US010576168B2

(12) United States Patent
Gaspar et al.

(10) Patent No.: US 10,576,168 B2
(45) Date of Patent: Mar. 3, 2020

(54) TREATMENT OF LYSOSOMAL STORAGE DISEASES

(71) Applicant: UCL Business PLC, London (GB)

(72) Inventors: Bobby Gaspar, London (GB); Adrian Thrasher, London (GB); Michael Antoniou, London (GB); Claudia Montiel-Equihua, London (GB)

(73) Assignee: UCL Business LTD, London (GB)

( * ) Notice: Subject to any disclaimer, the term of this patent is extended or adjusted under 35 U.S.C. 154(b) by 0 days.

(21) Appl. No.: 15/382,303

(22) Filed: Dec. 16, 2016

(65) Prior Publication Data
US 2017/0173184 A1 Jun. 22, 2017

(30) Foreign Application Priority Data

Dec. 16, 2015 (GB) .................................. 1522243.3

(51) Int. Cl.
A61K 48/00 (2006.01)
C12N 15/00 (2006.01)
C12N 15/63 (2006.01)
A61K 35/28 (2015.01)
A61K 38/47 (2006.01)
C12N 5/0789 (2010.01)
C12N 9/24 (2006.01)
C12N 9/26 (2006.01)
C12N 15/86 (2006.01)
A61K 35/12 (2015.01)

(52) U.S. Cl.
CPC .......... A61K 48/0058 (2013.01); A61K 35/28 (2013.01); A61K 38/47 (2013.01); A61K 48/00 (2013.01); A61K 48/0091 (2013.01); C12N 5/0647 (2013.01); C12N 9/2402 (2013.01); C12N 9/2408 (2013.01); C12N 15/86 (2013.01); C12Y 302/0102 (2013.01); C12Y 302/01076 (2013.01); A61K 2035/124 (2013.01); C12N 2510/00 (2013.01); C12N 2740/15043 (2013.01); C12N 2740/16043 (2013.01); C12N 2830/008 (2013.01)

(58) Field of Classification Search
None
See application file for complete search history.

(56) References Cited

U.S. PATENT DOCUMENTS

| 6,812,339 | B1 * | 11/2004 | Venter | ................... | C12Q 1/6883 |
| | | | | | 435/6.11 |
| 2014/0010861 | A1 * | 1/2014 | Bancel | ................. | A61K 48/005 |
| | | | | | 424/450 |
| 2014/0093485 | A1 | 4/2014 | Medin et al. | | |
| 2014/0220678 | A1 | 8/2014 | Trono et al. | | |
| 2014/0249208 | A1 * | 9/2014 | Bancel | ................. | A61K 48/005 |
| | | | | | 514/44 R |
| 2015/0315611 | A1 | 11/2015 | Van Der Loo et al. | | |

OTHER PUBLICATIONS

Voet, Biochemistry John Wiley and Sons, 1990, pp. 126-128.*
Ngo, in The Protein Folding Problem and Tertiary Structure Prediction, Merz et al. (eds.), Birkhauser Boston: Boston, MA, pp. 433 and 492-495, 1994.*
Kimchi-Sarfaty C et al., A "silent" polymorphism in the MDR1 gene changes substrate specificity.Science. Jan. 26, 2007;315(5811): 525-8.*
Aldenhoven et al., "Hematopoietic Cell Transplantation for Mucopolysaccharidosis Patients is Safe and Effective: Results after Implementation of International Guidelines," Biol Blood Marrow Transplant. 21:1106-1109 (2015).
Arumugam et al., "Genotoxic potential of lineage-specific lentivirus vectors carrying the beta-globin locus control region," Mol Ther. 17(11):1929-1937 (2009).
Bruni et al., "Update on treatment of lysosomal storage diseases," Acta Myol. 26:87-92 (2007).
Demaison et al., "High-level transduction and gene expression in hematopoietic repopulating cells using a human imunodeficiency virus type 1-based lentiviral vector containing an internal spleen focus forming virus promoter," Hum Gene Ther. 13:803-13 (2002).
El-Amouri et al., "Normalization and Improvement of CNS Deficits in Mice With Hurler Syndrome After Long-term Peripheral Delivery of BBB-targeted Iduronidase," Molecular Therapy. 22(12):2028-2037 (2014).
Giarrantana et al., "Proof of principle for transfusion of in vitro-generated red blood cells," Blood. 118(19):5071-9 (2011).
Knight et al., "Effect of the internal promoter on insertional gene activation by lentiviral vectors with an intact HIV long terminal repeat" J Virol. 84(9):4856-4859 (2010).
Montiel-Equihua et al., "The beta-Globin Locus Control Region in Combination With the EF1alpha Short Promoter Allows Enhanced Lentiviral Vector-mediated Erythroid Gene Expression With Conserved Multilineage Activity," Molecular Therapy. 20(7):1400-1409 (2012).
Tabiot-Dameron et al.,"Association of the 5' HS4 sequence of the chicken beta-globin locus control region with human EF1alpha gene promoter induces ubiquitous and high expression of human CD55 and CD59 cDNAs in transgenic rabbits," Transgenic Res. 8:223-235 (1999).
Visigalli et al., "Gene therapy augments the efficacy of hematopoietic cell transplantation and fully corrects mucopolysaccharidosis type I phenotype in the mouse model," Blood. 116(24):5130-5139 (2010).
Wang et al., "Reprogramming erythroid cells for lysosomal enzyme production leads to visceral and CAN cross-correction in mice with Hurler syndrome" PNAS. 106(47):19958-19963 (2009).
Wilkinson, F.L. et al., "Busulfan conditioning enhances engraftment of hematopoietic donor-derived cells in the brain compared with irradiation" Mol Ther. 21(4):868-876 (2013).
Winchester et al., "The molecular basis of lysosomal storage diseases and their treatment," Biochem. Soc. Trans. 28:150-4 (2000).
Partial International Search Report for International Patent Application No. PCT/G82016/053969, dated Apr. 18, 2017 (11 pages).
International Search Report and Written Opinion for International Patent Application No. PCT/GB2016/053969, dated Jun. 1, 2017 (19 pages).

(Continued)

Primary Examiner — Maria G Leavitt
(74) Attorney, Agent, or Firm — Clark & Elbing LLP

(57) ABSTRACT

The present invention relates to the prevention and/or treatment of lysosomal storage diseases in a patient.

9 Claims, 26 Drawing Sheets
Specification includes a Sequence Listing.

(56) References Cited

OTHER PUBLICATIONS

Adams et al., "Adenosine deaminase activity in thymus and other human tissues," Clin Exp Immunol. 26(3):647-49 (1976).
Antoine et al., "Long-term survival and transplantation of haemopoietic stem cells for immunodeficiencies: report of the European experience 1968-99," Lancet. 361(9357):553-560 (2003).
Ariga et al., "T-cell lines from 2 patients with adenosine deaminase (ADA) deficiency showed the restoration of ADA activity resulted from the reversion of an inherited mutation" Blood. 97(9):2896-2899 (2001).
Aiuti et al., "Gene therapy for immunodeficiency due to adenosine deaminase deficiency," N Engl J Med. 360(5):447-58 (2009).
Aiuti et al., "Multilineage hematopoietic reconstitution without clonal selection in ADA-SCID patients treated with stem cell gene therapy," J Clin Invest. 117(8):2233-40 (2007).
Apasov et al., "Adenosine deaminase deficiency increases thymic apoptosis and causes defective T cell receptor signalling," J Clin Invest. 108(1):131-41 (2001).
Arredondo-Vega et al., "Adenosine deaminase deficiency: genotype-phenotype correlations based on expressed activity of 29 mutant alleles," Am J Hum Genet. 63(4):1049-1059 (1998).
Bartelink et al.,"Body weight-dependent pharmacokinetics of busulfan in paediatric haematopoietic stem cell transplantation patients: towards individualized dosing," Clin Pharmacokinet. 51(5):331-45 (2012).
Benveniste et al., "p53 expression is required for thymocyte apoptosis induced by adenosine deaminase deficiency," Proc Natl Acad Sci USA. 92(18):8373-7 (1995).
Benveniste et al., "Interference with thymocyte differentiation by an inhibitor of S-adenosylhomocysteine hydrolase," J Immunol. 155(2):536-44 (1995).
Blackburn et al., "Adenosine deaminase-deficient mice generated using a two-stage genetic engineering strategy exhibit a combined immunodeficiency," J Biol Chem. 273(9):5093-100 (1998) (9 pages).
Blaese et al., "T lymphocyte-directed gene therapy for ADA-SCID: initial trial results after 4 years," Science. 270(5235):475-80 (1995).
Bollinger et al.,"Brief report: hepatic dysfunction as a complication of adenosine deaminase deficiency," N Engl J Med. 334(21):1367-71 (1996).
Booth et al., "Management options for adenosine deaminase deficiency; proceedings of the EBMT satellite workshop (Hamburg, Mar. 2006)," Clin Immunol. 123(2):139-47 (2007).
Bordignon et al., "Gene therapy in peripheral blood lymphocytes and bone marrow for ADA-immunodeficient patients," Science. 270(5235):470-5 (1995).
Borkowsky et al., "Adenosine deaminase deficiency without immunodeficiency: clinical and metabolic studies," Pediatr Res. 14(7):885-9 (1980).
Boztug et al., "Stem-cell gene therapy for the Wiskott-Aldrich syndrome," N Engl J Med. 363(20):1918-27 (2010).
Candotti et al., "Gene therapy for adenosine deaminase-deficient severe combined immune deficiency: clinical comparison of retroviral vectors and treatment plans," Blood. 120(18):3635-46 (2012).
Carson et al., "Lymphospecific toxicity in adenosine deaminase deficiency and purine nucleoside phosphorylase deficiency: possible role of nucleoside kinase(s)," Proc Natl Acad Sci USA. 74(12):5677-81 (1977).
Chaffee et al., "IgG antibody response to polyethylene glycol-modified adenosine deaminase in patients with adenosine deaminase deficiency," J Clin Invest. 89(5):1643-51 (1992).
Chan et al., "Long-term efficacy of enzyme replacement therapy for adenosine deaminase (ADA)-deficient Severe Combined Immunodeficiency (SCID)," Clin Immunol. 117(2): 133-143 (2005).
Daddona et al., "Adenosine deaminase deficiency with normal immune function: An acidic enzyme mutation," J Clin Invest. 72(2):483-492 (1983).
Dinjens et al., "Distribution of adenosine deaminase complexing protein (ADCP) in human tissues," J Histochem Cytochem. 37(12):1869-1875 (1989).

Dong et al., "Determination of adenosine deaminase binding domain on CD26 and its immunoregulatory effect on T cell activation," J Immunol. 159(12): 6070-6076 (1997).
Dooley et al., "First trimester diagnosis of adenosine deaminase deficiency," Prenat Diagn. 7(8):561-565 (1987).
Dull et al., "A third-generation lentivirus vector with a conditional packaging system," J Virol. 72(11):8463-71 (1998).
Fischer et al., "Naturally occurring primary deficiencies of the immune system," Annu Rev Immunol. 15:93-124 (1997).
Fox et al., "$Ta_1$, a novel 105 KD human T cell activation antigen defined by a monoclonal antibody," J Immunol. 133(3):1250-1256 (1984).
Gaspar et al., "Successful reconstitution of immunity in ADA-SCID by stem cell gene therapy following cessation of PEG-ADA and use of mild preconditioning," Mol Ther. 14(4):505-513 (2006).
Gaspar et al., "How I treat ADA deficiency," Blood. 114(17):3524-32 (2009).
Gaspar et al., "Hematopoietic stem cell gene therapy for adenosine deaminase-deficient severe combined immunodeficiency leads to long-term immunological recovery and metabolic correction," Sci Transl Med. 3(97):97ra80 (2011) (9 pages).
Giblett et al., "Adenosine-deaminase deficiency in two patients with severely impaired cellular immunity," Lancet. 2(7786):1067-1069 (1972).
Hacein-Bey-Abina et al., "Insertional oncogenesis in 4 patients after retrovirus-mediated gene therapy of SCID-X1," J Clin Invest. 118(9):3132-3142 (2008).
Hacein-Bey-Abina et al., "LMO2-associated clonal T cell proliferation in two patients after gene therapy for SCID-X1," Science. 302(5644):415-9 (2003) (6 pages).
Hershfield et al., "In vivo inactivation of erythrocyte S-adenosylhomocysteine hydrolase by 2'-deoxyadenosine in adenosine deaminase-deficient patients," J Clin Invest. 63(4):807-11 (1979).
Hershfield, "Adenosine deaminase deficiency," GeneReviews[Internet], NCBI Bookshelf, posted Oct. 3, 2006 (36 pages).
Hirschhorn et al., "Amelioration of neurologic abnormalities after 'enzyme replacement' in adenosine deaminase deficiency," N Engl J Med. 303(7):377-80 (1980).
Hirschhorn, "Overview of biochemical abnormalities and molecular genetics of adenosine deaminase deficiency," Pediatr Res. 33(1 Suppl):S35-41 (1993).
Hirschhorn et al., "Spontaneous in vivo reversion to normal of an inherited mutation in a patient with adenosine deaminase deficiency," Nat Genet. 13(3):290-295 (1996).
Howe et al., "Insertional mutagenesis combined with acquired somatic mutations causes leukemogenesis following gene therapy of SCID-X1 patients," J Clin Invest. 118(9):3143-50 (2008).
Husain et al., "Burkitt's lymphoma in a patient with adenosine deaminase deficiency-severe combined immunodeficiency treated with polyethylene glycol-adenosine deaminase," J Pediatr. 151(1):93-5 (2007).
Ingolia et al., "Molecular cloning of the murine adenosine deaminase gene from a genetically enriched source: identification and characterization of the promoter region," Mol Cell Biol. 6(12): 4458-4466 (1986).
Kadonaga et al., "Isolation of cDNA encoding transcription factor Sp1 and functional analysis of the DNA binding domain," Cell. 51(6):1079-1090 (1987).
Kaufman et al., "Cerebral lymphoma in an adenosine deaminase-deficient patient with severe combined immunodeficiency receiving polyethylene glycol-conjugated adenosine deaminase," Pediatrics. 116(6):e876-9 (2005) (6 pages).
Kohn et al., "T lymphocytes with a normal ADA gene accumulate after transplantation of transduced autologous umbilical cord blood CD34+ cells in ADA-deficient SCID neonates," available in PMC Sep. 19, 2013, published in final edited form as: Nat Med. 4(7):775-780 (1998) (13 pages).
Lee et al., "Mechanisms of deoxyadenosine toxicity in human lymphoid cells in vitro: relevance to the therapeutic use of inhibitors of adenosine deaminase," Br J Haematol. 56(1):107-119 (1984).
Macchi et al., "Mutations of Jak-3 gene in patients with autosomal severe combined immune deficiency (SCID)," Nature. 377(6544):65-8 (1995).

(56) References Cited

OTHER PUBLICATIONS

Marwaha et al., "Extreme thrombocytosis in response to PEG-ADA: early therapeutic and risk indicator," Clin Pediatr (Phila). 39(3):183-186 (2000).
Markert et al., "Adenosine deaminase (ADA) deficiency due to deletion of the ADA gene promoter and first exon by homologous recombination between two Alu elements," J Clin Invest. 81(5):1323-1327 (1988).
Migchielsen et al., "Adenosine-deaminase-deficient mice die perinatally and exhibit liver-cell degeneration, atelectasis and small intestinal cell death," Nat Genet. 10(3):279-87 (1995).
Morgan et al., "Heterogeneity of biochemical, clinical and immunological parameters in severe combined immunodeficiency due to adenosine deaminase deficiency," Clin Exp Immunol. 70(3):491-9 (1987).
Morrison et al., "A marker for neoplastic progression of human melanocytes is a cell surface ectopeptidase," J Exp Med. 177(4):1135-1143 (1993).
Moshous et al., "Artemis, a novel DNA double-strand break repair/V(D)J recombination protein, is mutated in human severe combined immune deficiency," Cell. 105(2):177-186 (2001).
Noguchi et al., "Interleukin-2 receptor gamma chain mutation results in X-linked severe combined immunodeficiency in humans," Cell. 73(1):147-57 (1993).
Ott et al., "Correction of X-linked chronic granulomatous disease by gene therapy, augmented by insertional activation of MDS1-EVI1, PRDM16 or SETBP1," Nat Med. 12(4):401-409 (2006).
Ozsahin et al., "Adenosine deaminase deficiency in adults," Blood. 89(8):2849-2855 (1997).
Petersen et al., "New assignment of the adenosine deaminase gene locus to chromosome 20q13 X 11 by study of a patient with interstitial deletion 20q," J Med Genet. 24(2):93-96 (1987).
Philip et al., "Regional assignment of the ADA locus on 20q13.2 leads to qter by gene dosage studies," Cytogenet Cell Genet. 27(2-3):187-189 (1980).
Puel et al., "Defective IL7R expression in T(−)B(+)NK(+) severe combined immunodeficiency," Nat Genet. 20(4):394-397 (1998).
Ratech et al., "Pathologic findings in adenosine-deaminase-deficient severe combined immunodeficiency. I. Kidney, adrenal, and chondroosseous tissue alterations," Am J Pathol. 120(1):157-69 (1985).
Revy et al., "Cernunnos-XLF, a recently identified non-homologous end-joining factor required for the development of the immune system," Curr Opin Allergy Clin Immunol. 6(6):416-20 (2006).
Richard et al., "The binding site of human adenosine deaminase for CD26/Dipeptidyl peptidase IV: the Arg142Gln mutation impairs binding to CD26 but does not cause immune deficiency," J Exp Med. 192(9):1223-35 (2000).
Rieux-Laucat et al., "Inherited and somatic CD3zeta mutations in a patient with T-cell deficiency," N Engl J Med. 354(18):1913-1921 (2006).
Sanchez et al., "Carrier frequency of a nonsense mutation in the adenosine deaminase (ADA) gene implies a high incidence of ADA-deficient severe combined immunodeficiency (SCID) in Somalia and a single, common haplotype indicates common ancestry," Ann Hum Genet. 71(Pt 3):336-347 (2007).
Schambach et al., "Woodchuck hepatitis virus post-transcriptional regulatory element deleted from X protein and promoter sequences enhances retroviral vector titer and expression," Gene Ther. 13(7):641-645 (2006).
Schambach et al., "Context dependence of different modules for posttranscriptional enhancement of gene expression from retroviral vectors," Mol Ther. 2(5): 435-445 (2000).
Schrader et al., "Characterization of the adenosine deaminase-adenosine deaminase complexing protein binding reaction," J Biol Chem. 265(31):19312-8 (1990) (8 pages).
Shultz et al., "Human lymphoid and myeloid cell development in NOD/LtSz-scid IL2R gamma null mice engrafted with mobilized human hemopoietic stem cells," J Immunol. 174(10):6477-6489 (2005).
SenGupta et al.,"A flow cytometric method for the detection of adenosine deaminase in mononuclear cells," J Immunol Methods. 80(2): 155-162 (1985).
Shovlin et al., "Adult onset immunodeficiency caused by inherited adenosine deaminase deficiency," J Immunol. 153(5):2331-2339 (1994).
Soudais et al., "Independent mutations of the human CD3-epsilon gene resulting in a T cell receptor/CD3 complex immunodeficiency," Nat Genet. 3(1):77-81 (1993).
Stein et al., "Genomic instability and myelodysplasia with monosomy 7 consequent to EVI1 activation after gene therapy for chronic granulomatous disease," Nat Med. 16(2):198-204 (2010).
Stephan et al., "Atypical X-linked severe combined immunodeficiency due to possible spontaneous reversion of the genetic defect in T cells," N Engl J Med. 335(21):1563-1567 (1996).
Tanaka et al., "Sensorineural deafness in siblings with adenosine deaminase deficiency," Brain Dev. 18(4):304-306 (1996).
Thrasher et al., "Failure of SCID-X1 gene therapy in older patients," Blood. 105(11):4255-4257 (2005).
Tischfield et al., "Assignment of a gene for adenosine deaminase to human chromosome 20," Hum Hered. 24(1):1-11 (1974).
Titman et al., "Cognitive and behavioral abnormalities in children after hematopoietic stem cell transplantation for severe congenital immunodeficiencies," Blood. 112(9):3907-13 (2008).
Trotta, "Identification of a membrane adenosine deaminase binding protein from human placenta," Biochemistry. 21(17):4014-4023 (1982).
Van der Weyden et al., "Human adenosine deaminase. Distribution and properties," J Biol Chem. 251(18):5448-56 (1976).
Van Lunzen et al., "Transfer of autologous gene-modified T cells in HIV-infected patients with advanced immunodeficiency and drug-resistant virus," Mol Ther. 15(5):1024-33 (2007).
Valerio et al., "Isolation of cDNA clones for human adenosine deaminase" Gene. 25(2-3):231-240 (1983).
Zychlinski et al., "Physiological promoters reduce the genotoxic risk of integrating gene vectors," Mol Ther. 16(4):718-25 (2008).
Carbonaro et al., "Preclinical demonstration of lentiviral vector-mediated correction of immunological and metabolic abnormalities in models of adenosine deaminase deficiency," Mol Ther. 22(3):607-22 (2014).
Montiel-Equihua et al., "The beta-globin locus control region in combination with the EF1(alpha) short promoter allows enhanced lentiviral vector-mediated erythroid gene expression with conserved multilineage activity," Mol Ther. 20(7):1400-9 (2012).
International Search Report and Written Opinion for International Patent Application No. PCT/GB2016/053970, dated Feb. 24, 2017 (14 pages).
Aiuti et al., "Gene therapy for ADA-SCID, the first marketing approval of an ex vivo gene therapy in Europe: paving the road for the next generation of advanced therapy medicinal products," EMBO Mol Med. 9(6):737-40 (2017).
ADAGEN® (pegademase bovine) Injection, Leadiant Biosciences, Inc., <http://www.adagen.com/gene_therapy.html>, retrieved Nov. 8, 2018 (3 pages).
Braid et al., "Intramuscular administration potentiates extended dwell time of mesenchymal stromal cells compared to other routes," Cytotherapy. 20(2):232-44 (2018).

\* cited by examiner

Ctrl WT

Ctrl IDUA-/-

LCR EFS treated

WT (T3B 7LR)

Control WT (P2 5L)

MPS Control (P1 3R)

LCR (T3B 9R)

FIG. 20
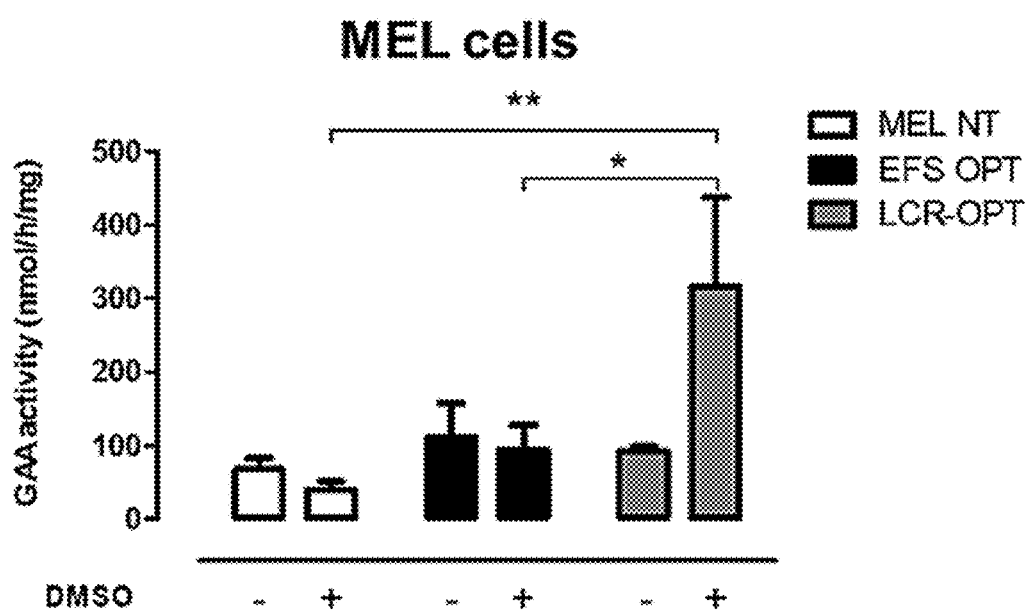
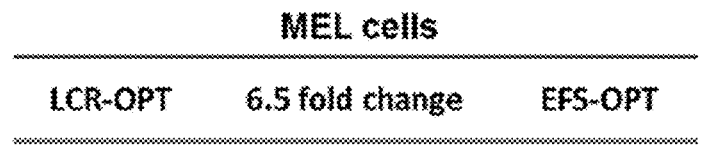

| Human erythroid-like cells | | |
|---|---|---|
| LCR-OPT | 4 fold change | EFS-OPT |

SEQUENCE LISTING

<160> NUMBER OF SEQ ID NOS: 20

<210> SEQ ID NO 1
<211> LENGTH: 4020
<212> TYPE: DNA
<213> ORGANISM: Artificial Sequence
<220> FEATURE:
<223> OTHER INFORMATION: BLCR-EFS SEQUENCE

<400> SEQUENCE: 1

```
gcggccgcta tctcattgct gttcgtaatt gttagattaa ttttgtaata ttgatattat    60
tcctagaaag ctgaggcctc aagatgataa cttttatttt ctggacttgt aatagctttc   120
tcttgtattc accatgttgt aactttctta gagtagtaac aatataaagt tattgtgagt   180
ttttgcaaac acagcaaaca caacgaccca tatagacatt gatgtgaaat tgtctattgt   240
caatttatgg gaaacaagt atgtactttt tctactaagc cattgaaaca ggaataacag    300
aacaagattg aaagaataca ttttccgaaa ttacttgagt attatacaaa gacaagcacg   360
tggacctggg aggagggtta ttgtccatga ctggtgtgtg gagacaaatg caggtttata   420
atagatggga tggcatctag cgcaatgact ttgccatcac ttttagagag ctcttggggg   480
ccccagtaca caagagggga cgcagggtat atgtagacat ctcattcttt tcttagtgt    540 gagaataaga atagccatga cctgagttta tagacaatga gccctttct ctctcccact    600 cagcagctat gagatggctt gccctgcctc tctactaggc tgactcactc caaggcccag   660
caatgggcag ggctctgtca gggctttgat agcactatct gcagagccag ggccgagaag   720
gggtggactc cagagactct ccctcccatt cccgagcagg gtttgcttat ttatgcattt   780
aaatgatata tttatttaa aagaaataac aggagactgc ccagccctgg ctgtgacatg   840
gaaactatgt agaatatttt gggttccatt ttttttcct tctttcagtt agaggaaaag   900
```

```
gggctcactg cacatacact agacagaaag tcaggagctt tgaatccaag cctgatcatt    960
tccatgtcat actgagaaag tccccaccct tctctgagcc tcagtttctc tttttataag   1020
taggagtctg gagtaaatga tttccaatgg ctctcatttc aatacaaaat ttccgtttat   1080
taaatgcatg agcttctgtg cggccgctct agaactagtg gatccccgc ttctttgaga    1140
aacatcttct tcgttagtgg cctgcccctc attcccactt taatatccag aatcactata   1200
agaagaatat aataagagga ataactctta ttataggtaa gggaaaatta agaggcatac   1260
gtgatgggat gagtaagaga ggagagggaa ggattaatgg atgataaaat ctactactat   1320
ttgttgagac cttttatagt ctaatcaatt ttgctattgt tttccatcct cacgctaact   1380
ccataaaaaa acactattat tatctttatt ttgccatgac aagactgagc tcagaagagt   1440
caagcatttg cctaaggtcg acatgtcag aggcagtgcc agacctatgt gagactctgc     1500
agctactgct catgggccct gtgctgcact gatgaggagg atcagatgga tggggcaatg   1560
aagcaaagga atcattctgt ggataaagga acagccatg aagaagtcta tgactgtaaa     1620
tttgggagca ggagtctcta aggacttgga tttcaaggaa ttttgactca gcaaacacaa   1680
gaccctcacg tgactttgc gagctggtgt gccagatgtg tctatcagag gttccaggga    1740
gggtggggtg gggtcagggc tggccaccag ctatcagggc ccagatgggt tataggctgg   1800
caggctcaga taggtggtta ggtcaggttg gtggtgctgg gtggagtcca tgactcccag   1860
gagccaggag agatagacca tgagtagagg gcagacatgg gaaaggtggg ggaggcacag   1920
catagcagca tttttcattc tactactaca tgggactgct cccctatacc cccagctagg   1980
ggcaagtgcc ttgactccta tgttttcagg atcatcatct ataaagtaag agtaataatt   2040
gtgtctatct catagggtta ttatgaggat caaaggagat gcacactctc tggaccagtg   2100
gcctaacagt tcaggacaga gctatgggct tcctatgtat gggtcagtgg tctcaatgta   2160
gcaggcaagt tccagaagat agcatcaacc actgttagag atatactgcc agtctcagag   2220
cctgatgtta atttagcaat gggctgggac cctcctccag tagaaccttc taaccagctg   2280
ctgcagtcaa agtcgaatgc agctggttag actttttta atgaagcttg gtgaccgtcg     2340
taccagtggg gcctctaaga ctaagtcact ctgtctcact gtgtcttagc cagttcctta   2400
cagcttgccc tgatgggaga tagagaatgg gtatcctcca acaaaaaat aaattttcat     2460
ttctcaaggt ccaacttatg ttttcttaat ttttaaaaaa atcttgacca ttctccactc   2520
tctaaaataa tccacagtga gagaaacatt cttttccccc atcccataaa tacctctatt   2580
aaatatggaa aatctgggca tggtgtctca cacctgtaat cccagcactt tgggaggctg   2640
aggtgggtgg actgcttgga gctcaggagt tcaagaccat cttggacaac atggtgatac   2700
cctgcctcta caaaagtac aaaaattagc ctggcatggt ggtgtgcacc tgtaatccca    2760
gctattaggg tggctgaggc aggagaattg cttgaacccg ggaggcggag gttgcagtga   2820
gctgagatcg tgccactgca ctccagcctg ggggacagag cacattataa ttaactgtta   2880
tttttactt ggactcttgt ggggaataag atacatgttt tattcttatt tatgattcaa     2940
gcactgaaaa tagtgtttag catccagcag gtgcttcaaa accatttgct gaatgattac   3000
tatacttttt acaagctcag ctccctctat cccttccagc atcctcatct ctgattaaat   3060
aagcttcagt ttttccttag ttcctgttac atttctgtgt gtctccatta gtgacctccc   3120
atagtccaag catgagcagt tctggccagg cccctgtcgg ggtcagtgcc ccaccccgc     3180
cttctggttc tgtgtaacct tctaagcaaa ccttctggct caagcacagc aatgctgagt   3240
catgatgagt catgctgagg cttagggtgt gtgcccagat gttctcagcc tagagtgatg   3300
```

```
actcctatct gggtccccag caggatgctt acagggcaga tggcaaaaaa aaggagaagc    3360
tgaccacctg actaaaactc cacctcaaac ggcatcataa agaaaatgga tgcctgagac    3420
agaatgtgac atattctaga atatattatt tcctgaatat atatatatat atatacacat    3480
atacgtatat atatatatat atatatttgt tgttatcaat tgccatagaa tgattagtta    3540
ttgtgaatca aatatttatc ttgcaggtgg cctctatacc tagaagcggc agaatcaggc    3600
tttattaata catgtgtata gattttagg atctatacac atgtattaat atgaaacaag    3660
gatatggaag aggaaggcat gaaaacagga aagaaaaca aaccttgttt gccatttaa    3720 ggcacccctg acagctagg tggcaaaagg gggctgcagg aattcgatat cacgattggc    3780
tccggtgccc gtcagtgggc agagcgcaca tcgcccacag tccccgagaa gttgggggga    3840
ggggtcggca attgaaccgg tgcctagaga aggtggcgcg gggtaaactg ggaaagtgat    3900
gtcgtgtact ggctccgcct ttttcccgag ggtgggggag aaccgtatat aagtgcagta    3960
gtcgccgtga acgttctttt tcgcaacggg tttgccgcca aacacaggt gtcgtgacgc    4020
```

<210> SEQ ID NO 2
<211> LENGTH: 1974
<212> TYPE: DNA
<213> ORGANISM: Artificial Sequence
<220> FEATURE:
<223> OTHER INFORMATION: cDNA of codon optimised IDUA

<400> SEQUENCE: 2

```
agcgctatgc ggccgctgag gcctagagct gccctgctgg ctctgctggc ctctctgctg      60
gctgcccctc ctgtggcccc tgccgaagcc cctcacctgg tgcatgtgga tgccgccagg     120
gctctgtggc cactgcggag attctggcgg agcaccggct tttgccccc actgcctcac     180 agccaggccg accagtacgt gctgagctgg gaccagcagc tgaacctggc ctacgtcggc     240
gccgtgcccc acagaggcat caaacaagtg cgcacccact ggctgctgga actggtgaca     300
acccggggca gcaccggcag aggactgagc tacaacttca cccacctgga cggctacctg     360
gacctgctga gagagaacca gctgctgccc ggcttcgagc tgatgggcag cgccagcggc     420
cacttcaccg acttcgagga caagcagcag gtgttcgagt ggaaggacct ggtgtccagc     480
ctggccagac ggtacatcgg cagatacggc ctggcccacg tgtccaagtg aacttcgag     540 acatggaacg agcccgacca ccacgacttc gacaacgtgt caatgaccat gcagggcttt     600
ctgaactact acgacgcctg cagcgagggc ctgagagccg cctcctgc cctgagactg     660 ggcggacccg cgatagctt ccacaccccc cccagaagcc cctgagctg gggcctgctg     720 agacactgcc acgacggcac caatttcttc accggcgagg ccggcgtgcg gctggactac     780
atcagcctgc accggaaggg cgccagaagc agcatcagca tcctggaaca ggaaaaggtc     840
gtcgcccagc agatccggca gctgttcccc aagttcgccg acaccccat ctacaacgac     900 gaggccgacc cctggtcgg atggtcactg cctcagcctt ggagagccga cgtgacctac     960
gccgccatgg tggtgaaagt gatcgcccag caccagaacc tgctgctggc caacaccacc    1020
agcgccttcc cttacgccct gctgagcaac gacaacgcct tcctgagcta ccaccccac    1080 cccttcgccc agagaaccct gaccgccgg ttccaggtca caacaccag accccccac    1140 gtgcagctgc tgagaaagcc cgtgctgacc gccatgggac tgctggccct gctggacgag    1200
gaacagctgt gggccgaggt gtcccaggcc ggcaccgtgc tggactccaa tcacacagtg    1260
ggcgtgctgg ctagcgccca cagacctcag ggacccgccg atgcttggcg gctgccgtg    1320
```

| | | | |
|---|---|---|---|
| ctgatctacg | ccagcgacga | caccagagcc | caccccaaca gatccgtggc cgtgaccctg | 1380 |
| cggctgagag | gcgtgccacc | tggccctggc | ctggtgtacg tgaccagata cctggacaac | 1440 |
| ggcctgtgca | gccccgacgg | cgaatggcgc | agactgggca gacctgtgtt ccccaccgcc | 1500 |
| gagcagttcc | ggcggatgag | agccgctgag | gaccctgtgg ctgccgcccc tagacctctg | 1560 |
| cctgctggcg | gcagactgac | cctgaggccc | gctctgagac tgccttctct gctgctggtg | 1620 |
| cacgtgtgcg | ccaggcccga | gaagcctccc | ggccaggtca aagactgag agccctgcct | 1680 |
| ctgacccagg | gacagctggt | gctggtctgg | tccgatgagc acgtgggcag caagtgcctg | 1740 |
| tggacctacg | agatccagtt | cagccaggac | ggcaaggcct acaccccgt gtcccggaag | 1800 |
| cccagcacct | tcaacctgtt | cgtgttcagc | cccgacactg gcgctgtgtc cggctcttat | 1860 |
| agagtgcggg | ccctggacta | ctgggccaga | cccggccctt tcagcgaccc cgtgccctac | 1920 |
| ctggaagtgc | ccgtgcctag | aggccccct | agccccggca cccttgagt cgac | 1974 |

<210> SEQ ID NO 3
<211> LENGTH: 26591
<212> TYPE: DNA
<213> ORGANISM: Homo sapiens

<400> SEQUENCE: 3

| | | | |
|---|---|---|---|
| agaacccgcc | ccggagggga | gggacgcagg | gaagagtcgc acggacgcac tcgcgctgcg | 60 |
| gccagcgccc | gggcctgcgg | gccccggcgg | cggctgtgtt gcgcagtctt catgggttcc | 120 |
| cgacgaggag | gtctctgtgg | ctgcggcggc | ggctgctaac tgcgccacct gctgcagcct | 180 |
| gtccccgccg | ctctgaagcg | gccgcgtcga | agccgaaatg ccgccacccc ggaccggccg | 240 |
| aggccttctc | tggctgggtc | tggttctgag | ctccgtctgc gtcgccctcg gatccgaaac | 300 |
| gcaggccaac | tcgaccacag | gtgccgccca | cgccctccct gccatctctt ctcccttcct | 360 |
| ccctcccttc | cttcctcctt | ccttcttcc | ttccttcttt gtttatatcc attctttta | 420 |
| cccttcctct | ctcctaccat | tccttctttc | atccatcatt cgttccctcc ctccattttt | 480 |
| cactccttcc | taccgtccct | tcatccctcc | cttccctctt tccatctatt catccatcca | 540 |
| tctcctatcc | ctccgtgctt | cccttcctct | ttcccccat cttcccatc tctatccatc | 600 |
| catctttccc | cctcctttcc | tccctccatt | ggtccatccg tccctttac cttctatcca | 660 |
| ttcatatttc | tctctcttct | cccctccttc | tctccatcct ttcttccctt cagctattca | 720 |
| tctttttcctc | cttatcttcc | tccatccaac | catctgtcct ttcctgcata catcattctc | 780 |
| ttttttcct | aaattcatct | ttcctttcca | ccatctttca ctcactatct cgcttcctca | 840 |
| cccaggttgg | aggccatgac | caaagcctaa | ccctgccacc caggactcag gcttcctcct | 900 |
| cgagccccac | tcccacccctt | gctgaggcac | agcgccctcc ctggctaggc tgttaaggtg | 960 |
| cagggtccag | ccttgggcct | cttagtaacc | tagcacctac catgagggag ggttcagtgt | 1020 |
| cagtgcaggt | tacctcacca | aagccctcc | ctctgtgta gatgctctga acgttcttct | 1080 |
| catcatcgtg | gatgacctgc | gccctccct | gggctgttat ggggataagc tggtgaggtc | 1140 |
| cccaaatatt | gaccaactgg | catcccacag | cctcctcttc cagaatgcct ttgcgcaggt | 1200 |
| atgtctggga | acctctagct | gtgggtgtgt | gctgcttcgt gcactgaggg ttggggcgg | 1260 |
| ggagcttcag | ctattgtcag | atggcacaga | ttgtgcggga catcttgtta gagggaagca | 1320 |
| tagtctggaa | aatggtagtg | gagaaaatct | ggttttccac tcatgggaaa gcttgacctt | 1380 |
| caagggtggc | cttctccttg | ggtgcaaggt | gcgccctggc cctgatgtgt tcatggcagc | 1440 |
| cctggccagc | tttctcccag | aacgggcgct | tgcctggtgc tcagaaggaa ggggtgctgc | 1500 |

-continued

```
agaagggcac ccacaggtct gcaggctggg cctcaggtga gagctagcca gggtggccct    1560
gctccctgaa cccccctcatg gctctgcccc cagcaacact ggccgctctg tgtgcctggg   1620
gaggccattg cgtaggagga gataagcatc tgctggtttc aggggctgat tgcttccctt    1680
ttctctcccg gaagcagtct gttgcctagg tgacacccaa atcccagtgt ctggtttgag    1740
ctctgcatga ctcagctacc aagctgtttg ctaggagcct cgggagggcg gttgcttggt    1800
tacctaagag atggcagaca tgttttgctg tggcgatgct tacctctgct tctgctccct    1860
aacagcaagc agtgtgcgcc ccgagccgcg tttctttcct cactggcagg agacctgaca    1920
ccacccgcct gtacgacttc aactcctact ggagggtgca cgctggaaac ttctccacca    1980
tcccccagta cttcaaggag aatggctatg tgaccatgtc ggtgggaaaa gtctttcacc    2040
ctggtactgc tccatgtcca gagtctgggt tctcttggtt tgtggtgtct gaatccagca    2100
ttcccatcct ggggatgggg ctgtctttgc agagccctct tctggctggg cgagtccctc    2160
gctagtcagt gcttcctttc taaaaaactg acttgtcaac ccagccacgt tttcacccaa    2220
agtgaaaaag ggtagaaaga gctttgcttc ctttcagaaa ccactgaggg tgtgctgttg    2280
ggtctttcag ctcctcgggt ggtagggagg acacaggctg gggaggtggc agtgttgggt    2340
ggagtccagc tcagggcccc accctctccc ctgcagggta cctgtcagta aacctagggg    2400
tggggtgagg acacctgagg gcctcccgtg tggccagcat tgctgttgct gacttattgc    2460
ccaatgaggg ggctgtgctt aggtaggggc tgctatccac tctggaaatt aagtcagaaa    2520
gatgagtgta atctggtacc caggatctat agggtcccag agacggacat tccttacctc    2580
aaatgctgcc tgataaactg gctctcttta atgccaatat ggggatagtg aaaagcaaac    2640
aaactttaaa acttttatt tatagaagta atgcatgagt atttgagaaa aaaaatggag     2700
aaaaaagtat tggaagacaa gagcaccata gggacaataa tgcttatcat ttgggaatga    2760
cgaatgtttt cagtctcttt cccttttgctc agtggttaca ccggcaggct tggcagcctt    2820
ctgcaggagc tcagctggcc agcccaggtt gagagtgaca ttcagctcta ctaagtcagg    2880
ccagtttcag aggtgaacct gtcaggaatc atattgcaca gccaaaagtc cagtgtcagg    2940
agaactttct gcagtttggt gttctcatta ccatacccct tgcccaaatg cagctggagg    3000
gaagtgatga ttttggagag aggaggaaac acagcagagg gaggagattg tgctttggga   3060
ggggaaacca ggcaaggact gagtgatgtt gcttgacctc ctccctcctg atgattggat    3120
tttggcacca ggctctaagc accatgtcct tctcagagaa taaacctttc cctgcagccc    3180
ttgtgggaac acatttttca gctgaatctt tgttctcaag acctttttct gttagcattg    3240
ggcctgcttc aagatgacag tagccaccac tgtgtgccag gtatgtaccg tttaccatgc    3300
tggccactcc tttaatcctc ccaacagcaa gcaaggtggg ttttatcat catcatcatt     3360 tcccaaggaa gacatgaagg ctcatgggag tcaagtagct tgccagaggt tgcaaggatg    3420
ctaagaggca gcatcaggat ttggacctgt ggttgttggc ttcctgtgtg ctctttccac    3480
agtgcttgct gtcttcatag gccctccacc cgctgccctc tttctctcca ttcctgtctc    3540
ttctggtact cccttatggga gtcccactgt gtgactgctg ctgatgcttt ctcacgaggt   3600
tctgcctgtg atcccctcca ctcccagcta accactatag gcagcacttc ccttcagatc    3660
cctcacaggc ctcactggct cctagaagtc ctccctgcca gtcctcacct gactcacaat    3720
aacctctgtg cttggaggat cccccacttg gcacttcgat gcttttgaaa gctgaagtc    3780 cttccttggt ttccagtgct gttatactgt cttcacaaat aaactataaa ctactaagct    3840
```

```
taagggtggg tttctgcttc atgaatgagc acttgaactt ggaattctaa acaaggtttt      3900
tgagtcctgg ctcccttatc taatatctgg ttagcatagg taagtcacat accttccctg      3960
agcctccctc tcctgccccc atcggctccc tgatggtgct gatgcctctg ctgcctcctt      4020
cataggtgta gagataggtt tcagcatggg ctctaaggag ctgactgatc ttgtccttgt      4080
gggtcccttc cacagagcct agcacaaatc atcagggctt agggaccagg aagtcagatg      4140
cttagttctc aaatagaaac tagagagttt ggctttagag ggaccttttt gtagatgagg      4200
aaactgagcc ccaaagaagg gaggttccac ttgcccattt gtttacagag tttttaattat      4260 ggggagtggg gtgttgaaag actcatcatg ttttaacaac cttttttttt ttccaaggga      4320
tatcttctaa ccataccgat gattctccgt atagctggtc ttttccacct tatcatcctt      4380
cctctgagaa gtatgaaaac actaaggtaa ggctgtgaaa gggacatttc tgaagaggaa      4440 ccacttttttc ctttgtcaca taaactactg ggtatactgc atgttctgtg aagctggtta    4500
tataccacga agttgtgggt ttcatttgtg ataatgtttt gacagaagta agtgttggga      4560
tcttcagcat taggcccgac aggagcagtg gcttcattct agaagctggt gggtgctact      4620
tgttctaaaa ccttgggctc taacgtgtca gactcattga atagctcccc agtgctcacg      4680
ctggatgaga ctgagagttg taggagatgc tgagacatgg gagggagaaa agaggctgag      4740
ctccaggagc ctcagcccag aatgggagaa aggcatgccg tgtatctgtc tctgacctaa      4800
tgtgtatgtt cagcagctga gacctctgat aggggttttg aattttttaga gcattatgaa      4860 aaaaagtaac ctacaaagaa aatcttggtt tagaggaatc ccaaatgtat aaatgaaact      4920
aaaacccaca tttaagaaac tcagaaaacc agctagggaa ctgagacatg aaatgtatct      4980
ctgaggtttt agtaaacatc gtgttgggaa gggtgaggat ttggaagtga ggtggaaggt      5040
attgttctaa gttcttgaca gctttccatt tcagaataca gtgaaaactg tgagctctgg      5100
cctttggctt gtggcttgaa tagggaagat cccatcttaa ttccctgaag ccatcttgct      5160 tcttttttagt ggcctcactt acgaatgcca ggtccctgcc ctaactgccc cctacccatt    5220
tcttctcaaa gtggtgggtc tgacaatact aaatctccct cgagtgctgc aaatcgtgta      5280
tatatagatg atgaacaagt ggtctgaggc gggtgctggg ctgtcctgcc caagggtggg      5340
gtgagcaagg cagggctgtg aaaaggcaac actctttgag atggaacagc agctgacaca      5400
gcccctcggt ctttgtggta tacaaatcat ggtcagaact aactttggtc tcacggccag      5460
catgtctact ttaggaagca aagcaggagg tttcattctg tgcctagtgt agctgaagtt      5520
ctggaaattc catggactgt caccttatca agttgattgg gaccctgtca cttacaagcc      5580
ttagcctgtc tttgaaattt gaaatggggtt ttttttttct ttttaaattt ttaattaaaa     5640
tagagttcat ataccataaa actctccctt ttgaagtata taatttaatg gttttttagca     5700 tactcacgga gctatgcagc catcacccaa atcgatctta gatcattttt atcgctctca      5760
aaagaaaccc tgtacccatt accagtcgtt cctcattttg tctcagcacc cagcgtggga      5820
caacaactga actatttttg gtctccatgg atttgcctat tttgtccatt tggtataaat      5880
agagtcatac actatgtagc catttgtttc tggcttcttt cacttagaat aatgttttttg     5940 aggttcagcc acataacagt ataaattggt acttcattcc ttttttttttt ttttttttgag    6000 atggagtttc actcttgtca cccaggctgg agtgcaatgg cgcaatctca gctcactgta      6060
gcctccacct cccaggttca agcgatgatt ctcctgcctc agccttccga gtagctggga      6120
ttacaggtgc ccaccaccac acccagctaa tgtttgtatt tttagtagag acggggtttc      6180
accatgttgg tcaggctggt ctcgaactcc ttacctcagg caatccactc atctcccaga      6240
```

```
gtgctgggat tagaggtgtg agccaccgca cccagccttt cattcctttt tatggctgca    6300
taattgtcta ttgtaccaca ttttgtttat cagttcatca cttgatggat atttgggttg    6360
tttctacttt tgactattag gaataatgct gccctcgaca ttttgtaca agtgttttta    6420
tgggcatatg ttttaatt ttttgggtat aataactatg tttaactgtt tgaggaattg    6480
ccagactggc tttcaaagtg gctgcactat tttacattcc caccagcaat gtgagagggt    6540
tctaattttt ctgcatcctc gtcaacactt gttattttcc atcttaaaaa attataacca    6600
tccttttggg tgtgaagtgg ttttgatttg catttcccta atgactaatg atgttagcca    6660
catttccatg ttcaattggc catttgtata tcatctttgg agaaatgtct atccaaatcc    6720
tttgcccatt tttaattggc attttttaat tgttgaatta gagatggatt ttttttata    6780
attagtctat cggggtttct tttaattagt tatgatctgg agaaagagta ttagtagcaa    6840
gaaaccaagt gctagtggat ttctggcccc tgcctggaaa acaagaaaca ccttttctgt    6900
cttagttcta cttctgatgt ctctgttcag tctgagtgac taaacgtga agggctgatt    6960
atgtgaacat taaatctgtg tgtgtagcct tcatggcttc atttcttgca cttaaaaagc    7020
tgatgttata ttattttgtt ttgaaagaca tgtcgagggc cagatggaga actccatgcc    7080
aacctgcttt gccctgtgga tgtgctggat gttcccgagg gcaccttgcc tgacaaacag    7140
agcactgagc aagccataca gttgttggaa aagatgaaaa cgtcagccag tccttttcttc   7200
ctggccgttg ggtatcataa gccacacatc cccttcagat accccaaggt gaagagctgg    7260
ttgagggctg atccagcaca gctgtgacag ctgtgttgtt tgttgaggga gggatttgca    7320
cagggaaggt ggctacatcc tgccatcgcc aggcaccatg gttgctgat gggcactagt    7380
gtcctcagtg gagtaaagat gggatttaga ggtcaaggcc aagaacatgt aagaatcttg    7440
taagaaatgc ttggctttcc gcttcactcc actggagggt ttgatttcct ttccttgaac    7500
ttattgagca gatgttgggt tggatggtga gatcaccaca gagtagtgaa tcagagctgg    7560
ctgccaaagc ctgtaataag ggatggccct tccaaaacag ccccagggaa tgtgaaactc    7620
tcttcaaaaa ctgcctgttc cccctgagcc tgtcaggtta gatcatctaa acacaaagca    7680
ctgcattgct tcttggaacc tcaaatcctg tacttgcttg tatgtcatt agagcatgta    7740
gtcttttctg tttagaaatc cttttccatt tttccctatc atgttttatg agggcctgag    7800
catcccatcc ttttgacttt gcagagaatg cccctcacat gtaatgagag tagagaccag    7860
cagtatgctc tttgatgttg caggtatctt gctttgattg gcccagggga tcttgctttc    7920
ctagtaggag ctgtcagccc ccttgataga agaaggctgt gaggttcacc tctcctgcct    7980
ctttgcagaa aacagttaac aaagctggcc tggctgtgat tctttgaaag gcctgcttat    8040
aagtctagcc cttggctggc atctgggaac tttgatttct gaagtgttct cactattccc    8100
agaattggct tactatgctt aaaccgttta gacaaacatt atggttgatg ataaaccct    8160
gggtttgttt ttttttttct gggagcctgg aattttgata tgttccagac agatagtacc    8220
tacctgacca gccccaaata aaaactggat aatgaggctt taatgagctt ccctagttag    8280
cagcatttca catgtattgt cacacaactc gttgctggga gaagtaagta tcctatgtga    8340
cttccctgga agaggacttg aagcttgtgc ctagtttcct ctagactttg cctcatgtgc    8400
cttttttctt tgctgagtgt gtttcactgt aataagtcat agctgtgagt gagactaaat    8460
gctgaatcct atgagttccc ctagtgaatt gctgaacctg agggtggttt tgggaaccca    8520
acacctcacc acactttct agccaggcag gaggtgggga caggaacaga agggcgtctg    8580
```

```
tttgtatgaa ggaagagagt tgttgctgct cagtttgtag gaaacagaag tcgtatgatt    8640
tcattgccat tggcatctca tgagagtaac ttaaggctgg acttccaggt cagggccgag    8700
cacgtgggga atgctagtga gccaccactc aaatgcatcc caggcttaga gaaaaggcag    8760
tatagacagt gatagagcca caagcttgtg cttttgctaa aagagtgaca actttgtggc    8820
tttgtgtttt tccccaagga atttcagaag ttgtatccct tggagaacat caccctggcc    8880
cccgatcccg aggtccctga tggcctaccc cctgtggcct acaacccctg gatggacatc    8940
aggcaacggg aagacgtcca agccttaaac atcagtgtgc cgtatggtcc aattcctgtg    9000
gactttcagg tatcaaggac atagtttggg gatgtattgg acactgatga catagtgtcg    9060
taggtgaaac cactcttctc agtagacaca actccaccta taatgtctta ttaagagctt    9120
tctttgtgtg agttatcagg caaagtgctg gggtggaggt gtcctatagg tatttaggac    9180
acaggcagtg ttgcctggat caggactctc ccaaccagtg tcttactttc taaagaaggg    9240
aatgtccaga gagttggtga cttgttgtgt gtggacacag aggtggggaa ccagcctggg    9300
tgaccgttcc taacccaggg gatactgttc aggtgacagc tcattaattg tagagtgatg    9360
ggcaactccc gagcagccca gaatgcttgg tttgctggta cttgcaggtt ccctctgtgg    9420
gaaagcccat cctggctagc tgtcactctc aggggtggc ttggtgaaca ggcccttggt    9480
gcagagggaa ctgggacacc atcatggcca gtgccaccca gctgtgatgt ccggcattcc    9540
tttgccatga tttaggggcg gagcaaccac acaattagaa tcctcacact gactcatcag    9600 tcacccttc tccctggaga gcagaataca cattgactaa tgctctttct ggaatattcc    9660
acacagaacc ctgcccttct cttaccacat gaatgctgtg gcaggcaagc tatagcggat    9720
ggaagatggc agtgttttca aagtgtgcat cctggactac ctgccttaga atttctggga    9780
gggcttgttg gaaatgcaaa gtcttggccc actcagattt acacaattgg aagctggagg    9840
tggaacttga cctgacaacc gacatttctt aaaaaaaaaa aaaaaaagca caccaggtga    9900
ttctgattca tcagaagttt gagagcctct gctgtagagt attgtttaaa gcaaacacag    9960
aacaaaacca ctgcatacag atatcccttg ctatccaaac ttacttggcc cctgagtttg    10020
cacaacaaga gtttggttgg tgagaggtgt acattcctca aatgtatttg attcctgttt    10080
cactgagagt ttggaaagca atgcatccat ctgtttgttt tctaattttg tgtttctggg    10140
ctcctgatgg tgaagtggct tgaactggct ctgaggctgc acctggatgc tttattagtg    10200
atggtcactt aaaatgaccc ttcaaaatgg actgtgtgcc aggaagggcg ctgattcatg    10260
tgtggtatcg cctttagtcc tcatggggac ttagtgaggt acctgctctc tgttgtctag    10320
gtgaggaaac tcaaggcatg ggaggtgtgc tgacttgtct gacagcacaa aattagtgct    10380
gggtggagcc aattcatccc cagggactgt aactccaaag ccccatggtt ggatctgttg    10440
gttcccagca gtgtgggttc gaattcatgt tctacctcat accagctgcc taacctctgt    10500
caagtcatgt tacctccctg agcctccctg agttttcttc tctataaaac tgaaacaagg    10560
taggtaaagt ttttccatga taacacctac tttagagatt ttcagcaaga accaaagaga    10620
gcatgtagaa gtatctagga ccgtgtcggc tgcacggagc tatctccttc aagttctctt    10680
agtcccctcc ttacacacag tggacagcat gactcagagg gcctccctga tgcctgcatg    10740
tgctggtctc agccctgtgt tccccttgaa ctctggcctg ctcactgtcc tcttgtagct    10800
ttggatgtcc gcatccaagc ccatctcact gcacccttga gactcagctc tgggatctct    10860
tcagctccag ccctctaact cagctctaca tgagccagtc acctcagggg ccacactcag    10920
gagtttgttg cctgctcctt ccgagtcacc atactgacca caacctcttc tcctagcact    10980
```

```
tcccttgctc tacctcacgg ggattgctag agtatggatt tctatctccc ccttgtgtcc   11040
aggtcctgtt ggctttgttg cttccctaaa tagctaaggc ctggtggcag gtgacttact   11100
gtacttccca gccgcccagc tcaccatact tgtccattta ccttgcccc tcctgcagta    11160
cctttatcgt cagacactcc agccacaccc tctgctctgt agtccaagtc ctgaaagctg   11220
ctggagaaaa tccatgcccc cacgaagcag ggaggccctc agatgccccg cctccagccc   11280
cagcagccca ggcaagctct ctgctcagct cacctcactt gtcctctgca gctgctccgt   11340
ttgcatgacc tcttctctac tccctttcac tgctccccte caggccttg ccacccctgt    11400
gccccatttc tcagtggata gcacctttcc tcttgtagaa atggaagctg gtggacagcc   11460
agaggtaggg gatcggacag ggtggatgtg ggtacgcatc ctggctgtgc cccttatcag   11520
ctgtgtgact ctgggcaagt taacctttct gagtcttgga gtccttaatg tgccgttcac   11580
aggatcagat gccacctagt gtgtacttgc tgaatgggct ctattaataa tctctgtcac   11640
tgagacctgg aattttgtgt atgcatgttc tgggctcgag gcctcttccc tcaactcccc   11700
accactgtcc ctgcttccca cgtctgcaag cagaatgagc aagatcttcc ttctcaccta   11760
cctaccctgc agcctctcca tccactctca tccctcccag ctgcaaaagt gccagccccc   11820
ttgcccctgc ctgtttctgc tttccactcc ttcacctgac ctccaaggca gagcgagtgc   11880
acactgggct gttctggctg tgtctgtggc ctcattgtcc atttgttctt caccatcctc   11940
tacacaggct tccacctccc caatccacta aactctcacc tcagcactga ccttggtggc   12000
cagtaaaatc tatctgtgta ggtcctgacc ttccttgagc tctgtgtcac ttcctcactg   12060
ttggccagct ccacccttc tgggactgtt ggcctcccaa tcctttctgt gtctgccact    12120
taggtgccac ttcccaggcc ccccactata tcctttccac ctcttcttcc cctgctgggc   12180
tcagttgagc cttggcagat gactccagaa ctacccctc agcccaggtc tctcctgatt    12240
ttcagatatg tgtgttgacc tgcctgtgag agccattcct aggcagatga ccctggagac   12300
ctcagctcca taggcttccg cgtggtcagg ccaccacccc tgccctgcct tttctccttc   12360
ctcctcctcc tcttgcgccc cctgccccca aatgccagcg aattatgcca ccagctgaat   12420
gtgaaacctg gagtcaccct tgggttcctc aacacctcct cctcctctgc tccctgcccc   12480
catgtctgct tgatgcccct gaattcctct cacatccaca cagtcctctg gatccttcag   12540
cacattgttc tggaccacct cagtgggcct tgctttgttt tgttcattca gcaagtgtag   12600
tgagcacctc ttatgtaccc agcagtggcc tagtaccatt ttgtctaaag cctctggaat   12660
ctgtgtctgt gtcctgttgc aacaggactc ttaataactt gaagcccaga tcatgtcaat   12720
ttctcgcctt gaaagacctc agtgactcca ttggcctaga acttggagtc tccactccct   12780
ggatagaccc accaggtcca tattatctgg cccggaccta actttctagt caccccctctg  12840
ccctcccatt tgattctcca gtcacatggg cctttcattg gccccaaatg caacctgctc   12900
tgtcacaact ccacactgtt ccgtgccctg cagcccctgc ttggagcatc tgagcccat    12960
ttgtctgact gcaggtgctt cttgtcaaat tctaactcct ctgtgaagcc ttccctgaat   13020
ctcccaggca gatttgaggg cttattcccc tgtgtcaccc ctgggcctct gtggggatc    13080
ggtcagagtg gtgggaaaaa ctatagggaa aggatgcaaa ccttctgaaa ggtcagaagg   13140
ttctgcagag ccccagggga gaatagctgt tctataaccc tgaggcagag ggcaaggagt   13200
aggtacaagg gagtgtggga gaatttatct taaacaggct tgtttactta tgttgaccag   13260
gaactgacct ttgatcgtct gtgcttgtga ggttccctga aaggggaaca ataaatgtta   13320
```

-continued

```
attacctgca ggttggctct aggttttttgg cattatgcct gcactgaata aaagccagca    13380
gctccagctt ctcggggctg ctctctggcc actagagcca ggcagtaacc tagctgctct    13440
tatgctgcat acctgtgtct gagtactcat ttcatccata ggccagggtc tgcaggacag    13500
acccagcagg cctcactgat aattaagcat tttcttgtct ccatgattgt gtcctcactg    13560
gatgggtgg ctcatcaagg gtgaggacct tgtctgctta ttgccttacg tccaggggct    13620
agcataggaa ggagggaata cctttgtata ggacatagcc atcctgacag gtgtctttca    13680
tccccaggag gaccaaagtt ccacaggttt cagactgaag acttcatcta ccagaaagta    13740
taagtaggcc agggctcagc ataatcctgc tggaaggcta gatgtatatc ttttctcttg    13800
actgcaagtg agaacgggtg agtctcatga ttgtcctcac cctggcagtg atgagaagaa    13860
gctggtgggt ccagctgata agtcagggc tggtctgcga agacacggct ctcttctcac    13920
ccctctttgg ggtggaagat taattttttgt ccttagcatt tgtgaaccag gttgggaatg    13980
agagtcagcc caggagggc cggtggctca tttacttcag ggcatgatct ggctgttccc    14040
aaagtgcctc ttgggttcag ggactgtgaa ggacgtgctg ctctctggta tctcctttgc    14100
tcttctcctg cctgctgaca gtttgttaga aatgagctcc acgtaacggc catagttcat    14160
gaagatatgc agttgtaatc tgctgttggg ttagcaagtg atcagaggga aaggctcagt    14220
cagggttgct gttatgtgtt aaattatgaa tttttttttc cctgaaaagg gctgttgaca    14280
tcctaaccc ccagtactgc tgaatgtaac catatttgga aataggttta ttgcagatgt    14340
aattagttaa gatcaggtca tattggagta aggtgggctc ctaatccaat atgatcggtg    14400
tcctttaaga agaggggaga gagacacggg aagaacacat gaagatggag acacagtgat    14460
acagctgcaa gctgaggaat gccagggact gacagccacc accaccagct agggagaggc    14520
aagattcttc tacttagagc cttcaggag agaatgccc tcccagcacc ttgatcttgg    14580
acttctagcc tccagagcta ggagacaata catttcagct taaaacaaca gagcagtagg    14640
tgacacattc atccactgtg atctgtgccc taaagtgaaa tctgatttgc ttagaaatgt    14700
atcttatttg tagacctaca gattttgctg tgactctgtg ggtgaagtga tgctgatggt    14760
agggaaagga gtgttacatt ttggctgaga aaatcattaa gggcatcaac taaggggtag    14820
ggattgggag agatgcacag gcaagcatta tctctgtatg ccttggcaat ttaaattgca    14880
gtcactctca ttttttatttt ttttcaattt gcagcggaaa atccgccaga gctactttgc    14940
ctctgtgtca tatttggata cacaggtcgg ccgcctcttg agtgctttgg acgatcttca    15000
gctggccaac agcaccatca ttgcatttac ctcggatcat ggtaagcatt ttgaaattcc    15060
ctggtgagtc aaaacatctg aactttcctg tgaaacatgc tttgcaaaat tgccattgac    15120
ataaacatgg gtgtgttctc ttttgtgaac cagtggttca caaacaaagt gggatcctgg    15180
ggcatttta tgatcagctt gttagtcctg agacctctgt cttagatgct tgacggatag    15240
gtgtgggtgg gtgggggagg gtcttgcagc aacttttttt ttttcttga tgaatgcagc    15300
aggaaccctc catttgtgtg gcagagctct tgtaaccccc atttttaacc tggagggttg    15360
gaggactttt agtttgggtg gagaggatcc agaacaatcc tggcagagcc cagcaagctc    15420
ttcacgcctg gctccagccc tcccacccct atccccgctg tcttctctgc cgagagcctg    15480
ggcttttcaa gtctttatct cccctaagg ctgtttccta cttttccaaa aatgaaacta    15540
tcttttttaaa agcatttttt aaattcttca acattccaag agcagggaat aaaacagcag    15600
ctcccccgt ttcccactca catagtcttg ttcctctcat cctcacccac tccccatct    15660
ctgaattgtt tcgaagcaaa tcccagatgg ttccattttc cgatcactgt ctctgaaaaa    15720
```

```
tattgcctct tttgaagtat aaccataata ctgttatact tagagaaagg aaaataattt    15780
tcatatcatc aaatatgaaa taggataata gtaaatcata acatgtgctt atcatgaaaa    15840
gaaaaaagga tacagagcat gtaattcagg gccagaacat cctgcccttt tctcccacct    15900
gctcagggct aacagatgac aatggattag ggatccatct gccagccatc agttgtgcac    15960
atatgcacac agggatatat gttatacatg tgtatgtttg taacatgtat gtcacaagat    16020
gtgattgctt gttctgtgtg tactgttaac gttccctggt tttgtacact taatgtcata    16080
ggcaatctct gtgtcatttc tcagaagcct accttttccc ttagaaatgt ctgtaatatt    16140
ttattatata tggaggtgcc ataatttttc acatattcct gattatctgc catctgcttc    16200
tgagccctcg gtgcccagtt tcctcttctc cacgaacaca ctctgttgtg aggcagttgc    16260
cgtagattac aaatagccca tctcagagtc ccctcctggg acatcctcca tcagaaccgc    16320
ctgggagcca gtaaaacatg ctggtttctg caactggtct caggagctcg cagttctggg    16380
catgggaaag tgcactttaa caggtgtctc aggtggtctg gccacctctc cctgagctca    16440
tcattccctg ggcctcccta tgttgccacg tcctcatctt gggcctctgg ggcaggagcc    16500
agaaacctcc tgagctgcct gtcaaggtca tcgggcttgt tcctcctgat ctggagatgg    16560
atccttgggg cccacacagg cacgcgttct ccttagccag acttccccgt atttgctcct    16620
ggctgcagca gcacaggctg aggcccggca ccagatgttc aatacgatct tgcagtcagg    16680
cggtccacag ctatttctgt agcatttgcc atgtgtcaga ccctgtgcca ggcctggggg    16740
cccctctgc ctggtgcagg gcagctcaca aaagctggca gaggccgaag gctgcgtgcc     16800
agtattcaga atgccacaga gcgcctggct gctgtaccctt cagagcctcc acaggcaccc   16860
cagtcagagt tccgggagtg gattcctgag gtcgcactgc caggttccct cacgttgcca    16920
tcctgcaggc ttctcgatcc ttgacctttt agattcccgc cacactgaat ctaaaaggga    16980
caatgtgacc tctaagctgg tggcctagga gcctgccgat aacctaccca ttcatcagcc    17040
ctcgtgggtc aaggctgcct cgtcctcccc gagagagtgg agaggtcgag cagtggggat    17100
gcccctcagg ccccgggggct tactgactgg ggcgggtgtc aggggaact ccctctcttt    17160
ctgagctcca ctgagctatc tgaaagtccc caccatactc cccagtactg acagccagag    17220
ggaggaacgg ctcaccagaa tcattgggca tctctgatgg gcatcaagtc tgctttgatt    17280
attgatgagt gggtaagagg gtcctctcaa cttggggtct ccttgggaaa gcactgtcaa    17340
ctcagaacag gtttcagccc tgttctggag accacaggcc ctggaaggct gggacatcat    17400
ttgcagcccc agcgtcatct attagacgga gccagcaagg tctcatgctg tgcggtacat    17460
ttcaacactt tctcaaattt acccgtggca gcttttggtg tgtttggtta tttttataac    17520
actactcact gtacaatttc tgtcatgcac attttttgta tcaaaagggg tgctgtaact    17580
ttaaaagact gggtatttcc aacttggaat attcaaacca tctttttgcaa gggatgtttt    17640
aaataggcat gaagggttgt ttttaattga ggttaaggat ctgaaatgag aggttttggt    17700
ttaccctatc tatggtatgt cttaaaaatc aacgaagatg tccttgtctt ttttgaattt    17760
gccgagtgtg ttgcagttcc acagctcact gttaggtggc atacacccca aactgaaaac    17820
ctgacctcgt agggcatgag tcaaaagaca ggtaggcaca ggacagggca gtggtgacac    17880
tacagctttc agggttccca gcctgtcaag aatgagcatg tcttagcagg ggaggaacgc    17940
atgtgtggga accgccacag agtcctacgt taggtatatg ttgctagtag tttgttaaga    18000
tatttgagtt tgggaattta attatttttt cttttttaaa ggtttcctca tgaggacaaa    18060
```

```
tacctgattt tgaataaagc agcattcagt tgaaataacc ctttctgtgg taattccaag   18120
tgaatatttt tcttctaggt gatgagtttc tacttcctct ggttttttaca acaggaaatg   18180
aaatggtatc taaaataaac aagctgtggt atgatgatta ttcattttct gtcattctgt   18240
gcttttatg aactagggtg ggctctaggt gaacatggag aatgggccaa atacagcaat   18300
tttgatgttg ctacccatgt tcccctgata ttctatgttc ctggaaggac ggcttcactt   18360
ccggaggcag gcgagaagct tttcccttac ctcgaccctt ttgattccgc ctcacagttg   18420
atggagccag gtataaaata tgctgaaatg atattgcttg acagtaagat cacctttagt   18480
ttatatgtga accactttat tgaatcatag gctttggggg ttacacagac ccccccttcc   18540
tgccttgtgt tggaatttct tctcaacatt ttgtggtcag cacacgcttt ctgaacatct   18600
cccatactct gggtggggaa agagtgacag aaccagaatt gacaagtatg gcccctgtcc   18660
acaaggagcc ttgtgggatg atgatggaca aaggaacagg tgcatcccca agatggggag   18720
ggctgtggta cagtctacaa gagcctgctc cagagcttag agtaaggggc tgcccccgta   18780
acagacgagg agaatccttt ccctcgatgc gcacttttgg tagggactca gccttctttg   18840
tgggggcac attttccatt ttgacagctc atcaatctag tgaaccacta gatctgtaaa   18900
atctaccagg tgattctact ctgccctccc cagcagtgaa gggcaagttt actttgactt   18960
ccatgtgcca gtccttcaaa gctttgaaaa cagcactgat gccccgacc ctgtccatcc   19020
accaatatct tctcttctct aggctgaaat ccccagccct tcaaccattc gtcacaaggt   19080
agtgtttaga cgcgtggttg tcctggtctc tgtcttccaa aaagtttcag tttgagaaag   19140
cacttccaga ataccagttg gaccagatac ccctcctgga tgtgtgggca acctgtatgg   19200
gttcttgtga gttctatcct gacttgatct gcccagtgca tttcagggac aggttgtaca   19260
ctgtctctga aatgacgtat gacgtttgct cttttttggag tgcctcttct atgaactatg   19320
ctaaaccaga ttgccccctt tctggactta agcatttaat ccatccttaa catctaaatc   19380
ttgtactgta tattgattcc tgtttaaatt tgtcttggtt ctggaccatc attcgggcct   19440
ttctggatct ttctgagctt gctttatact acccaatttt attttttgca ctttgatttt   19500
tgtgcactgc atgtcctgtc ttcttttcatg tcattgatag aaaggttaaa cagtttcaag   19560
gcatgatttt agcccttgt ttgctgggaa agatcttctg attggttgag aatcttttct   19620
gaaactttg ttgggaagtg ttcagcaatt tagaaattga tgtaactgca cggccttttca   19680
gtttatttcc aaattttatc tctagctgtg tcttttccct gaacttcaga cttttgtttc   19740
caatagtctt tcccacttag ccagcctaac atatccaaag ctggacttca catctttcat   19800
cttcagcttt tccttcaaca ctcttcttgt cctcaagaaa tgagaatagt cactcatgcc   19860
aaaaaatcat ggaataatct caaccccgt tcttctctta ctccatatgc aatattcagt   19920
ctatgagaaa gcctgtcaca ctccattcag actctgtgta ccacttccca ccacttcgcc   19980
tgccactgtc ttggaccaga ctgccactgt cttgtgctga agtactgcaa gagcttgcta   20040
aatggtcccc ttgcttgtgc cctggatccc ttggaggttt cctcctcag agcagccaca   20100
gtgattccat taaaacccaa gtcaagtcat gtcacagccc ggcacaggag cctcttatgt   20160
acccttcttg atctgagtaa aagtcgtcac agtggcctta catgttctgg ccccattatc   20220
tccctgacct catcttttta taagtatcca ggccagttgt cctataacag tgtcccacag   20280
cctggattta tctgattgct tccacatgac tacattcagg gtaacatttt tgacacgtgt   20340
gctacatggg ctgttgtatt ctcccattgt gtcacatggt gggggcactt catgccagc   20400
gttactagta ttgtaagttt gaacactcgg ttgaagagct agctagcatc agccagatct   20460
```

```
tgccattgta aaggtacctt tttcaacttt ctttacttgt tttcttttta ttttacttaa   20520
aaattaagtg tctagaaaat gaaatcaagc atgataaagc actgtcttaa agatccagaa   20580
gggccagaat ggtagtgcaa atccaattgc aattttaaca ggaatcaata taaagtacag   20640
tatttagact ttaaatatgg atgaaccgca atgaaatact acttcatacc cactaggatg   20700
gctattaata aaaacaaca acaaaagctg tgaaaggctg ggcgtggtgg ctcacgccag   20760
taatcccagc actttgggag gccaaggtgg gcggatcacg aggtcaggag atcaagacca   20820
tcctggccaa caaggagaaa ccccatctct actaaaaata caaaaattag ctgggtgtgg   20880
cggtgcatgc ctgtaatccc agctactcag gaggctgagg caggagaatc acttgaacct   20940
gggagacgga ggttgcagtg agctgagccg agattgcgcc actgaactcc atcctggaga   21000
cagggctaga ccccgtctaa aaaaaagaa tgaaacaagt gttaagagtg ttagtgatta   21060
tatggaaaaa ttggaacact tgtgcattgc tggtaagaat gtaaatggt gcagccactg   21120 tggaaaagaa tttggtggat cctcagagtt aaacatagaa ttactctatg cccagaagt   21180 tccactccta ggtatatatc cacagagctg aaaacaggta ttcaatcaaa ggttgtacat   21240
tactgttcat agcagcacta ttcacagtaa ccagaaagtg gaagcaattc agatgtctat   21300
tgacagaaga acagacaaaa tgtggtccgt ccatgcaatg gaatattatt cagtcttaaa   21360
aaggaaggaa actgacacat gctacatcat ggatgagcct tgaggacatt atgctaagtg   21420
aaaaaagtca gtcacaaaag gacaaatact gtataatccc actcctatga ggtatctaga   21480
gtagtccagt tcatagacat agaaagtaga atggtggttt ccagttgctg ggtgaggatg   21540
gagaaagggg agttgttact taatggggac agagtttcag ttgtgtaaat taagaggagt   21600
tctggagata gatggtggta atgatggcac aacagtataa gtgtacttaa ttccactgaa   21660
ctgtatacta aaaagtggtt acgatggtaa atgtcatggt gtgtgtattt gatcgtaata   21720
aaatgcaaag ataactctaa tgcagacatc cagaagggag taatgtgtgg ggtgatcctg   21780
tgggagtcag aatatcctgt tcctcaacag actcttttac ctagtggttg tagccttaat   21840
tgatgatcct tgtctgagtc agttattaaa tcggtggttc caaaattcag gttgttttaa   21900
aaagcgccaa cagcctcgtg gggccctaat tttgcatcct gctatttgat tggatgagta   21960
attaatgcag ggtgaggtgc cgaggtggtg tttctaaacg tctgttgcta aagataaatg   22020
ttgtaaatta aaaaaagaaa acatatggag cccagacagg ttcctttact gctcctgcct   22080
ggccatggca ggcttttata atgtaaccca ttctgctctg tcgcttcctg tttcaggcag   22140
gcaatccatg gaccttgtgg aacttgtgtc tcttttccc acgctggctg gacttgcagg   22200
actgcaggtt ccacctcgct gccccgttcc ttcatttcac gttgagctgt gcagagaagg   22260
caagaacctt ctgaagcatt ttcgattccg tgacttggaa gaggatccgt acctccctgg   22320
taatccccgt gaactgattg cctatagcca gtatccccgg ccttcagaca tccctcagtg   22380
gaattctgac aagccgagtt taaaagatat aaagatcatg ggctattcca tacgcaccat   22440
agactatagg tatactgtgt gggttggctt caatcctgat gaatttctag ctaacttttc   22500
tgacatccat gcaggggaac tgtattttgt ggattctgac ccattgcagg atcacaatat   22560
gtataatgat tcccaaggtg gagatctttt ccagttgttg atgccttgag ttttgccaac   22620
catggatggc aaatgtgatg tgctcccttc cagctggtga gaggaggagt tagagctggt   22680
cgttttgtga ttacccataa tattggaagc agcctgaggg ctagttaatc caaacatgca   22740
tcaacaattt ggcctgagaa tatgtaacag ccaaaccttt tcgtttagtc tttattaaaa   22800
```

-continued

```
tttataattg gtaattggac cagttttttt tttaatttcc ctcttttta aacagttacg    22860
gcttatttac tgaataaata caaagcaaac aaactcaagt tatgtcatac ctttggatac    22920
gaagaccata cataataacc aaacataaca ttatacacaa agaatacttt cattatttgt    22980
ggaatttagt gcatttcaaa aagtaatcat atatcaaact aggcaccaca ctaagttcct    23040
gattattttg tttataattt aataatatat cttatgagcc ctatatattc aaaatattat    23100
gttaacatgt aatccatgtt tcttttcaa atctaaagtt aaaaaaaaat agcagaagcc    23160
agtgtcttaa agtctatctt ttgtttctaa gaccatggga tttcataatc tcaagataaa    23220
atatgtatga agtaattaat gtagaatttt tacaccaaat aataaataat gcttaataaa    23280
ctagagatat gagatgtgta ggaaatttgg ttaaacttt ttcagatact ttctggccca    23340
aataataatt tgttagcaaa taatgatgacc cttgaactca atggccatct attaaaagac    23400
tgttgttcac actggaaaac atttaaagat gtgactatat ccatgggtgg attgaatcac    23460
tcaaaatata ttagtatcct tctttaggga tggttggtta cagacatgta tttattcagg    23520
aggcagaaaa tattccattt taattgctta ttaaagaaaa cattaaattc taattattt    23580
tgaggactgt gaagactttt cattagtgta atattaggtc attgtcaatc tcccagaatg    23640
tagttctata ttctctaaat atgaaagtat ccagaaaggc cagtggtagt aaaaagctta    23700
gtgtatataa tctcaaaagg gatggaatat ttacaactca tatttataac atgttgaatc    23760
ttctcagtta tcagtagtca tcagaagtgt caatagcttt ctaaataaat attaaatatc    23820
tactgtcctg tagtgaagga gtaatttta gtaattttct ctttacaaag tctccagtgt    23880
ttccaggtaa atatttgtga aacaaaatac agcaaactac attgttactt cagtgtattg    23940
ttgccaaaaa tgacaagata ttatattaaa atcagtaaat tttagacaga tttaaaaat    24000
taattagcct acaatagagg ttatatggta acacggtgat cttctaagca gttaagtgac    24060
tgactgttct ggcaacaacg acttctccgt gactgaaggg ccctgttcat ttcctgatcc    24120
tgaagctcgt ctctcttttg agcctccgct tgctttggtc gatggtttcc ctcagctttt    24180
tctttgctgt tcttcatcct cgttgttgct gtcatcatgt tcactgtggc ttttacaata    24240
cagcctgtaa attccttatg acatagttca gtgcatttgg ctttattgcc tgctccacag    24300
ttctttacct ttacttggct tagagaaact gtatctttgt tgcttcatat aacctttccc    24360
caaccccact aagctggaca taacttatta gtggtcctcc cgtcacttta tttgtagaaa    24420
tctctctttc acatgagcag gggttctttc atgtggttta gctgacagca gaactagtga    24480
ttctagacat tttgcatggc cctcattcag tggctcacaa acatgaggga gcatcagaac    24540
tacttgaggg gcttgttaaa acccagtgcg ttagaagtcg gatgcggtgg ctcacacctg    24600
taatcccagc actttgggag gcccaggcag gcggatcact tgaggttagg agttcaagac    24660
cagcctggcc aacatggtga aaccccgtct ctactaaaaa tacaaaagtt agccgggtgt    24720
ggtggtgcat gcctgtaatc ccagcttctt gggaggccaa ggcacaagaa tcgcttgaac    24780
caggagacgg aggtttcagt gaatgaagat cgtgccattg tattccagcc tcggcaacac    24840
agcaggactg tgattttctt tggagactcc tagattttct gtggttttga actgaatttg    24900
ttggatgttg gcaagtgcct cttatgagct gtttctttat cctgcatttg ccccacaaag    24960
acttatctgg aggtgagcaa agtatgtttg gtagtgaggt cacaaaggca atcagcccct    25020
tcctccccac tcccattgcc atcttctcag tccttctccc tttctttcca agtagtttac    25080
ccaccccctcc tctttcctcc cctgtcccta aaataatcca cgtgtcttcc taaaatctct    25140
ctttgatcct gtcctttgat aacaccgtca gtgcctacta ctgggtctag acagacctct    25200
```

```
gttgagcagt cagagtcttc cctgactcca caatgcccct ttccttggct gaccagtatg    25260
actactggtc cccaccttc ccttgcctat ccctacctcc ctcctactag gttgtcccat    25320
ccctctcttc acccattcat tcatgaccat ttttcactac caagctcccc ccctcccgaa    25380
ggaggctgag gttttgtga ctctctagac tctattgtgg gatggaatga acattgctaa    25440
agaatcttgt gttcgcttta ctttaaaaag gtatttttt cctaattata aaactgatgt    25500
gtcagttacg gaaaaattag aaatgcagca caaatacatg aatattttac cacaaaattg    25560
ccatataata tcttgtcttt ttggggggtg tgaattttt gcattgttct ggtcatattc    25620
tttatcatgt aatttatgtt ctttttact aagtattatg tgtggttatt atagatttc    25680 acaaagatat attgctggta atatattta ttgtgtagtc ttataattta cttaaccttc    25740
tttcaattgt tagaaattta ggctatttcc agatttcag tattgtaaat aatgctgtga    25800
tgaccaattt tgtgaataaa atgtttttat gtatttcaga ttattcccctt aggatagtct    25860 ctcagtgcca agtgtcaaa acatctcta ttttgcttat cttcctgctc tcttgctgcc    25920 ttaggggta gtaaactgaa acataaagta aacatgcata caaataaaaa acataaaaca    25980
aaaataagca acctgatggt aataggtgaa agtggtaacc tgttttaact ttgaattctt    26040
gccgggcgcg gtggctcacg cctgtaatcc cagcactttg ggaggctgag gcgggtggat    26100
cacgaggtca ggagttcaaa accagcctgg ccaagatggt gaaatcccgt ctctactaaa    26160
aatacaaaaa ttagccgggc gtggtggcgg gcgcctgtaa tcccagctac ttgggaggct    26220
gaggcagaga attgcttgaa cccaggaggc ggaggttgca gtgagccaag atcgcgccac    26280
tgcactccag cctgggtgac agagcgagac tccgtctcaa ataaaaaaca caaaaaaca    26340 aaaaaaactt aaaattcttt gcttgttagt gaccttgatc atggttctct ttgtacgata    26400
gttgggcatc tgtatttcca cttgtgtgaa tttgccttta aattttggtt atgggtttca    26460
ccttttaaaa taatcaaaca tatttatctt ttcctgtgtg ataggttttt ttctgtatct    26520
tttcctgtta aacacacaga cccctcccca atctggacat tgaataaata ttcattttcc    26580
tttgcattgt t                                                      26591
```

<210> SEQ ID NO 4
<211> LENGTH: 43233
<212> TYPE: DNA
<213> ORGANISM: Homo sapiens

<400> SEQUENCE: 4

```
aggccccgcc ccgcagccca gccggaaggg ccggcggacg ctcgctaggt cggctcgctg      60
gccggggctc cgcggctccc gtggttgcca tggcggcggt tgtcgcggcg acgaggtggt     120
ggcagctgtt gctggtgctc agcgccgcgg ggatggggggc ctcgggcgcc ccgcagcccc     180
ccaacatcct gctcctgctc atggacgacg tgagtgcggg cggtgggacg gggcagggcc     240
ggggtggggc ggggaggga ggggcggatg gaggaggag cgaggtgggg gaagggcggg     300
cggggtgggg ggagaggtga ggggaggccc cttggggaag ggggaggcc ccgcgcgggg     360 aggaggaggg ggaggggacg gggggtatcc ccgtgcgggg aggggggaggc ccctcggggga     420 gtggccgcgg ggtccaggcg tggggtctcg gcggtcaccg atcaccacac gcgctgccac     480
tgtgctgcat gaccgggaca gcgtcctccc tggcaggtgg gtggccggcg tgctaccggg     540
ccctgcctcc cccgtctgac ctttcccgcc ctctactctt gggaaaggtg ggcgcgcagc     600
gtggcctccc caagggagg aagaggctgc tcctgccgcc ctgcctgaga gctgcgtcgc     660
```

```
cctaggaatc actcccgcca cctcgggccg ccgggtcccc ccgctgggct ccagtcttac    720
ctgacggctg tctctgtcct ctggagaatg ctgagcgaag gtcaggtgtc cctaaggtct    780
gaagaactga aaggctggaa tgtctcctgg tgggcaagtg cggggtcagg ggtcacagcc    840
agcctggagg cctccttccc taactccttg tgggagccac ctggagactc aggaatgagc    900
ctgcctgggg catgggtcac cgtgcaggac cccagacaca cctgggttga aaccctactg    960
tctccaagct tgggggtcac ttccattctt gaacctcagc tgccacacct gggggttac   1020
acctgtcccg ccgtgctcac gttgtgtgtg aggactggga cgacaccgag taccagacag   1080
ttttgggccg tcggtgtcgc tcagcccctg tgtgctggct ccgaccagca gagaccctga   1140
caggtgcctt cagacccacc tgtgctgacc agtgggggcc acgggccaca cccaagggct   1200
gggcagtcgt ggctgtcgga attggaaggt gctggtagtg taaaatacac agatttagaa   1260
gacttggtga agaaaaata atgtaaaata tctcacttaa caattttatt aaattaatgg   1320
tttttttaaca taaagatata cttgaaaaga taacagacac cacccataat ttccccaccc   1380
aggggtgaca gccgacagtc ctgggcagct gcttttccat ctcatatgtc ttatttgtgt   1440
gcagtgactg cttccagag cacgctctcc agcgcccagg ggtccgtgtc ctgacagcag   1500
tagccgggcc tttctctgca ctgagtgcca tctccctcct aaagatactt tgcttcagaa   1560
tttcatcctt tcacttttga agttcctctg ggccagtgta gatactttgt ttcagaattt   1620
cttcttttca ttgtgtaact ccttctgggc cagcatagct tcgctggatg agctgggctc   1680
tgcaggtgaa gcctccctgt taagtttctg cttttcctga ctttctcaga ggacagaggg   1740
gtgaggcggg gcagctcatg aataattttt tatgttgaag acttgtcgaa ataatatttt   1800
ggttatgttg ggttaaataa aatataaagt tagtctgtat ttcacctact tctgcttttc   1860
taatgtggct cccggtaaat agggaattgc atgtggactc accctacgtt tccataggac   1920
agcaagggtt caggccgtgc agggtggagg ggtggggtgt ggccaccggg gcacatgtgg   1980
gggagggtga caggaagccc cgcccacctg ggcacctgtt ctgtggcctc cactgtgtgg   2040
cttgtggggt cgtttggcag ctgacgccta agaaccccca gaggagctgt gtcctggccg   2100
gtaggtgtac ttgtaaggac tttctgatgc agacagcaga agatgaagtc aaagtgacaa   2160
gcaacagtgg ggattccctg gccctcctga gtcgacagac cagggccgcc tggcgagttt   2220
cccctttcgt ggctctgctg cctctgaact ggccacatcc tcactcagcc tgtgatggtc   2280
ctaggtgact ccaagtcacc cctgcagtca gcagacccag tgggaggttg gctctgcccg   2340
tgtcatgtta gcgtgatgtg gtctcagcc ctgcgccaag cacactgggg gaggggcaca   2400
tgctgacctg tccagcccag gcctcggagc ctcgggccta ccccagaagg gagactgccc   2460
ctgatcatct catctgcctg gacccagcag agagggggtt ccctgaaggg cccatggtgc   2520
agctgccagg acagggcagg gatgctggca ggtgagagcc acagaagctc acagtggagc   2580
cccgaggtgc cctgacgtgg cccagggtgc aaggggggtcc tcacaggctg tcttctctcc   2640
ttggagtccg gggcttcctc cgcagccctg tccacacctc ttcctgcact gcagaccggt   2700
tgtttctgcc agggcgctgg cgtctgaacc tgcaacaggt cattcggcct ctggcatgac   2760
atgggatggt tgatgacccc acagctctgg gcccagcacc acttgaggac gagtgtgcat   2820
gtctcaagtt cagattttgg agcatggccc tccagggacc ggctgcctcc agcccagtct   2880
cccctatcc agtcctctgt ggctgggcag tggggggcct gggccccct ttcgtctaag   2940
caagtgcagt ttcagaaaag ggttgtcccc aaaactagct tattgcaccc ctcatggcca   3000
gaagccactc tccaactggt cacactgacc cgggagagaa ccattgcccc cagagtcggg   3060
```

```
accagaaggg gaagctggga ctcaggggtg agagcagctg gcaagagccc ccacctgtcc   3120 aggggggagct gagccgggca aggacgggtc tacctgcact ccccagggct gccctgccct   3180
ggcctttcac tgacccacgg tccagcgcgg cctggcttcg tagtaccctg ggcacctgct   3240
gcgtgagtga ggaaacctgc gtggcccact ctgctctcca gggcttctgg ggccttggag   3300
acaggtgaga cccagtgaca agttccactc tggcccacac acagctcctg cctcccaggg   3360
cgagcagcac tctgtgtctc cactccttat ttggaaaata gggttaagga gggtcagccc   3420
tgaccacaga ggaagtggag agtcagggcc acccaggcca gctcctgttg ccacagcagc   3480
ctcgtcgagc caccagagtc cggggagggt tgctcagtgc ccctcgtttg aaacagacaa   3540
gcactggcct gctcgtcttc ataataatcc catagcaacc agtaggaatg aaactgcgt   3600 ttcttaaaac tctgaaattc tgaaggatac tgatccatgg ctcacagctg tgctcgctga   3660
acgtggacaa tcatttgggg gcttttaggc cttttttttt ttttttttt ttttttgagat   3720 ggagtctcac tctggtcacc caggctggat tgcagtggtg tgatctcagc tcactgcaac   3780
ctccgtctcc caggttcaag caattctcct gcctcagcct cccgagtagc tgggactaca   3840
ggctcccacc accgtgccca gctaatttt gtatttctag tggagacggg gtttcaccat   3900
attggccagt ctggcctgaa actcctgacc tcaggtgatc tgcctgcctc agcctcccaa   3960
agtgctggga ttacaggcat gagccaccac acccagccag gactttttt ttgagacaag   4020 gtctggctct gtcacccagg ctggagtgca gtagctcgat cacagctcac tgcagcctca   4080
aactactggg ctcaagcaat tttcctgcct cagcctcctg agtagctggg attatagccg   4140
cccatcacca cactcggcta attaatttga tcttcaatca ctgataccct tcttccact   4200 agatcgaatc ggctactgaa gcttgtgcat gcgtcacgta gttctggtgc catggttttc   4260
agctccatca ggtcatctaa ggtcttctct acactgttga ttctagttag ccattcgtct   4320 catcttttt caaggttttt agcttcctta ccatggattc aaacatcttc ctctagttcg   4380
gagaagttgg ttattaccga cttttctgaag cctacttctg tcagctcgtc agagtcattc   4440
tctgtccagc tttgttccct tgctggcgag gagctgcgat cctttggagg agaagaggtg   4500
ctctggtttt tagaattttc agcttttctg ctctggtttc tccccatctt tgtggtttta   4560
tctgcctttg gtctttgatg ctggtggcct aaagatgggg ttttggcgta gatgtccttt   4620
ttgttgatgt tgatgctatt cctttctgtt tgttaatttt cctataaga gtcaggtccc   4680 tcagctgcag gtctgttgga gtttgctgaa ggtccactcc agaccctgtt tgcctgggta   4740
tcaccagtgg aggctgcaga acagcaacta ttgcagaata gtaaatattg ctgcctgatc   4800
cttcttctgg aagctttgtc ccagaggggc acctgcctgt atgaggtgtc agtgggcccc   4860
tactgggaag tatctcccag ttaggctaca cggggggtcag ggacccactt gaggaggcaa   4920
tgtgtccgtt ctcagagctc aaacactgtg ccgggagaac cactgctctc ttcagagctg   4980
tcagacgggg acgtttaagt ctgccgaagt ttctgctgcc ttttgttcag ctattccctg   5040
ctcctagagg tggggtctac agaggcagca ggctttgcag agctgcggtg ggctctgccc   5100
ggttcgagct tccctgccgc tttgtttacc tactcaagcc tcagcaatgg cggacgcccc   5160
tccccaggca ggctgccacc tcgcaggtgg atctcagact gctgtgctag cagtgagcaa   5220
ggctccgtgg gcatgagacc ctccgagcca ggcccgggat ataatctcct ggtgtgtcgt   5280
tagctaagac cgttggaaaa gcgcactatt tgggcgggag tgtcctgatt ttccaggtgc   5340
agtctgtcac ggcttccctt ggctaggaaa gggaaatccc ccaaccctc gcacttcctg   5400
```

```
agtgaggcga tgccccaccc tgcttcggct caccctccat gggctgcact cactgtccaa    5460
ccagtcccag taggatgaac caggcacctc agttggaaat gcagaaatcg ccgtcttctg    5520
cgtcaatcac gctgggagct gcagcccgga gctgttccta ttcagccatg ttggaacgga    5580
atccccacac ccggctaatt aaaaaaaaag ttttttttag tgacagtgtc tgtctgtgag    5640
acccaggttg gtcttgactt cctgagctca agcgatcctc cctcctcagc ctcccaaagt    5700
gttgggataa cagacgtgaa ccactggatc cagcccgttt aggactttta agggagagaa    5760
gaaaggtggt tcctgcccgt ggtgccctgt ggggttttta tgatgttcaat ggtaacctgc    5820 tcactctgca gggaggctgt ccacacctgc ttttcatagc caagaaaggc gccgataaat    5880
aatgaaagaa cagggtcagc agatgagagc tggcccagca gcctgggacg ctgtcctcag    5940
aaggcccacg tgtgggacgt tgccctcggc tggtcagaag gcacatgtgt gggaggtttt    6000
tgccctcggc tggcgtctgg aacaggagg tcccccgct gttcgctgat aggagcagct    6060
caccttgcca cactgttttt gcacatgcca cgatttatgc ccagcatcct ccttctgggc    6120
ataaagagtc tcggcacatg ccaggcagag gcggccgcac tgccagccta ggcaaaagcc    6180
ctgggaactg agtctcgcac agcttccccg tcagcatccc gcacctgtgc tcgcagcccg    6240
agcgtcccgt gtggctccgc ctggggaggg ttccacgctg cggctggtct ccccggcccc    6300
gcccgcacct tctcccctgg ctgatgccct cccgttgta agtcatggca gtgagtagga    6360
ctgtcgccaa gacctgggac tcctcccagc gagagtgctc ccttgcggta tcttctgagt    6420
cagtggtgag cgtggagccc ctcccctcaa gccctgggac tcctccccgc agtatttct    6480 ggtgagtgat gagcgtggag cccactccct ttacagcatt ttccgctgca tccattcatg    6540
ttatttgtgg cctggaacag gtaggaggat acccaggtg agcacaagca gatccggacg    6600
cagctctgct gactgccgac cttctgggga ggccagaccc gcctcgggaa gcctcaggac    6660
gcagcctgca gggagggtcg ggcacatggc acccagtatt cagatgtgcg gcctcactcc    6720
cagcccgaag ggagcccagc agtggtcctg ggcatgggca gacagtgtaa cgggcgaaac    6780
atactgctcc ctcccatccc aggccttgtg cccccggccc acctgccatt ctgtactctc    6840
ccacctggac tggagacagc aggaagtgca gaagccacct gagaggatga atctgcactc    6900
ggggaggtgg agggcaagga gctttgggcg tgtgtggcca gtcccctca ggctggcctc    6960 agggagctgt accgtcccag cctgcactgc aggtttctgc tgcctcagtg ggatgcacct    7020
caccctgaca tgggcgcatt cgcccactgt gactaggtgc cactgagccc aaggtccctt    7080
ctcagcccat gagcagctct gcgggcgtcc tgcccctgt cctccacct ccttttcttc    7140 ctcatcagct tcagggaca cctctctcta ggtcctcctt tcattccagc ctccattgtc    7200
ctcagaaaag ccatttcagt gacttcaaaa taaaccatct cagggctggg cgtggtggct    7260
cacacctggg atctcagcac tttgggaggt ggaggcgggt ggactgcttg agctcagttc    7320
actcaagacc agcctgggca acgtggcaaa actccatctc taccaaaaat acaaaaaagt    7380
tggcctgaca cggtggttca cacctgtaat cccagcactt gggaggctg aggcaggtgg    7440 atcacctgag gtcagtattc aagaccagcc tggccaacat ggtgaaaccc catctctata    7500
aaaaaaatac aaaaattaga tgagcttggt ggtgggtgcc tataattcca gctactcagg    7560
aggctgaggc aggcgaattg cttgaaccca agagccggag gttgcagtga gccaagacca    7620
cgccactgca ctccaacctg gtgacagag tgagactcca tctcaaaaaa taatgataat    7680
aataattaac tgggcatggt ggcatgtgcc tgtagtccca gctactcagg aggctgaggt    7740
gggaggatca cctgagcccg gaaggcagag gttgcagtga gccaagatcg cgccactgta    7800
```

```
cttcagcctg tttgtcagag tgagaccctg tctcaaaaaa ataaaccatc tcaaagggga   7860
tccaaagcta aaagggccaa acagaattgt gtcccatgag acatggaggg cctttgagag   7920
gaaaaagccc agacctggcc cagctctggg actccacacg ttaggagggg ctgaggcaag   7980
gagcggccac cctgccaagc tgagccttac aggcaggggc catgtagcct gccgtccacc   8040
ggggaaatgg atcattgcat ccagacaaag accaaggtgt gaccacgcag acctggatgt   8100
ccagccaccc acgtgcgccc agagcggccc actgtcctcc cgcggtcccc ggggcccagc   8160
gcccatccct ccagcagccg ttcccagtca gcacgctgcc acccccgccc ccggtgaggg   8220
cttcccctct gttcagaccc ctgtcacttc acacaggccc cgaggctgct gcttctttga   8280
cttaccagga cccagcgagt caaacgccca ccggccccga cccagcagtg tcagggagc   8340 ccctggtcca tctgcagaaa accaggatgc ccgcacttcc ttttttttt ttttcagac   8400 ggagtctcac tgtcacccag gctgtcctgc ctcagcctcc cgagtagctg ggaccacagg   8460
cgcctgcaac cacgcctggc taattttttg tattttggt agagacgggg tttcactgtg   8520
ttagcaagga tggtctcgat ctcctgacca cctcgtgatc cacctgcctc ggcctcccaa   8580
agtgctggga ttacaggcgt gaaccaccgc gcccggcctt tcattctttt atagccgctt   8640
tactgagacg gaattcgctg gtgaaagtgt gcgggtcatt tttagtgtgt tctcagagtc   8700
gtcctgccac cacacatcgt cacatcatct ttgtcaccac ggaaggaagc cccagccctg   8760 atggggggtca ctcccttgtg ctccccgaag cccctggccg acccgctccc ctttctgtct   8820
ctaaggatct gccttttctg acgtgtccgg tgaatggaat cttacggctc atgggccttg   8880
tgtctatttt cccctcacac agggttttg ggcttcacac acacagcctg tgtgaggact   8940
ccattccttt tcgtggctga gtcatggtcc acagtgtgga gggaccacgt gtggctgagg   9000
cttccaccca tggatgggca tccgggtgtt tccagcttgg ctgccaggga gcgagccgct   9060
gtgggtgttg gttcatgcac aggtttccac gtggacacac ttttcagttc tgttgggcgt   9120
gtaccaggga ggcgctgccg ggcggcgtgg ccaccctgcg tggcgctgcc ggacctctca   9180
ccaggtgctg cgtgtcacgt tcttacatgg tgtgtgaggg ctccagtttc cagtgagttc   9240
acttttaatg ttttgttttg tttggtaaaa atcaaccttta gacaatcagc gatcagactc   9300
tagtccctgt cgtggtgaac tgtggagaga ccaaagtgag cctctctccg gctcttggag   9360
caccagggcc catgcagcct gtcttggggt catttgaaat ggtggaaact ttacaagggc   9420
ccgatgggca ggtgagcccc actcggcctc caggcacagc cctcctcaag gtccctgctg   9480
tccatgcagg tggcagtcct actctgtggg tgagtcctgg agccacttgt gacaggagga   9540
ggctggatgg ggtgaatttg gagaaaagtg gcaggttttt gttttttatt tttttgagac   9600
agggttctct gtctgttacc taggctggac tgccgtggcg cgatctcagc tcactgcagc   9660
ctctgcctcc tgagctcagg ggattctcct gcctcagcct cccaagtagc tgggattaca   9720
ggtgtgtgcc accatgccca gctgattttt tgatttttta tagagatggg gtctcacctt   9780
gttgcccagg ctggtcaacg agagagaaaa gtatttcaga gacttaaaaa aagaaccatc   9840
ggtggtctcc agtgtgctta agagctgcgg gtggagctgt ttgcgttcct cctgaaggct   9900
ttggctgcca gacatggctg ggctgcagat acttgcttta ctaagaggtt ttccctccct   9960
gccgtccagg tgtgtccaca ggtgtccaca caaccaggtg tcgtgaatgt ctgttcacac  10020
taagtgggct tctcagtaac cccctggcca caccccatc tcacccatcc caggagcctc  10080
ctgggaccac acacgggggt cgggagctta aaagaacaga aacacggccg ggcacagtgc  10140
```

```
tcacacctgt aatcccagca ctttgggagg ccaaggcagg cagatcaccg gaggtcagga    10200
gttcgagacc agcctggcca acatggcgaa accccgtctc tactaaaaat acaaaaacta    10260
gctgagcatg atggagggcg cctataatcc cagctacttg ggaggctgag gcaggagtaa    10320
tcgcttgaac ccgagaggca aaggttgccg tgagccgaga tcgtgcaggc aaaggttgca    10380
gtgagtcgag attgtgccct ccagcctggg cgacaacagc aagacttcgt ctcaaaaaaa    10440
aaaaaaaaaa aaaaaagcc agaaacgcat tctgtctcgg tctggaggcc ggaagtctga    10500
gctcaaggtg tgggcaggac ctcgctccct cggaaacctg caagggacct cttgcccctg    10560
cagcttctgg tggcccccag ccgtccggag cccatggctg tgtgtctccc gcctctgacc    10620
ccattgccac acggccacct tcgccctgtc tcctataagg actgcagtgt gtgggatgag    10680
ggtccacccc catgttagtg acctcatctt actgaatcat atctgcggca accctgtttc    10740
taactaaggt cacatgctga gctacactgg ggccatgatt tcagcataac ttttggggat    10800
acagctccac ccattaacac agatgaactg tgatttattt aaccaaattt ctgttcccag    10860
tatctcaacc acaattttaa attggcataa tgggttatac atagctgtaa ttattttctt    10920
aggataaact cctacaagtg gaattgctgg gccatgatct tttttgtttt gtttgtttag    10980
tgagagtgtc tcaccctgtt gcccaggctg gagtgctgtg gtgtgatcat ggctcacggc    11040
agcctcaacc tcctggcctc aagtgatcct cctacctcag cctcctgagt agttgggacc    11100
acaggtacac accaccacac ttggcttttt tttttttttt agagttggag tcttgctgtg    11160
ttgtccaggc tggtctcgaa ctcctggctt taagtgatcc tctcatgccc tttttttttt    11220
tttgagacgg agtcttgctc tgtcacccag gctggagtgc ggtggcacaa tctcggctca    11280
ctgcaacctc cgcctcccgg gttgaagcga ttctcctgcc tcagcctccc aagtagctgg    11340
tacaggtgcc cgccaccatg cccagctaat tcttgtgttt ttagtagaga ctgggtttca    11400
tcatattggc caggctggtc tcgaactcct aaccttgtga tccgcctacc tcggcctccc    11460
aaagtactag gattacaggc gtgagccacc gcacccagcc ccatgattgc cttttaagat    11520
agggtagctg cactttcact aagacagagg ttggccaact ccagcccatg ggtcaaatgt    11580
gaaccacctg ctgggttttg ttgttgttgt ggttttggga cggagtctcc ctctgttgcc    11640
caggctggag tgcagtggta caatcttggc tcactgcaac ctccgcctcc caggttcaag    11700
cgattctcct gccggctact gtactccgag tagccgggac tacaggtgcc caccaccatg    11760
cctggctaat ttttgtatt tttagtagag gcggggtttc accatgttag ccaggatggt    11820
ctcgatctcc tgacctggtg atccgcccgc ctcggcctcc cacggtgctg ggattacagg    11880
cgtgagccac cgagcccggc ccaccacctg ccgttttta aacccataag ccaggcatgg    11940 gtttttataat tttaaattgt tcaaaaaacc aaaagagtaa tattttgtga catgaaaaat    12000
tatatgaaat tcagatgttg atgaataaag ttttattggc acagagcgtg cacatctgct    12060
cgcatgctgg cttgtggcag ggctgagggg ctgtgacagc cccatatggc ccacaaagct    12120
gaaaggattt gctgtgaggc cctttacata atgcatttgc tgatgccagc tctaaatatc    12180
catatttgca ttcagattgg tttcagaaat aaatatgcgt tgaatgcagc tgggcctgtg    12240
aacgtggtgg ttgaattcag ctgggcctgt gaacttggtc gttgtgttta gaatgtgttg    12300
tctttcccag gtgttgtgtg tttgtgctgc cgaagctgct gaaggcggcc tgtagagggc    12360
aggggcccag gcaggcacag tcacttcact ggtgtcttgg ttggtgcttg gagcacctca    12420
ggagggaata tgtcccttaag gaaggaagac aggccagaca gaggggcctc ggagtgttgg    12480
cttctaccag gctcctgctg aggtgggcgc tcagggagac ggctggagga tccgaggaga    12540
```

```
gccaaagccc caggcggtgc cctcccttc tccttctaga gcaaagtcct ggcccactgc   12600
ctgtttaaaa gcactttttt ccaacaatac acactgtaaa atttgaagaa gttttcagtg   12660
aacaccgccg ctgccactca cctccggagt ttgccgtggg catttgctgt gctggtgcca   12720
tcacacctgg catcaccccg gcctcctggc atcaccccag cctccgtgct tcctgccctg   12780
tgctcacccg tcctcctgct tggggttttt attgtaaaat acacagaacg taaaattgac   12840
catgacagcc accttaacgt gcaccactcg ggcacagtcc attcacagcg tggtgcctcc   12900
atcccttcta cctgcttcca aacagtccat cccaagaaga aaccggtact catcagcagg   12960
ccctccccag cacccacccc cagccccggc agccactcag ccgcctcctg cctctgcgga   13020
ccggcctgtt ccggaggctt aatgagcaaa tcacagcctg tgtggcccct gtgtctgctt   13080
ccttccctca catgaagctt tccagggccg tgcgcggtgt ggggtgccct tcctttcgat   13140
ggttgggtag tgtgccgcgg tacgtgcgtg agtttcctga cataacac gttaccacag    13200 gccaggtggc cttagcggaa atggattctt gccggattct ggaggccaga agtgcaaaat   13260
caaggtgtca gccgggcccc tccccctcag gctctccagg aaggtccttg ctgtcccctg   13320
gctggtggct gcgtcactcc agtctcggcc tcggccttca cccggcatct ctactgcatg   13380
tctgcgtctc taagggccca gtcataggat tgagggccca ccctggccca gcgtgacctc   13440
atcttagctc actacatctg cagagaccct acttccaaat gtggccacac ccacgtagta   13500
cacgccggcc gcactttgtc gtctgccgat gggcgctcag ggtgctcctg ccttttggcc   13560
actgagtcgt gctgccctgg acgctcgtat gcaggcctgc gtgtggacgt aagtttcagt   13620
ctcttgggtg tacagctagg agtggagttg cagcgtggaa ctgcagggtc acacgataac   13680
tgggcttctg ggggacagtt accagttgac tttgaaatct agacgtgtac agacatcga    13740 gggcctgtgt atttatgttg aaaatagatg cacgtgttta gaggccagct cctgcgagca   13800
tgcagatgct ggtgtcaggc tgggaggagg cagacggaca cattcccac ctgaagacca    13860 agcagaagtg gaggcgaaag acagcgtggg ctgaccgtgg agcggcccca tcgtgcacgc   13920
acgcaggcga tgctgaggtt tgggctggcg tggagcggcc ccatcgtgca cgcacgcagg   13980
cgatgctggg gtttggccga gctctgccgc tggctgggac acaggtggt gctggcttcc    14040 acggtccccg acacgctctt ggccacatgg gcagctcccc aggccagaag cacctgcaga   14100
aggcgctcat tcctcctccc cgtgctcttc cctgcagatg ggatgggtg acctcggggt    14160 gtatggagag ccctccagag agaccccgaa tttggaccgg atggctgcag aagggctgct   14220
tttcccaaac ttctattctg ccaaccctct gtgctcgcca tgtaagtcag cggggccctc   14280
gcccccagga agggtgagc ccaacaggcc gaggcctccc gggtccttcc agccctgact    14340
ctgggcggct gcatcaacct tgtctattcc tactactgca ggagggtgg caggtgggct    14400 caggcctttc tcatcaaatc ccagcccggc tccgtgccat gtggggtgcg gcacctgctg   14460
ggttttcagg gtcgaagttg cggtattgtt ggtggctgct gttctgtttc ccagagtcga   14520
gtgctgtggc cgcctgggga gaggtgctgc agtgtggctc cgtctcaggg tacctgggaa   14580
gcaggagtcc cactccctcc ctccctgggg agagtctctc ctgctggaga cagaaacatg   14640
tggtgttgat cgtgaggaag aggagaaggc aggggcacggg gctggtgctc gaggatgggg  14700
gcgtgtggac ctgcacgccc agtgggtgtc ccaggagcct gcgaaaggag gcggggtctt   14760
ggggacaacg ctgagctgca gggcccaagg gccacgcgtc tttcagtgga atgggtgccg   14820
tgccccaccc aggtggtgga gacgctaacg gggattgaca ggcgtggcag cccttgtaa   14880
```

```
acctgcgcgt gcctcgtctg tcacgcgtct gtctactcgt tggggctctt gttgacgccc   14940
ggggtctgag ccacacccett cttatccagt ttctgtttct gtcacctcca catagcgagg   15000
gcggcactgc tcacaggacg gctacccatc cgcaatggct tctacaccac caacgcccat   15060
gccagaaacg gtaggctgcc caccgcctcc agggacaccc ttggggtgca gggttgggca   15120
ggtgggctac gggtggtgcc cgtgtctccg ggactcgggt ggcaagctgc aggtgggta    15180
ccgctggtgc ctgggtctct gggacttagg tggaagtgca ggcccccta gctggcttcc    15240
ttccctgccc tggcccagtg gggactgagc ggagggtgcc cagtctggcc taaggagctg   15300
agccggcacc cccaccccag aagctcccac tccccaggcg ggtgagccgc acacccacag   15360
ggaggccggg gctgtggcat cagcggcagt tctggaatgt tctggaatcg ctgtgcttga   15420
ggggttgga tgggctcccc aggggcatct cacaggggaa gtgggatttc cagtggcatt    15480
tgaggaaagg gaaggacggg ggaggcaggg gtggggcagt gcagcatcac gtggcatatt   15540
ccagagaccc ctggagacca ggcaggtggg aggctggcct gagaggcagg gtggggcctg   15600
agggtgggca ggagtcccaa ggaaggcgct gggggcacg gagtctgccc cgtccccacc    15660
ctctggtgat ggcactggct ctgagggtg cctggaaaaa tcttgggaag tgccatgccc    15720
tgtggacgcg cagcccccag gcacagcctt tgacccgag gggccagtgt cctgttagga    15780
tgtgtggacg cagcccccag tgtcctgtta ggatggggtt ggtggcagct tctcggggtc   15840
tcctcggggc tcacccagcg ctgctcttcc agcctacaca ccgcaggaga ttgtgggcgg   15900
catcccagac tcggagcagc cctgccgga gcttctgaag aaggccggct acgtcagcaa    15960
gattgtcggc aagtggtaag tctcctggcc acgcctgccc aggcgtcctg ctccatccac   16020
ttcctggcct tggttccaag ggacatggcc acaagtttcc aaatgaggag ggtgtcttgg   16080
gtgggaaacg gcagctgatt ctgggtgtgt tcaggtgtct ccagcgtccc tgtgcaggcc   16140
agcgtgacct tgccagcagg atctcaggtc accaggctgg tcccacggcc gcgagtatcc   16200
tgcggcatca gactccgcag gcctgtcacc gtcatccctc gagtcacagc ccctagcacc   16260
cgccaccact gcccccggc tgcctcctgc cacgtcgtcc ttggagggggc cacgtcatta   16320
cacacaggag ctgtggcgga ggagctgcct gtccaccta ggggcctgtt ggatggtgaa    16380
agctctggtc taaaccacaa agaagccacc aggaaggaga gtaacagcct agcagttgat   16440
gaaatcctga gctgatgaga gcttgggtgc tacacagccc ccacgctgcg gttttaggcg   16500
cacaggatgt ttcatttctt ttactccctg ggacgcctga gtgagcctag agggttgggt   16560
aggagtcacc tgtcccgaat ttctctccac ttgttggagc gttccccgcc tgtcaggtcc   16620
gcatgccgcc tcctccagga agcccttgct gctttcccag cctctgtgat ccccagtcgg   16680
ctgcctgtgg ctcctgccgg tccccttcag atggatgctc cttggatgta gatggtcatg   16740
gcagccagga atttgctgag cttgatcact ggatgaggag gacccagagg ctgtctaggg   16800
agcacttcat cattcttcag atgagaggaa gcagcctgcc gagctgagct ctcagaaagc   16860
acagggcaga gctgatgggc acagcagctg cagagtcctc acacagggag gttgggcccc   16920
acgcagcctg catagtccct gagccagtgc caggggccat ggcggaagtc agcccccgag   16980
ggccactgga gcgcgtgagt actgtgccaa caggaggaag agccggtggc ctctccaagt   17040
gacaagcccc acagtgaccc agagctctcc gcctggcctg cagctctgt cttgggccca    17100
gcggcctcct atgcatggtc attggtgccg gtggccagag ctagacaggg agtgggtctc   17160
catagaggcc tcgaggctcc tgaacagctg tcgacgggga agaggggacc ccaaggagtg   17220
ggagcaggag ccaggcagac ctcagagccc caggctcctc ccgcacatgg tgcagtggct   17280
```

```
ggatggcccg ggctgggtcc tacagcggct gctcagtcag gtgggggggt ccctatccca   17340
gcagggtccc ctctcagggc agtaggggtg ttgtcagcca tgactcagac ttccctgagg   17400
cccctcacct ggactcaaaa agaggctgct tgatctgcat gaagccacgc gggtgtgcag   17460
ggcagggact tgagtcccag agggccgcgg acactccctg ctccaggtca cctgctggtg   17520
agtgccaggc cccactgctg ctttcggaca aggacgttga gctgacagct taatttgtgt   17580
agcgtcctgc ccatgtgctt ccctgagca aggcctttgt gctgcggacg tggaagcacg    17640
agtgtcccct gtggccgggc ggtgacctgc ggacgttggc gcacgagtgt cccctgtggc   17700
cgggcggtga cctgcggacg tgggcgcacg agtgtcccct gtggccgggc ggtgacctgt   17760
ggacgtgggc gcacgagtgt cccctgtggc cgggcggtga ccagcggacg tgggcgcacg   17820 agtgtccct gtggttgggc ggtgacctgc ggacgtggac gcacgagtgt cccctgtggc    17880
tgggtggtga cctgcctggg gtgttcaggg atgtcggggt gctctagcaa tgggcccaag   17940
tgctgaagac ccaaaggaaa cagcccggag ttggcagcca agggagctct gaggtcacag   18000
agaggtccag gcgtgcttac ctgagagagg agatggggag aggcagctcg ggaggtccag   18060
ggtacagagg ccatgtccag ggaggcagca gaaatctgct gtggtgaaat ctgcctcggg   18120
gaaatctgcg tcggggatgc tgctttcaaa gccgtagctg cagaagaact ttcctcagac   18180
gacacgcaac tgacgtgaga cccgcccacg gccgtgccta gaagccatct cataccacct   18240
ctcctgcagc ccgttctgaa gagcagccgc aagctggatt cgttccagga caggacaggc   18300
tgcgcaagga aacccggaca gctggcctgg gggccagggc gagtgggcac agaggtgtgg   18360
cctgcagggc tgctgtgggc cggaggatga gattaggtgc caccagaggg tgggagcaca   18420
aggtctgcgg gggattgtca gaaggggagt gcgggacggg gtctggaggg gttcccacag   18480
gcctggggtg tgatgcctgg cgatggccat tcccagcagg tgaaccccgg tcccaggaga   18540
gcggttggtg gaggtcacca gtgtggccac actgtcacgt tctcttgtcg tcactctaat   18600
ccctgcctct gccagggtcc tggggatgtg ggtacagctg gcaggcccg gggctcccgc    18660 acggcacaca cgccccgcc cagtcgtcat cctgggggcca ttgccctgaa ctggagatg    18720 agactctgag cgcctcggtg tggagagacc cagtaattac ctggcaggaa atattttctg   18780
ccctggaaaa cccagaggag acacacttgg gttcgaggca tgaccgcaa aactctcctg    18840 ggagttcaga aaacgtggaa ggaaggagcc ggggccacga ggggcatgtc aggcgggttc   18900
caggcggctg ggaggctcct cacgatgcac caccccttcac cgtgcaggga accccggccg   18960
ccgccatgcc tgccgccctc ggttgtgccc agacgctctg cagggtaggc gggcagtgcc   19020
agcaccctcc tcgggtgagg ccttggtctt ttgtccctgc cgtgcccagg catagcccat   19080
actcagtgct ggagggtgct cgtcttacca agaattttgt gaaggtggta tctgttgctg   19140
ctcagaactt ccgagtgtcc ccacgtgggg tccctgaagt gtcctgggtt cctgtttcca   19200
ggcatctggg tcacaggccc cagttccacc ccctgaagca cggatttgat gagtggtttg   19260
gatcccccaa ctgccacttt ggaccttatg acaacaaggc caggcccaac atccctgtgt   19320
acagggactg ggagatggtt ggcaggtaat ggagccccac cccttcccct cccacgtcct   19380
gaactgctgt gccggcgtg cctgcccccc gcctctagca ctggtgggct caagtcgcca    19440
ctcatgaggg ctggtctgtc cctgggtccc cgggcaccga gggctttggt ttggtggctt   19500
ctgtcccacc aagttttgcc ccagagccta tgagactcct gcctgggggtt tccacccttt   19560 tcagggtcgt agatccctgt agctgtcctg agagaggaag gcccccagca gagcgagccc   19620
```

```
acacggtctg ccctagctgt cagggtactg cccatgtggt ctacgggtgg ggaggccggc   19680
tgtgctccag acatccaggg acatgggcag acaggaggt gggatgaaac ccccactggg    19740
agccacacca ggagcaaaag ccgctgtcca gacagagccg tcctggtgcc cgggcgtggg   19800
ggcagcacct cttgacacgg cagtgccggg tccgggaccc tcatcttttg tgaattttat   19860
tttgcttaac ttgactcttc ttggcggaag tgctcattca ttacatgacg gtgaccagaa   19920
gcagcaccag cttgctgcct cttttctagat agagccccgt ggaggtgtgg gagtcgcacc  19980
acgcagcccc catttgaagt gtgcagttct gtggttggca ttagtcacag gctgggacaa   20040
ccagcactgt agctgcttca gaacgagccc catggcctga gcggcggctc cccagcccca   20100
gccgagtgac cacagccgcc tcactgcctt caccttggtg tcgtgccctc agccccattc   20160
ccccatcttc ccatgtggca ggttattgca gcaccggcct cagccaggtc atcagatgca   20220
agaccgtgcc ctgggggagc gagggatgcg tccagcttgg ttgttccctg agtggacatt   20280
tcatttccag gcttcctttt ttttttttt cttgagacag gatcttgctc tgtcacccag    20340
ggtggattgc agtggcgcga tctcggctca ctgcaacctc cgcctcctgg gttcaagcaa   20400
ttctcctgcc tcagcctctc aagtagctgg gattacaggc gtgcgccacc acgcccagct   20460
aatttttgta ttttagtag agacagagtt tcaccatgtt gcccaggctg gtctcaaatt    20520
cctgacctca tgatccacct tcctcagcct cccaaaatgc tgggattaca ggcatgagcc   20580
atgacgccca gccctagcct tcttttaaat gaagcccatg gctttgctgg tgaaatcagg   20640
gagaacggga ctttcttggc ctaaattctg aagtctgtct ggatctgtgt tcttttcaga   20700
tattatgaag aatttcctat taatctgaag acggggaag ccaacctcac ccagatctac    20760
ctgcaggtga tggggaccgc accatcctcg ccctgtggga cgcatgggga cggggaccgc   20820
accaacctca tcctgtggga ggcgtgggga caggaatgca tcaacctcac cccgtgggag   20880
gcatgggttc agggacctca tcaccctcgc cccgtgggac gcgtggggac ggggaccgca   20940
ccatcctcgc cccgtgggac gcgtggggac ggggaccgca ccaaccttgc cccgtgggac   21000
gcgtggggac ggggaccgca ccaacctcgc cccgtgggac gtgtggggac ggggaccgtg   21060
ggaggcatga ggaggtcggc ctgaggctgg aggacgacgg tgtggctctc tccataggaa   21120
gccctggact tcattaagag acaggcacgg caccacccct ttttcctcta ctgggctgtc   21180
gacgccacgc acgcacccgt ctatgcctcc aaacccttct tgggcaccag tcagcgaggg   21240
cggtgagtcc tggctccatg gagcatagac ctcgctggag gccccagctg tgcttgactc   21300
cagagatggg acactcagta ccgtggcatt taggccaatt atggaaaggc cagagcaacc   21360
ccaccccttt gaagccgtcc actggcctgg gatcagcaga ggagggctgt ggtggggtg    21420 ctggctctgt ccttcataag ccacatgaac ttgaactgag gccattcctc ttctgggaag   21480
aggccggcca gtttcactgt ggtctgtgaa gttatgattt aatgaactcc gtgaatcaca   21540
gtatgccgtt ggctgcctga tccatttgtc accatcctcc aggtatggag atgcctttg    21600 tcaccatcct gcaggtatgg agacgccgtc cgggagattg atgacagcat gggaagata    21660 ctggagctcc tccaagacct gcacgtcgcg gacaacacct tcgtcttctt cacgtcggac   21720 aacgcgctg ccctcatttc cgcccccgaa caaggtgagt gctcgctgtc acttctcacg    21780
gtttccccac agccagcgtg tcagcgaaga gtgcctggac cggctgtgcc cacggggtct   21840
gtggtgggca gagcatgaag ggtccctctg ggtccagcgg gaggagcaga tgtcaccgag   21900
cctcgagcaa ggcccttctg gcccaggact aacctggaag caggagtgac cttgaacttg   21960
ggggtgggga ggaggtgaca caggggagag ggtttgtctt ggaagaggct gacgcctccc   22020
```

```
gaagggtgac cccggaggcc ggaggctttg gaggccgcat ggaaacagca gggccggtgg    22080
agcagggtgt ccctgctgag gtgggggccg gcacccccaga ccccgagcag ccctgtgagt   22140
gtggcctgga cctggtcacc caggggccgg gctgcctcca tgaagatgga ctcctgcccc    22200
caccacagcc ctgtcaagtg gttcctggga tggagcttca gcctttcccc cgctcggcac   22260
tgatgaatgc ctgacccatc cccagcgcca acaaacctga acccgcctct tcccagacca   22320
cgcggggggg ggccctgcag cctcttccca gaccacacgg ggggggccct acagcctctt   22380
cccagaccac gctgaggggg gccctgcagc ctcttcccag accacgcggt ggggagagcc   22440
ctacagcctc ttcccagacc acgctgaggg gggccctgca gcctcttccc agaccacacg   22500 ggggggccc tacagcctct tcccagacca cgctgagggg ggccctgcag cctcttccca   22560
gaccacgcgg gggggccctg cagcctcttc ccagaccacg cggggggggg ccctgcagcc   22620
tcttcccaga ccacgtggtg gggagagccc tacagcctcg tcccagacca tgtcggggggg   22680 cgcctacagc ccagtgtgct gcggggattg ggggcttcag agtttcaagt gatagaaacc   22740
agcacagctg aaagccaaaa cagaagcata ggctccctcg cgccacgtcc caccagatag   22800
ctcccctggg tgagcctggc tctcgtgcag gccctccgga cagctccatc tcccgcccac   22860
tggagtcaga cccacgagtc gaggcccccca acagacccat gtgtggaggg ctacaggcag   22920
ctcccaggag gcagggtgct gggtgggggg agggtggtgt tggccgtcat tccccatggg   22980
gagcccgggg gggcccacct cgacgccagc acccacaacc accagccagc aggggcaagg   23040
gtcccagcga cctgagtctt catttctaaa tgatggaatg tttcatacca acaaatggca   23100
tgtttcatac caacaaatgg tatatgtacc tatttgtaac aagatgagaa cccacacacc   23160
cagcacccag cacaagacta gaaacagaac atcccagaga aagaaagcag gggaggggc   23220 tgggcgtggt ggctcacacc tgtaatccca gcactttggg aggctgaggc gggtggatca   23280
cgaggtcagg aggtcgagac catcctggct aacacggtga acccccatct ctactgaaaa   23340
acaaaaaatt agccaggcgt ggtggcgggc acctgtagtc ccagctgctg ggcaggctaa   23400
gtcaagagaa tgacttgaac ccgggaggcg gagcttgcag tgagccgaga tcgcaccact   23460
gcactccagc ctgggcgaca gagcgagact ccatgtcaaa aaaaaaaaa aagggggatgg   23520 gagagagaag gaaagaaagg gagggaggga aggagaagaa gcacagcatg gcctcctgtg   23580
agcctgagtg tcccctagaa gtggccagtg tccccagctc agtgtccatt gtcccttcac   23640
aggttctgtg gctctgctgc tgtgagcagg gccctccctg agacaggccg ggttgcgggt   23700
gttggcgtgt ttgcccgtga ggggctctga gcagagctgc ctgcgaggtt ccgttcagag   23760
gcttccccac gctgccgctc ggggttggat ggcagcgcag gaaggagctg cggtgacttt   23820
gcctcccctg gatggttcac ttttttcactg ccggaaaaat atttctcttt tttttttttt   23880 ttttttttg agaaggagtc tcgctctgtt gcccaggctg gagtgcagtg gcgcgatctc   23940
agctcactgt agccttgacc tcctgggctc agcaatcct cccacctcag cctcctgagt   24000
agctgggact acaggacgtg ccgccacacc cagctaattt ttgtattttt gtagagatgg   24060
ggtttagccg tggtctctct ttggtagaaa ccagtctagg ctagtcttga actcccgagt   24120
tcaagcagtc cccctgcttc ggcctcccaa ggtactggga tgacaggtat gagccaccgc   24180
agccggcccc ttcgtttcct ttttcccttt tattcagggg acccgaagct gagagagcct   24240
caagtggctc aggctacagc agcaggggtg gcttttgtcc ctgacgtggg cccccaccc   24300 ccttcttcca tgtctgggag tgagccaggg atggtgtagt cacctgagat ggcctttgcc   24360
```

```
ccgtgaccac ttcccacaag tgatggttca gaaaccaaaa tccggtcttg ggggcttgtc    24420
agaaacacag attcctacgc cccaccgtga ctgactgagt cagaaccatg gggaggccag    24480
aagttggctg cattttaagt accccaaaca ccgggaggct tgtgaacatt cacgttcggg    24540
aagcaccagt cggcagctgc gcacgtggca cccagggcct ctgctgcggg agtgtacctc    24600
tctgagtctt gctgacaccg tatggttgtg tttccatttc ctcagtgggc atgatgtccc    24660
cactttctcc aggagacttt gcagccgcgg catctcagat gagcccctgg agagccaccc    24720
cgaggctcgg atcatgcact ccagccagag tgccttggcc gggccctttg tccctatgac    24780
cagtctcagt gactcagtgg ggagggaggg ggagggcctg gggacatctg gtcccagtgg    24840
cctgacaagg gcccctctct cccaggtggc agcaacggcc cctttctgtg tgggaagcag    24900
accacgtttg aaggagggat gagggagcct gccctcgcat ggtggccagg gcacgtcact    24960
gcaggccagg tgagtcagcg tccaccggtc tgccgggcag caggtccagg cctgcagcca    25020
tcccagggtg tgtgcgcccc tcactggcca cctcccccat gcaccccgtg ctcatcctca    25080
ccgctctcct ccccacgcac cctgtgctca gcctccacgc accccatgct cagcctcacc    25140
accctcctcc ccacgctccc cgtgctcggc ctcaccgctc tcctcccac gcaccccgtg    25200 ctcggcctca ccgctctcct ccccacgcac cccgtgctcg gctcaccgc tctcctcccc    25260 acgcaccccg tgctcggcct caccgctctc ctcccacgc accccgtgct cggcctcacc    25320
gctctcctcc ccacgctccc cgtgctcggc ctcaccgctc tcctcccac gcaccccgtg    25380 ctcggcctca ccgctctcct ccccacgcac cccgtgctcg gctcaccgc tctcctcccc    25440 acgcaccccg tgctcggcct caccgctctc ctcccacgc accccgtgct cggcctcacc    25500
gctctcctcc ccacgcaccc cgtgctcggc ctcaccgctc tcctcccac gcaccccgtg    25560 ctcggcctca ccgctctcct ccccacgcac cccgtgctcg gcctcaccgc tctcctcccc    25620 acgctcccg tgctcggcct caccgctctc ctcccacgc accccgtgct cggcctcacc    25680
gctctcctcc ccacgcaccc cgtgctcggc ctcaccgctc tcctcccac gcaccccgtg    25740 ctcggcctca ccgctctcct cggaaccagg tccctctcgg tggctctcgg tgtgtagggc    25800
ttgctgtgct tggtcagaca ggcaggaagg ctctcggtgg ggactggagc cacgtatact    25860
gccgtgtgtc acgtgggtgc tggtaatgac tgtgtggtga ggagacatcc gtggtccagt    25920
caccgcagca gtcctgagtt aaatggagct aaacaggttt cttccctgca ggacttatca    25980
gtgcctttag catgctggtg ggcaccatga gcttctagaa ggggcttaga gcaggctgag    26040
tgtttaaaaa cctgtctgtc tactacgaaa tcggtcgttt ttccccaa agcacatctt    26100 ctcaggccag tgtcctaagg acactcagag aacagcagca gcccgacacg agaccgttgg    26160
tgtctgtctg ccgcatgggg tgcggacctc ggtggtggcc tgggtcctgg ctgggcgagg    26220
gtgcgccctg ccatctcagt gtgaccacct tcatgctgtc actgcatctc ctctggccca    26280
ggaagctgcc cctcggttga gaatcacacc gtgtggtctt ctgtaacagg cacttgagcc    26340
agacataccc atcaacacgc ggggctgagt ctggtgtttg taaacgaccg ctgtttcttc    26400
actgtttctt agtcttttgc cctcccaatg gcctccagag gcagccatcc ccttcaagtg    26460
gccccacgag gatggggggg gctcccagtg gcagctggaa catcacacat gacgacagcc    26520
agagtcaaca tggggctcat ggggctgagt gaagacgtgc gtggggccag ctccttctgg    26580
aggctccagg agatgttctg ttccctgcct tttcccaatc ctagtagctg ccccattcct    26640
gagctcctgg cccctccacc gtcaaagcca gcagcacgca ggcatctgtc cctgccttc    26700 ctgttccacg ttttttttt ttttttttt ttttttgaga tgaagtctca ctctgttgcc    26760
```

```
caggctggag tgcagtagtg caatctcggc tcactgcaac ttctacctcc cagattcaag   26820
cgattctcct gcctcagcct cccgagtagc tgggactaca ggcatgctct accatgcccg   26880
gctaattttt gtattttag tagagacgga gtttcactat gttggccagt atggtctcaa    26940
tctcctgacc tcgtgatctg cccgcctcgg cctccgaaag tgttgggatt acaggcgtga   27000
gccaccgcgc ccggcgcctg ttccactttt gaggaccctg tggctgtgtc ccacccacc    27060 ccctgctcac ccaggctggc ctccctgttt cgagcctcgc tgatgagcgg cctgcgttgt   27120
gtctgccgcc tcaattgcct ggcctggtcg cgcgcctgaa gcccaggga ttggctgctg     27180 ttctgccaga tcctcctctt ccccactcat tctacacatc aggaaactga ggccagagag   27240
gaagtcgtct gtcagggtcc cccaattact agggagcaga ggtgggagca ggcgcctggc   27300
tgtggatcct gcactcctgc ccaccatgcc tgggcagtcc cctgtgtccc cagcagccag   27360
tgggactggg ggcggcaact gccaagggcg cctgttctct acagctgtct gggcctccct   27420
cagaccctgc ccagggcagc ctttgtctga catgggactc ctgggccacc ccaagttccc   27480
aggaccctga aggtggaaga gaccccacgg ttcactgaaa aggcagctgc ggctccgtgt   27540
gaagggcaga gtggctgtga gagtgaccgc cttgttgtgc aggagaagca tgggtggtgg   27600
gcacggcctc ctttgtggtg tggggtgccc ctaggacaga atgcagctgt ccgccccct    27660 ccactccct gagcgccatc cccctgaggg tagggatggg ccatttggtt tcttgtgtgg    27720
gggcacctgc agggagtggc cggtggtcac tcagtgaaca ctgtgacgtt ggcatgagac   27780
tcaggaactg tgtagctctg ggagacgttg catgagact cgggaccgc gtagctctgg     27840 gagacgttgg catgagactc aggaactgtg tagctctggg agacgttggc atgagactcg   27900
ggacccgtgt agctctggga gacgttggcg tgagactcgg gacccgcgta ggtctgggag   27960
acgatggcgt gagacccggg acccgcgtag gtctgggaga cgatggcatg agactcggga   28020
cctgcgtagg tctgggagat gtgaggttcc ccactgcagt gggtgcccac caggccggga   28080
cagggctggg gctctgctcc ccaggctggg agccacccgt ggctgtgctc agcagcagcc   28140
tggaaaaggt gagggagcc accccagcgc cgcccggctc catgcgtagt gggttcaggg    28200
acgtctgtac cccacagacc tccccaccca cctgcccacg gaaaggctcc agctgagaaa   28260
aatgccaatt tcagcgtttt ggaaccttgc catctgcctc gctccctgaa gagggaaac    28320 cctctcccca cctgaggaag ggaaaccctc ttcccagagc caccaagttg cctttcccg    28380 tgggccacaa agtgaaattg aattcgatgg catcaggcct gtgcaccagg acaccacgac   28440
ggggtttcag tgaaagcgcc tgacgtctgt cccgacagtt ccctctgggc aggggaggct   28500
ttagtccctg cagccctgga ttctgagtga agtctcgaaa gcgctgataa cggtttcagt   28560
gacttctccc acagccgcag ctgcccactg catttctgga tgtttctgga aggcatcgct   28620
gcctggagag ttcttcgaaa acgctccacg aggaccctgc ctgtgctgac accactcccg   28680 cccgcccgc ctgccggcac cacaagcact gctccgcagt tatttttca gatgacaaaa     28740 gcatctggat ttctttcctt tattattctg tcctttaaag acacgggaa ggacgggaag    28800 cagtcgcaca gacactgctg accagacctg gggaagcttc tcaccttctg caaagcttcc   28860
tgaactttcc tggcaaacgc tgagctttgc attccctgcc ccacactggg cgctgcagac   28920
cccacatccc gtgagcggct gcagcgcgga gtgagtgtcc ctgtgaggcc agggctcctc   28980
tgttggagaa gctggcgatc gccgtctgcc ctagcgagga gctggctgca ggcggcgagg   29040
gtgcccctgg accgtgggga gggctgtcga cactgggtgg gagctccagg gcctggcagc   29100
```

```
ggatggcggt ccctgcccag ctgccccagg ggctgagctt gccaggcagg ggtgtctctc      29160
cagccccacc ccagtctccc cgtcgagtga cccaagcctg agcccccga gttaagaaag       29220 agacagggcc gccgggctca tgcctgtaat cccagcactt tgggaggctg aggcgggcag      29280
atcacctgag gttgggagtt cgagaccagc ctgaccaaca tggagaaacc ccgtctctac      29340
taaaagtaca aaattagccg ggcgtagtga cacatacctg taatcccagc ttctcgggag      29400
actgagtcag gagaatcact tgaacctgga aggcagaggt tgtggtgagc tgagatcgca      29460
ccactgcact ccagcctggg tgacaagaac aaaactccat ctcaaaaaac aaaaacaaaa      29520
aacaagaagc agacagggcc actgagggaa gccagatggc acgctctgct catggctggt      29580
cagcagtgcc cacgccctcc ggaggtcaag gcacggcggg aaagacagcc tcctgcctgt      29640
cctggagctc tctgggtgtg tcaggagccg tccccacccc agccactcgg agctgctcct      29700
gtccagcctc agctgcccct ccacatctgg tttttctcca cctgctcctc tgacttaagg      29760
ggcagggctc acagtggcct tagggcattc agtgttagag cgaggctgat cctctccgga      29820
caggtgggcc tggaggggca tctccctggg agggctgtga ttctcctttc atctgatcca      29880
cagaggcaga aagggtgcc agggagtgag ggcgtggcct ggctctgggg tctttgggcc      29940
tggtttgagg ctcctctgtc tctcacaggc cttgtgaccc cgctcagtcc ctgctgtggg      30000
cgtgtgagca tgtatgcata tctgtagacc cagctgggca gcggggctca cgccccccca      30060
gggattggcc cccagcccca tcgggtcggt gcagagtgcc ctgaccgtgt tgctgccatg      30120
tgtttcaggt gagccaccag ctgggcagca tcatggacct cttcaccacc agcctggccc      30180
ttgcgggcct gacgccgccc agcgacaggg ccattgatgg cctcaacctc ctccccaccc      30240
tcctgcaggg ccggctgatg gacaggttgg tgctagacct gccccggccc cttccccga       30300 tccaagtagt gaagcccaga gctgctaatc aggtgcaacc cccaggccca gcagccctcc      30360
tggttctgga cacaggcgtg ctcgtgccca gggcaggagg aggcaggggt gcctgagacg      30420
agaggacctg gggacctgcc tgtggggcag gggccatcct gggagggtcc aagcacagcg      30480
aggccctggc tttcaagaaa gccttaggag ggagggcaag gccaggagag gggcctcatc      30540
cctgcctgta cccgggcaca tgccgcccct gcccgcccca cccctgttcc ctgcctgtac      30600
ccagacacac gccacccctg tccgccgcac ccctgttccc tgcctgtacc cagacacacg      30660
ccgcccctgt ccgccccacc cctgttccct gcctgcagcc cgggcacatg ccaccctgc       30720 ctgccccacc cctgttgcct gcctgtacct gggcacacgc cgccctgcc cgccccaccc       30780 ctgttccctg tctgtagccc gggcacacgc tgccctgtc tgcccaccc ctgttccctg        30840 cccagcctgg ttttggtgc ctcatggctt cctgtagctt ccttcttcct tccatccaag       30900
tcgctgctct gccaagtcca tggcccagct cttaccttct gtccaaatcc ttagtgtcca      30960
aagtccattt cctacccct gagagcagcc accattccac tcaaaccacg tttcctgggt       31020
ggtcctgaag ggatgaggat tccaaaggct caacggaaag caaggtgggg acggcccaag      31080
gcagctgccg cctccggcta tctggggccg ggtagaggga gttttgctca cttgtcccct      31140
ctcgagacct ggcacaagtg gttggtcact gtggggagag acggtgccca gctgcgtccc      31200
ccactccccg ttcctgactc gcaggcccaa catggtcagg agaccccgtg ccgcctgctt      31260
atcctcttgt ctgcccaccc tccccagggt ctggcccagc cttgccaagg accagcaatg      31320
aggggacgcc caggcaccct agcccggcc gccagcac cccagacacc caggcacccc         31380
agccccagct gccaggaat cccagtcccg gacacccagg cacccagcc ccggctgccc        31440 agaaacccca gccccagaca tccaggcacc ccagccccgg ccgcccagac acccaggtac      31500
```

```
cccagccctg gccgcccagg cactccagcc ctagacaccc aggcacccca gacacccagt    31560
caccccagcc ccggccaccc agacacccag ccacccccagc cccggttgcc cagacacccc   31620
agccccagac acccaggcac cccagatacc cagtcgcccc ggccacccag gcacccccagc   31680 cccggctgcc caaacaccca ggcacccccag ccctggccac ccagacaccc cagccccaga   31740
cacccaggcg ccccagacac ccaggcaccc tagacaccca gtcacccccag ccccggccgc   31800 ccaaacaccc agtcacccca gcccggccg cccagacacc ccagccccag acacccaggc    31860
gccccagata cccagtcacc ccagccctgg ccacccagga gctccagccc cggccgccca   31920
ggcaccccag ccccagccac cttgcgggcc ttttttacttt tcaatcatct ttgtaaagta   31980
tcaaccaaga cctcacgtgg aggcatgagc cactgatgac agacgcagcc cagagcctcc   32040
aggtggcccc agcgtgtcct tcctgtcatt acatggtcct cccctcccat cccacaggcc    32100
tatcttctat taccgtggcg acacgctgat ggcggccacc ctcgggcagc acaaggctca   32160 cttctgacc tggaccaact cctgggagaa cttcagacag gtacagggct cgggacgtgg   32220
gcgcaggcgg agctgccccc atctctatcc agacgtggcc cctgagcacc gtcctggggg    32280
aggcacagga gggtgagaca ggcaggaact ccaccccctc cacagccttc tctgtgtggc    32340
ccccagtcgt tcagcgtggc ctagggcatg gcagctgaca ggctggagag gaggaaggag    32400
cctcttcctg ccccgcgtga tgacagtagc cccgcggcat agctacaggc gtggcctaga   32460
ccctggtcag gtggccccca tgggcctctc catcctgcca gggcatctga gcctccccca   32520 cacccccaggc tggaggcgac agagacgtgg cctgcttggc ccaggtgcta catgggggcc   32580
gcagcattgg catcaccaca gcaaccccca gtgtgggagg gtgaaacgcc acacgcacag   32640
ggcctggggc tcctgccgcc ccaggctacc ccagcattgt cagcgccagg ctttctccca    32700
cgagccctcg cctcaagcct cctgctccct ccccacggtc ttttctggcc cctgctgacc    32760
cctacgctcc agcatccccc agccctcct gagaggtctc tctcagcccc acccactccc    32820
agcatcaaag tcttgagata tgaaccccct gctaatctgc cttaattggg aagaaaatca    32880
tttagtgtaa tggagagtct aaagactgga agtgagaact ggggctgagg gctgagcacc    32940
caggctgagg agggaagctg ctcgtggggc agtgtctgga gggcaatgat gcccaggagt    33000
gttttggctc ctccccaccc tgtgcaggcc ccgcacccgc tcttctttcg ggttttaccc    33060
agcactgtca cctgcaaggg ccatcctggg catcggtccc cggcattgcc gcctgtgagg   33120
gccgtcctgg gcatcggtcc ccggcattgc cgcctgcgag ggccgtcctg ggcatcggtc   33180
cccgggcatt gccgcctgcg agggccgtcc tgggcatcgt tccccgggca ttgccgcctg   33240
cgagggccgt cctgggcatc ggtccccggc attgccgcct gcgagggccg tcctgggcat   33300
cggtccccgg cattgccgcc tgcgagggcc gtcctgggca tcggtccccg gcattgccgc   33360
ctgcgagggc cgtcctgggc atcggtcccc ggcattgccg cctgcgaggg ccgtcctggg   33420
catcggtccc cggcattgcc gcctgcgagg gccgtcctgg gcatcggtcc ccggcattgc   33480
cgcctgcgag ggccgtcctg gcacagtcc tcggacgagc cccttggcct gcagcacccg   33540
ctctgggaat gttagaggca tacctcgcct ttcccgaatc aggaggccca ggggcagcag    33600
aaagagaatt gtggttactg taaaatcctt gccccttcttg agtgtgtgaa tctgtgtcag    33660
ctccctgggt ctgttttgt tttctgtgtt ttctcttgcc tttcacatgt tggtcctgct    33720
cctccctgtc ttagggtttc tgtagggatt ctgagcgttg tggctctccc ttctcccagg    33780
gcagggcctc ccttcccgtc cctttccctc cctccccttc cccagcagag agtaggctgt   33840
```

```
taaaaggggc tttcctccat gaaattagtg gcagtccaga tctgaggctg gctaaggtgt    33900
tttaaataca ctcacctgcc tcgcaaagaa gaggggtaca tgaaaacagg gtacgtgagg    33960
catgccagct acgcatctcg ggcccagagc gggtggcttc acctcctcca caggatgctt    34020
atgggcccgc tagtccttca gcgtttagcc agcgccctgc accatgctga gtaccaggga    34080
cgctgctagg cacaggcaga cgagaccccc ccacggcccc cagttagggg ctccaggaca    34140
caggcagaca aggcccctca cggccgcagt caggggctcc aggacacggg cagacgaggc    34200
ccctcacggc cgcaggtcag gggctccagg acacaccttc cctcttctca ttgcagggca    34260
ttgatttctg ccctgggcag aacgtttcag gggtcacaac tcacaatctg aagaccaca    34320
cgaagctgcc cctgatcttc cacctgggac gggacccagg ggagaggttc cccctcaggt    34380
gagtcggtgc agggcctcct ggctgctgag gcagtgccag ccggactccc caaaatgcag    34440
gctccacagg gacagagccc tctgcaccct gcccgccgcc tccccttgcc tgcatctgct    34500
gttgctattc atacccacac gtgcttggtg gcctgccctc ctcccagggt gcctgctgct    34560
gcccacccctg gtggtctccc cacttctgcc ccttctgggc caccatccac ctggcccca    34620
gtgatgtatc ccctactctg agctgcattt ggggatggct gaggccagag gggaggggtc    34680
caggccctgg ggcaagtagg aggtacaagg acacaggtca gctagcagga ggaatggcag    34740
aaagccacca gccccagctc caccctctgc tctctgggcc ttgtcctcac cccaccgagg    34800
atgccggagt ctgcgccatc acctgccagt tttcagggaa gccctcccct taccctcagg    34860
agtcttgagg gtcatggtcg ccagtaccag actcacctgc tggcagctcc ttaggggcga    34920
cacagaggcc ccaacacttg gctggagacc ccgccctggc ttcctttttt tttgtccgaa    34980
cccatctccc tgggctaggg ctacctggag gcttcccccc ctcacccccag caggatgagc    35040
aggtccccaa ttcctgctcc tggcctgggg gtcctggggc acgtgcatgc ctagtggtct    35100
ccagcattcc tgccctatcg agttggtcct gggaagaccc aggagcatca ggggagtggc    35160
gtgcagaggc agaaccaggc ctgagcacag cggttgctcc ctgcccaggc tttctatgct    35220
ccccgatggg cctgggtttg agtagggccg gtgggaggca gcagagagca gtacaggacc    35280
gagggtggca gcaccaccgc caaggtgccc tgaggctcct gcaccctctg gacggggcag    35340
ccgccttccc acggggctga gcctgcggtg aggctcctgg gctgcagccc ctcagggatc    35400
ccttgggcac ttcctcggca gcacctctcc tccaccgagc gtccagctca gaagcccagg    35460
atggtgactg cgggaaggca gcatggagcc tggagtggac agcagtgtcc ccaggcccag    35520
gtccacccac acctcccagc ttggcctgaa gggaagtagg gcctgtgcct tgtgattaag    35580
gcacgggtgg cgctgggtcc aaggccaaat gccctgagtc cagagggagg agacacagac    35640
atggtgaagg ccacgggacg agacggggac tggacagagc gccaccagcc tcggctcacc    35700
tggggccact ggagctggaa gaggcaggaa ggagcccag ttcctccagg ggtgcacagc    35760
cctgagaccc ttggtttcag cctctggcct ctggaaaagt gaggggcatc tgcagtttca    35820
ttgttttaag ccccagttca tggtcatatg ttgtgggggt gccgagatac agagacagac    35880
gcccccgggg gactcgtgat cacccatggg ggtgagaccc gtgaaaccat ggggggcctg    35940
gagcttgggg ccttgtggag ctggaggggc tgtctgggag ccccctgtgc ccgcagaagt    36000
cactgaggag ccaacagccc ccccagctgg aagcgccgtc caggggagac cacggggagc    36060
agattgcagg ccccagttac acagaacaag ctgctggcca caccggtgcc cgccacaccc    36120
cccacaggct ggtcgctcca gggaccaccc gaggttaaag cctggatggc ggtgcccct    36180
cgcgtccact gggcgtgatt ggcatccaca ggggggtcct cagggccact gctccccgcc    36240
```

```
tgttgcgttt gctggagccc ctccagccag gccagagcag agacacagtc ccacccacca   36300
cagccaccca gccccgccct cacagctgga gaaggcaggg ttatttcaaa gcaaacccag   36360
gcagcaggca gagcttccca gagggggtca caaggaggcc cagctgtcgg ccatgccttt   36420
gagaaccact gtccctgagg tcacacaccc atgacacagc ctgattcacc gtgggctgct   36480
tctcagacac agacacacat gtcactttgc caggagcctc tctaaattaa agacgggtgg   36540
ccggtcgcca tggttcatgc ctgtaatccc agcactttgg gaggctgagg tgagtggatc   36600
acctgaggtc aggagtttga gaccagcctg gcctacatgg tgaaatccca tctctaccaa   36660
aatacaaaaa attagctgga tgtgttggtc ggtgcctgta atcccagcta ctcgagaagg   36720
tgaggcggga gaattgcttg aacccaggag gcggaggttg cagtgagctg agatcgcacc   36780
actgcactcc agcctgggtg acagagcaag actccgtcta agaaaaaaaa gacgacgggg   36840
ccaggcatgg tcactcacac ctgtgatccc agcactttgg gaggccgagg taggaggatc   36900
tcttgagccc caggagtttg agaccagcct ggtcaacaca gcaagacctt actggtacag   36960
aaaataaaaa attaaggccg ggcacagtgg ctcacacctg taatcccagc actttgggag   37020
gccgaggcag gcagatcatg aggtcaggag ttcgagacca gcctgaccaa catggtgaaa   37080
ccccgtctct actaaaaata taaaaattag ccaggcgtgg tggcgggcgc ctgtactccc   37140
agctactcag gaggctgagg caggagaatc gcttgaacca gggaggcgga ggttgcagtg   37200
agctgagatc atgccattgc actccagcct aggtgacagc gcgagactct ctctcaaaaa   37260
ataataatta aaattagcca ggcacagtga tctatggtcc cagctactca agagactgag   37320
gcaggaagat cgcttgagcc tggaaggtca aggctgcagt gagctgctgt ctcaccactc   37380
cagcctgggt aacagagcaa gatcctgtct ctaaaaaata aatgaaataa acaagattaa   37440
agcaacaagc caggccacgg ccttcgggga cgctcaccgt cagaaagtgc acgtgcagtt   37500
cacgccagtt ctcaaccagc agtatttggc cacagaatcc tgcagaaaca caaatgcacc   37560
tgagaccctc ctggattaaa aatggaccct gtgctcaggg gcgctgtgtg aagcccaggc   37620
tgggaccagg acaggcatct ccgcgggcac caagcgggga gccctgaagg accccagctc   37680
tcctgaaggt cgccctctga tgcaaccccca ggcctgagcc ctaagcaggg agtgggtgga   37740
tcgagcagaa agaggctggg gcaggtggcc ggggtgggg agggggcgc atccccgtcc   37800 ctgttgcatg cagcttccgt gtgaagcctc attttaggg aaggttctgg agcaaaaagc   37860
cagttctcac agactgctga gcgtccaagg cagaagactg ggcttcagtg ggtccgggct   37920
cacctcccag aaggtactgg gcctggacag gtgctgccat caggagggga gctgactcac   37980
ctggtaaccc cgtctctagc tttgtaagga gctgccacac caccttccag agtggctgct   38040
ccggtccacg tccccaccag cagcaacgca gctcccagcc tgggcattga gaaactccag   38100
cttcagccac actcgcagaa gttcctccct gcatctccgc tatggcagcg atggcaggtg   38160 tcttttttatg tggatgttgt cgatattaga agtgattgaa aatggtgaaa aggcatcatc   38220
tgtgcagatg tcctcagagc acagcatgac ggcgccgtgg acccaagatt cacagcatcg   38280
caaactgcgg ccctgacatc gcgaaccgtg gcacctcgtc gagccgtgta atcgtatctt   38340
cgtgaagatg aaaggaatcc aaacactccg cagcttgcat tggaatttta gaactgcaga   38400
tgccgttccc ctccattttcc tgcttttttgg caatgggatg acgttgcttt tgtaatgaaa   38460
gaagggtgtg tcatatttgt aaatgtttac gtagtagtga gtgctgggga gacccacagg   38520
ccccagccca catatcccgg gtcctggtca caggcaggga caggatggga cggctctact   38580
```

```
cacagcctct ctgccagggc ttggcctgct gagccttcat ttcctctctt gcccgtgagt   38640
ctgagggcag aggatggctc gggtgcctgc tgcctgtcct agcgaggccc ggggccgctg   38700
caggcttgag cacatggtcc cagtgactgc tcactgtggt tctcagcccg ttagagctct   38760
gcagcctcag cctgtccagg ccagcccctc tccgtccttc gctgtcagcc ccagccgtgt   38820
gaccagagct ctctgtcccc agctttgcca gcgccgagta ccaggaggcc ctcagcagga   38880
tcacctcggt cgtccagcag caccaggagg ccttggtccc cgcgcagccc cagctcaacg   38940
tgtgcaactg ggcggtcatg gtaagtggct ggtgtgtggg cggccgtctc tttgccgggg   39000
ctgcagccac ccaccegggg cccaggatga accgtggcca gcacagggca gaggcaggcg   39060
tgcttccccg cctccgtcag tggtgaggcc ctcgtgcctc agagcacacg cggcggcgtc   39120
cgggattcgg gaggcaggag ccaagcgact cggggaccag acaacgctg caccagggca   39180 gccgcaggtc cacagccggc cacccgggcc tctgcctggc tgagctgaga ctggggagct   39240
ccaaggcccc tctcctgccc cccacaagtc actgagggac agcagggcgc gtgagagggt   39300
ccggggtccc ctggtcctcg actcccacac gggcagcttc tccttgcagg ggccctgtga   39360
tgacctccaa actcccgggc tctgaaggca ccgaggcagg aacggcactg cccggtgggt   39420
cccgggtggg ctggtgggca ctgttgagtg gcggcggccc cagggcccac ctgcgaggtt   39480
ctcatttgtg cctccttcat gctgggccag ccccagagac cttcgcatca gacctgatct   39540
cactcatagg cacccaccca gagcagcacc tccgtgcagc ctgacaagac caggccttgt   39600
tcacctccag tagagaaacg gcctcatcac gccagcatcg ccagaaaaca caagcacaga   39660
cgtgcctcca aagtttcact gaagtctgtg ttcaggccac aaaggatgcg tcgtcgtctt   39720
gtccagccct gggggccgca gcagtcaggg cctctcagga gcagctttc tgtcccctgc   39780 ttgggggtcc catagggtgg catgtggacg gcccagccat cccgcgtgtg cagtggccgc   39840
aaaggcctgt ttcccagcac agctgatgtg ggtcccagca gggcaggtct tcacagctcc   39900
ttcagatggg acacgtgcgg ccctcgctct agtcggcaaa aacgagccac acacaggtct   39960
gcggtgtcgc tcctgggtgc ccagagccca ccgagcacag tggagatggc cgagcccagc   40020
ctcgaggccc ctgggccgtc gctcaccegt ttacacgggc tgggcgtggc tgcccacagc   40080
ccctggatct gccgcgcagg attcgggaag aaggcccctc ggcagctgca gacttcagcc   40140
tgggctcctg ctgtgcgggc gaaaaggccc agctgaagcc tctttccagg gccagacccg   40200
gctgcagcgt gggagccgct gggtgcccgc cgtgccgtgg aaggaaggt ggtggctctg   40260 aacagccagg gagccacagc gtgggccggc ggatgtaaca ggagagcacc ggccatcggg   40320
agcacctacc agcagtgagg accatggagg gcagatggcc ttgtccctgc ccagggacag   40380
tccaccctgc agggttattt aggactgggc agggcagggc cacctccgtt agttgggggg   40440
cggggggcgg gggtgcctgg caagtttcat aggaagatat tcagggccct tccttcaaag   40500
ggacctgggc agctggcgtc cccgcctctg gactcagtgg tggagcaggg aggtccctgt   40560
ctcaggaccc ctgagtctcg gggccccagg agccagggc caccagccgt ggaggagccc   40620
tggccttctg ccttccacac ccaatcccac tccgtgctgc tgggtccttc tctacgaccc   40680
aggctgcagt ggctccacgg gcgcaggcca cacctgccat ggacagtg gcacagggc   40740 aggggaggtg ggcgcacaca gcctggctgc cactgccatc tcctgggcac tggggggaact   40800 gcccccaccg ccacacctgt gctctctgca gggggaaaag tgccaactca gacctggcga   40860
gctgagccca tggggtctga ggggcccaga tgccaccgtg agcagagcca tggggagat   40920 gcacagacac gcgtgtgaag cctgggggcc ctccttaccc cttccctgcc ctctgtcccc   40980
```

```
gccaactcca ggccagcccc aggagagggg ctcagtggcg tctctggcac agaggagagg    41040
gagtgtggcc acctggaccc ctgcttctgg gacagctgag cggcctttga gaaatgcaga    41100
tcccccatcc agactcaaac acaccctgcg gctgcctctg ctgcccctgg agtttgggag    41160
cagcttcctc acccaaaccc actcctgctc tggtggccaa gggggcaggg acactcatgc    41220
ggcatccctg ctgccgccta gggctggaga ctgtccttag taccctgagc agcacccaga    41280
atccaaagtc tgtccccgga aagtgccctc agggccatgc ggcgtctgac gtggcacaga    41340
agtggcctgg atgggacac agaaccaaac tgcactcatt tcagccaaga aggctcctct    41400
tagcggcata agtctcccTT tctgttgcca ggaaaagtgc cctcccatca agcaaggctt    41460
ccgctaagca aggctgcact gtgaggtcca cacacaccca ggcgatggag gggtgcgggc    41520
tccgctcagc accgcactga actgagccca gcagcgcagt agggactggc ttctccctgg    41580
gaaaggcttc ttgagaggct gaagctgcag gagagggtga tgagttgaga agctcagggt    41640
gggccctcct ggGaggaccg cctgcccttt ctaacactgc tggccctcgg aggccctcag    41700
ccacttggca gctgcatccc ccataccCgg gacctcccca ccaagttctc atttctccaa    41760
tggcagcctt cagagctgag aggccgagtc aagaggGTGc catctcccaa gttcccatga    41820
ttcctgggga gcgtctgtgt agctgcccac ctggaccgag gtggtcccca cactgaggcc    41880
aattggttgg ggtccggggt tgacctggGc aggGgacaca tcaaaactgc tcgaggccaa    41940
gcgcggtggc tcacgcctat aatcccagca ctttgggagg ccaaggcagg tggatcacct    42000
gaggtcagaa gtttgagacc agcctggcca acttggggaa ccctTgtctc taccaaaaat    42060
acaaaaatgg ttgggcgtgg tggctcacac ctgtaatccc agcacttgg gaggccaagg    42120
caggtggatc acgaggtcag gagttcaaga ccagcctggt caagatggtg aaactccgtc    42180
tctactaaaa atacaaaaat tagccaggcg tggtggcgcg tgcctgtaat cccagcagct    42240
actcactcag gaggctgagg caggagaatc tcttgaaccc ggaaggcaga ggttgcagtg    42300
agccaagatc gcgccactga actccagcct gggtgacaga gtgagactgt ctcagaacag    42360
caacaacaaa atgcccgctg ctgctgggtc cagaagagct tgaataactg catgttcttt    42420
ttctcaattt tcatttccca gaactgggca cctccgggct gtgaaaagtt agggaagtgt    42480
ctgacacctc cagaatccat tcccaagaag tgcctctggt cccactagca cctgcgcaga    42540
ctcaggccag gcctagaatc tccggttggc cctgcaagtg cctggaggaa ggatggctct    42600
ggcctcggtc ctcccccaac cctgcccaag ccagacagac agcacctgca gacgcagggg    42660
gactgcacaa ttccacctgc ccaggacctg accctggcgt gtgcttggcc ctcctcctcg    42720
cccacggcgc ctcagatttc aggaccctcc tcctcgccca cggcgcctca gacctcagga    42780
ccctgccgtc tcacgccttt gtgaaccca aatatctgag accagtctca gtttatttTG    42840
ccaaggttaa ggatgcacct gtgacagcct caggaggtcc tgacaacagg tgcctgaggt    42900
ggctggggat acagtttgcc tttatacatc ttagggagac acaagatcag tatgtgtatg    42960
gcgtacattg gttcagtcag ccttccactg aatacacgat tgagtctggc ccagtgaatc    43020
cgcattttta tgtaaacagt aagggaacgg ggcaatcata taagcgtttg tctcagggga    43080
gccccagagg gatgacttcc agttccgtct gtcctttgtc cacaaggaat ttccctggac    43140
gctaattatg agggaggcgt gtagcttctt atcattgtaa ctatgttatt tagaaataaa    43200
acgggaggca ggtttgccta attcccagct tga                                 43233
```

<210> SEQ ID NO 5

```
<211> LENGTH: 209326
<212> TYPE: DNA
<213> ORGANISM: Homo sapiens

<400> SEQUENCE: 5
aaaagtgaat acatgatttt atttaactca ttaataagga aattggtaag gtgttaaaac      60
caattcaaag gacaatccaa agaacagatc aggaatacta aaataaatat gcaagcggag     120
gtgaaactgt tttccttggt agtggtggag gggaaggatt gctactccgc tggataaagt     180
tcatttgtgt atatataaat aagaattatt ttccattgtt atttatctat aacttataaa     240
gttgtaaaca acttccacgg aatcagactc aacctggaag ggtatggtct ctaggcaatg     300
caaaatttt cccctacacc tgttaacaac tataatatct ccagacagag tagacagaaa     360
gtctggatgg caacgggaat ctactggtca tacggctaac ttcctaattc aataagcacg     420
tgactaaagg attttttcct tccactcaga tatttcaggc taactagata ctgtgtgctt     480
cttagtgtca ctgcttagtg ggggagccag ctctgagtgg ggtcatatcc ggacaagcga     540
atgagctatt tattcaatga ccacgcaaca ctccaaatcc tcccagggca acttgaaagt     600
aaccgcacct tccaaagggc accgtgcaat cagactgtgt gtttggcctc ctgtttgcta     660
gtggggagga agcggcttca tgggtgtaca ctacgcataa atgaatgtga aaggctattt     720
agacctctgc cttttcaccg tcctcccacc tgccacaggc tgggctcttg tgctagaaat     780
gacttgctag ctagacatca tggttcagga tctgagtcag aggtttaacc atttataagc     840
ttttttctta tgaaaaattg gcactaatta taatgtctaa ctgtcagagt tgttgcaggc     900
tttacaggag acgcgggctg tgaagatgct ttgtaaattg tgaagcgtta ttaaagaaca     960
catcttttt ttttaggaaa ccacagtgca aatttaattg ccggggaaga taacgggcct    1020
tggtgccctc caagcgtcag ctgagtttcc aagaagccgg gcagcgggcg cccgcgggtt    1080
cgtctctggc tcctcctccg ccacagcagc cgggggcccg ggtcggaggc ggcggggcc     1140
gagcgccccg cctcgcaagc ccacggcccg ctggggtgc cgtcccgcgc cggggcggag    1200
caggccccgg cagcccagtt cctcattcta tcagcggtac aaggggctgg tggcgccaca    1260
ggcgctggga ccgcgggcgg acaaggatgg gtccgcgcgg cgcggcgagc ttgccccgag    1320
gccccggacc tcggcggctg ctcctccccg tcgtcctccc gctgctgctg ctgctgttgt    1380
tggcgccgcc gggctcgggc gccgggcca gccggccgcc ccacctggtc ttcttgctgg    1440
cagacgacct aggctggaac gacgtcggct tccacggctc ccgcatccgc acgccgcacc    1500
tggacgcgct ggcggccggc ggggtgctcc tggacaacta ctacacgcag ccgctgtgca    1560
cgccgtcgcg gagccagctg ctcactggcc gctaccaggt acgcggcgcc cccgccgccc    1620
gcgccgcccc cgccccgcct ttcgccggcg ccctgccgct cctacccggc ccttgaggcc    1680
gcgggcgctg gcaggcgggg ctcggaccgc cgacccagtt atgggtcccg gcggcttctc    1740
gccccaacct cgctcttcca ggccggcagc ccgccgcggc ctctgcgcat gcccggctct    1800
ggcgccccgc ggacccgcgc cccggccgcc gggttgggcg ggtggctttg tctttcgttt    1860
tctgaagctc cgggcgaagg ggtttatggg aatgccgggt gctgggcgcc gcggccggca    1920
ggcgagcgcg tcctgaggtg ggaggctggg gagggcgtgg gctgggagca aagacgaggg    1980
gagaggtaaa atgaagggt gctcgccgtg ggtgcgaccc tggcccgtgg gaacccagcg    2040
gtgataggtt aggagtgtcc caccaaagat tattttttc caggttctca acacccctgg    2100
aatgaaacct gatgctaggt tgattttct taggctgctg acattccttt cacatgtaac    2160
cttgtattga actcttctga gcatcttcat tatcgcttta aaagcttccc tttaggaacg    2220
```

```
gctccacagt taacgaagga aatataaatg tagagcgtgc atagatgtta gatggctaag    2280
aatatcaaga acatttgcat agcactttgt tgtttttaaa gtgaattatt gaaacagtgc    2340
atgaggtagt tgtttttacc ccgttttaca gacgaggcag gaagcctgta aaggctcgtt    2400
ggcataagaa tcgcacagct agaaagtggt caaggcagtg tccgttgtgc ttttcctgca    2460
tccactggtc gtcccgggct tatgaaattg gccttttttc ccctcaatct gaatacgatt    2520
gtcatatttc taagaccctg aagttattat gaccatatta atacagtaa atgggaactg    2580 ttggatacca cctgcatgcc ttcacagagt acatatgctg tttactcaac aaaaatattt    2640
tgagcttact gtgctactga cagggatat atatttgaat gttgccctcc caagtgtgtg    2700
ttcgcataac ctgtcagatc aaccctagcc tcacgtggtc ctaagatcaa gagaagggag    2760
ggcttacttg tgataaagat atgcgcagtg gtctgaaggc ttttataaag aggaaagatt    2820
gggtgttgct aagggtgaga aatagctgta gccaaggtta gaaatgggag taaaggatgc    2880
ttcccttcac catccacctt agtacttttg gcggttctga ccttggctgc tacgtgtaat    2940
taggaatccc ctacattgtg taaatctcac cctggacact ttgtgggagt aaagggatgt    3000
gccagtaaag aagaagaaga agggaaaggt gaggtttgcc caaagggttc tgcatttgct    3060
ttgaagtaag agaactgaac tcagattgca aaagaatgga agggccattc atttctccaa    3120
cttcctccct tccaacagag ttggacagga aagcaaatac caacttcaga acccattcc    3180 tgggccggga acggtggctc acgcctgtaa tcccagcact ttggaggctg aggcaggtgg    3240
atcacctgag gtcaggagtt cgagaccagc ctgaccaaca cggcgaaacc ccgtctctac    3300
taaaactaca aaaattagcc gagtgtggtg gcatgcgtct atagtcctag ctactcggga    3360
gactgagtca ggagaatcgc ttgaactcgg gaggcagagg ttgcagtgag ccgagatcgc    3420
accactgcac tccagcctgg gcgacagagc aagactccat ctcaaaacaa aataaaataa    3480
aaaacccatt cccgtaatca gttgcttttg tcccctaaca tcctccccca ccagtcacca    3540
aaattatgtc ttggagaaca aactttagta tttagagtac cccatggtta tgaagtaaag    3600
gatgagtaga gaagctgggc actctgaaag gtttagaggc ctctcagtgt agctgattct    3660
aaagcagcct tgcttcccca acatttttt ttcctccagt tttctcaccc actttattct    3720
cttagagttc atgagaccca agtagatgtt acccagggtg agcaagtgtc cacttttaat    3780
gaagtagaaa tttcagggaa ggctcaggag tctccgtcag atactatatg ctggtattgt    3840
tctgagcact tacaagtgtt aactcatttg attctcacaa caactctatc atctctgttc    3900
tgtaacaagg aaaactgatgc tggaagaggt taagaaactt gcccaaggtt acagggctag    3960
tatatgttgg accaggattt gacccagggc acgtggccct agggttgatg cctataacca    4020
ctaagccata ttgcctactc aaaattatta aaaataacat cccaaggact gcttcataca    4080
tactaaataa tccctgtatt acttttggac atttgggtca ttcctaaata tctcaaggta    4140
aagaatcaac ccatcatatt tctgagttag gaattgccta tattccatgt aaaataaaaa    4200
tagattttat ttctgagtca tttgttatgc ataattttag acaataaaat gaaggaattt    4260
tttgactgtc tcaaaatgag ttacttgaag gaagttgtta agagtcatat ctggccgggc    4320
gcggtggctc acgcctgtaa tcccagcact ttggaggcc gaggcgggtg gatcatgagg    4380
tcaggagatc gagaccatcc tggctaacaa ggtgaaaccc cgtctctact aaaaatacaa    4440
aaaattagct gggcgcggtg gcgggcgcct gtagtcccag ctactcggga ggctgaggca    4500
ggagaatggc gtgaacccgg gaagcggagc ttgcagtgag ccgagattgc gccactgcag    4560
```

```
tccgcagtcc ggcctgggcg acagagcgag actccgtctc aaaaaaaaaa aaaaaaaaaa    4620
gagtcatatc tatgaacttg gcagtcatgc tttaagttaa tatttacaga cccctttccc    4680
ataattattt aactttagaa aagaaaagca caagttgata aacaagccta gactgactgg    4740
actttatact ctcatgaaat cctgagtttt agttttttg gtttcagaaa ttatttattg     4800
agtaaagagg actggttagg aactgagatg taggttttgg tcttggctgg tcagactgtg    4860
acctcgctgg ccatcatttc cacatctgtg aaacagagga gttgggctga actctagact    4920
ttgtctagct ctaaattaat ttaactctaa ggctcttgtg tccattaggg cgagtttcta    4980
acttggcaaa tgcacattat catacctatc atactaaccc catctactgg tagaaagatt    5040
aatcttgccc aacacagtgt atcttacaaa ttgcgtgtac tacttgttct gctgctagga    5100
acttacttaa ttcagccttt tatagtgaga catttaattg ttcacagccc tcacaaatga    5160 actatttaa atgtgcatgc tatggtgaaa tatgtgtagg gactgggtac aggttggagg     5220
caatggagga gactaattag cagatggggt aagtagttac tggtaaattc aagaactaga    5280
aattcggccg ggcgcggtgg ctcacgcctg taatcccagc actttgggag gccgaggcgg    5340
gcggatcacg aggtcaggag atcgagacca tcccggctaa aacggtgaaa ccccgtctct    5400
actaaaaata caaaaaatta gccgggcgta gtggcgggcg cctgtagtcc cagctacttg    5460
ggaggctgag gcaggagaat ggcgtgaacc cgggaggcgg agcttgcagt gagccgagat    5520
tgcgccactg cactccagcc tgggcgacag agcgagactc cgtctcaaaa aaaaaaaaaa    5580
aaaaaaaaaa aaaaagaac tagaaattca ggtctctcta cactcaggct aggggccttc     5640
ccacagccct atgactcatt cattcattat ttgtgaaatc tttaaaaaaa tccgtatttt    5700 attttaaaa tagaaaatac attcacatgg cttaaaaact aaaagctgc aaaagggctt      5760 acagtgaaaa tctaccaaaa cacacacaca cacacacaca tacacacact tccttagaca    5820
ttcagttcct atgtttgtag acaaataatg ctctgaatta tatattttta tatatcattt    5880
ctctcttttt tctgtatgaa tggtaacata ctcttcacac tgatctgcag ctccattttt    5940
gtttgtttgt ttttacttaa catttgcaat cattccattt tgttgactaa agattatcct    6000
cacagctttt agggctgcat aatatttttgt taaatggata cattgtagtt tatttagcca   6060
gttgcatact gatgaacatg taggttgttt ccagcctttt gatatatcaa agaatggtga    6120
agtgaatact ttgcacatat gtcattttgt acatattgga acgtatatga aggataagtt    6180
cctagaaatg gaattttctg ggtttaagga tagatgcatt tgtaattttg ataaatattg    6240
caaaattgca tcttaaggga ttgtaccaat ttacattccc actggcaata ttaagttata    6300
gttcacatcc tatataattt accattttaa agtatccaat tcaatggttt tttgtacatt    6360
cacaaggttg tgtaaccaat attttcatca cctcagaaag aaaccactca actattagca    6420
gtcactcttc atttcctcat tccaccagcc cttggaaacc accagccttc ttattatcta    6480
tgtgacttta cctatttgg acatttcata taaatggaat acaatagatg tcctttcatc     6540
tatgttgtag catgtattgt tcccttttat ggctcaataa tattccatga tatggacatg    6600
ccacattttg ttcatacatt catcaattca tggacattag gttgtttgcg ctttttggct    6660
attatgaata atgctgctgt gaacatccat gtacaagttt ttgtatcagc atatttttta    6720
agttcttttg ggttaatatg taggagtgaa acgccgtatt gttgcaggac ttctccttag    6780
ttcagctaac gatgaggtcc ttgtctgtcc catggccatg aaaattcagg ctcgcagatg    6840
gtttgaaggg tgagtaaagc aggggtttat tgggtgaaaa ggaaaaaagg gggaacagg     6900 gacccactga aaggtcagag tccctgctac agtgcttccc tcattgcccg tttgaatccc    6960
```

```
aggtgccata ggaagaggag aggccaggcg ccacctccgt ggctccaccc cagtgcacag    7020
tccagctgga gttttgccag ggacccctc ccacctggct gtcttagtat catgtggtaa     7080
ctctatgttt aactctttga ggaattggaa attgttttcc acagcagcta taccacgtta    7140
tatttccact agcaacgtat gtgggtttta gcgtctccac atccttgcca acacttgtca    7200 ttatctttt gattatagcc ttcaagtcat cctagtgagt aggaagtggt atttaattgt     7260
agttttgatt ttcatttccc taatgactaa tgatgttgaa catcttttaa tgtcttattg    7320 atcatttta tgtcttcttt ggagaaatgt ttactcagat cctttgcctg ttttaaaatt     7380
gggtaattta tcttctcatt cttgagttgt aagatttctt tatgtattct ggatactatt    7440
aaataaaccc ttactagata gattatttgc aaatattttc tcccattctg tggattgctt    7500
tttactttcc tgatagtgtc ctttgatgta acaaaagtt acaaatttt atgtacaact      7560 tacctatttt tctttggttg cttatattgt tggtaccatg tctaagaaac cattttctaa    7620
tccaagatta tgaagattta cctctatgtt ttatagtatt ttatagtttt cagttttac    7680 atttaggtct ttgatccatt tggagttcat ttttatgtac aatttgaggt atgtggatgc    7740
atgtaggtgt ccaaatattt cagtgctatt tgttgaaaag agtgttcttt cctcattgca    7800 cccttgcac ccttgtcaag actcaattga ccatagacgt atgacttaca attctattcc     7860
attgatctac atgcctatcc ttatgccagt gcctcactgt cttgattgct gtagctttgt    7920
attacaaagg tttcagaatt agaaaatgca agtcttccaa ttttgttatt cttttcgag    7980 atagtttggc tattctcggc cccttgcatt tccacataaa ttttaggatc aacttgtaca    8040
tttctattaa aaaaagga agtggaattt tggtagacag ggatttcagt gatctgtaaa     8100
actatttgga gagtattact acctcaacaa tataactctt ccaatttaag aatatgagat    8160
gtctttctgt ttatttagag ggttttttt tttttttta agacagagtc tcactctgct      8220
ctgttgccca ggctggagca cagtgttggc tcactataac ctctgcctca tgggttcaaa    8280
caattctcct gcctcagcct cctgagtagc tgggactata ggcacccacc accacgccta    8340
cctagttttt gtatttttaa tagagatggg gtttcaccat gttggccagg ctggtcttga    8400
actcctgacc tcaaatgatc cacctgcctt ggcctcccaa agtgttggga ttatagacgt    8460
gagccaccac acccagccta tttaggtctt ctttaatttc tttcaacaat attttataat    8520
ttttagtgtg taagcattgt gctttggtta aatttattcc tgttttacta ttttcagtgg    8580
tattgtaaat ggacttcctt tcttaatttt attttcagta gttcattgct gttacataga    8640
aatgcaactg atatatgtac attgatcatt ttgcaacctt aatgaacttg ttagccctaa    8700
ttgtgtgtgt gtgtataatc tttagagttt tttagtgcaa gatcatgtca tctgcaagta    8760
gaagaagttt tacttcctcc tttctaatct agatacctt tatttcattg tcttgcctaa     8820
ttaccctgga taggacctcc agtgcaatat tgagtagaag tggcatgagt ggacatactt    8880
gtcttgtttc caatcttaga ggggaagctt tcagtcgatc accattaagt gtgatatatt    8940
cattcattct ttcattcaac aaatgtttac tgagcagcaa gttacgccac tgtactctgg    9000
gaatctcttg gtgcttataa tctgaagggg gtgaggtaag gagaaggagt aaccaagagg    9060
gaagtgaaat aaatacaaac aggccaggcg tggtggctca cgtctgtaat cccagcactt    9120
tgggaggccg aggcaggcgg atccctgag gtcaggagtt tgagaccagc ctggccaaca    9180
tggtgaaacc ctgtctctac taaaaataca aaaattagcc aggtatgatg gtgcgcacct    9240
gtaatcccag ctactcatga ggctgaggcg ggagaattgc ttgaacccgg gagacggaga    9300
```

```
ttgcagtgag ccgagattgc gccactgcac tccagcctga gcaacagagc aagactccat   9360
ctcgcggggg ggaagtgggg aaagaaagaa atacaaacaa gtaaggtgaa tttaaatagc   9420
atgacaatac atgtggagaa gaaaataaag taggtcaagt gatcttgact caggaaggtg   9480
tcttcaagga ggtagtatga gcagaggcct gaatgaaggg agtcagccat gcacatatcc   9540
tagcaaagtt taacgtggag gaaggagcaa cagaagcaaa gctcttgagg ctggaacgag   9600
cttgttgtaa gaatgagatg gtagctgagt gaatgagggt gccagaggca ggccaagagc   9660
tagaggaggg aggctgggtc tccctgggtt taatgctgcc cacccattaa aaagtgttaa   9720
aacttgaact ttttttgtgt cagtttttat agtaaggtga cattgaggct attatacact   9780
aaagaacatt tcgaatctaa cagtgttcta aatgggcata ttttaaggaa atacagtcaa   9840
gtgccatgtg gcattctttg gatgcatgta attccaatta gaattaattg tacatattct   9900 ctcttttttct ttaaaagaaa taagcttggc tgggcgcagt ggctcatgcc tgtaatccca   9960
gcaatttggg aggcctaggt gggtggatca ctggagtcca ggagttcgag agcagcctcg   10020
gtgaaattcc atctctataa aaagttaaaa aattaaccaa gtgtggtggt aagcgcctgt   10080
agtcccagct acacaggaga ctgaggttga gacccggggg caggggggta gatggcggga   10140
aatcgcttga gcctggggag gcagagtttg cagtgagcca ggatggtgcc actgcactcc   10200
agtccaggtg acagagtgag actctgtctc aaaaaaaaaa aaaaaaaaaa aaaaagtag   10260 cctgttttta aaatcatctc caggaaatac attcaaaacc ttcaaatata aagatgtaa   10320 aaaatataaa catgtagatg aggatctttt cagcctgtct ccccaccctc cttcccatag   10380
gcagctcctg tttattggtt tcttgatatc gcttggaggc atgttatgca tatgagaaaa   10440
tcgattttat atttatttttt cccttgttta aaacctcaag attaaaaata ttaatttaaa   10500
aattctccag cttttctaat agaatttgtg tactgcattt agttcaaata gaaaacttaa   10560
tattactaat tttccatatt cttacaaatt gactttattc tatacaaaat attcattata   10620
cctttgttat tcctaataca tatttttaatt gtgataagtg gttctgaggt ctgacttctc   10680
cattagattg ccttgtctgt tctctgggcta aagaagcact cagtgttgga caattaaatg   10740
atcaaatgtg agaagcactt ttacacagtt cgtgaaagag ctcaccatct taattaaact   10800
gcttgaaatt gccatgtcat ttctaatgcc tttacttctt ttttaagaaa ttgaaaagat   10860
taaagagtaa gaaagtgata ggccttaaag gaaaacactc ttctgggaaa atagttaaga   10920
aaagtaactc tggtcctcaa ctgggaatgt ccttaccttg ggtaccaagg gggccactcc   10980
accagaactc cataaaacctt ggcacagaat agaagcaatg aaagatgact ccaaggtttc   11040
attcttaagg gatccaaacc acattttttct taatcacact gataaatgga caagacattt   11100
tcacggcttt tcactcaccc ctgaggcgga accttggaca ggaaatatag gaaggaggct   11160
gtgctggagc atcgtgggta atttttgact tttgcttcaa gtttgcttca agaaggtgag   11220
caggaaagat gcatgctgca ggcagaagag ggcatggtgg tgcaggcgct ctgcctgagc   11280
atgccctccc tttcctgctt cttgtcctcc tcgccctcac tgtcctgcct gctcctcgcc   11340
tgctggcctc tcagtggact cctgccagtg gtcgcctctc cctggacttt gaggttcaga   11400
agtggggcac aggagagtgc agagctgaa gaaatgttta cagggtgcag ggattgggga   11460
aagtgcatgt ctcaaggtgg gcgctcctag gatcccctgg caaaggcaca ggaggaggga   11520
gctgtcagag gaccatgtag ccttgagacc atgggtgcct cctaagagaa aacagtgtct   11580
ttatttctgt gctcctttag ggggagaaac aaaggatgca ttagctccat agggacaagc   11640
aagatggcct cactaaagca cagcagagcc ctggggtgac tttcatgggt ttgctaaagc   11700
```

```
caggtgtcct tcctaagcct agccaaatcc aagagacatt ttcccaggag ggaaggggag    11760
tgcggaggcc tcattctgca aacattgcag ctattttaaa gaaacaattc cagattttat    11820
atcttttacc tgccaggaaa ttgcaaatga ggaaataagg aaataagttt ggagctaagt    11880
ggaatatgac cagtggagtt agaggatttt ctggttgctt gatttacgag gtttgtcatt    11940
tcaggaatca ctttgagcat aagctgttgc tctctggtca ttatcttttg tttgcgtttc    12000
cttaatcata tcacctttg agagattcct ttccctcagc tttcttcata ttttccttcc    12060
ttttccattt gggctttctt tggaattata atttaaacag agggaggcac tgaaaccctt    12120
tctgacttgt ttattctttt ttacaaacaa catcccttg tgggtttagt cagagatttg    12180
cactcttcac taatcaacac caaaataaat agactcttaa aactgtcagt gacacgggcc    12240
agttctgcag cccgagtcct gaagggccaa gccagatggc aaagccaggc ccctagcaca    12300
cataatgcgt gtctgtaggc tcttggcttc agcagcatgg gcagctgact gcttttcaga    12360
tggcttctgt ggggagggag cagattttcc actatccatt tgttctttgg gcatctccag    12420
gaataaaccc taaggtggca caagtgttac ttgaccgtga ttaaaacctg ctgtgtactg    12480
gccgaggcac aggctagaaa ttctgaactc ctgcttgcc accagcatgt tctgtgattg    12540
cgttctgatc atgaagcttc ccataggctc tctggtgtat aaggtggagg ggtagagtgg    12600 cccattttc tgaattttta agtactgcag caggaggtat tgcacacata tgtgggcaca    12660
tgaggatatg agttcatttt gctcagacca gactgactgg acagaacctc ccttctgttc    12720
aacgggatat tatctcaaca ctgttgaggt gaggagagaa agagcatcta tcgccttctg    12780
tgcagcagtg gtttgcttcg ctcttgggag agtttgagtg tagctgaaat attgtgctct    12840
gaactcccat atagataact aatcaattga ctgtctggac ctctgaaagg ggagttgaaa    12900
gagattctga tatgggagct gccatcttcc tctcccccag caagagattg gattttctcc    12960
tttaagctca tgagactata ctgcaaggaa ctcctaggtg tgcagaagac agaataacac    13020
actggaccaa ataaattgtt acgtgcaacc aatatgtaaa taaggatctc tcagttatgt    13080
cacagaaaga gcctagaaca agccaggtcc tccactggat ttgcagacct tttgcctttg    13140
tggagaggat ttttgatggt caagtaaaat cttaggagaa gttgtttttt gagagaagat    13200
ttggtttaat gaagaggaga cagccacaca tggtagatag ggaagtaacc ccttggactt    13260
tcgtatatta catgtagaac cttctccatt cacacacact tctttggaca ttgcagatgg    13320
gtgttagaat gaaattgttt tatattctgt tgtgtttatc agggcaccct tattttttc    13380 ttttgattcc tattggtgcc cggttgcctt cctgcccctt gcagcatggc gtggctctgt    13440
agttctgtgc tgaagtgctg ggttggaacc agttcggcat ttgcctgttt actgcttctc    13500
tacacattac agcttcctc cttcagatag tgtttgaaca gaccgaaaac atgttttgg    13560 atgtcatcca gggtttggct tctgcttccc aataatgcca taaaaatgct ctgtcaaata    13620
aattctcagg aactgaaaag aacacattcc ctgctccata tgattgtcag taatggagga    13680
aggcttcagc tgaccacctg gcttggtgcc cacggcttag gaaaaccaaa tcacacaaca    13740
tctcttggca gtgctttcta gcaatcagaa ttaattctct gcatgtgatg gatgagcttt    13800
ccatttaagg gaattttcgc agagcattta tctccactgg ggcttttgga ttccataaaa    13860
tattatcttt acttatcctg cctggttgcc aattagcata ctatatgcta tgaagttttt    13920
gagtcctagg gtcaatttc tcttcagtaa gcttccagag ttaaccatgg aaagaatact    13980
ttgatttggg gtgtgtgtgt gtgtgtgtgt gtgtgtgtac gtatgcgtgc aaatgtgcta    14040
```

```
agaggaatgc ttcccttcc cagcctggat attataacat ccttatcatt cagggtccca   14100
gctggaaaga ggtggcacat tcaaattagg gagggtttat ttacaaaggg accatttaa   14160
aaggtgtgaa tgtgtggggc aaaatgctag ggatagtgta gtaatccagt ggagctgtta   14220
ctactcctag accagaagag aagaaaggaa gggccaatta ccagaaccta aaggagaga   14280
ggcagataga gaaagaagtc tgcttccaga gtgacctttg gtagagagac tcatgtagcc   14340
aggctaagca gcgtgtcagg tgaggccatg cactctcctc tttccctctc actcctgcca   14400
gggctcccca ttggctaagc ccaatcagaa acctgaagac aagtgtcctt tgacttgatc   14460
ctcataggtc agcctcctag ggcagagagc aggactgaga aagcagcgtg gatttgaagg   14520
gcaaacagaa ggtatctgac acatctccca atgtagatag gtgtctaatt atttctagga   14580
gaggcataac aatctcagta ggaaacttaa actcactttt atttttaaac agttttattg   14640
agatatgatt gacatacaat gaactgtaca cacttcaagt atacaattcg ataaactttg   14700
ataggtatat acctgtgaaa ccatcaccac atcaagatag tgaacttaac tatcatcctc   14760
aagataaacc cactttaact taaacacttaa gatattccat gtggttcttt taggaggatg   14820
tggaaagaga tcatgcagta aagcaatagc aggtgcaatt cctaacttac taaagttatt   14880
gaagttagtg agttactgaa tgaagttact gcccggggtt acaaagctca taagtgataa   14940
agccaggatg ggatttaatc ctctgagcct tatgctattc cacttaaat tataaggcaa   15000
ataaatact cacaaacact tataaaatc atttgttagc aacaagtttc ttgctctcca   15060
ccttatagct gatgaaggga ccagccgtgg cctgggttga gaactggcac tcttacctcc   15120
tgtgtcccca gagcctgttt attctataaa tcaagagctc ccagggctgg ggaaggctgg   15180
tgtctggtgc agagttgaat ttgagacccc agtcccactt tctacaaaga agagcatctc   15240
cctggctaag ccaggacaag gaggcaggag gtgttaagtt ttagggaagg gtgggactgg   15300
gtagacaagg agggataccc tgtcatgccg cagcaggggc tacagtggca cccaccagca   15360
caagagctgt gacagggcca aactgggttc tgggcgggcc ttttgaactt gtctagtaag   15420
ctcaggtctc agggcctttg aagtttttat tccttaggtc tggattgctc ttaccccgga   15480
tttctccaag tctcactgcc tcactttatt ctggtcactg ctcaaatatc tcctcttcag   15540
aaaaggtttc tttctttctt tctcttttg agacagggtc ttgctctgtt gcccaggctg   15600
gagtgcagtg cagtggtatg atcacagctc actgcagcct cgacctccca ggctcaagtg   15660
atcctcccac ctcagtctcc ttggtagctg ggactacagg cacaggccac catgccttgc   15720
taatttttc tatttttatt tttagtagag atgagatcat ggcatgttgc ccaggctggt   15780
ctggaattcc tggagtcaag ctagcctcct gccttagcct cccaaagtgt tgggattgta   15840
gggataagcc accccgcctg gcccagagaa gctttctttt gccactctat cacaagtgcc   15900
acctctgtca ctgtctccct ctccttcttt acttttcctc atggcaatga tcactgttgg   15960
acattagagt atcagttctc aaactttttg gtcttagggt tttgcacttg cttaaaaatt   16020
attgaggacc ccagggagca tagatttaaa tgggttgtta ccattcaaaa tttgccccat   16080
aagttaaaac aaattataaa tttttttatt caatgaaaaa tagtaataaa cccactatat   16140
taacataaat aacttatgaa aaaagctcta tttttcaaaa ccaaatagtt aagtgagaag   16200
aatggcattg ttttatattt tttgtacatc ttttctacta atagaagttt gctaggttgt   16260
tgtatctgct tctgcattta acctgttatg atatattatt tttagtaaaa gttgaagaaa   16320
aatctggccc cacaaagatg tgtagttgga aagggaggg ctattttaat atcctttca   16380
tataattgtg ggtattctac tcaatattac accaaaagtt aagaagtggt cattgcttaa   16440
```

```
agtttagttg ctgtatggac cttatgccct gggcatactt gtgtgagcca ctcccaagca   16500
gcagtcagat ggccgctttt tataagaaaa agttgaacac tctctttga gataatgatt    16560 tacataaagt agaataaaaa atgcaataat cgttttatta tactgttaaa taactcagcc   16620
aggcacggtg gcttaagcct gtaatcccaa cacattggga ggccaaggca ggcagatcac   16680
ctgaggtcag gagttcgaga ccagcctggc caacatggtg aaaccccgtc tctactaaaa   16740
atacaaataa attagttagg tatggtggtg ggcgcctgta atcccagcta ctcaggaggc   16800
tgaggcagga gaatcacttg aacctgggag gtggaggttg caatgagcca agattgcgcc   16860
attgcactcc agcctgggca acaagagtga actccatct caaacaaaa acaaaaacaa     16920 aaccacttgt aaaaaaatca ccaagttttc gaagattaca gaagtgtctt ctaatcaaac   16980
accaacttct tgtgtgccca aaattggaac gctttttct tgttagattc acaccacata    17040
ttattgctac ttttttgag gcaaaagta acaagttaat ggtttctaac atagtgcctt     17100
gataaatatt gaaatatct gttcgttgga atggttttat ttgtctttca aatcctgttt    17160
atgtccacta cttcatttga ataagagaat tctgcctttc agaaatatcc tcaagccagt   17220
acaggaatag agttaaacat ccaagtcaac agatatgatc agtaaggtag aaggccattt   17280
tatctgcttg ttcacaatat ttcaatgtca ttaatctata attttatgtt tatctctgta   17340
agatccgtac aggtttacag caccaaataa tctggccctg tcagcccagc tgtgttcctc   17400
tggatgaaaa actcctgccc cagctcctaa aagaagcagg ttatactacc catatggtcg   17460
gaaaatggca cctgggaatg taccggaaag aatgccttcc aacccgccga ggatttgata   17520
cctactttgg taatggaaat gcacatgttt ctttaacaac ttagactaac tgcagccatc   17580
tcataaaaca cacccaagtg caatcaaatg aaagaactgg atatttgaac acagagtgaa   17640
tcagtcggca ctgtaatggg gctgctttct aatgttacct ctgtaaacag gctctgtgc    17700 tgaccttatg gtgggcaaac ccattacctt tgttggagtt ctaaatgcca ccttagggcc   17760
ttgcaagagt ttactatcca cgttggagac cgctgtactc tcagagaccc ttattaccaa   17820
aaagggatat ggattgattt tttatttttt taatgcctgg caaaacctaa tgtaagaata   17880
tttccaggct gggtgcggtg gctcacgcct gtaatcccag cactttggga ggccgaagca   17940
ggcggatcac gaggtcagga gatggagacc atcctgacta acacggtgaa actctgtctc   18000
tactaaaaat acaaaaaat taaccgggca tggtggcact tgcccatagt cccagctact    18060
caggaggctg aggcaggaga atgggcatga acccaggagg tggagcttgc agtgagccga   18120
gatcatgcca ctgcactcta gcctgggcaa cagagcaaga ctctgtctca aaataataa    18180 taataataat aataataata ataataaa taataataaa ataaaaatg aatatttcct      18240 tcacaaaggt ttggtgtgtt ttttctccc tgtggaatgt attcacaatt tttccttttt    18300
ttttgaaggg ggtgggggaa gactcttcca ttggcattct tccacctgtg aaatctgttt   18360
ttgcaatcac aaagttgggg aagataggtt ttaaaaaaca aaggaaaatg aggaggccaa   18420
ataaatggta ataagaagga taataagaaa taataataag tattttataa acttgatagc   18480
cctatgaaac taaatgtgaa acctagagtt tgttttaaaa tatgccctct ttaaacctgt   18540
aataacctgt gcctgaatta ataacctgtg tatcttgcca gtagctatat atctttcttt   18600
caagttcttt ttatagtgag ctatctgttt agctatttag ctacctacct acctcccatc   18660
tgttcattta tttatttaca accctccgta gccaaaaagg aacacatatt gaacatagaa   18720
agtttaaaca ggattaaata atcaggatga gtagaaaaag atggaatagg ttaatggcat   18780
```

```
caaattacag aaaagttgca tggctctagg ctgtcttcat attcatctct gatatttgaa    18840
atttctttt ttttttttt tatatacgga gtctcgctct gttgcccagg ctggagtgct     18900
gtgtcatgat ctcggctcac tgcaacctcc gcctcccggg ttcaagcagt tctcctgcct    18960
cagcctcctg agtagctggg attataggtg tgtgccacca cgctcagcta attttatat    19020
ttttagtaga datagggttt caccatgttg gtcaggctgg tctcgaactc ctgacctcgt    19080
gacccaccca tcttggcctc ccaaagtgct gggattacag gtgtgagcca ccgcgcccag    19140
cctgagattt gaaatttatt tgtccgaaga gggagaaaga aaggaaaaga ctataagagt    19200
tacattattt acaagataaa tggaaaccag atgttcagga aaagcaaaag cattttctgg    19260
ctcttaggcc tgacagaaat ttctccttg ggagaaggag aaggtaaggt ggacaacatc    19320
tttaaaaatg tcattttaat aatacgttag gtggttttct tgtagatgtt ttgaggtatt    19380
ttcttctgtt caagctaggg ccagagcacc aaagtgcaat tcagtaaaag taattatatg    19440
ggggccaaaa caatgcagct gaagcacatg gctctgtaat gcctcattgg attcagggtt    19500
aaaatcaaga tgcaaggatg tcagacagga gggtgtgtgt gccccactct catccaggtc    19560
caccagcaga cctcactact caatcttagc ttttttttt tttttttaa atggacccgg    19620
atgtattctc agtacctcaa atagctgtta aaattagact tgatgtaaga tcactttgtc    19680
atcttggaaa ttctagagga gcaaacagcc tgtacatcct tagaaatttt tcaatcaggc    19740
ctttgctaaa agatgagtca atatctatac tctgggaaga ggatgggctg tagatatttt    19800
gaattgttta ttaaaaccaa gttaggtact taaaaattca gctggacaga aggtagaaat    19860
gatatccttt tatgagaatt aagaagccta acctggattt agatgaacac acaccccaaa    19920
ttcatttgaa gggagacttg cagccaagaa ggttatgatg accacacagc tcttctcact    19980
gttacatctc agctcttttg ctaaaaatca ggtgatggtg ggatagttgc acaagcctgt    20040
gaatacacta gaaaccaatg tcttttacac tttaaatgag tgacttgtgt ggtatgtgaa    20100
ttatatctca atgcagctgg tacataaagc atcagagaag atttggttgt tcaagaagca    20160
ttttctattt ttttcccca aaagcatagg ctgccatcat ctttaggctc agtattgaag    20220
ttcaaatttg tgaatcatta ttatgaagaa aagcttcatg tgattgtcac atggttgctt    20280
ggtattagtt ttgccaagta tgtgaatagt tttatttctg gaattctcct atctgtatta    20340
tcttttaaat atttgtagtt catgccttg ctaatgaagt gtatctgtcc tatattctgc    20400
taactgatag aaagcagctc acacttaaca gttaaagaac ctgaagtgat ttcctcaagc    20460
tttaatgccc agtagttatt aaaaacctta aatagacctc cagtgttctg acattctaat    20520
cacccatgta agggctgaaa ttattttat ggatacattt cttctctgt tacacattaa    20580
ttaacaagta ctttgtattt cgttttccat tatatacata ggagaaaaga ttgccatata    20640
aaagttattt taagaccaaa gtattaattg tattcaagat cttgaattta ttgagtcata    20700
gaaaggaga atttaattta aaatgaattg atttattata taaactatgt aaagctctta    20760
attttcatta tagggaaagt tcaggactga agaaagagct aggtcaattt tatcatcctc    20820
attttaaggt taataagcag tatatgtcag gagatagcta agagtctagc aaatatttct    20880
ttttaataac tttatcaaag tataattcac atatcataca attcacccaa ttaaagtgta    20940
caattcaatg attttaata aattcagaag gttgtgccac tatcatggca atccaattgt    21000
agaacatttt tatcatcccc aaaaaagaaa ctcatccacc tcagcaatca ctccccattt    21060
cccctagtc cctccagccc taggcagcca ctaatctatt ttctgtctct atagatttac    21120
atgttgtggg catttaatac aagtggaatc atacgtagca cagcttattt taatacttta    21180
```

```
aaatatagaa atataatatt ttaaaatata gaaaagatgg aacatttgca gaaacaacta   21240
tatttgagaa aacccatttt cttccatgtg aagtctaaat tatgggatag gccgttgatg   21300
ccatttaaat ctggggtgaa attgagatca ttttaggtag aaaagtctta tttcagtgct   21360
cactttagtt tgatctgttg gctctgttat gtctagagat cctctattag gaaaggtttg   21420
tatctttcac cagtgggtgt cagcatctga ctaaagatga ctcttcctag aaccacttct   21480
gtaaataacc ttgaagccag tctcgcaaca tcagtaacaa caaacattgt ttgaatcctg   21540
cactcattta tgtgatcacc ttagagtaaa aacctgtaac aagtcacatt aactgtacat   21600
tattttacc attatatagc tttgaaggat tgagatttta tcacccttac tgagtttcaa   21660
ctctgataaa aaaaaaaact gttagtgtta catgatagcg cctatattct aaaggcgaat   21720
gaggaataga tttgagtttt tatgcagtaa tgttttaatg ccttctgcca ccagatatag   21780
acatgttgag aaatggtgct gattagcctt gtcatttgat tagcctcgtc acgggtaatc   21840
aattgcatta ggcaattaaa tgctgaaaca ttagtttgtt taacaagttt tatgctatgc   21900
tgactatttt cgtcttccat tcttgcagga tatctcctgg gtagtgaaga ttattattcc   21960
catgaacgct gtacattaat tgacgctctg aatgtcacac gatgtgctct tgattttcga   22020
gatggcgaag aagttgcaac aggatataaa aatatgtatt caacaaacat attcaccaaa   22080
agggctatag ccctcataac taaccatcca ccagagaagg taagttttgc ttctatttac   22140
tgatagcaaa atcttgttac actaatgtct tttcagacaa atgtaggaaa aggccattgt   22200
tgtttaggga aaaatctaat aaattctagg gaagtccttt tcaaattata cagtatccca   22260
gaatcagcct gggaagcttg ttaaaaagga agattcctgg agcccacctc tagggtgtga   22320
tttattaggc gtgggagaaa tccgtacatc agcattttag agaaactctt aaaaggtgat   22380
tcttaagagt ggtccccaga tcacactttg aggaatacta tgttggtagt atttcaatag   22440
aaatatagtt taaaatttt ggtatattac gtgcatgtgc tgtgagtaat taataaaatg   22500
acttaaaaaa tgattggctt aggtgtaagg tgaggcttta ttatgacaaa cttttggtta   22560
agggatccat aaattttggg atcagggcag ttcctctaac cttgtacttc ctccctacaa   22620
gaatattttg ctattctaga tcttttgcat ttccatgtta attttagaat catctagtca   22680
atttctatat gccagctccc ccctgcccaa agtgtctgct tggatttata tttgaaacta   22740
tagaacaact tggggagaat ggatgtctta acaatattgg gtcttctaat ccatatacct   22800
ggtataccaa tgagcttatt tttcacattt actatactga tgcttttgtg taacacatga   22860
ataatcttat tattatgatt attttgttaa cctagagtta acttcatgag gtaaagttta   22920
agctaagttc tctggattta gcttataaat gcttttgaaa tgggaacaaa tatttgtatt   22980
gtcagacact gggctcaaaa tatggcttca ttaagaacac ccataaaaat aatacttcag   23040
tgggaccctg acacaacaaa ttatagaata tgcagtgctc cctggttctt ccaatttcct   23100
gcactttgcc tctttgacaa tgcctgaagg tccttggtgc aggtctgtct tagtctgttt   23160
gtgttgctat aaaggaatag ctgaggctgg gtaatttata aagaaaagag gtttatttgg   23220
ctcgtggtgc tgcagactct acaagaagca tggcaccagc atttgcttct gggtaagggc   23280
ttcaggaagc ttccagtcat aatggaaggt gaagttgagc tggcgtgtgc agatcacatg   23340
gcaggagagg agagagagag agatgccagg ctctttctaa caaccagccc tctcaggaac   23400
taatacagtg agaacttata actgcaaaga tggcatgaag ccattcgtga gggatccacc   23460
tccatgaccc agacagctgc cattaggctc ccactgggga tcaaatttaa acatgaggtt   23520
```

```
tggaggaggg tcaaatatct aaactataag aagatcaccg tgtggattct ggtttacata   23580
cctgtttgga cttggtatgt ggctgctggt tccccttcca gtttctgcct gtttgaactc   23640
agtattggaa atcttccctg aatgagttaa atgccagatt gctggcatcc ttatttgact   23700
tccacaagct aaggtaaaat cttccagaag acaactttac ctcgaacttc aaattatatt   23760
tacactatca aatgttatac aactcctgac attcattaaa aataataga aaccccgtct    23820 ctactaaaaa tacaaaaaaa attagccggg tgcagtggtg ggtgcctgta gtccagctac   23880
tctggaggtt gaggcaggag aatggcgtga acccgggagg cggagcttgc agtgagccga   23940
gatcgcacca ctacactcca gcctgggcga cagagcaaga ctccgtctca aaaaaaaaa   24000 aaaaaaaaa tcgagcacat gtagaagtga aaacacagat agaggtgtct gtcctcagct   24060
gcgtcccact tttggcgatc actctcctat gctgatatct tgaagcaacc atgctttctg   24120
tggaacacga agaaatggga acattctctc aaatatgtgg aaatacacag attttaaatt   24180
taaatctaaa caaatattca gataattgga aaaatagttg ctaggtaatt ggcttaaatc   24240
ctcagttttc ttctacatat ttgacatttt atggatgcac cttaacactt aacaaggtaa   24300
agtcttaaga gaactgtgta ttattctttg agggagccac cattttacac ataagcaaac   24360
tggcttagag aagttaagta acttgttcaa ggtcacagag ctattgagag tcagaatcag   24420
aatttaaact catgctctct gactccagac ctcatgtact taatcagcct ccctagttca   24480
cagctaatat ccaagaccag agattctgag tcccagctca tgattcacct taatgatttc   24540
agtcctgacc atatattaga atcatctggg aaacttataa gaaatactga tgccaaatat   24600
tgtgattcat tggtctgagg tgggacccaa tcattggtgt ttcattattc ctcctcctgg   24660
gctcctacca gtgattctaa tgtgcagtca tcactgacac ctggtgcagt gacagccatt   24720
ctcggatggg tcattcaggg cattcctctc aaatatggag aggcaagcag aagccagcta   24780
cctattacag gttcacaatc tgccatacct taatctgtgc aacaactgta atctgcccac   24840
aatacaaatt cattcctact gaagaacgat ggaatattcc ctcacagggt tccataacat   24900
taagcagata agaggaagca actggagtga aataatagat cttttgtgggt gggctctctt   24960 aactagggtg gtgggaaaa cacggaactg aggacaatag gaggccctaa aagcttgcta   25020
gccatggaag gagtgttatt accatagccg ctgttcgtag gtaactgttt ggaaattgcc   25080
agatgagagg atggtcattt tcctattgtg tctgaaacat gctatagcag tatccagcat   25140
tcccagtatc ttcaaaggaa agtttcagtc atagacataa gtgaatgaaa taatcaatag   25200
tcaagctgta acccaagaat gtttaagaca gctaatacat gtttacattt tcaattctgt   25260
ataaaatgat gcaactcacc agtttgagga gctgagcttt tcacgatttt atcccgatgt   25320
tgaatctaat tctgggctaa tttctcaggt actatatata gattgtagca taaggaactt   25380
gttctaagat aaaaatcatt aaagaaagcc acatgaagaa tccacaggct aacttaaaat   25440
tgtgcctatt ttaaaaagca cttaagagga aaaagcatt tggaggcagt tcataactga   25500
aacacagttg ctgatgctgg actcaggaag gtactgctaa ttaccatttc acatatgtta   25560
agaaggaacc ttctttctct ttttcagcag gataattccc catactagtg acactacaga   25620
ctgaaagtaa catattcata aaatatcttt cttttaaaaa cagccccccg tcagccgggt   25680
gcactggccc acacctgtaa tcccagcact ttgggaggcc gaggcgggtg gattgtgagg   25740
ttaggagttt gagaccaccc tgaccaacat agttaaaccc catctctact aaaaatacaa   25800
aaattagcca ggcctggtgg catgcacctg taatcccagc tagtcaggag gctgaggcag   25860
gagaatcgct tgaacccggg aggaagagtt gcagtgagcc aagctcgtgc cactgaactc   25920
```

```
cagcctgggt gacagagcaa gactccatct caagaaaaac aaacaaaaaa acaccccat    25980
gtcagcactt tgcagaatgg aagcaaatgt aatgttatac acctgatcta ctagaagctt   26040
cttaaagaaa atgttaattt ctagtggaag actcttactt ttctgtgaca caatttggaa   26100
aagaatgtct taatttagaa gtcaaagaaa aacaatttca aaacctatca tatgcttttt   26160
ttttcattta tactttaaat taggagaata cactaaagaa atgaaaataa gactttcttc   26220
ctcactgaaa taagttttct tagcatggtg aggatattta cagtatatat cttaggaacc   26280
atgtagcata aataaaggga aaagaacccc caatatctca aacatgaata tgctaatagc   26340
tctaggtgat aatgtcttgc ttttatgtaa tacttagata tttagtaatg atttcatgcc   26400
taggatttca tttcacattc ccaagacact ggaaagggtt acaggtaggg ttggagctaa   26460
ggcagtaact gtgacagttg atgagaacag ggatctggac ctaagaaaaa gcaggggaga   26520
gatcaggctc cagtgatggc agctgctggc tttaggctga cagtgagccg agctctggtt   26580
ggcaggagtg ggaaaattga ccacagctgt tcacaggcag ggtcctagga atagtggctg   26640
caggtggggt cctcactgtg attggagaac cttggagtcc tagttaattc attccactag   26700
gctaccatat agtattaaaa acactactct ttctcttttt tcaatttaaa aatagtatag   26760
aaatatttca catttactac tgttggggaa tgagttataa tatttcatga ataaagttca   26820
ccttctgagt gttgaaactt tattttttgt agtatgggat ggaaatatct aaaatgtgca   26880
tcagtcctga cctcttgaaa tgggctatag taccgacatg gactggtata gtttcttatt   26940
tttaacccct caagagtgtc aacttaaaat aatcaaaagg atcagaatct agtttaaaga   27000
gagtttattc aagtacagag tttaaggatg gcctcttggg aagcacagat tccaaagaat   27060
ggaagtccgt gtttcaaagt gtagaagttt gggatttctt actgtattag tccattctca   27120
cgctgttata aagaactgcc tgagttccac tggccctcca gtgagctgag ggttttttgca  27180
ggaaaaaaaa aaaagctgcc tgagactggg taatttataa aggaaagagg tttaattgac   27240
tcagttccac atggctgggg aggcctcagg aaacttacaa tggtgtggaa ggggaagcaa   27300
acaagtcttt cttcacgtgg cagcaggaga gagaagtgcc aagcaaaggg ggaaaagcgc   27360
cttataaaac cagcagacct tgtgagaact tattcactgt caagagaaca gtatgggggt   27420
aaccacccc atgattccat taactcccac tgggtccctc ccctgacaca tgggggattat  27480
gggaactaca attaaagatg aaatttgggt ggggacacag ccaaaccata tcacttacat   27540
agacaaaatt tagggagct taaaagaatt tcaacatctt tctgtacaag gcttaatgca    27600
taattacaat gatctgatta gtcaaggtgg tggttttctt ttgggaaagg tatgtttaac   27660
attccacact gaagatgtaa cagtcatggt gttttttggg tcatctggtc tgagttaggt   27720
acaggacaat aaaggaggtg gttaatctat aacaaagatc ttcaataaga aggggaggag   27780
tcctggtctc tggtctttcc tagttattta cagaagaaga acaataagga agagagttac   27840
tctataatct aagaaacaga agttgcaaac atgctacgtg acacagtctc caggacttaa   27900
tttttcccctt ggcataattt agagggtcct gaaaatttat attctttttat aaaagtgatg  27960
gtaatgtctt tagctactaa ggaataatta taggaaagat tttcagatta tttttcacca   28020
tatttaacaa agtgagtaga atgatttcta tactgaatat ttataagaac ctttaataat   28080
gatccccaaa tcttttttttc cctggtcatt gttcaagaac tcccctgtcc gccttcccag   28140
ccattgcctt tagtaatcaa ttgctggctg ggaatcacct accctctttc tcctttctct    28200
ccttcgccag gtggttgcca tgttgctgct aatgacctgg atgagaacat cttctcctta   28260
```

| | | | | | |
|---|---|---|---|---|---|
| agctgtgggc | ccctctctc | cccactgtat | ccctgcccc | ctgccactgt | taagagtcca | 28320 |
| gatcagagtc | acaaaatctc | gtgtttgcaa | gggccaggct | gctaacctaa | agaagtgaag | 28380 |
| cagtttatgt | agaacagtgg | gaaactagaa | aattggatag | catttgaggg | ggatggggcc | 28440 |
| cctgtttctc | atactccagc | cttttgttac | cagatggagt | gtggacaaag | agtagtcaga | 28500 |
| aattctgatt | tttccaaaaa | agttttttta | tataaaaaca | gatcgatgtg | atatttcctg | 28560 |
| atttttttta | aaactttacg | tgggctgcaa | attgttgtag | acttccgatt | tttaatccta | 28620 |
| tccccatctg | gaccttggct | ggtggctgga | gttggctcag | tctagtgctg | aagacccaga | 28680 |
| tagcagtacc | cagagcagac | ccatactgca | ctgtcaggtc | agcgatgcac | ctgcacgttc | 28740 |
| ttccctccag | acatcgcagc | caagaccttc | atcacccca | ggcagggcat | ctgttgggat | 28800 |
| gtcctgcacc | atggtctaca | cgaacataga | cgcttcagca | tgaccatgca | gctggagtag | 28860 |
| aaggtgtatg | tgtgtcgagt | ggaagcagag | gcagaactga | aatggtgtca | gaggttatag | 28920 |
| aatagacttt | tggagtggga | atttggaatg | ttttcccatg | gaaataatgg | aagtacgggt | 28980 |
| tctacattat | catcattttc | actccatcag | ctgcgtcctt | agtttaatag | gttttaaagc | 29040 |
| aacgactttg | acatttagca | gctatttta | actttgtgag | tttagggaaa | acgtatttct | 29100 |
| gagttccaaa | gacctgaaca | ataaataaac | ttttgggggg | tctatttgag | ctctatgtat | 29160 |
| ggatactcct | ttttgcatta | caaggatgtg | taatataaaa | tttaaaacaa | cttgtcaaca | 29220 |
| atgaagaatg | aaatatgagc | accacccccc | caccaaagtc | tgtttctaac | cattttcatt | 29280 |
| catttatgag | atttaaatgc | ctcaaatact | ttaacagaat | tatacgttta | tttttgggtt | 29340 |
| aaactagttg | ttgtctcttt | gaggcttttc | aactcattaa | agaattctgt | agcactatga | 29400 |
| agagaatgcc | ttcagaaagg | ctcattaaaa | aggagaagct | gacctggtat | gccactaatg | 29460 |
| ttaaatgttg | caaattgatg | taagtggtaa | atagaatca | gtgtgtcata | cttcttagtt | 29520 |
| tcaggaatta | aactggtctt | atgtttggtc | ctgcatcaaa | gactaacaag | gcatggtgtt | 29580 |
| cactttttt | ctcataaaat | atagtttaaa | aatactaaac | ctcttctaaa | agatgagggc | 29640 |
| ttatttcag | ctaaagcaaa | aagctaaagc | ctctattggt | acacatccat | atcgtaatag | 29700 |
| tgggttttcc | aataggaaat | tgctcttcgg | ttaatgtgga | gttggacaag | tcacacatat | 29760 |
| aaccttcta | agcctcagtt | aactcatctg | taaaattgct | gtaacatagg | gtggtttcat | 29820 |
| taaatgagat | agaatgtgta | aattattatc | atactgtcta | gtatgtagac | aacatttaat | 29880 |
| atgtggttgc | cattactgat | attattattt | gtttggatta | ggtccattga | ggccgttctg | 29940 |
| ggactctggc | ttttattttc | aattttttgt | cttgtgtctt | ttgttatatt | ttttaatatc | 30000 |
| tttattgaaa | caaaatttac | atatcataaa | attcactcat | ttaaagtata | cagttcaata | 30060 |
| gtaaattttc | agttatgcaa | ccataccaca | atctaagttt | aaaacatgtt | catcatcccc | 30120 |
| ccaaaaaaac | cttgtatctg | ttagcaatca | ctcaccattc | ctctccccca | caatttccta | 30180 |
| cagccccagg | caaccaccct | ctgtctctat | agatttgcct | atatttctgg | aatttcatat | 30240 |
| aaatgaaatt | acataatatg | aggactttta | cgattgactg | atttcactta | gtataatgtt | 30300 |
| ttcaaggttt | atctatgttg | tagtatgtat | caatacttta | tttcatttat | tgccatatgt | 30360 |
| tgctgaaaat | ataccatatt | ttgttttatcc | attcatcaat | tgatagatgt | ttgggttgtt | 30420 |
| tctactcttt | ggctattatg | aataatgttg | cagtgaatat | tcatggaagt | ttttgggtgg | 30480 |
| atgtatgctt | tgatttctct | aggaatggaa | atgctgggtc | atatggtaac | tctatgtttt | 30540 |
| acaatttcag | gaactgccaa | aatgtttctt | caaagtggct | atgtgtgcca | ttttacattc | 30600 |
| ctgctagtaa | tgaatgacag | ttccaatttc | tccatatcct | caccaatact | tgttctttc | 30660 |

```
cattttttaaa ttatcaccat cctaacagat gtgaagtgtt acctcattgt ggttttaatt    30720
tgcatcttaa taatgactga tgatgttgac tgtctttaca tgtgtttatt gccttttgtg    30780
tatcctctct ggagaaattg ctattcagat tctttgccca ttttgtagtt gagttatcat    30840
tgagttgtaa gggttcttta tatattctgg agatgagtcc cttatcatac atgtgattca    30900
caaatacttt caatgcattc tgtaggttgt cttgatatta ttttattaa tgcataaatc    30960 tgaactgtct tatccttcta tatttaatgc ttcaatatcc tcttaactgg tttgcacaaa    31020 cttttcttttcc agcctctgtt tctctacctt gctctccagt ctgtgcatga gccccttcag    31080
gtccctgagg aatacttgaa gccatatgac tttatccaag acaagaacag gcatcactat    31140
gcaggaatgg tgtcccttat ggatgaagca gtaggaaatg tcactgcagc tttaaaaagc    31200
agtgggctct ggaacaacac ggtgttcatc ttttctacag gtaagtctgt caataggaaa    31260
atcatctctt ggcaaagcct aggacatggt atttgataag tggaatgaag acaaattgga    31320
gcggttagca ttgccttatt aaaataaatg caaactgcaa tagtggagac atggtaattg    31380
tggatggaaa gatatatcta aggaaaaaga atgatgggct tccccccgttc cctcagatat    31440 caaaatattc tgggactgtg gcttgaaaac acatgttcac taactgagta agtatgagtg    31500
gacatcactc atatacaggg ctgctgggta gtgaatccct agagtggctt gttcccagct    31560
ctctctacaa cccagacatc ctctatggtc acaactccca ccaactagaa gggtctctgt    31620
atcactgcaa agagacagat tgtgacatta tgaagacaaa taatggagcc atttaaatct    31680
atgaaagtgt ctccaagttt agatttttt ggtattaaaa ttgttttttgg ggccgggcgc    31740 ggtggctcac gcctgtaatc ccagcacttt gggagaccga ggtgggtgga tcaactgagg    31800
tcaggagttc gagaccagcc tgaccaatat ggtgaaacct cttctctact aaaaatgcaa    31860
aaattagccg ggcatggtgg cgagtgcatg tagtcccagc tactcgggag gctgagacag    31920
gagaactgct tgaatccagg aggcagaggt tgcagtgagc cgaaactgtg ccactgcact    31980
ccagtctggg caacagagtg agactgtgtc tcaaaaaaaa tatttttttt ctgacagtaa    32040
aagttatata tgttattata gacaaattag aaaagggaga aataaaactc ataatctcag    32100
agattacttt tgaaaatcat tttcattatg gcgatgccat tctgtttcct aatctgttac    32160
atgtgcaact tcccctctc attagagacg gttttctgaa atttcactgt gatgtgcttt    32220
gggtgtagat catcatttat tcatcatgct gagtactcag agagcacttt caatctgaaa    32280
atgcagatcc ttttgttatg gggaattttc ttatatgatt tattttggaa ttgtgtggcc    32340
ctccgtccca ccttccccta ttttttctgt acagaactcc tattatttgg tcaccaggtc    32400
agtcctctaa ttttttcctag ttttttttt ccctctcctg ttttctttat ttttcttcta    32460
gtatttggga aatcttactg ttttgtaagc ttcctattga atttatttta actgccatgt    32520
ctgttaatta ccagcaactc ttttgtgttt tctgataatt ccttttttgt gaagttctgt    32580
ttttaattta tagatgtcat aacttgtttc cccaaagcct gtgctcttaa ccattactct    32640
taaatgtgta ttatgtgtgt gtgtatatat atgtatgtat actttttt taaagtttgc    32700 tgatattgcc aacattatct ctcttccttt tgagttcttt ttttcagttt gtttatatct    32760
ttgttatagt ctgtctttaa tgagagtggt ttggttttct caaatcccta gagattcttg    32820
gctgaaatct aacaatttga ttggaaactc caagtgccag gtcagggctt gtcatctggt    32880
gagttttact gtaacatgac catgtagggg tgaggtgaca tgttgaggaa ttcattttgg    32940
tattctactc atacttttgt ggttttgttt tttcacgagt tgttttgttt tgctttcaat    33000
```

```
caggcatagt tattgaacgt ggcatttgtt gagcagttac tatgtgtggg acgcagttct    33060
aagtgtttca tgcgaattag ttcagtgaat cctcatgata atggattctc tgggaactat    33120
tattgtccca tcttgcagat gtgagaactg aagcacaaag ggcataagta acttgcccca    33180
ggtcatgcag ccaggcagag cctggctcca ctacagtatc ctgcctccca gatgatgatc    33240
tcagtgttct cataggacct catggtatag cagagctttc catatggtgt gctgcaatat    33300
tgatctactg aggagcctgg gcagggccag aatagcatct accctgagca gccttgttca    33360
cttgtgtggg tgctatccaa atactataat tttctaagta tgtcctgctg tgaaaaaggt    33420
taaaatttgt ttttctccca aaacttactc ttcagaaaaa aaggtagac atatttcagc     33480 ccttaacaag atctctcaga ttctgggagt cattctcaat ttaatttatt ttgaatatcc    33540
tggcatagca ttttgatcag tgctggtttt gaatgcctag agaagtcact agaaagaatc    33600
aattaaaaaa aagatgctag gacatgtaac actggtgtag caaaattatt cctgggaaat    33660
gacctcattg ttgcaagaat tggaagtcat aagtttataa aacaagtctt tgttctagag    33720
atcacaatta gacaatttca ggacaaatga ttttctaaag tgaaagtata tatgattaa     33780 tgtattgtac gtgggcttaa atgtgctcag acagaagtga agatgctagt tctggaagac    33840
tgtattaaat atctctaagt ggctcttgtg ataacattcc catcaagaat gcatgggagg    33900
ctgggtctgg tggctgacgc ttgtgatccc agcactttgg gaggccgagg caggcaggtc    33960
acttgagttc aggagttcaa caccagcctg ggaaacatgg tgaaaccctg tctctacaaa    34020
aaatacaaaa attagccagg tgtggtggca tgtgcctgta gtccaagcta ctggaggggc    34080
tgaggctgga ggattgcttg agcctaggag gttgaggctg cagtgagctg agattgcgcc    34140
actgtactcc agcctgggta acagagcgag accttgtttc aaaagaaaga aagaaagaaa    34200
gaaagaagag tgcatgggaa gaggtggaat acaattttt tcatgatatt tgagaatgga    34260
aaaatatttt aagataaata tttcctttat tatatgattg caaatgtgta tgtataattg    34320
tactttcaaa cagatagttg actatttcat aaacatctat atttattcaa gctggtagta    34380
gtaacatttg gagcttctca ctgagaaaat gaggatcacc ttaaatagga ttgtcttata    34440
ttttgatact atattaatag atatcttaat cttggatcat ctttgctttg ttaggttaaa    34500
tccaacttga ccgtgcctat gtattttttat tatactgatg aattcagttt gctagggttt    34560
catttaggat ttttgcatca attcagaagt ggaagtagag ttagtggttt cttttttgtg    34620
tcaggttttg ttgtcttggt tgtgctcact tcataaaata atgtggttag ttttgccatc    34680
tttttctatg ctctggaata gtttatagaa tgttggaaag atcttctgt  ttagctggtc    34740 cctgaagcct tttgtggagg catttaaaaa attatttcca tagtttacat tttttgctga    34800
attatatcta ggtgtgtgtc tttaaaatgt tttgaaatta attttgcctg aaatatagtg    34860
agccctgaaa ctgcatgctg agatgattat tcactccagg aggctttcct tgttcctatt    34920
ttagcttatt gcttttgttc tacttgattt atgtctcaaa aatatcttta attactgtgt    34980
tgaatccctg attcagcttt tctctcatcc ttttcatttt ttttgtcctt tttctcaggc    35040
tttggagctc ttctgcatta ccagtttaga cacttttgca attttaatcc tacaccttaa    35100
tatctccaac atagattatt gttgattgta tttttagttt ttttgcaatg ctgtctctgt    35160
ttcaatcagt acccttttct tccaagcttg ttagtatagt atagtatagt atttagtagc    35220
attaaacctc aatgtaaccc tgtgagatag taaatggttt cttgatccca tttaccaatg    35280
aagaaatcaa aacttctttt taaaaataa aataaaaaa taaagatagg gtcttgctat      35340
gttgcccaga ctggtctcaa actcctgggc tcaagtgatc ctcccacctc agactcccaa    35400
```

```
aatgctagga ttatcagtgt gagccgctta agaaaattaa gcgattagtc caaggccaca   35460
cagctaacaa ctgaaaaagc cagaattcaa acccagatct acttgaggtc aaaacccaat   35520
taacctaatc agttgtcttt ttgcatctca ttttcttttc catttatttc atcccattgt   35580
actgcatttc tacgcttgtg ttcacaggac ccatccttt  cctgaacctt tctgaataga   35640
acttttctaa aatctttatt tttataggaa gtcattgcca gctagatgct cttccttgga   35700
gtatagtggt gaaggatctg cacacacaga atgtgtggcc gtcttgtggc ctctggtcac   35760
tgtttcctgg ttgattcctt ctcaaatctg cagcttgagg tcaggttgat gcatacacct   35820
cacagagttc ctggtggcat ataggcatta agtgttctac tctattgaac ctgacccacc   35880
tagttacagt ttcttctttt ttggcactct aattctttga caggctaaaa gaaccccaga   35940
ctcttcctat ctccacattt tcagggcttt atttttgggg acattcctca ggatacagtg   36000
tgccagcact gccagacctt ctctttttcct gcctattgtc ttctgggagt tgtgatctct   36060
aagcacacag aagtagagga ggtaataatt ctcctctgct taaattagtg ccatcccttc   36120
tcaggctgtc ttcctgcctc tcttaatcta ggtgaagggc tctgtgtcat gaggcaaagc   36180
agggtgggcc agttcttatt tcctcagccc agcttctctg gtcttgtagt ttctggacat   36240
gtttccaaga ttctggcatt ataagctgtc tgtccatctt ggtttcttat gttgtgatgg   36300
ggtttcatct tgttctgtgt ttgttgtttt cgcagggtag tggtccagag aagcagcact   36360
agtggctgtt aggaagacac cattgtattc tggatgcttg tcaccatggc tgatctttgt   36420
agttgctaaa ttccaggaac ctgcacagga atctgacctg gagtaaaatg agttaaggtt   36480
agggacaact cttgagtaac taggtcatga gttaagacta ggaaaaccga ttctgcaacc   36540
ctgaaaacag tgattgacct caacatctta atgcagccat tgtgtattta tattaactct   36600
tttttttgtt tgttttgttt ttttttgagat ggagtctcgc tctgtcactc aggctggagt   36660
acagtagcat gatcttggct tgctgcaatc actgcctccc gggttcaagt gattctcctg   36720
cctcagcctc ccaaatagct gggattacag gcgtgtacca ccatgcctgg ctaattttg   36780 tatttttagg agagacaagg tttcgccatg ttggccagac tggtctcgaa ctcctgagct   36840
caggcaatcc acccacctca gcctctcaga gtgctcggat tacagtcatg agccaccacg   36900
cccagcctgt attaagcctt accagaataa ttagttttac ttacatttag atgagggttt   36960
gaatataagg agaaacctaa tttgcatttc tttctccaga gacttctgtg tttattgaca   37020
atttcatttc ctgaagttga aattaataat gtgctataat aatgtaatta tacccaagg    37080 acctggacta actaatcaca gagcagtgat tcatttttttc ccacttctct cactttactt   37140
cacttagccc tgtacttctt tataaggata agaatactgg ttgcattcaa atcaataaat   37200
gttgagtcca ttagtacaga aaccatgaa  acaatctag cttcctggtg ttggattata    37260
tttggtgatc ggtaaaggca aaggcataat ttttagattt tgatgtttga taaagctaac   37320
ttttaaaaat ttctgttata atctgagaga aatccatgat tcattccttg ccacctctac   37380
ccatcatctt agcatagtta ttctcagtgc gctgtctggg gaccacctgc agcagtggag   37440
catttgttaa aaatgcaatt ttcaaggtga tggctgcaca acattgtgcc atgttctaaa   37500
tgtcactgaa ttggatactt taaaatggct aatttcatgt aatgtgaatt tcaccacaat   37560
cttaaaaatt cagttttctca gactctatca cagcccagct gaattagaaa cccagaggcc   37620
caaaaatctc cattttttaac aagaattcag gtgattctttt tgtacacaga aatttgaaga   37680
cctctgagct aaggtaactc ttattcaaac tttaggaatt taccttacaa ggaatgtatg   37740
```

```
tggttattta aatttgacat atatttatgt ttatacatat atcctcctca ctaggaggaa   37800
tatatatatg acagctggaa accaactggg tttgaagttc aggcgctcct aggtagtttt   37860
catttcaggt aaatgcacct atttctagaa atagactctt caaaaagctg acgagaaaag   37920
tttaaattta attattctgc tttccatgtt cttactgcat ataaatcaca accttaattg   37980
attcatgcca tttcttctgc agtgtgtgat taataccact gttaacaaat attgtctttc   38040
tcattacaca catactattc tgggtttgtt ttttttattc tatttttttat ttttatgggt   38100 atatagtagg tataaatata tatttatgga gtacatgaga tattttgata caggcacaca   38160
atgcatagta atcatatctg ggtaatgggg atatctatgc cctcaagcat ttatcatttc   38220
tttgtgttac caacattcca attaaactct tttgattatt taaaaatgta caataaatta   38280
ttattaactg tagtcaccct attgtgttat taaatactag ctcttattca ttctatctaa   38340
gtatatttgt gtacccatta accatacccca cttccccccct accctcaccc cactacccctt   38400 tccagcctct agtaaccatc cttctattct ctacctctat gagttctatt gttttaattt   38460
ttagctctta caaataagtg agaacatgtg atgtttgtct ttgtgcttgg cttatttcac   38520
ttaatataat gacctccagt tccctccatg ttgttgcacg tggttgatct cattctttta   38580
tgtgactgaa tagtactcca ttgtgtatat gtagcacatt ttctttatcc atgcatctgt   38640
tgatggacac ttaggttgtt ttcaaatctt ggctattgtg aatagtgctg caataaacat   38700
ggcagtgcaa gtgtatgttt gatatactga tattctttct tttgggtata cttagcag    38760 tgggattact ggatcatgtg gtagttttgt ttttagtttc ctgaggaacc tccaaactgt   38820
tctccatagt ggctgtacta actcacattc ccaccaacat tgtacaaaag tacccttttc   38880
tccacatcct cgccagcatt cattattacc tgtctttttgg ataaaagccca ttttaactgg  38940 ggtgagagga tatctcactg cagttttgat tggcatttct ctgatagcca atcatgttga   39000
gcaccttttc atatacctgt ttgccgttta tatgtcttct tttaagaaat gtctattcag   39060
atcttttgcc cattttttaat cagattatta gattttttttt ccccatagag ttgtttgagt   39120
tccttatata gtctggttat ttgtcccttg tcaaatggat agtttgcaga tattttctcc   39180
cattccatgg cttatctctt cactttgttg gtcattttct ttactgtgca ggagcttttt   39240
aactcaatgg aatcctattt gtccattttt gctttggtta cctgtgcttg tgggatatta   39300
cacaagaagt ctttgcctag tccaatgtcc tggagagttt ccccaatgtt ttctattagt   39360
agttgcatag tttgtgttct tagacttaag tctttaatcc attttgattt gattttttcta  39420 tatggtgaga gatagggggtc tagtttcatt cttctgcata tggatatcca gttttcccag  39480
caccatttat tgaagagact atcctttctc cagtgtctgt tcttggtact tttgttgaaa   39540
atgggttcac tgtagatgta tggatttatt tttgggttct ctattctctt ccttttgtct   39600
aggtgtctgt ttttatgcta gtaccgtgct gttttggtta ctataactct atagtataat   39660
ttgaaatcag gtaatgtgat tcctacagtt ttgttctttt tgctcaggat agctttggct   39720
attctgggtc ttttgtggtt ccatataaat tttagaatta ttttttctct ttctatgaag   39780
aatgtctttg gtattttgat agggattgca ttgaatctgt agattgcttt gggtagtatg   39840
gacgttttaa caatattgat tgttccaatc atgaacatga aatatctttc cattactttg   39900
tgtctgcttc aatttccttc atcaatgttt tatagttttc attgtagagc cctttcacta   39960
ctttggttaa gtagtgatct acttactact tattcctagg tatcttatttt tattggtagc   40020 tattgtaaaa gggataactt tcttgatttc ttttttctgat tgttcactgt tggcacatag   40080
aaatgttacc gattttttata tgttactgat ttttgtatgt tgattttgta tcttgtaact   40140
```

```
ttactgaatt tgcttatcag tcctaatagt ttttttgtgg aggctatagg tttttccaaa    40200
tgtaagatcg tatcatctgc aaacaaggat aatttgactt ctttctttcc aatctggatg    40260
cctttatttc tttctcttgt ctgattactc tagctagcac ttttaattc caggttttt      40320 aaatccaagg atgacacttc taatccttct ctgatagaac atgatcagag tttgagtccc    40380
aactttcctg ccaatgagtt atatgtagag tctagcctcg gtttcattat ctgttaaacg    40440
caagttgatt gaccattcat ttattcactc cgtctttcat tgcagataaa aagataactg    40500
ggacatattg ctcccttagg aaactcacac tctagtgaag tagacaggta catgtattat    40560
tattatgcag tgggaatatt aggatgaagc ccagggtgct gtctgcacac aataagagcc    40620
acctctcaga gcccagggtg tggggaggct ttctgagatg gaaaggttgg gaatggcttg    40680
gccagataag cagaacacag gtggggagga gattgggcag cattctagcc tgtgagaaag    40740
gaacataaat aaagacaggg aggttggag agcagtcctg gaggggggtc tgcattgctg     40800
gagcctggac tgcaaggtgg agagcagcga gatgtgaggc tagagagcat gacccagggg    40860
tccactcaga agggcctgt gcacatgcag ggaggaattg tgaagggtct catggtgaca     40920
gtgaggcact taaagttttt aagcaggatc agattttcac tttagaactg aaatggaggg    40980
tgattggaag caggccgacc ttttaggagg ctctgacaat aaagagagga gagaagataa    41040
ggagcacttg agtaaaggca gagggaaggt ggatggagat aagaggacag atttaagaaa    41100
tacataggag gggtggagcc aagatggccg aataggaaca gctccagtct acagcttcca    41160
acatgtgcga cgcagaagac gaatgatttc tgcatttcca actgaggtac tgggttcatc    41220
tcactgggga ttgttggaca gtgggtgcag gacaatgggt gtggtgcact gagcctgagg    41280
caaagcaggg cgaggcatcg cctcacccgg aagcgcaag gggtcaggga attccctttc     41340
ctactcaaag aaagggtga cagacggcac ctggaaaatc gggtcactcc caccctaata    41400
ctgcgctttt ccaatggtct tagcaaacg cacaccagga gattgtatcc cgcgcctggc     41460
tcagagggtc ctacgcccat ggagcctcgc tcattgctag tacagcagtc tgagatcaaa    41520
ctgcaaggtg gcagcgagga tggggaggg gcgcccacca ttgccaaggc ttgagtaggt     41580
aaacaaagtg gccgggaagc tcgaactggg tagagcccac cgcagctcaa ggaggcctgt    41640
ctgcctctgt agactccacc tctgggggca gggcatagct gaacaaaagg cagcagaaac    41700
ctctgcagac ttaaatgtcc ctgtctaaca gctttgaaga gagtagtggt tctcccagca    41760
cgcagcttga gatctgagaa cggacagact gcctcctcaa gtgggtccct gaccccgag     41820 tagcctaaca gggaggcacc cccttgtagg ggcagactga catctcacat ggccgggtaa    41880
ccctctgaga caaaacttcc agaggaatga tcatgcagca acatttgctg ttcaccaata    41940
tccgctgttc tgcagcctcc actgctgata cccaggcaaa cagggtctgg agtggacctc    42000
cagcaaactc caacagacct gcagctgacg gtcctgactg ttagaaggaa aactaacaaa    42060
cagaaaggac atccacacca aaaccccatc tgtaaatcac catcatcaaa gaccaaaggt    42120
aaataaaacc acaaagatgg ggaaaaaaca gagcagaaaa actgaaaatt ctaaaaatca    42180
gagtgcctct cctcctccaa aggaatgcag ctcctcacca gcaacggaac aaagctggat    42240
ggagaatgag tttgatgagt tgagagaaga aggcttcaga cgatcaaact tctccgagct    42300
aaaggaggaa gttcgaaccc atggcaagga agttaaaaac cttgaaaaaa gattagatga    42360
atggctaact agaataacca atgcagagaa gtccttaaag gacctgatgg agctgaaaac    42420
cacggcacga gaactacgtg acgaatgcac aagactcagt agccgatttg atcaactgga    42480
```

```
agaaagggta tcagtgattc aagatcaaat gaatgtaatg aagtgagaag agaagtttag    42540
agaaaaaaga ataaaaagaa acgaacaaag cctccatgaa atatgggact atgtgaaaag    42600
accaaatcta catctgattg gtgtacctga aagtgacagg gagaatggaa ccaagttgga    42660
aaacactctg caggatacta tccaggagaa cttccccagt ctagcaaggc aggccaacat    42720
tcagattcag gaaatacaga gaatgccaca aagatactcc ttgagaagag caactccaag    42780
acacataatt gtcagattca ccaaagttga aatgaaggaa aaaatgttaa cggcagccag    42840
agagaaaggt caggttaccc acaaagggaa gcccatcaga ctaacagtcg gtctctcggc    42900
agaaactcta caagccagaa gacagtgggg gccaatattc aacattctta aagaaaagaa    42960
ttttcaacct agactttcat atccagccaa actaagcttc ataagtgaag gagaaataaa    43020
atactttaca gacaagcaaa tgctgagaga ttttgtcacc accagtcctg ccctgcaaga    43080
gctcctgaag gaagcactaa acatggaaag gaacaactga taccagccac tgcaaaaaca    43140
tgccaaattg taaagaccat cgaggctagg aagaaactac atcaactaac gagcaaaata    43200
accagctaac atcatgacag gatcaaattc acacataaca atatgaacct taaatgtaaa    43260
tgggctaaat gctccaatta aaagacacag actggcaaat tggataaaga gtcaagaccc    43320
atcagtatgc tgtattcagg agatgcatct cacgtgcaaa gacacacata ggctcaaaat    43380
aaagggatgg aggaagatct accaagcaaa tgaaaaacaa aaaaggcag ggattgcaat    43440 cctagtctct gataaaacag actttaaacc aacaaagatc aaaggagaca agaaggcca    43500 ttacataatg gtaaagggat caattcaaca agaagagcta actctcctaa atatatatgc    43560
acccaataca ggagcaccca gattcataaa gcaagtcctt agagacctac aaagagactt    43620
agactcccac acaataataa tgggagacat taaccccca ctgttaacat tagacagatc    43680
aatgagacag aaagttaaca aggatatcca ggaattgaac tcagctctgc accaagcgga    43740
cctaatagac atctacagaa ctctccaccc caaatcaaca gaatatacat tcttttcagc    43800
accacaccac acctattcca aaattgacca catagttgga agtaaagcac tcagcaaatg    43860
taaaagaaca gaaattatag caaactgtct ctcagaccac agtgcaatca aactagaact    43920
caggattaag aaactcactc aaaaccattc aactacatgg aaaccgaaca acccgctcct    43980
gagtgactac tgggtacata atgaaatgaa ggcagaaata aagatgttct ttgaaaccaa    44040
tgagaaaaaa gatacaacat accagaatct ctgggcacac ttcaaagcag tgtgtagagg    44100
gaaatttgta gcactaaatg cccacgagag aaagcaggaa aggtctacaa ttgacaccct    44160
aacatcacaa ttaaaagaac tagagaagca agagcaaacc cattcaaaag ctagcagaag    44220
gcaaggaata actaagatca gagcagaact gaaggagata gagacacaaa aaacccttca    44280
aaatatcaat gaatccagga gctggttttt tgaaaagatc aacaaaattg atagaccgct    44340
agcaagacta ataaagaaga aaagagagaa gaatcaaata gatgcaataa aaaatgataa    44400
aggggatatc accactgatc ccacagaaat acaaactacc atcagagaat actacaaaca    44460
cctctacgca aacaaactag aaaatctaga agaaacggat aaattactgg atacatacac    44520
cctcccaaga ctaaaccagg aagaagttga atctctgaat agaccaataa caggctctga    44580
aattgtgaca ataatcaata gcttaccaaa caaaaagagt ccaggaccag atggattcac    44640
aaccgaattc taccagaggt acaaggagga actggtacca ttccttctga aactattcca    44700
atcaatagaa aaagagggaa tcctccctaa ctcattttat gagtccagca tcatcctgat    44760
accaaagcca ggcagagaca caaccaaaaa agagaatttt agaccaatat ccttgatgaa    44820
cattgatgca aaaatcctca ataaaatact ggcaaaccaa atccagcagc acatcaaaaa    44880
```

```
gcttatccac catgatcaag tgggcttcat ccctgggatg caaggctggt tcaatatatg   44940
caaatcaata aaggtaatcc agcatataaa gagaaccaaa gacaaaaacc acatgattat   45000
ctcaatagat gcagaaaagg cctttgacaa aattcaacaa cccttcatgc taaaaactct   45060
caataaatta gatattgatg ggacgtatct caaaagaata agagctatct atgacaaacc   45120
cacagccaat atactgaatg ggcagaaact gaaagcattc cctttgaaaa ctggcacaag   45180
acagggatgc cctctctcac cactcctatt caacatagtt ttggaagttc tggccagggc   45240
aattaggcag gagaaggaaa taaagggcat tcaattagga aaagaggaag tcaaattgtc   45300
cctgtttgca gatgacatga ttgtatatct agaaaacccc atcgtctcag ccccaaatct   45360
ccttaagctg ataagcaact tcagcaaagt ctcaggatac aaaatcaata tacaaaaatc   45420
acaagcattc ttatacacca ataacagaca aacagagagc caaatcatga gtgaactccc   45480
attcacaatt gcttcaaaga gaataaaata cctaggaatc caacttacaa gggatgtgaa   45540
ggacctcttc aaggagaact acaaaccact gctcaatgaa ataaaagagg ataccaacaa   45600
atggaagaac attccatgct catgggtagg aagaatcaat attgtgaaaa tggccatact   45660
gcccaaggta atttatagat tcaatgccat ccccatcaag ctaccaatga ctttcttcac   45720
agaactggaa aaaactactt taaagttcat atggaaccaa aatgagcccg cattgccaag   45780
tcaatcctaa gccaaaagaa caaagctgga ggcatcacac tacctgactt caaactatgc   45840
tacaaggcta cagtgactga acagcatgg tactggtacc aaaacagaga tatagaccaa   45900
tggaacagaa cagagccctc agaaataatg ccacatatct ttaactatct gatctttgac   45960
aaacctgaca gaaacaagaa atggggaaag gattccctat ttaataaatg gtgctgggaa   46020
agctggctag ccatatgtag aaagctgaaa ctggatcctt tccttacacc ttatacaaaa   46080
attatttcaa gatggattaa agacttaaat gttagaccta aaaccataag aaccctagaa   46140 gaaaaaacg taggcaatac cattcaggac ataggcatgg gcaaggactt catgtctaaa   46200
acaccaaaag caatggcagc aaaagccaaa atagacaaat gggatctaat taaactaaag   46260
agcttctgca cagcaaaaga aactaccatc agagtgaaca ggcaaccttc agaatgggta g   46320 aaaatttttg caatctactc atctgacaaa gggctaatat ccagaatcta caatgaactc   46380
aaacaaattt acaagaaaaa acaaacaacc ccatcaaaaa gtgggcgaag gatatgaaca   46440
gacacttctc aaaagaagac atttatgcag ccaaaagaca catgaaaaaa tgctcatcat   46500
tactggccat cagagaaatg caaaacaaaa tcacaatgag ataccatctc acaccagtta   46560
gaatggcaat cattagaaag tcaggaaaca acaggtgctg gagaggatgt ggagaaatag   46620
gaacactttt acactgttgg tgggactata actagttca accattgtgg aagtcagtgt   46680
ggcgattcct cagggatcta gaactagaaa taccatttga cccagccatc ccattactgg   46740
gtatataccc aaaggattat aaatcatgct gctataaaga cacatgcaca tgtatgttta   46800
ttgcggcact attcacaata gcaaagactt ggaaccaacc caaatgtcca ccaatgatag   46860
actggattaa gaaaatgtgg cacatacaca ccatggaata cttgcagcca taaaaaatga   46920
tgagttcatg tcctttatag ggacacggat gaagctggaa accatcattt tcagcaatct   46980
atcgcaaaga gaaaaaacca aacaccacat gttctcactc ataggtggga attgaacaat   47040
gagaaaacat ggacacagga agggaaacat cacacaccgg ggcctgttgt ggggtcgggg   47100
gaaggggtga gggatagcat taggagatat acctaatgct aaatgatgag ttaatgggtg   47160
cagcacacca acatggcaca tgtatacata tgtaacaaac ctgcacgtta tgcacatgta   47220
```

```
ccctagaact taaagtatta aaaaaaaaaa aagaaataca taggagagct tggaccactt   47280
gatgttgaga gctcttttta ctaggaaagc tgatggtttt gtaattctgc cagttttcag   47340
gatgttgtca gtgctaatga aagcctttca tgttctcccc atggcatgga tacatctgca   47400
aagagctgga aagagtgaag cccatggcca gagtacccac ataatccaca tagcagtagt   47460
gcatcagagt gcatagattc atagtacaca tgagacggag agcagaagtg gtttggttgt   47520
cacagtgact tgagggtgaa gtttccattt agtgaacagg catctgcagt gctcaggcca   47580
gtcctgcagt gaagtgtcct gcctcagatg tcagtagcac aaccattaag ggacagtgac   47640
cggatcctgt tcaataacac atttctactt agacaaatag agcaatttat tgcagagtct   47700
aaacttttag cacttattat ctgagctttc acaatattac atgtgattta atactcaaat   47760
ggagttaata atcttaacta attcctctaa atcttacgtc cctttcccc ttacatataa    47820 gaatttcctt caaaactggt agttggcaaa gagagagctc attcaaggtt ttaaatatac   47880
ttatgcaatt ggcagactta taaaatatta tagaaattct gtgccaggaa caaagttata   47940
tgtgctagga aaccaatctc actgggttct tcagacactt aaatgaattt ctgacaaagc   48000
taaggaaaag ctgttatgtg aataaatcag tgagtgtgtc cacattctat tactctttgc   48060
aattatgcat ttatttggcg cgtctatcat agaggaaaat tacaacccat gcctcagaat   48120
aatgagactt gaatgaactt ttccatagcc agtcattaat tcatgccacc tctttagatt   48180
tcacctgtta atgtccacac tgagagcatg ttggatcact ttaaaatttt attagtaata   48240
ggtactaatt tgttgattat tttattgagt gaaaataata accaatacat tttactgaac   48300
agccatgctg atttggtgtc cctggctgag ttacaaagca gaggttccag ggctggggat   48360
ggtagtccca cctcccctct ttgtctctgg ctgttctcag ggatgtgttg cccttttgggt  48420 actcgtgttg cttcccatgg gttaaagcat gggcaggcct cctgccaggg aacccaggat   48480
ggtggggaag ctggttgttt acctccatct cactttttcc agtgtagaaa ccatgagttg   48540
ggccacagtg ggtgggggt gtagcagata tggacatttg attcttttac catctcctca    48600
gagtttttca cttctctgtg accctggaaa tggaatcatc ctcatgtttg agttctgcga   48660
tgttgctggt gataatcttg gcaccttata tttgttttgg ttttctgtgg agaggagtga   48720
acctagattg tgtctgtgtt atcatttttgg aactagaagt tccgaaatca ataaccaata   48780 catttttaaaa ccaccccac cccgcaccaa agggtcttgc atttgtattc tctgtgtcaa    48840
accattgaat tcataatccc agagtcgaag gaaaaaatgc ctctcaatct ctatgtttat   48900
cagatcttca atgttttatt atagtactta atatatacta tgctataatg tcttattgtt   48960
gatattatga acttttagca ggagaaacat gaagtagtca tgattttcac aattctgtga   49020
gaagagagca ctgtggcctt tctatgagtt tataattaat gaatatatat attcattata   49080
tatataagat atatatatca tatatatgat atatatatct tacatatata tatcttacat   49140
atatatgata tatatcttt acatatatat atcttacata tatgatatat atatatcttta   49200 catatatata tcttacatat atatgatata tatatcttac atatatatat cttacatata   49260
tatgtaagat atatatatat cgaacttcct tgaactgagc atatttattg actaaattgc   49320
aagaaacttt ccaatttgtt tgggttttact ttaatctcat ctttttgcact ccattttgaa  49380 ggtcacattt aagatgaatc cgtttcttat attttatgct cctctcagaa ctcactggag   49440
ccaaaattct ctgtgaggca agagctatgt tatgttggac aggctgcact ggaggatgaa   49500
gcaaaatgaa aagtagattc tatgtagaaa taatcacctg gaaactacag tgacagcaag   49560
aagaaggagc tgaaataaat tcaggttgtc acaagctgct aaaaaaatgc atttacttac   49620
```

```
attgcttctt atctggtacc catatctgct gtctcctaca gtcgtctagc caaatatta    49680 aagatataga atctacaaag acaaactaat tattaatgtg tctgtgaact ctgcaaacaa    49740
acattattga atgcattact gttaggactc ctatttggac aagtagctag gtgagccctg    49800
tctaagcata aagacctatg cagggcttat caaacttcaa gactctgctg actagagatg    49860
caaaataaaa tcatgaggga attagcaggc accagtgaga cctgcaggct ttgagaaatc    49920
tcttgaggta agtgagaaag acagcttcct atgtgagcag aggttcattt attttgattc    49980
aagttaaggg ttaagggcaa cttgacattt tgtattacac ctatcccttc cccacccctc    50040 ttttttttt tttcttagga gttgtaagga tcttacaaga tcatctgatc ttagaaagaa    50100
ataaagaccc tggccaggca cagtggctcg cacctgtaat cccagcactt tgggaggcag    50160
aggcaggcag atcacttgag gtcaggagtt cgagaccagc ctggccaaca tggcaaaacc    50220
ttatgtctac taaaaataca aaaataaccc agcatgatgc cttgtgcctg caattccagc    50280
tacttgggag gttgaggcag gagaatcgct tgaacccggg aggcggaggt tgcagtgagc    50340
tgagatagcg ccactgcact ccagcctggg caatagagtg agaatccacc aaaaaaaaaa    50400
aaaaagagag agagagagga agggatggag ggaaagagag agaggcgggg aggaagggaa    50460
agagagggag ggagggaggg aaagagagag ggagggaggt gggggggag agacagagag    50520 aaagacagaa agaaaagaaa ggaggaaaga aaggaaggaa aggaagggaa ggagagaagg    50580
ggggagggga ggggaggggga gtggaggaga ggggaggaga gagaacgaaa aatacccaga    50640
gagggacgtt gggactttg taaatactca ggaggcagat ggcctgagtc caacactcac    50700
tgatgcctat gcaatcttgg gtaagatact aaaacttcca gtgccttatt tcttcatca    50760 gcaaagtgtg gataaaaatt ataactaccc gatagtactg atgagattgc agcacttcct    50820
gacacatact gagtgcttta ttgttattag gttgtgtgat ataataatag ctaagtggct    50880
agagattaaa ccatttctag cctttggtct ccggtttgct ttttattgt ttttatggct    50940 tctgtttcct cttgttactc tcatcaggct atttgctact acctatgctt attattcatt    51000
cattcattca cttgttcact catcagcggc acacctgcca cgggccaagc tctctgctag    51060
gccctgggaa acagtaggga atgaggctga ctatgcacag gacgaagtgg cttatttcct    51120
aattcaatag tctgttaatg agcatcagga atgtcaagaa tcctccttct tctactgaag    51180
atggttagca gcctgtaaca attattatga cacatttttc atttatattt tagcttctga    51240
aaatcatgag gaattatttt ttaaagcagt cttgattt gattactgag aatacaatat    51300
gttttgagaa cctcattatt tcctctgata ctttcttctt ttcttcatat ttcttatatt    51360
ctttatgttt aaattgaagg tgatttatta tgcaagctat tggatatgat tttggagttt    51420
tttgtaccat taattattga gggagcaaag ttgaaattct gcttttaatt catctccttt    51480
ttttgaaaaa tgtatgactt aaaaatgaaa ttaaataatc aaaaattaaa tgtgatgctt    51540
aaaggtcatt tgtttaaag tgatgaatgc tagtttacca tatactacta gaaaaatcaa    51600
aattatataa tctatttgcc atgtattatt atttaatttt aataaatatt tatggtttca    51660
taaatataca aggttcttcc taaagttatc tatctaccac attttctcat ttatttattt    51720
atttttattt tttattttgg agacagaatc tcgctctgtc acccaggccg tagtgcagtg    51780
gcgtgatctc agctcattgc aacctctgcc ttcccagttc aagtaattct cctgcctcag    51840
cctccacctc acaagtagct gggattacag gtgcccacca tcacgcctgc caaatttttg    51900
tatttttagt agagacaggg tttcaccatg ttggccaggc tggtctcaaa ctcctagcct    51960
```

-continued

```
caggcaatcc acctgccttg gccttccaaa gtaacatttt ctctttcatt aactattcat    52020
tcattttcct attttttaac tctgaaagtt cttaagtata tatattatta taatatcagc    52080
aatcatattt ataacaaaat attaaccatt aatgattgta gtattttatt tttattatac    52140
taaacagcta tactttgatt aaaattgtaa catatatagt aaaggacata ggaggttttt    52200
tgctccaaat gacatccaga atgcttatct atatttgaaa gagactattc agatattaat    52260
actaacacca ataatgtgc cttgttttac tgtgatgtag ctacactgat tatctgtgct    52320
ggtaaactgt acctcaccat tattgatgtt ccaggatgcc agaaatggca ttaaagtaag    52380
cattgggcta tttggtcttc tagggctaat gcagagacca tttgggtttt ttgggagaac    52440
tcaactccct gtggtcctat gaccaagacc ctcattgtct ggctgtcagc ttaaggctca    52500
ttctagcttc tggaggcttc cccttattct ttgactttct ccttccacct tcagagcctt    52560
taacagtggg ttgagtcctc ctcatgtttt gaatctctcc tccttttct tctctctcgt     52620
cactctagtc tattcttcct tctttaactt ttagagctca taacctatgc cctctccaat    52680
aatccaggat aatctcccta tatttaggtc agctagttag caacttcaat tccatggcaa    52740
ctttaactcc ccgttgccat gtaaggtaac atattcacag ttctgaggt taggacatct    52800
ttggggacca taattccatg cagtcacttt ggaatgattg aaatttttta gtattctttc    52860
tgatcacctc ccatcctcta ctagttcttt tcctaggaga aacattcacc acacatgcaa    52920
atgctcgtcc taatacttgt gtgatagtcc cagtgtcccc atccacaagg cagctcagca    52980
gacttctctg aaaaacagac aatagcgact ctatcgccat tgacctccac aaaaaaagt    53040
aattgttgtg ggcctgggaa taattgttta aaatattgtg acttgtgagt gactgtgaag    53100
ataagaacaa ctttgggcaa atagatgctt ttaacagcat cacacctcag agcctttgaa    53160
acttgagcgg gagctggctc tagttttctt ggggatccat ggactgattt cttctactta    53220
gggattttgt tgtaaatcca gaaaaatacg taggaagctg taaacgatta taaaaattca    53280
ggcccattct tcaatccatg ggtatatatt tgacaccttg ggaacttgca ttaatacttt    53340
ttcggtaaaa taaaaccctc aactcacctt catttattga gcatcttctg tgtgatgagc    53400
agtgtcacct ctgtgtttac gcacatataa aagttccagg ttctgctttc aagagtttac    53460
attcttatat gagcagtaag gctagctatc caacccactt gctaatagtg taagacttta    53520
tacaactaat ttctaaatgg tgtgacattg acaatgacag taagtgctgt ttcgtagtag    53580
ggaggggaaa tatgagtgga gttgtgtgag aagacttcac agaggagctg gggcttgagc    53640
tgttggcgga aggatgctag agtttgaata ggcagagaga gagagaatgg tccattccag    53700
atgcctccat ggagaaaata atggagaatg attatgacag taacaaccaa aaatttatga    53760
gtacttcctg taacctagtt gttgtgccaa gcactttaca tgtatctacc catttaatag    53820
gtactactat tatccccaat ttctagatga agaagtaggt gcttagagag taatataact    53880
cattcaaagc atagcacttc ctaagtggag gaatggagtc aaactcaggc ctgtctgatt    53940
tcagagctca agcttataat cactgtgtca gtaggctgtg atccaggtca gcttagagta    54000
tgggagccat gcagagaaat cctggataat tgaagttcta gaaagataga gctggaaagg    54060
gttttagaga caatcccac acaatgtttt catttttaaaa acagagaccc agagaggcta    54120
agtgcaacca cttatgttag aatggagact tagccttgtc tcttacactt gtcctcttac    54180
cacagttagg tgagtccatc tgataatgat gcagaaaggt tagcgttgcc ttgatgactg    54240
tcagaaggca gctataggct gcctcagtca catgggaggt aaagcggtat ctgacataat    54300
accccctggga atggattcca ccatgggaga atgtagttca ctgaattcca actaaaacaa    54360
```

```
agagctatta gactgctcgt gacttttttgg ctgaagtatg ccttttttgat acatatgcag   54420
ccatcttttg gaattgggtg aaaatcagtg tattagtcca ttctcacact gctataaaga   54480
aatacctgag ctgggtaatt tataaaggaa agaggtttaa gagccagttc cacatggctg   54540
gggaggcctc aggaaactta caatcacggc ggaagggaaa gcaagcacat cttacatggt   54600
ggcaggagag agagagaaag tgaaggggga agagccctt  ataaaaccat cagctcttgt   54660
gagaacttac tcactatcat gtgaacagca tgggagaacc agcccccatg atccagtcac   54720
ctcccaccag gtcccttctt caacacctgg ggattacaat tcgagatgag atttgggtgg   54780
ggacacagcc aaaccatacc aatcagcata ggacaaacta tatttgccaa agaataatga   54840
aattttgtag agtcatgttt tcatatcact tcatgtgaaa acatgactct ctacaaaatt   54900
tcatattctt ttctagcttg cattctaccc agaaaccagt ggtaaaaatg ggctgattgt   54960
gttttttatc tttctcaagt tctcctcccc ttccagtaga aatattaatg agcagtgaaa   55020
tggccagaga caggcagctg gaggaagatg ggggcactaa gtgaggaata tgcattcatg   55080
aatgagcgga aaatagatgc tggtgctttt ggtctggaat cttttttaaca ttgtcattag   55140
taatagattc aagatagaca tttaggtttc aaagggggca ccagtattat cagttgaaaa   55200
aacaaaagtg atgcattgtt tatactcatc tcttctagaa tgtaaaaatg aggatttacc   55260
ctgtagtaat atttctaaga aaaaaaatga aagttggtta gattttagct actaaagaac   55320
caaaacagac taatactttc ccattttact ctccttgtgt ggggttctcc ttgagggcag   55380
tggtaactgc tgcacatatg tgtgcaatat atttgtatca aggcattcgc tccagaaaac   55440
gagagagaga tttcccgggc tagcctttgt tggcattctg tcccagattc ctctccgctt   55500
tggggttata caaagattac tgtggttctc tgacttgatt tgaagctctg gcttagtcag   55560
ctgaggaaag actacagtcg ccttcctccc caggagttta tcagagactt gctcttccgt   55620
ggagggcctg ggaacgcagt gcctaagctc ttggtggggg accacccgc  tgtgcttggc   55680
ttcaaacagg ctgctgtcca ttgctttcag aagcatgaga ttgccccatc aggcttaaaa   55740
acaataataa aaatatattt gaaaaaaatc cccagtcgct tctcttgctg tctttggcag   55800
ttaggtacaa agcatcaaca aaatgttgta tacagaaatt ctgccttcca ggcttgttcc   55860
tttcttacag aacaatcctt aaccttgtag gactcttttt tcatgttttc ttaatgagaa   55920
aatatttcag agattattgg caccacaggt ttattccttt ccagtggttt acactcttaa   55980
ctgactgtaa tctttatgat cttttttttgt atttttcttt cacagtatgg gccatatcta   56040
atcagcctct cctaccgtga ctattcaaag aaaaggatct tttttttcttt ttcttttttct   56100
tttgtttcca tctcagaaca ctttcttgtc aatatcttct tttttaaaaaa tgaggattgt   56160
tgtaacaaat ttagcaaaca ttaagaatga catccattgc cgtggaagct accaaaaaag   56220
ttatatacct gtcctcaaaa tagcctgtga tctggtgaac tattcagata catgcaaatt   56280
agtcaaaata taaagaaat  agaggtgggg aacaaaggga gtgctgtgtt tgcgctgaca   56340
gtgctggccg taggttgcca ttttaaactc ccactttggt gtcccctttt gtttgaaggt   56400
ccctctggag tccagaggta atagagcagg ctgagtagtg gggcctaagg aaaactcagg   56460
gctgcaaata accctgtgta cagtgcattc agatcacatc tgtgagtcgc tggagggagt   56520
ggcctgaccg gttggtgtct atggtgggtt gtgatcatca ggctggtccc aggtgaggtc   56580
acctgaccac tcattatttt cttttttggta acagaaatta gtcagttaac aagcataact   56640
ttaacaagca taactctact tgttatttaa gacaatgtac tgtcctgagg agttctgaag   56700
```

| | |
|---|---|
| atcagtaaga tacagtctcc ctctttttt tttttttt ttgagacaga gtcttgcttt | 56760 |
| gtcacccagg ctggagtgca gtggcgcgat ctcggctgac tgcaatctca gcccccaggg | 56820 |
| ttctagtgac tctcctgcct cagcctctct agtagctggg attacaggca cccaccacca | 56880 |
| cactgggcaa attttttgt attttagta gaaacgggt tttgctatgt gggccaggct | 56940 |
| gttttctaac tcctgtcctc aggagaacca cctgtctcgg cctcccaaag tgctaggatt | 57000 |
| acaggagtga gccactgcgc cgggccagtc tcctctctta aagcacacct agaatcatgg | 57060 |
| tagtggtctc taattcagtg tgaggcacaa gtctcagatt cctctgtggg tgaagagggg | 57120 |
| gtcaggcaag tgtgtggtgt ggagatttcc tttcccgtgt ctgaggccat gatccatccc | 57180 |
| ctgtaaagac tgtgttgatt ccttgccctc tagactgaaa atcacttagt atgagaagaa | 57240 |
| atgttaccaa agggagtgtg aattgtgaag gagggaccaa aaacatgtca ggcactagtc | 57300 |
| tagcacaatg cctagcaaag aactcgggga ctgtgtgagg tacaggagta tgcgtggatt | 57360 |
| caagattcag ctacacatct gcaggagcca cggttcccca ggttaagggc agaacagaaa | 57420 |
| gatgaagtct ggacagcaga ggggtcattg aggagcttct taggggaggc gggacatcca | 57480 |
| ttaaactgtg cttgagtgat tgttaagatg taggtaggca atggacacgg agagcaggac | 57540 |
| gttttgggca tggggagtga gcaggatgt aggaagagga agtgaaggtg tgttctgagc | 57600 |
| atgttgacta ggcctgtcca gccttggtg ttcaaagagg cacacaagac cacaggagaa | 57660 |
| atggggcaca tcttcctgga gtgttcattt tgcttgaata tatagaaggg aaaataaata | 57720 |
| atttatctgg ttaataattt aaaacattgt tatattaaaa caggcaaatt atggaagaga | 57780 |
| atacaattaa tttcatggat ttttgttaaa gttcaaaatc tcaggttcc attgtttct | 57840 |
| tttgattctt cgatggaaga attttaaatt ctttaaagga gatcaacttt attccttcat | 57900 |
| tcacaaaaat agcaaaagca gccgggcatg gcggctcacg cctgtaatcc cagcactttg | 57960 |
| ggaggccgag gtgggcggat cacctgaagt cagcagttcg agaccagcct ggccaacatg | 58020 |
| gcgaaacccc atctctacta aaaatataaa aaattagcca gatgtggtgg tatgcccctg | 58080 |
| tagtcccagc tactcagagg ctgaggcagg agaatcgctt gaacctggga ggcggagatt | 58140 |
| gcagtgagct gagatggcac cactgcactc cagcctgtgt gacagagcaa gactctgtct | 58200 |
| caaaaaaaa aaaaaaaaa aaaaaaaag caaaagcaaa tggcaatcac agttgcccac | 58260 |
| agatccttac ttcatcatg aggcacgagc tatggtttcc cttagctccc tgtgggcagt | 58320 |
| ggggaagcag tctagcatgt ggccatgggg tttgcttggc tgttagacag ccctcttcag | 58380 |
| gtcccaggcc ctttgaccc atcatactca tcctgtgctt cttgacactg gcaaatcttg | 58440 |
| atgatggtta atgtgactcc ccgaaggatg tgcctccatc ccatgtgaca gatatgaagt | 58500 |
| ctgtctgcgc acagtctggg ccatggagtc tgcactccta agaatgcaca gaggcctggc | 58560 |
| tgccttggtc tcttgagata atgaaattaa gagtcttcag aggcatttct tgagtcttca | 58620 |
| atttcatctc ctttctcccc ttctggtcct aagcatgaca ttcctgtctc agcttttct | 58680 |
| ggccccctgc tgtctctgga ttctggtctt gtgagtttcc tttgtttggg ttgtgaatca | 58740 |
| ttaggcaatt tagataacag gttctgtttt tcctaggcag aggcaaactc ctctggttca | 58800 |
| aagctgcctc tggccttttc ccagctttga ggaagctgca tacagtctct ccaagctagt | 58860 |
| gtggcatcag aggccaatca gaggcagaat tggtggtggg tgaaagagcc tctaagcctt | 58920 |
| tctttactat ctctgttttg acttctattc tttccggtgt gtgttggatt gacctaagat | 58980 |
| tttctttgtt agaacaccaa actgcccagt gttatagata gtgttttat actttatcta | 59040 |
| ctcataaatt aaaggaatta agaaaatggc aggaagagct cagttattca atactaaata | 59100 |

```
gtgccctggc cttcattatt caggggagaa aagggcctgg gtctgtgctg ttcaacaggt    59160
agccactagt catacatggc tattgagcat ttgaaatgtg gtaaagttga attgagatgt    59220
gctgtaaggg taaatactg aatttcaaag atgatatgaa aaataatga aaaataatac      59280 ctccataatt tttatatgaa ttacatattg aaatgataat attttatat attgggttga    59340 ataaaatata ttattaaaat taatttcagc caggcaggcg tggtggctca cgcctgcaat    59400
cccagaactt gatcacttga gcccaggaat tagagaccag ccttggaaac agggtgaaac    59460
cccatctgta caaaaagata caaaaattag ctgggtgtga tggcacatgc ctgtggtcct    59520
agctactcgg gaggctgagg tgggaggatt gactgagcca gggaggtcaa ggctgcagtg    59580
agtggtgatc atgccattgc actccagcct gggcaacaga gcaaaccct gtctcaaaaa     59640 aaattaattt caacagttta ttttatctt ttcatgatct ggccactaga agattttaaa     59700
ttacatttgt ggctcacatt ttgtttccat tagacagtgc tgctttagat ggtagcttca    59760
taattgcagt aattcatacc tcttgagagt tctccaggga ttattttgtt gaagattttc    59820
tcttgcaatg atcaggctgg gtgagaataa cacatagtag actgtaagag tcttcaaggc    59880
aaaagctgtg tctgtttaat gtactttgga ggcaggagta gtaaagtcat tttgcttagg    59940
aaactcataa actggcttcg aaggcaattc caaaaccagt tttgagcatc atctttgaaa    60000
taagggtatt gcctcccagt gactccattg aaagatgcaa ttcatttggt tgcataagac    60060
tggggttgga atgttaaaga aaaaaaaaaa gtggggaag caagtttcat ttcttatagt     60120
ccatacctcc agtggggact cagcatgtag aaaggcactt ggacaggaac cacgatcata    60180
cctattgtta tttcatcaat gcagaatgca acataatgga ggcagaatgg ggaaagaaag    60240
cctttccagc tgcttcaaag aaaacccaga tgcttaactt gtttgctgtg atgtgctatc    60300 cttttcttcct tggtgccaga agagaaatta ttacaacata taaaaaatag gattatggcc    60360
ggaagaaaag ttattataac atacaacaaa taggattgtg ggatcctgaa tatgttattc    60420
aggatccata ttgtaaaaca tattttcttt gaaattttaa tcattagaaa ctatatagtt    60480
caaatatatt ctcaaggcta atccatccat attcaggaat ctttctttt taatattata     60540 aaatctttct atggacaaac tcacgattag taaagtattt ccccataaaa tagaaacaat    60600 cttttttcc aaaaagagg gttgttatta ttaaggtctt ttaaaaatac tttttgttct      60660
ggagcatgct ttatcttcta cttctctggg gtaggttaga ataattatc accgttttgt     60720 aaatcgggaa ataacacag ggaagtcatt tgtcgaaaag cacaggggac cagtgccaga     60780
aatggtttga aaatttagat cttttacttt ccatttcagg tgctgcaatc atagtatcac    60840
atggctatgt gaatagtaaa gtgtcttgtt tacgacagaa catactgttc tgaaaagtgg    60900
ggaggtatat ctcattttta ggggcattcc ttttctctaa attctaccct gtgctttgct    60960
tagtaataca gttatttata aaaatttata gaactgtaac agaggtaaag aattctcaat    61020
cttgctactt ctttcctccc aatagtaata aaaaggattt aggcatcctt gctagcttct    61080
cggaggcaaa gtccctgtga agctatgaga ccttcattat cacattccca ctgctttgtc    61140
agcttatatt tgtgaggaat ttaatcagtt ttattgctgt atatgactgg aaatgaatgg    61200
catttatttt ctctgcaggg atttatttgc ttttttcctt gggtggctat tcctttgttg    61260
ataatatttt cccaagtctt gaagcactaa ttgattttgg gacttaagca agatcacttt    61320
ttacattgaa tgcagaaact gtgttcctat ggattagggc acggtctgtg tagccatcaa    61380
ctggagatcc tgctgagaac tgtaaatgag gaagaaatta tgggtcatga taataaggtg    61440
```

```
ttccaagtct caagattcag acaggagcag acataaacag cctcttcctt ggagatatgc    61500
aaccagtcag ccaaggtgta ttttcttaag cattgaggcc ttgaaaaaca tatggaactt    61560
tgagaatatg tttgcaggtg tgaaaataat ggtcggtgga tctttctccc tgtcatgtat    61620
atatacagtg tgtagagagt aagagacaca ttttggaaaa gaaaaatgat tttaattgtt    61680
ggtgtttcag gacaatgctt tgcttttaaa gttacatgtc attatctcaa ccccaattca    61740
gtctattccc tgaagcacat tctccttgct ctcttactag tcttagcttt ggcatatat    61800 tgctcatcgt aggaacttgg taataaacct agatttaatc gtaactcaaa gaatacatga    61860
ggactttata tcacttttg atttcaaaga ctgctcaagt caaatgactg atacggaaat    61920
gtaccaaaaa gattccaggt ccagtcaatt ccttggaaaa tattgttaat agtagactca    61980
acttggcatg ttgggaacag ggagaaggtg ggaagccaag gctgggcaaa gccatagata    62040
ggaggctgag ctggctatag gacaggctcc agaaaattga caaggagtct gacttatcac    62100
ggccaagtag acatggcagg tttaggaccc atcttggaga gactgtgtag cacaatgatt    62160
aaatcggaat agaggctctg taattgtaca gacctgaggc tcaggccctc attctaccac    62220
ttactaattt ggtgatatgg ataaattact tttctgagca tctgttttgt tatctgcaaa    62280
atagggataa agcttgctca gcggactatt gtgaggatta aatgagagaa ttcacataaa    62340
gcacctagca ccaggcctgg cataagcagg aatttaataa atacagctat tattattatc    62400
ttcatcatca tcactatctg ggcttttgcc attttgcact ggttggtgag gatactgcag    62460
cagtaatctc tgggcaatta caaatattat atccatgttt aggttccgta ggtccaggaa    62520
gaagcaggat catattcagc catgctatgt ggacagagcc cagcaccccc tggaaaagga    62580
ggttcataag ggctgggcag gccttggaac ctcgctttca ggaaactgga atgtacattt    62640
ggaaagcagg cagatgccca cacataatac tgtagggtag cagagaaaac tgtagactca    62700
acatgaagct gtcagtctct agggcctgag cagagctgaa cctattcact gaagtcctca    62760
gaatttgcaa ctgggtagga ttggggcaag caggagctaa tgactcaata gccaattgct    62820
gtctttaaat cttactgaaa ttcttaaaac tattgaatgg cagcatttta gttttaagtc    62880
ttttccagaa tgtgaggtag gtatgttatt ctctgttttt cagatgacga cgtgagctta    62940
agggactgtg atccatagtt aaagcaaaag ccacaattgc atccttcagc tccaggctgt    63000
catttagaaa ccacacttac taagacagtg tctcttgtag acgcgtctat gcatcactgc    63060
agatgcttga agcaccatat tttgttccag ctgctgctat ggtgaccagg tcagagcagg    63120
ctttcgtgag tttctcacag gggcaatcac agtgccttgc cctgagccca tgttttctga    63180
cactgagggg ctcacatgtg cataacccag gtgtgctggg agtcagtgcc catggggcca    63240
cacttactca ttgggaacca gtggatggat gtttccccca tggatccccc agctgtgaga    63300
tgaatcttat tggaattctc aaagggtccc agtgagatgg agcatgagcc acctgtggcg    63360
gtggtcagcc aacttgataa cacatccagg tgttgctttt tccctccctc cctgtttggc    63420
tctcccagcc tttccctcct gctctctggg atcacttcca acataaacta cctacatgca    63480
aacttctgcc tttggtccaa gcaaagataa tttcaaaaag cgtttcctta tagtcacatg    63540
ttcatactga ctcccttgtc ctgaccaact cacagcaggt tggagcttga aagattaaga    63600
atctgttatt atagtccagg tgcggtggtt catgcctgta atcccagcac tttgggaggc    63660
cgaggcggga ggatcacgag gtcaggagat caagaccatc ctggtcaaca tggtgaaacc    63720
ccgtcactgc ccaggggcag ctccagaaat gctaagaacc aaggcctgga atcagggata    63780
tcaagagtca gcttggtact ttacctcact gtggctgagc tgatgcttaa gctgcaagac    63840
```

```
aaaagtccgc tttacaattc cctctccttt tctcaagcag aagacatccc tccttatagg   63900
caccacagct gggaatgtgc tgggtcacac ctgaagccag cctggctctg aatcccgttc   63960
aaggcctact gcaagtactg cctgggtatt gctgctgact attcagagcc caagggctct   64020
taagttagca ggtgatgaat gctgccagga ctgggttctt cccttcaagg tagtgggctc   64080
ccttctggcc caggatatat ctagacatgt cctccaggag gtagggcctg gaatggggac   64140
ctcaggactc tgtctggtgc cctatcctgc tgtggctgag ctggtatcca agttgttaga   64200
cagaggcctc tttagtcatc cctctcctct tcttgagtgg aaagaagtag tctttcccag   64260
ggctgcgagc tgcactccct tggccatcct agctggtgtc tcagtaggtc acgtgccccc   64320 tcctccccccc ccaccaaatc cactggctct aagcccagca tggtattagg atttgcctag   64380
aaattgcagt ccttgtaccc tggactacct taaagtttat ttagaatccc agagcacttg   64440
agcccatggt ggtgagcctt gctggaactt cgattccaac cactgggatt gttgatcccc   64500
tctggccagg gctggtctaa atgctccctc cacgggtgcc agctgaattc tgccggtgtt   64560
gctttccact gttttagggc agcactgagt tccagtgcac agtcccacaa tcgctacacc   64620
ttccttcccc caagaacaca gattctgtct ctgtgccacg cagctgctac tggggagatg   64680
tgtgaggcat ggcagcaatt cgtgactgtc tttcctaccc tcttcaatgc ctctttagt    64740 gatatgaagg agacatttaa gtgatatgtc tcaagatatt tttgacttcc cttttgattt   64800
cttctttaac ccattggtta ttcaagagca tgttgtataa tttccacata ctgtatttgt   64860
gaattttcca gatctcttct gttactgatt tctggtttca aagcattgtg gtcagaaaag   64920
atacatgata tgatttttaat cttctccaca tatgtaattt taaatagcca cattaaaaaa   64980
ctaaaaagaa acacgtgaaa ttaattttag taattagata ttccgtatat ccaaaatatt   65040
atttcagttt ataatcaata taaaaagtta ttgatgagat gttttacagt cttttacaca   65100
cacatatata cacatacata tgtatgtaca tacacatata tgtgtgtgta tacacacaca   65160
cacacgcaca gtctgttgtg tattttatac ttacagaaca cctcaattca gactagccac   65220
atttctagcc gcatgtgccc agtgggtatt gttttgaaca gctcagctct aaaggaagtg   65280
agctggaaga tggttggtgg tcattggaga gtgagacttg aaactgagat tgtggagggt   65340
ttgcaaatat ttataatctt aagatctagg atacaactct gggattgagt ttctttagca   65400
gagtggaaat ttagatcatg gaaggagaaa aggacaggtc attgagcgtc caggttttgg   65460
gaaagatcat ctgtgtcagc tttgaattca tcaaggttta tgagagagtg gagagactga   65520
taggatgtta ggtcttaaaa tcttcaaaag agaatctaca aactcctggc aggtctgatc   65580
caggagtttg taaatccctg taatcaagta gtatagtctg atagcatggg cttctaacct   65640 ggcgggcag cagttagaaa ggagggtggg aaaaagttag gaagtgcagt aacaagcaac    65700
aaggctgcag aggaagcagt tgtcctctgg ggagagccag atctcaatgt gagccagagg   65760
ttctggctgt aaggacttct gatggtgatc tatgaggagc tgaagcacag aggaatggtt   65820
ttaggagtca gatcaccaga tgtgcagagc tctatgggga caagagtcca ggtgccgagg   65880
gatgctcacc ccatcccctg tggtggaggt gtgtcccca ctgctgtccc agccttattg    65940
ccttctgagg gttctgataa cccgccgcag gtatggcctg tggctagcag ggtagaggac   66000
cactaagacc taagtctcac agtgtatctt tctaccccctg acttccatcc tgtctcctgt   66060
ttgaagtgtt gctcagatga ctgcacagta gtccttattcc agataaatga cttcatccag   66120
agttcacttt taaataataa tttatttttat ttttttattag agacagtctt gctatgttgc   66180
```

```
tcaggctggt ctcaaactcc tgggttcaag cgatcctccc accttggcct cccaaagtgc    66240
tgggattaca ggtgtgagcc accgcatcca gcctatttta tttttgaacc aacagtgcac    66300
aaagtacaaa attttaaaat gacaagagca tctgaatgaa aagtaagtct gcctccctcc    66360
agccacccaa tttcttttct cagagaacac acttgttacc ctttctggaa ttcatttgta    66420
acaggtggct cctctgtcca aattccctcc tcctatctct tgggggtttg gatgtgaagc    66480 tggcctttt ttccctgaaa atgcattcat gctccctagg acactggctt gccaaacagg    66540
agtctgggca cttagcagcc agtgctctgt gcaaaccagc cagtgctctg aattcagatg    66600
agagctttgt gtttgcctta ttggaaagcc cttgattcct gggcttctag aggtatgtat    66660
cactcaaaat ctctgcagtt cttttagggt aagtgaacgc tttacttctt catctattag    66720
aaaattattc tctcagcagg gtgcggtggc tcactcctgt aaacccagct cactcctgta    66780
ctttgggagg ccgaggcggg cagatcatga ggtcaggagt tcgagaccag cctgaccaac    66840
atggtgaatc cccgtctcta ctaaaaatac aaaaattatc cgggtgtggt ggcacacacc    66900
tgtaatccca gctactcagg aggctgaggc tggagaatca cttgaatccg ggaggcggag    66960
gttgcaatga gccaagatcg tgccactgca ctccagcctg ggtgacagag cgagactccc    67020
tctcaaaaat aaataaataa ataaataaat gaataaatga ataaataagt aactctctca    67080
gtggttcctc aatgcagggc tgcacactaa gcacacaaaa gtgaatcaaa cttgaccaaa    67140
cttgggtatt tggatcatac atgaactctg cctgaagtcc aatcccaggc tagctactgg    67200
cactggcagc ttctccacat tcaagaacca cggggatgtt gcaagtgcgc tgatgtttgt    67260
ggtaagcaga cattaatgga ataaggacta tgtggtcccc acagcttgcc ctgtcatgat    67320
cattctccag tgtgggtcac aggttcaccg gaacatcagc taacatgctg tataaagtca    67380
cagcaggtga gccacgagg gaatattgag ctccattctc tctgcaactc caccttcttc    67440
tctcagattg gagagtgggg ttcctagctt cctgtattga aattgtagcc aatcaatagg    67500
aaatctcaca cttatggaaa atcccaaatc ttaattgact ctgttcctta tcctctatta    67560
ccagtactca actgcagcat tttatgttgc tgttgtcatg cagaagagaa aggattaatc    67620
acggtaactt tcatcggcag aggggtgaaa caaatgaaaa aaatgttcag gcacttaatg    67680
cttctgtgaa aacccaatta gcaccccttc atggttataa tttctaatta cttttttgaac    67740 tgagaaaaaa atgttcttgc taattagcta attatttggt agtgaccttt tgataaaaat    67800
tgctttgact ctaaaaatgt ctgaagaaga gttacttaat ttaataaatc actgttattc    67860
taacatttta gaaaatcagg cattaagaag aggtcttgaa agtttctaag tttcagaaat    67920
accatgttgg gttgaaagtt ctttagatgt gtatttgtgc atgcatgtgt gtgtgtgtgt    67980
gtgtgcacat gatattgaga ttttgccac ttaaaattta tgagactaat gtcagttgtt    68040
agcaatagag aaaactgggc ttggggcata tggaaacttt ctgcaacatt tctgtatatc    68100
taaaactatt ctaaataag gaattttatt ttttcagtgt aagaaagtcc cttgaaataa    68160
aatttgatac agtctgcaat gaactgaatt aaaacatccc tgaaaagttt ctataaagtt    68220
taattccacg tagaaaataa cttaataaaa aaacctcaca atgtgttgcc ttcctaaagc    68280
ttctgacttc agctaacaga agcattaaga gtagtggttt taatatgtat gtaatagtgc    68340
catcagaaat ccctaatgtg cagatatatt aactataaaa ttacatgtca aatatttagt    68400
tgctgtattt agaagacaat acaattccta agagaaacaa taagcctatt tactaataca    68460 tctatttct acacctcagt caaatttata gttaaaaact agaatgaatt gtctttaggg    68520
ttgaaagcct gtctcatgat gctgatgagc cagcgtaagg aagtgtggtg actgtttgag    68580
```

```
ttgtgtctgt ctcttggtct gttctcttat aagtttctaa gaaattaact gatggtggcc      68640
aaatttgatt gaagtatatc tagtcttcct tgattccccc ttgaacctgt ggtttaatat      68700 tccacccttta aacataactg caggctgggc acagtggctc actcctgtaa tcccagcact     68760
ttgggaggcc gaggtgggtg gatcacttga ggttaggaat tcgagaccag cctggccaac     68820
atggcaaaac ctcgtctttta ctgaaaacat aaaaattagc tgggtgtggt ggcacacaac     68880
tgtaatccga gctactctgg aggctgaggc atgagaatca cttcaaccca ggaggcgagag    68940 gttgcgatga gccaagattg tgccaccaca ctccagcctg gatgatagag tgagactctg    69000
tctcaaaata aaataaaata aaataaaaca aacacaattg cattttaaaa aaccagtgat    69060
ttaattgaga aaaatgcgta tgctcagaca aaaagaaaa aaaaatgact tcagatgggc     69120
atgtatccta tcagataaat aaatttcaat aaaattaagt aggtgggtta tacagataat    69180
gagagagaag taatgataat cataaaattt gagttgacgt tcctttgtgc tttatgcatt    69240
tagcttaagt ttttcttgac aacagacaac tataggaata tagaatatag tctgtagttt    69300
aaaaggaact ttggcacaat gtatccaact acctaatact gtattagaga gggcctttga    69360
acttgagctt cctctgccta gagctctctt catcctgacc tgacagggtt gactcctggt    69420
cattttaatt ctcagctcag aagtcaactc ctctatcttc tgcaccctct ccctttttccc   69480 tcatggtctg ccccatcaca gtgtttggtt tctgtcctgg cactcaccac agtgggaatt    69540
ctctcaacgt ttattatttg ctttccttat ttatcacctg tctccttcac cagaattcag    69600
ctttatagga gcaggggcct tgtctgtctt gttcaccact atatcattcc ctgtgcttgg    69660
cacatagcaa gttggtaatt taaagtttga cattgaaata catgtgtgtg tgtatctatg    69720
tgtttataat tactggtaga aacaggccaa aaagatcccc ccaagaatga ataacaacct    69780
ccacttacta aacctttgtc tcattctttg ctccattcct gattttctta cacacttgta    69840
ttgcttttag gacatgataa atgatacaac ttaataggaa aatgataaat ctcaaggaga    69900
aaacttggca ttaatgtaac atttaatctg cagaacaaat tgatgttgta gcttccttct    69960
tatctttctg tttttatcaa taagagaaag atgtctttgg ggatgggaag gaaacagagg   70020
gtcttgaggt aggattccca ggggtcctca tctcagtgac ctcttgttct acgtgcatttt  70080 tcccggaaga caggcaagtt tagtgttttta ccacattaac cctgaaatct gataaagtct   70140
gttctcctct ttaaactaaa gacagtttgt ctgtgtgccc aggcccagtc tcctttcttc   70200
tggactggaa caggccaggg aagatttctg ggccttttttt ctctttctttt ccgtagtcag  70260 ggcacctggc cacagctttg tctcttatct tgccttagaa cttgcatggg aagctgtcat   70320
agaccgcctg ctgagagcct taaaagaaat gtaaggtaga gtgtgtaatt attatcagct    70380
gttcacatat gagatgtaag tatcttggat attttggatt ttatgaagt catacgcgct     70440 taccacatta tattcatccc gaacttcagt aattttacaa tgaatcattg atcttaagga    70500
agacttgtaa taaatgctaa tctcagagca ttaatgaaga cacaaactaa gactacataa    70560
aggctataca ggatgagcat ccctaacctg aaaatccacc atctgaaatg ctcccaaatc    70620
tggaacttct tgagccgata tgatgccaca agtggaaggt tccacacgtg accttctttg    70680
actagtcgca ttcaaaatgc agtcaaactt tgtttcatgc acaaaattat ttaaaatatt    70740
gtataaaatt accttcaggc tatgtgtata tgaaacataa atgaattttg tgtttagatt   70800
tgatcccagc cccaagatgt atcattatgt atatgcaaat atcccacaaa aaaaatttta   70860
aatcccaaac acttctggtc ctaagtgttt tggacaagga gtattcaacc tgtagtgtcc    70920
```

| | |
|---|---|
| acttagatct ggttggtgtt agcttccatt ttaccttctt attcatacc tcactctcct | 70980 |
| tttcttttt tccccaaatt aatgtagtat ccatatttag tagaaagcct atttgacctt | 71040 |
| tctcattatt gcctgtagga catctttct tttagtgtgt agagttagct tgccttcgac | 71100 |
| tgacattaac aaagtgcttt cctaatcacg atcctcaatg cagatagtct tttcctggaa | 71160 |
| tcacttgttt tccttttagt tacggtatca atgcagctca gaaaggtcct aaggtcatga | 71220 |
| ctgatgaaac ttcaagaaaa aaaaaaagcc aagggcctag aaattgtgtc aattttaatt | 71280 |
| gattagaggt ggcagcagta gttcttggtc aagtaattat caaataactc aaaaaggtat | 71340 |
| ccaggaaatg actgggaagc agaaaccaag ctgattgcgc attgatagtg aaaaccagat | 71400 |
| ttgtttgaca aaagggaaag tttctgccag aattgaatta tgtctcttct aggcaaaaat | 71460 |
| acacacataa ggaacaagga gcaagctcaa aaactaaaga aagtagccca ttgcctggca | 71520 |
| aattactaga aaaataatag gaacgtttaa tgtccataag aagactttca tgaggccagg | 71580 |
| tgtggtggct accacctata aatcccagca ctttgggagg ccaaggcagg tcacttgagc | 71640 |
| cagagttaaa gaacagcctg gccaacatga ccaaaccctg cctctactga aaacagaaaa | 71700 |
| attagctggg cgtggtggca ggtacctgta gtcccagcta ctcgggaggc tgaggcagga | 71760 |
| gaatcgcttg aacctggcgg agattgtagt gagctgagat catgcacgcc agcctgagtg | 71820 |
| acagagcgag actctgtctc aaaaacaaag actttcatga aataaaacga ataatgaggt | 71880 |
| atccttggca tcatctgatg gctctgagta tttgttgggc tgctccattc tgatacgtgg | 71940 |
| gccattctgt ccaacaaggt gtggcattga gaaggattgg tggtcacatt aagggcttgt | 72000 |
| tttctttat attgttaaat aatagactct gaaatgttac ttttctctgt aaaacaaggt | 72060 |
| agtacttcct agttcatttc tttcttcttt gtaaattaat atttaaaata atactttcta | 72120 |
| acttttggat taccagatta gactttattg tataataaac cacatgattt tagatttaaa | 72180 |
| gtcagctttt gaaagaaatc cttattattt gttcattaat tttaattaaa aatttgataa | 72240 |
| tgtttctgat aaaaaatatt aatatgtggc tgctgggcac agtggttcat gcttgtaatc | 72300 |
| ccagcacttt gggaggccaa ggcaggaaga ttacttgagg ccaggaattt gagaccagcc | 72360 |
| tgagcaacat agtgagaccc tgtctcgaaa aaaaagtttt aaatattagc tgggtgtggt | 72420 |
| ggcacatatc tgtaatccca gctactcaga aggctgaggt gagaagatga cttgagccca | 72480 |
| ggagtttgag gttacaacgt actatgattg caccaccgca ctcctgcctg ggtgataaag | 72540 |
| tggtatcttg tctaaaaaaa aaaaaaaaaa atcatggtat tgaaaggtat aaagaggaaa | 72600 |
| atgtgaatta ttattattct actcctaagg taaatattta acctttata gtgaaaattt | 72660 |
| ttctgacact aaaaattttt ttaaaaacat gagtttaac aatagcagtc atcttaagaa | 72720 |
| atcattattg aggtgactac agctagcaaa gaaatttttt ttcccccagc tgaaatcttg | 72780 |
| ggtacccttta tactttggta taaacatgta cacatagtag cagagaataa ttgtgatgca | 72840 |
| ctaagctggc aggtctgtgg atttcagctc caaacacaaa tatgtaacac tgagcctata | 72900 |
| ttgaaatatg gattaagagg ctctaactca cttttgtaaa ataaaatgat aggagccaca | 72960 |
| tttgtgttta attatagcat gagaaacctg agaatcaaaa gaataagta agttccatca | 73020 |
| cacaacagga taggaaaaat agaaagtcta cctcacactg ctgcatttgt ctgtaacttg | 73080 |
| gcctacttta tgaaactcaa aagcgaatta agccgggcgc ggtggctcac gcctgtaatc | 73140 |
| ccaagcactt tgagaggctg aggcgggcgg atcacgaggt caggagatcg agaccatcct | 73200 |
| ggctaacacg gtgaaacccc gtctctacta aaaacacaaa aaattagccg ggcgaggtgg | 73260 |
| cgggcgcctg tagtcccagc tacttgggag gctgaggcag gagaatggcg tgaacctggg | 73320 |

```
aggcggagcc tgcagtgagc ggagatcgcg ccactgcact ccagcctggg cgacagcgag   73380
actctgtctc aacaaaagaa aaaaaaaaaa aaagcgaatt aaaactacat tttaaaagcc   73440
tggttctcat cacagttttt ggctgttagg gataggactg gtgcaggcaa cattgctcca   73500
gctgaccagg aaatggtctt ccagaatccc tctgatttaa tgagccctat ctcctagctc   73560
tgcgtgggtt ttgagtaacc atgaaaaaaa gcttttaagt gatcaaaatg atatattgat   73620
tcttcttttc taatgccttg aatattcttt cagcaaagct gctttaaaaa taatttctga   73680
ttttctatttt ggttttatc aagacatgga aatggataga ggtattgtga attgatccca   73740
agaggaagaa attcctgtaa aatgtagatg cgttggtcac atgggggaga agctcctgtc   73800
tgacctctat ttcatattat gagctcaaaa catgctttct catgggccat gtgacatcat   73860
gtttggttga gcaaaatgtt aatgttgcag tgattgggat cagtgctgtg cttcctgacc   73920
cacctgctgc attggtaaac ctgaaaccac cgcagcaaat atgtttattt gctttccct    73980
gaaatgtgct gttccttttt acctcctaca gataaaactg acaggccctt ttcctgctag   74040
ccaaaaacag tgaggagaac caggtggaag acacagcttt taaaatgtag ttttaattca   74100
ctttgagtcc cataaagtag gctgagttac agacgagctg tgggcttcac caaatcactc   74160
catgacctca ctttccttct ggcaaacctc tcccagtgca atatgttgat atcgttgatg   74220
gagtatgaga aacagcttgc tggagaagag cctgcctgtg atctcttaag gttgccagac   74280
aacatcactg taggccatct tctctcttt tccttatgct tcaatttccc atggcttttg    74340
tgtactacaa taacgtcagt aaccaacctc actggaacca cttggcttgt agatagtgaa   74400
agctctgttt acattagagg tagtttcaga attgatgaaa gcctgtgttg acttcttagt   74460
ttcttatagt ggatattttg attgaaaaca ctggaatctc caatgtgata attgaccta    74520
ctgttgtgta ctgagatctc tattttagat tctccccaaa taccacctt tttctattt     74580
taaaattatt attgcaaatt cagtcaaata atatggtaga cagaaatttg gatgggcttc   74640
aggaaaagag gtttaatagt ggatttgccc ctaactagct gtacagcctc ttgcatatca   74700
tttaatctat cttgacctca ttgtctttgt attgagattc tgtggtccag tcatgggaat   74760
taaaatcacc atccatagaa agctgtgtct ctcgtctctt tgtgattcaa cacttcatct   74820
tttctgcaga gtagaacacc ttgtaggcag gttcataatc ttctctgtac ttggaaatca   74880
cccggaaagc ccccttttcaa gtttctaatt gcccaagtta ttctttttt ttttttttt    74940
ttttttttt tttttttttt ttagagggag tctcactctg ttcccaggc tggagtgcag     75000
ttgtgcgatc tgagctcact gcaacctccg cctcctggtt tcaagcgatt ctagtgcctc   75060
agcctcctga gtagctggaa ttacaggcgt gcaccaccac acccggctaa ttttttgtatt  75120
tttagtagag acgggtttc accatgttgg ccaggctggt ctcaaactcc tgacctcaga    75180
tgatccatct gcgttggcct cccaaagtgt gcccaagtaa ttctataatg tagccaggat   75240
gagaaccact ggtatcaggt ctagacccag ggactcatta ttataaaaca ttccccttg    75300
acatacctt tcatccttga gtcaggacaa ttttacctt cagaaagtag ctacagtcct    75360
tttataattt actcctcacc aaaggtaaaa tacatccatt ttctctgtgt gtgacttctg   75420
actattctgc actgattcaa tacccctccg ttttttgctt atttttttcat tctcaccatt  75480
caaccacact tgacacttga atacttttg ttgatttaaa agaacaacaa caacaaaaat    75540
acagagtaag atcacttgac tttattgtat tagccattaa atctctttct ggagcaatag   75600
ttctctaagt atggtcccag gagcagcaat atcactatca cctggaaact tgttagaaag   75660
```

```
gcaaattctc aggcccttt ctggaccaga agctctggag atggttccca gcagtctgtt      75720
ttcacaagac ttctaggtga ttcgacacac tattgcttga gagctgttct agagagattt      75780
tatattttca gatagttgga ttttaaaaa ttttttagt gtgctcagat atttttgaag      75840
taatcgttgt ctgaacttac ttggtctaga aatagaagag atgttctatt tctaaagggg      75900
atatttccca atcctaccca tcttttatc ctttagaagt tttcatcttc ttttctgctt      75960
ttagaagacc tatccatatc tctcttattt ttacactgaa aatttagtct tacattctat      76020
tatcatggaa actttaataa tcaatgctat ttcaatgatg tattatgatg tgatgtaaca      76080
atagatgggg cagtgactaa tacaacatta atttctactt cttcatttgt ttatttttat      76140
tggaccttca gatgacattc ttcttacttt atgaaggggg ccagcccctc cacacctgtg      76200
ggtatttctc atcgggtggg acgagagact gagaaaagaa ataagacaca gagacaaagt      76260
atagagaaag aacagcgggc ccaggagacc ggtgcttagc atacagagga cctgcaccgg      76320
caccggtccc cgggtttcct cagtatttat tgattactat tttcactatc tcagcaagag      76380
gaatgcggca ggagaacagg gtgatagtgg ggagaaggtc agcaagaaaa catgtgagca      76440
aaggaatctg tgtcacaaat aagttcaagg gaaggtacta tgcctggatg tgcatgtagg      76500
ccacatttat gcttctctcc acccaaacat ctcagtggag taaagagtag cagagcagca      76560
ttgctgccaa catgtctcgc ctcccgccac agggcggctt ttctcctatc tcagaattga      76620
acaaatgtac aatcgggttt tataccgaga cattcagttc ccaggggcag gcaggagaca      76680
gtggccttcc tctatctcaa ctgcaagagg ccttcctctt ttgctaatcc tcctcagcac      76740
agacccttca cgggtctcgg gctgggggga tggtcaggtc tttcccatcc cacaaggcca      76800
tatttcagac tatcacatgg ggagaaacct tggataatac ccagttttcc tgggcagagg      76860
tccctgtggc tttctgcagt gcattgtgcc cctggtttat cgagaatgga gaatggcgat      76920
gacttttacc aaacatactg cctgtaaaca ttttgttaac aaggcacatc ccacacagcc      76980
ctagatccct taaaccttga ttccataaa cacatgtttc tgtgagctca aggttggggc      77040
aaagttacag attaacagca tctcagggca aagcaattgt tcagggtaca gatcaaaatg      77100
gagtttctta tgtcttccc tttctacata gagacagtaa tggtctgatc tctctctctt      77160
ttccctacaa cttaagaaca cagacacaga ttatttttta aagttattct taaacatgtg      77220
gaattacttt ataataaacc caaaagttgc tgttgttaga gggaaatttt tactaagtca      77280
agtactctct ggaaaaaaaa atgtgtgagc ataagctaat atcataaatg aaatgatgaa      77340
gaagaggata agggcacatg gtcctaagtg aggaaacttt gacccagaaa ccttttgcag      77400
tgacagaagt agaccaagag tccaagtctc catgcttcca attcagtatt ccttgcatga      77460
aatgtcactg cctttcgaga ctataccgtt tacctaattg gttggatctt tgtcaagagc      77520
ttgatccaag tggagtttct ttgtttaata tataaagcat ttgcaagtcc tttcaagggc      77580
agcacatagt tttatttaac tccctcaagc cctctcacct ctgtcaagtt gcaccaggaa      77640
attcaaggtc tagccaaagg cccccaatga gttaaaaacc caaccatcct gcagagtaga      77700
agaaattaat gtcaaaacca gatgttcctc tgtgggcctt gctggattca taagtcagga      77760
taaagccagc gtggatgcat gcatgtcaaa aaaaaaaaaa aaagtcttgg ccagtgttgt      77820
agagaaatga agtgttgttt catctgcagt tcctctccag tccttgctgg ttgggagcac      77880
tggctcccgg gagactggtg gccctgacac tcaagccatt aactgagaat gctctctaat      77940
cccttgtttt cattgttggt gttccggcca ggctgcccgc acagagcctg cccgttttca      78000
ttggctgcag gaattgttat tggagtggct gacagctgtc tgccaggctg cctgaaactg      78060
```

```
ccttcctgtg ctctccgctg ctgctccact tcacagcgct attgttcctg ttgagccttt    78120
tcttaaaatc tttcccagct gtatcctgat atggtaaacc acttaaatta gctccagatt    78180
gttctgttta ttttgtgtta gataagcgac aaaatacagt cccagcggca gaccaagagg    78240
agagtggaag tcgggggagg ggggtcagag gacacaaggg cttttacaac acaaggtaga    78300
gttcccagac aaaactgtga gaggcacaag tatgatacag tcactggcct gaccatttat    78360
acgtgactct gatgggccag gtgagcaata acgttgcatc tgcgcacacc tcattccaga    78420
aaagaaaatc aagacccag catacagcta cactggaagg gagctaaatt tctattattg    78480
gaaatagaca cagtattgct gtcaggttgg ttgccatgcc agctgtccag gtaccatgct    78540
tgatgccctg attaccacaa gacttccccc ttcccctgc ttttaattat ccttctgtag    78600
tgcagtgtat ggtaactgat gggctcaaaa ctggcccaca tttgccagtc tccctatatg    78660
ctcagcactt gaaatgagt cttctctgct gtaatttaaa gctagaaatc caaagacatt    78720
gagtcaccag cataggtatt ttccacacag ctgcaagtga acttcacaa tggacttggc    78780 cgctatttgc ttacacttgc catctgtgca accgctctac ccgtggcctc ccccgctttg    78840
tggttgtctt ctaacaggag cagtccacgc aaagccttcc tgaatactta acaaaatttt    78900
aaaaaatata atagatactg tcctagcatg aaggcgctgc ctttgtgatt tttaggaatt    78960
aacccaaata aaatatgaaa ataaactac cgagtgcttt aacgcagcta aagcatgcaa    79020
gcaaaaccag caaccagctg agttccgaca gttactgaga gttttgtatg tggtaattca    79080
agactcccca ggaaagatct catgactcac tccagtgtgg ctgggcctcc agtcctcact    79140
ctgaaccaaa gtcctggaaa cacttttcca ccacgttgag agaaggcgag ggaagaacag    79200
ggtcaggagt gatcaaatgc ccttagaaac agtctctttc tttccttttg ggaaaacaaa    79260
ctcactgtgt aataaaaagg tacaaagcca actttggaat aataatcacc ccgccccatc    79320
cccttgccct ctgatggaaa gtgccttgtc ttctccatca aggtctagct gggggcttga    79380
acggcctccg tgtcacctct aattccccag ttttaccttt gtttcctttc tctgtatctt    79440
ttttgccctt agttgtgtac agtcttgtat tttttcacat aggctatgct ttctgtggat    79500
gttgcctccc tcgaaagcag ggaccatgtg ttgaacccct gttgccttt cccagagtag    79560 cgggcaccta gcaggtgctt aattaaggtg tgtcaaataa ttgtttcctt ttttattctt    79620
acctgacatg aagtatgctc ctgtatcaat tcagatgaag gtttaaaaaa aatcaagaca    79680
agtatcacaa gttcccttag cccattctca ttaaaatcat gggcaccacc ttcccgtgct    79740
caccaggatg gaggaagtca acaaatatct ttctcattga ttaaaaactc tggataatac    79800
tgaaagcaac tatctgaggc ttcttaaaag tacttaggtt ggtgctaaag taattgaggt    79860
tttcgaaaac tgcaattact tttgcaccaa cctaatataa cagcagggat gataagaata    79920
gggacagaga agaaaacaaa atcaggtgaa tggagaatgg ggaataaagt caaagcttca    79980
tgaatccctt gtgtggtgag ttttggaggt ttattttctc tcctctatct cttggctttg    80040
acctaagagc caatggaatt atggaactat gcagcaggca ctggcagcaa catctccaag    80100
agaaacctcc tacttctaac cagaggtcta ggaaagtggg ctcttgctca agaatatggg    80160
gaattcctat tttatttgtt ttttctttc ttttaatttt ttgagattga gtctcacgct    80220
gttgcccagg ctggagtaca gtggtgtaac catagctcac tgcagcctct acctcctggg    80280
ctcaagtgat cctcctgcct tagcttccca aatagctggg actgcagtca tgcaccacta    80340
cacttggcta atttttttttt tttttaattt tttatgtttg gttagcgatt ggatcacact    80400
```

```
atgttgcctg gctggtgtga gccacagtgt ccagactgtt ttttcttttt ctttcccttt    80460
tctttcttaa ctctacccca agacaggccc cagttgaaga tctgcattgg tgttgtggtg    80520
gggtgcaggc acctaaaatc tcaaaagaag acccacattt ctgaccggag tgtgagataa    80580
tctctgttat tttcctcttt tttttttttt tttttttttt ttttgctact ttgctcccaa    80640
aggcaacctc agttatgcag aagtgcatga cagaatgggg aactacaacc taacagaaac    80700
ctgttttcct gatcagagaa accacataaa ggggcccctg gagcggaggt tggggtggga    80760
tctgaaggat ctaaagggag agaagaactg agaagaggga tccctgatt ctgtgtatga     80820 gctaagcccc aggctcacct ccaagtgcat atatgccaca caggcccaaa ggagcaaagc    80880
agaggcttcg aaaactcaac tgccatgtga accactgccc aggtcctaga ttaacccctg    80940
agtggcacat gcgctgggca aacccaaacc tcatagcaaa ggctttaaaa actaaactga    81000
cattagagcc actgtccaca gaaggtgaga caaaacttgt ggtctgagtc tcactaggtt    81060
gattctctgc ttaaccaaac aaacatcaac accctcgaga ggattttaac tagacctaga    81120
ggctcagaac atggtattca aaatgtctaa tagacagtcc aaaattactc attatacaaa    81180
aaaaaaaaaa caggaaaata cgagcagtac tcaagggaaa agactaaaaa tagattattt    81240
cagctgtgat gagctcattt gagatgatca tccaaatatt ggtgttgtca gacaaaaact    81300
ttaatgcagc tattgtaacc attctccatg agacaaagtt gaacactctt gaaatgaatg    81360
gaaaaatagc agtgaaatag aaactaaagc caaacaaatg aacaaacaaa acaaatgaaa    81420
attatagaac tgaaaaacac aatatctgaa atttaaaatt aactctatgg gtccaatagc    81480
agaatggagc tgataaagaa gagtcggtga acttcaagat agatcaatag aaattataca    81540
gtctgggctg gtcgtggtgg ctcgtgcctg taatcccagc actttgggag gctgaggtgg    81600
gcagattgct taaggctagg agttcaagac cagcctggcc aacatgatga acccccatct    81660
ctaccaaaaa atacaaaaat tagtcaggtg tggtggcaca cgcctgtcgt cccagctact    81720
caggaggctg aggcaggaga attgcttgaa cccaggaggg cagaggttgc agtgagctga    81780
gatagcgcca ctgcattcca gcctgggcaa cagagtgaga ccctctctca aaaaaaaaa     81840 aaaaaaaaag aaagaaagaa aagaaagaaa attatacagc ctgaaacaca gaaaaaagga    81900
agaaaaacag tgctgcaggg acctatggaa taatatcaaa aggtctagca tttatgtcat    81960
tagagtccag aaagagagca gaaatattag tgtagaaaaa atatataaag gaataatgtg    82020
tgaaaacttc acaaatttgg tgcaagatac atgtacaaat tcaagaagct cagtgaaatc    82080
caaacaggat aaactcaaag aaaactcacac cagcatcata atggaactgc tgaaaactaa    82140
agatgaaaaa aaaaaatacc ttgaaagcag cagtctcatt catgggattg aatgaaattg    82200
aatgaaagca tgttcacaca aaaaacaata cccatatatt tatagcatct ttattgataa    82260
ttactaaaaa ctgaaaaacc caaatgtcct tcaactagca aatagataaa cagatgtggt    82320
acttctgtgc agtggactac tactcagtag tgtaatgaac tgttgataca cacattagca    82380
tggatgaatc acaaatgcat tatgctgaat gcaggaagcc agactgaaaa gattacacac    82440
actatgattt ttttatatga cattctggaa aaagcaaaac cttaacgaca gagaagcatc    82500
agtggttgcc aggggttaag gctggtgtca aatttgtct acaaagaggt ggtacaaagg     82560
agttatatca cagtgataga atgttctatc ctgattgtgg tggtatttat atgactctat    82620
ttgttaaaat ccataatgat gcacaccaaa ataagtgaat tttactgtat gtaaattaaa    82680
aagaaatcac cagcacatga tttcatatct gatatggtta atatatcttc atgactatgt    82740
gaagtataga aaagattcat gtaatctctt atctattttg aagtcatttt ccatttgatt    82800
```

```
ccataaactt tcaggaagcc aaaaatggaa taaacaatga aatggtctct gatacataca    82860
gaaagctttc caaaaaagaa ttttgtgttt catatgccag gcagatgttt tgtagggtca    82920
gcttaccaca aaaggcctcg ctgaaaaaat gcagtataaa agtaggggcc tgtaagagaa    82980
agagaagcac attgactcca gaggaggtct actgttttat aaaagaagcc aagcaaattt    83040
gatggactgg tgaaaacaag aacaaagaat ctgacatgtc ttggaagctc tgggttttga    83100
taattaggga agtatttaga atgctgtctc gaggaatcac atcttttgtg ctgagatata    83160
tccctgcttg tgttctgaaa tatacatgga gtgggcaggc ttggactgtt taaatgaagc    83220 agattttta cattcttgtg acactaggaa gacttttcct gaatgtagga ttttttcttt    83280
aacgcacctc tcatccaaat ggcaaaacat ccaggatggg tgcttacttg caatgagatc    83340
tccccagctg accagagctg tactttctcc cactgcttat tccccctctg aagttacatc    83400
atcattttgc tccctggtac accattatgg gtcttatcta tttttataca taaatatatt    83460
aaacaaaact gttggtttta agaaactttt gacctattct aagacctatt ctctgttttt    83520
ctataaaagt tttatggttt tagctgttgc atttaggtct ttgatctatc ttcttttttcc   83580 tcatacagta ttgtttttat tgagatataa ttcatatacc atgaaattca tccttttaaa    83640
gtatacagtt cactggtttt tagtatattc acaaagttgt gcaatcatca ccattgtcta    83700
attctagaac attttaaaaa ttaaacatac aagaaattct ctacccctta gcagttactc    83760
ccaactccct ttcctccctc tgtcaatcac ataatctatg ttttgtcctt atggatttta    83820
ctaagctaga catttcgtaa aaatggaatc atacaatata tggcttttttg tgtctggctt    83880 cttttatttg gcataatgtt ttagatgttc atccattttg tagcataaat cagtatttca    83940 tttcttttg ctgatgcata atatcccttt tattgctata cattgctgaa aatatacatt    84000
ttaaaaaatc cattaatcag ttaatggata tttgggttgt tcctactttt ttgggctatt    84060
atgaataatg ctgctatgac cattcaggta ccaattttg tgtggacata tattttact    84120 tctcttgggt atatacctag gtgtggaatt ggtggatcat gtggtaaatc tatgtttaac    84180
tttatgagga actgctaaac cctttgccat ggtttgaagg tatctcccaa aagttcatgt    84240
gttggaaacc gaatccttct gtcctcatga atggattaat gagggttttg ccatcatgaa    84300
tagattaatg tcactgtcac aggaatgggt tcattacatt gagagtggct ttgttataaa    84360
agtgagttct ctcagtctct cttgctcttg ccctcttatc atatgatgcc ctctgtcatg    84420
ttatgacacc acatgaaggc cctcacctgg tgccagcacc atgttcttag acttcccagc    84480
ctccagaacc atgagctaaa taaacttgtt ttctatataa attaaccagc ctatggtatt    84540
ctgttacagc aacagaaaac aagactaaga cactgttttt caaagcagct gcatcatgtt    84600
acactcccac cagcaatta tgagtgttcc agtttctcca cgtccttacc accacttgtc    84660
aattgtctgt ctttttttgtt atatagtaat cctattgggt ataaagtggt atcttcttat    84720
ggttttagtt tgtgcctctt ggatgactaa tgtgggacat cttttttgtgt atctattgac   84780 catctatttt tgtgtatctt ctttagagaa atgtctattt aaatcctgtg tcaatatttt    84840
aatttggtta tcttttatta ttgagttgta atatgattca tctttaattt ttatgtgtgt    84900
tatgaagtag ggtttgtcaa ggtttttgttt gttttttta acgtagatat cagaatactc    84960
tagcattatt ttttttgaa aaaactattt ccctattggt tggtttggca cccttgctaa    85020
aaagcaaatg accatttaaa tgtggttgtt ttactaggca ctccattcca gttccatgaa    85080
atcttgatta ctgtagcttt atagtagttc ttgaaattgg atagtataat tcttctaact    85140
```

```
ctgttcttct atttgaaaat tgattgcagt cttgggataa atatcacttt atcatcatgt   85200
ttgtggtagg cagagtaatc ccccgtctcc ctcctgcctc caaacatgcc ctaaagcctg   85260
gaacctgtga atatgttatg ttatatgaca aggggaatta agattgcaga ccaaattaag   85320
gtttctgata aactgacctg aagatgagga gattgtcctg gattatctgg ttggaccagt   85380
gcaatcggtg accttaaaag tggaagaggg aggcagaaga ggaggtcggg taatatgata   85440
tgaaaaggat tcaaccatca ttgatgactt tttttttttt ttttttttcct gagacggagt   85500 cttgctctgt cgccaggctg gagggcagtg gcgcgatctc ggctcactgc aagctctgcc   85560
tcccaggtcc cgggttcaca ccattctcct gcctcagcct cccaagtagc tggcactaca   85620
ggcgcccgct accatgccca gctaattttt ttgtattttt agtagagacg gcttcactg   85680 tgttagccag gatggtctcg atctcctgac ctcgtgatct gcctccttag gcctcccaaa   85740
gtgctgggat tacaggcgtg agctactgcg cccgcccatt gctgactttg aaggtgaagg   85800
aagagggcat gaatcaagga atgcaggatt tcaaaatggt agtatagaag caagccagct   85860
tcaatccctc aatagaagac caaaaacaaa tatatagcat tgagattttc accagcaaca   85920
acccagagtt caagtatgag gatgagacag cccccagggc cacagagaag tggaaaaacc   85980
ttgagcatat gattggagaa tcagatttcc acgtctgcga gtcccctccc ctacattctt   86040
tcagcaccaa gcatgtggaa aatctccctc aattctgttt ttacactgga aaagtgaaa   86100 ttgagtggtc aaccagcttc ctcaccttct tgggttccgt agcaggagtc ctgtccctgc   86160
cttaactcat gggaagcatt gtgagtgcct gtagggagaa atatctctga ggacaggctg   86220
caacaaaggt cagaaggtga gactaccatc cccaaccctg gaaactctgc tctgtaactc   86280
agccaaatga gacaccaaat cagagtggct attcagcagc accacactgt aggaggtaca   86340
ttccacaggt tccatgggc aggaaccct agccagtctt cccacactgc tgactagggg   86400
ttcctgccta ggagcctgta aacatacct gggataatcc ctttggtgac tccccatt   86460 gggacaggca gcactgcaac cgtttactag agccaaagtg aacctgggct tatagcgcca   86520
cctagagccg aaaaggaggc agcaatctag ttgcaaagat taagcaaata tattcaatga   86580
aagacaaaac aagctggaca gagaaaacta gaatcaataa ttaatccttc aatgcaaaga   86640
catagacata tacccgcaag taacaacagc aaacagggaa ccacagtctc cccaaaggac   86700
aaagcaaaaa tccaatgact gaccctaacg agatggcgac tattagcttc tgaccaataa   86760
tttaaaatag cagtttttaag gaaactcagg tatctccaag ataatacaga aaagcagaaa   86820
tttatcagag aaatctaaca aagagattga ataattttta aaaatcaaa cagaaatctt   86880 agaactgaga aatacatttg ccaaactgaa gaactcttaa gaggctctga gcagcagagt   86940
gagccaagca gaggaaagaa tctatgagct caaaaaccag ctgtgtgaaa atacacaatc   87000
agagaagaaa aaagaaataa gaataaatg taacaaagac cacctacaat atgtaaaaaa   87060
ttacctcaaa agaccaaatc taagaattac tgctgttggt gttcaagaga gagtgaagcg   87120
agagcaaggg gtagaaagtt gattcaaaag gataagaact gaaaactttc caaaacttga   87180
gaaagagaaa tatccagcta cagaaaggtc agagaacacc aaacagattt gacccaaata   87240
agactactcc aaggcataga aaatgaaac tctcaaggt caaggacaaa gagaggatcc   87300
taaaagcagc agagaaaaga agcaaataac acgtaaagta gctctaattc atgtggcaac   87360
ggattactct aaggaaacta aacaggccag gagggagtgg aatggcattt tcagattgct   87420
caaagagaga caaaaaaagc ctgccatcca agaatattgt atccagcaaa attatcattc   87480
aaatataaag gagagataaa atctttccca gacaaacaaa agctgagaga attcaccacc   87540
```

```
actagatcca tcttgcaaga aatactaaag gcagttcttc agtctgaaag aaaaaacgct    87600
aatgtgcaaa agaaaacttt tcaaagtata aaacctacag gtaaaattaa gtacctggac    87660
aaactcagaa tactctctta ctgtattgct ggtatgcaat ccactcataa ctctactatg    87720
aagctcaaaa gacatgagcc aaggagtgaa aacagcctct agaagctaga aaggcaagga    87780
aatggatttg ctagaaaggc aaggaaatgg aacttccaga agggaatgca gccctctcaa    87840
caccttgaca ttagcccagt gagacctgca tcagacttgt acaggcctca gcagctgaat    87900
gtattgtaca gcctgcagaa ctgtacaata ataagtgtgt attgtttaag ctgctaagtg    87960
tgtggtaata gaaaactaat gtatgttttt ttatataaag ctaaatttga tttcctaaat    88020
attgttaaag attttacac ctgtgttcat tgtggttttc ttttctgta atgtctttgt      88080
ttcattttgg tgtcagagta atgctggcct catagaataa gttgggaagt acaggattcc    88140
tatctatttt ttgaaagagt ttgtatagaa ctagtattat tcctttctta aatgtttggt    88200
agaatttgcc aatgaaggca tttgggcctg aaattttctt ggtgagaagg ttttgttttg    88260
ttttgttttg agacagagcc tcactctgtc gcccaggctg gagtgcagtg gcacagtctc    88320
ggcactgcaa cctttgcctc ccgggttcaa gcgattctcc tgcctccgcc tcctgagtag    88380
cttggattat aggtgcctgc caccacacct ggctaatttt tgtatttta gtagagccgg      88440
ggtttctcca tgttggccag gctggtctcg aactcctggc ctcatgtgat ccatccacct    88500
cagcctccca aagtgctggg attacaggcg tcagccaccg cacccggcct gtggggaggt    88560
ttttaattac taatttcaat gtctttaatg ggtatagggc atgtacgtta tctatttttt    88620
cctgaatgaa cttagattaa tcatttttga agtcttagtt gctagaaaaa aatatttaaa    88680
aattggtgaa ttttctcatt aaagcagctt ttagtgcatt tttgaatata gtaaatataa    88740
atatttata tttatagaat atatttaga tctgaaaaat aattattatg agagtccaca       88800
tattacaaaa atacaaatat tatatctgag tccttactta ccaggagatc tgattataac    88860
ttgatttccc atacatttat gccactccca tgggccataa acatgccagt cactgtgata    88920
aatttacttt gtaaatcaat taattgactt tgtgattata tatatatcat ttacagtgat    88980
tctgcttcta aaaagtggaa cctctttcca tatgctgtta gaattattta taagcttaca    89040
gaggtttagg ccagacccca aactgtgtta aattcacaag gtaatgagtg ctaacctgtg    89100
aagcctcttg aaagagaggt cactacctat ctctggccat atgtcccaat cctgccattg    89160
tatagggcag tggttttac tgagagtatt ttagaaattc acttgagtgt tactgatagt      89220
tagtgagtag ggggctcagg atgcaatgcc cgtaataacc ccacacagtg aggaattgtc    89280
ccaagtcctg tacaacttac aaaatatcct gctggttagt catgaagatt aaaagcttgt    89340
ttacaattt ctgagactag aacctaagtc tagtctctat gttttacaca taaacacaaa      89400
gtattttttg cgtggtttta atatataatt aatattctaa tctttatttt agcatttatc     89460
cctgctctct ctttttttt gtatttctac tatagaatgg cctaagtcc aaatttattt      89520
cgtctataac tgtatgcact catctaacca ctttgctatg tcttttaggg ttgaacctgc    89580
gcatttccct atgaaataca tgctatttta ttattaattg cctttttcta ctctgtatta    89640
cactgagagt tatttttttt aattagacat atagttacag tattgtatat aaattccatt    89700
tcaggacaaa ggagcatcac aaaatatttg ttatgaaaag ggtggggatg ttagatttga    89760
aaagcctgag aggcatgtta tagaaacaaa ctttcttctg atttcagtac ttttcctatc    89820
attatagttg ctattacata aaaatgtaaa gtcttggaat gagtccatat tactgcttca    89880
```

```
aaataaccaa acaataaaa atggatttaa cttctatttc gcctacaaaa tagcctaaca    89940
caattattat atccatcaag tctaggacat ccagccatag tgctcacaca tatgcatagt    90000
aatcacaaat ttcagtgcac aaacttagat ctgcaaagaa tataacttac ttcttttta    90060
ccctgtcact gaacgcagta cctctgggt ccctattctg ctgggtggag gaaacctggt    90120
tccagtcaat tcagatcatc tcagttaatt catgatctca tcctggctcc cctccaggga    90180
gccagtgcgt tggagctgaa ggaagtgtgt ggtccatagt catccttgca caagcctctg    90240
cagaaacatt cctgttcctg gctggccttt ttatatcatc catctagatc atgctgcgac    90300
ctccttgcct gcggagactc tttgaccat ctctgtgcca catttgtgct cttctcaaca    90360
ccaaatcaaa aacattcatc agttcagctg caacccttc cacactgtgg tgtgagaagc    90420
ctctgagcct gccttccatc accttgtgca accattgtca tctgctgctg ccacactata    90480
ctgggcacaa gaaccgcagg gagtcttgct atcctctcat ctgcccccg gctcctccag    90540
gggatgaggc atggttcttt ccactcttgt atccctccgt ccattatttc ttctacacta    90600
gatccagtcc tggggggcaga gcccaagatg tgtgcttaag gtcacagcca tgtcctttag    90660
cttcgtttcc agtcctctct cttcccctgg ctctgagtga ttgcttaagc taaatctatt    90720
agctcatcca cctgctgact atccatttcc ggagcccaga catggatctc cctgcctgct    90780
tcctgggttg agggtcacag ggtgacaaaa ttactaggaa tgagaaaagc tgttacttaa    90840
tatttggaaa catcattcca gtggagatgc agggcacatg aggcatactg cttagcctgt    90900
aataattttc tctcttttca gtctatatgc ctaactttat gccaggatag tgaaagtttt    90960
catgtgctta tcgttgtgac ctttgcaagg tatcaggtga agaaggcagg cacattgtat    91020
tgctgtagat aaataggatt aatgacagga atatgggata taaaccttt tgctaggtct    91080
aaaccatcct taactatgcc atgagtctct cactatctta atgatgtagg gtcatcattt    91140
taatttttt attgtagtat gcatctttca gtggtgtctt caatatacgt cagtgtggat    91200
catttaatgt tggaaaaaca ggtaaagaca ctttagtttg tggtctactt ttacaattta    91260
tactttctt ctcctttcct ccttctacaa agattatgtc cagcagtatg catcttcctg    91320
acttgcagat tctagcctgc tataaaatta ggacaccaga caccgcacat attgctagaa    91380
ttgcgtctga gactgaatag gtcctgagtt agtctctaat tgcatggact tcgtggtgcc    91440
tattgtggta actcagggc atttgttttg atttgtttgt ttgtttgttt ggttggttgg    91500
tttggttttt tatcctggcc cttggctgtt catcccttg tctcctgctg caaggcctcc    91560
tgttagccat ttgcctctca ttaggcatgg agctccaggc tgccttccat gttctttcct    91620
cctgagtggc ctcctcacct gcttgggatg tccagtgtca atcacctgga ttctgccctc    91680
actcccactg tgcatgccct ggtcagaggt gggctgctg cccaggactc tgggggctca    91740
cagagtttat ttcactttgg ccttggagca agtgttatct gcagatccga agaggttctt    91800
gttattattg attaagtatg cattcaatat ttgaaatgct ttaaacaaac tgcttcatgt    91860
ttggatatat tgagttattt ttgtttctgc cattaaatgt tttactctcc ggttattctt    91920
cagggaggat tgtgctcatc agtgttctcg tgacttttgt ttgcctctct ctgcattaaa    91980
cacccaaaca tcagtgagat cctttagaat ctggcaaaac ttcagagaac tctgaggaaa    92040
tgaaactgcc tgtccactca gtttcattga ttttttctgag taaccttaaa ggcatatctt    92100
actacttaag aagtagagat tcagtaaaat gttgttctg ttccaaggat aaaaattgag    92160
aacatttaac ttgtattata tacttggaat cataaagaca aattgaaata gttgatgtct    92220
gcccagatag aatgtgctag cttctctctgg cttaaccatc tctgaaaaca cattgacata    92280
```

```
aatttccatc tttctcacca cgcaagttgt tagtacacct gttcttttga aaccacaatt   92340
ctgtttgttc ctgtgtgttg atggtatttt cactttctc ctgctgccct tgaacttgcc    92400
agactctcca gcacttgtgt ggtacttttc tcattcatta cttctctagt ggcattactg   92460
aaggataaac agctgtctag tcaaaattat ctggccacgt tcagtgggtt ttaggtctga   92520
aaggggagcc aaataatgtg tgagtaaact gtaacactcc ctaagagtgc caaaaaaatt   92580
agtttgcctg gaaatccatt agtaaaaaat atcaaacatt cctaaaaatt aaacaatagg   92640
aaaaacaaac agggttttag ttgttaaaaa ggacagacca aatatttggt acttttactc   92700
gcttaataca tcaaacatgg gtcttctgtg ctacttgtca gggggattct gaatatgaag   92760
atcaaacctt gcattaccca tacctcctaa gtgagagcac ctcaacattt tgtgcttacc   92820
ttacaacttt catctaaaga tctccaagat ctgtgaatac ttatgtttta aattacagga   92880
aaaagttaag ttgttgcttg ccaatatgta ataaattagg acactgtttt ccagtttcca   92940
gttccatttt aacttgtaga gaataaacgt tttcaatctt tcaacagact ttggagtctt   93000
ttcatcctta ataaatgtta aaggagagat aaaaccccat tgatatctca gcattataag   93060
caatggcatt agcctcatta aagtgaggaa atattttact acaaactttt ataacatttt   93120 tcttttaat cctcattcat ccctgatttt gcccttccc tgcatgcatc ttttttaaat     93180
ctccacatct tttggtggct acatccgtgt attagtccat tttcacactg ctgataaaga   93240
catacccaag actgggtaat ttataaagaa aaaggtttaa tggactcaca gttccatgtg   93300
gcttgggaga cctcacaatc acggtggaag gtgagggaag aacaaaggca catcttacat   93360
ggcagcaggc aaaagcaaaa tgagagccag gtgaaagggg aaacccctt taaaatcatc    93420 agctctcgtg aagcttgttc actaccacga gaacagtatg ggggaatctg cccctgtgat   93480
tcaattatct cccactgggt ctcccctaca acacatggga attatgggag ctacaattca   93540
agatgagatt tgggtaggga cacagccaaa ccgtatcaat cggttatttg gtgcctggct   93600
gccagtcgca ctccaccaga accctcctct tgctagccca gctggacatt ctccttgctg   93660
gtgctcttag tcaagatgta aagtctggtt agtgtctgag ctggtggtca gagcacttat   93720
ctgccctgaa tgctgcaaac cattttaaac ccctacgaat aatcaaatgt gtatttgaac   93780
aaatcttcag tttctggtgt ttaatttgaa tcccaggcta ttgttatagt gttttttct    93840 atgataattg atgtccttta tttaaactca tgggaacaga aaggagttat cctggctctc   93900
ccctgatagt aacaaccccc ctcacaattc actgtgttgt tgcacttctc aagaaattac   93960
ctatagaata gagaatgcag gctgggcgtg gtggcttctg cctgtaatcc cagcactatg   94020
ggaagccgag gtggatgaat cacctgaggt ctggagttca agaccagcct ggccgacaag   94080
gcgaaaccct gtcttcacta aaaatgcaaa aattagctgg gcatggtggt gggcacctgt   94140
agacccagct actcaggaag ttgaggcatg agaatcgctt gaaccctgga ggcggaggtt   94200
gcagtgagcc aagattgcac cactgtactc cagcctggga gacagagtga gactctgtct   94260
caaaaaaaaa aaaaaaaaaa aaaaagaat agagaatgca atctaggagg actctatgct   94320
tagaatactt tggtcttatg aaaacgtgat gttttggagt gtggctatga tacttaaatc   94380
taatatatgt ttagtaaata tccagatagg agcctattct gttctgtgta ctttgctggt   94440
gctgatgact agcatacata aaaatagcta atattattta gcactgcttc tatgccaggc   94500
acaatattaa ggtgggtatt ttgttatcct catttctcaa ataaggaaac ttaggctcag   94560
agattgagta cttgcccaaa cccacagtgc ttagctcctc tcagttccct gcatttcagt   94620
```

| | |
|---|---|
| gaaattagac atggggcagt aggggtgata ggggaaagtg atgatggtca taaaacacct | 94680 |
| agacctatac cttttttgttt atacctagtc atcatttagc tcaagttttc cttaacttct | 94740 |
| ggcagcagag tatacctaat agtataacta gtctttaatt aagaagcagc cttgacacag | 94800 |
| acaccctagt ctctaatgtg cgattgcata aggcctcctg ctccctgtgc ctgggctctc | 94860 |
| atctctctgg tggtcacttg gctggctctg tcctgtcctt atggtttcag ctcctccaca | 94920 |
| aagcccagtc attgcctccc atgaatggag agatcttatc tcttttctc actcactccg | 94980 |
| tgagggacag gaccttgtcc atcctgtttg ctgccctttt tccagatctg gagtggtccc | 95040 |
| tggaacatgg cagcactcaa gaaagatgtg ttaaaggaat aagtgagttc tttcttccag | 95100 |
| gccaagactg atgcttcttg aaatgctccc aatcaaccct cttagactcc aacataactg | 95160 |
| accagggacc agattagaca aacaattctg atatttgagg gtttgattta cttaaattct | 95220 |
| cactggggtc caagagcacc ccttgccagc tcctatagtt taagcagcag tatgtagaat | 95280 |
| agccaatgaa aagtcaaggt cacagagtag ctggacaaag cttagaaaaa aacaatgcag | 95340 |
| tgacctaagt taatgtttag tgcctttaac ctctatttc ggtgagtggc cttttcccta | 95400 |
| attatttgtt cctccaaatc attgagccct tctgtgtggt aggtcctgtg ctaggtcttg | 95460 |
| gaaataaaaa cattaagaaa ctttttgctc ttgagaagca gagttcatgg ggaagacaaa | 95520 |
| gccatgaaca actgattaac aatagacaga gctaagtata gtagaaaatg tgcacataaa | 95580 |
| atgtagcaga aatacagagc agagatgaag accatctagg gcactaagtg gcaggttcac | 95640 |
| agaagatatg atctttaacc cgtggcactt taggcaaggg agccaacatg tgcaaaggca | 95700 |
| aaattagcat gaaagggcat gacatattct aacaacaggg agaagttagt tctacgtgac | 95760 |
| tgaagctcag ggcactttt atggggggagg acaggagttg atacccaaaa aggaggttgg | 95820 |
| gggcagatat gaaggattct atatgtgggc ctgaagttgg aactttttcc ctgattggaa | 95880 |
| agcaatcagg tctttaaaca tgcatgtggc ctgattgatt ttgggtttta caaacacctc | 95940 |
| tggtgggaac ttgaagcggt atataaatta gcccaggagc ccagacagag gagtgcctga | 96000 |
| cctaaagcaa tgggctgcag aagggggggat gattggaaag ctgttttaaa ggtagacttg | 96060 |
| gcagaatcaa atgcacattc tgtcagaaat gattcaatgt agtgcaacag ggaaagagta | 96120 |
| gccaagcgtg gtggcacaca cttgtagtcc cagctacttg ggaggctgaa gtgggaggat | 96180 |
| tgattgagcc caggagatcg aggctgcagt gagctgtgat cctgccactg cactccatcc | 96240 |
| tggttggagg agtgagactt tgtctcaaaa aaaaaaaaa aaagataaga tttgagaata | 96300 |
| tcagaatgta atttgaatat ctaggtagat aatgtctcca aaatctttta gcaggagaag | 96360 |
| attgaattta ccgaatcctt tagatgtgta ctaagacata tattagcact ccagtttgcc | 96420 |
| tctcagtaat ttaaaaaaaa atccaaagaa tcaaccatca acaagcagat acttttctgg | 96480 |
| gacaaagagg cttctccatt tttgaaacga tgttgcctac tcatctgtta gtcacccttg | 96540 |
| catcagggcc gtgttcaaag agatgtccag gcttggtatg aggctgctag agccttcctt | 96600 |
| gcttttcctt ttgtgatctt tgagtcaggt tgggaaggat gactagggta agccccagct | 96660 |
| gaagcatgca cagggatgtt ggggtagaga tgatgtttca gggcagccct ccacggccaa | 96720 |
| gccacacatt aaattgtttg gggagtagtt ctaaaaatta atgctgttgt catggtttca | 96780 |
| ttttgatttt tatcagctgg atatggatga ggcttcattg tcatatactt aatgttttg | 96840 |
| cttagatctt tggcaaacca atatttttcc atgactttt gacagttatt tttgttcaat | 96900 |
| agtgaataat aaagtgagat ttacggtctg tatatgataa tgtttgtctt acttttgacat | 96960 |
| ttctttttcta gacagtaaag gccttataat tagattttcc ctgtgccaaa acattgctgc | 97020 |

```
aaaaccatct ccctgaaaaa acgtttcttt gcttcttta ggagctggcg tcatcttatt   97080
ttgatttgga atttttttca tatgtcagtc aggaaatgaa acaaaatttt ctcttgaata   97140
tgaattctta acaagaaaga aattaacttt tgccgaaaaa taaaactaga agggaaaatg   97200
agaagaaacg tctttgaaat gctgatggtt ccattgtctt tttaaattct aatttatgtc   97260
aaacttcagt gagcaatata ggaaactccc ttttccacct tgttgcaaaa gagcttattt   97320
tattcttgtt gctactccta ccagtttat gttgaattct ttgaaatacc caggagactg   97380
aactagaact tatggaccgc accctatttc tcatatagtt aaccaactaa tgtcctaact   97440
cagtggattc tgccccattg ctgataagtg gcaaccatcg gccaggtgcc atctgtgggg   97500
gtacaaggac aggcgaagct gaactgccct tctgctgagg ccacatctgc agttggcgct   97560
atgccaggag agccttggag aagttgcaca tgtgtccatt gacagtgctt tctctttgga   97620
gtgctcttaa aaagaataac tgttgataga atcgcttatt gctaatggca aaacatcaca   97680
gagaactaat tgcaaaaaca gtcacactta ctacatccgt ggcctcccct aatgatatgt   97740
ggaaacacct tccctttcct acagtagcaa aagtggccaa attctctgta caacccggag   97800
aattttccta tctgagtcat aactgaagag ctgctcctag aatcagattc cagatccagc   97860
caccettgtc cccatcatct ccactcttat ttccaccacc atcttcatcc aatactttcc   97920
gttgagcact aacaaatatg tgcaactgaa ggacactaca taatacctca gagaagtgta   97980
tctatttaaa acagagacaa caggcttctt ctaaagtatt gagccagcat cacttacagc   98040
aatccagaca acagagtgaa ataatcgttc tgtctcagcc tttcttgata tcacgggaag   98100
agtgtaggta tttctttcca gtgtatttt gtatcacatg aatagcacct tcttctaagt   98160
ttcgatacat tggttatgag tgattgctac tctgtgcagt atcatgaaca tggaggaatt   98220
tcttctttct actgatggtg accttttgtt gttttgaata tacgggtctg ctcagcttca   98280
atatgaaatg gaatgtgtat ttcaacaact ggcctgagtg aatgtttggg ccttgagttt   98340
ttgtcaagaa gtgatgtggg gaggtttgaa gaaagattct tgtaagtctg tgatgtcaaa   98400
tgatgagatt gtctgtcacc gacccatgtg ttgaagaatt gtttcctcac ctgatctaac   98460
tcaagactct tctctactcc ctttcgagaa gcacagaaaa gaactgagaa ctggtgtgtt   98520
aagggcgcca ccaaaagttt ccttggcagt agagccttga atttcttccc caacagcagc   98580
taagcccttct ctaaaaggaa ttaccattac cttgaaataa cttcctatgt acactcatag   98640
gaagagtgta cactttgctg aggttgaccg tacttgtggt tttcatcagg aagtgaaagt   98700
ttatgtggcc tacatgtgtg agcccactct atactaggga tagcaggagt gtggtgctct   98760
aggggcagag gcctggggtg tcacacagac cttgttggaa tcctagcatt gccatctatt   98820
cactgtttgg cttttccaaa cttccttta aaaacgtga caaaatggtt ataatactaa   98880
actatttggg ttgttgtaaa ttttaagaac aacagcagtt actaccatgt attgagcact   98940
taggttgtgt caggtaccct gccaagaaaa gatcataagc aatgtcactt catttccatc   99000
ataatacatg aagtagtgct atggtttgga tgtggtttgt ttccaccaaa gctcatgtgg   99060
aagtctaatt gccactgcat cttgggaggt ggggcccagt aggaagtgtt tgggtcatgg   99120
gggcgggttc ctcatgaata gatcaatgct gtctcccagg atcgagttct caatctcaag   99180
ggaatggatt agtcgccatg agagtgggtt gttataaagt gaggctcttc ctgctctttg   99240
gtccctcttt acctgcacct gcctctcctt ccacttctct gccatgttat gatgcagcac   99300
aaaagccctc accagcaact gatgccagtg cctagcgctt ggacttatca gtcatcagaa   99360
```

```
ttgtgagcca aataaacctg ttttctttat aaattaccta gtctcagtat tctgttatag    99420
caacacaaaa tggactaaat caattagtga ttgttatttc cacatgaaga cgaggaaact    99480
gaggtggtat atcacccctg ccacacagc tagtgagtgt ctggcctcag gcttctattc    99540
caggtctgcc aacccagat tctgtgagag ataatgcaaa atcagagtca ctcctagtgc     99600
agtcagtgct taacaagtgt tcattctctt tcctcccaga tgcatcttgt agctttgata    99660
gatctctgat ttcttaataa attttatat gtaacattct atacagcagg tggtctgtca     99720
tactgccctc atgtggctca tttgggtaat agtgggtttt tttttaaag tttaatgcaa     99780 aatatgtgtt atttaaaatg tgtctctaaa gtcacctaaa tctgtggata ctttgggagt    99840
ttgtatgatt ctataacccc agtatgtaag aaatggcact ttttcttttc tactgcccac    99900
tttaatgtct taactctgag ccctcatttg gctgggaaga tacttaactt cagttactct    99960
agtagcttct accctgtctt tgccaagatc tcccattcct tctgttgtct tggaagagaa   100020
accttctctt ccctggtatt gtgcataatg aaactttatt tcaccatcct gtcaagaggg   100080
gaaaattttt tttcacaatt atattttcc atctaatgtt ctgtttacag agacatttat   100140
caaccactgg agaaatactc agctttcaca cttaagaaag agatattatt gccagagtgt   100200
agagtgttaa ttcattttcc agtttaaatt gtagaatttt ttttccaaga ggaaaagaaa   100260
aaggtcagtt tttgtctcca cctataagga gcattaagtc actaagtgaa attcccttag   100320
ttttctcttc atgcatggag agggtcccag cttccatgga ctcattctcc catgctatac   100380
aaagttacac aggtgtattt aaagtttagt ggattgttta gcttagggat ctccaaagcg   100440
catatcatcg agggactgcc ttgttttcca gtggctctct ccatggagga tttaaaggta   100500
gatatgtatc acactgggcc ttacttatgt ctgaataatg aaaggctatg tcaatgggaa   100560
aagggaattt agggtgggaa aaggcaagga attttctttt tttttattat ttaagcacca   100620
tttagtaaca atgtacatac agtctctgtt cttaaatgta tttaagagtt aacatcatcc   100680
tcatgccaag accttactgt gtttcagata acggagggca gactttggca gggggtaata   100740
actggcccct tcgaggaaga aaatggagcc tgtgggaagg aggcgtccga ggggtgggct   100800
ttgtggcaag ccccttgctg aagcagaagg gcgtgaagaa ccgggagctc atccacatct   100860
ctgactggct gccaacactc gtgaagctgg ccaggggaca caccaatggc acaaagcctc   100920
tggatggctt cgacgtgtgg aaaaccatca ggtacctaca ccctgccctt tttcctccca   100980
ggacagaaac tccaagagca gcctgactcc attgagcaag aatgatagct tttgtgttaa   101040
aatgatagtt cagcttacaa atacatgatt tttaagaaaa ataagtgcct ttagagacat   101100
tgtaagtata tatttttta aattataaat ttgagattgt gggcctgtgt tttacgtgaa    101160
gaacaagatt gtcctcagcc catcgccctc catggaaggt cttttgaagct gcgacgtttt  101220 gcttagaagt aggctagggt attgttagct tcctgcaggg ggtcagggaa ctagtcctgt   101280
tgtctgctgg aagaatggag acaaaacag caggaaaaa gctggaatag gaactaggga    101340
tatgtttatt tccatttatt agcaagtatc taacaagcac ctactatgtg ccataccttc   101400
ttctagatgc tgagaaatta ggaatgaaca agtcagtcaa gatcctgcct ctcaggaagc   101460
tgtattctag ttgggggaga aagatgttgg acaaatgaac acacagatga gcaagatgac   101520
tgccagttgt gataagtgcc aggaaggcaa aaaagtatgt tgtgatagat agagctggct   101580
gatgtgaaga agatacatca gggaacagga cccagactca gatttgggaaa tcgtgatggt  101640 cttttttcctg tttaaccccc acagtgtaga gcaatagccc ccaaggttgg gaggcacatg  101700
ccttagaggt tgcaagatgt tcccttggag tacaggaaga aaatttcaat cttgtatttg   101760
```

```
tattaatatc taatttcatc tcatcctttt taaagtatat gttttttaag acacataata  101820
tattagtaga cttgtacata aatctaattt ataaataaat atgcatatat tggaggtatt  101880
atttttacgg gtggaatgac ctagtgcaat ggttttcaac ctctgtttgg tgttacagct  101940
ctgtttgggg ttagcagctg attgactgtc ccttagtggc caggggggaga ggacttcctc  102000 aggccatctc ttcatcccac tccaggtatc ccagctcaag aatagcaggt ttcaggtctc  102060
tagttatagg aaatacacaa tggagtattt aggagcaaaa agccatgata tatttaacat  102120
accctcaaat ggttcagaaa aaaattgtgt gtgtgtgtgt gtgtgtatgt atgtacatgt  102180
gcacagagag aattcaaatg gactgcaaaa ttaaataaaa gaatataggt aaggtgcata  102240
agtattcttt tgttatgtct tattttttgca actttttgta aatttgaaat tatttccaaa  102300
taaaagtgtt ttaaaaatag gaaggtctga cagcactgca cccacatttc cagaaggcca  102360
acaactgact agaatcaaat agctgctgcc ttctgtagat gaagtatcca cccttcaaat  102420
cttcaatctc tattgttccc aagttccaat acagatccac tgcactcatt taggttacct  102480
acttagtctc tgtaggcatt taagtttata gtccctgctg aacataatca tagtattcaa  102540
cactctggaa ataccatact ttgaccaatt tccagttgca aaatatatag attatttctt  102600 atcttttttat attatcaatt tttctgtaat taataattaa tgttaaaaaa tagtagggtt  102660
cagcagccta agattagttt ttacaaagga agtttgatag ctattcaagt ttaaacatta  102720
aagtttaaag tcctgtgagt tcaggaatgg atagaagaag tgttcagcca ggccgctcaa  102780
cctctcacaa cgtggagtct atgggttcct ctctaatggg cctcacccag aagggtgaga  102840
ctagggaagg tcctcatctc ttacaaaccc aagggaaaat ctgatttaat tagctttata  102900
accttctttc aattattttg caactcaaag ttccatgttt tccttcgaga atttattaaa  102960
ttttaaagat cacttttcaa gcagcaacat ttatagtatt gggtagccat ttcttcacca  103020
tttctaaaca ttattttggt tcttatgagt catattattt tcatattatt ttaaaatcct  103080
cactagcctc aaaattgttcc ctcttattct tgcctgaaaa gttgatttgt cagtttggag  103140
acagtgatca gttatgatt tgtcatttca agaacactct acagcatcca agtcacagaa  103200
aaagtaatgc cactgaacag ctaagctgag aagcaaagca gtaaaacctt ttctctcacc  103260
agaaattttg aagctttgtg ctcattatgt gctcattcat atgcgatgac ttttttttct  103320
ttttctttga aacattctg cctctatcca tgatctaaac ttgatatgtt aaatttaaat  103380
ttaatttccc caagcgtgag tactatatgt cattgtagat aatttgcaaa ctacaaaaaa  103440
taaaaataat tggctgggcg tggtggctca tgcctgtaat cccagcactt tgggagactg  103500
aggtgggtgg accacctgag gtcaggagtt caagaccagc ctggccaaca tggtgaaacc  103560
ccgtctctac taaaaatata aaaactagcc gggtgtggtg gtgggcacct gtaattccag  103620
ctactcagga ggctgaggca ggagaattgc ttgaacccag gagatggagg ttgcagtgag  103680
ccaacacggt gccactgcac tccagcctcg gcgacagagt aagactccgt ctcaaaaaaa  103740 aaaaaaaaa aaaaaaaat cactcaaatc ttacctagaa acaactacta taaacatttt  103800
gtcatatttc cttagaattt ttcttttcag cattttttta ctacatcttt tttccttatt  103860
taacagacca ttggttttttg attgtgtcat ccaagaaact tactgcaaac actatttcag  103920
tcactgcaca ttcaatcgca tggatatacc ttgatatact tacccattcc cttgactttc  103980
ttttttagtt ttttaaaaca ttagctctga aatgagctct ttctacatga actgtttgtc  104040 tacatttttgg acttttccc ttagatataa atgatttgaa attaaatcat tgagctaaag  104100
```

-continued

```
aaagtgacca atgttggggc ttgaaaaaca ataccccaaa ctggaggccc cagaagcagc    104160
ctctacaaca gaagtttttc tctgacctcc tcctgctctc ttgtctctca gtctcatttt    104220
ttcctgaggc aagccatgga aaccagaatc cttcttcccc agggcaggtc atagaaacca    104280 gaacccttc tccccagggc taatcataaa acctagaaat attattctaa ttttccctct     104340
gccctatttg tgtaaaaagt ggccataaaa aagttatctg gcctaacttg ttttaactgt    104400
aggtcataac attcccattc cagagcgggt ccaaccccac atccagaagg aaggaatgca    104460
tgcccagaga ggccgagaag aatccagaga gacagacctt gctgggtttc cccactcagg    104520
ctattagcat tagagcatac cctttatcc aatcatgttt ctatatggct gtccatactt     104580
tgttaaacct atacataaaa atgaacgatt tcctctatat ctttgggtct tcattctaaa    104640
ggctcccatg tatacacatt aaatacattt gtatgccttt tctcctgtta attcacctt     104700 tgtgaactga ttttcagtg aacttgcgga gggccaaggg tggcccctac atgatttaa      104760 aagcatttga taaacattac caaactgctt tctaaaaagg ctgtatcaat gtactcttgt    104820
acaggtgtag aaagtgctca tcttcctcat agcttttcct tatcaagctt tttaaaaaac    104880
ctttgctaat gttatagaca aaatagtctt gtattaactt gatttttat tattatggag     104940 attaatattt aacttttat attccatttg tattttgtct ttgaaagtat tcattccatg     105000
tgcttttcca cttatttac tgaaaagtag gtgttttttg tggatttgtt tgcttcttta     105060
tgtcaggttt ttggattgtt gtatttcttg caaatattt tccttttttt ttgtcttttt     105120
attttgttta tgtcttctac atggatgtct ttcccatgtt tatttgtcaa tgaaatgttt    105180
ttctcttgct tttttgttca gaatatttt tctcagcttc aaatgtgcta atatctatt      105240 ttcttctagg tgttgtggtt tgagtttctt ccatgtattt ctttttctt ttttttctt      105300 tttaagacag agtcttgctc tgtcacccag actggagtgc agtgatatga tcttggctca    105360
ctgcgatctc tgcctcctgg gttcaagcgg ttctcatgtc tcagcttccc gagtagttgg    105420
aattacaggt atgcatcaac atacccagct aattttgta ttttagtag agcctggggtt     105480 ttgccatgtt ggtccaacca gtcttgaact cctggcctca agtgatccac ctgccttggc    105540
ctcccaaagc gctggaatta caggtgtgag ccattgtgct cagccataat tcttaaattg    105600
ttgcaagatg gtgtgcgtgt tatgtgaggt cagtgtctaa atcagaggag taatgttttt    105660
tgcagttttt taagattgta ggcctctta agaccgatga aaactatgaa cttacaggaa     105720
aaaagtacct aaacataggc acaaaaatct agatattacc tattttgtga tattagaaat    105780
tgattacaca ttcttttcta aaacattctt tacaagccta tgccccttt gcttattta     105840 atgcaaaact taatgcccac ttcatggtaa aaataaaaca aagatttcca agcaaagcaa    105900
atcttgaact ttaattcagt ttatcatcaa ctttcaatat aaaggctgta gcggtttggc    105960
ttggagtagg agaaagcttt gagtgacttt gagatggcaa catttgtggc atgcttgata    106020
tccaatcatt tttgattttt cttttgtttt gttttggtgg caaaaatgtt gtaaccctg     106080 gcttgcataa ggacataata gcatgtggaa tcaaagcttt ataggacact ttgccaggtg    106140
agggtgggat tgaatcgaaa aatagttgaa ttcattttga gtcccaaatt tactgaggtt    106200
attatctttg gcaaagttca catcattgat gtttgtccat atagctaaat tttggattac    106260
aaatgcacat ttcaacctta agattatgtt gatcagaagt aacctttaag aatttggctc    106320
atgtttgctt ctgactgcag agaaattggg aaaagtctaa tcactcttag ctccaaattg    106380
cagatctttc ttcggtgtta gcacgttctc ctagcggcca atctcttatg gaacaggggc    106440
acgttcttca gtaccgtaca tagtggtgac tgcgggggctt taaccaaaag atatggccaa   106500
```

```
aattattgtc caagtaggct aaatcatgag ataatgggct ttcttttttt tttttattta 106560
aaagtaaaat ttctgcccaa agtttgatca tacatttcaa gacttgtttt ctggaaattc 106620
agcaaatttc tatttagaaa gcaaaaaacc gctctcattc tgttcccatt gcttgagaaa 106680
aattcctgaa ataataattc agcctcgagc ctaatgaagt tggtgcttct cacagcatta 106740
ggcaagttcg gaatcggtgg cagaacattt ggcacccctg cctgctgata cagaaatcgc 106800
ccagtcacat tgacgtctgt tgtgtctttt ccaaagcagc aaaaacaaat ggacagccaa 106860
atgtcagaga cacccgatct gtgcccagag gtctgaaact ttttccaga aatggaaata 106920 ccactttcga gatgatggta gtttttgaaa atttgaagag gctcgtgaaa taggaatgcc 106980
agtaacggat gaaaaacagt tgtctgtgct gagagcatca gaagttttat tagctgtata 107040
gttacaaatt tctcttagga ctgcttcaaa atattaaaat gttagaagaa atagtagttc 107100
tggagtgggt gacattattt acaataggag ctccttcgac tgcttcagtt tttctttgtt 107160
gcaagccaca gactatgttt gccatttcta ggggacatga cttctctaag ctcttttcca 107220
ttctgtgtag ttttttctgct tttcagctca ataatcagcc tataggttgt ttgaagacat 107280
ttcataaggt tgattgacaa aaaggaaaac caaaggatta aaaccttgca agtttctttt 107340
taattatttt atatttaatt aaacaatgta aaacataagc agactaggcg tggtggctca 107400
cgcctataat cccagcacta tgggaggccg aggagggagg attgcttgag cccaggagtt 107460
cgagaccagc ctgggcaaca tagcgaaacc ctgtctctac aaaaaataca aaaattagct 107520
gggtgtgttg gcacacacct gtagtcccag ctactcagga ggctgaggca ggaggttcac 107580
ttgagcccag gagcttgagg ctacagtgag ttgtgatcat gccactgcac tccagcctgg 107640
gcaacagagc aagatcctgt ttcaggaaaa aaaaaaagca atctcctgat cataatgata 107700
ggaatttctt ttttatcatc aatgggaaac actttaagat gtcataacat gacagtggtg 107760
acaactgaat attaaaatat cttaaaaact tagtatgtca ttataaagac ttttccccca 107820
ctatcaatat catttcaaga agaaagttaa aggaaaaaca aatctttca cctcaatttt 107880 acagatgcca tgaagccaaa taaagcatga tggtccatga gctaaatgtt aacctctgat 107940
ctaaaatgga tacttcaaga aaaaaaaaaa acacataaaa tgatacttca ttccacatac 108000
taacaagaga actcagacta attattgaat aatatttctc ttttcactga cttatggcac 108060
tattttaggt tttaagttct tatgagtact gtgctctgtc ttggggcccc ctgttttagc 108120
ccactgactt atctgttctc atgctggcat ctgactatta atcattgtct ttttcgagta 108180
tatttaaata tctggtagaa atggttatcg gcctgtcctt cattatattg tctttataaa 108240
attttcttga caactctcac tttttaattt ttcttggtga actctagaat tattttgtta 108300
aattaaaaga aaagcttctc aaaaattata ctgagtgaga ttaagcctgt aaattaatct 108360
ggcaacaatg tacatattca tgcttttcac ttggacactt aaagttgtcc cccagtttac 108420
taatgctctc tttatttaaa aaaaattctg ttttctcttt atttcatttt gggcagtttc 108480
tatttctaag cctttaaggt ttttgatttt tttctcaatg tctgatcttt catcaatttc 108540
atgcaatgta tttttcatct cacacattgt agctttcact tcttgaagct ccacttgggt 108600
ctttttaata tcctccctgt aactacttaa cttcctgaac atatagaata cagttataat 108660
aaatatttta atgtcccctg ctaattccaa catctatatc acttctcagt tggttgtgat 108720
tgattattct cctcattata ccggtcatat ttctatccct tttggtcttt gattcaatgc 108780
caagcattgt acatttttacc ctgttgagtg ctggatattt ttgtattctt gtaaagcttc 108840
```

-continued

| | | | | | |
|---|---|---|---|---|---|
|tagctaggca|gggtgtggtg|gctcacacct|gtaatcccag|cactttggga|ggccaaggcg 108900|
|ggtggatcac|ctgaggtcaa|gagttcaaga|ctatcctggc|caacatggtg|aaacccgtc 108960|
|tctaataaaa|atataaaaat|tagctgagca|tggtggcggg|cgcctgtgat|cccagctact 109020|
|agggaggctg|aggcaggaga|atcgcttgaa|cccgggaggc|agaggttgca|gtgatccgag 109080|
|attgcaccac|tgcactccaa|cctgagcaac|agactgagac|cctgcctcaa|aataaataaa 109140|
|taaataaata|aaaataaagc|ttctggcttt|gttctgagat|gcagttaagt|tatttggaaa 109200|
|cagtttgatc|gttttgagca|ttgcttttag|gatttattag|gcaactgcag|agcagtgctc 109260|
|agtctacagc|taattatact|ccactgctga|gtcaaatcct|ctctagtcaa|accttctcac 109320|
|agcagcctgt|gagttttttca|aggctggctg|atgggaacgg|gtactgttcc|caactctgtg 109380|
|tgaatgctga|gcagtcttcc|ccttaatcct|tacaggtagt|tctttcccgt|gttgtgagta 109440|
|gttcactcac|aggcatcttt|ttctaagaca|atggtcccca|aactctctgg|caccagggac 109500|
|tggttttgtg|agagacaatt|tttccaccga|ccagggttgg|tcggggata|gtttcaggat 109560|
|gaaactcaga|tcataaggca|ttagttagat|tctcataaga|agcatacacc|gtagatccct 109620|
|cgcatgcgca|gttcacagta|ggattcgcac|tcctatgagg|atttagtgct|gccactaatc 109680|
|tgacagaagg|cagaactcag|gcagtaaagc|ttgctagccc|accgctcacc|tcctgctgtg 109740|
|aggtccagtt|cctaataggc|cacagatggg|taccggtcca|cagtctttgt|tgggggacct 109800|
|ctgctctaag|gggatcctct|gcagatttcc|aggattctca|ttctgtgcag|ctttctcttc 109860|
|tctggtcctc|tgtcctaaga|gctcaagctc|ccttggtctc|tggactcagc|tctgtctgct 109920|
|caactcaagg|aattcattgg|actacatttc|agttgcccct|ccctgcacca|gggcttagaa 109980|
|attctctcaa|ggcagtaaac|tgggcaatga|ttaaaaactc|acctgctttg|ttttcatct 110040|
|tggaataatc|attgttcttt|gcctgatatc|cagtgttttg|aatactgttt|taaatattct 110100|
|gtccatttttt|ctttgggttg|ttttaggcaa|gagggttaag|taaatctaat|ttggctggaa 110160|
|gcagaagtat|ccaaagaaaa|atttattgtg|cctttacttt|ctttaccagt|attttcttgc 110220|
|ctatttctca|ctttcaagtg|ttttaaattc|aatctatcag|tacagaccca|gcttttttgca 110280|
|attgaatact|ttaaatctta|taactcttct|tccaaagcaa|gtttcttctt|cattctactt 110340|
|tgtaatcaca|tgttgcgaaa|ttttatatat|atatatttaa|ttatgtttaa|tgttaccaac 110400|
|atttttattt|ataactttcc|ttagttctta|agtttgatta|atcttttgat|tagttgatta 110460|
|atattttaaa|gtaattttttc|agtagaggta|cataaatggt|gagttcttcc|aaattttttca 110520|
|tatgaaagaa|tatatttcta|ttaccatcaa|acataaatag|taatataggt|caggcgcagt 110580|
|ggcttatgcc|tgtaatccca|atactttggg|agcctgaggc|aggtagatca|cttgaggtca 110640|
|ggagtttgag|accaggctgg|ccaacctggt|gaaaccctgc|tctaccaaa|aatacaaaag 110700|
|ttgactgggt|gtggtggcac|acacctgtag|tcccagctac|ttgggagact|gagggaggag 110760|
|aatcgcttga|acccatgagg|tggaagttgc|agtgagccga|gattgcgccg|ctgcacttca 110820|
|gcctgggtaa|aagagcgaga|ctctgtctca|aaaaaaaaa|taataataat|ataataatt 110880|
|attgttaaaa|atgaaagaat|gtatttattt|catctttcga|tcatgatact|taccaacaat 110940|
|gttggcataa|actccacctt|gtcaaatacc|aaaactgcaa|tcctgtcttg|ttttgtttg 111000|
|cctttaccctg|gttcactttg|ctataataat|actcaccagt|agacaataaa|ctaacgtcta 111060|
|cagcatcttg|agcagaaagg|atttaacaag|aattctgtat|attattaata|ttattttttgt 111120|
|ttgaatgtaa|tatgttgaat|gtatttatgt|ttgaatgtta|gaatattaat|attatttatg 111180|
|tttgaatgta|attatttatg|tttgagttct|ttcatttgaa|agaatgtatt|ctatggggaa 111240|

```
tggtgcaaat ggtgattttt ttctttgaac catgtattta gaagtgcatt gttaagtttc    111300
caaattttgg ttttttccct agttaaatta ttgatttcta gtttatttca gttgtggttt    111360
tgaggaccac aaataattga aatgctttgt attatttcaa ttattattat tgtttttaa     111420 cagagacaag gtctcaattt gtcacccaag ctagagtgca gtggtgcaat catagctcac    111480
tgcaacttct gcctcctggg ctcaagcaat ccttccaccc cagcctccca agtagctggc    111540
actacaggca tgtactgcta taaccagcta attttaaat ttttattttg tagaggcagg     111600
gtctcactat gttgcctcag ctggtctcaa actcctgggc tcaagcaatc ctcctgcctc    111660
agcctcccaa agcgctggga ttacaggtgt gagccatcac tcctgggcta attgttttaa    111720
atttgagact tggcctagta gatggtcttt cttgttgtcc acatcaggtg taattgaaaa    111780
gaatgcgtat tctgtagttg ttaagtatag tgttaggttt ttctttatga tccagtctgt    111840
aatgttttag tagatgaatt tatacatatt tataaatatt tttatttcta ttcttagttt    111900
tttcattgtt ttgttacatt tacttttat ctttgacctt ttatttagta gttctttaat     111960
atttagaaaa atttatattt tatcctactg tttatcatta tacaaatatc tttatataat    112020
tccttagtcc ctttttttctt acttaggttc cactatttgg tttgtcacat ttaaatgaca   112080
tcttcagctt ccacttatta cccataagga aatcaagcaa cttatgtaac ttttcattct    112140
cttccagttt tgtgatttaa gtagtgttat tcctactgta tcagagcatg taatatgtaa    112200
tactgttctc tctttatcca caattttgtt ttagttttag atcttcaata atatattcaa    112260
tactgaccac ccatccactt ctaaagtgtt cacaattatc tcttagttgg aggaattcat    112320
ccttgaatag atttctcagg attctttgaa ttcttgcatg tttattaaaa catttctac     112380 aaccttgata attgaacacc agctcaaccg gttaaaataa aacccttgtc ccacactttc    112440
ttgctttgag tttcttgaaa atgttaccct aatctttgct tgttttctat gttactgttg    112500
ataagtctaa tatcagcctg attttattcc tttgcaagtg actttgtgtt ttttgtctgg    112560
gcacccagaa gatttttat tatcactatt attatagtta tgatttaaaa tctaagaatt     112620
tttccagatg tgtcacaaag gtgaccctac tgtgtcagtt ttctcagata aaagtgagtt    112680
atttcacttt gtatattcag atcttctttt atttcagagt ttttaaaaat tacagtttta    112740
ggccgggtgc ggtggctcac gcctgtaatc ccagcacttt gggaggccga ggcgggcgga    112800
tcacaaggtc aggagatcga gaccatcccg gctaaaacgg tgaaacccg tctctactaa     112860 aaatacaaaa aattagccgg gcgtagtggc gggcgcctgt agtcccagct ccttgggagg    112920
ctgaggcagg agaatggcgt gaacccggga ggcggagctt gcagtgagcc gagatcccgc    112980
cactgcactc cagcctgggc gacagagcga gactccgtct caaaaaaaaa aaaaaattac    113040
agttttaaat attatattct actgttttgt ttttcttctt caggaactcc tagttatagg    113100
tattattgaa tcttctttac ataaatttgg tttctgtcaa tttctctcgt atcctctttg    113160
cctctttatt ttttctttat tttgaattaa ttatcctttc tcttttaatt tctattctct    113220
acacgctttc acatagagaa tgtcatgtat aatgttttgt catttctaag attttgtcct    113280
ttttttccca gttcccttcc tttaaaaagt gtgatgtctg agtttacaa tttctgaatc     113340 atggttgttg tttctttaat attggcagtt gatgatttca ttatatttaa ttcatgttga    113400
aatatcctgt aatggttttc ttctgcctta tgactgtttt tccatagtag gagaatgttt    113460
tcatttgcca aattttgaa ttctcatttt ctatttttt taactcgtat ggtaactttg      113520
catagatgct gagttctttt tggttttgtt cacgtttatg tatgttggcg tttcctggat    113580
```

```
ctaagatagc aggcaatccg taggagtggg atttggacac tttcatttac ttcaggtgct    113640
tcaagagcgc tgtgtattgc tatagtgaag tgcagtttct ttgctaaatg tagcccctt     113700 ctttttttt tttttttaa ttatactta agttttaggg tacatgtgca cattgtgcag      113760
gttagttaca tatgtataca tgtgccatgc tggtacgctg cacccactaa ctcgtcatct    113820
agcattaggt atatctccca atgctatccc tccccctcc cctcccac cacagtcccc     113880 agggtgtgat attccccttc ctgtgtccat gtgatctcat tgttcaattc ccacctatga    113940
gtgagaatat gcggtgtttg gttttttgtt cttgcgatag tttactgaga atgatggttt    114000 ccaattcat ccatgtccct acaaaggaca tgaactcatc attttttatg ctgcatagt     114060 attccatggt gtatatgtgc cacattttct taatccagtc tatcattgtt ggacatttgg    114120
gttggttcca agtctttgct attgtgaata atgccacaat aaacatacgt gtgcatgtgt    114180
ctttatagca gcatgattta tagtcatttg ggtatatgcc cagtaatggg atggctgggt    114240
caaatggtat ttctagttct ggatccctga ggaatcgcca cactgacttc cacaatggtt    114300
gaactagttt acagtcccac caacagtgta aaagtgttcc tgtttctcca catcctctcc    114360
agcacctgtt gtttcctgac ttttaatga ttaccgttct aactggtgtg agatgatatc    114420
tcatagtggt tttgatttgc atttctctga tggccagtga tggtgagcat tttttcatgt    114480
gttttttggc tgcataaatg tcttcttttg agaagtgtct gttcatgtcc ttcgcccgct    114540
ttttgatggg gttgtttgtt tttttcttgt aatttgttg agttcattgt agattctgga    114600
tattagccct ttgtcagatg agtaggttgc gaaaatttc tcccattttg taggttgcct    114660
gttcactctg atggtagttt cctttgctgt gcagaagctc tttagtttaa ttagatccca    114720
tttgtcaatt ttggctttg ttgccattgc ttttggtgtt ttggacatga agtccttgcc    114780
cacgcctatg tcctgaatgg taatgcctag gttttcttct agggttttta tggttttagg    114840
tctaacgttt aaatctttaa tccatcttga attgattttt gtataaggtg taaggaaggg    114900
atccagtttc agctttctac atatggctag ccagttttcc cagcaccatt tattaaatag    114960
ggaatccttt cccatagct tgttttctc aggtttgtca aagatcagat agttgtaggt     115020
aagcggcgtt atttctgagg gctctgttct gttccattga tctatatctc tgttttggta    115080
ccagtaccat gctgttttgg ttactgaagc cttgtagtat agtttgaagt caggtagtgt    115140
gatgcctcca gctttgttct tttggcttag gattgacttg gcaatgaggg ctcttttttg    115200
gttccatatg aacttgaaag tagtttttc caattctgtg aagaaagtca ttggtagctt     115260
gatggggttg gcattgaacc tgtaaattac ctgggcagt atggccattt tcacgatatt     115320
gattcttcct acccatgagc atggaatgtt cttccatttg tttgtatcct cttttatttc    115380
cttgagcagt ggtttgtagt tctccttgaa gaggtccttc acatcccttg taagttggat    115440
tcctaggtat tttattctct tgaagcaat tgtgaatggg agttcactca tgatttggct     115500
ctctgtttgt ctgttgttgg tgtataggaa tgcttgtgat ttttgtatat tgatttgta    115560 tcctgagact ttgctgaagt tgcttatcag cttaaggaga tttggggctg agacaatggg    115620
gttttctaga taaacaatca tgtaatctgc aaacagggac aatttgactt cctcttttcc    115680
taattgaata ccctttattt ccttccctg cctaattgcc ctggccagaa cttccaacac    115740
tatgttgaat aggagtggtg agagagggca tccctgtctt gtgccagttt tcaaagggaa    115800
tgcttccagt ttttgcccat tcagtatgat attggctgtg ggtttgtcat agatagctct    115860
tattattttg aaatacgtcc catcaatacc taatttattg agagttttta acatgaagtg    115920
ttgttgaatt ttgtcaaagg cttttttctgc atctattgag ataatcatgt ggttttttgtc   115980
```

-continued

```
tttggctctg tttatatgct ggattacatt tattgatttg cgtatattga agcagccttg 116040
catcccaggg atgaagccca cttgatcatg gtggataagc tttttgatgt gctgctggat 116100
ttggtttgcc agtatttat tgaggatttt tgcatcaatg ttcatcaagg atattggtct 116160
aaaattctct tttttggttg tgtctctgcc tggctttggt atcaggatga tgctggactc 116220
ataaaatgag ttagggagga ttctctcttt ttctattgat tggaatagtt tcagaaagaa 116280
tggtaccagt tcctccttgt acctctggta gaattcggct gtgaatcctt ctggtcctgg 116340
actcttttg gttggtaaaa tattgattat tgccacaatt tcagctcctg ttattggtct 116400
attcagagat tcaacttctt cctggtttag tcttgggaga gtgtatgtgt cgaggaatgt 116460
atccatttct tctagatttt ctagtttatt tgcgtagagg tgtttgtagt attctctgat 116520
ggtagtttgt atttctgtgg gatcggtggt gatatcccct ttatcatttt ttattgtgtc 116580
tatttgattc ttctctcttt tcttctttgt tagtcttgct agcggtctat caattttgtt 116640
gatcctttca aaaaccagc tcctggattc attgattttt tgaagggttt tttgtgtctc 116700
tatttccttc agttctgctc tgattttagt tatttcttgc cttctgctag cttttgaatg 116760
tgtttgctct tgcttttcta gttgttttaa ttgtgatgtt agggtgtcaa ttttggatct 116820
ttcctgcttt ctcttgtggg catttagtgc tataaattc cctctacaca ctgctttgaa 116880
tgcgtcccag agattctggt atgttgtgtc tttgttctcg ctggtttcaa agaacatctt 116940
tacttctgcc ttcatttcgt tatgtaccca gtagtcattc aggagcaggt tgttcagttt 117000
ccatgtagtt gagcggcttt gagtgagatt cttaatcctg agttctagtt tgattgcact 117060
gtggtctgag agatagtttg ttataatttc tgttcttta catttgctga ggagagcttt 117120
acttccaact atgtggtcaa ttttggaata ggtgtggtgt ggtgctgaaa aaatgtata 117180
ttctgttgac ttggggtgga gagttctgta gatgtctatt aggtccgctt ggtgcagagc 117240
tgagttcaat tcctgggtat ccttgttgac tttctgtctc gttgatctgt ctaatgttga 117300
cagtggggta ttgaagtctc ccattattaa tgtgtgggag tctaagtctc tttgtaggtc 117360
actcaggact tgctttatga atctgggtgc tcctgtattg ggtgcatata tatttaggat 117420
agttagctct tcttgttgaa ttgatcccct taccagtatg taatggcctt ctttgtctct 117480
tttgatcttt gttggtttaa agtctgtttt atcagagact aggattgcaa cccctgcctt 117540
ttttgtttt ccatttgctt ggtagatctt cctccttcct ttcatttga gcctatgtgt 117600
gtctctgcac gtgagatggg tttcctgaat acagcacact gatgggtctt gactctttat 117660
ccaacttgcc agtctgtgtc ttttaattgt agcatttagt ccatttacat ttaaagttaa 117720
tattgttatg tgtgaatttg atcctgtcat tatgatgtta gctggtgatt tgctcgtta 117780
gttgatgcag tttcttccta gtctcgatgg tctttacatt ttggcatgat tttgcagcgg 117840
ctggtaccgg ttgttccttt ccatgtttag tgcttccttc aggagctctt ttagggcagg 117900
cctggtggtg acaaaatcgg tcagcatttg cttgtctgta aagtatttta tttctccttc 117960
acttatgaag cttagtttgg ctggatatga aattctgggt tgaaaattct tttctttaag 118020
aatgttgaat attggccccc actctcctct ggcttgtagg gtttctgcca agagatccac 118080
tgttagtctg atgggcttcc ctttgagggt aacccgacct ttctctctgg ctgccctaa 118140
cattttttcc ttcatttcaa ctttggtgaa tctgacaatt atgtgtcttg gagttgctct 118200
tctcgaggag tatctttgtg gcgttctctg tatttcctga atctgaacgt tggcctgcct 118260
tgctagattg gggaagttct cctggataat atcctgcaga gtgtttgcca acttggttcc 118320
```

```
attctccgca tcactttcag gtacaccaat cagacgtaga tttggtcttt tcacatagtc   118380
ccatatttct tggaggcttt gctcatttct ttttattctt ttttctctaa acgtcccttc   118440
ttgcttcatt tcattcattt catcttccat tgctgatacc ctttcttcca gttgatcgca   118500
tcggctcctg aggcttctgc attcttcacg tagttctcga gccttggttt tcagctccat   118560
cagctccttt aagcacttct ctgtattggt tattctagtt atacattctt ctaaattttt   118620
ttcaaagttt tcaacttctt tgcctttggt ttgaatgtcc tcccgtagct cagagtaatt   118680
tgatcgtctg aagccttctt ctctcagctc gtcaaaatca ttctccatcc agctttgttc   118740
cattgctggt gaggaactgc gttcctttgg aggaggagag gcgctctgcg ttttagagtt   118800
cccagttttt ctgttctgtt ttttccccac ctttgtggtt ttatctactt ttggtctttg   118860
atgatggtga tgtacagatg ggttttcggt gtcctttctg tttgtgagtt ttccttctaa   118920
cagacaggac cctcagctgc aggtctgttg gaatacctg ccgtgtgagg tgtcagtgtg    118980
cccctgctgg ggggtgcctc ccagttaggc tgctcggggg tcaggggtca gggacccact   119040
tgtggaggca gtctacccgt tctcagatct ccagctgcgt gctgggagaa ccactgctct   119100
cttcaaggct gtcagacagg gacatttaag tctgcagagg ttactgctgt cttttgttt    119160
gtctgtgccc tgcccccaga ggtggagcct acagaggcag gcaggcctcc ttgagctgtg   119220
gtgggctcca cccagttcga gcttcccggc tgctttgttt acctaagcaa gcctgggcaa   119280
tggcgggcgc ctctcccca gcctcgctgc cgccttgca tttgatctca gactgctgtg    119340
ctagcaatca gcgagattcc gtgggtgtag gaccctccga gccaggtgtg ggatatagtc   119400
tcgtggtacg ccgttttta agccagtctg aaaagcgcaa tattcgggtg ggagtgaccc    119460
gattttccag gtgcgtctgt cacccctttc tttgactcgg aaagggaact ccctgacccc   119520
ttgcgcttcc caggtgaggc aatgcctcgc cctgctttgg ctcgcgcacg gtgtgcgcac   119580
ccactggcct gcgcccactg tcttgcactc cctggtgaga tgaacccggt acctcagatg   119640
gaaatgcaga aatcacccgt cttctgcgtc gctcatgctg ggagccgtag accggaactg   119700
tccctattcg gccatcttgg ctcagcccct ttcttttgg tctgccttct catgattctc     119760
tgacactgtg ttattataat ggaaccctga tcttggcca tgtccttcct tccctttacc     119820
atccatcttc caaaggacac ttgttcttca gctgctcctc tctcagcatc tcagctgccc   119880
aaggcagcca ctctcgtcct gcacacttcc ttatccaagc tacttccttg gactcccttt   119940
tgactcccca ctagccagtg ctttgatctg tcaggtatga gacctctatc aacatttgt    120000
cccctggggtg tgaccttctc tttctggagt ttatcttatc agacgttatt tgagtccttt   120060
cccccttgata tggtttggct gtgtccccac ccaaatctca tcttgaattc ccatgtgttg   120120
tggcagggac ccagtgggag gtaattgaat catgggcag gtctttccta tgctgttctc    120180
atgatagtga atagggctca caagatctga tggtaatata aggggaaatt tccctgtgca   120240
agctctcgtt ttgcctgctg ccattcatgt aaaacgtgac tggctcctcc ttgccttcca   120300
ccatgactgt gaggcctccc cagccaagtg aaactgtaag tccaaataaa cctctttctt   120360
tggtaaatta cccagtcttg ggtatgtctt tatcagcagc atgaaaacag agtaatacag   120420
taaattggcc cagtagagtg gggcactgat gaaaagatac ctgaaaatgt ggaagccact   120480
ttggaactgg gtaataggca gaggttggaa cagtttggag ggctcagaag aagacaggaa   120540
aatgtgggaa agtttggaac ctcctagaga tttgttgaat ggctttaccc aaaatgctga   120600
tagcaatatg gacaatgaaa tccaggctga ggtggtcttg gatggagatg aggcacttgt   120660
tgggaactgg agcaaaggtg actcttgcta tgttttaaca aagagattgg tgacatttg    120720
```

```
ccctgccct agagatttgt ggaactttga atttgagaga gatgatttag ggtatctggc  120780
agaggaaatt tctaagcagc aaagcattca agaggttatt tgggttctgt taaaggcatt  120840
cagttttata agggaagcag agcataaaag tttgaataat ttgcagcctg acaatgtgat  120900
agaaaagaaa attccatttt ctgagtagaa attcaagcag gctgtggaaa tttgcataag  120960
taatcaggag ccaaatgttg attctcaaga caatgggaaa aatgtctcca gggcgtgtca  121020
gaggtcttca tggcagcccc tcctataaca ggactggagg cctaggagca aaaagtggtt  121080
tcagggccca ggcctagggt ccctgtgctg tgtacagcct agggatttgg tgccctgtgt  121140
cccagccact ccagccatgg ccaaaagggg ccaatgtaga gcttgggcca tggtttcaga  121200
gggtgtaagc cccaagcctt ggcagcttcc acgtggtgtt gagcctgcca gtgcacagaa  121260
gttgagaatt ggggtttggg aacctctgcc tatatttcag aagatgtgtg gaaatgcctg  121320
gatgcccagg caagagtttg ctgcaggggt gggatactca cggagaacct ctgctagggc  121380
aggatggaag ggaaatgtgg ggccagaacc cctatacgga gtcctagtgg agctgtgaga  121440
agagggccac tatcctccag accccagaat gatagaccca cgacagcttg caccatgcac  121500
ctggaaaagc cacagacact caatgccagc ccatgaaagc agccaggagg gaggttgtac  121560
cctgcaaagc cacaggggca gagctgccca agaccatggg aacccacctc ttgcatcagc  121620
gtgacctgga tgtgagacat ggagtttgag atcatttctg gagctttaag atttgactgc  121680
cccactggat tttggacttg catgggccct gtagccactt tgttttggcc aatttctccc  121740
atttggaatg gtcggattta cccaatgtct gtatccccct tgtatttagg aaataactag  121800
cttgcttttg attttacagg ctcataggca taagggactt gccttgtctc agatgagact  121860
ttggaatgtg gactttgag ttaatgctga aacaagttaa gactttgggg gactgttggg  121920
aaggcatgat tggttttgaa atgggaggac atgagatttg ggaggggcca ggggtggaat  121980
gatatggttt ggctctgtgt ccccaccaga tctcatctgg aactgtactc ccataattct  122040
catgtgtcat gggagggacc cggtggcaga taattgaatc atgggggcag tttcctccat  122100
actgttctcg tggtagtgaa taagtctcat gagatctgat ggttttgtca ggggtttctc  122160
cttttgcatc ttcctcattc tctctttgcc tgctgccatc catgtaagat gggacttgct  122220
cctccttgcc ttccaccatg attgtgaggc ttcgccagcc atgtgtaact gtagtccaat  122280
taatcctctt tcttttgtaa attgtccagt cttggggatg tctttatcag cagcatgaaa  122340
acggactaat acactcctct tgtaccccct aaccctcttt tgcataattc tagcctgact  122400
ctgcccttgg gtgggtacca gtcctgactc ttcaggtctc agagggttgt ttcctcactt  122460
cacccagggt ttaaataggc cttgtctcct gcttgtgtca taggcttctg ctttggttga  122520
tattactttc tttctttatc aatatggttt ttaaagagaa tgtatgaagg gattttaaat  122580
ttagatggcc accattattc tatgaaaatc taaaaattca catgttctta ggttcttatt  122640
ccactttaag aaaaacagca ctagaaacta tagataaaac attatagata tggtttatga  122700
aataaagatg ataggaacaa caatcagtag ccctgcatgc aaagactatg aagtgactat  122760
ctattttttt ttattattat tatactttaa gttctagggt acatgtgcac aatgtgcagg  122820
tttgttacat atgtatacat gtgccatgtt ggtgtcctgc acccattaac acatcattta  122880
caataggtat ttctcttaat gccatcccta cccccacccc ccaccccaca acaggcccca  122940
gtgtgtgatg ttccccgccc cgtgtccaag tgtcctcatt gttcaattcc cacctatgag  123000
tgagaacatg cagtgtttgg ttttctgtcc ttgctatagt ttgctcagag tgatggtttt  123060
```

-continued

```
cagcttcatc catgtcccta caaaggacat gaactcgtcc ttttttatgg ctgtacagta   123120
ttccatggtg tatatgtgcc atgttttctt aatccagtct atcattgatg acatgtgag    123180 ttgattccaa gtcttcgcta ttgtgaatag tgctgcaata acatacgtg tgcatgtgtc    123240 tttatagtag catgatttat aatcctttgg gtatataccc agtaatggga tcactgggtc   123300
aaacgatttt tctagttcta gatccttgag gaatcgccac actgtcttcc acaatggttg   123360
aactagttta cactcccacc agcaatgtaa aagccttccc atttctccac atcctctcca   123420
gcacctgttg tttcctgact ttttaatgat cgccattcta actaatgtga gatagtatct   123480
cattgtggtt ttgatttgca tttctctgat gaccagtgat gatgagcatt ttttcatgc    123540 gtctgttggc tgcataaatg tcttcttttg agaagtgtct gttcatatcc tttgcccacc   123600
ttttgatggg gttacttgat tttttcctat aaatttgttt aagttctttg tagattctgg   123660
atattagccc tttgttacat gggtaaattg taaaaatttt ctcccattct gtaggttgcc   123720
tgttcacttt gatggtagtt tcttttttgct gtgcagaagc tctttagttt aattagatcc   123780
catttgtcta ttttggcttt tgttgccatt gcttttggtg tttagacgt gaagtccttg    123840 cccatgccta tgtcctgaat ggtaatgcct aggtttttt cttctagggt ttctatggtt    123900
ttaggtcaaa catttaagtc tttaatccat cttgaattaa ttttgtata aggtgtaagg    123960 aagggatcca gtttcagctt tctacatatg gctagccagt tttcccagca ccatgtatta   124020
aatagggaat actttcctta tttcttgttt ttgtcaggtt tgtcaaagat cagaaggttg   124080
tatttctgag ggctctgttc tgttccattg gtctatatct ctgttttggt accagtacca   124140
tgctgttttg gttactgtag ccttgtagta tagtttgaag tcaggtagcg tgatgcctcc   124200
agctttgttc ttttggctta ggattgtctt ggcaacgcgg gctttttttg cttccatctg   124260
aactttaaag tagttttttc caattctgtg aagaaagtca ttggtagctt gatgggatg    124320 gcactgaatg tataaattac ctcgggcagt atggccattt tcactatatt gattcttcct   124380
atccatgagc atggaatgtt ctcccatttg tttgtgtcct cttttatttc gttgagcagt    124440
ggtttgtagt tctccttgaa gaggtccttc acatcccttg taagttggat tcctaggtat   124500
tttattctct tgaagcaat tgtgaatggg agttcagttg tgatttggtt ctctgttgt     124560 ctgttatttg tgtataggaa tgcttgtgat ttttgcacat tgattttgta tcttgagaca   124620
ctttgttgaa gttgcttatc agcttaagga gattttgggc tgagatgatg gggttttcta   124680
gatatacaat catgtcatgt gcaaacaggg acaatttgac ttcctctttt cctaattgaa   124740
tgcccttatt ttcttctct tgcctgattg ccctgaccag aatttccaac attatattga    124800
ataggagtgg tgaaagaggg catccctgtc ttgtgccagt tttcaaaggg aatgcttcca   124860 gttttttgccc attcagtatg atattggctg tgggtttgtc atagatagct cttattgttt   124920
ttagatatgt cccatcaata cctagttttcc tgagagtttt tagcatgaag cattgttgaa   124980
ttttgtcgaa ggccttttgt gcatctattg agataatcat acagttttg tgtttggttc    125040 tgtttatatg atggattacg ttcattgatt tgcatatgtt gaaccagcca tgcatcccag   125100
ggatgaagcc aacttgatct tggtggataa gcttttgat gtgctgctgg attcggtttg    125160
ccagtatttt attgaggatt tttgcatcga tgttcatcag ggatattggt ctaaaattct   125220
ctttttttgt tgtgtctctg ccaggctttg gtatcaggat gatgctggcc tcataaaatg   125280
agttagggag gattccctct ttttctgttg attggaatag tttcagaagc aatggtacca   125340
gctcctcttt gtacctctgg tagaattcgg ctgtgaatcc gtctggtcct ggactgtttt   125400
tggttggtag gctattaatt tattgcctca atttcagagc ctgttattgg tctattcagg   125460
```

```
attcagcttc ttcctggttt agtcttggga gggtgtgtgt gtcgaggaat ttatccattt   125520
cttctagatt ttctagttta tttgcataga ggtgtttgta gtattctctg acggtagttt   125580
gtatttctgt gggattggtg ctgatatacc ctttatcatt ttttattgtg tctatttgat   125640
tcttctctct tttcttcttt attagtcttg ctagtggtct atcaattttg ttgatctttt   125700
cagaaaacca gctcctggat tcattgattt ttttgaaggg ttttttgtgtc tccatctcct   125760
tcagttctgc tctgctgtta gttatttctt gccttctgct agcttttgaa tgtgtttgct   125820
cttgcttctt tagttctttt aattgtgatg ttagggtgtc aagttttaga tctttcctgc   125880
tttctcttgt gggcatttag tgctatagat ttccctctac acagtgcttt aaatgtgtcc   125940
cagaggttct ggtatgttgt gtctttgctc tcattggttt caaagaacat ctttatttct   126000
gccttcattt cattatttat gcagtagtcc ttcaggatta ggttgttcag tttccatgta   126060
gtagtgcagt tttgagtgag tttcttaatc ctgagttcta atttaattgc actgtggtct   126120
gaaagacagt ttgttataat ttctgttcta ttacatttgc tgaggagtgc tttacttcaa   126180
ttcagcaaga agagctagct atcctaaata tatatgcacc caatacagga gcacccagat   126240
tcataaagca agtccttaga gacctacaaa gagacttaga ctcccacaca ataataatgg   126300
gagactttaa caccccactg tcaacattag acagatcaac gagacagaaa gttaacaaag   126360
atatccagga cttgaactca gctctggacc aagcggacct aatagacatc tacagaactc   126420
tgcaccccaa atcaacagaa tatacattct tctcagcacc acgttgcact tattccaaaa   126480
ttgacaacat agttggaagt atctatgttt ttaagttcaa actaaatgtt taaggaatgc   126540
tatattattt gattccctaa tttcccaacc ttttggataa aagggcttct atcctacact   126600
cacagtatgg agtgttctga ggttgtttca gattgttttg ttaggtggtt ccatgttcca   126660
ggaagctaca tctcatgcct gatctcttcc atgttagtct gctgcttgct gtggggtgg    126720
acatagagag gaaagcagcc agcattcggg gtgagaggag gcacaatggt gcctctctaa   126780
ggacagttca tggaagatca tcactctttt ttttttgttt gtttagcata gccctgagt    126840
cccatcattc gatggaggca aagcaaatcc atcttcttct actttctttg ggatcatgtt   126900
ttgattctta tggcagaatc caagaatgtg ttgttcgtct cttcagcatt ggcattagtg   126960
aaaatcccct tgggactttg gcatatggtc ttctctttag tttccaacgc tgttgccagt   127020
tttcatcttt ttgtaattct tcgtggatat taaaatggaa attggaagaa aggcatatta   127080
gtccctgaag tttatcctga attaacccag aagtcctacc aattattttt tagtaatgaa   127140
taggaaagaa ttatattaag ggtatgattc agtgattttt gattacttt ttctctagac    127200
tacttaaaaa acttaataaa ccttcttaat aacaatctat atgaaaaata tctttccata   127260
tataactcta gacccagtga attcaactta catatttcct cactgaattt catcaacatt   127320
ttctaatttc cgtgcctata ctcttaattt atggtaatat ttgcatgttg aaatggcttt   127380
tcaggaagca tgggatttac acaaaccaaa tatcacctgc cccccataca cacacaccct   127440
taacaaagga aataagtcct gtaaggagtt tcaccgggat agtggttaaa aatcggtact   127500
ttttgattag atctggttta aatcctgtct cctccattaa ttacttgtgc aatctttaag   127560
cattgatttc cttgtgtaaa atgtaataat agttacattt gtctgtaaca aatgtaacaa   127620
ataacaacct atcctgtaga cacctatgtg aggatttagt gagagagtgt gtttgaaaca   127680
tttagcacca tgcctggaac attgtaagaa ctcggtagct ggtagtgaag atgataacaa   127740
ggatgatggt gcttccaaag ggttaacagg tcggacatta ccctgtggat gtgttggtca   127800
```

```
atgttttcat tagtaactgg ggttattttt tttcttcaaa atttcttctc agaaagtatt   127860
gtcattgcta tttctaaaaa tttgatactg cctttcaggg tgtgtctttt atgacagatg   127920
gtcagcagtt agtggtaaaa gaagtatgga atgtaatacc atttcattta tttatgggaa   127980
atgttttgtt gccccaccct tcaactaata ggaaaatgaa aatcaaaaac tggaaactat   128040
ttataaatgg acagtgctgt gatctcagtg tctgaaactg tagactttta gaaaatattt   128100
atagcatatt ggaaactggt cactggtcag tggctgtctc cttgccctgt ttttgtaaat   128160
aaaaatactc tagcaaatgt gaaatttggg gtaaattcaa acagaatact gaaaatatca   128220
tcagagacaa tgatatacta ctttataagt tttcaagaga agagggtgaa gaaaaatgtt   128280
taacttttat taatagaagc atttgcagtt aatagagata tttgtttatg gagccttaaa   128340
aataaaccaa atgaatggaa acaccataca ttcaaggaga cactgaggcc atgtgtacat   128400
cttactgagc agagaattta gcatagaagg ttagagatgg gatttggggg tcagtctgcc   128460
tgagctccaa acccagtcct gtcacctgct caaccacatg attgtgtaag tcacttaacc   128520
atgccatgcc aagcttgtct ctacctcaca gtgttgaagg ttgaatgaaa tgatacgtgt   128580
aaagtatttt aaatggtgtg ttgcacataa aaaatgttct atcagtgcaa gctactgtta   128640
tccaaactag cctagccaaa acaaatgaaa ccccaaaata actagtttgg ttgttatagg   128700
catgggtaaa acttgccaac ttcaccggtt tagaggtagg tcttcatcac taagtggcaa   128760
atggcaaaca agatagttct gttatttct ttacataggt ctttgtctac ttactgccat   128820
agccaataat atgtgctggg atggggtaa acattgtacg gtggcaatcc ttgaactgtc   128880
ccatgggtgc ctaccttaaa gaagctaatt agagagctct gctttgttcc tataagcctg   128940
gagcccaagt atttgctgta ataaaaacac ccattacctt gattcacgta aaaccaggac   129000
atttcatgaa cttgtgtgat tattgaaaac ccgtttatca ttaacaccgt cagtcattat   129060
ttagagattt ttatttcaca aataaaatca acaatctgat aaagacagta tagctcatgc   129120
agctaaacta tagcatctac caaaaccaaa aaataaggaa aatacctaga taacagattg   129180
caatatgtat ttttaatat acagtctata atgagtagac tgtgtgactt gactatattg   129240
acactgatat ttttccaaaa agagactctc atattggaga gaacatcata aaatgtctta   129300
gaaattaaaa ttacatctac cccagtgtgt ttcataaagg gagcacttgc cagcaagaag   129360
aataggtagg aatattaatg tttcatttta tcttcatatt attccttgtgt ctgtgtccca   129420 ggttatagtc tttgaggtta tattatttcc atgtctgcag aatctggatc tatattttac   129480
aataaagggg cttttgttgc ctcatgcaat tctcataaca actctgtaag ataggtactt   129540
ttatctagat tctgctgatg agaaaaacaa cacccaagtt tatatagcca gtaatttctg   129600
gagttgggat gcacaccctg aaaggctttg ctcccaaaga caatgctata cttcttatga   129660
gagagtgatg tcttcagaaa ttggtcagga ggaaagttca ttttctgatg attgtatgga   129720
aatgaaactt tggaactgta tgatgtcctg gaatactata gtatttgtag cattacctaa   129780
aaatgaatac atgcatatat gtgtgtgtgt gtagagagag acatagagaa gatagaagct   129840
aacacatgat tatagtatag caataatcaa ccccacaacc attttatggt tctgatagggg   129900 ccactgttta ttctgcaaga tcacaagtga tcacaagagt tgatattgct gaaactgtgt   129960
tatgaacata caacatacac tttttctcca acccactttg gtatacacac ctttgtggaa   130020
gaaattgtgt cattgtgata aagctttgtg ttcaaggtac taatatccct atatggcata   130080
tattaagata ttgattatag aaagttatca acagatttct taagatactt tctgggaaac   130140
caggacttgt tttcaagggg aagccattat cattatatat ggacttctta cctaagtgtc   130200
```

```
ctaaaagcta gatacccatc ttttgctcta taggaacaaa atcaagaatt tagaacatgt   130260
aatcacatat ggtgacctct ataacaaggc cagagagcag tgattcttaa tcttagatgt   130320
gggttaaaat cagattgcat ttttgacaag ggtgccaaga tagttccatt ggaactattg   130380
aaaagactat tggaaaaaat agtcctttca aaaaaatagt gctgggataa ctggctaccc   130440
acatgcagaa gaatgaagtt gaagaagcat gacatcagca agatggtaga ctagaagacc   130500
ctagtgctat tctccctcaa aaagatagcc agaacaatga ataaacaact tcattttaac   130560
aaaaataact gaggaggagc acagtggtgc acaagagaag taacagatac cctggtgagc   130620
acagaaactt gggatggcca catagagaat gggaagaaat gccaggcctc cattacccta   130680
accccaattg gaagcagctg ggaatgaact aggaggaacg tttccctact gcaaggaggt   130740
aaacaaaagg atcccagcag ccccatcaac accgtggata cctacagacc tgagcactgg   130800
ggtcccctgc aatcctcaca gacactaagc ctagctgagg gagctgcctg aagtccacat   130860
gtccgtgctt cccccagaga aggagccaat actatgatcc acaccctgtg gcccacatag   130920
ctaccatgct atgccatctt ggagttggaa ctatggctgg atgtgtcttg ctctggggc   130980 aagtatgcat ggctctcttt tatccctgag gctaagccat tgctgaactg ccccagccca   131040
atggcctgac atccccaagt cgagcaactg ttttgtgctc ccctgtgggg ccaagcagag   131100
gtggagctgc tccacctccc caccccttt cctcctcagg ccagagctga agcagtgtcc   131160
tgattcctgg gaaaacagta cttttgactgc tcagagaaat catgcccctc caatgcctaa   131220
gtcaaagcag cacgctgcat cctagggaaa tggtgcctgg tccacccaga gcagtcatac   131280
ctgttggact caagccgaaa tgacacatca ccctctgggg aatttgtacc ctggctgagc   131340
tgaatagctg caaatcccag ggctgtgctg acatggtatc ctgtgtccca gggaaacaga   131400
gcagtggctg agctgagaca ccccatcctg caggccaaac agctctagtg tccttccttc   131460
ctggggctgt actagcctcc tgaagtctga gctgctgaga tacccttgac tctggggagt   131520
ggagtcattg ctgtgctgca cattgtcttc cagggcccaa ataacagctg tgttctgcca   131580
ttctagggta cagcatattt ctctgcagaa acctgacaag ccaggagaga agtggatgat   131640
gtattcaaag taccaaaaga aaaaaaaatt gtcagctaag catgcgatac ccagcaaatc   131700 taccccttcag aaatgagaga gaaagaaagt ctcccagaca agtaaaaact gagggaattc   131760
atcaccacta gactggcttt acaagaaaca gtcaagggag tcctgtatct ggaagaaaaa   131820
agatgataat cattctcatg aaaacacaca caagtgtaaa actcgctggt agagcagatg   131880
cacaaaggag aaagagaaac aagagaaaac cttgttactg cagaaaacca ccaaactgca   131940
atgatctcaa atatctttcc tgaccacaat gaaatcaata acaagaggaa cttttgaaat   132000
tttacaaaca catggaaatg gaagttaaac acgttcctga atggtcaatg ggtcaataaa   132060
gaaattaaga aggaaaatgt taaatgtctt gaaagaaatg aaaatagaca tacagcatat   132120 caaaaccta tggtatacag caaaagaagt gttaagagga aaatgtatag caatagatgc   132180
ctacatccaa aaagtagaag gatttccaat cagcaacgta gcaatgtatc tcaagaaact   132240
agaaaagcaa gaacaagcca aatccaaaat tagtagaagg aaagaaataa tgatgaaagc   132300
agaaataaac aaaattcacg gagatctggc agccaagatg gctgaatagg aacagctccg   132360
gtctacagct cccagcgtga gcgacacaga agacgggtga tttctgcatt tccctctgag   132420
gtaccggatt catctcacta gggagtgcaa gacagtgggc acaggacagt gggtgcagcg   132480
caccatgcgc aagcctaagc agggcgaggc attgcctcac tcgggaagtg caaggggtca   132540
```

```
gggagttccc tttcctagtc aaagaaaggg gtgacagacg gcacctggaa aattgggtca   132600
ctcccaccct aatactgcac ttttccaatg ggcttaaaaa acggcacact aggagattat   132660
atcccgcacc tggctcagag ggtcctatgc ccacagagtt tcgctgattg ctagcacagc   132720
agtctgagat caaactgcaa ggcggcagcg aggctggggg aggggcaccc accattgccc   132780
aggcttgctt aggtaaacaa agcagccagg aagctcaaac ttggtggagc ccaccacagc   132840
tcaaggaggc ctgcctgcct ctgtaggctc cacctctggg ggcagggcac agacaaacaa   132900
aaagacatca gtaacatctg cagacttaaa tatccctgtc tgacagcttt gaagagagca   132960
gtggttctcc cagcacgcag ctggagatct gagaacgggc agactgcctc ctcaagtggg   133020
tccctgatcc ctgaaccccg agcaacctaa ccgggaggca ccccccagta ggggcagact   133080
gacacctcac acggccgggt attcctctga gacaaaactt ccagaggaat gatcagacag   133140
cagcattcat ggttcacgaa aatccgctgt tctgcagcca ccgctgctga tacccaggca   133200
aacagggtct ggagtggacc tctagcaaac tccaacagac ctgcagctga gggtcctgtc   133260
tgttagaagg aaaactaaca aacagaaagg acatccacac caaaaaccca tctgtacatc   133320
accatcatca aagaccaaaa gcagataaag ccacaaagat ggggaaaaaa cagagcagaa   133380
aaactggaaa ctctaaaaac agagcgcctc tcctcttcca aaggaacgca gttccacacc   133440
agcaacggaa caaagctgga cggagaatta ctttgacgag ttgagaaaag aaggcttcag   133500
actatcaaac tactctgagc tacaggagga aattcaaacc aaaggcaaag aagttaaaaa   133560
ctttgaaaaa aatttagacg aatgtataac tagaataacc aatacagaga agtgcttaaa   133620
ggagctgatg gagctgaaag ccaaggctcg agaactacat gaagaatgca gaagcctcag   133680
gagctgatgc aatcaactgg aagaaagggt atcagtgatg gaagatgaaa tgaatgaaat   133740
gaagcgagaa gggaagttta gagaaaaaag aataaaaaga aacgaacaaa gcctccaaga   133800
aatatgggac tatgtgaaaa gaccaaatct acgtctgatt ggtgtacctg aaagtgacgg   133860
ggagaatgga agcaagttgg aaaacactct gcaggatatt atccaggaga acttccccaa   133920
tctagcaagg caggccaaca ttcagattca ggaaatacag aaaatgccac aaagatactc   133980
ctcgagaaga gcaactccaa gacacataat tgtcagattc atcaaagttg aaatgaagga   134040
aaaaatgtta agggcagcca gagagaaagg tcgggttacc cacaaaggga agcccatcag   134100
actaacagca gatctcttgg cagaaactct acaagccaga ggagagtggg ggccaatatt   134160
caacattctt aaagaaaaga ttttcaacc cagaatttca tatccagcca aactaagctt   134220
cataagtgaa ggagaaataa aatactatac agacaagcaa atgctgagag attttgtcac   134280
caccaggcct gtcctaaaag agctcctgaa gcactaaaca tggaaggaa caatcggtac   134340 cagccgctgc aaaatcatgc caaattgtaa agaccatcga ggctaggaag aaactgcatc   134400
aactaacgag caaaataacc agctaatatc ataatgacaa gatcaaattc acacataaca   134460
atattaactt taaatgtaaa tgggctaaat gctccaatta aaagacacag actggcaaat   134520
tggataaaga gtcaagaccc attagtgtgc tgtattcagg aaacccatct catgtgcaga   134580
gacacacaaa ggctcaaaat aaaaggatgg aggaagatct accaagcaaa tggaaaacaa   134640
aaaaaggcag gggttgcaat cctagtctct gataaaacag actttaaacc aacaaagatc   134700
aaaagagaca agaaggcca ttacataatg gtaaagggat caattcaaca agaagagcta   134760
actatcctaa atatatatgc aaccaataca ggagcaccca gatgcataaa gcaagtcctg   134820
agtgacctac aaagagactt agactcccac acaataataa taggagactt taacaccccca   134880 ctatcaacat taaacagatc aatgagacag aaagttaaca aagatacca ggaattgaac   134940
```

```
tcagctctgc accaagcgga cctaatagac atctacagac ctctccaccc caagtcaaca 135000
gaatatacat ttttttcagc accacaccac acctattcca aaattgacca catagttgga 135060
agtaaagcac tcctcagcaa atgtaataga acagaaatta taacaaactg tctctcagac 135120
cacagtgcaa tcaaactaga actcaggatt cagaaactca ctcaaaactg ctcaactaca 135180
tggaaactga acaacctact cctgaatgac tactgggtac ttaacgaaat gaaggcagaa 135240
gtaaagatgt tctttgaaac cagcgagaac aaagacacaa cataccagaa tctctgggac 135300
acattcaaag cagtgtgtag tgggaaattt atagcactga atgcccacaa gagaaagcag 135360
gaaagatcca aaattgacac cctaacatca caattaaaac aactagaaaa gcaagagcaa 135420
acacattcaa aagctagcag aaggcaagaa ataactaaga tcagagcaga actgaaggag 135480
atagaggcac aaaaaaccct tcaaaaaatt aatgaatcca ggagctggtt ttttgaaaag 135540
atcaacaaaa ttgatagacc gctagcaaga ctaacaaaga agaaaagaga gaagaatcaa 135600
atagacgcaa taaaaaatga taaaggggat atcaccactg ataccacaga aatacaaact 135660
accatcagag aatactacaa acacctctat gcaaataaac tagaaaatct agaagaaacg 135720
gataaattac tggatacgta caccctccca agactaaacc aggaagaagt tgaatctctg 135780
aatagaccaa taacaggctc tgaaattgtg acaataatca atagcttacc aaccaaaaag 135840
agtccaagac cagttggatt cacaaccaaa ttctaccaga ggtacaagga ggaactggta 135900
ccattccttc tgaaactatt ccaatcaata gaaaagaga gaatcctccc taactcattt 135960
tatgagtcca gcatcatcct gataccaaag ccaggcagag acacaaccaa aaagagaat 136020
tttagaccaa tatccttgat gaacattgat gcaaaaatcc tcaataaaat actggcaaac 136080
caaatccagc agcacatcaa aaagcttatc caccatgatc aagtgggctt catccctggg 136140
atgcaaggct ggttcaatat acgcaaatca ataaatgtaa tccagcatat aaccagaacc 136200
aaagacaaaa accacatgat tatctcaata gatgcagaaa aggcctttga caaaactcaa 136260
caacacttca tgctaaaaac tctcaataaa ttaggtattg atgggacgta tctcaaaata 136320
ataagagcta tctatgacaa acccacagcc aatatactga atgggcaaaa actggaagca 136380
ttccctttga aaactggcac aagacaggga tgccctctct caccactcct attcaacata 136440
gtgttggaag ttctggccag ggcaattagg caggagaagg aaataaaggg cattcaatta 136500
ggaaaagagg aagtcaaatt gtccctgttt gcagatgaca tgattgtata tctagaaaac 136560
cccatcgtct cagccccaaa tctccttaag ctgataagca acttcagcaa agtctcagga 136620
tgcaaaatca atgtacaaaa atcacaagca ttcttataca ccaataacag acaaacagag 136680
agccaaatca tgagtgaact cccattcaca attgcttcaa agagaataaa atacctagga 136740
atccaactta caagggatgt gaaggacctc ttcaaggaga actacaaacc actgctcaag 136800
gaaataaaag aggatacaaa caaatggaag aacattccat gctcatggac aggaagaatc 136860
aatattgtga aaatggccat actgcccaag gtaatttata gattcaatgc catccccatc 136920
aagctaccaa tgactttctt cacagaattg gaaaaaacta agttcatat ggaaccaaaa 136980
aagagcccac attgccaagt caatcctaag ccaaaagaac aaagctggag gcatcacgct 137040
acctgacttc aaactatact acaaggctac agtaaccaaa acagcatggt actggtacca 137100
aaacagagat atagatcaat ggaacagaac agagccctca gaaataatgc cgcttaccta 137160
caactatctg atctttgaca aacctgagaa aaacaagcaa tggggaaagg attccccatt 137220
taataaatgg tgctgggaaa actggctagc catatgtaga aagctgaaac tggatcccctt 137280
```

```
ccttacacct tatacaaaaa ttaattcaag atggattaaa gacttaaacg ttagacctaa    137340
aaccataaaa acccgagaag aaaacctagg cattaccatt caggacatag gcatgggcaa    137400
ggacttcatg tctaaaacac caaaagcaat ggcaacaaaa accaaaactg acaaatggga    137460
tctaattaaa ctaaagagct tctgcacagc aaaagaaact accatcaaag tgaacaggca    137520
accttcagaa tgggagaaaa ttttttgcaat ctactcatct gacaaagggc taatatccag    137580
aatctacaat gaactcaaac aaatttacga gaaaaaacaa cgccatcaac aagtgggcaa    137640
aggatatgaa cagacgcttc tcaaaagaag acatttatgc agccaaaaga cacgtgaaaa    137700
aatgctcatc attactggcc atcagagaaa tgcaaatcaa aaccacaatg agataccgtc    137760
tcacaccagt tagaatggca atcattaaaa agtcaggaaa caacaggtgc tagagaggat    137820
gtggagaaat agaaatactt ttgcactgtt ggtgggactg taaactagtt caaccattgt    137880
ggaagtcagt gtgatgattc ctcagggatc tagaactaga ctagaaatac catttgaccc    137940
agccatccca ttacggggta tatcccaaa ggactataaa tcatgctgct ataaagacac    138000
atgcacacgt atgtttattg cggcactatt cacaatagca aagacttgga accaacccaa    138060
acgtccaaca atgatagact ggattaagaa aatgtggcac atatacacca tggaatacta    138120
tgcagccata aaaaatgatg agttcatgtc ctttgtacgg acatggatga aattggaaat    138180
cattctcagt aaactatcgc aaggacaaaa aaccaaacac cgcatgttct cactcatagg    138240
tgggaattga acaatgagaa ctcatggaca caggaagggg aacatcacac tctggggagt    138300
gttgtggggt ggggggaggg gggaggatag cattaggaga tatacctaat gctaaatgac    138360
gagttaatgg gtgcagcaca acagcatggc acatgtatac atatgtaact aacctgcaca    138420
ttgtgcacat gtaccctaaa acttaaagta taataataat aaaataataa taataataaa    138480
ataaaaaaat tcacgctaaa aaataataca aaagatcgat gaaattaaaa gttggttttt    138540
gaaacgatta acaaaactga caaataatta gctagatgaa tcaagaatgt aaatggtcca    138600
aataaaatca ccaacaaaaa aggagacatt gcaactgata ccatagaaat acaagtgatc    138660
atgagagact attatgaaca actatatgcc aacaaattag aaaatctagt ggaaatggat    138720
aaattcatgt atacatgcaa tgtgccatga ttgaaccaag aagaaataga aaacctgaat    138780
agaccaatta taagtaatga gattgaatct tgtaataaaa agtctcccat tgaagagaag    138840
cccaggacct gatgacctca ttgcagaatt ctacaaaaca tttaaagaac taataaaaat    138900
tcttctcaaa ctcttccaga aaattgaaga ggagggaatt cttctaaact tattccacaa    138960
gaccagcatt atgttgatac caaaactaga cagagataca caagaaaag aaaactttag    139020 gccagtatcc ccaatgaaca tagacacaca aagcctcaac aaaatgctag caaactgaat    139080
ccagcaacac attaaaaga tcgttcacag ccaggtgtgg tgtctcatgc ctgtaatctc    139140
agggctttgg gaggccaagg caggaggatc acttgaacct aggagttcaa gaccagcctg    139200
ggcagcagag ggagatccca tttctgcaaa aaatttaaaa attagccagg catggtggca    139260
tgctcctata gcccaggtac tagggaggct gaggtgggag gattgcttga gtctgggaga    139320
ttgagactgc aatgagccat gatcaagcca ctgtactcca gtctgggcaa caaatgaga    139380 ccccatctca aaaataaaa ataaatttaa aagatcattc accattatca agtgggattt    139440
atcccaaagt tgcaagaatg gttcaacata tacaaatcca taaacatgac acattacatc    139500
aacagaatga agtataaaaa ccacatgacc atctcaatag atacataaaa aggatttgat    139560
acaattcaac atcgcttcat aatcaaaaca ctcaactaat tagttataga aggaccacag    139620
ctcaacacga taaaggccat atatcataag cccatagcaa acatcgcact gaatgggaaa    139680
```

```
aagttgacag cctttcccct aacatctgaa acaagacaac gatgctcact tttaccactt 139740
ttgttcaaca gagtaatgga agtcctagcc agagcaatca ggcaatagaa agaaataaag 139800
gacctccaaa atggaaagga ggatgtcaaa ttgtccctat ttgcagatga tatcatcata 139860
tatacagaaa accctaaaag ctctaccaaa aaactcttac aactgataaa caaattcagt 139920
aaagttgcag gatacagaat caacatacag aaatcagtag catttctata tgccagcaac 139980
aagctagcag aagagaacac acaaaaaatg aaaagatatc tcatattcat agatttgaag 140040
aataaatatt gtgaaaatga tcttactacc aaaagcaatc tacagagtca atgcaatccc 140100
tatctaaata ccaataacat tctcaacaga aattaaaaaa tcctaaaatt tacatgcacc 140160
cacaaaagac cctatagcca aagcaatcct gaatgaaaag aacaaagttg gaggcatcac 140220
actgccaggt ttcaaaagat actataaagg tatagtaacc aatacagcat gttacttgtg 140280
taaaatacag attcatatac caatggaaca aaatagagaa cctagaaata aattcgtgta 140340
tgtatagcct actgatcctt gacaaaggca ccaagaacat ttattgagga agagacagtc 140400 tttttcaataa atggtgctgg gaaaattgga tatccacatg cataaaaatg aaaccaaacc 140460
tgtatctctc accatatata aaaatcaact caaaatgggt taatgactta aatataagac 140520
ctgaagctat gaaactcctg aaagaaaaca taggagaaat gcttcagaac attggtctgg 140580
gcaaagattt tatggagaag acctcaaagg cacaggcaac aaaagcaaaa atagacaaat 140640
gggattatat caagctaaaa tctcctgcac agcaaaggaa acaatcaaca gagcaaatag 140700
acagcctgca taatgggaga aaatatttgc taactcttca ttcaacaaag gattaatatc 140760
cagaatatat aaggaactga aacaattcaa cagaaaaacc ccccaaataa tccagtttaa 140820
aatgggtaaa tgagctgaat agacacctct caaaataaga aatacaaatg gctagtagat 140880
ttatttttaa aaatgctcaa catcactaat catgagagaa tgcaaattta aaaccacgat 140940
gagatatgat ctcaacccgg ttagaatggc cattatcaaa aagttaaaaa ataacagatc 141000
ctggcgaggt tgtagagaaa ggggtactct tatccaccac tggtgagaat gcaaattagt 141060
ctagccattg tggaaaacaa tatgaaggct cctcaaaaaa ctaaaaatag aactaccata 141120
tgatccagca atcccgctac tgggtatata tgcaaaggaa atgaaatcag tatatcaagg 141180
agatatgtgc actcccatat ttattgcagt actattcaca ataccccaaga tatagaatca 141240 acttaagggt ccatcagtgg gtgaatgaag aaaaatatggt atatatacac aatggaatac 141300
tctttagcca taaacaaaa tgaaatcctg tcattcacag taacatggat gaaactgaag 141360
gtcactatgt taagtgaaat aagccaggca cagaaagata aataccacat gttctctac 141420 atggaagcta aaaaacgttg atctcataga agcaaagagt agagtagtgt ttttcctgag 141480
gggtgggaag ggtaggggag aggagaatag ccaaaggtta gttaatggat ataaaagtac 141540
aattaaatag gaggaataag gtctagtgct ctatagcact ataggatgac tatcattaac 141600
aacaatttat tgtatatttt tgaaaagtta caagagtgaa ttttgaatgt tcccaacaca 141660
gagaaatgat aaatatttga ggtgatggtt atgctaatta cactgactta tcattacaca 141720
ttgtacacat atattgaaat atactctagc ccataaatat gtatatttat atgtcaatta 141780
aacataataa aaaagaaga taatgaagtt ggatctctac ctcacagcat acacaaaaat 141840
taacttaaaa tggatcatag acctaaatgt aagaattaaa actataaaac tcttagaaga 141900
aaactcagga gtaaagcttt tgtgatcttgg gtcagacagt agtttcttag ataaaagcaa 141960
cacaggagaa aatacataag tcgaactaca tcaaaatgca aacttttatt ctcaaaatga 142020
```

```
tattctcaag gaagtgaaaa atcaacccac agaataggag aaaatattag caaatcatgt  142080
atcagataag ggacttgcaa atagaatata taaagaattc atgcaactca atcataaaaa  142140
gacaagtagc cccattaaaa tacgagcaaa tgatctgaat agacatttct ccaaagagga  142200
tatataaatg gccaatacat acatgaaaag atgctcatca ttaattatta ggaaaatgca  142260
aatcaaatcg caatgagata tcactttaca ccaactagaa tggctacatt caaaaagaca  142320
cattaataag tgttgtcaaa gatgtggaga aattgaagca cttattcctg gtgagagtgt  142380
gaaatggcgt agctgctttg gaaaattgtt cggcaagtcc tcaaaatgtt gtagagttac  142440
catatgacct ggcaattcca ctcctagtta tagacccaag agatatgaaa acgaatgccc  142500
acacaaaaaa ttgtacatga atgttcatag taggattatt cataatagcc aaatattgaa  142560
aacaatcaaa atactaacca agtaaatgga taaagaaaat gtgatatctt caagcaatgg  142620
gatattattt agccatataa aggaatgaaa tatttgatgc atgctaccac attgatgatc  142680
cttgaaaaca ttatgctaag tgaaagaagc cagccacaaa aggccaagta ttgtgtggtt  142740
ccagttatat gaaatgtcca gaataggcaa atctgtagag acagattaac aatcggctag  142800
ggctggggag gggagtgaag tagaaaatga agaatgactg ctaatgggta cagtatttct  142860 tttggagga taaaaatgtt ctaaaattag actgttgatg attgtgcaac catgtgaata  142920
taccaaaaac atttaactgt gcagtttaaa tgggtgattg tatggtttta aaattatact  142980
tcaataaagc taagtttggg tgcttttata aatcttatg cccaggctga aactcagaac  143040
tcagtctcct gggattgaac ccatgcatca gtattttta agagttcttc aggtgattgt  143100
attgtgcagc caaggttgag aatcattatg tttgaatcag ccctaatcca aataagattt  143160
taatttaaga gactccaaaa gagttgagat cccatgtgga aggactccgg gaggcttcct  143220
caaaccatga tacctcaagt gtggttctga gaccagcagc atcaatgtca cctgggaaac  143280
tgttagaaat gcagattatt gggcccatt cagttcaagt acatcaggat ccacagttta  143340
acaagctccc cagatgattc atatgtacat taaggtttgg gaagcactgc ttaggagcag  143400
cggttcccat gcttggctgc acattggaat catctggaga gtccaaaagt accaatgctt  143460
gggttccacc gccagtgatc ttacgggtat gagatgcagc ctgtgcatct gggatttaaa  143520
agcttcccag gtaattctaa tgtacagcaa agtttgagaa tgagtactgc aaaaaacaag  143580
atacctaatg gcaaataaga tggttaataa aattttctta ttttgttttt aacagaagga  143640
tagatgaaca tgcataagaa agtggagatt attgatatca aaaatttcca gaggagtgag  143700
gaagggatgg cagtgagaca acaatggaaa acgttttctc taaaaaaaaa aaagggaaa  143760 aaacaaaaa caaaaacaga aaactcacca cacaccaggc attttccttc taaatccaag  143820
agagggatct ttcatgtgat tattggagac tactcaaatt taagtggcca agaatttgtg  143880
ggttcttaag agggtcttta atgctgaaaa catatgggta tttactgaac ttcccttct  143940 ttgaatttat aaagagaaag tttattaata tggtggtgaa catttcttcc caagctgtgt  144000
acccatgtcc agcttcttcg gtctggggaa attttaactc ctcagtagac agtgggccct  144060
gcgcagggtc tggggcatgc tcttcctata tatggcattc agccctgagg attctcctcc  144120
ccagcaatcg gccatgtctc tctaatgacc attgtctctg ccatttactg gtcttttcaa  144180
aattatgact ctgaaatatc tcctaggcaa aatttatgagg cttgcagagt tagctttgag  144240
acttctcatc acccacccct tccctcctt ccgacaagct ccgttctgt cccatgcccc  144300 cagattgtct tctccaggtg acttgaaccc accttcttgg ttgcagtatc agtacactgt  144360
acccttgtct gcactgaaat taaccatgca gtttctgtgc cttcttaagt tgatgtgtgt  144420
```

```
gtgtgtgtgt gtgtggtggt ggagggtata attacttgaa tctgtgttaa taaagtgtta   144480
actattaacg gaaatccaca atccctctct acctcccct caggaagtcc ctaatggtgt    144540
ttggtcattg tttcaatcac ttgtcatata ttgtgttttc ttggcccata tctctaacca   144600
catccttatc aaaatattct gatgagtgca ttttaaaagt agaatgacaa catacttaag   144660
atagttggag gggttggctc ctatttgcat catgatgatt ctgcctatga agattttttcc  144720 taacaatcaa ctaggattat acacaacgct tggtttcaaa aaatcatctc atcgtattaa   144780
atttacttat tttaaaatac ctgtgactct tctgaataat gaaaaaaatg acatgaatga   144840
agagtatgta tataaactct ctctaaagtt attaggaaaa tgtttttatt taattgtgcc   144900
taatattttg gggtattaca gtgaactcta cttttaaagc tgcgtagtta tgtattaata   144960
tactggccct gaaattttg agttttcaac ctatagtcca gaaaaagcct ttatttttaa    145020
tagttgccct aaaaatttaa cacaaaagtt ttacttagct aaatctaaat ttaatcagta   145080
gctttacccc acttccaaac aatataaata ctttaaaatg ctttcatttg atttcctttc   145140
cttgcttgct attattttcc aggattttaa ctctgtttgc ttggttttat ttgtttgttt   145200
gttttaagac agagtctcac tttgtcatct aggctggagt gcagtggtgt gatcatagct   145260
cactacagcc ttgaactcct gggctcaagg gatcctcttg cctcagcctc ctgtgttgct   145320
gggactacag gcatgcacca ccatgctcaa attattatta ttattagtag tagtagtagt   145380
agtagtagta gtagtagtag tacagaccag gtctcagtat gttgcctaag cttgtctcaa   145440
actcctggct ggcctcaagg gatcctccca tctcagcctc ccaaagtgct gggattatag   145500
gcgtgagcca ttgtacctgg catacttgtt tggttttaag cccacaaatt agacatcatc   145560
atcattctat ttagattttc tcatatttac cattttcttt acatatcatt tctacttcca   145620
ttcagagctt ctgggatcaa accgtagttc ctggcatttt ggactggttg atagtctcca   145680
ggatattcag gcagttaagt gtctccgaaa gaaaatgaga aaagaaaggt cctgggaaat   145740
atgccccacc cccacccctg cagtgctgcc gctgctgtcc caggaccgtg ggcacccctg   145800
aatgtttctc ttccactgtc tctgatcact gtgatttatg gagtagaggg ggacaatgac   145860
atctgataga ataccaaagt taaatatgct caatttaagg agctgttatt tattcagaga   145920
tcgtgtcttt cctacctttt ttgctgttta ttttataaaa taatggtgat ggtagttgaa   145980
gtttgttatt ttgttttgtt ttaaattaat tcattaagat ttgtttttat atttccttac   146040
ttggcaaata caaagttgtg aatcacaacc cagatttttt gaaattgtat tgggcattga   146100
aatcccaaac cactgctatc aacagctaac tgtgagtttg gcgtgtggac actgggacac   146160
ctgaaaccat gtcttggtta cgtcaggagc cttattgatt atttatatta tgtatgaatc   146220
ctgtggtgtt aacagtactt tgcaacccttt agtacttagc tgaactgtat tagattatca   146280
gggagtcctc agtacacccct caatgattta aattgttttt agctacttct gtaaggctga   146340
gtctacacta gcaaaatgac ctgggtgcct attgtgctcc ctacatacat ctggtgatgt   146400
ttatgctccc aatttcttaa gaacactgct ttgagagtca cacacccaa tattctacca    146460 ataacttact atgtaccttc atcatttgta agaagagggg gttgaactaa gcgatctcca   146520
agtcactttt cagcacaaat gtaggttgtg attgtatttg tgtgtacaca tttttttaaag  146580 ccttaaagag atctaggtat ttctcatgta tttatattaa atctaagatc cgtgttgcaa   146640
atttggacat ggaggacatt aattttttctg atgtaggtta ctctttaaga ggcatgttgc   146700
atctgtaata ttggtgccac catttttggca gatgcagttt cttcatttac tcgtaagtgt   146760
```

```
tcagtatgaa gtctatatga ggtgacttga gttctcattt ctctggtgta aaaaatggtc 146820
atgtttaaat aaggccacaa tatttatttc aaagggtccc agaatcattt tttaaaatat 146880
cttcatatgc ttgacactga agttcttatg taaagggttc ggtcaatgta aacaaacgat 146940
gactgcttga agatgcacca gccgtgattg tggagacctc caaattcatg acagagttgt 147000
taactggcag gtttgttatt cctataagt acaaggaagg gaagtattaa ataattcat 147060 gcccattaga gagaggaaat taacattccc ttaaaaattg ttttccagtg aaggaagccc 147120
atcccccaga attgagctgc tgcataatat tgacccgaac ttcgtggact cttcaccgtg 147180
tgagtaccag tgcattgcta ctagattaaa tctaattggc ccaccaagat ggtttgatta 147240
cctagtgtgt ctctagccta gctttctctt ttttcctgag ttgctataaa ggtaaacagt 147300
tcttcgggac atatctcccg ctcatctcag agggcagtgt gctgtgaaag caacaccagc 147360
ttatgaaata agaaaggtga attctattct tgctctgccg cttactagcc tttaagccat 147420
tgaactctcc ctgccccagc cttccccatt tacaaaagaa gaactcatgg catctctgag 147480
gctccttctc actgtagatg tcatgttgct gccctgttct tacctgagag ctccagagcc 147540
accttccaga aaactcacag tcagataagc cacagttggg ttccaggtag tgtgagcaac 147600
cacattatct gattgggctg gtcaggtact gcccaacacc tgctgggtgt cacaagtgtg 147660
actttcctag cagtcctgga agtgattccg cttgattctg cctcctgcct aaattaacct 147720
gtaaagagcc ttaccatttc cttcagggca ggcatgcatg tagtgcttcc agatcacaac 147780
ggactgtaat aggcctgtat aaataccatg cgagtggccc taatgccctc agcatagtga 147840
gtttgggcat agaaagcctt agcaattaga ccctttgccc agctttcatc ataatgctca 147900
tcttgcaaac agtgccctta tattccctta ttcacatggg ggctcccatc cgctcctttc 147960
tggacatact gctgcccact tagttcaggc tctccttact tctttgtttt ttccaaactg 148020
cattatagct caccacaaaa tattctcatt cagagattcc tgctcagaga attaccccac 148080
agtcattcta aatgtgtcac caggcactcg ggccccactt gcccggccag cctcactcca 148140
ggcactcctt gtcatgttct cacttcctag acacttgtca tctccatgca gatcatcgta 148200
ctgtcatgaa tatgcttttc cctatgcctg aaacacattt tccctacctg tctataatct 148260
ctctcatccc ttaaaaaccc agccccatgt ctccctctgt gaatgctttc cagagcccca 148320
gaaggagcag tcactccttc ctgtgtgcat gtgtctccgt atagcatccc tcacatgttc 148380
gtgtttgtgc ctgcatttcc aagctgagag ctcctggaag tcagcatctc ctgtatttt 148440 ttatccttgt cagttaacac aaatactggg agcttgctag gcactcagta atgattactt 148500
gatgactcag tggacaattg gagagttgag atgcaataaa gaccaagtgg acacattaag 148560
acctggacag gaaagggccc tgagacaggc gagaatggct acatcgtgga gaaatttcta 148620
tttcttttgg agtaaacgca tgtcagtgag agaggcaagg gcaaggtttg agccctaagg 148680
actgtaagaa cagtctagat ttgtgctgtc cagtatagta gccacaggcc acatgtggct 148740
gtcaggtact taaaatatgg ctaactgtgg attgagatgt gctgtgagta gaatatatac 148800
atccgatttt caagacttag tacacctatg tattatatgc atacaatatt atagatttat 148860
tatttgttga aaggataata ctttggatat attgaattaa atatattgtt agtgttttac 148920
ttctctcctc ttccttttctt aatgtggcta ataagaaaatt taattttaat taacttacat 148980
aagtgacttg cattatattt ctattggcct aaaaacccct tctagaaggt gctaggaagt 149040
aagttgatca gctgagctga tcacagagct gtgaatagtt actgtgaggc tacatcaatg 149100
actcctaaac ttttctctac cccagtacac ctaagagata catttcagtc atatcaaagt 149160
```

```
ctctaagggt ggctggaaga gaatagtggg gaggcaggaa tggctttaaa actttctgag 149220
taatttaatg cactgcaaag cccagtataa cctaggtcta ggggatatgt ggaatatgcc 149280
acccacatta taatggttgt aaatgtcttc acctgctaaa ttccacctac aaatgaaaaa 149340
ccttaagacc cctcactcac taagctgtat tttggtttgg catttgaagt aggagcttga 149400
gaactatact cctatgtgat atggttggga tttgtgtccc acccaagtgt catgtcgaat 149460
tgtaatcccc catgctggag gaggggcccg gcgggaggtg actggatcat aggcatggat 149520
tcccccttgc tgttcttgtg atagtgagtg agttctcatg agatctggtt gtttgaaagt 149580
gtgtggcacc tcccccttcg ctctcttcct cctgctccag ccatgtagga catacctgcc 149640
tcctcttcac cttctgtcat gattgtaagt tcctgaggcc tccccagcca tgattcctgt 149700
acagcctgtg gaaccctgaa ccaattaaac ctctcttatt tatacctagt ctcaggtagt 149760
tctttataac aatgcaagga cggacgaata cactatcacc acagcactgt gtgctgcagg 149820
gttcttggtg caacttgctg tgctttctcc tgtcttacct aaagggccct agcaaaataa 149880
cagcacaggc aaaaggtttc tccagagtaa aagttggtaa gagcatggaa attagaatag 149940
aaaattttcc taatcttgcc atccatagac tgtaaggaca tttacttctc ttggactcag 150000
tttcctatgt attatgtggt agaattataa gacccagtac tgccgccaca aatttaggca 150060 tcctcttttgg ccttctgctg ctcttccttc cctctctgga gcccacccag gccttcatgt 150120
tggcttcccc accagcttgg gactcctgct ctgactcctg cagataacga aggacattgt 150180
cagctcttgc aaggatgtag aaccacattc actgttgctt cacacacaca cagcgttctc 150240
tgctgtctgt gcctgcaggt agcaaggtgc cacccacctc ctcacacatg gcaatcccat 150300
gggccttttc tgcccagttt ttatattcac ttcactctac tgagaggcag aagaagaaac 150360
aagaagagct gtctttgggt gcctgctcat ttttaggatg atgatacaag cccgtttcct 150420
tttctatgca attcatttat gaggaaaaat taaatccagc tataaaaaaa catgtactta 150480
ggggacagcc aagtctggat atcatattca tagagcacag aggcttttgt ggagttaaat 150540
cagaagtagc caatctcggg tgtaaactga gggttaacaa tggagtcagt gttatcacag 150600
aagcatttct gtggtttctc actccagctc ttcccagatc gttggtgctt actgcgggag 150660
aagaaggtag cgttccacct ccaccttccc taaagccact tcgtcagttt cctcacctgt 150720
ggagtaaaga aggaattaaa tgatctccaa ggtccctctg gcttcagtgt tctgtgggtc 150780
tctatatgaa tgggacctca aaggagcaaa gctgcttact ctgcttctct ccttttttctg 150840 cctgctagaa ggagtgtgtc cattgataag cagtgatgtt gccaaaggca tgatcataaa 150900
tagataaaca caagtgcaaa tgctagaaac attatatgca ctagaggaat ttgaattatt 150960
ttatgagttt cttattacta tatcctggcc acctttctga tttccgttcc gaaacatcac 151020
cgtatcgatc cgcttttcta tctcctcttt cccttagtgg gtcatcctgg ggtttgttga 151080
ccaatgtctc ctctgattgt gaatcatacg aataggcatt acgcacttcc caggagattt 151140
ctgccctctg cctagcacca catgctccca gaagctggcc tcttggattt cagcagctac 151200
acctcccccg ctccctgcca acacacaccc cattccccta gtcaaattat agggtgccca 151260
gaggcccatc ctgctggtgg agtcaggatt tttttcatgg tcacatgcac atggtaggtt 151320
gtggcttgga tactaacagt aaaaatactc aaagatcggc acaaaatatt gatacacgta 151380
cacattcata gagaaacatg cacacacacc aggggtcacc aaatctctca tagatcagga 151440
gattcaccat tctgcagtaa agcataaagt ctcaaggatg catacgtaaa ttataccatt 151500
```

```
aggatgacta caatttaaaa aatgaaagaa agaaaaggag agagagtgga aaaaggaagg  151560
aagggaggga gggagggagg ggaaaataag aattgttgag gatgtagaga aattggaacc  151620
cttattcact gttaatggga aagtaaaata atgtagcctc tatggacaat aacattgtgt  151680
gattactcaa aatattaaaa atagaattat cataggatcc agcaatccca cttctgagta  151740
tatacctaaa agaattaaaa gcaggggctt gaacaggtat ttgtacactc atgtttgtag  151800
cagcattact cagcattact cagaacagcc aaaaggtagt agcaacccaa atgtccatca  151860
gtgaatggat gaataaacaa aatgtggcat atatatatat atatatatat atatatatat  151920
atatatacac atatatatac catgaaaatag tatccagcac taacagtgaa agaaattcta  151980
atacatgcta caacatggat gaaccttaaa gacattatgc taagcaagtc acaaaaggaa  152040
aaactatatg actccactta catgaggtac ctaaagtggt cagattcata gggacagaaa  152100
atagaatggt ggttgcctga ggttgtgggg aggggagaat ggggcatgat tgttgagtgg  152160
gtgtagagat ggatggtgat gatgacagca taacaacgtg aatgtattta atgccactgg  152220
accatacaat taaaagtggt taggatagta aattttatgt tgtttgtatt ttaccacaat  152280
ttaaaaatat aaaaaataaa taaaacgtaa ctttccctcc ttccaaaact gaagagaaac  152340
tgcatgagaa tagggtctct atcttttca tttactgcca tatgcacagt aaggtctccg  152400
tagcacagaa cctaacatcg tagtaagttg ttgggttaat atcagtaaat atctgctaat  152460
gaatgataaa cagatcaacc tgtcaaagtc attgttttat tgtcttacag cctttcctga  152520
gcctaaaagt acctccagat ggccacttat actccttta aaccccaaac ctacctttg  152580 tgcctaagta aaaataactt agaagctaca agtcacttat taagttgtaa ttgacattat  152640
atacagatgt ttgaaactgt tcattcagct tctaagtgcc caccctcatc gctccctgca  152700
ttgaaaagat cggccagaaa agatgatgtg ggatttccct gcccaacttc atcccttttc  152760
ccagacctcc tcaatagaca aatagagatt tataaagcct ttgcctctgg cctggctcgg  152820
cctgacttcc ctctgagtct ggggctctgc ctcttcttgc tgttctgagt tcggttctgt  152880
tcctgttttc tgggatgttc cctctggttg tttcatcatt cactggttat ctcagtgccc  152940
caaccctagc tctgcttta tccccttcct ccctccactg cctcccagct tcatgacctg  153000
tgtcagagtg tgggatgtaa ttgctttcct gtgtgctttg aggagacttt ttattcattt  153060
ttgaaggctt tgttctgaag taaccttgga agtgctttgg tctctgttca gatagtaccc  153120
ttctcttttc ctttgttccc ttctgagaaa actcctaaga attatttatt cctccatgtc  153180
tttaaaatac ttctgtcttc gtccagcagc acagggtggt cagtgtaaga aacccgtgag  153240
agagcctggg gaatagcacc attgaagctg attagtggga aagcctggaa acctctaaag  153300
tggtggggaa cagccataat cccagggtag gcaagaggtc ctgcaggtct gaattcagct  153360
ctacatggtt ccaaggagag ctccagcccc aaattccaca ctcctgcaag gccccagcaa  153420
gcatggctca gaccacaagg agaactgctt caaaggcatt attttgcctg aggaaaaaca  153480
tatacaccta tcctgcaggt gccgggcttg atcttggctg ttctgcagta atgatcctgc  153540
cccatctgag accacgactc actttggaag tcagacgtgg cattctatga tggctggaac  153600
acacatatcc gatcatgtaa cataggtgta tatatttaaa acgtacgcac acacaggaga  153660
cacacacatt ctgctggtag aagcttgatt atagatgaag ggcagtgaca gatgttagca  153720
ttttccaccc caccaaaggc cagctcttca aagtgattcc atacagcttt gttactattt  153780
catttaaagg ccctcttctc tttaaagttt ctaatgagat gttatttctg ctcctgatta  153840
tagggtgaaa gaacagcctt cttcccaccc tctcctctct cacacacaca ttttctgtgg  153900
```

```
tgcaattgcc aaatccatgc ttgagatcca agagtcgtcc aggttggaat gcttggagct 153960
gctccctgtt tcctcctcag agcgacattc agagccattt cccagtatta tgttgccatt 154020
tccaagattg tttattcagt aaataaataa acgatgatgg cctgggatgc atgaggtact 154080
gttataaata ctcgagatca gttaagctaa agccaaacct aaaggtctgg ctaaaaccca 154140
gtctggaaga gtctggaaga gggcatggac acagcctctc ccaccctgc tggaaggctg 154200
ttggtggttc ccagctgtcc actagcaagc cctcctacaa cgcccaccat tcagcaccat 154260
tgcaatgccc tccttcagtc ctgtttatct cccttgttgc cctgcgcctt ctgtagagtt 154320
cagtgcacat tcctactcct ccgtgaagcc ctctctgatt cttttgaact tgagtcccct 154380
gagtttctct ggagcttccc aggacggtga gctcttgctg cctcatagtg cagtatttat 154440
attcacgtgt tttccccatc cggagctata aggagagcaa ggcttcattg tatagttctc 154500
tcggtgtctt atgtataaga gattaataca tattgaaaga atgcacgcta ataaatgaat 154560
aatttatcat cagctgattc gattagaatc agtctaatga gaacaatagt aatttcatac 154620
atcattttca aggcattttt atttcttttt gggtctatta gagaagtagt gacacagagg 154680
catctttctt tcagcctgaa attagatatt aagcagaatc aagagttagg gggaatgcat 154740
ggggctcacc ctgctacaga ttgctcagca ttgcatagaa tgccagaggc taagggcccc 154800
ttggcagttt gttcactctt tataatccaa gtgaagaaac tgaggcacca ggtcatgcat 154860
gctgttaaat atcagagctg gaactcaggg ctgttcagac ccggcatgta catcatgtcc 154920
tactgatttc gcaggtctca tcgctttgtg tcctacccctt gtcttgtggg agaagggcac 154980
ccagatatga gttacgatca tctcacctat ataatagcat gttgatggga catgactcat 155040
ttaaaggagg ctggaaaaat gggtcgagta gtcacattag ccttgctaga ttcacatgta 155100
atctgactct gcagatggtg gtagcttctg cttgtagagc tagtcatgga agccctgtca 155160
gtgccttgta ttcactccac tggagggtgc tgggggatg agggagctgt gtgtggggtg 155220
ggcagtgtca cctagtaaaa caggtagagt ttgggggtgc cagaaagccc tgggttttat 155280
tcaataccag ctctgactta tttcctgtga gcttgtgggt aagttcttcc agccatctgt 155340
ttcatcacct atacgttggg aacgattata acaatatctc ctgtaaatat gtccaaacaa 155400
cagtgaacaa caattacatt ctggctgcta cgattgggc agggtgggaa agttgcactt 155460
ttcactttat gtatttctct agtttttaatt ttaaattatg agcacatgtg acttccttaa 155520
tcaggaataa agccataaag ctttatttgt gaaaaccacc tccaaggagg gttccggtaa 155580
gcatggaata tctgaaatct gctgggttct tatagagtgg gagttgctgc ttccgtgcct 155640
gcctgtacta ggtcagagca gttagaattt tgtgtcgtct ctagttgcca atatttgtct 155700
ttagcagctc gtcaaatttt ccttggtgtg ggttgctaca tgccctcaat cacagagcca 155760
aaacacagat agctttctcc ttttttaattt tcaaaggctt ctagtctgcc ccctccgctt 155820
tggggagcac taaagtctgt ttggaaatgt ggccttttg atgccaaagg cagtcccaca 155880
agcctcgtat ccctccacc ccacttcaca cagcacatct caaggagcac gcatgaaacc 155940
ttcactgtta acacttggtg ctggcatcct ggctttcatc ccgagaaaat acacaaacca 156000
aaccaaatcc acagcacttt aaaaacacta attaactctc accactggcc taggctacgc 156060
agaaatggca atcccgctg ccccaatttt atgtttggag aaatcagggt aagcaacatt 156120
ttctagggct tctctgagcc agatcacaga agctgacctg aaggacttgg cctgccctg 156180
catctggagt taggccattt gatgaagggc cagctgcctc accagatccc ttctctacag 156240
```

```
caccacgtgg ttagtggccc ataactccat ttgtacatca gcgtttgttt ttttttcccc 156300
agggttactt tgatgccaaa ctgtctcatg tccaactgac catttattta tttgcttact 156360
tttctttaat tctggtacag cctagaaatt ttagccatag cttccaagtg tagcctgtta 156420
attatagttg attaaaggtt ctatgctgat tttgaatttc aacacaaaag cagactaact 156480
tccaaacagt ccctctcagg tccagtggct ccgcccctcc cgtcttccac cctggagcct 156540
ccccaggtct ggtaaagatt tggtggtgtc cagactcctt ttttcctctc ccagtctgga 156600
ccagtcattc tcctacctca gttccccagt cttaccatct gtaaagataa atatatccat 156660
ctttcttgaa agagtctacc ataaaattct gtaaaaacat aaaacctcat aaaattttag 156720
ggaacatatc caatgaaatt aaaatttaca aagtaaatct attttgtaaa tatttattga 156780
tcttgtcaga attttagggg gttttagggt gcttgtgtat aaggctgaaa taaaactttt 156840
gaaaacattt ctgggacgtt gttgaaaaca gactaaacgg cctgtttagt aacccataat 156900
gtaagatgtt agtaatcagg catttataga ctgaagtctg ttacctctgg cagaaaatac 156960
ctagggaatg agtatatggc ccctgcttct aaagattctt ttgaatcaga ggaaaacata 157020
tgcccaggaa aggatattaa cacagttata aataaagta gaacaaatga taagtgatat 157080
aatataagca gtaaggacaa atgaagaagt gacagcattt gggagtgatt aggaaaggtg 157140
ttctcaaaaa ggatatcttt aaatttgtcc attacttcaa caactttagt tttatctttc 157200
ttgattttaa tgtgaatgaa ggaaaagaat atttaacact attagttttc tatcactgat 157260
caaacaaatt accataaact caatggctta aaacaaccaa tacttaacca tcactctatt 157320
ttcgtatttt ttgaatgttt tcagttctgt aggtcagaag tctgacatgg gtctcactgg 157380
actaaatcca gggtaccgat tggcagggct gcagtcccct ccaaaggctg aggggacatc 157440
ccatttcctt gcctttttcct gcttctagag gctgcctaca ttccttggcc catggcctcc 157500
ttcctccatc ttcaaagcca gcaatggaag gttgggtcct tttctagcac attctttgaa 157560
cctggcttcc atcatctcat cttgtctgac ctgttctgcc tccttcttca acttttctgg 157620
actcttgtga taacattggg cccacctgga taaataatct agaatcacct ccctatttga 157680
aagtcagctg attagcaatc ttaattccat ctgcagcctg aatgccccctt tgccgtgtaa 157740
cctaacatat tcacaggtcc tggggattgg gacgtggata tctttagggg gccattattc 157800
tgctaccaca aatacctgct gtgttgccct agacttcatg aaaaatacaa caagtcgctt 157860
ataacctagt tggagagaac aagaacatac aaaaagttaa aagaaaatca gataacagtt 157920
gaaagctatg gtggtagaga cgttacaagt tgtacttaat tgtcagatca tttccatgga 157980
gtctgatagt tgctatgaga gtgaaggagg gctaaaacac tcaggccctc tttcacctcc 158040
actgaacctc aaagagttcc taggtggaaa agaccatcaa aggaaataga aaaggctgtg 158100
agcaaaaggt gtgtgagcct atttggggga caaaggggag gcatgaaaga agagatggga 158160
aagctaaaca aggacaatat gtcacactaa ggagatggga tttcatcctg tatgcagcag 158220
ggaagctcct tttgtacaaa taatagatgg ggggtggtg caagaaattt ttaaaaatac 158280
agaaaagctc aaaattttta aaaatacaca caaaaaaaat caccctaaac ctattattct 158340
gctacccaga aataagcatt gttaatattt tggtgggctt tttctatttc tatttaggga 158400
gagctttcaa catttcaccg ttcagtatga tatcgattgc agatttttt tatactcttt 158460
atcagtgtaa gaaaactccc tcctattctt agtttgtaga attttaaaa cagctattgc 158520
tgttgtccac aggaaagtcc ctttgtgtct gcactatttt aatcccaaaa taagaaaaa 158580
tctgctaatt ccacaggtgg ttatatagat gctggggttt cagcacttcc tgtttgaccg 158640
```

```
gaaactctca gtgaagtaaa aaaaaaaaaa aatcagaaat tgtggaagtt tatttgtaga  158700
gactcttgtt ttgccgttag gactgtgggt cccagaattc tttggaatga cagccctagt  158760
caaagtctag ccatttctct cccaattatc caaacaaagg ctggtttagg cactgcctga  158820
aaggacttga tagatgtaat ccaagtccca tatccttaag tgcctcaacc aagaggaagt  158880
cctgggtggg cctgattcag tcatatgagt aaaatataaa ttttcctttg taggctggtt  158940
tttactaaaa atgatattgc tggattatcc ttggaatcca tctcagcaaa gtgttagaat  159000
aatctcaagt ataaaggcag gaggggctgg gcacagtggc tcatgcttgt aatcccagca  159060
ctttgggatg ccaaggtggg tggattgcat gaggccagga gctcaagacc agcctggcca  159120
acatggcaaa accccgtctt tactaaaaaa tacaaaaaag tagccgggca tggtggcaca  159180
cacctgtagt cccagttact agggaggcta aggtgggagg attgcttgaa ccggggaggc  159240
agaggttgca gtgagctgag agtgcaccac tgcactccag cctgggcgac agagcaagac  159300
tctatttcaa aaaaaaggca ggagaagtag tttatataag atatttataa ctagtttagt  159360
ggtctaatag cctatggatg agaagtgact ggtacagtgg gccatcctag aaagagaaaa  159420
tcatgtctag gtgggctcta tttgatggag ccgttgatct ggggccaggt ttacagtctc  159480
ttgtcactat ctggactctg ttctaggtat gcagctggct gtgcccctat taggatgaac  159540
cccctgtagg tgccctttcc ttctgatatg ccagggatgc tctgggactt cctgtcatag  159600
gtgattccta atgctcctga cccatggcag ccaaataggt tcccccttgg aggcttccat  159660
tctgccctgt tacctgccct tattttcaaa tttggaatgt ttgtagaagt ctgttagtat  159720
ctctctcact tattttgggg gtatcatact gttttcacag caaagagct tgcagtcagc  159780 tttagcttct tcctttaata catgaggggt aacacctgtg ctatttgttt tctttcctaa  159840
atgccttcac agaagcagtt tgaaccagaa gaatatacac aattaagtaa aaggagttga  159900
gagaaatcac atggagagca ataaagaaaa gaaactaacc attgttgaca gtgcactgtg  159960
ttctaggcac tgtgtagcta ccccctgccc ccagtacctg cctttcttta gagcacatat  160020 tatttttaa atatttattt atcatcctcc tgtctccatt aaatacaag ttccacgagg  160080 gcagacaatt tagtcttttg tgttcttttc tatcccaaa catctagaac agtagcacaa  160140
taagtagttg ttgaataaat gtcttttctt aaagaaaaaa tgaaaaaagg ggccaggcat  160200
ggtggctcat gcctgtaatc ccagcacttt gggaggctga ggcgagcaga tcacaaggtc  160260 agggggtttaa gaccagcctg accaaaatgg tgaaacccca tctctactga aaatacaaaa  160320
agtagtcagg catggtggtg cacgcctgta gtcccagctg cttgggaggc taaggcagaa  160380 gaatccttg aactcaggag gcagaggttg cagtgagcca agatcgtgcc actgcactcc  160440
agcctgggca acagagcgag actccatcaa aaaaaaaaa agaaagaaaa aggaaagaca  160500 tgggggttaac ttttttaacc tttaaaaaag atctatggaa aagattggat agatgtcaga  160560
ggtacttgat tgtaatagct aatgcttgtt tgtaaagtga gacgtaagaa agcttagatt  160620
tggcttaatt gatggcaagt ttaagagact gaggtttact tgagactgac attagtataa  160680
atttaaaatg acttaaagag gaagtcatgg gtatttgaac tatttatatt catttcagat  160740
cctttctttt acatcatttt gtaaaaactc cttcgaaaaa aatagttcag tgcttatagc  160800 tgactttta cttcttttctc aaaaagaaa aaataataa aagaggaatg agaaagtcag  160860
cttaagtact accttcccctt atcttttgac tgagatataa gaattatttg tgacataaat  160920 acattttat taaagaaagt tgaagattgg atctggttta ttttttggac aagttagaat  160980
```

```
atagtacttg atttctaatt gttaacaact aatgttttaa aaaacaaatg ttagagactg   161040
aaaaggaatc taaaccttte cettttttcta attgtaatca tattttcaaa tgtatatggg   161100 attttttct tagtctttcc acaaattata aacagcagca tttaccctgc attgagctga    161160
aatgaataaa cattttttaa atgaaaataa tgacagtgaa aaccaattta gaaaagaaag   161220 gaaaagatg cccataaatc acagacactt ggaagagcat gtaagaaaag ctaagaacta    161280 cattttcat attttacatt ttctctttaa aatcgctttc caaattgttg atggtttggc    161340
agctccaagg atgacatcaa ctcttccatt gtgcagtatc tgcttgcttt tagataactt   161400
ggtggcactt tatcaggttt tggtgattaa gctgaattaa aaaccaactg gatttgagtt   161460
taaattctcc taactgctaa accaaacaca ttcctgaccg taggcctact tttgaatact   161520
tctgaaaact tattattacc cataggctgt tttacttcta gaaacaaaag taagcaagtg   161580
agagaaaaat gcactcctta gagttactaa ccacatctgt caaaatgcag tatattacca   161640
gtgcagctgt taaatgctt ttaaaccagc catcttcttt tctgcctatc ttaacctgac    161700
tgaaaaccaa gaggacaata atcttggcat tgttttccta cttcagaaaa tcacagatag   161760
ttatgagcta ctgtctctct cagcagttgg gggcagattc tgatgattag ttaagtcatg    161820
atgaaaagat aataccagaa attaggctat taatgaggaa gaaaacagca ggctgtgaac   161880
aggtctgata actttcctgt atatcctagg aactcacctg ggaatactag gtgaaaacat   161940
tggcattcca cacatctggt ctattaccct acacttaaag cagtgccttt catacctgaa   162000
tgtgcacacg aatcacctga ttcagtcagg ctggggtggg gcccaaattc agcatttcta   162060
acagactcct gagtggtgcc aatactgctg ggtctctgac tacaatttga atattgagcc   162120
cctagtctag aggactttca cccaatttga agctcaatct ttagaattta aaatatttgt    162180
ataagtattt aagactaaat attttttcta agatatctaa ttaaagacag agatgtaaga   162240
ccttgaattt cagaactgtt ttataaattg tattagtctg ttttgcgttg ctgtaaagga   162300
atgtctgaga ctgggtaatt taaaagaggt ttatttcgct catgattctg caggctgtac   162360
aagcatggca ccagcatctg ctcagcttat gatgaggcct cagacagaag gcaaagggag   162420
agcaggtatg cacatggcaa gagtggcagc aagagagatg ccaggctctt ttaaagaaca   162480
gctctttaaa acatgaacag aacaagactc aaggagggca tcaagccatt tatgagagat   162540
ctgcccctat ggcccaaaca ctccccactg tgccccccct ccaacattgg ggatcacatt   162600
tcaacatgag atttggagga aacagatatc caaattatat cataagtatt tataatctct   162660 tccccccacat ttctatttaa gctagttgta tagcaattta cattatcttt cagattatcc   162720
aaatgccaaa atgttttctg atcctaaagt aacatgatgc atttgctgaa aaaaagttta   162780
agatatattc aagccagcaa gacatgaaga tttagagct catcacagaa gcttggtctc    162840
ttttcctttt gttcctggtt ttctccttat gtgaacattc agaaagaaaa cccaagcttc   162900
taaaaaatgg caaggagctc agtatctacc accctagaag aaggtccctg gaaatcaaga   162960
atcaggtagc agatttcttc tcctatgaac attcttgggg aaacctactt aggctatggg   163020
ttctgacttc tttcaagtac ttcctctgat cttgcggaag tactatggat gggtataggc   163080 aaacccaaa aagtccccag aaagagttt agtagagaaa ctaggtgatt aggagtgcca    163140
ctactttgtg caaaagagga aaattcccca tgctcatgcc tcttaaatgg ctgagagatt   163200
tctgtggcct ggtattacac accaggccaa agtagtcact gggacaccca ttggtcagtt   163260
actgtgtctc caagggacac agagcatctt gcccagtgtc atcattatgt gagcttggcc   163320
tgcctcctgg actcagtgaa cctgtttct cacctcccaa aaataaaagc aaaaacacac    163380
```

```
ctacaatttc agagcatgtg aaaaatggat ctaatcatca cattcatagg gacaatggta    163440
gaatttatta atgttcctac agttttcctt taaagtgttt tgagattaga aacaaaacat    163500
tatatgcaat atttgagagg aaaaaccaca aaataataaa attttgtatt cagtatctca    163560
gttgtgtaaa aataatatag acattaaaac aggattagag gccaggcgtg ttggctcacg    163620
cctgtaatcc cagcactttg ggaggccgag gcgggcggat catgaggtca agagatcgag    163680
accatcctgg ccaacatggt gaaaccctgc ctctactaaa aatacaaaaa ttagctgggc    163740
atggtggcac acatctgtag tcccagctac tcaggaggct gaggcaggag aatggcgtga    163800
acccggaagg cagagcttgc agtaagccga gatcacgcca ctgcactcca gcctgggtga    163860
cagagcaaga ctccgtctca aaaacaaac aaacgaagaa aaaacagga ttagaaagag    163920
aataccaaat tgttataatg gtcagttagc tttagagggt gagattatgt ataattttta    163980
gtatcgtttt tattcaattc agtgtaccta ttacttttgc aactaaattt ttgaaaaaga    164040
acaaagaaaa aaggcaacaa agcaacactg atcaggctga aggtctcctg ggcctaaacc    164100
tcccaaccac caagagtgtc aaaatctctg ttcagggact tgggtctgta gttaattgtt    164160
ggatgttttt atgtggtata aatctgtgta ctgccttgat gacagtaata aactagagtg    164220
tcttgataaa gaccaaagtc atcaattttc caaaatctgt atttgattaa ttctccaaag    164280
gtccaggtca atgttattcc tcaaacttta ttattttaac atagaagccc aaagtttcca    164340
agtctgtcag aaaattcatt atcactgtaa aacagcaaaa ggtcacaaaa tgtctctttc    164400
tacaataaaa tagcatataa gaaaaaatct cttttctca acaattcatt acccccaacag    164460
aaccaaaaaa acctttgaca tttcaggtct ttttgcttca ggggaaataa atgttccata    164520
gatcatggag aaaatgaca aacaaattaa tgaaaaacaa atacactcct gcagtatccc    164580
cagccacgcc agaccaaaca agtcagagtc agcttttatt cttgggtctt tccaactctg    164640
aagagtgaca gtttccataa tggcatcagc agtttagtta gagaaagctg tacacacacc    164700
aaagaaacac aaattaaaga aacatgtggt agaaaaacag aaagaggaat tctgttattt    164760
catgcatatt taattctagt gggaaagtca ttgctggcaa agtgttattg aaatcttgag    164820
ctaataagta gaagcattct agaagatatg caccgcctcc tcatagtgct ttatacaaaa    164880
ttgtaacttg actgaattta gcagtgctca attttcccac attctaaaaa ttccttcctt    164940
gaattctgcc tcactctcac cactaaacct tgtcagaagt agtttgcatg tgctttctcc    165000
atatcttcaa tttccattca tttactaatt ttaacaccaa atacatttcc attttcatta    165060
tttgtttaaa cacagccata caaataaaac caaaattggc ccagtgcagt ggctcacgcc    165120
tgtaatccca gcactttggg aggctgaggt gggtggatca tctgaggtca ggagttcgag    165180
accaacctgg ctgacatggt gaaactctgt ctctactaaa attacaaaaa aattagctgg    165240
gcgtgctggt ggatgcctgt aatcccagct actcaggagg ctgaggcagg agaatagctt    165300
gaacccggga ggcagaggtt gcagtgagct gagatcacgc tattgcactc tagcctgggt    165360
gacaagagca aaactccgtc tcagataaat aaataaataa aacaaaacaa agttcactat    165420
gacccttatt ccctgtcccc ctccacagag gtgaccactg ctaacagttt tgactttata    165480
gaccacttta gatgtgctta tgtatacaat atggatttat ggagcagtgg tgtgtacaat    165540
acttttttt tttttacatag ataatatcat ataaaatgtt gtgggttttt tttttgcca    165600
catacttttt tctgtcaatg atctgtcttg gagatctttc cagatccgta agtataaatc    165660
agtggttttc aaccaggggc tagtgagccc cccaggggag atttggcaat ttttgcaggc    165720
```

```
attttttggtg gtcacgacct gagtggggaa tgctattggc atctagtagg tagaagtcag   165780
ggatgtacta aacatcccac aatgcacaga acagccctat gacaaagagt tttccacctg   165840
aaatgtcaat aatgctgagg ctgagaaacc ctgataaagg tctactttat tcttttaact   165900
gctgcatggt attctgtagt ttatttagcc agtcatgtag cagtgtatat ttacatgatt   165960 ttttttttctt ttttgagttg gagtcttgct ctgttgccca ggctggagtg cagtggtgcg   166020
atttcgactc actgcaacct ctacctcccg ggttcaagcg attctcctgc ctcagcctcc   166080
cgagtaggtg ggactatagg cgtccaccac cacacccagc taatttctgt atttttagta   166140 gagacttttta aaaacatgtt tatttgtaga tatcagtgaa tgtttcttcc atttactttt   166200
gacccaactg caatcaacct tgtttcctaa atatccctaa atccattgct actgctttaa   166260
caaaatacca cagactgggt aatttataaa taataaaact ttatttctca cagttctgga   166320
ggctgggaag tctaagactg aggtgccggc agatttggtg tctggtgagg ctcctttct   166380 gcttccaaga tggtgccctg tggctgcatc ttccagagga gagaaacatt gagtcctcac   166440
gtggcagaag ggacaaaagg ggaaaaggga agaactctct tcctcaggtt cttggataaa   166500
ggcactaatc ctatccatga gggtggagcc cccagggcct aatcacttcc caatggcccc   166560
acctcttaat gccatcacct tggggggttcc aacatatgga ttttggagca acaaaccata   166620
gcagccccct gcaggtgacc agtgggtttt ctgaatccct tggctccttt tcagcatgag   166680
ctgacttggc ccttctgtgc catttgccag tgcttgtcct aaagcacttg gcctcccagg   166740
ccccttggct ctgcctttttt cctctctacc tctgtggccc ccttcagtct ctgtggctct   166800
gccatctcct gagctcttgc tgtcacagtg ctaggcatta gggatatgaa gacgaactgt   166860
ggaaggtccc agccctggag accctccagt ctagaagaca agcacataca caaatctccc   166920
aaagggaagc atcacctagt cagggcacat ttgaagtgtg ctgagtgatt gaataaataa   166980
ctaaatatag tagattttag aggacagtgg gaaatgtttt tccttcatga ttcagaattt   167040
actgcatatt ttatcttcat gacaccttttt ctcacaacat acgttttgaa aaaaaataag   167100
tcacgaaaaa gactttcctc atattttccc acccacagtc tttttgtctg ccttgaaaca   167160
gcaactgcat tgtttcacat acagggaatg cacttggtct ttgccaaggc agagaacaga   167220
tcaaatttga gaagcagccc tgcttgctgc tggctgaggg atgggaagtg aggttggccc   167280
tcggagcttc cttcccctac cctttctttc aacctcctca tgatggtagg accatcacct   167340
cccagcagcc ccttccttac tcctgtgggg agatttcaga agcagactga gtggcaactg   167400
ccgcctggcc cttttctccc tggatcaagg gatcttaagc acctacctga aacctaacag   167460
caaaggaaat ctcaactata aatctaactc catgcagaaa ttaaactcct tcaacgggta   167520
ttcactgctc actgtgcagg ccccagggaa gtgtaaagat caatgggaca tggcctctgc   167580
ccctaaggag ccagagaggg ccagggcaag ggtgggaggg ggcatctata aacaactgct   167640
tgcaatgcaa aacagaatca agttagtcct aaaaagagga ttgagcaagg ttgcttaagg   167700
agaaaggaag gattcattat gataggagat caagcaagac acttgaaaag catgtccctt   167760
ctggtagcgg gcgcctgaag tcccagctac tcaagaggct gaggcaggag aatggcatgg   167820
acccaggagg cggagcttgc agtgagccga gattgagatc acgccactgc actccagcct   167880
gggcgacaga gcgagactct gtctcaaaaa aaaaaaaaa aaaaaaaaa aaaaagagc   167940 tttattttat gggttcttc catttaaacc caaggaaagt ggggtttctg aaagaagaaa   168000
tgaaatgcga accgtgcaag attctagatg gccattctgc tgagcaccat gtagtttggg   168060
taaagccctg aaccttacaa atgggagttt ttatctcaga tatgtatctc agatgcagga   168120
```

```
cttttatctc agatataact aaagagtatcc aagattgcag ctgtctcggc cctagatgct  168180
caagcctgtg cagccttagt tgtatatcag agatctacag agatcttagt tgtgtatcag  168240
agatctacag agatcttagt tgtgtatcag agatctacag agatcttagt tgtgtatcag  168300
agatctacag agatcttagc tgtatatcag agatccacag agatcttaat tgtatatcag  168360
agatctttct ttgggggcg gcacaggggg acggagtctt gctctgtcac ccaggctgga  168420
gtgcagtggt gtgatcttgg ttcactgcaa cctctgtctc ctgggttcaa gtcattctcc  168480
tacctcagcc agctgagtag ctgggaccac aggtacgtgc tgccatgccc agctaatttt  168540
tttgtatttt tagtagagac gaggatttac catgttggcc aggctggtct tgaactcctg  168600
acctcaagtg atccacctgc cttggcctcc caaagtgttg ggattacaga tgtaagccac  168660
tgtgcccagc cctagttgt atatcagaga cattttttgt tttgttttt tgggttttt  168720 gaggcagagt ctcgctgtca ctctgttgcc caggctggag tacagtggcg tactctcagc  168780
tcgctgcaac cctgcctcc caggttcagg agattctcct gcctcagcct cctgagtagc  168840
tgggagtaca ggcatatggc accacaccca gctaattctt gtattttag tagagaggtg  168900 gtttcaccat attggtcagg ctggtctcgg actcctgacc ttaggtgatt caccctctt  168960 ggcctcccaa agtgctggga gtacaggtgt gagccaccgc gcccggccta tcagagatct  169020
taatttgatt tatttctgtt caaatcagat ctgactctta aaggcaccca tttattgccc  169080
cagacctgac tgtagatatt ctgcaggatc tacacatact tttatcttta tttatatttc  169140
tatttgctta tgttgaagcc gagtgggtcc tgggaacata aaggatatag ctcaaggata  169200
gaggctttta ccataaattg ccaaagctca cctagagaaa gaacagagag gaagctgtga  169260
aggatgtgtg ggtttgggga gggaagcata aaccagagag agtgaagcag ttggattatt  169320
ggtcagtgaa caaggacaac agtggtcacc atagctgttg ttattttgtg cctactaatg  169380
atcattcttt atctctccca gtagagaact gattgaactg aagtccggaa gacaaggagg  169440
gtactgctac agaagggccc agagggctgc tgcatttatt cctatcgct gtatagcaaa  169500 ttaccacaaa tttagcagct taaaataaca cctgtttact acctcacagt tctgtaggtc  169560
tgaaggctgg gcaggctcaa ctgggttctc tgcttagggt ctcagagggc tgaattcaag  169620
gtgtcagtca ggttgggctc ttacctggag gctttgcaga agaaccttct tccaagcttg  169680
ctcaggttgt tggcagaatt cagttgctgt ggttgtagga ctgaagtccc tgttgtctcc  169740
gcaaggacta ccctcagctt ctcaagttct tgtcccattg acccttcat ggtaaagtca  169800 gcaatggaga agcttcctct tgttgaatcc ctctcacaat tagaatctct caactgtaac  169860
aagaatctcg cttctgtaac aagctggaga aaattccta cttttaaaag gctcatgtga  169920
ttaggttagg cccatgcaga tgctctctga ttagtaaccct taatgcatc tgcagaattc  169980 cttttcccac caaacataac ataatctcag gagtaacacc aggggtgaa gaccatggag  170040 cccttggttc cacctgacct tggaatgaca cctggaaatc cagggttcag ggaccagaaa  170100
tctgtgactg agggtggggc tggggagtga cacacagaag ggaaatattc tccgggagcc  170160
aaacagagaa ggactttgg aggcagaatt tgctgacaga gctaatcaag cccccttaat  170220
cagtaagagt ctttgttgag caccttcttt tctaggccct gttaggcact agaataatga  170280
aggagacagt ccttgccctt taggaattca cagtctagtg agattgtaag aaatctcctg  170340
gactagaaat gcagtcctga tacaaccgta ccctgagaaa tctgtatatc ttcaggaaag  170400 tcatttgtg tgttttacag actggcctga gtgctcgctg ctgttgtagc taccaccaac  170460
```

```
tttctactga agatgataac ccagggcata agaaatgact tcagacccaa ggttctgaaa    170520
gggcccctca aggcctcggg tggctcctgc agaagtggca gaagaggcgg gaactaggaa    170580
cctggcatca taggaaaagt gccttctcca agaaagaagg ggcccagga ggctgtctta     170640 cttagatcaa ccataaacta ccacagatgg gtcatttctt atattatttc aaaatatctt    170700
tgaagatgag aattcatttg tgtccttcat agaccaaagt tctttgtgtt acctttttccc   170760 aaaagtaaat tcctttccct ttattcattc cttgtggaaa taaaatgcaa gccctttata    170820
cttgtcttac agtaatatgg cacatgtagc ttacttttga gcatcccagt gaataatgtt    170880 tggaacttttt cttattacct aatagcatat agagaagagt gaagtcagct aaaaacagaa   170940
attttgaaaa gccatcttca ggaaaatgta ggcccagatg ctttcctcca cctttttttga   171000 caggctgcca catacagttt cacaggttgc taactgcaca ggggcacagc ctgtcctcca    171060
tttgccaagt cacactttct ggcacagaga ggggtgtctt gttctaattt gtctttgtgg    171120
cctgctctct tctgttcttg aagctgcaag ccacagtgag atgagtgaaa agcagtcagt    171180
ctcatagaaa aaagcaggga aaaagcaata gagacaagaa ggaaagccaa ggaaaggatt    171240
cttggggaag gtcaacaggg aagggtggag aaggggaaag gagatgacca ttatgatctt    171300
ctaattagga gtttagggga gatcgtttgc cttattcagc aaccatgcga ctagaaaata    171360
agcaatctct ttaaaataat gctttactac agtcaacttc aataatcttt tcgataattg    171420
ggttgtgatt aaacttacag gcacaagact aaataatccc aacgccttta actttgcaca    171480 ttgtttttttg tttgtttggt tggttttgtt gttttagttt ggggttttttt ttactttgtg  171540 tgcccttata tattcaacaa atacttcttg gtacccattc tattcatagc actctcttag    171600
tccttgtata caggggtcct caatccttga tgtgaattaa agtcacctgg gcagcatgct    171660
gaaaatgcag cttcctaggc cctcccttca tgcagcttca ggatctctca gctatatttt    171720
gatcaaacat ccaaggaatt tctggtgatt caaggaccac actttgagga agcttgctgt    171780
agacatggaa agcatataat ccatagttct ttgtcctgta agaccgtata actgagttag    171840
ggaacaggag gtagacatac ataaagataa cgaacaacac ccaacagtgg gtgctacaga    171900
agcaagtgag taacagagaa aatgatgaac cagtgacata ttaggtggga agaggaagaa    171960
tgttcctaca tggaattccc tgaagacttc aaaaaaaaga gtgggccttt aaaagagagg    172020
agagaccatt tcagttggga aaaatatgta aataaaggcg cagtagccttt atgtggtgag   172080 agacttaggg aaagactgac tcaacatctc ttggcttcat gatgatcctt tttgacccac    172140
aggttctttc tccttttctta ttaggttgct tttaagacta tttcataagg gatcgcagat   172200
gtgcatgtaa aaagagatta atcactattg aaatgtatgt gctgactgat ttgtgtgtta    172260
cactattgaa aaactgtata gactccaaat ggcatctgat tattaaattc agatgccaga    172320
gtctttgatt aacagcatgt cttttttgctc tgtatatttt ccttcagaag tagcagggct   172380
tgcagacatc tcaagctatg ccacagaaga gtcaaacaga ggaagtggtc atgaaattaa    172440
atgtgaagac agtctattaa cttttgcaat acagaacctt tgtttactca taaaatccat    172500
atttggagct cattctttcc aaatggatta ttatctaagt gttttttattg gagactgttt    172560 ggtacttgtg ttttatagtt cttttttcttt cactcaaaca attttgtata ttagaaaaca   172620
atttcagcaa atattttatg tttaaaaaat cagaagaaaa tgaagatgac cctctctttt    172680
gccagtactc ataataaata caaaatgaga agagattttt atagtactgc atgactctat    172740
tatctggagt acaaatcact gcttttttttt ttgtttgtg agacagggtc tccctctgtc    172800
ctccaggatg agcacaaagg catcctctcg gctcactgca gccttgagct ccctggctca    172860
```

```
agtgatcctc ccacctcagc ctcctgaata gctgggacca caggcatgtg ctaccatgcc  172920
caactaattt tttatttttt gtagagatgg ggactcactg tgctgcccag gctggtcttg  172980
aattcctgga ctcaagtaat cctcctacct cagcctcaca aagtgttggg attacaggtg  173040
tgagtcactg tgcctggcct tgcattttt aaaagtgata agtaaatgct atatgacttc  173100
aggtagagat tatatctcat gtttaatttg tataactgca taagtagaaa aactgttcat  173160
gaaaatatat tggctgggcg tggtggatca cacctgtaaa ctcagcactt tgggaggctg  173220
aggtgggtgg atctcctgag gtcaggagtt caagactagc ctggccaaca tggagaaacc  173280
ccatctctac taaaaataca aaaattagcc ggtgtggtgg cacatgcctg taatcccagc  173340
tacctgggag gctgaggcag gagaatcact tgaacccggg aggcagaggt tgcagtgagc  173400
cgagattgca ccactgcact ccagcctggg tgacagagca agagaaaaaa aaagaaagg  173460 aaggaaggaa gaaatttact tattccatct ctgtacacat aatttgtaaa cttttttatc  173520
atcaattatt attataaatt ttttgagaca gggtctcact gtgttcccca ggctggagcg  173580
tagtggtgtg agcacggctc actgcagcct cgatcacctg gctccagca atcctcccat  173640 atcagcctcc tgagtaactg agactatagg cacatgccac catgcccggt taatttttgt  173700
attttgtaga gacagggttt cgccatgtta cccaggctgg tcttgaactc ctgagctcaa  173760
gcaatccacc tgcctcagcc tcccaaagtg ctgggattac aggcatgagc caccacatca  173820
gcccatcaat tattattaaa ctcatgtgta ccagtacaat ttcaagccct ctaagctgca  173880
tttaatgcta aattgtgata tcatgtgtgt gtgtgtgtgt gtgtgtgtgt gtgtgtgtgt  173940
gtttgaacag aatgttcata tgacttcatt tctataataa tgtgataata caaatatttg  174000
gggtcatttt aatcgtatta gcatttatct ttaccaaatt gatttgattg ttgtgtagcc  174060
acttctcatc tgttacatat acacgttta catatcattc aaacttgaaa tttccttaaa  174120
caactttccc agcctggttt cggatgattg cttgttgaga cttttgtccat gctctgtcct  174180 cccctcccca ctgtaaatac tcttctttg ggctagggg ctgtgccctc cagggtattg  174240
ttttccttcc tgttcagtgc ccatgctctt gcctgtgttt ctcctgtacc tttcccagga  174300
cctagcagac agccgagcac ctgcccactg ctctgtaaat actgacctgc atctcaagtg  174360
gggtagcctt tgtgtacttt cccatttcca agttgatttg cctgtgaatc ccatatgtga  174420
acacatatgc agatgtccct gatgtgctct ttcctgcttg gaggcacatg caaggatgtg  174480 gcacttttc taattgcttg aacagtcaag tggatctctc ttaggcagca cttggccaaa  174540
aattctgaat atttaatcac tggtacagga ttagttcagt tggccaaaaa gaaaaaaaaa  174600
atgtatggat gaaatgtgaa tacactgtta acttttcat ctgcctttat aattagtgtt  174660
ttttcaatat taagtttctg ctttttatac tgagttttta gggaaaaat atgggaagga  174720 ttccatattc attgcttcac acgatctata gttcctgaga taactatata attatgaatg  174780
ttgatacacc cataagagac tttgctttt cctctcacac atctgttttg ctttaggcaa  174840
gagaactttc tcatgccaga atggctgcag tggatgtagg caatctgctt tatgttgagc  174900
cgctacaatt cacagatgca aatgttaaa aggttaacat ggttatttct tcatctgaaa  174960
caaacgtccc tagtcactac ttttgtcctt taaaaaaat tgtattcttt tataaatcca  175020
ttgtgtgtaa tccttatacc cttgtctcat aatcctcata tcagagctga attaactctt  175080
ttgtggcctc ctgtgatgaa tttcagttgt cctactagtt tctcttgctg gtgtgattgt  175140
gtcctcttga tggaatttag gttcttaggg agagaatgag ggaagcagct tctctaccca  175200
```

```
gaacagaatc ccactaaccg aaagaatgct gccctgcaaa aaagtttcta gtgtatccat 175260
gtgtgatctc aattatttaa tcaacaaaca ttccagagca tccattgttt cactgtacta 175320
ggaaatgggg gcaagaccag gatagtatac ggaggctaac ctcagcaact gcagtccagt 175380
tggaaagatg aaacctaaca tgatgatagg atggcagcgg gttgtgagtg tcaaacgcat 175440
gcttctgtac tgcgctcctg ctgcctccaa aagcagggg agccttcagt tcatcacacc 175500
tacagctctg gacattttt catgttgtta aattaatcta acattgtagg atctgaattt 175560
tctatagaaa ctttacctaa cttttcttgt attgctaatt tgttgtattg agtaagcctt 175620
ctgtgtagaa aacagtttaa ctatgttaac aacactatgt caaagattca agcctttga 175680
gagcttagga gaaatccaac cccagtcatt ttctgacaca actgaacaca gtactctgtg 175740
gttgaaagtt cctgaaactc ccaaagcaca ggaaggctga ctacagatcc taaagatgtt 175800
taactcacat agtccttggt ggcacttact gtttgcagct ggagggcctt gtattttctt 175860
aaaatgcatc ctaaataaaa actcaaaagc cattcaatgc taattcaagt ttcatggtta 175920
aaggcgcagc tttgctggca tctagaatta gaaccgtgtg gtgtgtcccc cagaaaacga 175980
gctctcatgg caaaaacaga caaactctac cccctgccaa actaactgtc agcagaaatc 176040
tggtctgctt tctgaaatgg gatgtaggtt tccaaattct ctagacaatc tctttccaaa 176100
gcaaaggaga aacaaataac tcacaggcac caactgcatt ttctgttcaa agcaagaagg 176160
gttttcactg tgctgttttt acctgtcatt tcacaactca gttctctctg gagcacttgt 176220
accaagggta caagaaagtc atgagatcag agagctggtt ttggacatgc acttaatcac 176280
tcccatcctt atttcccctg cttccctgat gcccctgaat agcaggctct gtccccgaaa 176340
gagaaatgag agttaaagaa atgaccactt aaccttttcc tttggtaggg aggttctagg 176400
aggccagtga agcttgcggg ggtcgggaaa tttgagaagt gaatgagat taggagaaca 176460
gagtttgctc cagatgagct ttggagctgt gccttttctt ctggaactca ctaccggatc 176520
aagggggtcta gtggggtgcc caccacactg gccaccagac caggcttgat ggaaagggcc 176580
cagagatggg tcctgcttgt gcagtctaca actgccagca tcagctgccc cctattcctc 176640
tctgtggccc atggtcagcc agaatcgagg ggccaaagca atgggcctgt agcttgagaa 176700
gcatgtcagc aggctggggt tcaaggccag gcctacaggc ccgcagtgga gagggcaagg 176760
ctggctccag gtccgatggg caggttgcca ggacgtgatt ttcagagcag gaaagtggag 176820
tgaagcgtga ctggcagtga gtgtgagcag acagctgcag agtcgtctct gcctagtgtt 176880
aggcctggcc gcaggctctg gcggccctca gcctgaccgt aggatgggtc tcccagcttc 176940
agctgaaggc aagaagtgcc gctgacttgg ggagctgagc cagacctggc tcctgccctc 177000
ctccctgaac gtgctccagg atcatctgtc tgcctgttgt tcctcactct ttttagctct 177060
ccacggggct ggcctttgtt gtagacagag aagagaggca ctgtgttatg tgccgaaagc 177120
tctgtcacaa gacacctaca ccaccaatgt gctgccgtgc ttttcctcat gctgttcccg 177180
ttgcccaagt gacctttcct gccttctgt gcctggtaaa atctggcttg ttctttgaga 177240
tccagttcaa atgtaagctt ccttggcaag tccttcccag ccgctctgac caccacctt 177300
cctggcagga ttgcatactg attgcaaccc cctcggtgcc cgctcagcgt gttctatgca 177360
cctgtagctc tagcccatta tgatagagtt atttattcac attctttgtt agatgctgaa 177420
tctgtccaag acagggacct ggacatctgt ccattcatct ctgtatccct cccagcacag 177480
tggctgaaac acagtttgtc atttatacat gtctgttttg caaatccgtt atctgagatg 177540
aaagcctgta gatttcatta acatcttagc tctgactagt tgagaaatca aagtagggc 177600
```

```
acatggcaca gctaacacat attggcgtct tgctgtgtgc tgccctagac accccgtgtc  177660
cagcaaaaag tcacacatcg ttgacccgag cagagggagc caggggggcc atcctgtgtc  177720
cctccagcat cactgcaaac agggtggggg caccagtgga ggcaggagcg ctgacctgtc  177780
ttgaaggctg agagtaagat gggtcccttg tggccttcaa aagtatttgg acttctgaag  177840
ctgcctgtgg ctccggaaat tagggaaatg ctttagtggg agtgcttctg tgtgcgggga  177900
ggtgtaagtg caacatgaac tgaatctcac tccacccagt acaggatgtg cccggagagc  177960
atgctgagct accctgtgcc agctacgtgc tctagaacag catcctccca gccacccagg  178020
aggtcatgca ggcctcgtca tcagaaaagt ggcttaaaaa ccatgtggag tcagaccatt  178080
tgaacactaa ctagaaatgg gaggctatta gggaattatt gtgaatgttc taggaaacat  178140
tgctcatctt tgcacattaa attcctacta atataatagt atcatgatta tgagggtttt  178200
atttttttaa ggatccttgt cttttaggga tatatgccaa aatatttacc gatgaaatat  178260
gatggttgga atttgcttgg aaataatatg gggaggaggg ggtgggaggt aaagataaag  178320
aaaattggcc acaagttgat gattgttggg tacatggtgt ttattatgat gctcagtcta  178380
cttctgtgca tgttttgacat ttttcatggc aaggtgtttt tttttttttt tttttttttt  178440
ttgagacgga gtctcgctct gtcgcccagg ctggagtgca gtggcgggat ctcggctcac  178500
tgcaagctcc gcctcccggg ttcacgccat tctcctgcct cagcctccca agtagctggg  178560
actacaggcg cccgccacta cgcccggcta attttttgta tttttagtag agacggggtt  178620
tcaccgtttt agccgggatg gtctcgatct cctgacctcg tgatccgccc gcctcggcct  178680
cccaaagtgc tgggattaca ggcgtgagcc accgcgcccg gcctatgttt tttaagtatt  178740
tgagagatta aggggaaaca gtattttgtt ctcatcccct cgtttcttgg atttgcttta  178800
ttgtcccttt tcctcacccc tggttacctc tgaggatctc ctagttagag aagagggtcc  178860
aaattgttgt tctatctacc cttttggtac cttcttaaaa ggccttccct taaggttccc  178920
caaatatgtt taaaagtctt tggaaattag gtgcatttcc tcccattggc tcaggaaggg  178980
gtggggagca gcatatggta ctggaaacca ggctcccttg aagtgctcct tgcccgggct  179040
taggctctgt tgaggtgaat cacttgcctc cctccaatga ggagtatgct ttcctgaggt  179100
tgtagaagag aaatgtgcca tttttcactgt gcctgtaccc aagggagcca gaatgggagc  179160 atttttaaaag aaagacactt tcatatgact aaatcaacct ggaagccaac tgatgaagat  179220
gtgctatctg atagagcttg gggaccacca accaactggg aacataaaat gtggagggca  179280
ggcttggccc tggattattg actctctcaa atgtttctat tatgtctcac tcttaaggag  179340
ggagactaga agctcttaag tccagtagct taacatttt cagagtggat ttttttcttg  179400
gccttatttc taccaccctc gtgttcccaa aacaccccctt ccatcaccac accccaacac  179460
ggaatgctct gcactcactg tattgtcctc agccatttcc caccttcatg gcccagcttt  179520
ctgccagtgc agaccacaga tatggttgca ggaaagtgga gaaagagtag ctaatcggag  179580
gtgacaggga gcggaagagt aagcatggcg agagcatgcc agctggtgga gtcttaaatg  179640
gaactgtaga gttcttgggg atgtctgccc atttgaggta accgtcttgt ctagcttcct  179700
gtccacatgg cacattccgg tggtgtgact tgaaggaagc taccaaaacc atatttatca  179760
cattccagag gccagagggc ctatgagtaa tcgtgagtat ggagacgatg aagttggaat  179820
ccaggagaag ctgatggtgg agcataatga ggcaaatcta ataggccaga atgtcatcag  179880
gtcaatgtag agtgctgtgc gtgggccacc tgcaaagcgc agggtgagga ggagtgactg  179940
```

```
acaaggaact taataggagg caacagtgtg atgtggctgc acagacctac aaatgcttta    180000
aaatccagtt gcatggatac aggaggctga aagcatcaat cctgtaatat atccagatga    180060
gaagtgccag tccaggaatc acattttgtt ccctgtaagt ttctgaaggg ggccatctca    180120
gtaaatgatg gttgttcata tgaaagatat tattatttct ctgatggtat ctgatactgc    180180
atgttgcatg cagaagaaga tctctaaaga tctttacata ttaacagcct atgacatcct    180240
tcaggtatac agttgttaca catgccaggg gacactgtga ctttgttatt gttttgtatt    180300
ttctctgcat ttgggttaat tttgtttgat tattgtcatc cctttagttc ctaacttaca    180360
cactagggtg ttagagagga aggtaatcca gaacagattt tataataata acaataaagg    180420
ccaccctatt ttctctctat tgtattgctc agtactcata gcgcattagt gcatttaacg    180480
ctcacagaaa cccaatgaag gtaggtggta gtattagtct cattttacag aaaagtaaaa    180540
tattagaaag ttaagcaatt tgcccccaag gccgcacagc tagaaagcaa caaggcaggg    180600
actctgggag cccaagctca cagtgcctct ccctggtgtt gcttttttcca cagcagtgaa    180660
taactgctcc cctgaagtgc tccttgcctg gggttcggca ccgcgaccag ttccacaggc    180720
atcgtgtcta agtgtgactg tgccccggaa cccacagagc cacccggctg ctcagtcgat    180780
gataatcaaa aattttaaat ttgcttccat tggacattcc tgctcatcca gccactttc    180840
ttatcagaag acaaaggcat gctgaccata tgtttattat cattcctcct ctttcctgct    180900
tgttttctta gtcaaggtca gagaggacca gaaacaccca gtgctgagaa gagtgagcct    180960
tgctttctca gaaatggttc ctacctctgt ggaaagcagt gaaagagcct ccagtagcct    181020
cttcctggag tggtggaggg tggatagaag gaaaacaat tagaagtaac aataacgaat    181080
agaaacagaa agacgtcttt cttcctaaca acctcatttt gttttccttc taatcttatt    181140
aaattttcac atacttggta taaaatcaca acagtttagg ttctgataat gtcttatagc    181200
tgcctgtgtg cctcgttggc tgacttatgc tctgatatgt ccctaatatg gcagattctc    181260
catacagata agtggaaagt aactcctcct acaggtaaac ttgatgggac tgtaggatta    181320
agccttttgc ttgttatgcg actcagcaat tattaggaaa aggctgggtg ttttcagcag    181380
cccctgggaa atgtgattta tgacatgaca acgttggttg gtcggggtct ctgttttcact    181440
ctccagtgtg cactcatttg agtaagtctg tgaggaactt cccacttgta agaaacagta    181500
tcttgcgtgt tgctatcact aaaccctgga ggccggatgc tgtgtccctg ctaatggtct    181560
ctggttggca aatatacatg tgactctttc tgagcaaagt gctatgtgta atatgaaagg    181620
agcttgaatg ggtagtccct gccctcaagt ggccttgatt ttacaggaga cttgccatgg    181680
acctggaaga tgcatggagc acggggcagc atttgcccat tccctcagcg tgcacaggta    181740
taatggccac tgtccgggag ctgggaggtc agaggcaat gactgcagcc aaccatactg    181800
gggacagaaa ggccagtccc taccaggcta tccacattgg ttaaaatagg aaccacccat    181860
ttttgtctcc tctccaggct ttgaaagcat ttgggtaatt acagcttgcc tttctgcctt    181920
tggttgttag ttttagtgtc ttaattatct gccatgtcaa aagatttctc ctgatccctc    181980
tgagctctct ccccttttgct cctagtggtg ttttcaccct gcttgataag ttagaattgt    182040
acagtggttt ccatttcttc tgtcatataa acagtaggca gttctcaacc ttcccatcct    182100
ctctaactta ctctctactt ttttttcctta agagaggctt atgtgatgac attgaccaag    182160
taagtcctct aacctcagtg ataggtgggt tcggatgggg tggcaaggaa aggaaaaggg    182220
aattgaatca gttttgattt tttaaaaatc atgctgagct gaagtgaaac acttttttt    182280
ttccacaaaa actgagtctg aagggatctt tttttttttt tcattccaca ttttggttac    182340
```

```
atctgcagtg agcagttgca aatcctgaga gacttctctt ccctggcatt tgtttcattt   182400
tgcaagagtc tcactgtgcc tgtgtcttat gtgagctcct tgaaatgaaa gaacgttaat   182460
ggctgaagac tgttagagcc atttgggtgc ctgcttatac ctttcactca gcaggactgc   182520
caggggccct gtctggctct gccaggtgcc ctcgggtggg agaataaggg cactgaaaca   182580
acaaataggc ccttgaccag acctccagct ccttgcctgc agggaatagc actggagtac   182640
aacgtctagt acaaagtagg tgttcaataa ataaccatca aatgggataa aaccagttcc   182700
tagcccagca caggtgcagg gtagatgctc agtaaatatt tgttgaagaa acgaatacat   182760
tactatatcc catgggggaa gacctctggt cttcatagca cttgcatcat ttgtagctct   182820
gcaagggctc tgggctggat cgactaggaa agcagcctga gcagggaagc agatggctga   182880
tcaagccctc cagccgagga gaccagcact gtttctgtgg gaacttggat gccactgacc   182940
tcactcatgg aagcttgcaa gagtggtgca ggccccagtg gaccaaggcc agggctctgt   183000
ctgctccctt tggcagtcgg aaagcagcac acacttagct ttgccaggac ccagcttcag   183060
cggccttcat agcccagtaa ttacctcgtg atcaagggag ggagggatgt gtgtagaaat   183120
cactttttag tagcacatat ttctcttgga aaagccccag taagctgccg actttctctc   183180
aagtgttcaa aggataccag ggaactgacg ggctaattta attgtattaa tacaagaggc   183240
ggccgtccct agtgcagagg ggagtgcgtt agggagaatt gtctgtcggg aggctggagt   183300
tccagcttca acatggaagt gaaaacactc tccaggaaag cagacgagtc ccactgggga   183360
ggaaactgac tctctccatg gcccacaggg cctgctcttc atctgtctga agaagcctct   183420
ttattgcatt cagataagtg tttcacttga aggagagcaa acacaaccaa ataatgacct   183480
agatgtccct tcctcatgtt ttcaaacagt ccccccttctc tttaatccct gcaggagaaa   183540
atgtcctgga gttgagatct taggagacat tggttcattt aagtccatta tgagaccttc   183600
acaaggcacc ccttaaatct ggcagtagga ccacagtttt atcctggcca caaatttaaa   183660
gactttgatc ctattccctc tcaggtatca atgcaaacag aacaattcta acatttttag   183720
tatggccacc ccaacgtgga caccaattag ctaagccagg gaactttact tctatttcct   183780
catctatgca aaggggagaa caggttagat gatgtctaag gcccctcaag aacttgagtg   183840
ctcttcattc tgtaatcatt atctctctaa ttagtttctc ttctctaaac tttattctcc   183900
tccacggcct ctgtttaggg gtggaaggta gatgctgtac cctagtgtgt gtttcccggg   183960
gctgtttctc agcctgctgc tctgttctct ccactctcta tctgtcccta ttgcgatcat   184020
tctcaaatct aactgtgact gcagcactcc agttcattca tttattccat aatatttctc   184080
aaacacccac acgtgctag gtgctgaatg aacagtacac tggtgaacaa gagtcatgat   184140
ccctgctttt tttggatcat atacttttct agggagacat gtattaaata tatttaattt   184200
aatttaacaa atataattta aataatatta aatatattaa atgaatatat aatgataaat   184260
tgtaagacgt gttatggaag atgaacaggg gttgccctga tttaatttgg gaggtcaaaa   184320
aatatctgct ctgaggaagt gttatttgat ctgagacctg gaaaggagt tatcaggcaa   184380 ggagttgtag aaagtgctcc aggtagagga aagagctaac acaaagacct tgcagcagg   184440 gaagggctag actggatgaa cagagcttcg tgtgcccaaa gaactgaagg aaaccagtgt   184500
ggttggaaca tacacagtga gagcagtggg gtgagatgag actgggagaa tgacagatta   184560
gttaagataa cgctggctgc tggaacaaac caaaactgac attcgaacag tatagacatt   184620
tatttctcat ttgcagaagt gcaaactaga tattcctgag cagttagata tccctgttca   184680
```

```
aagcagtgtc ttggagacca cagctccttt cattttgcag ctctgccatt tttaatgacc   184740
tgccaaggcc agcgtgcttc tctgcatgga aggctgtgca tgagagggtt ttctgggccc   184800
aggcctgcct ggaagtggtg ctcccaaccg cactcacatt ccgccagcac acacccaact   184860
gcaagggagg ccgagaaatg tggtcagagt gtgatcccaa gaaggagaca gggcagatga   184920
cgcagacact gtgggccatg ttgcagtttc agttttattc ctagcgtgct gaggagtgtg   184980
agtgagagtg cacctgtggc aaatccatca gcacttctaa acctacacgt tcaattgcta   185040
atgtcatgca attcatcttc ctccaaaagc aacatctctc acgtgttctt ccagtgatgc   185100
cattccagac ctagcagtcc ttttcctgc tctattcatc gtctagactt acttgaccaa    185160
tccaaccctg gactggttca gtacttcccc gactaggctc ttcaattggt ttctttctgc   185220
tctgatacag aatgctaagg tacgtattta caatgtagac tatccccttc cagtgacaga   185280
gttattcctg gctgttgtat agagcaactt ttttgtacta tcaggtcatc ctagaaactt   185340
aattagtaat cagagtataa tgaacatgga gatgtgtctt tctaaaacag gcctttcatc   185400
cctgctaaaa aaaatttta cttgcttcca agtacctact gaataaagtt ctaacttcta    185460
tatgttggag gtactaacgc aacccatctt ttcctaacaa ttcttacttt gtcctcctca   185520
agccagccag ggtgctcaac tatccagagt ccaaacaaac ttggtgaatt ctcaccttgt   185580
actcttccac actctgcctg ggatgtcctg ttcctgctca tcctcctctc tgaatcctac   185640
tgatgtttta gtgcaagcct tcatcccta gtctcacct tctctgggaa gtctcccctc     185700
caaccaacca gaaatagact ttccatctct ggagttctgt agtgcttact cttcaaagta   185760
attaatgctt aaattaactt gtgtcttacc actcctttgg catttatcat gtattgcctt   185820
ttattgacat ttattctccc aattcattct aagcttctta agtagagata cttttcctgg   185880
tatctaaaac agtaccttgc acaccctcca aaaaattatt aattaattta atgtttttct   185940
gtaattcctg tgcacacctta tacagtttct taaacatggc agatgctcaa aaaattcttg  186000
ttgatttgtt attattgtta ttttaatgta taacccctg taaaatgcaa agtcttggtc    186060
agttaagggg gagtgctttt tctgggaatt ccagccccaa acggaggtct gggtaaaatg   186120
catggtggag aggggagtct gtgagtgctc ctccagcctc tgtgcacagc ttcctacttt   186180
gctgctgctg ctgctgcttt tttttttt tttaattgag atggagtctt gctctgtcac     186240
ccgggctgga gtgcagtggt gtgatcttgg tttactgcaa cctctgcctc ctgggttcaa   186300
gcaatcttct cacctcagcc tcctgagtag ctgggactac aggtgcacac caccacgccc   186360
agctaatttt tgtatttta gtagaaatgg ggttttacca tgttggccag gctagtcttg    186420
aactcctgac ctcaagtgat tgcctgcct cggcctccca aagtgccggg attacagacg    186480
tgagccaccg cgactggccg ctactttgct tctcttgctc attcagaaag ccaactctgg   186540
gtttgtcaca gattgtttgc ttacaaatat tcccactttt tcattcacaa tccttctttc   186600
cccaagaaag aggttggtcg caaggtgtag gggtgttgcc ctggggctct gtctttccaa   186660
ttttcccttc tatccagatt tttcatctgc caaaccctat gagagccagg agagggcatc   186720
agatcaacca gccaaagctt caaaatctgc cttgactctg tggggttctg ctcacctaca   186780
cctttgtagg gtaccatcct ctagtaaaat gagcctctac tatgatagca ggctcctgca   186840
ttctatttct aaatctgcct gattctaaac attcttgttt gagtcagatg ggaaatacag   186900
ttctgtttca ttttctccc cgtcttaatt ggttttccgt atgcgggttc agaagtagga    186960
ttttgccata cacatcatcc ttcatgtgag taggtgagca ccagcatcag gggaaggaaa   187020
agagacaaac tgactgttag ggagggagtc tctctccaga ctcggctagc cagcacagct   187080
```

-continued

```
tcagatcctg cccctcaagt gagtcacttc atgaatgtgg ctaaagtgtc taacggttgg 187140
catttctcag gaagcatgct gggattatgg atgtgaaagt taacatgggt tgagagagga 187200
ctgaggcttc agcaatctca gaatgtctgt ctgttgagct tcataaccaa gctgccaaat 187260
tcaaatctgc atctacagat tcttgagcac ttgaggcggg tgccctctga agctggacct 187320
tttcaaagct gctctgaaga gctgggtggc acctccttca tatttcattc taagtcaatt 187380
gcagagctaa gaaaccgtct ttgcttactg tctcagatgt gtttccagtt ttcattggaa 187440
agagaaattg tgttctgaat cccagttcat gtgaaaccct gataacttct caaaatataa 187500
aacgtcctta ctttcggggg ctgctgtcaa gaactagagg aggctggaaa gagttgtctc 187560
aaatgtttgc ttttttacct ttggcaagca tcacctagtg gccctcatgt cagtgactac 187620
agggtttgtg taacatgcct gggtttgggc catggacagc aatgttgtgg agggctgccc 187680
ttggaagaac accagccagc ttcagttttc tgcactgtaa ttgttgccac tgctacccca 187740
gtatgggctc ctggggtcag gagggatggc atcaccaagc ttcccggagg gggcaggccc 187800
acctgacagc cattaaaagg ctgattccgt gggcagggcc cttttttccaa attaagtatt 187860
aaatgaacat tatttcatcc ttatccaaaa ctgtgctcag agcctagaca cgtctttcct 187920
gcacaccgga atatgaaccg tacaacacag ggtgagctca gccttcagca aggcgttttg 187980
gatggtgagg ctttgtggtt gggattgcac taaatgccat gtaggggcg ggggggtctt 188040
tctcctttca tcccttgcca gagactcagc ctgggccatg ctcatcatca taatcacagg 188100
ctgaagagga atattttggg tttagtttcc ctttttttt ttttttttac acacaatgcc 188160
tatttataac catttgttga cagactctac caattactta aaaaaacgtg tatttagaca 188220
gagacagacc aaaaatgtga attcaatggt ggccctagtt ctgtattcga ttagcatctg 188280
ctggtgccag aactggagat ggctgtctgt tgtcacttta attggaggat gattagaaaa 188340
aaatacttgc ttttcttcca atcttatctt tgttgttacc agctcatcag atccgcaagt 188400
tcatgtttat tatggccatt atatgttaaa agctcagtgc attttctgtc tccacatcat 188460
ctataacatc ctgttgccaa atccagttat ctcctttcct gctttctcat actttccctc 188520
tctttgacat taaccatttt ctccatggag tatttcccct ggcttctgag gccttcttct 188580
agtctaactc ctccttctca gccttttaga ggccccttcc cctatgcttt gcctttcaaa 188640
tggtgtttct ttccagaatt ccatcctcct ccctgttctt ttctcagtcc atatattttt 188700
tccaccttaa atacagccag aagaagtgga gacaaggcac ccagtttgag agtccaggac 188760
ttggcagtgc acatcggaca ttagagaggg gttacccata aagctatctt aggggcagct 188820
gaatatacag gatctctgtg attcctaccc ttaccccaaa aagcaggatg gctcacgggg 188880
gcagcagaaa ggtgatggag ccagagagag taggtaagct attgtccatg gtggatacag 188940
ggagagacaa gctgaagagg ttgaacctgt tttgatggcc aaggccagca gatggatgtc 189000
aatatcccta tgtgaaatac aggagtggag caccatcgaa ggaatgatgt gagaaggaag 189060
tgagaaggct gggctttgtt actgtgcagg ttcacctggg ctagaggcac tatggttgga 189120
tacacaaaac aacagtctgg gttagagata agattctgga gtctagaata cccagcgaaa 189180
tgttgggcat ggaaactaga ggaacgaaaa cattgaagag atgaacagtg aaaaaagaat 189240
aagcaaatga ggctgaaaag aatggcaggt agaggccggg cgcagtggct cgtgcctgta 189300
atcccggcac tttcggagac caaggcaggc ggatcacaag gtcaagagat cgagacctgc 189360
cgggcgcggt ggctcacgcc tgtaatccca gcactttggg aggccgaggc gggcggatca 189420
```

```
cgaggtcagg agatcgagac catcccggct aaaacggtga aaccccgtct ctactaaaaa  189480
atacaaaaaa ttagccaggc atagtggcgg gcgcctgtag tcccagctac ttgggaggct  189540
gaggcaggag aatggcgtga acccgggagg cggagcttgc agtgagccga gatcccgcca  189600
ctgcactcca gcctgggcga cagagcgaga ctctgtctca aaaaaaaaaa aaaaagagat  189660
cgagaccatc ctggccaaca tggtgaaacc ccgtctctac taaaaataca aaaattagct  189720
gggcatggtg gcgtgtgcct gtagtcccag ctactcggga ggctgaggca ggagaatcac  189780
ttgaacccag gaggcagagg ttgcagtgag ccaagattgt gccaccgcac tccagcctgg  189840
tgacagagtg agactccgtc aaaaaaaaaa gaatggcagg tagaaatgag actcccaaag  189900
atgaacccag atggagcatt ttctctatgc caggcactgc agtaagtgct ttgcacgcat  189960
tgtctcactt agagactgaa aaggggaagg acaccttaga aagaagaaaa tttcaaaaag  190020
agagaccctc cttctgcctt gatcatattt gtcactcttt ctttacctat tgcattggcc  190080
tatccatagg gctcttcctg gatcctcctg gggaattggt atgtcttttg gaatctccta  190140
gcactttgtg cgttttattt attcaggcaa caaatgttta ttccactatt ttagaattta  190200
tggtggttaa acaaaattat tttattatta cctgctgaac tccagcttat tcattctgaa  190260
gatttagtgt ctaacacata tagtgatcaa caacataggt atttgtttag taagtaaatg  190320
aataatatga aataagttat tttttcaaga ctcaaattta aaccaaagca tgagaagagc  190380
tcttgtcaac ctatttcagg tataggtggc ttaatttact acaacggtca tgagttgagg  190440
attcattgaa tggttgtttt ctgtcatttt tggtttacac tgctcaatca acactgctgg  190500
ctgatgtcag accttaacca attgttgaag ttccctgtaa caccagcaca ttctctgaat  190560
acttactatg cacaatgcaa taatgattaa catttgaact ctgtctaggc tgagtaagcc  190620
acatcaaagc tctttttttca ctaggacttt taaaatatca gatatgaact gagtgagtag  190680
gtgtcagaga aattgacttt gtaaactgaa aatcataaac ttaagattca tttgaaatac  190740
gtcatgtgga gtgcatatat aaaaattatg agcatttttaa tttgtcccct gtaggtaata  190800
aataacatct gcaatattcc tcctcacctt tttctgatta gcttcatgtc tggcatattt  190860
ttcccaacac tcctgttttcg tgttgtaaga atttctccaa ggacagacag gattctaagt  190920
aagtagtgag ggtctaacag aaaacttgca gcaaccaggt tcaagttcag aaatgaggga  190980
agtatttaat ggtggtcagg cctcccctatt ttactcttct ttggtacacg ctggcagagc  191040
tgcacaggcc ccgaggggtg gcagtgcctg tgaaaggcac agtgcctgtg aaaggtctat  191100
aatctagacc cacaagccag cccctcctc cccaaagctg gtgtggctcc caggcccct  191160
cactccccac atgtacctgc acccacatgg gggcatccag cagagtgccc taggccacca  191220
gcatccccct agggtccatg gagctggagg gacctctgga gactcccaaa gatgaaccaa  191280
ggtggacatt ggccacctct gctgggcagc tgcatagagt ttgtttggga ggaagatttt  191340
gtccttaaaa gtttgaaaac cactgcctta actgtgtaat ttcaataact actatatgat  191400
gatgataaca ataatagcta acattatttg agagcttact ctctgccagg gaccctatta  191460
tgggctttca atgtactatc tcatttaatt ctcccaaaaa aatctctgag gcacttactg  191520
attttatcag ctagaaaaca gaggctaagt aaaatgccca tggttacaga gttatgaagt  191580
aggagagctg gcccatttag tctggctcca aagccaggga tctcaatctt gctgctaata  191640
ctgctattaa ttagctctgg taaaagtgaa gaggcagcct ggacaactgg aaaacagaac  191700
agcacatgtt tagtaagtgc ctatgacagt caggcgttaa atgatgcttg agccttagtt  191760
actctgagct tcactctatc cctctcaccc cagtggcctc acctaatttt ggaaaagttg  191820
```

```
gacaagcagt gagacagaca gggtaaaaag aaaaaattgg cttgtaaata ctccccgaat 191880
atcctgcctg ataaaacatt cttcctcctc tccctcctcc tccttcctat cacctctccc 191940
tttgcctttc tccccaaccc cacctctctt ctttgttttc tgttttcttt ttgcctccct 192000
tatcggtcct gtcttctttg ccttgtgtta gattctttag gctcctattt caggacaggt 192060
cacatttact cttgcttcta cactaggaca caccctcccc tcttactact cagtgttagt 192120
tcactggcct caataaacac tggatgtttt tattttattt catgtttgtg cacttgaaga 192180
ctattgaatt cattctgtgt gtttttttt ccaaaatgat atatgaatta gaattgccct 192240
tttgagccaa gaaccctggt gggttttgtt ttgttttta acagagccgc aagcccagga 192300
atgagaaatc agttcataaa atcaatagca agcaaattta gaatccacta cagcacctat 192360
acccagctta tagtaagcct gagaagcaga ctcctacagg atgagattga ttccagcagt 192420
gtggttagat atttggaaat gcctaaagaa atgtttatgc tcaagttaag gttgcagcag 192480
aaaccatata acttgagaat ttctggggcc taaatgtacg ggctctacag aatgtactac 192540
gttgctttgt gcctctgccc agatcactat tctccttttc cactttcctc ccatgctgcc 192600
cccagcacac gcatacttgc ctcatcgcct caaaaaaaaa ataataaaaa ttgaaatctt 192660
tctaatgcca attcagcctt ccagtttcat ctgagacatc acttcttcag ggagatcttc 192720
tcctttccct agactaatca aggtccccac cttgccttcc tagagccccc atccctagcc 192780
acaacaccca tcaaaattga tcatcactgc ttgtctcctt gccttcctcc acctggctgt 192840
gtgcccagca actaggacta gttcaagaag tatttgttga cgaagtaaat caatttagtt 192900 tgggggggacc atggccacag gatcaagaca cttctcagct ctctgctgtc tccttactct 192960
tgctttccag actctgattc ccgagcagtt gggaagacat cttttttgttt cttccattct 193020 gaaattcact gaccaactgc gtacatccat gctcataaac atttgattta gctataaaat 193080
ctattttaaa taaaaatgcc aattagagta gaaacttcct gctcctccct gtccccacta 193140
tgtgtaaggt aagtgtggag gtgggaaaaa gagcgttgtc ttctaaggag tgggagttga 193200
atgtctccta ggtgcccact gcaggcagca tgaaaataat aggatggata ctataggagg 193260
cacatttgag atctttcaaa ttgctccagc tgaccatcca tgacatgggc tacctggtga 193320
ggcaggaagt cctgtgtggg actgtcctag ggcaatagct gtgcaaagac catcataagt 193380
gcaacagatg ctgctgaaga tggtaatttc aggcagccta tgttaggcca gggctcagct 193440
gggctagact aagggaacca aagacaggta tgaaagggac tgtaggctcc agtgaccccca 193500 aggcagaacc agaattggga atctctgttc tattgcactc tgttttaca attctggcca 193560 gacctgtagt gtggcatacc actacaggtt atgtggggaa aatgttacca catattcccc 193620
acataatttt ctaacaatac ctcgttccct ttgcagctgg ttcagatctc acagtcataa 193680
gagggttgag cagttggtca caccttgact tgacagctgt cagtcagagg ccataggttc 193740
aacatatatt gaaatgatt ctttcagttg gtcagttggt tttacctatt tgcctgggct 193800
tatggcgacc accgtggaaa ttcaagagac ctgtacccag aatccgtgca cttatggtgc 193860
acagaatgct cactacgtgt agaatcttat ttcctcttca cactcattct atttaggtag 193920
tattttggtt ctcatttttg catacaagga aacaggaact cagagtggtt aaatgacttt 193980
ataagataag aaaaagagct tgttctaaag gctattgaaa tgccagtgat tgatttctct 194040
gagttacttt tcagaactag agtgatggca tagggcaagc ttattcaaac ccatggccca 194100
cgggctgcac gtggcccagg atggccttga atgcgtaact tttttttttt tttttgcga  194160
```

```
cagattctca ctctgtcgtc caggctggag tacagtgatg cgatctcggc tcgctgcaac   194220
ctccacctcc tgggttcaag tgcttctcat gcctcagcct cctgagtagc tgggattaca   194280
ggcatgcacc gtcacacctg gctaattttt gtattttag tagagatggg gttttaccac    194340
agtggcccgg ctggtctcga actcctggcc tcaagtgatc tgcccgcctc agcctcccaa   194400
agtgctggga ttacaggcgt gagccaccat gcctgtaaac tttctgaaaa ttcataagct   194460
ttcttaaaac attatgagtt ttcttgcaat ttcttttttt ttttagctca tcagctgtca   194520
ttagtgttag tgtatttat gtgtggccca agacaattct tcttcttcca gtgtggctca    194580
aggaagccag aagattggac acgcctggca tacggcatac cactgcgcca tccaaaacag   194640
ctgtgcacag ccccacttcc cagctgttag gggcttttt catcttcaaa aattaagcaa    194700
agaggttcac taaagcatca gttcagagtg tgggcttct agtcagtgta ttttaggaa     194760
ttaattttag gaagaaacta ttttaggtc cacgattatt tttaaaaaca aaaatctaga    194820
caacagtgca tacatgcacg tctggatatg taagccctta ccacacagcg agatgagagg   194880
gtggccttgg ccaaagcctg cagttgttgg gacattcaaa accatgagca gactggagat   194940
ttgagccaca tgtgcaccag cgcagtcgct cagatgcggc ctgggtgcgc tgatctggga   195000
gggggactca cgggctctgg gtctctgact agctggcaca tgaaggacct taatgacttg   195060
aacctcactt tcagtttgag atcctttgaa cttttgttag agtgagccat aaagaagtgg   195120
tcagccaatc agatgtttag tataaactga actttagcgt aaataagctt taagagacac   195180
atttgattta cataataaat aaacaagcta cttttaggaa cttttaagta caaaagttga   195240
agatagttgc taattaaacc taaatcttgc ctgtacatta aaaacatact cgacagaatt   195300
tccagtttag aaaactcctc aagaaccaaa tttctgggac agctggggtg tttttctcac   195360
ttagcccaag tgagtaagtt ttactgtaag taaatatgca tacatcatta agtgaaggtg   195420
gcatcacact ggcagggaaa gtcagatggg ttattggcga agaatgaaat tttgctgatc   195480
ttcataaatt gtgaaatgat aaaaaacaaa tagaactcag tagaaatgaa tggcaggcca   195540
aacaaaccgg acagaaaagg ggctacagac taaaagtggt aaattacagc ttctacacat   195600
aaatcctttt taccccaacc ctctttaaat tctggaacat aaatggggga acaaatatag   195660
acccttcta aatccacacc agagaagtga ctttggttgt tttttgttt ggttttatt    195720
tgttttctg atataatagt gattttgcc tcctttcctc ctctttgtaa ggtcttgggt     195780
agaagaggtt gtaaagaaa atgaaactat attatactga tgataatagc taccattcag    195840
tgatagttat tgacagatgt taatatctgt ttcatagagc aaggattaaa tgagttatac   195900
atagaacact taaagcagtg ttttatgttt ataagcatgt agtatttaag tattagatat   195960
tattatcttt aatgttggca attgtcttaa caatataaca gatattctac taagcactat   196020
atatgtctta tctcacttgc tactgttatg ttaattttat agatagtaat ctgaggcatg   196080
ggaagtttaa aaagttgcct gagattgcac gggtggtaat aactgcgcac tttctatatg   196140
ctgtacttag tactagacat ttttaatgta tcgttgcatt tagacctcac aacaatactg   196200
aaactgaggc ctagggaggc cagctaacac caagatcaca cagccagtga gtgatggagc   196260
tgagattcaa acccaagcag tctggctcca aaagtgcatg ttctatgcta ctgtgtacta   196320
tggcctcctg gagaagggct ggtaggatgc cacttcaatg atacagccct ttcctccatc   196380
ctcattacca tccctagcac tgctttcctt cagggtcaca acagtaggtc ttcctaagcc   196440
ccattctcca atcatgtcca gctcattgta cttgagcagc atttcggaga ggaaatgcct   196500
ctagaccctc ccgttcaccc tacagcgctg tttgtgccac gcttccctca ccaccctgcc   196560
```

```
aagcccttgc ttgcacacct ctaatgccag aaaatcatcc tcccaaggaa actcattctt  196620
tctgtcttgg ggaagctctg tctggtggaa acatattcct catattgacc caaatggtgc  196680
tatgtgcctt taacctttct gtgcctcagt ttattcatcc atgggacttt cacgaggatt  196740
aaattagaca ccaagtgctt aaaacaatgc ctcatctgta ttatgtttgc taaatattag  196800
ctgctattac tattttatta ttattagttc tctctatggc ttccacccca aatgctttat  196860
agtacaaatt gagtccttct tgaattcact cttttcacc cttttgtcag ctgcagcctg  196920
ccctccagga tatgatggtg gcctttgtga tgactttgta gactcaatac catatcactc  196980
cagtctgctg tacatgcatc gttaagaact gtctttctgg gatattgctt ttgtacatca  197040
tttccctctt cagaagccaa actggttctt ggttgctttc atactttgga tggattatta  197100
gattctctac taatttcttg ctgatctcta cccatgctct tctctctgag catgaaaact  197160
tcctgtcttc catggacttt cctcttctta tttgcaggtc agctcacata tttattttgt  197220
ttaaacatta tgtagttaaa agtctcaaag gctatatacg aaaatgttaa cagcaactaa  197280
taaattaaca ggtcattttt attttccttt tcatgttttt ctgtgttttc caacatatat  197340
acaacaaaca tataaattgc attgttatga aaaatactgt gtttcctaaa agtacaatca  197400
tagactgtat tatacaatac tttccaaggt caagaggatg ccttgtgcag tcaagagagt  197460
aggattgcct ttcatgaaga tcagaagtat ctccagccct cccctcagtc ccttccctt  197520
ttggtgaacc cattggaatc actaattagt gtatttcaaa ctatatatat tagccataga  197580
cccttcttc aaacaaaaat gtaggccagg tgtggtggct cacacttata atacctcagc  197640
actttgggaa gccaaggtgg gaggatggct tgaggccagg agtttcagac cagccaggta  197700
acgtagggaa acaattacaa aaatcatagt ggcctcttta aaaatttttt ttctaatttt  197760
tttaaaatta gctaggtatg gtagcacatg cctgtggtcc taaccactca ggaggctgag  197820
gtaggaggat catttgagcc aagaagttca aggctgcagt aagctagtaa gctgtgatct  197880
caccactgta ttttagcctg agcaacagtg taagaccta tctcaaaaaa taaaaaaata  197940
aattaaaaaa atgtagagaa gtacaacata tttagcagat attatagatt cttccttaag  198000
gagttgaact ctgttgaaat ggagatggtg aacctggacc ccgacccact aactcaccat  198060
cctatttcaa dacaacttct gagttacttc cagaacctac tttgggtctg gagaacacag  198120
ttctccactg aaaccaccac caggccacct cattctggta acaaacaact cccaatttct  198180
agggggttgct cagataagga gtgctgtaag tttactacgt attatgtaac atatttcatc  198240
agtcctaaaa ttttctgctg atctccttt tcccatccaa aatcaataca cacggctaat  198300
ccatcttata gctgaatatt tctgtctggc cagaaagctt tattatctca gaggtggctt  198360
tcagctcaga aggaaacgag aaaaatttgt ttgtttatac ttctctctta actccctagc  198420
ttctgctcat tcatcaagct aatagatgga atatttggct cttctgattc gccatctgaa  198480
accctctgct ctcttggctt ctgtaatgtc ctgtttaact ggttcacttc ctcatattat  198540
tttcctctct actccgtttg ctgttttcct ttggccctca gtgctctgtt tctgggcgtc  198600
tgctttcttg cttccctccc taggcagcga atccacttct agggttaagc aatcactgca  198660
ttgcgggtgg tgcttagtgt gtgcctcagt ctgtcagaca gaggccagtc ctatagctcc  198720
aatatgttgt ggagccgtct accttgagct caagttaatt cctaaaatca gtatgtctca  198780
ttccagaatc ctttactccc cactatttcc cgtctgaaca tctctattct gccaatatca  198840
acagtattct ctcaatcacc aaactcaaaa ccttggattt tatttatctt ttatattctt  198900
```

```
ttgtcaccaa atatcttggc tttcaccttg ggaacttctc ttagatgtct ctttgctcat 198960
cacttcatgt catggaattc cagaacacag tgctgtatta ccacatacag ttgttaatca 199020
acaaatattt cttaaattgg catctagtcc aactctgtca acgaaatttt aaaagtttgt 199080
taacattcta agaaacctct gcctcctgtc ttgggtcctg acagtttatc caatacactg 199140
tcaagttaat agtgaaaaca cccagtgcgg ccaaagcaat cttgggaaaa aataaaagtg 199200
ggaggactca ggcttgctga tttctaaggt tactactaag cttgacaagt cctggtagtg 199260
tggtactggc ataagaatag acatagatca gctatgtgtg tggctcacac ctgtaatccc 199320
agcactttgg gaggctggat cgcttgaggc caggagctag agaccagcct ggccaacata 199380
gtgaaacctg tatctatata gatagataga tagatagata gatagataga tagatagata 199440
gatggttatc gattttttaa taactataga tcaatggaat ggcatcgaga gtccagaaat 199500
aaaccctcat gcttatggtc aattgggttt tgacaaggat accaagacaa ttaaagagga 199560
aaaaaatact ctctcagaca aatggttctg gagacaactg agatatctat atacaaaagg 199620
atgaaattgg gtgggtatgg tggctcatgc ctgtaatccc agcactttgg aaggctggag 199680
tgagaggatt gcttgaggcc agaagacaag cctgggtaac attgcaagac ccccatctct 199740
ataaaaaatc agctgggcat gatggcatgt gcctgtagtc cccgctattc tggaggctaa 199800
ggtgagagga tcgcttgagc ctaggagttt aaggatgcag tgagctaaag ctaagatcgc 199860
actccagcct gggtgatgga gtgagatcct gtctctaaaa agaataaaat tgagaatgta 199920
atacagaaca catttcagcc attttttaat gctctgcagt tactcgaaag gttaaacata 199980
gacttaccat ataactcagc aattctgctt ctagatatat acccaagaga ggtgaagatg 200040
tacatccaca ctgaaattgt acatgaatgt taatggtaca ttactcgtag tcgccaaaaa 200100
gtataaacaa agaagtgtcc attaattgat gaataaagaa aatgtggtat attttttggca 200160
atatacagga atgaaaggaa tattattcat tatttaaaaa gaatgaagta ctgatacgtg 200220
ctacaaaatg aatgaacctt gagaacatta tgccaagtga aagaagccag acacgaaagg 200280
ccacatattg tctgatccta tttatataaa atgtccagaa taggtaaatc cagagcacaa 200340
agtgggttaa gggttgccta gggctggagg gtgtgggagt aaatgggggat taactgccaa 200400
tggtgcaggg tttctttctg gggtgataaa aatgttctaa aatatgttac agtgatggtt 200460
atacaacttt gtgaatatat catactaaaa accatagaat tttacactaa aaatgggtga 200520
atttgatcat atgtgaacta tatgatatac tctttaaaaa atatatttaa attcctctta 200580
tgtctcccta ttgattagaa ggaaaagttg ccacctctct gacccttctt ctgcagccac 200640
atctccctct gaccataatc aagaagtact ccttgcattt atgaactcat gtcattagat 200700
cgggcccatc cagataaatc tgagataatc ctcacatctt acaggtctta cctataatca 200760
tacctgcaga gtcccttatg gcatggaagg tgatgtattc ataggttctg ggagattagg 200820
atgttgacat tttgaggaac cattatcctg cctatcatac cctgttttat acttctttct 200880
attgcataag agtctcacac atgttgacag atggatggaa aaaatatatt atgcaggtac 200940
taacagcagc aacaatgaca gctaaaaact gagctatcta tacatcagat aaagtagatt 201000
taaaggagga aagcactatt agaattaaag agggagtttt caaaataatt atccagtcat 201060
agaagagatt tttaacatac ctctctcagt aactgataga acaagcaaac aaacaaaaat 201120
gtccataaag atataaaaga tttgaacacc atagttaaca aacttgacct aaatgatata 201180
cagagcattg agcccaacaa cttcagacta catgtttttt acattggtgc ttggataatt 201240
catagtccgt attagaaatg aaaatgttga atatctgtta ttcaaaaggt tataaaaaaa 201300
```

```
ataacaaatt aagcccaaag aaaataaaag gagggaaata ataaagataa aagaagttaa    201360
tgaaatagaa aacaaacata ctacagatag gatctacaag gccaaaagtt tgttgtttga    201420
aaagaccaat aaaatcaggc caggtgcggt gactcacgcc tgtaatccca gcactttggg    201480
aggccaaggc gggcggatca tgaggtcagg agttccagac cagcctggcc aacatggtga    201540
aactctgtct ctactaaaaa tacaaaaaat tagctgggca tggtggcatg cacctgtaat    201600
cccagctact caggaggctg aggcaggaga attgcttgaa ctccagaggc agaggttgca    201660
gtgagccaag atcgcaccac tgcactccag cctgggtgac agagcaagac tccatctaaa    201720
aaaaaaaaaa aaaaaagact aataaaatca attaaacact agcaaaacgt atcttgggaa    201780
aaaatgaaaa gcatgaattg ccaatatcag gaataaacag gcaatattac tacagatgct    201840
acaaacattt aaaagataat acaaaacaaa agttcacatg tactacacaa attcctaata    201900
aaatacaagt tatcaaaact gacaaaggga gaaatagaag atctaaatgg tcctatacct    201960
gctcaggaaa ttaaatcaat aatttcaaac cttcccacaa agaaaactct aggcctagat    202020
ggctttacca acaaactctt ttttgtggat gaatagtatt ccattgtgtc tatatatcac    202080 attttctttta tccattcatc tattgatgga cacttaggtt gattccatat cttgactatt    202140
ataaatagtg ttgcaataaa catggaggtg caggtaaccc tttagtatac cgatttcctt    202200
tcgtttggat aaatacctag tggtgggatt actgcactgt atggtagttc tatttttaat    202260
tttttgagga acctccatac tgtcttccat aatacctttta ctaatttaca ctcccaccaa    202320
cagtacacac atacattttt aaagcataaa acagtgctat atattatccc ttggcacata    202380
tgtattctgc atttttaaaat ggctgaagga tgcactgaag tcacaatagc agcagcctct    202440
agaggagtaa atgaaaggac agggtttgag gataagaaca aaggagactt caacttcatt    202500
tttattgtcc agtttctttt atttttttta aaaaaggca aacatggtaa aatgttaaca    202560
tctgttcatt ttgggtgatg gctcataggg tgttagtcat attattcttt gtaattttcc    202620
ctttgtttaa tttctcaaaa tgaaaacaat aaagtcaaga taatagtatc tttcatagtt    202680
tagtcttagg cttatttatt gtttaggtat tttatgttcc tgtttgtctt aagaaaaaaa    202740
tgtgtataaa tataagtata gatgagatag ttaaattttcc ttttttttgtt tgtgttcaca    202800 aaacatgctt gttttattta acattctttg gtatcaaaat gtggccttca tacaaacttg    202860
tgaggagtaa accatgaggg ttcacagttt taccacagtc tgtatgttag caaccatttc    202920
ctgtgataga catgctcatg cacctcaagt actagaagta tccatttgta ttggagccaa    202980
aatatccgca agcagagaaa caagaagtca aaaatatttt cctctttggt gctaaagatt    203040
tgctgctgtg tgattgttga gactgaagtt ctgaaagcac cagtgtttgc cggatctgtc    203100 tccagccttgt ctctacaagg tcatttccaa aagactgtca aaagaatggc atgtcccgcc    203160
ttttccacca ccgacacacc ctgcatgaaa accccaggag cacagaagtc ctgcttgggt    203220
gaggataagg gctctctcaa agtctattat cgaaggaagg cagacagatg ggttaaccac    203280
tccaatggag tctatacttt tacagacata tcacatatta tgacaattaa ttattaggct    203340
ggtggttcag caacctttcg aagtgatccc aagatgattg ctgtgaccat atttgaaaag    203400
ctaacagata aatgtgggct taaaacagac tatatgttat tcagctaggc ctcaaccata    203460
ggcataagta ggagtgaggt gagggccctt gtggacccac cagggtcttc cacaagagta    203520
gaactcttgc cttgttcact cctttcataa tcaggcaaag gaaggagtta ttcaaaagga    203580
ggaactgagc atgttcaacc gagacccttt ttgctgtcca atttccagcc agcctgtcac    203640
```

```
ctggatatat gtaagcactc tggtctgctc ttggctgtgt gctctaaggg agcccactgg 203700
gtgttcagca agatcaatgg tgaggattaa atctttctaa gtcaagggtc agttacaaac 203760
aagatctctc tgctacagat ctgaagctgt attctctcca gtcaattttg tcagtaacaa 203820
aagcagtatt ttttgttcca tctgtctatc ttctacctct taattggttt caaacttaag 203880
aggtggtaga gattagtaat tgctccccac aaaagcaaaa aaccaacctg atgatcaatt 203940
aagatctcaa aaatgataaa ttaatataat ccatgatacc agccaaaaat ttgtatacca 204000
aatttgttct taccccata gttatcctgt ctgaatagtt aactgagcac tgctcacttt 204060
tagattcctt aagagttgtt aaaaaataag tctttgtact ctatcatggc atgcatgaac 204120
tctcatagct tgaaatgact gcatgaaaat gtacatttta taatttctta tactatttac 204180
ataggtataa gtatacacag aaagtgtgtt taaatgttta acagccaaaa acaaaaacca 204240 aaaaaagtc actctgctgt aacagaacac tgttctgcat atggctagct gtacattggc 204300
agaacatagc gattttaagg atgaattagt gttgtaatct cttgggatt tcctttatat 204360 ttgcggtggt ttatgactga catttcatgt aactatagct ttctgtttgg atttaataaa 204420
agattcattt ctgtggcaag atacacattt gcactccagt gttgaataaa agctactgtt 204480
ctgcaagggt ataaaatgct gatttataac aacacgttcc aataacagtg atctaattct 204540
ttcaaactat ttcttcccag gtcccaggaa cagcatggct ccagcaaagg atgactcttc 204600
tcttccagaa tattcagcct ttaacacatc tgtccatgct gcaattagac atggaaattg 204660
gaaactcctc acgggctacc caggtagagt ccttagctta gcaaacttcc cttcccgtgg 204720
tagacaaagc agggctgtgt cctcagggca gtatctccag tctatctgcc ctcctgggat 204780
ttgattccca cggccatttc tctggaaaga gaggacatta tcactcttgt tctaaccgtt 204840
tcccacctct tcctctgtgg ctcctcctca aggcccctaa gccctaccac ttacctcact 204900
ttgctcagat acctgaaatc ttaatttgtc tttctaatct ttcatgatcc ctcctgatat 204960
atgtcctaga aagacaacta tttattcagg gttttctttt cccaattcta agactccgcc 205020
tgttcccaat tacacagctt ccatcattgt catggtgcaa gtaagctttc ccagtggatc 205080
atcaaggaga agcttaccga agtaacaaat gccttttgca aaacatatct ctggggctgc 205140
tgaatgagga gataggaaga aatggtttaa cctactcgtc ctaaccaaaa aaaaaaaaaa 205200
aaaaaaaaaa agagagagag agagaaagac agagagaatt aactgtagca ggggtgaaag 205260
gaagaaatgt cactcttatg cttcatggaa aatacggatt ttaaatatat gtggctatca 205320
agcacagcac atttagctaa caaagagagt ctctgagagc tacaccctca accagtggta 205380
tagctgggga aggaggttgc tcctctgatt atattctcta agagtgatat cttttcaata 205440
cttttaaaat atgtgggatg atggttaagg ctgtgatgta attaatcaat gtttacaatg 205500
agaacatttt tggcgtttgc aatatgacaa gtctttttg actgggattg tcccatgtat 205560
tgcaagactt tagcatcact agctcatgcc cactaaatgc caggagcacc cctatgccct 205620
agtccttgtg acaaggacat acacacatgc acacgtttt ctgggtgtcc ttgcttgtga 205680
agcagtgaga catgtctagt taaagcacca gaagtcaagt ctgagaagca tctagagaca 205740
gcatctaggg ccgcatcttt ttatgtttcc acacccacaa cccagtgcag ccttggcctc 205800
agactccttc cctgaaatta gaacctgcct ctgtgcttct ccctcagtaa actgttttgt 205860
tttctttgct aggctgtggt tactggttcc ctccaccgtc tcaatacaat gtttctgaga 205920
taccctcatc agacccacca accaagaccc tctggctctt tgatattgat cgggaccctg 205980
aagaaagaca tgacctgtcc agagaatatc ctcacatcgt cacaaagctc ctgtcccgcc 206040
```

```
tacagttcta ccataaacac tcagtccccg tgtacttccc tgcacaggac ccccgctgtg  206100
atcccaaggc cactggggtg tggggccctt ggatgtagga tttcagggag ctagaaaac   206160 ctttcaattg gaagttggac ctcaggcctt ttctcacgac tcttgtctca tttgttatcc  206220
caacctgggt tcacttggcc cttctcttgc tcttaaacca caccgagagtg tctaatttca 206280 acccctaatg catttaagaa gctgataaaa tctgcaacac tcctgctgtt ggctggagca  206340
tgtgtctaga ggtgggggtg gctgggttta tcccccttttc ctaagccttg ggacagctgg 206400
gaacttaact tgaaatagga agttctcact gaatcctgga ggctggaaca gctggctctt  206460
ttagactcac aagtcagacg ttcgattccc ctctgccaat agccagtttt attggagtga  206520
atcacatttc ttacgcaaat gaagggagca gacagtgatt aatggttctg ttggccaagg  206580
cttctccctg tcggtgaagg atcatgttca ggcactccaa gtgaaccacc cctcttggtt  206640
caccccttac tcacttatct catcacagag cataaggccc attttgttgt tcaggtcaac  206700
agcaaaatgc ctgcaccatg actgtggctt taaaataaa  gaaatgtgtt tttatcgtaa  206760
tttatttccc cccagccatt gctcactctg tctagacttc ctgccacttc caattcttct  206820
gtggcttttc ctgcctttcc ttttgacctc agtagtccta tccctgggaa ggccactttg  206880
cttctctacc tgagcacccc tgatttctgg aacgctgctg agccctgcct tacttttgcc  206940
cctagggctg aagctagagg cctccccgta ataggcggtg gagttgctct gtgaggatgt  207000
tcatggtaga cactaagagg gctgggtggg agatgcttgg ctctgtggca tctgttcagc  207060
gaggcttttc ctatattgca tggagttagt cattgtgatt gtagcttttat ttcataatat 207120 attaagactt gcactgctat ttactagcag tgagaagaaa cctcaggaaa ggatatgaaa  207180
aagcaagtgg ccagtgtctg ggatactggg ccttggtaaa gcagaggagg gcacacccac  207240
agtcctctta ttctctgttt tactgcttgt tttgaggttc tggggtctgg caaagaggat  207300
gcagtttgac acctgcagcc ctttctcaat cccactaatg tcttactaat gtggaacagt  207360
ccatattagc tccagagagt gtcaaaccca gagaaatgtg tgcaaaaatg atactctttt  207420
ctgcattagc cccaccattg tgttcaccaa tgcttggaac actgcctgaa ggcactcatt  207480
ttttaatttt tattttatt ttaattttttt atatctttat gagacgatct cactctgtca   207540
ccaggttgga gtacagtggt acaatcacaa ctcaccgtag cctcaaactc ctgggctcaa  207600
gtgattctcc cacctcaggc acccaaatag ctggaactac aggcatatac cgccacaccc  207660
agctaatttt attttttgaa aagacaaggt tccctatgtt gcccagctgg tcttaaactc  207720
ctgggctcca gcaattatcc cagcttgggc tccaaaagtg ctgggattac aggcatgagt  207780
caccatgcct ggcctcattt tttaaaacaa atgaataaat ggacaaatga gtaaatgaga  207840
aagtctcaca ccatgaaaga tgctagtcca atgagctgaa tacagaggta atataaatgt  207900
cttccagctg ttgcttttct gttctcaagc tgcccctcct ggggtaggag cataatctac  207960
atcactgggc agtcacagga cactctatag caaggttgta gcgtcctctc cagtgggggg  208020
agaaaaggaa ctgtgcctac caaaggtact ctcttgtcag caatttccat ttctatactt  208080
tatgggacac tagaaactaa aagcaacaaa taatctgata taagtccttg tatagtcatc  208140
cttcaattca gtagcaatat tttctggtca ctactaacct gtattgtatt aaaatgagac  208200
tattggaagg aaatggtgct aaaactaata acatctctta ccaacctta  cccaactcct   208260 gggttggcaa acagctgacc aaaactgccat cacctcccac ttggaagtgt atggccgaca  208320
gcatgaaata gctgagccca gatgttcctt ctgcatcctc cgaatcccag ggctgggtgt  208380
```

```
aggtagccgt tggaggccat cgctacaggg cacctatctg ttatcgctgc tgtcctccca    208440
acagctgtct ccagttctag ttccttggtt ttcaggcaca gtgggggatg ttctgcaccc    208500
agtggacttc aaaagagttt tgaagactta attttttgta aaacaagtac ttgagatttt    208560
ggtttatcca taatagaatg tatttcatta gattctctga ttctatataa gaatgtgaaa    208620
agattgatat attgttgtta gaaataatgt tatttctttc caattttttt ttttttttt     208680 tttgagatgg agtctcgctc tgtcacccag gctggagtgc agtggtgtga tctcggctca    208740
ctgcagcctc taactcccag gttcaagcta ttctcctgcc tcagcctccc aagtagctgg    208800
attacaggca tacaccacca cgcctggcta tgttttgtat ttttcgtaga gatgggttt     208860 caccatgttg gccaggctgg tctcaaactc ctgacctcaa gtgatccacc cacttcagct    208920
tcccaaagca ctgggattac aggtgtgagc cactgtgccc ggcaaatttt tttaccttta    208980
cagaaggttt tgcttattta attgtgagct catttttctt tgttacttt gtcccccag      209040 atttgggga caaaataaaa ttaatctttt aaaatgtgtc agccatatgt atgggcttc      209100 catttggggt gaggagaaag ttctggaact agatagtggt catggttata caacatcata    209160
aatgcaatta ctgccactga attgtatgtt ttaaagtggt taaaatgtta agttttatgt    209220
tttattacaa tttttaaatg tgtcaaccaa ctttatagta cataaattat atctcagtaa    209280
agctgttaaa taaataaata tagtaaaaat tttagaacta aaaaaa                   209326

<210> SEQ ID NO 6
<211> LENGTH: 21631
<212> TYPE: DNA
<213> ORGANISM: Homo sapiens

<400> SEQUENCE: 6
gtcctcaacc aagatggcgc ggatggcttc aggcgcatca cgacaccggc gcgtcacgcg         60
acccgcccta cgggcacctc ccgcgctttt cttagcgccg cagacggtgg ccgagcgggg        120
gaccgggaag catggcccgg gggtcggcgg ttgcctgggc ggcgctcggg ccgttgttgt        180
ggggctgcgc gctggggctg cagggcggga tgctgtaccc ccaggagagc ccgtcgcggg        240
agtgcaagga gctggacggc ctctggagct tccgcgccga cttctctgac aaccgacgcc        300
ggggcttcga ggagcagtgg taccggcggc cgctgtggga ggtgcgatct cggggcaggg        360
ccgggaggcg cccgaaagcc cggcggtggg agtaggggag cccgggcccc ccgcagactt        420
cttcccctgg gcgtctccga gctggggccc gcaggaggtt aaaggtcaac gggcttgggg        480
gcgccggctt gggggacggg ggaacaggag caccctggag ggccggggcg gattaggcag        540
gaggagaaaa ggctcttgcc gagccctttc ccgaggtaaa ggctgagtct gtgcagtatc        600
cttcctttca atatttattt ttaattttta aaaattttt tgagactggg tttgcacctg         660
tttcccaggc tggggcggag tggcgccagc ctaacttctg agctcaagcg attctcccgc        720
cccagccttg caatttaggg ggtgccaaca cgcctggcta attgaaaaaa aaaaaattat        780
ctgggctcgg tggctcacac ctgtaatccc agcactttgg gaggtggagg cgggcgaatc        840
gcctgaggcc aggagtttga ccaggctg ccaacataa cagggtgaaa cctcatctct          900
actaaaaata taaaaattag ccaagtgtgg tggttcatgc ctgtaatccc agctacttgg        960
gaggctgagt caggagaatt gcttgaaccc gggagtagag gttgcagtga gctgagatca       1020
ggatgccact gcactccaac ttgggcgaca tagtgagact acgtctccaa aaaaaaaaa        1080 aaggcaaaaa aacttaaaaa aaaaaaaaag atacaggggtg tcactattta cccagggtgg     1140
tctcgaactc ctggcctcaa gccatcctcc cacgttgacc tcccaaagcg ctgattactg       1200
```

```
gcatgagcca cccacacact ctggccacag cggcatgcac tgcacagagc tgggcccggg   1260
gatcgggaga aggtgacagt ttagatgtcc tgaggtcagc tctgccgagg caggaagtcc   1320
cttggttttc aaggttcaca tagaggacag gacatgacat caggcccagg acgccacccc   1380
tgttcccctc ctgacttgga tgtgatctgc agagaagtgg aactgggtga ggtctgggcg   1440
gcttttgcct ggtctacatc ctcttattct gactttgcag cattcagtac aggagggaaa   1500
gaggaggggg ctgggtgcca gtgtgcaccc cactcacagt gtcctaagca agctccccc    1560 cattcctcca accagccttc ctccctgtga caggcagtgg ccatctgcct cttagtcaca   1620
ggtctgaacc ttcttgcctc tggctgggat gtggccctgg gcttgctcct gtctcaggag   1680
atattgtgcc ccatccactc tgaggaggaa ctcctggccc cactggccca ggtgcacaga   1740
tcgccctggc agttgacctg tcatcagcaa gttatctgtc ctttctgcca agaatccccg   1800
ctatgtgtca gggcttgtgc taggcctggg ggcacagccg tgcagcacac tggtcctgga   1860
ccctttgggg ggcctaggag ctgagcccgg ctcttctctc cacagtcagg ccccaccgtg   1920
gacatgccag ttccctccag cttcaatgac atcagccagg actggcgtct gcggcatttt   1980
gtcggctggg tgtggtacga acgggaggtg atcctgccgg agcgatggac ccaggacctg   2040
cgcacaagag tggtgctgag gattggcagt gcccattcct atgccatcgt ggtcagtgcg   2100
gccaggagca ggcagggcgg gtggggggggc acggctgctg aacagcatgg gacctccagc   2160
tgccacccac ggcatgtatg ctggggtggg atggtggggg gtcctgccct gccctgccct   2220
gggggctgtg ccctgtatag ggggataggt agcctgatct accccattgg gatgtcattc   2280
ttcccgtctg gctggaaggc cccggagccc catgctgcag gttatgtgag ggagtgcccg   2340
atagtagggc gcctcctcat gccctgacct gcagccccct ccccgtatct cctgtgtctg   2400
cagtgggtga atggggtcga cacgctagag catgaggggg gctacctccc cttcgaggcc   2460
gacatcagca acctggtcca ggtggggccc ctgccctccc ggctccgaat cactatcgcc   2520
atcaacaaca cactcacccc caccaccctg ccaccaggga ccatccaata cctgactgac   2580
acctccaagt gggtaccatc ctgcctccat tgcacacacc caccttcccg ccccacccct   2640
tggtcttcct ggtagggact gggtggcctt cacagagtgg aggccttgga tctggggagg   2700
ccagggaggc ctgtgagctg aggtcagggg acccagagca agggcccagc aaaccacagt   2760
cctcccatcc taggtatccc aagggttact ttgtccagaa cacatatttt gactttttca   2820
actacgctgg actgcagcgg tctgtacttc tgtacacgac acccaccacc tacatcgatg   2880
acatcaccgt caccaccagc gtggagcaag acagtggtga gggcttctgg taggatcctc   2940
tcagcggggc cagggtggc tctgtttgtt ccctgtttgg aaagctctcc caggaaaaag    3000
gtgctcccag catctctaca ccctcacaga ttcccttcca cctatgaagc taaaattcag   3060
cctgtgtgag cggatacggg ctcccaaaat cacccgtgtg gttgacctcg ctaggagaag   3120
aggggtctgg cctaacgtca cacagctcgg ggtggcaatc ctgtcccttc tctatggtgc   3180
tactctcact ccatctcccc ttgctacaca tcgtgctcaa ggaacaggca gcttcggtgg   3240
ggggggcgcc gggcatggtg gcttatgcct gtcatccagc actttgcaag gaggccctgg   3300
tataaggatc acttgaggcc agtagttcaa gagcagcctg gcaacatag tgaggccatc    3360 accacaaaaa attaaaaaat tagccaggga tggtgatgtg tgccggtagt cccagctgct   3420
gaggcaggag aatcacttga gcctgggatg tcaagggtgc agtgagctat gaccacacca   3480
ctgcactctg gtctgggcaa cagacgcaga ccctgtcttt ctttttttct tcttttttt    3540
```

```
ttttgagctg gagtctcgct ctgtcgccag gctggagtgc gatggcgtga tcttggctca   3600
ctgcaacctc tgcctcccgg gttcaagcga ttctcctgcc tcagcctccc gagtaactgg   3660
gattataggc acccgccacc acgcccggct aattttttcta ttttttttta gtagagacag   3720
ggtttcactc tattggcctg actggtcttg aactcctaac ctcaggtgat ccaccctcct   3780
cggcctgcca aaatgcaagg gttacaggcg tgagccactg tgcccagctg ggatacctg    3840
ttttttttgt ttttgttttt tgttttgag atggagtctt gctctgttgt ccaggctgga    3900
gtgctgtggc gtgttcttgg ctcactgcaa cctccgcctc ccgggttcaa acaattctct   3960
tgcctcagcc tcctgagcag ctgggattac aggcgtgtgc caccacgtcc agctaatttt   4020
tgtatttttta gtagagatgg ggtttcacca tgttggccag gctggttcaa ctcctgactt   4080
cgggatccac ccgcctcagt ctcccaaaat gctgggatta caggaatgag ccacagcgct   4140
cggtctgtat ttaagaaaaa ttttttgtttt aagttttttt tcttttttaaa aatatatctt   4200
tttcagggcg ggcgcggtgg ctcatgcctg taatcccagc actttgggag gccaaggtgg   4260
ggggatcacg aggtcaggag atcgcgacca tcctgactaa catggtgaaa ctccgtctct   4320
actaaaaatg caaaaaatta gccgggcatg gtggcagggg cctgtagtcc cagcgactcg   4380
ggaggctgag gcaggagaat ggcgtgaacc tgggaggcag agcttgcagt gagctgagat   4440
tgcatcactg cactccagcc tagggacag agcgagactc catgtcaaaa aataaaaata    4500
aaaaatata tatatatctt tttcttttttc tgagatgagg cttgcactgt ggcccaggct   4560
ggagtgcagt ggtgagatta ttgacagccg ttgtggggcc gcggttctaa gtttaaaaga   4620
atttaggctg ggtgtggtgg ctaatgcctg tcatcccagc actttgggag tccaaggtgg   4680
atggatcgct ttagctgcaa agtttgagac cagcctgggc aacatactga gaccctatct   4740
aagaaaaaaa taaataaata aaataaaaata aatgaataaa aaagaattta aaaaagaatc    4800
ccacagcaaa gacaatgcac catagagcaa tttattgcca aggaaaggta ttttggaagt   4860
taagtttaga acagcctggg tgcactggct catgcctgta atcccagcac ttttggaggc    4920
cgagatgggt ggatcacttg agctcagaag ttcaaaccag cttagccaac attagctgga   4980
cattgtggtg tgagcctgca atcccggcta ctcaggaggt tgagatggga gaattgtttg   5040
aacccgggag gtggaggttg cagtcagctg agattgcaac actgcactcc agcctaggtg   5100
acagagtgac ccccccatct caaaaaaaat agtgaagtgc aaaatgcaca gttcaccctg   5160
agacacagaa ttcaggacag gctgctcgta aggatgagac agcaccgatt attactgggg   5220
aaactccctt tctgggagtc ttccgtgatg aattcctaag gagctgggaa gaggtgttac   5280
tgtaagcacg ttctgggccg tcctctggtt gcacatgcgt agtagctgta catgcttgtt   5340
cacacgtcac gtgtctcagt gccgtggttg gcatgtctga gggacacggt cacttccttg   5400
actacctatc ctgcctcaag atcatagctc actgcagccc cgaactcctg gctcaagcaa   5460
tcctcccact tcagcctccc aagtagctgg ggctgccggg gctgcaagca cgcaccacca   5520
cgaccggctg attgtttgta ttttttaggga agaagtggtt tccctatgtt acccaggctg   5580
gtcttgaact cctggtctca agcgatcctc ccaccccagc ctcctcaagt gttgggatta   5640
caggtgtgac cactgcacct ggccaaaatc ttttttttaaa ttaaaaaaag caccgggtgc   5700
ggtggctcac acctgtaatc ccagcacttt gggaggccaa ggcgggtgga tcacctgagg   5760
tcaggggttc aagaccagcc tggccaatat gacaaaaccc atctctacta aaaatataaa   5820
aattcgccaa gcatggtggt gcacgtctat aatcccaggc acttgggagg ctgagacagg   5880
agaatcacct gaaccccaga ggtggaggtt gcagtgagcc gagatcatgc cactgcactc   5940
```

```
cagcctgggg gacagagtga gactccgtct caaaaaaaaa aaataagaaa ttaaatttaa    6000
aaaaagcaac agaaacaaat ggctgcctgg cagcggtggc tgcagggcgc tcctgtttgt    6060
gtgactcagg tcgtgtccct ccctcagccc tggtctctct tgtttcttgc agggctggtg    6120
aattaccaga tctctgtcaa gggcagtaac ctgttcaagt tggaagtgcg tcttttggat    6180
gcagaaaaca aagtcgtggc gaatgggact gggacccagg ccaacttaa ggtgccaggt     6240 gtcagcctct ggtggccgta cctgatgcac gaacgccctg cctatctgta ttcattggag    6300
gtaatggtgg tttgggacat gcctaaggga ggtcttttgc ccccatgtgg tgaccctggc    6360
ttcagcagga gcccaagaca ggtggatggg caggcatggt cctctgagct ttctgatgtt    6420
tctcacccTT ggtgggaggc ccattttctt tttttttttt tttttgaga tggtctcact     6480 ctgtcaccca ggctggagtg caatggcctg atcacagctc actgcagcct tgaactctca    6540
gcctgcagca gtcctcctgc cttggcctcc tgagtagctg ggactacagg cacatgccac    6600
catgtctggc taaataaaa aaattttgta gcctgggcag agtgactcat gcctgtaatc      6660
tcagcatttt gggaggctga ggtgggtgga tcacttgagg ccaagagttc aagaccagcc    6720
tggccaacat ggtgaaaccc catctctact aaaaatatga aaatttgctg ggcatggtgg    6780
cgaacacctg taattccagc cactcgggag gctgaggcag gagaattgct tgaactcagg    6840
aggcagaggc tgcagtgagc tgagatcaca ccactgcact ccagcctggg ggacagactg    6900
agactgtctc agaagaaaaa cattttttt ttatagagat ggggtctcag tctgtcagca      6960
ggctggtctt caactcctgg actcaagtga tcctcctgcc ttagcctccc aaagtgtggg    7020
aactccaggc atgagccacc ttgtcttgtc aaagggaagg ccatgttttg aagggcaggt    7080
tcccagggtc agccaggta gggcagaacc tctgattgct gcatctctgc ttacaggccc      7140
agaggcagct gctgggtgc acgaggggcc ttcctgctgg agggcaggcc ggatgggct       7200 caggctgtcg gggtgctcac acctggtgct ttggctgtca taggtgcagc tgactgcaca    7260
gacgtcactg gggcctgtgt ctgacttcta cacactccct gtggggatcc gcactgtggc    7320
tgtcaccaag agccagttcc tcatcaatgg gaaacctttc tatttccacg gtgtcaacaa    7380
gcatgaggat gcggacgtgt gttggggctc ctgggtcctt gtcggggctg cttctggtca    7440
ccctccactt tcgccttccc tgtgtcctgc agttgagggc agctcagggc aatgaggcaa    7500
atggctccaa atggagaggg ggctcatggg gtggctctcc agggtcctgg ctctcagagg    7560
aagtgcagct tcgacaggga caggggtcac ttggctctgc tatctcctag atccgaggga    7620
agggcttcga ctggccgctg ctggtgaagg acttcaacct gcttcgctgg cttggtgcca    7680
acgctttccg taccagccac taccctatg cagaggaagt gatgcagatg tgtgaccgct      7740
atgggattgt ggtcatcgat gagtgtcccg gcgtgggcct ggcgctgccg tgagtctctg    7800
ctgtgcacct gctccgcctg cccagcccgg gggcgtcacc gtgaccctct gtcccttccc    7860
tcctggcccg caggcagttc ttcaacaacg tttctctgca tcaccacatg caggtgatgg    7920
aagaagtggt gcgtagggac aagaaccacc ccgcggtcgt gatgtggtct gtggccaacg    7980
agcctgcgtc ccacctagaa tctgctggct actacttgaa gtgagtgctc cctccctgcc    8040
ctcggctaga gtgggaagga gaccctgcca ggtggctggc ctcggtgggc atgtgctgtt    8100
caagatcggc ctcgtgtcca gcccaatggg aaggccgtcc atacccagat agttcagggg    8160
accaaatatc tacccaccca aattgtggtt ttcttttttg ttcttttttt ttcttttga      8220 gatggagtct cactatatgg cccaggctgg agtgcagtgg ggtgatctcc gctcattaca    8280
```

```
acctctgcct cctgggttca agtgattctc ctgcctcagt ctcctgagta gctaggatta    8340
caggcaccca tgaaccactg tgctggggct gtttttttt ttcaaaatgg gttctcactc    8400
tggttgccca ggttggagtg cagcggtgca gttttggctt actgcagcct tgacttccca   8460
ggctcaggtg atcctcctgt ctcagcctcc caagtagctg ggattctaga tgtgtgtcat   8520
cacgcccagc taattttgc tttattttt atttttgga tatgcagtct ccctctattg      8580
cccaggatgg agtgcagggg catgatctca gctcactgca acctctgccg ctcaggttca   8640
agtgattctc cagcctcagc ctcccgagta gctgggatta caggcacatg ccaccacgcc   8700
cagctaagtt ttcctttttt cctttttatg agatggagtc tcactccgtg gccaggctgg   8760
agtgcagtgg cgcaatctcg tctcactgca accttcacct tccaggttca agtgattctc   8820
ctgcctcagc ctcctgagga gttgggatta caggcacacg ccaacatacc ctgctaattt   8880
ttgtattttt agcagagacg gggtttcacc attttggcta ggatggtctc gatctcttga   8940
actcatgatc cgcctgcctc ggcctcctga agtgctcgga ttacaggcgt gagctaccac   9000
gcctggccaa cttttgcatt tttcagtaga cgggggtttt cactatgttg gccaggctgg   9060
gtcttggact actgacctca ggagatccac ttacctcggc ctcccagagt gctgggatta   9120
caggcgtgag ccaccgtgcc cggctaatta gagactgggt tcaccatgt tgccaggct    9180
ggcgtggaac tcctggcctc tagtgatcct cctgcctcac cttcccaaag tgctgggatt   9240
acaggtgtga accaccacac ctggcccccct tttcttcctt acaatcgtgc agttctaact  9300
cagcgttcag agttggattt tcacttggg gtagaagcag gagaggtggt agaaatgcct    9360
cttgactcat acagcacacc ccaatttcat gcagtgcttt gggctgagcc aagtctgcag   9420
caggcagaag gctctgagaa gttgttgcag cctgggccaa ggacaattca gagcttgggg   9480
gcacaggggt gtgctcagca ggactgggtg gacaggccct tgttgcgaa ggggaagagt    9540
acaggcttcc aggagcaggt gttttgaggct ctttgggag gtggccagag gagatgcctg   9600
ttttctgggg caggatttgg agggagccac ccaggctgga gaggttcagc caggctgtca   9660
caggctttga agtttcccat ctgagagcct ggctgttgga gagtgtgggt ttggaacttg    9720
aggctagggg gttcttttct gatctgtgcc agccacagcc ttcggatagg cagagcaatg   9780
atgggggagg gcgtaaaaga agaaatgaac tgaggaaaga gaagaggaaa acaggcttca   9840
acaacagtct aggctgggtg cggtggctca cgcctgtaat cccagcactt tgggaggcca   9900
aggtgggtgg atcacctgag gtcaggagtt tgagaccggc gtggccaaca gatattgaaa   9960
ccctgtctct actaaaaata aaacaattag ccggaacacag aggtgggcgt ctgtaatccc  10020
agctacttgg gaggctgagg caggagaatt gcttgagccc aggaggtgga ggttgcagtg   10080
agccaagatc atgtcattgc actccagcct gggctacaga gtgagattct gtctctcaaa   10140
aaaacaaaaa caaaaacagt ctgtactgtg gaggcctcgg gcaggtgcca ggagctctga   10200
gcacagacgg gtccctctgt tgggttttttc ttcccttcta agggccattt cttcttattt   10260
atttatttat ttttgagat ggagttttgc acttgttgcc caggctggag tgcaatggca    10320
caatctcggc tcaccacaac ctctgcctcc tgggttcaag tgattctccc gcctcagcct   10380
cccgagtagc tgggattaca ggcatgcgcc accacgccca gctaatttgt atttttagta   10440
gatatgggggt ttctccgtgt tggtcaggct ggtctcgaac tcccaacctc aggttatctg   10500
cctgcctcag cctcccaaat agctgggggc acaggtgtgt gcggccatgt caggctaagt   10560
ttaaattttt tttttttttt ccgcaagatg gagtcttgct tgttgcccag gctggagagc   10620
actggtgcaa ttttggctca ctacaacctc tacctcctgg gttcaggcaa ttcttctgcc   10680
```

```
tcagcctcat gagtagctgg gattccaggc gcatgccacc atgcccagct aggttttttt    10740
tgtatttttt tgtagagata gacttttacc atgttgacca ggctggtctc aaactcttga    10800
cctcatgatc cacccgcctc ggcctcccaa agtgttggga ttacaggcgt gagccaccat    10860
gcccgcccct aattttttaaa tttgttgtag aaacaaggtc ttgctatgtt gcccaggctg    10920
gtcttgaact cctggtctct ggtaaaactc ccaaagtgct gggattctag gcgtgagccg    10980
ccttgcccgg cacttgcacc atttctctgc atgcgtctcc actcccactg cccaggacct    11040
gtggacttag atttgagtca ctgctgagca cctcgcacct agcccatgc ctgcctccca     11100 gcctgcactc cgtttgcttg atgcattaat aaatatccct cccaaatctg catccatcca    11160
cctcctgtgt tcaagagctg tttcagggcg tcaacctcat ttttgccagt gtccagccta    11220
gtgacctcag ctctgtgtac ctggaagagt ggctgctcct ctgggggtat aggattcgga    11280
gatgggggta aaggagtga tgttagagag ctcggtctag gactagagga tcatatgccc     11340
ttatgtaaaa tacatctcaa gttagggaag aaagcagcgg ctccatgctt tttttttttt    11400
cccctttgtt tttgtttgtt tgtttgaga cagggtcttg ctctgtggac caggctggag    11460
tgcagtggca tgatcttggc ccactgcaga ctcctccttc tgggttcacg ccattcttct    11520
gcctcagcct cctgagtagc tcagactata ggcgccggcc accacgcccg gctaattttt    11580 tgtatttta gtagagacgg ggttttaccg tgttaggatg gtatcgatct cctgaccttg     11640
tgatctgccc gcctcggcct cccaaagtgc tgggattaca ggcgtgagcc actgcgcctg    11700
gccgctaatt tttgtatttg tagtagatag agttgggggtt tcaccatgtt ggccaggctg    11760
atcttgaact cctgacctca agtgatccac ccacctcggc ctcccaaagt gctgggatta    11820
caggtgtgaa ccatcgtgcc tggccccgtg ttgtgttctg gcggtggaag atgggacaga    11880
gaggatggga gggtgtctga gccattcctg gactgatgga acctgtttct tctgcctttt    11940
gtggacagga tggtgatcgc tcacaccaaa tccttggacc cctcccggcc tgtgaccttt    12000
gtgagcaact ctaactatgc agcagacaag ggggtgagcc tgggggtccc caccccactt    12060
ctccctgcct ttgcctgggc ttgtcctgaa gcctggtcat gggaacagcc aggaagaacc    12120
atgcgctgcc agtctgggtt ttatttcatt ttctttttta cttaaaaaga tagagacagg    12180
gtcttgccat gttgcccagg ctggtctcca actcctgggc tcaagcaatc ctcctgcctt    12240
ggcctcccaa agggctgggg ttacaggtgt gggccaccac accccggccg cagccagtct    12300
gttttcacag atggtctttg ggttaatgag aattctcccc ctgcttactc gccaggcagt    12360
gtggcttcct caatccaagg aggctgggca tagggagatg ggatttgttt gctcagtttg    12420
gactcagcat ttttgcact tcgatttaat agactcataa aacatcaaag atttaaggga     12480
gcttagagtt catctggccc acacctggct gatgagaatc tctagggga gttttatga     12540 aatgccagat ctctgcattc tgaggtcctg atttagtacg tccagggttg aacttgagt     12600 ttttcttttt cttttgtaga ggcaaggtct tactctcttg ccctggctgg agtgcagtgg    12660
tgcaatcaca gctcactgca gccttgaatt cctgagccca agtgatcctc ctgcctcagc    12720
ctcccgagta gctgggactc caggttttca ccactgcgcc tagctaattt tatatctttt    12780
tgtagaggtg gcatctctct atgttgccca ggctggtctc aaagtcttga gctcaagtga    12840
tctcctgcct tggcctccca aagtgctgtg attacaggca tgagttgcag tgcctggctg    12900
acattagcat tctttatta tttatttatt tattttgaga tggaatcttg ctctgttgcc    12960
caggcttgag tgaaatggtg caatctcagc tcgctgcaac ctcgtcctcc caggttcaag    13020
```

```
caattctgcc tcggcctcct gagtagctgg gattacaggt gcatgccacc acacccagct   13080 aattttttgta tttttttagta gagatggggt tttgccatgt tagccaggct ggtctcaaac   13140
tgctgatctc aggtgatctg cccactttgg cctcccaacg tgctgggatt acaggcgtga   13200
gccaccacac ccggccagca tttttactag aaagaaatgt gttcaggacg cattagaaac   13260
tagccagttg gacacagaag cccctgctgc tcagctgtaa gcaccgctat gctgaagctt   13320
ggggtggtcc tactcggtcg tcaccgccct gctccttgga gtgacttttc tggccctctg   13380
cagtccacag tgctgccttg tgaaagctcc ctcaagatcc tctgtgacag ccgggcatgg   13440
tggcttacac ctatcatccc agcactttgg gaggccgagg caggcagatt acttgagatc   13500
aggagttcaa gaccagccca gccaactggt gaaacttcat ttctaccaaa aatacaaaaa   13560
attagctggg cgtggtggcg cacgcctgta atcctagcta ctcgggagac tgaggcatga   13620
gaagcacctg atggtgggag gcagaggttg cagtgagctg agatcgcacc actaacattc   13680
tagcctgggc gacagagcga gactctgtct ccaaaacaaa acaaaagatt ttctgtgaga   13740
atgactgcat cggcccctcg ggtggcagcg cttctccagg gcaaggtgag gggaagccca   13800
gtgatgggag tgctgcctgg agaggagtca gttccagtgg tgggggccct gggctttggc   13860
tgagggctgt gcgttggcag ctgctgtgcc tctcacagcc cttcccagcg cgcacgtca    13920 tgagtgtcag tgtggagtcc caggcctacc tcctctgggc cactttgtga ccatgtttct   13980
tgcctatggc agggtaattt caggatctaa attggtacac ttggacgttc tcagccccag   14040
gaggcagctg ttcccgttct aggttttttt tttttttttt ttttggtaga aatgggggct   14100
tgtgatgttg cccaggctgg tctcgaactc ctgggatcaa gtgatcctcc catcttggcc   14160
tcccaatgtg ctgggattac aggcatgagc caccgtgccc tgctaatttt cttactacta   14220
ttttttgtaa tgctgcagtc ttgctgtgtt gcccaggctg gtcttaagcc atcctcctgc   14280
ctcagcctcc cagagtgctg ggattacatc ccccttacct tctctgccag aggagccccc   14340
gcagtgtgtg aatgctgagt catgctgtct actgagtgct gaacgggctc tgctgctctg   14400
gtcctaggct ccgtatgtgg atgtgatctg tttgaacagc tactactctt ggtatcacga   14460
ctacgggcac ctggagttga ttcagctgca gctggccacc cagtttgaga actggtataa   14520
gaagtatcag aagcccatta ttcagagcga gtatggagca gaaacgattg cagggtttca   14580
ccaggtaagc agtgttgagc tttctgcttg tgtgttctct cagggcagag atgtcactca   14640
cctcctccag cctgacctgc gcccactgca ctgctcccct cgcttcagct tgggctctc    14700 ctcccacggc cccgtccacg ttccctcacc gccaacagcc aggcctgtgc cccactcact   14760
tggtcctcag aggtggcctc cttactggct ttgtttccag atagcctcct atcacccgtg   14820
cccaagtggt ctttctaaca gatccaaatt tgtatttgtt tttgagaccg gatctctctg   14880
tcacccaggc tggagtgtgg tggtgcgatc actgctcact gcagccttaa cctcctgggc   14940
tcaagtgatc ctcccacctc agcctcctga gtagctggga ccataggcac atgccaacac   15000
gcctggctaa ttttttttact tttgtagaga tggggtcttg ccatgttgcc cagactggtc   15060
ttgaactcct ggcctcaagt gatctgcctc aggctcccaa agtgctggga ttacaggtgt   15120
gagcctctgc accagccaca gttgaaaatt tggagtgtcc tgtcattggc tcccccaggc   15180
ccacaggaca aagccctaac ctctggtcag gacactcagt gtcctctgct ctctcctggg   15240
ttttcatccc cttctcccct ctatcccagc cactgatctg tttccactgc cctcgcttgc   15300
tctcctgctc ttgcttgagc tgtttcttct gcctggaatg cccatgttgg caccataatc   15360
accaactaaa atatcctttt tcttaatttt catattttag atataggggtc ttgctatgtt   15420
```

```
gtccaggctg gtctcaaact cctggactca attgatcttc ctgccttggc ctccaaaagt   15480
gctggaatta caggcatgat ccactgtgct agcctttttt tcttttttctt tttttcaggg   15540 tcttgttgtg ttgcccaggc tggagtgcag tggtgtcatc atagctcact gcagccttga   15600
actaaagggc tgaagtaatt cttccacctc agcctcctga gtagctggga cgacaggcat   15660
gaaccaccat gtgcagccta ttttaaatt tttttgtaaa gatggagtct atcaggctgg   15720
tctagaactc ctggccttac gtgattgtcc tgcctcagac tcccaaagtg ctgggaatcc   15780
aggcatgaga caccatgccc agcctgtcgt cattttttta atctatctca tttttttgtc   15840
ctcctcacca aagatatgtt ggtttgtctt gtgaggtttt ttttttcctg tggattcctg   15900
aaccccatcc agccctcat tcccacccca gccagctcac acttgtttgt cacagctcct   15960
ggttgacaca cagggaacag ccacccacag tggactgcgc tgttctgttt gcacccttaa   16020
atttatcgtg cttacagaat gccacttctg caaactagtc aagtagggga agtggctctt   16080
ggatatattt gcttgcgcat cctctttgaa aaggtaacca gctctgaatt cttttttttt   16140
ttttgacaca gagtttcgct ctcgttgcct aggctggagt gcagtggcgc gatctcggct   16200
cactgcaatg tccacctccc tggttcaagc gattctcatg cctcagcctc ccgagtagct   16260
gggattacag gcatgcgcca ccacgcccac ctcatttgt atttttagta gagatgaggt   16320
ttcaccatgt tggtcaggct ggtcttgaac tcctgacctc aagtgatccg cccgccttgg   16380
cctcccaaag tgctgggatt acaggcatga gccaccgtgc caagccctag ctctgaattc   16440
ttaagaaact cttgagaggg tctaggtcag tgctgataga acctctgcag tgctgggcat   16500
ggtggctcac acctggaatg ctggcacttt gggaggccaa ggtcagagga tctcttgagc   16560
ccaggagttt gagaccagtc tgtgcaacat agaccccatc tctacaaaaa atttaaaatt   16620
agttgggcat ggttatgagt gcttgtagtc caagccactt gggaggctga ggtgggagga   16680
ttgtttgagc ccagtaggtc aaggctgcat tcagctatga ttgcaccact gtactcccac   16740
ctgggtgaca gagtgagacc ttgttcaaa aaataaaaaa aaacaaactt gcaatgatgg   16800
aaatgttcta tatttgcact gtctgaaatg gtacacacta gctacacatg gctactgagg   16860
tcttgatata tgactaggat aactgaattg atttagttta attaaataaa tttttttgag   16920
acagcctcac tctgttgccc aggctggagt gcagtggcat aatcacagct cactgctcaa   16980
cctcctgggc tcaagcgatc ctccctcctt agccccaagt agcttgaact gcaggcgtgc   17040
gccaccacac ctggctaata ttttgacttt ttgtagagac tgggtctcac tgtgttgcct   17100
agactagtct tgaaatcctg ggctgaagtg atcctcctgt ctcgacctcc aaaagtgctg   17160
gcattacaga cctgaggtac catgcccagc ctggtttggt tgagtttaat ttaatttaat   17220
ttttatatat atatatatat ttattagaga cagggtctca ctgtgtcacc caaactggag   17280
tgcagtggtg tgaacacagc tcactgtcgc tttgatctct ggggctcaag cagtcctcca   17340
acctcagcct cccaagtagc tgggaccaca gatgtgtgcc actaggcttg gctaattttt   17400 gtacttttg tagagatggg gtcttgctat gttgcccagg ctggtcttga acacctgggc   17460
tcaagcagtc ctcccacctc agcctcccaa attgctggga tgacagacat gagccactgc   17520
acctgactga aagacatatt tttgcctgta gtgtagttta gccttaagac tgtaccagca   17580
gatagaggtg gaaaagtaat gtgaaacgaa tgtcaaatta cgtttataaa taaagcagct   17640
gctcattaag gttgttttttt ttttaaacc tcctttttta ttctggggtta catcattccc   17700 tggctgtctt taccccagca tcagtgagtc ctgcagtcac tatagccccc tgtgaagaca   17760
```

```
gatattttgg tcaccatcaa gtggatcttt attttatct aacatttaca attctgccag    17820
ttctgactct tacattctct ttgccttgaa tcctaggatc cacctctgat gttcactgaa    17880
gagtaccaga aaagtctgct agagcagtac catctgggtc tggatcaaaa acgcagaaaa    17940
tacgtggttg gagagctcat ttggaatttt gccgatttca tgactgaaca gtgtaagtgg    18000
cagtttggct catgggataa cgtacccgtc ctcatttttt caggttgcct ttccaattct    18060
ggccatttca attgtaagaa tattggaaac aaagttgggg aagctggttt aatccatgta    18120
ggttgcgttg agaattttct aggaaaagta agttgtgttt aggaagtagg aaagcaatca    18180
ggccccccgcc tcccaaatac ggtcaaaaag caaacaggag agtcagctat agtgaatcgg    18240
aaatggctgg cttgcctttt ccttgtctat tttgtagcca aggaggaacg aaaaacggga    18300
cctcatcatg gatttacttt tgggatacac tcattattcc atagaagggt acaaagcctg    18360
agaaacttaa ggtatttcag tctgttgtat attacttgcg aaaagcaggc ttatcaaata    18420
caggtgagtt tcaacgcatc ttgaatttgg cagcatttac aagtcttcag gccaggtgta    18480
gtggctcacg cctgtaatcc cagcactttg ggaggtcagg gtgggaggat cgcttgaggc    18540
caggagttca agaccagcct gttcagcata gcaagacccc atctctacaa aaaataaaca    18600
gattagctag gcgtggtggt gtgtgcctgt agtctcagct gcttgggagg ctgaggcagg    18660
cggataacct gagcacagga gttggaggct gcagtgaact atgattgcac cactgcacaa    18720
gagcctggac aacagagtga gacttgtctt taaaacacaa gattggtctt caaagagaat    18780
aacatctgcg gtgtcttgtg aggatggatg aggggctgcc aagttcgcaa tgaatgtgtc    18840
ccatttcttc ttagttatg gacttaccat aaactgaaga tagcagtttg gtgggttgga    18900
gaagcatgtg gtaatggtgg gaattataat acattactta cagggaaaga caggcctttg    18960
aaaggtaaag cgtaagagtg agaatggaat acggatgaat gaatgaacaa gatgaggtga    19020
gaaggaagag gtaaagggaa aaggagaaca ggaagctgtc ctctgcgtgg cacctgtgat    19080
aaatggtttc tggggacatc cctgatggca gttttgtgga gaggtgcgag gctttatgcg    19140
gtaagaaatg agctgcaggc tgggcgcagt ggctcaagcc tgtgatccca gcactttggg    19200
aggccaaggt ggacagatca cctgaggtca ggagtttgag accagcatgg ccaacatgga    19260
gaaaccccat ctctactaaa aatacaaaat tagccgggtg tggtagcgca tgcctgtaat    19320
gccagccact tgggagactg aggcatgaga atctgttgaa cctgggagat ggaggttgca    19380
atgagctaag atcacagcac tgtactccag cttgagcaat agagtgagac tctttttttt    19440
ttttgagacg gagttttgct cgtttcccag gctggagtgc agtggcgcta tctcagccta    19500
ctgcaacctc cacctcccag gttcaagcaa ttctcctgcc tcagcctccc gattaactgg    19560
gattgcaggc atgcgccacc acacccggct aattttgtat ttttagtaga cgggggttt    19620
ctccatgttg gtcaggctgg gcttgaacta ccgacctcag gtgatccgca catctgggcc    19680
tcccaaagtg ctgggattac aggcatgagc caccatggcc agctgaaact cggtcttaaa    19740
aagaaaaaag aaatgagctg catcacgttg ggcaagtcac ctaagctttt cataagcctg    19800
tccagtgggg ataatgccac ctccttgttg gtgtcgtaag ggctgcattt gatgaagtac    19860
ttggcgatgc ctgtgttcac ttatggaaga aacagtcttg aaccttttgg tggggaaagc    19920
cccttttcca tttaacattt ccatttagtg gtggtcttac tggggacaga gaatgtcctg    19980
agagcacagc cctgacaggt cgttgccagc tgtgctcctc caccaggctc agctcaggcc    20040
taatgaccac cagtggtggg tgctgccaag ctggacgtca gccccggcgg actttgaact    20100
ccatgagtag gtcccacgca gggacctgtg gctggtcagg accctggctc ccactaggcg    20160
```

```
ctatctcttc agaaaggccc aaggcttttc aagggtaact gtcccagata cccctagccc    20220
tctgcctacc cagttaccag acagctgggt acccagcatg taaaccttag tttgcaaata    20280
aaagataaac ttttagtgct ttttttttt ttggagatgg agtctcactc tgtcgcccag    20340
gctggagtgc agtggcacaa tctcagctca ctgcaacctc tgcgtcctgg gttcaagcga    20400
ttctcctgcc ccagcctcct gagtagctgg gaccacaggc acccaccacc atgcctgtat    20460 aattttttgta ttttttagtag agatgaggtt tcaccatatt gtccaggctg gtcttaatct    20520
cctgaccttg tgatccgcct gctttgtcct cccagagtgc tgggattaca ggcatgagcc    20580
aatgtgccca gccagttttt gtattttaa tagaggcggg tttcctcatg ttggccaggc    20640
tgatcttgaa ctcctgacct caggtgatcc acctgcctca gcctcccaaa gcactgggat    20700
tacaggcgtt ggccaccaca cctggccact gttttgggtt ttttcccct aacagactag    20760 aaaactagaa attaacacac cagggaacct gggtgtttgg gcagagcagt ggtatttaaa    20820
tatttcaacc cataaattgt cacttcagag caagcatcct gaaactgtaa gaggacattt    20880
ggctgagcat ggtggcttgt gcttataatc ccagcacttt agggaggcta aggagggcag    20940
attgcttgag cccagtagtt tgagaccagc ctggacaaca taatgagacc ttgtctttac    21000 taaaaataa aataaaaga ttaccgggca tggtggtgct ggagaggctg aggcaggagg    21060
attgcctgag cccaggaggt tgaggctgca gtgagctatg attgtgtcac cgcattccag    21120
cctgggcaac agggagaaaa aagaaaaaaa aagacatttc tatttagtgc ctaccttagc    21180
tccagactgg ttctaacttg acccatcaga agacatctga atcgctttgt gtcttttttt    21240 ttttttttgta gcaccgacga gagtgctggg gaataaaaag gggatcttca ctcggcagag    21300
acaaccaaaa agtgcagcgt tccttttgcg agagagatac tggaagattg ccaatgaaac    21360
caggtatccc cactcagtag ccaagtcaca atgtttggaa aacagcctgt ttacttgagc    21420
aagactgata ccacctgcgt gtcccttcct ccccgagtca gggcgacttc cacagcagca    21480
gaacaagtgc ctcctggact gttcacggca gaccagaacg tttctggcct gggttttgtg    21540
gtcatctatt ctagcaggga acactaaagg tggaaataaa agattttcta ttatggaaat    21600
aaagagttgg catgaaagtg gctactgaaa a                                   21631
```

<210> SEQ ID NO 7
<211> LENGTH: 10415
<212> TYPE: DNA
<213> ORGANISM: Homo sapiens

<400> SEQUENCE: 7

```
ctctctctct ctcgctcgct ctctcgctct ctcgctctct ctcgctcgct ctctcgctct      60
cgctctctct ctctctccgg ctcgccagcg acacttgttc gttcaacttg accaatgaga    120
cttgaggaag ggctctgagt cccgcctctg catgagtgac cgtctctttt ccaatccagg    180
tcccgccccg actccccagg gctgcttttc tcgcggctgc gggtggtcgg gctgcatcct    240
gccttcagag tcttactgcg cggggcccca gtctccagtc ccgcccaggc gcctttgcag    300
gctgcggtgg gatttcgttt tgcctccggt tggggctgct gtttctcttc gccgacggta    360
ggcgtaatga atatttcgac ctttggatct tagctgtccc ctccctgcgt tcgcacttaa    420
cctttttcac cattattatt attattgtta ttattattat ttttgaggg agtctcgccc    480 tgtcgcccag gctggagtgt aatgcgcct tcttggctca ctgcaacctc cgcctccgg    540 gttcaggcga ttctccgacc tcagcctccc aagtacgtgg gattacaggc acccgccacc    600
```

```
acgcacggct aatttttgt atcttttagt agagacgggg tttcaccatg ttggtcaggc    660
tggtctccaa ttcctgacct cgtgatccgc ccgcctcggc ctgccaaaca gctgtgatta    720
taggcgtgag ccaccgcgcc cggccaacca tcattattat ttttaacggt aaggatggtc    780
agattttact aatgaagaag agattataaa atcttcaagt ctttatatcc acttgctttt    840
tgaggggtgg agtgggaaga aggttatgta attcatacgt tcttcagaca tgtgacaaac    900
attcacggag cccggcgacg agcgtcgggg ttgggattcg cactggagct gcagatgggt    960
gccaggatgg actggtccct accctccgct tgaacctagg aggcggaggt tgcagtgaac   1020
cgagatcgtg ccactgcact ccagcctggg tgacagagat actccgtctc aaaaaaaaaa   1080
acaaaacaaa aaacaagcgg actgggcgca gtgcctcacc ctgtaatccc agcactttgc   1140
aaagccaagg cgggaggatc ctttgagttt aggagtttga gaccaacctg cgcaacacag   1200
taagaccccg tctctacaaa aaatacagaa attagccagg tgtggtggtg tgcgcctata   1260
gtcccagcta ttctggaggc tgaggtggga ggattgctta ttctggaggc agaggttgca   1320
ctgagccgaa atcaagctac tacactccat ccagggcaac atacgagac cctgtctcaa   1380 acaaacaaac aaaaaattgc tcagtacctg gccaaaaaag aagaggctca ctatgcagag   1440
gggaagtgga aggagatgtt tggacttcta aactcaatag agcaggagag gcaaatgtag   1500
aatgtgctca ggaaatatct gtgagatgaa tgaacttgag ggaagtaagg tactagatat   1560
tacctgccct acccagaaca atcctgtgc aatgtttcct tgaaaagtga gaagtctgga   1620
aggggtggct actgacatag tgaagcaact agttcaattc tacaacttga cagctacccc   1680
tgtgccaggc tatctacgag gatacttaga atgcataaga cattccttca aggaactcca   1740
ggaacagagg cctgacatgt tgcaatgttt agtgtcaagc agtgtactag agacacatta   1800
tcacactcaa acctcacaac aattctgtga ggtaggagtt atcactcccc ttttatagat   1860
gaaacagagg cttagagtga ttgatttatt gaaagtcaaa cagccagtaa atggtgtagc   1920
caggattcca aacttgctgt ctcactgaga ctgtacttaa ttactggagg gaccgggtgt   1980
ggtggctcat tgctataatc ccaacacctt gggaggctga ggctggtgga tcacctgagg   2040 tcagggttc gagaccagcc tggccaacat ggtgaaaccc catctctact aaaaatacaa   2100
aaattagctg ggcatggtgg tgggctcctg taatcccagc tactcaggag gctgaggcag   2160
ggcaattgct tgagccgaga tcacactgca ctccagcctg gcaacaggg caagactctg   2220 tctcaaaacc aaaaaaaaaa aaattactgg aggaacctag aagaagaaat gatcaatttt   2280
gcttggagtg tatctagaaa gacttcactg agatcattta aagaacaaaa aggatggctg   2340
gggtccagcg cagtggctca tgcctgtaat cccagcactt tcggatacca aggcagcaga   2400
tcacctgagg tccagagttt cagaccagcc tggccaacat agtgaaaccc catctctact   2460
aaaaataaaa aaattagctg agcatgttgg agggcacctg taatcccagc tacttgggag   2520
gctgaggcag gagaatcact cgaacccagg aggtggaggt tgcagtgagc caagatcacg   2580
ccactgcact ccagcctggg caacagagtg agactctgtc tcaaaaaaca acaacaacaa   2640
aaaatacaaa caagagacaa gtagttccca ggtgcctacc aagtggtcag gcactgcact   2700
tacctcactg actgcagtaa ccacccttg aggttgtggc attgcctcca ttttccaggc   2760
aaggaaatgg gctgagagct gggattagtc aggtcatgac tgtgtgtgcc actcccgcta   2820
aatctcattt gatgtggttc atgaggccac accatggaca gcttcctcct tgtgtccact   2880
gaggatatgc ctttgtacaa cactttggtt tttgaacgac tttacaaacc tccctgtctt   2940
gtgaggaagg aagaacagtt attaccatct gcatctgatg atgaaacaag ggacgctgca   3000
```

```
gaggagccgc actgaccact ccctccctcc agtcctgtca tcccactgcc agtgtcccac   3060
cctcttgtgc cctgcacttc actggctaat aaccccctc acttttttcct ctgtgaagcc    3120 atcctggata attccccacc cacgaatggt ccctcctcat ctcagagagc tctccatgca    3180
cacctgttac cgtttctgtc tttatctgta aatatctgtg tgtctgactt ccatgcctca    3240
cacacctcta tagggcaaag actgtcttaa acatcttggt agtgtcagta ttttgcacag    3300
tgaagttttt ttttttaaat tatatcagct ttatttgtac cttttttgaca tttctatcaa   3360 aaaagaagtg tgcctgctgt ggttcccatc tctgggatt taggagcctc taccccattc     3420
tccatgcaaa tctgtgttct aggctcttcc taaagttgtc acccatacat gccctccaga    3480
gttttatagg gcatataatc tgtaacagat gagaggaagc caattgccct ttagaaatat    3540
ggctgtgatt gcctcacttc ctgtgtcatg tgacgctcct agtcatcaca tgacccatcc    3600
acatcgggaa gccggaatta cttgcagggc taacctagtg cctatagcta aggcaggtac    3660
ctgcatcctt gttttttgttt agtggatcct ctatccttca gagactctgg aaccctgtg    3720 gtcttctctt catctaatga ccctgagggg atggagtttt caagtccttc cagagaggta    3780
agagagagag ctcccaatca gcattgtcac agtgcttctg gaatcctggc actgaatttt   3840
aatgaatgac agactctctt tgaatccagg gccatcatgg ctcttttgagc aaggcacaga   3900 tggagggagg ggtcgaagtt gaaatgggtg ggaagagtgg tggggagcat cctgatttgg    3960
ggtgggcaga gagttgtcat cagaagggtt gcagggagag ctgcacccag gtttctgtgg    4020
gccttgtcct aatgaatgtg ggagaccggg ccatgggcac ccaaaggcag ctaagccctg    4080
cccaggagag tagttgaggg gtggagaggg gcttgctttt cagtcattcc tcattctgtc    4140
ctcaggaatg tcccaagcct ttgagtaggg taagcatcat ggctggcagc ctcacaggat    4200
tgcttctact tcaggcagtg tcgtgggcat caggtgagtg agtcaaggca gtggggaggt    4260
agcacagagc ctcccttctg cctcatagtc ctttggtagc cttccagtaa gctggtggta    4320 gactttagt aggtgctcaa taaatccttt tgagtgactg agaccaactt tggggtgagg     4380
attttgtttt ttttcttttg aaacagagtc ttactctgtt gcctgggctg gagtgcagtg    4440
gtgcaatttt ggctcattcc aacctctgcc tcccagattc aagcgattct cttgcttcag    4500
cttcccaggt agctgggatt acaggcggcc accactacgc ccagctaatt tttgtatttt    4560
tagtagagac ggggtttcac catgctggca aggcaggtct caaactcctc acctcaggtg    4620
atccgcccac ctcggcctcc taaagtgcta ggattacagg tgtgagcccc tgcgcccggc    4680
caaggggtga ggaattttga aaccgtgttc agtctctcct agcagatgtg tccattctcc    4740
atgtcttcat cagacctcac tctgcttgta ctccctccct cccaggtgcc cgcccctgca    4800
tccctaaaag cttcggctac agctcggtgg tgtgtgtctg caatgccaca tactgtgact    4860
cctttgaccc ccgaccttt cctgcccttg gtaccttcag ccgctatgag agtacacgca    4920
gtgggcgacg gatggagctg agtatggggc ccatccaggc taatcacacg ggcacaggta    4980
accattacac ccctcacccc ctgggccagg ctgggtcctc ctagaggtaa atggtgtcag    5040
tgatcaccat ggagtttccc gctgggtact gataccctta ttccctgtgg atgtcctcag    5100
gcctgctact gaccctgcag ccagaacaga agttccagaa agtgaaggga tttggagggg    5160
ccatgacaga tgctgctgct ctcaacatcc ttgccctgtc accccctgcc caaaatttgc    5220
tacttaaatc gtacttctct gaagaaggtg aggaggaagg ggacaagatg acatagagcc    5280
attgaaactt ttcgtttttc tttcttttt ttaaaatttt tttgaggcag aatctcactc     5340
```

-continued

| | |
|---|---|
| tgcccattct gtcggcgaga caggagtgca gtggtgtgat ctcccctcac agcaacctct | 5400 |
| gcctcccagg ctatagtgat tctcctgcct cagcctcctg agtagctgga attataggcg | 5460 |
| tgcgccacta ccacctggct aattttttgta ttttttagtag agacagggtt tcatcatgtt | 5520 |
| gaccaggcta gtcttaaact cctgacctca aatgatatac ctgccttggc ctcccgaagt | 5580 |
| gctggaatta caagtgtgag ccaccgagcc cagcagacac ttttcttttt tctttttttt | 5640 |
| tttttgagac agagtctcgc actgtcaccc aggctggagt gcagtggcac aatctcagct | 5700 |
| cactgcaacc tccacctccc gggttcaggt gattctcctg tctcagcctc tcgagtacct | 5760 |
| gggattacag gtgcctgcca ccacgcccgg ctaattttttt gtattttttag tagagacagg | 5820 |
| gtttcactat gttggccagg atgattgcga actcctgacc tcgtgatctg cccacatcgg | 5880 |
| cctcccaaag tgctgggatt acatgcgtga gccactgaca ctttttctttg ccctttcttt | 5940 |
| ggaccctgac ttctgcccat ccctgacatt tggttcctgt tttaatgccc tgtgaaataa | 6000 |
| gatttcaccg cctatcatct gctaactgct acggactcag gctcagaaag gcctgcgctt | 6060 |
| cacccaggtg ccagcctcca caggttccaa cccaggagcc caagttccct ttggccctga | 6120 |
| ctcagacact attaggactg gcaagtgata agcagagtcc catactctcc tattgactcg | 6180 |
| gactaccata tcttgatcat ccttttctgt aggaatcgga tataacatca tccgggtacc | 6240 |
| catggccagc tgtgacttct ccatccgcac ctacacctat gcagacaccc ctgatgattt | 6300 |
| ccagttgcac aacttcagcc tcccagagga agataccaag ctcaaggtag gcattctagc | 6360 |
| ttttttcaggc cctgagggcc ctgatgtctg ggggttgaga aactgtaggg taggtctgct | 6420 |
| tgtacagaca ttttgtcccc tgctgttttg tcctgggggt gggagggtgg aggctaatgg | 6480 |
| ctgaaccgga tgcactggtt gggctagtat gtgttccaac tctgggtgct tctctcttca | 6540 |
| ctacctttgt ctctagatac ccctgattca ccgagccctg cagttggccc agcgtcccgt | 6600 |
| ttcactcctt gccagcccct ggacatcacc cacttggctc aagaccaatg gagcggtgaa | 6660 |
| tgggaagggg tcactcaagg gacagcccgg agacatctac caccgacct gggccagata | 6720 |
| ctttgtgaag taagggatca gcaaggatgt gggatcagga ctggcctccc atttagccat | 6780 |
| gctgatctgt gtcccaaccc tcaacctagt tccacttcca gatctgcctg tcctcagctc | 6840 |
| acctttctac cttctgggcc tttcagccttt gggcctgtca atcttgccca ctccatcagg | 6900 |
| cttcctgttc tctcggtctg gcccactttc ttttattttt tcttctttt tttttttttg | 6960 |
| agaaggagtc tctctctctg tcacccaggc tggagtgctg tggcgccatc ttcactcact | 7020 |
| gtaacctctg cctcctgagt tcaagcaatt ctcctgcctc agccttccaa gtagctggga | 7080 |
| ttataggcgc ctgccaccag gcccagctga ttttttctatt tttagtagag acggggtttc | 7140 |
| gccaggctgt tctcgaactc ctgaactcaa gtgatccacc tgcctcggct tcccaaagtg | 7200 |
| ctgggattac aggtgtgagc caccacaccc agctggtctg gtccactttc ttggccggat | 7260 |
| cattcatgac ctttctcttg ccaggttcct ggatgcctat gctgagcaca agttacagtt | 7320 |
| ctgggcagtg acagctgaaa atgagccttc tgctgggctg ttgagtggat accccttcca | 7380 |
| gtgcctgggc ttcacccctg aacatcagcg agacttcatt gcccgtgacc taggtcctac | 7440 |
| cctcgccaac agtactcacc acaatgtccg cctactcatg ctggatgacc aacgcttgct | 7500 |
| gctgcccac tgggcaaagg tggtaaggcc tggacctcca tggtgctcca gtgaccttca | 7560 |
| aatccagcat ccaaatgact ggctcccaaa cttagagcga tttctctacc caactatgga | 7620 |
| ttcctagagc accattcccc tggacctcca gggtgccatg gatcccacag ttgtcgcttg | 7680 |
| aaacctttct aggggctggg cgaggtggct cactcatgca aacccagcac tttgggaagc | 7740 |

```
cgaggcgggt gatcacctga ggtcaggagt ttaagaccac cctggccaac gtgttgaaac    7800
cctgtgtcta ctaaaataca aaaaaaaaaa attatctggg catgatggtg ggtgtctgta    7860
atcccagcta ctcaggaggc tgagaaggga gaatcagttg aacccgggag atggtggttg    7920
cggtgagccg agatcgcgcc actgcactcc agcctgggag gctgagcgag actccatctc    7980
gaaacaaaac aaaacaaaac tatctaggct gggggtggtg gttcatgtat gtatgtgtat    8040
atacatatat atgtgtttat atgtatatat atatacacac acacacatac atacacacac    8100
atacacacac aaattagctg ggtgtggcac ccgtgtagtc ccagctactc aggaggctaa    8160
tgtgggagga tcagttgacc ctaggaagtc aaggctgcag tgagtcgtga ttgcgccact    8220
gtactccagc ccgagtgaca gagtgacatc ctgtctcaaa acaaaaaaa aatctcccca    8280 aacctctcta gttgcattct tcccgtcacc caactccagg attcctacaa caggaactag    8340
aagttccaga agcctgtgtg caaggtccag gatcagttgc tcttcctttg caggtactga    8400
cagacccaga agcagctaaa tatgttcatg gcattgctgt acattggtac ctggactttc    8460
tggctccagc caaagccacc ctaggggaga cacaccgcct gttccccaac accatgctct    8520
ttgcctcaga ggcctgtgtg ggctccaagt tctgggagca gagtgtgcgg ctaggctcct    8580
gggatcgagg gatgcagtac agccacagca tcatcacggt aagccacccc agtctccctt    8640
cctgcaaagc agacctcaga cctcttacta gtttcaccaa agactgacag aagcccttcc    8700
tgtccagctt tccccagcta gcctgccctt ttgagcaact ctggggaacc atgattccct    8760
atcttccctt tccttcacag gtctgcacac ctcattgccc cttttgcaac tactgaggca    8820
cttgcagctg cctcagactt tcagctcccc cttgagatgc ctggatcttc acacccccaa    8880
ctccttagct actaaggaat gtgccctca cagggctgac ctacccacag ctgcctctcc    8940
cacatgtgac ccttacctac actctctggg accccagt gttgcgcctt tgtctctttg    9000
cctttgtcct tacctagaa cctcctgtac catgtggtcg gctggaccga ctggaacctt    9060
gccctgaacc ccgaaggagg acccaattgg gtgcgtaact ttgtcgacag tcccatcatt    9120
gtagacatca ccaaggacac gttttacaaa cagcccatgt tctaccacct tggccacttc    9180
aggtgagtgg agggcgggca cccccattcc ataccaggcc tatcatctcc tacatcggat    9240
ggcttacatc actctacacc acgagggagc aggaaggtgt tcagggtgga acctcggaag    9300
aggcacaccc atcccctttt gcaccatgga ggcaggaagt gactaggtag caacagaaaa    9360
ccccaatgcc tgaggctgga ctgcgatgca gaaaagcagg gtcagtgccc agcagcatgg    9420
ctccaggcct agagagccag ggcagagcct ctgcaggagt tatggggtgg gtccgtgggt    9480
gggtgacttc ttagatgagg gtttcatggg aggtaccccg agggactctg accatctgtt    9540
cccacattca gcaagttcat tcctgagggc tcccagagag tggggctggt tgccagtcag    9600
aagaacgacc tggacgcagt ggcactgatg catcccgatg gctctgctgt tgtggtcgtg    9660
ctaaaccggt gagggcaatg gtgaggtctg ggaagtgggc tgaagacagc gttggggggcc    9720 ttggcaggat cacactctca gcttctcctc cctgctccct agctcctcta aggatgtgcc    9780
tcttaccatc aaggatcctg ctgtgggctt cctggagaca atctcacctg gctactccat    9840
tcacacctac ctgtggcgtc gccagtgatg gagcagatac tcaaggaggc actgggctca    9900
gcctgggcat taagggaca gagtcagctc acacgctgtc tgtgactaaa gagggcacag    9960
cagggccagt gtgagcttac agcgacgtaa gcccagggc aatggtttgg gtgactcact   10020
ttcccctcta ggtggtgcca ggggctggag gcccctagaa aaagatcagt aagcccagt   10080
```

| | |
|---|---:|
| gtcccccag ccccatgct tatgtgaaca tgcgctgtgt gctgcttgct ttggaaactg | 10140 |
| ggcctgggtc caggcctagg gtgagctcac tgtccgtaca aacacaagat cagggctgag | 10200 |
| ggtaaggaaa agaagagact aggaaagctg ggcccaaaac tggagactgt ttgtctttcc | 10260 |
| tggagatgca gaactgggcc cgtggagcag cagtgtcagc atcagggcgg aagccttaaa | 10320 |
| gcagcagcgg gtgtgcccag gcacccagat gattcctatg gcaccagcca ggaaaaatgg | 10380 |
| cagctcttaa aggagaaaat gtttgagccc agtca | 10415 |

<210> SEQ ID NO 8
<211> LENGTH: 10223
<212> TYPE: DNA
<213> ORGANISM: Homo sapiens

<400> SEQUENCE: 8

| | |
|---|---:|
| aaacaataac gtcattattt aataagtcat cggtgattgg tccgcccctg aggttaatct | 60 |
| taaaagccca ggttacccgc ggaaatttat gctgtccggt caccgtgaca atgcagctga | 120 |
| ggaacccaga actacatctg gctgcgcgc ttgcgcttcg cttcctggcc ctcgtttcct | 180 |
| gggacatccc tggggctaga gcactggaca atggattggc aaggacgcct accatgggct | 240 |
| ggctgcactg ggagcgcttc atgtgcaacc ttgactgcca ggaagagcca gattcctgca | 300 |
| tcaggtatca gatattgggt actcccttcc ctttgctttt ccatgtgttt gggtgtgttt | 360 |
| ggggaactgg agagtctcaa cgggaacagt tgagcccgag ggagagctcc cccacccgac | 420 |
| tctgctgctg ctttttatc cccagcaaac tgtcccgaat caggactagc cctaaacttt | 480 |
| ctctgtgtga cctttcctgg gatgggagtc cggccagcgg cccctgtttc tttctctctc | 540 |
| tctctctctc tcgttctcct tctctttctc tttctcttct ttcctctctc tttctctctc | 600 |
| tccctgcccg gttctctttt ttcactgctc cttgcagagc agggccaccc cataggcagt | 660 |
| gtgcccaaag tagccctgcc cggttctatt cagacccttc ttgtgaactt ctgctcttcc | 720 |
| tctgccgggt gctaaccgtt agaacatcta gggtgggtag gaggaatggg gaactaagat | 780 |
| tcgtgccatt ttttctcctt ttggggtcgt ggatttctcg gcagtatctc gagggagtta | 840 |
| gagagaccat aaggtcgctg agatctctcc cacctcgccc atgagcgtgg catcaggctg | 900 |
| gaaggttgac atggaggaac tttatacatt tacacctttg cgtgagggtt gaggctggat | 960 |
| tagataggta ttgaacatat ctgaccctca caatccttat ctgtaaattg ggattacaac | 1020 |
| cttttaattt cagggagctg acaaaaaaaa tctgaaaaat agttcttatc tcacacaggt | 1080 |
| gagttttcaa ggagataacc tatttaaagt acatagcaca gcgcttgacc attcaactgc | 1140 |
| gcttacagag caaatgttca atgggaaaat gaatgtaaat ctacaaatct gaatgaatat | 1200 |
| gtgtattttt ctggagagag gatatttacc tttcttcaaa ttctcaaagg gctctgtgat | 1260 |
| ttaaaaaagg ttaggaatca ctgatagatg ttggtaaaag gtggcagtca cagtacattt | 1320 |
| ctgtgtccat aagttattcc tatgaatatc tttatagata aagtcaggat gttggtcaga | 1380 |
| catcacagaa gaaattggcc ttgtaagttt catgtgaccc tgtggtacag tatgtgtggc | 1440 |
| aatttttgccc atcacggatt ttttttttatt ggtatttgca tctgattata aaactaatgc | 1500 |
| atgatcattg caaaaaatgt agataaagaa gagcaaaatg aaaataaaga tttcccccca | 1560 |
| ccgttccacc acccagaaat aatcatggtt taaatgttaa tatacaacct tacaattgtt | 1620 |
| ttctatataa atgaaaacat agatttcttt atttcattat tttccataaa aaatggatca | 1680 |
| tgtttatgtc atgtttggct aatggcaaga ccctggcacc cagtctgggc tcaaattctg | 1740 |
| cctcattgtt acttagccct gtgacattgg gtaaattaca cttttttttt tttttttttt | 1800 |

```
ttgagacggg gtctcgctct gtcgcccagg ctggagtgca gtggcacgat ctcggctcac    1860
tgcaagctcc gcctcctggg ttcacgccat tcttctgcct cagcctcccg agtagctggg    1920
actacaggcg cctgccacca cgcctggctc tttttttttt tttttttttt tttagtacag    1980
acggggtttc accatgttag ccagggtggt ctcaatctcc tgacctcgtg attcgcccgc    2040
ctcagcctcc caaagtgctg gtgtgagcca ccgtgcccag ccttactttt tttttttgaga    2100 ggggtctca ctctgtcacc caggttggag tgcagtggcg cgatctctgc tcagtgcaaa     2160
ctccacctcc cgggtttaag cagttctcct gtcgtagtct cctgagtagc tgggattaca    2220
ggcacaccac cacggccagc taattttgt attttcagta gagacgggtt tcaccatgtt     2280
gcccaagctg gtctcgaact cctggcctca agtgatctgc ccgccttggc ctcccagagt    2340
gctgggatta caggtgtgag ccaccgcacc cggcctcttt tttcttttt agtctatcat     2400 accttgcaaa tacagtggtt cttcctatgt gttggttttg atatttatgt aatcaaacac    2460
atcagttttt cctttctgat ttctgacttt ggggtcatgc tgagaaagtc ctttcctacc    2520
tgaagataat acagtatata cgtttcttac tagtattttt gtggattttt aaaatattta    2580 aatcttagt ccatctgaac tttgttcttc tatcagaaat gccacattta ataataata     2640 agtcccatgg tatcagatgg ctggaaggac ctctttcgaa actttgttta attccattaa    2700
tctgtgtatt cttattctaa tgctaatagt tccacactag cttcctttat ctttttttc    2760 tttttttttt ttttttgag ctggagttc gctcttgttg cccaggctgg agtacaatgt     2820
cacgatctcg gttcaccgca acctccgcct cccaggttca agcaattctc ctgcctcatc    2880
ctcgcgagta gctggaatta caggcatgcg ccaccacgcc tagctatttt gtattttag    2940 tagagatggg gtttctccat gttggtcagg ctggtctcaa actcccagcc tcaggtgatc    3000
tgcctgcctc ggcctcccaa aatgctgtta ttacaggcgt gagccaccac gcccagcctt    3060
catcttttaa tgaatgtaca tgtatgtaat cttttaggtg aacttttgt aatgttgtgc     3120 caagttcctt aaaaagccct tttggaagct gggcaggtgg cccacgcctg taatcccagc    3180
attttgggag tctgaggcag gtggatcact tgaggccagg agttcaagac tagcctagcc    3240
aaaatgcaaa accctgtctc tactaaagat acaaaaatta gccggatgcg atggcacatg    3300
cctgtaatct cagctactcg ggaggctgag gtagaagaat cgcttgaacc ggggaggcag    3360
aggttgcagt gagccaagat ggcgccactg cactccagcc tgggtgacag agggagactc    3420
catctcaaaa aaaaaaaaa aaaaaagat aaaaggaaa cctaagtact cttgggcttt       3480
gttaaggatt ttgttaaata tacaaaggat tgcagggaaa attaacttat ttttaatatt   3540
gagtatgctt atccaagagc aaaataatat ttctccattt attcaaatca tttaggagca    3600 tcatagttttt aacatatggg ccttgcacgt atcttaaatt tatctctagg cattttaggt   3660
tgttcagttg ttcttgtgaa tgggatcttt ttctccaaat aggattattg ttgatatctg    3720
ttgattatgt taactttgta gtttctgact ttactgaact gtcttcttag atctaatact    3780
cttttcaatt tcatcatata tttctcattc ctattttgtt tggggttttt agggcgggaa    3840
tattaacggg ataagagaga caaaagaaaa tctggaaaaa caattcattt taccttacat    3900
tgcttgtgat tactaccaca ctattactgg gttggaaaaa attgtgaaat cccaaggtgc    3960
ctaataaatg ggaggtacct aagtgttcat ttaatgaatt gtaatgatta ttggaatttc    4020
tctttcagtg agaagctctt catggagatg gcagagctca tggtctcaga aggctggaag    4080
gatgcaggtt atgagtacct ctgcattgat gactgttgga tggctcccca aagagattca    4140
```

```
gaaggcagac ttcaggcaga ccctcagcgc tttcctcatg ggattcgcca gctagctaat    4200
tatgtgagtt tatagataat gttcttgttc attcagagga ctgtaagcac ttctgtacag    4260
aagcttgttt agaaacagcc ctcatggccg ggcgtggtgg ctcacgcctg taatcccaac    4320
actttgggag gccgaggcgg gtggatcacc tgaggtcaag agttcaagac cagcctggcc    4380
aacatggtga accccaact ctattaaaag tacaaaaaat tagctgggca tggtggtgaa    4440
cgcctgtaac cccagctact tgggaggctg aggcaggaga tcgcttgaa cccaggaggt    4500
ggaagtttca gtgagctgag atcacgccat tgcactctag cctgggcaac aaaagagaaa    4560
ctccatctca aaaaaaaaaa caaggaaaaa aagaaacagc cctcatgaca cttagaaagt    4620
agaatagctg gctgttatct gaacattgaa ttgtaaggct tatcaggtgg actttgcatt    4680
ccatcagcag acaatttttt tttttttttt ttttgagat ggagtctcat tctgtctccc    4740
aggctggagg gcagtggtgc gatctcggct cactgcaagc tccacctcct gggttcatgc    4800
cattctcctg cctcagcctc caagtagct gggaccacag gcacccgcca ccatgcccag    4860
ttaattttt gtattttag tagagacggg gtttcaccat gttagccaag atggtctcga    4920
tctcctgacc tcgtgatccg cccacctcgg cctcccaaag tgctgggatt acaggcatga    4980
gccaccgcgc ctagcctaca aatgttttgt aatagctctt gaggcccatc ttggagttct    5040
ccttttgcta aaaccactga actctctagg aggaaaaagg aacttggttc ttgacatatg    5100
tgtgcatgta tttccatata acctttagga agctattgca atggtactat aaactagaat    5160
tttagaagat agaaggaaaa tattctggag atcattgaag agaaatggag tccaacacta    5220
gttaaagatg atgaagacag atttttttt ttgacggagt ctcgctctgt cgcccaggct    5280
ggagtgcagt ggcacaatct cagctcactg caaccctcca cctcttgggt tcaagtgatt    5340
ctcctgcctc agcctcccaa gtagctggga ctacaggcgc acaccaccac gcccggctaa    5400
tttttgtatt tttagtagag acaaggtttc accatattcg ccaggctggt ctcgaactcc    5460
tgaccttgta atccgcccac cttggcctcc caaagtgctg ggattacagg catgagccac    5520
cacgcccggc cgatgaagac agatttatt cagtactacc acagtagagg aaagagccaa    5580
gttcaattcc aaatacaaca aagacaggtg gagatttata gccaatgagc agattgaggg    5640
ggtcagtgga tggaatattt aagaagacat caagggtagg gagcttcttg ctaaagcttc    5700
atgtacttaa acaagaaggg tggggatga gggaaattga tcagatatca atggtggcag    5760
tattgactta gcaggattct tgctaagagg tcttgctagg acagacatag gaagccaagg    5820
tggaggtcta gtcgaaaaga aggctcatca gagaagtcta actaaagttt ggtcaagaag    5880
agtctttgtc aaggtaaatc tatcatttcc ctcaaaaggt aattttcagg atcccatcag    5940
gaagattagc atggctgcta gctttctcct cagttctggg ctatagctca catgcctagt    6000
ttgaactagc tcagcagaac tgggggattt attcttgtc ttccaacaaa ctcatctgga    6060
tgattttggg ggtttgtggg gaaaagcccc caatacctgg tgaagtaacc ttgtctcttc    6120
ccccagcctg gaatggttct ctctttctgc tacctcacga ttgtgcttct acaatggtga    6180
ctcttttcct ccctctcatt tcaggttcac agcaaaggac tgaagctagg gatttatgca    6240
gatgttggaa ataaaacctg cgcaggcttc cctgggagtt ttggatacta cgacattgat    6300
gcccagacct ttgctgactg gggagtagat ctgctaaaat ttgatggttg ttactgtgac    6360
agtttggaaa atttggcaga tggtaatgtt tcattccaga gatttagcca caaaggaaag    6420
aactttgagg ccatggtagc tgagccaaag aaccaatctt cagaattta aatacccctgt    6480
cacaatactg gaaataatta ttctccatgt gccagagctc ccatctcttc tctttcagtt    6540
```

```
cattaattaa ttaattaatt catgtaaaat ccatgcatac ctaaccatag ctaatattgt   6600
gcacttataa ttcaagaggg ctctaagagt taattagtaa ttgtaactct ctataacatc   6660
atttagggga gtccaggttg tcaatcggtc acagagaaag aagcatcttc attcctgcct   6720
ttcctcaata tacacaccat ctctgcacta cttcctcaga acaatcccag cagtctggga   6780
ggtactttac acaatttaag cacagagcaa ctgcctgtcc ctgctgctag tttaaacatg   6840
aaccttccag gtagcctctt cttaaaatat acagccccag ctgggcatga tggctcatgc   6900
ctgtaatcct agcactttgg gaggctgagg cgggtggatt acttgaggtc aggagttcga   6960
gaccaccctg gccaacatgg tgaaacccca tctctagtaa aaatacaaaa attagctgac   7020
tttggtggca catgcctgta atcccagcta cttgggaagc tgagacagaa gagtcacttg   7080
aacctgggaa acagaggttg cagtgagcca agatcgcacc actgcactcc accctggatg   7140
acagactgaa ccccatctca aaaaattaaa ataaaataaa ataaaataac tatatatata   7200
gccccagctg gaaattcatt tctttccctt atttaccca ttgttttctc atacaggtta    7260
taagcacatg tccttggccc tgaataggac tggcagaagc attgtgtact cctgtgagtg   7320
gcctctttat atgtggccct ttcaaaaggt gagatagtga gcccagaatc caatagaact   7380
gtactgatag atagaacttg acaacaaagg aaaccaaggt ctccttcaaa gtccaacgtt   7440
acttactatc atcctaccat ctctcccagg ttccaaccac ttctcaccat ccccactgct   7500
gtaattatag cctaagctac catcacctgg aaagtcatcc ttgtgtcttc ccctttattt   7560
caccattcat gtcctgtcta tcaacagtcc ttccaccagt atctctaaaa tatctcctga   7620
atcagcccac ttccttccat cttcactaca tgcaccctgg ccttccaagc tactatcggc   7680
tctcaaccag actgctggga ccacctgatc tctctgcttc cactctgtct caaccccat    7740 ctattttcca agcagcacta gagttatcat attaaaatgt aaatatcagt ttttttttta   7800
aagaaaaaaa ccctgagact taacagagtt ataaaaaata taaatgtcat catcagttcc   7860
ctgcttaaaa cccttaactc gcttccaatt gcacttggaa tgaaaccaaa ctgcactgat   7920
ccagcccttg cctgcctccc caaagtccaa ggggtcatgg ctctttccct ggctacactg   7980
gttttctttc tgtccctcaa cactgcaagc ctattgctgc cccagggcct ttacacttgc   8040 ttttttttctg cctagaacag ttcttcccca aagattttta aagggccggg ctccttaaca   8100
ttgaagtcgc agaccaaacg ccacatatgc agacagttct tctctaacta ctttaaaata   8160
gccctctgtc cattcattct tcatcacatt aacctgttta attttcttct cagagctcca   8220
cactatttgg aagtatttgt tgacttgtta ccatgtctcc ccactagagt gtaagtttca   8280
tgagggcagg gaccttgtct gactttgact gtatctctcg catatggtta agtgttgaat   8340
agttatttat ggaatgaatc cctattattc cctcattatc tctgcaaaat agtctttttt   8400
ctcaacatct taaacctgat atcccacctg cctatctaca aactttttt ttgcgacaga    8460 gtctcactgt cacccaggct agagtgcagt ggcgccatct cggctcactg caacctccgc   8520
ctcccgggtt taagcgattc tcttgcctca gcctcccagt agctgggatt ataggcgtgc   8580
gctaccacat ctggctaatt tttgtatttt tagtagagat ggtttcacca tgttggccag   8640
gcttgtctcg aactcctgac ctcagatgat ccacctgcct cggcctccca agtgctggg    8700 attacaggca tgagccaccg tgcccagcct ctacaaactt tttattccat taacaaacta   8760
tatgcctggg atttaagttt tcttaatact tgatggagtc ctatgtaatt ttgcagcttt   8820 taatttttact aagaccattt tagttctgat tatagaagta aattaacttt aagggatttc   8880
```

| | |
|---|---:|
| aagttatatg gcctacttct gaagcaaact tcttacagtg aaaattcatt ataagggttt | 8940 |
| agacctcctt atggagacgt tcaatctgta aactcaagag aaggctacaa gtgcctcctt | 9000 |
| taaactgttt tcatctcaca aggatgttag tagaaagtaa acagaagagt catatctgtt | 9060 |
| ttcacagccc aattatacag aaatccgaca gtactgcaat cactggcgaa attttgctga | 9120 |
| cattgatgat tcctggaaaa gtataaagag tatcttggac tggacatctt ttaaccagga | 9180 |
| gagaattgtt gatgttgctg gaccaggggg ttggaatgac ccagatatgg taaaaacttg | 9240 |
| agccctcctt gttcaagacc ctgcggtagg cttgtttcct attttgacat tcaaggtaaa | 9300 |
| tacaggtaaa gttcctggga ggaggcttta tgtgagagta cttagagcag gatgctgtgg | 9360 |
| aaagtggttt ctccatatgg gtcatctagg taactttaag aatgtttcct cctctcttgt | 9420 |
| ttgaattatt tcattctttt tctcagttag tgattggcaa ctttggcctc agctggaatc | 9480 |
| agcaagtaac tcagatggcc ctctgggcta tcatggctgc tcctttattc atgtctaatg | 9540 |
| acctccgaca catcagccct caagccaaag ctctccttca ggataaggac gtaattgcca | 9600 |
| tcaatcagga ccccttgggc aagcaagggt accagcttag acaggtaaat aagagtatat | 9660 |
| attttaagat ggctttatat acccaatacc aactttgtct tgggcctaaa tctattttt | 9720 |
| tcccttgctc ttgatgttac tatcagtaat aaagcttctt gctagaaaca ttactttatt | 9780 |
| tccaaaataa tgctacagga tcattttaat ttttcctaca agtgcttgat agttctgaca | 9840 |
| ttaagaatga atgccaaact aacagggcca cttatcacta gttgctaagc aaccacactt | 9900 |
| tcttggtttt tcagggagac aactttgaag tgtgggaacg acctctctca ggcttagcct | 9960 |
| gggctgtagc tatgataaac cggcaggaga ttggtggacc tcgctcttat accatcgcag | 10020 |
| ttgcttccct gggtaaagga gtggcctgta atcctgcctg cttcatcaca cagctcctcc | 10080 |
| ctgtgaaaag gaagctaggg ttctatgaat ggacttcaag gttaagaagt cacataaatc | 10140 |
| ccacaggcac tgttttgctt cagctagaaa atacaatgca gatgtcatta aaagacttac | 10200 |
| tttaaaatgt ttatttatt gcc | 10223 |

```
<210> SEQ ID NO 9
<211> LENGTH: 2906
<212> TYPE: DNA
<213> ORGANISM: Artificial Sequence
<220> FEATURE:
<223> OTHER INFORMATION: cDNA of codon-optimised GAA gene

<400> SEQUENCE: 9
```

| | |
|---|---:|
| ccaatccaat agcgctgccg ccgcgatcgc catgggggtc cgacatcctc cttgttctca | 60 |
| ccgcctgctg gccgtctgtg ctctggtctc cctggctact gctgctctgc tggggcatat | 120 |
| cctgctgcat gatttcctgc tggtgcctag ggagctgagt ggaagctccc ccgtcctgga | 180 |
| ggaaacccac cctgctcatc agcagggagc atcccgaccc ggacctcgag atgctcaggc | 240 |
| acacccaggg cggcctagag ctgtgcccac tcagtgcgac gtgcccccta acagccggtt | 300 |
| tgactgtgcc cctgataagg ctatcacaca ggagcagtgc gaagcagag ctgctgtta | 360 |
| tattccagca aaacagggac tgcagggagc acagatggga cagccctggt gtttctttcc | 420 |
| accctcctac ccttcttata agctggaaaa tctgtctagt tcagagatgg gctacacagc | 480 |
| cactctgacc cggaccacac ccaccttctt tcctaaggat atcctgacac tgcgactgga | 540 |
| cgtgatgatg gagactgaaa accggctgca cttcaccatc aaggatcccg ccaatcggag | 600 |
| atatgaagtg ccactggaga ccccccacgt tccattctcg gctccaagtc ccctgtactc | 660 |
| agtggagttc agcgaggaac ccttcggcgt gatcgtgcgg cggcagctgg atggaagagt | 720 |

```
gctgctgaac actaccgtcg cccctctgtt ctttgctgac cagtttctgc agctgagtac    780
ttcactgcct tctcagtata tcaccggcct ggccgaacac ctgagtccac tgatgctgag    840
cacctcctgg acaagaatta ctctgtggaa cagggacctg cacctaccc caggagccaa    900
tctgtacggc tctcacccct tctatctggc tctggaggat ggcgggagcg cacatggcgt    960
gtttctgctg aactccaatg ctatggacgt ggtcctgcag ccctctcctg cactgagttg   1020
gcggtcaacc ggaggcatcc tggacgtgta cattttcctg gggccagagc ccaaaagcgt   1080
ggtccagcag tacctggacg tggtcggata ccattcatg cctccatact ggggctggg    1140
atttcacctg tgcagatggg ggtatagctc caccgcaatc acacggcagg tggtcgaaaa   1200
catgaccaga gcccattttc ccctggatgt gcagtggaat gacctggatt acatggacag   1260
ccgacgggac ttcaccttca acaaggacgc cttcagggat tttcctgcca tggtgcagga   1320
gctgcatcag gggggaagaa ggtacatgat gatcgtggat ccagccattt ctagttcagg   1380
accagctggc agctaccgac catatgacga aggactgcga cgaggggtgt tcatcactaa   1440
cgagaccggg cagccactga ttggaaaagt gtggccaggc tccaccgcat tcccagactt   1500
caccaatcct actgccctgg cttggtggga agacatggtg gccgagttcc acgaccaggt   1560
cccatttgat ggaatgtgga tcgacatgaa cgaacccagt aatttcatta ggggatcaga   1620
ggacggctgc cctaacaatg agctggaaaa tccaccttat gtgccaggag tggtcggagg   1680
gaccctgcag gccgctacaa tctgtgccag ctcccaccag tttctgtcca cacactataa   1740
cctgcataat ctgtacggac tgactgaggc aatcgcctct catcgcgcac tggtgaaggc   1800
aaggggaaca cgaccattcg tcatttctag gagtactttt gctggacacg ggcgctacgc   1860
aggacattgg accggcgacg tgtggtctag ttgggaacag ctggcttcaa gcgtgcccga   1920
gattctgcag ttcaacctgc tgggagtgcc tctggtcgga gcagacgtgt gcgggtttct   1980
gggaaatacc tccgaggaac tgtgcgtgcg gtggacacag ctgggagcct tctatccttt   2040
tatgcgaaac cacaatagcc tgctgtccct gccacaggaa ccctactcat tcagcgagcc   2100
agcccagcag gctatgcgca aagccctgac cctgcgatat gctctgctgc ccatctgta   2160
cacactgttt caccaggcac atgtggccgg cgaaactgtc gctcggcctc tgttcctgga   2220
gtttccaaag gattcctcta catggactgt ggaccaccag ctgctgtggg gagaagccct   2280
gctgatcacc cccgtgctgc aggctgggaa agcagaggtc acaggctatt cccactggg   2340
gacatggtac gatctgcaga ctgtgccagt cgaggctctg ggatcactgc caccacctcc   2400
agcagcacct agagaaccag caatccacag cgagggacag tgggtgacac tgcctgcccc   2460
actggacact attaacgtgc atctgaggggc tggctatatc attcctctgc agggaccagg   2520
cctgacaact accgagtctc gccagcagcc aatggctctg cagtggccc tgaccaaggg   2580
aggagaagca aggggagagc tgttctggga cgatggagag agcctggaag tgctggagcg   2640
aggagcatac acacaggtca tctttctggc cagaaacaat actattgtga atgaactggt   2700
gagggtcacc agcgagggag caggactgca gctgcagaag gtgaccgtcc tgggagtggc   2760
tacagcacct cagcaggtcc tgtccaacgg cgtgcctgtc tccaattca cttactctcc   2820
agacaccaaa gtgctggaca tctgcgtgag cctgctgatg ggcgaacagt ttctggtctc   2880
ctggtgctga gtcgacattg gattgg                                        2906
```

<210> SEQ ID NO 10
<211> LENGTH: 3742
<212> TYPE: DNA

<213> ORGANISM: Homo sapiens

<400> SEQUENCE: 10

| | |
|---|---|
| atctcattgc tgttcgtaat tgttagatta attttgtaat attgatatta ttcctagaaa | 60 |
| gctgaggcct caagatgata acttttattt tctggacttg taatagcttt ctcttgtatt | 120 |
| caccatgttg taactttctt agagtagtaa caatataaag ttattgtgag tttttgcaaa | 180 |
| cacagcaaac acaacgaccc atatagacat tgatgtgaaa ttgtctattg tcaatttatg | 240 |
| ggaaaacaag tatgtacttt ttctactaag ccattgaaac aggaataaca gaacaagatt | 300 |
| gaaagaatac attttccgaa attacttgag tattatacaa agacaagcac gtggacctgg | 360 |
| gaggagggtt attgtccatg actggtgtgt ggagacaaat gcaggtttat aatagatggg | 420 |
| atggcatcta gcgcaatgac tttgccatca cttttagaga gctcttgggg gccccagtac | 480 |
| acaagagggg acgcagggta tatgtagaca tctcattctt tttcttagtg tgagaataag | 540 |
| aatagccatg acctgagttt atagacaatg agcccttttc tctctcccac tcagcagcta | 600 |
| tgagatggct tgccctgcct ctctactagg ctgactcact ccaaggccca gcaatgggca | 660 |
| gggctctgtc agggctttga tagcactatc tgcagagcca gggccgagaa ggggtggact | 720 |
| ccagagactc tccctcccat tcccgagcag ggtttgctta tttatgcatt taaatgatat | 780 |
| atttatttta aaagaaataa caggagactg cccagccctg gctgtgacat ggaaactatg | 840 |
| tagaatattt tgggttccat ttttttttcc ttctttcagt tagaggaaaa ggggctcact | 900 |
| gcacatacac tagacagaaa gtcaggagct ttgaatccaa gcctgatcat ttccatgtca | 960 |
| tactgagaaa gtccccaccc ttctctgagc ctcagtttct cttttataa gtaggagtct | 1020 |
| ggagtaaatg atttccaatg gctctcattt caatacaaaa tttccgttta ttaaatgcat | 1080 |
| gagcttctgt gcggccgctc tagaactagt ggatccccccg cttctttgag aaacatcttc | 1140 |
| ttcgttagtg gcctgcccct cattcccact ttaatatcca gaatcactat aagaagaata | 1200 |
| taataagagg aataactctt attataggta agggaaaatt aagaggcata cgtgatggga | 1260 |
| tgagtaagag aggagaggga aggattaatg gatgataaaa tctactacta tttgttgaga | 1320 |
| ccttttatag tctaatcaat tttgctattg ttttccatcc tcacgctaac tccataaaaa | 1380 |
| aacactatta ttatctttat tttgccatga caagactgag ctcagaagag tcaagcatttt | 1440 |
| gcctaaggtc ggacatgtca gaggcagtgc cagacctatg tgagactctg cagctactgc | 1500 |
| tcatgggccc tgtgctgcac tgatgaggag gatcagatgg atggggcaat gaagcaaagg | 1560 |
| aatcattctg tggataaagg agacagccat gaagaagtct atgactgtaa atttgggagc | 1620 |
| aggagtctct aaggacttgg atttcaagga attttgactc agcaaacaca agaccctcac | 1680 |
| ggtgactttg cgagctggtg tgccagatgt gtctatcaga ggttccaggg agggtggggt | 1740 |
| ggggtcaggg ctggccacca gctatcaggg cccagatggg ttataggctg gcaggctcag | 1800 |
| ataggtggtt aggtcaggtt ggtggtgctg ggtggagtcc atgactccca ggagccagga | 1860 |
| gagatagacc atgagtagag ggcagacatg ggaaaggtgg gggaggcaca gcatagcagc | 1920 |
| attttttcatt ctactactac atgggactgc tcccctatac ccccagctag ggcaagtgc | 1980 |
| cttgactcct atgttttcag gatcatcatc tataaagtaa gagtaataat tgtgtctatc | 2040 |
| tcatagggtt attatgagga tcaaaggaga tgcacactct ctggaccagt ggcctaacag | 2100 |
| ttcaggacag agctatgggc ttcctatgta tgggtcagtg gtctcaatgt agcaggcaag | 2160 |
| ttccagaaga tagcatcaac cactgttaga gatatactgc cagtctcaga gcctgatgtt | 2220 |
| aatttagcaa tgggctggga ccctcctcca gtagaacctt ctaaccagct gctgcagtca | 2280 |

```
aagtcgaatg cagctggtta gactttttt aatgaagctt ggtgaccgtc gtaccagtgg    2340
ggcctctaag actaagtcac tctgtctcac tgtgtcttag ccagttcctt acagcttgcc    2400
ctgatgggag atagagaatg ggtatcctcc aacaaaaaaa taaattttca tttctcaagg    2460
tccaacttat gttttcttaa ttttaaaaa atcttgacc attctccact ctctaaaata    2520
atccacagtg agagaaacat tcttttcccc catcccataa atacctctat taaatatgga    2580
aaatctgggc atggtgtctc acacctgtaa tcccagcact tgggaggct gaggtgggtg    2640 gactgcttgg agctcaggag ttcaagacca tcttggacaa catggtgata ccctgcctct    2700
acaaaaagta caaaaattag cctggcatgg tggtgtgcac ctgtaatccc agctattagg    2760
gtggctgagg caggagaatt gcttgaaccc gggaggcgga ggttgcagtg agctgagatc    2820
gtgccactgc actccagcct gggggacaga gcacattata attaactgtt attttttact    2880
tggactcttg tggggaataa gatacatgtt ttattcttat ttatgattca agcactgaaa    2940
atagtgttta gcatccagca ggtgcttcaa aaccatttgc tgaatgatta ctatactttt    3000
tacaagctca gctccctcta tcccttccag catcctcatc tctgattaaa taagcttcag    3060
tttttcctta gttcctgtta catttctgtg tgtctccatt agtgacctcc catagtccaa    3120
gcatgagcag ttctggccag gcccctgtcg gggtcagtgc ccacccccg ccttctggtt    3180 ctgtgtaacc ttctaagcaa accttctggc tcaagcacag caatgctgag tcatgatgag    3240
tcatgctgag gcttagggtg tgtgcccaga tgttctcagc ctagagtgat gactcctatc    3300
tgggtcccca gcaggatgct tacagggcag atggcaaaaa aaggagaag ctgaccacct    3360 gactaaaact ccacctcaaa cggcatcata agaaaatgg atgcctgaga cagaatgtga    3420
catattctag aatatattat ttcctgaata tatatatata tatatacaca tatacgtata    3480
tatatatata tatatatttg ttgttatcaa ttgccataga atgattagtt attgtgaatc    3540
aaatatttat cttgcaggtg gcctctatac ctagaagcgg cagaatcagg ctttattaat    3600
acatgtgtat agattttag gatctataca catgtattaa tatgaaacaa ggatatggaa    3660
gaggaaggca tgaaaacagg aaaagaaaac aaaccttgtt tgccatttta aggcaccct    3720 ggacagctag gtggcaaaag gg                                            3742
```

<210> SEQ ID NO 11
<211> LENGTH: 15523
<212> TYPE: DNA
<213> ORGANISM: Artificial Sequence
<220> FEATURE:
<223> OTHER INFORMATION: BGLOBIN LCR CONTAINING ONLY ESSENTIAL ELEMENTS

<400> SEQUENCE: 11

```
tttattttgt tttgttttct aatcaacaga gatgggcaaa cccattattt ttttctttag      60
acttgggatg gtgatagctg gcagcgtca gaaactgtgt gtggatatag ataagagctc     120
aggactatgc tgagctgtga tgagggaggg gcctagctaa aggcagtgag agtcagaatg     180
ctcctgctat tgccttctca gtccccacgc ttggtttcta cacaagtaga tacatagaaa     240
aggctatagg ttagtgtttg agagtcctgc atgattagtt gctcagaaat gcccgataaa     300
tatgttatgt gtgtttatgt atatatatgt tttatatata tatatgtg tgtgtgtgtg      360 tgtgtgtgtg ttgtgtttac aaatatgtga ttatcatcaa aacgtgaggg ctaaagtgac     420
cagataactt gcaagtccta ggataccagg aaaataaatt acattccaaa aatttaactg     480
agactttaaa aaaaaaaaaa aaacaaaaaa aaaccagtga tccatggaca cagggagggg     540
```

-continued

```
aacatcacac actggggcct gttggggtg gggggctagg ggaaggatag cattaggaga    600
aatacctaat gtagatgacg ggttgatggg tgcagcaaac caccatggca catgtacccc   660
agaacttaaa gcatattaaa aaaacagtga tcataaaga agctcaaatt taactataag   720
agacggaatg gctcccacaa ttcttaacta taatcttaca gaatattctc attgaataga   780
agtatgctta tcattagaga tttggacagc caggaaagca cagaaaaaaa aaaaaggagc   840
tctgttgcct tatagcctag aggtgttttg aacctcacat aacactgatg tccaggccaa   900
ggccatcctt cccatgaaga tggatgaata agccatatct gacacctatg aaataatgtt   960
tactttagtg gcatattgca ttaggctacc tgccttggca cagttttttct ttacttttac  1020 ctgactgatg aaacaattaa ttgcttacat aaacatgagt gctctagtta taaattccag  1080
tgtaaaaaac accctggttt cgatattcat cttttgagcc ttttattttg gtcagaacaa  1140
gttttcaaga gcaaatctca gcctacaaaa caaatgagtc caattctaga actcagtaat  1200
cccatcaagg ctctgcctgc ggagggctaa ctagctctat gcaggcttag cacttccagc  1260
tctactccac tgatttctttt gtgtgtgcat agcagtggat gtgtcagcat acatcctttt  1320
aattatagtt gtatatgtgt ttgactgctc attcattcat tcaaaattgt aaaattgcta  1380
agaatacagc acaaaaacag aatagaggaa taaagttcct gttttcatgg acttgatagt  1440
ggaaagagct tgacattaaa taagcaaatg aaacatgtta tataccaatg agattaggtg  1500
ctatggagaa aaaaaaaaaa ctgaaatgaa ggccagagtg tgattaggac agggtgaaag  1560
ggtatcgcta ctttaagtag tatggcagga aagtcctcac tataaagtta acacctgaga  1620
gagtacccat agatgatgag gaacccattt atatgaaact atgattaaat atttagggca  1680
tagggaatgg caaatgtaaa taccctaaag atgtaagatg cttagaattt tcaaggaata  1740
tcaataaggc caatgtagga tgagattcgg tgaaggggag aataaaagat gagatcatag  1800
aagtcctaaa ttataaaatt tgggacacta ataatcccta catcatagag ttgtaagaaa  1860
aaacactcta cacacataca cataaatata tatatttatt tatatgagag ctatatatat  1920
gtatctgtaa taaacataat atatgcatga acaactattg tagagaattg taaggatttg  1980
gttttattat aaatgatata ggaaactatc agaaagacttt gaacaaagag gtgaccatat  2040
atgacttaca ttttgaaaag actaatttgg atagtatatt gggaagaaat tgtagtgggg  2100
cagtggtaga agcaggaaga ttgttatgag tcaacagcta taatttaggt ggtggtgaca  2160
gtgacttaga ccagagtggt agcattggag gtgaaggcaa ggggtcagcc tctgaaaaca  2220
tcctttcacg aaaaaccaac aggattttct gacagagaat atggaattgg tgtgtgtgtg  2280
tgttgcactc atgcacactc tagtgcatgc taatttctgg ctgtgagtat atgtcagagt  2340
aaggattttg aagctaggca aagtgagtct ttgggttgaa ttttgtcaag gtgtttgttc  2400
atcacagtct ctacctcaga attggcttta aaattggaaa gctgggtggg tggatatgga  2460
aatgagaaac catctctgga gcttgtctac acatcatacc tttagccaaa gtgacatcaa  2520
gtatttcttg gatgctgacc agaggcttct gagccaggcc cctctagctg aaggaagttc  2580
acagtttctt taaggaggga aaatggtaga taagtcagag aacaatcaga cagaattctg  2640
ttcggtcagg gaatttgatg ggttttgttt gtttgtttgt ttgtttgttt tcgttttttct  2700 ttagacagag tctcgctctg gaggctggag tgcaatggca tgatctctgc tcagtgcaaa  2760
ctccacctcc ccggttcaag cgattctcct gcctcagcct cccaagtagt tggattacag  2820
gctcccgtca ccacgtccag ctaattttta tattttaag cagagaccag gtttcactat  2880
gttggctggg ctggtgtcca actcctgacc tcaagtgatc tgcccacctt ggcgtcccaa  2940
```

```
actgctgtga ttacaggagt gagccaccgc acctcaagga atttgatgtt taggctgtga    3000
cctctgcact aggaatggaa ggttagccac tcccacccca cccttcgtcc tgcaagtacc    3060
caatcacact gcagagccac acctgccttc cttagaggcg tgcctccatc cctgatgagt    3120
ttttcctcca tgtgtagaat tgaataagaa ggatagaatt caatttaaca gctttgagt    3180 acttcctata gcctaggcat tgtgctgaca actatgttag agagagaaat agacaagcta    3240
taaacttttc ctcaggacca tctacataat ttctaggccc aatataaaat gaaatgaat    3300 agcccctttg tcaaaaatta aggatttcat gtcaggaaca gcaaggatgt taaaccaagc    3360
atggggccat caagctatat ctgctattca tgatacgaaa aaataaagag tattctagtt    3420
atttagccac atatttcaag tttagtctga tatcacccct taaacactgc cactcaacct    3480
aaaacaatgc tagtctttct agacccatcc atggaatttt ttccccactg ttttttttct    3540
aattaatttg tgatttaaat ggctcatatt ccagcctgtg ccacagttat tacacattta    3600
actcactctc tgtattttgt tatctgtata aatactcttc aggttgattt cctttcttaa    3660
tgtttgtgtt tatgttagat atgcatcatg tagcctgtct tcatttctat cacaaacata    3720
cacttgaacc aaaaggaag ttttacata gcatcactaa atcttctctc tgtgctctta    3780
gcgaaaccaa gtaggctgac aagacatcat tcattcacag cgaaaccgag tagactgaca    3840
agaggtcatt cattcacaaa tgaatacaaa aaacagtgtc aagtatacgt gaggtcctgt    3900
aatgggtcct gggcctgcaa aaccctcaca gctgctaacc tcaagaagct cagtggagac    3960
ataacattca tctgaaaatt ccttgcatgt ctgttgaact aatttatctg cctctcctta    4020
aatttgttcc tttttgtata gttccttaag tcatgtcaca tttctgaaac atctttgcca    4080
ctgtgaactc ctacagaagc cagcttcaaa gccattcttc tggaagcctt ctctatcccc    4140
ttgacctcct gttttttctc ccacaagcat tatgtctgtc tgtcattgtt tttcatcctc    4200
ttgtagtcct tcacagttac ccacacaggt gaaccctttt agctctcctg gaggaatgtt    4260
tctttcctct caggatcaga gttgcctaca tcttcctaat gcaccaagac tggcctgaga    4320
tgtatcctta agatgagagc ttcccagtag caccccaagt cagatctgac cccgtatgtg    4380
agcatgtgtc ctctaacagc acaggccttt tgccacctag ctgtccaggg gtgccttaaa    4440
atggcaaaca aggtttgttt tcttttcctg ttttcatgcc ttcctcttcc atatccttgt    4500
ttcatattaa tacatgtgta tagatcctaa aaatctatac acatgtatta ataaagcctg    4560
attctgccgc ttctaggtat agaggccacc tgcaagataa atatttgatt cacaataact    4620
aatcattcta tggcaattga taacaacaaa tatatatata tatatatata tacgtatatg    4680
tgtatatata tatatatatt caggaaataa tatattctag aatatgtcac attctgtctc    4740
aggcatccat tttctttatg atgccgtttg aggtggagtt ttagtcaggt ggtcagcttc    4800 tcctttttt tgccatctgc cctgtaagca tcctgctggg gacccagata ggagtcatca    4860
ctctaggctg agaacatctg gcacacacc ctaagcctca gcatgactca tcatgactca    4920
gcattgctgt gcttgagcca gaaggtttgc ttagaaggtt acacagaacc agaaggcggg    4980
ggtggggcac tgaccccgac aggggcctgg ccagaactgc tcatgcttgg actatgggag    5040
gtcactaatg gagacacaca gaaatgtaac aggaactaag gaaaaactga agcttattta    5100
atcagagatg aggatgctgg aagggataga gggagctgag cttgtaaaaa gtatagtaat    5160
cattcagcaa atggttttga agcacctgct ggatgctaaa cactattttc agtgcttgaa    5220
tcataaataa gaataaaaca tgtatcttat tccccacaag agtccaagta aaaaataaca    5280
```

```
gttaattata atgtgctctg tcccccaggc tggagtgcag tggcacgatc tcagctcact    5340
gcaacctccg cctcccgggt tcaagcaatt ctcctgcctc agccacccta atagctggga    5400
ttacaggtgc acaccaccat gccaggctaa ttttttgtact ttttgtagag cagggtatc    5460 accatgttgt ccaagatggt cttgaactcc tgagctccaa gcagtccacc cacctcagcc    5520
tcccaaagtg ctgggattac aggtgtgaga caccatgccc agattttcca tatttaatag    5580
aggtatttat gggatggggg aaaagaatgt ttctctcact gtggattatt ttagagagtg    5640
gagaatggtc aagatttttt taaaaattaa gaaaacataa gttggacctt gagaaatgaa    5700
aatttatttt tttgttggag gatacccatt ctctatctcc catcagggca agctgtaagg    5760
aactggctaa gacacagtga gacagagtga cttagtctta gaggccccac tggtacccag    5820
atgagaaggc accttcatca ctcatcacag tcagctctgc cttctcctc tctcctttct    5880 catcagaaat ttcataagtc tactagggtc aggcagatca cataagaaaa gaggatgcca    5940
gttaaggtct gcagtgagta tgagcccatc cctgatgaat taaggcaatc aacactttag    6000
gcagccatgt tgccatgaga gattaggagg ggccaaatga gcccagaaat accacctact    6060
tcttagatga tcttgagcaa gttgcttaac ttcttgaagt ctctgaaata taggatgata    6120
atatgtatta gctaatagaa ttatgaggat gagattagtt tattgtgtaa agaactaggg    6180
acacagtata tattcagtaa gtgttttctg ttacagtatt atgataaata tatacatgca    6240
actattacag ttgcatgcta ccttaaagaa taattggagg tacagttatt cggaggtatt    6300
tcttgactgt taatgttggc agcagattca gcttatttta caacactatt cagacctctc    6360
acaataattc cctaggagat atttagacaa caagccatca tgttgtaact tctcatttgt    6420
cttttctcac ttaccctctc attcacccac ctcttttgct ctctgttcct gtgaaagtac    6480
ccttctactt agcctacttt tgaccagtgt gcatgtcact gggcaataca agacctctga    6540
gctttggctt agaaggaaat acaataatgg ctaattttg agaaagagga actctagccc    6600
atcagggaag acatagggag ttctgtagga atgagttctt ccattctttt tacagatgag    6660
aaagacaatg tgaagcccca aatgatttta agtagttag catatggaga aatggcttgc    6720
attggtaaaa tttggggaaa ctttgttgtc agacccggca aagggagatg cagagaatct    6780
gcagtttctt ctcatttctt gtgtacctat cacagcacca cagcactatt cctagcatag    6840
tttagggccc tcagttcttg acgctagtta gaatttcaca caaacttaaa ctagacaaac    6900
atatgtatgt ttctgaggca ctgaggtcac tgcaggatga agacggagcc aatgggttag    6960
accagaagag taaatgaaca ctataacaca taaacactcc ctttaaccaa agttgcagct    7020
tgaccaaggg gtcaaagggt aatttgggca ggcatgggcc ttcagttttc tcaagtgtct    7080
gcttataatt tgtcatatga caatctctgt aacccaagag aaaatctctt tattctgaag    7140
ttgtttctaa atttttcttt acctttttct ccctcaaact ttcctgaaga aatgcaatta    7200
tggttgagga agtatggtct gcaactgtgg cttggaccac aacttccaat cgacaagaag    7260
taaaagtaag aagcaagggc cacagggcag gaatatctac ttctaatttc tcgcatccac    7320
aatatctgag tttgtgtttt gctgtggaaa aaacactgtc ttcagaggta gcagaactgg    7380
gtctacatcc tagccttact acttggtggt tctgtaagct tggacaaatt atttcatgtc    7440
tttgattttc gagtccccag ttaataagag ctcatgtaat gtagacagta ggagagctca    7500
gaccatctga cttctaatta ctaattgtct acttattagc ttgtgctttc aataagttga    7560
tctacactac aagtacattg ggctcctcat caataaatga ggtaataatc tacttctgag    7620
tattggtgtg agtaaaacta agttaattca tataataaac ttcttttttt ttttttgaga    7680
```

```
tggagtctca ctctgtcgcc taggctggag tgcagtggtg caatcttagc tcactgcaac  7740
ctccacctcc tgggttcaag tgattctcct gcctcagcct cctgagtagc tgggattata  7800
gacgcgtgcc accacacctg gctgattttt tgtatttttt agtagagaag gggtttcacc  7860
atgttggcca ggctggtctg gaactcctga cctcaggtga tccaattgcc ttggcctccc  7920
aaagtgctgg gattacaggc atgtaatccc atatatgagc caccgtgccc ggcctcatat  7980
gataaactta aatttgattc tagcatatac taagtactca agaggtgtta cttatcatta  8040
gtattaatta tagtatgttc aataatacat atctcacaga attaccatat gtaatgagat  8100
tattaaatat cataaaatgg cacctgacat atagaaagat ttcagtaagt attaattccc  8160
acttctcttt catttacctc cagcctaaat ctacactatt tcctcgtgtc tctcatgtgg  8220
tttctagtcc cttcaccatc ttgtttccct ctcaactcct gtgcagattc ctaaaaattt  8280
ctcatgttca gaaccttggg cttccatgtt tccagtgaag tcagattttt ttagatggca  8340
aagttgctgt tagacaattt catctgtgcc ctgcttagga gcttaatctt taatgaaagc  8400
taagctttca ttaaaaaaag tctaaccagc tgcattcgac tttgactgca gcagctggtt  8460
agaaggttct actggaggag ggtcccagcc cattgctaaa ttaacatcag gctctgagac  8520
tggcagtata tctctaacag tggttgatgc tatcttctgg aacttgcctg ctacattgag  8580
accactgacc catacatagg aagcccatag ctctgtcctg aactgttagg ccactggtcc  8640
agagagtgtg catctccttt gatcctcata ataacccctat gagatagaca caattattac  8700
tcttacttta tagatgatga tcctgaaaac ataggagtca aggcacttgc ccctagctgg  8760
gggtataggg gagcagtccc atgtagtagt agaatgaaaa atgctgctat gctgtgcctc  8820 ccccacctttt cccatgtctg ccctctactc atggtctatc tctcctggct ctgggagtc  8880 atggactcca cccagcacca ccaacctgac ctaaccacct atctgagcct gccagcctat  8940
aacccatctg ggccctgata gctggtggcc agccctgacc ccaccccacc ctccctggaa  9000
cctctgatag acacatctgg cacaccagct cgcaaagtca ccgtgagggt cttgtgtttg  9060
ctgagtcaaa attccttgaa atccaagtcc ttagagactc ctgctcccaa atttacagtc  9120
atagacttct tcatggctgt ctcctttatc cacagaatga ttcctttgct tcattgcccc  9180
atccatctga tcctcctcat cagtgcagca cagggcccat gagcagtagc tgcagagtct  9240
cacataggtc tggcactgcc tctgacatgt ccgaccttag gcaaatgctt gactcttctg  9300
agctcagtct tgtcatggca aaataaagat aataatagtg ttttttttatg gagttagcgt  9360 gaggatggaa aacaatagca aaattgatta gactataaaa ggtctcaaca aatagtagta  9420
gattttatcg tccattaatc cttccctctc ctctcttact catcccatca cgtatgcctc  9480
ttaattttcc cttacctata ataagagtta ttcctcttat tatattcttc ttatagtgat  9540
tctggatatt aaagtgggaa tgaggggcag gccactaacg aagaagatgt ttctcaaaga  9600
agccattctc cccacataga tcatctcagc agggttcagg aagataaagg aggatcaagg  9660
tcgaaggtag gaactaagga agaacactgg gcaagtggat ccaggttgtc caacgctgaa  9720
agtaggaatc taagcactag tctctggatg ctaggagggc ctctgcatgg gtaactcttt  9780
caactagcca ggggctggac tgtggagaaa ccatttccag atagaagtga ggagattcca  9840
gcaggaaaca cttaagagag gatccctgga agttcggggc aggaggctcc ctgtcacatg  9900
aaggaaacct gctcagcgta ggctctaggt tcttccctac tcttatccaa tggggcttct  9960
gattttaagc cagtcttcac aaagccccag atttctacat gctggagccc tgaatgggca  10020
```

```
ggaagcattg cggtttccat ttcattcaga gctctttcat accctgcttc cccatagttt   10080
gtctcaacat ttctgttgat aatctgattc atgcaaccaa gaattatgag agagccttca   10140
gtcatgccta ggcctgcatt tattgttgtg catatgatgg ggtagcagac aagaaaacgt   10200
taacagcata gactttctca gagctatatg agtttgggaa ttaatcaaga ccagcctttt   10260
gctcagggta gaaatcccct atagggattt attcaatgat gggttaaaag ctttctatat   10320
ggtgaggagc tcacagattt tccaagccct tgcttttgct agacagctta atgtttatga   10380
aattcttaca cacagaagaa tcttctaatc ctgggttaca taatataact tgattcccta   10440
ttccagaaga taatattccc atattctgaa gcattcatgc atttgttaaa aataggcat    10500 agtgacaagt gccagaactc taacagtcaa ccagagagcc acagttttca acttcacaaa   10560
gttaaccatc taactgaaga cagcagcaat caaaaccacc accccttctc cacatggtgt   10620
agtctttcct gatgtcaggg atgttaggct caggttagga aagtcagact atcatcccag   10680
agcaggacac agacgaataa agtgtaattt tttagtcact taggaaaaac agtggaatgc   10740
aaagagtaaa aaatgctttc tgaatggata acttggcctg ggaggccttt ggaagcagag   10800
actggagctt aaatttaaac atctttgtat ccccagcatc cagcatacag actgccaaga   10860
agtacatgtc aataaatatt tattggatag tgagcaaaga cataattagg accaaatctc   10920
aattctacta tttgctagta gtttatgttt gtgtgtgtga gagtgtatgc ttgagcaagt   10980
tgagaggtag ttttttttaac tgtagtaaaa tggggataat aatagtatct acctgaaaga   11040
atccaagagt attaaatatg attaattatg caaagcacta attacagtct ctgatagcct   11100
tcaataaatg tcagttattt ttattattac agttaaagat gaatgggcat aaagtacaga   11160
acactagttt tcacctgcag caagaatgat tgcagttaaa caaaaaatac tagcaaacat   11220
ttctagagta gttagcattt ataagtcact gctttaaact ctttgcatgt attaactcac   11280
tcgggctgca gaacaatctt atgagcctgt taaaactcct gtaatcatgc ttataatccc   11340
agcactttgg aaggctgagg tgggcagatt gcttgagctc cggagtctga gaccatcctg   11400
tgtaacatgt gaaaccccat ctctaccaaa aatacaaaaa attagcgagg tatggtggtg   11460
tgtacctgtg gttccagcta ctcaggatgt tgaggtggga ggaccgcttg agcctgggaa   11520
gtgcaagttg cagtgagccg agattttgcc actacactcc catttgggtg acagagtgag   11580
accctttctc aaaaacaaac taattaaaaa accctccatt ttacagatga agaaactgag   11640
tcatacaact actaagagaa actgagtcac taatcactca ggtggtctgg ctccagcatc   11700
tgtactctta atctctgctc tatactgccc aagactttta taaagtcaag ggttgagtca   11760
ctgaaatgag ttattgggat ggctgtgtgg gaagggtgct aagttctttc ctaaaggtat   11820
gtgagaatac aaaggaaaga agcatcctcc tttttacaca cgtgaactag tgcatgcaaa   11880
tctgacactc agtgggcctg ggtgaaggtg agaatttat tgctgaatga gagcctctgg   11940
ggacatcttg ccagtcaatg agtctcaggt tcaatttcct tctcagtctt ggagtaacag   12000
aagctcatgc atttaataaa cggaaatttt gtattgaaat gagagccatt ggaaatcatt   12060
tactccagac tcctacttat aaaaagagaa actgaggctc agagaagggt ggggactttc   12120
tcagtatgac atgaaatga tcaggcttgg attcaaagct cctgactttc tgtcagtgt    12180 atgtgcagtg agccccttt cctctaactg aaagaaggaa aaaaaaatgg aacccaaaat    12240
attctacata gtttccastg tcacagccag ggctgggcag tctcctgtta tttcttttaa   12300
aataaatata tcatttaaat gcataaataa gcaaaccctg ctcgggaatg ggagggagag   12360
tctctggagt ccaccccttc tcggccctgg ctctgcagat agtgctatca aagccctgac   12420
```

```
agagccctgc ccattgctgg gccttggagt gagtcagcct agtagagagg cagggcaagc   12480
catctcatag ctgctgagtg ggagagagaa aagggctcat tgtctataaa ctcaggtcat   12540
ggctattctt attctcacac taagaaaaag aatgagatgt ctacatatac cctgcgtccc   12600
ctcttgtgta ctggggtccc caagagctct ctaaaagtga tggcaaagtc attgcgctag   12660
atgccatccc atctattata aacctgcatt tgtctccaca caccagtcat ggacaataac   12720
cctcctccca ggtccacgtg cttgtctttg tataatactc aagtaatttc ggaaaatgta   12780
ttctttcaat cttgttctgt tattcctgtt tcaatggctt agtagaaaaa gtacatactt   12840
gttttcccat aaattgacaa tagacaattt cacatcaatg tctatatggg tcgttgtgtt   12900
tgctgtgttt gcaaaaactc acaataactt tatattgtta ctactctaag aaagttacaa   12960
catggtgaat acaagagaaa gctattacaa gtccagaaaa taaagttat catcttgagg    13020 cctcagcttt ctaggaataa tatcaatatt acaaaattaa tctaacaatt atgaacagca   13080
atgagataat gtgtacaaag tacccagacc tatgtggtag agcatcaagg aagcgcattg   13140
cggagcagtt ttttgtttgt ttgttttgt attctgtttc gtgaggcaag gtttcactct    13200
gctgtccagg ctggagtgca gtggcaagat catgtctcac tgcagccttg acctcctgag   13260
ctcaagggat cctcccattt cggcctcctg agtagctggg actacaggtg tacatcacat   13320
gcctggctaa ttttttttt tttttaagt agagacgagg tcttgctatg ttgtccagga     13380
taatatcaaa ctcttgagct caagcagtcc tcccacttct acctctcaag tgctggaatt   13440
acagacatga gccaccactc ctggcttgca gactatttaa atgactaatt cctgacacta   13500
cttgagggat actagacagt agacaacaca tctttaatat accaaatggg tgactgtagg   13560
gttgagaggg agattagaat tcaatgtttt atgaccaaaa aggcttaaat caggcacaag   13620
cttaggtctt ttcaactgtg aggaccggac tgaaagtgtg cagttcaagg ccctgtagtt   13680
gctgtttaac tgttcccagg tggaagtctc ttcaaagaac cactggtgca aaagggaac    13740 tacctgggga taaatatttc ctccagaaag ggggaaagtg caagctcccc taccaaaagc   13800
accaggcaag tccttgtcta ttttccctga agttctcaaa gaaatgagac ccttgtttac   13860
ctttaagatt agagaaggct tgaaaagttt gagctgtgcc tttggaggcc aacaaacttt   13920
tctcctttgt tgaccaagtt cagctctcct gtatgcttcc aaggtctgtt gcatcaagag   13980
tgagaattga aggtcttaga agctgggatc tcagatgtag ggaaaagagg agatttcctg   14040
ttcactcact gttaagatat ggctgaaatt ttttgatcta gtcatctaca aagcatgagt   14100
tgtgggtcag aaattgtttt tcacatcttt tgacttcctt tgacatcaga atataaccta   14160
ggaattgatt acttaagtga aggcaaggta ctttggtctg acaggaaca ttttgaacaa    14220 ggtagggaga cagctatgaa ggcaagcatt tattctatct atcatctatc tgtctatcta   14280
tctatctatt ctttcatcca cttatttata catttaaaca aaaagtatag agcgtagtat   14340
aatttgtaag tgctcagggc tgtgtgtgta tggattgttt gaaatgaaac taaagtggga   14400
gtataattct actgccccct taaccctgtg gtccctacac taccctgcaa gactcttagc   14460
tgcttagctt aattgtgagg ctgatttggg gcatagcacc ccatcctctc tgtctttcaa   14520
catcctcata ataacttgag aataatttta taaaatatca caatagggtc atgttcagta   14580
gggtgatata taaaattaga caagccatag tttgagttta cccttttgaa taaatatatg   14640
acaaaaggca atttaattat ctttatgagt ttggaggtat ccagtatgaa atttagataa   14700
tacctgcctt ctagtgttga aattagaact taatgatata atgcatcaat gaacttatta   14760
```

| | |
|---|---|
| tagttcctag cacaaagtaa gaatcctttc aatgtgtgtg tgtgtgtatg tatttatctg | 14820 |
| ttattaatag gaatcttatg ggcattatct cacttaatcc ttattaataa ctatgaagca | 14880 |
| ggtatttatt tgagttttcc aagtgagtta agtatagctt gtaatactta aggaaatatc | 14940 |
| cacaggttac atagctagta tataactgag aaataatttt atttatatta taaaacattc | 15000 |
| taacaataca gatgtatata aactaaaaaa ctgaaagggc tcatgcaacc ctaccttctc | 15060 |
| aatatcactt cttcacttag aaaaaaccag ccttagctgt ctgctatgaa tcctttcaaa | 15120 |
| atatacttct gagaaatgag agagagaaat ggggagggta gaaggaagga agatagggta | 15180 |
| agagacaggg aaggaggtgt ggggaaagaa attaaattat tcttttctct gtctcttgaa | 15240 |
| agagctcttt ccattacatt gaatcaaagg taatgttgcc atttctggac tcttgaaata | 15300 |
| aagaaagacc gatgtatgaa ataatttga aagtctatgg cattttcaaa atgcaaggtg | 15360 |
| atgtcttact aactagcctt tgctttatta ttagaaatgg ggaagtgagt atagacattt | 15420 |
| tatcaggaga tatattagga aaagggaaa ctggagaaac tgggaggagt atccagatgt | 15480 |
| cctgtccctg taaggtgggg gcacccacct tcaatcaaaa ggg | 15523 |

<210> SEQ ID NO 12
<211> LENGTH: 5283
<212> TYPE: DNA
<213> ORGANISM: Artificial Sequence
<220> FEATURE:
<223> OTHER INFORMATION: EF1A FULL LENGTH SEQUENCE

<400> SEQUENCE: 12

| | |
|---|---|
| ttaaagctta aaattcattt attgtagtga gcaagtttgt aatgaatacc agcaggtggt | 60 |
| gctcaagcca cagttgtcta agacactggg tttcacagga agttaatctc aatctcagta | 120 |
| tatgcaagta aactgactca ttcctgcttc cagtgggaac aattttcag ttaaatcttg | 180 |
| cttccttgca tgtcaagaat tctctactgg taaatcttac aggtgtcaac tttcattatc | 240 |
| agggcatcta ttggccatct attaaaggcc ttacctgttt tttctgtcat ccagcaaatc | 300 |
| ttagactatt tacttgtgta aacattagat agcaaagaaa ctaaggacaa aaatctctag | 360 |
| ttcaatttag acttgatacc tcagagcact ggctgatggg aaggcatttt atctaattca | 420 |
| gactcagatg agggaaaacg ataacacttc attacagact tgtctatggc caattcaagt | 480 |
| acctttgaat cttgagcaat acacattgcc agtcacttta agaggcctta tctcttgggc | 540 |
| tgctttaact cctgcttagc atgtccttaa gaacacatgt cctggccagg catggtggct | 600 |
| catgcctgta attccagcac tttaggaggc cgaggcgatc acctaaggtc aggagtttga | 660 |
| gaccagcctg accaacatgg aaaaacctca tctctattaa aaacaccaaa ttagcacatg | 720 |
| cctgtaatcc cagctacttg ggaggctgaa gtaggagaat tgcttgaacc catgaggagg | 780 |
| agattgcagt gagattttgc cattgcattc tagcctgggc aacaagaact ccatcttaaa | 840 |
| aaaaattttt aaaaaccatc acacaaacag aaagcatgtc ctttaatttt acctatcctt | 900 |
| caaacttaag caaaaatttt cctttttataa ccaaaaaaaa accttaagac acttttacat | 960 |
| atgggaggtc aggcacagtg gctcatgcct gtaatcccag caggaagatc gcgaaaagca | 1020 |
| tttttcaaat gcacaaatgc ttaaagattc aggagtaagt gggctattac acctgttaag | 1080 |
| cctattacca tgtagtttca ttcctagtga ccaagtagac aaactgctaa ttatcaaagc | 1140 |
| ataaaaggta ttagactctg caggagaaaa gcaatgtaga ttagtctaat tttatagcta | 1200 |
| cttcaaattg ccatcttttt ctattagaac cttgttccta ttctgaatag cactcaatag | 1260 |
| aacttgtgaa accatcaaac tggcataaag cttactccac tgacttcaaa atggacccct | 1320 |

-continued

| | |
|---|---|
| ccactcatag ggtgtacact agccactaca cttatttctt atgtcatggc aaatagtcaa | 1380 |
| cttcactgc ccagtcattt taacccacgt ttcaacatgc acatcccagt aatttggaaa | 1440 |
| cattttgttt ccaaagattc acttaacatt ggtttagcaa catgaagctt tctatgcaac | 1500 |
| acaaggactc agttttggc ctgttttagt gacaggcaat cagcaacatg ctgcatttct | 1560 |
| ctccagtgtt gtaatcaaag caaccctccc atagctttaa atgatattcc ttccccttcc | 1620 |
| aattatgtgg ggggaaaaca accctattct ccacccagaa gtgttaactc aagaattaca | 1680 |
| ttttcaagaa gtttccagat tcgtaaaacc agaattagat gtctttcacc taaatgtctc | 1740 |
| ggtgttgacc aaaggaacac acaggtttct catttaactt ttttaatggg tctcaaaatt | 1800 |
| ctgtgacaaa ttttggtca agttgtttcc attaaaaagt actgatttta aaaactaata | 1860 |
| acttaaaact gccacacgca aaaagaaaa ccaaagtggt ccacaaaaca ttctcctttc | 1920 |
| cttctgaagg ttttacgatg cattgttatc attaaccagt cttttactac taaacttaaa | 1980 |
| tggccaattg aaacaaacag ttctgagacc gttcttccac cactgattaa gagtggggtg | 2040 |
| gcaggtatta gggataatat tcatttagcc ttctgagctt tctgggcaga cttggtgacc | 2100 |
| ttgccagctc cagcagcctt cttgtccact gctttgatga cacccaccgc aactgtctgt | 2160 |
| ctcatatcac gaacagcaaa gcgacctatt aaaaaaaag ttaattatta cccaaagtac | 2220 |
| tgttcagttg tattttcat cttaacaca acttttttac atttaagtag tcatccttac | 2280 |
| ccaaaggtgg atagtctgag aagctctcaa cacacatggg cttgccagga accatatcaa | 2340 |
| caatggcagc atcaccagac ttcaagaatt tagggccatc ttccagcttt ttaccagaac | 2400 |
| ggcgatcaat cttttccttc agctcagcaa acttgcatgc aatgtgagcc gtgtggcaat | 2460 |
| ccaatacagg ggcatagccg gcgcttattt ggcctggatg gttcaggata atcaccttgg | 2520 |
| aaaaaagatt tgcgttcagt gcaaatccaa agtctcaaat gactttagcc tctgcagtaa | 2580 |
| gttaatgtta ctttaaattg ttacctgagc agtgaagcca gctgcttcca ttggtgggtc | 2640 |
| attttttgctg tcaccagcaa cgttgccacg acgaacatcc ttgacagaca cattcttgac | 2700 |
| attgaagccc acattgtccc caggaagagc ttcactcaaa gcttcatggt gcatttcgac | 2760 |
| agattttact tccgttgtaa cgttgactgg agcaaaggtg accaccatac cgggtttgag | 2820 |
| aacaccagtc tccactcggc caacaggaac agtaccaata cctaaaaata tttacagcat | 2880 |
| actaaatacc tatgaaggca gacagtactc tatcaactca aattcaactt tgtttacagc | 2940 |
| caacttacca ccaattttgt agacatcctg gagaggcagg cgcaagggct tgtcagttgg | 3000 |
| acgagttggt ggtaggatgc agtccagagc ctcaagcagc gtggttccac tggcattgcc | 3060 |
| atccttacgg gtgactttcc atcccttgaa ccaaggcatc tgaaacacaa gcatgccaat | 3120 |
| ttgtgtaagc atgaaatcgc cattcccaga gcttttaac aatggtcttg aaagccactt | 3180 |
| acgttagcac ttggctccag catgttgtca ccattccaac cagaaattgg cacaaatgct | 3240 |
| actgtgtcgg ggttgtagcc aattttctta atgtaagtgc tgacttcctt aacaatttcc | 3300 |
| tcatatctct tctggctgta gggtggctca gtggaatcca ttttgttaac accgacaatt | 3360 |
| agttgtttca cacccagtgt gtaagccaga agggcatgct ctcgggtctg cccattcttg | 3420 |
| gagataccag cttcaaattc accaacacca gcagcaacaa tcaggacagc acagtcagcc | 3480 |
| tttaaagaaa gcaaagacat atccctgtca actctccaaa tgacaaaacc agtgtacaaa | 3540 |
| gcaagccttt tgggataaag aaacctagaa ttattaatcc caccaacctg agatgtccct | 3600 |
| gtaatcatgt ttttgataaa gtctctgtgt cctggggcat caatgatagt cacatagtac | 3660 |

```
ttgctggtct caaatttcca caaggagata tcaatggtga taccacgttc acgctcagct    3720
ttcagtttat ccaagaccca ggcatacttg aaggagccct ttcccatctg taaggattaa    3780
gagtctttac ttggttacta aaacacaaac tccagcttca atttccttgt ccccagccct    3840
taattggcag tttccacttt acaactccaa gtccaaagtg attttagtca ctttgggtta    3900
cagaagcaac caaaaatcaa acttttataa gtaggatctt aactattaac atccaaatct    3960
actcactagc aatacgatta cagaagtcac caaaagcaaa attatttcat aagtaaggtc    4020
ttaactatta gcattcagat ctaaaccact cactagttct ggggaaatca cctaatgatt    4080
ctgctggtaa aactcatttt agttgatctt tcccttctg gtattaaaca tacctcagca     4140
gcctccttct caaattttc aatggttctt ttgtcgatgc caccgcattt atagatcaga     4200
tggccagtag tggtggactt gcccgaatct acgtgtccaa tgacgacaat gttgatatga    4260 gtctttcct ttcccatttt ggcttttagg ggtagttttc acgacacctg aaatggaaga     4320 aaaaacttt gaaccactgt ctgaggcttg agaatgaacc aagatccaaa ctcaaaaagg     4380
gcaaattcca aggagaatta catcaagtgc caagctggcc taacttcagt ctccacccac    4440
tcagtgtggg gaaactccat cgcataaaac ccctccccc aacctaaaga cgacgtactc     4500
caaaagctcg agaactaatc gaggtgcctg gacggcgccc ggtactccgt ggagtcacat    4560
gaagcgacgg ctgaggacgg aaaggccctt ttcctttgtg tgggtgactc acccgcccgc    4620
tctcccgagc gccgcgtcct ccattttgag ctccctgcag cagggccggg aagcggccat    4680 cttcgctc acgcaactgg tgccgaccgg gccagccttg ccgcccaggg cggggcgata     4740
cacggcggcg cgaggccagg caccagagca ggccggccag cttgagacta cccccgtccg    4800
attctcggtg gccgcgctcg caggccccgc ctcgccgaac atgtgcgctg gacgcacgg    4860 gccccgtcgc cgcccgcggc cccaaaaacc gaaataccag tgtgcagatc ttggcccgca    4920
tttacaagac tatcttgcca gaaaaaagc gtcgcagcag gtcatcaaaa attttaaatg     4980
gctagagact tatcgaaagc agcgagacag gcgcgaaggt gccaccagat cgcacgcg     5040 cggccccagc gccaggcca ggcctcaact caagcacgag gcgaaggggc tccttaagcg     5100
caaggcctcg aactctccca cccacttcca acccgaagct cgggatcaag aatcacgtac    5160
tgcagccagg ggcgtggaag taattcaagg cacgcaaggg ccataacccg taagagggcc    5220 aggccccgcgg gaaccacaca cggcacttac ctgtgttctg gcggcaaacc cgttgcgaaa   5280
aag                                                                  5283

<210> SEQ ID NO 13
<211> LENGTH: 243
<212> TYPE: DNA
<213> ORGANISM: Artificial Sequence
<220> FEATURE:
<223> OTHER INFORMATION: EF1A SEQUENCE USED IN THE VECTOR

<400> SEQUENCE: 13
ggctccggtg cccgtcagtg ggcagagcgc acatcgccca cagtccccga gaagttgggg      60
ggaggggtcg gcaattgaac cggtgcctag agaaggtggc gcggggtaaa ctgggaaagt     120
gatgtcgtgt actggctccg cctttttccc gagggtgggg gagaaccgta taagtgca      180 gtagtcgccg tgaacgttct ttttcgcaac gggtttgccg ccagaacaca ggtgtcgtga    240
cgc                                                                  243

<210> SEQ ID NO 14
<211> LENGTH: 29
```

-continued

<212> TYPE: DNA
<213> ORGANISM: Artificial Sequence
<220> FEATURE:
<223> OTHER INFORMATION: HS4 PCR FORWARD PRIMER

<400> SEQUENCE: 14
tttgcggccg ctatctcatt gctgttcgt                                           29

<210> SEQ ID NO 15
<211> LENGTH: 28
<212> TYPE: DNA
<213> ORGANISM: Artificial Sequence
<220> FEATURE:
<223> OTHER INFORMATION: HS4 PCR REVERSE PRIMER

<400> SEQUENCE: 15
tttgcggccg cacagaagct catgcatt                                            28

<210> SEQ ID NO 16
<211> LENGTH: 26
<212> TYPE: DNA
<213> ORGANISM: Artificial Sequence
<220> FEATURE:
<223> OTHER INFORMATION: MCS FORWARD PRIMER

<400> SEQUENCE: 16
cgatctcgag cctgcaggga tatcat                                              26

<210> SEQ ID NO 17
<211> LENGTH: 26
<212> TYPE: DNA
<213> ORGANISM: Artificial Sequence
<220> FEATURE:
<223> OTHER INFORMATION: MCS REVERSE PRIMER

<400> SEQUENCE: 17
cgatgatatc cctgcaggct cgagat                                              26

<210> SEQ ID NO 18
<211> LENGTH: 20
<212> TYPE: DNA
<213> ORGANISM: Artificial Sequence
<220> FEATURE:
<223> OTHER INFORMATION: WP FORWARD PRMER

<400> SEQUENCE: 18
cgggccacaa ctcctcataa                                                     20

<210> SEQ ID NO 19
<211> LENGTH: 20
<212> TYPE: DNA
<213> ORGANISM: Artificial Sequence
<220> FEATURE:
<223> OTHER INFORMATION: WP REVERSE PRIMER

<400> SEQUENCE: 19
ttgcttcccg tatggctttc                                                     20

<210> SEQ ID NO 20
<211> LENGTH: 33
<212> TYPE: DNA
<213> ORGANISM: Artificial Sequence
<220> FEATURE:
<223> OTHER INFORMATION: 5'FAM,TAMRA-3' PROBE
<220> FEATURE:
<221> NAME/KEY: misc_feature
<222> LOCATION: (1)..(1)

```
<223> OTHER INFORMATION: FAM-
<220> FEATURE:
<221> NAME/KEY: misc_feature
<222> LOCATION: (33)..(33)
<223> OTHER INFORMATION: -TAMRA

<400> SEQUENCE: 20
tctcctcctt gtataaatcc tggttgctgt ctc                                    33
```

TREATMENT OF LYSOSOMAL STORAGE DISEASES

FIELD OF THE INVENTION

The present invention relates to gene therapy for the treatment and/or prevention of lysosomal storage diseases (LSDs), in particular various Mucopolysaccharidosis, Gaucher's disease, Fabry's disease, and Pompe disease.

BACKGROUND OF THE INVENTION

Lysosomal Storage Diseases (LSD) are a group of rare genetically and phenotypically heterogeneous metabolic disorders, including inherited metabolic disorders, that are characterised by defects in lysosomal function and abnormal accumulation of substances inside the lysosome (Winchester et al. 2000). Lysosomes are subcellular compartments of enzymes that facilitate the degradation of and cellular recycling of molecules. Both intracellular and extracellular substrates can be targeted to lysosomes. Several enzymes contained within the lysosome are involved in degradation. Defects in one or more of such enzymes, such as genetic mutations leading to reduced or absent production of lysosomal enzymes, result in the accumulation of within the cell of biological molecules, leading to cellular toxicity (Reece and Campbell 2002).

Typically, LSD are monogenic conditions, caused by deficiency in a single lysosomal enzyme. The incidence of specific LSD is less than 1 in 100,000 people, but as a class of diseases, the incidence is about 1 in 5,000 to 1 in 10,000 people. LSD mostly affect children who often as a result die unpredictably, such as within a few month or years from birth. Particular examples of LSD include Hurler syndrome or mucopolysaccharidosis type I (MPS-I). MPS-I is a progressive lysosomal storage disorder with systemic and central nervous system (CNS) involvement due to deficiency of $\alpha$-l-iduronidase (IDUA). It has effects on the CNS and also peripherally, for example, involving cardiac defects.

Pre-clinical gene-replacement therapy studies have shown that reprogramming erythroid cells for lysosomal enzyme production leads to visceral correction of enzyme levels, for example, in a murine model of Hurler syndrome (Wang et al. 2009 and El-Amouri et al. 2014). Expression of enzyme more widely in haematopoietic cells corrects systemic and CNS pathology of MPS-I in a murine model (Visigalli et al. 2010). However, the translation of gene therapy strategies to clinical settings are currently often compromised by the levels and duration of gene expression achieved, by the breadth of cell types, tissues, organs, and organ systems that require correction and/or by the safety profile of the gene therapy vector. There are currently no cures for LSD and other related metabolic disorders, such as glycogen storage disease (GSD). This may be because treatment strategies rely on the uptake of exogenously introduced functional enzyme by affected cells, or endogenous production of functional enzyme. Although bone marrow transplantation, enzyme replacement therapy (ERT), and umbilical cord blood transplantation are used clinically to try and manage the progression of disease (Clarke et al. 2005 and Bruni et al. 2007), effectiveness of these treatment options is often limited by the availability of suitable donor tissue, and adverse immune responses such as Graft versus Host Disease (GvHD) and incomplete correction of organ pathology which has been demonstrated to be related to insufficient enzyme production (Aldenhoven et al. 2015). Thus, allogenic bone marrow transplant is not effective. Therefore, there is a need for improvements in gene-replacement therapies for LSDs and GSDs and related metabolic conditions, and more generally for other monogenic diseases.

SUMMARY OF THE INVENTION

We have designed a lentiviral (LV) gene therapy vector in which a therapeutic gene is under the control of the short form of the elongation factor 1 $\alpha$ (EFS) promoter and essential elements (hypersensitivity sites—HS 2,3,4) of the $\beta$-globin locus control region (bLCR). The advantages of this vector are that following correction of haematopoietic stem cells (HSCs), the EFS promoter drives expression of the transgene in lymphoid and myeloid cells but the bLCR elements upregulate EFS promoter activity in erythroid lineages. This leads to expression of the transgene in lymphoid and myeloid cells (due to the activity of EFS alone) but also importantly very high levels (~20-50 times in vivo) in red blood cells (due to the upregulation of EFS activity by the LCR). This provides a very effective systemic delivery system, since red blood cells can circulate around the body and are not confined to any one tissue.

A vector design of this nature can provide high levels of systemic therapeutic gene delivery for correction of diseases where the gene needs to be expressed in many different parts of the body and not just in haematopoietic cells. This pertains to many metabolic diseases where there are often numerous different tissue abnormalities. The high level of erythroid expression of transgene will provide higher systemic levels of therapeutic gene expression than vectors without the LCR and offer better disease correction. The skilled person would readily be able to determine whether correction and/or enhancement of the various parameters and/or disease states disclosed herein (such as aortic valve peak pressure, aortic flow rate, aortic dilation, bone modelling, enzyme activity, motor coordination, muscle strength, hypertrophic cardiomyopathy and concentration of glucose in urine) had occurred.

We have already shown using lentiviral vectors containing either bLCR+EFS or EFS alone, that reporter genes and a therapeutic gene are expressed at similar levels in myeloid and lymphoid cells following transduction with both vectors, but that there is significant upregulation of gene expression in erythroid lineages in cells transduced with the bLCR+EFS vector. In particular, we have previously shown that the bLCR in combination with the EFS promoter allows enhanced lentiviral vector-mediated erythroid gene expression with conserved multi-lineage activity (Montiel-Equihua et al. 2012).

However, in a series of gene therapy experiments in a murine model of MPS-I (Hurler disease—defects in $\alpha$-l-iduronidase (IDUA)), we have now also shown that mice treated with the LCR EFS IDUA vector have a 2-3 log increase in IDUA activity in the plasma and in different organs, including the liver and spleen. Most surprisingly, we saw functional correction of cardiac defects to normal levels in comparison to untreated mice. There was normalisation of the aortic valve peak velocity, aortic valve peak pressure and the mitral valve E/A ratio (the E/A ratio is the ratio of the early (E) to late (A) ventricular filling velocities). In a healthy heart, the E velocity is greater than the A velocity. In certain pathologies and with aging, the left ventricular wall can become stiff, increasing the back pressure as it fills, which slows the E filling velocity, thus lowering the E/A ratio). Importantly correction of the cardiac defects has not been described in any previous publication of murine model gene therapy treatment for MPS-I (Wang et al. 2009, Visigalli et al. 2010, El Amouri et al. 2014). Given that cardiac defects are a major cause of mortality and morbidity in MPS-I, this is a major finding. We have also seen correction of the computerised tomography (CT) appearances of the mouse snout in LCR EFS IDUA treated mice in comparison to untreated mice and/or control mice. Correction of other bone phenotypes were also seen.

In a further series gene therapy experiments in a murine model of Pompe disease (defects in acid a glucosidase (GAA)), and of ex vivo cellular experiments, we have shown that mice treated with the LCR EFS GAA vectors demonstrate surprisingly enhanced correction of functional, biochemical and/or genetic defects associated with the murine model of Pompe disease. Mice treated with the LCR EFS GAA vector have 1-2 log increase in GAA activity in the white blood cells (WBCs) and blood plasma, an increase in GAA activity in various other tissues. Mice treated with the LCR EFS GAA vector have a 6-fold increase in GAA activity as demonstrated in dried blood spot testing (DBS) and an increase in GAA activity in various other tissues; and a 3.4-fold reduction in glucose in urine a decrease in glucose in various other tissues. These fold changes are surprising and represent a major finding. GAA activity was increased 4-fold in human erythroid-like cells treated with the LCR EFS GAA compared with the EFS GAA treated control human erythroid-like cells. In LCR EFS GAA treated GAA-null mice, motor coordination, grip strength, and heart mass were corrected to wild-type levels compared with untreated GAA-null mice.

The IDUA gene has previously been linked with a PGK promoter in a lentiviral vector (Visgalli et al. 2010), but no correction of the cardiac defects in MPS-I was seen in this study. Furthermore, in these vectors, high copy number transduction was required to achieve significant expression of the IDUA gene, which is undesirable from a safety standpoint because of the increased possibility of genomic disruption associated with the introduction of vectors that integrate into the genome.

By contrast, with vectors of the present invention, the levels of expression of the transgene are significantly greater than when expressed under the control of a constitutive promoter that is not operably linked to the bLCR. Thus, it is possible to achieve disease and/or biochemical correction with a lower vector copy number (VCN). Thus, the risk of genomic disruption can be minimised. The low VCN is achieved by infecting the target cells with reduced amounts of virus, i.e., a low multiplicity of infection (MOI).

Further, the present disclosure demonstrates remarkable functional, biochemical, and/or genetic correction of defects associated with LSDs and GSDs. These show that high-level systemic expression using the LCR-EFS strategy can correct major organ pathologies associated with certain inherited diseases, providing advantages of long-term correction, reduction of immunological reactions, and systemic release and action. Thus, this approach could have significant utility for a variety of metabolic enzyme defects in the future.

Accordingly, the invention provides the following aspects:

[1] a host cell that contains a vector or expression cassette, said vector or expression cassette comprising a regulatory region in which a LCR is operably linked to an EFS promoter or a PGK promoter, wherein said regulatory region regulates the expression of a transgene operably linked to said regulatory region and the vector or expression cassette is present at a copy number of 1, 2, 3, 4 or 5 copies per cell;

[2] a cell population that includes cells containing a vector or expression cassette, said vector or expression cassette comprising a regulatory region in which a LCR is operably linked to an EFS promoter or a PGK promoter, wherein said regulatory region regulates the expression of a transgene operably linked to said regulatory region and the vector or expression cassette is present at an average copy number of from 0.5 to 2 in said population;

[3] the host cell according to [1] or a population according to [2], wherein said vector or expression cassette comprises a regulatory region:
 (a) of SEQ ID NO: 1; or
 (b) having at least 90% sequence identity to SEQ ID NO: 1;

[4] the host cell or cell population of any of the previous aspects, wherein the cell is a mammalian cell or the population is a population of mammalian cells;

[5] the host cell or cell population of any of the previous aspects, wherein the cell is a human cell or the population is a population of human cells;

[6] the host cell or cell population of any of the previous aspects, wherein the cell is a bone marrow cell or the population comprises bone marrow cells;

[7] the host cell or cell population of any of the previous aspects, wherein the cell is a haematopoietic stem cell (HSC) or a haematopoietic progenitor cell or the population comprises HSCs or progenitor cells;

[8] the host cell or cell population of any of the previous aspects, for use in a method of preventing or treating a lysosomal storage disease or a glycogen storage disease;

[9] a method of treating or preventing a lysosomal storage diseases and/or a glycogen storage disease in a patient in need thereof, comprising administering a therapeutically effective amount of a host cell according to any of [1] to [7] to said patient;

[10] use of a host cell or cell population of any of claims [1] to [7] for the manufacture of a medicament for treating or preventing lysosomal storage disease and/or glycogen storage disease in a patient in need thereof;

[11] the host cell for use, cell population for use, method or use of any one of [10] to [12], wherein the disease is Hurler syndrome (MPS-I), Hunter syndrome (MPS-II), Morquio syndrome (MPS-IV), Maroteaus-Lamy syndrome (MPS-VI), Sly syndrome (MPS-VII), Gaucher disease, Fabry's disease, and/or Pompe disease;

[12] the host cell for use, population for use, method or use of any one of the previous claims, wherein the transgene encodes:
 (a) α-L-iduronidase (IDUA) (EC 3.2.1.76);
 (b) iduronate sulfatase (EC 3.1.6.13);
 (c) N-acetylgalactosamine 6-sulfatase (EC 3.1.6.4);
 (d) N-acetylgalactosamine 4-sulfatase (EC 3.1.6.12);
 (e) β-glucuronidase (3.2.1.31);
 (f) β-glucocerebrosidase (EC 3.2.1.45);
 (g) α-galactosidase A (EC 3.2.1.22); or
 (h) acid α-glucosidase (GAA) (EC 3.2.1.20);

[13] the host cell for use, population for use, method or use of any one of the previous aspects, wherein the disease is Hurler syndrome and the transgene encodes α-L-iduronidase; Hunter syndrome and the transgene encodes iduronate sulfatase; Morquio syndrome and the transgene encodes N-acetylgalactosamine 6-sulfatase; Maroteaus-Lamy syndrome and the transgene encodes N-acetylgalactosamine 4-sulfatase; Sly syndrome and the transgene encodes β-glucuronidase; Gaucher disease and the transgene encodes β-glucocerebrosidase; Fabry's disease and the transgene encodes α-galactosidase A; and/or Pompe disease and the transgene encodes acid α-glucosidase;

[14] the host cell, population, cell for use, cell population for use of any one of the previous aspects, wherein the transgene is selected from:
(a) SEQ ID NO: 2; SEQ ID NO:3; SEQ ID NO: 4; SEQ ID NO: 5; SEQ ID NO: 6; SEQ ID NO: 7; SEQ ID NO: 8; or SEQ ID NO: 9, or
(b) a sequence having at least 90% sequence identity to a sequence of SEQ ID NO: 2; SEQ ID NO:3; SEQ ID NO: 4; SEQ ID NO: 5; SEQ ID NO: 6; SEQ ID NO: 7; SEQ ID NO: 8; or SEQ ID NO: 9;

[15] the host cell, cell population, cell for use, cell population for use, method or use of any one of the preceding claims, wherein the cell is an erythrocyte or a macrophage;

[16] the host cell for use, population for use, method or use of any one of aspect [10] to [15], wherein the transgene is IDUA and one or more peripheral aspects of MPS-I are corrected; and/or IDUA activity is enhanced, corrected or partially corrected;

[17] the host cell for use, population for use, method or use of aspect [16], wherein the transgene is wherein cardiac aspects of MPS-I are corrected;

[18] the host cell for use, population for use, method or use of aspect [17], wherein:
(a) aortic valve peak pressure is corrected;
(b) aortic flow rate is corrected;
(c) aortic dilation is corrected;
(d) bone modelling is corrected and/or
(e) IDUA enzyme activity is corrected or enhanced;

[19] the host cell for use, population for use, method or use of any one of aspects [10] to [15] wherein the transgene is GAA and one or more peripheral aspects of Pompe are corrected; and/or GAA activity is enhanced, corrected or partially corrected;

[20] the host cell for use, population for use, method or use of aspect [19], wherein:
(a) motor coordination is corrected;
(b) muscle strength is corrected;
(c) hypertrophic cardiomyopathy is corrected;
(d) GAA enzyme activity is corrected or enhanced; and/or
(e) the concentration of glucose in urine is corrected;

[21] the host cell for use, population for use, method or use of according to any one of aspects [16] to [20], wherein correction is achieved after at least 100 days post-administration, or more preferably after at least 2 years post-administration;

[22] the host cell for use, population for use, method or use of any one of aspects [8] to [21], wherein the host cell or population of cells, is derived from the same patient, an individual who is related to the patient, or an individual who is a tissue type match for the patient.

[23] the host cell for use, population for use, method or use of any one of aspects [8] to [21], wherein the host cell or population of cells, is derived from an individual with a different genetic background from the patient to which it is administered;

[24] the host cell for use, cell population for use of any one of aspects [8] to [23], wherein the host cell is introduced into the blood and/or the bone marrow.

[25] the host cell for use, population for use, method or use according to any of the previous aspects, wherein:
(a) the vector or expression cassette is a lentivirus vector or expression cassette comprising a lentivirus genome or a derivative thereof, further wherein the vector or expression cassette is based on a third-generation CCL backbone; and
(b) the transgene is flanked by a long terminal repeat (LTR) and central polypurine tract (cPPT) at the 5' end, and a woodchuck hepatitis post-transcriptional regulatory element (wPRE) sequence and a LTR lacking the U3 region at the 3' end;

[26] a method of making the host cell of aspect [1], or the cell population of aspect [2], comprising:
(a) isolating a cell or cell population from a first organism; and
(b) introducing into said cell or cell population a vector or expression cassette comprising a regulatory region in which a β-globin LCR is operably linked to an EFS promoter or a PGK promoter, wherein said regulatory region regulates the expression of a transgene operably linked to said regulatory region;

[27] the method of aspect [26], further comprising culturing the isolated cell or cell population;

[28] the method of aspect [26] or [27], further comprising introducing the isolated or cultured cell or cell population into:
(a) the first organism;
(b) a second organism that is related to the first organism;
(c) a second organism that is a tissue type match for the first organism; or
(d) a second organism with a different genetic background to the first organism;

[29] a nucleic acid sequence comprising in operable linkage in the 5' to 3' direction a cPPT, the Dnase I hypersentitive sites, 4, 3, and 2 from the β globin LCR, the EFS or PGK promoter nucleic acid sequence, a transgene, and the wPRE, or a compliment, variant or fragment of said sequence;

[30] the nucleic acid sequence of aspect [29], wherein said nucleic acid sequence is:
(a) flanked at the 5' end by a LTR; and
(b) flanked at the 3' end by a LTR lacking the U3 region; and

[31] the nucleic acid sequence of aspect [29] or [30], wherein the transgene is selected from:
(a) SEQ ID NO: 2; SEQ ID NO:3; SEQ ID NO: 4; SEQ ID NO: 5; SEQ ID NO: 6; SEQ ID NO: 7; SEQ ID NO: 8; or SEQ ID NO: 9, or
(b) a sequence having at least 90% sequence identity to a sequence of SEQ ID NO: 2; SEQ ID NO:3; SEQ ID NO: 4; SEQ ID NO: 5; SEQ ID NO: 6; SEQ ID NO: 7; SEQ ID NO: 8; or SEQ ID NO: 9.

BRIEF DESCRIPTION OF THE DRAWINGS

FIG. 20 is a graph of GAA activity in MEL cells treated with or without the MEL cell differentiation agent DMSO, in non-transfected cell (NT), EFS-GAA (EFS OPT) cells and bLCR-EFS-GAA (LCR-OPT) cells.

BRIEF DESCRIPTION OF THE SEQUENCES

Figure 1A:
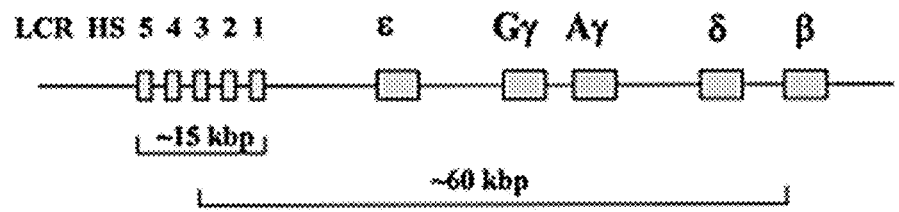
FIG. 1A is a schematic of the β-globin locus control region (bLCR). This is a cluster of genes whose expression is limited to erythroid cells and is controlled by a number of cis-acting elements, one of which is the LCR. The LCR is composed of five erythroid-specific hypersensitive sites (HS) upstream the globin genes and its job is to maintain an active chromatin domain, enhance expression in erythroid lineages and protect the locus from silencing. Most of the activity of the LCR resides in sites 2 and 3, and number 4 is important in adult globin expression.

SEQ ID NO: 1 shows the DNA sequence of the bLCR-EFS sequence.
SEQ ID NO: 2 shows the cDNA sequence of the codon-optimised IDUA gene.
SEQ ID NO: 3 shows the cDNA sequence of the iduronate sulfatase gene.
SEQ ID NO: 4 shows the cDNA sequence of the N-acetylgalactosamine 6-sulfatase gene.
SEQ ID NO: 5 shows the cDNA sequence of the N-acetylgalactosamine 4-sulfatase gene
SEQ ID NO: 6 shows the cDNA sequence of the β-glucuronidase gene.
SEQ ID NO: 7 shows the cDNA sequence of the β-glucocerebrosidase gene.
SEQ ID NO: 8 shows the cDNA sequence of the α-galactosidase A gene.
SEQ ID NO: 9 shows the cDNA sequence of the codon-optimised GAA gene.
SEQ ID NO: 10 shows the DNA sequence of the full length β globin LCR sequence.
SEQ ID NO: 11 shows the DNA sequence of the sequence of the β globin LCR containing only essential elements.
SEQ ID NO: 12 shows the DNA sequence of the EF1α full length sequence.
SEQ ID NO: 13 shows the DNA sequence of the EF1α sequence used in the vector (i.e., the EFS sequence).
SEQ ID NO: 14 shows the DNA sequence of the HS4 PCR forward primer.
SEQ ID NO: 15 shows the DNA sequence of the HS4 PCR reverse primer.
SEQ ID NO: 16 shows the DNA sequence of the MCS forward primer.
SEQ ID NO: 17 shows the DNA sequence of the MCS reverse primer.
SEQ ID NO: 18 shows the DNA sequence of the WP forward primer.
SEQ ID NO: 19 shows the DNA sequence of the WP reverse primer.
SEQ ID NO: 20 shows the sequence of the 5'-FAM, TAMRA-3' probe.

DETAILED DESCRIPTION OF THE INVENTION

It is to be understood that different applications of the disclosed host cell and/or cell population containing the vector and/or expression cassette of the invention, together with specific polynucleotide sequences, may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "a host cell" includes "host cells", reference to "vector" includes two or more such vectors, reference to "an expression cassette" includes two or more expression cassettes, and the like.

All publications, patents and patent applications cited herein, whether supra or infra, are hereby incorporated by reference in their entirety.

The present invention concerns gene therapy for the treatment and/or prevention of lysosomal storage diseases or glycogen storage diseases, in particular various Mucopolysaccharidosis, Gaucher disease, Fabry's disease and Pompe disease, in a patient.

The patient may be any suitable organism. The patient is preferably a mammal. The mammal may be a commercially farmed animal, such as a horse, a cow, a sheep or a pig, a laboratory animal, such as a mouse or a rat, or a pet, such as a cat, a dog, a rabbit or a guinea pig. The patient is more preferably a human.

The vectors and expression cassettes of the present invention can be used to treat lysosomal storage diseases or glycogen storage diseases. The lysosomal storage diseases and/or glycogen storage diseases may be inherited diseases. Lysosomal storage diseases and glycogen storage diseases can be defined as metabolic disorders, characterised by enzyme deficiency.

Lysosomal Storage Diseases (LSD)

Lysosomal Storage Diseases (LSD) are a group of rare genetically and phenotypically heterogeneous metabolic disorders, including inherited metabolic disorders, that are characterised by defects in lysosomal function and abnormal accumulation of substances inside the lysosome (Winchester et al. 2000). Lysosomes are subcellular compartments of enzymes that facilitate the degradation of and cellular recycling of molecules. Several enzymes contained within the lysosome are involved in degradation. Defects in one or more of such enzymes, such as genetic mutations can lead to reduced or absent production of lysosomal enzymes, which may result in the aberrant accumulation of within the cell of biological molecules, which may lead to cellular toxicity (Reece and Campbell 2002).

Typically, LSD are monogenic conditions, caused by deficiency in a single lysosomal enzyme. The incidence of specific LSD is less than 1 in 100,000 people, but as a class of diseases, the incidence is about 1 in 5,000 to 1 in 10,000 people. LSD mostly affect children who often as a result die unpredictably, such as within a few month or years from birth.

Table 1 provides particular examples of genes encoding enzymes whose deficiency causes LSD, together with the specific LSD caused.

TABLE 1

Examples of LSD and the causative gene

| Disease | Causative Gene and associated enzyme commission (EC) number based on the chemical reaction catalysed |
|---|---|
| MPS-I - Hurler syndrome | α-L-iduronidase (IDUA) (EC 3.2.1.76) |
| MPS-II - Hunter syndrome | iduronate sulfatase (IDS) (EC 3.1.6.13) |
| MPS-IV - Morquio syndrome | N-acetylgalactosamine 6-sulfatase (EC 3.1.6.4) |
| MPS-VI - Maroteaux-Lamy syndrome | N-acetylgalactosamine 4-sulfatase (3.1.6.12) |
| MPS-VII - Sly syndrome | β-glucuronidase (EC 3.2.1.31) |
| Gaucher disease | β-glucocerebrosidase (EC 3.2.1.45) |
| Fabry's disease | α-galactosidase A (EC 3.2.1.22) |
| Pompe disease | acid α-glucosidase (GAA) (EC 3.2.1.20) |

MPS-I—Hurler Syndrome

Hurler syndrome, also known as mucopolysaccharidosis type-I (MPS-I), Hurler's disease, also gargoylism, is an autosomal recessive genetic disorder that results in the build-up of glycosaminoglycans (GAGs) (or mucopolysaccharides) due to a deficiency or absence of α-L-iduronidase (IDUA), an enzyme responsible for the degradation of mucopolysaccharides in lysosomes. Without this enzyme, a build-up of heparan sulfate and dermatan sulfate occurs in the body. Heparan sulfate and dermatan sulfate are components of the extracellular matrix, participating in various biological processes such as cellular proliferation, differentiation and wound healing. Heparan sulfate is preferentially expressed in the lung, arteries and at cell surfaces. Dermatan sulfate is preferentially expressed in skin, blood vessels, the heart and heart valves.

Symptoms of MPS-I appear during childhood and early death can occur due to organ damage. Overall incidence is about 1 in 100,000 live births. MPS-I is divided into three subtypes based on severity of symptoms. All three types result from an absence of, or insufficient levels of, the enzyme α-L-iduronidase. MPS-I H or Hurler syndrome is the most severe of the MPS-I subtypes. The other two types are MPS-I S or Scheie syndrome and MPS-I H-S or Hurler-Scheie syndrome are both characterised by reduced expression of IDUA. Hurler syndrome is often classified as a LSD, and is clinically related to Hunter Syndrome. Hunter syndrome is X-linked while Hurler syndrome is autosomal recessive.

Children born to an MPS-I parent carry a defective IDUA gene, which has been mapped to the 4p16.3 site on chromosome 4. The gene is named IDUA because of its iduronidase enzyme protein product. There is a large genetic heterogeneity associated with IDUA with at least 30 non-pathogenic polymorphisms. As of 2001, 52 different mutations in the IDUA gene have been shown to cause Hurler syndrome. Because Hurler syndrome is an autosomal recessive disorder, affected persons have two non-working copies of the IDUA gene. If someone is born with one normal and one defective copy of the gene they are called a carrier and will produce less α-L-iduronidase than an individual with two normal copies of the gene. The slightly reduced production of the enzyme in carriers, however, remains sufficient for normal function and the person should not show any symptoms of the disease.

The condition is marked by progressive deterioration, hepatosplenomegaly, dwarfism and unique facial features. There is a progressive mental retardation, with death frequently occurring by the age of 10 years. Developmental delay is evident by the end of the first year, and patients usually stop developing between ages 2 and 4. This is followed by progressive mental decline and loss of physical skills. Language may be limited due to hearing loss and an enlarged tongue. In time, the clear layers of the cornea become clouded and retinas may begin to degenerate. Carpal tunnel syndrome (or similar compression of nerves elsewhere in the body) and restricted joint movement are common.

Affected children may be large at birth and appear normal but may have inguinal (in the groin) or umbilical (where the umbilical cord passes through the abdomen) hernias. Growth in height may be initially faster than normal, then begins to slow before the end of the first year and often ends around age 3. Many children develop a short body trunk and a maximum stature of less than 4 feet. Distinct facial features (including flat face, depressed nasal bridge, and bulging forehead) become more evident in the second year. By age 2, the ribs have widened and are oar-shaped. The liver, spleen and heart are often enlarged. Children may experience noisy breathing and recurring upper respiratory tract and ear infections. Feeding may be difficult for some children, and many experience periodic bowel problems. Children with Hurler syndrome often die before age 10 from obstructive airway disease, respiratory infections, or cardiac complications.

Diagnosis often can be made through clinical examination and urine tests (excess mucopolysaccharides are excreted in the urine). Enzyme assays (testing a variety of cells or body fluids in culture for enzyme deficiency) are also used to provide definitive diagnosis of one of the mucopolysaccharidoses. Prenatal diagnosis using amniocentesis and chorionic villus sampling can verify if a fetus either carries a copy of the defective gene or is affected with the disorder. Genetic counselling can help parents who have a family history of the mucopolysaccharidoses determine if they are carrying the mutated gene that causes the disorders.

Enzyme replacement therapies are currently in use. BioMarin Pharmaceutical provides therapeutics for mucopolysaccaradosis type I (MPS-I), by manufacturing laronidase (Aldurazyme), commercialized by Genzyme. Enzyme replacement therapy has proven useful in reducing non-neurological symptoms and pain. Bone marrow transplantation (BMT) and umbilical cord blood transplantation (UCBT) can be used as treatments for MPS. Abnormal physical characteristics, except for those affecting the skeleton and eyes, can be improved, and neurologic degeneration can often be halted. BMT and UCBT are high-risk procedures with high rates of morbidity and mortality. There is no cure for MPS-I.

MPS-II—Hunter Syndrome

Hunter syndrome, or mucopolysaccharidosis-II (MPS-II), is a LSD caused by a deficient (or absent) enzyme, iduronate sulfatase. The accumulated substrates in Hunter syndrome are heparan sulfate and dermatan sulfate. The syndrome has X-linked recessive inheritance. The symptoms of Hunter syndrome (MPS-II) are generally not apparent at birth, but usually start to become noticeable after the first year of life. Often, the first symptoms of Hunter syndrome may include abdominal hernias, ear infections, runny noses, and colds, but this in itself may not lead to a diagnosis of Hunter syndrome, since these symptoms are quite common among all infants. As the build-up of glycosaminoglycans (GAG) continues throughout the cells of the body, signs of Hunter syndrome become more visible. Physical appearances of many children with Hunter syndrome include a distinctive coarseness in their facial features, including a prominent forehead, a nose with a flattened bridge, and an enlarged tongue. For this reason, unrelated children with Hunter syndrome often look alike. They may also have a large head as well as an enlarged abdomen. Many continue to have frequent infections of the ears and respiratory tract.

The continued storage of GAG in cells can lead to organs being affected in important ways. The thickening of the heart valves along with the walls of the heart can result in progressive decline in cardiac function. The walls of the airway may become thickened as well, leading to breathing problems while sleeping (obstructive airway disease) and noisy breathing generally. People with Hunter syndrome may also have limited lung capacity due to pulmonary involvement. As the liver and spleen grow larger with time, the belly may become distended, making hernias more noticeable. All major joints (including the wrists, elbows, shoulders, hips, and knees) may be affected by Hunter syndrome, leading to joint stiffness and limited motion. Progressive involvement of the finger and thumb joints results in decreased ability to pick up small objects. The effects on other joints, such as hips and knees, can make it increasingly difficult to walk normally. If carpal tunnel syndrome develops, a common symptom even in young children with Hunter syndrome, a further decrease in hand function can occur. The bones may be affected, resulting in short stature. In addition, pebbly, ivory-colored skin lesions may be found on the upper arms and legs and upper back of some people with Hunter syndrome. The presence or absence of the skin lesions is not helpful, however, in predicting clinical severity in Hunter syndrome. Finally, the storage of GAG in the brain can lead to delayed development with subsequent mental retardation and progressive loss of function. The rate and degree of progression may be different for each person with Hunter syndrome.

Although Hunter syndrome is associated with a broad spectrum of clinical severity, two main forms can be recognized—severe and mild/attenuated. The differences between the severe and attenuated forms are mainly due to the progressive development of neurodegeneration in the severe form. It is important to note, however, that though the terms "attenuated" or "mild" are used by physicians in comparing people with Hunter syndrome, the effects of even mild disease are quite serious. Between the two main forms of disease, and even within them, two of the most significant areas of variability concern the degree of mental retardation and expected lifespan. Some people who have Hunter syndrome experience no mental handicaps and live into their 20s or 30s; there are occasional reports of people who have lived into their 50s or 60s. Since the implementation of enzyme replacement therapy for Hunter syndrome, lifespans for those without mental handicaps are expected to lengthen since their physical disease appears to improve or stabilize with such treatment. The quality of life remains high in a large number of people, and many adults are actively employed.

In contrast, others with Hunter syndrome develop severe mental impairment and have life expectancies of 15 years or fewer often due to neurodegeneration or physical complications from the disease. The age at onset of symptoms and the presence/absence of behavioural disturbances are predictive factors of ultimate disease severity in very young patients. Behavioural disturbances can often mimic combinations of symptoms of attention deficit hyperactivity disorder, autism, obsessive compulsive disorder, and/or sensory processing disorder, although the existence and level of symptoms may differ in each affected child. They often also include a lack of an appropriate sense of danger and aggression. The behavioral symptoms of Hunter syndrome generally precede neurodegeneration and often increase in severity until the mental handicaps become more pronounced.

Hunter syndrome, is a serious genetic disorder that primarily affects males (X-linked recessive). It interferes with the body's ability to break down and recycle specific mucopolysaccharides, also known as glycosaminoglycans or GAG. Hunter syndrome is one of several related lysosomal storage diseases.

In Hunter syndrome, GAG builds up in cells throughout the body due to a deficiency or absence of the enzyme iduronate sulfatase. This build-up interferes with the way certain cells and organs in the body function and leads to a number of serious symptoms. As the build-up of GAG continues throughout the cells of the body, signs of Hunter syndrome become more visible. Physical manifestations for some people with Hunter syndrome include distinct facial features and large head. In some cases of Hunter syndrome, central nervous system involvement leads to developmental delays and nervous system problems. Not all people with Hunter syndrome are affected by the disease in exactly the same way, and the rate of symptom progression varies widely. However, Hunter syndrome is always severe, progressive, and life-limiting.

Since Hunter syndrome is an inherited disorder (X-linked recessive) that primarily affects males, it is passed down from one generation to the next in a specific way. Nearly every cell in the human body has 46 chromosomes, with 23 derived from each parent. The causative gene is located on the X chromosome. Females have two X chromosomes, one inherited from each parent, whereas males have one X chromosome that they inherit from their mother and one Y chromosome that they inherit from their father. If a male has an abnormal copy of the IDS gene, he will develop Hunter syndrome. A male can obtain an abnormal copy of the causative gene in one of two ways. His mother is often a carrier; i.e., she has one abnormal and one normal IDS gene, and she passes along the abnormal gene to him. Alternatively, during egg and sperm formation, a mutation can develop in the IDS gene on his X chromosome. In this second case, the mother is not a carrier and the risk of a spontaneous mutation occurring again in a future sibling is low but not zero. Females can carry one abnormal copy of the IDS gene and are usually not affected.

The human body depends on a vast array of biochemical reactions to support critical functions, including the production of energy, growth and development, communication within the body, and protection from infection. Another critical function is the breakdown of large biomolecules, which is the underlying problem in Hunter syndrome (MPS-II) and related storage disorders. The biochemistry of Hunter syndrome is related to a problem in a part of the connective tissue of the body known as the extracellular matrix. This matrix is made up of a variety of sugars and proteins and helps to form the architectural framework of the body. The matrix surrounds the cells of the body in an organized meshwork and functions as the glue that holds the cells of the body together. One of the parts of the extracellular matrix is a complex molecule called a proteoglycan. Like many components of the body, proteoglycans need to be broken down and replaced. When the body breaks down proteoglycans, one of the resulting products is mucopolysaccharides, otherwise known as glycosaminoglycans (GAGs). There are several types of GAG, each found in certain characteristic places in the body In Hunter syndrome, the problem concerns the breakdown of two GAG: dermatan sulfate and heparan sulfate. The first step in the breakdown of dermatan sulfate and heparan sulfate requires the lysosomal enzyme iduronate sulfatase. In people with Hunter syndrome, this enzyme is either partially or completely inactive. As a result, GAG build up in cells throughout the body, particularly in tissues that contain large amounts of dermatan sulfate and heparan sulfate. As this build-up continues, it interferes with the way certain cells and organs in the body function and leads to a number of serious symptoms. The rate of GAG build-up is not the same for all people with Hunter syndrome, resulting in a wide spectrum of medical problems.

The visible signs and symptoms of Hunter syndrome (MPS-II) in younger people are usually the first clues leading to a diagnosis. In general, the time of diagnosis usually occurs from about 2 to 4 years of age. Doctors may use laboratory tests to provide additional evidence that an MPS disorder is present, before making a definitive diagnosis by measuring the iduronate sulfatase enzyme activity. The most commonly used laboratory screening test for an MPS disorder is a urine test for GAG. It is important to note that the urine test for GAG can occasionally be normal and yet the child still may have an MPS disorder. A definitive diagnosis of Hunter syndrome is made by measuring enzyme activity in serum, white blood cells, or fibroblasts from skin biopsy. In some people with Hunter syndrome, analysis of the causative gene can determine clinical severity. Prenatal diagnosis is routinely available by measuring iduronate sulfatase enzymatic activity in amniotic fluid or in chorionic villus tissue.

Because of the very specific nature of the illness, treatment has been proven very difficult. The treatment for this disorder can usually be diagnosed specifically for specific patients because all cases are different. Because of the nature of the illness, and absent a really efficient treatment, it is important to emphasize the need for extensive palliative treatment against the diverse symptoms. Their objective is to reduce the effects of the deterioration of many bodily functions. In light of the diversity of symptoms, it is quite common to use a wide spectrum of palliative strategies where surgery and therapies are often pivotal. For a long time, the most efficient approach had been to use bone marrow graft, emerging into hematopoietic stem cell transplantation. Based upon the same theory, they each have the advantage of procuring a new source of the affected causative gene. However, the results have been considered imperfect at best. While this treatment alternative is able to improve or stop the progression of some of the physical symptoms, it does not prevent the eventual cognitive regression that occurs in Hunter syndrome patients who are cognitively affected, although it may slow such regression early on. Therefore, for attenuated patients, this may still serve as a viable treatment option because of its more permanent nature, possibly even equivalent to weekly enzyme replacement therapy, resulting in much improved life expectancy. However, even for attenuated patients, it is a major intervention with not insignificant mortality risks and potential for life-threatening or altering complications such as graft-versus-host disease. For cognitively affected patients, without solving the challenge of cognitive regression, it is limited at best as a permanent treatment alternative. Because of all these reasons, grafts have seen a decrease in their application as Hunter syndrome treatment.

MPS-IV—Morquio's Syndrome

Morquio's syndrome (referred to as mucopolysaccharidosis-IV, MPS-IV, Morquio-Brailsford syndrome, or Morquio) is an autosomal recessive mucopolysaccharide storage disease (a LSD), usually inherited. It is a rare type of birth defect with serious consequences. When the body cannot process certain types of mucopolysaccharides, they build up or are eliminated, causing various symptoms. These involve accumulation of keratan sulfate.

The following signs are associated with Morquio's syndrome: Abnormal heart development, abnormal skeletal development, hypermobile joints, large fingers, knock-knees, widely spaced teeth, bell-shaped chest (flared ribs), compression of spinal cord, enlarged heart, dwarfism, heart murmur, and below average height for certain age. Patients with Morquio's syndrome appear healthy at birth. They often present with spinal deformity, and there is growth retardation and possibly genu valgum in the second or third year of life. A patient with Morquio's syndrome is likely to die at an early age. Other signs and symptoms of the disease may include: Short stature and short neck (caused by flat vertebrae), moderate kyphosis or scoliosis, mild pectus carinatum ("pigeon chest"), cervical spine: odontoid hypoplasia, atlanto-axial instability; may be associated with myelopathy with gradual loss of walking ability, joint laxity, mild dysostosis multiplex, dysplastic hips, large unstable knees, large elbows and wrists, and flat feet. The combined abnormalities usually result in a duck-waddling gait, mid-face hypoplasia and mandibular protrusion, thin tooth enamel, corneal clouding, and mild hepatosplenomegaly. Regarding the life span of people with Morquio, some can die as early as 2 or 3 years old, and some can live up to 60 or 70 years old. The treatment for Morquio's syndrome consists of prenatal identification and of enzyme replacement therapy.

MPS-VI—Maroteaux-Lamy Syndrome

Maroteaux-Lamy syndrome (also known as mucopolysaccharidosis type-VI, MPS-VI, or polydystrophic dwarfism) is a form of mucopolysaccharidosis. Children with Maroteaux-Lamy syndrome, usually have normal intellectual development but share many of the physical symptoms found in Hurler syndrome. Caused by the deficient enzyme N-acetylgalactosamine-4-sulfatase, Maroteaux-Lamy syndrome has a variable spectrum of severe symptoms. Neurological complications include clouded corneas, deafness, thickening of the dura (the membrane that surrounds and protects the brain and spinal cord), and pain caused by compressed or traumatized nerves and nerve roots.

Signs are revealed early in the affected child's life, with one of the first symptoms often being a significantly prolonged age of learning how to walk. By age 10 children have developed a shortened trunk, crouched stance, and restricted joint movement. In more severe cases, children also develop a protruding abdomen and forward-curving spine. Skeletal changes (particularly in the pelvic region) are progressive and limit movement. Many children also have umbilical MPS-VII—Sly Syndrome Sly syndrome, also called Mucopolysaccharidosis Type-VII or MPS, is an autosomal recessive LSD characterized by a deficiency of the enzyme β-glucuronidase, a lysosomal enzyme. Sly syndrome belongs to a group of disorders known as mucopolysaccharidoses, which are LSD. In Sly syndrome, the deficiency in β-glucuronidase leads to the accumulation of certain complex carbohydrates (mucopolysaccharides) in many tissues and organs of the body. Sly syndrome has an autosomal recessive pattern of inheritance. The defective gene responsible for Sly syndrome is located on chromosome 7.

The symptoms of Sly syndrome are similar to those of Hurler syndrome (MPS-I). The symptoms include; (i) in the head, neck, and face: coarse (Hurler-like) facies and macrocephaly, frontal prominence, premature closure of sagittal lambdoid sutures, and J-shaped sella turcica; (ii) in the eyes: corneal opacity and iris coloboma; (iii) in the nose: anteverted nostrils and a depressed nostril bridge; (iv) in the mouth and oral areas: prominent alveolar processes and cleft palate; (v) in the thorax: usually pectus carinatum or exacavatum and oar-shaped ribs; also a protruding abdomen and inguinal or umbilical hernia (vi) in the extremities: talipes, an underdeveloped ilium, aseptic necrosis of femoral head, and shortness of tubular bones occurs; (vii) in the spine: kyphosis or scoliosis and hook-like deformities in thoracic and lumbar vertebrate; and (viii) in the bones: dysostosis multiplex. In addition recurrent pulmonary infections occur. Hepatomegaly occurs in the gastrointestinal system. Splenomegaly occurs in the hematopoietic system. Inborn mucopolysaccharide metabolic disorders due to β-glucuronidase deficiency with granular inclusions in granulocytes occurs in the biochemical and metabolic systems. Growth and motor skills are affected, and mental retardation also occurs.

Mucopolysaccharidosis Type-VII is also known as β-glucuronidase deficiency, β-glucuronidase deficiency mucopolysaccharidosis, GUSB deficiency, mucopolysaccharide storage disease VII, MCA, and MR.

Gaucher's Disease

Gaucher's disease or Gaucher disease is a genetic disease in which fatty substances (sphingolipids) accumulate in cells and certain organs. The disorder is characterized by bruising, fatigue, anemia, low blood platelets, and enlargement of the liver and spleen. It is caused by a hereditary deficiency of the enzyme glucocerebrosidase. This enzyme acts on the glycolipid glucocerebroside. When the enzyme is defective, glucosylceramide accumulates, particularly in white blood cells, most often macrophages (mononuclear leukocytes). Glucosylceramide can collect in the spleen, liver, kidneys, lungs, brain, and bone marrow.

Manifestations may include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets, and yellow fatty deposits on the white of the eye (sclera). Persons affected most seriously may also be more susceptible to infection. Some forms of Gaucher's disease may be treated with enzyme replacement therapy. The disease is caused by a recessive mutation in a gene located on chromosome 1 and affects both males and females. Gaucher's disease is the most common of the LSD. It is a form of sphingolipidosis (a subgroup of LSD), as it involves dysfunctional metabolism of sphingolipids.

Gaucher's disease has three common clinical subtypes. Type I (non-neuropathic Gaucher's disease) is the most common form of the disease, occurring in about one in 50,000 live births. It occurs most often among persons of Ashkenazi Jewish heritage. Symptoms may begin early in life or in adulthood and include enlarged liver and grossly enlarged spleen (together hepatosplenomegaly); the spleen can rupture and cause additional complications. Skeletal weakness and bone disease may be extensive. Spleen enlargement and bone marrow replacement cause anemia, thrombocytopenia, and leukopenia. The brain is not affected pathologically, but lung and, rarely, kidney impairment may occur. Patients in this group usually bruise easily (due to low levels of platelets) and experience fatigue due to low numbers of red blood cells. Depending on disease onset and severity, type I patients may live well into adulthood. The range and severity of symptoms can vary dramatically between patients. Type II (acute infantile neuropathic Gaucher's disease) typically begins within 6 months of birth and has an incidence rate around one 1 in 100,000 live births. Symptoms include an enlarged liver and spleen, extensive and progressive brain damage, eye movement disorders, spasticity, seizures, limb rigidity, and a poor ability to suck and swallow. Affected children usually die by age two. Type III (chronic neuropathic Gaucher's disease) can begin at any time in childhood or even in adulthood, and occurs in about one in 100,000 live births. It is characterized by slowly progressive, but milder neurologic symptoms compared to the acute or type II version. Major symptoms include an enlarged spleen and/or liver, seizures, poor coordination, skeletal irregularities, eye movement disorders, blood disorders including anemia, and respiratory problems. Patients often live into their early teen years and adulthood. Also, compound heterozygous variations occur which considerably increase the complexity of predicting disease course.

Painless hepatomegaly and splenomegaly: the size of the spleen can be 1500-3000 ml, as opposed to the normal size of 50-200 ml. Splenomegaly may decrease the affected individual's capacity for eating by exerting pressure on the stomach. While painless, enlargement of spleen increases the risk of splenic rupture. Hypersplenism and pancytopenia, the rapid and premature destruction of blood cells, leads to anemia, neutropenia, leukopenia, and thrombocytopenia (with an increased risk of infection and bleeding). Cirrhosis of the liver is rare. Severe pain associated with joints and bones occurs, frequently presenting in hips and knees. Neurological symptoms occur only in some types of Gaucher's: Type I: impaired olfaction and cognition; Type II: serious convulsions, hypertonia, mental retardation, and apnea; Type III: muscle twitches known as myoclonus, convulsions, dementia, and ocular muscle apraxia. Parkinson's disease is recognised as being more common in Gaucher's disease patients and their heterozygous carrier relatives. Osteoporosis: 75% of patients develop visible bony abnormalities due to the accumulated glucosylceramide. A deformity of the distal femur in the shape of an Erlenmeyer flask is commonly described (aseptic necrosis of the femur joint).

The disease is caused by a defect in housekeeping gene for lysosomal glucocerebrosidase (also known as β-glucosidase, EC 3.2.1.45) on the first chromosome (1q22). The enzyme is a 55.6 kD, 497-amino acid-long protein that catalyses the breakdown of glucosylceramide, a cell membrane constituent of red and white blood cells. The macrophages that clear these cells are unable to eliminate the waste product, which accumulates in fibrils, and turn into 'Gaucher cells', which appear on light microscopy to resemble crumpled-up paper.

In the brain (type II and III), glucosylceramidase accumulates due to the turnover of complex lipids during brain development and the formation of the myelin sheath of nerves. Different mutations in the β-glucosidase gene determine the remaining activity of the enzyme, and, to a large extent, the phenotype. Heterozygotes for particular acid β-glucosidase mutations carry about a five-fold risk of developing Parkinson's disease, making this the most common known genetic risk factor for Parkinson's. The three types of Gaucher's disease are inherited in an autosomal recessive fashion. Both parents must be carriers for a child to be affected. If both parents are carriers, the chance of the disease is one in four, or 25%, with each pregnancy for an affected child. Genetic counselling and genetic testing are recommended for families who may be carriers of mutations.

Each type has been linked to particular mutations. In all, about 80 known mutations are grouped into three main types: Type I (N370S homozygote), the most common, also called the "non-neuropathic" type occurs mainly in Ashkenazi Jews, at 100 times the occurrence in the general populace. The median age at diagnosis is 28 years of age, and life expectancy is mildly decreased. There are no neurological symptoms. Type II (one or two alleles L444P) is characterized by neurological problems in small children. The enzyme is hardly released into the lysosomes. Prognosis is poor: most die before the age of three. Type III (also one or two copies of L444P, possibly delayed by protective polymorphisms) occurs in Swedish patients from the Norrbotten region. This group develops the disease somewhat later, but most die before their 30th birthday. The Gaucher-causing mutations may have entered the Ashkenazi Jewish gene pool in the early Middle Ages (48-55 generations ago).

Gaucher disease is suggested based on the overall clinical picture. Initial laboratory testing may include enzyme testing. Decreased enzyme levels will often be confirmed by genetic testing. Numerous different mutations occur; sequencing of the β-glucosidase gene is sometimes necessary to confirm the diagnosis. Prenatal diagnosis is available, and is useful when a known genetic risk factor is present. A diagnosis can also be implied by biochemical abnormalities such as high alkaline phosphatase, angiotensin-converting enzyme, and immunoglobulin levels, or by cell analysis showing "crinkled paper" cytoplasm and glycolipid-laden macrophages. Some lysosomal enzymes are elevated, including tartrate-resistant acid phosphatase, hexosaminidase, and a human chitinase, chitotriosidase. This latter enzyme has proved to be very useful for monitoring Gaucher's disease activity in response to treatment, and may reflect the severity of the disease For those with type-I and most type-III, life-long enzyme replacement treatment with intravenous recombinant glucocerebrosidase can decrease liver and spleen size, reduce skeletal abnormalities, and reverse other manifestations. The rarity of the disease means dose-finding studies have been difficult to conduct, so controversy remains over the optimal dose and dosing frequency.

Fabry Disease

Fabry disease (also known as Fabry's disease, Anderson-Fabry disease, angiokeratoma corporis diffusum, and α-galactosidase A deficiency) is a rare genetic LSD, inherited in an X-linked manner. Fabry disease can cause a wide range of systemic symptoms. It is a form of sphingolipidosis, as it involves dysfunctional metabolism of sphingolipids. A deficiency of the enzyme α galactosidase A (a-GAL A, encoded by GLA) due to mutation causes a glycolipid known as globotriaosylceramide (abbreviated as Gb3, GL-3, or ceramide trihexoside) to accumulate within the blood vessels, other tissues, and organs. This accumulation leads to an impairment of their proper functions.

The DNA mutations which cause the disease are X-linked recessive with incomplete penetrance in heterozygous females. The condition affects hemizygous males (i.e., all males), as well as homozygous, and in many cases heterozygous females. While males typically experience severe symptoms, women can range from being asymptomatic to having severe symptoms. New research suggests many women suffer with severe symptoms ranging from early cataracts or strokes to hypertrophic left ventricular heart problems and renal failure. This variability is thought to be due to X-inactivation patterns during embryonic development of the female.

Symptoms are typically first experienced in early childhood and can be very difficult to understand; the rarity of Fabry disease to many clinicians sometimes leads to misdiagnoses. Manifestations of the disease usually increase in number and severity as an individual ages. Full body or localized pain to the extremities (known as acroparesthesia) or gastrointestinal (GI) tract is common in patients with Fabry disease. This acroparesthesia is believed to be related to the damage of peripheral nerve fibers that transmit pain. GI tract pain is likely caused by accumulation of lipids in the small vasculature of the GI tract which obstructs blood flow and causes pain. Kidney complications are a common and serious effect of the disease; renal insufficiency and renal failure may worsen throughout life. Proteinuria (which causes foamy urine) is often the first sign of kidney involvement. End-stage renal failure in Fabry patients can typically occur in the third decade of life, and is a common cause of death due to the disease. Cardiac complications occur when glycolipids build up in different heart cells; heart-related effects worsen with age and may lead to increased risk of heart disease. High blood pressure and cardiomyopathy are commonly observed. Angiokeratomas (tiny, painless papules that can appear on any region of the body, but are predominant on the thighs, around the belly button, buttocks, lower abdomen, and groin) are common. Anhidrosis (lack of sweating) is a common symptom, and less commonly hyperhidrosis (excessive sweating). Additionally, patients can exhibit Raynaud's disease-like symptoms with neuropathy (in particular, burning extremity pain). Ocular involvement may be present showing cornea verticillata (also known as vortex keratopathy), i.e., clouding of the corneas. Keratopathy may be the presenting feature in asymptomatic patients, and must be differentiated from other causes of vortex keratopathy (e.g., drug deposition in the cornea). This clouding does not affect vision. Other ocular findings can include conjunctival and retinal vascular abnormalities, and anterior/posterior spoke-like cataract. Visual reduction from these manifestastions are uncommon. Fatigue, neuropathy (in particular, burning extremity pain), cerebrovascular effects leading to an increased risk of stroke, tinnitus (ringing in the ears), vertigo, nausea, inability to gain weight, chemical imbalances, and diarrhea are other common symptoms.

Fabry disease is suspected based on the individual's clinical presentation, and can be diagnosed by an enzyme assay (usually done on leukocytes) to measure the level of α-galactosidase activity. An enzyme assay is not reliable for the diagnosis of disease in females due to the random nature of X-inactivation. Molecular genetic analysis of the GLA gene is the most accurate method of diagnosis in females, particularly if the mutations have already been identified in male family members. Many disease-causing mutations have been noted. Kidney biopsy may also be suggestive of Fabry disease if excessive lipid build-up is noted. Pediatricians, as well as internists, commonly misdiagnose Fabry disease. Pain associated with Fabry disease can be partially alleviated by ERT, but pain management regimens may also include analgesics, anticonvulsants, and nonsteroidal anti-inflammatory drugs, though the latter are usually best avoided in renal disease.

Life expectancy with Fabry disease for males was 58.2 years, compared with 74.7 years in the general population, and for females 75.4 years compared with 80.0 years in the general population, according to registry data from 2001 to 2008. The most common cause of death was cardiovascular disease, and most of those had received kidney replacements.

Glycogen Storage Diseases (GSD)

Glycogen storage disease (GSD, also glycogenosis and dextrinosis) is the result of defects in the processing of glycogen synthesis or breakdown within muscles, liver, and other cell types. GSD has two classes of cause: genetic and acquired. Genetic GSD is caused by any inborn error of metabolism (genetically defective enzymes) involved in these processes. In livestock, acquired GSD is caused by intoxication with the alkaloid castanospermine. There are eleven distinct diseases that are commonly considered to be glycogen storage diseases (GSD types-I, -II, -III, -IV, -V, -VI, -VII, -IX, -XI, -XII, and -XIII).

GSD type-II (also called Pompe disease or acid maltase deficiency) is an autosomal recessive metabolic disorder which damages muscle and nerve cells throughout the body. It is caused by an accumulation of glycogen in the lysosome due to deficiency of the lysosomal acid α-glucosidase enzyme (GAA). Newly synthesised GAA is cleaved into give the mature form of GAA.

Pompe is the only GSD with a defect in lysosomal metabolism, and the first glycogen storage disease to be identified. Pompe may present during infancy (classic infantile-onset, or non-classic variant of infantile-onset) or later on in life. Typically, late-onset Pompe is less severe than infantile-onset Pompe. Pompe affects 5,000 to 10,000 people worldwide.

The build-up of glycogen causes progressive muscle weakness (myopathy) throughout the body and affects various body tissues, particularly in the heart, skeletal muscles, liver and nervous system. It can also causes macroglossia, muscle atrophy (including paraspinal muscle atrophy), respiratory distress, hypertrophic cardiomyopathy, and hepatomegaly. It has been reported in almost all ethnic populations. It has an autosomal recessive inheritance pattern. This means the defective gene is located on an autosome, and two copies of the gene—one from each parent—are required to be born with the disorder. As with all cases of autosomal recessive inheritance, children have a 1 in 4 chance of inheriting the disorder when both parents carry the defective gene, and although both parents carry one copy of the defective gene, they are usually not affected by the disorder.

The levels of α-glucosidase tend to determine the type of GSD-II an individual may have. More α-glucosidase present in the individuals' muscles means symptoms occur later in life and progress more slowly. GSD II is broadly divided into two onset forms based on the age symptoms occur. Infantile-onset form is usually diagnosed at 4-8 months; muscles appear normal but are limp and weak preventing them from lifting their head or rolling over. As the disease progresses heart muscles thicken and progressively fail. Without treatment death usually occurs due to heart failure and respiratory weakness. Late/later onset form occurs later than one to two years and progresses more slowly than infantile-onset form. One of the first symptoms is a progressive decrease in muscle strength starting with the legs and moving to smaller muscles in the trunk and arms, such as the diaphragm and other muscles required for breathing. Respiratory failure is the most common cause of death. Enlargement of the heart muscles and rhythm disturbances are not significant features but do occur in some cases.

The infantile form usually comes to medical attention within the first few months of life. The usual presenting features are cardiomegaly (92%), hypotonia (88%), cardiomyopathy (88%), respiratory distress (78%), muscle weakness (63%), feeding difficulties (57%) and failure to thrive (50%). The main clinical findings include floppy baby appearance, delayed motor milestones and feeding difficulties. Moderate hepatomegaly may be present. Facial features include macroglossia, wide open mouth, wide open eyes, nasal flaring (due to respiratory distress), and poor facial muscle tone. Cardiopulmonary involvement is manifest by increased respiratory rate, use of accessory muscles for respiration, recurrent chest infections, decreased air entry in the left lower zone (due to cardiomegaly), arrhythmias, and evidence of heart failure. Median age at death in untreated cases is 8.7 months and is usually due to cardiorespiratory failure.

Late-onset form differs from the infantile principally in the relative lack of cardiac involvement. The onset is more insidious and has a slower progression. Cardiac involvement may occur but is milder than in the infantile form. Skeletal involvement is more prominent with a predilection for the lower limbs. Late-onset features include impaired cough, recurrent chest infections, hypotonia, progressive muscle weakness, delayed motor milestones, difficulty swallowing or chewing, and reduced vital capacity. Prognosis depends on the age of onset of symptoms, with a better prognosis being associated with later-onset disease.

The usual initial investigations include chest X-ray, electrocardiogram and echocardiography. Typical findings are those of an enlarged heart with non-specific conduction defects. Biochemical investigations include serum creatine kinase (typically increased 10 fold) with lesser elevations of the serum aldolase, aspartate transaminase, alanine transaminase and lactic dehydrogenase. Diagnosis is made by estimating the acid a glucosidase activity in either skin biopsy (fibroblasts), muscle biopsy (muscle cells), or in white blood cells. The choice of sample depends on the facilities available at the diagnostic laboratory. In the late-onset form, the findings on investigation are similar to those of the infantile form with the caveat that the creatinine kinases may be normal in some cases. The diagnosis is by estimation of the enzyme activity in a suitable sample.

The disease is caused by a mutation in a gene (acid α-glucosidase: also known as acid maltase) on long arm of chromosome 17 at 17q25.2-q25.3 (base pair 75,689,876 to 75,708,272). The gene spans approximately 20 kb and contains 20 exons with the first exon being noncoding. The coding sequence of the putative catalytic site domain is interrupted in the middle by an intron of 101 bp. The promoter has features characteristic of a 'housekeeping' gene. The GC content is high (80%) and distinct TATA and CCAAT motifs are lacking. Most cases appear to be due to three mutations. A transversion (T→G) mutation is the most common among adults with this disorder. This mutation interrupts a site of RNA splicing. However, Table 2 below summarises some of the typical mutations seen in the clinic.

TABLE 2

Examples of disease causing mutations in Pompe

| Mutation | Pathologic Variant | Percentage of Affected Individuals |
|---|---|---|
| c.525delT | p.Glu176Argfs*45 | 34% of Dutch cases<br>9% of US cases |
| c.2482_2646del<br>(Exon 18 del) | p.Gly828_Asn882del | 25% of infantile Dutch and Canadian cases<br>5% of US cases |
| c.336-13T > G | | 36%-90% of late-onset cases |
| c.1935C > A | p.Asp645Glu | |
| c.2560C > T<br>(nonsense) | p.Arg854* | Up to 60% of individuals of African descent |

The mutated gene in Pompe encodes a protein—acid α-glucosidase (EC 3.2.1.20)—which is a lysosomal hydrolase. The protein is an enzyme that normally degrades the α-1,4 and α-1,6 linkages in glycogen, maltose, and isomaltose and is required for the degradation of 1-3% of cellular glycogen. The deficiency of this enzyme results in the accumulation of structurally normal glycogen in lysosomes and cytoplasm in affected individuals. Excessive glycogen storage within lysosomes may interrupt normal functioning of other organelles and lead to cellular injury.

Cardiac and respiratory complications are treated symptomatically. Physical and occupational therapy may be beneficial for some patients. Alterations in diet may provide temporary improvement but will not alter the course of the disease. Genetic counselling can provide families with information regarding risk in future pregnancies. The prognosis for individuals with Pompe disease varies according to the onset and severity of symptoms. Without treatment the disease is particularly lethal in infants and young children.

The β-globin Locus Control Region and the Elongation Factor 1-α Short Isoform Promoter The locus control region (LCR) is a long-range cis-regulatory element that enhances expression of linked genes at ectopic chromatin sites. It functions in a copy number-dependent manner and is tissue-specific, as seen in the selective expression of β-globin genes in erythroid cells in vitro, in vivo and ex vitro. Expression levels of genes can be modified by the LCR and gene-proximal elements, such as promoters, enhancers, and silencers. The LCR functions by recruiting chromatin-modifying, coactivator, and transcription complexes. Its sequence is conserved in many vertebrates, and conservation of specific sites may suggest importance in function. The bLCR is required for normal regulation of β-globin gene expression. It maintains active chromatin domains, enhances expression in erythroid lineages, and protects the locus from negative position effects. The bLCR in mice and humans is found 6-22 kb upstream of the first globin gene (epsilon). The bLCR consists of 5 regions of erythroid-specific DNase I hypersensitivity (HS) and is functionally defined by its ability to confer on a gene linked in cis, physiological levels of gene expression that are directly proportional to gene copy number regardless of integration site in mice. Each bLCR DNase I HS site possesses a functional core region of 200-300 bp, which contains a high density of erythroid-specific and ubiquitous transcription factor-binding elements. The bLCR can drive high levels of erythroid-specific expression from heterologous non-erythroid promoters. This may require CAAT and CACCA, or GC-rich (for example, Sp1) elements. In one embodiment, bLCR is the sequence of SEQ ID NO: 10 or a variant thereof. In a preferred embodiment, the β-globin LCR is SEQ ID NO: 11 [sequence containing essential elements of the LCR], or a variant thereof.

The EF1α promoter is a constitutive promoter of that can be used to drive constitutive ectopic gene expression in vitro, in vivo, and ex vivo. In one embodiment, the EF1α promoter is human. In another embodiment, it is the sequence of SEQ ID NO: 12 or a variant thereof. In a preferred embodiment, the first intron in the naturally occurring EF1α promoter has been deleted resulting in the EF1α promoter short version of SEQ ID NO: 13, or a variant thereof.

As used in the present invention, "variants" may include truncations, deletions, mutations, and/or the addition of sequences not found in the naturally occurring sequence, that do not substantially alter the function of the sequence. Suitable methods readily apparent to the skilled person can be used to assay function. Truncations may refer to removal of about 1, 2, 5, 10, 25, 50, 100, 250, 500, 750, 1000 nucleotides from the 5' and/or 3' end of a sequence. In one embodiment, the function of the sequence may be to drive constitutive expression. In another embodiment, the function of the sequence may be to drive tissue-specific expression. The term "tissue-specific expression" refers to expression of a nucleotide sequence and/or polypeptide sequence in a defined tissue that is about 2-fold, 5-fold, 10-fold, 25-fold, 50-fold, 100-fold, 250-fold, 500-fold, 1000-fold, 5000-fold or 10000-fold higher than expression in other tissues. The term "tissue-specific expression" may also refer to expression of a nucleotide sequence and/or polypeptide sequence in a defined tissue, where expression of the nucleotide sequence and/or polypeptide sequence is not detected in any other tissue.

Vectors and Expression Cassettes

Erythrocytes are the most abundant cell lineage in the bloodstream and offer an attractive vehicle for expressing and delivering therapeutic proteins to several tissues. Genetic modification of the erythroid lineage to express a therapeutic gene at high levels is an effective strategy for systemic delivery, such as systemic delivery of a gene therapy vector. However, restriction of activity to the erythroid lineage may also limit efficiency where multi-lineage gene expression is also desirable. To achieve these characteristics in combination, in one embodiment, a lentiviral construct, or derivative thereof, containing vector and/or expression cassette, in which the transgene is under the transcriptional control of a constitutively acting EFS (elongation factor 1α promoter short version, in which the first intron is deleted) has been created. Alternatively, the transgene may be under the control of a different constitutively active promoter selected from the group consisting of the cytomegalovirus (CMV) promoter, the phosphoglycerate kinase (PGK) promoter, the simian virus 40 (SV40) promoter, the Ubiquitin C (UbC) promoter, the CAG promoter, the ubiquitous chromatin opening element (UCOE) promoter, the CD11b promoter, the Wiskott-Aldrich syndrome (WAS) promoter, and the Glyceraldehyde 3-phosphate dehydrogenase (GAPDH) promoter.

The one embodiment, vector, and/or expression cassette may include the full locus control region of the β-globin gene, or a variant thereof. In another embodiment, the vector and/or expression cassette can include the essential elements of the locus control region of the β-LCR which is known to upregulate expression of the β-globin family to high levels specifically in erythroid cells. The expression cassette of the invention may be a gene, or variant thereof, operably linked to a regulatory region. The regulatory region may comprise a bLCR, or variant thereof, operably linked to an EFS, or variant thereof. Alternatively, operable linkage may be to a constitutively active promoter selected from the group consisting of the CMV promoter, the PGK promoter, the SV40 promoter, the UbC promoter, the CAG promoter, the UCOE promoter, the CD11b promoter, the WAS promoter and the GAPDH promoter.

In one embodiment, the bLCR is operably linked to an EFS promoter to form the regulatory region of the invention. In a further embodiment, the regulatory region regulates the expression of a transgene operably linked to the regulatory region. The regulatory region may comprise or consist of SEQ ID NO: 1 or a sequence having at least about 60%, 70%, 80%, 90%, 95%, 96%, 97%, 98%, or 99% sequence identity to SEQ ID NOs: 1.

In a further embodiment, the vector and/or expression cassette is present at a copy number of 1, 2, 3, 4, 5, 6, 7, 8, 9, 10, 11, 12, 13, 14, 15, 16, 17, 18, 19 or 20 copies per cell. In a preferred embodiment, the vector and/or expression cassette is present at a copy number of 1, 2 or 3 copies per cell. In another embodiment, the vector and/or expression cassette is present at an average copy number of 0.5, 1, 2, 3, 4, 5, 6, 7, 8, 9, or 10 copies in a population of cells. In another embodiment, the vector and/or expression cassette is present at an average copy number of from 0.5 to 1, 0.5 to 1.5, 0.5 to 2, 0.5 to 2.5, 0.5 to 3, 0.5 to 4, 0.5 to 5, 0.5 to 6, 0.5 to 7, 0.5 to 8, 0.5 to 9, 0.5 to 10, 1 to 1.5, 1 to 2, 1 to 2.5, 1 to 3, 1 to 4, 1 to 5, 1 to 6, 1 to 7, 1 to 8, 1 to 9, 1 to 10, 1.5 to 2, 1.5 to 2.5, 1.5 to 3, 1.5 to 4, 1.5 to 5, 1.5 to 6, 1.5 to 7, 1.5 to 8, 1.5 to 9, 1.5 to 10, 2 to 2.5, 2 to 3, 2 to 4, 2 to 5, 2 to 6, 2 to 7, 2 to 8, 2 to 9, 2 to 10, 2.5 to 3, 2.5 to 4, 2.5 to 5, 2.5 to 6, 2.5 to 7, 2.5 to 8, 2.5 to 9, 2.5 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10 copies per cell. In a preferred embodiment, the vector and/or expression cassette is present at an average copy number of from 0.5 to 2 in said population.

The transgene operably linked to the regulatory region may encode the enzymes α-L-iduronidase (IDUA) (EC 3.2.1.76); iduronate sulfatase (EC 3.1.6.13); N-acetylgalactosamine 6-sulfatase (EC 3.1.6.4); N-acetylgalactosamine 4-sulfatase (EC 3.1.6.12); β-glucuronidase (3.2.1.31); β-glucocerebrosidase (EC 3.2.1.45); α-galactosidase A (EC 3.2.1.22); and/or acid α-glucosidase (GAA) (EC 3.2.1.20). The transgene encoding the enzyme of the invention may be selected from any of SEQ ID NOs: 2 to 9, or a variant thereof. The variant may be defined as having at least about 60%, 70%, 80%, 90%, 95%, 96%, 97%, 98%, or 99% sequence identity to any one of SEQ ID NOs: 2 to 9, based on nucleotide identity over the entire sequence. In a preferred embodiment, the transgene is a sequence, or variant thereof, encoding the enzyme α-L-iduronidase (IDUA) (EC 3.2.1.76). In another preferred embodiment, the transgene is a sequence, or variant thereof, encoding the enzyme acid α-glucosidase (GAA) (EC 3.2.1.20).

Sequence identity may be calculated using any suitable algorithm. For example the PILEUP and BLAST algorithms can be used to calculate identity or line up sequences (such as identifying equivalent or corresponding sequences (typically on their default settings), for example as described in (Altschul 1993; and Altschul et al. 1990). Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al. supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (Henikoff and Henikoff 1992) alignments (B) of 50, expectation (E) of 10, M=5, N=4, and a comparison of both strands.

The BLAST algorithm performs a statistical analysis of the similarity between two sequences; see e.g., (Karlin and Altschul 1993). One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate identity (for example used on its default settings) (Devereux et al. 1984).

The vector and/or expression cassette of the invention may be prepared by standard means known in the art for provision of vectors and/or expression cassettes for gene therapy. Thus, well established public domain transfection and/or transduction, packaging and purification methods can be used to prepare a suitable vector preparations, and suitable viral particles (see below). In one embodiment, the vector may contain the full genome of a naturally occurring lentivirus, or a variant thereof. In an alternative embodiment, the vector may contain a partial genome of a naturally occurring lentivirus, or a variant thereof.

The present invention provides a vector comprising the expression cassette of the invention. In a preferred embodiment, the vector is a lentiviral vector. Lentiviral (and in particular human immunodeficiency virus (HIV)) vectors are well known in the art. These are plasmids that comprise a number of the elements of the lentivirus genome, but do not comprise packaging signals that are required for packaging the RNA produced from the plasmid into virions. In particular, vectors comprise all the elements of the HIV genome required to make replication incompetent viral particles (but without any of the packaging signals). These elements may be present on a single vector. Alternatively, these elements may be split across vectors. HIV vectors may comprise HIV structural proteins, but lacks the LTRs necessary for integration into the host cell genome. The vector may also typically lacks the Ψ signal necessary for packaging of viral RNA into virions. The vector of the invention may comprise the expression cassette of the invention (i.e., an expression cassette comprising a regulatory region in which a bLCR is operably linked to an EFS promoter, wherein said regulatory region regulates the expression of a transgene operably linked to said regulatory region). Alternatively, operable linkage may be to a constitutively active promoter selected from the group consisting of the CMV promoter, the PGK promoter, the SV40 promoter, the UbC promoter, the CAG promoter, the UCOE promoter, the CD11b promoter, the WAS promoter and the GAPDH promoter.

The term "operably linked" refers to a juxtaposition wherein the components described are in a relationship permitting them to function in their intended manner. A control sequence (e.g., an LCR and/or EFS sequence) "operably linked" to a coding sequence (i.e., selected from SEQ ID NOs: 2 to 9, or a variant thereof) is ligated in such a way that expression of the coding sequence is achieved under conditions compatible with the control sequences.

The vector may additionally comprise polynucleotides encoding additional elements of the HIV-1 genome, such as a polynucleotide encoding HIV-1 Rev, Tat, Vif, Vpr, Vpu and Nef. The vector may comprise all of the HIV viral proteins, except the envelope (Env) protein. The vector may additionally comprise polynucleotides encoding HIV-1 Rev and Tat. This vector may then additionally comprise polynucleotides encoding HIV-1 Vif, Vpr, Vpu and Nef. Vectors such as these are known in the art and are standard HIV vectors. All of the additional components described above, such as HIV-1 Pol, Rev, Tat, Vif, Vpr, Vpu and Nef may be present on the same vector as the construct of the invention, or may instead be present on one or more additional vectors. These components may be arranged in any suitable number of vectors and in any suitable way that results in production of replication incompetent HIV virions once the packaging plasmids are introduced into host cells (see below).

The vector or expression cassette may be of retrovirus, lentivirus, adenovirus or adeno-associated virus origin. In a preferred embodiment, the vector or expression cassette of lentivirus origin may be based on a third generation CCL backbone, in which the transgene may be is flanked by an LTR and cPPT at the 5' end, and a wPRE sequence and a LTR lacking the U3 region at the 3' end.

Lentiviral Production and Transduction of Host Cell

Lentiviruses are a subclass of retroviruses. They have been adapted as gene delivery vehicles thanks to their ability to integrate into the genome of non-dividing host cells, which is the unique feature of lentiviruses as other retroviruses can infect only dividing host cells. The viral genome in the form of RNA is reverse-transcribed when the virus enters the host cell to produce DNA, which is then inserted into the genome at a random position by the viral integrase enzyme. The interred genetic material remains in the genome and is passed on to the progeny of the host cell when it divides. For safety reasons lentiviral vectors usually does not carry the genes required for their replication. To produce a lentivirus, several plasmids are transfected into a so-called packaging cell line, commonly Human Embryonic Kidney (HEK) 293. One or more plasmids, generally referred to as packaging plasmids, encode virion proteins, such as the capsid and the reverse transcriptase. Another plasmid contains the genetic material to be delivered by the vector (i.e., the vector of the present invention). It is transcribed to produce the single-stranded RNA viral genome and is marked by the presence of the ψ (psi) sequence. This sequence is used to package the genome into the virion.

Packaging plasmids (including vectors and/or expression cassettes of the invention) may be constructed by standard methodology known in the art, for example using standard molecular biology techniques, sub-cloning using restriction enzymes and/or PCR. Any suitable cell can be used to produce lentiviral stocks containing the vectors and/or expression cassettes of the invention. In general, such cells will be transfected mammalian cells but other cell types, e.g., insect cells, can also be used. In one embodiment, the cell is a mammalian cell. In a preferred embodiment, the cell is a HEK293T cell. In further embodiment, the lentiviral stocks (i.e., viral suspensions) may be produced in HEK293T cells by cotransfection of the packaging plasmids pMD.G2 (VSVG envelope plasmid) and pCMVΔ8.91 (gag-pol plasmid) with the corresponding lentiviral construct (i.e., the expression cassette of the invention), using polyethylenimine (Sigma-Aldrich).

Vector titre can be determined by standard methodology known in the art, for example by harvesting HEK293T cells transduced with serial dilution of the viral suspension and use of flow cytometry and/or quantitative RT-PCT.

In a preferred embodiment, lentiviral stocks are used to transduce the host cell and/or cell populations of the invention by standard methodology known in the art. In one embodiment, the host cell and/or cell population is a mammalian cell. In another embodiment, the host cell and/or cell population is a human cell. In one embodiment, the host cell and/or cell population is a bone marrow cell. In one embodiment, the host cell and/or cell population is a haematopoietic stem cell (HSC) and/or a haematopoietic progenitor cell. In one embodiment, the host cell and/or cell population is a common myeloid progenitor. In one embodiment, the host cell and/or cell population is a granulocyte-macrophage progenitor. In one embodiment, the host cell and/or cell population is a megakaryocyte-erythroid progenitor cell. In one embodiment, the host cell and/or cell population is a macrophage.

In one embodiment, the vector and/or expression cassette design is used to drive transgene expression in a mammalian cell. In another embodiment, the vector and/or expression cassette design is used to drive transgene expression in a human cell. In another embodiment, the vector and/or expression cassette design is used to drive transgene expression in all haematopoietic lineages. In another embodiment, this vector and/or expression cassette design is used to drive transgene expression in HSCs and/or a haematopoietic progenitor cells and/or a population of HSCs and/or haematopoietic progenitor cells. In another embodiment, this vector and/or expression cassette design is used to drive transgene expression in a common myeloid progenitor. In another embodiment, this vector and/or expression cassette design is used to drive transgene expression in a granulocyte-macrophage progenitor. In another embodiment, this vector and/or expression cassette design is used to drive transgene expression in a megakaryocyte-erythroid progenitor cell. In another embodiment, this vector and/or expression cassette design is used to drive transgene expression in a macrophage. In another embodiment, this vector and/or expression cassette design is used to drive transgene expression in erythrocytes. In another embodiment, this vector and/or expression cassette design is used to drive transgene expression in any cells derived from a HSC. A cell derived from a HSC would be apparent to the skilled person.

In one embodiment, a method is provided to make the host cell and/or cell population of the invention by isolating by standard techniques known to the person skilled in the art a cell or cell population from a first organism. For example, the cells may be isolated from peripheral blood and/or by aspiration of the bone marrow. In a further embodiment, a vector and/or expression cassette of comprising the regulatory region of the invention, in which a bLCR is operably linked to an EFS promoter, which may regulate the expression of a transgene operably linked to the regulatory region, may be introduced into the cell or cell population. In a preferred embodiment, the vector is introduced into the host cell or cell population by viral transduction (see above). In a further embodiment, the isolated cell and/or cell population may be cultured, for example ex vivo using standard techniques. Suitable culture conditions would be apparent to the person skilled in the art. Cytokines selected from TPO, SCF, IL-3 and/or Flt-3 may be used to supplement culture media.

In a further embodiment, the isolated and/or cultured cell and/or cell population may be introduced into the first organism, a second organism that is related to the first organism, a second organism that is a tissue type match for the first organism, and/or a second organism with a different genetic background to the first organism. The isolated and/or cultured cell and/or cell population may be introduced into the first or second organism by direct injection into the blood and/or into the bone marrow.

As used here, a "cell population" refers to any group of two or more cells. A cell population may refer to about 10; 100; 500; 1000; 5000; 10,000; 50,000; 100,000; 500,000; 1,000,000; 5,000,000; 10,000,000; 50,000,000; 100,000,000; 500,000,000; or 1,000,000,000 cells. In another embodiment, a cell population may refer to about 100 or more cells. In another embodiment, individual cells in the cell population may be functionally distinct from each other, functionally similar to each other, and/or functionally identical to each other. Cells in the cell population may be from different lineages. In one preferred embodiment, the cells in the cell populations are from the same and/or similar lineages. In another embodiment, cells in the cell populations are from cells of the haematopoietic lineage. In another embodiment, cells in the cell population are from HSCs and/or haematopoietic progenitor cells. In another embodiment, cells in the cell population are from common myeloid progenitors, granulocyte-macrophage progenitors, megakaryocyte-erythroid progenitors, macrophages and/or erythrocytes. Cell populations may be derived from a single cell and/or population of cells, cultured ex vivo.

Methods of Therapy and Medical Uses

The promoters, regulatory regions, vectors, host cell, cell populations and/or expression cassettes of the invention may be used to treat LSD and GSD, in particular MSP-I or Pompe. Treatment may encompass correction of one or more peripheral aspects of MPS-I or Pompe. Treatment occurs through the sustained or transient release of enzyme from the host cell and/or a cell derived from the host cell. In one embodiment, release of the enzyme may be into the circulation. In another embodiment, release of the enzyme may be into a specific group of tissues and/or organs. In another embodiment, release of the enzyme may be into a specific tissue and/or organ. In one embodiment, the enzyme may be targeted to the central nervous system (CNS), heart, face, mouth, eye, bone, liver, spleen and/or lung. In one embodiment, treatment results in an about 2 log, 3 log, 4 log or 5 log increase in enzyme activity in the plasma and/or different organs and/or tissues. In one preferred embodiment, the activity of IDUA and/or GAA is increased. In one embodiment, levels of excreted glucose is reduced.

In one embodiment defects associated with LSDs, and in particular MPS-I are corrected. This may include cardiac aspects, in particular, peak velocity, transversal arch diameter, aortic valve peak pressure, aortic valve peak pressure, aortic flow rate, aortic dilation and/or mitral valve E/A ratio. In another embodiment, bone modelling defects of LSDs, and in particular MPS-I are corrected. Bone modelling defects can include bone volume fraction, trabecular thickness, trabecular separation, trabecular number, bone morphology, cortical bone area, total cross-sectional bone area, marrow area, cortical bone thickness, cortical bone porosity and/or bone length. In another embodiment, hearing defects associated with LSDs, and in particular MPS-I are corrected. In another embodiment, hepatosplenomegaly and/or dwarfism associated with LSDs, and in particular MPS-I is corrected. In another embodiment, facial defects associated with LSDs, and in particular MPS-I, such as flat face, depressed nasal bridge, and/or bulging forehead are corrected. In another embodiment, mental retardation, loss of physical skills and/or decline slowed associated with LSDs, and in particular MPS-I, are corrected. In another embodiment, an enlarged tongue associated with LSDs, and in particular MPS-I, is corrected. In another embodiment, clouded corneas and/or degenerated retinas associated with LSDs, and in particular MPS-I, are corrected. In another embodiment, carpal tunnel syndrome and/or restricted joint movement associated with LSDs, and in particular MPS-I, is corrected. In another embodiment, enlarged organs such as liver, spleen and/or heart associated with LSDs, and in particular MPS-I, are corrected. In another embodiment obstructive airway disease associated with LSDs, and in particular MPS-I, is corrected.

In one embodiment defects associated with GSDs, and in particular Pompe are corrected. They may include motor coordination, muscle strength, hypertrophic cardiomyopathy, cardiomegaly, hypotonia, respiratory function, feeding difficulties, and/or macroglossia.

Thus, the invention provides a means whereby the various phenotypes associated with MPS-I and Pompe can be correct, treated, arrested, palliated, and/or prevented. Correction can refer to both partial, total correction and hypercorrection. Correction may be achieved after about 10 days, 20 days, 30 days, 40 days, 50 days, 60 days, 70 days, 80 days, 90 days, 100 days, 125 days, 150 days, 175 days, 200 days, 250 days, 300 days, 1 year, 1.5 years, 2 years, 2.5 year, 3 years, 4 year or 5 years. In one particular embodiment, correction is achieved after 100 days. In another particular embodiment, correction is achieved after 200 days. In another particular embodiment, correction is achieved after 1 year. In another particular embodiment, correction is achieved after 2 years. In one embodiment, effects of correcting, treating, arresting, palliating and/or preventing a phenotype can be transient. In another embodiment, effects of correcting, treating, arresting, palliating and/or preventing a phenotype can be sustained.

In one embodiment, a method is provided to make the host cell and/or cell population of the invention for use in a method of preventing or treating LSD and/or GSD. In another embodiment, a method is provided to make the host cell and/or cell population of the invention in the manufacture of a medicament for the treatment and/or prevention of LSD and/or GSD. In another embodiment the host cell, population, cell for use, cell population for use, method or use of the invention, treat the disease Hurler syndrome when the transgene of the invention encodes α-L-iduronidase; Hunter syndrome when the transgene of the invention encodes iduronate sulfatase; Morquio syndrome when the transgene of the invention encodes N-acetylgalactosamine 6-sulfatase; Maroteaus-Lamy syndrome when the transgene of the invention encodes N-acetylgalactosamine 4-sulfatase; Sly syndrome when the transgene of the invention encodes β-glucuronidase; Gaucher disease when the transgene of the invention encodes β-glucocerebrosidase; Fabry's disease when the transgene of the invention encodes α-galactosidase A; and/or Pompe disease when the transgene of the invention encodes acid α-glucosidase.

The host cell and/or cell population of the invention may be made by isolating by standard techniques known to the person skilled in the art a cell or cell population from a first organism. For example, the cells may be isolated from peripheral blood and/or by aspiration of the bone marrow. In a further embodiment, a vector and/or expression cassette of comprising the regulatory region of the invention, in which a bLCR is operably linked to an EFS promoter, which may regulate the expression of a transgene operably linked to the regulatory region, may be introduced into the cell or cell population. Alternatively, operable linkage may be to a constitutively active promoter selected from the group consisting of the CMV promoter, the PGK promoter, the SV40 promoter, the UbC promoter, the CAG promoter, the UCOE promoter, the CD11b promoter, the WAS promoter and the GAPDH promoter.

In a preferred embodiment, the vector is introduced into the host cell or cell population by viral transduction (see above). In a further embodiment, the isolated cell and/or cell population may be cultured, for example ex vivo using standard techniques. Suitable culture conditions would be apparent to the person skilled in the art. Cytokines selected from TPO, SCF, IL-3 and/or Flt-3 may be used to supplement culture media.

In a further embodiment, the isolated and/or cultured cell and/or cell population may be introduced into the first organism, a second organism that is related to the first organism, a second organism that is a tissue type match for the first organism, and/or a second organism with a different genetic background to the first organism. The isolated and/or cultured cell and/or cell population may be introduced into the first or second organism by direct injection into the blood and/or into the bone marrow.

The invention provides a pharmaceutical composition comprising the host cell and/or cell population of the invention and a pharmaceutically acceptable carrier for use in a method of preventing or treating LSD or GSD.

The invention also provides a vector and/or expression cassette for use in a method of preventing and/or treating LSD and/or GSD.

The invention also provides the use of a host cell and/or cell population of the invention in the manufacture of a medicament for the treatment and/or prevention of LSD and/or GSD.

The invention also provides a method of treating or preventing LSD and/or GSD in a patient in need thereof comprising administering a therapeutically effective amount of a host cell and/or cell population of the invention to the patient.

The invention also provides a method of treating or preventing LSD and/or GSD in a patient in need thereof wherein: (i) the LSD is Hurler syndrome (MPS-I), Hunter syndrome (MPS-II), Morquio syndrome (MPS-IV), Maroteaux-Lamy syndrome (MPS-VI), Sly syndrome (MPS-VII), Gaucher disease and/or Fabry's disease; and/or (ii) the GSD is von Gierke's disease (GSD type I), Pompe disease (GSD type II), Cori's disease (GSD type III), Andersen disease (GSD type IV), McArdle disease (GSD type VI), Tarui's disease (GSD type VIII), GSD type IX, Fanconi-Bickel syndrome (GSD type XI), Red cell aldolase deficiency (GSD type XII), GSD type XIII and/or GSD type 0.

The invention also provides a method of treating or preventing LSD and/or GSD in a patient in need thereof, comprising administering a therapeutically effective amount of a cell and/or cell population of the invention to the patient by direct injection into the blood and/or bone marrow. Accordingly, LSD and/or GSD is thereby treated or prevented in said patient.

Additionally, the invention provides the use of the cell and/or cell population of the invention in the manufacture of a medicament for treating or preventing LSD and/or GSD by direct injection into the blood and/or bone marrow.

The invention also provides host cells and/or cell populations for use wherein said host cells and/or cell populations are administered directly into the blood and/or bone marrow.

In all these embodiments, the host cells and/or cell populations of the invention may be administered in order to prevent the onset of one or more symptoms of LSD and/or GSD. The patient may be asymptomatic. The subject may have a predisposition to the disease. The method or use may comprise a step of identifying whether or not a subject is at risk of developing, or has, LSD and/or GSD. A prophylactically effective amount of the cells and/or cell populations is administered to such a subject. A prophylactically effective amount is an amount which prevents the onset of one or more symptoms of the disease.

Alternatively, the host cells and/or cell populations may be administered once the symptoms of the disease have appeared in a subject i.e., to cure existing symptoms of the disease. A therapeutically effective amount is an amount which is effective to ameliorate one or more symptoms of the disease.

The subject may be male or female. The subject is preferably identified as being at risk of, or having, LSD and/or GSD.

The dose of the host cells and/or cell populations of the invention may be determined according to various parameters, especially according to the age, weight and condition of the patient to be treated; the route of administration; and the required regimen. A physician will be able to determine the required route of administration and dosage for any particular patient. The dose may be provided as a single dose, but may be repeated or in cases where vector may not have targeted the correct region and/or tissue (such as surgical complication). The treatment is preferably a single permanent treatment, but repeat injections, for example in future years and/or with different lentiviral serotypes may be considered.

Pharmaceutical Compositions and Dosages

The host cell and/or cell population of the invention can be formulated into pharmaceutical compositions. These compositions may comprise, in addition to the host cell and/or cell population, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may be determined by the skilled person according to the route of administration, for example direct injection into the blood and/or bone marrow.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as sodium chloride injection, Ringer's injection, lactated Ringer's injection, and Hartmann's solution. Preservatives, stabilisers, buffers, antioxidants, and/or other additives may be included, as required.

For delayed release, the vector may be included in a pharmaceutical composition which is formulated for slow release, such as in microcapsules formed from biocompatible polymers or in liposomal carrier systems according to methods known in the art.

Dosages and dosage regimes can be determined within the normal skill of the medical practitioner responsible for administration of the composition.

Combination Therapies

The promoters, expression cassettes, vectors, host cells, cell populations and/or pharmaceutical compositions can be used in combination with any other therapy for the treatment or prevention of LSD and/or GSD. The promoters, expression cassettes, vectors, host cells, cell populations and/or pharmaceutical compositions can be used in combination with any other targeted and non-targeted delivery mechanism, such as tagged enzymes and exosomes respectively.

Kits

The promoters, expression cassettes, vectors, host cells, cell populations and/or pharmaceutical compositions can be packaged into a kit.

Other Applications

The vector, expression cassette, lentiviral particle, host cell and/or cell population of the invention may be used in vitro, for example for molecular biology research purposes. In particular, the virus particles may be used to deliver a transgene (either in vitro, in vivo or ex vivo). Transgenes can include genes coding for therapeutic proteins (such as SEQ ID NOs: 2 to 9), RNAs and also nucleic acids involved in gene silencing, such as siRNAs or antisense RNAs. Virus particles of the invention may be used in gene silencing. In this case, the virus particles may be used to deliver a siRNA (in the form of a shRNA). Lentiviruses can also been used to transduce embryonic stem cells and to introduce transgenes into early embryos in order to generate transgenic animals. Lentiviruses have also been used to knock down targeted genes in vivo. Other applications of lentiviruses include immune modulation, cellular reprogramming and in vivo imaging.

EXAMPLES

Materials and Methods
Vector Construction
LV EFS GFP—the EFS promoter was obtained from the vector SIN-LV-EFS-γc as a HincII/BamHI fragment, subcloned into pBluescript SK, and then removed and inserted into the P'HR-cppt-SEW vector as an EcoRI/BamHI fragment replacing the SFFV promoter.

LV-LCR-EFS-GFP—the β-LCRHS4 element core (275 bp) and flanking regions of 5' 461 bp and 3' 352 bp were amplified by PCR with the primers HS4 PC forward-TTTGCGGCCGCTATCTCATTGCTGTTCGT (SEQ ID NO: 14) and HS4 PCR reverse-TTTGCGGCCGCACA-GAAGCTCATGCATT (SEQ ID NO: 15), giving the fragment NotI sites at each end. The PCR product was confirmed by sequencing and then inserted into the NotI site of the MA954 plasmid containing the HS3 (5' 570 bp, 223 bp core, 3' 400 bp) and the HS2 (5' 715 bp, 388 bp core, 3' 310 bp) fragments as employed in the GLOBE lentiviral construct. The β-LCR (HS4,3,2) was excised as an EcoRI fragment from the resulting MA954 HS4 and then linked upstream the EFS promoter in LV-EFS-GFP.

LV-EFS-ADA—a codon-optimised version of an ADAcDNA was commercially synthesized (GeneArt, Regensburg, Germany) and subcloned as an AfeI/SalI fragment into the pSRS11-EFS-γc vector, substituting the γc cDNA sequence. The fragment EFS-ADA was excised with ClaI/SalI and cloned into the plasmid pCCLsincpptW1.6hWasp-WPRE (Genethon, Evry-Cedex, France), substituting W1.6h-Wasp. LV-LCR-EFS-ADA: to insert the HS4, 3, 2 β-LCR fragment, a multicloning site was generated by aligning the primers MCS forward-CGATCTCGAGCCT-GCAGGGATATCAT (SEQ ID NO: 16) and MCS reverse-CGATGATATCCCTGCAGGCTCGAGAT (SEQ ID NO: 17), and cloning them into the ClaI site upstream EFS in the LV-EFS-ADA vector. The multicloning site provided the sites for XhoI and EcoRV. The β-LCR fragment was excised from the MA954 HS4 construct via XhoI/EcoRV digestion and inserted into LV-EFS-ADA.

Cell Lines

The Jurkat (human T cell leukemia), U937 (human leukemic monocyte lymphoma), and K562 (human erythroleukemia) cell lines were maintained in RPMI medium (Invitrogen, Paisley, UK) supplemented with 10% fetal bovine serum (Sigma-Aldrich, Poole, UK) and 10 μg/ml each of penicillin and streptomycin. MEL and human embryonic kidney (HEK293T) cells were maintained in Dulbecco's modified Eagle's medium medium (Invitrogen), serum and penicillin-streptomycin as above. MS5 (mouse bone marrow stroma) cells were maintained in α-MEM medium (Invitrogen) with 20% serum, penicillin-streptomycin (Invitrogen). Cells were transduced with virus at a MOI of 5 in their corresponding culture medium; transgene expression was typically analyzed 3 days after transduction. All cells were cultured at 37° C., 5% $CO_2$.

Mouse Erythroleukaemia (MEL) Cell Differentiation

MEL cells were seeded at a density of $2 \times 10^5$ cells/ml in Dulbecco's modified Eagle's medium supplemented with 10% fetal bovine serum (Sigma-Aldrich) and 10 μg/ml each of penicillin and streptomycin (Invitrogen). Half of the cultures were induced to undergo terminal erythroid differentiation for 4 days by addition of 2% DMSO (Sigma-Aldrich), with medium replenished on day 2 after the start of the procedure.

Lentiviral (LV) Vector Production and Titration

Lentiviral stocks were produced in HEK293T cells by cotransfection of the packaging plasmids pMD.G2 (VSVG envelope plasmid) and pCMVΔ8.91 (gag-pol plasmid) with the corresponding LV construct, using polyethylenimine (Sigma-Aldrich) as previously described (Demaison et al. 2002). The vector titre was determined in HEK293T cells transduced with serial dilutions of the viral suspension, harvested 3 days after exposure to the virus; the titer was determined by flow cytometry in the case of the GFP vectors (LV LCR EFS GFP: $0.86 \times 10^9$ virus particles/ml; LV EFS GFP: $2 \times 10^9$ virus particles/ml) or by quantitative-PCR of the wPRE region in the case of the IDUA or GAA vectors that do not express GFP (LV LCR EFS IDUA: $3.4 \times 10^8$ virus particles/ml, LV EFS IDUA: $3.8 \times 10^8$ virus particles/ml; LV LCR EFS GAA; LV EFS GAA).

DNA Isolation and Vector Copy Number Determination

DNA was isolated from cell pellets with the DNeasy Blood and Tissue kit (Qiagen, West Sussex, UK), following the manufacturer's instructions. Average vector copy number per cell was determined by wPRE quantitative-PCR in Platinum Quantitative-PCR SuperMix-UDG with ROX (Invitrogen). Primer sequences for the wPRE region were WP forward-CGGGCCACAACTCCTCATAA (SEQ ID NO: 18) and WP reverse-TTGCTTCCCGTATGGCTTTC (SEQ ID NO: 19) (Invitrogen), and FAM-TCTCCTCCTTG-TATAAATCCTGGTTGCTGTCTC-TAMRA probe (SEQ ID NO: 20) (Eurofins-MWG Operon, Ebersberg, Germany).

IDUA Enzyme Activity Assay

Principle: The activity of α-L-iduronidase is measured using 4-methylumbelliferyl-α-L-iduronide (4-MUI). The α-L-iduronidase cleaves α-L-iduronic acid from the substrate to yield the fluorescent product 4-methylumbelliferone (4-MU). The liberated 4-MU is measured using a luminescence spectrophotometer against a standard of known concentration.

Method: Tissues were homogenized in 0.5M NaCl/0.02M Tris pH 7-7.5 and sonicated 3 times for 5 sec at 5 µm amplitude on ice with 10 sec hold between each sonication step. 1 ml of homogenization buffer was used for 0.1-0.5 g tissue. Debris were removed by centrifugation at 2,045×g for 15 min at 4° C. 20 µl supernatants were transferred in microcentrifuge tubes and incubated with 20 µl 2 mM 4-MUI at 37° C. for 1 h in water bath. The assay was performed in duplicates. Reaction was stopped by adding 160 µl stopping buffer (1:2 ratio of 0.2M sodium carbonate and 0.2M sodium hydrogen carbonate, final pH 9.5). 200 µl samples were transferred in a black 96-well plate and fluorescence read at 360 ex/460 em against a 6.25 µM 4-MU standard curve. Blank values were subtracted from the averaged sample readings. The activity of GAA was determined by the nanograms of 4-MU produced per hour and normalized by milligrams of protein content (ng/h/mg protein).

GAA Enzyme Activity Assay

Principle: The activity of α-acid-glucosidase (GAA) is measured using the artificial substrate 4-methylumbelliferyl-α-D-glucopyranoside (4-MUG). At acid pH, GAA hydrolyses 4-MUG into the fluorescent product 4-methylumbelliferone (4-MU) and glucose. The liberated 4-MU is measured using a luminescence spectrophotometer against a standard of known concentration at 360 nm wavelength. The test is set up with and without acarbose which inhibits non-lysosomal α-glucosidase.

Method: Cell were lysed in TN buffer (150mM NaCl, 25mM Trizma, pH 6.4), 1% Triton X-100 and 1% protease inhibitor cocktail (P8340, Sigma-Aldrich®) using 200 µl buffer for 2-3×10$^6$ cells and pipetting cell suspension 5-6 times up and down. Cell debris were removed by centrifugation at 13,000 rpm for 5 min. Tissues were weighted and homogenized in D-PBS, 1% Triton X-100 and 2% protease inhibitor cocktail (P8340, Sigma-Aldrich®) using 1 ml buffer for 100-300 mg tissue. Tissues were transferred in 2 ml standard tubes containing 2.8 mm ceramic (zirconium oxide) beads (CK28-2 ml, KT03961-1-002.2, Precellys) and mechanically homogenized with 2 cycles of 30 sec at the 3D motion speed of 5,700 rpm with an interval of 10 sec between cycles using Precellys®24 homogenizer. Debris were pelleted down at 13,000 rpm for 5 min at 4° C. 5 µl supernatants were used for GAA activity assay and tested in duplicates with or without 5 µl 7.5 µM acarbose in 96-well plate round bottom. 10 µl 4 mM 4-MUG was added per well using a multichannel pipette. After 1 h of incubation at 37° C. in water bath, reactions were stopped with 200 µl of stopping buffer (0.25M glycine, pH 10.4). 200 µl samples were transferred in a black 96-well plate and fluorescence read at 360 ex/460 em against a 6.25 µM 4-MU standard curve. Blank values were subtracted from the averaged sample readings. The activity of GAA was determined by the nanograms of 4-MU produced per hour and normalized by milligrams of protein content (ng/h/mg protein).

Dried blood spot test (DBS): About 40 µl of whole blood were dropped in absorbent paper. 3.2 mm disk was punched from the center of the spot and used for analyses. Disks were incubated in 360 µl water for 1 h in cold room for sample extraction. GAA activity assay was automatically performed by Tecan Genesis Workstation 150 with Freedom EVOware program.

Human Haematopoietic Stem Cell (HSC) Selection and Transduction

Bone marrow samples from individuals and cord blood from a normal delivery were obtained with written, informed consent. The leukocytes were separated by density gradient centrifugation over a Ficoll-Paque layer (GE Healthcare, Little Chalfont, UK), and the CD34$^+$ population was isolated using CD34 selection microbeads (Miltenyi-Biotec, Woking, UK). The cells were cultured at 37° C., 5% $CO_2$, at a density of 1 million/ml in serum-free Stem Span medium (Stem Cell Technologies, Grenoble, France) supplemented with 300 ng/ml hFlt3, 300 ng/ml hSCF, 100 ng/ml hTPO and 20 ng/ml hIL-3 (all Peprotech, Rocky Hill, N.J.) for 16 hours and then transduced with lentivirus at a multiplicity of infection (MOI) of 20-25, for 16 hours.

Natural Killer (NK) and Erythroid In Vitro Differentiation

For NK differentiation, transduced, and control CD34+ cells were seeded onto MS5 monolayers in 24-well plates at a concentration of 10,000 cells/well if obtained from bone marrow, or 1,000 cells per well if obtained from cord blood. The culture medium consisted of α-MEM medium (Invitrogen), 10% serum, 10 mmol/l HEPES (Gibco-Invitrogen, Paisley, UK), 10 mmol/l sodium pyruvate (Gibco-Invitrogen), 0.5 mg/ml Gentamicin (Gibco-Invitrogen), 10 µg/ml each of penicillin and streptomycin, 20 mmol/l l-glutamine (Gibco-Invitrogen), 2-mercaptoethanol 0.5 mmol/l (Gibco-Invitrogen), hSCF 50 ng/ml, hFlt3 50 ng/ml, hIL-3 10 ng/ml, hIL-7 20 ng/ml, and hIL-15 20 ng/ml. The medium was changed every 2-3 days and the cells were transferred to a new MS5 monolayer every week. The cells were harvested after 3-4 weeks of culture and stained with APC-CD56+ (BD Bioscience, Oxford, UK).

For erythroid differentiation, an adapted version of the protocol published by (Giarratana et al. 2011) was followed. The basal medium formula was modified to contain serum-free Stem Span (Stem Cell Technologies), 4 mmol/l l-glutamine (Gibco-Invitrogen), 10 µg/ml each of penicillin and streptomycin, 20 mmol/l l-glutamine (Gibco-Invitrogen), ferrous nitrate 90 ng/ml (Sigma-Aldrich) and ferrous sulphate 900 ng/ml (Sigma-Aldrich). The cells were harvested on day 18 after the start of differentiation and stained for PE-Glycophorin A (eBioscience, Hatfield UK) and APC-CD71 (BD Bioscience).

Busulfan administration protocols for murine HSC transplants Full myeloablation was achieved by using 125 mg/kg busulfan, which has been reported to be comparable with 10 Gy of lethal irradiation (Wilkinson et al. 2013). This dose of busulfan was administered in 5 days using 25 mg/kg/day per mouse by intraperitoneal injection. Treated mice were 7-8 week old. Cells were transplanted into busulfan conditioned mice by standard methods known in the art. Typically, mice were 6 to 8 weeks old. Functional, genetic, and biochemical studies were then subsequently carried out.

Immortalisation (IM) Assay

IM assays were carried out as described in (Knight et al. 2010). $3.6 \times 10^7$ Bcl-15 cells were transduced with each vector at an MOI of 10 in the presence of IL-3 (10% WEHI supernatant). After 96 hours expansion the cells were replated in supernatant containing 1 µg/ml bGH (Prospec, East Brunswick, N.J.), in the absence of IL-3 to select IL-3 independent mutants.

IM-WST1 Assay

A version of the in vitro immortalisation (IVIM) protocol was followed, modified from (Arumugam et al. 2009). After the 2-week expansion in 96-well plates step, half of the cells in each "clone" well were transferred into a new well containing 10 µl of WST1 reagent (Roche, Penzberg, Germany), and incubated at 37° C., 5% $CO_2$ for 4 hours. The absorbance was measured with a FLUOstar Optima colorimeter (BMG Labtech, Offenburg, Germany) at a wavelength of 450 nm. Clones were considered positive when absorbance was over the baseline established with the mock-transduced cells. The replating efficiency was then calculated using L-Cal software (Stem Cell Technologies), normalized with the virus copy number and expressed as replating index.

MEL Cell Clones

MEL cells were transduced with LV LCR EFS GFP at an MOI of 3. The GFP+ cells were sorted on a MoFlo XDP (Beckman Coulter, High Wycombe, UK) using a 70 µm nozzle, voltage of 2,000-4,000 V and sheath pressure of 60Ψ, and seeded in limiting-dilution (1 cell/well) in a 96-well plate with conditioned medium (50% culture medium from unsorted transduced cells+50% fresh culture medium). Sixteen clones were chosen based on their GFP expression pattern (low, medium, or high) and the insertion sites were determined by nrLAM-PCR and pyrosequencing. Five clones with multiple insertions (4, 6, or 11), and four clones with single insertions were chosen for microarray analysis. The chosen clones were cultured in the presence or absence of 2% DMSO (basal or differentiated state) and RNA was isolated using the RNEasy kit (Qiagen).

Efficacy of the LV-βLCR-EFS-IDUA Vector in Correcting the Metabolic Abnormalities Seen in MPS I Mice Murine HSCs (lineage -ve) cells were isolated from eight week old IDUA-/- male mice and transduced with either the LV-βLCR-EFS-IDUA, LV EFS-IDUA or LV-βLCR-EFS-GFP vectors in established cytokine cultures before transplantation into busulfan-conditioned eight week old female recipients (n=6 per group). WT and/or IDUA-/- mice of similar ages acted as controls. Mice were bled at monthly intervals and IDUA activity in the serum analysed together with peripheral blood mononuclear cells (PBMCs) of all treatment groups. At 12 weeks and 24 weeks post-transplant, mice were culled, organs isolated and then analysed in a number of different ways. IDUA activity in PBMCs and in serum was determined and normalised to vector copy number. IDUA activity was in a variety of different tissues including liver, spleen, heart and brain. The level of total GAGs in the plasma and brain was determined together with the levels of specific substrates such as heparan sulfate (HS) and dermatan sulphate (DS), which may be more specific markers of metabolic correction.

Figure 8B:
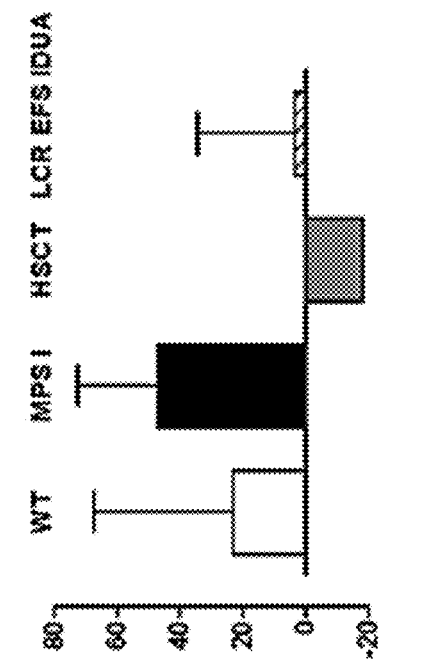
FIG. 8B is a graph of an open field test for non-associative memory (measuring % changen n. of rearing between between T1 and T3) in WT mice, a murine MPS-I model, mice that have undergone HSCT and mice treated with the LCR EFS IDUA gene therapy vector.
Figure 8A:
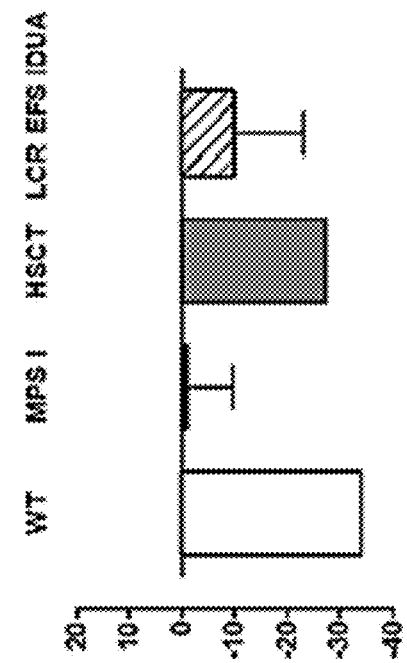
FIG. 8A is a graph of an open field test for non-associative memory (measuring % change cm_path between T1 and T3) in WT mice, a murine MPS-I model, mice that have undergone HSCT and mice treated with the LCR EFS IDUA gene therapy vector.
Figure 9A:
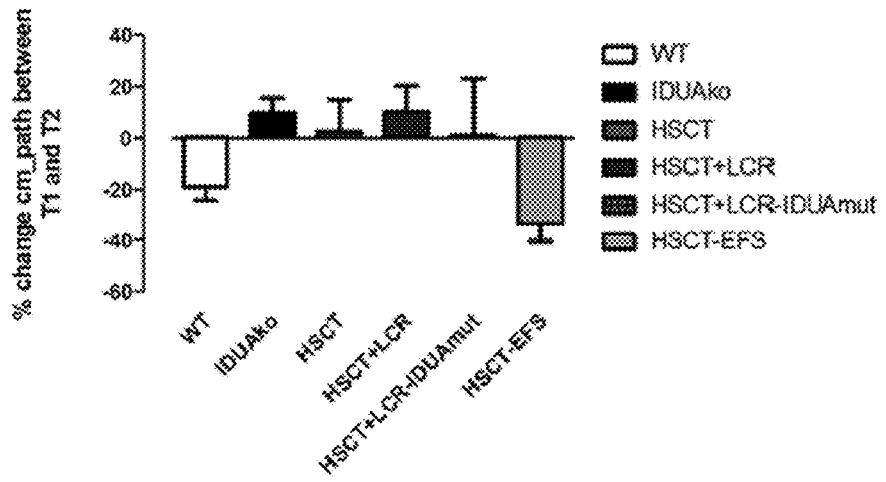
FIG. 9A is an open field test, testing non-associative memory (measuring % change in cm_path between T1 and T2) in WT mice, a murine MPS-I model (IDUAko); HSC transplanted mice (HSCT); HSCT+LCR treated mice (mice treated with the LCR-EFS-IDUA vector); HSCT+LCR-IDUAmut treated mice (LCR-EFS vector but with a mutant IDUA) and HSCT-EFS treated mice (mice treated with a vector containing only EFS-IDUA). WT n=11; IDUAko n=11; HSCT n=8; -LCR n=11; -LCR-IDUAmut n=3; -EFS n=2.
Figure 9B:
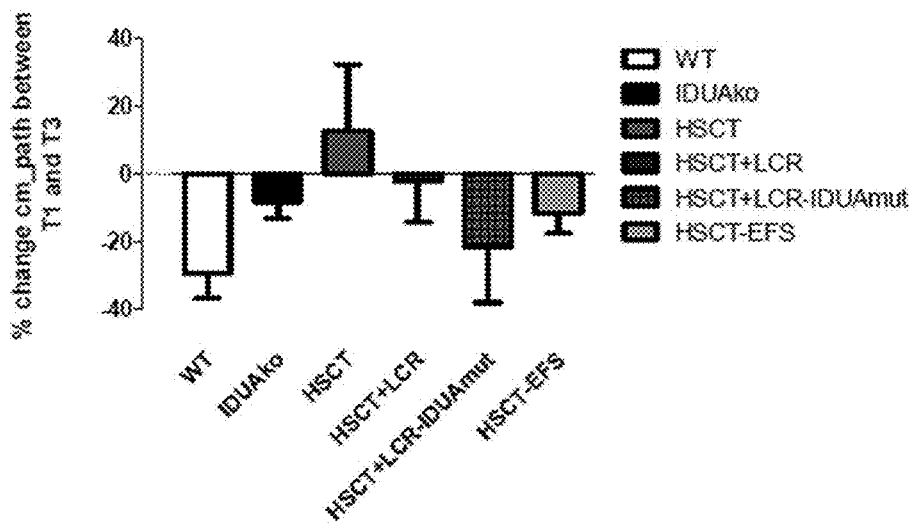
FIG. 9B is an open field test, testing non-associative memory (measuring % change in cm_path between T1 and T3) in WT mice, a murine MPS-I model (IDUAko); HSC transplanted mice (HSCT); HSCT+LCR treated mice (mice treated with the LCR-EFS-IDUA vector); HSCT+LCR-IDUAmut treated mice (LCR-EFS vector but with a mutant IDUA) and HSCT-EFS treated mice (mice treated with a vector containing only EFS-IDUA). WT n=11; IDUAko n=11; HSCT n=8; -LCR n=11; -LCR-IDUAmut n=3; -EFS n=2.

Efficacy of the LV-βLCR-EFS-IDUA Vector in Correcting the Functional Abnormalities Seen in MPS I Mice In further transplant studies functional recovery of different organ systems as assessed in reconstituted mice 6 months after transplantation/8 months of age. The 6 months post-transplant/8 months of age time point was chosen to study functional recovery of different organ systems, as at this time point any cardiac, behavioural, skeletal and hearing parameters in MPS-I mice were expected to be statistically significantly different from age-matched wild-type controls. Neurological assessment involved analysis of non-associative memory (repeat trial open field test) and spatial learning and memory deficits (Morris Water maze) (FIGS. 8A and 8B; 9A and 9B). Other murine organ specific abnormalities were also analysed, including correction of known skeletal defects by CT scans and cardiac defects by echocardiographic evaluation, and deafness through auditory brain stem responses. All these parameters were correlated to the level of IDUA activity in blood and storage material excretion in urine. Most importantly vector copy number (VCN) was determined in PBMCs and bone marrow by qPCR to demonstrate that these corrections can be made at low copy number (<2 VCN/cell).

Safety of the LV-βLCR-EFS-IDUA Vector in Comparison to a LV-EFS-IDUA Vector

A number of safety assays were undertaken as a prerequisite to progression to clinical development. This included (1) analysis of full blood counts in transplanted mice from the different cohorts to show that high level erythroid-specific IDUA expression does not alter erythroid lineage development; (2) analysis of the number and type of colony forming units following lineage negative cell transduction by different vectors, to demonstrate that vector transduction did not alter stem cell stability and commitment; and (3) analysis of genotoxicity in an in vitro murine stem cell model of immortalization, to demonstrate that the vector does not show increased potential for immortalization.

qPCR Protocol for Determining Vector Copy Number (VCN)

DNA was isolated by PBMC pellets using DNeasy Blood and Tissue kit (Qiagen, West Succex, UK). Following the manufacture's instruction. Average VCN per cell was determined by wPRE quantitative-PCR in Platinum Quantitative-PCR SuperMix-UDG with ROX (Invitrogen). Primer sequences for the wPRE region were WP forward-CGGGC-CACAACTCCTCATAA and WP reverse-TTGCTTCCCG-TATGGCTTTC (Invitrogen), and FAM-TCTCCTCCTTG-TATAAATCCTGGTTGCTGTCTC-TAMRA probe (Eurofins-MWG Operon, Ebersberg, Germany).

Codon Optimisation

A human codon optimised GAA and IDUA sequence were obtained by using GeneScript OptimumGene™ algorithm. This generates gene sequences with the highest possible level of expression by taking into account the variety of factors that influence gene expression level, i.e., changing codon usage bias or modifying GC content and secondary structures that would interfere with translational efficacy and mRNA stability.

Immunohistochemistry

For MPS-I data (Hurler syndrome): Liver, kidney, spleen, and top half of the heart were fixed in formalin. All tissues were then paraffin embedded or epoxy treated. These were cut in sections—particularly coronal sections for heart- and then stained for H&E and alcian blue to detect glycosaminoglycan storage in lysosomes.

Femur and tibia were collected in PBS, still joined, and fixed in 4% PFA overnight. Decalcification was performed in 10% acid acetic overnight and then paraffin embedded. Coronal sections of the growth plate (the region between the epiphysis and metaphysis of the bone) were stained for H&E and toluidine blue or alcian blue.

Half brain was fixed in 4% PFA overnight and then left in 15% sucrose solution before staining free floating brain sections.

For Pompe's data: Diaphragm, tibia anterior, soleus-gastrocnemius, liver, lung, half brain and top half of the heart were frozen in OCT using isopentane cooled in liquid nitrogen. All tissues were cryo-sectioned and stained for H&E, acid phosphatase and periodic acid-Schiff to determine vacuolization and glycogen accumulation in tissues.

Computerised Tomography (CT), Echocardiography (ECG) and High Frequency Ultrasound Standard methods known to the person skilled in the art were used to conduct CT and micro-CT, ECG and high frequency ultrasounds, and to measure parameters from the data acquired. High frequency ultrasound data was acquired on a Vevo® 2100 system.

Technique Optimisation

The pre-transplant conditioning regime, transcardial perfusion prior to tissue and sample harvest, brain sectioning and immunohistochemistry, enzymatic activity, and glycosaminoglycan assays were optimised. Functional assays were also set up, including the open field habituation test (OFT) more on this memory test if possible, computerized tomography (CT) and echocardiography (Echo) scans, as well as auditory brainstem responses (ABR).

Transplant Experiments

Four transplant experiments (TP1, TP2, TP3 and TP4) were carried out in the IDUA experiments. Three transplant experiments (TP1, TP2 and TP3) were carried out in the GAA experiments. Authorisation was granted by the by the Named Veterinary Surgeon to transfer transplanted mice to more than one UCL Biological Service Unit, allowing the same cohorts to be used for imaging and behaviour and reducing the number of animals used in these studies.

The first IDUA transplant experiment (TP1) reached the end point (6 months post-transplant). The mice were analysed in the open field test for habituation (a test that can measure memory), as well as CT and Echo for skeletal and cardiac functions, respectively.

In the second IDUA transplant experiment (TP2), the mice have recovered normal distribution of blood cell populations and the gene therapy group shows good engraftment of gene-modified cells in the periphery (above 50%).

In the GAA experiments, the first transplant experiment (TP1) reached the 6-month post-transplant end point.

Statistical Analysis

T-test or Mann-Whitney tests were run in the GraphPad Prism4 Software and the significance level is expressed as follows: (*) if P<0.001; () if 0.01>P>0.001; (*) if 0.05>P>0.01; (ns) if P>0.05.

Example 1

Enhancement of Expression of GFP and IDUA from a Lentiviral Vector

Figure 1B:
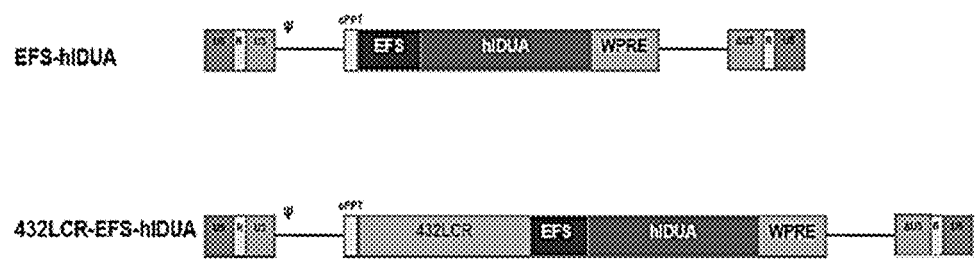
FIG. 1B is a schematic showing the EFS-human IDUA (hIDUA) construct (top); and the HS 4, 3, 2- (432)-LCR-EFS-hIDUA construct. In both constructs, the hIDUA gene has been codon optimized and the constructions are based on the CCL backbone.
Figure 1C:
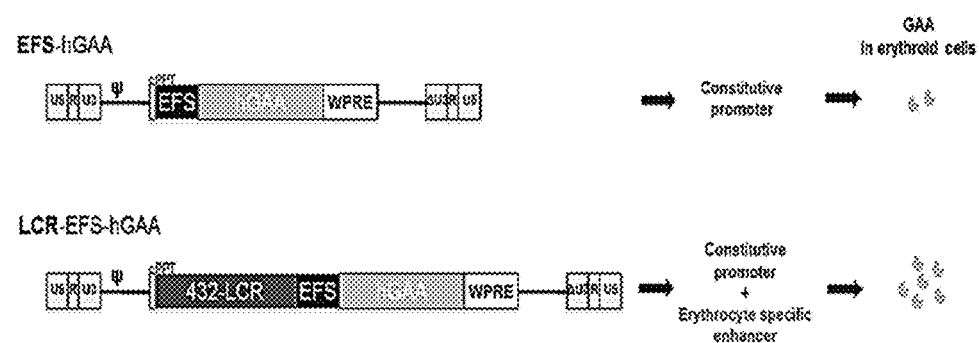
FIG. 1C is a schematic showing the EFS-human GAA (hGAA) construct (top); and the 432–LCR-EFS-hGAA construct (bottom). cPPT, central polypurine tract; wPRE, woodchuck hepatitis post-transcriptional regulatory element; U5-R-U3, 5' LTR (long terminal repeal); Ψ, Ψ packaging element; ΔU3-R-U5, 3' LTR lacking the U3 region.
Figure 2A:
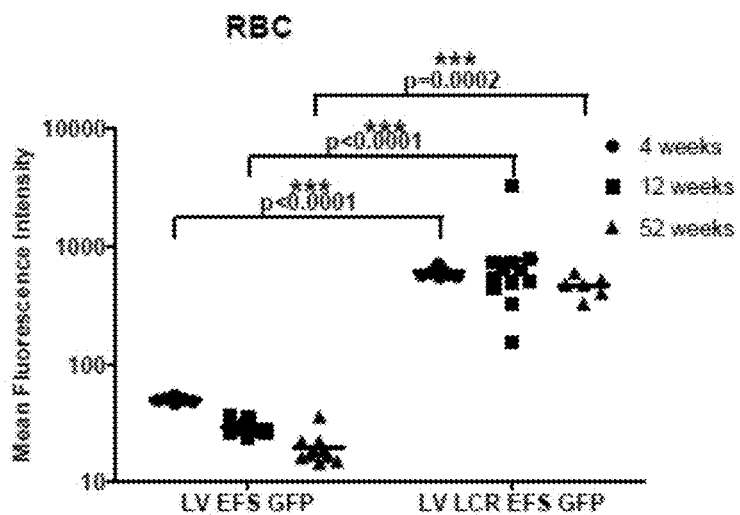
FIG. 2A is a graph of GFP intensity measured at 4, 12, and 52 weeks post-transplant in the red blood cell population of mice transplanted with cells transduced with either the LV-EFS-GFP (equivalent to LNT-EFS-GFP) or the LV-bLCR-EFS-GFP (equivalent to LNT-4321cr-EFS-GFP) constructs.
Figure 2B:
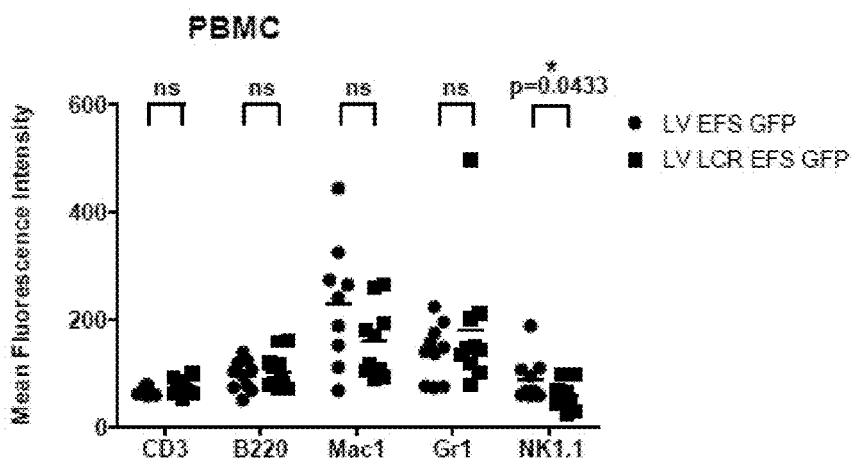
FIG. 2B is a graph of GFP intensity measured at 52 weeks post-transplant in peripheral blood mononuclear cell populations. B220 B cells; CD3 T cells; NK1.1 NK cells; Gr1 granulocytes; Mac1 myeloid population. Lin- cells were recovered from the bone marrow of male 8-week-old C57BL/6 mice and infected overnight at an MOI of 50.3× 105 cells/mouse were i.v. injected in lethally irradiated 12-week-old female C57BL/6 mice.
Figure 2C:
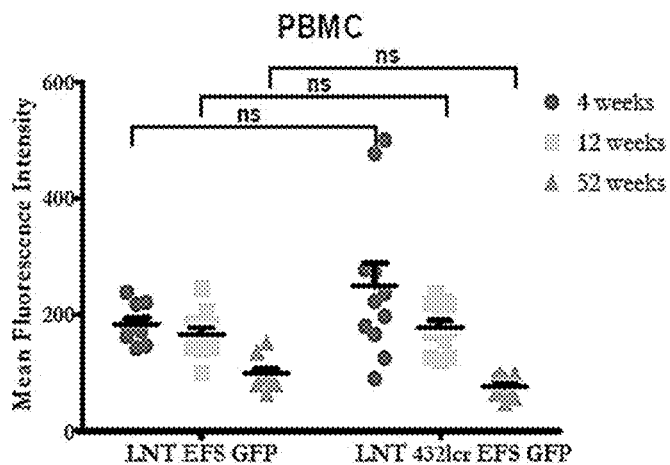
FIG. 2C is a graph of GFP intensity measured at 4, 12, and 52 weeks post-transplant in the peripheral blood mononuclear cell (PBMC) population of mice transplanted with cells transduced with either the LV-EFS-GFP (equivalent to LNT-EFS-GFP) or the LV-bLCR-EFS-GFP (equivalent to LNT-4321cr-EFS-GFP) constructs.

Experiments in C57BL/6 mice transplanted with lineage negative (lin -ve) cells (hematopoietic progenitors) transduced with either the LV-βLCR-EFS-GFP (FIGS. 1A-1C) or the LV-EFS-GFP vector demonstrated that βLCR-EFS enhanced GFP expression by 20-fold in red blood cells in vivo without affecting expression in non-erythroid lineages, even one year after transplant (FIGS. 2A-2C).

Figure 3:
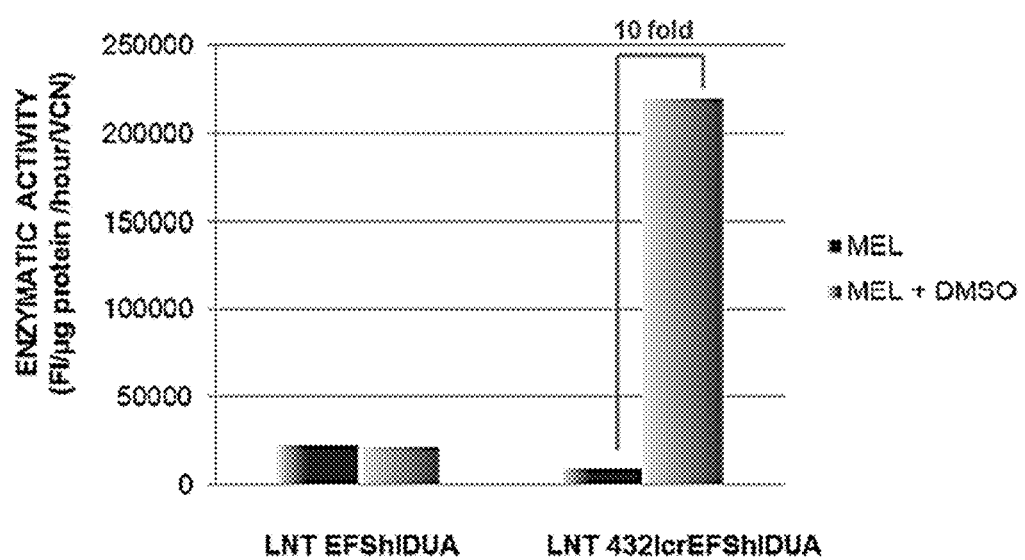
FIG. 3 is a graph of iduronidase activity (IDUA) enzyme activity in mouse erythroleukaemic (MEL) cells transformed with the LV-EFS-IDUA (equivalent to LNT-EFS-IDUA) and the LV-bLCR-EFS-IDUA (equivalent to LNT-4321cr-EFS-IDUA) constructs. MEL cells were induced to differentiate by the addition of DMSO, which resulted in a significant increase in IDUA enzyme activity in MEL cells transformed with the LNT-4321crEFS-hIDUA construct.
Figure 4:
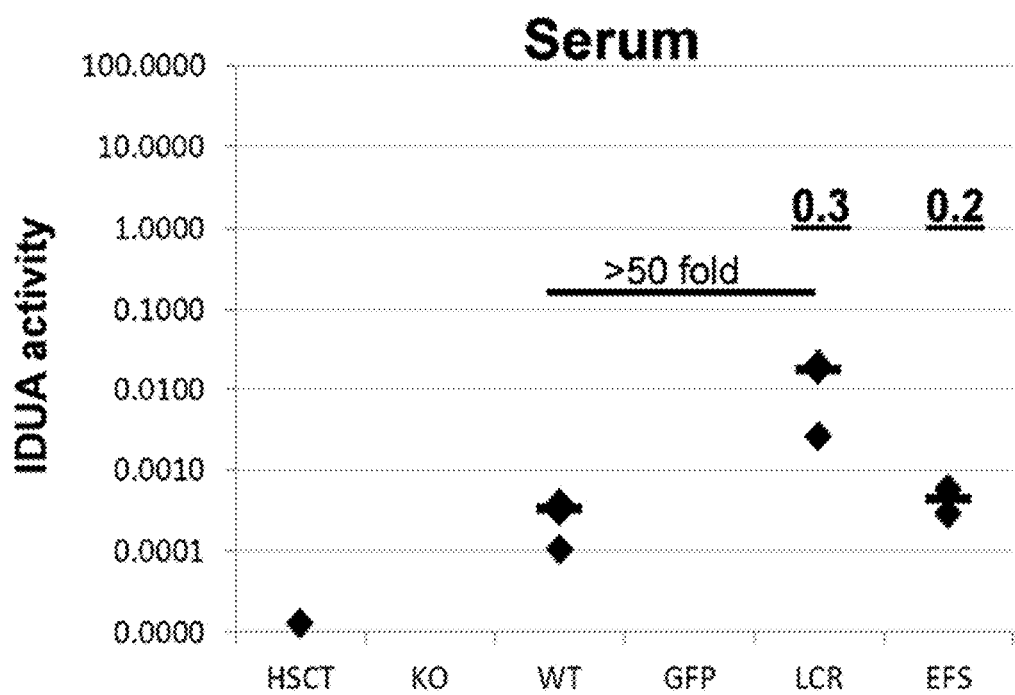
FIG. 4 is a graph of IDUA activity in the serum of transplanted mice. The average vector copy number is shown above the LCR and EFS groups. HSCT=recipients engrafted with WT donor cells; KO=IDUA-/- control mice; WT=wild-type control mice; GFP=recipients engrafted with GFP lentivirus-transduced donor cells; LCR=recipients engrafted with LCR lentivirus-transduced donor cells; EFS=recipients engrafted with EFS lentivirus-transduced cells. Lin- cells were recovered from the bone marrow of 80 week-old WT or IDUA-/- mice. The cells from the latter were transduced with LV-EFS-GFP, or LV-EFS-IDUA or LV-LCR-EFS-IDUA and injected into irradiated 80 week-old recipients. Analysis of serum at 12 weeks post-transplant.

Vectors were constructed in which the GFP reporter has been substituted for a codon optimised version of the human IDUA cDNA (FIG. 1A-1C). Experiments using these vectors in MEL cells again show upregulation of IDUA expression as a result of the bLCR containing vector (FIG. 3). We also performed an in vivo HSC transplant experiment (n=3) in IDUA−/− mice. It was shown that 12 weeks after transplant, the serum IDUA activity of mice receiving LV-bLCR-EFS-IDUA transduced HSCs was 40 times greater than the IDUA activity of mice receiving LV-EFS-IDUA transduced cells and 50 times greater than activity in WT mice (FIG. 4).

These data suggest very strongly that by upregulating expression in erythroid cells through the activity of the bLCR, high levels of IDUA are produced and then secreted into the plasma of corrected mice. Importantly, these high levels of expression were achieved using an average VCN in PBMCs of 0.3 vector copies per cell. The intragenic integrating nature of lentiviral vectors has been shown to have potential for adverse effects through disruption of gene splicing and therefore limiting the number of viral integrations of 5 or fewer per cell may have improved safety in clinical applications.

Example 2

Functional Characterisation of IDUA Treated Animals

Figure 6:
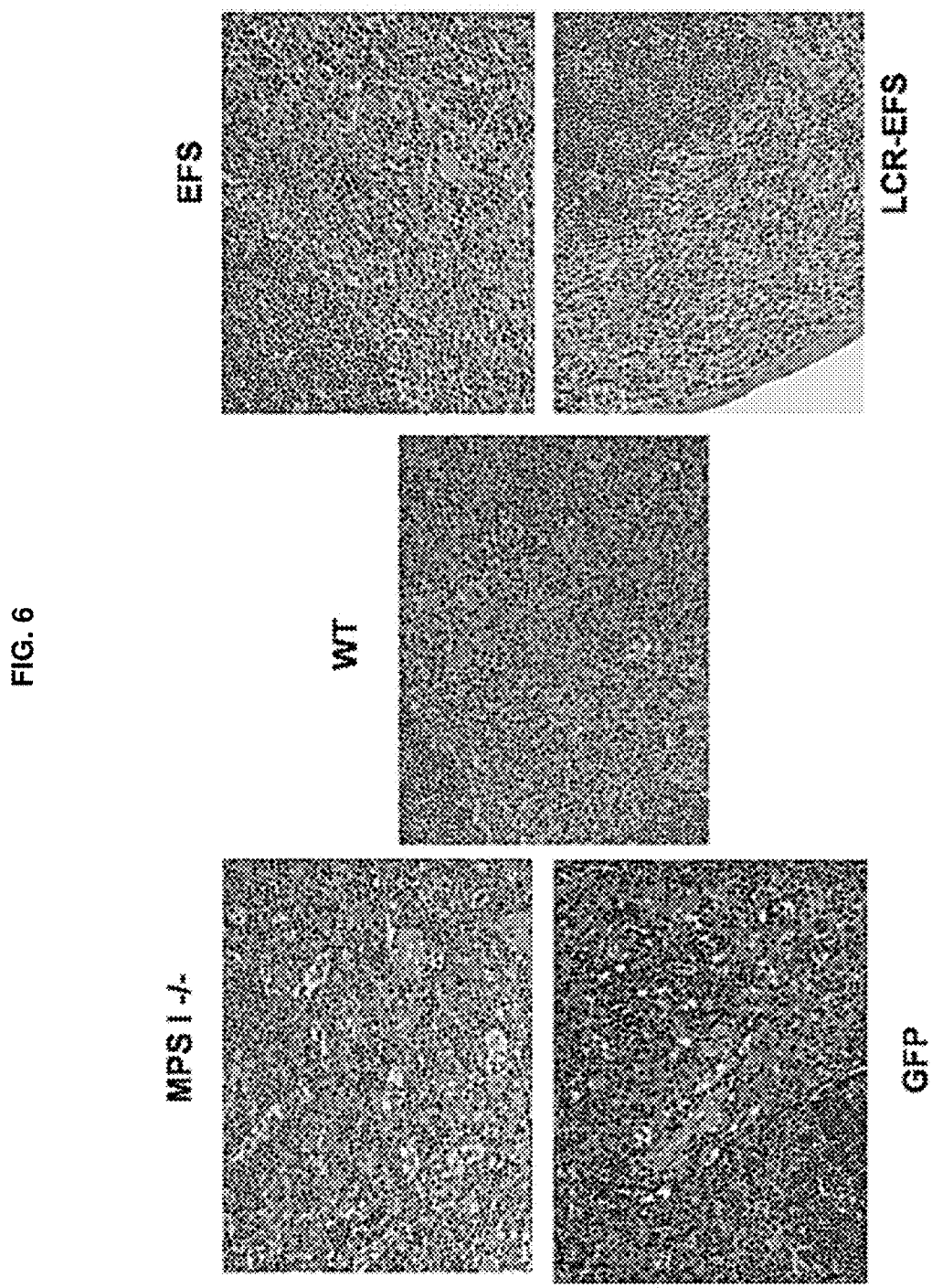
FIG. 6 is a photograph of hematoxylin and eosin (H&E) staining of spleen tissue sections from reconstituted mice and controls. Mice were MPS-I null (MPS I-/-), treated with LV-βLCR-EFS-GFP (GFP), wild-type (WT), treated with the EFS-IDUS containing construct (EFS), or treated with the bLCR-EFS-IDUA containing construct (LCR-EFS).

Macroscopic correction of the abnormal macrophage phenotype seen in the spleen of corrected mice in comparison to IDUA−/− or mock GFP-transduced mice was demonstrated by sectioning harvested spleens and staining with haematoxylin and eosin (H&E) (FIG. 6).

Figure 5A:
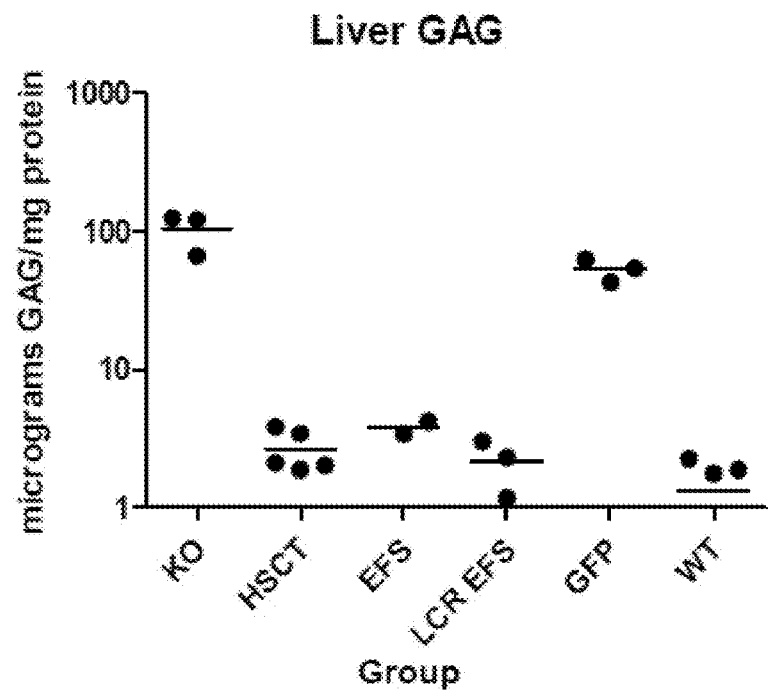
FIG. 5A is the total glycosaminoglycan (GAG) quantification in extracts from liver of reconstituted mice and controls. HSCT=recipients engrafted with WT donor cells; KO=IDUA-/- control mice; WT=wild-type control mice; GFP=recipients engrafted with GFP lentivirus-transduced donor cells; LCR=recipients engrafted with LCR lentivirus-transduced donor cells; EFS=recipients engrafted with EFS lentivirus-transduced cells. Tissues were dispersed in PBS using a hand-held homogeniser (T10 Ultraturrax IKA, Staufen, Germany). The lysates were spun, the supernatant separated from the debris, and half of the sample was treated for 20 hours with actinase E to break the protein. The protein-free lysate was separated by centrifugation and total GAGs were determined using the Blyscan kit (Bicolor Ltd, Carrickfergus UK). Good GAG clearance was observed in the liver with low multiplicity of infection (MOI).
Figure 5B:
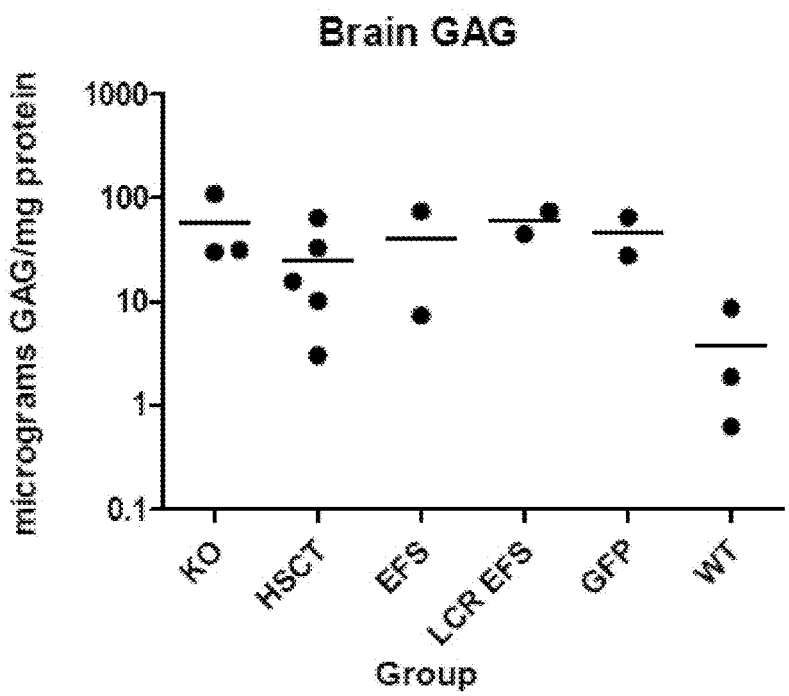
FIG. 5B is the total glycosaminoglycan (GAG) quantification in extracts from brain of reconstituted mice and controls. HSCT=recipients engrafted with WT donor cells; KO=IDUA-/- control mice; WT=wild-type control mice; GFP=recipients engrafted with GFP lentivirus-transduced donor cells; LCR=recipients engrafted with LCR lentivirus-transduced donor cells; EFS=recipients engrafted with EFS lentivirus-transduced cells. Tissues were dispersed in PBS using a hand-held homogeniser (T10 Ultraturrax IKA, Staufen, Germany). The lysates were spun, the supernatant separated from the debris, and half of the sample was treated for 20 hours with actinase E to break the protein. The protein-free lysate was separated by centrifugation and total GAGs were determined using the Blyscan kit (Bicolor Ltd, Carrickfergus UK). Compared to the KO, treated brains showed no difference, possible because the time point was too early.

We have also quantified the level of total glycosaminoglycans (GAGs) in the liver and brain of these animals after treatment (FIGS. 5A and 5B). Animals in the HSCT, EFS and LCR EFS treatment groups all showed GAG levels comparable to WT in the liver. In the brain, all treatment groups had GAG levels similar to the untreated MPS-I mice. As the clearance of storage compounds in brain relies on the activity of IDUA-expressing microglia and turnover of precursors from the blood into the brain is a slow process, it is possible that 12 weeks post-transplant is still early to see differences between treatments. In addition, it is possible that in the gene therapy treated animals, the fraction of transduced precursors giving rise to microglia is small, particularly considering that the average vector copy number in blood is low (0.2-0.3)

Example 3

Biochemical Analysis of IDUA Transplanted Animals and Age-Matched Controls

The data generated here corresponds to the first transplant experiment (TP1), including a HSC transplant (HSCT) group (IDUA−/− receiving WT cells, n=2), a LCR-IDUA group (IDUA−/− receiving IDUA−/− cells transduced with the lentivirus β LCR-EFS-IDUA, n=5), a MPS-I group (IDUA−/− untreated n=4) and a WT group (WT untreated n=2). The group sizes for transplanted mice were larger at the start of the experiment (HSCT n=6 and LCR-IDUA n=7), but we lost some of the mice due to chemotherapy toxicity or lack of stem cell engraftment. We have refined the transplant procedure to avoid this issue.

Figure 7A:
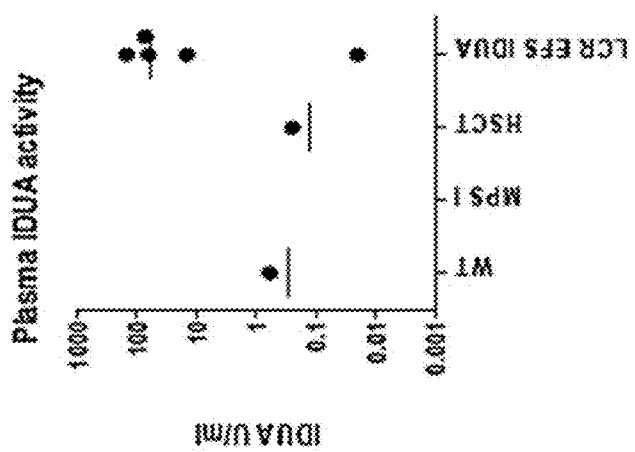
FIG. 7A is a graph of IDUA activity that has been measured in the plasma of transplanted animals and compared to the levels observed in MPS-I and WT controls. In plasma, the levels of enzymatic activity are in average 100-fold higher in gene therapy animals in comparison to WT and HSCT controls, at an average vector copy number of 0.73.
Figure 7B:
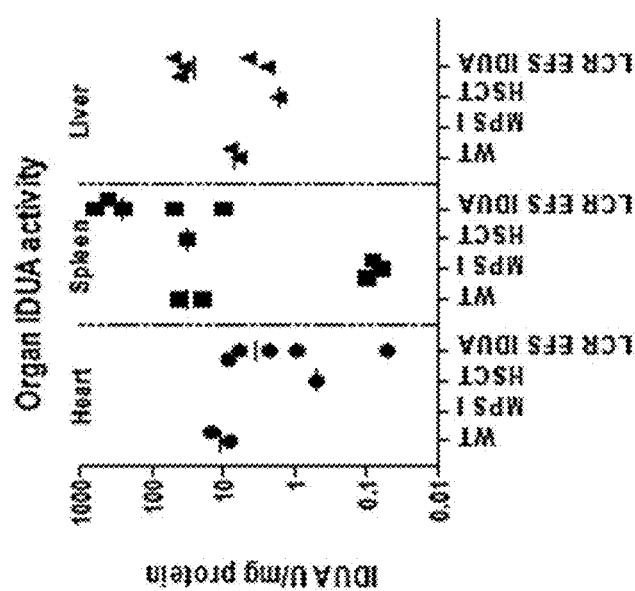
FIG. 7B is a graph of IDUA activity that has been measured in the heart, spleen, and liver of transplanted animals and compared to the levels observed in MPS-I and WT controls. In the spleen and liver the activity detected for the gene therapy group is about 10-fold higher than the activity detected in WT controls. The average activity detected in the heart for the transplanted group is below the normal activity (WT), and is higher than the activity obtained in a HSCT control mouse with similar levels of engraftment (90%).
Figure 7C:
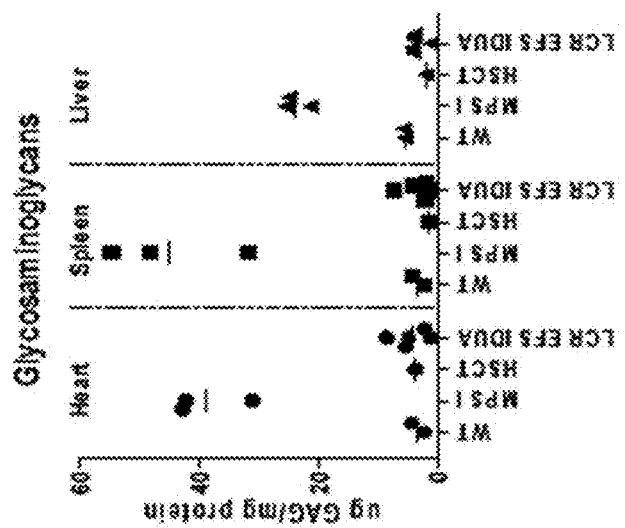
FIG. 7C is a graph of glycosaminoglycans (GAG) levels that have been measured in the heart, spleen, and liver of transplanted animals and compared to the levels observed in MPS-I and WT controls. GAG levels were measured in homogenates from the three major organs, for both HSCT and gene therapy-treated animals.

Iduronidase activity has been measured in plasma and major organs of transplanted animals and compared to the levels observed in MPS-I and WT controls. In plasma (FIG. 7A), the levels of enzymatic activity are in average 100-fold higher in Gene Therapy animals in comparison to WT and HSCT controls, this is at an average vector copy number of 0.73. The circulating enzyme is then internalized by other tissues (FIG. 7B); in spleen and liver the activity detected for the Gene Therapy group is about 10-fold higher than the activity detected in WT controls. Interestingly, although the average activity detected in heart for the transplanted group is below the normal activity (WT), it is higher than the activity obtained in a HSCT control mouse with similar levels of engraftment (90%). Glycosaminoglycan levels were measured in homogenates from the three major organs (FIG. 7C), for both HSCT and gene therapy-treated animals, the levels are back to normal.

Example 4

Open Field Test in IDUA-treated Animals

The data generated here corresponds to the first transplant experiment (TP1), including a HSC transplant (HSCT) group (IDUA−/− receiving WT cells, n=2), a LCR-IDUA group (IDUA−/− receiving IDUA−/− cells transduced with the lentivirus β LCR-EFS-IDUA, n=5), a MPS-I group (IDUA−/− untreated n=4) and a WT group (WT untreated n=2). The group sizes for transplanted mice were larger at the start of the experiment (HSCT n=6 and LCR-IDUA n=7), but we lost some of the mice due to chemotherapy toxicity or lack of stem cell engraftment. We have refined the transplant procedure to avoid this issue.

The size of each test group was not large enough for a meaningful statistical analysis to be carried out. However a tendency of the gene therapy group towards the wild-type behaviour was observed (FIGS. 8A, 8B, 9A, and 9B).

Example 5

Figure 10A:
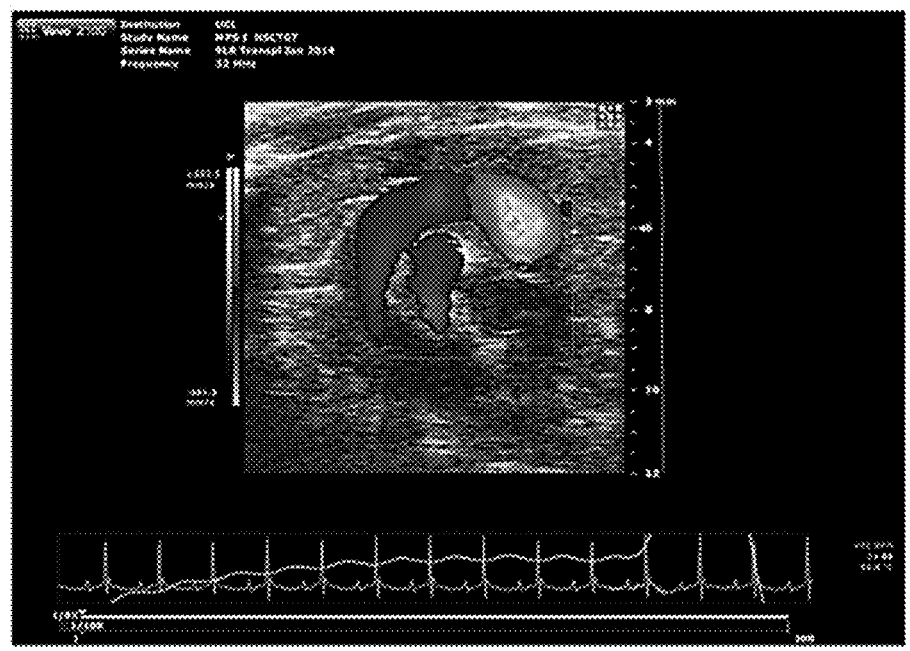
FIG. 10A is a photograph of an ultrasound view of an aortic arch with the corresponding electrocardiogram (ECG) traces in a LCR EFS IDUA gene therapy-treated age-matched MPS-I mouse.
Figure 10B:
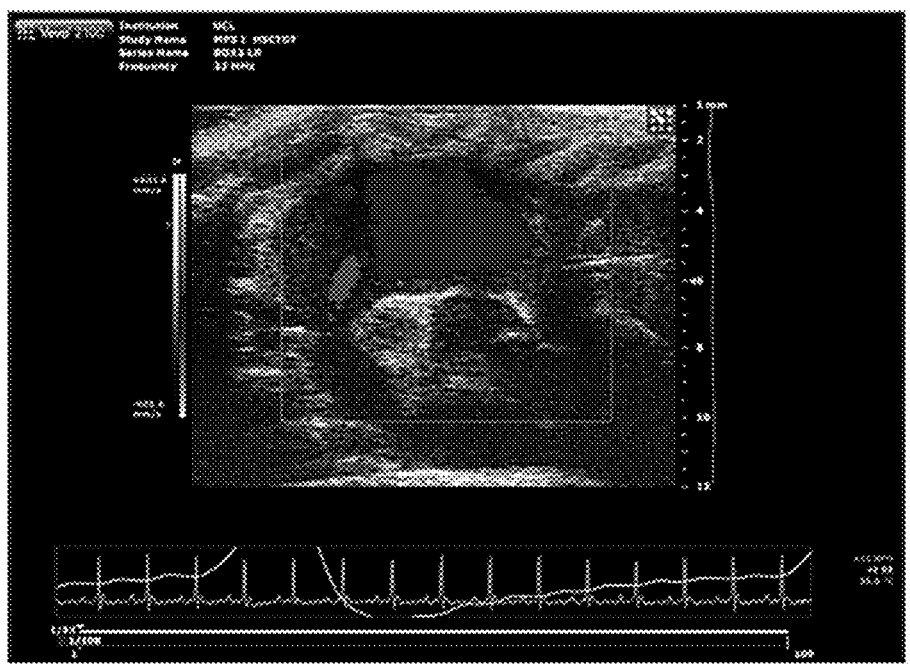
FIG. 10B is a photograph of an ultrasound view of an aortic arch with the corresponding electrocardiogram (ECG) traces in an age-matched MPS-I mouse.
Figure 11A:
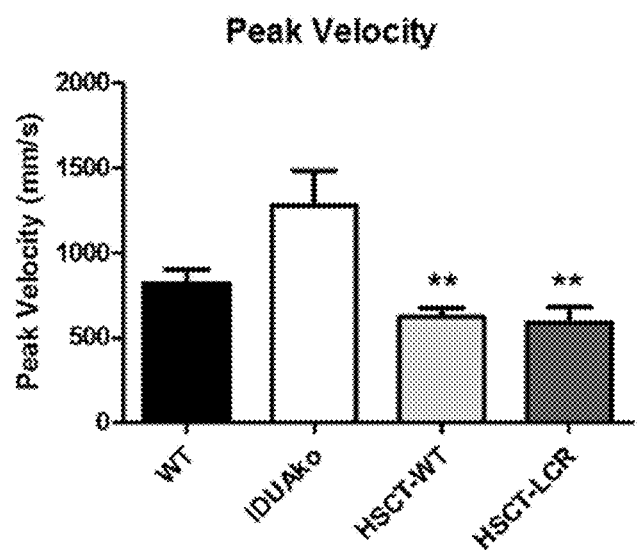
FIG. 11A is a graph of the peak velocity as measured by ultrasound in WT, IDUAko mice, HSCT-WT mice and HSCT-LCR-IDUA treated mice. Peak velocity was corrected in treated mice.
Figure 11B:
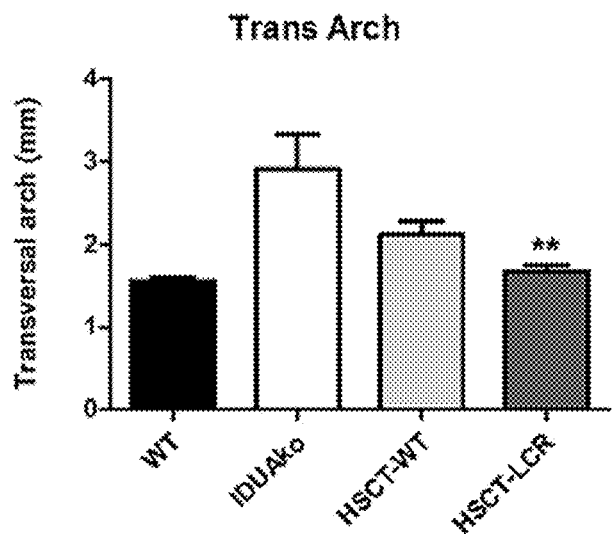
FIG. 11B is a graph of the transversal arch diameter as measured by ultrasound in WT, IDUAko mice, HSCT-WT mice and HSCT-LCR-IDUA treated mice. Transversal arch diameter was corrected in treated mice.
Figure 11C:
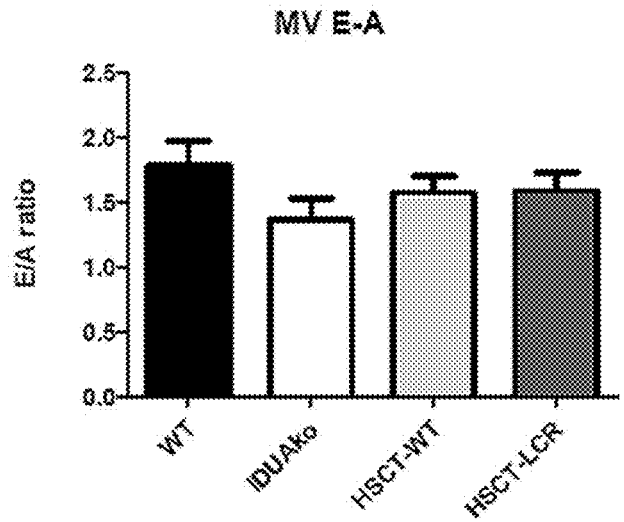
FIG. 11C is a graph of the mitral valve E/A ratio (MV E-A) as measured by ultrasound in WT, IDUAko mice, HSCT-WT mice and HSCT-LCR-IDUA treated mice.
Figure 12A:
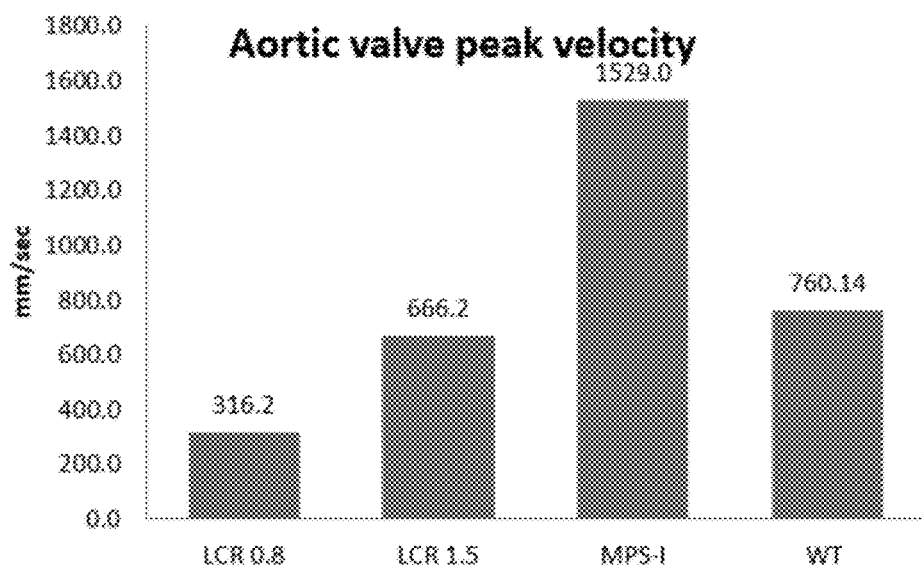
FIG. 12A is a graph representing the correction of aortic valve peak velocity in a murine model of MPS-I post gene therapy with the bLCR-EFS-IDUA construct, as measured by ultrasound after treatment with cells containing on average of 0.8 and 1.5 copies of the gene therapy vector (LCR 0.8 and LCR 1.5 respectively), compared to WT and MPS-I null mice.
Figure 12B:
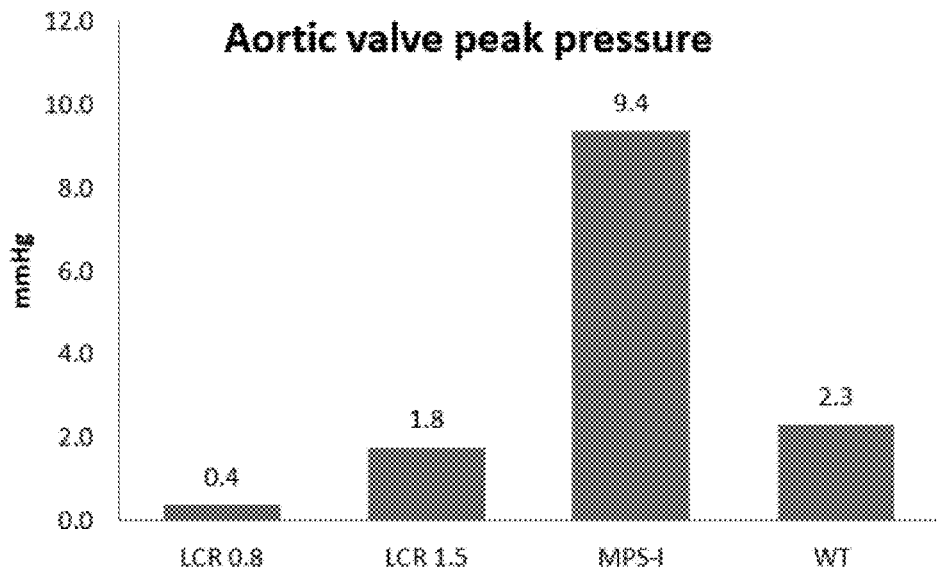
FIG. 12B is a graph representing the correction of aortic valve peak pressure in a murine model of MPS-I post gene therapy with the bLCR-EFS-IDUA construct, as measured by ultrasound after treatment with cells containing on average of 0.8 and 1.5 copies of the gene therapy vector (LCR 0.8 and LCR 1.5 respectively), compared to WT and MPS-I null mice.
Figure 13:
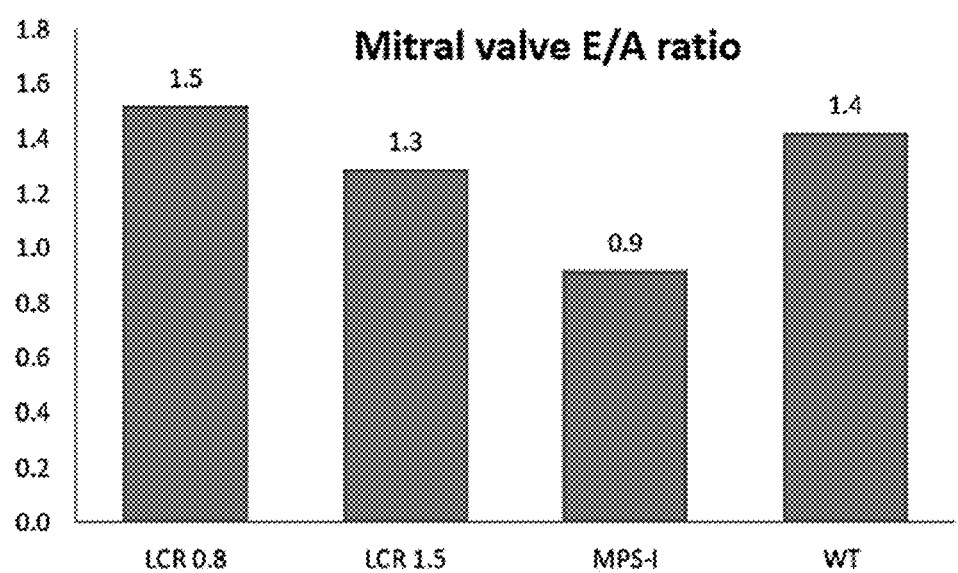
FIG. 13 is a graph representing the correction of mitral valve early to late ventricular filling velocities (E/A) ratio, as measure by ultrasound, post gene therapy with the bLCR-EFS-IDUA construct as measured by ECG after treatment with cells containing on average 0.8 and 1.5 copies of the LCR EFS vector (LCR 0.8 and LCR 1.5 respectively), compared to WT and MPS-I null mice.

Correction of Cardiac Parameters and Function as Measured by Ultrasound in IDUA Treated Animals The data generated here corresponds to the first transplant experiment (TP1), including a HSC transplant (HSCT) group (IDUA−/− receiving WT cells, n=2), a LCR-IDUA group (IDUA−/− receiving IDUA−/− cells transduced with the lentivirus β LCR-EFS-IDUA, n=5), a MPS-I group (IDUA−/− untreated n=4) and a WT group (WT untreated n=2). The group sizes for transplanted mice were larger at the start of the experiment (HSCT n=6 and LCR-IDUA n=7), but we lost some of the mice due to chemotherapy toxicity or lack of stem cell engraftment. We have refined the transplant procedure to avoid this issue. FIGS. 10A and 10B demonstrated that in the open field test we saw a tendency of the gene therapy treated animals to recover normal function. One of the most striking features observed in the MPS-I mouse model is the development of aortic dilation, FIGS. 10A and 10B show that this seems to be avoided with the treatment. Peak velocity and transversal arch diameter abnormalities were also strikingly corrected in Gene Therapy treated animals (FIGS. 11A-11C). The MPS-I murine model showed an elevated aortic valve peak pressure and velocity compared to wild-type animals, as shown in FIGS. 12A, 12B, and 8B, respectively. In addition, the mitral valve E/A ratio in the MPS-I murine model was reduced compared to wild-type animal, as shown in FIG. 13. Post gene therapy with the LCR EFS IDUA vector, functional correction of aortic valve peak pressure, aortic valve peak velocity, and mitral valve E/A ratio was observed (FIGS. 12A, 12B, and 13).

Example 7

Figure 14A:
FIG. 14A is a photograph demonstrating the bone modelling in a WT mouse. Snout bone morphology was measured by computerised tomography (CT). Top, anterior head; bottom, posterior head.
Figure 14B:
FIG. 14B is a photograph demonstrating the bone modelling in a murine model of MPS-I (IDUA–/–). Snout bone morphology was measured by computerised tomography (CT). Top, anterior head; bottom, posterior head.
Figure 14C:
FIG. 14C is a photograph demonstrating the correction of bone modelling post-gene therapy with the bLCR-EFS-IDUA construct in a murine model of MPS-I. Snout bone morphology was measured by computerised tomography (CT). Top, anterior head; bottom, posterior head.
Figure 15A:
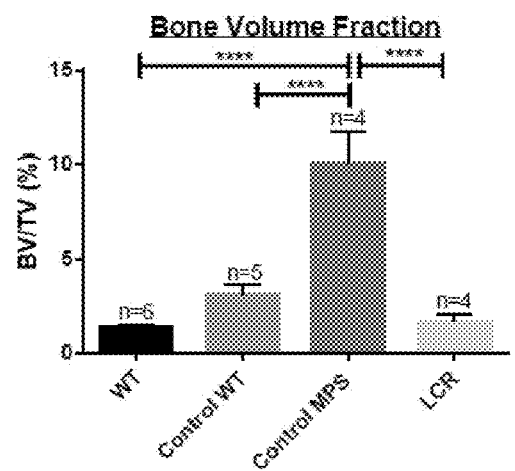
FIG. 15A is a graph demonstrating the correction of bone volume in bLCR-EFS-IDUA compared to control WT or MPS-null mice, as measured by micro-computerised tomography (micro-CT).
Figure 15B:
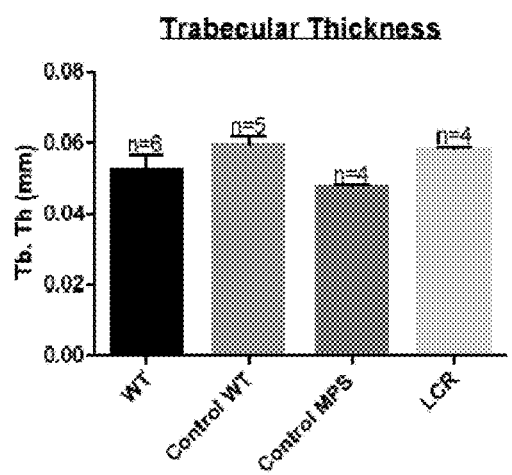
FIG. 15B is a graph demonstrating the correction of trabecular thickness in bLCR-EFS-IDUA compared to control WT or MPS-null mice, as measured by micro-computerised tomography (micro-CT).
Figure 15C:
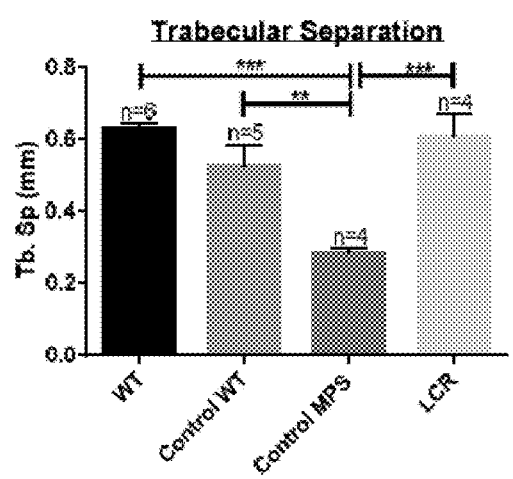
FIG. 15C is a graph demonstrating the correction of trabecular separation in bLCR-EFS-IDUA compared to control WT or MPS-null mice, as measured by micro-computerised tomography (micro-CT).
Figure 15D:
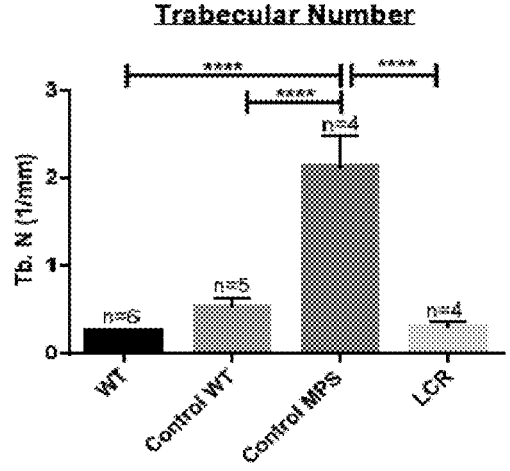
FIG. 15D is a graph demonstrating the correction of trabecular number in bLCR-EFS-IDUA compared to control WT or MPS-null mice, as measured by micro-computerised tomography (micro-CT).
Figure 16A:
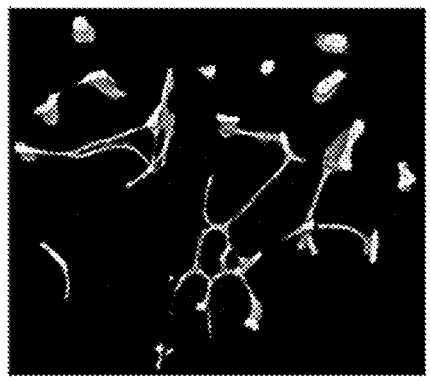
FIG. 16A is a photograph demonstrating the bone morphology in WT (T3B 7LR) mice, as measured by micro-CT.
Figure 16B:
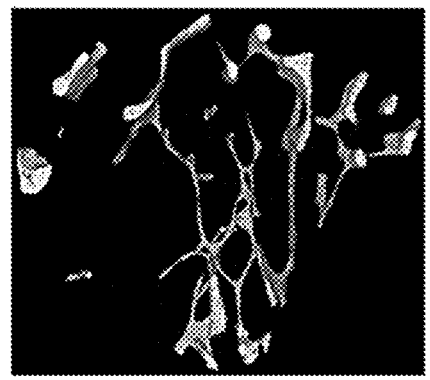
FIG. 16B is a photograph demonstrating the bone morphology in control WT (P2 5L) mice, as measured by micro-CT.
Figure 16C:
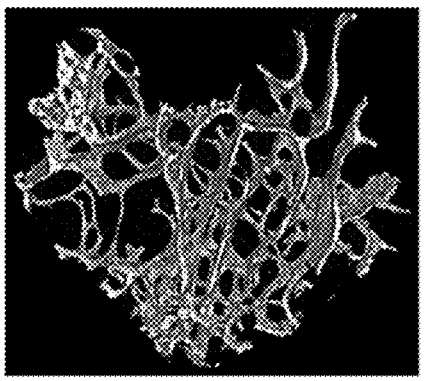
FIG. 16C is a photograph demonstrating the bone morphology in MPS control (P1 3R) mice, as measured by micro-CT.
Figure 16D:
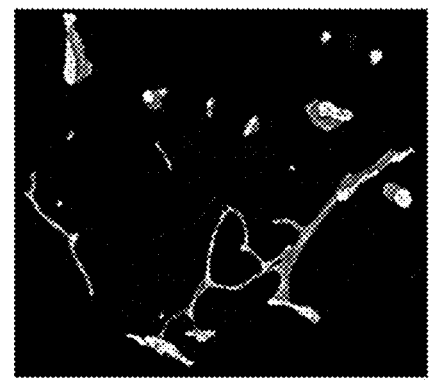
FIG. 16D is a photograph demonstrating the correction of bone morphology in bLCR-EFS-IDUA treated mice, as measured by micro-CT.
Figure 17A:
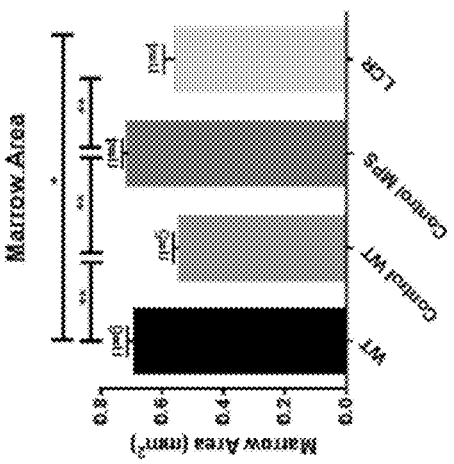
FIG. 17A is a graph demonstrating the correction of cortical bone area in bLCR-EFS-IDUA compared to control WT or MPS-null mice, as measured by micro-computerised tomography (micro-CT).
Figure 17B:
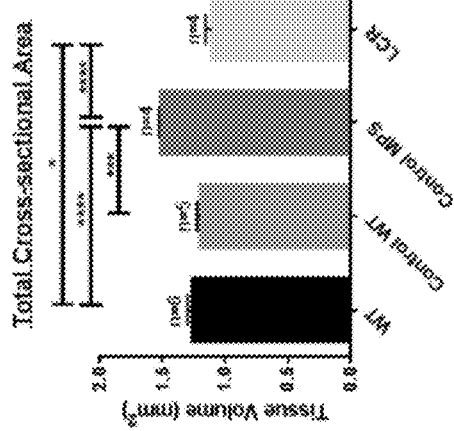
FIG. 17B is a graph demonstrating the correction of total bone cross-sectional area in bLCR-EFS-IDUA compared to control WT or MPS-null mice, as measured by micro-computerised tomography (micro-CT).
Figure 17C:
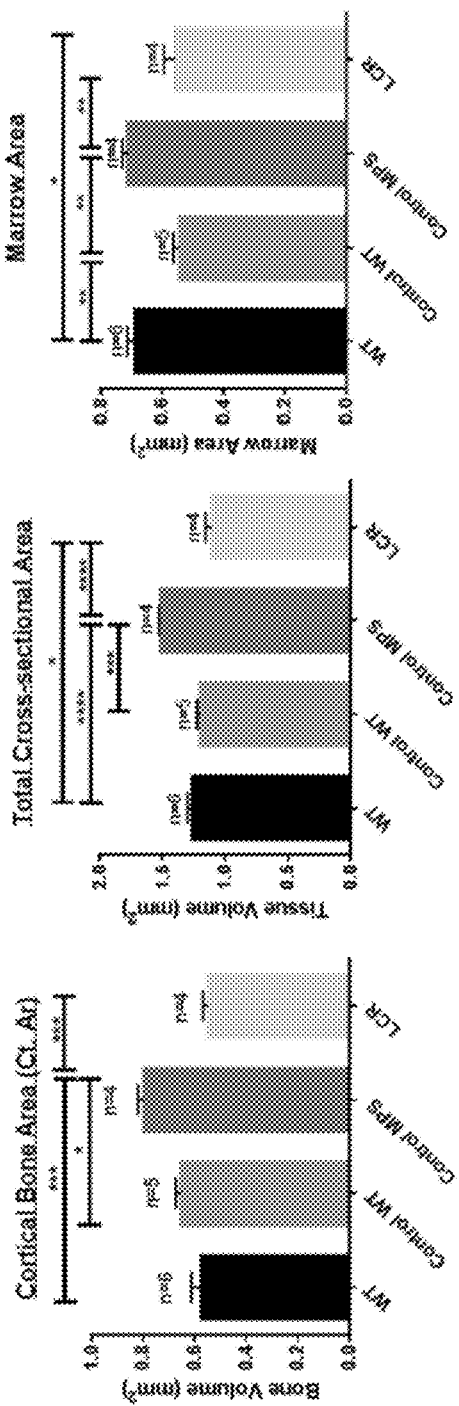
FIG. 17C is a graph demonstrating the correction of marrow area in bLCR-EFS-IDUA compared to control WT or MPS-null mice, as measured by micro-computerised tomography (micro-CT).
Figure 17D:
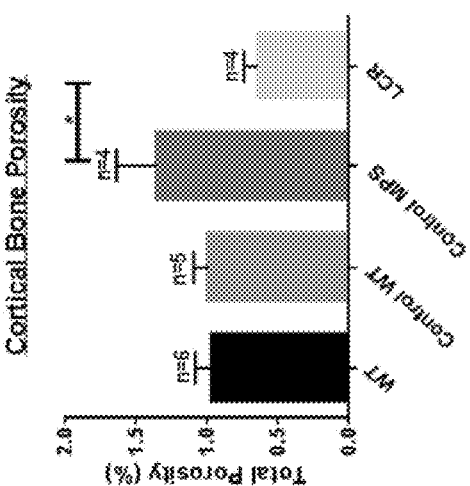
FIG. 17D is a graph demonstrating the correction of cortical bone thickness in bLCR-EFS-IDUA compared to control WT or MPS-null mice, as measured by micro-computerised tomography (micro-CT).
Figure 17E:
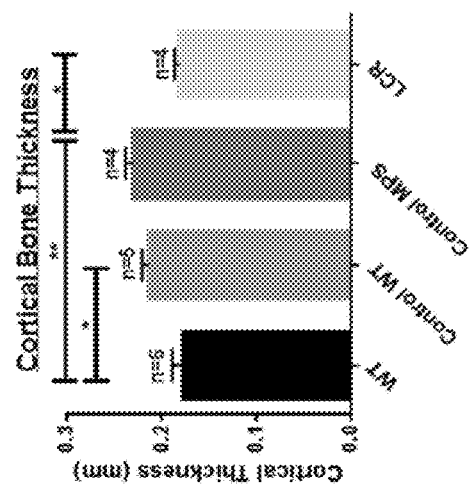
FIG. 17E is a graph demonstrating the correction of cortical bone porosity in bLCR-EFS-IDUA compared to control WT or MPS-null mice, as measured by micro-computerised tomography (micro-CT).
Figure 18:
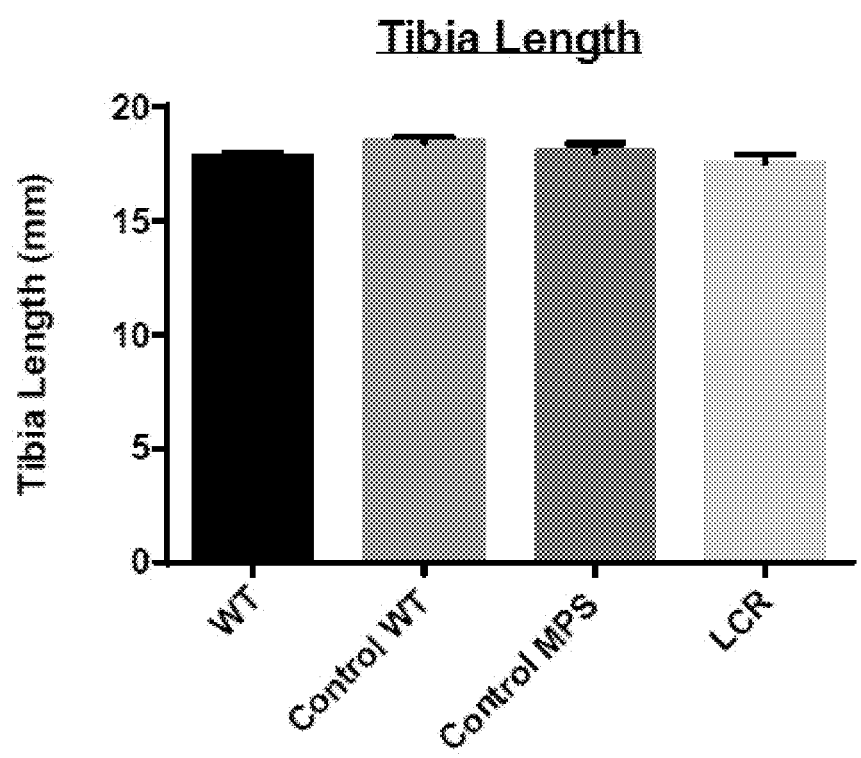
FIG. 18 is a graph demonstrating lack of significant difference in the gross length of the tibia in bLCR-EFS-IDUA compared to control WT or MPS-null mice.
Figure 19:
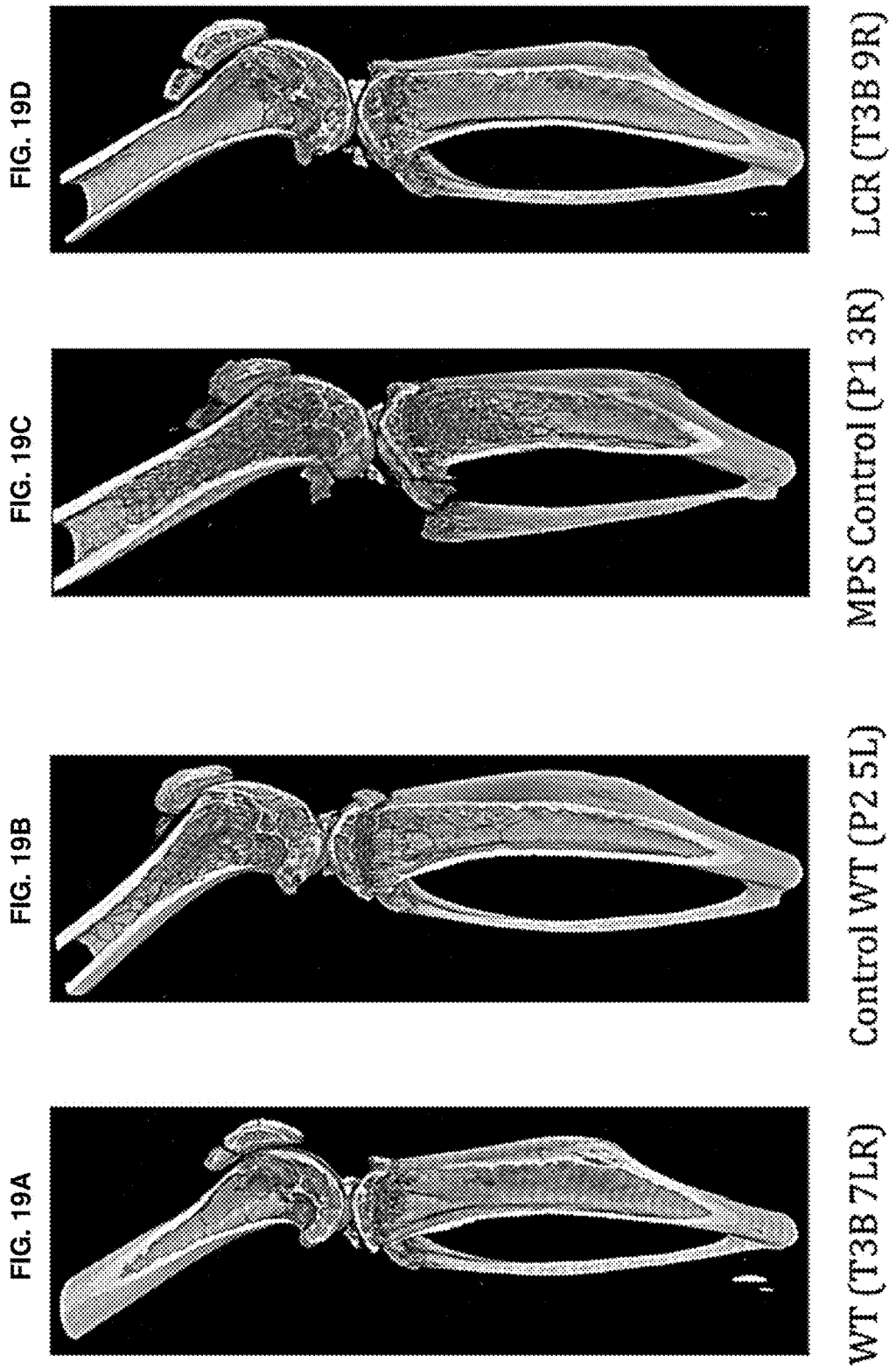
FIG. 19A is photograph of the gross morphology of sectioned hind-limbs from WT (T3B 7LR) mice.
FIG. 19B is photograph of the gross morphology of sectioned hind-limbs from control WT (P2 5L).
FIG. 19C is photograph of the gross morphology of sectioned hind-limbs from MPS-null (P1 3R) mice.
FIG. 19D is photograph of the gross morphology of sectioned hind-limbs from bLCR-EFS-IDUA-treated mice.

Correction of Bone Modelling Post Gene Therapy in a MPS-I Murine Model as Determined by CT and Gross Morphological Analysis The MPS-I murine model had fatter and shorter snouts, compared to wild-type mice (FIGS. 14A and 14B). Post gene therapy with the LCR EFS IDUA vector, correction in this bone modelling defect was observed by computerised tomography (CT) (FIG. 14C). The bone volume, trabecular thickness, trabecular separation, trabecular number gross morphology, cortical bone area, total cross-sectional area, marrow area, cortical bone thickness and cortical bone porosity were all corrected in LCR EFS GAA treated animals (FIGS. 15A-15D, 16A-16D, 17A-17E, 18, and 19A-19D).

Example 8

Enhancement of Expression of GAA from Lentiviral Vector

Figure 21A:
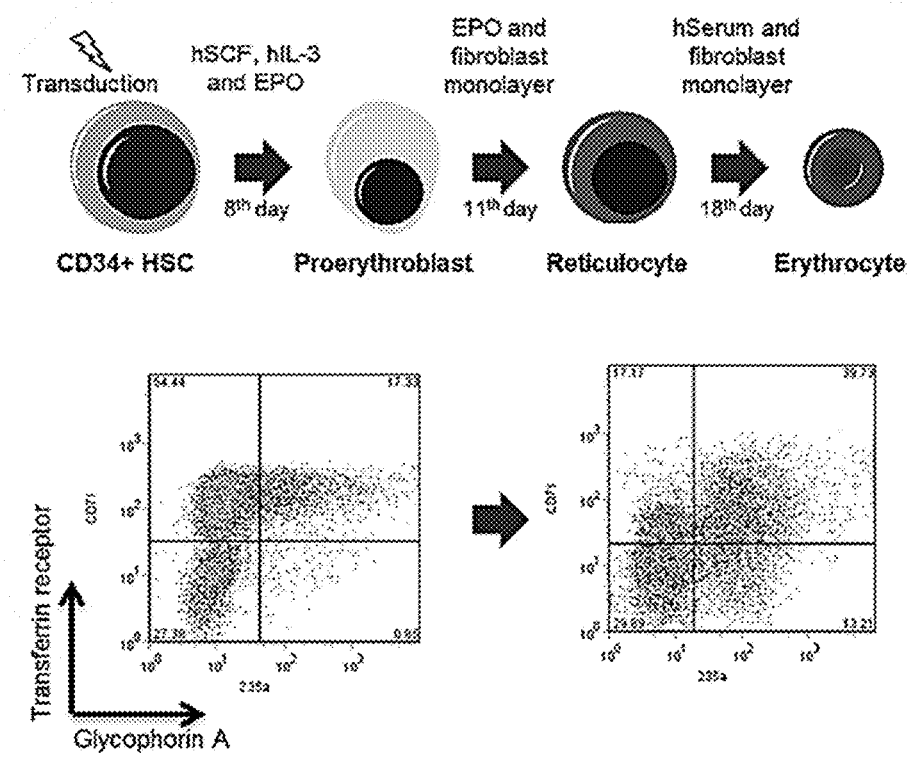
FIG. 21A is a schematic of the protocol for isolating erythroid-like cells and validation by FACS.
Figure 21B:
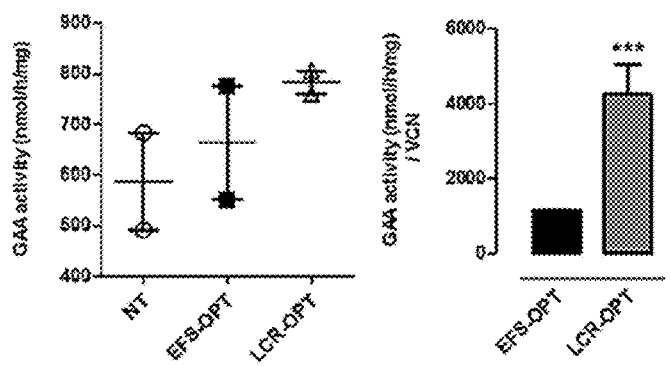
FIG. 21B is a graph of the GAA activity in EFS-GAA (EFS OPT) cells and bLCR-EFS-GAA (LCR-OPT) in human erythroid-like cells, showing a 4-fold increase in GAA activity in bLCR-EFS-GAA treated cells.

Experiments in MEL cells demonstrated that transduction with the bLCR-EFS-GAA construct resulted in a significant 6.5-fold increase in GAA activity differentiated MEL cells (MEL cell treated with DMSO) compared with non-transduced or EFS-GAA MEL differentiated MEL cells (FIG. 20). A 4-fold increase in GAA activity was shown in human erythroid-like cells treated with the bLCR-EFS-GAA construct, compared to cells treated with the EFS-GAA construct or non-transduced cells (FIGS. 21A and 21B).

These data suggest very strongly that by upregulating expression in erythroid cells through the activity of the bLCR, high levels of GAA are produced and then secreted into the plasma of corrected mice.

Example 9

Functional and Biochemical Characterisation of GAA Treated Animals

Figure 22A:
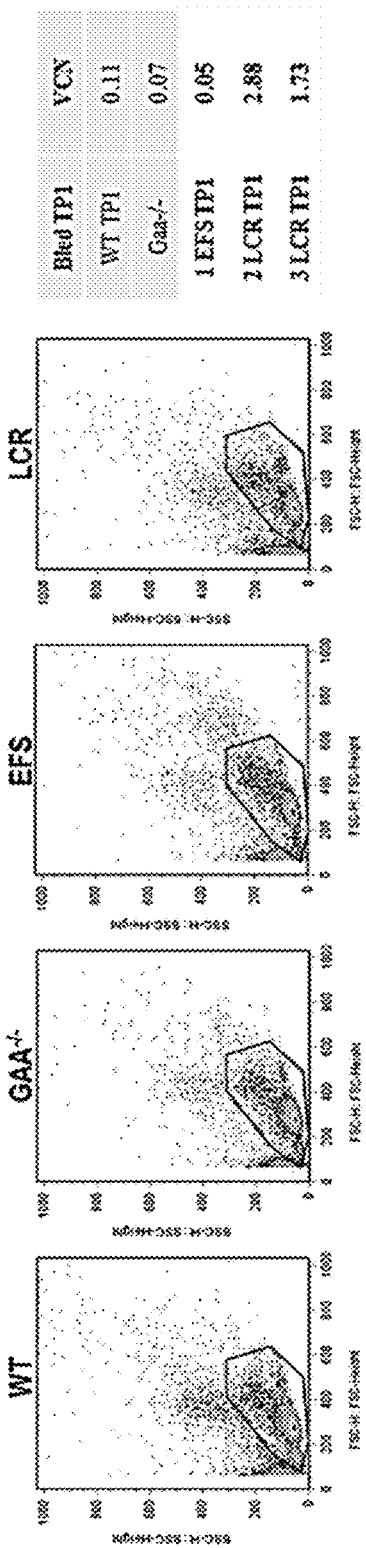
FIG. 22A is a series of graphs of pilot HSC transplant (TP) experiments identifying the indicated cell populations through FACS.
Figure 22B:
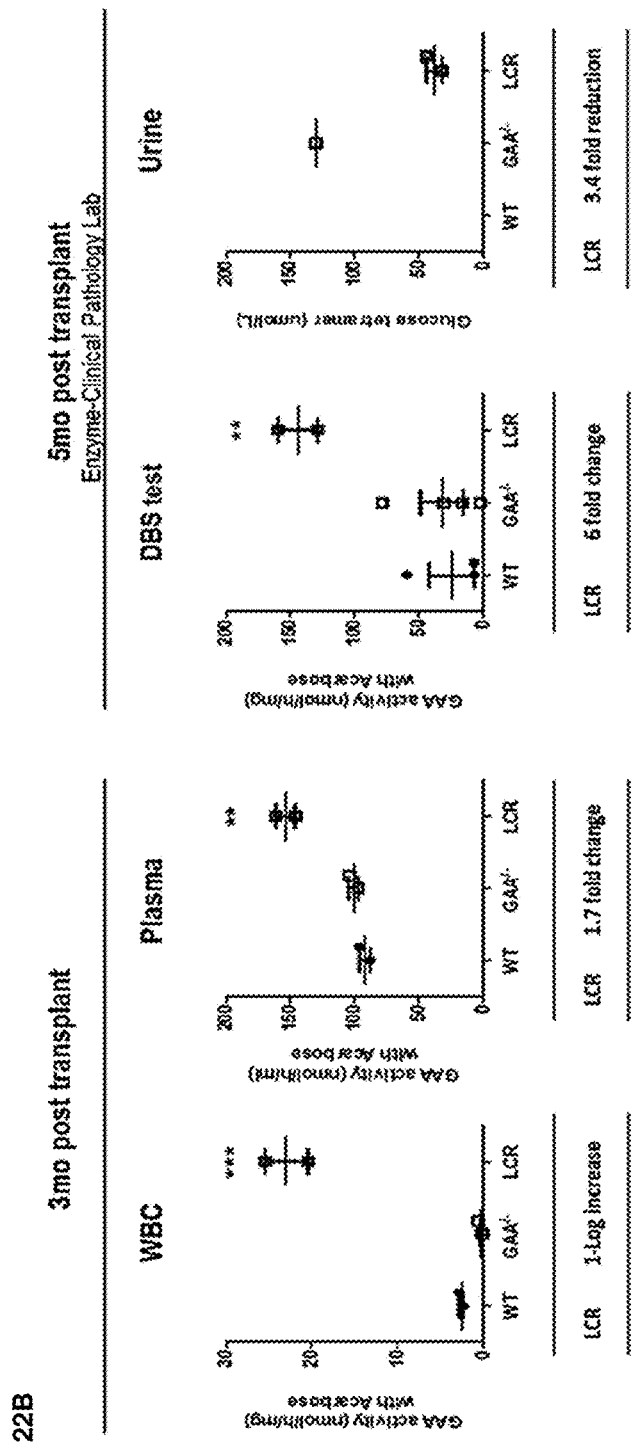
FIG. 22B is a series of graphs of GAA–/– mice with the bLCR-EFS-GAA construct depicting an increase in GAA enzyme activity and reduction in excreted glucose tetramers in urine.
Figure 23A:
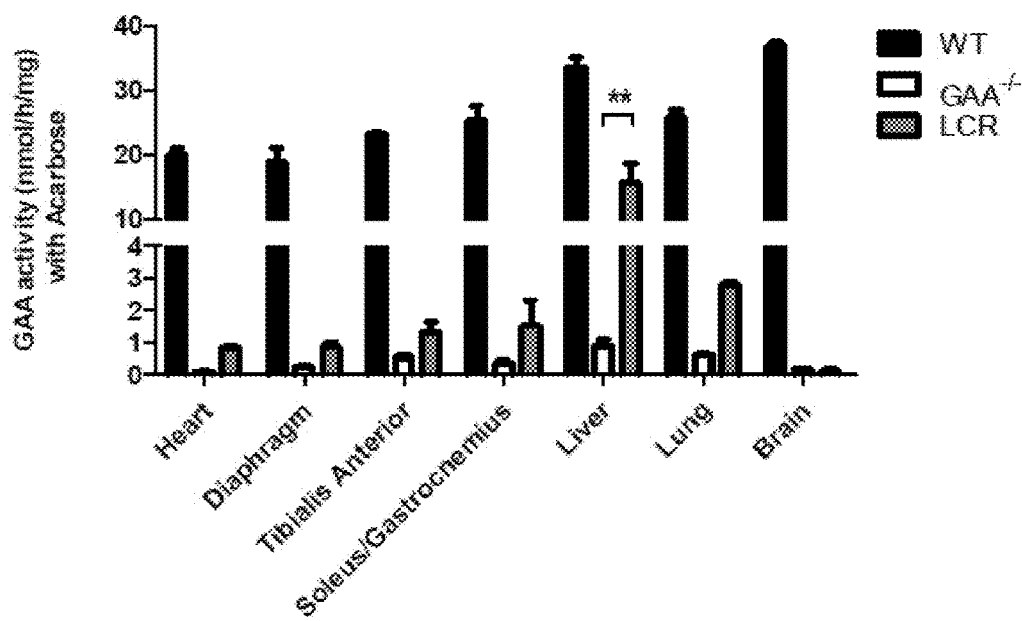
FIG. 23A is a graph depicting cross-correction of GAA activity and glycogen concentrations across multiple tissues in bLCR-EFS-GAA treated GAA–/– mice.
Figure 23B:
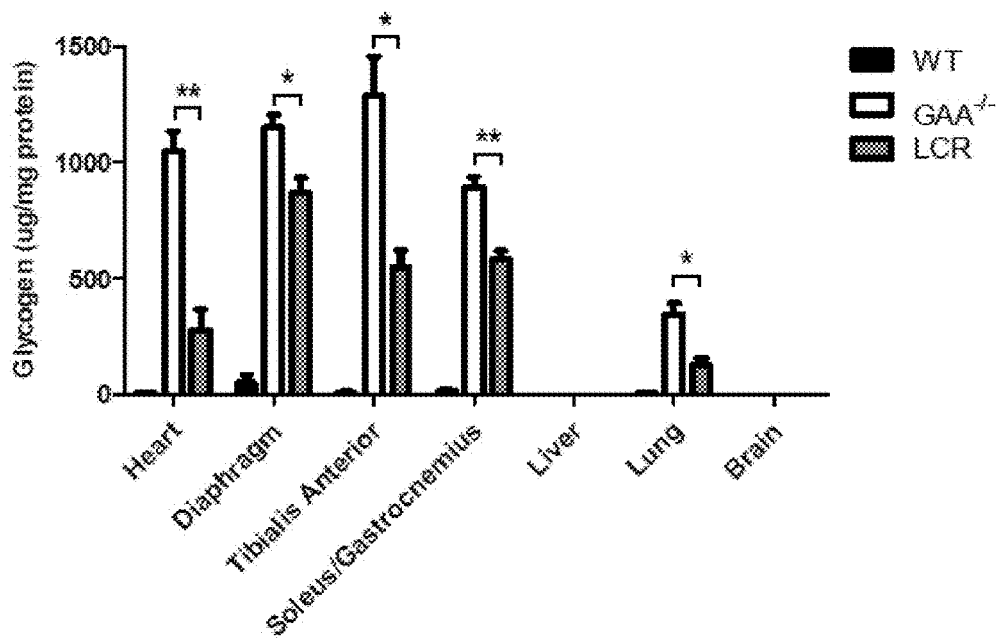
FIG. 23B is a graph depicting cross-correction of glycogen concentrations across multiple tissues in bLCR-EFS-GAA treated GAA-/- mice.
Figure 24A:
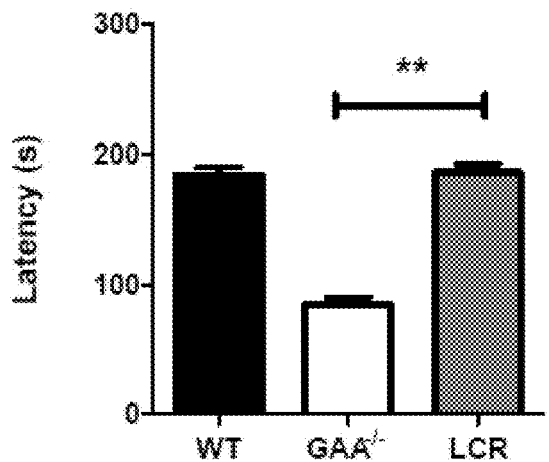
FIG. 24A is a graph depicting the results of a "Rotarod test" measuring motor coordination of GAA-/- mice and GAA-/- mice treated with the bLCR-EFS-GAA vector. All functional defects in the GAA-null mouse model were corrected with the bLCR-EFS-GAA vector.
Figure 24B:
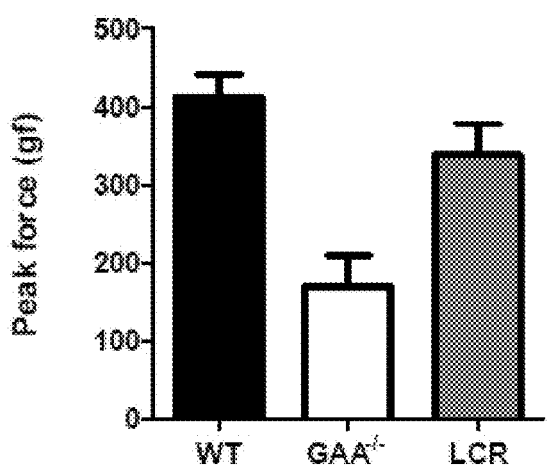
FIG. 24B is a graph depicting the results of a "Grip strength test" measuring muscle strength of GAA-/- mice and GAA-/- mice treated with the bLCR-EFS-GAA vector. All functional defects in the GAA-null mouse model were corrected with the bLCR-EFS-GAA vector.
Figure 24C:
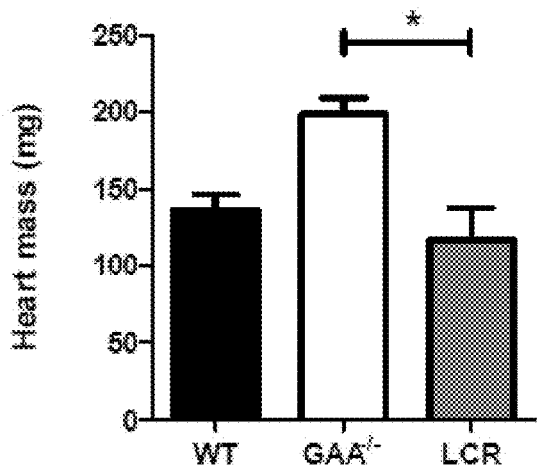
FIG. 24C is a graph depicting the heart mass measured by ultrasound of GAA-/- mice and GAA-/- mice treated with the bLCR-EFS-GAA vector. All functional defects in the GAA-null mouse model were corrected with the bLCR-EFS-GAA vector.

We have quantified the activity of GAA white blood cells, blood plasma, dried blood spot testing, heart, diaphragm, tibialis anterior, soleu/gastrocnemius, liver, lung, and brain in GAA-null animals after treatment with the bLCR-EFS-GAA construct (FIGS. 22A, 22B, and 23A). Enhanced, complete, or partial correction was observed in the bLCR-EFS-GAA treated group. We have also quantified the level of total glycogen in urine, heart, diaphragm, tibialis anterior, soleus/gastrocnemius, liver, lung and brain in GAA-null animals after treatment with the bLCR-EFS-GAA construct (FIGS. 22A, 22B, and 23B). Partial to complete correction was observed in the bLCR-EFS-GAA treated group. Correction of the GAA-null mouse model's motor coordination, muscle strength, and hypertrophic heart was also observed in animals treated with the bLCR-EFS-GAA construct (FIGS. 24A-24C).

Example 10

Comparison of Various CCL GT Constructs

We have quantified the activity of the specific enzyme IDUA under the control of various constructs in K562 cells (early erythroid-myeloid-like cells), U937 cells (monocyte-like cells), HEK 293T cells, and Jurkat cells (a T-cell line).

Figure 25:
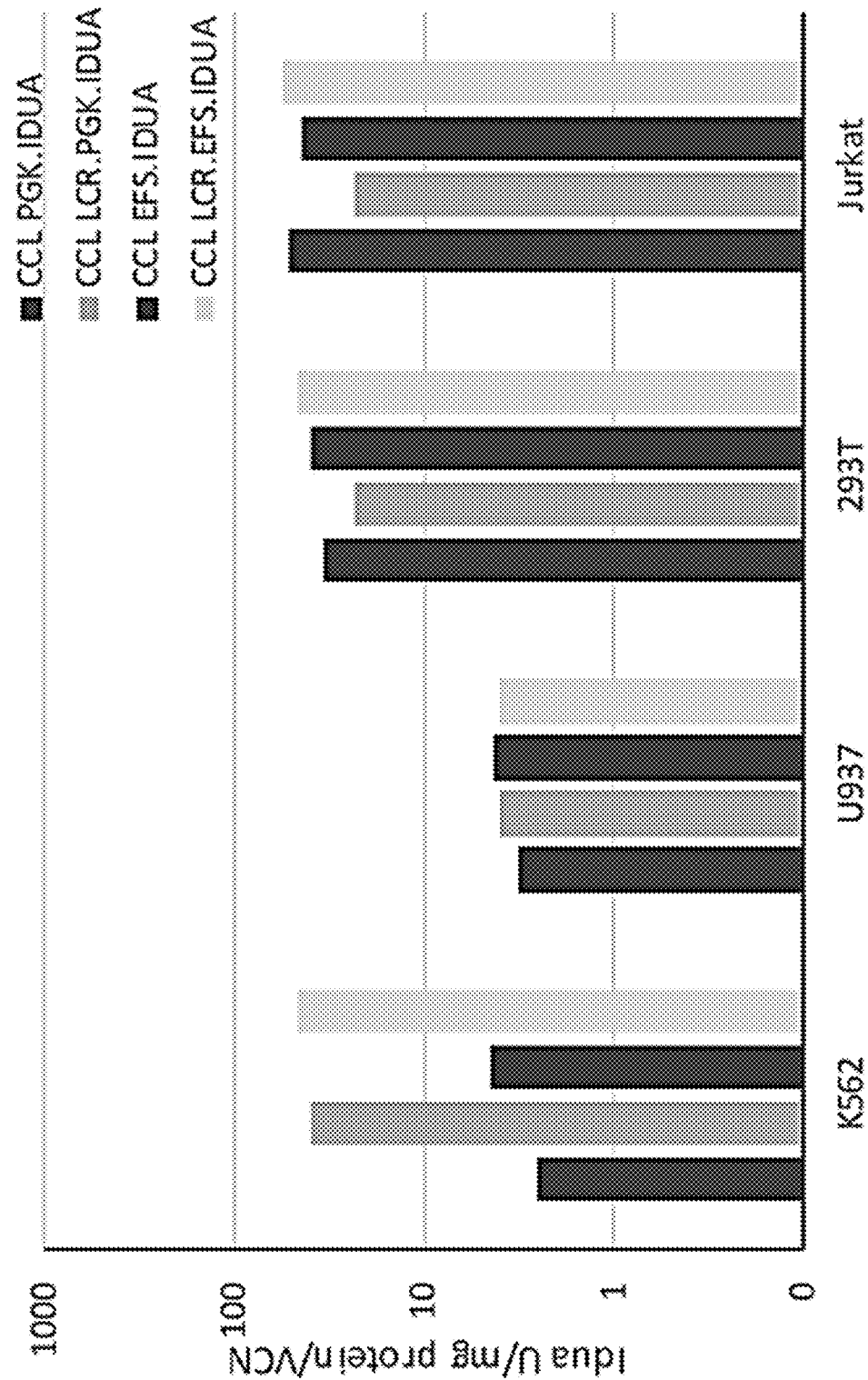
FIG. 25 is a graph of IDUA enzymatic activity in K562, U937, 293T and Jurkat cells were transduced with CCL PGK.IDUA, CCL LCR.PGK.IDUA, CCL EFS.IDUA or CCL LCR.EFS.IDUA lentiviral vectors. After 3 days, the cells were collected washed and frozen for IDUA activity assay and copy number. IDUA enzymatic activity was normalized with the copy number and protein concentration, and is presented on a log 10 scale.

As shown in FIG. 25, when IDUA was under the control of the LCR region operably linked to a suitable promoter (for example PGK or EFS), normalised expression was very substantially increased in an erythroid-like cell line, compared to when the IDUA gene was driven by the promoter alone (i.e., in the absence of an operably linked LCR regulatory element). This clearly demonstrates a combinatorial effect of the LCR regulatory region with the selected promoter.

Figure 26A:
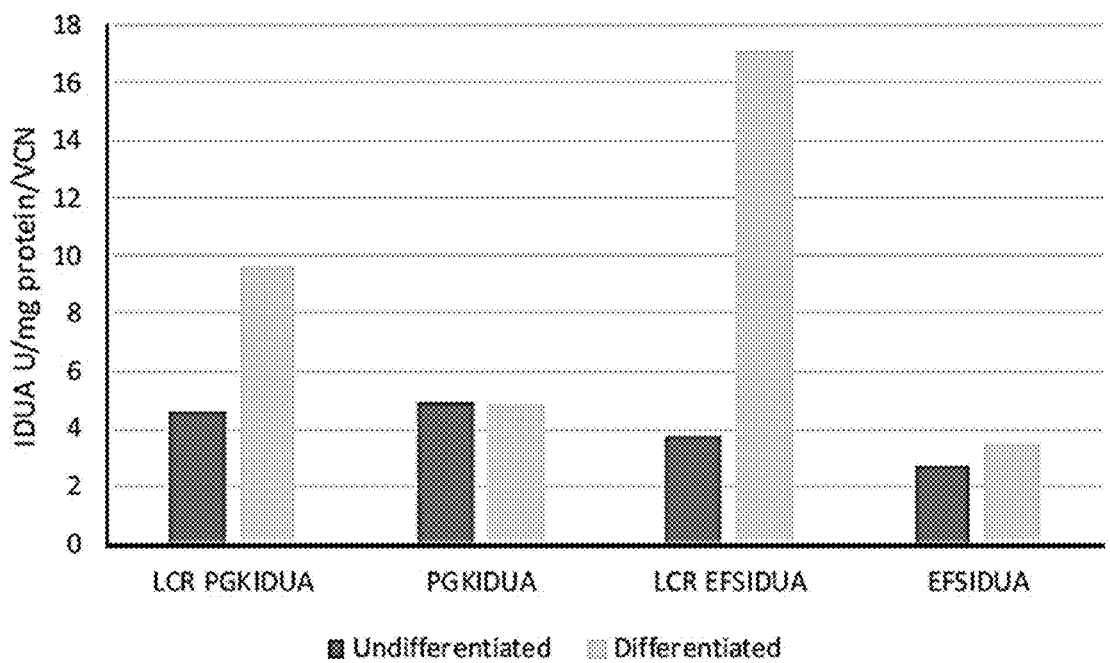
FIG. 26A is a graph of IDUA enzymatic activity in MEL cells transduced with CCL PGK.IDUA, CCL LCR.PGK.IDUA, CCL EFS.IDUA or CCL LCR.EFS.IDUA lentiviral vectors. After 4 days, half of the transduced cells were exposed to 2% dimethylsulphoxide (DMSO) for 4 days to induce erythroid differentiation. IDUA enzymatic activity was normalized with the copy number and protein concentration.
Figure 26B:
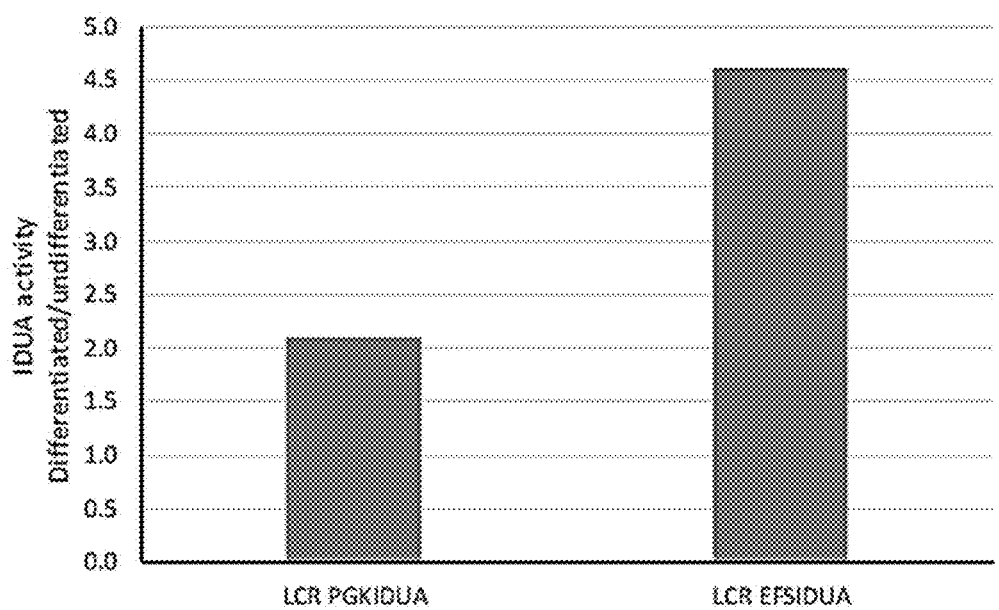
FIG. 26B is a graph of IDUA enzymatic activity in MEL cells transduced with the CCL LCR.PGK.IDUA and CCL LCR.EFS.IDUA lentiviral vectors, indicating a resulting at least a two-fold induction of IDUA activity upon differentiation of the MEL cells.

Looking in more detail in MEL cells (a specific early-erythroid cell line that can be driven to differentiate by the addition of DMSO), upon differentiation, the normalised IDUA activity increased significantly when under the control of the LCR-PGK or LCR-EFS regulatory element (FIG. 26A). An increase of at least 2-fold in normalised IDUA activity was observed (FIG. 26B). However, this effect was not observed when the IDUA gene was under the control of the PGK or EFS regulatory element alone (FIG. 26A).

Although these effects have been shown with the IDUA gene, it would be expected that a similar effect would be observed with other genes. Further, it would be expected that a similar erythroid-specific up-regulation of expression would be observed in in vivo systems, such as the human or the mouse.

REFERENCES

Altschul et al. (1990) "Basic local alignment search tool" *J Mol BIol* 215:403-410

Altschul et al. (1993) "A protein alignment scoring system sensitive at all evolutionary distances" *J Mol Evol* 36:290-300

Winchester et al. (2000) "The molecular basis of lysosomal storage diseases and their treatment". Biochem. Soc. Trans. 28:150-4

Reece and Campbell (2002) Biology. San Francisco: Benjamin Cummings. pp. 121-122 ISBN 0-8053-6624-5.

Wang et al. (2009) "Reprogramming erythroid cells for lysosomal enzyme production leads to visceral and CAN cross-correction in mice with Hurler syndrome" PNAS 106:19958-19963

El-Amouri et al. (2014) "Normalization and Improvement of CAN Deficits in Mice With Hurler Syndrome After Long-term Peripheral Delivery of BBB-targeted Iduronidase" Molecular Therapy 22:20-28-2037

Visigalli et al. (2010) "Gene therapy augments the efficacy of hematopoietic cell transplantation and fully corrects mucopolysaccharidosis type I phenotype in the mouse model" Blood 116:5130-5139

Clarke et al. (2005). "Enzyme replacement therapy of Fabry disease". Mol. Neurobiol. 32: 043-050

Bruni et al. (2007). "Update on treatment of lysosomal storage diseases". Acta Myol 26:87-92

Aldenhoven et al. (2015) "Hematopoietic Cell Transplantation for Mucopolysaccharidosis Patients Is Safe and Effective: Results after Implementation of International Guidelines." Biol Blood Marrow Transplant S1083-8791(15)00118-4

Montiel-Equihua et al. (2012) "The β-Globin Locus Control Region in Combination With the EF1α Short Promoter Allows Enhanced Lentiviral Vector-mediated Erythroid Gene Expression With Conserved Multilineage Activity" Molecular Therapy 20:1400-1409

Henikoff and Henikoff (1992) "Amino acid substitution matrices from protein blocks" PNAS 15:10915-9

Karlin and Altschul (1993) "Applications and statistics for multiple high-scoring segments in molecular sequences" PNAS 15:5873-7

Devereux et al. (1984) "A comprehensive set of sequence analysis programs for the VAX" Nucleic Acids Res. 12:387-395

Demaison et al. (2002) "High-level transduction and gene expression in hematopoietic repopulating cells using a human immunodeficiency [correction of imunodeficiency] virus type 1-based lentiviral vector containing an internal spleen focus forming virus promoter. Hum Gene Ther. 13:803-13

Giarrantana et al. (2011) "Proof of principle for transfusion of in vitro generated red blood cells" Blood 118:5071-9

Knight et al. (2010) "Effect of the internal promoter on insertional gene activation by lentiviral vectors with an intact HIV long terminal repeat" J Virol 84:4856-4859

Arumugam et al. (2009) "Genotoxic potential of lineage-specific lentivirus vectors carrying the β-globin locus control region" Mol Ther 17:1929-1937

Wilkinson, F. L. et al. (2013) "Busulfan conditioning enhances engraftment of hematopoietic donor-derived cells in the brain compared with irradiation" Mol Ther 21:868-876

```
Sequence Information
SEQ ID NO: 1-the DNA sequence of the bLCR-EFS sequence
GCGGCCGCTATCTCATTGCTGTTCGTAATTGTTAGATTAATTTTGTAATATTGATATTATTCCTAGA
AAGCTGAGGCCTCAAGATGATAACTTTTATTTTCTGGACTTGTAATAGCTTTCTCTTGTATTCACCA
TGTTGTAACTTTCTTAGAGTAGTAACAATATAAAGTTATTGTGAGTTTTTGCAAACACAGCAAACA
CAACGACCCATATAGACATTGATGTGAAATTGTCTATTGTCAATTTATGGGAAAACAAGTATGTAC
TTTTTCTACTAAGCCATTGAAACAGGAATAACAGAACAAGATTGAAAGAATACATTTTCCGAAATT
ACTTGAGTATTATACAAAGACAAGCACGTGGACCTGGGAGGAGGGTTATTGTCCATGACTGGTGT
GTGGAGACAAATGCAGGTTTATAATAGATGGGATGGCATCTAGCGCAATGACTTTGCCATCACTTT
TAGAGAGCTCTTGGGGGCCCCAGTACACAAGAGGGGACGCAGGGTATATGTAGACATCTCATTCT
TTTTCTTAGTGTGAGAATAAGAATAGCCATGACCTGAGTTTATAGACAATGAGCCCTTTTCTCTCTC
CCACTCAGCAGCTATGAGATGGCTTGCCCTGCCTCTCTACTAGGCTGACTCACTCCAAGGCCCAGC
AATGGGCAGGGCTCTGTCAGGGCTTTGATAGCACTATCTGCAGAGCCAGGGCCGAGAAGGGGTGG
ACTCCAGAGACTCTCCCTCCCATTCCCGAGCAGGGTTTGCTTATTTATGCATTTAAATGATATATTT
ATTTTAAAAGAAATAACAGGAGACTGCCCAGCCCTGGCTGTGACATGGAAACTATGTAGAATATT
TTGGGTTCCATTTTTTTTTCCTTCTTTCAGTTAGAGGAAAAGGGGCTCACTGCACATACACTAGACA
GAAAGTCAGGAGCTTTGAATCCAAGCCTGATCATTTCCATGTCATACTGAGAAAGTCCCCACCCTT
CTCTGAGCCTCAGTTTCTCTTTTTATAAGTAGGAGTCTGGAGTAAATGATTTCCAATGGCTCTCATT
TCAATACAAAATTTCCGTTTATTAAATGCATGAGCTTCTGTGCGGCCGCTCTAGAACTAGTGGATC
CCCCGCTTCTTTGAGAAACATCTTCTTCGTTAGTGGCCTGCCCCTCATTCCCACTTTAATATCCAGA
ATCACTATAAGAAGAATATAATAAGAGGAATAACTCTTATTATAGGTAAGGGAAAATTAAGAGGC
ATACGTGATGGGATGAGTAAGAGAGGAGAGGGAAGGATTAATGGATGATAAAATCTACTACTATT
TGTTGAGACCTTTTATAGTCTAATCAATTTTGCTATTGTTTTCCATCCTCACGCTAACTCCATAAAA
```

| Sequence Information |
|---|
| AAACACTATTATTATCTTTATTTTGCCATGACAAGACTGAGCTCAGAAGAGTCAAGCATTTGCCTA |
| AGGTCGGACATGTCAGAGGCAGTGCCAGACCTATGTGAGACTCTGCAGCTACTGCTCATGGGCCCT |
| GTGCTGCACTGATGAGGAGGATCAGATGGATGGGCAATGAAGCAAAGGAATCATTCTGTGGATA |
| AAGGAGGACAGCCATGAAGAAGTCTATGACTGTAAATTTGGGACAGGAGTCTCTAAGGACTTGGA |
| TTTCAAGGAATTTTGACTCAGCAAACACAAGACCCTCACGGTGACTTTGCGAGCTGGTGTGCCAGA |
| TGTGTCTATCAGAGGTTCCAGGGAGGGTGGGGTGGGGTCAGGGCTGGCCACCAGCTATCAGGGCC |
| CAGATGGGTTATAGGCTGGCAGGCTCAGATAGGTGGTTAGGTCAGGTTGGTGGTGCTGGGTGGAG |
| TCCATGACTCCCAGGAGCCAGGAGAGATAGACCATGAGTAGAGGGCAGACATGGGAAAGGTGGG |
| GGAGGCACAGCATAGCAGCATTTTTCATTCTACTACTACATGGGACTGCTCCCCTATACCCCCAGC |
| TAGGGGCAAGTGCCTTGACTCCTATGTTTTCAGGATCATCATCTATAAAGTAAGAGTAATAATTGT |
| GTCTATCTCATAGGGTTATTATGAGGATCAAAGGAGATGCACACTCTCTGGACCAGTGGCCTAACA |
| GTTCAGGACAGAGCTATGGGCTTCCTATGTATGGGTCAGTGGTCTCAATGTAGCAGGCAAGTTCCA |
| GAAGATAGCATCAACCACTGTTAGAGATATACTGCCAGTCTCAGAGCCTGATGTTAATTTAGCAAT |
| GGGCTGGGACCCTCCTCCAGTAGAACCTTCTAACCAGCTGCTGCAGTCAAAGTCGAATGCAGCTGG |
| TTAGACTTTTTTTAATGAAGCTTGGTGACCGTCGTACCAGTGGGGCCTCTAAGACTAAGTCACTCT |
| GTCTCACTGTGTCTTAGCCAGTTCCTTACAGCTTGCCCTGATGGGAGATAGAGAATGGGTATCCTC |
| CAACAAAAAATAAATTTTCATTTCTCAAGGTCCAACTTATGTTTTCTTAATTTTTAAAAAAATCTT |
| GACCATTCTCCACTCTCTAAAATAATCCACAGTGAGAGAAACATTCTTTTCCCCCATCCCATAAAT |
| ACCTCTATTAAATATGGAAAATCTGGGCATGGTGTCTCACACCTGTAATCCCAGCACTTTGGGAGG |
| CTGAGGTGGGTGGACTGCTTGGAGGTCAGGAGTTCAAGACCATCTTGGCAACATGGTGATACCCT |
| GCCTCTACAAAAAGTACAAAAATTAGCCTGGCATGGTGGTGTGCACCTGTAATCCCAGCTATTAGG |
| GTGGCTGAGGCAGGAGAATTGCTTGAACCCGGGAGGCGGAGGTTGCAGTGAGCTGAGATCGTGCC |
| ACTGCACTCCAGCCTGGGGACAGAGCACATTATAATTAACTGTTATTTTTTACTTGGACTCTTGTG |
| GGGAATAAGATACATGTTTTATTCTTATTTATGATTCAAGCACTGAAAATAGTGTTTAGCATCCAG |
| CAGGTGCTTCAAAACCATTTGCTGAATGATTACTATACTTTTTACAGCTCAGCTCCCTCTATCCCT |
| TCCAGCATCCTCATCTCTGATTAAATAAGCTTCAGTTTTTCCTTAGTTCCTGTTACATTTCTGTGTGT |
| CTCCATTAGTGACCTCCCATAGTCCAAGCATGAGCAGTTCTGGCCAGGCCCCTGTCGGGGTCAGTG |
| CCCCACCCCCGCCTTCTGGTTCTGTGTAACCTTCTAAGCAAACCTTCTGGCTCAAGCACAGCAATG |
| CTGAGTCATGATGAGTCATGCTGAGGCTTAGGGTGTGTGCCCAGATGTTCTCAGCCTAGAGTGATG |
| ACTCCTATCTGGGTCCCCAGCAGGATGCTTACAGGGCAGATGGCAAAAAAAAAGGAGAAGCTGACC |
| ACCTGACTAAAACTCCACCTCAAACGGCATCATAAAGAAAATGGATGCCTGAGACAGAATGTGAC |
| ATATTCTAGAATATATTATTTCCTGAATATATATATATATATATACACATATACGTATATATATA |
| TATATATATTTGTTGTTATCAATTGCCATAGAATGATTAGTTATTGTGAATCAAATATTTATCTTGC |
| AGGTGGCCTCTATACCTAGAAGCGGCAGAATCAGGCTTTATTAATACATGTGTATAGATTTTTAGG |
| ATCTATACACATGTATTAATATGAAACAAGGATATGGAAGAGGAAAGGCATGAAAACAGGAAAAG |
| AAAACAAACCTTGTTTGCCATTTTAAGGCACCCCTGGACAGCTAGGTGGCAAAAGGGGGCTGCAG |
| GAATTCGATATCACGATTGGCTCCGGTGCCCGTCAGTGGGCAGAGCGCACATCGCCCACAGTCCCC |
| GAGAAGTTGGGGGAGGGGTCGGCAATTGAACCGGTGCCTAGAGAAGGTGGCGCGGGGTAAACT |
| GGGAAAGTGATGTCGTGTACTGGCTCCGCCTTTTTCCCGAGGGTGGGGGAGAACCGTATATAAGTG |
| CAGTAGTCGCCGTGAACGTTCTTTTTCGCAACGGGTTTGCCGCCAGAACACAGGTGTCGTGACGC |

SEQ ID NO: 2-the cDNA sequence of the codon optimised IDUA gene
AGCGCTATGCGGCCCCTGAGGCCTAGAGCTGCCCTGCTGGCTCTGCTGGCCTCTCTGCTGGCTGCC
CCTCCTGTGGCCCCTGCCGAAGCCCCTCACCTGGTGCATGTGGATGCCGCCAGGGCTCTGTGGCCA
CTGCGGAGATTCTGGCGGAGCACCGGCTTTTGCCCCCCACTGCCTCACAGCCAGGCCGACCAGTAC
GTGCTGAGCTGGGACCAGCAGCTGAACCTGGCCTACGTCGGCGTGCCCCACAGAGGCATCAA
ACAAGTGCGCACCCACTGGCTGCTGGAACTGGTGACAACCCGGGGCAGCACCGGCAGAGGACTGA
GCTACAACTTCACCCACCTGGACGGCTACCTGGACCTGCTGAGAGAGAACCAGCTGCTGCCCGGCT
TCGAGCTGATGGGCAGCGCCAGCGGCCACTTCACCGACTTCGAGGACAAGCAGCAGGTGTTCGAG
TGGAAGGACCTGGTGTCCAGCCTGGCCAGACGGTACATCGGCAGATACGGCCTGGCCCACGTGTC
CAAGTGGAACTTCGAGACATGGAACGAGCCCGACCACCACGACTTCGACAACGTGTCAATGACA
TGCAGGGCTTTCTGAACTACTACGACGCCTGCAGCGAGGGCCTGAGAGCCGCCTCTCCTGCCCTGA
GACTGGGCGGACCCGGCGATAGCTTCCACACCCCCCCAGAAGCCCCCTGAGCTGGGCCTGCTG
AGACACTGCCACGACGGCACCAATTTCTTCACCGGCGAGGCCGGCGTGCGGCTGGACTACATCAG
CCTGCACCGGAAGGGCGCCAGAAGCAGCATCAGCATCCTGGAACAGGAAAAGGTCGTCGCCCAGC
AGATCCGGCAGCTGTTCCCCAAGTTCGCCGACACCCCCATCTACAACGACGAGGCCGACCCTCTGG
TCGGATGGTCACTGCCTCAGCCTTGGAGAGCCGACGTGACCTACGCCGCCATGGTGGTGAAAGTG
ATCGCCCAGCACCAGAACCTGCTGCTGGCCAACACCACCAGCGCCTTCCCTTACGCCCTGCTGAGC
AACGACAACGCCTTCCTGAGCTACCACCCCCACCCCTTCGCCCAGAGAACCCTGACCGCCCGGTTC
CAGGTCAACAACACCAGACCCCCCCACGTGCAGCTGCTGAGAAAGCCCGTGCTGACCGCCATGGG
ACTGCTGGCCCTGCTGGACGAGGAACAGCTGTGGGCCGAGGTGTCCAGGCCGGCACCGTGCTGG
ACTCCAATCACACAGTGGGCGTGCTGGCTAGCGCCCACAGACCTCAGGGACCCGCCGATGCTTGG
CGGGCTGCCGTGCTGATCTACGCCAGCGACGACACCAGAGCCCACCCCAACAGATCCGTGGCCGT
GACCCTGCGGCTGAGAGGCGTGCCACCTGGCCCTGGCCTGGTGTACGTGACCAGATACCTGGACA
ACGGCCTGTGCAGCCCCGACGGCGAATGGCGCAGACTGGGCAGACCTGTGTTCCCCACCGCCGAG
CAGTTCCGGCGGATGAGAGCCGCTGAGGACCCTGTGGCTGCCGCCCCTAGACCTCTGCCTGCTGGC
GGCAGACTGACCCTGAGGCCCGCTCTGAGACTGCCTTCTCTGCTGCTGGTGCACGTGTGCGCCAGG
CCCGAGAAGCCTCCCGGCCAGGTCACAAGACTGAGAGCCCTGCCTCTGACCCAGGGACAGCTGGT
GCTGGTCTGGTCCGATGAGCACGTGGGCAGCAAGTGCCTGTGGACCTACGAGATCCAGTTCAGCC
AGGACGGCAAGGCCTACACCCCCGTGTCCCGGAAGCCCAGCACCTTCAACCTGTTCGTGTTCAGCC
CCGACACTGGCGCTGTGTCCGGCTCTTATAGAGTGCGGGCCCTGGACTACTGGGCCAGACCCGGCC
CTTTCAGCGACCCCGTGCCCTACCTGGAAGTGCCCGTGCCTAGAGGGCCCCCCTAGCCCCGGCAACC
CTTGAGTCGAC -continued Sequence Information SEQ ID NO: 3-the cDNA sequence of the iduronate sulfatase gene
(Gene ID: 3423)
AGAACCCGCCCCGGAGGGGAGGGACGCAGGGAAGAGTCGCACGGACGCACTCGCGCTGCGGCCA
GCGCCCGGGCCTGCGGGCCCGGCGGCGGCTGTGTTGCGCAGTCTTCATGGGTTCCCGACGAGGA
GGTCTCTGTGGCTGCGGCGGCGGCTGCTAACTGCGCCACCTGCTGCAGCCTGTCCCCGCCGCTCTG
AAGCGGCCGCGTCGAAGCCGAAATGCCGCCACCCCGGACCGGCCGAGGCCTTCTCTGGCTGGGTC
TGGTTCTGAGCTCCGTCTGCGTCGCCCTCGGATCCGAAACGCAGGCCAACTCGACCACAGGTGCCG
CCCACGCCCTCCCTGCCATCTCTTCTCCCTTCCTCCCTCCCTTCCTTCCTCCTTCCTTCTTTCCTTCCT
TCTTTGTTTATATCCATTCTTTTTACCCTTCCTCTCTCCTACCATTCCTTCTTTCATCCATCATTCGTT
CCCTCCCTCCATTTTTCACTCCTTCCTACCGTCCCTTCATCCCTCCCTTCCCTCTTTCCATCTATTCAT
CCATCCATCTCCTATCCCTCCGTGCTTCCCTTCCTCTTTCCCCCCATCTTTCCCATCTCTATCCATCC
ATCTTTCCCCCTCCTTTCCTCCCTCCATTGGTCCATCCGTCCCTTTTACCTTCTATCCATTCATATTTC
TCTCTCTTCTCCCCTCCTTCTCTCCATCCTTTCTTCCCTTCAGCTATTCATCTTTTCCTCCTTATCTTC
CTCCATCCAACCATCTGTCCTTTCCTGCATACATCATTCTCTTTTTTTCCTAAATTCATCTTTCCTTTC
CACCATCTTTCACTCACTATCTCGCTTCCTCACCCAGGTTGGAGGCCATGACCAAAGCCTAACCCT
GCCACCCAGGACTCAGGCTTCCTCCTCGAGCCCCACTCCCACCCTTGCTGAGGCACAGCGCCCTCC
CTGGCTAGGCTGTTAAGGTGCAGGGTCCAGCCTTGGGCCTCTTAGTAACCTAGCACCTACCATGAG
GGAGGGTTCAGTGTCAGTGCAGGTTACCTCACCAAAGCCCCTCCCTCCTGTGTAGATGCTCTGAAC
GTTCTTCTCATCATCGTGGATGACCTGCGCCCTCCCTGGGCTGTTATGGGGATAAGCTGGTGAGG
TCCCCAAATATTGACCAACTGGCATCCCACAGCCTCCTCTTCCAGAATGCCTTTGCGCAGGTATGT
CTGGGAACCTCAGCTGTGGGTGTGTGCTGCTTCGTGCACTGAGGGTTGGGGCGGGAGCTTCAG
CTATTGTCAGATGGCACAGATTGTGCGGGACATCTTGTTAGAGGGAAGCATAGTCTGGAAAATGG
TAGTGGAGAAAATCTGGTTTTCCACTCATGGGAAAGCTTGACCTTCAAGGGTGGCCTTCTCCTTGG
GTGCAAGGTGCGCCCTGGCCCTGATGTGTTCATGGCAGCCCTGGCCAGCTTTCTCCCAGAACGGGC
GCTTGCCTGGTGCTCAGAAGGAAGGGGTGCTGCAGAAGGGCACCCACAGGTCTGCAGGCTGGGCC
TCAGGTGAGAGCTAGCCAGGGTGGCCCTGCTCCCTGAACCCCCTCATGGCTCTGCCCCAGCAACA
CTGGCCGCTCTGTGTGCCTGGGGAGGCCATTGCGTAGGAGGAGATAAGCATCTGCTGGTTTCAGGG
GCTGATTGCTTCCCTTTTCTCTCCCGGAAGCAGTCTGTTGCCTAGGTGACACCCAAATCCCAGTGTC
TGGTTTGAGCTCTGCATGACTCAGCTACCAAGCTGTTTGCTAGGAGCCTCGGGAGGGCGGTTGCTT
GGTTACCTAAGAGATGGCAGACATGTTTTGCTGTGGCGATGCTTACCTCTGCTTCTGCTCCCTAACA
GCAAGCAGTGTGCGCCCCGAGCCGCGTTTCTTTCCTCACTGGCAGGAGACCTGACACCACCCGCCT
GTACGACTTCAACTCCTACTGGAGGGTGCACGCTGGAAACTTCTCCACCATCCCCCAGTACTTCAA
GGAGAATGGCTATGTGACCATGTCGGTGGGAAAAGTCTTTCACCCTGGTACTGCTCCATGTCCAGA
GTCTGGGTTCTCTTGGTTTGTGGTGTCTGAATCCAGCATTCCCATCTGGGGATGGGGCTGTCTTTG
CAGAGCCCTCTTCTGGCTGGGCGAGTCCCTCGCTAGTCAGTGCTTCCTTTCTAAAAAACTGACTTGT
CAACCCAGCCACGTTTTCACCCAAAGTGAAAAAGGGTAGAAAGAGCTTTGCTTCCTTTCAGAAACC
ACTGAGGGTGTGCTGTTGGGTCTTTCAGCTCCTCGGGTGGTAGGGAGGACACAGGCTGGGGAGGT
GGCAGTGTTGGGTGGAGTCCAGCTCAGGGCCCACCCTCTCCCCTGCAGGGTACCTGTCAGTAAAC
CTAGGGTGGGGTGAGGACACCTGAGGGCCTCCCGTGTGGCCAGCATTGCTGTTGCTGACTTATTG
CCCAATGAGGGGGCTGTGCTTAGGTAGGGGCTGCTATCCACTCTGGAAATTAAGTCAGAAAGATG
AGTGTAATCTGGTACCCAGGATCTATAGGGTCCCAGAGACGGACATTCCTTACCTCAAATGCTGCC
TGATAAACTGGCTCTCTTTAATGCCAATATGGGGATAGTGAAAAGCAAACAAACTTTAAAACTTTT
TATTTATAGAAGTAATGCATGAGTATTTGAGAAAAAAAATGGAGAAAAAAGTATTGGAAGACAAG
AGCACCATAGGGACAATAATGCTTATCATTTGGGAATGACGAGTGTTTTCAGTCTCTTTCCCTTTGC
TCAGTGGTTACACCGGCAGGCTTGGCAGCCTTCTGCAGGAGCTCAGCTGGCCAGCCCAGGTTGAG
AGTGACATTCAGCTCTACTAAGTCAGGCCAGTTTCAGAGGTGAACCTGTCAGGAATCATATTGCAC
AGCCAAAGTCCAGTGTCAGGAGAACTTTCTGCAGTTTGGTGTTCTCATTACCATACCCCTTGCCC
AAATGCAGCTGGAGGAAGTGATTTTGGAGAGAGGAGGAAACACAGCAGAGGGAGGAGATT
GTGCTTTGGGAGGGGAAACCAGGCAAGGACTGAGTGATGTTGCTTGACCTCCTCCCTCCTGATGAT
TGGATTTTGGCACCAGGCTCTAAGCACCATGTCCTTCTCAGAGAATAAACCTTTCCCTGCAGCCCTT
GTGGGAACACATTTTTCAGCTGAATCTTTGTTCTCAAGACCTTTTTCTGTTAGCATTGGGCCTGCTT
CAAGATGACAGTAGCCACCACTGTGTGCCAGGTATGTACCGTTTACCATGCTGGCCACTCCTTTAA
TCCTCCCAACAGCAAGCAAGGTGGGTTTTTATCATCATCATCATTTCCCAAGGAAGACATGAAGGC
TCATGGGAGTCAAGTAGCTTGCCAGAGGTTGCAAGGATGCTAAGAGGCAGCATCAGGATTTGGAC
CTGTGGTTGTTGGCTTCCTGTGTGCTCTTTCCACAGTGCTTGCTGTCTTCATAGGCCCTCCACCCGCT
GCCCTCTTTCTCTCCATTCCTGTCTCTTCTGGTACTCCCTATGGGAGTCCCCACTGTGACTGCTGCT
GATGCTTTCTCACGAGGTTCTGCCTGTGATCCCCTCCACTCCCAGCTAACCACTATAGGCAGCACTT
CCCTTCAGATCCCTCACAGGCCTCACTGGCTCCTAGAAGTCCTCCCTGCCAGTCCTCACCTGACTCA
CAATAACCTCTGTGCTTGGAGGATCCCCCACTTGGCACTTCGATGCTTTGAAAGCTGGAAGTCCT
TCCTTGGTTTCCAGTGCTGTTATACTGTCTTCACAAATAAACTATAAACTACTAAGCTTAAGGGTGG
GTTTCTGCTTCATGAATGAGCACTTGAACTTGGAATTCTAAAACAAGGTTTTGAGTCCTGGCTCCCT
TATCTAATATCTGGTTAGCATAGGTAAGTCACATACCTTCCCTGAGCCTCCCTCTCCTGCCCCCATC
GGCTCCCTGATGGTGCTGATGCCTCTGCTGCCTCCTTCATAGGGTGAGAGATAGGTTTCAGCATGG
GCTCTAAGGAGCTGACTGATCTTGTCCTTGTGGGTCCCTTCCACAGAGCCTAGCACAAATCATCAG
GGCTTAGGGACCAGGAAGTCAGATGCTTAGTTCTCAAATAGAAACTAGAGAGTTTGGCTTTAGAG
GGGACCTTTTGTAGATGAGGAAACTGAGCCCCAAAGAAGGGAGGTTCCACTTGCCCATTTGTTTAC
AGAGTTTTAATTATGGGGAGTGGGGTGTTGAAAGACTCATCATGTTTTAACAACCTTTTTTTTTTTC
CAAGGGATATCTTCTAACCATACCGATGATTCTCCGTATAGCTGGTCTTTTCCACCTTATCATCCTT
CCTCTGAGAAGTATGAAAACACTAAGGTAAGGCTGTGAAAGGGACATTTCTGAAGAGGAACCACT
TTTTCCTTTGTCACATAAACTACTGGGTATACTGCATGTTCTGTGAAGCTGGTTATATACCACGAAG
TTGTGGGTTTCATTTGTGATAATGTTTTGACAGAAGTAAGTGTTGGGATCTTCAGCATTAGGCCCG
ACAGGAGCAGTGGCTTCATTCTAGAAGCTGGTGGGTGCTACTTGTTCTAAAACCTTGGGCTCTAAC
GTGTCAGACTCATTGAATAGCTCCCAGTGCTCACGCTGGATGAGACTGAGAGTTGTAGGAGATGC
TGAGACATGGGAGGGAGAAAAGAGGCTGAGCTCCAGGAGCCTCAGCCCAGAATGGGAGAAAGGC
ATGCCGTGTATCTGTCTCTGACCTAATGTGTATGTTCAGCAGCTGAGACCTCTGATAGGGGTTTGA
ATTTTTAGAGCATTATGAAAAAAAGTAACCTACAAAGAAAATCTTGGTTTAGAGGAATCCCAAAT

```
GTATAAATGAAACTAAAACCCACATTTAAGAAACTCAGAAAACCAGCTAGGGAACTGAGACATGA
AATGTATCTCTGAGGTTTTAGTAAACATCGTGTTGGGAAGGGTGAGGATTTGGAAGTGAGGTGGA
AGGTATTGTTCTAAGTTCTTGACAGCTTTCCATTTCAGAATACAGTGAAAACTGTGAGCTCTGGCCT
TTGGCTTGTGGCTTGAATAGGGAAGATCCCATCTTAATTCCCTGAAGCCATCTTGCTTCTTTTTAGT
GGCCTCACTTACGAATGCCAGGTCCCTGCCCTAACTGCCCCCTACCCATTTCTTCTCAAAGTGGTGG
GTCTGACAATACTAAATCTCCCTCGAGTGCTGCAAATCGTGTATATATAGATGATGAACAAGTGGT
CTGAGGCGGGTGCTGGGCTGTCCTGCCCAAGGGTGGGGTGAGCAAGGCAGGGCTGTGAAAAGGCA
ACACTCTTTGAGATGGAACAGCAGCTGACACAGCCCCTCGGTCTTTGTGGTATACAAATCATGGTC
AGAACTAACTTTGGTCTCACGGCCAGCATGTCTACTTTAGGAAGCAAAGCAGGAGGTTTCATTCTG
TGCCTAGTGTAGCTGAAGTTCTGGAAATTCCATGGACTGTCACCTTATCAAGTTGATTGGGACCCT
GTCACTTACAAGCCTTAGCCTGTCTTTGAAATTTGAAATGGGTTTTTTTTTTCTTTTTAAATTTTTAA
TTAAAATAGAGTTCATATACCATAAAACTCTCCCTTTTGAAGTATATAATTTAATGGTTTTTAGCAT
ACTCACGGAGCTATGCAGCCATCACCCAAATCGATCTTAGATCATTTTTATCGCTCTCAAAAGAAA
CCCTGTACCCATTACCAGTCGTTCCTCATTTTGTCTCAGCACCCAGCGTGGGACAACAACTGAACT
ATTTTTGGTCTCCATGGATTTGCCTATTTTGTCCATTTGGTATAAATAGAGTCATACACTATGTAGC
CATTTGTTTCTGGCTTCTTTCACTTAGAATAATGTTTTTGAGGTTCAGCCACATAACAGTATAAATT
GGTACTTCATTCCTTTTTTTTTTTTTTTGAGATGGAGTTTCACTCTTGTCACCCAGGCTGGAGTGC
AATGGCGCAATCTCAGCTCACTGTAGCCTCCACCTCCCAGGTTCAAGCGATGATTCTCCTGCCTCA
GCCTTCCGAGTAGCTGGGATTACAGGTGCCCACCACCACACCCAGCTAATGTTTGTATTTTTAGTA
GAGACGGGGTTTCACCATGTTGGTCAGGCTGGTCTCGAACTCCTTACCTCAGGCAATCCACTCATC
TCCCAGAGTGCTGGGATTAGAGGTGTGAGCCACCGCACCCAGCCTTTCATTCCTTTTTATGGCTGC
ATAATTGTCTATTGTACCACATTTTGTTTATCAGTTCATCACTTGATGGATATTTGGGTTGTTTCTAC
TTTTGACTATTAGGAATAATGCTGCCCTCGACATTTTGTACAAGTGTTTTTATGGGCATATGTTTT
TAATTTTTTGGGTATAATAACTATGTTTAACTGTTTGAGGAATTGCCAGACTGGCTTTCAAAGTGG
CTGCACTATTTTACATTCCCACCAGCAATGTGAGAGGGTTCAATTTTTCTGCATCCTCGTCAACAC
TTGTTATTTTCCATCTTAAAAAATTATAACCATCCTTTTGGGTGTGAAGTGGTTTTGATTTGCATTTC
CCTAATGACTAATGATGTTAGCCACATTTCCATGTTCAATTGGCCATTTGTATATCATCTTTGGAGA
AATGTCTATCCAAATCCTTTGCCCATTTTTAATTGGCATTTTTTAATTGTTGAATTAGAGATGGATT
TTTTTTTATAATTAGTCTATCGGGGTTTCTTTTAATTAGTTATGATCTGGAGAAAGAGTATTAGTAG
CAAGAAACCAAGTGCTAGTGGATTTCTGGCCCCTGCCTGGAAAACAAGAAACACCTTTTCTGTCTT
AGTTCTACTTCTGATGTCTCTGTTCAGTCTGAGTGACTAACACGTGAAGGGCTGATTATGTGAACA
TTAAATCTGTGTGTGTAGCCTTCATGGCTTCATTTCTTGCACTTAAAAAGCTGATGTTATATTATTTT
GTTTTGAAAGACATGTCGAGGGCCAGATGGAGAACTCCATGCCAACCTGCTTTGCCCTGTGGATGT
GCTGGATGTTCCCGAGGGCACCTTGCCTGACAAACAGAGCACTGAGCAAGCCATACAGTTGTTGG
AAAAGATGAAAACGTCAGCCAGTCCTTTCTTCCTGGCCGTTGGGTATCATAAGCCACACATCCCCT
TCAGATACCCCAAGGTGAAGAGCTGGTTGAGGGCTGATCAGACAGCCAGCTGTGACAGCTGTGTTGTT
TGTTGAGGGAGGGATTTGCACAGGGAAGGTGGCTACATCCTGCCATCGCCAGGCACCATGGTTGC
CTGATGGGCACTAGTGTCCTCAGTGGAGTAAAGATGGGATTTAGAGGTCAAGGCCAAGAACATGT
AAGAATCTTGTAAGAAATGCTTGGCTTTCCGCTTCACTCCACTGGAGGGTTTGATTTCCTTTCCTTG
AACTTATTGAGCAGATGTTGGGTTGGATGGTGAGATCACCACAGAGTAGTGAATCAGAGCTGGCT
GCCAAAGCCTGTAATAAGGGATGGCCCTTCCAAAACAGCCCCAGGGAATGTGAAACTCTCTTCAA
AAACTGCCTGTTCCCCCTGAGCCTGTCAGGTTAGATCATCTAAACACAAAGCACTGCATTGCTTCT
TGGAACCTCAAATCCTGTACTTGCTTGTATGTCATTTAGAGCATGTAGTCTTTTCTGTTTTAGAATC
CTTTTCCATTTTTCCCTATCATGTTTTATGAGGGCCTGAGCATCCCATCCTTTTGACTTTGCAGAGA
ATGCCCCTCACATGTAATGAGAGTAGAGACCAGCAGTATGCTCTTTGATGTTGCAGGTATCTTGCT
TTGATTGGCCCAGGGGATCTTGCTTTCCTAGTAGGAGCTGTCAGCCCCCTTGATAGAAGAAGGCTG
TGAGGTTCACCTCTCCTGCCTCTTTGCAGAAAACAGTTAACAAAGCTGGCCTGGCTGTGATTCTTTG
AAAGGCCTGCTTATAAGTCTAGCCCTTGGCTGGCATCTGGGAACTTTGATTTCTGAAGTGTTCTCAC
TATTCCCAGAATTGGCTTACTATGCTTAAACCGTTTAGACAAACATTATGGTTGATGATAAACCCC
TGGGTTTGTTTTTTTTTTTCTGGGAGCCTGGAATTTTGATATGTTCCAGACAGATAGTACCTACCTG
ACCAGCCCCAAATAAAAACTGGATAATGAGGCTTTAATGAGCTTCCCTAGTTAGCAGCATTTCACA
TGTATTGTCACACAACTCGTTGCTGGGAGAAGTAAGTATCCTATGTGACTTCCTGGAAGAGGACT
TGAAGCTTGTGCCTAGTTTCCTCTAGACTTTGCCTCATGTGCCTTTTTCTTTGCTGAGTGTGTTTCA
CTGTAATAAGTCATAGCTGTGAGTGAGACTAAATGCTGAATCCTATGAGTTCCCCTAGTGAATTGC
TGAACCTGAGGGTGGTTTTGGGAACCCAACACCTCACCCACTTTTCTAGCCAGGCAGGAGGTGG
GGACAGGAACAGAAGGGCGTCTGTTTGTATGAAGGAAGAGAGTTGTTGCTGCTCAGTTTGTAGGA
AACAGAAGTCGTATGATTTCATTGCCATTGGCATCTCATGAGAGTAACTTAAGGCTGGACTTCCAG
GTCAGGGCCGAGCACGTGGGGAATGCTAGTGAGCCACCACTCAAATGCATCCCAGGCTTAGAGAA
AAGGCAGTATAGACAGTGATAGAGCCACAAGCTTGTGCTTTTGCTAAAAGAGTGACAACTTTGTG
GCTTTGTGTTTTCCCCAAGGAATTTCAGAAGTTGTATCCCTTGGAGAACATCACCCTGGCCCCCGA
TCCCGAGGTCCCTGATGGCCTACCCCCTGTGGCCTACAACCCCTGGATGGACATCAGGCAACGGGA
AGACGTCCAAGCCTTAAACATCAGTGTGCCGTATGGTCCAATTCCTGTGGACTTTCAGGTATCAAG
GACATAGTTTGGGGATGTATTGGACACTGATGACATAGTGTCGTAGGTGAAACCACTCTTCTCAGT
AGACACAACTCCACCTATAATGTCTTATTAAGAGCTTTCTTTGTGTGAGTTATCAGGCAAAGTGCT
GGGGTGGAGGTGTCCTATAGGTATTTAGGACACAGGCAGTGTTGCCTGGATCAGGACTCTCCCAAC
CAGTGTCTTACTTTCTAAAGAAGGGAATGTCCAGAGAGTTGGTGACTTGGTGTGTGGACACAGA
GGTGGGGAACCAGCCTGGGTGACCGTTCCTAACCCAGGGGATACTGTTCAGGTGACAGCTCATTA
ATTGTAGAGTGATGGGCAACTCCCGAGCAGCCCAGAATGCTTGGTTTGCTGGTACTTGCAGGTTCC
CTCTGTGGGAAAGCCCATCCTGGCTAGCTGTCACTCTCAGGGGGTGGCTTGGTGAACAGGCCCTTG
GTGCAGAGGGAACTGGGACACCATCATGGCCAGTGCCACCCAGCTGTGATGTCCGGCATTCCTTTG
CCATGATTTAGGGGCGGAGCAACCACACAATTAGAATCCTCGACTGACTCATCAGTCACCCTTTC
TCCCTGGAGAGCAGAATACACATTGACTAATGCTCTTTCTGGAATATTCCACACAGAACCCTGCCC
TTCTCTTACCACATGAATGCTGTGGCAGGCAAGCTATAGCGGATGGAAGATGGCAGTGTTTTCAAA
GTGTGCATCCTGGACTACCTGCCTTAGAATTTCTGGGAGGGCTTGTTGGAAATGCAAAGTCTTGGC
CCACTCAGATTTACACAATTGGAAGCTGGAGGTGGAACTTGACCTGACAACCGACATTTCTTAAAA
AAAAAAAAAAAAAGCACACCAGGTGATTCTGATTCATCAGAAGTTTGAGAGCCTCTGCTGTAGAG
TATTGTTTAAAGCAAACACAGAACAAAACCACTGCATACAGATATCCCTTGCTATCCAAACTTACT
```

-continued

| Sequence Information |
|---|
| TGGCCCCTGAGTTTGCACAACAAGAGTTTGGTTGGTGAGAGGTGTACATTCCTCAAATGTATTTGA |
| TTCCTGTTTCACTGAGAGTTTGGAAAGCAATGCATCCATCTGTTTGTTTTCTAATTTTGTGTTTCTGG |
| GCTCCTGATGGTGAAGTGGCTTGAACTGGCTCTGAGGCTGCACCTGGACTGTGCTGCTTTATTAGTGATGGT |
| CACTTAAAATGACCCTTCAAAATGGACTGTGTGCCAGGAAGGGCGCTGATTCATGTGTGGTATCGC |
| CTTTAGTCCTCATGGGGACTTAGTGAGGTACCTGCTCTCTGTTGTCTAGGTGAGGAAACTCAAGGC |
| ATGGGAGGTGTGCTGACTTGTCTGACAGCACAAAATTAGTGCTGGGTGGAGCCAATTCATCCCCAG |
| GGACTGTAACTCCAAAGCCCCATGGTTGGATCTGTTGGTTCCCAGCAGTGTGGGTTCGAATTCATG |
| TTCTACCTCATACCAGCTGCCTAACCTCTGTCAAGTCATGTTACCTCCCTGAGCCTCCCTGAGTTTT |
| CTTCTCTATAAAACTGAAACAAGGTAGGTAAAGTTTTTCCATGATAACACCTACTTTAGAGATTTT |
| CAGCAAGAACCAAAGAGAGCATGTAGAAGTATCTAGGACCGTGTCGGCTGCACGGAGCTATCTCC |
| TTCAAGTTCTCTTAGTCCCCTCCTTACACACAGTGGACAGCATGACTCAGAGGGCCTCCCTGATGC |
| CTGCATGTGCTGGTCTCAGCCCTGTGTTCCCCTTGAACTCTGGCCTGCTCACTGTCCTCTTGTAGCT |
| TTGGATGTCCGCATCCAAGCCCATCTCACTGCACCCTTGAGACTCAGCTCTGGGATCTCTTCAGCTC |
| CAGCCCTCTAACTCAGCTCTACATGAGCCAGTGACCTCAGGGGCCACACTCAGGAGTTTGTTGCCT |
| GCTCCTTCCGAGTCACCATACTGACCACAACCTCTTCTCCTAGCACTTCCCTTGCTCTACCTCACGG |
| GGATTGCTAGAGTATGGATTTCTATCTCCCCCTTGTGTCCAGGTCCTGTTGGCTTTGTTGCTTCCCT |
| AAATAGCTAAGGCCTGGTGGCAGGTGACTTACTGTACTTCCCAGCCGCCCAGCTCACCATACTTGT |
| CCATTTATCCTTGCCCCTCCTGCAGTACCTTTATCGTCAGACACTCCAGCCACACCCTCTGCTCTGT |
| AGTCCAAGTCCTGAAAGCTGCTGGAGAAAATCCATGCCCCCACGAAGCAGGGAGGCCCTCAGATG |
| CCCCGCCTCCAGCCCCAGCAGCCCAGGCAAGCTCTCTGCTCAGCTCACCTCACTTGTCCTCTGCAG |
| CTGCTCCGTTTGCATGACCTCTTCTCTACTCCCTTTCACTGCTCCCCTCCAGGCCTTTGCCACCCCTG |
| TGCCCCATTTCTCAGTGGATAGCACCTTTCCTCTTGTAGAAATGGAAGCTGGTGGACAGCCAGAGG |
| TAGGGGATCGGACAGGGTGGATGTGGGTACGCATCCTGGCTGTGCCCCTTATCAGCTGTGTGACTC |
| TGGGCAAGTTAACCTTTCTGAGTCTTGGAGTCCTTAATGTGCCGTTCACAGGATCAGATGCCACTT |
| AGTGTGTACTTGCTGAATGGGCTCTATTAATAATCTCTGTCACTGAGACCTGGAATTTTGTGTATGC |
| ATGTTCTGGGCTCGAGGCCTCTTCCCTCAACTCCCCACCACTGTCCCTGCTTCCCACGTCTGCAAGC |
| AGAATGAGCAAGATCTTCCTTCTCACCTACCTACCCTGCAGCCTCTCCATCCACTCTCATCCCTCCC |
| AGCTGCAAAAGTGCCAGCCCCCTTGCCCCTGCCTGTTTCTGCTTTCCACTCCTTCACCTGACCTCCA |
| AGGCAGAGCGAGTGCACACTGGGCTGTTCTGGCTGTGTCTGTGGCCTCATTGTCCATTTGTTCTTCA |
| CCATCCTCTACACAGGCTTCCACCTCCCAATCCACTAAACTCTCACCTCAGCACTGACCTTGGTGG |
| CCAGTAAAATCTATCTGTGTAGGTCCTGACCTTCCTTGAGCTCTGTGTCACTTCCTCACTGTTGGCC |
| AGCTCCACCCCTTCTGGGACTGTTGGCCTCCCAATCCTTTCTGTGTCTGCCACTTAGGTGCCACTTC |
| CCAGGCCCCCCACTATATCCTTTCCACCTCTTCTTCCCCTGCTGGGCTCAGTTGAGCCTTGGCAGAT |
| GACTCCAGAACTACCCCTTCAGCCCAGGTCTCTCCTGATTTTCAGATATGTGTGTTGACCTGCCTGT |
| GAGAGCCATTCCTAGGCAGATGACCCTGGAGACCTCAGCTCCATAGGCTTCCGCGTGGTCAGGCC |
| ACCACCCCTGCCCTGCCTTTTCTCCTTCCTCCTCCTCCTCTTGCGCCCCCTGCCCCCAAATGCCAGC |
| GAATTATGCCACCAGCTGAATGTGAAACCTGGAGTCACCCTTGGGTTCCTCAACACCTCCTCCTCC |
| TCTGCTCCCTGCCCCCATGTCTGCTTGATGCCCCTGAATTCCTCTCACATCCACACAGTCCTCTGGA |
| TCCTTCAGCACATTGTTCTGGACCACCTCAGTGGGCCTTGCTTTGTTTTGTTCATTCAGCAAGTGTA |
| GTGAGCACCTCTTATGTACCCAGCAGTGGCCTAGTACCATTTTGTCTAAAGCCTCTGGAATCTGTGT |
| CTGTGTCCTGTTGCAACAGGACTCTTAATAACTTGAAGCCCAGATCATGTCAATTTCTCGCCTTGAA |
| AGACCTCAGTGACTCCATTGGCCTAGAACTTGGAGTCTCCACTCCCTGGATAGACCCACCAGGTCC |
| ATATTATCTGGCCCGGACCTAACTTTCTAGTCACCCCTCTGCCCTCCCATTTGATTCTCCAGTCACA |
| TGGGCCTTTCATTGGCCCCAAATGCAACCTGCTCTGTCACAACTCCACACTGTTCCGTGCCCTGCAG |
| CCCCTGCTTGGAGCATCTGAGCCCCATTTGTCTGACTGCAGGTGCTTCTTGTCAAATTCTAACTCCT |
| CTGTGAAGCCTTCCCTGAATCTCCCAGGCAGATTTGAGGGCTTATTCCCCTGTGTCACCCCTGGGCC |
| TCTGTGGGGATCGGTCAGAGTGGTGGGAAAAACTATAGGGAAAGGATGCAAACCTTCTGAAAGG |
| TCAGAAGGTTCTGCAGAGCCCCAGGGGAGAATAGCTGTTCTATAACCCTGAGGCAGAGGGCAAGG |
| AGTAGGTACAAGGGAGTGTGGGAGAATTTATCTTAAACAGGCTTGTTTACTTATGTTGACCAGGAA |
| CTGACCTTTGATCGTCTGTGCTTGTGAGGTTCCCTGAAAGGGGAACAATAAATGTTAATTACCTGC |
| AGGTTGGCTCTAGGTTTTTGGCATTATGCCTGCACTGAATAAAAGCCAGCAGCTCCAGCTTCTCGG |
| GGCTGCTCTCTGGCCACTAGAGCCAGGCAGTAACCTAGCTGCTCTTATGCTGCATACCTGTGTCTG |
| AGTACTCATTTCATCCATAGGCCAGGGTCTGCAGGACAGACCCAGCAGGCCTCACTGATAATTAAG |
| CATTTTCTTGTCTCCATGATTGTGTCCTCACTGGATGGGGTGGCTCATCAAGGGTGAGGACCTTGTC |
| TGCTTATTGCCTTACGTCCAGGGGCTAGCATAGGAAGGAGGGAATACCTTTGTATAGGACATAGCC |
| ATCCTGACAGGTGTCTTTCATCCCCAGGAGGACCAAAGTTCCACAGGTTTCAGACTGAAGACTTCA |
| TCTACCAGAAAGTATAAGTAGGCCAGGGCTCAGCATAATCCTGCTGGAAGGCTAGATGTATATCTT |
| TTCTCTTGACTGCAAGTGAGAACGGGTGAGTCTCATGATTGTCCTCACCCTGGCAGTGATGAGAAG |
| AAGCTGGTGGGTCCAGCTGATAAGTCAGGGGCTGGTCTGCGAAGACACGGCTCTCTTCTCACCCCT |
| CTTTGGGGTGGAAGATTAATTTTTGTCCTTAGCATTTGTGAACCAGGTTGGGAATGAGAGTCAGCC |
| CAGGAGGGGCCGGTGGCTCATTTACTTCAGGGCATGATCTGGCTGTTCCCAAAGTGCCTCTTGGGT |
| TCAGGGACTGTGAAGGACGTGCTGCTCTCTGGTATCTCCTTTGCTCTTCTCCTGCCTGCTGACAGTT |
| TGTTAGAAATGAGCTCCACGTAACGGCCATAGTTCATGAAGATATGCAGTTGTAATCTGCTGTTGG |
| GTTAGCAAGTGATCAGAGGGAAAGGCTCAGTCAGGGTTGCTGTTATGTGTTAAATTATGAATTTTT |
| TTTTCCCTGAAAAGGGCTGTTGACATCCTAACCCCCCAGTACTGCTGAATGTAACCATATTTGGAA |
| ATAGGTTTATTGCAGATGTAATTAGTTAAGATCAGGTCATATTGGAGTAAGGTGGGCTCCTAATCC |
| AATATGATCGGTGTCCTTTAAGAAGAGGGGAGAGAGACACGGGAAGAACACATGAAGATGGAGA |
| CACAGTGATACAGCTGCAAGCTGAGGAATGCCAGGGACTGACAGCCACCACCACCAGCTAGGGAG |
| AGGCAAGATTCTTCTACTTAGAGCCTTCAGGGAGAGAATGGCCCTCCCAGCACCTTGATCTTGGAC |
| TTCTAGCCTCCAGAGCTAGGAGACAATACATTTCAGCTTAAAACAACAGAGCAGTAGGTGACACA |
| TTCATCCACTGTGATCTGTGCCCTAAAGTGAAATCTGATTTGCTTAGAAATGTATCTTATTTGTAGA |
| CCTACAGATTTTGCTGTGACTCTGTGGGTGAAGTGATGCTGATGGTAGGGAAAGGAGTGTTACATT |
| TTGGCTGAGAAAATCATTAAGGGCATCAACTAAGGGGTAGGGATTGGGAGAGATGCACAGGCAA |
| GCATTATCTCTGTATGCCTTGGCAATTTAAATTGCAGTCACTCTCATTTTTATTTTTTTCAATTTGC |
| AGCGGAAAATCCGCCAGAGCTACTTTGCCTCTGTGTCATATTTGGATACACAGGTCGGCCGCCTCT |
| TGAGTGCTTTGGACGATCTTCAGCTGGCCAACAGCACCATCATTGCATTTACCTCGGATCATGGTA |
| AGCATTTTGAAATTCCCTGGTGAGTCAAAACATCTGAACTTTCCTGTGAAACATGCTTTGCAAAAT |

Sequence Information

```
TGCCATTGACATAAACATGGGTGTGTTCTCTTTTGTGAACCAGTGGTTCACAAACAAAGTGGGATC
CTGGGGCATTTTTATGATCAGCTTGTTAGTCCTGAGACCTCTGTCTTAGATGCTTGACGGATAGGTG
TGGGTGGGTGGGGAGGGTCTTGCAGCAACTTTTTTTTTTTCTTGATGAATGCAGCAGGAACCCT
CCATTTGTGTGGCAGAGCTCTTGTAACCCCCATTTTTAACCTGGAGGGTTGGAGGACTTTTAGTTTG
GGTGGAGAGGATCCAGAACAATCCTGGCAGAGCCCAGCCAAGCTCTTCACGCCTGGCTCCAGCCCT
CCCACCCCTATCCCCGCTGTCTTCTCTGCCGAGAGCCTGGGCTTTTCAAGTCTTTATCTCCCCCTAA
GGCTGTTTCCTACTTTTCCAAAAATGAAACTATCTTTTTAAAAGCATTTTTTAAATTCTTCAACATT
CCAAGAGCAGGGAATAAAACAGCAGCTCCCCCCGTTTCCCACTCACATAGTCTTGTTCCTCTCATC
CTCACCCACTCCCCCATCTCTGAATTGTTTCGAAGCAAATCCCAGATGGTTCCATTTTCCGATCACT
GTCTCTGAAAAATATTGCCTCTTTTGAAGTATAACCATAATACTGTTATACTTAGAGAAAGGAAAA
TAATTTTCATATCATCAAATATGAAATAGGATAATAGTAAATCATAACATGTGCTTATCATGAAAA
GAAAAAAGGATACAGAGCATGTAATTCAGGGCCAGAACATCCTGCCCTTTTCTCCCACCTGCTCAG
GGCTAACAGATGACAATGGATTAGGGATCCATCTGCCAGCCATCAGTTGTGCACATATGCACACA
GGGATATATGTTATACATGTGTATGTTTGTAACATGTATGTCACAAGATGTGATTGCTTGTTCTGTG
TGTACTGTTAACGTTCCCTGGTTTTGTACACTTAATGTCATAGGCAATCTCTGTGTCATTTCTCAGA
AGCCTACCTTTTCCCTTAGAAATGTCTGTAATATTTTATTATATATGGAGGTGCCATAATTTTTCAC
ATATTCCTGATTATCTGCCATCTGCTTCTGAGCCCTCGGTGCCCAGTTTCCTCTTCTCCACGAACAC
ACTCTGTTGTGAGGCAGTTGCCGTAGATTACAAATAGCCCATCTCAGAGTCCCCTCCTGGGACATC
CTCCATCAGAACCGCCTGGGAGCCAGTAAAACATGCTGGTTTCTGCAACTGGTCTCAGGAGCTCGC
AGTTCTGGGCATGGGAAAGTGCACTTTAACAGGTGTCTCAGGTGGTCTGGCCACCTCTCCCTGAGC
TCATCATTCCCTGGGCCTCCCTATGTTGCCACGTCCTCATCTTGGGCCTCTGGGGCAGGAGCCAGA
AACCTCCTGAGCTGCCTGTCAAGGTCATCGGGCTTGTTCCTCCTGATCTGGAGATGGATCCTTGGG
GCCCACACAGGCACGCGTTCTCCTTAGCCAGACTTCCCCGTATTTGCTCCTGGCTGCAGCAGCACA
GGCTGAGGCCCGGCACCAGATGTTCAATACGATCTTGCAGTCAGGCGGTCCACAGCTATTTCTGTA
GCATTTGCCATGTGTCAGACCCTGTGCCAGGCCTGGGGGCCCCCTCTGCCTGGTGCAGGGCAGCTC
ACAAAAGCTGGCAGAGGCCGAAGGCTGCGTGCCAGTATTCAGAATGCCACAGAGCGCCTGGCTGC
TGTACCTTCAGAGCCTCCACAGGCACCCCAGTCAGAGTTCCGGGAGTGGATTCCTGAGGTCGCACT
GCCAGGTTCCCTCACGTTGCCATCCTGCAGGCTTCTCGATCCTTGACCTTTTAGATTCCCGCCACAC
TGAATCTAAAAGGGACAATGTGACCTCTAAGCTGGTGGCCTAGGAGCCTGCCGATAACCTACCCA
TTCATCAGCCCTCGTGGGTCAAGGCTGCCTCGTCCTCCCCGAGAGAGTGGAGAGGTCGAGCAGTG
GGGATGCCCCTCAGGCCCCGGGGCTTACTGACTGGGGCGGGTGTCAGGGGGAACTCCCTCTCTTTC
TGAGCTCCACTGAGCTATCTGAAAGTCCCCACCATACTCCCCAGTACTGACAGCCAGAGGGAGGA
ACGGCTCACCAGAATCATTGGGCATCTCTGATGGGCATCAAGTCTGCTTTGATTATTGATGAGTGG
GTAAGAGGGTCCTCTCAACTTGGGGTCTCCTTGGGAAAGCACTGTCAACTCAGAACAGGTTTCAGC
CCTGTTCTGGAGACCACAGGCCCTGGAAGGCTGGGACATCATTTGCAGCCCAGCGTCATCTATTA
GACGGAGCCAGCAAGGTCTCATGCTGTGCGGTACATTTCAACACTTTCTCAAAGTTTACCCGTGGCA
GCTTTTGGTGTGTTTGGTTATTTTTATAACACTACTCACTGTACAATTTCTGTCATGCACATTTTTG
TATCAAAAAGGGTGCTGTAACTTTAAAAGACTGGGTATTTCCAACTTGGAATATTCAAACCATCTT
TTGCAAGGGATGTTTTAAATAGGCATGAAGGGTTGTTTTAATTGAGGTTAAGGATCTGAAATGAG
AGGTTTTGGTTTACCCTATCTATGGTATGTCTTAAAAATCAACGAAGATGTCCTTGTCTTTTTTGAA
TTTGCCGAGTGTGTTGCAGTTCCACAGCTCACTGTTAGGTGGCACATACCCAAACTGAAAACCTG
ACCTCGTAGGGCATGAGTCAAAAGACAGGTAGGCACAGGACAGGGCAGTGGTGACACTACAGCTT
TCAGGGTTCCCAGCCTGTCAAGAATGAGCATGTCTTAGCAGGGGAGGAACGCATGTGTGGGAACC
GCCACAGAGTCCTACGTTAGGTATATGTTGCTAGTAGTTTGTTAAGATATTTGAGTTTGGGAATTTA
ATTATTTTTTCTTTTTTAAAGGTTTCCTCATGAGGACAAATACCTGATTTTGAATAAAGCAGCATTC
AGTTGAAATAACCCTTTCTGTGGTAATTCCAAGTGAATATTTTTCTTCTAGGTGATGAGTTTCTACT
TCCTCTGGTTTTTACAACAGGAAATGAAATGGTATCTAAAATAAACAAGCTGTGGTATGATGATTA
TTCATTTTCTGTCATTCTGTGCTTTTTATGAACTAGGGTGGGCTCTAGGTGAACATGGAGAATGGGC
CAAATACAGCAATTTTGATGTTGCTACCCATGTTCCCCTGATATTCTATGTTCCTGGAAGGACGGCT
TCACTTCCGGAGGCAGGCGAGAAGCTTTTCCCTTACCTCGACCCTTTTGATTCCGCCTCACAGTTGA
TGGAGCCAGGTATAAAATATGCTGAAATGATATTGCTTGACAGTAAGATCACCTTTAGTTTATATG
TGAACCACTTTATTGAATCATAGGCTTTGGGGGTTACACAGACCCCCCCTTCCTGCCTTGTGTTGGA
ATTTCTTCTCAACATTTTGTGGTCAGCACACGCTTTCTGAACATCTCCCATACTCTGGGTGGGGAAA
GAGTGACAGAACCAGAATTGACAAGTATGGCCCCTGTCCACAAGGAGCCTTGTGGGATGATGATG
GACAAAGGAACAGGTGCATCCCCAAGATGGGGAGGGCTGTGGTACAGTCTACAAGAGCCTGCTCC
AGAGCTTAGAGTAAGGGGCTGCCCCCGTAACAGACGAGGAGAATCCTTTCCCTCGATGCGCACTTT
TGGTAGGGACTCAGCCTTCTTTGTGGGGGGCACATTTTCCATTTTGACAGCTCATCAATCTAGTGA
ACCACTAGATCTGTAAAATCTACCAGGTGATTCTACTCTGCCCTCCCCAGCAGTGAAGGGCAAGTT
TACTTTGACTTCCATGTGCCAGTCCTTCAAAGCTTTGAAAACAGCACTGATGCCCCCGACCCTGTCC
ATCCACCAATATCTTCTCTTCTCTAGGCTGAAATCCCCAGCCCTTCAACCATTCGTCACAAGGTAGT
GTTTAGACGCGTGGTTGTCCTGGTCTCTGTCTTCCAAAAAGTTTCAGTTTGAGAAAGCACTTCCAG
AATACCAGTTGGACCAGATACCCCTCCTGGATGTGTGGGCAACCTGTATGGGTTCTTGTGAGTTCT
ATCCTGACTTGATCTGCCCAGTGCATTTCAGGGACAGGTTGTACACTGTCTCTGAAATGACGTATG
ACGTTTGCTCTTTTTGGAGTGCCTCTTCTATGAACTATGCTAAACCAGATTGCCCCCTTTCTGGACT
TAAGCATTTAATCCATCCTTAACATCTAAATCTTGTACTGTATATTGATTCCTGTTTAAATTTGTCTT
GGTTCTGGACCATCATTCGGGCCTTTCTGGATCTTTCTGAGCTTGCTTTATACTACCCAATTTTATTT
TTTGCACTTTGATTTTTGTGCACTGCATGTCCTGTCTTCTTTCATGTCATTGATAGAAAGGTTAAAC
AGTTTCAAGGCATGATTTTAGCCCTTTGTTTGCTGGGAAAGATCTTCTGATTGGTTGAGAATCTTTT
CTGAAACTTTTGTTGGGAAGTGTTCAGCAATTTAGAAATTGATGTAACTGCACGGCCTTTCAGTTT
ATTTCCAAATTTTATCTCTAGCTGTGTCTTTTCCCTGAACTTCAGACTTTTGTTTCCAATAGTCTTTC
CCACTTAGCCAGCCTAACATATCCAAAGCTGGACTTCACATCTTTCATCTTCAGCTTTTCCTTCAAC
ACTCTTCTTGTCCTCAAGAAATGAGAATAGTCACTCATGCCAAAAAATCATGGAATAATCTCAACC
CCTGTTCTTCTCTTACTCCATATGCAATATTCAGTCTATGAGAAAGCCTGTCACACTCCATTCAGAC
TCTGTGTACCACTTCCCACCACTTCGCCTGCCACTGTCTTGACCAGACTGCCACTGTCTTGTGCTG
AAGTACTGCAAGAGCTTGCTAAATGGTCCCCTTGCTTGTGCCCTGGATCCCTTGGAGGTTTTCCTCC
TCAGAGCAGCCACAGTGATTCCATTAAAACCCAAGTCAAGTCATGTCACAGCCCGGCACAGGAGC
CTCTTATGTACCCTTCTTGATCTGAGTAAAAGTCGTCACAGTGGCCTTACATGTTCTGGCCCCATTA
```

-continued

Sequence Information

```
TCTCCCTGACCTCATCTTTTTATAAGTATCCAGGCCAGTTGTCCTATAACAGTGTCCCACAGCCTGG
ATTTATCTGATTGCTTCCACATGACTACATTCAGGGTAACATTTTTGACACGTGTGCTACATGGGCT
GTTGTATTCTCCCATTGTGTCACATGGTGGGGGCACTTCAGGCCAGCGTTACTAGTATTGTAAGTT
TGAACACTCGGTTGAAGAGCTAGCTAGCATCAGCCAGATCTTGCCATTGTAAAGGTACCTTTTTCA
ACTTTCTTTACTTGTTTTCTTTTTATTTTACTTAAAAATTAAGTGTCTAGAAAATGAAATCAAGCAT
GATAAAGCACTGTCTTAAAGATCCAGAAGGGCCAGAATGGTAGTGCAAATCCAATTGCAATTTTA
ACAGGAATCAATATAAAGTACAGTATTTAGACTTTAAATATGGATGAACCGCAATGAAATACTAC
TTCATACCCACTAGGATGGCTATTAATAAAAAACAACAACAAAAGCTGTGAAAGGCTGGGCGTGG
TGGCTCACGCCAGTAATCCCAGCACTTTGGGAGGCCAAGGTGGGCGGATCACGAGGTCAGGAGAT
CAAGACCATCCTGGCCAACAAGGAGAAACCCCATCTCTACTAAAAATACAAAAATTAGCTGGGTG
TGGCGGTGCATGCCTGTAATCCCAGCTACTCAGGAGGCTGAGGCAGGAGAATCACTTGAACCTGG
GAGACGGAGGTTGCAGTGAGCTGAGCCGAGATTGCGCCACTGAACTCCATCCTGGAGACAGGGCT
AGACCCCGTCTAAAAAAAAGAATGAAACAAGTGTTAAGAGTGTTAGTGATTATATGGAAAAATT
GGAACACTTGTGCATTGCTGGTAAGAATGTAAATGGTGCAGCCACTGTGGAAAAGAATTTGGTG
GATCCTCAGAGTTAAACATAGAATTACTCTATGGCCCAGAAGTTCCACTCCTAGGTATATATCCAC
AGAGCTGAAAACAGGTATTCAATCAAAGGTTGTACATTACTGTTCATAGCAGCACTATTCACAGTA
ACCAGAAAGTGGAAGCAATTCAGATGTCTATTGACAGAAGAACAGACAAAATGTGGTCCGTCCAT
GCAATGGAATATTATTCAGTCTTAAAAAGGAAGGAAACTGACACATGCTACATCATGGATGAGCC
TTGAGGACATTATGCTAAGTGAAAAAGTCAGTCACAAAAGGACAAATACTGTATAATCCCACTC
CTATGAGGTATCTAGAGTAGTCCAGTTCATAGACATAGAAAGTAGAATGGTGGTTTCCAGTTGCTG
GGTGAGGATGGAGAAAGGGGAGTTGTTACTTAATGGGGACAGAGTTTCAGTTGTGTAAATTAAGA
GGAGTTCTGGAGATAGATGGTGGTAATGATGGCACAACAGTATAAGTGTACTTAATTCCACTGAA
CTGTATACTAAAAAGTGGTTACGATGGTAAATGTCATGGTGTGTGTATTTGATCGTAATAAAATGC
AAAGATAACTCTAATGCAGACATCCAGAAGGGAGTAATGTGTGGGGTGATCCTGTGGGAGTCAGA
ATATCCTGTTCCTCAACAGACTCTTTTACCTAGTGGTTGTAGCCTTAATTGATGATCCTTGTCTGAG
TCAGTTATTAAATCGGTGGTTCCAAAATTCAGGTTGTTTTAAAAAGCGCCAACAGCCTCGTGGGGC
CCTAATTTTGCATCCTGCTATTTGATTGGATGAGTAATTAATGCAGGGTGAGGTGCCGAGGTGGTG
TTTCTAAACGTCTGTTGCTAAAGATAAATGTTGTAAATTAAAAAAAGAAAACATATGGAGCCCAG
ACAGGTTCCTTTACTGCTCCTGCCTGGCCATGGCAGGCTTTTATAATGTAACCCATTCTGCTCTGTC
GCTTCCTGTTTCAGGCAGGCAATCCATGGACCTTGTGGAACTTGTGTCTCTTTTTCCCACGCTGGCT
GGACTTGCAGGACTGCAGGTTCCACCTCGCTGCCCCGTTCCTTCATTTCACGTTGAGCTGTGCAGA
GAAGGCAAGAACCTTCTGAAGCATTTTCGATTCCGTGACTTGGAAGAGGATCCGTACCTCCCTGGT
AATCCCCGTGAACTGATTGCCTATAGCCAGTATCCCCGGCCTTCAGACATCCCTCAGTGGAATTCT
GACAAGCCGAGTTTAAAAGATATAAAGATCATGGGCTATTCCATACGCACCATAGACTATAGGTA
TACTGTGTGGGTTGGCTTCAATCCTGATGAATTTCTAGCTAACTTTTCTGACATCCATGCAGGGGAA
CTGTATTTTGTGGATTCTGACCCATTGCAGGATCACAATATGATTATGATTCCCAAGGTGGAGAT
CTTTTCCAGTTGTTGATGCCTTGAGTTTTGCCAACCATGGATGGCAAATGTGATGTGCTCCCTTCCA
GCTGGTGAGAGGAGGAGTTAGAGCTGGTCGTTTTGTGATTACCCATAATATTGGAAGCAGCCTGA
GGGCTAGTTAATCCAAACATGCATCAACAATTTGGCCTGAGAATATGTAACAGCCAAACCTTTTCG
TTTAGTCTTTATTAAAATTTATAATTGGTAATTGGACCAGTTTTTTTTTAATTTCCCTCTTTTTAAA
ACAGTTACGGCTTATTTACTGAATAAATACAAAGCAAACAAACTCAAGTTATGTCATACCTTTGA
TACGAAGACCATACATAATAACCAAACATAACATTATACACAAAGAATACTTTCATTATTTGTGGA
ATTTAGTGCATTTCAAAAGTAATCATATATCAAACTAGGCACCACACTAAGTTCCTGATTATTTT
GTTTATAATTTAATAATATATCTTATGAGCCCTATATATTCAAAATATTATGTTAACATGTAATCCA
TGTTTCTTTTTCAAATCTAAAGTTAAAAAAAAATAGCAGAAGCCAGTGTCTTAAAGTCTATCTTTTG
TTTCTAAGACCATGGGATTTCATAATCTCAAGATAAAATATGTATGAAGTAATTAATGTAGAATTT
TTACACCAAATAATAAATAATGCTTAATAAACTAGAGATATGAGATGTGTAGGAAATTTGGTTAA
ACTTTTTTCAGATACTTTCTGGCCCAAATAATAATTTGTTAGCAAATAATATGACCCTTGAACTCAA
TGGCCATCTATTAAAAGACTGTTGTTCACACTGGAAAACATTTAAAGATGTGACTATATCCATGGG
TGGATTGAATCACTCAAAATATATTAGTATCCTTCTTTAGGGATGGTTGGTTACAGACATGTATTTA
TTCAGGAGGCAGAAAATATTCCATTTTAATTGCTTATTAAAGAAAACATTAAATTCTAAATTATTTT
GAGGACTGTGAAGACTTTTCATTAGTGTAATATTAGGTCATTGTCAATCTCCCAGAATGTAGTTCT
ATATTCTCTAAATATGAAAGTATCCAGAAAGGCCAGTGGTAGTAAAAAGCTTAGTGTATATAATCT
CAAAAGGGATGGAATATTTACAACTCATATTTATAACATGTTGAATCTTCTCAGTTATCAGTAGTC
ATCAGAAGTGTCAATAGCTTTCTAAATAAATATTAAATATCTACTGTCCTGTAGTGAAGGAGTAAT
TTTTAGTAATTTTCTCTTTACAAAGTCTCCAGTGTTTCCAGGTAAATATTTGTGAAACAAAATACAG
CAAACTACATTGTTACTTCAGTGTATTGTTGCCAAAAATGACAAGATATTATATTAAAATCAGTAA
ATTTTGACAGATTTTAAAAATTAATTAGCCTACAATAGAGGTTATATGGTAACACGGTGATCTTC
TAAGCAGTTAAGTGACTGACTGTTCTGGCAACAACGACTTCTCCGTGACTGAAGGGCCCTGTTCAT
TTCCTGATCCTGAAGCTCGTCTCTCTTTTGAGCCTCCGCTTGCTTTGGTCGATGGTTTCCCTCAGCTT
TTTCTTTGCTGTTCTTCATCCTCGTTGTTGCTGTCATCATGTTCACTGTGGCTTTTACAATACAGCCT
GTAAATTCCTTATGACATAGTTCAGTGCATTTGGCTTTATTGCCTGCTCCACAGTTCTTTACCTTTAC
TTGGCTTAGAGAAACTGTATCTTTGTTGCTTCATATAACCTTTCCCCAACCCCACTAAGCTGGACAT
AACTTATTAGTGGTCCTCCCGTCACTTTATTTGTAGAAATCTCTCTTTCACATGAGCAGGGGTTCTT
TCATGTGGTTTAGCTGACAGCAGAACTAGTGATTCTAGACATTTTGCATGGCCCTCATTCAGTGGC
TCACAAACATGAGGGAGCATCAGAACTACTTGAGGGGCTTGTTAAAACCCAGTGCGTTAGAAGTC
GGATGCGGTGGCTCACACCTGTAATCCCAGCACTTTGGGAGGCCCAGGCAGGCGGATCACTTGAG
GTTAGGAGTTCAAGACCAGCCTGGCCAACATGGTGAAACCCCGTCTCTACTAAAAATACAAAAGT
TAGCCGGGTGTGGTGGTGCATGCCTGTAATCCCAGCTTCTTGGGAGGCCAAGGCACAAGAATCGCT
TGAACCAGGAGACGGAGGTTTCAGTGAATGAAGATCGTGCCATTGTATTCCAGCCTCGGCAACAC
AGCAGGACTGTGATTTTCTTTGGAGACTCCTAGATTTTCTGTGGTTTTGTGAACTGAATTTGTTGGATG
TTGGCAAGTGCCTCTTATGAGCTGTTTCTTTATCCTGCATTTGCCCCACAAAGACTTATCTGGAGGT
GAGCAAAGTATGTTTGGTAGTGAGGTCACAAAGGCAATCAGCCCCTTCCTCCCCACTCCCATTGCC
ATCTTCTCAGTCCTTCTCCCTTTCTTTCCAAGTAGTTTACCCACCCCTCCTCTTTCCTCCCCTGTCCCT
AAAATAATCCACGTGTCTTCCTAAAATCTCTCTTTGATCCTGTCCTTTGATAACACCGTCAGTGCCT
ACTACTGGGTCTAGACAGACCTCTGTTGAGCAGTCAGAGTCTTCCCTGACTCCACAATGCCCCTTT
CCTTGGCTGACCAGTATGACTACTGGTCCCCACCTTTCCCTTGCCTATCCCTACCTCCCTCCTACTA
```

| Sequence Information |
|---|
| GGTTGTCCCATCCCTCTCTTCACCCATTCATTCATGACCATTTTTCACTACCAAGCTCCCCCCTCCC
GAAGGAGGCTGAGGTTTTTGTGACTCTCTAGACTCTATTGTGGGATGGAATGAACATTGCTAAAGA
ATCTTGTGTTCGCTTTACTTTAAAAAGGTATTTTTTTCCTAATTATAAAACTGATGTGTCAGTTACG
GAAAAATTAGAAATGCAGCACAAATACATGAATATTTTACCACAAAATTGCCATATAATATCTTGT
CTTTTTTGGGGGTGTGAATTTTTTGCATTGTTCTGGTCATATTCTTTATCATGTAATTTATGTTCTTTT
TTACTAAGTATTATGTGTGGTTATTATAGATTTTCACAAAGATATATTGCTGGTAATATATTTTATT
GTGTAGTCTTATAATTTACTTAACCTTCTTTCAATTGTTAGAAATTTAGGCTATTTCCAGATTTTCAG
TATTGTAAATAATGCTGTGATGACCAATTTTGTGAATAAAATGTTTTTATGTATTTCAGATTATTCC
CTTAGGATAGTCTCTCAGTGCCAAGTTGTCAAAAACATCTCTATTTTGCTTATCTTCCTGCTCTCTT
GCTGCCTTAGGGGGTAGTAAACTGAAACATAAAGTAAACATGCATACAAATAAAAAACATAAAAC
AAAAATAAGCAACCTGATGGTAATAGGTGAAAGTGGTAACCTGTTTTAACTTTGAATTCTTGCCGG
GCGCGGTGGCTCACGCCTGTAATCCCAGCACTTTGGGAGGCTGAGGCGGGTGGATCACGAGGTCA
GGAGTTCAAAACCAGCCTGGCCAAGATGGTGAAATCCCGTCTCTACTAAAAATACAAAAATTAGC
CGGGCGTGGTGGCGGGCGCCTGTAATCCCAGCTACTTGGGAGGCTGAGGCAGAGAATTGCTTGAA
CCCAGGAGGCGGAGGTTGCAGTGAGCCAAGATCGCGCCACTGCACTCCAGCCTGGGTGACAGAGC
GAGACTCCGTCTCAAATAAAAAACAACAAAAAACAAAAAAAACTTAAAATTCTTTGCTTGTTAGT
GACCTTGATCATGGTTCTCTTTGTACGATAGTTGGGCATCTGTATTTCCACTTGTGTGAATTTGCCT
TTAAATTTTGGTTATGGGTTTCACCTTTTAAAATAATCAAACATATTTATCTTTTCCTGTGTGATAG
GTTTTTTTCTGTATCTTTTCCTGTTAAACACACAGACCCCTCCCCAATCTGGACATTGAATAAATAT
TCATTTTCCTTTGCATTGTT |
| SEQ ID NO: 4-the cDNA sequence of the N-acetylgalactosamine 6-sulfatase
gene (Gene ID:: 2588)
AGGCCCCGCCCCGCAGCCCAGCCGGAAGGGCCGGCGGACGCTCGCTAGGTCGGCTCGCTGGCCGG
GGCTCCGCGGCTCCCGTGGTTGCCATGGCGGCGGTTGTCGCGGCGACGAGGTGGTGGCAGCTGTTG
CTGGTGCTCAGCGCCGCGGGGATGGGGGCCTCGGGCGCCCCGCAGCCCCCCAACATCCTGCTCCTG
CTCATGGACGACGTGAGTGCGGGCGGTGGGACGGGGCAGGGCCGGGGTGGGGCGGGGAGGGGAG
GGGCGGATGGAGGGAGGAGCGAGGTGGGGGAAGGGCGGGCGGGGTGGGGGGAGAGGTGAGGGG
AGGCCCCTTGGGGAAGGGGGAGGCCCCGCGCGGGGAGGAGGAGGGGGAGGGGACGGGGGGTA
TCCCCGTGCGGGGAGGGGGAGGCCCCTCGGGGAGTGGCCGCGGGGTCCAGGCGTGGGGTCTCGGC
GGTCACCGATCACCACACGCGCTGCCACTGTGCTGCATGACCGGGACAGCGTCCTCCCTGGCAGGT
GGGTGGCCGGCGTGCTACCGGGCCCTGCCTCCCCCGTCTGACCTTTCCCGCCCTCTACTCTTGGGA
AAGGTGGGCGCGCAGCGTGGCCTCCCCAAAGGGAGGAAGAGGCTGCTCCTGCCGCCCTGCCTGAG
AGCTGCGTCGCCCTAGGAATCACTCCCGCCACCTCGGGCCGCCGGGTCCCCCGCTGGGCTCCAGT
CTTACCTGACGGCTGTCTCTGTCCTCTGGAGAATGCTGAGCGAAGGTCAGGTGTCCCTAAGGTCTG
AAGAACTGAAAGGCTGGAATGTCTCCTGGTGGGCAAGTGCGGGGCTCAGGGGTCACAGCCAGCCTG
GAGGCCTCCTTCCCTAACTCCTTGTGGGAGCCACCTGGAGACTCAGGAATGAGCCTGCCTGGGGCA
TGGGTCACCGTGCAGGACCCCAGACACACCTGGGTTGAAACCCTACTGTCTCCAAGCTTGGGGGTC
ACTTCCATTCTTGAACCTCAGCTGCCACACCTGGGGGGTTACACCTGTCCCGCCGTGCTCACGTTGT
GTGTGAGGACTGGGACGACACCGAGTACCAGACAGTTTTGGGCCGTCGGTGTCGCTCAGCCCCTGT
GTGCTGGCCTCCGACCAGCAGGACCCCTGACAGGTGCCTTCAGACCCCACCTGTGCTGACCAGTGGG
GGCCACGGGCCACACCCAAGGGCTGGGCAGTCGTGGCTGTCGGAATTGGAAGGTGCTGGTAGTGT
AAAATACACAGATTTAGAAGACTTGGTGAAAGAAAAATAATGTAAAATATCTCACTTAACAATTT
TATTAAATTAATGGTTTTTTAACATAAAGATATACTTGAAAAGATAACAGACACCACCCATAATTT
CCCCACCCAGGGGTGACAGCCGACAGTCCTGGGCAGCTGCTTTTCCATCTCATATGTCTTATTTGTG
TGCAGTGACTGCTTTCAGAGCACGCTCTCCAGCGCCCAGGGGTCCGTGTCCTGACAGCAGTAGCC
GGGCCTTTCTCTGCACTGAGTGGCATCTCCCTCCTAAAGATACTTTGCTTCAGAATTTCATCCTTTC
ACTTTTGAAGTTCCTCTGGGCCAGTGTAGATACTTTGTTTCAGAATTTCTTCTTTTCATTGTGTAACT
CCTTCTGGGCCAGCATAGCTTCGCTGGATGAGCTGGGCTCTGCAGGTGAAGCCTCCCTGTTAAGTT
TCTGCTTTTCCTGACTTTCTCAGAGGACAGAGGGGTGAGGCGGGGCAGCTCATGAATAATTTTTTA
TGTTGAAGACTTGTCGAAATAATATTTTGGTTATGTTGGGTTAAATAAAATATAAAGTTAGTCTGT
ATTTCACCTACTTCTGCTTTTCTAATGTGGCTCCCGGTAAATAGGGAATTGCATGTGGACTCACCCT
ACGTTTCCATAGGACAGCAAGGGTTCAGGCCGTGCAGGGTGGAGGGGTGGGGTGTGGCCACCGGG
GCACATGTGGGGGAGGGTGACAGGAAGCCCCGCCCACCTGGGCACCTGTTCTGTGGCCTCCACTG
TGTGGCTTGTGGGGTCGTTTGGCAGCTGACGCCTAAAGAACCCCAGAGGAGCTGTGTCCTGGCCGG
TAGGTGTACTTGTAAGGACTTTCTGATGCAGACAGCAGAAGATGAAGTCAAAGTGACAAGCAACA
GTGGGGATTCCCTGGCCCTCCTGAGTCGACAGACCAGGGCCGCCTGGCGAGTTTCCCCTTTCGTGG
CTCTGCTGCCTCTGAACTGGCCACATCCTCACTCAGCCTGTGATGGTCCTAGGTGACTCCAAGTCA
CCCCTGCAGTCAGCAGACCCAGTGGGAGGTTGCCTCTGCCCGTGTCATGTTAGCGTGATGTGGGTC
TCAGCCCTGCGCCAAGCACACTGGGGAGGGGCACATGCTGACCTGTCCAGCCCAGGCCTCGGAG
CCTCGGGCCTACCCCAGAAGGGAGACTGCCCCTGATCATCATCTGCCTGGACCCAGCAGAGAG
GGGGTTCCCTGAAGGGCCCATGGTGCAGCTGCCAGGACAGGGCAGGGATGCTGGCAGGTGAGAGC
CACAGAAGCTCACAGTGGAGCCCCGAGGTGCCCTGACGTGGCCCAGGGTGCAAGGGGGTCCTCAC
AGGCTGTCTTCTCTCCTTGGAGTCCGGGGCTTCCTCCGCAGCCCTGTCCACACCTCTTCCTGCACTG
CAGACCGGTTGTTTCTGCCAGGGCGCTGGCGTCTGAACCTGCAACAGGTCATTCGGCCTCTGGCAT
GACATGGGATGGCTTGATGACCCACAGCTCTGGGCCCAGCACCACTTGAGGACGAGTGTGCATGT
CTCAAGTTCAGATTTTGGAGCATGGCCCTCCAGGGACCGGCTGCCTCCAGCCCAGTCTCCCCCTAT
CCAGTCCTCTGTGGCTGGGCAGTGGGGGCCTGGGCCCCCTTTCGTCTAAGCAAGTGCAGTTTCA
GAAAAGGGTTGTCCCCAAAACTAGCTTATTGCACCCCTCATGGCCAGAAGCCACTCTCCAACTGGT
CACACTGACCCGGGAGAGAACCATTGCCCCCAGAGTCGGGACCAGAAGGGGAAGCTGGGACTCA
GGGGTGAGAGCAGCTGGCAAGAGCCCCCACCTGTCCAGGGGGAGCTGAGCCGGGCAAGGACGGG
TCTACCTGCACTCCCCAGGGCTGCCCTGCCCTGGCCTTTCACTGACCCACGGTCCAGCGCGGCCTG
GCTTCGTAGTACCCCTGGGCACCTGCTGCGTGAGTGAGGAAACCTGCGTGGCCCACTCTGCTCTCCA
GGGCTTCTGGGGCCTTGGAGACAGGTGAGACCCAGTGACAAGTTCCACTCTGGCCCACACACAGC
TCCTGCCTCCCAGGGCGAGCAGCACTCTGTGTCTCCACTCCTTATTTGGAAAATAGGGTTAAGGAG
GGTCAGCCCTGACCACAGAGGAAGTGGAGAGTCAGGGCCACCCAGGCCAGCTCCTGTTGCCACAG
CAGCCTCGTCGAGCCACCAGAGTCCGGGGAGGGTTGCTCAGTGCCCCTCGTTTGAAACAGACAAG |

-continued

Sequence Information

```
CACTGGCCTGCTCGTCTTCATAATAATCCCATAGCAACCAGTAGGAATGGAAACTGCGTTTCTTAA
AACTCTGAAATTCTGAAGGATACTGATCCATGGCTCACAGCTGTGCTCGCTGAACGTGGACAATCA
TTTGGGGGCTTTTAGGCCTTTTTTTTTTTTTTTTTTTGAGATGGAGTCTCACTCTGGTCACCCA
GGCTGGATTGCAGTGGTGTGATCTCAGCTCACTGCAACCTCCGTCTCCCAGGTTCAAGCAATTCTC
CTGCCTCAGCCTCCCGAGTAGCTGGGACTACAGGCTCCACCACCGTGCCCAGCTAATTTTTGTAT
TTCTAGTGGAGACGGGGTTTCACCATATTGGCCAGTCTGGCCTGAAACTCCTGACCTCAGGTGATC
TGCCTGCCTCAGCCTCCCAAAGTGCTGGGATTACAGGCATGAGCCACCACACCCAGCCAGGACTTT
TTTTTTGAGACAAGGTCTGGCTCTGTCACCCAGGCTGGAGTGCAGTAGCTCGATCACAGCTCACTG
CAGCCTCAAACTACTGGGCTCAAGCAATTTTCCTGCCTCAGCCTCCTGAGTAGCTGGGATTATAGC
CGCCCATCACCACACTCGGCTAATTAATTTGATCTTCAATCACTGATACCCTTTCTTCCACTAGATC
GAATCGGCTACTGAAGCTTGTGCATGCGTCACGTAGTTCTGGTGCCATGGTTTTCAGCTCCATCAG
GTCATCTAAGGTCTTCTCTACACTGTTGATTCTAGTTAGCCATTCGTCTCATCTTTTTTCAAGGTTTT
TAGCTTCCTTACCATGGATTCAAACATCTTCCTCTAGTTCGGAGAAGTTGGTTATTACCGACTTTCT
GAAGCCTACTTCTGTCAGCTCGTCAGAGTCATTCTCTGTCCAGCTTTGTTCCCTTGCTGGCGAGGAG
CTGCGATCCTTTGGAGGAGAAGAGGTGCTCTGGTTTTTAGAATTTTCAGCTTTTCTGCTCTGGTTTC
TCCCCATCTTTGTGGTTTTATCTGCCTTTGGTCTTTGATGCTGGTGGCCTAAAGATGGGGTTTTGGC
GTAGATGTCCTTTTTGTTGATGTTGATGCTATTCCTTTCTGTTTGTTAATTTTCCTTATAAGAGTCAG
GTCCCTCAGCTGCAGGTCTGTTGGAGTTTGCTGAAGGTCCACTCCAGACCCTGTTTGCCTGGGTATC
ACCAGTGGAGGCTGCAGAACAGCAACTATTGCAGAATAGTAAATATTGCTGCCTGATCCTTCTTCT
GGAAGCTTTGTCCCAGAGGGGCACCTGCCTGTATGAGGTGTCAGTGGGCCCCTACTGGGAAGTATC
TCCCAGTTAGGCTACACGGGGGTCAGGGACCCACTTGAGGAGGCAATGTGTCCGTTCTCAGAGCTC
AAACACTGTGCCGGGAGAACCACTGCTCTCTTCAGAGCTGTCAGACGGGGACGTTTAAGTCTGCCG
AAGTTTCTGCTGCCTTTTGTTCAGCTATTCCCTGCTCCTAGAGGTGGGGTCTACAGAGGCAGCAGG
CTTTGCAGAGCTGCGGTGGGCTCTGCCCGGTTCGAGCTTCCCTGCCGCTTTGTTTACCTACTCAAGC
CTCAGCAATGGCGGACGCCCCTCCCCAGGCAGGCTGCCACCTCGCAGGTGGATCTCAGACTGCTGT
GCTAGCAGTGAGCAAGGCTCCGTGGGCATGAGACCCTCCGAGCCAGGCCCGGGATATAATCTCCT
GGTGTGTCGTTAGCTAAGACCGTTGGAAAAGCGCACTATTTGGGCGGGAGTGTCCTGATTTTCCAG
GTGCAGTCTGTCACGGCTTCCCTTGGCTAGGAAAGGGAAATCCCCCAACCCCTCGCACTTCCTGAG
TGAGGCGATGCCCCACCCTGCTTCGGCTCACCCTCCATGGGCTGCACTCACTGTCCAACCAGTCCC
AGTAGGATGAACCAGGCACCTCAGTTGGAAATGCAGAAATCGCCGTCTTCTGCGTCAATCACGCT
GGGAGCTGCAGCCCGGAGCTGTTCCTATTCAGCCATGTTGGAACGGAATCCCCACACCCGGCTAAT
TAAAAAAAAAGTTTTTTTAGTGACAGTGTCTGTCTGTGAGCCCCAGGTTGGTCTTGACTTCCTGA
GCTCAAGCGATCCTCCCTCCTCAGCCTCCCAAAGTGTTGGGATAACAGACGTGAACCACTGGATCC
AGCCCTTTTAGGACTTTTAAGGGAGAGAAGAAAGGTGGTTCCTGCCCGTGGTGCCCTGTGGGGGTT
TTAGATGTTCAATGGTAACCTGCTCACTCTGCAGGGAGGCTGTCCACACCTGCTTTTCATAGCCAA
GAAAGGCGCCGATAAATAATGAAAGAACAGGGTCAGCAGATGAGAGCTGGCCCAGCAGCCTGGG
ACGCTGTCCTCAGAAGGCCCACGTGTGGGACGTTGCCCTCGGCTGGTCAGAAGGCACATGTGTGG
GAGGTTTTTGCCCTCGGCTGGCGTCTGGGAACAGGAGGTCCCCCCGCTGTTCGCTGATAGGAGCAG
CTCACCTTGCCACACTGTTTTTGCACATGCCACGATTTATGCCCAGCATCCTCCTTCTGGGCATAAA
GAGTCTCGGCACATGCCAGGCAGAGGCGGCCGCACTGCCAGCCTAGGCAAAAGCCCTGGGAACTG
AGTCTCGCACAGCTTCCCCGTCAGCATCCCGCACCTGTGCTCGCAGCCCGAGCGTCCCGTGTGGCT
CCGCCTGGGGAGGGTTCCACGCTGCGGCTGGTCTCCCCGGCCCCGCCCGCACCTTCTCCCCTGGCT
GATGCCCTCCCCGTTGTAAGTCATGGCAGTGAGTAGGACTGTCGCCAAGACCTGGGACTCCTCCCA
GCGAGAGTGCTCCCTTGCGGTATCTTCTGAGTCAGTGGTGAGCGTGGAGCCCCCTCCCTCAAGCCC
TGGGACTCCTCCCCGCAGTATTTTCTGGTGAGTGATGAGCGTGGAGCCCCACTCCCTTTACAGCATTT
TCCGCTGCATCCATTCATGTTATTTGTGGCCTGGAACAGGTAGGAGGATGACCCAGGTGAGCACAA
GCAGATCCGGACGCAGCTCTGCTGACTGCCGACCTTCTGGGGAGGCCAGACCCGCCTCGGGAAGC
CTCAGGACGCAGCCTGCAGGGAGGGTCGGGCACATGGCACCCAGTATTCAGATGTGCGGCCTCAC
TCCCAGCCCGAAGGGAGCCCAGCAGTGGTCCTGGGCATGGGCAGACAGTGTAACGGGCGAAACAT
ACTGCTCCCTCCCATCCCAGGCCTTGTGCCCCGGCCCACCTGCCATTCTGTACTCTCCCACCTGGA
CTGGAGACAGCAGGAAGTGCAGAAGCCACCTGAGAGGATGAATCTGCACTCGGGGAGGTGGAGG
GCAAGGAGCTTTGGGCGTGTGTGGCCAGTCCCCTCAGGCTGGCCTCAGGGAGCTGTACCGTCCCA
GCCTGCACTGCAGGTTTCTGCTGCCTCAGTGGGATGCACCTCACCCTGACATGGGCGCATTCGCCC
ACTGTGACTAGGTGCCACTGAGCCCAAGGTCCCTTCTCAGCCCATGAGCAGCTCTGCGGGCGTCCT
GCCCCCTGTCCTCCCACCTCCCTTTCTTCCTCATCAGCTTCAGGGGACACCTCTCTAGGTCCTCCT
TTCATTCCAGCCTCCATTGTCCTCAGAAAAGCCATTTCAGTGACTTCAAAATAAACCATCTCAGGG
CTGGGCGTGGTGGCTCACACCTGGGATCTCAGCACTTTGGGAGGTGGAGGCGGGTGGACTGCTTG
AGCTCAGTTCACTCAAGACCAGCCTGGGCAACGTGGCAAAACTCCATCTCTACCAAAAATACAAA
AAAGTTGGCCTGACACGGTGGTTCACACCTGTAATCCCAGCACTTTGGGAGGCTGAGGCAGGTGG
ATCACCTGAGGTCAGTATTCAAGACCAGCCTGGCCAACATGGTGAAACCCCATCTCTATAAAAAA
AATACAAAATTAGATGAGCTTGGTGGTGGGTGCCTATAATTCCAGCTACTCAGGAGGCTGAGGC
AGGCGAATTGCTTGAACCCAAGAGCCGGAGGTTGCAGTGAGCCAAGACCACGCCACTGCACTCCA
ACCTGGGTGACAGAGTGAGACTCCATCTCAAAAAATAATGATAATAATAATTAACTGGGCATGGT
GGCATGTGCCTGTAGTCCCAGCTACTCAGGAGGCTGAGGTGGGAGGATCACCTGAGCCCGGAAGG
CAGAGGTTGCAGTGAGCCAAGATCGCGCCACTGTACTTCAGCCTGTTTGTCAGAGTGAGACCCTGT
CTCAAAAAAATAAACCATCTCAAAAGGGATCAAAGCTAAAAGGGCCAAACAGAATTGTGTCCCA
TGAGACATGGAGGGCCTTTGAGAGGAAAAAGCCCAGACCTGGCCCAGCTCTGGGACTCCACACGT
TAGGAGGGGCTGAGGCAAGGAGCGGCCACCCTGCCAAGCTGAGCCTTACAGGCAGGGGCCATGTA
GCCTGCCGTCCACCGGGGAAATGGATCATTGCATCCAGACAAAGACCAAGGTGTGACCACGCAGA
CCTGGATGTCCAGCCACCCACGTGCGCCCAGAGCGGCCCACTGTCCTCCCGCGGTCCCCGGGCCC
AGCGCCCATCCCTCCAGCAGCCGTTCCCAGTCAGCACGCTGCCACCCCCGCCCCCGGTGAGGGCTT
CCCCTCTGTTCAGACCCCTGTCACTTCACACAGGCCCCGAGGCTGCTGCTTCTTTGACTTACCAGGA
CCCAGCGAGTCAAACGCCCACCGGCCCCGACCCAGCAGTGTCAGGGGAGCCCCTGGTCCATCTGC
AGAAAACCAGGATGCCCGCACTTCCTTTTTTTTTTTTCAGACGGAGTCTCACTGTCACCCAGGC
TGTCCTGCCTCAGCCTCCCGAGTAGCTGGGACCACAGGCGCCTGCAACCACGCCTGGCTAATTTTT
TGTATTTTTGGTAGAGACGGGGTTTCACTGTGTTAGCAAGGATGGTCTCGATCTCCTGACCACCTC
GTGATCCACCTGCCTCGGCCTCCCAAAGTGCTGGGATTACAGGCGTGAACCACCGCGCCCGGCCTT
```

| Sequence Information |
|---|
| TCATTCTTTTATAGCCGCTTTACTGAGACGGAATTCGCTGGTGAAAGTGTGCGGGTCATTTTTAGTG |
| TGTTCTCAGAGTCGTCCTGCCACCACACATCGTCACATCATCTTTGTCACCACGGAAGGAAGCCCC |
| AGCCCTGATGGGGGTCACTCCCTTGTGCTCCCCGAAGCCCTGGCCGACCCGCTCCCCTTTCTGTCT |
| CTAAGGATCTGCCTTTTCTGACGTGTCCGGTGAATGGAATCTTACGGCTCATGGGCCTTGTGTCTAT |
| TTTCCCCTCACACAGGGTTTTTGGGCTTCACACACACAGCCTGTGTGAGGACTCCATTCCTTTTCGT |
| GGCTGAGTCATGGTCCACAGTGTGGAGGGACCACGTGTGGCTGAGGCTTCCACCCATGGATGGGC |
| ATCCGGGTGTTTCCAGCTTGGCTGCCAGGGAGCGAGCCGCTGTGGGTGTTGGTTCATGCACAGGTT |
| TCCACGTGGACACACTTTTCAGTTCTGTTGGGCGTGTACCAGGGAGGCGCTGCCGGGCGGCGTGGC |
| CACCCTGCGTGGCGCTGCCGGACCTCTCACCAGGTGCTGCGTGTCACGTTCTTACATGGTGTGTGA |
| GGGCTCCAGTTTCCAGTGAGTTCACTTTTAATGTTTTGTTTTGTTTGGTAAAAATCAACCTTAGACA |
| ATCAGCGATCAGACTCTAGTCCCTGTCGTGGTGAACTGTGGAGAGACCAAAGTGAGCCTCTCTCCG |
| GCTCTTGGAGCACCAGGGCCCATGCAGCCTGTCTTGGGGTCATTTGAAATGGTGGAAACTTTACAA |
| GGGCCCGATGGGCAGGTGAGCCCCACTCGGCCTCCAGGCACAGCCCTCCTCAAGGTCCCTGCTGTC |
| CATGCAGGTGGCAGTCCTACTCTGTGGGTGAGTCCTGGAGCCACTTGTGACAGGAGGAGGCTGGA |
| TGGGGTGAATTTGGAGAAAAGTGGCAGGTTTTTGTTTTTTATTTTTTTGAGACAGGGTTCTCTGTCT |
| GTTACCTAGGCTGGACTGCCGTGGCGCGATCTCAGCTCACTGCAGCCTCTGCCTCCTGAGCTCAGG |
| GGATTCTCCTGCCTCAGCCTCCCAAGTAGCTGGGATTACAGGTGTGTGCCACCATGCCCAGCTGAT |
| TTTTTGATTTTTTATAGAGATGGGGTCTCACCTTGTTGCCCAGGCTGGTCAACGAGAGAGAAAAGT |
| ATTTCAGAGACTTAAAAAAAGAACCATCGGTGGTCTCCAGTGTGCTTAAGAGCTGCGGGTGGAGC |
| TGTTTGCGTTCCTCCTGAAGGCTTTGGCTGCCAGACATGGCTGGGCTGCAGATACTTGCTTTACTAA |
| GAGGTTTTCCCTCCCTGCCGTCCAGGTGTGTCCACAGGTGTCCACACAACCAGGTGTCGTGAATGT |
| CTGTTCACACTAAGTGGGCTTCTCAGTAACCCCCTGGCCACACCCCCATCTCACCCATCCCAGGAG |
| CCTCCTGGGACCACACACGGGGGTCGGGAGCTTAAAAGAACAGAAACACGGCCGGGCACAGTGCT |
| CACACCTGTAATCCCAGCACTTTGGGAGGCCAAGGCAGGCAGATCACCGGAGGTCAGGAGTTCGA |
| GACCAGCCTGGCCAACATGGCGAAACCCCGTCTCTACTAAAAATACAAAAACTAGCTGAGCATGA |
| TGGAGGGCGCCTATAATCCCAGCTACTTGGGAGGCTGAGGCAGGAGTAATCGCTTGAACCCGAGA |
| GGCAAAGGTTGCCGTGAGCCGAGATCGTGCAGGCAAAGGTTGCAGTGAGTCGAGATTGTGCCCTC |
| CAGCCTGGGCGACAACAGCAAGACTTCGTCTCAAAAAAAAAAAAAAAAAAAAAAGCCAGAAA |
| CGCATTCTGTCTCGGTCTGGAGGCCGGAAGTCTGAGCTCAAGGTGTGGGCAGGACCTCGCTCCCTC |
| GGAAACCTGCAAGGGACCTCTTGCCCCTGCAGCTTCTGGTGGCCCCCAGCCGTCCGGAGCCCATGG |
| CTGTGTGTCTCCCGCCTCTGACCCCATTGCCACACGGCCACCTTCGCCCTGTCTCCTATAAGGACTG |
| CAGTGTGTGGGATGAGGGTCCACCCCCATGTTAGTGACCTCATCTTACTGAATCATATCTGCGGCA |
| ACCCTGTTTCTAACTAAGGTCACATGCTGAGCTACACTGGGGCCATGATTTCAGCATAACTTTTGG |
| GGATACAGCTCCACCCATTAACACAGATGAACTGTGATTTATTTAACCAAATTTCTGTTCCCAGTA |
| TCTCAACCACAATTTTAAATTGGCATAATGGGTTATACATAGCTGTAATTATTTCTTAGGATAAAC |
| TCCTACAAGTGGAATTGCTGGGCATGATCTTTTTTTGTTTGTTTGTTTAGTGAGAGTGTCTCACCC |
| TGTTGCCCAGGCTGGAGTGCTGTGGTGTGATCATGGCTCACGGCAGCCTCAACCTCCTGGCCTCAA |
| GTGATCCTCCTACCTCAGCCTCCTGAGTAGTTGGGACCACAGGTACACACCACCACACTTGGCTTT |
| TTTTTTTTTTTTAGAGTTGGAGTCTTGCTGTGTTGTCCAGGCTGGTCTGAACTCCTGGCTTTAAGTG |
| ATCCTCTCATGCCCTTTTTTTTTTTTGAGACGGAGTCTTGCTCTGTCACCCAGGCTGGAGTGCGGT |
| GGCACAATCTCGGCTCACTGCAACCTCCGCCTCCCGGGTTGAAGCGATTCTCCTGCCTCAGCCTCC |
| CAAGTAGCTGGGTACAGGTGCCCGCCACCATGCCCAGCTAATTCTTGTGTTTTTAGTAGAGACTGGG |
| TTTCATCATATTGGCCAGGCTGGTCTCGAACTCCTAACCTTGTGATCCGCCTACCTCGGCCTCCCAA |
| AGTACTAGGATTACAGGCGTGAGCCACCGCACCCAGCCCCATGATTGCCTTTTAAGATAGGGTAGC |
| TGCACTTTCACTAAGACAGAGGTTGGCCAACTCCAGCCCATGGGTCAAATGTGAACCACCTGCTGG |
| GTTTTGTTGTTGTTGTGGTTTTGGGACGGAGTCTCCCTCTGTTGCCCAGGCTGGAGTGCAGTGGTAC |
| AATCTTGGCTCACTGCAACCTCCGCCTCCCAGGTTCAAGCGATTCTCCTGCCGGCTACTGTACTCCG |
| AGTAGCCGGGACTACAGGTGCCCACCACCATGCCTGGCTAATTTTTTGTATTTTTAGTAGAGGCGG |
| GGTTTCACCATGTTAGCCAGGATGGTCTCGATCTCCTGACCTGGTGATCCGCCCGCCTCGGCCTCCC |
| ACGGTGCTGGGATTACAGGCGTGAGCCACCGAGCCCGGCCCACCACCTGCCGTTTTTTAAACCCAT |
| AAGCCAGGCATGGGTTTTATAATTTTAAATTGTTCAAAAAACCAAAAGAGTAATATTTTGTGACAT |
| GAAAAATTATATGAAATTCAGATGTTGATGAATAAAGTTTTATTGGCACAGAGCGTGCACATCTGC |
| TCGCATGCTGGCTTGTGGCAGGGCTGAGGGGCTGTGACAGCCCCATATGGCCCACAAAGCTGAAA |
| GGATTTGCTGTGAGGCCCTTTACATAATGCATTTGCTGATGCCAGCTCTAAATATCCATATTTGCAT |
| TCAGATTGGTTTCAGAAATAAATATGCGTTGAATGCAGCTGGGCCTGTGAACGTGGTGGTTGAATT |
| CAGCTGGGCCTGTGAACTTGGTCGTTGTGTTTAGAATGTGTTGTCTTTCCCAGGTGTTGTGTGTTTG |
| TGCTGCCGAAGCTGCTGAAGGCGGCCTGTAGAGGGCAGGGGCCCAGGAGGCACAGTCACTTCAC |
| TGGTGTCTTGGTTGGTGCTTGGAGCACCTCAGGAGGGAATATGTCCTTAAGGAAGGAAGACAGGC |
| CAGACAGAGGGGCCTCGGAGTGTTGGCTTCTACCAGGCTCCTGCTGAGGTGGGCGCTCAGGGAGA |
| CGGCTGGAGGATCCGAGGAGAGCCAAAGCCCCAGGCGGTGCCCTCCCCTTCTCCTTCTAGAGCAA |
| AGTCCTGGCCCACTGCCTGTTAAAAGCACTTTTTTCCAACAATACACACTGTAAAATTTGAAGA |
| GTTTTCAGTGAACACCGCCGCTGCCACTCACCTTCCGGAGTTTGCCGTGGGCATTTGCTGTGCTGGT |
| GCCATCACACCTGGCATCACCCCGGCTCCTGGCATCACCCCAGCCTCCGTGCTTCCTGCCCTGTGC |
| TCACCCGTCCTCCTGCTTGGGGTTTTTATTGTAAAATACACAGAACGTAAAATTGACCATGACAGC |
| CACCTTAACGTGCACCACTCGGGCACAGTCCATTCACAGCGTGGTGCCTCCATCCCTTCTACCTGCT |
| TCCAAACAGTCCATCCCAAGAAGAAACCGGTACTCATCAGCAGGCCTCCCCACCCCCACCCCCC |
| AGCCCCGGCAGCCACTCAGCCGCCTCCTGCCTCTGCGGACCGGCCTGTTCCGGAGGCTTAATGAGC |
| AAATCACAGCCTGTGTGGCCCTTGTGTCTGCTTCCTTCCCTCACATGAAGCTTTCCAGGGCCGTGCG |
| CGGTGTGGGGTGCCCTTCCTTTCGATGGTTGGGTAGTGTGCCGCGGTACGTGCGTGAGTTCCTGA |
| GACATAACACGTTACCACAGGCCAGGTGGCCTTAGCGGAAATGGATTCTTGCCGGATTCTGGAGG |
| CCAGAAGTGCAAAATCAAGGTGTCAGCCGGGCCCTCCCCCTGGGCTCTCCAGGAAGGTCCTTGC |
| TGTCCCCTGGCTGGTGGCTGCGTCACTCCAGTCTCGGCCTCGGCCTTTCACCCGGCATCTCTACTGCA |
| TGTCTGCGTCTCTAAGGGCCCAGTCATAGGATTGAGGGCCCACCCTGGCCCAGCGTGACCTCATCT |
| TAGCTCACTACATCTGCAGAGACCCTACTTCCAAATGTGGCCACACCCACGTAGTACACGCCGGCC |
| GCACTTTGTCGTCTGCCGATGGGCGCTCAGGGTGCTCCTGCCTTTTGGCCACTGAGTCGTGCTGCCC |
| TGGACGCTCGTATGCAGGCCTGCGTGTGGACGTAAGTTTCAGTCTCTTGGGTGTACAGCTAGGAGT |
| GGAGTTGCAGCGTGGAACTGCAGGGTCACACGATAACTGGGCTTCTGGGGGACAGTTACCAGTTG |

-continued

| Sequence Information |
|---|
| ACTTTGAAATCTAGACGTGTACAGACATACGAGGGCCTGTGTATTTATGTTGAAAATAGATGCACG |
| TGTTTAGAGGCCAGCTCCTGCGAGCATGCAGATGCTGGTGTCAGGCTGGGAGGAGGCAGACGGAC |
| ACATTCCCCACCTGAAGACCAAGCAGAAGTGGAGGCGAAAGACAGCGTGGGCTGACCGTGGAGC |
| GGCCCCATCGTGCACGCACGCAGGCGATGCTGAGGTTTGGGCTGGCGTGGAGCGGCCCCATCGTG |
| CACGCACGCAGGCGATGCTGGGGTTTGGCCGAGCTCTGCCGCTGGCTGGGACACAGGGTGGTGCT |
| GGCTTCCACGGTCCCCGACACGCTCTTGGCACCATGGGCAGCTCCCCAGGCCAGAAGCACCTGCA |
| GAAGGCGCTCATTCCTCCTCCCCGTGCTCTTCCCTGCAGATGGGATGGGGTGACCTCGGGGTGTAT |
| GGAGAGCCCTCCAGAGAGACCCCGAATTTGGACCGGATGGCTGCAGAAGGGCTGCTTTTCCCAAA |
| CTTCTATTCTGCCAACCCTCTGTGCTCGCCATGTAAGTCAGCGGGGCCCTCGCCCCCAGGAAGGGG |
| TGAGCCCAACAGGCCGAGGCCTCCCGGGTCCTTCCAGCCCTGACTCTGGGCGGCTGCATCAACCTT |
| GTCTATTCCTACTACTGCAGGGAGGGTGGCAGGTGGGCTCAGGCCTTTCTCATCAAATCCCAGCCC |
| GGCTCCGTGCCATGTGGGGTGCGGCACCTGCTGGGTTTTCAGGGTCGAAGTTGCGGTATTGTTGGT |
| GGCTGCTGTTCTGTTTCCCAGAGTCGAGTGCTGTGGCCGCCTGGGGAGAGGTGCTGCAGTGTGGCT |
| CCGTCTCAGGGTACCTGGGAAGCAGGAGTCCCACTCCCTCCCTCCCTGGGGAGAGTCTCTCCTGCT |
| GGAGACAGAAACATGTGGTGTTGATCGTGAGGAAGAGGAGAAGGCAGGGCACGGGGCTGGTGCT |
| CGAGGATGGGGGCGTGTGGACCTGCACGCCCAGTGGGTGTCCCAGGAGCCTGCGAAAGGAGGCG |
| GGGTCTTGGGGACAACGCTGAGCTGCAGGGCCCAAGGGCCACGCGTCTTTCAGTGGAATGGGTGC |
| CGTGCCCCACCCAGGTGGTGGAGACGCTAACGGGGATTGACAGGCGTGGCAGCCCCTTGTAAACC |
| TGCGCGTGCCTCGTCTGTCACGCGTCTGTCTACTCGTTGGGGCTCTTGTTGACGCCCGGGGTCTGAG |
| CCACACCCTTCTTATCCAGTTTCTGTTTCTGTCACCTCCACATAGCGAGGGCGGCACTGCTCACAGG |
| ACGGCTACCCATCCGCAATGGCTTCTACACCACCAACGCCCATGCCAGAAACGGTAGGCTGCCCA |
| CCGCCTCCAGGGACACCCTTGGGGTGCAGGGTTGGGCAGGTGGGCTACGGGTGGTGCCCGTGTCT |
| CCGGGACTCGGGTGGCAAGCTGCAGGTGGGGTACCGCTGGTGCCTGGGTCTCTGGGACTTAGGTG |
| GAAGTGCAGGCCCCCCTAGCTGGCTTCCTTCCCTGCCCTGGCCCAGTGGGGACTGAGCGGAGGGTG |
| CCCAGTCTGGCCTAAGGAGCTGAGCCGGCACCCCCACCCCAGAAGCTCCCACTCCCCAGGCGGGT |
| GAGCCGCACACCCACAGGGAGGCCGGGGCTGTGGCATCAGCGGCAGTTCTGGAATGTTCTGGAAT |
| CGCTGTGCTTGAGGGGTTTGGATGGGCTCCCCAGGGGCATCTCACAGGGGAAGTGGGATTTCCAGT |
| GGCATTTGAGGAAAGGGAAGGACGGGGGAGGCAGGGGTGGGGCAGTGCAGCATCACGTGGCATA |
| TTCCAGAGACCCCTGGAGACCAGGCAGGTGGGAGGCTGGCCTGAGAGGCAGGGTGGGGCCTGAG |
| GGTGGGCAGGAGTCCCAAGGAAGGCGCTGGGGGGCACGGAGTCTGCCCCGTCCCACCCTCTGGT |
| GATGGCACTGGCTCTGAGGGGTGCCTGGAAAAATCTTGGGAAGTGCCATGCCCTGTGGACGCGCA |
| GCCCCCAGGCACAGCCTTTGACCCCGAGGGGCCAGTGTCCTGTTAGGATGTGTGGACGCAGCCCCC |
| AGTGTCCTGTTAGGATGGGGTTGGTGGCAGCTTCTCGGGGTCTCCTCGGGGCTCACCCAGCGCTGC |
| TCTTCCAGCCTACACACCGCAGGAGATTGTGGGCGGCATCCCAGACTCGGAGCAGCTCCTGCCGG |
| AGCTTCTGAAGAAGGCCGGCTACGTCAGCAAGATTGTCGGCAAGTGGTAAGTCTCCTGGCCACGC |
| CTGCCCAGGCGTCCTGCTCCATCCACTTCCTGGCCTTGGTTCCAAGGGACATGGCCACAAGTTTCC |
| AAATGAGGAGGGTGTCTTGGGTGGGAAACGGCAGCTGATTCTGGGTGTGTTCAGGTGTCTCCAGC |
| GTCCCTGTGCAGGCCAGCGTGACCTTGCCAGCAGGATCTCAGGTCACCAGGCTGGTCCCACGGCCG |
| CGAGTATCCTGCGGCATCAGACTCCGCAGGCCTGTCACCGTCATCCCTCGAGTCACAGCCCCTAGC |
| ACCCGCCACCACTGCCCCCCGGCTGCCTCCTGCCACGTCGTCCTTGGAGGGGCCACGTCATTACAC |
| ACAGGAGCTGTGGCGGAGGAGCTGCCTGTCCACCCTAGGGGCTGTTGGATGGTGAAAGCTCTGG |
| TCTAAACCACAAAGAAGCCACCAGGAAGGAGAGTAACAGCCTAGCAGTTGATGAAATCCTGAGCT |
| GATGAGAGCTTGGGTGCTACACAGCCCCCACGCTGCGGTTTTAGGCGCACAGGATGTTTCATTTCT |
| TTTACTCCCTGGGACGCCTGAGTGAGCCTAGAGGGTTGGGTAGGAGTCACCTGTCCCGAATTTCTC |
| TCCACTTGTTGGAGCGTTCCCGCCTGTCAGGTCCGCATGCCGCTCCTCCAGGAAGCCCTTGCTGC |
| TTTCCCAGCCTCTGTGATCCCCAGTCGGCTGCCTGTGGCTCCTGCCGGTCCCCTTCAGATGGATGCT |
| CCTTGGATGTAGATGGTCATGGCAGCCAGGAATTTGCTGAGCTTGATCACTGGATGAGGAGGACC |
| CAGAGGCTGTCTAGGGAGCACTTCATCATTCTTCAGATGAGAGGAAGCAGCCTGCCGAGCTGAGC |
| TCTCAGAAAGCACAGGGCAGAGCTGATGGGCACAGCAGCTGCAGAGTCCTCACACAGGGAGGTTG |
| GGCCCCACGCAGCCTGCATAGTCCCTGAGCCAGTGCCAGGGGCCATGCGGAAGTCAGCCCCCGA |
| GGGCCACTGGAGCGCGTGAGTACTGTGCCAACAGGAGGAAGAGCCGGTGGCCTCTCCAAGTGACA |
| AGCCCCACAGTGACCCAGAGCTCTCCGCCTGGCCTGGCAGCTCTGTCTTGGGCCCAGCGGCCTCCT |
| ATGCATGGTCATTGGTGCCGGTGGCCAGAGCTAGACAGGGAGTGGGTCTCCATAGAGGCCTCGAG |
| GCTCCTGAACAGCTGTCGACGGGAGAGAGGGGACCCCAAGGAGTGGGAGCAGGAGCCAGGCAGA |
| CCTCAGAGCCCAGGCTCCTCCCGCACATGGTGCAGTGGCTGGATGGCCCGGCTGGGTCCTACAG |
| CGGCTGCTCAGTCAGGTGGGGGGTCCCTATCCCAGCAGGGTCCCCTCTCAGGGCAGTAGGGGTG |
| TTGTCAGCCATGACTCAGACTTCCCTGAGGCCCCTCACCTGGACTCAAAAAGAGGCTGCTTGATCT |
| GCATGAAGCCACGCGGGTGTGCAGGGCAGGGACTTGAGTCCCAGAGGGCCGCGGACACTCCCTGC |
| TCCAGGTCACCTGCTGGTGAGTGCCAGGCCCCACTGCTGCTTTCGGACAAGGACGTTGAGCTGACA |
| GCTTAATTTGTGTAGCGTCCTGCCCATGTGCTTCCCCTGAGCAAGGCCTTTGTGCTGCGGACGTGG |
| AAGCACGAGTGTCCCCTGTGGCCGGGCGGTGACCTGCGGACGTTGGCGCACGAGTGTCCCCTGTG |
| GCCGGGCGGTGACCTGCGGACGTGGGCACGAGTGTCCCCTGTGGCCGGGCGGTGACCTGTGGA |
| CGTGGGCGCACGAGTGTCCCCTGTGGCCGGGCGGTGACCAGCGGACGTGGGCGCACGAGTGTCCC |
| CTGTGGTTGGGCGGTGACCTGCGGACGTGGACGCACGAGTGTCCCCTGTGGCTGGGTGGTGACCTG |
| CCTGGGGTGTTCAGGGATGTCGGGGTGCTCTAGCAATGGGCCCAAGTGCTGAAGACCCAAAGGAA |
| ACAGCCCGGAGTTGGCAGCCAAGGGAGCTCTGAGGTCACAGAGAGGTCCAGGCGTGCTTACCTGA |
| GAGAGGAGATGGGGAGAGGCAGCTCGGGAGGTCCAGGGTACAGAGGCCATGTCCAGGGAGGCAG |
| CAGAAATCTGCTGTGGTGAAATCTGCCTCGGGGAAATCTGCGTCGGGGATGCTGCTTTCAAAGCCG |
| TAGCTGCAGAAGAACTTTCCTCAGACGACACGCAACTGACGTGAGACCCGCCCACGCCGTGCCT |
| AGAAGCCATCTCATACCACCTCTCCTGCAGCCCGTTCTGAAGAGCAGCCGCAAGCTGGATTCGTTC |
| CAGGACAGGACAGGCTGCGCAAGGAAACCCGGACAGCTGGCCTGGGGGCCAGGGCGAGTGGGCA |
| CAGAGGGTGTGGCCTGCAGGGCTGCTGTGGGCCGGAGGATGAGATTAGGTGCCACCAGAGGGTGGG |
| AGCACAAGGTCTGCGGGGGATTGTCAGAAGGGGAGTGCGGGACGGGGTCTGGAGGGGTTCCCAC |
| AGGCCTGGGGTGTGATGCCTGGCGATGGCCATTCCCAGCAGGTGAACCCCGGTCCCAGGAGAGCG |
| GTTGGTGGAGGTCACCAGTGTGGCCACACTGTCACGTTCTCTTGTCGTCACTCTAATCCCTGCCTCT |
| GCCAGGGTCCTGGGGATGTGGGTACAGCTGGCAGGCCCCGGGGCTCCCGCACGGCACACAACGCC |
| CCGCCCAGTCGTCATCCTGGGGCCATTGCCCTGAACTGGGAGATGAGACTCTGAGCGCCTCGGTGT |

-continued

Sequence Information

```
GGAGAGACCCAGTAATTACCTGGCAGGAAATATTTTCTGCCCTGGAAAACCCAGAGGAGACACAC
TTGGGTTCGAGGCATGACCCGCAAAACTCTCCTGGGAGTTCAGAAAACGTGGAAGGAAGGAGCCG
GGGCCACGAGGGGCATGTCAGGCGGGTTCCAGGCGGCTGGGAGGCTCCTCACGATGCACCACCCT
TCACCGTGCAGGGAACCCCGGCCGCCGCCATGCCTGCCGCCCTCGGTTGTGCCCAGACGCTCTGCA
GGGTAGGCGGGCAGTGCCAGCACCCTCCTCGGGTGAGGCCTTGGTCTTTTGTCCCTGCCGTGCCCA
GGCATAGCCCATACTCAGTGCTGGAGGGTGCTCGTCTTACCAAGAATTTTGTGAAGGTGGTATCTG
TTGCTGCTCAGAACTTCCGAGTGTCCCCACGTGGGGTCCCTGAAGTGTCCTGGGTTCCTGTTTCCAG
GCATCTGGGTCACAGGCCCCAGTTCCACCCCCTGAAGCACGGATTTGATGAGTGGTTTGGATCCCC
CAACTGCCACTTTGGACCTTATGACAACAAGGCCAGGCCCAACATCCCTGTGTACAGGGACTGGG
AGATGGTTGGCAGGTAATGGAGCCCCACCCCTTCCCCTCCCACGTCCTGAACTGCTGTGCCCGGCG
TGCCTGCCCCCCGCCTCTAGCACTGGTGGGCTCAAGTCGCCACTCATGAGGGCTGGTCTGTCCCTG
GGTCCCCGGGCACCGAGGGCTTTGGTTTGGTGGCTTCTGTCCCACCAAGTTTTGCCCCAGAGCCTA
TGAGACTCCTGCCTGGGGTTTCCCACCTTTTCAGGGTCGTAGATCCCTGTAGCTGTCCTGAGAGAG
GAAGGCCCCAGCAGAGCGAGCCCACACGGTCTGCCCTAGCTGTCAGGGTACTGCCCATGTGGTC
TACGGGTGGGGAGGCCGGCTGTGCTCCAGACATCCAGGGACATGGGCAGGACAGGAGGTGGGAT
GAAACCCCCACTGGGAGCCACACCAGGAGCAAAAGCCGCTGTCCAGACAGAGCCGTCCTGGTGCC
CGGGCGTGGGGGCAGCACCTCTTGACACGGCAGTGCCGGGTCCGGGACCCTCATCTTTTGTGAATT
TTATTTTGCTTAACTTGACTCTTCTTGGCGGAAGTGCTCATTCATTACATGACGGTGACCAGAAGCA
GCACCAGCTTGCTGCCTCTTTCTAGATAGAGCCCCGTGGAGGTGTGGGAGTCGCACCACGCAGCCC
CCATTTGAAGTGTGCAGTTCTGTGGTTGGCATTAGTCACAGGCTGGGACAACCAGCACTGTAGCTG
CTTCAGAACGAGCCCCATGGCCTGAGCGGCGGCTCCCCAGCCCCAGCCGAGTGACCACAGCCGCC
TCACTGCCTTCACCTTGGTGTCGTGCCCTCAGCCCCATTCCCCCATCTTCCCATGTGGCAGGTTATT
GCAGCACCGGCCTCAGCCAGGTCATCAGATGCAAGACCGTGCCCTGGGGAGCGAGGGATGCGTC
CAGCTTGGTTGTTCCCTGAGTGGACATTTCATTTCCAGGCTTCCTTTTTTTTTTTTTTTCTTGAGACAG
GATCTTGCTCTGTCACCCAGGGTGGATTGCAGTGGCGCGATCTCGGCTCACTGCAACCTCCGCCTC
CTGGGTTCAAGCAATTCTCCTGCCTCAGCCTCTCAAGTAGCTGGGATTACAGGCGTGCGCCACCAC
GCCCAGCTAATTTTTGTATTTTTAGTAGAGACAGAGTTTCACCATGTTGCCCAGGCTGGTCTCAAAT
TCCTGACCTCATGATCCACCTTCCTCAGCCTCCCAAAATGCTGGGATTACAGGCATGAGCCATGAC
GCCCAGCCCTAGCCTTCTTTTAAATGAAGCCCATGGCTTTGCTGGTGAAATCAGGGAGAACGGGAC
TTTCTTGGCCTAAATTCTGAAGTCTGTCTGGATCTGTGTTCTTTTCAGATATTATGAAGAATTTCCT
ATTAATCTGAAGACGGGGGAAGCCAACCTCACCCAGATCTACCTGCAGGTGATGGGGACCGCACC
ATCCTCGCCCTGTGGGACGCATGGGGACGGGGACCGCACCAACCTCATCCTGTGGGAGGCGTGGG
GACAGGAATGCATCAACCTCACCCCGTGGGAGGCATGGGTTCAGGGACCTCATCACCCTCGCCCC
GTGGGACGCGTGGGGACGGGGACCGCACCATCCTCGCCCCGTGGGACGCGTGGGGACGGGGACC
GCACCAACCTTGCCCCGTGGGACGCGTGGGGACGGGGACCGCACCAACCTCGCCCCGTGGGACGT
GTGGGGACGGGGACCGTGGGAGGCATGAGGAGGTCGGCCTGAGGCTGGAGGACGACGGTGTGGC
TCTCTCCATAGGAAGCCCTGGACTTCATTAAGAGACAGGCACGGCACCACCCCTTTTTCCTCTACT
GGGCTGTCGACGCCACGCACGCACCCGTCTATGCCTCCAAACCCTTCTTGGGCACCAGTCAGCGAG
GGCGGTGAGTCCTGGCTCCATGGAGCATAGACCTCGCTGGAGGCCCCAGCTGTGCTTGACTCCAGA
GATGGGACACTCAGTACCGTGGCATTTAGGCCAATTATGGAAAGGCCAGAGCAACCCCACCCCTT
TGAAGCCGTCCACTGGCCTGGGATCAGCAGAGGAGGGCTGTGGTGGGGGTGCTGGCTCTGTCCTTC
ATAAGCCACATGAACTTGAACTGAGGCCATTCCTCTTCTGGGAAGAGGCCGGCCAGTTTCACTGTG
GTCTGTGAAGTTATGATTTAATGAACTCCGTGAATCACAGTATGCCGTTGGCTGCCTGATCATTTG
TCACCATCCTCCAGGTATGGAGATGCCTTTTGTCACCATCCTGCAGGTATGGAGACGCCGTCCGGG
AGATTGATGACAGCATTGGGAAGATACTGGAGCTCCTCCAAGACCTGCACGTCGCGGACAACACC
TTCGTCTTCTTCACGTCGGACAACGGCGCTGCCCTCATTTCCGCCCCCGAACAAGGTGAGTGCTCG
CTGTCACTTCTCACGGTTTCCCCACAGCCAGCGTGTCAGCGAAGAGTGCCTGGACCGGCTGTGCCC
ACGGGGTCTGTGGTGGGCAGAGCATGAAGGGTCCCTCTGGGTCCAGCGGGAGGAGCAGATGTCAC
CGAGCCTCGAGCAAGGCCCTTCTGGCCCAGGACTAACCTGGAAGCAGGAGTGACCTTGAACTTGG
GGGTGGGGAGGAGGTGACACAGGGGAGAGGGTTTGTCTTGGAAGAGGCTGACGCCTCCCGAAGG
GTGACCCCGGAGGCCGGAGGCTTTGGAGGCCGCATGGAAACAGCAGGGCCGGTGGAGCAGGGTG
TCCCTGCTGAGGTGGGGGCCGGCACCCCAGACCCCGAGCAGCCCTGTGAGTGTGGCCTGGACCTG
GTCACCCAGGGGCCGGGCTGCCTCCATGAAGATGGACTCCTGCCCCCACCCACAGCCCTGTCAAGTG
GTTCCTGGGATGGAGCTTCAGCCTTTCCCCCGCTCGGCACTGATGAATGCCTGACCCATCCCCAGC
GCCAACAAACCTGAACCCGCCTCTTCCCAGACCACGCGGGGGGGGCCCTGCAGCCTCTTCCCAG
ACCACACGGGGGGGCCCTACAGCCTCTTCCCAGACCACGCTGAGGGGGCCCTGCAGCCTCTTC
CCAGACCACGCGGTGGGAGAGCCCTACAGCCTCTTCCCAGACCACGCTGAGGGGGCCCTGCAG
CCTCTTCCCAGACCACACGGGGGGGCCCTACAGCCTCTTCCCAGACCACGCTGAGGGGGCCCT
GCAGCCTCTTCCCAGACCACGCGGGGGGCCCTGCAGCCTCTTCCCAGACCACGCGGGGGGGC
CCTGCAGCCTCTTCCCAGACCACGTGGTGGGAGAGCCCTACAGCCTCGTCCCAGACCATGTCGGG
GGGCGCCTACAGCCCAGTGTGCTGCGGGGATTGGGGGCTTCAGAGTTTCAAGTGATAGAAACCAG
CACAGCTGAAAGCCAAAACAGAAGCATAGGCTCCCTCGCGCCACGTCCCACCAGATAGCTCCCCT
GGGTGAGCCTGGCTCTCGTGCAGGCCCTCCGGACAGCTCCATCTCCCGCCCACTGGAGTCAGACCC
ACGAGTCGAGGCCCCCAACAGACCCATGTGTGGAGGGCTACAGGCAGCTCCCAGGAGGCAGGGTG
CTGGGTGGGGGAGGGTGGTGTTGGCCGTCATTCCCCATGGGGAGCCCGGGGGGGCCCACCTCGA
CGCCAGCACCCACAACCACCAGCCAGCAGGGGCAAGGGTCCCAGCCTGAGTCTTCATTTCTA
AATGATGGAATGTTTCATACCAACAAATGGCATGTTTCATACCAACAAATGGTATATGTACCTATT
TGTAACAAGATGAGAACCCACACACCCAGCACCCAGCACAAGACTAGAAACAGAACATCCCAGA
GAAAGAAAGCAGGGGAGGGGCTGGGCGTGGTGGCTCACACCTGTAATCCCAGCACTTTGGGAGG
CTGAGGCGGGTGGATCACGAGGTCAGGAGGTCGAGACCATCCTGGCTAACACGGTGAAACCCCAT
CTCTACTGAAAAACAAAAAATTAGCCAGGCGTGGTGGCGGGCACCTGTAGTCCAGCTGCTGGGC
AGGCTAAGTCAAGAGAATGACTTGAACCCGGGAGGCGGAGCTTGCAGTGAGCCGAGATCGCACCA
CTGCACTCCAGCCTGGGCGACAGAGCGAGACTCCATGTCAAAAAAAAAAAAAAAGGGGATGGGA
GAGAGAGGAAAGAAAGGGAGGGAGGGAAGGAGAAGAAGCACAGCATGGCCTCCTGTGAGCCT
GAGTGTCCCCTAGAAGTGGCCAGTGTCCCCAGCTCAGTGTCCATTGTCCCTTCACAGGTTCTGTGG
CTCTGCTGCTGTGAGCAGGGCCCTCCCTGAGACAGGCCGGGTTGCGGGTGTTGGCGTGTTTGCCCG
TGAGGGGCTCTGAGCAGAGCTGCCTGCGAGGTTCCGTTCAGAGGCTTCCCCACGCTGCCGCTCGGG
```

| Sequence Information |
|---|
| GTTGGATGGCAGCGCAGGAAGGAGCTGCGGTGACTTTGCCTCCCCTGGATGGTTCACTTTTTCACT |
| GCCGGAAAAATATTTTCTTTTTTTTTTTTTTTTTTTGAGAAGGAGTCTCGCTCTGTTGCCCAGG |
| CTGGAGTGCAGTGGCGCGATCTCAGCTCACTGTAGCCTTGACCTCCTGGGCTCCAGCAATCCTCCC |
| ACCTCAGCCTCCTGAGTAGCTGGGACTACAGGACGTGCCGCCACACCCAGCTAATTTTTGTATTTT |
| TGTAGAGATGGGGTTTAGCCGTGGTCTCTCTTTGGTAGAAACCAGTCTAGGCTAGTCTTGAACTCC |
| CGAGTTCAAGCAGTCCCCCTGCTTCGGCCTCCCAAGGTACTGGGATGACAGGTATGAGCCACCGCA |
| GCCGGCCCCTTCGTTTCCTTTTTCCCTTTTATTCAGGGGACCCGAAGCTGAGAGAGCCTCAAGTGGC |
| TCAGGCTACAGCAGCAGGGGTGGCTTTTGTCCCTGACGTGGGCCCCCACCCCCTTCTTCCATGTCT |
| GGGAGTGAGCCAGGGATGGTGTAGTCACCTGAGATGGCCTTTGCCCCGTGACCACTTCCCACAAGT |
| GATGGTTCAGAAACCAAAATCCGGTCTTGGGGGCTTGTCAGAAACACAGATTCCTACGCCCCACC |
| GTGACTGACTGAGTCAGAACCATGGGGAGGCCAGAAGTTGGCTGCATTTTAAGTACCCCAAACAC |
| CGGGAGGCTTGTGAACATTCACGTTCGGGAAGCACCAGTCGGCAGCTGCGCACGTGGCACCCAGG |
| GCCTCTGCTGCGGGAGTGTACCTCTCTGAGTCTTGCTGACACCGTATGGTTGTGTTTCCATTTCCTC |
| AGTGGGCATGATGTCCCCACTTTCTCCAGGAGACTTTGCAGCCGCGGCATCTCAGATGAGCCCCTG |
| GAGAGCCACCCCGAGGCTCGGATCATGCACTCCAGCCAGAGTGCCTTGGCCGGGCCCTTTGTCCCT |
| ATGACCAGTCTCAGTGACTCAGTGGGGAGGGAGGGGGAGGGCTTGGGGACATCTGGTCCCAGTGG |
| CCTGACAAGGGCCCCTCTCTCCCAGGTGGCAGCAACGGCCCCTTTCTGTGTGGGAAGCAGACCACG |
| TTTGAAGGAGGGATGAGGGAGCCTGCCCTCGCATGGTGGCCAGGGCACGTCACTGCAGGCCAGGT |
| GAGTCAGCGTCCACCGGTCTGCCGGGCAGCAGGTCCAGGCCTGCAGCCATCCCAGGGTGTGTGCG |
| CCCCTCACTGGCCACCTCCCCCATGCACCCCGTGCTCATCCTCACCGCTCTCCTCCCCACGCACCCT |
| GTGCTCAGCCTCCACGCACCCCATGCTCAGCCTCACCACCCTCCTCCCCACGCTCCCCGTGCTCGGC |
| CTCACCGCTCTCCTCCCCACGCACCCCGTGCTCGGCCTCACCGCTCTCCTCCCCACGCACCCCGTGC |
| TCGGCCTCACCGCTCTCCTCCCCACGCACCCCGTGCTCGGCCTCACCGCTCTCCTCCCCACGCACCC |
| CGTGCTCGGCCTCACCGCTCTCCTCCCCACGCTCCCGTGCTCGGCCTCACCGCTCTCCTCCCCACG |
| CACCCCGTGCTCGGCCTCACCGCTCTCCTCCCCACGCACCCCGTGCTCGGCCTCACCGCTCTCCTCC |
| CCACGCACCCCGTGCTCGGCCTCACCGCTCTCCTCCCCACGCACCCCGTGCTCGGCCTCACCGCTCT |
| CCTCCCCACGCACCCCGTGCTCGGCCTCACCGCTCTCCTCCCCACGCACCCCGTGCTCGGCCTCACC |
| GCTCTCCTCCCCACGCACCCCGTGCTCGGCCTCACCGCTCTCCTCCCCACGCTCCCGTGCTCGGCC |
| TCACCGCTCTCCTCCCCACGCACCCCGTGCTCGGCCTCACCGCTCTCCTCCCCACGCACCCCGTGCT |
| CGGCCTCACCGCTCTCCTCCCCACGCACCCCGTGCTCGGCCTCACCGCTCTCCTCGGAACCAGGTC |
| CCTCTCGGTGGCTCTCGGTGTGTAGGGCTTGCTGTGCTTGGTCAGACAGGCAGGAAGGCTCTCGGT |
| GGGGACTGGAGCCACGTATACTGCCGTGTGTCACGTGGGTGCTGGTAATGACTGTGTGGTGAGGA |
| GACATCCGTGGTCCAGTCACCGCAGCAGTCCTGAGTTAAATGGAGCTAAACAGGTTTCTTCCCTGC |
| AGGACTTATCAGTGCCTTTAGCATGCTGGTGGGCACCATGAGCTTCTAGAAGGGGCTTAGAGCAG |
| GCTGAGTGTTTAAAAACCTGTCTGTCTACTACAGAATCGGTCGTTTTTCCCCAAAGCACATCTTC |
| TCAGGCCAGTGTCCTAAGGACACTCAGAGAACAGCAGCAGCCCGACAGGAAGACCGTTGGTGTCTG |
| TCTGCCGCATGGGGTGCGGACCTCGGTGGTGGCCTGGGTCCTGGCTGGGCGAGGGTGCGCCCTGCC |
| ATCTCAGTGTGACCACCTTCATGCTGTCACTGCATCTCCTCTGGCCCAGGAAGCTGCCCCTCGGTTG |
| AGAATCACACCGTGTGGTCTTCTGTAACAGGCACTTGAGCCAGACATACCCATCAACACGCGGGG |
| CTGAGTCTGGTGTTTGTAAACGACCGCTGTTTCTTCACTGTTTCTTAGTCTTTTGCCCTCCCAATGGC |
| CTCCAGAGGCAGCCATCCCCTTCAAGTGGCCCCCACGAGGATGGGGGGGGCTCCCAGTGGCAGCTG |
| GAACATCACACATGACGACAGCCAGAGTCAACATGGGGCTCATGGGGCTGAGTGAAGACGTGCGT |
| GGGGCCAGCTCCTTCTGGAGGCTCCAGGAGATGTTCTGTTCCCTGCCTTTTCCCAATCCTAGTAGCT |
| GCCCCATTCCTGAGCTCCTGGCCCCTCCACCGTCAAAGCCAGCAGCACGCAGGCATCTGTCCCTGG |
| CCTTCCTGTTCCACGTTTTTTTTTTTTTTTTTTTTTTTGAGATGAAGTCTCACTCTGTTGCCCAGG |
| CTGGAGTGCAGTAGTGCAATCTCGGCTCACTGCAACTTCTACCTCCCAGATTCAAGCGATTCTCCT |
| GCCTCAGCCTCCCGAGTAGCTGGGACTACAGGCATGCTTACCATGCCCGGCTAATTTTTGTATTTT |
| TAGTAGAGACGGAGTTTCACTATGTTGGCCAGTATGGTCTCAATCTCCTGACCTCGTGATCTGCCC |
| GCCTCGGCCTCCGAAAGTGTTGGGATTACAGGCGTGAGCCACCGCGCCCGGCCCTGTTCCACTTT |
| TGAGGACCCTGTGGCTGTGTCCCACCCCACCCCCTGCTCACCCAGGCTGGCCTCCTGTTTCGAGC |
| CTCGCTGATGAGCGGCCTGCGTTGTGTCTGCCGCCTCAATTGCCTGGCCTGGTCGCGCGCCTGAAG |
| GCCCAGGGATTGGCTGCTGTTCTGCCAGATCCTCCTCTTCCCCACTCATTCTACACATCAGGAAACT |
| GAGGCCAGAGAGGAAGTCGTCTGTCAGGGTCCCCCAATTACTAGGGAGCAGAGGTGGGAGCAGG |
| CGCCTGGCTGTGGATCCTGCACTCCTGCCCACCATGCCTGGGCAGTCCCCTGTGTCCCCAGCAGCC |
| AGTGGGACTGGGGGCGGCAACTGCCAAGGGCGCCTGTTCTCTACAGCTGTCTGGGCCTCCCTCAGA |
| CCCTGCCCAGGGCAGCCTTTGTCTGACATGGGACTCCTGGGCCACCCCAAGTTCCCAGGACCCTGA |
| AGGTGGAAGAGACCCCACGGTTCACTGAAAAGGCAGCTGCGGCTCCGTGTGAAGGGCAGAGTGGC |
| TGTGAGAGTGACCGCCTTGTTGTGCAGGAGAAGCATGGGTGGTGGGCACGGCCTCCTTTGTGGTGT |
| GGGGTGCCCTAGGACAGAATGCAGCTGTGCCGCCCCTCCACTCCCTGAGCGCCATCCCCTGA |
| GGGTAGGGATGGGCCATTTGGTTTCTTGTGTGGGGGCACCTGCAGGGAGTGGCCGGTGGTCACTCA |
| GTGAACACTGTGACGTTGGCATGAGACTCAGGAACTGTGTAGCTCTGGGAGACTGTTGGCATGGA |
| CTCGGGACCCGCGTAGCTCTGGGAGACGTTGGCATGAGACTCAGGACCGTGTAGCTCTGGGAGA |
| CGTTGGCATGAGACTCGGGACCCGTGTAGCTCTGGGAGACGTTGGCGTGAGACTCGGGACCCGCG |
| TAGGTCTGGGAGACGATGGCGTGAGACCCGGGACCCGCGTAGGTCTGGGAGACGATGGCATGAGA |
| CTCGGGACCTGCGTAGGTCTGGGAGATGTGAGGTTCCCCACTGCAGTGGGTGCCCACCAGGCCGG |
| GACAGGGCTGGGGCTCTGCTCCCCAGGCTGGGAGCCACCCGTGCTGTCTCAGCAGCAGCCTGG |
| AAAAGGTGAGGGGAGCCACCCCAGCGCCGCCCGGCTCCATGCGTAGTGGGTTCAGGGACGTCTGT |
| ACCCCACAGACCTCCCCACCCACCTGCCCACGGAAAGGCTCCAGCTGAGAAAAATGCCAATTTCA |
| GCGTTTTGGAACCTTGCCATCTGCCTCGCTCCCTGAAGAAGGGAAACCCTCTCCCCACCTGAGGAA |
| GGGAAACCCTCTTCCCAGAGCCACCAAGTTGCCTTTTCCCGTGGGCCACAAAGTGAAATTGAATTC |
| GATGGCATCAGGCCTGTGCACCAGGACACCACGACGGGGTTTCAGTGAAAGCGCCTGACGTCTGT |
| CCCGACAGTTCCCTCTGGGCAGGGGAGGCTTTAGTCCTGCAGCCCTGGATTCTGAGTGAAGTCTC |
| GAAAGCGCTGATAACGGTTTCAGTGACTTCTCCCACAGCCGCAGCTGCCCACTGCATTTCTGGATG |
| TTTCTGAAGGCATCGCTGCCTGGAGAGTTCTTCGAAAACGCTCCACGAGGACCCTGCCTGTGCTG |
| ACACCACTCCCGCCCGCCCGCCCTGCCGGCACCACAAGCACTGCTCCGCAGTTATTTTTCAGATG |
| ACAAAAGCATCTGGATTTCTTTCCTTTATTATTCTGTCCTTTAAAGGACACGGGAAGGACGGGAAG |
| CAGTCGCACAGACACTGCTGACCAGACCTGGGGAAGCTTCTCACCTTCTGCAAAGCTTCCTGAACT |

-continued

| Sequence Information |
|---|
| TTCCTGGCAAACGCTGAGCTTTGCATTCCCTGCCCCACACTGGGCGCTGCAGACCCCACATCCCGT |
| GAGCGGCTGCAGCGCGGAGTGAGTGTCCCTGTGAGGCCAGGGCTCCTCTGTTGGAGAAGCTGGCG |
| ATCGCCGTCTGCCCTAGCGAGGAGCTGGCTGCAGGCGGCAGGGGTGCCCCTGGACCGTGGGGAGG |
| GCTGTCGACACTGGGTGGGAGCTCCAGGGCCTGGCAGCGGATGGCGGTCCCTGCCCAGCTGCCCC |
| AGGGGCTGAGCTTGCCAGGCAGGGGTGTCTCTCCAGCCCCACCCCAGTCTCCCCGTCGAGTGACCC |
| AAGCCTGGAGCCCCCGAGTTAAGAAAGAGACAGGGCCGCCGGGCTCATGCCTGTAATCCCAGCAC |
| TTTGGGAGGCTGAGGCGGGCAGATCACCTGAGGTTGGGAGTTCGAGACCAGCCTGACCAACATGG |
| AGAAACCCCGTCTCTACTAAAAGTACAAAATTAGCCGGGCGTAGTGACACATACCTGTAATCCCA |
| GCTTCTCGGGAGACTGAGTCAGGAGAATCACTTGAACCTGGAAGGCAGAGGTTGTGGTGAGCTGA |
| GATCGCACCACTGCACTCCAGCCTGGGTGACAAGAACAAAACTCCATCTCAAAAAACAAAAACAA |
| AAAACAAGAAGCAGACAGGGCCACTGAGGGAAGCCAGATGGCACGCTCTGCTCATGGCTGGTCA |
| GCAGTGCCCACGCCCTCCGGAGGTCAAGGCACGGCGGGAAAGACAGCCTCCTGCCTGTCCTGGAG |
| CTCTCTGGGTGTGTCAGGAGCCGTCCCCACCCCAGCCACTGGAGCTGCTCCTGTCCAGCCTCAGC |
| TGCCCCTCCACATCTGGTTTTTCTCCACCTGCTCCTCTGACTTAAGGGGCAGGGCTCACAGTGGCCT |
| TAGGGCATTCAGTGTTAGAGCGAGGCTGATCCTCTCCGGACAGGTGGGCTGGAGGGGCATCTCC |
| CTGGGAGGGCTGTGATTCTCCTTTCATCTGATCCACAGAGGCAGAGAAGGGTGCCAGGGAGTGAG |
| GGCGTGGCCTGGCTCTGGGGTCTTTGGGCCTGGTTTGAGGCTCCTCTGTCTCTCACAGGCCTTGTGA |
| CCCCGCTCAGTCCCTGCTGTGGGCGTGTGAGCATGTATGCATATCTGTAGACCCAGCTGGGCAGCG |
| GGGCTCACGCCCCCCAGGGATTGGCCCCCAGCCCCATCGGGTCGGTGCAGAGTGCCCTGACCGT |
| GTTGCTGCCATGTGTTTCAGGTGAGCCACCAGCTGGGCAGCATCATGGACCTCTTTCACCACCAGCC |
| TGGCCCTTGCGGGCCTGACGCCGCCCAGCGACAGGGCCATTGATGGCCTCAACCTCCTCCCCACCC |
| TCCTGCAGGGCCGGCTGATGGACAGGTTGGTGCTAGACCTGCCCCGGCCCCTTCCCCGATCCAAG |
| TAGTGAAGCCCAGAGCTGCTAATCAGGTGCAACCCCAGGCCCAGCAGCCCTCCTGGTTCTGGAC |
| ACAGGCGTGCTCGTGCCCAGGGCAGGAGGAGGCAGGGGTGCCTGAGACGAGAGGACCTGGGGAC |
| CTGCCTGTGGGGCAGGGGCCATCCTGGGAGGGTCCAAGCACAGCGAGGCCCTGGCTTTCAAGAAA |
| GCCTTAGGAGGGAGGGCAAGGCCAGGAGAGGGGCCTCATCCCTGCCTGTACCCGGGCACATGCCG |
| CCCCTGCCCGCCCCACCCCTGTTCCCTGCCTGTACCCAGACACACGCCACCCCTGTCCGCCGCACC |
| CCTGTTCCCTGCCTGTACCCAGACACACGCCGCCCCTGTCCGCCCACCCCTGTTCCCTGCCTGCAG |
| CCCGGGCACATGCCACCCCTGCCTGCCCCACCCCTGTTGCCTGCCTGTACCTGGGCACACGCCGCC |
| CCTGCCCGCCCCACCCCTGTTCCCTGTCTGTAGCCCGGGCACACGCTGCCCCTGTCGCCCCACCCC |
| TGTTCCCTGCCCAGCCTGGTTTTTGGTGCCTCATGGCTTCCTGTAGCTTCCTTCTTCCTTCCATCCAA |
| GTCGCTGCTCTGCCAAGTCATGGCCCAGCTCTTACCTTCGTCCAAATCCTTAGTGTCCAAAGTCC |
| ATTTCCTACCCCCTGAGAGCAGCCACCATTCCACTCAAACCACGTTTCCTGGGTGGTCCTGAAGGG |
| ATGAGGATTCCAAAGGCTCAACGGGAAGCAAGGTGGGGACGGCCCAAGGCAGCTGCCGCCTCCG |
| GCTATCTGGGGCCGGGTAGAGGGAGTTTTGCTCACTTGTCCCCTCTCGAGACCTGGCACAAGTGGT |
| TGGTCACTGTGGGGAGAGACGGTGCCCAGCTGCGTCCCCACTCCCCGTTCCTGACTCGCAGGCCC |
| AACATGGTCAGGAGACCCCGTGCCGCCTGCTTATCCTCTTGTCTGCCCACCCTCCCCAGGGTCTGG |
| CCCAGCCTTGCCAAGGACCAGCAATGAGGGGACGCCCAGGCACCCTAGCCCCGGCCGCCCAGGCA |
| CCCCAGACACCCAGGCACCCCAGCCCCAGCTGCCCAGGAATCCCAGTCCCGGACACCCAGGCACC |
| CCAGCCCCGGCTGCCCAGAAACCCCAGCCCCAGACATCCAGGCACCCCAGCCCCGGCCGCCCAGA |
| CACCCAGGTACCCCAGCCCTGGCCGCCCAGGCACTCCAGCCCTAGACACCCAGGCACCCCAGACA |
| CCCAGTCACCCCAGCCCCGGCCACCCAGACACCCAGCCACCCCAGCCCCGGTTGCCCAGACACCC |
| CAGCCCCAGACACCCAGGCACCCCAGATACCCAGTCGCCCCGGCCACCCAGGCACCCCAGCCCCG |
| GCTGCCCAAACACCCAGGCACCCCAGCCCTGGCCACCCAGACACCCCAGCCCCAGACACCCAGGC |
| GCCCCAGACACCCAGGCACCCCTAGACACCCAGTCACCCCAGCCCGCCCAAACACCCAGTC |
| ACCCCAGCCCCGGCCGCCCAGACACCCCAGCCCCAGACACCCAGGCGCCCCAGATACCCAGTCAC |
| CCCAGCCCTGGCCACCCAGGAGCTCCAGCCCCGGCCGCCCAGGCACCCCAGCCCCAGCCACCTTG |
| CGGGCCTTTTTACTTTTCAATCATCTTTGTAAAGTATCAACCAAGACCTCACGTGGAGGCATGAGC |
| CACTGATGACAGACGCAGCCCAGAGCCTCCAGGTGGCCCCAGGCTGTCCTTCCTGTCATTACATGG |
| TCCTCCCCTCCCATCCCACAGGCCTATCTTCTATTACCGTGGCGACACGCTGATGGCGGCCACCCTC |
| GGGCAGCACAAGGCTCACTTCTGGACCTGGACCAACTCCTGGGAGAACTTCAGACAGGTACAGGG |
| CTCGGGACGTGGGCGCAGGCGGAGCTGCCCCATCTCTATCCAGACGTGGCCCCTGAGCACCGTCC |
| TGGGGGAGGCACAGGAGGGTGAGACAGGCAGGAACTCCACCCCCTCCACAGCCTTCTCTGTGTGG |
| CCCCCAGTCGTTCAGCGTGGCCTAGGGCATGGCAGCTGACAGGCTGGAGAGGAGGGAGGGACCTC |
| TTCCTGCCCCGCGTGATGACAGTAGCCCCGCGGCATAGCTACAGGCGTGGCCTAGACCCTGGTCAG |
| GTGGCCCCCATGGGCCTCTCCATCCTGCCAGGGCATCTGAGCCTCCCCCACACCCCAGGCTGGAGG |
| CGACAGAGACGTGGCCTGCTTGGCCCAGGTGCTACATGGGGGCCGCAGCATTGGCATCACCACAG |
| CAACCCCCAGTGTGGGAGGGTGAAACGCCACACGCACAGGGCCTGGGGCTCCTGCCGCCCCAGGC |
| TACCCCAGCATTGTCAGCGCCAGGCTTTCTCCCACGAGCCCTCGCCTCAAGCCTCCTGCTCCTCCC |
| CACGGTCTTTTCTGGCCCCTGCTGACCCCTACGCTCCAGCATCCCCAGCCCCTCCTGAGAGGTCTC |
| TCTCAGCCCCACCCACTCCCAGCATCAAAGTCTTGAGATATGAACCCCTGCTAATCTGCCTTAATT |
| GGGAAGAAAATCATTTAGTGTAATGGAGAGTCTAAAGACTGGAAGTGAGAACTGGGGCTGAGGG |
| CTGAGCACCCAGGCTGAGGAGGAAGCTGCTCGTGGGCAGTGTCTGGAGGGCAATGATGCCCAG |
| GAGTGTTTGCTCCTCCCCACCCTGTGCAGGCCCCGCACCCGCTCTTCTTTCGGGTTTTACCCAGC |
| ACTGTCACCTGCAAGGGCCATCCTGGGCATCGGTCCCCGGCATTGCCGCCTGTGAGGGCCGTCCTG |
| GGCATCGGTCCCCGGCATTGCCGCCTGCGAGGGCCGTCCTGGGCATCGGTCCCCGGCATTGCCGCC |
| CTGCGAGGGCCGTCCTGGGCATCGTTCCCCGGGCATTGCCGCCTGCGAGGGCCGTCCTGGGCATCG |
| GTCCCCGGCATTGCCGCCTGCGAGGGCCGTCCTGGGCATCGGTCCCCGGCATTGCCGCCTGCGAGG |
| GCCGTCCTGGGCATCGGTCCCCGGCATTGCCGCCTGCGAGGGCCGTCCTGGGCATCGGTCCCCGGC |
| ATTGCCGCCTGCGAGGGCCGTCCTGGGCATCGGTCCCCGGCATTGCCGCCTGCGAGGGCCGTCCTG |
| GGCATCGGTCCCCGGCATTGCCGCCTGCGAGGGCCGTCCTGGGCACAGTCCTCGGACGAGCCCCTT |
| GGCCTGCAGCACCCGCTCTGGGAATGTTAGAGGCATACCTCGCCTTTCCCGAATCAGGAGGCCCAG |
| GGGCAGCAGAAAGAGAATTGTGGTTACTGTAAAATCCTTGCCCTTCTTGAGTGTGTGAATCTGTGT |
| CAGCTCCCTGGGTCTGTTTTTGTTTTCTGTGTTTTCTTGCCTTTCACATGTTGGTCCTGCTCCTCCC |
| TGTCTTAGGGTTTCTGTAGGGATTCTGAGCGTTGTGGCTCTCCCTTCTCCCAGGGCAGGGCCTCCCT |
| TCCCGTCCCTTTCCCTCCCCTCCCTTCCCCAGCAGAGAGTAGGCTGTTAAAAGGGGCTTTCCTCCAT |
| GAAATTAGTGGCAGTCCAGATCTGAGGCTGGCTAAGGTGTTTTAAATACACTCACCTGCCTCGCAA |

Sequence Information

```
AGAAGAGGGGTACATGAAAACAGGGTACGTGAGGCATGCCAGCTACGCATCTCGGGCCCAGAGC
GGGTGGCTTCACCTCCTCCACAGGATGCTTATGGGCCCGCTAGTCCTTCAGCGTTTAGCCAGCGCC
CTGCACCATGCTGAGTACCAGGGACGCTGCTAGGCACAGGCAGACGAGACCCCCCACGGCCCCC
AGTTAGGGGCTCCAGGACACAGGCAGACAAGGCCCCTCACGGCCGCAGTCAGGGGCTCCAGGACA
CGGGCAGACGAGGCCCCTCACGGCCGCAGGTCAGGGGCTCCAGGACACACCTTCCCTCTTCTCATT
GCAGGGCATTGATTTCTGCCCTGGGCAGAACGTTTCAGGGGTCACAACTCACAATCTGGAAGACC
ACACGAAGCTGCCCCTGATCTTCCACCTGGGACGGGACCCAGGGGAGAGGTTCCCCCTCAGGTGA
GTCGGTGCAGGGCCTCCTGGCTGCTGAGGCAGTGCCAGCCGGACTCCCCCAAATGCAGGCTCCAC
AGGGACAGAGCCCTCTGCACCCTGCCCGCCGCCTCCCCTTGCCTGCATCTGCTGTTGCTATTCATAC
CCACACGTGCTTGGTGGCCTGCCCTCCTCCCAGGGTGCCTGCTGCTGCCCACCCTGGTGGTCTCCCC
ACTTCTGCCCCTTCTGGGCCACCATCCACCTGGCCCCCAGTGATGTATCCCCTACTCTGAGCTGCAT
TTGGGGATGGCTGAGGCCAGAGGGGAGGGGTCCAGGCCCTGGGGCAAGTAGGAGGTACAAGGAC
ACAGGTCAGCTAGCAGGAGGAATGGCAGAAAGCCACCAGCCCCAGCTCCACCCTCTGCTCTCTGG
GCCTTGTCCTCACCCCACCGAGGATGCCGGAGTCTGCGCCATCACCTGCCAGTTTTCAGGGAAGCC
CTCCCCTTACCCTCAGGAGTCTTGAGGGTCATGGTCGCCAGTACCAGACTCACCTGCTGGCAGCTC
CTTAGGGGCGACACAGAGGCCCCAACACTTGGCTGGAGACCCCGCCCTGGCTTCCTTTTTTTTTGT
CCGAACCCATCTCCCTGGGCTAGGGCTACCTGGAGGCTTCCCCCCCCTCCACCCCAGCAGGATGAGCA
GGTCCCCAATTCCTGCTCCTGGCCTGGGGGTCCTGGGGCACGTGCATGCCTAGTGGTCTCCAGCAT
TCCTGCCCTATCGAGTTGGTCCTGGGAAGACCCAGGAGCATCAGGGGAGTGGCGTGCAGAGGCAG
AACCAGGCCTGAGCACAGCGGTTGCTCCCTGCCCAGGCTTTCTAGCTCCCCGATGGGCCTGGGTT
TGAGTAGGGCCGGTGGGAGGCAGCAGAGAGCAGTACAGGACCGAGGGTGGCAGCACCACCGCCA
AGGTGCCCTGAGGCTCCTGCACCCTCTGGACGGGGCAGCCGCCTTCCCACGGGGCTGAGCCTGCG
GTGAGGCTCCTGGGCTGCAGCCCCTCAGGGATCCCTTGGGCACTTCCTCGGCAGCACCTCTCCTCC
ACCGAGCGTCCAGCTCAGAAGCCCAGGATGGTGACTGCGGGAAGGCAGCATGGAGCCTGGAGTG
GACAGCAGTGTCCCCAGGCCCAGGTCCACCCACACCTCCCAGCTTGGCCTGAAGGGAAGTAGGGC
CTGTGCCTTGTGATTAAGGCACGGGTGGCGCTGGGTCCAAGGCCAAATGCCCTGAGTCCAGAGGG
AGGAGACACAGACATGGTGAAGGCCACGGGACGAGACGGGGACTGGACAGAGCGCCACCAGCCT
CGGCTCACCTGGGGCCACTGGAGCTGGAAGAGGCAGGAAGGAGCCCCAGTTCCTCCAGGGGTGCA
CAGCCCTGAGACCCTTGGTTTCAGCCTCTGGCCTCTGGAAAAGTGAGGGGCATCTGCAGTTTCATT
GTTTTAAGCCCCAGTTCATGGTCATATGTTGTGGGGGTGCCGAGATACAGAGACAGACGCCCCCGG
GGGACTCGTGATCACCCATGGGGGTGAGACCCGTGAAACCATGGGGGGCCTGGAGCTTGGGGCCT
TGTGGAGCTGGAGGGGCTGTCTGGGAGCCCCCTGTGCCCGCAGAAGTCACTGAGGAGCCAACAGC
CCCCCCAGCTGGAAGCGCCGTCCCAGGGGGACCACGGGGAGCAGATTGCAGGCCCCAGTTACACA
GAACAAGCTGCTGGCCACACCGGTGCCCGCCACACCCCCACAGGCTGGTCGCTCCAGGGACCAC
CCGAGGTTAAAGCCTGGATGGCGGTGCCCCTCGCGTCCACTGGGCGTGATTGGCATCCACAGGG
GGGTCCTCAGGGCCACTGCTCCCCGCCTGTTGCGTTTGCTGGAGCCCCTCCAGCCAGGCCAGAGCA
GAGACACAGTCCCACCCACCACAGCCACCCAGCCCCGCCCTCACAGCTGGAGAAGGCAGGGTTAT
TTCAAAGCAAACCCAGGCAGCAGGCAGAGCTTCCCAGAGGGGGTCACAAGGAGGCCCAGCTGTCG
GCCATGCCTTTGAGAACCACTGTCCCTGAGGTCACACACCCATGACACAGCCTGATTCACCGTGGG
CTGCTTCTCAGACACAGACACACATGTCACTTTGCCCAGGAGCCTCTCTAAATTAAAGACGGGTGGC
CGGTCGCCATGGTTCATGCCTGTAATCCCAGCACTTTGGGAGGTCGAGGTGAGTGGATCACCTGAG
GTCAGGAGTTTGAGACCAGCCTGGCCTACATGGTGAAATCCCATCTCTACCAAAATACAAAAAATT
AGCTGGATGTGTTGGTCGGTGCCTGTAATCCCAGCTACTCGAGAAGGTGAGGCGGGAGAATTGCTT
GAACCCAGGAGGCGGAGGTTGCAGTGAGCTGAGATCGCACCACTGCACTCCAGCCTGGGTGACAG
AGCAAGACTCCGTCTAAAGAAAAAAAGACGACGGGGCCAGGCATGGTCACTCACACCTGTGATCC
CAGCACTTTGGGAGGCCGAGGTAGGAGGATCTCTTGAGCCCCAGGAGTTTGAGACCAGCCTGGTC
AACACAGCAAGACCTTACTGGTACAGAAAATAAAAAATTAAGGCCGGGCACAGTGGCTCACACCT
GTAATCCCAGCACTTTGGGAGGCCGAGGCAGGCAGATCATGAGGTCAGGAGTTCGAGACCAGCCT
GACCAACATGGTGAAACCCGTCTCTACTAAAAATATAAAAATTAGCCAGGCGTGGTGGCGGGCG
CCTGTACTCCCAGCTACTCAGGAGGCTGAGGCAGGAGAATCGCTTGAACCAGGGAGGCGGAGGTT
GCAGTGAGCTGAGATCATGCCATTGCACTCCAGCCTAGGTGACAGCGCGAGACTCTCTCTCAAAA
AATAATAATTAAAATTAGCCAGGCACAGTGATCTATGGTCCCAGCTACTCAAGAGACTGAGGCAG
GAAGATCGCTTGAGCCTGGAAGGTCAAGGCTGCAGTGAGCTGCTCTCACCACTCCAGCCTGGGT
AACAGAGCAAGATCCTGTCTCTAAAAAATAAATGAAATAAACAAGATTAAAGCAACAAGCCAGG
CCACGGCCTTCGGGGACGCTCACCGTCAGAAAGTGCACGTGCAGTTCACGCCAGTTCTCAACCAGC
AGTATTTGGCCACAGAATCCTGCAGAAACACAAATGCACCTGAGACCCTCCTGGATTAAAAATGG
ACCCTGTGCTCAGGGGCGCTGTGTGAAGCCCAGGCTGGGACCAGGACAGGCATCTCCGCGGGCAC
CAAGCGGGGAGCCCTGAAGGACCCCAGCTCTCCTGAAGGTCGCCCTCTGATGCAACCCCAGGCCT
GAGGCCTAAGCAGGGAGTGGGTGGATCGAGCAGAAAGAGGCTGGGGCAGGTGGCCGGGGGTGGG
GAGGGGGCGCATCCCCGTCCCTGTTGCATGCAGCTTCCGTGTGAAGCCTCATTTTTAGGGAAGGT
TCTGGAGCAAAAAGCCAGTTCTCACAGACTGCTGAGCGTCCAAGGCAGAAGACTGGGCTTCAGTG
GGTCCGGGCTCACCTCCCAGAAGGTACTGGGCTGGACAGGTGCTGCCATCAGGAGGGGAGCTGA
CTCACCTGGTAACCCCGTCTCTAGCTTTGTAAGGAGCTGCCACACCACCTTCCAGAGTGGCTGCTC
CGGTCCACGTCCCCACCAGCAGCAACGCAGCTCCCAGCCTGGGCATTGAGAAACTCCAGCTTCAG
CCACACTCGCAGAAGTTCCTCCCTGCATCTCCGCTATGGCAGCGATGGCAGGTGTCTTTTTATGTG
GATGTTGTCGATATTAGAAGTGATTGAAAATGGTGAAAAGGCATCATCTGTCAGATGTCCTCAGA
GCACAGCATGACGGCGCCGTGGACCCAAGATTCACAGCATCGCAAACTGCCGCCCTGACATCGCG
AACCGTGGCACCTCGTCGAGCCGTGTAATCGTATCTTCGTGAAGATGAAAGGAATCCAAACACTCC
GCAGCTTGCATTGGAATTTTAGAACTGCAGATGCCGTTCCCCTCCATTTCCTGCTTTTTGGCAATGG
GATGACGTTGCTTTTGTAATGAAAGAAAGGGTGTGTCATATTTGTAAATGTTTACGTAGTAGTGAGT
GCTGGGGAGACCCACAGGCCCCAGCCCACATATCCCGGGTCCTGGTCACAGGCAGGGACAGGATG
GGACGGCTCTACTCACAGCCTCTCTGCAGGGCTTGGCCTGCTGAGCCTTCATTTCCTCTCTTGCCC
GTGAGTCTGAGGGCAGAGGATGGCTCGGGTGCCTGCTGCCTGTCCTAGCGAGGCCCGGGGCCGCT
GCAGGCTTGAGCACATGGTCCCAGTGACTGCTCACTGTGGTTCTCAGCCCGTTAGAGCTCTGCAGC
CTCAGCCTGTCCAGGCCAGCCCCTCTCCGTCCTTCGCTGTCAGCCCCAGCCGTGTGACCAGAGCTC
TCTGTCCCCAGCTTTGCCAGCGCCGAGTACCAGGAGGCCCTCAGCAGGATCACCTCGGTCGTCCAG
CAGCACCAGGAGGCCTTGGTCCCCGCGCAGCCCCAGCTCAACGTGTGCAACTGGGCGGTCATGGT
```

| Sequence Information |
|---|
| AAGTGGCTGGTGTGTGGGCGGCCGTCTCTTTGCCGGGGCTGCAGCCACCCACCCGGGGCCCAGGA |
| TGAACCGTGGCCAGCACAGGGCAGAGGCAGGCGTGCTTCCCCGCCTCCGTCAGTGGTGAGGCCCT |
| CGTGCCTCAGAGCACACGCGGCGGCGTCCGGGATTCGGGAGGCAGGAGCCAAGCGACTCGGGGA |
| CCAGAACAACGCTGCACCAGGGCAGCCGCAGGTCCACAGCCGGCCACCCGGGCCTCTGCCTGGCT |
| GAGCTGAGACTGGGGAGCTCCAAGGCCCCTCTCCTGCCCCCCACAAGTCACTGAGGGACAGCAGG |
| GCGCGTGAGAGGGTCCGGGGTCCCCTGGTCCTCGACTCCCACACGGGCAGCTTCTCCTTGCAGGGG |
| CCCTGTGATGACCTCCAAACTCCCGGGCTCTGAAGGCACCGAGGCAGGAACGGCACTGCCCGGTG |
| GGTCCCGGGTGGGCTGGTGGGCACTGTTGAGTGGCGGCGGCCCCAGGGCCCACCTGCGAGGTTCT |
| CATTTGTGCCTCCTTCATGCTGGGCCAGCCCCAGAGACCTTCGCATCAGACCTGATCTCACTCATA |
| GGCACCCACCCAGAGCAGCACCTCCGTGCAGCCTGACAAGACCAGGCCTTGTTCACCTCCAGTAG |
| AGAAACGGCCTCATCACGCCAGCATCGGCCAGAAACACAAGCACAGACGTGCCTCCAAAGTTTCA |
| CTGAAGTCTGTGTTCAGGCCACAAAGGATGCGTCGTCGTCTTGTCCAGCCCTGGGGGCCGCAGCAG |
| TCAGGGCCTCTCAGGAGCAGCTTTTCTGTCCCCTGCTTGGGGGTCCCATAGGGTGGCATGTGGACG |
| GCCCAGCCATCCCGCGTGTGCAGTGGCCGCAAAGGCCTGTTTCCCAGCACAGCTGATGTGGGTCCC |
| AGCAGGGCAGGTCTTCACAGCTCCTTCAGATGGGACACGTGCGGCCCTCGCTCTAGTCGGCAAAA |
| ACGAGCCACACACAGGTCTGCGGTGTCGCTCCTGGGTGCCCAGAGCCCACCGAGCACAGTGGAGA |
| TGGCCGAGCCCAGCCTCGAGGCCCCTGGGCCGTCGCTCACCTGTTTACACGGGCTGGGCGTGGCTG |
| CCCACAGCCCCTGGATCTGCCGCGCAGGATTCGGGAAGAAGGCCCCTCGGCAGCTGCAGACTTCA |
| GCCTGGGCTCCTGCTGTGCGGGCGAAAAGGCCCAGCTGAAGCCTCTTTCCAGGGCCAGACCCGGC |
| TGCAGCGTGGGAGCCGCTGGGTGCCCGCCGTGCCGTGGGAAGGAAGGTGGTGGCTCTGAACAGCC |
| AGGGAGCCACAGCGTGGGCCGGCGGATGTAACAGGAGAGCACCGGCCATCGGGAGCACCTACCA |
| GCAGTGAGGACCATGGAGGGCAGATGGCCTTGTCCCTGCCCAGGGACAGTCCACCCTGCAGGGTT |
| ATTTAGGACTGGGCAGGGCAGGGCCACCTCCGTTAGTTGGGGGGCGGGGGCGGGGTGCCTGGC |
| AAGTTTCATAGGAAGATATTCAGGGCCCTTCCTTCAAAGGGACCTGGGCAGCTGGCGTCCCCGCCT |
| CTGGACTCAGTGGTGGAGCAGGGAGGTCCCTGTCTCAGGACCCCTGAGTCTCGGGGCCCCAGGAG |
| CCCAGGGCCACCAGCCGTGGAGGAGCCCTGGCCTTCTGCCTTCCACACCCAATCCCACTCCGTGCT |
| GCTGGGTCCTTCTCTACGACCCAGGCTGCAGTGGCTCCACGGGCGCAGGCCACACCTGCCATGGAG |
| ACAGTGGGCACAGGGCAGGGGAGGTGGGCGCACACAGCCTGGCTGCCACTGCCATCTCCTGGGCA |
| CTGGGGGAACTGCCCCCACCGCCACACCTGTGCTCTCTGCAGGGGGAAAAGTGCCAACTCAGACC |
| TGGCGAGCTGAGCCACTGGGTCTGAGGGGCCCAGATGCCACCGTGAGCAGAGCCATGGGGGAG |
| ATGCACAGACACGCGTGTGAAGCCTGGGGGCCCTCCTTACCCCTTCCCTGCCCTCTGTCCCCGCCA |
| ACTCCAGGCCAGCCCCAGGAGAGGGGCTCAGTGGCGTCTCTGGCACAGAGGAGAGGGAGTGTGGC |
| CACCTGGACCCCTGCTTCTGGGACAGCTGAGCGGCCTTTGAGAAATGCAGATCCCCCATCCAGACT |
| CAAACACACCCTGCGGCTGCCTCTGCTGCCCCTGGAGTTTGGGAGCAGCTTCCTCACCCAAACCCA |
| CTCCTGCTCTGGTGGCCAAGGGGGCAGGGACACTCATGCGGCATCCCTGCTGCCGCCTAGGGCTGG |
| AGACTGTCCTTAGTACCCTGAGCAGCACCCAGAATCCAAAGTCTGTCCCCGGAAAGTGCCCTCAGG |
| GCCATGCGGCGTCTGACGTGGCACAGAAGTGGCCTGGATGGGACACAGAACCAAACTGCACTCA |
| TTTCAGCCAAGAAGGCTCCTCTTAGCGGCATAAGTCTCCCTTTTCTGTTGCCAGGAAAAGTGCCCTC |
| CCATCAAGCAAGGCTTCCGCTAAGCAAGGCTGCACTGTGAGGTCCACACACACCCAGGCGATGGA |
| GGGGTGCGGGCTCCGCTCAGCACCGCACTGAACTGAGCCCAGCAGCCGCAGTAGGGACTGGCTTCT |
| CCCTGGGAAAGGCTTCTTGAGAGGCTGAAGCTGCAGGAGAGGGTGATGAGTTGAGAAGCTCAGGG |
| TGGGCCCTCCTGGGAGGACCGCCTGCCCTTTCTAACACTGCTGGCCCTCGGAGGCCCTCAGCCACT |
| TGGCAGCTGCATCCCCCATACCCGGGACCTCCCCACCAAGTTCTCATTTCTCCAATGGCAGCCTTC |
| AGAGCTGAGAGGCCGAGTCAAGAGGGTGCCATCTCCCAAGTTCCCATGATTCCTGGGGAGCGTCT |
| GTGTAGCTGCCCACCTGGACCGAGGTGGTCCCCACACTGAGGCCAATTGGTTGGGGTCCGGGGTTG |
| ACCTGGGCAGGGGACACATCAAAACTGCTCGAGGCCAAGCGCGGTGGCTCACGCCTATAATCCCA |
| GCACTTTGGGAGGCCAAGGCAGGTGGATCACCTGAGGTCAGAAGTTTGAGACCAGCCTGGCCAAC |
| TTGGGGAACCCTTGTCTCTACCAAAAATACAAAAATGGTTGGGCGTGGTGGCTCACACCTGTAATC |
| CCAGCACCTTGGGAGGCCAAGGCAGGTGGATCACGAGGTCAGGAGTTCAAGACCAGCCTGGTCAA |
| GATGGTGAAACTCCGTCTCTACTAAAAATACAAAAATTAGCCAGGCGTGGTGGCGCGTGCCTGTA |
| ATCCCAGCAGCTACTCACTCAGGAGGCTGAGGCAGGAGAATCTCTTGAACCCGGAAGGCAGAGGT |
| TGCAGTGAGCCAAGATCGCGCCACTGAACTCCAGCCTGGGTGACAGAGTGAGACTGTCTCAGAAC |
| AGCAACAACAAAATGCCCGCTGCTGCTGGGTCCAGAAGAGCTTGAATAACTGCATGTTCTTTTTCT |
| CAATTTTCATTTCCCAGAACTGGGCACCTCCGGGCTGTGAAAAGTTAGGGAAGTGTCTGACACCTC |
| CAGAATCCATTCCCAAGAAGTGCCTCTGGTCCCACTAGCACCTGCGCAGACTCAGGCCAGGCCTAG |
| AATCTCCGGTTGGCCCTGCAAGTGCCTGGAGGAAGGATGGCTCTGGCCTCGGTCCTCCCCCAACCC |
| TGCCCAAGCCAGACAGACAGCACCTGCAGACGCAGGGGGACTGCACAATTCCACCTGCCCAGGAC |
| CTGACCCTGGCGTGTGCTTGGCCCTCCTCCTCGCCCACGGCGCCTCAGATTTCAGGACCCTCCTCCT |
| CGCCCACGGCGCCTCAGACCTCAGGACCCTGCCGTCTCACGCCTTTGTGAACCCCAAATATCTGAG |
| ACCAGTCTCAGTTTATTTTGCCAAGGTTAAGGATGCACCTGTGACAGCCTCAGGAGGTCCTGACAA |
| CAGGTGCCTGAGGTGGCTGGGGATACAGTTTGCCTTTATACATCTTAGGGAGACACAAGATCAGTA |
| TGTGTATGGCGTACATTGGTTCAGTCAGCCTTCCACTGAATACACGATTGAGTCTGGCCCAGTGAA |
| TCCGCATTTTTATGTAAACAGTAAGGGAACGGGGCAATCATATAAGCGTTTGTCTCAGGGGAGCCC |
| CAGAGGGATGACTTCCAGTTCCGTCTGTCCTTTGTCCACAAGGAATTTCCCTGGACGCTAATTATG |
| AGGGAGGCGTGTAGCTTCTTATCATTGTAACTATGTTATTTAGAAATAAAACGGGAGGCAGGTTTG |
| CCTAATTCCCAGCTTGA |
| SEQ ID NO: 5-the cDNA sequence of the N-acetylgalactosamine 4-sulfatase gene (Gene ID: 411) |
| AAAAGTGAATACATGATTTTATTTAACTCATTAATAAGGAAATTGGTAAGGTGTTAAAACCAATTC |
| AAAGGACAATCCAAAGAACAGATCAGGAATACTAAAATAAATATGCAAGCGGAGGTGAAACTGT |
| TTTCCTTGGTAGTGGTGGAGGGGAAGGATTGCTACTCCGCTGGATAAAGTTCATTTGTGTATATAT |
| AAATAAGAATTATTTTCCATTGTTATTTATCTATAACTTATAAAGTTGTAAACAACTTCCACGGAAT |
| CAGACTCAACCTGGAAGGGTATGGTCTCTAGGCAATGCAAAAATTTTCCCCTACACCTGTTAACAA |
| CTATAATATCTCCAGACAGAGTAGACAGAAAGTCTGGATGGCAACGGGAATCTACTGGTCATACG |
| GCTAACTTCCTAATTCAATAAGCACGTGACTAAAGGATTTTTTCCTTCCACTCAGATATTTCAGGCT |
| AACTAGATACTGTGTGCTTCTTAGTGTCACTGCTTAGTGGGGGAGCCAGCTCTGAGTGGGGTCATA |

Sequence Information

```
TCCGGACAAGCGAATGAGCTATTTATTCAATGACCACGCAACACTCCAAATCCTCCCAGGGCAACT
TGAAAGTAACCGCACCTTCCAAAGGGCACCGTGCAATCAGACTGTGTGTTTGGCCTCCTGTTTGCT
AGTGGGGAGGAAGCGGCTTCATGGGTGTACACTACGCATAAATGAATGTGAAAGGCTATTTAGAC
CTCTGCCTTTTCACCGTCCTCCCACCTGCCACAGGCTGGGCTCTTGTGCTAGAAATGACTTGCTAGC
TAGACATCATGGTTCAGGATCTGAGTCAGAGGTTTAACCATTTATAAGCTTTTTTCTTATGAAAAT
TGGCACTAATTATAATGTCTAACTGTCAGAGTTGTTGCAGGCTTTACAGGAGACGCGGGCTGTGAA
GATGCTTTGTAAATTGTGAAGCGTTATTAAAGAACACATCTTTTTTTTTAGGAAACCACAGTGCA
AATTTAATTGCCGGGGAAGATAACGGGCCTTGGTGCCCTCCAAGCGTCAGCTGAGTTTCCAAGAA
GCCGGGCAGGGCGCCCGCGGGTTCGTCTCTGGCTCCTCCTCCGCCACAGCAGCCGGGGCCCG
GGTCGGAGGCGGCGGGGCCGAGCGCCCGGCCTCGCAAGCCCACGGCCCGCTGGGGGTGCCGTCC
CGCGCCGGGGCGGAGCAGGCCCCGGCAGCCCAGTTCCTCATTCTATCAGCGGTACAAGGGGCTGG
TGGCGCCACAGGCGCTGGGACCGCGGGCGGACAAGGATGGGTCCGCGCGGCGCGGCGAGCTTGCC
CCGAGGCCCCGGACCTCGGCGGCTGCTCCTCCCCGTCGTCCTCCCCGCTGCTGCTGCTGTTGTTG
GCGCCGCCGGGCTCGGGCGCCGGGGCCAGCCGGCCGCCCCACCTGGTCTTCTTGCTGGCAGACGA
CCTAGGCTGGAACGACGTCGGCTTCCACGGCTCCCGCATCCGCACGCGCACCTGGACGGCGCTGGC
GGCCGGCGGGGTGCTCCTGGACAACTACTACACGCAGCCGCTGTGCACGCCGTCGCGGAGCCAGC
TGCTCACTGGCCGCTACCAGGTACGCGGCGCCCCGCCGCCCGCGCCGCCCCGCCCCGCCTTTCG
CCGGCGCCCTGCCGCTCCTACCCGGCCCTTGAGGCCGCGGGCGCTGGCAGGCGGGGCTCGGACCG
CCGACCCAGTTATGGGTCCCGGCGGCTTCTCGCCCCAACCTCGCTCTTCCAGGCCGGCAGCCCGCC
GCGGCCTCTGCGCATGCCCGGCTCTGGCGCCCCGCGGACCCGCGCCTCGGCCGCCGGGTTGGGCG
GGTGGCTTTGTCTTTCGTTTTCTGAAGCTCCGGGCGAAGGGGTTTATGGGAATGCCGGGTGCTGGG
CGCCGCGGCCGGCAGGCGGAGCGGTCCTGAGGTGGGAGGCTGGGAGGGCGTGGGCTGGGAGCA
AAGACGAGGGGAGAGGTAAAATGAAGGGGTGCTCGCCGTGGGTGCGACCCTGGCCCGTGGGAAC
CCAGCGGTGATAGGTTAGGAGTGTCCCACCAAAGATTATTTTTTTCCAGGTTCTCAACACCCCTGG
AATGAAACCTGATGCTAGGTTGATTTTTCTTAGGCTGCTGACATTCCTTTCACATGTAACCTTGTAT
TGAACTCTTCTGAGCATCTTCATTATCGCTTTAAAAGCTTCCCTTTAGGAACGGCTCCACAGTTAAC
GAAGGAAATATAAATGTAGAGCGTGCATAGATGTTAGATGGCTAAGAATATCAAGAACATTTGCA
TAGCACTTTGTTGTTTTTAAAGTGAATTATTGAAACAGTGCATGAGGTAGTTGTTTTTACCCCGTTT
TACAGACGAGGCAGGAAGCCTGTAAAGGCTCGTTGGCATAAGAATCGCACAGCTAGAAAGTGGTC
AAGGCAGTGTCCGTTGTGCTTTTCCTGCATCCACTGGTCGTCCCGGGCTTATGAAATTGGCCTTTTT
TCCCCTCAATCTGAATACGATTGTCATATTTCTAAGACCCTGAAGTTATTATGACCATATTAAATAC
AGTAAATGGGAACTGTTGGATACCACCTGCATGCCTTCACAGAGTACATATGCTGTTTACTCAACA
AAAATATTTTGAGCTTACTGTGCTACTGACAGGGGATATATATTTGAATGTTGCCCTCCCAAGTGT
GTGTTCGCATAACCTGTCAGATCAACCCTAGCCTCACGTGGTCCTAAGATCAAGAGAAGGGAGGG
CTTACTTGTGATAAAGATATGCGCAGTGGTCTGAAGGCTTTTATAAAGAGGAAAGATTGGGTGTTG
CTAAGGGTGAGAAATAGCTGTAGCCAAGGTTAGAAATGGGAGTAAAGGATGCTTCCCTTCACCAT
CCACCTTAGTACTTTTGGCGGTTCTGACCTTGGCTGCTACGTGTAATTAGGAATCCCCTACATTGTG
TAAATCTCACCCTGGACACTTTGTGGGAGTAAAGGGATGTGCCAGTAAAGAAGAAGAAGAAGGGA
AAGGTGAGGTTTGCCCAAAGGGTTCTGCATTTGCTTTGAAGTAAGAGAACTGAACTCAGATTGCAA
AAGAATGGAAGGGCCATTCATTTCTCCAACTTCCTCCCTTCCAACAGAGTTGGACAGGAAAGCAA
ATACCAACTTCAGAAACCCATTCCTGGGCCGGGAACGGTGGCTCACGCCTGTAATCCCAGCACTTT
GGAGGCTGAGGCAGGTGGATCACCTGAGGTCAGGAGTTCGAGACCAGCCTGACCAACACGGCGA
AACCCCGTCTCTACTAAAACTACAAAAATTAGCCGAGTGTGGTGGCATGCGTCTATAGTCCTAGCT
ACTCGGGAGACTGAGTCAGGAGAATCGCTTGAACTCGGGAGGCAGAGGTTGCAGTGAGCCGAGAT
CGCACCACTGCACTCCAGCCTGGGCGACAGAGCAAGACTCCATCTCAAAACAAAATAAAATAAAA
AACCCATTCCCGTAATCAGTTGCTTTTGTCCCCTAACATCCTCCCCCACCAGTCACCAAAATTATGT
CTTGGAGAACAAACTTTAGTATTTAGAGTACCCCATGGTTATGAAGTAAAGGATGAGTAGAGAAG
CTGGGCACTCTGAAAGGTTTAGAGGCCTCTCAGTGTAGCTGATTCTAAAGCAGCCTTGCTTCCCCA
AACATTTTTTTCCTCCAGTTTTCTCACCCACTTTATTCTCTTAGAGTTCATGAGACCCAAGTAGAT
GTTACCCAGGGTGAGCAAGTGTCCACTTTTAATGAAGTAGAAATTTCAGGGAAGGCTCAGGAGTC
TCCGTCAGATACTATATGCTGGTATTGTTCTGAGCACTTACAAGTGTTAACTCATTTGATTCTCACA
ACAACTCTATCATCTCTGTTCTGTAACAAGGAAACTGATGCTGGAAGAGGTTAAGAAACTTGCCCA
AGGTTACAGGGCTAGTATATGTTGACCAGGATTTGACCCAGGGCACGTGGCCCTAGGGTTGATG
CCTATAACCACTAAGCCATATTGCCTACTCAAAATTATTAAAAATAACATCCCAAGGACTGCTTCA
TACATACTAAATAATCCCTGTATTACTTTTGGACATTTGGGTCATTCCTAAATATCTCAAGGTAAAG
AATCAACCCATCATATTTCTGAGTTAGGAATTGCCTATATTCCATGTAAAATAAAAATAGATTTTA
TTTCTGAGTCATTTGTTATGCATAATTTTAGACAATAAAATGAAGGAATTTTTGACTGTCTCAAAA
TGAGTTACTTGAAGGAAGTTGTTAAGAGTCATATCTGGCCGGGCGCGGTGGCTCACGCCTGTAATC
CCAGCACTTTGGGAGGCCGAGGCGGGTGGATCATGAGGTCAGGAGATCGAGACCATCCTGGCTAA
CAAGGTGAAACCCCGTCTCTACTAAAAATACAAAAAATTAGCTGGGCGCGGTGGCGGGCGCCTGT
AGTCCCAGCTACTCGGGAGGCTGAGGCAGGAGAATGGCGTGAACCCGGGAAGCGGAGCTTGCAGT
GAGCCGAGATTGCGCCACTGCAGTCCGCAGTCCGGCCTGGGCGACAGAGCGAGACTCCGTCTCAA
AAAAAAAAAAAAAAAAGAGTCATATCTATGAACTTGGCAGTCATGCTTTAAGTTAATATTTAC
AGACCCCTTTCCCATAATTATTTAACTTTAGAAAAGAAAAGCACAAGTTGATAAACAAGCCTAGAC
TGACTGGACTTTATACTCTCATGAAATCCTGAGTTTTAGTTTTTTGGTTTCAGAAATTATTTATTGA
GTAAAGAGGACTGGTTAGGAACTGAGATGTAGGTTTTGGTCTTTGGCTGGTCAGACTGTGACCTCGC
TGGCCATCATTTCCACATCTGTGAAACAGAGGAGTTGGGCTGAACTCTAGACTTTGTCTAGCTCTA
AATTAATTTAACTCTAAGGCTCTTGTGTCCATTAGGGCGAGTTTCTAACTTGGCAAATGCACATTAT
CATACCTATCATACTAACCCCATCTACTGGTAGAAAGATTAATCTTGCCCAACACAGTGTATCTTA
CAAATTGCGTGTACTACTTGTTCTGCTGCTAGGAACTTACTTAATTCAGCCTTTTATAGTGAGACAT
TTAATTGTTCACAGCCCTCACAAATGAACTATTTTAAATGTCATGCTATGGTGAAATATGTGTAG
GGACTGGGTACAGGTTGGAGGCAATGAGGAGACTAATTAGCAGATGGGGTAAGTAGTTACTGGT
AAATTCAAGAACTAGAAATTCGGCCGGGCGCGGTGGCTCACGCCTGTAATCCCAGCACTTTGGGA
GGCCGAGGCGGGCGGATCACGAGGTCAGGAGATCGAGACCATCCCGGCTAAAACGGTGAAACCC
CGTCTCTACTAAAAATACAAAAAATTAGCCGGGCGTAGTGGCGGGCGCCTGTAGTCCCAGCTACTT
GGGAGGCTGAGGCAGGAGAATGGCGTGAACCCGGGAGGCGGAGCTTGCAGTGAGCCGAGATTGC
GCCACTGCACTCCAGCCTGGGCGACAGAGCGAGACTCCGTCTCAAAAAAAAAAAAAAAAAAAAAA
```

-continued

| Sequence Information |
|---|
| AAAAAAAAAGAACTAGAAATTCAGGTCTCTCTACACTCAGGCTAGGGGCCTTCCCACAGCCCTAT |
| GACTCATTCATTCATTATTTGTGAAATCTTTAAAAAAATCCGTATTTTATTTTTAAAATAGAAAATA |
| CATTCACATGGCTTAAAAACTTAAAAGCTGCAAAAGGGCTTACAGTGAAAATCTACCAAAACACA |
| CACACACACACACACATACACACACTTCCTTAGACATTCAGTTCCTATGTTTGTAGACAAATAATG |
| CTCTGAATTATATATTTTTATATATCATTTCTCTCTTTTTTCTGTATGAATGGTAACATACTCTTCAC |
| ACTGATCTGCAGCTCCTATTTTGTTTGTTTGTTTTTACTTAACATTTGCAATCATTCCATTTTGTTGA |
| CTAAAGATTATCCTCACAGCTTTTAGGGCTGCATAATATTTTGTTAAATGGATACATTGTAGTTTAT |
| TTAGCCAGTTGCATACTGATGAACATGTAGGTTGTTTCCAGCCTTTTGATATATCAAAGAATGGTG |
| AAGTGAATACTTTGCACATATGTCATTTTGTACATATTGGAACGTATATGAAGGATAAGTTCCTAG |
| AAATGGAATTTTCTGGGTTTAAGGATAGATGCATTTGTAATTTTGATAAATATTGCAAAATTGCAT |
| CTTAAGGGATTGTACCAATTTACATTCCCACTGGCAATATTAAGTTATAGTTCACATCCTATATAAT |
| TTACCATTTTAAAGTATCCAATTCAATGGTTTTTTGTACATTCACAAGGTTGTGTAACCAATATTTT |
| CATCACCTCAGAAAGAAACCACTCAACTATTAGCAGTCACTCTTCATTTCCTCATTCCACCAGCCCT |
| TGGAAACCACCAGCCTTCTTATTATCTATGTGACTTTACCTATTTTGGACATTTCATATAAATGGAA |
| TACAATAGATGTCCTTTCATCTATGTTGTAGCATGTATTGTTCCCTTTTATGGCTCAATAATATTCC |
| ATGATATGGACATGCCACATTTTGTTCATACATTCATCAATTCATGGACATTAGGTTGTTTGCGCTT |
| TTTGGCTATTATGAATAATGCTGCTGTGAACATCCATGTACAAGTTTTTGTATCAGCATATTTTTTA |
| AGTTCTTTTGGGTTAATATGTAGGAGTGAAACGCCGTATTGTTGCAGGACTTCTCCTTAGTTCAGCT |
| AACGATGAGGTCCTTGTCTGTCCCATGGCCATGAAAATTCAGGCTCGCAGATGGTTTGAAGGGTGA |
| GTAAAGCAGGGTTTTATTGGGTGAAAAGGAAAAAAGGGGGAAACAGGGACCCACTGAAAGGTCA |
| GAGTCCCTGCTACAGTGCTTCCCTCATTGCCCGTTTGAATCCCAGGTGCCATAGGAAGAGGAGAGG |
| CCAGGCGCCACCTCCGTGGCTCCACCCCAGTGCACAGTCCAGCTGGAGTTTTGCCAGGGACCCCCT |
| CCCACCTGGCTGTCTTAGTATCATGTGGTAACTCTATGTTTAACTCTTTGAGGAATTGGAAATTGTT |
| TTCCACAGCAGCTATACCACGTTATATTTCCACTAGCAACGTATGTGGGTTTTAGCGTCTCCACATC |
| CTTGCCAACACTTGTCATTATCTTTTTGATTATAGCCTTCAAGTCATCCTAGTGAGTAGGAAGTGGT |
| ATTTAATTGTAGTTTTGATTTTCATTTCCCTAATGACTAATGATGTTGAACATCTTTTAATGTCTTAT |
| TGATCATTTTTATGTCTTCTTTGGAGAAATGTTTACTCAGATCCTTTGCCTGTTTTAAAATTGGGTA |
| ATTTATCTTCTCATTCTTGAGTTGTAAGATTTCTTTATGTATTCTGGATACTATTAAATAAACCCTTA |
| CTAGATAGATTATTTGCAAATATTTTCTCCCATTCTGTGGATTGCTTTTTACTTTCCTGATAGTGTCC |
| TTTGATGTAAACAAAAGTTACAAATTTTTATGTACAACTTACCTATTTTTCTTTGGTTGCTTATATTG |
| TTGGTACCATGTCTAAGAAACCATTTTCTAATCCAAGATTATGAAGATTTACCTCTATGTTTTATAG |
| TATTTTATAGTTTTCAGTTTTTACATTTAGGTCTTTGATCCATTTGGAGTTTCATTTTTATGTACAATT |
| TGAGGTATGTGGATGCATGTAGGTGTCCAAATATTTCAGTGCTATTTGTTGAAAAGAGTGTTCTTTC |
| CTCATTGCACCCTTTGCACCCTTGTCAAGACTCAATTGACCATAGACGTATGACTTACAATTCTATT |
| CCATTGATCTACATGCCTATCCTTATGCCAGTGCCTCACTGTCTTGATTGCTGTAGCTTTGTATTAC |
| AAAGGTTTCAGAATTAGAAAATGCAAGTCTTCCAATTTTGTTATTCTTTTTCGAGATAGTTTGGCTA |
| TTCTCGGCCCCTTGCATTTCCACATAAATTTTAGGATCAACTTGTACATTTCTATTAAAAAAAAGGG |
| AAGTGGAATTTTGGTAGACAGGGATTTCAGTGATCTGTAAAACTATTTGGAGAGTATTACTACCTC |
| AACAATATAACTCTTCCAATTTAAGAATATGAGATGCTTTCTGTTTATTTAGAGGGTTTTTTTTTTT |
| TTTTTTAAGACAGAGTCTCACTCTGCTCTGTTGCCCAGGCTGGAGCACAGTGTTGGCTCACTATAAC |
| CTCTGCCTCATGGGTTCAAACAATTCTCCTGCCTCAGCCTCCTGAGTAGCTGGGACTATAGGCACC |
| CACCACCACGCCTACCTAGTTTTTGTATTTTAATAGAGATGGGGTTTCACCATGTTGGCCAGGCTG |
| GTCTTGAACTCCTGACCTCAAATGATCCACCTGCCTTGGCCTCCCAAAGTGTTGGGATTATAGACG |
| TGAGCCACCACACCCAGCCTATTTAGGTCTTCTTTAATTTCTTTCAACAATATTTTATAATTTTTAGT |
| GTGTAAGCATTGTGCTTTGGTTAAATTTATTCCTGTTTTACTATTTTCAGTGGTATTGTAAATGGAC |
| TTCCTTTCTTAATTTTATTTTCAGTAGTTCATTGCTGTTACATAGAAATGCAACTGATATATGTACAT |
| TGATCATTTTGCAACCTTAATGAACTTGTTAGCCCTAATTGTGTGTGTGTATAATCTTTAGAGTT |
| TTTTAGTGCAAGATCATGTCATCTGCAAGTAGAAGAAGTTTTACTTCCTCCTTTCTAATCTAGATAC |
| CTTTTATTTCATTGTCTTGCCTAATTACCCTGGATAGGACCTCCAGTCTGCAATATTGAGTAGAAGTGG |
| CATGAGTGGACATACTTGTCTTGTTTCCAATCTTAGAGGGGAAGCTTTCAGTCGATCACCATTAAG |
| TGTGATATATTCATTCATTCTTTCATTCAACAAATGTTTACTGAGCAGCAAGTTACGCCACTGTACT |
| CTGGGAATCTCTTGGTGCTTATAATCTGAAGGGGGTGAGGTAAGGAGAAGGAGTAACCAAGAGGG |
| AAGTGAAATAAATACAAACAGGCCAGGCGTGGTGGCTCACGTCTGTAATCCCAGCACTTTGGGAG |
| GCCGAGGCAGGCGGATCACCTGAGGTCAGGAGTTTGAGACCAGCCTGGCCAACATGGTGAAACCC |
| TGTCTCTACTAAAAATACAAAAATTAGCCAGGTATGATGGTGCGCACCTGTAATCCCAGCTACTCA |
| TGAGGCTGAGGCGGGAGAATTGCTTGAACCCGGGAGACGGAGATTGCAGTGAGCCGAGATTGCGC |
| CACTGCACTCCAGCCTGAGCAACAGAGCAAGACTCCATCTCGCGGGGGGAAGTGGGGAAAGAA |
| AGAAATACAAACAAGTAAGGTGAATTTAAATAGCATGACAATACATGGAGAAGAAAATAAAG |
| TAGGTCAAGTGATCTTGACTCAGGAAGGTGTCTTCAAGGAGGTAGTATGAGCAGAGGCCTGAATG |
| AAGGGAGTCAGCCATGCACATATCCTAGCAAAGTTTAACGTGGAGGAAGGAGCAACAGAAGCAA |
| AGCTCTTGAGGCTGGAACGAGCTTGTTGTAAGAATGAGATGGTAGCTGAGTGAATGAGGGTGCCA |
| GAGGCAGGCCAAGAGCTAGAGGAGGGAGGCTGGGTCTCCCTGGGTTTAATGCTGCCCACCCATTA |
| AAAAGTGTTAAAACTTGAACTTTTTTGTGTCAGTTTTTATAGTAAGGTGACATTGAGGCTATTATA |
| CACTAAAGAACATTTCGAATCTAACAGTGTTCTAAATGGGCATATTTTAAGGAAATACAGTCAAGT |
| GCCATGTGGCATTCTTTGGATGCATGTAATTCCAATTAGAATTAATTGTACATATTCTCTCTTTTTCT |
| TTAAAAGAAATAAGCTTGGCTGGGCGCAGTGGCTCATGCCTGTAATCCCAGCAATTTGGGAGGCCT |
| AGGTGGGTGGATCACTGGAGTCCAGGAGTTCGAGAGCAGCCTCGGTGAAATTCCATCTCTATAAA |
| AAGTTAAAAAATTAACCAAGTGTGGTGGTAAGCGCCTGTAGTCCCAGCTACACAGGAGACTGAGG |
| TTGAGACCCGGGGCAGGGGGGTAGATGGCGGGAAATCGCTTGAGCCTGGGGAGGCAGAGTTTGC |
| AGTGAGCCAGGATGGTGCCACTGCACTCCAGTCCAGGTGACAGAGTGAGACTCTGTCTCAAAAAA |
| AAAAAAAAAAAAAAAAAGTAGCCCTGTTTTTAAAATCATCTCCAGGAAATACATTCAAAACCT |
| TCAAATATAAAAGATGTAAAAAATATAAACATGTAGATGAGGATCTTTTCAGCCTGTCTCCCCACC |
| CTCCTTCCCATAGGCAGCTCCTGTTTATTGGTTTCTTGATATCGCTTGGAGGCATGTTATGCATATG |
| AGAAAATCGATTTTATATTTATTTTTCCCTGTTTAAAACCTCAAGATTAAAAATATTTAATTTAAAA |
| ATTCTCCAGCTTTTCTAATAGAATTTGTGTACTGCATTTAGTTCAAATAGAAAACTTAATATTACTA |
| ATTTTCATATTCTTACAAATTGACTTTATTCTATACAAAATATTCATTATACCTTTGTTATTCCTAA |
| TACATATTTTAATTGTGATAAGTGGTTCTGAGGTCTGACTTCTCCATTAGATTGCCTTGTCTGTCTCT |

-continued

Sequence Information

```
GGGCTAAAGAAGCACTCAGTGTTGGACAATTAAATGATCAAATGTGAGAAGCACTTTTACACAGT
TCGTGAAAGAGCTCACCATCTTAATTAAACTGCTTGAAATTGCCATGTCATTTCTAATGCCTTTACT
TCTTTTTTAAGAAATTGAAAAGATTAAAGAGTAAGAAAGTGATAGGCCTTAAAGGAAAACACTCT
TCTGGGAAAATAGTTAAGAAAAGTAACTCTGGTCCTCAACTGGGAATGTCCTTACCTTGGGTACCA
AGGGGGCCACTCCACCAGAACTCCATAAACCTTGGCACAGAATAGAAGCAATGAAAGATGACTCC
AAGGTTTCATTCTTAAGGGATCCAAACCACATTTTTCTTAATCACACTGATAAATGGACAAGACAT
TTTCACGGCTTTTCACTCACCCCTGAGGCGGAACCTTGGACAGGAAATATAGGAAGGAGGCTGTGC
TGGAGCATCGTGGGTAATTTTTGACTTTTGCTTCAAGTTTGCTTCAAGAAGGTGAGCAGGAAAGAT
GCATGCTGCAGGCAGAAGAGGGCATGGTGGTGCAGGCGCTCTGCCTGAGCATGCCCTCCCTTTCCT
GCTTCTTGTCCTCCTCGCCCTCACTGTCCTGCCTGCTCCTCGCCTGCTGGCCTCTCAGTGGACTCCTG
CCAGTGGTCGCCTCTCCCTGGACTTTGAGGTTCAGAAGTGGGGCACAGGAGAGTGCAGAGCTGGA
AGAAATGTTTACAGGGTGCAGGGATTGGGGAAAGTGCATGTCTCAAGGTGGGCGCTCCTAGGATC
CCCTGGCAAAGGCACAGGAGGAGGGAGCTGTCAGAGGACCATGTAGCCTTGAGACCATGGGTGCC
TCCTAAGAGAAAACAGTGTCTTTATTTCTGTGCTCCTTTAGGGGGAGAAACAAAGGATGCATTAGC
TCCATAGGGACAAGCAAGATGGCCTCACTAAAGCACAGCAGAGCCCTGGGGTGACTTTCATGGGT
TTGCTAAAGCCAGGTGTCCTTCCTAAGCCTAGCCAAATCCAAGAGACATTTTCCCAGGAGGGAAG
GGGAGTGCGGAGGCCTCATTCTGCAAACATTGCAGCTATTTTAAAGAAACAATTCCAGATTTTATA
TCTTTTACCTGCCAGGAAATTGCAAATGAGGAAATAAGGAAATAAGTTTGGAGCTAAGTGGAATA
TGACCAGTGGAGTTAGAGGATTTTCTGGTTGCTTGATTTACGAGGTTTGTCATTTCAGGAATCACTT
TGAGCATAAGCTGTTGCTCTCTGGTCATTATCTTTTGTTTGCGTTTCCTTAATCATATCACCTTTTGA
GAGATTCCTTTCCCTCAGCTTTCTTCATATTTTCCTTCCTTTTCCATTTGGGCTTTCTTTGGAATTATA
ATTTAAACAGAGGGAGGCACTGAAACCCTTTCTGACTTGTTTATTCTTTTTTACAAACAACATCCCT
TTGTGGGTTTAGTCAGAGATTTGCACTCTTCACTAATCAACACCAAAATAAATAGACTCTTAAAAC
TGTCAGTGACACGGGCCAGTTCTGCAGCCCGAGTCCTGAAGGGCCAAGCCAGATGGCAAAGCCAG
GCCCCTAGCACACATAATGCGTGTCTGTAGGCTCTTGGCTTCAGCAGCATGGGCAGCTGACTGCTT
TTCAGATGGCTTCTGTGGGGAGGGAGCAGATTTTCCACTATCCATTTGTTCTTTGGGCATCTCCAGG
AATAAACCCTAAGGTGGCACAAGTGTTACTTGACCGTGATTAAAACCTGCTGTGTACTGGCCGAGG
CACAGGCTAGAAATTCTGAACTCCTGCTTTGCCACCAGCATGTTCTGTGATTGCGTTCTGATCATGA
AGCTTCCCATAGGCTCTCTGGTGTATAAGGTGGAGGGGTAGAGTGGCCCATTTTTCTGAATTTTTA
AGTACTGCAGCAGGAGGTATTGCACACATATGTGGGCACATGAGGATATGAGTTCATTTGCTCAG
ACCAGACTGACTGGACAGAACCTCCCTTCTGTTCAACGGGATATTATCTCAACACTGTTGAGGTGA
GGAGAGAAAGAGCATCTATCGCCTTCTGTGCAGCAGTGGTTTGCTTCGCTCTTGGGAGTTTGAG
TGTAGCTGAAATATTGTGCTCTGAACTCCCATATAGATAACTAATCAATTGACTGTCTGGACCTCT
GAAAGGGGAGTTGAAAGAGATTCTGATATGGGAGCTGCCATCTTCCTCTCCCCAGCAAGAGATT
GGATTTTCTCCTTTAAGCTCATGAGACTATACTGCAAGGAACTCCTAGGTGTGCAGAAGACAGAAT
AACACACTGGACCAAATAAATTGTTACGTGCAACCAATATGTAAATAAGGATCTCTCAGTTATGTC
ACAGAAAGAGCCTAGAACAAGCCAGGTCCTCCACTGGATTTGCAGACCTTTTGCCTTTGTGGAGAG
GATTTTTGATGGTCAAGTAAAATCTTAGGAGAAGTTGTTTTTTGAGAGAAGATTTGGTTTAATGAA
GAGGAGACAGCCACACATGGTAGATAGGGAAGTAACCCCTTGGACTTTCGTATATTACATGTAGA
ACCTTCTCCATTCACACACACTTCTTTGGACATTGCAGATGGGTGTTAGAATGAAATTGTTTTATAT
TCTGTTGTGTTTATCAGGGCACCCTTATTTTTTCTTTTGATTCCTATTGGTGCCCGGTTGCTTTCCT
GCCCCTTGCAGCATGGCGTGGCTCTGTAGTTCTGTGCTGAAGTGCTGGGTTGGAACCAGTTCGGCA
TTTGCCTGTTTACTGCTTCTCTACACATTACAGCTTCCTTCCTTCAGATAGTGTTTGAACAGACCGA
AAACATGTTTTTGGATGTCATCCAGGGTTTGGCTTCTGCTTCCCAATAATGCCATAAAAATGCTCTG
TCAAATAAATTCTCAGGAACTGAAAAGAACACATTCCCTGCTCCATATGATTGTCAGTAATGGAGG
AAGGCTTCAGCTGACCACCTGGCTTGGTGCCCACGGCTTAGGAAAACCAAATCACACAACATCTCT
TGGCAGTGCTTTCTAGCAATCAGAATTAATTCTCTGCATGTGATGGATGAGCTTTCATTTAAGGG
AATTTTCGCAGAGCATTTATCTCCACTGGGGCTTTTGGATTCCATAAAATATTATCTTTACTTATCC
TGCCTGGTTGCCAATTAGCATACTATATGCTATGAAGTTTTTGAGTCCTAGGGTCAATTTTCTCTTC
AGTAAGCTTCCAGAGTTAACCATGGAAAGAATACTTTGATTTGGGGTGTGTGTGTGTGTGTGTG
TGTGTGTACGTATGCGTGCAAATGTGCTAAGAGGAATGCTTCCCTTTCCCAGCCTGGATATTATAA
CATCCTTATCATTCAGGGTCCCAGCTGGAAAGAGGTGGCACATTCAAATTAGGGAGGGTTTATTTA
CAAAGGGACCATTTTAAAAGGTGTGAATGTGTGGGGCAAAATGCTAGGGATAGTGTAGTAATCCA
GTGGAGCTGTTACTACTCCTAGACCAGAAGAGAAGAAAGGAAGGGCCAATTACCAGAACCTAGAA
GGAGAGAGGCAGATAGAGAAAGAAGTCTGCTTCCAGAGTGACCTTTGGTAGAGAGACTCATGTAG
CCAGGCTAAGCAGCGTGTCAGGTGAGGCCATGCACTCTCCTCTTTCCCTCTCACTCCTGCCAGGGC
TCCCCATTGGCTAAGCCCAATCAGAAACCTGAAGACAAGTGTCCTTTGACTTGATCCTCATAGGTC
AGCCTCCTAGGGCAGAGAGCAGGACTGAGAAAGCAGCGTGGATTTGAAGGGCAAACAGAAGGTA
TCTGACACATCTCCCAATGTAGATAGGTGTCTAATTATTTCTAGGAGAGGCATAACAATCTCAGTA
GGAAACTTAAACTCACTTTTATTTTTAAACAGTTTTATTGAGATATGATTGACATACAATGAACTGT
ACACACTTCAAGTATACAATTCGATAAACTTTGATAGGTATATACCTGTAGAACCATCACCACATC
AAGATAGTGAACTTAACTATCATCCTCAAGATAAACCCACTTTAACTTAACACTTAAGATATTCCA
TGTGGTTCTTTTAGGAGGATGTGGAAAGAGATCATGCAGTAAAGCAATAGCAGGTGCAATTCCTA
ACTTACTAAAGTTATTGAAGTTAGTGAGTTACTGAATGAAGTTACTGCCCGGGGTTACAAAGCTCA
TAAGTGATAAAGCCAGGATGGGATTTAATCCTCTGAGCCTTATGCTATTCCACTTTAAATTATAAG
GCAAATAAAATACTCACAAACACTTATAAAAATCATTTGTTAGCAACAAGTTTCTTGCTCTCCACC
TTATAGCTGATGAAGGGACCAGCCGTGGCCTGGGTTGAGAACTGGCACTCTTACCTCCTGTGTCCC
CAGAGCCTGTTTATTCTATAAATCAAGAGCTCCCAGGGCTGGGAAGGCTGGTGTCTGGTGCAGA
GTTGAATTTGAGACCCCAGTCCCACTTTCTACAAAGAAGAGCATCTCCCTGGCTAAGCCAGGACAA
GGAGGCAGGAGGTGTTAAGTTTTAGGGAAGGGTGGGACTGGGTAGACAAGGAGGGATACCCTGTC
ATGCCGCAGCAGGGGCTACAGTGGCACCCACCAGCACAAGAGCTGTGACAGGGCCAAACTGGGTT
CTGGGCGGGCCTTTTGAACTTGTCTAGTAAGCTCAGGTCTCAGGGCTTTGAAGTTTTTATTCCTTA
GGTCTGGATTGCTCTTACCCCGGATTTCTCCAAGTCTCACTGCCTCACTTTATTCTGGTCACTGCTC
AAATATCTCCTCTTCAGAAAAGGTTTCTTTCTTTCTTTTTGAGACAGGGTCTTGCTCTGTTG
CCCAGGCTGGAGTGCAGTGCAGTGGTATGATCACAGCTCACTGCAGCCTCGACCTCCCAGGCTCAA
GTGATCCTCCCACCTCAGTCTCCTTGGTAGCTGGGACTACAGGCACAGGCCACCATGCCTTGCTAA
TTTTTTCTATTTTTATTTTTAGTAGAGATGAGATCATGGCATGTTGCCCAGGCTGGTCTGGAATTCC
```

Sequence Information

```
TGGAGTCAAGCTAGCCTCCTGCCTTAGCCTCCCAAAGTGTTGGGATTGTAGGGATAAGCCACCCCG
CCTGGCCCAGAGAAGCTTTCTTTTGCCACTCTATCACAAGTGCCACCTCTGTCACTGTCCCTCTC
CTTCTTTACTTTTCCTCATGGCAATGATCACTGTTGGACATTAGAGTATCAGTTCTCAAACTTTTG
GTCTTAGGGTTTTGCACTTGCTTAAAAATTATTGAGGACCCCAGGGAGCATAGATTTAAATGGGTT
GTTACCATTCAAAATTTGCCCCATAAGTTAAAACAAATTATAAATTTTTTTATTCAATGAAAATA
GTAATAAACCCACTATATTAACATAAATAACTTATGAAAAAGCTCTATTTTTCAAAACCAAATAG
TTAAGTGAGAAGAATGGCATTGTTTTATATTTTTTGTACATCTTTTCTACTAATAGAAGTTTGCTAG
GTTGTTGTATCTGCTTCTGCATTTAACCTGTTATGATATATTATTTTTAGTAAAAGTTGAAGAAAAA
TCTGGCCCCACAAAGATGTGTAGTTGGAAAAGGGAGGGCTATTTTAATATCCTTTTCATATAATTG
TGGGTATTCTACTCAATATTACACCAAAAGTTAAGAAGTGGTCATTGCTTAAAGTTTAGTTGCTGT
ATGGACCTTATGCCCTGGGCATACTTGTGTGAGCCACTCCCAAGCAGCAGTCAGATGGCCGCTTTT
TATAAGAAAAAGTTGAACACTCTCTTTTGAGATAATGATTTACATAAAGTAGAATAAAAAATGCA
ATAATCGTTTTATTATACTGTTAAATAACTCAGCCAGGCACGGTGGCTTAAGCCTGTAATCCCAAC
ACATTGGGAGGCCAAGGCAGGCAGATCACCTGAGGTCAGGAGTTCGAGACCAGCCTGGCCAACAT
GGTGAAACCCCGTCTCTACTAAAAATACAAATAAATTAGTTAGGTATGGTGGTGGGCGCCTGTAAT
CCCAGCTACTCAGGAGGCTGAGGCAGGAGAATCACTTGAACCTGGGAGGTGGAGGTTGCAATGAG
CCAAGATTGCGCCATTGCACTCCAGCCTGGGCAACAAGAGTGAAACTCCATCTCAAAACAAAAC
AAAAACAAAACCACTTGTAAAAAAATCACCAAGTTTTCGAAGATTACAGAAGTGTCTTCTAATCA
AACACCAACTTCTTGTGTGCCCAAAATTGGAACGCTTTTTTCTTGTTAGATTCACACCACATATTAT
TGCTACTTTTTTTGAGGCAAAAAGTAACAAGTTAATGGTTTCTAACATAGTGCCTTGATAAATATT
GAAAATATCTGTTCGTTGGAATGGTTTTATTTGTCTTTCAAATCCTGTTTATGTCCACTACTTCATTT
GAATAAGAGAATTCTGCCTTTCAGAAATATCCTCAAGCCAGTACAGGAATAGAGTTAAACATCCA
AGTCAACAGATATGATCAGTAAGGTAGAAGGCCATTTTATCTGCTTGTTCACAATATTTCAATGTC
ATTAATCTATAATTTTATGTTTATCTCTGTAAGATCCGTACAGGTTTACAGCACCAAATAATCTGGC
CCTGTCAGCCCAGCTGTGTTCCTCTGGATGAAAAACTCCTGCCCCAGCTCCTAAAAGAAGCAGGTT
ATACTACCCATATGGTCGGAAAATGGCACCTGGGAATGTACCGGAAGAATGCCTTCCAACCCGC
CGAGGATTTGATACCTACTTTGGTAATGGAAATGCACATGTTTCTTTAACAACTTAGACTAACTGC
AGCCATCTCATAAAACACACCCAAGTGCAATCAAATGAAAGAACTGGATATTTGAACACAGAGTG
AATCAGTCGGCACTGTAATGGGGCTGCTTTCTAATGTTACCTCTGTAAACAGGGCTCTGTGCTGAC
CTTATGGTGGGCAAACCCATTACCTTTGTTGGAGTTCTAAATGCCACCTTAGGGCCTTGCAAGAGT
TTACTATCCACGTTGGAGACCGCTGTACTCTCAGAGACCCTTATTACCAAAAAGGGATATGGATTG
ATTTTTTATTTTTTAATGCCTGGCAAAACCTAATGTAAGAATATTTCCAGGCTGGGTGCCGGTGGCT
CACGCCTGTAATCCCAGCACTTTGGGAGGCCGAAGCAGGCGGATCACGAGGTCAGGAGATGGAGA
CCATCCTGACTAACACGGTGAAACTCTGTCTCTACTAAAAATACAAAAAATTAACCGGGCATGGT
GGCACTTGCCCATAGTCCCAGCTACTCAGGAGGCTGAGGCAGGAGAATGGGCATGAACCCAGGAG
GTGGAGCTTGCAGTGAGCCGAGATCATGCCACTGCACTCTAGCCTGGGCAACAGAGCAAGACTCT
GTCTCAAAAATAATAATAATAATAATAATAATAATAATAATAATAATAATAATAAAATAAAAAT
GAATATTTCCTTCACAAAGGTTTGGTGTGTTTTTTTCTCCCTGTGGAATGTATTCACAATTTTTCCTT
TTTTTTTGAAGGGGGTGGGGGAAGACTCTTCCATTGGCATTCTTCCACCTGTGAAATCTGTTTTTGC
AATCACAAAGTTGGGGAAGATAGGTTTTAAAAAACAAAGGAAAATGGGAGGCCAAATAAATGG
TAATAAGAAGGATAATAAGAAATAATAATAAGTATTTTATAAACTTGATAGCCCTATGAAACTAA
ATGTGAAACCTAGAGTTTGTTTTAAAATATGCCCTCTTTAAACCTGTAATAACCTGTGCCTGAATTA
ATAACCTGTGTATCTTGCCAGTAGCTATATATCTTTCTTTCAAGTTCTTTTTATAGTGAGCTATCTGT
TTAGCTATTTAGCTACCTACCTACCTCCCATCTGTTCATTTATTTATTTACAACCCTCCGTAGCCAA
AAAGGAACACATATTGAACATAGAAAGTTTAAACAGGATTAAATACAGGATGAGTAGAAAAA
GATGGAATAGGTTAATGGCATCAAATTACAGAAAAGTTGCATGGCTCTAGGCTGTCTTCATATTCA
TCTCTGATATTTGAAATTTCTTTTTTTTTTTTTTTATATACGGAGTCTCGCTCTGTTGCCCAGGCTG
GAGTGCTGTGTCATGATCTCGGCTCACTGCAACCTCCGCCTCCCGGGTTCAAGCAGTTCTCCTGCCT
CAGCCTCCTGAGTAGCTGGGATTATAGGTGTGTGCCACCACGCTCAGCTAATTTTTATATTTTTAGT
AGAGATAGGGTTTCACCATGTTGGTCAGGCTGGTCTCGAACTCCTGACCTCGTGACCCACCCATCT
TGGCCTCCCAAAGTGCTGGGATTACAGGTGTGAGCCACCGCGCCCAGCCTGAGATTTGAATTTAT
TTGTCCGAAGAGGGAGAAAGAAAGGAAAAGACTATAAGAGTTACATTATTTACAAGATAAATGGA
AACCAGATGTTCAGGAAAAGCAAAAGCATTTTCTGGCTCTTAGGCCTGACAGAAATTTCTCCTTTG
GGAGAAGGAGAAGGTAAGGTGGACAACATCTTTAAAAATGTCATTTTAATAATACGTTAGGTGGT
TTTCTTGTAGATGTTTTGAGGTATTTCTTCTGTTCAAGCTAGGGCCAGAGCACCAAAGTGCAATTC
AGTAAAAGTAATTATATGGGGGCCAAAACAATGCAGCTGAAGCACATGGCTCTGTAATGCCTCAT
TGGATTCAGGGTTAAAATCAAGATGCAAGGATGTCAGACAGGAGGGTGTGTGCCCCACTCTCA
TCCAGGTCCACCAGCAGACCTCACTACTCAATCTTAGCTTTTTTTTTTTTTTTTAAATGGACCCGG
ATGTATTCTCAGTACCTCAAATAGCTGTTAAAATTAGACTTGATGTAAGATCACTTTGTCATCTTGG
AAATTCTAGAGGAGCAAACAGCCTGTACATCCTTAGAAATTTTTCAATCAGGCCTTTGCTAAAAGA
TGAGTCAATATCTATACTCTGGGAAGAGGATGGGCTGTAGATATTTTGAATTGTTTATTAAAACCA
AGTTAGGTACTTAAAAATTCAGCTGGACAGAAGGTAGAAATGATATCCTTTTATGAGAATTAAGA
AGCCTAACCTGGATTTAGATGAACACACACCCCAAATTCATTTGAAGGGAGACTTGCAGCCAAGA
AGGTTATGATGACCACACAGCTCTTCTCACTGTTACATCTCAGCTCTTTTGCTAAAAATCAGGTGAT
GGTGGGATAGTTGCACAAGCCTGTAATACACTAGAAACCAATGTCTTTTACACTTTAAATGAGTG
ACTTGTGTGGTATGTGAATTATATCTCAATGCAGCTGGTACATAAAGCATCAGAGAAGATTTGGTT
GTTCAAGAAGCATTTTCTATTTTTTCCCCAAAAGCATAGGCTGCCATCATCTTTAGGCTCAGTAT
TGAAGTTCAAATTTGTGAATCATTATTATGAAGAAAAGCTTCATGTGATTGTCACATGGTTGCTTG
GTATTAGTTTTGCCAAGTATGTGAATAGTTTTATTTCTGGAATTCTCCTATCTGTATTATCTTTTAAA
TATTTGTAGTTCATGCCTTTGCTAATGAAGTGTATCTGTCCTATATTCTGCTAACTGATAGAAAGCA
GCTCACACTTAACAGTTAAAGAACCTGAAGTGATTTCCTCAAGCTTTAATGCCCAGTAGTTATTAA
AAACCTTAAATAGACCTCCAGTGTTCTGACATTCTAATCACCCATGTAAGGGCTGAAATTATTTTT
ATGGATACATTTCTTTCTCTGTTACACATTAATTAACAAGTACTTTGTATTTCGTTTTCCATTATATA
CATAGGAGAAAAGATTGCCATATAAAAGTTATTTTAAGACCAAAGTATTAATTGTATTCAAGATCT
TGAATTTATTGAGTCATAGAAAAGGAGAATTTAATTTAAAATGAATTGATTTATTATATAAACTAT
GTAAAGCTCTTAATTTTCATTATAGGGAAAGTTCAGGACTGAAGAAAGAGCTAGGTCAATTTATC
ATCCTCATTTTAAGGTTAATAAGCAGTATATGTCAGGAGATAGCTAAGAGTCTAGCAAATATTTCT
```

-continued

Sequence Information

```
TTTTAATAACTTTATCAAAGTATAATTCACATATCATACAATTCACCCAATTAAAGTGTACAATTCA
ATGATTTTTAATAAATTCAGAAGGTTGTGCCACTATCATGGCAATCCAATTGTAGAACATTTTTATC
ATCCCCAAAAAAGAAACTCATCCACCTCAGCAATCACTCCCCATTTCCCCCTAGTCCCTCCAGCCC
TAGGCAGCCACTAATCTATTTTCTGTCTCTATAGATTTACATGTTGTGGGCATTTAATACAAGTGGA
ATCATACGTAGCACAGCTTATTTTAATACTTTAAAATATAGAAATATAATATTTTAAATATAGAA
AAGATGGAACATTTGCAGAAACAACTATATTTGAGAAAACCCATTTTCTTCCATGTGAAGTCTAAA
TTATGGGATAGGCCGTTGATGCCATTTAAATCTGGGGTGAAATTGAGATCATTTTAGGTAGAAAAG
TCTTATTTCAGTGCTCACTTTAGTTTGATCTGTTGGCTCTGTTATGTCTAGAGATCCTCTATTAGGAA
AGGTTTGTATCTTTCACCAGTGGGTGTCAGCATCTGACTAAAGATGACTCTTCCTAGAACCACTTCT
GTAAATAACCTTGAAGCCAGTCTCGCAACATCAGTAACAACAAACATTGTTTGAATCCTGCACTCA
TTTATGTGATCACCTTAGAGTAAAAACCTGTAACAAGTCACATTAACTGTACATTATTTTTACCATT
ATATAGCTTTGAAGGATTGAGATTTTATCACCCTTACTGAGTTTCAACTCTGATAAAAAAAAAAAC
TGTTAGTGTTACATGATAGCGCCTATATTCTAAAGGCGAATGAGGAATAGATTTGAGTTTTATGC
AGTAATGTTTTAATGCCTTCTGCCACCAGATATAGACATGTTGAGAAATGGTGCTGATTAGCCTTG
TCATTTGATTAGCCTCGTCACGGGTAATCAATTGCATTAGGCATTTAAATGCTGAAACATTAGTTT
GTTTAACAAGTTTTATGCTATGCTGACTATTTTCGTCTTCCATTCTTGCAGGATATCTCCTGGGTAG
TGAAGATTATTATTCCCATGAACGCTGTACATTAATTGACGCTCTGAATGTCACACGATGTGCTCTT
GATTTTCGAGATGGCGAAGAAGTTGCAACAGGATATAAAAATATGTATTCAACAAACATATTCAC
CAAAAGGGCTATAGCCCTCATAACTAACCATCCACCAGAGAAGGTAAGTTTTGCTTCTATTTACTG
ATAGCAAAATCTTGTTACACTAATGTCTTTTCAGACAAATGTAGGAAAAGGCCATTGTTGTTTAGG
GAAAAATCTAATAAATTCTAGGGAAGTCCTTTTCAAATTATACAGTATCCCAGAATCAGCCTGGGA
AGCTTGTTAAAAAGGAAGATTCCTGGAGCCCACCTCTAGGGTGTGATTTATTAGGCGTGGGAGAA
ATCCGTACATCAGCATTTTAGAGAAACTCTTAAAAGGTGATTCTTAAGAGTGGTCCCCAGATCACA
CTTTGAGGAATACTATGTTGGTAGTATTTCAATAGAAATATAGTTTAAAAATTTTGGTATATTACGT
GCATGTGCTGTGAGTAATTAATAAAATGACTTAAAAAATGATTGGCTTAGGTGTAAGGTGAGGCTT
TATTATGACAAACTTTTGGTTAAGGGATCCATAAATTTTGGGATCAGGGCAGTTCCTCTAACCTTGT
ACTTCCTCCCTACAAGAATATTTTGCTATTCTAGATCTTTTGCATTTCCATGTTAATTTTAGAATCAT
CTAGTCAATTTCTATATGCCAGCTCCCCCCTGCCCAAAGTGTCTGCTTGGATTTATATTTGAAACTA
TAGAACAACTTGGGGAGAATGGATGTCTTAACAATATTGGGTCTTCTAATCCATATACCTGGTATA
CCAATGAGCTTATTTTTCACATTTACTATACTGATGCTTTTGTGTAACACATGAATAATCTTATTAT
TATGATTATTTTGTTAACCTAGAGTTAACTTCATGAGGTAAAGTTTAAGCTAAGTTCTCTGGATTTA
GCTTATAAATGCTTTTGAAATGGGAACAAATATTTGTATTGTCAAATATGGCTCAAAATATGGC
TTCATTAAGAACACCCATAAAAATAATACTTCAGTGGGACCCTGACACAACAAATTATAGAATAT
GCAGTGCTCCCTGGTTCTTCCAATTTCCTGCACTTTGCCTCTTTGACAATGCCTGAAGGTCCTTGGT
GCAGGTCTGTCTTAGTCTGTTTGTGTTGCTATAAAGGAATAGCTGAGGCTGGGTAATTTATAAAGA
AAAGAGGTTTATTTGGCTCGTGGTGCTGCAGACTCTACAGGAACATGGCACCAGCATTTGCTTCT
GGGTAAGGGCTTCAGGAAGCTTCCAGTCATAATGGAAGGTGAAGTTGAGCTGGCGTGTGCAGATC
ACATGGCAGGAGAGGAGAGAGAGAGAGATGCCAGGCTCTTTCTAACAACCAGCCCTCTCAGGAAC
TAATACAGTGAGAACTTATAACTGCAAAGATGGCATGAAGCCATTCGTGAGGGATCCACCTCCAT
GACCCAGACAGCTGCCATTAGGCTCCCACTGGGGATCAAATTTAAACATGAGGTTTGGAGGAGGG
TCAAATATCTAAACTATAAGAAGATCACCGTGTGGATTCTGGTTTACATACCTGTTTGGACTTGGT
ATGTGGCTGCTGGTTCCCCCTTCCAGTTTCTGCCTGTTTGAACTCAGTATTGGAAATCTTCCCTGAAT
GAGTTAAATGCCAGATTGCTGGCATCCTTATTTGACTTCCACAAGCTAAGGTAAAATCTTTCAGAA
GACAACTTTACCTCGAACTTCAAATTATATTTACACTATCAAATGTTATACAACTCCTGACATTCAT
TAAAAAATAATAGAAACCCGTCTCTACTAAAAATACAAAAAAAATTAGCCGGGTGCAGTGGTGG
GTGCCTGTAGTCCAGCTACTCTGGAGGTTGAGGCAGGAGAATGGCGTGAACCCGGGAGGCGGAGC
TTGCAGTGAGCCGAGATCGCACCACTACACTCCAGCCTGGGCGACAGAGCAAGACTCCGTCTCAA
AAAAAAAAAAAAAAAAAATCGAGCACATGTAGAAGTGAAAACACAGATAGAGGTGTCTGTCCT
CAGCTGCGTCCCACTTTTGGCGATCACTCTCCTATGCTGATATCTTGAAGCAACCATGCTTTCTGTG
GAACACGAAGAAATGGGAACATTCTCTCAAATATGTGGAAATACACAGATTTTAAATTTAAATCT
AAACAAATATTCAGATAATTGGAAAAATAGTTGCTAGGTAATTGGCTTAAATCCTCAGTTTTCTTC
TACATATTTGACATTTTATGGATGCACCTTAACACTTAACAAGGTAAAGTCTTAAGAGAACTGTGT
ATTATTCTTTGAGGGAGCCACCATTTTACACATAAGCAAACTGGCTTAGAGAAGTTAAGTAACTTG
TTCAAGGTCACAGAGCTATTGAGAGTCAGAATCAGAATTTAAACTCATGCTCTCTGACTCCAGACC
TCATGTACTTAATCAGCCTCCCTAGTTCACAGCTAATATCCAAGACCAGAGATTCTGAGTCCCAGC
TCATGATTCACCTTAATGATTTCAGTCCTGACCATATATTAGAATCATCTGGGAAACTTATAAGAA
ATACTGATGCCAAATATTGTGATTCATTGGTCTGAGGTGGGACCCAATCATTGGTGTTTCATTATTC
CTCCTCCTGGGCTCCTACCAGTGATTCTAATGTGCAGTCATCACTGACACCTGGTGCAGTGACAGC
CATTCTCGGATGGGTCATTCAGGGCATTCCTCTCAAATATGGAGAGGCAAGCAGAAGCCAGCTAC
CTATTACAGGTTCACAATCTGCCATACCTTAATCTGTGCAACAACTGTAATCTGCCCACAATACAA
ATTCATTCCTACTGAAGAACGATGGAATATTCCCTCACAGGGTTCCATAACATTAAGCAGATAAGA
GGAAGCAACTGGAGTGAAATAATAGATCTTTGTGGGTGGGCTCTCTTAACTAGGGTGGTGGGGAA
AACACGGAACTGAGGACAATAGGAGGCCCTAAAAGCTTGCTAGCCATGGAAGGAGTGTTATTACC
ATAGCCGCTGTTCGTAGGTAACTGTTTGGAAATTGCCAGATGAGAGGATGGTCATTTTCCTATTGT
GTCTGAAACATGCTATAGCAGTATCCAGCATTCCCAGTATCTTCAAAGGAAAGTTTCAGTCATAGA
CATAAGTGAATGAAATAATCAATAGTCAAGCTGTAACCCAAGAATGTTTAAGACAGCTAATACAT
GTTTACATTTTCAATTCTGTATAAAATGATGCAACTCACCAGTTTGAGGAGCTGAGCTTTTCACGAT
TTTATCCCGATGTTGAATCTAATTCTGGGCTAATTTCTCAGGTACTATATATAGATTGTAGCATAAG
GAACTTGTTCTAAGATAAAAATCATTAAAGAAAGCCACATGAAGAATCCACAGGCTAACTTAAA
TTGTGCCTATTTTAAAAAGCACTTAAGAGGAAAAAGCATTTGGAGGCAGTTCATAACTGAAACA
CAGTTGCTGATGCTGGACTCAGGAAGGTACTGCTAATTACCATTTCACATATGTTAAGAAGGACC
TTCTTTCTCTTTTTCAGCAGGATAATTCCCCATACTAGTGACACTACAGACTGAAAGTAACATATTC
ATAAAATATCTTTCTTTTAAAAACAGCCCCCCGTCAGCCGGGTGCACTGGCCCACACCTGTAATCC
CAGCACTTTGGGAGGCCGAGGCGGGTGGATTGTGAGGTTAGGAGTTTGAGACCACCCTGACCAAC
ATAGTTAAACCCCATCTCTACTAAAAATACAAAAATTAGCCAGGCCTGGTGGCATGCACCTGTAAT
CCCAGCTAGTCAGGAGGCTGAGGCAGGAGAATCGCTTGAACCCGGGAGGAAGAGTTGCAGTGAG
CCAAGCTCGTGCCACTGAACTCCAGCCTGGGTGACAGAGCAAGACTCCATCTCAAGAAAAACAAA
```

| Sequence Information |
|---|
| CAAAAAAACACCCCCATGTCAGCACTTTGCAGAATGGAAGCAAATGTAATGTTATACACCTGATCT |
| ACTAGAAGCTTCTTAAAGAAAATGTTAATTTCTAGTGGAAGACTCTTACTTTTCTGTGACACAATTT |
| GGAAAAGAATGTCTTAATTTAGAAGTCAAAGAAAAACAATTTCAAAACCTATCATATGCTTTTTTT |
| TTCATTTATACTTTAAATTAGGAGAATACACTAAAGAAATGAAAATAAGACTTTCTTCCTCACTGA |
| AATAAGTTTTCTTAGCATGGTGAGGATATTTACAGTATATATCTTAGGAACCATGTAGCATAAATA |
| AAGGGAAAAGAACCCCCAATATCTCAAACATGAATATGCTAATAGCTCTAGGTGATAATGTCTTG |
| CTTTTATGTAATACTTAGATATTTAGTAATGATTTCATGCCTAGGATTTCATTTCACATTCCCAAGA |
| CACTGGAAAGGGTTACAGGTAGGGTTGGAGCTAAGGCAGTAACTGTGACAGTTGATGAGAACAGG |
| GATCTGGACCTAAGAAAAGCAGGGGAGAGATCAGGCTCCAGTGATGGCAGCTGCTGGCTTTAGG |
| CTGACAGTGAGCCGAGCTCTGGTTGGCAGGAGTGGGAAAATTGACCACAGCTGTTCACAGGCAGG |
| GTCCTAGGAATAGTGGCTGCAGGTGGGGTCCTCACTGTGATTGGAGAACCTTGGAGTCCTAGTTAA |
| TTCATTCCACTAGGCTACCATATAGTATTAAAAACACTACTCTTTCTCTTTTTTCAATTTAAAAATA |
| GTATAGAAATATTTCACATTTACTACTGTTGGGGAATGAGTTATAATATTTCATGAATAAAGTTCA |
| CCTTCTGAGTGTTGAAACTTTATTTTTTGTAGTATGGGATGGAAATATCTAAATGTGCATCAGTCC |
| TGACCTCTTGAAATGGGCTATAGTACCGACATGGACTGGTATAGTTTCTTATTTTTAACCCCTCAAG |
| AGTGTCAACTTAAAATAATCAAAAGGATCAGAATCTAGTTTAAAGAGAGTTTATTCAAGTACAGA |
| GTTTAAGGATGGCCTCTTGGGAAGCACAGATTCCAAAGAATGGAAGTCCGTGTTTCAAAGTGTAG |
| AAGTTTGGGATTTCTTACTGTATTAGTCCATTCTCACGCTGTTATAAAGAACTGCCTGAGTTCCACT |
| GGCCCTCCAGTGAGCTGAGGGTTTTTGCAGGAAAAAAAAAAAAGCTGCCTGAGACTGGGTAATTT |
| ATAAAGGAAAGAGGTTTAATTGACTCAGTTCCACATGGCTGGGGAGGCCTCAGGAAACTTACAAT |
| GGTGTGGAAGGGGAAGCAAACAAGTCTTTCTTCACGTGGCAGCAGGAGAGAGAAGTGCCAAGCA |
| AAGGGGGAAAAGCGCCTTATAAAACCAGCAGACCTTGTGAGAACTTATTCACTGTCAAGAGAACA |
| GTATGGGGGTAACCACCCCCATGATTCCATTAACTCCCACTGGGTCCCTCCCCTGACACATGGGA |
| TTATGGGAACTACAATTAAAGATGAAATTTGGGTGGGGACACAGCCAAACATATTCACTTACATA |
| GACAAAATTTAGGGGAGCTTAAAAGAATTTCAACATCTTTCTGTACAAGGCTTAATGCATAATTAC |
| AATGATCTGATTAGTCAAGGTGGTGGTTTTCTTTTGGGAAAGGTATGTTTAACATTCCACACTGAA |
| GATGTAACAGTCATGGTGTTTTTGGGTCATCTGGTCTGAGTTAGGTACAGGACAATAAAGGAGGT |
| GGTTAATCTATAACAAAGATCTTCAATAAGAAGGGGAGGAGTCCTGGTCTCTGGTCTTTCCTAGTT |
| ATTTACAGAAGAAGAACAATAAGGAAGAGAGTTACTCTATAATCTAAGAAACAGAAGTTGCAAAC |
| ATGCTACGTGACACAGTCTCCAGGACTTAATTTTCCCCTTGGCATAATTTAGAGGGTCCTGAAAAT |
| TTATATTCTTTTATAAAAGTGATGGTAATGTCTTTAGCTACTAAGGAATAATTATAGGAAAGATTTT |
| CAGATTATTTTTCACCATATTTAACAAAGTGAGTAGAATGATTTCTATACTGAATATTTATAAGAA |
| CCTTTAATAATGATCCCCAAATCTTTTTTTCCCTGGTCATTGTTCAAGAACTCCCCTGTCCGCCTTCC |
| CAGCCATTGCCTTTAGTAATCAATTGCTGGCTGGGAATCACCTACCCTCTTTCTCCTTTCTCTCCTTC |
| GCCAGGTGGTTGCCATGTTGCTGCTAATGACCTGGATGAGAACATCTTCTCCTTAAGCTGTGGGCC |
| CCCTCTCTCCCCACTGTATCCCCTGCCCCCTGCCACTGTTAAGAGTCCAGATCAGAGTCACAAAAT |
| CTCGTGTTTGCAAGGGCCAGGCTGCTAACCTAAAGAAGTGAAGCAGTTTATGTAGAACAGTGGGA |
| AACTAGAAAATTGGATAGCATTTGAGGGGGATGGGGCCCCTGTTTCTCATACTCCAGCCTTTTGTT |
| ACCAGATGGAGTGTGGACAAAGAGTAGTCAGAAATTCTGATTTTTCCAAAAAAGTTTTTTTATATA |
| AAAACAGATCGATGTGATATTTCCTGATTTTTTTAAAACTTTACGTGGGCTGCAAATTGTTGTAGA |
| CTTCCGATTTTTAATCCTATCCCCATCTGGACCTTGGCTGGTGGTGGCTGGAGTTGGCTCAGTCTAGTGC |
| TGAAGACCCAGATAGCAGTACCCAGAGCAGACCCATACTGCACTGTCAGGTCAGCGATGCACCTG |
| CACGTTCTTCCCTCCAGACATCGCAGCCAAGACCTTCATCACCCCCAGGCAGGGCATCTGTTGGGA |
| TGTCCTGCACCATGGTCTACACGAACATAGACGCTTCAGCATGACCATGCAGCTGGAGTAGAAGG |
| TGTATGTGTCGAGTGGAAGCAGAGGCAGAACTGAAATGGTGTCAGAGGTTATAGAATAGACTT |
| TTGGAGTGGGAATTTGGAATGTTTTCCCATGGAAATAATGGAAGTACGGGTTCTACATTATCATCA |
| TTTTCACTCCATCAGCTGCGTCCTTAGTTTAATAGGTTTTAAAGCAACGACTTTGACATTTAGCAGC |
| TATTTTTAACTTTGTGAGTTTAGGGAAAACGTATTTCTGAGTTCCAAAGACCTGAACAATAAATAA |
| ACTTTTGGGGGTCTATTTGAGCTCTATGTATGGATACTCCTTTTTGCATTACAAGGATGTGTAATA |
| TAAAATTTAAAACAACTTGTCAACAATGAAGAATGAAATATGAGCACCACCCCCCCACCAAAGTC |
| TGTTTCTAACCATTTTCATTCATTTATGAGATTTAAATGCCTCAAATACTTTAACAGAATTATACGT |
| TTATTTTTGGGTTAAACTAGTTGTTGTCTCTTTGAGGCTTTTCAACTCATTAAAGAATTCTGTAGCA |
| CTATGAAGAGAATGCCTTCAGAAAGGCTCATTAAAAAGGAGAAGCTGACCTGGTATGCCACTAAT |
| GTTAAATGTTGCAAATTGATGTAAGTGGTAAAATAGAATCAGTGTGTCATACTTCTTAGTTTCAGG |
| AATTAAACTGGTCTTATGTTTGGTCCTGCATCAAAGACTAACAAGGCATGGTGTTCACTTTTTTCT |
| CATAAAATATAGTTTAAAAATACTAAACCTCTTCTAAAAGATGAGGGCTTATTTCAGCTAAAGCA |
| AAAAGCTAAAGCCTCTATTGGTACACATCCATATCGTAATAGTGGTTTTATCTATGGAAATTGCT |
| CTTCGGTTAATGTGGAGTTGGACAAGTCACACATATAACCTTTCTAAGCCTCAGTTAACTCATCTGT |
| AAAATTGCTGTAACATAGGGTGGTTTCATTAAATGAGATAGAATGTGTAAATTATTATCATACTGT |
| CTAGTATGTAGACAACATTTAATATGTGGTTGCCATTACTGATATTATTATTTGTTTGGATTAGGTC |
| CATTGAGGCCGTTCTGGGACTCTGGCTTTTATTTTCAATTTTTTGTGTCTTTTGTTATATTTTT |
| TAATATCTTTATTGAAACAAAATTTACATATCATAAAATTCACTCATTTAAAGTATACAGTTCAATA |
| GTAAATTTTCAGTTATGCAACCATACCACAATCTAAGTTTAAAACATGTTCATCATCCCCCCAAAA |
| AAACCTTGTATCTGTTAGCAATCACTCACCATTCCTCTCCCCCACAATTTCCTACAGCCCCAGGCAA |
| CCACCCTCTGTCTCTATAGATTTGCCTATATTTCTGGAATTTCATATAAATGAAATTACATAATATG |
| AGGACTTTTACGATTGACTGATTTCACTTAGTATAATGTTTTCAAGGTTTATCTATGTTGTAGTATG |
| TATCAATACTTTATTTCATTTATTGCCATATGTTGCTGAAAATATACCATATTTTGTTTATCCATTCA |
| TCAATTGATAGATGTTTGGGTTGTTTCTACTCTTTGGCTATTATGAATAATGTTGCAGTGAATATTC |
| ATGGAAGTTTTTGGGTGGATGTATGCTTTGATTTCTCTAGGAATGGAAATGCTGGGTCATATGGTA |
| ACTCTATGTTTTACAATTTCAGGAACTGCCAAAATGTTTCTTCAAAGTGGCTATGTGTGCCATTTTA |
| CATTCCTGCTAGTAATGAATGACAGTTCCAATTTCTCCATATCCTCACCAATACTTGTTCTTTTCCA |
| TTTTTAAATTATCACCATCCTAACAGATGTGAAGTGTTACCTCATTGTGGTTTTAATTTGCATCTTA |
| ATAATGACTGATGATGTTGACTGTCTTTACATGTGTTTATTGCCTTTTGTGTATCCTCTTTGGAGAA |
| ATTGCTATTCAGATTCTTTGCCCATTTTGTAGTTGAGTTATCATTGAGTTGTAAGGGTTCTTTATATA |
| TTCTGGAGATGAGTCCCTTATCACATGTGATTCACAAATACTTTCAATGCATTCTGTAGGTTGTC |
| TTGATATTATTTTTATTAATGCATAAATCTGAACTGTCTTATCCTTCTATATTTAATGCTTCAATATC |
| CTCTTAACTGGTTTGCACAAACTTTCTTTCCAGCCTCTGTTTCTCTACCTTGCTCTCCAGTCTGTGCA |

```
TGAGCCCCTTCAGGTCCCTGAGGAATACTTGAAGCCATATGACTTTATCCAAGACAAGAACAGGC
ATCACTATGCAGGAATGGTGTCCCTTATGGATGAAGCAGTAGGAAATGTCACTGCAGCTTTAAAA
AGCAGTGGGCTCTGGAACAACACGGTGTTCATCTTTTCTACAGGTAAGTCTGTCAATAGGAAAATC
ATCTCTTGGCAAAGCCTAGGACATGGTATTTGATAAGTGGAATGAAGACAAATTGGAGCGGTTAG
CATTGCCTTATTAAATAAATGCAAACTGCAATAGTGGAGACATGGTAATTGTGGATGGAAAGAT
ATATCTAAGGAAAAGAATGATGGGCTTCCCCCGTTCCCTCAGATATCAAAATATTCTGGGACTGT
GGCTTGAAAACACATGTTCACTAACTGAGTAAGTATGAGTGGACATCACTCATATACAGGGCTGCT
GGGTAGTGAATCCCTAGAGTGGCTTGTTCCCAGCTCTCTCTACAACCCAGACATCCTCTATGGTCA
CAACTCCCACCAACTAGAAGGGTCTCTGTATCACTGCAAAGAGACAGATTGTGACATTATGAAGA
CAAATAATGGAGCCATTTAAATCTATGAAAGTGTCTCCAAGTTTAGATTTTTTGGTATTAAAATTG
TTTTTGGGGCCGGGCGCGGTGGCTCACGCCTGTAATCCCAGCACTTTGGGAGACCGAGGTGGGTGG
ATCAACTGAGGTCAGGAGTTCGAGACCAGCCTGACCAATATGGTGAAACCTCTTCTCTACTAAAAA
TGCAAAAATTAGCCGGGCATGGTGGCGAGTGCATGTAGTCCCAGCTACTCGGGAGGCTGAGACAG
GAGAACTGCTTGAATCCAGGAGGCAGAGGTTGCAGTGAGCCGAAACTGTGCCACTGCACTCCAGT
CTGGGCAACAGAGTGAGACTGTGTCTCAAAAAAAATATTTTTCTGACAGTAAAAGTTATATAT
GTTATTATAGACAAATTAGAAAAGGGAGAAATAAAACTCATAATCTCAGAGATTACTTTTGAAAA
TCATTTTCATTATGGCGATGCCATTCTGTTTCCTAATCTGTTACATGTGCAACTTCCCCCTCTCATTA
GAGACGGTTTTCTGAAATTTCACTGTGATGTGCTTTGGGTGTAGATCATCATTTATTCATCATGCTG
AGTACTCAGAGAGCACTTTCAATCTGAAAATGCAGATCCTTTTGTTATGGGGAATTTTCTTATATG
ATTTATTTTGGAATTGTGTGGCCCTCCGTCCCACCTTCCCCTATTTTTTCTGTACAGAACTCCTATTA
TTTGGTCACCAGGTCAGTCCTCTAATTTTTCCTAGTTTTTTTTTTCCCTCTCCTGTTTTCTTTATTTTT
CTTCTAGTATTTGGGAAATCTTACTGTTTTGTAAGCTTCCTATTGAATTTATTTTAACTGCCATGTCT
GTTAATTACCAGCAACTCTTTTGTGTTTTCTGATAATTCCTTTTTTGTGAAGTTCTGTTTTTAATTTA
TAGATGTCATAACTTGTTTCCCCAAAGCCTGTGCTCTTAACCATTACTCTTAAATGTGTATTTATGTG
TGTGTGTATATATATGTATGTATATACTTTTTTTAAAGTTTGCTGATATTGCCAACATTATCTCTCTT
CCTTTTGAGTTCTTTTTTTCAGTTTGTTTATATCTTTGTTATAGTCTGTCTTTAATGAGAGTGGTTTG
GTTTTCTCAAATCCCTAGAGATTCTTGGCTGAAATCTAACAATTTGATTGGAAACTCCAAGTGCCA
GGTCAGGGCTTGTCATCTGGTGAGTTTTACTGTAACATGACCATGTAGGGGTGAGGTGACATGTTG
AGGAATTCATTTTGGTATTCTACTCATACTTTTGTGGTTTTGTTTTTTCACGAGTTGTTTTGTTTTGC
TTTCAATCAGGCATAGTTATTGAACGTGGCATTTGTTGAGCAGTTACTATGTGTGGGACGCAGTTC
TAAGTGTTTCATGCGAATTAGTTCAGTGAATCCTCATGATAATGGATTCTCTGGGAACTATTATTGT
CCCATCTTGCAGATGTGAGAACTGAAGCACAAAGGGCATAAGTAACTTGCCCCAGGTCATGCAGC
CAGGCAGAGCCTGGCTCCACTACAGTATCCTGCCTCCCAGATGATGATCTCAGTGTTCTCATAGGA
CCTCATGGTATAGCAGAGCTTTCCATATGGTGTGCTGCAATATTGATCTACTGAGGAGCCTGGGCA
GGGCCAGAATAGCATCTACCCTGAGCAGCCTTGTTCACTTGTGTGGGTGCTATCCAAATACTATAA
TTTTCTAAGTATGTCCTGCTGTGAAAAAGGTTAAAATTTGTTTTTCTCCCAAAACTTACTCTTCAGA
AAAAAAAGGTAGACATATTTCAGCCCTTAACAAGATCTCTCAGATTCTGGGAGTCATTCTCAATTT
AATTTATTTTGAATATCCTGGCATAGCATTTTGATCAGTGCTGGTTTTGAATGCCTAGAGAAGTCAC
TAGAAAGAATCAATTAAAAAAAAGATGCTAGGACATGTAACACTGGTGTAGCAAAATTATTCCTG
GGAAATGACCTCATTGTTGCAAGAATTGGAAGTCATAAGTTTATAAAACAAGTCTTTGTTCTAGAG
ATCACAATTAGACAATTTCAGGACAAATGATTTTCTAAAGTGAAAGTATATATGGATTAATGTATT
GTACGTGGGCTTAAATGTGCTCAGACAGAAGTGAAGATGCTAGTTCTGGAAGACTGTATTAAATAT
CTCTAAGTGGCTCTTGTGATAACATTCCCATCAAGAATGCATGGGAGGCTGGGTCTGGTGGCTGAC
GCTTGTGATCCCAGCACTTTGGGAGGCCGAGGCAGGCAGGTCACTTGAGTTCAGGAGTTCAACAC
CAGCCTGGGAAACATGGTGAAACCCTGTCTCTACAAAAAATACAAAAATTAGCCAGGTGTGGTGG
CATGTGCCTGTAGTCCAAGCTACTGGAGGGGCTGAGGCTGGAGGATTGCTTGAGCCTAGGAGGTT
GAGGCTGCAGTGAGCTGAGATTGCGCCACTGTACTCCAGCCTGGGTAACAGAGCGAGACCTTGTTT
CAAAAGAAAGAAAGAAAGAAAGAAGAGTGCATGGGAAGAGGTGGAATACAATTTTTTTCA
TGATATTTGAGAATGGAAAATATTTTAAGATAAATATTTCCTTTATTATATGATTGCAAATGTGTA
TGTATAATTGTACTTTCAAACAGATAGTTGACTATTTCATAAACATCTATATTTATTCAAGCTGGTA
GTAGTAACATTTGGAGCTTCTCACTGAGAAAATGAGGATCACCTTAAATAGGATTGTCTTATATTT
TGATACTATATTAATAGATATCTTAATCTTGGATCATCTTTGCTTTGTTAGGTTAAATCCAACTTGA
CCGTGCCTATGTATTTTTATTATACTGATGAATTCAGTTTTGCTAGGGTTTCATTTAGGATTTTTGCAT
CAATTCAGAAGTGGAAGTAGAGTTAGTGGTTTCTTTTTTGTGTCAGGTTTTGTTGTCTTGGTTGTGC
TCACTTCATAAAATAATGTGGTTAGTTTTGCCATCTTTTTCTATGCTCTGGAATAGTTTATAGAATG
TTGGAAAGATCTTTCTGTTTAGCTGGTCCCTGAAGCCTTTTGTGGAGGCATTTAAAAAATTATTTCC
ATAGTTTACATTTTTTGCTGAATTATATCTAGGTGTGTGTCTTTAAAATGTTTTGAAATTAATTTTGC
CTGAAATATAGTGAGCCCTGAAACTGCATGCTGAGATGATTATTCACTCCAGGAGGCTTTCCTTGT
TCCTATTTTAGCTTATTGCTTTTGTTCTACTTGATTTATGTCTCAAAAATATCTTTAATTACTGTGTT
GAATCCCTGATTCAGCTTTTCTCTCATCCTTTTCATTTTTTTGTCCTTTTTCTCAGGCTTTGGAGCTC
TTCTGCATTACCAGTTTAGACACTTTTGCAATTTTAATCCTACACCTTAATATCTCCAACATAGATT
ATTGTTGATTGTATTTTTAGTTTTTTTGCAATGCTGTCTCTGTTTCAATCAGTACCCTTTTCTTCCAA
GCTTGTTAGTATAGTATAGTATAGTATTTAGTAGCATTAAACCTCAATGTAACCCTGTGAGATAGT
AAATGGTTTCTTGATCCCATTTACCAATGAAGAAATCAAAACTTCTTTTTAAAAAATAAAATAAAA
AAATAAAGATAGGGTCTTGCTATGTTGCCCAGACTGGTCTCAAACTCCTGGGCTCAAGTGATCCTC
CCACCTCAGACTCCCAAAATGCTAGGATTATCAGTGTGAGCCGTTAAAGAAAATTAAGCGATTAGT
CCAAGGCCACACAGCTAACAACTGAAAAAGCCAGAATTCAAACCCAGATCTACTTGAGGTCAAAA
CCCAATTAACCTAATCAGTTGTCTTTTTGCATCTCATTTTCTTTTCCATTTATTTCATCCCATTGTAC
TGCATTTCTACGCTTGTGTTCACAGGACCCATCCTTTTCCTGAACCTTTCTGAATAGAACTTTTCTA
AAATCTTTATTTTATAGGAAGTCATTGCCAGCTAGATGCTCTTCCTTGGAGTATAGTGGTGAAGG
ATCTGCACACACAGAATGTGTGGCCGTCTTGTGGCCTCTGGTCACTGTTTCCTGGTTGATTCCTTCT
CAAATCTGCAGCTTGAGGTCAGGTTGATGCATACACCTCACAGAGTTCCTGGTGGCATATAGGCAT
TAAGTGTTCTACTCTATTGAACCTGACCCACCTAGTTACAGTTTCTTCTTTTTTGGCACTCTAATTCT
TTGACAGGCTAAAAGAACCCCAGACTCTTCCTATCTCCACATTTTCAGGGCTTTATTTTTGGGGACA
TTCCTCAGGATACAGTGTGCCAGCACTGCCAGACCTTCTCTTTTCCTGCCTATTGTCTTCTGGGAGT
TGTGATCTCTAAGCACACAGAAGTAGAGGAGGTAATAATTCTCCTCTGCTTAAATTAGTGCCATCC
CTTCTCAGGCTGTCTTCCTGCCTCTCTTAATCTAGGTGAAGGGCTCTGTGTCATGAGGCAAAGCAG
```

-continued

Sequence Information

```
GGTGGGCCAGTTCTTATTTCCTCAGCCCAGCTTCTCTGGTCTTGTAGTTTCTGGACATGTTTCCAAG
ATTCTGGCATTATAAGCTGTCTGTCCATCTTGGTTTCTTATGTTGTGATGGGGTTTCATCTTGTTCTG
TGTTTGTTGTTTTCGCAGGGTAGTGGTCCAGAGAAGCAGCACTAGTGGCTGTTAGGAAGACACCAT
TGTATTCTGGATGCTTGTCACCATGGCTGATCTTTGTAGTTGCTAAATTCCAGGAACCTGCACAGG
AATCTGACCTGGAGTAAAATGAGTTAAGGTTAGGGACAACTCTTGAGTAACTAGGTCATGAGTTA
AGACTAGGAAAACCGATTCTGCAACCCTGAAAACAGTGATTGACCTCAACATCTTAATGCAGCCA
TTGTGTATTTATATTAACTCTTTTTTTTGTTTGTTTTGTTTTTTTTGAGATGGAGTCTCGCTCTGTCAC
TCAGGCTGGAGTACAGTAGCATGATCTTGGCTTGCTGCAATCACTGCCTCCCGGGTTCAAGTGATT
CTCCTGCCTCAGCCTCCCAAATAGCTGGGATTACAGGCGTGTACCACCATGCCTGGCTAATTTTTGT
ATTTTTAGGAGAGACAAGGTTTCGCCATGTTGGCCAGACTGGTCTCGAACTCCTGAGCTCAGGCAA
TCCACCCACCTCAGCCTCTCAGAGTGCTCGGATTACAGTCATGAGCCACCACGCCCAGCCTGTATT
AAGCCTTACCAGAATAATTAGTTTTACTTACATTTAGATGAGGGTTTGAATATAAGGAGAAACCTA
ATTTGCATTTCTTTCTCCAGAGACTTCTGTGTTTATTGACAATTTCATTTCCTGAAGTTGAAATTAAT
AATGTGCTATAATAATGTAATTATAACCCAAGGACCTGGACTAACTAATCACAGAGCAGTGATTCA
TTTTTTCCCACTTCTCTCACTTTACTTCACTTAGCCCTGTACTTCTTTATAAGGATAAGAATACTGGT
TGCATTCAAATCAATAAATGTTGAGTCCATTAGTACAGAAAACCATGAAAACAATCTAGCTTCCTG
GTGTTGGATTATATTTGGTGATCGGTAAAGGCAAAGGCATAATTTTTAGATTTTGATGTTTGATAA
AGCTAACTTTTAAAAATTTCTGTTATAATCTGAGAGAAATCCATGATTCATTCCTTGCCACCTCTAC
CCATCATCTTAGCATAGTTATTCTCAGTGCGCTGTCTGGGGACCACCTGCAGCAGTGGAGCATTTG
TTAAAAATGCAATTTTCAAGGTGATGGCTGCACAACATTGTGCCATGTTCTAAATGTCACTGAATT
GGATACTTTAAAATGGCTAATTTCATGTAATGTGAATTTCACCACAATCTTAAAAATTCAGTTTCTC
AGACTCTATCACAGCCCAGCTGAATTAGAAACCCAGAGGCCCAAAAATCTCCATTTTTAACAAGA
ATTCAGGTGATTCTTTTGTACACAGAAATTTGAGAACCTCTGAGCTAAGGTAACTCTTATTCAAAC
TTTAGGAATTTACCTTACAAGGAATGTATGTGGTTATTTAAATTTGACATATATTTATGTTTATACA
TATATCCTCCTCACTAGGAGGAATATATATATGACAGCTGGAAACCAACTGGGTTTGAAGTTCAGG
CGCTCCTAGGTAGTTTTCATTTCAGGTAAATGCACCTATTTCTAGAAATAGACTCTTCAAAAAGCT
GACGAGAAAAGTTTAAATTTAATTATTCTGCTTTCCATGTTCTTACTGCATATAAATCACAACCTTA
ATTGATTCATGCCATTTCTTCTGCAGTGTGTGATTAATACCACTGTTAACAAATATTGTCTTTCTCA
TTACACACATACTATTCTGGGTTTGTTTTTTTATTTCTATTTTTTATTTTTATGGGTATATAGTAGGT
ATAAATATATTTATGGAGTACATGAGATATTTTGATACAGGCACACAATGCATAGTAATCATAT
CTGGGTAATGGGGATATCTATGCCCTCAAGCATTTATCATTTCTTTGTGTTACCAACATTCCAATTA
AACTCTTTTGATTATTTAAAAATGTACAATAAATTATTATTAACTGTAGTCACCCTATTGTGTTATT
AAATACTAGCTCTTATTCATTCTATCTAAGTATATTTGTGTACCCATTAACCATACCCACTTCCCCC
CTACCCTCACCCCACTACCCTTTCCAGCCTCTAGTAACCATCCTTCTATTCTCTACCTCTATGAGTTC
TATTGTTTTAATTTTTAGCTCTTACAAATAAGTGAGAACATGTGATGTTTGTCTTTGTGCTTGGCTT
ATTTCACTTAATATAATGACCTCCAGTTCCCTCCATGTTGTTGCACGTGGTTGATCTCATTCTTTTAT
GTGACTGAATAGTACTCCATTGTGTATATGTAGCACATTTTCTTTATCCATGCATCTGTTGATGGAC
ACTTAGGTTGTTTTCAAATCTTGGCTATTGTGAATAGTGCTGCAATAAACATGGCAGTGCAAGTGT
ATGTTTGATATACTGATATTCTTTCTTTGGGTATATACTTAGCAGTGGGATTACTGGATCATGTGG
TAGTTTTGTTTTTAGTTTCCTGAGGAACCTCCAAACTGTTCTCCATAGTGGCTGTACTAACTCACAT
TCCCACCAACATTGTACAAAAGTACCCTTTTCTCCACATCCTCGCCAGCATTCATTATTACCTGTCT
TTTGGATAAAAGCCATTTTAACTGGGGTGAGAGGATATCTCACTGCAGTTTTGATTGGCATTTCTCT
GATAGCCAATCATGTTGAGCACCTTTTCATATACCTGTTTGCCGTTTATATGTCTTCTTTTAAGAAA
TGTCTATTCAGATCTTTTGCCCATTTTTAATCAGATTATTAGATTTTTTTCCCCATAGAGTTGTTTG
AGTTCCTTATATAGTCTGGTTATTTGTCCCTTGTCAAATGGATAGTTTGCAGATATTTTCTCCCATTC
CATGGCTTATCTCTTCACTTTGTTGGTCATTTTCTTTACTGTGCAGGAGCTTTTTAACTCAATGGAAT
CCTATTTGTCCATTTTTGCTTTGGTTACCTGTGCTTGTGGGATATTACAAGAAGTCTTTGCCTAG
TCCAATGTCCTGGAGAGTTTCCCCAATGTTTTCTATTAGTAGTTGCATAGTTTGTGTTCTTAGACTTT
AAGTCTTTAATCCATTTTGATTTGATTTTTCTATATGGTGAGAGATAGGGGTCTAGTTTCATTCTTCT
GCATATGGATATCCAGTTTTCCCAGCACCATTTATTGAAGAGACTATCCTTTCTCCAGTGTCTGTTC
TTGGTACTTTTGTTGAAATGGGTTCACTGTAGATGTATGGATTTATTTTTGGGTTCTCTATTCTCTT
CCTTTTGTCTAGGTGTCTGTTTTTATGCTAGTACCGTGCTGTTTTGGTTACTATAACTCTATAGTATA
ATTTGAAATCAGGTAATGTGATTCCTACAGTTTTGTTCTTTTTGCTCAGGATAGCTTTGGCTATTCT
GGGTCTTTTGTGGTTCCATATAAATTTTAGAATTATTTTTTCTCTTTCTATGAAGAATGTCTTTGGTA
TTTTGATAGGGATTGCATTGAATCTGTAGATTGCTTTGGGTAGTATGGACGTTTTAACAATATTGAT
TGTTCCAATCATGAACATGAAATATCTTTCCATTACTTTGTGTCTGCTTCAATTTCCTTCATCAATGT
TTTATAGTTTTCATTGTAGAGCCCTTTCCACTACTTTGGTTAAGTAGTGATCTACTTACTACTTATTCC
TAGGTATCTTATTTTATTGGTAGCTATTGTAAAAGGGATAACTTTCTTGATTTCTTTTTCTGATTGTT
CACTGTTGGCACATAGAAATGTTACCGATTTTTATATGTTACTGATTTTTGTATGTTGATTTTGTATC
TTGTAACTTTACTGAATTTGCTTATCAGTCCTAATAGTTTTTTGTGGAGGCTATAGGTTTTCCAA
ATGTAAGATCGTATCATCTGCAAACAAGGATAATTTGACTTCTTTCCAATCTGGATGCCTTTA
TTTCTTTCTCTTGTCTGATTACTCTAGCTAGCACTTTTTAATTCCAGGTTTTTTAAATCCAAGGATGA
CACTTCTAATCCTTCTCTGATAGAACATGATCAGAGTTTGAGTCCCAACTTTCCTGCCAATGAGTTA
TATGTAGAGTCTAGCCTCGGTTTCATTATCTGTTAAACGCAAGTTGATTGACCATTCATTTATTCAC
TCCGTCTTTCATTGCAGATAAAAGATAACTGGGACATATTGCTCCCTTAGGAAACTCACACTCTA
GTGAAGTAGACAGGTACATGTATTATTATTATGCAGTGGGAATATTAGGATGAAGCCCAGGGTGC
TGTCTGCACACAATAAGAGCCACCTCTCAGAGCCCAGGGTGTGGGGAGGCTTTCTGAGATGGAAA
GGTTGGGAATGGCTTGGCCAGATAAGCAGAACACAGGTGGGGAGGAGATTGGGCAGCATTCTAGC
CTGTGAGAAAGGAACATAAATAAAGACAGGGAGGTTGGGAGAGCAGTCCTGGAGGGGGTCTGC
ATTGCTGGAGCCTGGACTGCAAGGTGGAGAGCAGCGAGATGTGAGGCTAGAGAGCATGACCCAG
GGGTCCACTCAGAAGGGGCCTGTGCACATGCAGGGAGGAATTGGAAGGGTCTCATGGTGACAGT
GAGGCACTTAAAAGTTTTAAGCAGGATCAGATTTTCACTTTAGAACTGAAATGGAGGGTGATTGG
AAGCAGGCCGACCTTTTAGGAGGCTCTGACAATAAAGAGAGGAGAGAAGATAAGGAGCACTTGA
GTAAAGGCAGAGGGAAGGTGGATGAGATAAGGGACAGATTTAAGAAATACATAGGAGGGGTG
GAGCCAAGATGGCCGAATAGGAACAGCTCCAGTCTACAGCTTCCAACATGTGCGACGCAGAAGAC
GAATGATTTCTGCATTTCCAACTGAGGTACTGGGTTCATCTCACTGGGGATTGTTGGACAGTGGGT
GCAGGACAATGGGTGTGGTGCACTGAGCCTGAGGCAAAGCAGGGCGAGGCATCGCCTCACCCGGG
```

-continued

Sequence Information

```
AAGCGCAAGGGGTCAGGGAATTCCCTTTCCTACTCAAAGAAAGGGGTGACAGACGGCACCTGGAA
AATCGGGTCACTCCCACCCTAATACTGCGCTTTTCCAATGGTCTTAGCAAACGGCACACCAGGAGA
TTGTATCCCGCGCCTGGCTCAGAGGGTCCTACGCCCATGGAGCCTCGCTCATTGCTAGTACAGCAG
TCTGAGATCAAACTGCAAGGTGGCAGCGAGGATGGGGGAGGGGCGCCCACCCATTGCCAAGGCTTG
AGTAGGTAAACAAAGTGGCCGGGAAGCTCGAACTGGGTAGAGCCCACCGCAGCTCAAGGAGGCC
TGTCTGCCTCTGTAGACTCCACCTCTGGGGGCAGGGCATAGCTGAACAAAAGGCAGCAGAAACCT
CTGCAGACTTAAATGTCCCTGTCTAACAGCTTTGAAGAGAGTAGTGGTTCTCCCAGCACGCAGCTT
GAGATCTGAGAACGGACAGACTGCCTCCTCAAGTGGGTCCCTGACCCCCGAGTAGCCTAACAGGG
AGGCACCCCTTGTAGGGGCAGACTGACATCTCACATGGCCGGGTAACCCTCTGAGACAAAACTT
CCAGAGGAATGATCATGCAGCAACATTTGCTGTTCACCAATATCCGCTGTTCTGCAGCCTCCACTG
CTGATACCCAGGCAAACAGGGTCTGGAGTGGACCTCCAGCAAACTCCAACAGACCTGCAGCTGAC
GGTCCTGACTGTTAGAAGGAAAACTAACAAACAGAAAGGACATCCACACCAAAACCCCATCTGTA
AATCACCATCATCAAAGACCAAAGGTAAATAAAACCACAAAGATGGGGAAAAAACAGAGCAGAA
AAACTGAAAATTCTAAAAATCAGAGTGCCTCTCCTCCTCCAAAGGAATGCAGCTCCTCACCAGCAA
CGGAACAAAGCTGGATGGAGAATGAGTTTGATGAGTTGAGAGAAGAAGGCTTCAGACGATCAAA
CTTCTCCGAGCTAAAGGAGGAAGTTCGAACCCATGGCAAGGAAGTTAAAAACCTTGAAAAAAGAT
TAGATGAATGGCTAACTAGAATAACCAATGCAGAGAAGTCCTTAAAGGACCTGATGGAGCTGAAA
ACCACGGCACGAGAACTACGTGACGAATGCACAAGACTCAGTAGCCGATTTGATCAACTGGAAGA
AAGGGTATCAGTGATTCAAGATCAAATGAATGTAATGAAGTGAGAAGAGAAGTTTAGAGAAAAA
AGAATAAAAAGAAACGAACAAAGCCTCCATGAAATATGGGACTATGTGAAAAGACCAAATCTAC
ATCTGATTGGTGTACCTGAAAGTGACAGGGAGAATGGAACCAAGTTGGAAAAACACTCTGCAGGAT
ACTATCCAGGAGAACTTCCCCAGTCTAGCAAGGCAGGCCAACATTCAGATTCAGGAAATACAGAG
AATGCCACAAAGATACTCCTTGAGAAGAGCAACTCCAAGACACATAATTGTCAGATTCACCAAAG
TTGAAATGAAGGAAAAAATGTTAACGGCAGCCAGAGAGAAAGGTCAGGTTACCCACAAAGGGAA
GCCCATCAGACTAACAGTCGGTCTCTCGGCAGAAACTCTACAAGCCAGAAGACAGTGGGGGCCAA
TATTCAACATTCTTAAAGAAAAGAATTTTCAACCTAGACTTTCTATATCCAGCCAAACTAAGCTTCA
TAAGTGAAGGAGAAATAAAATACTTTACAGACAAGCAAATGCTGAGAGATTTTGTCACCACCAGT
CCTGCCCTGCAAGAGCTCCTGAAGGAAGCACTAAACATGGAAAGGAACAACTGATACCAGCCACT
GCAAAAACATGCCAAATTGTAAAGACCATCGAGGCTAGGAAGAAACTACATCAACTAACGAGCA
AAATAACCAGCTAACATCATGACAGGATCAAATTCACACATAACAATATGAACCTTAAATGTAAA
TGGGCTAAATGCTCCAATTAAAAGACACAGACTGGCAAATTGGATAAAGAGTCAAGACCCATCAG
TATGCTGTATTCAGGAGATGCATCTCACGTGCAAAGACACACATAGGCTCAAATAAAGGGATGG
AGGAAGATCTACCAAGCAAATGAAAAACAAAAAAAGGCAGGGATTGCAATCCTAGTCTCTGATAA
AACAGACTTTAAACCAACAAAGATCAAAGGAGACAAAGAAGGCCATTACATAATGGTAAAGGGA
TCAATTCAACAAGAAGAGCTAACTCTCCTAAATATATATGCACCCAATACAGGAGCACCCAGATTC
ATAAAGCAAGTCCTTAGAGACCTACAAAGAGACTTAGACTCCCACACAATAATAATGGGAGACAT
TAACACCCCACTGTTAACATTAGACAGATCAATGAGACAGAAAGTTAACAAGGATATCCAGGAAT
TGAACTCAGCTCTGCACCAAGCGGACCTAATAGACATCTACAGAACTCTCCACCCCAAATCAACA
GAATATACATTCTTTTCAGCACCACACCACACCTATTCCAAAATTGACCACATAGTTGGAAGTAAA
GCACTCAGCAAATGTAAAAGAACAGAAATTATAGCAAACTGTCTCTCAGACCACAGTGCAATCAA
ACTAGAACTCAGGATTAAGAAACTCACTCAAAACCATTCAACTACATGGAAACCGAACAACCCGC
TCCTGAGTGACTACTGGGTACATAATGAAATGAAGGCAGAAATAAAGATGTTCTTTGAAACCAAT
GAGAAAAAAGATACAACATACCAGAATCTCTGGGACACATTCAAAGCAGTGTGTAGAGGGAAATT
TGTAGCACTAAATGCCCACGAGAGAAAGCAGGAAAGGTCTACAATTGACACCCTAACATCACAAT
TAAAAGAACTAGAAAAGCAAGAGCAAACCCATTCAAAAGCTAGCAGAAGGCAAGAATAACTAA
GATCAGAGCAGAACTGAAGGAGATAGAGACACAAAAAACCCTTCAAAATATCAATGAATCCAGG
AGCTGGTTTTTTGAAAAGATCAACAAAATTGATAGACCGCTAGCAAGACTAATAAAGAAGAAAG
AGAGAAGAATCAAATAGATGCAATAAAAAATGATAAAGGGGATATCACCACTGATCCCACAGAA
ATACAAACTACCATCAGAGAATACTACAAACACCTCTACGCAAACAAACTAGAAAATCTAGAAGA
AACGGATAAATTACTGGATACATACACCCTCCCAAGACTAAACCAGGAAGAAGTTGAATCTCTGA
ATAGACCAATAACAGGCTCTGAAATTGTGACAATAATCAATAGCTTACCAAACAAAAGAGTCCA
GGACCAGATGGATTCACAACCGAATTCTACCAGAGGTACAAGGAGGAACTGGTACCATTCCTTCT
GAAACTATTCCAATCAATAGAAAAAGAGGGAATCCTCCCTAACTCATTTTATGAGTCCAGCATCAT
CCTGATACCAAAGCCAGGCAGAGACACAACCAAAAAAGAGAATTTTAGACCAATATCCTTGATGA
ACATTGATGCAAAAATCCTCAATAAAATACTGGCAAACCAAATCCAGCAGCACATCAAAAAGCTT
ATCCACCATGATCAAGTGGGCTTCATCCCTGGGATGCAAGGCTGGTTCAATATATGCAAATCAATA
AAGGTAATCCAGCATATAAAGAGAACCAAAGACAAAACCACATGATTATCTCAATAGATGCAGA
AAAGGCCTTTGACAAAATTCAACAACCCTTCATGCTAAAAACTCTCAATAAATTAGATATTGATGG
GACGTATCTCAAAAGAATAAGAGCTATCTATGACAAACCCACAGCCAATATACTGAATGGGCAGA
AACTGAAAGCATTCCCTTTGAAAACTGGCACAAGACAGGGATGCCCTCTCTCACCACTCCTATTCA
ACATAGTGTTGGAAGTTCTGGCCAGGGCAATTAGGCAGGAGAGGAAATAAAGGGCATTCAATTA
GGAAAAGAGGAAGTCAAATTGTCCCTGTTTGCAGATGACATGATTGTATATCTAGAAAACCCCATC
GTCTCAGCCCCAAATCTCCTTAAGCTGATAAGCAACTTCAGCAAAGTCTCAGGATACAAAATCAAT
ATACAAAAATCACAAGCATTCTTATACACCAATAACAGACAAACAGAGAGCCAAATCATGAGTGA
ACTCCCATTCACAATTGCTTCAAAGAGAATAAAATACCTAGGAATCCAACTTACAAGGGATGTGA
AGGACCTCTTCAAGGAGAACTACAAACCACTGCTCAATGAAATAAAAGAGGATACCAAATGG
AAGAACATTCCATGCTCATGGGTAGGAAGAATCAATATTGTGAAAATGGCCATACTGCCCAAGGT
AATTTATAGATTCAATGCCATCCCCATCAAGCTACCAATGACTTTCTTCACAGAACTGGAAAAAAC
TACTTTAAAGTTCATATGGAACCAAAATGAGCCCGCATTGCCAAGTCAATCCTAAGCCAAAAGAA
CAAAGCTGGAGGCATCACACTACCTGACTTCAAACTATGCTACAAGGCTACAGTGACTGAAACAG
CATGGTACTGGTACCAAAACAGAGATATAGACCAATGGAACAGAACAGAGCCCTCAGAAATAATG
CCACATATCTTTAACTATCTGATCTTTGACAAACCTGACAGAAACAAGAAATGGGGAAAGGATTCC
CTATTTAATAAATGGTGCTGGGAAAGCTGGCTAGCCATATGTAGAAAGCTGAAACTGGATCCTTTC
CTTACACCTTATACAAAAATTATTTCAAGATGGATTAAAGACTTAAATGTTAGACCTAAAACCATA
AGAACCCTAGAAGAAAAAACGTAGGCAATACCATTCAGGACATAGGCATGGGCAAGGACTTCAT
GTCTAAAACACCAAAAGCAATGGCAGCAAAAGCCAAAATAGACAAATGGGATCTAATTAAACTA
AAGAGCTTCTGCACAGCAAAAGAAACTACCATCAGAGTGAACAGGCAACCTTCAGAATGGTAGAA
```

Sequence Information

```
AATTTTTGCAATCTACTCATCTGACAAAGGGCTAATATCCAGAATCTACAATGAACTCAAACAAAT
TTACAAGAAAAACAAACAACCCCATCAAAAAGTGGGCGAAGGATATGAACAGACACTTCTCAA
AAGAAGACATTTATGCAGCCAAAAGACACATGAAAAAATGCTCATCATTACTGGCCATCAGAGAA
ATGCAAAACAAAATCACAATGAGATACCATCTCACACCAGTTAGAATGGCAATCATTAGAAAGTC
AGGAAACAACAGGTGCTGGAGAGGATGTGGAGAAATAGGAACACTTTTACACTGTTGGTGGGACT
ATAAACTAGTTCAACCATTGTGGAAGTCAGTGTGGCGATTCCTCAGGGATCTAGAACTAGAAATAC
CATTTGACCCAGCCATCCCATTACTGGGTATATACCCAAAGGATTATAAATCATGCTGCTATAAAG
ACACATGCACATGTATGTTTATTGCGGCACTATTCACAATAGCAAAGACTTGGAACCAACCCAAAT
GTCCACCAATGATAGACTGGATTAAGAAAATGTGGCACATACACACCATGGAATACTTGCAGCCA
TAAAAAATGATGAGTTCATGTCCTTTATAGGGACACGGATGAAGCTGGAAACCATCATTTTCAGCA
ATCTATCGCAAAGAGAAAAAACCAAACACCACATGTTCTCACTCATAGGTGGGAATTGAACAATG
AGAAAACATGGACACAGGAAGGGAAACATCACACACCGGGGCCTGTTGTGGGGTCGGGGGAAGG
GGTGAGGGATAGCATTAGGAGATATACCTAATGCTAAATGATGAGTTAATGGGTGCAGCACACCA
ACATGGCACATGTATACATATGTAACAAACCTGCACGTTATGCACATGTACCCTAGAACTTAAAGT
ATTAAAAAAAAAAAAGAAATACATAGGAGAGCTTGGACCACTTGATGTTGAGAGCTCTTTTTAC
TAGGGAAAGCTGATGGTTTTGTAATTCTGCCAGTTTTTCAGGATGTTGTCAGTGCTAATGAAAGCCTTT
CATGTTCTCCCCATGGCATGGATACATCTGCAAAGAGCTGGAAAGAGTGAAGCCCATGGCCAGAG
TACCCACATAATCCACATAGCAGTAGTGCATCAGAGTGCATAGATTCATAGTACACATGAGACGG
AGAGCAGAAGTGGTTTGGTTGTCACAGTGACTTGAGGGTGAAGTTTCCATTTAGTGAACAGGCATC
TGCAGTGCTCAGGCCAGTCCTGCAGTGAAGTGTCCTGCCTCAGATGTCAGTAGCACAACCATTAAG
GGACAGTGACCGGATCCTGTTCAATAACACATTTCTACTTAGACAAATAGAGCAATTTATTGCAGA
GTCTAAACTTTTAGCACTTATTATCTGAGCTTTCACAATATTACATGTGATTTAATACTCAAATGGA
GTTAATAATCTTAACTAATTCCTCTAAATCTTACGTCCCTTTTCCCCTTACATATAAGAATTTCCTTC
AAAACTGGTAGTTGGCAAAGAGAGAGCTCATTCAAGGTTTTAAATATACTTATGCAATTGGCAGA
CTTATAAAATATTATAGAAATTCTGTGCCAGGAACAAAGTTATATGTGCTAGGAAACCAATCTCAC
TGGGTTCTTCAGACACTTAAATGAATTTCTGACAAAGCTAAGGAAAAGCTGTTATGTGAATAAATC
AGTGAGTGTGTCCACATTCTATTACTCTTTGCAATTATGCATTTATTTGGCGCGTCTATCATAGAGG
AAAATTACAACCCATGCCTCAGAATAATGAGACTTGAATGAACTTTTCCATAGCCAGTCATTAATT
CATGCCACCTCTTTAGATTTCACCTGTTAATGTCCACACTGAGAGCATGTTGGATCACTTTAAAATT
TTATTAGTAATAGGTACTAATTTGTTGATTATTTTATTGAGTGAAAATAATAACCAATACATTTTAC
TGAACAGCCATGCTGATTTGGTGTCCCTGGCTGAGTTACAAAGCAGAGGTTCCAGGGCTGGGGAT
GGTAGTCCCACCTCCCCTCTTTGTCTCTGGCTGTTCTCAGGGATGTGTTGCCCTTTGGGTACTCGTG
TTGCTTCCCATGGGTTAAAGCATGGGCAGGCCTCCTGCCAGGGAACCCAGGATGGTGGGGAAGCT
GGTTGTTTACCTCCATCTCACTTTTTCCAGTGTAGAAACCATGAGTTGGGCCACAGTGGGTGGGGG
GTGTAGCAGATATGGACATTTGATTCTTTTACCATCTCCTCAGAGTTTTTCACTTCTCTGTGACCCT
GGGAAATGGAATCATCCTCATGTTTGAGTTCTGCGATGTTGCTGGTGATAATCTTGGCACCTTATATT
TGTTTTGGTTTTCTGTGGAGAGGAGTGAACCTAGATTGTGTCTGTGTTATCATTTTGGAACTAGAAG
TTCCGAAATCAATAACCAATACATTTTAAAACCACCCCACCCCGCACCAAAGGGTCTTGCATTTG
TATTCTCTGTGTCAAACCATTGAATTCATAATCCCAGAGTCGAAGGAAAAAATGCCTCTCAATCTC
TATGTTTATCAGATCTTCAATGTTTTATTATAGTACTTAATATATACTATGCTATAATGTCTTATTGT
TGATATTATGAACTTTTAGCAGGAGAAACATGAAGTAGTCATGATTTTCACAATTCTGTGAGAAGA
GAGCACTGTGGCCTTTCTATGAGTTTATAATTAATGAATATATATATTCATTATATATATAAGATAT
ATATATCATATATATGATATATATATCTTACATATATATATCTTACATATATATGATATATATATCT
TACATATATATATCTTACATATATATGATATATATATCTTACATATATATATCTTACATATATATGA
TATATATATCTTACATATATATCTTACATATATATGTAAGATATATATATATATCGAACTTCCTTGA
ACTGAGCATATTTATTGACTAAATTGCAAGAAACTTTCCAATTTGTTTGGGTTTACTTTAATCTCAT
CTTTTGCACTCCATTTTGAAGGTCACATTTAAGATGAATCCGTTTCTTATATTTTATGCTCCTCTCAG
AACTCACTGGAGCCAAAATTCTCTGTGAGGCAAGAGCTATGTTATGTGGACAGGCTGCACTGGA
GGATGAAGCAAAATGAAAAGTAGATTCTATGTAGAAATAATCACCTGGAAACTACAGTGACAGCA
AGAAGAAGGAGCTGAAATAAATTCAGGTTGTCACAAGCTGCTAAAAAAATGCATTTACTTACATT
GCTTCTTATCTGGTACCCATATCTGCTGTCTCCTACAGTCGTCTAGCCAAATATTTAAAGATATAGA
ATCTACAAAGACAAACTAATTATTAATGTGTCTGTGAACTCTGCAAACAAACATTATTGAATGCAT
TACTGTTAAGGACTCCTATTTGGACAAGTAGCTAGGTGAGCCCTGTCTAAGCATAAAGACCTATGCA
GGGCTTATCAAACTTCAAGACTCTGCTGACTAGAGATGCAAAATAAAATCATGAGGGAATTAGCA
GGCACCAGTGAGACCTGCAGGCTTTGAGAAATCTCTTGAGGTAAGTGAGAAAGACAGCTTCCTAT
GTGAGCAGAGGTTCATTTATTTTGATTCAAGTTAAGGGTTAAGGGCAACTTGACATTTTGTATTAC
ACCTATCCCTTCCCCACCCCTCTTTTTTTTTTTTCTTAGGAGTTGTAAGGATCTTACAAGATCATCT
GATCTTAGAAAGAAATAAAGACCCTGGCCAGGCACAGTGGCTCGCACCTGTAATCCCAGCACTTT
GGGAGGCAGAGGCAGGCAGATCACTTGAGGTCAGGAGTTCGAGACCAGCCTGGCCAACATGGCA
AAACCTTATGTCTACTAAAAATACAAAAATAACCCAGCATGATGCCTTGTGCCTGCAATTCCAGCT
ACTTGGGAGGTTGAGGCAGGAGAATCGCTTGAACCCGGGAGGCGGAGGTTGCAGTGAGCTGAGAT
AGCGCCACTGCACTCCAGCCTGGGCAATAGAGTGAGAATCCACCAAAAAAAAAAAAAAGAGAG
AGAGAGAGGAAGGGATGGAGGGAAAGAGAGAGAGGCGGGAGGAAGGGAAAGAGAGGGAGGG
AGGGAGGGAAAGAGAGGGAGGGAGGTGGGGGGGAGAGACAGAGAGAAAGACAGAAAGAA
AAGAAAGGAGGAAAGAAAAGGAAGGAAGGAAGGAAGGAGAGAAGGGGGAGGGAGGGGAG
GGGAGTGGAGGAGAGGGAGGAGAGAACGAAAAATACCCAGAGGGGACGTTGGGACTTTTG
TAAATACTCAGGAGGCAGATGGCCTGAGTCCAACACTCACTGATGCCTATGCAATCTTGGGTAAG
ATACTTAAACTTCCAGTGCCTTATTTTCTTCATCAGCAAAGTGTGGATAAAAATTATAACTACCCG
ATAGTACTGATGAGATTGCAGCACTTCCTGACACATACTGAGTGCTTTATTGTTATTAGGTTGTGTG
ATATAATAATAGCTAAGTGGCTAGAGATTAAACCATTTCTAGCCTTTGGTCTCCGGTTTGCTTTTA
TTTGTTTTTATGGCTTCTGTTTTCCTCTTGTTACTCTCATCAGGCTATTTGCTACTACCTATGCTTATTA
TTCATTCATTCATTCACTTGTTCACTCATCAGCGGCACACCTGCCACGGGCCAAGCTCTCTGCTAGG
CCCTGGGAAACAGTAGGGAATGAGGCTGACTATGCACAGGACGAAGTGGCTTATTTCCTAATTCA
ATAGTCTGTTAATGAGCATCAGGAATGTCAAGAATCCTCCTTCTTCTACTGAAGATGGTTAGCAGC
CTGTAACAATTATTATGACACATTTTTCATTTATATTTTAGCTTCTGAAAATCATGAGGAATTATTT
TTTAAAGCAGTCTTTGATTTTGATTACTGAGAATACAATATGTTTTGAGAACCTCATTATTTCCTCT
GATACTTTCTTCTTTTCTTCATATTTCTTATATTCTTTATGTTTAAATTGAAGGTGATTTATTATGCA
```

-continued

Sequence Information

```
AGCTATTGGATATGATTTTGGAGTTTTTTGTACCATTAATTATTGAGGGAGCAAAGTTGAAATTCTG
CTTTTAATTCATCTCCTTTTTTTGAAAAATGTATGACTTAAAAATGAAATTAAATAATCAAAAATTA
AATGTGATGCTTAAAGGTCATTTTGTTTAAAGTGATGAATGCTAGTTTACCATATACTACTAGAAA
AATCAAAATTATATAATCTATTTGCCATGTATTATTATTTAATTTTAATAAATATTTATGGTTTCAT
AAATATACAAGGTTCTTCCTAAAGTTATCTATCTACCACATTTTCTCATTTATTTATTTATTTTTATT
TTTTATTTTGGAGACAGAATCTCGCTCTGTCACCCAGGCCGTAGTGCAGTGGCGTGATCTCAGCTC
ATTGCAACCTCTGCCTTCCCAGTTCAAGTAATTCTCCTGCCTCAGCCTCCACCTCACAAGTAGCTGG
GATTACAGGTGCCCACCATCACGCCTGCCAAATTTTTGTATTTTTAGTAGAGACAGGGTTTCACCA
TGTTGGCCAGGCTGGTCTCAAACTCCTAGCCTCAGGCAATCCACCTGCCTTGGCCTTCCAAAGTAA
CATTTTCTCTTTCATTAACTATTCATTCATTTTCCTATTTTTTAACTCTGAAAGTTCTTAAGTATATA
TATTATTATAATATCAGCAATCATATTTATAACAAAATATTAACCATTAATGATTGTAGTATTTTAT
TTTTATTATACTAAACAGCTATACTTTGATTAAAATTGTAACATATATAGTAAAGGACATAGGAGG
TTTTTTGCTCCAAATGACATCCAGAATGCTTATCTATATTTGAAAGAGACTATTCAGATATTAATAC
TAACACCAAATAATGTGCCTTGTTTTACTGTGATGTAGCTACACTGATTATCTGTGCTGGTAAACTG
TACCTCACCATTATTGATGTTCCAGGATGCCAGAAATGGCATTAAAGTAAGCATTGGGCTATTTGG
TCTTCTAGGGCTAATGCAGAGACCATTTGGGTTTTTTGGGAGAACTCAACTCCCTGTGGTCCTATG
ACCAAGACCCTCATTGTCTGGCTGTCAGCTTAAGGCTCATTCTAGCTTCTGGAGGCTTCCCCTTATT
CTTTGACTTTCTCCTTCCACCTTCAGAGCCTTTAACAGTGGGTTGAGTCCTCCTCATGTTTTGAATCT
CTCCTCCTTTTCTTCTCTCGTCACTCTAGTCTATTCTTCCTTCTTTAACTTTTAGAGCTCATAACC
TATGCCCTCTCCAATAATCCAGGATAATCTCCCTATATTTAGGTCAGCTAGTTAGCAACTTCAATTC
CATGGCAACTTTAACTCCCCGTTGCCATGTAAGGTAACATATTCACAGGTTCTGAGGTTAGGACAT
CTTTGGGACCATAATTCCATGCAGTCACTTTGGAATGATTGAAATTTTTTAGTATTCTTTCTGATC
ACCTCCCATCCTCTACTAGTTCTTTTCCTAGGAGAAACATTCACCACACATGCAAATGCTCGTCCTA
ATACTTGTGTGATAGTCCCAGTGTCCCCATCCACAAGGCAGCTCAGCAGACTTCTCTGAAAAACAG
ACAATAGCGACTCTATCGCCATTGACCTCCACAAAAAAAAGTAATTGTTGTGGGCCTGGGAATAAT
TGTTTAAAATATTGTGACTTGTGAGTGACTGTGAAGATAAGAACAACTTTGGGCAAATAGATGCTT
TTAACAGCATCACACCTCAGAGCCTTTGAAACTTGAGCGGGAGCTGGCTCTAGTTTTCTTGGGGAT
CCATGGACTGATTTCTTCTACTTAGGGATTTTGTTGTAAATCCAGAAAAATACGTAGGAAGCTGTA
AACGATTATAAAAATTCAGGCCCATTCTTCAATCCATGGGTATATATTTGACACCTTGGGAACTTG
CATTAATACTTTTTCGGTAAAATAAAAACCTCAACTCACCTTCATTTATTGAGCATCTTCTGTGTGA
TGAGCAGTGTCACCTCTGTGTTTACGCACATATAAAAGTTCCAGGTTCTGCTTTCAAGAGTTTACAT
TCTTATATGAGCAGTAAGGCTAGCTATCCAACCCACTTGCTAATAGTGTAAGACTTTTATACAACTA
ATTTCTAAATGGTGTGACATTGACAATGACAGTAAGTGCTGTTTCGTAGTAGGGAGGGGAAATATG
AGTGGAGTTGTGTGAGAAGACTTCACAGAGGGAGCTGGGGCTTGAGCTGTTGGCGGAAGGATGCTA
GAGTTTGAATAGGCAGAGAGAGAGAGAATGGTCCATTCCAGATGCCTCCATGGAGAAAATAATGG
AGAATGATTATGACAGTAACAACCAAAAATTTATGAGTACTTCCTGTAACCTAGTTGTTGTGCCAA
GCACTTTACATGTATCTACCCATTTAATAGGTACTACTATTATCCCCAATTTCTAGATGAAGAAGTA
GGTGCTTAGAGAGTAATATAACTCATTCAAAGCATAGCACTTCCTAAGTGGAGGAATGGAGTCAA
ACTCAGGCCTGTCTGATTTCAGAGCTCAAGCTTATAATCACTGTGTCAGTAGGCTGTGATCCAGGT
CAGCTTAGAGTATGGGAGCCATGCAGAGAAATCCTGGATAATTGAAGTTCTAGAAAGATAGAGCT
GGAAAGGGTTTTAGAGACAATCCCCACACAATGTTTTCATTTTAAAAACAGAGACCCAGAGAGGC
TAAGTGCAACCACTTATGTTAGAATGGAGACTTAGCCTTGTCTCTTACACTTGTCCTCTTACCACAG
TTAGGTGAGTCCATCTGATAATGATGCAGAAAGGTTAGCGTTGCCTTGATGACTGTCAGAAGGCAG
CTATAGGCTGCCTCAGTCACATGGGAGGTAAAGCGGTATCTGACATAATACCCCTGGGAATGGATT
CCACCATGGGAGAATGTAGTTCACTGAATTCCAACTAAAACAAAGAGCTATTAGACTGCTCGTGA
CTTTTTGGCTGAAGTATGCCTTTTTGATACATATGCAGCCATCTTTTGGAATTGGGTGAAAATCAGT
GTATTAGTCCATTCTCACACTGCTATAAAGAAATACCTGAGCTGGGTAATTTATAAAGGAAAGAGG
TTTAAGAGCCAGTTCCACATGGCTGGGGAGGCCTCAGGAAACTTACAATCACGGCGGAAGGGAAA
GCAAGCACATCTTACATGGTGGCAGGAGAGAGAGAGAAAGTGAAGGGGGAAGAGCCCTTTATAA
AACCATCAGCTCTTGTGAGAACTTACTCACTATCATGTGAACAGCATGGGAGAACCAGCCCCCATG
ATCCAGTCACCTCCCACCAGGTCCCTTCTTCAACACCTGGGGATTACAATTCGAGATGAGATTTGG
GTGGGGACACAGCCAAACCATACCAATCAGCATAGGACAAACTATATTTGCCAAAGAATAATGAA
ATTTTGTAGAGTCATGTTTTCATATCACTTCATGTGAAAACATGACTCTCTACAAAATTTCATATTC
TTTTCTAGCTTGCATTCTACCCAGAAACCAGTGGTAAAAATGGGCTGATTGTGTTTTTTATCTTTCT
CAAGTTCTCCTCCCCTTCCAGTAGAAATATTAATGAGCAGTGAAATGGCCAGAGACAGGCAGCTG
GAGGAAGATGGGGGCACTAAGTGAGGAATATGCATTCATGAATGAGCGGAAAATAGATGCTGGT
GCTTTTGGTCTGGAATCTTTTTAACATTGTCATTAGTAATAGATTCAAGATAGACATTTAGGTTTCA
AAGGGGGCACCAGTATTATCAGTTGAAAAAACAAAAGTGATGCATTGTTTATACTCATCTCTTCTA
GAATGTAAAAATGAGGATTTACCCTGTAGTAATATTTCTAAGAAAAAAAATGAAAGTTGGTTAGA
TTTTAGCTACTAAAGAACCAAAACAGACTAATACTTTCCCATTTTACTCTCCTTGTGTGGGGTTCTC
CTTGAGGGCAGTGGTAACTGCTGCACATATGTGTGCAATATATTTGTATCAAGGCATTCGCTCCAG
AAAACGAGAGAGAGATTTCCCGGGCTAGCCTTTGTTGGCATTCTGTCCCAGATTCCTCTCCGCTTT
GGGGTTATACAAAGATTACTGTGGTTCTCTGACTTGATTTGAAGCTCTGGCTTAGTCAGCTGAGGA
AAGACTACAGTCGCCTTCCTCCCCAGGAGTTTATCAGAGACTTGCTCTTCCGTGGAGGGCCTGGGA
ACGCAGTGCCTAAGCTCTTGGTGGGGGACCACCCCGCTGTGCTTGGCTTCAAACAGGCTGCTGTCC
ATTGCTTTCAGAAGCATGAGATTGCCCCATCAGGCTTAAAAACAATAATAAAAATATATTTGAAAA
AAATCCCCAGTCGCTTCTCTTGCTGTCTTTGGCAGTTAGGTACAAAGCATCAACAAAATGTTGTAT
ACAGAAATTCTGCCTTCCAGGCTTGTTCCTTTCTTACAGAACAATCCTTAACCTTGTAGGACTCTTT
TTTCATGTTTTCTTAATGAGAAAATATTTCAGAGATTATTGGCACCACAGGTTTATTCCTTTCCAGT
GGTTTACACTCTTAACTGACTGTAATCTTTATGATCTTTTTTGTATTTTTCTTTCACAGTATGGGCC
ATATCTAATCAGCCTCTCCTACCGTGACTATTCAAAGAAAAAGGATCTTTTTTTCTTTTTCTTTTTCTT
TTGTTTCCATCTCAGAACACTTTCTTGTCAATATCTTCTTTTTAAAAAATGAGGATTGTTGTAACAA
ATTTAGCAAACATTAAGAATGACATCCATTGCCGTGGAAGCTACCAAAAAAGTTATATACCTGTCC
TCAAAATAGCCTGTGATCTGGTGAACTATTCAGATACATGCAAATTAGTCAAAATATAAAGAAA
TAGAGGTGGGGAACAAAGGGAGTGCTGTGTTTGCGCTGACAGTGCTGGCCGTAGGTTGCCATTTTA
AACTCCCACTTTGGTGTCCCCTTTTGTTTGAAGGTCCCTCTGGAGTCCAGAGGTAATAGAGCAGGC
TGAGTAGTGGGGCCTAAGGAAAACTCAGGGCTGCAAATAACCCTGTGTACAGTGCATTCAGATCA
```

-continued

Sequence Information

```
CATCTGTGAGTCGCTGGAGGGAGTGGCCTGACCGGTTGGTGTCTATGGTGGGTTGTGATCATCAGG
CTGGTCCCAGGTGAGGTCACCTGACCACTCATTATTTTCTTTTTGGTAACAGAAATTAGTCAGTTAA
CAAGCATAACTTTAACAAGCATAACTCTACTTGTTATTTAAGACAATGTACTGTCCTGAGGAGTTC
TGAAGATCAGTAAGATACAGTCTCCCTCTTTTTTTTTTTTTTTTTGAGACAGAGTCTTGCTTTGTC
ACCCAGGCTGGAGTGCAGTGGCGCGATCTCGGCTGACTGCAATCTCAGCCCCCAGGGTTCTAGTGA
CTCTCCTGCCTCAGCCTCTCTAGTAGCTGGGATTACAGGCACCCACCACCACACTGGGCAAATTTT
TTTGTATTTTTAGTAGAAACGGGGTTTTGCTATGTGGGCCAGGCTGTTTTCTAACTCCTGTCCTCAG
GAGAACCACCTGTCTCGGCCTCCCAAAGTGCTAGGATTACAGGAGTGAGCCACTGCGCCGGGCCA
GTCTCCTCTCTTAAAGCACACCTAGAATCATGGTAGTGGTCTCTAATTCAGTGTGAGGCACAAGTC
TCAGATTCCTCTGTGGGTGAAGAGGGGGTCAGGCAAGTGTGTGGTGTGGAGATTTCCTTTCCCGTG
TCTGAGGCCATGATCCATCCCCTGTAAAGACTGTGTTGATTCCTTGCCCTCTAGACTGAAATCACT
TAGTATGAAGAAATGTTACCAAAGGGAGTGTGAATTGTGAAGGAGGGACCAAAAACATGTCA
GGCACTAGTCTAGCACAATGCCTAGCAAAGAACTCGGGGACTGTGTGAGGTACAGGAGTATGCGT
GGATTCAAGATTCAGCTACACATCTGCAGGAGCCACGGTTCCCCAGGTTAAGGGCAGAACAGAAA
GATGAAGTCTGGACAGCAGAGGGGTCATTGAGGAGCTTCTTAGGGGAGGCGGGACATCCATTAAA
CTGTGCTTGAGTGATTGTTAAGATGTAGGTAGGCAATGGACACGGAGACGGGACGTTTTGGGCA
TGGGGAGTGAGCAGGGATGTAGGAAGAGGAAGTGAAGGTGTGTTCTGAGCATGTTGACTAGGCCT
GTCCAGCCTTTGGTGTTCAAAGAGGCACACAAGACCACAGGAGAAATGGGGCACATCTTCCTGGA
GTGTTCATTTTGCTTGAATATATAGAAGGGAAAATAAATAATTTATCTGGTTAATAATTTAAAACA
TTGTTATATTAAAACAGGCAAATTATGGAAGAGAATACAATTAATTTCATGGATTTTTGTTAAAGT
TCAAAATCTCAGGTTTCCATTGTTTTCTTTTGATTCTTCGATGGAAGAATTTTAAATTCTTTAAAGG
AGATCAACTTTATTCCTTCATTCACAAAAATAGCAAAAGCAGCCGGGCATGGCGGCTCACGCCTGT
AATCCCAGCACTTTGGGAGGCCGAGGTGGGCGGATCACCTGAAGTCAGCAGTTCGAGACCAGCCT
GGCCAACATGGCGAAACCCATCTCTACTAAAAATATAAAAATTAGCCAGATGTGGTGGTATGC
CCCTGTAGTCCCAGCTACTCAGAGGCTGAGGCAGGAGAATCGCTTGAACCTGGGAGGCGGAGATT
GCAGTGAGCTGAGATGGCACCACTGCACTCCAGCCTGTGTGACAGACCAAGACTCTGTCTCAAAA
AAAAAAAAAAAAAAAAAAAAAGCAAAAGCAAATGGCAATCACAGTTGCCCACAGATCCTTA
CTTACATCATGAGGCACGAGCTATGGTTTCCCTTAGCTCCCTGTGGGCAGTGGGGAAGCAGTCTAG
CATGTGGCCATGGGGTTTGCTTGGCTGTTAGACAGCCCTCTTCAGGTCCCAGGCCCTTTGGACCCA
TCATACTCATCCTGTGCTTCTTGACACTGGCAAATCTTGATGATGGTTAATGTGACTCCCCGAAGG
ATGTGCCTCCATCCCATGTGACAGATATGAAGTCTGTCTGCGCACAGTCTGGGCCATGGAGTCTGC
ACTCCTAAGAATGCACAGAGGCCTGGCTGCCTTGGTCTCTTGAGATAATGAAATTAAGAGTCTTCA
GAGGCATTTCTTGAGTCTTCAATTTCATCTCCTTTCTCCCCTTCTGGTCCTAAGCATGACATTCCTGT
CTCAGCTTTTTCTGGCCCCCTGCTGTCTCTGGATTCTGGTCTTGTGAGTTTCCTTTGTTTGGGTTGTG
AATCATTAGGCAATTTAGATAACAGGTTCTGTTTTTCCTAGGCAGAGGCAAACTCCTCTGGTTCAA
AGCTGCCTCTGGCCTTTTCCCAGCTTTGAGGAAGCTGCATACAGTCTCTCCAAGCTAGTGTGGCAT
CAGAGGCCAATCAGAGGCAGAATTGGTGGTGGGTGAAAGAGCCTCTAAGCCCTTTCTTTACTATCTC
TGTTTTGACTTCTATTCTTTCCGGTGTGTGTTGGATTGACCTAAGATTTTCTTTGTTAGAACACCAA
ACTGCCCAGTGTTATAGATAGTGTTTTTATACTTTATCTACTCATAAATTAAAGGAATTAAGAAAA
TGGCAGGAAGAGCTCAGTTATTCAATACTAAATAGTGCCCTGGCCTTCATTATTCAGGGGAGAAAA
GGGCCTGGGTCTGTGCTGTTCAACAGGTAGCCACTAGTCATACATGGCTATTGAGCATTTGAAATG
TGGTAAAGTTGAATTGAGATGTGCTGTAAGGGTAAAATACTGAATTTCAAAGATGATATGAAAAA
ATAATGAAAAATAATACCTCCATAATTTTTATATGAATTACATATTGAAATGATAATATTTTTATAT
ATTGGGTTGAATAAAATATATTATTAAAATTAATTTCAGCCAGGCAGGCGTGGTGGCTCACGCCTG
CAATCCCAGAACTTGATCACTTGAGCCCAGGAATTAGAGACCAGCCTTGGAACAGGGTGAAACC
CCATCTGTACAAAAAGATACAAAAATTAGCTGGGTGTGATGGCACATGCCTGTGGTCCTAGCTACT
CGGGAGGCTGAGGTGGGAGGATTGACTGAGCCAGGGAGGTCAAGGCTGCAGTGAGTGGTGATCAT
GCCATTGCACTCCAGCCTGGGCAACAGAGCAAAACCCTGTCTCAAAAAAAATTAATTTCAACAGTT
TATTTTTATCTTTTCATGATCTGGCCACTAGAAGATTTTAAATTACATTTGTGGCTCACATTTTGTTT
CCATTAGACAGTGCTGCTTTAGATGGTAGCTTCATAATTGCAGTAATTCATACCTCTTGAGAGTTCT
CCAGGGATTATTTTGTTGAAGATTTTCTCTTGCAATGATCAGGCTGGGTGAGAATAACACATAGTA
GACTGTAAGAGTCTTCAAGGCAAAAGCTGTGTCTGTTTAATGTACTTTGGAGGCAGGAGTAGTAAA
GTCATTTTGCTTAGGAAACTCATAAACTGGCTTCGAAGGCAATTCCAAAACCAGTTTTGAGCATCA
TCTTTGAAATAAGGGTATTGCCTCCCAGTGACTCCATTGAAAGATGCAATTCATTTGGTTGCATAA
GACTGGGGTTGGAATGTTAAAGAAAAAAAAAAGTGGGGAAGCAAGTTTCATTTCTTATAGTCC
ATACCTCCAGTGGGGACTCAGCATGTAGAAAGGCACTTGGACAGGAACCACGATCATACCTATTG
TTATTTCATCAATGCAGAATGCAACATAATGGAGGCAGAATGGGGAAAGAAAGCCTTTCCAGCTG
CTTCAAAGAAAACCCAGATGCTTAACTTGTTTGCTGTGATGTGCTATCCTTTCTTCCTTGGTGCCAG
AAGAGAAATTATTACAACATATAAAAATAGGATTATGGCCGGAAGAAAGTTATTATAACATAC
AACAAATAGGATTGTGGGATCCTGAATATGTTATTCAGGATCCATATTGTAAAACATATTTTCTTT
GAAATTTTAATCATTAGAAACTATATAGTTCAAATATATTCTCAAGGCTAATCCATCCATATTCAG
GAATCTTTCTTTTTTAATATTATAAAATCTTTCTATGGACAAACTCACGATTAGTAAAGTATTTCCC
CATAAAATAGAAACAATCTTTTTTTCCAAAAAAGAGGGTTGTTATTATTAAGGTCTTTTAAAAATA
CTTTTTGTTCTGGAGCATGCTTTATCTTCTACTTCTCTGGGGTAGGTTAGAAATAATTATCACCGTTT
TGTAAATCGGGAAATAAACACAGGGAAGTCATTTGTCGAAAAGCACAGGGGACCAGTGCCAGAA
ATGGTTTGAAAATTTAGATCTTTTACTTTCCATTTCAGGTGCTGCAATCATAGTATCACATGGCTAT
GTGAATAGTAAAGTGTCTTGTTTACGACAGAACATACTGTTCTGAAAAGTGGGGAGGTATATCTCA
TTTTTAGGGGCATTCCTTTTTCTTAAATTCTACCCTGTGCTTTGCTTAGTAATACAGTTATTTATAAA
AATTTATAGAACTGTAACAGAGGTAAAGAATTCTCAATCTTGCTACTTCTTTCCTCCCAATAGTAAT
AAAAAGGATTTAGGCATCCTTGCTAGCTTCTCGGAGGCAAAGTCCCTGTGAAGCTATGAGACCTTC
ATTATCACATTCCCACTGCTTTGTCAGCTTATATTTGTGAGGAATTTAATCAGTTTTATTGCTGTAT
ATGACTGGAAATGAATGGCATTTATTTTCTCTGCAGGGATTTATTTGCTTTTTTCCTTGGGTGGCTA
TTCCTTTGTTGATAATATTTTCCCAAGTCTTGAAGCACTAATTGATTTTGGGACTTAAGCAAGATCA
CTTTTTACATTGAATGCAGAAACTGTGTTCCTATGGATTAGGGCACGGTCTGTGTAGCCATCAACT
GGAGATCCTGCTGAGAACTGTAAATGAGGAAGAAATTATGGGTCATGATAATAAGGTGTTCCAAG
TCTCAAGATTCAGACAGGAGCAGACATAAACAGCCTCTTCCTTGGAGATATGCAACCAGTCAGCC
AAGGTGTATTTTCTTAAGCATTGAGGCCTTGAAAAACATATGGAACTTTGAGAATATGTTTGCAGG
```

Sequence Information

```
TGTGAAAATAATGGTCGGTGGATCTTTCTCCCTGTCATGTATATATACAGTGTGTAGAGAGTAAGA
GACACATTTTGGAAAAGAAAAATGATTTTAATTGTTGGTGTTTCAGGACAATGCTTTGCTTTTAAA
GTTACATGTCATTATCTCAACCCCAATTCAGTCTATTCCCTGAAGCACATTCTCCTTGCTCTCTTACT
AGTCTTAGCTTTGGGCATATATTGCTCATCGTAGGAACTTGGTAATAAACCTAGATTTAATCGTAA
CTCAAAGAATACATGAGGACTTTATATCACTTTTTGATTTCAAAGACTGCTCAAGTCAAATGACTG
ATACGGAAATGTACCAAAAAGATTCCAGGTCCAGTCAATTCCTTGGAAAATATTGTTAATAGTAGA
CTCAACTTGGCATGTTGGGAACAGGGAGAAGGTGGGAAGCCAAGGCTGGGCAAAGCCATAGATA
GGAGGCTGAGCTGGCTATAGGACAGGCTCCAGAAAATTGACAAGGAGTCTGACTTATCACGGCCA
AGTAGACATGGCAGGTTTAGGACCCATCTTGGAGAGACTGTGTAGCACAATGATTAAATCGGAAT
AGAGGCTCTGTAATTGTACAGACCTGAGGCTCAGGCCCTCATTCTACCACTTACTAATTTGGTGAT
ATGGATAAATTACTTTTCTGAGCATCTGTTTTGTTATCTGCAAAATAGGGATAAAGCTTGCTCAGC
GGACTATTGTGAGGATTAAATGAGAGAATTCACATAAAGCACCTAGCACCAGGCCTGGCATAAGC
AGGAATTTAATAAATACAGCTATTATTATTATCTTCATCATCATCACTATCTGGGCTTTTGCCATTT
TGCACTGGTTGGTGAGGATACTGCAGCAGTAATCTCTGGGCAATTACAAATATTATATCCATGTTT
AGGTTCCGTAGGTCCAGGAAGAAGCAGGATCATATTCAGCCATGCTATGTGGACAGAGCCCAGCA
CCCCCTGGAAAAGGAGGTTCATAAGGGCTGGGCAGGCCTTGGAACCTCGCTTTCAGGAAACTGGA
ATGTACATTTGGAAAGCAGGCAGATGCCCACACATAATACTGTAGGGTAGCAGAGAAAACTGTAG
ACTCAACATGAAGCTGTCAGTCTCTAGGGCCTGAGCAGAGCTGAACCTATTCACTGAAGTCCTCAG
AATTTGCAACTGGGTAGGATTGGGGCAAGCAGGAGCTAATGACTCAATAGCCAATTGCTGTCTTTA
AATCTTACTGAAATTCTTAAAACTATTGAATGGCAGCATTTTAGTTTTTAAGTCTTTTTCCAGAATGTG
AGGTAGGTATGTTATTCTCTGTTTTTCAGATGACGACGTGAGCTTAAGGGACTGTGATCCATAGTT
AAAGCAAAAGCCACAATTGCATCCTTCAGCTCCAGGCTGTCATTTAGAAACCACACTTACTAAGAC
AGTGTCTCTTGTAGACGCGTCTATGCATCACTGCAGATGCTTGAAGCACCATATTTTGTTCCAGCTG
CTGCTATGGTGACCAGGTCAGAGCAGGCTTTCGTGAGTTTCTCACAGGGGCAATCACAGTGCCTTG
CCCTGAGCCCATGTTTTCTGACACTGAGGGGCTCACATGTGCATAACCCAGGTGTGCTGGGAGTCA
GTGCCCATGGGCCACACTTACTCATTGGGAACCAGTGGATGGATGTTTCCCCATGGATCCCCCA
GCTGTGAGATGAATCTTATTGGAATTCTCAAAGGGTCCCAGTGAGATGGAGCATGAGCCACCTGTG
GCGGTGGTCAGCCAACTTGATAACACATCCAGGTGTTGCTTTTTCCCTCCCTCCCTCCCTGTTTGGCTCTC
CCAGCCTTTCCCTCCTGCTCTCTGGGATCACTTCCAACATAAACTACCTACATGCAAACTTCTGCCT
TTGGTCCAAGCAAAGATAATTTCAAAAAGCGTTTCCTTATAGTCACATGTTCATACTGACTCCCTTG
TCCTGACCAACTCACAGCAGGTTGGAGCTTGAAAGATTAAGAATCTGTTATTATAGTCCAGGTGCG
GTGGTTCATGCCTGTAATCCCAGCACTTTGGGAGGCCGAGGCGGGAGGATCACGAGGTCAGGAGA
TCAAGACCATCCTGGTCAACATGGTGAAACCCCGTCACTGCCCAGGGGCAGCTCCAGAAATGCTA
AGAACCAAGGCCTGGAATCAGGGATATCAAGAGTCAGCTTGGTACTTTACCTCACTGTGGCTGAG
CTGATGCTTAAGCTGCAAGACAAAAGTCCGCTTTACAATTCCCTCTCCTTTTCTCAAGCAGAAGAC
ATCCCTCCTTATAGGCACCACAGCTGGGAATGTGCTGGGTCACACCTGAAGCCAGCCTGGCTCTGA
ATCCCGTTCAAGGCCTACTGCAAGTACTGCCTGGGTATTGCTGCTGACTATTCAGAGCCCAAGGGC
TCTTAAGTTAGCAGGTGATGAATGCTGCCAGGACTGGGTTCTTCCCTTCAAGGTAGTGGGCTCCCT
TCTGGCCCAGGATATATCTAGACATGTCCTCCAGGAGGTAGGGCCTGGAATGGGGACCTCAGGAC
TCTGTCTGGTGCCCTATCCTGCTGTGGCTGAGCTGGTATCCAAGTTGTTAGACAGAGGCCTCTTTAG
TCATCCCTCTCCTCTTCTTGAGTGGAAAGAAGTAGTCTTTCCCAGGGCTGCGAGCTGCACTCCCTTG
GCCATCCTAGCTGGTGTCTCAGTAGGTCACGTGCCCCCTCCTCCCCCCCCACCAAATCCACTGGCTC
TAAGCCCAGCATGGTATTAGGATTTGCCTAGAAATTGCAGTCCTTGTACCCTGGACTACCTTAAAG
TTTATTTAGAATCCCAGAGCACTTGAGCCCATGGTGGTGAGCCTTGCTGGAACTTCGATTCCAACC
ACTGGGATTGTTGATCCCCTCTGGCCAGGGCTGGTCTAAATGCTCCCTCCACGGGTGCCAGCTGAA
TTCTGCCGGTGTTGCTTTCCACTGTTTTAGGGCAGCACTGAGTTCCAGTGCACAGTCCCACAATCGC
TACACCTTCCTTCCCCAAGAACACAGATTCTGTCTCTGTGCCACGCAGCTGCTACTGGGGAGATG
TGTGAGGCATGGCAGCAATTCGTGACTGTCTTTCCTACCCTCTTCAATGCCTCTTTTAGTGATATGA
AGGAGACATTTAAGTGATATGTCTCAAGATATTTTTTGACTTCCCTTTTGATTTCTTCTTTAACCCATT
GGTTATTCAAGAGCATGTTGTATAATTTCCACATACTGTATTTGTGAATTTTCCAGATCTCTTCTGT
TACTGATTTCTGGTTTCAAAGCATTGTGGTCAGAAAAGATACATGATATGATTTTAATCTTCTCCAC
ATATGTAATTTTAAATAGCCACATTAAAAAACTAAAAAGAAACACGTGAAATTAATTTTAGTAATT
AGATATTCCGTATATCCAAAATATTATTTCAGTTTATAATCAATATAAAAAGTTATTGATGAGATG
TTTTACAGTCTTTTACACACACATATATACACATACATATGTATGTACATACACATATATGTGTGTG
TATACACACACACACGCACAGTCTGTTGTGTATTTTATACTTACAGAACACCTCAATTCAGACT
AGCCACATTTCTAGCCGCATGTGCCCAGTGGGTATTGTTTTGAACAGCTCAGCTCTAAAGGAAGTG
AGCTGGAAGATGGTTGGTGGTCATTGGAGAGTGAGACTTGAAACTGAGATTGTGGAGGGTTTGCA
AATATTTATAATCTTAAGATCTAGGATACAACTCTGGGATTGAGTTTCTTTAGCAGAGTGGAAATT
TAGATCATGGAAGGAGAAAAGGACAGGTCATTGAGCGTCCAGGTTTTGGGAAAGATCATCTGTGT
CAGCTTTGAATTCATCAAGGTTTATGAGAGAGTGGAGAGACTGATAGGATGTTAGGTCTTAAAATC
TTCAAAAGAGAATCTACAAACTCCTGGCAGGTCTGATCCAGGAGTTTGTAAATCCCTGTAATCAAG
TAGTATAGTCTGATAGCATGGGCTTCTAACCTGGCGGGGCAGCAGTTAGAAAGGAGGGTGGGAAA
AAGTTAGGAAGTGCAGTAACAAGCAACAAGGCTGCAGAGGAAGCAGTTGTCCTCTGGGGAGAGC
CAGATCTCAATGTGAGCCAGAGGTTCTGGCTGTAAGGACTTCTGATGGTGATCTATGAGGAGCTGA
AGCACAGAGGAATGGTTTAGGAGTCAGATCACCAGATGTGCAGAGCTCTATGGGGACAAGAGTC
CAGGTGCCGAGGGATGCTCACCCCATCCCCTGTGGTGGAGGTGTGTCCCCCACTGCTGTCCCAGCC
TTATTGCCTTCTGAGGGTTCTGATAACCCGCCGCAGGTATGGCCTGTGGCTAGCAGGGTAGAGGAC
CACTAAGACCTAAGTCTCACAGTGTATCTTTCTACCCCTGACTTCCATCCTGTCTCCTGTTTGAAGT
GTTGCTCAGATGACTGCACAGTAGTCTTATTCCAGATAAATGACTTCATCCAGAGTTCACTTTTAA
ATAATAATTTATTTTATTTTTTATTAGAGACAGTCTTGCTATGTTGCTCAGGCTGGTCTCAAACTCC
TGGGTTCAAGCGATCCTCCCACCTTGGCCTCCCAAAGTGCTGGGATTACAGGTGTGAGCCACCGA
TCCAGCCTATTTTATTTTTGAACCAACAGTGCACAAAGTACAAAATTTTAAAATGACAAGAGCATC
TGAATGAAAAGTAAGTCTGCCTCCCTCCAGCCACCCAATTTCTTTTCTCAGAGAACACACTTGTTA
CCCTTTTCTGGAATTCATTTGTAACAGGTGGCTCCTCTGTCCAAATTCCCTCCTCCTATCTCTTGGGG
GTTTGGATGTGAAGCTGGCCTTTTTTTCCCTGAAAATGCATTCATGCTCCCTAGGACACTGGCTTGC
CAAACAGGAGTCTGGGCACTTAGCAGCCAGTGCTCTGTGCAAACCAGCCAGTGCTCTGAATTCAG
ATGAGAGCTTTGTGTTTGCCTTATTGGAAAGCCCTTGATTCCTGGGCTTCTAGAGGGTATGTATCACT
```

-continued

Sequence Information

```
CAAAATCTCTGCAGTTCTTTTAGGGTAAGTGAACGCTTTACTTCTTCATCTATTAGAAAATTATTCT
CTCAGCAGGGTGCGGTGGCTCACTCCTGTAAACCCAGCTCACTCCTGTACTTTGGGAGGCCGAGGC
GGGCAGATCATGAGGTCAGGAGTTCGAGACCAGCCTGACCAACATGGTGAATCCCCGTCTCTACT
AAAAATACAAAAATTATCCGGGTGTGGTGGCACACACCTGTAATCCCAGCTACTCAGGAGGCTGA
GGCTGGAGAATCACTTGAATCCGGGAGGCGGAGGTTGCAATGAGCCAAGATCGTGCCACTGCACT
CCAGCCTGGGTGACAGAGCGAGACTCCCTCTCAAAAATAAATAAATAAATAAATAAATGAATAAA
TGAATAAATAAGTAACTCTCTCAGTGGTTCCTCAATGCAGGGCTGCACACTAAGCACACAAAAGT
GAATCAAACTTGACCAAACTTGGGTATTTGGATCATACATGAACTCTGCCTGAAGTCCAATCCCAG
GCTAGCTACTGGCACTGGCAGCTTCTCCACATTCAAGAACCACGGGGATGTTGCAAGTGCGCTGAT
GTTTGTGGTAAGCAGACATTAATGGAATAAGGACTATGTGGTCCCCACAGCTTGCCCTGTCATGAT
CATTCTCCAGTGTGGGTCACAGGTTCACCGGAACATCAGCTAACATGCTGTATAAAGTCACAGCAG
GTGAGCCCACGAGGGAATATTGAGCTCCATTCTCTCTGCAACTCCACCTTCTTCTCTCAGATTGGA
GAGTGGGGTTCCTAGCTTCCTGTATTGAAATTGTAGCCAATCAATAGGAAATCTCACACTTATGGA
AAATCCCAAATCTTAATTGACTCTGTTCCTTATCCTCTATTACCAGTACTCAACTGCAGCATTTTAT
GTTGCTGTTGTCATGCAGAAGAGAAAGGATTAATCACGGTAACTTTCATCGGCAGAGGGGTGAAA
CAAATGAAAAAAATGTTCAGGCACTTAATGCTTCTGTGAAAACCCAATTAGCACCCCTTCATGGTT
ATAATTTCTAATTACTTTTTGAACTGAGAAAAAAATGTTCTTGCTAATTAGCTAATTATTTGGTAGT
GACCTTTTGATAAAAATTGCTTTGACTCTAAAAATGTCTGAAGAAGAGTTACTTAATTTAATAAAT
CACTGTTATTCTAACATTTTAGAAAATCAGGCATTAAGAAGAGGTCTTGAAAGTTTCTAAGTTTCA
GAAATACCATGTTGGGTTGAAAGTTCTTTAGATGTGTATTTGTGCATGCATGTGTGTGTGTGTGT
GTGCACATGATATTGAGATTTTTGCCACTTAAAATTTATGAGACTAATGTCAGTTGTTAGCAATAG
AGAAAACTGGGCTTGGGGCATATGGAAACTTTCTGCAACATTTCTGTATATCTAAAACTATTCTAA
AATAAGGAATTTATTTTTTTCAGTGTAAGAAAGTCCCTTGAAATAAAATTTGATACAGTCTGCAAT
GAACTGAATTAAAACATCCCTGAAAAGTTTCTATAAAGTTTAATTCCACGTAGAAAATAACTTAAT
AAAAAAACCTCACAATGTGTTGCCTTCCTAAAGCTTCTGACTTCAGCTAACAGAAGCATTAAGAGT
AGTGGTTTTAATATGTATGTAATAGTGCCATCAGAAATCCCTAATGTGCAGATATATTAACTATAA
AATTACATGTCAAATATTTAGTTGCTGTATTTAGAAGACAATACAATTCCTAAGAGAAACAATAAG
CCTATTTACTAATACATCTATTTTCTACACCTCAGTCAAATTTATAGTTAAAAACTAGAATGAATTG
TCTTTAGGGTTGAAAGCCTGTCTCATGATGCTGATGAGCCAGCGTAAGGAAGTGTGGTGACTGTTT
GAGTTGTGTCTGTCTCTTGGTCTGTTCTCTTATAAGTTTCTAAGAAATTAACTGATGGTGGCCAAAT
TTGATTGAAGTATATCTAGTCTTCCTTGATTCCCCCTTGAACCTGTGGTTTAATATTCCACCTTTAA
ACATAACTGCAGGCTGGGCACAGTGGCTCACTCCTGTAATCCCAGCACTTTGGGAGGCCGAGGTG
GGTGGATCACTTGAGGTTAGGAATTCGAGACCAGCCTGGCCAACATGGCAAAACCTCGTCTTTACT
GAAAACATAAAAATTAGCTGGGTGTGGTGGCACACAACTGTAATCCGAGCTACTCTGGAGGCTGA
GGCATGAGAATCACTTCAACCCAGGAGGCAGAGGTTGCGATGAGCCAAGATTGTGCCACCACACT
CCAGCCTGGATGATAGAGTGAGACTCTGTCTCAAAATAAAATAAAATAAAATAAACAAACACAA
TTGCATTTTAAAAAACCAGTGATTTAATTGAGAAAAATGCGTATGCTCAGACAAAAAAGAAAAAA
AAATGACTTCAGATGGGCATGTATCCTATCAGATAAATAAATTTCAATAAAATTAAGTAGGTGGGT
TATACAGATAATGAGAGAGAAGTAATGATAATCATAAAATTTGAGTTGACGTTCCTTTGTGCTTTA
TGCATTTAGCTTAAGTTTTTCTTGACAACAGACAACTATAGGAATATAGAATATAGTCTGTAGTTT
AAAAGGAACTTTGGCACAATGTATCCAACTACCTAATACTGTATTAGAGAGGGCCTTTGAACTTGA
GCTTCCTCTGCCTAGAGCTCTCTTCATCCTGACCTGACAGGGTTGACTCCTGGTCATTTTAATTCTC
AGCTCAGAAGTCAACTCCTCTATCTTCTGCACCCTCTCCCTTTTCCCTCATGGTCTGCCCCATCACA
GTGTTTGGTTTCTGTCCTGGCACTCACCACAGTGGGAATTCTCTCAACGTTTATTATTTGCTTTCCTT
ATTTATCACCTGTCTCCTTCACCAGAATTCAGCTTTATAGGAGCAGGGGCCTTGTCTGTCTTGTTCA
CCACTATATCATTCCCTGTGCTTGGCACATAGCAAGTTGGTAATTTAAAGTTTGACATTGAAATAC
ATGTGTGTGTGTATCTATGTGTTTATAATTACTGGTAGAAACAGGCCAAAAGATCCCCCCAAGAA
TGAATAACAACCTCCACTTACTAAACCTTTGTCTCATTCTTTGCTCCATTCCTGATTTTCTTACACAC
TTGTATTGCTTTTAGGACATGATAAATGATCAACTTAATAGGAAATGATAAATCTCAAGGAGAA
AACTTGGCATTAATGTAACATTTAATCTGCAGAACAAATTGATGTTGTAGCTTCCTTCTTATCTTTC
TGTTTTTATCAATAAGAGAAAGATGTCTTTGGGGATGGGAAGGAAACAGAGGGTCTTGAGGTAGG
ATTCCCAGGGGTCCTCATCTCAGTGACCTCTTGTTCTACGTGCATTTTCCCGGAAGACAGGCAAGTT
TAGTGTTTTACCACATTAACCCTGAAATCTGATAAAGTCTGTTCTCCTCTTTAAACTAAAGACAGTT
TGTCTGTGTGCCCAGGCCCAGTCTCCTTTCTTCTGGACTGGAACAGGCCAGGGAAGATTTCTGGGC
CTTTTTTCTCTTTCTTTCCGTAGTCAGGGCACCTGGCCACAGCTTTGTCTCTTATCTTGCCTTAGAAC
TTGCATGGGAAGCTGTCATAGACCGCCTGCTGAGAGCCTTAAAAGAAATGTAAGGTAGAGTGTGT
AATTATTATCAGCTGTTCACATATGAGATGTAAGTATCTTGGATATTTTGGATTTTATGGAAGTCAT
ACGCGCTTACCACATTATATTCATCCCGAACTTCAGTAATTTTACAATGAATCATTGATCTTAAGGA
AGACTTGTAATAAATGCTAATCTCAGAGCATTAATGAAGACACAAACTAAGACTACATAAAGGCT
ATACAGGATGAGCATCCCTAACCTGAAAATCCACCATCTGAAATGCTCCCAAATCTGGAACTTCTT
GAGCCGATATGATGCCACAAGTGGAAGGTTCCACACGTGACCTTCTTTGACTAGTCGCATTCAAAA
TGCAGTCAAACTTTGTTTCATGCACAAAATTATTTAAAATATTGTATAAAATTACCTTCAGGCTATG
TGTATATGAAACATAAATGAATTTTGTGTTTAGATTTGATCCCAGCCCCAAGATGTATCATTATGTA
TATGCAAATATCCCACAAAAAAAATTTTAAATCCCAAACACTTCTGGTCCTAAGTGTTTTGGACAA
GGAGTATTCAACCTGTAGTGTCCACTTAGATCTGGTTGGTGTTAGCTTCCATTTTACCTTCTTATTC
ATACCCTCACTCTCCTTTTCTTTTTTTCCCCAAATTAATGTAGTATCATATTTAGTAGAAAGCCTAT
TTGACCTTTCTCATTATTGCCTGTAGGACATCTTTTCTTTTAGTGTGTAGAGTTAGCTTGCCTTCGAC
TGACATTAACAAAGTGCTTTCCTAATCACGATCCTCAATGCAGATAGTCTTTTCCTGGAATCACTTG
TTTTCCTTTTAGTTACGGTATCAATGCAGCTCAGAAAGGTCCTAAGGTCATGACTGATGAAACTTC
AAGAAAAAAAAAAGCCAAGGGCCTAGAAATTGTGTCAATTTTAATTGATTAGAGGTGGCAGCAG
TAGTTCTTGGTCAAGTAATTATCAAATAACTCAAAAAGGTATCCAGGAAATGACTGGGAAGCAGA
AACCAAGCTGATTGCGCATTGATAGTGAAAACCAGATTTGTTTGACAAAAGGGAAAGTTTCTGCC
AGAATTGAATTATGTCTCTTCTAGGCAAAAATACACACATAAGGAACAAGGAGCAAGCTCAAAAA
CTAAAGAAAGTAGCCCATTGCCTGGCAAATTACTAGAAAAATAATAGGAACGTTTAATGTCCATA
AGAAGACTTTCATGAGGCCAGGTGTGGTGGCTACCACCTATAAATCCCAGCACTTTGGGAGGCCA
AGGCAGGTCACTTGAGCCAGAGTTAAAGAACAGCCTGGCCAACATGACCAAACCCTGCCTCTACT
GAAAACAGAAAAATTAGCTGGGCGTGGTGGCAGGTACCTGTAGTCCCAGCTACTCGGGAGGCTGA
```

Sequence Information

```
GGCAGGAGAATCGCTTGAACCTGGCGGAGATTGTAGTGAGCTGAGATCATGCACGCCAGCCTGAG
TGACAGAGCGAGACTCTGTCTCAAAAACAAAGACTTTCATGAAATAAAACGAATAATGAGGTATC
CTTGGCATCATCTGATGGCTCTGAGTATTTGTTGGGCTGCTCCATTCTGATACGTGGGCCATTCTGT
CCAACAAGGTGTGGCATTGAGAAGGATTGGTGGTCACATTAAGGGCTTGTTTTCTTTTATATTGTT
AAATAATAGACTCTGAAATGTTACTTTTCTCTGTAAAACAAGGTAGTACTTCCTAGTTCATTTCTTT
CTTCTTTGTAAATTAATATTTAAAATAATACTTTCTAACTTTTGGATTACCAGATTAGACTTTATTGT
ATAATAAACCACATGATTTTAGATTTAAAGTCAGCTTTTGAAAGAAATCCTTATTATTTGTTCATTA
ATTTTAATTAAAAATTTGATAATGTTTCTGATAAAAATATTAATATGTGGCTGCTGGGCACAGTG
GTTCATGCTTGTAATCCCAGCACTTTGGGAGGCCAAGGCAGGAAGATTACTTGAGGCCAGGAATTT
GAGACCAGCCTGAGCAACATAGTGAGACCCTGTCTCGAAAAAAAAGTTTTAAATATTAGCTGGGT
GTGGTGGCACATATCTGTAATCCCAGCTACTCAGAAGGCTGAGGTGAGAAGATGACTTGAGCCCA
GGAGTTTGAGGTTACAACGTACTATGATTGCACCACCGCACTCCTGCCTGGGTGATAAAGTGGTAT
CTTGTCTAAAAAAAAAAAAAAAAAAATCATGGTATTGAAAGGTATAAAGAGGAAAATGTGAATTAT
TATTATTCTACTCCTAAGGTAAATATTTAACCTTTTATAGTGAAAATTTTTCTGACACTAAAAATTT
TTTTAAAAACATGAGTTTTAACAATAGCAGTCATCTTAAGAAATCATTATTGAGGTGACTACAGCT
AGCAAAGAAATTTTTTTTCCCCCAGCTGAAATCTTGGGTACCTTTATACTTTGGTATAAACATGTAC
ACATAGTAGCAGAGAATAATTGTGATGCACTAAGCTGGCAGGTCTGTGGATTTCAGCTCCAAACA
CAAATATGTAACACTGAGCCTATATTGAAATATGGATTAAGAGGCTCTAACTCACTTTTGTAAAAT
AAAATGATAGGAGCCACATTTGTGTTTAATTATAGCATGAGAAACCTGAGAATCAAAAGAAATAA
GTAAGTTCCATCACACAACAGGATAGGAAAAATAGAAAGTCTACCTCACACTGCTGCATTTGTCTG
TAACTTGGCCTACTTTATGAAACTCAAAAGCGAATTAAGCCGGGCGCGGTGGCTCACGCCTGTAAT
CCCAAGCACTTTGAGAGGCTGAGGCGGGCGGATCACGAGGTCAGGAGATCGAGACCATCCTGGCT
AACACGGTGAAACCCCGTCTCTACTAAAAACACAAAAAATTAGCCGGGCGAGGTGGCGGGCGCCT
GTAGTCCCAGCTACTTGGGAGGCTGAGGCAGGAGAATGGCGTGAACCTGGGAGGCGGAGCCTGCA
GTGAGCGGAGATCGCGCCACTGCACTCCAGCCTGGGCGACAGCGAGACTCTGTCTCAACAAAAGA
AAAAAAAAAAAAAAGCGAATTAAAACTACATTTTAAAAGCCTGGTTCTCATCACAGTTTTTGGCTG
TTAGGGATAGGACTGGTGCAGGCAACATTGCTCCAGCTGACCAGGAAATGGTCTTCCAGAATCCCT
CTGATTTAATGAGCCCTATCTCCTAGCTCTGCGTGGGTTTTGAGTAACCATGAAAAAAAGCTTTTA
AGTGATCAAAATGATATATTGATTCTTTCTTTCTAATGCCTTGAATATTCTTTCAGCAAAGCTGCTT
TAAAAATAATTTCTGATTTTCTATTTGGTTTTTATCAAGACATGGAAATGGATAGAGGTATTGTGA
ATTGATCCCAAGAGGAAGAAATTCCTGTAAAATGTAGATGCGTTGGTCACATGGGGGAGAAGCTC
CTGTCTGACCTCTATTTCATATTATGAGCTCAAAACATGCTTTCTCATGGGCCATGTGACATCATGT
TTGGTTGAGCAAAATGTTAATGTTGCAGTGATTGGGATCAGTGCTGTGCTTCCTGACCCACCTGCT
GCATTGGTAAACCTGAAACCACCGCAGCAAATATGTTTATTTGCTTTTCCCTGAAATGTGCTGTTCC
TTTTTACCTCCTACAGATAAAACTGACAGGCCCTTTTCCTGCTAGCCAAAAACAGTGAGGAGAACC
AGGTGGAAGACACAGCTTTTAAAATGTAGTTTTAATTCACTTTGAGTCCCATAAAGTAGGCTGAGT
TACAGACGAGCTGTGGGCTTCACCAAATCACTCCATGACCTCACTTTCCTTCTGGCAAACCTCTCCC
AGTGCAATATGTTGATATCGTTGATGGAGTATGAGAACAGCTTGCTGGAGAAGAGCCTGCCTGT
GATCTCTTAAGGTTGCCAGACAACATCACTGTAGGCCATCTTCTCTCTTTTTCCTTATGCTTCAATTT
CCCATGGCTTTTGTGTACTACAATAACGTCAGTAACCAACCTCACTGGAACCACTTGGCTTGTAGA
TAGTGAAAGCTCTGTTTACATTAGAGGTAGTTTCAGAATTGATGAAAGCCTGTGTTGACTTCTTAG
TTTCTTATAGTGGATATTTGATTGAAAACACTGGAATCTCCAATGTGATAATTGACCTTACTGTTG
TGTACTGAGATCTCTATTTTAGATTCTCCCAAATACCACCTTTTTTCTATTTTTAAAATTATTATTG
CAAATTCAGTCAAATAATATGGTAGACAGAAATTTGGATGGGCTTCAGGAAAAGAGGTTTAATAG
TGGATTTGCCCCTAACTAGCTGTACAGCCTCTTGCATATCATTTAATCTATCTTGACCTCATTGTCTT
TGTATTGAGATTCTGTGGTCCAGTCATGGGAATTAAAATCACCATCCATAGAAAGCTGTGTCTCTC
GTCTCTTTGTGATTCAACACTTCATCTTTTCTGCAGAGTAGAACACCTTGTAGGCAGGTTCATAATC
TTCTCTGTACTTGGAAATCACCCGGAAAGCCCCCTTTCAAGTTTCTAATTGCCCAAGTTATTCTTTT
TTTTTTTTTTTTTTTTTTTTTTTTTTTTTTTTAGAGGGAGTCTCACTCTGTTCCCCAGGCTGGAGT
GCAGTTGTGCGATCTGAGCTCACTGCAACCTCCGCCTCCTGGTTTCAAGCGATTCTAGTGCCTCAG
CCTCCTGAGTAGCTGGAATTACAGGCGTGCACCACCACACCCGGCTAATTTTTGTATTTTTAGTAG
AGACGGGGTTTCACCATGTTGGCCAGGCTGGTCTCAAACTCCTGACCTCAGATGATCCATCTGCGT
TGGCCTCCCAAAGTGTGCCCAAGTAATTCTATAATGTAGCCAGGATGAGAACCACTGGTATCAGGT
CTAGACCCAGGGACTCATTATTATAAAACATTCCCCTTTGACATACCTTTTCATCCTTGAGTCAGGA
CAATTTTACCTTTCAGAAAGTAGCTACAGTCCTTTTATAATTTACTCCTCACCAAAGGTAAAATACA
TCCATTTTCTCTGTGTGTGACTTCTGACTATTCTGCACTGATTCAATACCCCTTCGTTTTTTGCTTAT
TTTTTCATTCTCACCATTCAACCACACTTGACACTTGAATCATTAATTTCTACTTCTTCATTTGTT
ACAACAAAAATACAGAGTAAGATCACTTGACTTTATTGTATTAGCCATTAAATCTCTTTCTGGAGC
AATAGTTCTCTAAGTATGGTCCCAGGAGCAGCAATATCACTATCACCTGGAACTTGTTAGAAAGG
CAAATTCTCAGGCCCCTTTCTGGACCAGAAGCTCTGGAGATGGTTCCCAGCAGTCTGTTTTCACAA
GACTTCTAGGTGATTCGACACACTATTGCTTGAGAGCTGTTCTAGAGAGATTTTATATTTTCAGATA
GTTGGATTTTTAAAAATTTTTTTAGTGTGCTCAGATATTTTTGAAGTAATCGTTGTCTGAACTTACTT
GGTCTAGAAATAGAAGAGATGTTCTATTTCTAAAGGGGATATTTCCCAATCCTACCCATCTTTTTAT
CCTTTAGAAGTTTTCATCTTCTTTTCTGCTTTTAGAAGACCTATCCATATCTCTCTTATTTTTACACT
GAAAATTTAGTCTTACATTCTATTATCATGGAAACTTTAATAATCAATGCTATTTCAATGATGTATT
ATGATGTGATGTAACAATAGATGGGGCAGTGACTAATACAACATTAATTTCTACTTCTTCATTTGTT
TATTTTTATTGGACCTTCAGATGACATTCTTCTTACTTTATGAAGGGGGCCAGCCCCTCCACACCTG
TGGGTATTTCTCATCGGGTGGGACAGAGACTGAGAAAAGAAATAAGACACAGAGACAAAGTAT
AGAGAAAGAACAGCGGGCCCAGGAGACCGGTGCTTAGCATACAGAGGACCTGCACCGGCACCGG
TCCCCGGGTTTCCTCAGTATTTATTGATTACTATTTTCACTATCTCAGCAAGAGGAATGCGGCAGGA
GAACAGGGTGATAGTGGGGAGAAGGTCAGCAAGAAAACATGTGGCAAAGGAATCTGTGTCACA
AATAAGTTCAAGGGAAGGTACTATGCCTGGATGTGCATGTAGGCCACATTTATGCTTCTCTCCACC
CAAACATCTCAGTGGAGTAAAGAGTAGCAGAGCAGCATTGCTGCCAACATGTCTCGCCTCCCGCC
ACAGGGCGGCTTTTCTCCTATCTCAGAATTGAACAAATGTACAATCGGGTTTTATACCGAGACATT
CAGTTCCCAGGGGCAGGCAGGAGACAGTGGCCTTCCTCTATCTCAACTGCAAGAGGCCTTCCTCTT
TTGCTAATCCTCCTCAGCACAGACCCTTCACGGGTCTCGGGCTGGGGGATGGTCAGGTCTTTCCC
ATCCCACAAGGCCATATTTCAGACTATCACATGGGGAGAAACCTTGGATAATACCCAGTTTTCCTG
```

```
GGCAGAGGTCCCTGTGGCTTTCTGCAGTGCATTGTGCCCCTGGTTTATCGAGAATGGAGAATGGCG
ATGACTTTTACCAAACATACTGCCTGTAAACATTTTGTTAACAAGGCACATCCCACACAGCCCTAG
ATCCCTTAAACCTTGATTCCATACAACACATGTTTCTGTGAGCTCAAGGTTGGGGCAAAGTTACAG
ATTAACAGCATCTCAGGGCAAAGCAATTGTTCAGGGTACAGATCAAAATGGAGTTTCTTATGTCTT
TCCCTTTCTACATAGAGACAGTAATGGTCTGATCTCTCTCTTTTCCCTACAACTTAAGAACACAG
ACACAGATTATTTTTTAAAGTTATTCTTAAACATGTGGAATTACTTTATAATAAACCCAAAAGTTGC
TGTTGTTAGAGGGAAATTTTTACTAAGTCAAGTACTCTCTGGAAAAAAAAAATGTGTGAGCATAAGC
TAATATCATAAATGAAATGATGAAGAAGAGGATAAGGGCACATGGTCCTAAGTGAGGAAACTTTG
ACCCAGAAACCTTTTGCAGTGACAGAAGTAGACCAAGAGTCCAAGTCTCCATGCTTCCAATTCAGT
ATTCCTTGCATGAAATGTCACTGCCTTTCGAGACTATACCGTTTACCTAATTGGTTGGATCTTTGTC
AAGAGCTTGATCCAAGTGGAGTTTCTTTGTTTAATATATAAAGCATTTGCAAGTCCTTTCAAGGGC
AGCACATAGTTTTATTTAACTCCCTCAAGCCCTCTCACCTCTGTCAAGTTGCACCAGGAAATTCAA
GGTCTAGCCAAAGGCCCCCAATGAGTTAAAAACCCAACCATCCTGCAGAGTAGAAGAATTAATG
TCAAAACCAGATGTTCCTCTGTGGGCCTTGCTGGATTCATAAGTCAGGATAAAGCCAGCGTGGATG
CATGCATGTCAAAAAAAAAAAAAAAAGTCTTGGCCAGTGTTGTAGAGAAATGAAGTGTTGTTTCA
TCTGCAGTTCCTCTCCAGTCCTTGCTGGTTGGGAGCACTGGCTCCCGGGAGACTGGTGGCCCTGAC
ACTCAAGCCATTAACTGAGAATGCTCTCTAATCCCTTGTTTTCATTGTTGGTGTTCCGGCCAGGCTG
CCCGCACAGAGCCTGCCCGTTTTCATTGGCTGCAGGAATTGTTATTGGAGTGGCTGACAGCTGTCT
GCCAGGCTGCCTGAAACTGCCTTCCTGTGCTCTCCGCTGCTGCTCCACTTCACAGCGCTATTGTTCC
TGTTGAGCCTTTTCTTAAAATCTTTCCCAGCTGTATCCTGATATGGTAAACCACTTAAATTAGCTCC
AGATTGTTCTGTTTATTTTGTGTTAGATAAGCGACAAAATACAGTCCCAGCGGCAGACCAAGAGGA
GAGTGGAAGTCGGGGGAGGGGGTCAGAGGACACAAGGTCTTTTACAACACAAGGTAGAGTTCCC
AGACAAAACTGTGAGAGGCACAAGTATGATACAGTCACTGGCCTGACCATTTATACGTGACTCTG
ATGGGCCAGGTGAGCAATAACGTTGCATCTGCGCACACCTCATTCCAGAAAAGAAAATCAAGACC
CCAGCATACAGCTACACTGGAAGGGAGCTAAATTTCTATTATTGGAAATAGACACAGTATTGCTGT
CAGGTTGGTTGCCATGCCAGCTGTCCAGGTACCATGCTTGATGCCCTGATTACCACAAGACTTCCC
CCTTCCCCCTGCTTTTAATTATCCTTCTGTAGTGCAGTGTATGGTAACTGATGGGCTCAAAACTGGC
CCACATTTGCCAGTCTCCCTATATGCTCAGCACTTGAAAATGAGTCTTCTCTGCTGTAATTTAAAGC
TAGAAATCCAAAGACATTGAGTCACCAGCATAGGTATTTTCCACACAGCTGCAAGTGAAACTTCAC
AATGGACTTGGCCGCTATTTGCTTACACTTGCCATCTGTGCAACCGCTCTACCCGTGGCCTCCCCCG
CTTTGTGGTTGTCTTCTAACAGGAGCAGTCCACGCAAAGCCTTCCTGAATACTTAACAAAATTTTA
AAAAATATAATAGATACTGTCCTAGCATGAAGGCGCTGCCTTTGTGATTTTTAGGAATTAACCCAA
ATAAAATATGAAAAATAAACTACCGAGTGCTTTAACGCAGCTAAAGCATGCAAGCAAAACCAGCA
ACCAGCTGAGTTCCGACAGTTACTGAGAGTTTTGTATGTGGTAATTCAAGACTCCCAGGAAAGAT
CTCATGACTCACTCCAGTGTGGCTGGGCCTCCAGTCCTCACTCTGAACCAAAGTCCTGGAAACACT
TTTCCACCACGTTGAGAGAAGGCGAGGGAAGAACAGGGTCAGGAGTGATCAAATGCCCTTAGAAA
CAGTCTCTTTCTTTCCTTTTGGGAAAACAAACTCACTGTGTAATAAAAAGGTACAAAGCCAACTTT
GGAATAATAATCACCCCGCCCCATCCCCTTGCCCTCTGATGGAAAGTGCCTTGTCTTCTCCATCAA
GGTCTAGCTGGGGGCTTGAACGGCCTCCGTGTCACCTCTAATTCCCCAGTTTTTACCTTGTTTCCTT
TCTCTGTATCTTTTTTGCCCTTAGTTGTGTACAGTCTTGTATTTTTTCACATAGGCTATGCTTTCTGT
GGATGTTGCCTCCCTCGAAAGCAGGGACCATGTGTTGAACCCCTGTTGCCTTTTCCCAGAGTAGCG
GGCACCTAGCAGGTGCTTAATTAAGGTGTGTCAAATAATTGTTTCCTTTTTTATTCTTACCTGACAT
GAAGTATGCTCCTGTATCAATTCAGATGAAGGTTTAAAAAAAATCAAGACAAGTATCACAAGTTC
CCTTAGCCCATTCTCATTAAAATCATGGGCACCACCTTCCCGTGCTCACCAGGATGGAGGAAGTCA
ACAAATATCTTTCTCATTGATTAAAAACTCTGGATAATACTGAAAGCAACTATCTGAGGCTTCTTA
AAAGTACTTAGGTTGGTGCTAAAGTAATTGAGGTTTTCGAAAACTGCAATTACTTTTGCACCAACC
TAATATAACAGCAGGGATGATAAGAATAGGGACAGAGAAGAAAACAAAATCAGGTGAATGGAGA
ATGGGGAATAAAGTCAAAGCTTCATGAATCCCTTGTGTGGTGAGTTTTGGAGGTTTATTTTCTCTCC
TCTATCTCTTGGCTTTGACCTAAGAGCCAATGGAATTATGGAACTATGCAGCAGGCACTGGCAGCA
ACATCTCCAAGAGAAACCTCCTACTTCTAACCAGAGGTCTAGGAAAGTGGGCTCTTGCTCAAGAAT
ATGGGGAATTCCTATTTTATTTGTTTTTTCTTTTCTTTTAATTTTTTGAGATTGAGTCTCACGCTGTT
GCCCAGGCTGGAGTACAGTGGTGTAACCATAGCTCACTGCAGCCTCTACCTCCTGGGCTCAAGTGA
TCCTCCTGCCTTAGCTTCCCAAATAGCTGGGACTGCAGTCATGCACCACTACACTTGGCTAATTTTT
TTTTTTTTTTAATTTTTTATGTTTGGTTAGCGATTGGATCACACTATGTTGCCTGGCTGGTGTGAGCCA
CAGTGTCCAGACTGTTTTTCTTTTTCTTTCCCTTTTCTTTCTTAACTCTACCCCAAGACAGGCCCCA
GTTGAAGATCTGCATTGGTGTTGTGGTGGGGTGCAGGCACCTAAAATCTCAAAAGAAGACCCACA
TTTCTGACCGGAGTGTGAGATAATCTCTGTTATTTTCCTCTTTTTTTTTTTTTTTTTTTTTTTGCT
ACTTTGCTCCCAAAGGCAACCTCAGTTATGCAGAAGTGCATGACAGAATGGGGAACTACAACCTA
ACAGAAACCTGTTTTTCTGATCAGAGAAACCACATAAAGGGGCCCCTGGAGCGGAGGTTGGGGGT
GGATCTGAAGGATCTAAAGGGAGAAGAACTGGAGAAGAGGATCCCCTGATTCTGTGTATGAGC
TAAGCCCCAGGCTCACCTCCAAGTGCATATATGCCACACAGGCCCAAAGGAGCAAAGCAGAGGCT
TCGAAAACTCAACTGCCATGTGAACCACTGCCCAGGTCCTGATTAACCCCTGAGTGGCACATGCG
CTGGGCAAACCCAAACCTCATAGCAAAGGCTTTAAAAACTAAACTGACATTAGAGCCACTGTCCA
CAGAAGGTGAGACAAAACTTGTGGTCTGAGTCTCACTAGGTTGATTCTCTGCTTAACCAAACAAAC
ATCAACACCCTCGAGAGGATTTTAACTAGACCTAGAGGCTCAGAACATGGTATTCAAAATGTCTAA
TAGACAGTCCAAAATTACTCATTATACAAAAAAAAAAAAACAGGAAAATACGAGCAGTACTCAAG
GGAAAAGACTAAAAATAGATTATTTCAGCTGTGATGAGCTCATTTGAGATGATCATCCAAATATTG
GTGTTGTCAGACAAAAACTTTAATGCAGCTATTGTAACCATTCTCCATGAGACAAAGTTGAACACT
CTTGAAATGAATGGAAAATAGCAGTGAAATAGAAACTAAAGCCAAACAAATGAACAAACAAAA
CAAATGAAAATTATAGAACTGAAAACACAATATCTGAAATTTAAAATTAACTCTATGGGTCCAA
TAGCAGAATGGAGCTGATAAAGAAGAGTCGGTGAACTTCAAGATAGATCAATAGAAATTATACAG
TCTGGGCTGGTCGTGGTGGCTCGTGCCTGTAATCCCAGCACTTTGGGAGGCTGAGGTGGGCAGATT
GCTTAAGGCTAGGAGTTCAAGACCAGCCTGGCCAACATGATGAAACCCCATCTCTACCAAAAAAT
ACAAAAATTAGTCAGGTGTGGTGGCACACGCCTGTCGTCCCAGCTACTCAGGAGGCTGAGGCAGG
AGAATTGCTTGAACCCAGGAGGGCAGAGGTTGCAGTGAGCTGAGATAGCGCCACTGCATTCCAGC
CTGGGCAACAGAGTGAGACCCTCTCTCAAAAAAAAAAAAAAAAAAAAAGAAAGAAAGAAAGAA
AGAAAATTATACAGCCTGAAACACAGAAAAAGGAAGAAAAACAGTGCTGCAGGGACCCTATGGA
```

| Sequence Information |
|---|
| ATAATATCAAAAGGTCTAGCATTTATGTCATTAGAGTCCAGAAAGAGAGCAGAAATATTAGTGTA |
| GAAAAAATATATAAAGGAATAATGTGTGAAAACTTCACAAATTTGGTGCAAGATACATGTACAAA |
| TTCAAGAAGCTCAGTGAAATCCAAACAGGATAAACTCAAAGAAAACTACACCAGCATCATAATGG |
| AACTGCTGAAAACTAAAGATGAAAAAAAAAAATACCTTGAAAGCAGCAGTCTCATTCATGGGATT |
| GAATGAAATTGAATGAAAGCATGTTCACACAAAAAACAATACCCATATATTTATAGCATCTTTATT |
| GATAATTACTAAAAACTGAAAAACCCAAATGTCCTTCAACTAGCAAATAGATAAACAGATGTGGT |
| ACTTCTGTGCAGTGGACTACTACTCAGTAGTGTAATGAACTGTTGATACACACATTAGCATGGATG |
| AATCACAAATGCATTATGCTGAATGCAGGAAGCCAGACTGAAAAGATTACACACACTATGATTTTT |
| TTATATGACATTCTGGAAAAAGCAAAACCTTAACGACAGAGAAGCATCAGTGGTTGCCAGGGGTT |
| AAGGCTGGGTGTACAATTTGTCTACAAAGAGGTGGTACAAAGGAGTTATATCACAGTGATAGAAT |
| GTTCTATCCTGATTGTGGTGGTATTTATATGACTCTATTTGTTAAAATCCATAATGATGCACACCAA |
| AATAAGTGAATTTTACTGTATGTAAATTAAAAAGAAATCACCAGCACATGATTTCATATCTGATAT |
| GGTTAATATATCTTCATGACTATGTGAAGTATAGAAAAGATTCATGTAATCTCTTATCTATTTTGAA |
| GTCATTTTCCATTTGATTCCATAAACTTTCAGGAAGCCAAAAATGGAATAAACAATGAAATGGTCT |
| CTGATACATACAGAAAGCTTTCCAAAAAAGAATTTTGTGTTTCATATGCCAGGCAGATGTTTTGTA |
| GGGTCAGCTTACCACAAAAGGCCTCGCTGAAAAAATGCAGTATAAAAGTAGGGGCCTGTAAGAGA |
| AAGAGAAGCACATTGACTCCAGAGGAGGTCTACTGTTTTATAAAAGAAGCCAAGCAAATTTGATG |
| GACTGGTGAAAACAAGAACAAAGAATCTGACATGTCTTGGAAGCTCTGGGTTTTGATAATTAGGG |
| AAGTATTTAGAATGCTGTCTCGAGGAATCACATCTTTTGTGCTGAGATATATCCCTGCTTGTGTTCT |
| GAAATATACATGGAGTGGGCAGGCTTGGACTGTTTAAATGAAGACAGATTTTTTACATTCTTGTGAC |
| ACTAGGAAGACTTTTCCTGAATGTAGGATTTTTTCTTTAACGCACCTCTCATCCAAATGGCAAAAC |
| ATCCAGGATGGGTGCTTACTTGCAATGAGATCTCCCCAGCTGACCAGAGCTGTACTTTCTCCCACT |
| GCTTATTCCCCCTCTGAAGTTACATCATCATTTTGCTCCCTGGTACACCATTATGGGTCTTATCTATT |
| TTTATACATAAATATATTAAACAAAACTGTTGGTTTTAAGAAACTTTTGACCTATTCTAAGACCTAT |
| TCTCTGTTTTTCTATAAAAGTTTTATGGTTTTAGCTGTTGCATTTAGGTCTTTGATCTATCTTCTTTTT |
| CCTCATACAGTATTGTTTTATTGAGATATAATTCATATACCATGAAATTCATCCTTTTAAAGTATA |
| CAGTTCACTGGTTTTTAGTATATTCACAAAGTTGTGCAATCATCACCATTGTCTAATTCTAGAACAT |
| TTTAAAAATTAAACATACAAGAAATTCTCTACCCCTTAGCAGTTACTCCCAACTCCCTTTCCTCCCT |
| CTGTCAATCACATAATCTATGTTTTGTCCTTATGGATTTTACTAAGCTAGACATTTCGTAAAAATGG |
| AATCATACAATATATGGCTTTTTGTGTCTGGCTTCTTTTATTTGGCATAATGTTTTAGATGTTCATCC |
| ATTTTGTAGCATAAATCAGTATTTCATTTCTTTTTGCTGATGCATAATATCCCTTTTATTGCTATACA |
| TTGCTGAAAATATACATTTTAAAAAATCCATTAATCAGTTAATGAGATATTTGGGTTGTTCCTACTTT |
| TTTGGGCTATTATGAATAATGCTGCTATGACCATTCAGGTACCAATTTTTGTGTGGACATATATTTT |
| TACTTCTCTTGGGTATATACCTAGGTGTGGAATTGGTGGATCATGTGGTAAATCTATGTTTAACTTT |
| ATGAGGAACTGCTAAACCCTTTGCCATGGTTTGAAGGTATCTCCCAAAAGTTCATGTGTTGGAAAC |
| CGAATCCTTCTGTCCTCATGAATGGATTAATGAGGGTTTTGCCATCATGAATAGATTAATGTCACT |
| GTCACAGGAATGGGTTCATTACATTGAGAGTGGCTTTGTTATAAAAGTGAGTTCTCTCAGTCTCTCT |
| TGCTCTTGCCCTCTTATCATATGATGCCCTCTGTCATGTTATGACACCACATGAAGGCCCTCACCTG |
| GTGCCAGCACCATGTTCTTAGACTTCCCAGCCTCCAGAACCATGAGCTAAATAAACTTGTTTTCTAT |
| ATAAATTAACCAGCCTATGGTATTCTGTTACAGCAACAGAAAACAAGACTAAGACACTGTTTTCA |
| AAGCAGCTGCATCATGTTACACTCCCACCAGCAATTTATGAGTGTTCCAGTTTCTCCACGTCCTTAC |
| CACCCACTTGTCAATTGTCTGTCTTTTTTGTTATATAGTAATCCTATTGGGTATAAAGTGGTATCTTCT |
| TATGGTTTTAGTTTGTGCCTCTTGGATGACTAATGTGGGACATCTTTTTGTGTATCTATTGACCATCT |
| ATTTTTGTGTATCTTCTTTAGAGAAATGTCTATTTAAATCCTGTGTCAATATTTTAATTTGGTTATCT |
| TTTATTATTGAGTTGTAATATGATTCATCTTTAATTTTTATGTGTGTTATGAAGTAGGGTTTGTCAA |
| GGTTTTGTTTGTTTTTTTAACGTAGATATCAGAATACTCTAGCATTATTTTTTTTGAAAAAACTAT |
| TTCCCTATTGGTTGGTTTGGCACCCTTGCTAAAAAGCAAATGACCATTTAAATGTGGTTGTTTTACT |
| AGGCACTCCATTCCAGTTCCATGAAATCTTGATTACTGTAGCTTTATAGTAGTTCTTGAAATTGGAT |
| AGTATAATTCTTCTAACTCTGTTCTTCTATTTGAAAATTGATTGCAGTCTTTGGGATAAATATCACTT |
| TATCATCATGTTTGTGGTAGGCAGAGTAATCCCCCGTCTCCCTCCTGCCTCCAAACATGCCCTAAA |
| GCCTGGAACCTGTGAATATGTTATGTTATATGACAAGGGGAATTAAGATTGCAGACCAAATTAAG |
| GTTTCTGATAAACTGACCTGAAGATGAGGAGATTGTCCTGGATTATCTGGTTGGACCAGTGCAATC |
| GGTGACCTTAAAAGTGGAAGAGGGAGGCAGAAGAGGAGGTGGGTAATATGATATGAAAAGGAT |
| TCAACCATCATTGATGACTTTTTTTTTTTTTTTTTCCTGAGACGGAGTCTTGCTCTGTCGCCAGGC |
| TGGAGGGCAGTGGCGCGATCTCGGCTCACTGCAAGCTCTGCCTCCCAGGTCCCGGGTTCACACCAT |
| TCTCCTGCCTCAGCCTCCCAAGTAGCTGGCACTACAGGCGCCCGCTACCATGCCCAGCTAATTTTTT |
| TGTATTTTTAGTAGAGACGGGCTTCACTGTGTTAGCCAGGATGGTCTCGATCTCCTGACCTCGTGAT |
| CTGCCTCCTTAGGCCTCCCAAAGTGCTGGGATTACAGGCGTGAGCTACTGCGCCCGCCATTGCTG |
| ACTTTGAAGGTGAAGGAAGAGGGCATGAATCAAGGAATGCAGGATTTCAAAATGGTAGTATAGAA |
| GCAAGCCAGCTTCAATCCCTCAATAGAAGACCAAAAACAAATATATAGCATTGAGATTTTCACCA |
| GCAACAACCCAGAGTTCAAGTATGAGGATGAGACAGCCCCCAGGGCCACAGAGAAGTGGAAAAA |
| CCTTGAGCATATGATTGGAGAATCAGATTTCCACGTCTGCGAGTCCCCTCCCCTACATTCTTTCAGC |
| ACCAAGCATGTGGAAAATCTCCCTCAATTCTGTTTTTACACTGGAAAAAGTGAAATTGAGTGGTCA |
| ACCAGCTTCCTCACCTTCTTGGGTTCCGTAGCAGGAGTCCTGTCCCTGCCTTAACTCATGGGAAGC |
| ATTGTGAGTGCCTGTAGGGAGAAATATCTCTGAGGACAGGCTGCAACAAAGGTCAGAAGGTGAGA |
| CTACCATCCCCAACCCTGGAAACTCTGCTCTGTAACTCAGCCAAATGAGACACCAAATCAGAGTGG |
| CTATTCAGCAGCACCACACTGTAGGAGGTACATTCCACAGGTTCCCATGGGCAGGAACCCCTAGCC |
| AGTCTTCCCACACTGCTGACTAGGGGTTCCTGCCTAGGAGCCTGTAGAACATACCTGGGATAATCC |
| CTTTGGTGACTCCCCCATTTGGGACAGGCAGCACTGCAACCGTTTACTAGAGCCAAAGTGAACCTG |
| GGCTTATAGCGCCACCTAGAGCCGAAAAGGAGGCAGCAATCTAGTTGCAAAGATTAAGCAAATAT |
| ATTCAATGAAAGACAAAACAAGCTGGACAGAGAAAACTAGAATCAATAATTAATCCTTCAATGCA |
| AAGACATAGACATATACCCGCAAGTAACAACAGCAAACAGGGAACCACAGTCTCCCCAAAGGAC |
| AAAGCAAAAATCCAATGACTGACCCTAACGAGATGGCGACTATTAGCTTCTGACCAATAATTTAA |
| AATAGCAGTTTAAGGAAACTCAGGTATCTCCAAGATAATACAGAAAAGCAGAAATTTATCAGAG |
| AAATCTAACAAAGAGATTGAAATAATTTTAAAAAAATCAAACAGAAATCTTAGAACTGAGAAATAC |
| ATTTGCCAAACTGAAGAACTCTTAAGAGGGCTCTGAGCAGCAGAGTGAGCCAAGCAGAGGAAAGA |
| ATCTATGAGCTCAAAAACCAGCTGTGTGAAAATACACAATCAGAGAAGAAAAAAGAAATAAGAA |

Sequence Information

```
TAAAATGTAACAAAGACCACCTACAATATGTAAAAAATTACCTCAAAAGACCAAATCTAAGAATT
ACTGCTGTTGGTGTTCAAGAGAGAGTGAAGCGAGAGCAAGGGGTAGAAAGTTGATTCAAAAGGAT
AAGAACTGAAAACTTTCCAAAACTTGAGAAAGAGAAATATCCAGCTACAGAAAGGTCAGAGAAC
ACCAAACAGATTTGACCCAAATAAGACTACTCCAAGGCATAGAAAAATGAAACTCTCAAAGGTCA
AGGACAAAGAGAGGATCCTAAAAGCAGCAGAGAAAAGAAGCAAATAACACGTAAAGTAGCTCTA
ATTCATGTGGCAACGGATTACTCTAAGGAAACTAAACAGGCCAGGAGGGAGTGGAATGGCATTTT
CAGATTGCTCAAAGAGAGACAAAAAAAGCCTGCCATCCAAGAATATTGTATCCAGCAAAATTATC
ATTCAAATATAAAGGAGAGATAAAATCTTTCCCAGACAAACAAAAGCTGAGAGAATTCACCACCA
CTAGATCCATCTTGCAAGAAATACTAAAGGCAGTTCTTCAGTCTGAAAGAAAAACGCTAATGTG
CAAAAGAAAACTTTTCAAAGTATAAAACCTACAGGTAAAATTAAGTACCTGGACAAACTCAGAAT
ACTCTCTTACTGTATTGCTGGTATGCAATCCACTCATAACTCTACTATGAAGCTCAAAAGACATGA
GCCAAGGAGTGAAAACAGCCTCTAGAAGCTAGAAAGGCAAGGAAATGGATTTGCTAGAAAAGCA
AGGAAATGGAACTTCCAGAAGGGAATGCAGCCCTCTCAACACCTTGACATTAGCCCAGTGAGACC
TGCATCAGACTTGTACAGGCCTCAGCAGCTGAATGTATTGTACAGCCTGCAGAACTGTACAATAAT
AAGTGTGTATTGTTTAAGCTGCTAAGTGTGTGGTAATAGAAAACTAATGTATGTTTTTTTATATAAA
GCTAAATTTGATTTCCTAAATATTGTTAAAGATTTTTACACCTGTGTTCATTGTGGTTTTCTTTTTCT
GTAATGTCTTTGTTTCATTTTGGTGTCAGAGTAATGCTGGCCTCATAGAATAAGTTGGGAAGTACA
GGATTCCTATCTATTTTTTGAAAGAGTTTGTATAGAACTAGTATTATTCCTTTCTTAAATGTTTGGT
AGAATTTGCCAATGAAGGCATTTGGGCCTGAAATTTTCTTGGTGAGAAGGTTTTGTTTTGTTTTGTT
TTGAGACAGAGCCTCACTCTGTCGCCCAGGCTGGAGTGCAGTGGCACAGTCTCGGCACTGCAACCT
TTGCCTCCCGGGTTCAAGCGATTCTCCTGCCTCCGCCTCCTGAGTAGCTTGGATTATAGGTGCCTGC
CACCACACCTGGCTAATTTTTGTATTTTTAGTAGAGCCGGGGTTTCTCCATGTTGGCCAGGCTGGTC
TCGAACTCCTGGCCTCATGTGATCCATCCACCTCAGCCTCCCAAAGTGCTGGGATTACAGGCGTCA
GCCACCGCACCCGGCCTGTGGGGAGGTTTTAATTACTAATTTCAATGTCTTTAATGGGTATAGGG
CATGTACGTTATCTATTTTTTCCTGAATGAACTTAGATTAATCATTTTTGAAGTCTTAGTTGCTAGA
AAAAAATATTTAAAAATTGGTGAATTTTCTCATTAAAGCAGCTTTTAGTGCATTTTTGAATATAGTA
AATATAAATATTTTATATTTATAGAATATATTTTAGATCTGAAAAATAATTATTATGAGAGTCCAC
ATATTACAAAAATACAAATATTATATCTGAGTCCTTACTTACCAGGAGATCTGATTATAACTTGAT
TTCCCATACATTTATGCCACTCCCATGGGCCATAAACATGCCAGTCACTGTGATAAATTTACTTTGT
AAATCAATTAATTGACTTTGTGATTATATATATATCATTTACAGTGATTCTGCTTCTAAAAAGTGGA
ACCTCTTTCCATATGCTGTTAGAATTATTTATAAGCTTACAGAGGTTTAGGCCAGACCCCAAACTGT
GTTAAATTCACAAGGTAATGAGTGCTAACCTGTGAAGCCTCTTGAAAGAGAGGTCACTACCTATCT
CTGGCCATATGTCCCAATCCTGCCATTGTATAGGGCAGTGGTTTTTACTGAGAGTATTTTAGAAATT
CACTTGAGTGTTACTGATAGTTAGTGAGTAGGGGGCTCAGGATGCAATGCCCGTAATAACCCCACA
CAGTGAGGAATTGTCCCAAGTCCTGTACAACTTACAAAATATCCTGCTGGTTAGTCATGAAGATTA
AAAGCTTGTTTACAATTTTCTGAGACTAGAACCTAAGTCTAGTCTCTATGTTTTACACATAAACACA
AAGTATTTTTTGCGTGGTTTTAATATATAATTAATATTCTAATCTTTATTTTAGCATTTATCCCTGCT
CTCTCTTTTTTTTGTATTTCTACTATAGAATGGCCTTAAGTCCAAATTTATTTCGTCTATAACTGTA
TGCACTCATCTAACCACTTTGCTATGTCTTTTAGGGTTGAACCTGCGCATTTTCCTATGAAATACAT
GCTATTTTATTATTAATTGCCTTTTTCTACTCTGTATTACACTGAGAGTTATTTTTTTTAATTAGACA
TATAGTTACAGTATTGTATATAAATTCCATTTCAGGACAAAGGAGCATCACAAATATTTGTTATG
AAAAGGGTGGGGATGTTAGATTTGAAAAGCCTGAGAGGCATGTTATAGAAACAAACTTTCTTCTG
ATTTCAGTACTTTTCCTATCATTATAGTTGCTATTACATAAAAATGTAAAGTCTTGGAATGAGTCCA
TATTACTGCTTCAAAATAACCAAAACAATAAAAATGGATTTAACTTCTATTTCGCCTACAAAATAG
CCTAACACAATTATTATATCCATCAAGTCTAGGACATCCAGCCATAGTGCTCACACATATGCATAG
TAATCACAAATTTCAGTGCACAAACTTAGATCTGCAAAGAATATAACTTACTTCTTTTTTACCCTGT
CACTGAACGCAGTACCTCTGGGGTCCCTATTCTGCTGGGTGGAGGAAACCTGGTTCCAGTCAATTC
AGATCATCTCAGTTAATTCATGATCTCATCCTGGCTCCCCTCCAGGGAGCCAGTGCGTTGGAGCTG
AAGGAAGTGTGTGGTCCATAGTCATCCTTGCACAAGCCTCTGCAGAAACATTCCTGTTCCTGGCTG
GCCTTTTTATATCATCCATCTAGATCATGCTGCGACCTCCTTGCCTGCGGAGACTCTTTGGACCATC
TCTGTGCCACATTTGTGCTCTTCTCAACACCCAAATCAAAACATTCATCAGTTCAGCTGCAACCCCT
TCCACACTGTGGTGTGAGAAGCCTCTGAGCCTGCCTTCCATCACCTTGTGCAACCATTGTCATCTGC
TGCTGCCACACTATACTGGGCACAAGAACCGCAGGGAGTCTTGCTATCCTCTCATCTGCCCCCCGG
CTCCTCAGGGGATGAGGCATGGTTCTTTCCACTCTTGTATCCCTCCGTCCATTATTTCTTCTACACT
AGATCCAGTCCTGGGGGCAGAGCCCAAGATGTGTGCTTAAGGTCACAGCCATGTCCTTTAGCTTCG
TTTCCAGTCCTCTCTCTTCCCCTGGCTCTGAGTGATTGCTTAAGCTAAATCTATTAGCTCATCCACCT
GCTGACTATCCATTTCCGGAGCCCAGACATGGATCTCCCTGCCTGCTTCCTGGGTTGAGGGTCACA
GGGTGACAAAATTACTAGGAATGAGAAAAGCTGTTACTTAATATTTGGAAACATCATTCCAGTGG
AGATGCAGGGCACATGAGGCATACTGCTTAGCCTGTAATAATTTTCTCTCTTTTCAGTCTATATGCC
TAACTTTATGCCAGGATAGTGAAAGTTTTCATGTGCTTATCGTTGTGACCTTTGCAAGGTATCAGGT
GAAGAAGGCAGGCACATTGTATTGCTGTAGATAAATAGGATTAGTGACAGGAATATGGGATATAA
ACCTTTTTGCTAGGTCTAAACCATCCTTAACTATGCCATGAGTCTCTCACTATCTTAATGATGTAGG
GTCATCATTTTAATTTTTTATTGTAGTATGCATCTTTCAGTGGTGTCTTCAATATACGTCAGTGTGG
ATCATTTAATGTTGGAAAAACAGGTAAAGACACTTTAGTTTGTGGTCTACTTTTACAATTTATACTT
TTCTTCTCCTTTCCTCCTTCTACAAAGATTATGTCCAGCAGTATGCATCTTCCTGACTTGCAGATTCT
AGCCTGCTATAAAATTAGGACACCAGACACCGCACATATTGCTAGAATTGCGTCTGAGACTGAAT
AGGTCCTGAGTTAGTCTCTAATTGCATGGACTTCGTGGTGCCTATTGTGGTAACTCAGGGGCATTT
GTTTTGATTTGTTTGTTTGTTTGGTTGGTTGGTTTGGTTTTTTATCCTGGCCCTTGGCTGTTCAT
CCCTTTGTCTCCTGCTGCAAGGCCTCCTGTTAGCCATTTGCCTCTCATTAGGCATGGAGCTCCAGGC
TGCCTTCCATGTTCTTTCCTCCTGAGTGGCCTCCTCACCTGCTTGGGATGTCCAGTGTCAATCACCT
GGATTCTGCCCTCACTCCCACTGTGCATGCCCTGGTCAGAGGTGGGGCTGCTGCCCAGGACTCTGG
GGGCTCACAGAGTTTATTTCACTTTGGCCTTGGAGCAAGTGTTATCTGCAGATCCGAAGAGGTTCT
TGTTATTATTGATTAAGTATGCATTCAATATTTGAAATGCTTTAAACAAACTGCTTCATGTTTGGAT
ATATTGAGTTATTTTTGTTTCTGCCATTAAATGTTTTACTCTCCGGTTATTCTTCAGGGAGGATTGTG
CTCATCAGTGTTCTCGTGACTTTTGTTTGCCTCTCTCTGCATTAAACACCCAAACATCAGTGAGATC
CTTTAGAATCTGGCAAAACTTCAGAGAACTCTGAGGAAATGAAACTGCCTGTCCACTCAGTTTCAT
TGATTTTTCTGAGTAACCTTAAAGGCATATCTTACTACTTAAGAAGTAGAGATTCAGTAAAATGTT
```

-continued

Sequence Information

```
GTTTCTGTTCCAAGGATAAAAATTGAGAACATTTAACTTGTATTATATACTTGGAATCATAAAGAC
AAAATTGAAATAGTTGATGTCTGCCCAGATAGAATGTGCTAGCTTTCTCTGGCTTAACCATCTCTGA
AAACACATTGACATAAATTTCCATCTTTCTCACCACGCAAGTTGTTAGTACACCTGTTCTTTTGAAA
CCACAATTCTGTTTGTTCCTGTGTGTTGATGGTATTTTCACTTTTCTCCTGCTGCCCTTGAACTTGCC
AGACTCTCCAGCACTTGTGTGGTACTTTTCTCATTCATTACTTCTCTAGTGGCATTACTGAAGGATA
AACAGCTGTCTAGTCAAAATTATCTGGCCACGTTCAGTGGGTTTAGGTCTGAAAGGGGAGCCAAA
TAATGTGTGAGTAAACTGTAACACTCCCTAAGAGTGCCAAAAAAATTAGTTTGCCTGGAAATCCAT
TAGTAAAAAATATCAAACATTCCTAAAAATTAAACAATAGGAAAACAAACAGGGTTTTAGTTGT
TAAAAAGGACAGACCAAATATTTGGTACTTTTACTCGCTTAATACATCAAACATGGGTCTTCTGTG
CTACTTGTCAGGGGATTCTGAATATGAAGATCAAACCTTGCATTACCCATACCTCCTAAGTGAGA
GCACCTCAACATTTTGTGCTTACCTTACAACTTTCATCTAAAGATCTCCAAGATCTGTGAATACTTA
TGTTTTAAATTACAGGAAAAGTTAAGTTGTTGCTTGCCAATATGTAATAAATTAGGACACTGTTT
TCCAGTTTCCAGTTCCATTTTAACTTGTAGAGAATAAACGTTTTCAATCTTTCAACAGACTTTGGAG
TCTTTTCATCCTTAATAAATGTTAAAGGAGAGATAAAACCCCATTGATATCTCAGCATTATAAGCA
ATGGCATTAGCCTCATTAAAGTGAGGAAATATTTTACTACAAACTTTTATAACATTTTTCTTTTTAA
TCCTCATTCATCCCTGATTTTGCCCTTTCCCTGCATGCATCTTTTTTAAATCTCCACATCTTTTGGTG
GCTACATCCGTGTATTAGTCCATTTTCACACTGCTGATAAAGACATACCCAAGACTGGGTAATTTA
TAAAGAAAAGGTTTAATGGACTCACAGTTCCATGTGGCTTGGGAGACCTCACAATCACGGTGGA
AGGTGAGGGAAGAACAAAGGCACATCTTACATGGCAGCAGGCAAAAGCAAAATGAGAGCCAGGT
GAAAGGGGAAACCCTTTTAAAATCATCAGCTCTCGTGAAGCTTGTTCACTACCACGAGAACAGTA
TGGGGGAATCTGCCCCTGTGATTCAATTATCTCCCACTGGGTCTCCCCTACAACACATGGGAATTA
TGGGAGCTACAATTCAAGATGAGATTTGGGTAGGGACACAGCCAAACCGTATCAATCGGTTATTT
GGTGCCTGGCTGCCAGTCGCACTCCACCAGAAACCCTCCTCTTGCTAGCCCAGCTGGACATTCTCCTT
GCTGGTGCTCTTAGTCAAGATGTAAAGTCTGGTTAGTGTCTGAGCTGGTGGTCAGAGCACTTATCT
GCCCTGAATGCTGCAAACCATTTTAAACCCCTACGAATAATCAAATGTGTATTTGAACAAATCTTC
AGTTTCTGGTGTTTAATTTGAATCCCAGGCTATTGTTATAGTGTTTTTTCTATGATAATTGATGTCC
TTTATTTAAACTCATGGGAACAGAAAGGAGTTATCCTGGCTCTCCCCTGATAGTAACAACCCCCCT
CACAATTCACTGTGTTGTTGCACTTCTCAAGAAATTACCTATAGAATAGAGAATGCAGGCTGGGCG
TGGTGGCTTCTGCCTGTAATCCCAGCACTATGGGAAGCCGAGGTGGATGAATCACCTGAGGTCTGG
AGTTCAAGACCAGCCTGGCCGACAAGGCGAAACCCTGTCTTCACTAAAAATGCAAAAATTAGCTG
GGCATGGTGGTGGGCACCTGTAGACCCAGCTACTCAGGAAGTTGAGGCATGAGAATCGCTTGAAC
CCTGGAGGCGGAGGTTGCAGTGAGCCAAGATTGCACCACTGTACTCCAGCCTGGGAGACAGAGTG
AGACACTGTCTCAAAAAAAAAAAAAAAAAAAAAAAAGAATAGAGAATGCAATCTAGGAGGACT
CTATGCTTAGAATACTTTGGTCTTATGAAAACGTGATGTTTGGAGTGTGGCTATGATACTTAAATC
TAATATATGTTTAGTAAATATCCAGATAGGAGCCTATTCTGTTCTGTGTACTTTGCTGGTGCTGATG
ACTAGCATACATAAAAATAGCTAATATTATTTAGCACTGCTTCTATGCCAGGCACAATATTAAGGT
GGGTATTTTGTTATCCTCATTTCTCAAATAAGGAAACTTAGGCTCAGAGATTGAGTACTTGCCAA
ACCCACAGTGCTTAGCTCCTCTCAGTTCCCTGCATTTCAGTGAAATTAGACATGGGGCAGTAGGGG
TGATAGGGGAAAGTGATGATGGTCATAAAACACCTAGACCTATACCTTTTGTTTATACCTAGTCA
TCATTTAGCTCAAGTTTTCCTTAACTTCTGGCAGCAGAGTATACCTAATAGTATAACTAGTCTTTAA
TTAAGAAGCAGCCTTGACACAGACACCCTAGTCTCTAATGTGCGATTGCATAAGGCCTCCTGCTCC
CTGTGCCTGGGCTCTCATCTCTCTGGTGGTCACTTGGCTGGCTCTGTCCTGTCCTTATGGTTTCAGCT
CCTCCACAAAGCCCAGTCATTGCCTCCCATGAATGGAGAGATCTTATCTCTTTTTCTCACTCACTCC
GTGAGGGACAGGACCTTGTCCATCCTGTTTGCTGCCCTTTTTCCAGATCTGGAGTGGTCCCTGGAA
CATGGCAGCACTCAAGAAAGATGTGTTAAAGGAATAAGTGAGTTCTTTCTTCCAGGCCAAGACTG
ATGCTTCTTGAAATGCTCCCAATCAACCCTCTTAGACTCCAACATAACTGACCAGGGACCAGATTA
GACAAACAATTCTGATATTTGAGGGTTTGATTTACTTAAATTCTCACTGGGGTCAAGAGCACCCC
TTGCCAGCTCCTATAGTTTAAGCAGCAGTATGTAGAATAGCCAATGAAAAGTCAAGGTCACAGAG
TAGCTGGACAAAGGCTTAGAAAAAACAATGCAGTGACCTAAGTTAATGTTTAGTGCCTTTAACCTC
TATTTTCGGTGAGTGGCCTTTTCCCTAATTATTTGTTCCTCCAAATCATTGAGCCCTTCTGTGTGGTA
GGTCCTGTGCTAGGTCTTGGAAATAAAAACATTAAGAAACTTTTTGCTCTTGAGAAGCAGAGTTCA
TGGGGAAGACAAAGCCATGAACAACTGATTAACAATAGACAGAGCTAAGTATAGTAGAAAATGT
GCACATAAAATGTAGCAGAAATACAGAGCAGAGATGAAGACCATCTAGGGCACTAAGTGGCAGG
TTCACAGAAGATATGATCTTTAACCCGTGGCACTTTAGGCAAGGGAGCCAACATGTGCAAAGGCA
AAATTAGCATGAAAGGGCATGACATATTCTAACAACAGGGAGAAGTTAGTTCTACGTGACTGAAG
CTCAGGGCACTTTTTATGGGGAGGACAGGAGTTGATACCCAAAAGGAGGTTGGGGGCAGATAT
GAAGGATTCTATATGTGGGCCTGAAGTTGGAACTTTTTCCCTGATTGGAAAGCAATCAGGTCTTTA
AACATGCATGTGGCCTGATTGATTTTGGGTTTTACAAACACCTCTGGTGGGAACTTGAAGCGGTAT
ATAAATTAGCCCAGGAGCCCAGACAGAGGAGTGCCTGACCTAAAGCAATGGGCTGCAGAAGGGG
GGATGATTGGAAAGCTGTTTTAAAGGTAGACTTGGCAGAATCAAATGCACATTCGTCAGAAATG
ATTCAATGTAGTGCAACAGGGAAAGAGTAGCCAAGCGTGGTGGCACACACTTGTAGTCCCAGCTA
CTTGGGAGGCTGAAGTGGGAGGATTGATTGAGCCCAGGAGATCGAGGCTGCAGTGAGCTGTGATC
CTGCCACTGCACTCCATCCTGGTTGGAGGAGTGAGACTTTGTCTCAAAAAAAAAAAAAAAAGAT
AAGATTTGAGAATATCAGAATGTAATTTGAATATCTAGGTAGATAATGTCTCCAAATCTTTTAGC
AGGAGAAGATTGAATTTACCGAATCCTTTAGATGTGTACTAAGACATATATTAGCACTCCAGTTTG
CCTCTCAGTAATTTAAAAAAAAATCCAAAGAATCAACCATCAACAAGCAGATACTTTTCTGGGAC
AAAGAGGCTTCTCCATTTTTGAAACGATGTTGCCTACTCATCTGTTAGTCACCCTTGCATCAGGGCC
GTGTTCAAAGAGATGTCCAGGCTTGGTATGAGGCTGCTAGAGCCTTCCTTGCTTTTCCTTTTGTGAT
CTTTGAGTCAGGTTGGAAGGATGACTAGGGTAAGCCCCAGCTGAAGCATGCACAGGGATGTTGG
GGTAGAGATGATGTTTCAGGGCAGCCCTCCACGGCCAAGCCACACATTAAATTGTTTGGGGAGTA
GTTCTAAAAATTAATGCTGTTGTCATGGTTTCATTTTGATTTTTATCAGCTGGATATGGATGAGGCT
TCATTGTCATATACTTAATGTTTTTGCTTAGATCTTTGGCAAACCAATATTTTTCCATGACTTTTTGA
CAGTTATTTTTGTTCAATAGTGAATAATAAAGTGAGATTTACGGTCTGTATATGATAATGTTTGTCT
TACTTTGACATTTCTTTTCTAGACAGTAAAGGCCTTATAATTAGATTTTCCCTGTGCCAAAACATTG
CTGCAAAACCATCTCCCTGAAAAAACGTTTCTTTGCTTCTTTTAGGAGCTGGCGTCATCTTATTTTG
ATTTGGAATTTTTTTCATATGTCAGTCAGGAAATGAAACAAAATTTCTCTTGAATATGAATTCTTA
ACAAGAAAGAAATTAACTTTTGCCGAAAAATAAAACTAGAAGGGAAAATGAGAAGAAACGTCTTT
```

-continued

Sequence Information

```
GAAATGCTGATGGTTCCATTGTCTTTTTAAATTCTAATTTATGTCAAACTTCAGTGAGCAATATAGG
AAACTCCCTTTTCCACCTTGTTGCAAAAGAGCTTATTTTATTCTTGTTGCTACTCCTACCAGTTTTAT
GTTGAATTCTTTGAAATACCCAGGAGACTGAACTAGAACTTATGGACCGCACCCTATTTCTCATAT
AGTTAACCAACTAATGTCCTAACTCAGTGGATTCTGCCCCATTGCTGATAAGTGGCAACCATCGGC
CAGGTGCCATCTGTGGGGGTACAAGGACAGGCGAAGCTGAACTGCCCTTCTGCTGAGGCCACATC
TGCAGTTGGCGCTATGCCAGGAGAGCCTTGGAGAAGTTGCACATGTGTCCATTGACAGTGCTTTCT
CTTTGGAGTGCTCTTAAAAAGAATAACTGTTGATAGAATCGCTTATTGCTAATGGCAAAACATCAC
AGAGAACTAATTGCAAAACAGTCACACTTACTACATCCGTGGCCTCCCCTAATGATATGTGGAAA
CACCTTCCCTTTCCTACAGTAGCAAAAGTGGCCAAATTCTCTGTACAACCCGGAGAATTTTCCTATC
TGAGTCATAACTGAAGAGCTGCTCCTAGAATCAGATTCCAGATCCAGCCACCCTTGTCCCCATCAT
CTCCACTCTTATTTCCACCACCATCTTCATCCAATACTTTCCGTTGAGCACTAACAAATATGTGCAA
CTGAAGGACACTACATAATACCTCAGAGAAGTGTATCTATTTAAACAGAGACAACAGGCTTCTTC
TAAAGTATTGAGCCAGCATCACTTACAGCAATCCAGACAACAGAGTGAAATAATCGTTCTGTCTCA
GCCTTTCTTGATATCACGGGAAGAGTGTAGGTATTTCTTTCCAGTGTATTTTTGTATCACATGAATA
GCACCTTCTTCTAAGTTTCGATACATTGGTTATGAGTGATTGCTACTCTGTGCAGTATCATGAACAT
GGAGGAATTTCTTCTTTCTACTGATGGTGACCTTTTGTTGTTTTGAATATACGGGTCTGCTCAGCTT
CAATATGAAATGGAATGTGTATTTCAACAACTGGCCTGAGTGAATGTTTGGGCCTTGAGTTTTTGT
CAAGAAGTGATGTGGGGAGGTTTGAAGAAAGATTCTTGTAAGTCTGTGATGTCAAATGATGAGAT
TGTCTGTCACCGACCCATGTGTTGAAGAATTGTTTCCTCACCTGATCTAACTCAAGACTCTTCTCTA
CTCCCTTTCGAGAAGCACAGAAAAGAACTGAGAACTGGTGTGTTAAGGGCGCCACCAAAAGTTTC
CTTGGCAGTAGAGCCTTGAATTTCTTCCCCAACAGCAGCTAAGCCTTCTCTAAAAGGAATTACCAT
TACCTTGAAATAACTTCCTATGTACACTCATAGGAAGAGTGTACACTTTGCTGAGGTTGACCGTAC
TTGTGGTTTTCATCAGGAAGTGAAAGTTTATGTGGCCTACATGTGTGAGCCCACTCTATACTAGGG
ATAGCAGGAGTGTGGTGCTCTAGGGGCAGAGGCCTGGGGTGTCACACAGACCTTGTTGGAATCCT
AGCATTGCCATCTATTCACTGTTTGGCTTTTTCAAACTTCCTTTTAAAAAACGTGACAAAATGGTTA
TAATACTAAACTATTTGGGTTGTTGTAAATTTTAAGAACAACAGCAGTTACTACCATGTATTGAGC
ACTTAGGTTGTGTCAGGTACCCTGCCAAGAAAAGATCATAAGCAATGTCACTTCATTTCCATCATA
ATACATGAAGTAGTGCTATGGTTTGGATGTGGTTTGTTTCCACCAAAGCTCATGTGGAAGTCTAAT
TGCCACTGCATCTTGGGAGGTGGGGCCCAGTAGGAAGTGTTTGGGTCATGGGGGCGGGTTCCTCAT
GAATAGATCAATGCTGTCTCCCAGGATCGAGTTCTCAATCTCAAGGGAATGGATTAGTCGCCATGA
GAGTGGGTTGTTATAAAGTGAGGCTCTTCCTGCTCTTTGGTCCCTCTTTACCTGCACCTGCCTCTCC
TTCCACTTCTCTGCCATGTTATGATGCAGCACAAAAGCCCTCACCAGCAACTGATGCCAGTGCCTA
GCGCTTGGACTTATCAGTCATCAGAATTGTGAGCCAAATAAACCTGTTTTCTTTATAAATTACCTAG
TCTCAGTATTCTGTTATAGCAACACAAAATGGACTAAATCAATTAGTGATTGTTATTTCCACATGA
AGACGAGGAAACTGAGGTGGTATATCACCCCTGGCCACACAGCTAGTGAGTGTCTGGCCTCAGGC
TTCTATTCCAGGTCTGCCAACCCCAGATTCTGTGAGAGATAATGCAAAATCAGAGTCACTCCTAGT
GCAGTCAGTGCTTAACAAGTGTTCATTCTCTTTCCTCCCAGATGCATCTTGTAGCTTTGATAGATCT
CTGATTTCTTAATAAATTTTTATATGTAACATTCTATACAGCAGGTGGTCTGTCATACTGCCCTCAT
GTGGCTCATTTGGGTAATAGTGGGTTTTTTTTTAAAGTTTAATGCAAAATATGTGTTATTTAAAT
GTGTCTCTAAAGTCACCTAAATCTGTGGATACTTTGGGAGTTTGTAACTCTTAAGTCTATAACCCCAGTATG
TAAGAAATGGCACTTTTTCTTTTCTACTGCCCACTTTAATGTCTTAACTCTGAGCCCTCATTTGGCT
GGGAAGATACTTAACTTCAGTTACTCTAGTAGCTTCTACCCTGTCTTTGCCAAGATCTCCCATTCCT
TCTGTTGTCTTGGAAGAGAAACCTTCTCTTCCCTGGTATTGTGCATAATGAAACTTTATTTCACCAT
CCTGTCAAGAGGGGAAAATTTTTTTCACAATTATATTTTTCCATCTAATGTTCTGTTTACAGAGAC
ATTTATCAACCACTGGAGAAATACTCAGCTTTCACACTTAAGAAGAGATATTATTGCCAGAGTGT
AGAGTGTTAATTCATTTTCCAGTTTAAATTGTAGAATTTTTTTTCCAAGAGGAAAAGAAAAAGGTC
AGTTTTTGTCTCCACCTATAAGGAGCATTAAGTCACTAAGTGAAATTCCCTTAGTTTTCTCTTCATG
CATGGAGAGGGTCCCAGCTTCCATGGACTCATTCTCCCATGCTATACAAAGTTACACAGGTGTATT
TAAAGTTTAGTGGATTGTTTAGCTTAGGGATCTCCAAAGCGCATATCATCGAGGGACTGCCTTGTT
TTCCAGTGGCTCTCTCCATGGAGGATTTAAAGGTAGATATGTATCACACTGGGCCTTACTTATGTCT
GAATAATGAAAGGCTATGTCAATGGGAAAAGGGAATTTAGGGTGGGAAAAGGCAAGGAATTTTCT
TTTTTTTTATTATTTAAGCACCATTTAGTAACAATGTACATACAGTCTCTGTTCTTAAATGTATTTAA
GAGTTAACATCATCCTCATGCCAAGACCTTACTGTGTTTCAGATAACGGAGGCAGACTTTGGCAG
GGGGTAATAACTGGCCCCTTCGAGGAAGAAAATGGAGCCTGTGGGAAGGAGGCGTCCGAGGGGT
GGGCTTTGTGGCAAGCCCCTTGCTGAAGCAGAAGGGCGTGAAGAACCGGGAGCTCATCCACATCT
CTGACTGGCTGCCAACACTCGTGAAGCTGGCCAGGGGACACACCAATGGCACAAAGCCTCTGGAT
GGCTTCGACGTGTGGAAAACCATCAGGTACCTACACCCTGCCCTTTTTCCTCCCAGGACAGAAACT
CCAAGAGCAGCCTGACTCCATTGAGCAAGAATGATAGCTTTTGTGTTAAAATGATAGTTCAGCTTA
CAAATACATGATTTTTAAGAAAAATAAGTGCCTTTAGAGACATTGTAAGTATATATATTTTTAAAT
TATAAATTTGAGATTGTGGGCCTGTGTTTTACGTGAAGAACAAGATTGTCCTCAGCCCATCGCCCT
CCATGGAAGGTCTTTGAAGCTGCGACGTTTTGCTTAGAAGTAGGGCTAGGGTATTGTTAGCTTCCTG
CAGGGGGTCAGGGAACTAGGGATATGTTTATTTCCATTTATTTGCAAGTATCTAACAAGCACCTACT
ATGTGCCATACCTTCTTCTAGATGCTGAGAAATTAGGAATGAACAAGTCAGTCAAGATCCTGCCTC
TCAGGAAGCTGTATTCTAGTTGGGGGAGAAAGATGTTGGACAAATGAACACACAGATGAGCAAGA
TGACTGCCAGTTGTGATAAGTGCCAGGAAGGCAAAAAAGTATGTTGTGATAGATAGAGCTGGCTG
ATGTGAAGAAGATACATCAGGGAACAGGACCCAGACTCAGATTTGGAAATCGTGATGGTCTTTTT
CCTGTTTAACCCCCACAGTGTAGAGCAATAGCCCCCAAGGTTGGGAGGCACATGCCTTAGAGGTTG
CAAGATGTTCCCTTGGAGTACAGGAAGAAAATTTCAATCTTGTATTTGTATTAATATCTAATTTCAT
CTCATCCTTTTTAAAGTATATGTTTTTAAGCACATAATATATTAGTAGACTTGTACATAAATCTA
ATTTATAAATAAATATGCATATATTGGAGGTATTATTTTTACGGGTGGAATGACCTAGTGCAATGG
TTTTCAACCTCTGTTTGGTGTTACAGCTCTGTTTGGGGTTAGCAGCTGATTGACTGTCCCTTAGTGG
CCAGGGGGAGAGGACTTCCTCAGGCCATCTCTTCATCCCACTCCAGGTATCCCAGCTCAAGAATAG
CAGGTTTCAGGTCTCTAGTTATAGGAAATACACAATGGAGTATTTAGGAGCAAAAAGCCATGATA
TATTTAACATACCCTCAAATGGTTCAGAAAAAATTGTGTGTGTGTGTGTGTATGTATGTAC
ATGTGCACAGAGAGAATTCAAATGGACTGCAAAATTAAATAAAAGAATATAGGTAAGGTGCATAA
GTATTCTTTTGTTATGTCTTATTTTTGCAACTTTTTGTAAATTTGAAATTATTTCCAAATAAAGTGT
```

Sequence Information

```
TTTAAAAATAGGAAGGTCTGACAGCACTGCACCCACATTTCCAGAAGGCCAACAACTGACTAGAA
TCAAATAGCTGCTGCCTTCTGTAGATGAAGTATCCACCCTTCAAATCTTCAATCTCTATTGTTCCCA
AGTTCCAATACAGATCCACTGCACTCATTTAGGTTACCTACTTAGTCTCTGTAGGCATTTAAGTTTA
TAGTCCCTGCTGAACATAATCATAGTATTCAACACTCTGGAAATACCATACTTTGACCAATTTCCA
GTTGCAAAATATATAGATTATTTCTTATCTTTTTATATTATCAATTTTTCTGTAATTAATAATTAATG
TTAAAAAATAGTAGGGTTCAGCAGCCTAAGATTAGTTTTTACAAAGGAAGTTTGATAGCTATTCAA
GTTTAAACATTAAAGTTTAAAGTCCTGTGAGTTCAGGAATGGATAGAAGAAGTGTTCAGCCAGGC
CGCTCAACCTCTCACAACGTGGAGTCTATGGGTTCCTCTCTAATGGGCCTCACCCAGAAGGGTGAG
ACTAGGGAAGGTCCTCATCTCTTACAAACCCAAGGGAAAATCTGATTTAATTAGCTTTATAACCTT
CTTTTCAATTATTTTGCAACTCAAAGTTCCATGTTTTCCTTCGAGAATTTATTAAATTTTAAAGATCA
CTTTTCAAGCAGCAACATTTATAGTATTGGGTAGCCATTTCTTCACCATTTCTAAACATTATTTTGG
TTCTTATGAGTCATATTATTTTCATATTATTTTAAAATCCTCACTAGCCTCAAATTGTTCCCTCTTAT
TCTTGCCTGAAAAGTTGATTTGTCAGTTTGGAGACAGTGATCAGTTTATGATTTGTCATTTCAAGAA
CACTCTACAGCATCCAAGTCACAGAAAAGTAATGCCACTGAACAGCTAAGCTGAGAAGCAAAGC
AGTAAAACCTTTTCTCTCACCAGAAATTTTGAAGCTTTGTGCTCATTATGTGCTCATTCATATGCGA
TGACTTTTTTTTTCTTTTTCTTTGAAACATTTCTGCCTCTATCCATGATCTAAACTTGATATGTTAAAT
TTAAATTTAATTTCCCCAAGCGTGAGTACTATATGTCATTGTAGATAATTTGCAAACTACAAAAAA
TAAAAATAATTGGCTGGGCGTGGTGGCTCATGCCTGTAATCCCAGCACTTTGGGAGACTGAGGTGG
GTGGACCACCTGAGGTCAGGAGTTCAAGACCAGCCTGGCCAACATGGTGAAACCCCGTCTCTACT
AAAAATATAAAAACTAGCCGGGTGTGGTGGTGGGCACCTGTAATTCCAGCTACTCAGGAGGCTGA
GGCAGGAGAATTGCTTGAACCCAGGAGATGGAGGTTGCAGTGAGCCAACACGGTGCCACTGCACT
CCAGCCTCGGCGACAGAGTAAGACTCCGTCTCAAAAAAAAAAAAAAAAAAAAAAAATCACTC
AAATCTTACCTAGAAACAACTACTATAAACATTTTGTCATATTTCCTTAGAATTTTTCTTTTCAGCA
TTTTTTTACTACATCTTTTTTCCTTATTTAACAGACCATTGTTTTTGATTGTGTCATCCAAGAAACT
TACTGCAAACACTATTTCAGTCACTGCACATTCAATCGCATGGATATACCTTGATATACTTACCCAT
TCCCTTGACTTTCTTTTTTAGTTTTTTAAAACATTAGCTCTGAAATGAGCTCTTTCTACATGAACTGT
TTGTCTACATTTTGGACTTTTTCCCTTAGATATAAATGATTTGAAATTAAATCATTGAGCTAAAGAA
AGTGACCAATGTTGGGGCTTGAAAAACAATACCCCAAACTGGAGGCCCCAGAAGCAGCCTCTACA
ACAGAAGTTTTTCTCTGACCTCCTCCTGCTCTCTTGTCTCTCAGTCTCATTTTTTCCTGAGGCAAGCC
ATGGAAACCAGAATCCTTCTTCCCCAGGGCAGGTCATAGAAACCAGAACCCCTTCTCCCCAGGGCT
AATCATAAAACCTAGAAATATTATTCTAATTTTCCCTCTGCCCTATTTGTGTAAAAAGTGGCCATAA
AAAAGTTATCTGGCCTAACTTGTTTTAACTGTAGGTCATAACATTTCCATTCCAGACGGGTCCAA
CCCCACATCCAGAAGGAAGGAATGCATGCCCAGAGAGGCCGAGAAGAATCCAGAGAGACAGACC
TTGCTGGGTTTCCCCACTCAGGCTATTAGCATTAGAGCATACCCTTTTATCCAATCATGTTTCTATA
TGGCTGTCCATACTTTGTTAAACCTATACATAAAAATGAACGATTTCCTCTATATCTTTGGGTCTTC
ATTCTAAAGGCTCCCATGTATACACATTAAATACATTTGTATGCCTTTTCTCCTGTTAATTCACCTTT
TGTGAACTGATTTTTCAGTGAACTTGCGGAGGGCCAAGGGTGGCCCCTACATGATTTTAAAAGCAT
TTGATAAACATTACCAAACTGCTTTCTAAAAAGGCTGTATCAATGTACTCTTGTACAGGTGTAGAA
AGTGCTCATCTTCCTCATAGCTTTTCCTTATCAAGCTTTTTAAAAAACCTTTGCTAATGTTATAGAC
AAAATAGTCTTGTATTAACTTGATTTTTTATTATTATGGAGATTAATATTTAACTTTTTATATTCCAT
TTGTATTTTGTCTTTGAAAGTATTCATTCCATGTGCTTTTCCACTTATTTTACTGAAAAGTAGGTGTT
TTTTGTGGATTTGTTTGCTTCTTTATGTCAGGTTTTTGGATTGTTGTATTTCTTGCAAATATTTTCCT
TTTTTTTTTGTCTTTTTATTTTGTTTATGTCTTCTACATGGATGTCTTTCCCATGTTTATTTGTCAATGA
AATGTTTTTCTCTTGCTTTTTGTTCAGAAATATTTTTCTCAGCTTCAAATGTGCTAAATATCTATTT
TCTTCTAGGTGTTGTGGTTTGAGTTCTTCCATGTATTTCTTTTTCTTTTTTTTCTTTTTAAGACAG
AGTCTTGCTCTGTCACCCAGACTGGAGTGCAGTGATATGATCTTGGCTCACTGCGATCTCTGCCTCC
TGGGTTCAAGCGGTTCTCATGTCTCAGCTTCCCGAGTAGTTGGAATTACAGGTATGCATCAACATA
CCCAGCTAATTTTTGTATTTTTAGTAGAGCCTGGGTTTTGCCATGTTGGTCCAACCAGTCTTGAACT
CCTGGCCTCAAGTGATCCACCTGCCTTGGCCTCCCAAAGCGCTGGGATTACAGGTGTGAGCCATTG
TGCTCAGCCATAATTCTTAAATTGTTGCAAGATGGTGTGCGTGTTATGTGAGGTCAGTGTCTAAAT
CAGAGGAGTAATGTTTTTTGCAGTTTTTTAAGATTGTAGGCCTCTTTAAGACCGATGAAAACTATG
AACTTACAGGAAAAAGTACCTAAACATAGGCACAAAAATCTAGATATTACCTATTTTGTGATATT
AGAAATTGATTACACATTCTTTTCTAAAACATTCTTTACAAGCCTATGCCCCTTTTGCTTATTTTAAT
GCAAAACTTAATGCCCACTTCATGGTAAAAATAAAACAAAGATTTCCAAGCAAAGCAAATCTTGA
ACTTTAATTCAGTTTATCATCAACTTTCAATATAAAGGCTGTAGCGGTTTGGCTTGGAGTAGGAGA
AAGCTTTGAGTGACTTTGAGATGGCAACATTTGTGGCATGCTTGATATCCAATCATTTTTGATTTTT
CTTTTGTTTTGTTTTGGTGGCAAAAATGTTGTAAACCCTGGCTTGCATAAGGACATAATAGCATGTG
GAATCAAAGCTTTATAGGACACTTTGCCAGGTGAGGGTGGGATTGAATCGAAAAATAGTTGAATT
CATTTTGAGTCCCAAATTTACTGAGGTTATTATCTTTGGCAAAGTTCACATCATTGATGTTTGTCCA
TATAGCTAAATTTTGGATTACAAATGCACATTTCAACCTTAAGATTATGTTGATCAGAAGTAACCT
TTAAGAATTTGGCTCATGTTTGCTTCTGACTGCAGAGAAATTGGGAAAAGTCTAATCACTCTTAGC
TCCAAATTGCAGATCTTTCTTCGGTGTTAGCACGTTCTCCTAGCGGCCAATCTCTTATGGAACAGGG
GCACGTTCTTCAGTACCGTACATAGTGGTGACTGCGGGGCTTTAACCAAAAGATATGGCCAAATT
ATTGTCCAAGTAGGCTAAATCATGAGATAATGGGCTTTCTTTTTTTTTTTATTTAAAAGTAAAATT
TCTGCCCAAAGTTTGATCATACATTTCAAGACTTGTTTTCTGGAAATTCAGCAAATTTCTATTTAGA
AAGCAAAAAACCGCTCTCATTCTGTTCCCATTGCTTGAGAAAAATTCCTGAAATAATAATTCAGCC
TCGAGCCTAATGAAGTTGGTGCTTCTCACAGCATTAGGCAAGTTCGGAATCGGTGGCAGAACATTT
GGCACCCCTGCCTGCTGATACAGAAATCGCCCAGTCACATTGACGTCTGTTGTGTCTTTTCAAAG
CAGCAAAACAAATGGACAGCCAAATGTCAGAGACACCCGATCTGTGCCCAGAGGTCTGAAACTT
TTTTCCAGAAATGGAAATACCACTTTCGAGATGATGGTAGTTTTGAAAATTTGAAGAGGCTCGTG
AAATAGGAATGCCAGTAACGGATGGAAAAACAGTTGTCTGTGCTGGAGCATCAGAAGTTTTATTA
GCTGTATAGTTACAAATTTCTCTTAGGACTGCTTCAAAATATTAAAATGTTAGAAGAAATAGTAGT
TCTGGAGTGGGTGACATTATTTACAATAGGAGCTCCTTGACTGCTTCAGTTTTTCTTTGTTGCAAG
CCACAGACTATGTTTGCCATTTCTAGGGGACATGACTTCTCTAAGCTCTTTCCAATTCTGTGTAGTT
TTTCTGCTTTTCAGCTCAATAATCAGCCTATAGGTTGTTGAAGACATTTCATAAGGTTGATTGACA
AAAAGGAAACCAAAGGATTAAAACCTTGCAAGTTTCTTTTTAATTATTTTATATTTAATTAAACA
ATGTAAAACATAAGCAGACTAGGCGTGGTGGCTCACGCCTATAATCCCAGCACTATGGGAGGCCG
```

-continued

Sequence Information

```
AGGAGGGAGGATTGCTTGAGCCCAGGAGTTCGAGACCAGCCTGGGCAACATAGCGAAACCCTGTC
TCTACAAAAAATACAAAAATTAGCTGGGTGTGTTGGCACACACCTGTAGTCCCAGCTACTCAGGA
GGCTGAGGCAGGAGGTTCACTTGAGCCCAGGAGCTTGAGGCTACAGTGAGTTGTGATCATGCCAC
TGCACTCCAGCCTGGGCAACAGAGCAAGATCCTGTTTCAGGAAAAAAAAAAAGCAATCTCCTGAT
CATAATGATAGGAATTTCTTTTTTATCATCAATGGGAAACACTTTAAGATGTCATAACATGACAGT
GGTGACAACTGAATATTAAAATATCTTAAAAACTTAGTATGTCATTATAAAGACTTTTCCCCCACT
ATCAATATCATTTCAAGAAGAAAGTTAAAGGAAAAACAAATCTTTTCACCTCAATTTTACAGATGC
CATGAAGCCAAATAAAGCATGATGGTCCATGAGCTAAATGTTAACCTCTGATCTAAAATGGATACT
TCAAGAAAAAAAAAAACACATAAAATGATACTTCATTCCACATACTAACAAGAGAACTCAGACT
AATTATTGAATAATATTTCTCTTTTCACTGACTTATGGCACTATTTTAGGTTTTAAGTTCTTATGAGT
ACTGTGCTCTGTCTTGGGGCCCCCTGTTTTAGCCCACTGACTTATCTGTTCTCATGCTGGCATCTGA
CTATTAATCATTGTCTTTTTCGAGTATATTTAAATATCTGGTAGAAATGGTTATCGGCCTGTCCTTC
ATTATATTGTCTTTATAAAATTTTCTTGACAACTCTCACTTTTTAATTTTTCTTGGTGAACTCTAGAA
TTATTTTGTTAAATTAAAAGAAAAGCTTCTCAAAAATTATACTGAGTGAGATTAAGCCTGTAAATT
AATCTGGCAACAATGTACATATTCATGCTTTTCACTTGGACACTTAAAGTTGTCCCCCAGTTTACTA
ATGCTCTTTTTATTTAAAAAAAATTCTGTTTTCTCTTTATTTCATTTTGGGCAGTTTCTATTTCTAAG
CCTTTAAGGTTTTTGATTTTTTTCTCAATGTCTGATCTTTCATCAATTTCATGCAATGTATTTTTCAT
CTCACACATTGTAGCTTTCACTTCTTGAAGCTCCACTTGGGTCTTTTTAATATCCTCCCTGTAACTAC
TTAACTTCCTGAACATATAGAATACAGTTATAATAAATATTTTAATGTCCCCTGCTAATTCCAACAT
CTATATCACTTCTCAGTTGGTTGTGATTGATTATTCTCCTCATTATACCGGTCATATTTCTATCCCTT
TTGGTCTTTGATTCAATGCCAAGCATTGTACATTTTACCCTGTTGAGTGCTGGATATTTTGTATTCT
TGTAAAGCTTCTAGCTAGGCAGGGTGTGGTGGCTCACACCTGTAATCCCAGCACTTTGGGAGGCCA
AGGCGGGTGGATCACCTGAGGTCAAGAGTTCAAGACTATCCTGGCCAACATGGTGAAACCCCGTC
TCTAATAAAAATATAAAAATTAGCTGAGCATGGTGGCGGGCGCCTGTGATCCCAGCTACTAGGGA
GGCTGAGGCAGGAGAATCGCTTGAACCCGGGAGGCAGAGGTTGCAGTGATCCGAGATTGCACCAC
TGCACTCCAACCTGAGCAACAGACTGAGACCCTGCCTCAAAATAAATAAATAAATAAATAAAAAT
AAAGCTTCTGGCTTTGTTCTGAGATGCAGTTAAGTTATTTGGAAACAGTTTGATCGTTTTGAGCATT
GCTTTTAGGATTTATTAGGCAACTGCAGAGCAGTGCTCAGTCTACAGCTAATTATACTCCACTGCT
GAGTCAAATCCTCTCTAGTCAAACCTTCTCACAGCAGCCTGTGAGTTTTTCAAGGCTGGCTGATGG
GAACGGGTACTGTTCCCAACTCTGTGTGAATGCTGAGCAGTCTTCCCCTTAATCCTTACAGGTAGTT
CTTTCCCGTGTTGTGAGTAGTTCACTCACAGGCATCTTTTTCTAAGACAATGGTCCCCAAACTCTCT
GGCACCAGGGACTGGTTTTGTGAGAGACAATTTTTCCACCGACCAGGGTTGGTCGGGGATAGTTT
CAGGATGAAACTCAGATCATAAGGCATTAGTTAGATTCTCATAAGAAGCATACACCGTAGATCCCT
CGCATGCGCAGTTCACAGTAGGATTCGCACTCCTATGAGGATTTAGTGCTGCCACTAATCTGACAG
AAGGCAGAACTCAGGCAGTAAAGCTTGCTAGCCCACCGCTCACCTCCTGCTGTGAGGTCCAGTTCC
TAATAGGCCACAGATGGGTACCGGTCCACAGTCTTTGTTGGGGGACCTCTGCTCTAAGGGGATCCT
CTGCAGATTTCCAGGATTCTCATTCTGTGCAGCTTTCTCTTCTCTGGTCCTCTGTCCTAAGAGCTCA
AGCTCCCTTGGTCTCTGGACTCAGCTCTGTCTGCTCAACTCAAGGAATTCATTGGACTACATTTCAG
TTGCCCTTCCCTGCACCAGGGCTTAGAAATTCTCTCAAGGCAGTAAACTGGGCAATGATTAAAAAC
TCACCTGCTTTGTTTTTCATCTTGGAATAATCATTGTTCTTTGCCTGATATCCAGTGTTTTGAATACT
GTTTTAAATATTCTGTCCATTTTTCTTTGGGTTGTTTTAGGCAAGAGGGTTAAGTAAATCTAATTTG
GCTGGAAGCAGAAGTATCCAAAGAAAAATTTATTGTGCCTTTACTTTCTTTACCAGTATTTTCTTGC
CTATTTCTCACTTTCAAGTGTTTTAAATTCAATCTATCAGTACAGACCCAGCTTTTTGCAATTGAAT
ACTTTAAATCTTATAACTCTTCTTCCAAAGCAAGTTTCTTCTTCATTCTACTTTGTAATCACATGTTG
CGAAATTTTATATATATATATTTAATTATGTTTAATGTTACCAACATTTTTATTTATTATAACTTTCCTTA
GTTCTTAAGTTTGATTAATCTTTTGATTAGTTGATTAATATTTTAAAGTAATTTTTCAGTAGAGGTA
CATAAATGGTGAGTTCTTCCAAATTTTTCATATGAAAGAATATATTTCTATTACCATCAAACATAA
ATAGTAATATAGGTCAGGCGCAGTGGCTTATGCCTGTAATCCCAATACTTTGGGAGCCTGAGGCAG
GTAGATCACTTGAGGTCAGGAGTTTGAGACCAGGCTGGCCAACCTGGTGAAACCCTGCCTCTACCA
AAAATACAAAAGTTGACTGGGTGTGGTGGCACACACCTGTAGTCCCAGCTACTTGGGAGACTGAG
GGAGGAGAATCGCTTGAACCCATGAGGTGGAAGTTGCAGTGAGCCGAGATTGCGCCGCTGCACTT
CAGCCTGGGTAAAGAGCGAGACTCTGTCTCAAAAAAAAAAAATAATAATAATATAAATAATTATT
GTTAAAAATGAAAGAATGTATTTATTTCATCTTTCGATCATGAATACTTACCAACAATGTTGGCATA
AACTCCACCTTGTCAAATACCAAAACTGCAATCCTGTCTTGTTTTTGTTTGCCTTTACCTGGTTCAC
TTTGCTATAATAATACTCACCAGTAGACAATAAACTAACGTCTACAGCATCTTGAGCAGAAAGGAT
TTAACAAGAATTCTGTATATTATTAATATTATTTTGTTTGAATGTAATATGTTGAATGTATTTATGT
TTGAATGTTAGAATATTAATATTTATTTATGTTTGAATGTAATTATTTATGTTTGAGTTCTTTCATTTG
AAAGAATGTATTCTATGGGGAATGGTGCAAATGGTGATTTTTTTCTTTGAACCATGTATTTAGAAG
TGCATTGTTAAGTTTCCAAATTTTGGGTTTTTCCCTAGTTAAATTATTGATTTCTAGTTTATTTCAGT
TGTGGTTTTGAGGACCACAAATAATTGAAATGCTTTGTATTATTTCAATTATTATTATTGTTTTTA
ACAGAGACAAGGTCTCAATTTGTCACCCAAGCTAGAGTGCAGTGGTGCAATCATAGCTCACTGCA
ACTTCTGCCTCCTGGGCTCAAGCAATCCTTCCACCCCAGCCTCCCAAGTAGCTGGCACTACAGGCA
TGTACTGCTATAACCAGCTAATTTTTAAATTTTTATTTTGTAGAGGCAGGGTCTCACTATGTTGCCT
CAGCTGGTCTCAAACTCCTGGGCTCAAGCAATCCTCCTGCCTCAGCCTCCCAAAGCGCTGGGATTA
CAGGTGTGAGCCATCACTCCTGGGCTAATTGTTTAAATTTGAGACTTGGCCTAGTAGATGGTCTTT
CTTGTTGTCCACATCAGGTGTAATTGAAAAGAATGCGTATTCTGTAGTTGTTAAGTATAGTGTTAG
GTTTTTCTTTATGATCCAGTCTGTAATGTTTTAGTAGATGAATTTATACATATTTATAAATATTTTA
TTTCTATTCTTAGTTTTTTCATTGTTTTGTTACATTTACTTTTTATCTTTGACCTTTTATTTAGTAGTT
CTTTAATATTTAGAAAAATTTATATTTTATCCTACTGTTTATCATTATACAAATATCTTTATATAATT
CCTTAGTCCCTTTTTCTTACTTAGGTTCCACTATTTGGTTTGTCACATTTAAATGACATCTTCAGCT
TCCACTTATTACCCATAAGGAAATCAAGCAACTTATGTAACTTTTCATTTCCTTCCAGTTTTGTGAT
TTAAGTAGTGTTATTCCTACTGTATCAGAGCATGTAATATGTAATACTGTTCTCTCTTTATCCACAA
TTTTGTTTTAGTTTTAGATCTTCAATAATATATTCAATACTGACCACCCATCCACTTCTAAAGTGTTC
ACAATTATCTCTTAGTTGGAGGAATTCATCCTTGAATAGATTTCTCAGGATTCTTTGAATTCTTGCA
TGTTTATTAAAACATTTTCTACAACCTTGATAATTGAACACCAGCTCAACCGGTTAAAATAAACC
CTTGTCCCACACTTTCTTGCTTTGAGTTTCTTGAAAATGTTACCCTAATCTTTGCTTGTTTTCTATGT
TACTGTTGATAAGTCTAATATCAGCCTGATTTTATTCCTTTGCAAGTGACTTTGTGTTTTTTGTCTGG
```

Sequence Information

```
GCACCCAGAAGATTTTTTATTATCACTATTATTATAGTTATGATTTAAAATCTAAGAATTTTTCCAG
ATGTGTCACAAAGGTGACCCTACTGTGTCAGTTTTCTCAGATAAAAGTGAGTTATTTCACTTTGTAT
ATTCAGATCTTCTTTTATTTCAGAGTTTTTAAAAATTACAGTTTTAGGCCGGGTGCGGTGGCTCACG
CCTGTAATCCCAGCACTTTGGGAGGCCGAGGCGGGCGGATCACAAGGTCAGGAGATCGAGACCAT
CCCGGCTAAAACGGTGAAACCCCGTCTCTACTAAAAATACAAAAAATTAGCCGGGCGTAGTGGCG
GGCGCCTGTAGTCCCAGCTCCTTGGGAGGCTGAGGCAGGAGAATGGCGTGAACCCGGGAGGCGGA
GCTTGCAGTGAGCCGAGATCCCGCCACTGCACTCCAGCCTGGGCGACAGAGCGAGACTCCGTCTC
AAAAAAAAAAAAAAATTACAGTTTTAAATATTATATTCTACTGTTTTGTTTTTCTTCTTCAGGAACT
CCTAGTTATAGGTATTATTGAATCTTCTTTACATAAATTTGGTTTCTGTCAATTTCTCTCGTATCCTC
TTTGCCTCTTTATTTTTCTTTATTTTGAATTAATTATCCTTTCTCTTTTAATTTCTATTCTCTACACG
CTTTCACATAGAGAATGTCATGTATAATGTTTTGTCATTTCTAAGATTTTGTCCTTTTTTTCCCAGTT
CCCTTCCTTTAAAAAGTGTGATGTCTGAGTTTTACAATTTCTGAATCATGGTTGTTGTTTCTTTAATA
TTGGCAGTTGATGATTTCATTATATTTAATTCATGTTGAAATATCCTGTAATGGTTTTCTTCTGCCTT
ATGACTGTTTTTCCATAGTAGGAGAATGTTTTCATTTGCCAAATTTTTGAATTCTCATTTTCTATTTT
TTTTAACTCGTATGGTAACTTTGCATAGATGCTGAGTTCTTTTTGGTTTTGTTCACGTTTATGTATGT
TGGCGTTTCCTGGATCTAAGATAGCAGGCAATCCGTAGGAGTGGGATTTGGACACTTTCATTTACT
TCAGGTGCTTCAAGAGCGCTGTGTATTGCTATAGTGAAGTGCAGTTTCTTTGCTAAATGTAGCCCCT
TTCTTTTTTTTTTTTTTTAATTATACTTTAAGTTTTAGGGTACATGTGCACATTGTGCAGGTTAGT
TACATATGTATACATGTGCCATGCTGGTACGCTGCACCCACTAACTCGTCATCTAGCATTAGGTAT
ATCTCCCAATGCTATCCCTCCCCCCTCCCCCTCCCCACCACAGGGTGTGATATTCCCCTT
CCTGTGTCCATGTGATCTCATTGTTCAATTCCCACCTATGAGTGAGAATATGCGGTGTTTGGTTTTT
TGTTCTTGCGATAGTTTACTGAGAATGATGGTTTCCAATTTCATCCATGTCCCTACAAAGGACATGA
ACTCATCATTTTTTATGGCTGCATAGTATTCCATGGTGTATATGTGCCACATTTTCTTAATCCAGTCT
ATCATTGTTGGACATTTGGGTTGTTCCAAGTCTTTGCTATTGTGAATAATGCCACAATAAACATAC
GTGTGCATGTGTCTTTATAGCAGCATGATTTATAGTCATTTGGGTATATGCCCAGTAATGGGATGG
CTGGGTCAAATGGTATTTCTAGTTCTGGATCCCTGAGGAATCGCCACACTGACTTCCACAATGGTT
GAACTAGTTTACAGTCCCACCAACAGTGTAAAAGTGTTCCTGTTTCTCCACATCCTCTCCAGCACCT
GTTGTTTCCTGACTTTTTAATGATTACCGTTCTAACTGGTGTGAGATGATATCTCATAGTGGTTTTG
ATTTGCATTTCTCTGATGGCCAGTGATGGTGAGCATTTTTTCATGTGTTTTTGGCTGCATAAATGT
CTTCTTTTGAGAAGTGTCTGTTCATGTCCTTCGCCCGCTTTTTGATGGGGTTGTTTGTTTTTTTCTTG
TAATTTGTTTGAGTTCATTGTAGATTCTGGATATTAGCCCTTTGTCAGATGAGTAGGTTGCGAAAAT
TTTCTCCCATTTTGTAGGTTGCCTGTTCACTCTGATGGTAGTTTCCTTTGCTGTGCAGAAGCTCTTTA
GTTTAATTAGATCCCATTTGTCAATTTTGGCTTTTGTTGCCATTGCTTTTGGTGTTTTGGACATGAAG
TCCTTGCCCACGCCTATGTCCTGAATGGTAATGCCTAGGTTTTCTTCTAGGGTTTTTATGGTTTTAG
GTCTAACGTTTAAATCTTTAATCCATCTTGAATTGATTTTTGTATAAGGTGTAAGGAAGGGATCCA
GTTTCAGCTTTCTACATATGGCTAGCCAGTTTTCCCAGCACCATTTATTAAATAGGGAATCCTTTCC
CCATAGCTTGTTTTTCTCAGGTTTGTCAAAGATCAGATAGTTGTAGGTAAGCGGCGTTATTCTGAG
GGCTCTGTTCTGTTCCATTGATCTATATCTCTGTTTTGGTACCAGTACCATGCTGTTTTGGTTACTGA
AGCCTTGTAGTATAGTTTGAAGTCAGGTAGTGTGATGCCTCCAGCTTTGTTCTTTTGGCTTAGGATT
GACTTGGCAATGAGGGCTCTTTTTTGGTTCCATATGAACTTGAAAGTAGTTTTTTCCAATTCTGTGA
AGAAAGTCATTGGTAGCTTGATGGGGTTGGCATTGAACCTGTAAATTACCTTGGGCAGTATGGCCA
TTTTCACGATATTGATTCTTCCTACCCATGAGCATGGAATGTTCTTCCATTTGTTTGTATCCTCTTTT
ATTTCCTTGAGCAGTGGTTTGTAGTTCTCCTTGAAGAGGTCCTTCACATCCCTTGTAAGTTGGATTC
CTAGGTATTTTATTCTCTTTGAAGCAATTGTGAATGGGAGTTCACTCATGATTTGGCTCTCTGTTTG
TCTGTTGTTGGTGTATAGGAATGCTTGTGATTTTTGTATATTGATTTTGTATCCTGAGACTTTGCTGA
AGTTGCTTATCAGCTTAAGGAGATTTGGGGCTGAGACAATGGGGTTTTCTAGATAAACAATCATGT
AATCTGCAAACAGGGACAATTTGACTTCCTCTTTTCCTAATTGAATACCCTTTATTTCCTTCCCCTG
CCTAATTGCCCTGGCCAGAACTTCCAACACTATGTTGAATAGGAGTGGTGAGAGAGGGCATCCCTG
TCTTGTGCCAGTTTTCAAAGGGAATGCTTCCAGTTTTTGCCCATTCAGTATGATATTGGCTGTGGGT
TTGTCATAGATAGCTCTTATTATTTTGAAATACGTCCCATCAATACCTAATTTATTGAGAGTTTTTA
ACATGAAGTGTTGTTGAATTTTGTCAAAGGCTTTTTCTGCATCTATTGAGATAATCATGTGGTTTTT
GTCTTTGGCTCTGTTTATATGCTGGATTACATTTATTGATTTGCGTATATTGAAGCAGCCTTGCATC
CCAGGGATGAAGCCCACTTGATCATGGTGGATAAGCTTTTTGATGTGCTGCTGGATTTGGTTTGCC
AGTATTTTATTGAGGATTTTTGCATCAATGTTCATCAAGGATATTGGTCTAAAATTCTCTTTTTTGG
TTGTGTCTCTGCCTGGCTTTGGTATCAGGATGATGCTGGACTCATAAAATGAGTTAGGGAGGATTC
TCTCTTTTTCTATTGATTGGAATAGTTTCAGAAAGAATGGTACCAGTTCCTCCTTGTACCTCTGGTA
GAATTCGGCTGTGAATCCTTCTGGTCCTGGACTCTTTTTGGTTGGTAAAATATTGATTATTGCCACA
ATTTCAGCTCCTGTTATTGGTCTATTCAGAGATTCAACTTCTTCCTGGTTTAGTCTTGGGAGAGTGT
ATGTGTCGAGGAATGTATCCATTTCTTCTAGATTTTCTAGTTTATTTGCGTAGAGGTGTTTGTAGTA
TTCTCTGATGGTAGTTTGTATTTCTGTGGGATCGGTGGTGATATCCCCTTTATCATTTTTTATTGTGT
CTATTTGATTCTTCTCTCTTTTCTTCTTTGTTAGTCTTGCTAGCGGTCTATCAATTTTGTGATCCTTT
CAAAAAACCAGCTCCTGGATTCATTGATTTTTTGAAGGGTTTTTTGTGTCTCTATTTCCTTCAGTTCT
GCTCTGATTTAGTTATTTCTTGCCTTCTGCTAGCTTTTGAATGTGTTTGCTCTTGCTTTTCTAGTTGT
TTTAATTGTGATGTTAGGGTGTCAATTTTGGATCTTTCCTGCTTTCTCTTGTGGCATTTAGTGCTAT
AAATTTCCCTCTACACACTGCTTTGAATGCGTCCCAGAGATTCTGGTATGTTGTGTCTTTGTTCTCG
CTGGTTTCAAAGAACATCTTTACTTCTGCCTTCATTTCGTTATGTACCCCAATCATTCAGGAGCA
GGTTGTTCAGTTTCCATGTAGTTGAGCGGCTTTGAGTGAGATTCTTAATCCTGAGTTCTAGTTTGAT
TGCACTGTGGTCTGAGAGATAGTTTGTTATAAATTCTGTTCTTTTACATTTGCTGAGGAGAGCTTTA
CTTCCAACTATGTGGTCAATTTTGGAATAGGTGTGGTGGTGCTGAAAAAATGTATATTCTGTT
GACTTGGGGTGGAGAGTTCTGTAGATGTCTATTAGGTCCGCTTGGTCAGAGCTGAGTTCAATTCC
TGGGTATCCTTGTTGACTTTCTGTCTCGTTGATCTGTCTAATGTTGACAGTGGGGTATTGAAGTCTC
CCATTATTAATGTGTGGGAGTCTAAGTCTCTTTGTAGGTCACTCAGGACTTGCTTTATGAATCTGGG
TGCTCCTGTATTGGGTGCATATATATTTAGGATAGTTAGCTCTTCTTGTTGAATTGATCCCTTTACC
AGTATGTAATGGCCTTCTTTGTCTCTTTTGATCTTGTTGGTTTAAAGTCTGTTTTATCAGAGACTAG
GATTGCAACCCCTGCCTTTTTTGTTTTCCATTTGCTTGGTAGATCTTCCTCCTTCCTTTCATTTTGA
GCCTATGTGTGTCTCTGACACGTGAGATGGGTTTCCTGAATACAGCACACTGATGGGTCTTGACTCTT
TATCCAACTTGCCAGTCTGTGTCTTTTAATTGTAGCATTTAGTCCATTTACATTTAAAGTTAATATT
```

Sequence Information

```
GTTATGTGTGAATTTGATCCTGTCATTATGATGTTAGCTGGTGATTTTGCTCGTTAGTTGATGCAGT
TTCTTCCTAGTCTCGATGGTCTTTACATTTTGGCATGATTTTGCAGCGGCTGGTACCGGTTGTTCCTT
TCCATGTTTAGTGCTTCCTTCAGGAGCTCTTTTAGGGCAGGCCTGGTGGTGACAAATCGGTCGC
ATTTGCTTGTCTGTAAAGTATTTTATTTCTCCTTCACTTATGAAGCTTAGTTTGGCTGGATATGAAA
TTCTGGGTTGAAAATTCTTTTCTTTAAGAATGTTGAATATTGGCCCCCACTCTCCTCTGGCTTGTAG
GGTTTCTGCCAAGAGATCCACTGTTAGTCTGATGGGCTTCCCTTTGAGGGTAACCCGACCTTTCTCT
CTGGCTGCCCTTAACATTTTTTCCTTCATTTCAACTTTGGTGAATCTGACAATTATGTGTCTTGGAGT
TGCTCTTCTCGAGGAGTATCTTTGTGGCGTTCTCTGTATTTCCTGAATCTGAACGTTGGCCTGCCTT
GCTAGATTGGGGAAGTTCTCCTGGATAATATCCTGCAGAGTGTTTGCCAACTTGGTTCCATTCTCCG
CATCACTTTCAGGTACACCAATCAGACGTAGATTTGGTCTTTTCACATAGTCCCATATTTCTTGGAG
GCTTTGCTCATTTCTTTTTATTCTTTTTTCTCTAAACGTCCCTTCTTGCTTCATTTCATTCATTTCATC
TTCCATTGCTGATACCCTTTCTTCCAGTTGATCGCATCGGCTCCTGAGGCTTCTGCATTCTTCACGT
AGTTCTCGAGCCTTGGTTTTCAGCTCCATCAGCTCCTTTAAGCACTTCTCTGTATTGGTTATTCTAGT
TATACATTCTTCTAAATTTTTTCAAAGTTTTCAACTTCTTTGCCTTTGGTTTGAATGTCCTCCCGTA
GCTCAGAGTAATTTGATCGTCTGAAGCCTTCTTCTCTCAGCTCGTCAAAATCATTCTCCATCCAGCT
TTGTTCCATTGCTGGTGAGGAACTGCGTTCCTTTGGAGGAGGAGAGGCGCTCTGCGTTTTAGAGTT
CCCAGTTTTTCTGTTCTGTTTTTTCCCCACCTTTGTGGTTTTATCTACTTTTGGTCTTTGATGATGGTG
ATGTACAGATGGGTTTTCGGTGTCCTTTCTGTTTGTGAGTTTTCCTTCTAACAGACAGGACCCTCAG
CTGCAGGTCTGTTGGAATACCCTGCCGTGTGAGGTGTCAGTGTGCCCCTGCTGGGGGTGCCTCCC
AGTTAGGCTGCTCGGGGGTCAGGGGTCAGGGACCCACTTGTGGAGGCAGTCTACCCGTTCTCAGAT
CTCCAGCTGCGTGCTGGGAGAACCACTGCTCTCTTCAAGGCTGTCAGACAGGGACATTTAAGTCTG
CAGAGGTTACTGCTGTCTTTTTGTTTGTCTGTGCCCTGCCCCCAGAGGTGGAGCCTACAGAGGCAG
GCAGGCCTCCTTGAGCTGTGGTGGGCTCCACCCAGTTCGAGCTTCCCGGCTGCTTTGTTTACCTAAG
CAAGCCTGGGCAATGGCGGGCGCCTCTCCCCCAGCCTCGCTGCCGCCTTGCAGTTTGATCTCAGAC
TGCTGTGCTAGCAATCAGCGAGATTCCGTGGGTGTAGGACCCTCCGAGCCAGGTGTGGGATATAGT
CTCGTGGTACGCCGTTTTTAAGCCAGTCTGAAAAGCGCAATATTCGGGTGGGAGTGACCCGATTT
TCCAGGTGCGTCTGTCACCCCTTTCTTTGACTCGGAAAGGGAACTCCCTGACCCCTTGCGCTTCCCA
GGTGAGGCAATGCCTCGCCCTGCTTTGGCTCGCGCACGGTGTGCGCACCCACTGGCCTGCGCCCAC
TGTCTTGCACTCCCTGGTGAGATGAACCCGGTACCTCAGATGGAAATGCAGAAATCACCCGTCTTC
TGCGTCGCTCATGCTGGGAGCCGTAGACCGGAACTGTCCCTATTCGGCCATCTTGGCTCAGCCCT
TTCTTTTTGGTCTGCCTTCTCATGATTCTCTGACACTGTGTTATTATAATGGAACCCTGATCTTTGGC
CATGTCTTCCTTCCTTTACCATCCATCTTCCAAAGGACACTTGTTCTTCAGCTGCTCCTCTCTCAG
CATCTCAGCTGCCCAAGGCAGCCACTCTCGTCCTGCACACTTCCTTATCCAAGCTACTTCCTTGGAC
TCCCTTTTGACTCCCACTAGCCAGTGCTTTGATCTGTCAGGTATGAGACCTCTATCAACATTTTGT
CCCTTGGGTGTGACCTTCTCTTTCTGGAGTTTATCTTATCAGACGTTATTTGAGTCCTTTCCCCTTGA
TATGGTTTGGCTGTGTCCCCACCCAAATCTCATCTTGAATTCCCATGTGTTGTGGCAGGGACCCAGT
GGGAGGTAATTGAATCATGGGGCAGGTCTTTCCTATGCTGTTCTCATGATAGTGAATAGGGCTCAC
AAGATCTGATGGTAATATAAGGGGAAATTTCCCTGTGCAAGCTCTCGTTTTGCCTGCTGCCATTCA
TGTAAAACGTGACTGGCTCCTCCTTGCCTTCCACCATGACTGTGAGGCCTCCCCAGCCAAGTGAAA
CTGTAAGTCCAAATAAACCTCTTTCTTTGGTAAATTACCCAGTCTTGGGTATGTCTTTATCAGCAGC
ATGAAAACAGAGTAATACAGTAAATTGGCCCAGTAGAGTGGGGCACTGATGAAAAGATACCTGAA
AATGTGGAAGCCACTTTGGAACTGGGTAATAGGCAGAGGTTGGAACAGTTTGGAGGGCTCAGAAG
AAGACAGGAAAATGTGGGAAAGTTTGGAACCTCCTAGAGATTTGTTGAATGGCTTTACCCAAAAT
GCTGATAGCAATATGGACAATGAAATCCAGGCTGAGGTGGTCTTGGATGGAGATGAGGCACTTGT
TGGGAACTGGAGCAAAGGTGACTCTTGCTATGTTTTAACAAAGAGATTGGTGACATTTTGCCCCTG
CCCTAGAGATTTGTGGAACTTTGAATTTGAGAGAGATGATTTAGGGTATCTGGCAGAGGAAATTTC
TAAGCAGCAAAGCATTCAAGAGGTTATTTGGGTTCTGTTAAAGGCATTCAGTTTTATAAGGGAAGC
AGAGCATAAAAGTTTGAATAATTTGCAGCCTGACAATGTGATAGAAAAGAAAATTCCATTTTCTGA
GTAGAAATTCAAGCAGGCTGTGGAAATTTGCATAAGTAATCAGGAGCCAAATGTTGATTCTCAAG
ACAATGGGAAAAATGTCTCCAGGGCGTGTCAGAGGTCTTCATGGCAGCCCCTCCTATAACAGGAC
TGGAGGCCTAGGAGCAAAAGTGGTTTCAGGGGCCAGGCCTAGGGTCCCTGTGCTGTGTACAGCC
TAGGGATTTGGTGCCCTGTGTCCCAGCCACTCCAGCCATGGCCAAAAGGGGCAATGTAGAGCTTG
GGCCATGGTTTCAGAGGGTGTAAGCCCCAAGCCTTGGCAGCTTCCACGTGGTGTTGAGCCTGCCAG
TGCACAGAAGTTGAGAATTGGGGTTTGGGAACCTCTGCCTATATTTCAGAAGATGTGTGGAAATGC
CTGGATGCCCAGGCAAGAGTTTGCTGCAGGGGTGGGATACTCACGGAGAACCTCTGCTAGGGCAG
GATGGAAGGGAAATGTGGGGCAGAACCCCTATACGGAGTCCTAGTGGAGCTGTGAGAAGAGGG
CCACTATCCTCCAGACCCCAGAATGATAGACCCACGACAGCTTGCACCATGCACCTGGAAAAGCC
ACAGACACTCAATGCCAGCCCATGAAAGCAGCCAGGAGGGAGGTTGTACCCTGCAAAGCCACAGG
GGCAGAGCTGCCCAAGACCATGGGAACCCACCTCTTGCATCAGCGTGACCTGGATGTGAGACATG
GAGTTTGAGATCATTTCTGGAGCTTTAAGATTTGACTGCCCCACTGGATTTTGGACTTGCATGGGCC
CTGTAGCCACTTTGTTTTGGCCAATTTCTCCCATTTGGAATGGTCAGGCTGGATTTACCCAATGTCTGTATC
CCCCTTGTATTTAGGAAATAACTAGCTTGCTTTTGATTTTACAGGCTCATAGGCATAAGGGACTTGC
CTTGTCTCAGATGAGACTTTGGAATGTGGACTTTTGAGTTAATGCTGAAACAAGTTAAGACTTTGG
GGGACTGTTGGGAAGGCATGATTGGTTTTGAAATGGGAGGACATGAGATTTGGGAGGGGCCAGGG
GTGGAATGATATGGTTTGGCTCTGTGTCCCCACCAGATCTCATCTGGAACTGTACTCCCATAATTCT
CATGTGTCATGGGAGGGACCCGGTGGCAGATAATTGAATCATGGGGGCAGTTTCCTCCATACTGTT
CTCGTGGTAGTGAATAAGTCTCATGAGATCTGATGGTTTTGTCAGGGGTTTCTCCTTTTGCATCTTC
CTCATTCTCTCTTTGCCTGCTGCCATCCATGTAAGATGGGACTTGCTCCTCCTTGCCTTCCACCATG
ATTGTGAGGCTTCGCCAGCCATGTGTAACTGTAGTCCAATTAATCCTCTTTCTTTTGTAAATTGTCC
AGTCTTGGGGATGTCTTTATCAGCAGCATGAAAACGGACTAATACACTCCTCTTGTACCCCTAAC
CCTCTTTTGCATAATTCTAGCCTGACTCTGCCCTTGGGTGGGTACCAGTCCTGACTCTTCAGGTCTC
AGAGGGTTGTTTCCTCACTTCACCCAGGGTTTAAATAGGCCTTGTCTCCTGCTTGTGTCATAGGCTT
CTGCTTTGGTTGATATTACTTTCTTTCTTTATCAATATGGTTTTAAAGAGAATGTATGAAGGGATT
TTAAATTTAGATGGCCACCATTATTCTATGAAAATCTAAAAATTCACATGTTCTTAGGTTCTTATTC
CACTTTAAGAAAACAGCACTAGAAACTATAGATAAAACATTATAGATATGGTTTATGAAATAAA
GATGATAGGAACAACAATCAGTAGCCCTGCATGCAAAGACTATGAAGTGACTATCTATTTTTTTT
ATTATTATTATACTTTAAGTTCTAGGGTACATGTGCACAATGTGCAGGTTTGTTACATATGTATACA
```

-continued

| Sequence Information |
|---|
| TGTGCCATGTTGGTGTCCTGCACCCATTAACACATCATTTACAATAGGTATTTCTCTTAATGCCATC |
| CCTACCCCCACCCCCACCCCACAACAGGCCCCAGTGTGTGATGTTCCCCGCCCCGTGTCCAAGTG |
| TCCTCATTGTTCAATTCCCACCTATGAGTGAGAACATGCAGTGTTTGGTTTTCTGTCCTTGCTATAG |
| TTTGCTCAGAGTGATGGTTTTCAGCTTCATCCATGTCCCTACAAAGGACATGAACTCGTCCTTTTTT |
| ATGGCTGTACAGTATTCCATGGTGTATATGTGCCATGTTTTCTTAATCCAGTCTATCATTGATGGAC |
| ATGTGAGTTGATTCCAAGTCTTCGCTATTGTGAATAGTGCTGCAATAAACATACGTGTGCATGTGT |
| CTTTATAGTAGCATGATTTATAATCCTTTGGGTATATACCCAGTAATGGGATCACTGGGTCAAACG |
| ATTTTTCTAGTTCTAGATCCTTGAGGAATCGCCACACTGTCTTCCACAATGGTTGAACTAGTTTACA |
| CTCCCACCAGCAATGTAAAAGCCTTCCCATTTCTCCACATCCTCTCCAGCACCTGTTGTTTCCTGAC |
| TTTTTAATGATCGCCATTCTAACTAATGTGAGATAGTATCTCATTGTGGTTTTGATTTGCATTTCTCT |
| GATGACCAGTGATGATGAGCATTTTTTTCATGCGTCTGTTGGCTGCATAAATGTCTTCTTTTGAGAA |
| GTGTCTGTTCATATCCTTTGCCCACCTTTTGATGGGGTTACTTGATTTTTTCCTATAAATTTGTTTAA |
| GTTCTTTGTAGATTCTGGATATTAGCCCTTGTTACATGGGTAAATTGTAAAAATTTTCTCCCATTC |
| TGTAGGTTGCCTGTTCACTTTGATGGTAGTTTCTTTTTGCTGTGCAGAAGCTCTTTAGTTTAATTAG |
| ATCCCATTTGTCTATTTTGGCTTTTGTTGCCATTGCTTTTGGTGTTTTAGACGTGAAGTCCTTGCCCA |
| TGCCTATGTCCTGAATGGTAATGCCTAGGTTTTTTTCTTCTAGGGTTTCTATGGTTTTAGGTCAAAC |
| ATTTAAGTCTTTAATCCATCTTGAATTAATTTTTGTATAAGGTGTAAGGAAGGGATCCAGTTTCAGC |
| TTTCTACATATGGCTAGCCAGTTTTCCCAGCACCATGTATTAAATAGGGAATACTTTCCTTATTTCT |
| TGTTTTTGTCAGGTTTGTCAAAGATCAGAAGGTTGTATTTCTGAGGGCTCTGTTCTGTTCCATTGGT |
| CTATATCTCTGTTTTGGTACCAGTACCATGCTGTTTTGGTTACTGTAGCCTTGTAGTATAGTTTGAA |
| GTCAGGTAGCGTGATGCCTCCAGCTTTGTTCTTTTGGCTTAGGATTGTCTTGGCAACGCGGGCTTTT |
| TTTGCTTCCATCTGAACTTTAAAGTAGTTTTTTCCAATTCTGTGAAGAAAGTCATTGGTAGCTTGAT |
| GGGGATGGCACTGAATGTATAAATTACCTCGGGCAGTATGGCCATTTTCACTATATTGATTCTTCCT |
| ATCCATGAGCATGGAATGTTCTCCCATTTGTTTGTGTCCTCTTTTATTTCGTTGAGCAGTGGTTTGTA |
| GTTCTCCTTGAAGAGGTCCTTCACATCCCTTGTAAGTTGGATTCCTAGGTATTTTATTCTCTTTGAA |
| GCAATTGTGAATGGGAGTTCAGTTGTGATTGGTTCTCTGTTTGTCTGTTATTTGTGTATAGGAATG |
| CTTGTGATTTTTGCACATTGATTTTGTATCTTGAGACACTTTGTTGAAGTTGCTTATCAGCTTAAGG |
| AGATTTTGGGCTGAGATGATGGGGTTTTCTAGATATACAATCATGTCATGTGCAAACAGGGACAAT |
| TTGACTTCCTCTTTTCCTAATTGAATGCCCTTTATTTCTTTCTCTTGCCTGATTGCCCTGACCAGAAT |
| TTCCAACATTATATTGAATAGGAGTGGTGAAAGAGGGCATCCCTGTCTTGTGCCAGTTTTCAAAGG |
| GAATGCTTCCAGTTTTTGCCCATTCAGTATGATATTGGCTGTGGGTTTGTCATAGATAGCTCTTATT |
| GTTTTTAGATATGTCCCATCAATACCTAGTTTCCTGAGAGTTTTTAGATCATGAAGCATTGTTGAATTT |
| TGTCGAAGGCCTTTTGTGCATCTATTGAGATAATCATACAGTTTTTGTGTTTGGTTCTGTTTATATG |
| ATGGATTACGTTCATTGATTTGCATATGTTGAACCAGCCATGCATCCCAGGGATGAAGCCAACTTG |
| ATCTTGGTGGATAAGCTTTTTGATGTGCTGCTGGATTCGGTTTGCCAGTATTTTATTGAGGATTTTT |
| GCATCGATGTTCATCAGGGATATTGGTCTAAAATTCTCTTTTTTTGTGTGTCTCTGCCAGGCTTTG |
| GTATCAGGATGATGCTGGCCTCATAAAATGAGTTAGGGAGGATTCCCTCTTTTTCTGTTGATTGGA |
| ATAGTTTCAGAAGCAATGGTACCAGCTCCTCTTTGTACCTCTGGTAGAATTCGGCTGTGAATCCGT |
| CTGGTCCTGGACTGTTTTTGGTTGGTAGGCTATTAATTTATTGCCTCAATTTCAGAGCCTGTTATTG |
| GTCTATTCAGGATTCAGCTTCTTCCTGGTTTAGTCTTGGGAGGGTGTGTGTGTCAGGGAATTTATCC |
| ATTTCTTCTAGATTTTCTAGTTTATTTGCATAGAGGTGTTTGTAGTATTCTCTGACGGTAGTTTGTAT |
| TTCTGTGGGATTGGTGCTGATATACCCTTTATCATTTTTATTGTGTCTATTTGATTCTTCTCTCTTTT |
| CTTCTTTATTAGTCTTGCTAGTGGTCTATCAATTTTGTTGATCTTTTCAGAAAACCAGCTCCTGGATT |
| CATTGATTTTTTTGAAGGGTTTTTGTGTCTCCATCTCCTTCAGTTCTGCTCTGCTGTTAGTTATTTCTT |
| GCCTTCTGCTAGCTTTTGAATGTGTTTGCTCTTGCTTCTTTAGTTCTTTTAATTGTGATGTTAGGGTG |
| TCAAGTTTTAGATCTTTCCTGCTTTCTCTTGTGGGCATTTAGTGCTATAGATTTCCCTCTACACAGTG |
| CTTTAAATGTGTCCCAGAGGTTCTGGTATGTTGTGTCTTTGCTCTCATTGGTTTCAAAGAACATCTT |
| TATTTCTGCCTTCATTTCATTATTTATGCAGTAGTCCTTCAGGATTAGGTTGTTCAGTTTCCATGTAG |
| TAGTGCAGTTTTGAGTGAGTTTCTTAATCCTGAGTTCTAATTTAATTGCACTGTGGTCTGAAAGACA |
| GTTTGTTATAATTTCTGTTCTATTACATTTGCTGAGGAGTGCTTTACTTCAATTCAGCAAGAAGAGC |
| TAGCTATCCTAAATATATATGCACCCAATACAGGAGCACCCAGATTCATAAAGCAAGTCCTTAGAG |
| ACCTACAAAGAGACTTAGACTCCCACACAATAATAATGGGAGACTTTAACACCCCACTGTCAACA |
| TTAGACAGATCAACGAGACAGAAAGTTAACAAAGATATCCAGGACTTGAACTCAGCTCTGGACCA |
| AGCGGACCTAATAGACATCTACAGAACTCTGCACCCCAAATCAACAGAATATACATTCTTCTCAGC |
| ACCACGTTGCACTTATTCCAAAATTGACAACATAGTTGGAAGTATCTATGTTTTTAAGTTCAAACT |
| AAATGTTTAAGGAATGCTATATTATTTGATTCCCTAATTTCCCAACCTTTTGGATAAAAGGGCTTCT |
| ATCCTCACACTCACAGTATGGAGTGTTCTGAGGTTGTTTCAGATTGTTTTGTTAGGTGGTTCCATGTT |
| CCAGGAAGCTACATCTCATGCCTGATCTCTTCCATGTTAGTCTGCTGCTTGCTGTGGGGGTGGACAT |
| AGAGAGGAAAGCAGCCAGCATTCGGGGTGAGAGGAGGCACAATGGTGCCTCTCTAAGGACAGTTC |
| ATGGAAGATCATCACTCTTTTTTTTTGTTTGTTTAGCATAGCCCCTGAGTCCCATCATTCGATGGA |
| GGCAAAGCAAATCCATCTTCTTCTACTTTCTTTGGGATCATGTTTTGATTCTTATGGCAGAATCCAA |
| GAATGTGTTGTTCGTCTCTTCAGCATTGGCATTAGTGAAAATCCCCTTGGGACTTTGGCATATGGTC |
| TTCTCTTTAGTTTCCAACGCTGTTGCCAGTTTTCATCTTTTTGTAATTCTTCGTGGATATTAAAATGG |
| AAATTGGAAGAAAGCATATTAGTCCCTGAAGTTTATCCTGAATTAACCCAGAAGTCCTACCAATT |
| ATTTTTTAGTAATGAATAGGAAAGATTATATTAAGGGTATGATTCAGTGATTTTTGATTACTTTTT |
| TCTCTAGACTACTTAAAAAACTTAATAAACCTTCTTAATAACAATCTATATGAAAAATATCTTTCCA |
| TATATAACTCTAGACCCAGTGAATTCAACTTACATATTTCCTCACTGAATTTCATCAACATTTTCTA |
| ATTTCCGTGCCTATACTCTTAATTTATGGTAATATTTGCATGTTGAAATGGCTTTTCAGGAAGCATG |
| GGATTTACACAAACCAAATATCACCTGCCCCCCATACACACACACCCTTAACAAAGGAAATAAGT |
| CCTGTAAGGAGTTTCACCGGGATAGTGGTTAAAAATCGGTACTTTTTGATTAGATCTGGTTTAAAT |
| CCTGTCTCCTCCATTAATTACTTGTGCAATCTTTAAGCATTGATTTCCTTGTGTAAAATGTAATAAT |
| AGTTACATTTGTCTGTAACAAATGTAACAAATAACAACCTATCCTGTAGACACCTATGTGAGGATT |
| TAGTGAGAGAGTGTGTTTGAAACATTTAGCACCATGCCTGGAACATTGTAAGAACTCGGTAGCTGG |
| TAGTGAAGATGATAACAAGGATGATGGTCTTCCAAAGGGTTAACAGGTCGGACATTACCCTGTG |
| GATGTGTTGGTCAATGTTTTCATTAGTAACTGGGGTTATTTTTTTCTTCAAAATTTCTTCTCAGAAA |
| GTATTGTCATTGCTATTTCTAAAAATTTGATACTGCCTTTCAGGGTGTGTCTTTTATGACAGATGGT |
| CAGCAGTTAGTGGTAAAAGAAGTATGGAATGTAATACCATTTCATTTATTTATGGGAAATGTTTTG |

| Sequence Information |
|---|
| TTGCCCCACCCTTCAACTAATAGGAAAATGAAAATCAAAAACTGGAAACTATTTATAAATGGACA |
| GTGCTGTGATCTCAGTGTCTGAAACTGTAGACTTTTAGAAAATATTTATAGCATATTGGAAACTGG |
| TCACTGGTCAGTGGCTGTCTCCTTGCCCTGTTTTTGTAAATAAAAATACTCTAGCAAATGTGAAATT |
| TGGGGTAAATTCAAACAGAATACTGAAAATATCATCAGAGACAATGATATACTACTTTATAAGTTT |
| TCAAGAGAAGAGGGTGAAGAAAAATGTTTAACTTTTATTAATAGAAGCATTTGCAGTTAATAGAG |
| ATATTTGTTTATGGAGCCTTAAAAATAAACCAAATGAATGGAAACACCATACATTCAAGGAGACA |
| CTGAGGCCATGTGTACATCTTACTGAGCAGAGAATTTAGCATAGAAGGTTAGAGATGGGATTTGG |
| GGGTCAGTCTGCCTGAGCTCCAAACCCAGTCCTGTCACCTGCTCAACCACATGATTGTGTAAGTCA |
| CTTAACCATGCCATGCCAAGCTTGTCTCTACCTCACAGTGTTGAAGGTTGAATGAAATGATACGTG |
| TAAAGTATTTTAAATGGTGTGTTGCACATAAAAAATGTTCTATCAGTGCAAGCTACTGTTATCCAA |
| ACTAGCCTAGCCAAAACAAATGAAACCCCAAAATAACTAGTTTGGTTGTTATAGGCATGGGTAAA |
| ACTTGCCAACTTCACCGGTTTAGAGGTAGGTCTTCATCACTAAGTGGCAAATGGCAAACAAGATAG |
| TTCTGTTATTTTCTTTACATAGGTCTTTGTCTACTTACTGCCATAGCCAATAATATGTGCTGGGATG |
| GGGGTAAACATTGTACGGTGGCAATCCTTGAACTGTCCCATGGGTGCCTACCTTAAAGAAGCTAAT |
| TAGAGAGCTCTGCTTTGTTCCTATAAGCCTGGAGCCCAAGTATTTGCTGTAATAAAAACACCCATT |
| ACCTTGATTCACGTAAAACCAGGACATTTCATGAACTTGTGTGATTATTGAAAACCCGTTTATCATT |
| AACACCGTCAGTCATTATTTAGAGATTTTTATTTCACAAATAAAATCAACAATCTGATAAAGACAG |
| TATAGCTCATGCAGCTAAACTATAGCATCTACCAAAACCAAAAAATAAGGAAAATACCTAGATAA |
| CAGATTGCAATATGTATTTTTTAATATACAGTCTATAATGAGTAGACTGTGTGACTTGACTATATTG |
| ACACTGATATTTTTCCAAAAAGAGACTCTCATATTGGAGAGAACATCATAAAATGTCTTAGAAATT |
| AAAATTACATCTACCCCAGTGTGTTTCATAAAGGGAGCACTTGCCAGCAAGAAGAATAGGTAGGA |
| ATATTAATGTTTCATTTTATCTTCATATTATTCTTGTGTCTGTGTCCCAGGTTATAGTCTTTGAGGTT |
| ATATTATTTCCATGTCTGCAGAATCTGGATCTATATTTTACAATAAAAGGGCTTTTGTTGCCTCATG |
| CAATTCTCATAACAACTCTGTAAGATAGGTACTTTTATCTAGATTCTGCTGATGAGAAAAACAACA |
| CCCAAGTTTATATAGCCAGTAATTTCTGGAGTTGGGATGCACACCCTGAAAGGCTTTGCTCCCAAA |
| GACAATGCTATACTTCTTATGAGAGAGTGATGTCTTCAGAAATTGGTCAGGAGGAAAGTTCATTTT |
| CTGATGATTGTATGGAAATGAAACTTTGGAACTGTATGATGTCCTGGAATACTATAGTATTTGTAG |
| CATTACCTAAAAATGAATACATGCATATATGTGTGTGTGTAGAGAGAGACATAGAGAAGATAG |
| AAGCTAACACATGATTATAGTATAGCAATAATCAACCCCACAACCATTTTATGGTTCTGATAGGGC |
| CACTGTTTATTCTGCAAGATCACAAGTGATCACAAGAGTTGATATTGCTGAAACTGTGTTATGAAC |
| ATACAACATACACTTTTTCTCCAACCCACTTTGGTATACACACCTTTGTGGAAGAAATTGTGTCATT |
| GTGATAAAGCTTTGTGTTCAAGGTACTAATATCCCTATATGGCATATATTAAGATATTGATTATAG |
| AAAGTTATCAACAGATTTCTTAAGATACTTTCTGGGAAACCAGGACTTGTTTTCAAGGGGAAGCCA |
| TTATCATTATATATGGACTTCTTACCTAAGTGTCCTAAAAGCTAGATACCCATCTTTTGCTCTATAG |
| GAACAAAATCAAGAATTTAGAACATGTAATCACATATGGTGACCTCTATAACAAGGCCAGAGAGC |
| AGTGATTCTTAATCTTAGATGTGGGTTAAAATCAGATTGCATTTTTGACAAGGGTGCCAAGATAGT |
| TCCATTGGAACTATTGAAAAGACTATTGGAAAAAATAGTCCTTTCAAAAAAATAGTGCTGGGATA |
| ACTGGCTACCCACATGCAGAAGAATGAAGTTGAAGAAGCATGACATCAGCAAGATGGTAGACTAG |
| AAGACCCTAGTGCTATTCTCCCTCAAAAAGATAGCCAGAACAATGAATAAACAACTTCATTTTAAC |
| AAAAATAACTGAGGAGGAGCACAGTGGTGCACAAGAGAAGTAACAGATACCCTGGTGAGCACAG |
| AAACTTGGGATGGCCACATAGAGAATGGGAAGAAATGCCAGGCCTCCATTACCCTAACCCCAATT |
| GGAAGCAGCTGGGAATGAACTAGGAGGAACGTTTCCCTACTGCAAGGAGGTAAACAAAAGGATC |
| CCAGCAGCCCCATCAACACCGTGGATACCTACAGACCTGAGCACTGGGGTCCCCTGCAATCCTCAC |
| AGACACTAAGCCTAGCTGAGGGAGCTGCCTGAAGTCCACATGTCCGTGCTTCCCCAGAGAAGGA |
| GCCAATACTATGATCCACACCCTGTGGCCCACATAGCTACCATGCTATGCCATCTTGGAGTTGGAA |
| CTATGGCTGGATGTGTCTTGCTCTGGGGGCAAGTATGCATGGCTCTCTTTTATCCCTGAGGCTAAGC |
| CATTGCTGAACTGCCCCAGCCCAATGGCCTGACATCCCCAAGTCGAGCAACTGTTTTGTGCTCCCC |
| TGTGGGGCCAAGCAGAGGTGGAGCTGCTCCACCTCCCACCACCCTTTCCTCCTCAGGCCAGAGCTG |
| AAGCAGTGTCCTGATTCCTGGGAAAACAGTACTTTGACTGCTCAGAGAAATCATGCCCCTCCAATG |
| CCTAAGTCAAAGCAGCACGCTGCATCCTAGGGAAATGGTGCCTGGTCCACCCAGAGCAGTCCATAC |
| CTGTTGGACTCAAGCCGAAATGACACATCACCCTCTGGGGAATTTGTACCCTGGCTGAGCTGAATA |
| GCTGCAAATCCCAGGGCTGTGCTGACATGGTATCCTGTGTCCCAGGGAAACAGAGCAGTGGCTGA |
| GCTGAGACACCCCATCCTGCAGGCCAAACAGCTCTAGTGTCCTTCCTTCCTGGGGCTGTACTAGCC |
| TCCTGAAGTCTGAGCTGCTGAGATACCCTTGACTCTGGGGAGTGGAGTCATTGCTGTGCTGCACAT |
| TGTCTTCCAGGGCCCAAATAACAGCTGTGTTCTGCCATTCTAGGGTACAGCATATTTCTCTGCAGA |
| AACCTGACAAGCCAGGAGAAGTGGATGATGTATTCAAAGTACCAAAAGAAAAAAAATTGTC |
| AGCTAAGCATGCGATACCCAGCAAATCTACCCTTCAGAAATGAGAGAGAAAGAAAGTCTCCCAGA |
| CAAGTAAAAACTGAGGGAATTCATCACCACTAGACTGGCTTTACAAGAAACAGTCAAGGGAGTCC |
| TGTATCTGGAAGAAAAAGATGATAATCATTCTCATGAAAACACACACAAGTGTAAAACTCGCTG |
| GTAGAGCAGATGCACAAAGGAGAAAGAGAAACAAGAGAAAACCTTGTTACTGCAGAAAACCACC |
| AAACTGCAATGATCTCAAATATCTTTCCTGACCACAATGAAATCAATAACAAGAGGAACTTTGAA |
| ATTTTACAAACACATGGAAATGGAAGTTAAACACGTTCCTGAATGGTCAATGGGTCAATAAAGAA |
| ATTAAGAAGGAAATGTTAAATGTCTTGAAAGAAATGAAAATAGACATACAGCATATCAAAAACC |
| TATGGTATACAGCAAAAGAAGTGTTAAGAGGAAATGTATAGCAATAGATGCCTACATCCAAAAA |
| GTAGAAGGATTTCCAATCAGCAACGTAGCAATGTATCTCAAGAAACTAGAAAAGCAAGAACAAGC |
| CAAATCCAAAATTAGTAGAAGGAAAGAAATAATGATGAAAGCAAATAAACAAAATTCACGGA |
| GATCTGGCAGCCAAGATGGCTGAATAGGAACAGCTCCGGTCTACAGCTCCCAGCGTGAGCGACAC |
| AGAAGACGGGTGATTTCTGCATTTCCCTCTGAGGTACCGGATTCATCTCACTAGGGAGTGCAAGAC |
| AGTGGGCACAGGACAGTGGGTGCAGCGCACCATGCGCAAGCCTAAGCAGGGCGAGGCATTGCCTC |
| ACTCGGGAAGTGCAAGGGGTCAGGGAGTTCCCTTTCCTAGTCAAAGAAAGGGGTGACAGACGGCA |
| CCTGGAAAATTGGGTCACTCCCACCCTAATACTGCACTTTTCCAATGGGCTTAAAAAACGGCACA |
| TAGGAGATTATATCCCGCACCTGGCTCAGAGGGTCCTATGCCCACAGAGTTTCGCTGATTGCTAGC |
| ACAGCAGTCTGAGATCAAACTGCAAGGCGGCAGCGAGGCTGGGGAGGGGCACCCACCATTGCCC |
| AGGCTTGCTTAGGTAAACAAAGCAGCCAGGAAGCTCAAACTTGGTGGAGCCCACCACAGCTCAAG |
| GAGGCCTGCCTGCCTCTGTAGGCTCCACCTCTGGGGCAGGGCACAGACAAACAAAAAGACATCA |
| GTAACATCTGCAGACTTAAATATCCCTGTCTGACAGCTTTGAAGAGAGCAGTGGTTCTCCCAGCAC |
| GCAGCTGGAGATCTGAGAACGGGCAGACTGCCTCCTCAAGTGGGTCCCTGATCCCTGAACCCCGA |

```
GCAACCTAACCGGGAGGCACCCCCCAGTAGGGGCAGACTGACACCTCACACGGCCGGGTATTCCT
CTGAGACAAAACTTCCAGAGGAATGATCAGACAGCAGCATTCATGGTTCACGAAAATCCGCTGTT
CTGCAGCCACCGCTGCTGATACCCAGGCAAACAGGGTCTGGAGTGGACCTCTAGCAAACTCCAAC
AGACCTGCAGCTGAGGGTCCTGTCTGTTAGAAGGAAAACTAACAAACAGAAAGGACATCCACACC
AAAAACCCATCTGTACATCACCATCATCAAAGACCAAAGCAGATAAAGCCACAAAGATGGGGA
AAAAACAGAGCAGAAAAACTGGAAACTCTAAAAACAGAGCGCCTCTCCTCTTCCAAAGGAACGCA
GTTCCACACCAGCAACGGAACAAAGCTGGACGGAGAATTACTTTGACGAGTTGAGAAAAGAAGGC
TTCAGACTATCAAACTACTCTGAGCTACAGGAGGAAATTCAAACCAAAGGCAAAGAAGTTAAAAA
CTTTGAAAAAAATTTAGACGAATGTATAACTAGAATAACCAATACAGAGAAGTGCTTAAAGGAGC
TGATGGAGCTGAAAGCCAAGGCTCGAGAACTACATGAAGAATGCAGAAGCCTCAGGAGCTGATGC
AATCAACTGGAAGAAAGGGTATCAGTGATGGAAGATGAAATGAATGAAATGAAGCGAGAAGGGA
AGTTTAGAGAAAAAGAATAAAAAGAAACGAACAAAGCCTCCAAGAAATATGGGACTATGTGAA
AAGACCAAATCTACGTCTGATTGGTGTACCTGAAAGTGACGGGGAGAATGGAAGCAAGTTGGAAA
ACACTCTGCAGGATATTATCCAGGAGAACTTCCCCAATCTAGCAAGGCAGGCCAACATTCAGATTC
AGGAAATACAGAAAATGCCACAAAGATACTCCTCGAGAAGAGCAACTCCAAGACACATAATTGTC
AGATTCATCAAAGTTGAAATGAAGGAAAAAATGTTAAGGGCAGCCAGAGAGAAAGGTCGGGTTA
CCCACAAAGGGAAGCCCATCAGACTAACAGCAGATCTCTTGGCAGAAACTCTACAAGCCAGAGGA
GAGTGGGGGCCAATATTCAACATTCTTAAAGAAAAGAATTTTCAACCCAGAATTTCATATCCAGCC
AAACTAAGCTTCATAAGTGAAGGAGAAATAAAATACTATACAGACAAGCAAATGCTGAGAGATTT
TGTCACCACCAGGCCTGTCCTAAAAGAGCTCCTGAAGCACTAAACATGGAAAGGAACAATCGGTA
CCAGCCGCTGCAAAATCATGCCAAATTGTAAAGACCATCGAGGCTAGGAAGAAACTGCATCAACT
AACGAGCAAAATAACCAGCTAATATCATAATGACAAGATCAAATTCACACATAACAATATTAACT
TTAAATGTAAATGGGCTAAATGCTCCAATTAAAAGACACAGACTGGCAAATTGGATAAAGAGTCA
AGACCCATTAGTGTGCTGTATTCAGGAAACCCATCTCATGTGCAGAGACACACAAAGGCTCAAAA
TAAAAGGATGGAGGAAGATCTACCAAGCAAATGGAAAACAAAAAAAGGCAGGGGTTGCAATCCT
AGTCTCTGATAAAACAGACTTTAAACCAACAAAGATCAAAAGAGACAAAGAAGGCCATTACATAA
TGGTAAAGGGATCAATTCAACAAGAAGAGCTAACTATCCTAAATATATATGCAACCAATACAGGA
GCACCCAGATGCATAAAGCAAGTCCTGAGTGACCTACAAAGAGACTTAGACTCCCACACAATAAT
AATAGGAGACTTTAACACCCCACTATCAACATTAAACAGATCAATGAGACAGAAAGTTAACAAAG
ATACCCAGGAATTGAACTCAGCTCTGCACCAAGCGGACCTAATAGACATCTACAGACCTCTCCACC
CCAAGTCAACAGAATATACATTTTTTTCAGCACCACACCACACCTATTCCAAAATTGACCACATAG
TTGGAAGTAAAGCACTCCTCAGCAAATGTAATAGAACAGAAATTATAACAAACTGTCTCTCAGAC
CACAGTGCAATCAAACTAGAACTCAGGATTCAGAAACTCACTCAAAACTGCTCAACTACATGGAA
ACTGAACAACCTACTCCTGAATGACTACTGGGTACTTAACGAAATGAAGGCAGAAGTAAAGATGT
TCTTTGAAACCAGCGAGAACAAAGACACAACATACCAGAATCTCTGGGACACATTCAAAGCAGTG
TGTAGTGGGAAATTTATAGCACTGAATGCCCACAAGAGAAAGCAGGAAAGATCCAAAATTGACAC
CCTAACATCACAATTAAAACAACTAGAAAAGCAAGAGCAAACACATTCAAAAGCTAGCAGAAGG
CAAGAAATAACTAAGATCAGAGCAGAACTGAAGGAGATAGAGGCACAAAAAACCCTTCAAAAAA
TTAATGAATCCAGGAGCTGGTTTTTTGAAAAGATCAACAAAATTGATAGACCGCTAGCAAGACTA
ACAAAGAAGAAAGAGAGAAGAATCAAATAGACGCAATAAAAAATGATAAAGGGGATATCACCA
CTGATACCACAGAAATACAAACTACCATCAGAGAATACTACAAACACCTCTATGCAAATAAACTA
GAAAATCTAGAAGAAACGGATAAATTACTGGATACGTACACCCTCCCAAGACTAAACCAGGAAGA
AGTTGAATCTCTGAATAGACCAATAACAGGCTCTGAATTGTGACAATAATCAATAGCTTACCAAC
CAAAAAGAGTCCAAGACCAGTTGGATTCACAACCAAATTCTACCAGAGGTACAAGGAGGAACTGG
TACCATTCCTTCTGAAACTATTCCAATCAATAGAAAAAGAGGAGAATCCTCCCTAACTCATTTTATG
AGTCCAGCATCATCCTGATACCAAAGCCAGGCAGAGACACACCAAAAAAGAGAATTTTAGACCA
ATATCCTTGATGAACATTGATGCAAAAATCCTCAATAAAATACTGGCAAACCAAATCCAGCAGCA
CATCAAAAAGCTTATCCACCATGATCAAGTGGGCTTCATCCCTGGGATGCAAGGCTGGTTCAATAT
ACGCAAATCAATAAATGTAATCCAGCATATAACCAGAACCAAAGACAAAAACCACATGATTATCT
CAATAGATGCAGAAAAGGCCTTTGACAAAACTCAACAACACTTCATGCTAAAAACTCTCAATAAA
TTAGGTATTGATGGGACGTATCTCAAAATAATAAGAGCTATCTATGACAAACCCACAGCCAATATA
CTGAATGGGCAAAAACTGGAAGCATTCCCTTTGAAAACTGGCACAAGACAGGGATGCCCTCTCTC
ACCACTCCTATTCAACATAGTGTTGGAAGTTCTGGCCAGGGCAATTAGGCAGGAGAAGGAAATAA
AGGGCATTCAATTAGGAAAAGAGGAAGTCAAATTGTCCCTGTTTGCAGATGACATGATTGTATATC
TAGAAAACCCCATCGTCTCAGCCCCAAATCTCCTTAAGCTGATAAGCAACTTCAGCAAAGTCTCAG
GATGCAAAATCAATGTACAAAAATCACAAGCATTCTTATACACCAATAACAGACAAACAGAGAGC
CAAATCATGAGTGAACTCCCATTCACAATTGCTTCAAAGAGAATAAAATACCTAGGAATCCAACTT
ACAAGGGATGTGAAGGACCTCTTCAAGGAGAACTACAAACCACTGCTCAAGGAAATAAAAGAGG
ATACAAACAAATGGAAGAACATTCCATGCTCATGGACAGGAAGAATCAATATTGTGAAATGGCC
ATACTGCCCAAGGTAATTTATAGATTCAATGCCATCCCCATCAAGCTACCAATGACTTTCTTCACA
GAATTGGAAAAAACTAAAGTTCATATGGAACCAAAAAAGAGCCCACATTGCCAAGTCAATCCTAA
GCCAAAAGAACAAAGCTGGAGGCATCACGCTACCTGACTTCAAACTATACTACAAGGCTACAGTA
ACCAAAACAGCATGGTACTGGTACCAAAACAGAGATATAGATCAATGGAACAGAACAGAGCCCTC
AGAAATAATGCCGCTTACCTACAACTATCTGATCTTTGACAAACCTGAGAAAACAAGCAATGGG
GAAAGGATTCCCCATTTAATAAATGGTGCTGGGAAAACTGGCTAGCCATATGTAGAAAGCTGAAA
CTGGATCCCTTCCTTACACCTTATACAAAAATTAATTCAAGTGGATTAAAGACTTAAACGTTAGA
CCTAAAACCATAAAAACCCGAGAAGAAACCTAGGCATTACCATTCAGGACATAGGCATGGGCAA
GGACTTCATGTCTAAAACACCAAAAGCAATGGCAACAAAAACCAAAACTGACAAATGGGATCTAA
TTAAACTAAAGAGCTTCTGCACAGCAAAAGAAACTACCATCAAAGTGAACAGGCAACCTTCAGAA
TGGGAGAAAATTTTTGCAATCTACTCATCTGACAAAGGGCTAATATCCAGAATCTACAATGAACTC
AAACAAATTTACGAGAAAAAACAACGCCATCAACAAGTGGGCAAAGGATATGAACAGACGCTTCT
CAAAAGAAGACATTTATGCAGCCAAAAGACACGTGAAAAAATGCTCATCATTACTGGCCATCAGA
GAAATGCAAATCAAAACCACAATGAGATACCGTCTCACACCAGTTAGAATGGCAATCATTAAAAA
GTCAGGAAACAACAGGTGCTAGAGAGGATGTGGAGAAATAGAAATACTTTTGCACTGTTGGTGGG
ACTGTAAACTAGTTCAACCATTGTGGAAGTCAGTGTGATGATTCCTCAGGGATCTAGAACTAGACT
AGAAATACCATTTGACCCAGCCATCCCATTACGGGGTATATACCCAAAGGACTATAAATCATGCTG
CTATAAAGACACATGCACACGTATGTTTATTGCGGCACTATTCACAATAGCAAAGACTTGGAACCA
```

| Sequence Information |
|---|
| ACCCAAACGTCCAACAATGATAGACTGGATTAAGAAAATGTGGCACATATACACCATGGAATACT |
| ATGCAGCCATAAAAAATGATGAGTTCATGTCCTTTGTACGGACATGGATGAAATTGGAAATCATTC |
| TCAGTAAACTATCGCAAGGACAAAAAACCAAACACCGCATGTTCTCACTCATAGGTGGGAATTGA |
| ACAATGAGAACTCATGGACACAGGAAGGGGAACATCACACTCTGGGGAGTGTTGTGGGGTGGGG |
| GGAGGGGGGAGGATAGCATTAGGAGATATACCTAATGCTAAATGACGAGTTAATGGGTGCAGCAC |
| AACAGCATGGCACATGTATACATATGTAACTAACCTGCACATTGTGCACATGTACCCTAAAACTTA |
| AAGTATAATAATAATAAAATAATAATAATAATAAAATAAAAAAATTCACGCTAAAAAATAATACA |
| AAAGATCGATGAAATTAAAAGTTGGTTTTTGAAACGATTAACAAAACTGACAAATAATTAGCTAG |
| ATGAATCAAGAATGTAAATGGTCCAAATAAAATCACCAACAAAAAAGGAGACATTGCAACTGATA |
| CCATAGAAATACAAGTGATCATGAGAGACTATTATGAACAACTATATGCCAACAAATTAGAAAAT |
| CTAGTGGAAATGGATAAATTCATGTATACATGCAATGTGCCATGATTGAACCAAGAAGAAATAGA |
| AAACCTGAATAGACCAATTATAAGTAATGAGATTGAATCTTGTAATAAAAAGTCTCCCATTGAAG |
| AGAAGCCCAGGACCTGATGACCTCATTGCAGAATTCTACAAAACATTTAAAGAACTAATAAAAAT |
| TCTTCTCAAACTCTTCCAGAAAATTGAAGAGGAGGGAATTCTTCTAAACTTATTCCACAAGACCAG |
| CATTATGTTGATACCAAAACTAGACAGAGATACAACAAGAAAAGAAAACTTTAGGCCAGTATCCC |
| CAATGAACATAGACACACAAAGCCTCAACAAAATGCTAGCAAACTGAATCCAGCAACACATTAAA |
| AAGATCGTTCACAGCCAGGTGTGGTGTCTCATGCCTGTAATCTCAGGGCTTTGGGAGGCCAAGGCA |
| GGAGGATCACTTGAACCTAGGAGTTCAAGACCAGCCTGGGCAGCAGAGGGAGATCCCATTTCTGC |
| AAAAAATTTAAAAATTAGCCAGGCATGGTGGCATGCTCCTATAGCCCAGGTACTAGGGAGGCTGA |
| GGTGGGAGGATTGCTTGAGTCTGGGAGATTGAGACTGCAATGAGCCATGATCAAGCCACTGTACT |
| CCAGTCTGGGCAACAAAATGAGACCCCATCTCAAAAAATAAAAATAAATTTAAAAGATCATTCAC |
| CATTATCAAGTGGGATTTATCCCAAAGTTGCAAGAATGGTTCAACATATACAAATCCATAAACATG |
| ACACATTACATCAACAGAATGAAGTATAAAAACCACATGACCATCTCAATAGATACATAAAAAGG |
| ATTTGATACAATTCAACATCGCTTCATAATCAAAACACTCAACTAATTAGTTATAGAAGGACCACA |
| GCTCAACACGATAAAGGCCATATATCATAAGCCCATAGCAAACATCGCACTGAATGGGAAAAAGT |
| TGACAGCCTTTCCCCTAACATCTGAAACAAGACAACGATGCTCACTTTTACCACTTTTGTTCAACA |
| GAGTAATGGAAGTCCTAGCCAGAGCAATCAGGCAATAGAAAGAAATAAAGGACCTCCAAAATGG |
| AAAGGAGGATGTCAAATTGTCCCTATTTGCAGATGATATCATCATATATACAGAAAACCCTAAAA |
| GCTCTACCAAAAAACTCTTACAACTGATAAACAAATTCAGTAAAGTTGCAGGATACAGAATCAAC |
| ATACAGAAATCAGTAGCATTTCTATATGCCAGCAACAAGCTAGCAGAAGAGAACACACAAAAAAT |
| GAAAAGATATCTCATATTCATAGATTTGAAGAATAAATATTGTGAAAATGATCTTACTACCAAAAG |
| CAATCTACAGAGTCAATGCAATCCCTATCTAAATACCAATAACATTCTCAACAGAAATTAAAAAAT |
| CCTAAAATTTACATGCACCCACAAAAGACCCTATAGCCAAAGCAATCCTGAATGAAAAGAACAAA |
| GTTGGAGGCATCACACTGCCAGGTTTCAAAAGATACTATAAAGGTATAGTAACCAATACAGCATG |
| TTACTTGTGTAAAATACAGATTCATATACCAATGGAACAAAATAGAGAACCTAGAAATAAATTCG |
| TGTATGTATAGCCTACTGATCCTTGACAAAGGCACCAAGAACATTTATTGAGGAAGAGACAGTCTT |
| TTCAATAAATGGTGCTGGGAAAATTGGATATCCACATGCATAAAAATGAAACCAAACCTGTATCTC |
| TCACCATATATAAAAATCAACTCAAAATGGGTTAATGACTTAAATATAAGACCTGAAGCTATGAA |
| ACTCCTGAAAGAAAACATAGGAGAAATGCTTCAGAACATTGGTCTGGGCAAAGATTTTATGGAGA |
| AGACCTCAAAGGCACAGGCAACAAAAGCAAAAATAGACAAATGGGATTATATCAAGCTAAAATC |
| TCCTGCACAGCAAAGGAAACAATCAACAGAGCAAATAGACAGCCTGCATAATGGGAGAAAATATT |
| TGCTAACTCTTCATTCAACAAAGGATTAATATCCAGAATATATAAGGAACTGAAACAATTCAACAG |
| AAAAACCCCCCAAATAATCCAGTTTAAAATGGGTAAATGAGCTGAATAGACACCTCTCAAAATAA |
| GAAATACAAATGGCTAGTAGATTTATTTTTAAAAATGCTCAACATCACTAATCATGAGAGAATGCA |
| AATTTAAAACCACGATGAGATATGATCTCAACCCGGTTAGAATGGCCATTATCAAAAAGTTAAAA |
| AATAACAGATCCTGGCGAGGTTGTAGAGAAAGGGGTACTCTTATCCACCACTGGTGAGAATGCAA |
| ATTAGTCTAGCCATTGTGGAAAACAATATGAAGGCTCCTCAAAAAACTAAAAATAGAACTACCAT |
| ATGATCCAGCAATCCCGCTACTGGGTATATATGCAAAGGAAATGAAATCAGTATATCAAGGAGAT |
| ATGTGCACTCCCATATTTATTGCAGTACTATTCACAATACCCAAGATATAGAATCAACTTAAGGGT |
| CCATCAGTGGGTGAATGAAGAAAATATGGTATATATACACAATGGAATACTCTTTAGCCATAAAA |
| CAAAATGAAATCCTGTCATTCACAGTAACATGGATGAAACTGAAGGTCACTATGTTAAGTGAAAT |
| AAGCCAGGCACAGAAAGATAAATACCACATGTTCTCATACATGGAAGCTAAAAACGTTGATCTC |
| ATAGAAGCAAAGAGTAGAGTAGTGTTTTTCCTGAGGGGTGGGAAGGGTAGGGGAGAGGGAGAATA |
| GCCAAAGGTTAGTTAATGGATATAAAAGTACAATTAAATAGGAGGAATAAGGTCTAGTGCTCTAT |
| AGCACTATAGGGTGACTATCATTAACAACAATTTATTGTATATTTTTGAAAAGTTACAAGAGTGAA |
| TTTTGAATGTTCCCAACACAGAGAAATGATAAATATTTGAGGTGATGGTTATGCTAATTACACTGA |
| CTTATCATTACACATTGTACACATATATTGAAATATACTCTAAATATGTATATTTATATG |
| TCAATTAAACATAATAAAAAAGAAGATAATGAAGTTGGATCTCTACCTCACAGCATACACAAAA |
| ATTAACTTAAAATGGATCATAGACCTAAATGTAAGAATTAAAACTATAAAACTCTTAGAAGAAAA |
| CTCAGGAGTAAAGCTTTGTGATCTTGGGTCAGACAGTAGTTTCTTAGATAAAAGCAACACAGGAG |
| AAAATACATAAGTCGAACTACATCAAAATGCAAACTTTTATTCTCAAAATGATATTCTCAAGGAAG |
| TGAAAAATCAACCCACAGAATAGGAGAAAATATTAGCAAATCATGTATCAGATAAGGGACTTGCA |
| AATAGAATATAAAGAATTCATGCAACTCAATCATAAAAGACAAGTAGCCCCATTAAAATACG |
| AGCAAATGATCTGAATAGACATTTCTCCAAAGAGGATATATAAATGGCCAATACATACATGAAAA |
| GATGCTCATCATTAATTATTAGGAAATGCAAATCAAATCGCAATGAGATATCACTTTACACCAAC |
| TAGAATGGCTACATTCAAAAAGACACATTAATAAGTGTTGTCAAAGATGTGGAGAAATTGAAGCA |
| CTTATTCCTGGTGAGAGTGTGAAATGGCGTAGCTGCTTTGGAAAATTGTTCGGCAAGTCCTCAAAA |
| TGTTGTAGAGTTACCATATGACCTGGCAATTCCACTCCTAGTTATAGACCCAAGAGATATGAAAAC |
| GAATGCCCACACAAAAATTGTACATGAATGTTCATAGTAGGATTATTCATAATAGCCAAATATTG |
| AAAACAATCAAAATACTAACCAAGTAAATGGATAAAGAAAATGTGATATCTTCAAGCAATGGGAT |
| ATTATTTAGCCATATAAAGGAATGAAATATTTGATGCATGCTACCACATTGATGATCCTTGAAGAC |
| ATTATGCTAAGTGAAAGAAGCCAGCCACAAAAGGCCAAGTATTGTGTGGTTCCAGTTATATGAAA |
| TGTCCAGAATAGGCAAATCTGTAGAGACAGATTAACAATCGGCTAGGCTGGGAGGGGAGTGAA |
| GTAGAAAATGAAGAATGACTGCTAATGGGTACAGTATTTCTTTTGGGAGGATAAAAATGTTCTAA |
| AATTAGACTGTTGATGATTGTGCAACCATGTGAATATACCAAAAACATTTAACTGTGCAGTTTAAA |
| TGGGTGATTGTATGGTTTTAAAATTATACTTCAATAAAGCTAAGTTTGGGTGCTTTTATAAATCTTT |
| ATGCCCAGGCTGAAACTCAGAACTCAGTCTCCTGGGATTGAACCCATGCATCAGTATTTTTTAAGA |

Sequence Information

```
GTTCTTCAGGTGATTGTATTGTGCAGCCAAGGTTGAGAATCATTATGTTTGAATCAGCCCTAATCC
AAATAAGATTTTAATTTAAGAGACTCCAAAAGAGTTGAGATCCCATGTGGAAGGACTCCGGGAGG
CTTCCTCAAACCATGATACCTCAAGTGTGGTTCTGAGACCAGCAGCATCAATGTCACCTGGGAAAC
TGTTAGAAATGCAGATTATTGGGCCCCATTCAGTTCAAGTACATCAGGATCCACAGTTTAACAAGC
TCCCCAGATGATTCATATGTACATTAAGGTTTGGGAAGCACTGCTTAGGAGCAGCGGTTCCCATGC
TTGGCTGCACATTGGAATCATCTGGAGAGTCCAAAAGTACCAATGCTTGGGTTCCACCGCCAGTGA
TCTTACGGGTATGAGATGCAGCCTGTGCATCTGGGATTTAAAAGCTTCCCAGGTAATTCTAATGTA
CAGCAAAGTTTGAGAATGAGTACTGCAAAAAACAAGATACCTAATGGCAAATAAGATGGTTAATA
AAATTTTCTTATTTTGTTTTTAACAGAAGGATAGATGAACATGCATAAGAAAGTGGAGATTATTGA
TATCAAAAATTTCCAGAGGAGTGAGGAAGGGATGGCAGTGAGACAACAATGGAAAACGTTTTCTC
TAAAAAAAAAAAAGGGAAAAAAACAAAAACAAAAACAGAAAACTCACCACACACCAGGCATTT
TCCTTCTAAATCCAAGAGAGGGATCTTTCATGTGATTATTGGAGACTACTCAAATTTAAGTGGCCA
AGAATTTGTGGGTTCTTAAGAGGGTCTTTAATGCTGAAAACATATGGGTATTTACTGAACTTCCCTT
TCTTTGAATTTATAAAGAGAAAGTTTATTAATATGGTGGTGAACATTTCTTCCCAAGCTGTGTACCC
ATGTCCAGCTTCTTCGGTCTGGGGAAATTTTAACTCCTCAGTAGACAGTGGGCCCTGCGCAGGGTC
TGGGGCATGCTCTTCCTATATATGGCATTCAGCCCTGAGGATTCTCCTCCCCAGCAATCGGCCATGT
CTCTCTAATGACCATTGTCTCTGCCATTTACTGGTCTTTTCAAAATTATGACTCTGAAATATCTCCT
AGGCAAAATTATGAGGCTTGCAGAGTTAGCTTTGAGACTTCTCATCACCCACCCCTTCCCCTCCTTC
CGACAAGCTCCGTTTCTGTCCCATGCCCCAGATTGTCTTCTCCAGGTGACTTGAACCCACCTTCTT
GGTTGCAGTATCAGTACACTGTACCCTTGTCTGCACTGAAATTAACCATGCAGTTTCTGTGCCTTCT
TAAGTTGATGTGTGTGTGTGTGTGTGTGGTGGTGGAGGGTATAATTACTTGAATCTGTGTTAAT
AAAGTGTTAACTATTAACGGAAATCCACAATCCCTCTCTACCTCCCCCTCAGGAAGTCCCTAATGG
TGTTTGGTCATTGTTTCAATCACTTGTCATATATTGTGTTTTCTTGGCCCATATCTCTAACCACATCC
TTATCAAAATATTCTGATGAGTGCATTTTAAAAGTAGAATGACAACATACTTAAGATAGTTGGAGG
GGTTGGCTCCTATTTGCATCATGATGATTCTGCCTATGAAGATTTTTCCTAACAATCAACTAGGATT
ATACACAACGCTTGGTTTCAAAAAATCATCTCATCGTATTAAATTTACTTATTTTAAATACCTGTG
ACTCTTCTGAATAATGAAAAAAATGACATGAATGAAGAGTATGTATATAAACTCTCTCTAAAGTTA
TTAGGAAAATGTTTTTATTTAATTGTGCCTAATATTTTGGGGTATTACAGTGAACTCTACTTTTAAA
GCTGCGTAGTTATGTATTAATATACTGGCCCTGAAATTTTTGAGTTTTCAACCTATAGTCCAGAAAA
AGCCTTTATTTTAATAGTTGCCCTAAAAATTTAACACAAAAGTTTTACTTAGCTAAATCTAAATTT
AATCAGTAGCTTTACCCCACTTCCAAACAATATAAATACTTTAAAATGCTTTCATTTGATTTCCTTT
CCTTGCTTGCTATTATTTTCCAGGATTTTAACTCTGTTTGCTTGGTTTTATTTGTTTGTTTGTTTTAAG
ACAGAGTCTCACTTTGTCATCTAGGCTGGAGTGCAGTGGTGTGATCATAGCTCACTACAGCCTTGA
ACTCCTGGGCTCAAGGGATCCTCTTGCCTCAGCCTCCTGTGTTGCTGGGACTACAGGCATGCACCA
CCATGCTCAAATTATTATTATTATTAGTAGTAGTAGTAGTAGTAGTAGTAGTAGTAGTACAGA
CCAGGTCTCAGTATGTTGCCTAAGCTTGTCTCAAACTCCTGGCTGGCCTCAAGGGATCCTCCCATCT
CAGCCTCCCAAAGTGCTGGGATTATAGGCGTGAGCCATTGTACCTGGCATACTTGTTTGGTTTTAA
GCCCACAAATTAGACATCATCATCATTCTATTTAGATTTTCTCATATTTACCATTTTCTTTACATATC
ATTTCTACTTCCATTCAGAGCTTCTGGGATCAAACCGTAGTTCCTGGCATTTTGGACTGGTTGATAG
TCTCCAGGATATTCAGGCAGTTAAGTGTCTCCGAAAGAAAATGAGAAAAGAAAGGTCCTGGGAAA
TATGCCCCACCCCCACCCCTGCAGTGCTGCCGCTGCTGTCCCAGGACCGTGGGCACCCCTGAATGT
TTCTCTTCCACTGTCTCTGATCACTGTGATTTATGGAGTAGAGGGGGACAATGACATCTGATAGAA
TACCAAAGTTAAATATGCTCAATTTAAGGAGCTGTTATTTATTCAGAGATCGTGTCTTTCCTACCTT
TTTTGCTGTTTATTTTATAAAATAATGGTGATGGTAGTTGAAGTTTGTTATTTTGTTTGTTTTAAAT
TAATTCATTAAGATTTGTTTTTATATTTCCTTACTTGGCAAATACAAAGTTGAATCACAACCCAG
ATTTTTTGAAATTGTATTGGGCATTGAAATCCCAAACCACTGCTATCAACAGCTAACTGTGAGTTT
GGCGTGTGGACACTGGGACACCTGAAACCATGTCTTGGTTACGTCAGGAGCCTTATTGATTATTA
TATTATGTATGAATCCTGTGGTGTTAACAGTACTTTGCAACCTTTAGTACTTAGCTGAACTGTATTA
GATTATCAGGGAGTCCTCAGTACACCCTCAATGATTTAAATTGTTTTTAGCTACTTCTGTAAGGCTG
AGTCTACACTAGCAAAATGACCTGGGTGCCTATTGTGCTCCCTACATACATCTGGTGATGTTTATG
CTCCCAATTTCTTAAGAACACTGCTTTGAGAGTCACACAACCCAATATTCTACCAATAACTTACTAT
GTACCTTCATCATTTGTAAGAAGAGGGGGTTGAACTAAGCGATCTCCAAGTCACTTTTCAGCACAA
ATGTAGGTTGTGATTGTATTTGTGTGTACACATTTTTTAAAGCCTTAAAGAGATCTAGGTATTTCTC
ATGTATTTATATTAAATCTAAGATCCGTGTTGCAAATTTGGACATGGAGGACATTAATTTTTCTGAT
GTAGGTTACTCTTTAAGAGGCATGTTGCATCTGTAATATTGGTGCCACCATTTTGGCAGATGCAGTT
TCTTCATTTACTCGTAAGTGTTCAGTATGAAGTCTATATGAGGTGACTTGAGTTCTCATTTCTCTGG
TGTAAAAAAATGGTCATGTTTAAATAAGGCCACAATATTTATTTCAAAAGGTCCCAGAATCATTTTT
TAAAATATCTTCATATGCTTGACACTGAAGTTCTTATGTAAAGGGTTCGGTCAATGTAAACAAACG
ATGACTGCTTGAAGATGCACCAGCCGTGATTGTGGAGACCTCCAAATTCATGACAGAGTTGTTAAC
TGGCAGGTTTGTTATTTCCTATAAGTACAAGGAAGGGAAGTATTAAAATAATTCATGCCCATTAGA
GAGAGGAAATTAACATTCCCTTAAAAATTGTTTTCCAGTGAAGGAAGCCCATCCCCCAGAATTGAG
CTGCTGCATAATATTGACCCGAACTTCGTGGACTCTTCACCGTGTGAGTACCAGTGCATTGCTACT
AGATTAAATCTAATTGGCCCACCAAGATGGTTTGATTACCTAGTGTGTCTCTAGCCTAGCTTTCTCT
TTTTTCCTGAGTTGCTATAAAGGTAAACAGTTCTTCGGGACATATCTCCCGCTCATCTCAGAGGGC
AGTGTGCTGTGAAAGCAACACCAGCTTATGAAATAAGAAAGGTGAATTCTATTCTTGCTCTGCCGC
TTACTAGCCTTTAAGCCATTGAACTCTCCCTGCCCCAGCCTTCCCCATTTACAAAAGAAGAACTCAT
GGCATCTCTGAGGCTCCTTCTCACTGTAGATGTCATGTTGCTGCCCTGTTCTTACCTGAGAGCTCCA
GAGCCACCTTCCAGAAAACTCACAGTCAGATAAGCCACAGTTGGGTTCCAGGTAGTGTGAGCAAC
CACATTATCTGATTGGGCTGGTCAGGTACTGCCCAACACCTGCTGGGTGTCACAAGTGTGACTTTC
CTAGCAGTCCTGGAAGTGATTCCGCTTGATTCTGCCTCCTGCCTAAATTAACCTGTAAAGAGCCTT
ACCATTTCCTTCAGGGCAGGCATGCATGTAGTGCTTCCAGATCACAACGGACTGTAATAGGCCTGT
ATAAATACCATGCGAGTGGCCCTAATGCCCTCAGCATAGTGAGTTTGGGCATAGAAAGCCTTAGC
AATTAGACCCTTTGCCCAGCTTTCATCATAATGCTCATCTTGCAAACAGTGCCCTTATATTCCCTTA
TTCACATGGGGGCTCCCATCCGCTCCTTTCTGGACATACTGCTGCCCACTTAGTTCAGGCTCTCCTT
ACTTCTTTGTTTTTTCCAAACTGCATTATAGCTCACCACAAAATATTCTCATTCAGAGATTCCTGCT
CAGAGAATTACCCCACAGTCATTCTAAATGTGTCACCAGGCACTCGGGCCCCACTTGCCCGGCCAG
CCTCACTCCAGGCACTCCTTGTCATGTTCTCACTTCCTAGACACTTGTCATCTCCATGCAGATCATC
```

Sequence Information

```
GTACTGTCATGAATATGCTTTTCCCTATGCCTGAAACACATTTTCCCTACCTGTCTATAATCTCTCTC
ATCCCTTAAAAACCCAGCCCCATGTCTCCCTCTGTGAATGCTTTCCAGAGCCCCAGAAGGAGCAGT
CACTCCTTCCTGTGTGCATGTGTCTCCGTATAGCATCCCTCACATGTTCGTGTTTGTGCCTGCATTTC
CAAGCTGAGAGCTCCTGGAAGTCAGCATCTCCTGTATTTTTTTATCCTTGTCAGTTAACACAAATAC
TGGGAGCTTGCTAGGCACTCAGTAATGATTACTTGATGACTCAGTGGACAATTGGAGAGTTGAGAT
GCAATAAAGACCAAGTGGACACATTAAGACCTGGACAGGAAAGGGCCCTGAGACAGGCGAGAAT
GGCTACATCGTGGAGAAATTTCTATTTCTTTTGGAGTAAACGCATGTCAGTGAGAGAGGCAAGGGC
AAGGTTTGAGCCCTAAGGACTGTAAGAACAGTCTAGATTTGTGCTGTCCAGTATAGTAGCCACAGG
CCACATGTGGCTGTCAGGTACTTAAAATATGGCTAACTGTGGATTGAGATGTGCTGTGAGTAGAAT
ATATACATCCGATTTTCAAGACTTAGTACACCTATGTATTATATGCATACAATATTATAGATTTATT
ATTTGTTGAAAGGATAATACTTTGGATATATTGAATTAAATATATTGTTAGTGTTTTACTTCTCTCC
TCTTCCTTTCTTAATGTGGCTAATAGAAAATTTAATTTTAATTAACTTACATAAGTGACTTGCATTA
TATTTCTATTGGCCTAAAAACCCCTTCTAGAAGGTGCTAGGAAGTAAGTTGATCAGCTGAGCTGAT
CACAGAGCTGTGAATAGTTACTGTGAGGCTACATCAATGACTCCTAAACTTTTCTCTACCCCAGTA
CACCTAAGAGATACATTTCAGTCATATCAAAGTCTCTAAGGGTGGCTGGAAGAGAATAGTGGGGA
GGCAGGAATGGCTTTAAAACTTTCTGAGTAATTTAATGCACTGCAAAGCCCAGTATAACCTAGGTC
TAGGGGATATGTGGAATATGCCACCCACATTATAATGGTTGTAAATGTCTTCACCTGCTAAATTCC
ACCTACAAATGAAAAACCTTAAGACCCCTCACTCACTAAGCTGTATTTTGGTTTGGCATTTGAAGT
AGGAGCTTGAGAACTATACTCCTATGTGATATGGTTGGGATTTGTGTCCCACCCAAGTGTCATGTC
GAATTGTAATCCCCATGCTGGAGGAGGGGCCCGGCGGGAGGTGACTGGATCATAGGCATGGATT
CCCCCTTGCTGTTCTTGTGATAGTGAGTGAGTTCTCATGAGATCTGGTTGTTTGAAAGTGTGTGGCA
CCTCCCCCTTCGCTCTCTTCCTCCTGCTCCAGCCATGTAGGACATACCTGCCTCCTCTTCACCTTCTG
TCATGATTGTAAGTTCCTGAGGCCTCCCCAGCCATGATTCCTGTACAGCCTGTGGAACCCTGAACC
AATTAAACCTCTCTTATTTATACCTAGTCTCAGGTAGTTCTTTATAACAATGCAAGGACGGACGAA
TACACTATCACCACAGCACTGTGTGCTGCAGGGTTCTTGGTGCAACTTGCTGTGCTTTCTCCTGTCT
TACCTAAAGGGCCCTAGCAAAATAACAGCACAGGCAAAAGGTTTCTCCAGAGTAAAAGTTGGTAA
GAGCATGGAAATTAGAATAGAAAATTTTCCTAATCTTGCCATCCATAGACTGTAAGGACATTTACT
TCTCTTGGACTCAGTTTCCTATGTATTATGTGGTAGAATTATAAGACCCAGTACTGCCGCCACAAT
TTAGGCATCCTCTTTGGCCTTCTGCTGCTCTTCCTTCCCTCTCTGGAGCCCACCCAGGCCTTCATGTT
GGCTTCCCCACCAGCTTGGGACTCCTGCTCTGACTCCTGCAGATAACGAAGGACATTGTCAGCTCT
TGCAAGGATGTAGAACCACATTCACTGTTGCTTCACACACACACAGCGTTCTCTGCTGTCTGTGCC
TGCAGGTAGCAAGGTGCCACCCACCTCCTCACACATGGCAATCCCATGGGCCTTTTCTGCCCAGTT
TTTATATTCACTTCACTCTACTGAGAGGCAGAAGAAGAAACAAGAAGAGCTGTCTTTGGGTGCCTG
CTCATTTTAGGATGATGATACAAGCCCGTTTCCTTTTCTATGCAATTCATTTATGAGGAAAAATTA
AATCCAGCTATAAAAAAACATGTACTTAGGGGACAGCCAAGTCTGGATATCATATTCATAGAGCA
CAGAGGCTTTTGTGGAGTTAAATCAGAAGTAGCCAATCTCGGGTGTAAACTGAGGGTTAACAATG
GAGTCAGTGTTATCACAGAAGCATTTCTGTGGTTTCTCACTCCAGCTCTTCCCAGATCGTTGGTGCT
TACTGCGGGAGAAGAAGGTAGCGTTCCACCTCCACCTTCCCTAAAGCCACTTCGTCAGTTTCCTCA
CCTGTGGAGTAAAGAAGGAATTAAATGATCTCCAAGGTCCCTCTGGCTTCAGTGTTCTGTGGGTCT
CTATATGAATGGGACCTCAAAGGAGCAAAGCTGCTTACTCTGTCTCTCCTTTTTCTGCCTGCTAG
AAGGAGTGTGTCCATTGATAAGCAGTGATGTTGCCAAAGGCATGATCATAAATAGATAAACACAA
GTGCAAATGCTAGAAACATTATATGCACTAGAGGAATTTGAATTATTTTATGAGTTTCTTATTACTA
TATCCTGGCCACCTTTCTGATTTCCGTTCCGAAACATCACCGTATCGATCCGCTTTTCTATCTCCTCT
TTCCCTTAGTGGGTCATCCTGGGGTTTGTTGACCAATGTCTCCTCTGATTGTAATCATACGAATAG
GCATTACGCACTTCCCAGGAGATTTCTGCCCTCTGCCTAGCACCACATGCTCCCAGAAGCTGGCCT
CTTGGATTTCAGCAGCTACACCTCCCCCGCTCCCTGCCAACACACACCCCATTCCCCTAGTCAAATT
ATAGGGTGCCCAGAGGCCCATCCTGCTGGTGGAGTCAGGATTTTTTTCATGGTCACATGCACATGG
TAGGTTGTGGCTTGGATACTAACAGTAAAAATACTCAAAGATCGGCACAAAATATTGATACACGT
ACACATTCATAGAGAAACATGCACACACACCAGGGGTCACCAAATTCTCATAGATCAGGAGATT
CACCATTCTGCAGTAAAGCATAAAGTCTCAAGGATGCATACGTAAATTATACCATTAGGATGACTA
CAATTTAAAAAATGAAAGAAAGAAAAGGAGAGAGAGTGGAAAAAGGAAGGAAGGGAGGGAGGG
AGGGAGGGGAAAATAAGAATTGTTGAGGATGTAGAGAAATTGGAACCCTTATTCACTGTTAATGG
GAAAGTAAAATAATGTAGCCTCTATGGACAATAACATTGTGTGATTACTCAAAATATTAAAAATA
GAATTATCATAGGATCCAGCAATCCCACTTCTGAGTATATACCTAAAAGAATTAAAAGCAGGGGC
TTGAACAGGTATTTGTACACTCATGTTTGTAGCAGCATTACTCAGCATTACTCAGAACAGCCAAAA
GGTAGTAGCAACCCAAATGTCCATCAGTGAATGGATGAATAAACAAAATGTGGCATATATATATA
TATATATATATATATATATATATATATACACATATATATACCATGAAATAGTATCCAGCACTAACA
GTGAAAGAAATTCTAATACATGCTACAACATGGATGAACCTTAAAGACATTATGCTAAGCAAGTC
ACAAAAGGAAAACTATATGACTCCACTTACATGAGGTACCTAAAGTGGTCAGATTCATAGGGAC
AGAAAATAGAATGGTGGTTGCCTGAGGTTGTGGGAGGGGAGAATGGGGCATGATTGTTGAGTGG
GTGTAGAGATGGATGGTGATGATGACAGCATAACAACGTGAATGTATTTAATGCCACTGGACCAT
ACAATTAAAAGTGGTTAGGATAGTAAATTTTATGTTGTTTGTATTTTACCACAATTTAAAAATATA
AAAAATAAATAAAACGTAACTTTCCCTCCTTCCAAAACTGAAGAGAAACTGCATGAGAATAGGGT
CTCTATCTTTTTCATTTACTGCCATATGCACAGTAAGGTCTCCGTAGCACAGAACCTAACATCGTAG
TAAGTTGTTGGGTTAATATCAGTAAATATCTGCTAATGATGATAAACAGATCAACCTGTCAAAGT
CATTGTTTTATTGTCTTACAGCCTTTCCTGAGCCTAAAAGTACCTCCAGATGGCCACTTATACTCCT
TTTAAACCCCAAACCTACCTTTTGTGCCTAAGTAAAAATAACTTAGAAGCTACAAGTCACTTATTA
AGTTGTAATTGACATTATATACAGATGTTTGAAACTGTTCATTCAGCTTCTAAGTGCCCACCCTCAT
CGCTCCCTGCATTGAAAAGATCGGCCAGAAAAGATGATGTGGGATTTCCCTGCCCAACTTCATCCC
TTTTCCCAGACCTCCTCAATAGACAAATAGAGATTTATAAAGCCTTTGCCTCTGGCCTGGCTCGGC
CTGACTTCCCTCTGAGTCTGGGGCTCTGCCTCTTCTTGCTGTTCTGAGTTCGGTTCTGCTCCTGTTTT
CTGGGATGTTCCCTCTGGTTGTTTCATCATTCACTGGTTATCTCAGTGCCCCAACCCTAGCTCTGCT
TTTATCCCCTTCCTCCCTCCACTGCCTCCCAGCTTCATGACCTGTGTCAGAGTGTGGGATGTAATTG
CTTTCCTGTGTGCTTTGAGGAGACTTTTTATTCATTTTTGAAGGCTTTGTTCTGAAGTAACCTTGGA
AGTGCTTTGGTCTCTGTTCAGATAGTACCCTTCTCTTTTCCTTTGTTCCCTTCTGAGAAAACTCCTAA
GAATTATTTATTCCTCCATGTCTTTAAAATACTTCTGTCTTCGTCCAGCAGCACAGGGTGGTCAGTG
TAAGAAACCCGTGAGAGAGCCTGGGGAATAGCACCATTGAAGCTGATTAGTGGGAAAGCCTGGAA
```

-continued

Sequence Information

```
ACCTCTAAAGTGGTGGGGAACAGCCATAATCCCAGGGTAGGCAAGAGGTCCTGCAGGTCTGAATT
CAGCTCTACATGGTTCCAAGGAGAGCTCCAGCCCCAAATTCCACACTCCTGCAAGGCCCCAGCAA
GCATGGCTCAGACCACAAGGAGAACTGCTTCAAAGGCATTATTTTTGCCTGAGGAAAAACATATAC
ACCTATCCTGCAGGTGCCGGGCTTGATCTTGGCTGTTCTGCAGTAATGATCCTGCCCCATCTGAGA
CCACGACTCACTTTGGAAGTCAGACGTGGCATTCTATGATGGCTGGAACACACATATCCGATCATG
TAACATAGGTGTATATATTTAAAACGTACGCACACACAGGAGACACACACATTCTGCTGGTAGAA
GCTTGATTATAGATGAAGGGCAGTGACAGATGTTAGCATTTTCCACCCCACCAAAGGCCAGCTCTT
CAAAGTGATTCCATACAGCTTTGTTACTATTTCATTTAAAGGCCCTCTTCTCTTTAAAGTTTCTAAT
GAGATGTTATTTCTGCTCCTGATTATAGGGTGAAAGAACAGCCTTCTTCCCACCCTCTCCTCTCTCA
CACACACATTTTCTGTGGTGCAATTGCCAAATCCATGCTTGAGATCAAGAGTCGTCCAGGTTGGA
ATGCTTGGAGCTGCTCCCTGTTTCCTCCTCAGAGCGACATTCAGAGCCATTTCCCAGTATTATGTTG
CCATTTCCAAGATTGTTTATTCAGTAAATAAATAAACGATGATGGCCTGGGATGCATGAGGTACTG
TTATAAATACTCGAGATCAGTTAAGCTAAAGCCAAACCTAAAGGTCTGGCTAAAACCCAGTCTGG
AAGAGTCTGGAAGAGGGCATGGACACAGCCTCTCCCCACCCTGCTGGAAGGCTGTTGGTGGTTCC
CAGCTGTCCACTAGCAAGCCCTCCTACAACGCCCACCATTCAGCACCATTGCAATGCCCTCCTTCA
GTCCTGTTTATCTCCCTTGTTGCCCTGCGCCTTCTGTAGAGTTCAGTGCACATTCCTACTCCTCCGTG
AAGCCCTCTCTGATTCTTTTGAACTTGAGTCCCTTGAGTTTCTCTGGAGCTTCCCAGGACGGTGAGC
TCTTGCTGCCTCATAGTGCAGTATTTATATTCACGTGTTTTCCCCATCCGGAGCTATAAGGAGAGCA
AGGCTTCATTGTATAGTTCTCTCGGTGTCTTATGTATAAGAGATTAATACATATTGAAAGAATGCA
CGCTAATAAATGAATAATTTATCATCAGCTGATTCGATTAGAATCAGTCTAATGAGAACAATAGTA
ATTTCATACATCATTTTCAAGGCATTTTTATTTCTTTTTGGGTCTATTAGAGAAGTAGTGACACAGA
GGCATCTTTCTTTCAGCCTGAAATTAGATATTAAGCAGAATCAAGAGTTAGGGGGAATGCATGGG
GCTCACCCTGCTACAGATTGCTCAGCATTGCATAGAATGCCAGAGGCTAAGGGCCCCTTGGCAGTT
TGTTCACTCTTTATAATCCAAGTGAAGAAACTGAGGCACCAGGTCATGCATGCTGTTAAATATCAG
AGCTGGAACTCAGGGCTGTTCAGACCCGGCATGTACATCATGTCCTACTGATTTCGCAGGTCTCAT
CGCTTTGTGTCCTACCCTTGTCTTGTGGGAGAAGGGCACCCAGATATGAGTTACGATCATCTCACC
TATATAATAGCATGTTGATGGGACATGACTCATTTAAAGGAGGCTGGAAAAATGGGTCGAGTAGT
CACATTAGCCTTGCTAGATTCACATGTAATCTGACTCTGCAGATGGTGGTAGCTTCTGCTTGTAGA
GCTAGTCATGGAAGCCCTGTCAGTGCCTTGTATTCACTCCACTGGAGGGTGCTGGGGGGATGAGGG
AGCTGTGTGTGGGGTGGGCAGTGTCACCTAGTAAAACAGGTAGAGTTTGGGGGTGCCAGAAAGCC
CTGGGTTTTATTCAATACCAGCTCTGACTTATTTCCTGTGAGCTTGTGGGTAAGTTCTTCCAGCCAT
CTGTTTCATCACCTATACGTTGGGAACGATTATAACAATATCTCCTGTAAATATGTCCAAACAACA
GTGAACAACAATTACATTCTGGCTGCTACGATTGGGGCAGGGTGGGAAAGTTGCACTTTTCACTTT
ATGTATTTCTCTAGTTTTAATTTTAAATTATGAGCACATGTGACTTCTTAATCAGGAATAAAGCCA
TAAAGCTTTATTTGTGAAAACCACCTCCAAGGAGGGTTCCGGTAAGCATGGAATATCTGAAATCTG
CTGGGTTCTTATAGAGTGGGAGTTGCTGCTTCCGTGCCTGCCTGTACTAGGTCAGAGCAGTTAGAA
TTTTGTGTCGTCTCTAGTTGCCAATATTTGTCTTTAGCAGCTCGTCAAATTTTCCTTGGTGTGGGTTG
CTACATGCCCTCAATCACAGAGCCAAAACACAGATAGCTTTCTCCTTTTTAATTTTCAAAGGCTTCT
AGTCTGCCCCCTCCGCTTTGGGGAGCACTAAAGTCTGTTTGGAAATGTGGCCTTTTTGATGCCAAA
GGCAGTCCCACAAGCCTCGTATCCCCTCCACCCCACTTCACACAGCACATCTCAAGGAGCACGCAT
GAAACCTTCACTGTTAACACTTGGTGCTGGCATCCTGGCTTTCATCCCGAGAAAATACACAAACCA
AACCAAATCCACAGCACTTTAAAAACACTAATTAACTCTCACCACTGGCCTAGGCTACGCAGAAAT
GGCAAATCCCGCTGCCCCAATTTTATGTTTGGAGAAATCAGGGTAAGCAACATTTTCTAGGGCTTC
TCTGAGCCAGATCACAGAAGCTGACCTGAAGGACTTGGCCTGGCCCTGCATCTGGAGTTAGGCCAT
TTGATGAAGGGCCAGCTGCCTCACCAGATCCCTTCTCTACAGCACCACGTGGTTAGTGGCCCATAA
CTCCATTTGTACATCAGCGTTTGTTTTTTTTTCCCCAGGGTTACTTTGATGCCAAACTGTCTCATGTC
CAACTGACCATTTATTTATTTGCTTACTTTTCTTTAATTCTGGTACAGCCTAGAAATTTTAGCCATA
GCTTCCAAGTGTAGCCTGTTAATTATAGTTGATTAAAGGTTCTATGCTGATTTTGAATTTCAACACA
AAAGCAGACTAACTTCCAAACAGTCCCTCTCAGGTCCAGTGGCTCCGCCCCTTCCGTCTTCCACCC
TGGAGCCTCCCCAGGTCTGGTAAAGATTTGGTGGTGTCCAGACTCCTTTTTTCCTCTCCCAGTCTGG
ACCAGTCATTCTCCTACCTCAGTTCCCCAGTCTTACCATCTGTAAAGATAAATATATCCATCTTTCT
TGAAAGAGTCTACCATAAAATTCTGTAAAACATAAAACCTCATAAAATTTTAGGGAACATATCC
AATGAAATTAAAATTTACAAAGTAAATCTATTTTGTAAATATTTATTGATCTTGTCAGAATTTTTAG
GGGTTTTAGGGTGCTTGTGTATAAGGCTGAAATAAAACTTTTGAAAACATTTCTGGGACGTTGTTG
AAAACAGACTAAACGGCCTGTTTAGTAACCCATAATGTAAGATGTTAGTAATCAGGCATTTATAGA
CTGAAGTCTGTTACCTCTGGCAGAAAATACCTAGGGAATGAGTATATGGCCCCTGCTTCTAAAGAT
TCTTTTGAATCAGAGGAAAACATATGCCCAGGAAAGGATATTAACACAGTTATAAAATAAAGTAG
AACAAATGATAAGTGATATAATATAAGCAGTAAGGACAAATGAAGAAGTGACAGCATTTGGGAGT
GATTAGGAAAGGTGTTCTCAAAAAGGATATCTTTAAATTTGTCCATTACTTCAACAACTTTAGTTTT
ATCTTTCTTGATTTTAATGTGAATGAAGGAAAAGAATATTTAACACTATTAGTTTTCTATCACTGAT
CAAACAAATTACCATAAACTCAATGGCTTAAAACAACCAATACTTAACCATCACTCTATTTTCGTA
TTTTTTGAATGTTTTCAGTTCTGTAGGTCAGAAGTCTGACATGGGTCTCACTGGACTAAATCCAGGG
TACCGATTGGCAGGGCTGCAGTCCCTTCCAAAGGCTGAGGGGACATCCCATTTCCTTGCCTTTTCCT
GCTTCTAGAGGCTGCCTACATTCCTTGGCCCATGGCCTCCTTCCTCCATCTTCAAAGCCAGCAATGG
AAGGTTGGGTCCTTTTCTAGCACATTCTTTGAACCTGGCTTCCATCATCTCATCTTGTCTGACCTGTT
CTGCCTCCTTCTTCAACTTTTCTGGACTCTTGTGATAACATTGGGCCCACCTGGATAAATAATCTAG
AATCACCTCCCTATTTGAAAGTCAGCTGATTAGCAATCTTAATTCCATCTGCAGCCTGAATGCCCCT
TTGCCGTGTAACCTAACATATTCACAGGTCCTGGGGATTGGGACGTGGATATCTTTAGGGGGCCAT
TATTCTGCTACCACAAATACCTGCTGTGTTGCCCTAGACTTCATGAAAAATACAACAAGTCGCTTA
TAACCTAGTTGGAGAGAACAAGAACATACAAAAAGTTAAAAGAAAATCAGATAACAGTTGAAAG
CTATGGTGGTAGAGACGTTACAAGTTGTACTTAATTGTCAGATCATTTCCATGGAGTCTGATAGTT
GCTATGAGAGTGAAGGAGGGCTAAAACACTCAGGCCCTCTTTCACCTCCACTGAACCTCAAAGAG
TTCCTAGGTGGAAAAGACCATCAAAGGAAATAGAAAAGGCTGTGAGCAAAAGGTGTGTGAGCCTA
TTTGGGGGACAAAGGGGAGGCATGAAAGAAGAGATGGGAAAGCTAAACAAGGACAATATGTCAC
ACTAAGGAGATGGGATTTCATCCTGTATGCAGCAGGGAAGCTCCTTTTGTACAAATAATAGATGGG
GGGGTGGTGCAAGAATTTTTAAAAATACAGAAAAGCTCAAAATTTTTAAAAATACACACAAAAA
AAATCACCCTAAACCTATTATTCTGCTACCCAGAAATAAGCATTGTTAATATTTTGGTGGGCTTTTT
```

-continued

Sequence Information

```
CTATTTCTATTTAGGGAGAGCTTTCAACATTTCACCGTTCAGTATGATATCGATTGCAGATTTTTTT
TATACTCTTTATCAGTGTAAGAAAACTCCCTCCTATTCTTAGTTTGTAGAATTTTTAAAACAGCTAT
TGCTGTTGTCCACAGGAAAGTCCCTTTGTGTCTGCACTATTTTAATCCCAAAATAAAGAAAAATCT
GCTAATTCCACAGGTGGTTATATAGATGCTGGGGTTTCAGCACTTCCTGTTTGACCGGAAACTCTC
AGTGAAGTAAAAAAAAAAAAAAATCAGAAATTGTGGAAGTTTATTTGTAGAGACTCTTGTTTTGC
CGTTAGGACTGTGGGTCCCAGAATTCTTTGGAATGACAGCCCAGTCAAAGTCTAGCCATTTCTCT
CCCAATTATCCAAACAAAGGCTGGTTTAGGCACTGCCTGAAAGGACTTGATAGATGTAATCCAAGT
CCCATATCCTTAAGTGCCTCAACCAAGAGGAAGTCCTGGGTGGGCCTGATTCAGTCATATGAGTAA
AATATAAATTTTCCTTTGTAGGCTGGTTTTTACTAAAAATGATATTGCTGGATTATCCTTGGAATCC
ATCTCAGCAAAGTGTTAGAATAATCTCAAGTATAAAGGCAGGAGGGGCTGGGCACAGTGGCTCAT
GCTTGTAATCCCAGCACTTTGGGATGCCAAGGTGGGTGGATTGCATGAGGCCAGGAGCTCAAGAC
CAGCCTGGCCAACATGGCAAAACCCCGTCTTTACTAAAAAATACAAAAAAGTAGCCGGGCATGGT
GGCACACACCTGTAGTCCCAGTTACTAGGGAGGCTAAGGTGGGAGGATTGCTTGAACCGGGGAGG
CAGAGGTTGCAGTGAGCTGAGAGTGCACCACTGCACTCCAGCCTGGGCGACAGAGCAAGACTCTA
TTTCAAAAAAAAGGCAGGAGAAGTAGTTTATATAAGATATTTATAACTAGTTTAGTGGTCTAATAG
CCTATGGATGAGAAGTGACTGGTACAGTGGGCCATCCTAGAAAGAGAAAATCATGTCTAGGTGGG
CTCTATTTGATGGAGCCGTTGATCTGGGGCCAGGTTTACAGTCTCTTGTCACTATCTGGACTCTGTT
CTAGGTATGCAGCTGGCTGTGCCCCTATTAGGATGAACCCCCTGTAGGTGCCCTTTCCTTCTGATAT
GCCAGGGATGCTCTGGGACTTCCTGTCATAGGTGATTCCTAATGCTCCTGACCCATGGCAGCCAAA
TAGGTTCCCCCTTGGAGGCTTCCATTCTGCCCTGTTACCTGCCCTTATTTTCAAATTTGGAATGTTTG
TAGAAGTCTGTTAGTATCTCTCTCACTTATTTTGGGGGTATCATACTGTTTTCACAGCAAAAGAGCT
TGCAGTCAGCTTTAGCTTCTTCCTTTAATACATGAGGGGTAACACCTGTGCTATTTGTTTTCTTTCCT
AAATGCCTTCACAGAAGCAGTTTTGAACCAGAGAATATACACAATTAAGTAAAAGGAGTTGAGAG
AAATCACATGGAGAGCAATAAAGAAAAGAAACTAACCATTGTTGACATGGCACTGTGTTCTAGGC
ACTGTGTAGCTACCCCCTGCCCCCAGTACCTGCCTTTCTTTAGAGCACATATTATTTTTTAAATATT
TATTTATCATCCTCCTGTCTCATTAAAATACAAGTTCCACGAGGGCAGACAATTTAGTCTTTTGTG
TTCTTTTCTATACCCAAACATCTAGAACAGTAGCACAATAAGTAGTTGTTGAATAAATGTCTTTTCT
TAAAGAAAAAATGAAAAAAGGGGCCAGGCATGGTGGCTCATGCCTGTAATCCCAGCACTTTGGGA
GGCTGAGGCGAGCAGATCACAAGGTCAGGGGTTTAAGACCAGCCTGACCAAAATGGTGAAACCCC
ATCTCTACTGAAAATACAAAAAGTAGTCAGGCATGGTGGTGCACGCCTGTAGTCCCAGCTGCTTGG
GAGGCTAAGGCAGAAGAATCCCTTGAACTCAGGAGGCAGAGGTTGCAGTGAGCCAAGATCGTGCC
ACTGCACTCCAGCCTGGGCAACAGAGCGAGACTCCATCAAAAAAAAAAAAGAAAGAAAAAGGA
AAGACATGGGGTTAACTTTTTTAACCTTTAAAAAAGATCTATGGAAAAGATTGGATAGATGTCAGA
GGTACTTGATTGTAATAGCTAATGCTTGTTTGTAAAGTGAGACGTAAGAAAGCTTAGATTTGGCTT
AATTGATGGCAAGTTTAAGAGACTGAGGTTTACTTGAGACTGACATTAGTATAAATTTAAAATGAC
TTAAAGAGGAAGTCATGGGTATTTGAACTATTTATATTCATTTCAGATCCTTTCTTTTACATCATTT
TGTAAAAACTCCTTCGAAAAAAATAGTTCAGTGCTTATAGCTGACTTTTAGCTTCTTTCTCAAAAA
AGAAAAAAATAATAAAAGAGGAATGAGAAAGTCAGCTTAAGTACTACCTTCCCTTATCTTTTGACT
GAGATATAAGAATTATTTGTGACATAAATACATTTTATTTAAAGAAAGTTGAAGATTGGATCTGGG
TTATTTTTTGGACAAGTTAGAATATAGTACTTGATTTCTAATTGTTAACAACTAATGTTTTAAAAAA
CAAATGTTAGAGACTGAAAAGGAATCTAAACCTTTCCCTTTTTCTAATTGTAATCATATTTTCAAAT
GTATATGGGATTTTTTTCTTAGTCTTTCCACAAATTATAAACAGCAGCATTTACCCTGCATTGAGCT
GAAATGAATAAACATTTTTAAATGAAAATAATGACAGTGAAAACCAATTTAGAAAAGAAAGGAA
AAAGATGCCCATAAATCACAGACACTTGGAAGAGCATGTAAGAAAAGCTAAGAACTACATTTTTC
ATATTTTACATTTTCTCTTTAAAATCGCTTTCCAAATTGTTGATGGTTTGGCAGCTCCAAGGATGAC
ATCAACTCTTCCATTGTGCAGTATCTGCTTGCTTTTAGATAACTTGGTGGCACTTTATCAGGTTTTG
GTGATTAAGCTGAATTAAAAACCAACTGGATTTGAGTTTAAATTCTCCTAACTGCTAAACCAAACA
CATTCCTGACCGTAGGCCTACTTTTGAATACTTCTGAAAACTTATTATTACCCATAGGCTGTTTTAC
TTCTAGAAACAAAAGTAAGCAAGTGAGAGAAAAATGCACTCCTTAGAGTTACTAACCACATCTGT
CAAAATGCAGTATATTACCAGTGCAGCTGTTAAAATGCTTTTAAACCAGCCATCTTCTTTTCTGCCT
ATCTTAACCTGACTGAAAACCAAGAGGACAATAATCTTGGCATTGTTTTCCTACTTCAGAAAATCA
CAGATAGTTATGAGCTACTGTCTCTCTCAGCAGTTGGGGCAGATTCTGATGATTAGTTAAGTCAT
GATGAAAAGATAATACCAGAAATTAGGCTATTAATGAGGAAGAAAAACAGCAGGCTGTGAACAGG
TCTGATAACTTTCCTGTATATCCTAGGAACTCACCTGGGAATACTAGGTGAAAACATTGGCATTCC
ACACATCTGGTCTATTACCCTACACTTAAAGCAGTGCCTTTCATACCTGAATGTGCACACGAATCA
CCTGATTCAGTCAGGCTGGGGTGGGGCCCAAATTCAGCATTTCTAACAGACTCCTGAGTGGTGCCA
ATACTGCTGGGTCTCTGACTACAATTTGAATATTGAGCCCCTAGTCTAGAGGACTTTCACCCAATTT
GAAGCTCAATCTTTAGAATTTAAAATATTTGTATAAGTATTTAAGACTAAATATTTTTCTAAGATA
TCTAATTAAAGACAGAGATGTAAGACCTTGAATTTCAGAACTGTTTTATAAATTGTATTAGTCTGTT
TTGCGTTGCTGTAAAGGAATGTCTGAGACTGGGTAATTTAAAAGAGGTTTATTTCGCTCATGATTC
TGCAGGCTGTACAAGCATGGCACCAGCATCTGCTCAGCTTATGATGAGGCCTCAGACAGAAGGCA
AAGGGAGAGCAGGTATGCACATGCAAGAGTGGCAGCAAGAGAGATGCCAGGCTCTTTTAAAGA
ACAGCTCTTTAAAACATGAACAGAACAAGACTCAAGGAGGGCATCAAGCCATTTATGAGAGATCT
GCCCCTATGGCCCAAACACTCCCCACTGTGCCCCCCCTCCAACATTGGGGATCACATTTCAACATG
AGATTTGGAGGAAACAGATATCCAAATTATATCATAAGTATTTATAATCTCTTCCCCCACATTTCTA
TTTAAGCTAGTTGTATAGCAATTTACATTATCTTTCAGATTATCCAAATGCCAAATGTTTTCTGAT
CCTAAAGTAACATGATGCATTTGCTGAAAAAAAGTTTAAGATATATTCAAGCCAGCAAGACATGA
AGATTTAGAGCTCATCACAGAAGCTTGGTCTCTTTTCCTTTTGTTCCTGGTTTTCTCCTTATGTGAA
CATTCAGAAAGAAAACCCAAGCTTCTAAAAAATGGCAAGGAGCTCAGTATCTACCACCCTAGAAG
AAGGTCCCTGGAAATCAAGAATCAGGTAGCAGATTTCTTCTCCTATGAACATTCTTGGGGAAACCT
ACTTAGGCTATGGGTTCTGACTTCTTTCAAGTACTTCCTCTGATCTTGCGGAAGTACTATGGATGGG
TATAGGCAAACCCCAAAAAGTCCCCAGAAAGAGTTTTAGTAGAGAAACTAGGTGATTAGGAGTGC
CACTACTTTGTGCAAAAGAGGGAAAATTCCCCATGCTCATGCCTCTTAAATGGCTGAGAGATTTCTG
TGGCCTGGTATTACACACCAGGCCAAAGTAGTCACTGGGACACCCATTGGTCAGTTACTGTGTCTC
CAAGGGACACAGAGCATCTTGCCCAGTGTCATCATTATGTGAGCTTGGCCTGCCTCCTGGACTCAG
TGAACCTGTTTTCTCACCTCCCAAAAATAAAAGCAAAACACACCTACAATTTCAGAGCATGTGAA
AAATGGATCTAATCATCACATTCATAGGGACAATGGTAGAATTTATTAATGTTCCTACAGTTTTCCT
```

-continued

| Sequence Information |
|---|
| TTAAAGTGTTTTGAGATTAGAAACAAAACATTATATGCAATATTTGAGAGGAAAAACCACAAAAT |
| AATAAAATTTTGTATTCAGTATCTCAGTTGTGTAAAAATAATATAGACATTAAAACAGGATTAGAG |
| GCCAGGCGTGTTGGCTCACGCCTGTAATCCCAGCACTTTGGGAGGCCGAGGCGGGCGGATCATGA |
| GGTCAAGAGATCGAGACCATCCTGGCCAACATGGTGAAACCCTGCCTCTACTAAAAATACAAAAA |
| TTAGCTGGGCATGGTGGCACACATCTGTAGTCCCAGCTACTCAGGAGGCTGAGGCAGGAGAATGG |
| CGTGAACCCGGAAGGCAGAGCTTGCAGTAAGCCGAGATCACGCCACTGCACTCCAGCCTGGGTGA |
| CAGAGCAAGACTCCGTCTCAAAAAACAAACAAACGAAGAAAAAAACAGGATTAGAAAGAGAATA |
| CCAAATTGTTATAATGGTCAGTTAGCTTTAGAGGGTGAGATTATGTATAATTTTTAGTATCGTTTTT |
| ATTCAATTCAGTGTACCTATTACTTTTGCAACTAAATTTTTGAAAAAGAACAAAGAAAAAAGGCAA |
| CAAAGCAACACTGATCAGGCTGAAGGTCTCCTGGGCCTAAACCTCCCAACCACCAAGAGTGTCAA |
| AATCTCTGTTCAGGGACTTGGGTCTGTAGTTAATTGTTGGATGTTTTTATGTGGTATAAATCTGTGT |
| ACTGCCTTGATGACAGTAATAAACTAGAGTGTCTTGATAAAGACCAAAGTCATCAATTTTCCAAAA |
| TCTGTATTTGATTAATTCTCCAAAGGTCCAGGTCAATGTTATTCCTCAAACTTTATTATTTTAACAT |
| AGAAGCCCAAAGTTTCCAAGTCTGTCAGAAAATTCATTATCACTGTAAAACAGCAAAGGTCACA |
| AAATGTCTCTTTCTACAATAAAATAGCATATAAGAAAAAATCTCTTTTTCTCAACAATTCATTACCC |
| CAACAGAAACCAAAAAACCTTTGACATTTCAGGTCTTTTTGCTTCAGGGGAAATAAATGTTCCATA |
| GATCATGGAGAAAATGACAAACAAATTAATGAAAAACAAATACACTCCTGCAGTATCCCCAGCC |
| ACGCCAGACCAAACAAGTCAGAGTCAGCTTTTATTCTTGGGTCTTTCCAACTCTGAAGAGTGACAG |
| TTTCCATAATGGCATCAGCAGTTTAGTTAGAGAAAGCTGTACACACACCAAAGAAACACAAATTA |
| AAGAAACATGTGGTAGAAAAACAGAAAGAGGAATTCTGTTATTTCATGCATATTTAATTCTAGTGG |
| GAAAGTCATTGCTGGCAAAGTGTTATTGAAATCTTGAGCTAATAAGTAGAAGCATTCTAGAAGAT |
| ATGCACCGCCTCCTCATAGTGCTTTATACAAAATTGTAACTTGACTGAATTTAGCAGTGCTCAATTT |
| TCCCACATTCTAAAAATTCCTTCCTTGAATTCTGCCTCACTCTCACCACTAAACCTTGTCAGAAGTA |
| GTTTGCATGTGCTTTCTCCATATCTTCAATTTCCATTCATTTTACTAATTTTAACACCAAATACATTTC |
| CATTTTCATTATTTGTTTAAACACAGCCATACAAATAAAACCAAATTGGCCAGTGCAGTGGCTC |
| ACGCCTGTAATCCCAGCACTTTGGGAGGCTGAGGTGGGTGGATCATCTGAGGTCAGGAGTTCGAG |
| ACCAACCTGGCTGACATGGTGAAACTCTGTCTCTACTAAAATTACAAAAAAATTAGCTGGGCGTGC |
| TGGTGGATGCCTGTAATCCCAGCTACTCAGGAGGCTGAGGCAGGAGAATAGCTTGAACCCGGGAG |
| GCAGAGGTTGCAGTGAGCTGAGATCACGCTATTGCACTCTAGCCTGGGTGACAAGAGCAAAACTC |
| CGTCTCAGATAAATAAATAAATAAAACAAAACAAAGTTCACTATGACCCTTATTCCCTGTCCCCCT |
| CCACAGAGGTGACCACTGCTAACAGTTTTGACTTTATAGACCACTTTAGATGTGCTTATGTATACA |
| ATATGATTTATGGAGCAGTGGTGTGTACAATACTTTTTTTTTTTACATAGATAATATCATATAAA |
| ATGTTGTGGGGTTTTTTTTTGCCACATACTTTTTTCTGTCAATGATCTGTCTTGGAGATCTTTCCAG |
| ATCCGTAAGTATAAATCAGTGGTTTTCAACCAGGGGCTAGTGAGCCCCCAGGGGAGATTTGGCA |
| ATTTTTGCAGGCATTTTTGGTGGTCACGACCTGAGTGGGGAATGCTATTGGCATCTAGTAGGTAGA |
| AGTCAGGGATGTACTAAACATCCCACAATGCACAGAACAGCCCTATGACAAAGAGTTTTCCACCT |
| GAAATGTCAATAATGCTGAGGCTGAGAAACCCTGATAAAGGTCTACTTTATTCTTTTAACTGCTGC |
| ATGGTATTCTGTAGTTTATTTAGCCAGTCATGTAGCAGTGTATATTTACATGATTTTTTTTTCTTTTT |
| TGAGTTGGAGTCTTGCTCTGTTGCCCAGGCTGGAGTGCAGTGGTGCGATTTCGACTCACTGCAACC |
| TCTACCTCCCGGGTTCAAGCGATTCTCCTGCCTCAGCCTCCCGAGTAGGTGGGACTATAGGCGTCC |
| ACCACCACACCCAGCTAATTTCTGTATTTTTAGTAGAGACTTTTAAAAACATGTTTATTTGTAGATA |
| TCAGTGAATGTTTCTTCCATTTACTTTTGACCCAACTGCAATCAACCTTGTTTCCTAAATATCCCTA |
| AATCCATTGCTACTGCTTTAACAAAATACCACAGACTGGGTAATTTATAAATAATAAACTTTATT |
| TCTCACAGTTCTGGAGGCTGGGAAGTCTAAGACTGAGGTGCCGGCAGATTTGGTGTCTGGTGAGG |
| GCTCCTTTCTGCTTCCAAGATGGTGCCCTGTGGCTGCATCTTCCAGAGGAGAAACATTGAGTCC |
| TCACGTGGCAGAAGGGACAAAAGGGGAAAAGGGAAGAACTCTCTTCCTCAGGTTCTTGGATAAAG |
| GCACTAATCCTATCCATGAGGGTGGAGCCCCCAGGGCCTAATCACTTCCCAATGGCCCCACCTCTT |
| AATGCCATCACCTTGGGGGTTCCAACATATGGATTTTGGAGCAACAAACCATAGCAGCCCCCTGCA |
| GGTGACCAGTGGGTTTTCTGAATCCCTTGGCTCCTTTTCAGCATGAGCTGACTTGGCCCTTCTGTGC |
| CATTTGCCAGTGCTTGTCCTAAAGCACTTTGGCCTCCCAGGCCCCTTGGCTCTGCCTTTTTCCTCTCT |
| ACCTCTGTGGCCCCCTTCAGTCTCTGTGGCTCTGCCATCTCCTGAGCTCTTGCTGTCACAGTGCTAG |
| GCATTAGGGATATGAAGACGAACTGTGGAAGGTCCCAGCCCTGGAGACCCTCCAGTCTAGAAGAC |
| AAGCACATACACAAATCTCCCAAAGGGAAGCATCACCTAGTCAGGGCACATTTGAAGTGTGCTGA |
| GTGATTGAATAAATAACTAAATATAGTAGATTTTAGAGGACAGTGGGAAATGTTTTTCCTTCATGA |
| TTCAGAATTTACTGCATATTTTATCTTCATGACACCTTTTCTCACAACATACGTTTTGAAAAAAAT |
| AAGTCACGAAAAAGACTTTCCTCATATTTTCCCACCCACAGTCTTTTTGTCTGCCTTGAAACAGCAA |
| CTGCATTGTTTCACATACAGGGAATGCACTTGGTCTTTGCCAAGGCAGAGAACAGATCAAATTTGA |
| GAAGCAGCCCTGCTTGCTGCTGGCTGAGGGATGGGAAGTGAGGTTGGCCCTCGGAGCTTCCTTCCC |
| CTACCCTTTCTTTCAACCTCCTCATGATGGTAGGACCATCACCTCCCAGCAGCCCCTTCCTTACTCC |
| TGTGGGGAGATTTCAGAAGCAGACTGAGTGGCAACTGCCGCCTGGCCCTTTTCTCCCTGGATCAAG |
| GGATCTTAAGCACCTACCTGAAACCTAACAGCAAAGGAAATCTCAACTATAAATCTAACTCCATGC |
| AGAAATTAAACTCCTTCAACGGGTATTCACTGCTCACTGTGCAGGCCCCAGGGAAGTGTAAAGATC |
| AATGGGACATGGCCTCTGCCCCTAAGGAGCCAGAGAGGGCCAGGGCAAGGGTGGGAGGGGGCAT |
| CTATAAACAACTGCTTGCAATGCAAAACAGAATCAAGTTAGTCCTAAAAAGAGGATTGAGCAAGG |
| TTGCTTAAGGAGAAAGGAAGGATTCATTATGATAGGAGATCAAGCAAGACACTTGAAAAGCATGT |
| CCCTTCTGGTAGCGGGCGCCTGAAGTCCCAGCTACTCAAGAGGCTGAGGCAGGAGAATGGCATGG |
| ACCCAGGAGGCGGAGCTTGCAGTGAGCCGAGATTGAGATCACGCCACTGCACTCCAGCCTGGGCG |
| ACAGAGCGAGACTCTGTCTCAAAAAAAAAAAAAAAAAAAAAAAAAAAAAAAGAGCTTTATTTTA |
| TGGGTTCTTTCCATTTAAACCCAAGGAAAGTGGGGTTTCTGAAAGAAGAAATGAAATGCGAACCG |
| TGCAAGATTCTAGATGGCCATTCTGCTGAGCACCATGTAGTTTGGGTAAAGCCCTGAACCTTACAA |
| ATGGGAGTTTTTATCTCAGATATGTATCTCAGATGCAGGACTTTTATCTCAGATATAACTAAGAGT |
| ATCCAAGATTGCAGCTGTCTCGGCCCTAGATGCTCAAGCCTGTGCAGCCTTAGTTGTATATCAGAG |
| ATCTACAGAGATCTTAGTTGTGTATCAGAGATCTACAGAGATCTTAGTTGTGTATCAGAGATCTAC |
| AGAGATCTTAGTTGTGTATCAGAGATCTACAGAGATCTTAGCTGTATATCAGAGATCCACAGAGAT |
| CTTAATTGTATATCAGAGATCTTTCTTTGGGGGGCGGCACAGGGGGACGGAGTCTTGCTCTGTCAC |
| CCAGGCTGGAGTGCAGTGGTGTGATCTTGGTTCACTGCAACCTCTGTCTCCTGGGTTCAAGTCATTC |
| TCCTACCTCAGCCAGCTGAGTAGCTGGGACCACAGGTACGTGCTGCCATGCCCAGCTAATTTTTTT |

```
GTATTTTTAGTAGAGACGAGGATTTACCATGTTGGCCAGGCTGGTCTTGAACTCCTGACCTCAAGT
GATCCACCTGCCTTGGCCTCCCAAAGTGTTGGGATTACAGATGTAAGCCACTGTGCCCAGCCCTTA
GTTGTATATCAGAGACATTTTTTGTTTTGTTTTTTTGGGTTTTTTGAGGCAGAGTCTCGCTGTCACTC
TGTTGCCCAGGCTGGAGTACAGTGGCGTACTCTCAGCTCGCTGCAACCCTTGCCTCCCAGGTTCAG
GAGATTCTCCTGCCTCAGCCTCCTGAGTAGCTGGGAGTACAGGCATATGGCACCACACCCAGCTAA
TTCTTGTATTTTTAGTAGAGAGGTGGTTTCACCATATTGGTCAGGCTGGTCTCGGACTCCTGACCTT
AGGTGATTCACCCCTCTTGGCCTCCCAAAGTGCTGGGAGTACAGGTGTGAGCCACCGCGCCCGGCC
TATCAGAGATCTTAATTTGATTTATTTCTGTTCAAATCAGATCTGACTCTTAAAGGCACCCATTTAT
TGCCCCAGACCTGACTGTAGATATTCTGCAGGATCTACACATACTTTTATCTTTATTTATATTTCTA
TTTGCTTATGTTGAAGCCGAGTGGGTCCTGGGAACATAAAGGATATAGCTCAAGGATAGAGGCTTT
TACCATAAATTGCCAAAGCTCACCTAGAGAAAGAACAGAGAGGAAGCTGTGAAGGATGTGTGGGT
TTGGGGAGGGAAGCATAAACCAGAGAGAGTGAAGCAGTTGGATTATTGGTCAGTGAACAAGGAC
AACAGTGGTCACCATAGCTGTTGTTATTTTGTGCCTACTAATGATCATTCTTTATCTCTCCCAGTAG
AGAACTGATTGAACTGAAGTCCGGAAGACAAGGAGGGTACTGCTACAGAAGGGCCCAGAGGGCT
GCTGCATTTATTTCCTATCGCTGTATAGCAAATTACCACAAATTTAGCAGCTTAAAATAACACCTGT
TTACTACCTCACAGTTCTGTAGGTCTGAAGGCTGGGCAGGCTCAACTGGGTTCTCTGCTTAGGGTC
TCAGAGGGCTGAATTCAAGGTGTCAGTCAGGTTGGGCTCTTACCTGGAGGCTTTGCAGAAGAACCT
TCTTCCAAGCTTGCTCAGGTTGTTGGCAGAATTCAGTTGCTGTGGTTGTAGGACTGAAGTCCCTGTT
GTCTCCGCAAGGACTACCCTCAGCTTCTCAAGTTCTTGTCCCATTGACCCTTTCATGGTAAAGTCAG
CAATGGAGAAGCTTCCTCTTGTTGAATCCCTCTCACAATTAGAATCTCTCAACTGTAACAAGAATC
TCGCTTCTGTAACAAGCTGGAGAAAATTCCCTACTTTTAAAAGGCTCATGTGATTAGGTTAGGCCC
ATGCAGATGCTCTCTGATTAGTAACCTTAATGGCATCTGCAGAATTCCTTTTCCCACCAAACATAA
CATAATCTCAGGAGTAACACCAGGGGGTGAAGACCATGGAGCCCTTGGTTCCACCTGACCTTGGA
ATGACACCTGGAAATCAGGGTTCAGGGACCAGAAATCTGTGACTGAGGGTGGGGCTGGGGAGTG
ACACACAGAAGGGAAATATTCTCCGGGAGCCAAACAGAGAAGGACTTTTGGAGGCAGAATTTGCT
GACAGAGCTAATCAAGCCCCCTTAATCAGTAAGAGTCTTTGTTGAGCACCTTCTTTTCTAGGCCCT
GTTAGGCACTAGAATAATGAAGGAGACAGTCCTTGCCCTTTAGGAATTCACAGTCTAGTGAGATTG
TAAGAAATCTCCTGGACTAGAAATGCAGTCCTGATACAACCGTACCCTGAGAAATCTGTATATCTT
CAGGAAAGTCATTTTGTGTGTTTTACAGACTGGCCTGAGTGCTCGCTGCTGTTGTAGCTACCACCA
ACTTTCTACTGAAGATGATAACCCAGGGCATAAGAAATGACTTCAGACCCAAGGTTCTGAAAGGG
CCCCTCAAGGCCTCGGGTGGCTCCTGCAGAAGTGGCAGAAGAGGCGGGAACTAGGAACCTGGCAT
CATAGGAAAAGTGCCTTCTCCAAGAAAGAAGGGGCCCCAGGAGGCTGTCTTACTTAGATCAACCA
TAAACTACCACAGATGGGTCATTTCTTATATTATTTCAAAATATCTTTGAAGATGAGAATTCATTTG
TGTCCTTCATAGACCAAAGTTCTTTGTGTTACCTTTTCCCAAAAGTAAATTCCTTTCCCTTTATTCAT
TCCTTGTGGAAATAAAATGCAAGCCCTTTATACTTGTCTTACAGTAATATGGCACATGTAGCTTACT
TTTGAGCATCCCAGTGAATAATGTTTGGAACTTTTCTTATTAGCATACATATAGAAGAGTG
AAGTCAGCTAAAACAGAAATTTTGAAAAGCCATCTTCAGGAAAATGTAGGCCCAGATGCTTTCC
TCCACCTTTTTTGACAGGCTGCCACATACAGTTTCACAGGTTGCTAACTGCACAGGGGCACAGCCT
GTCCTCCATTTGCCAAGTCACACTTTCTGGCACAGAGAGGGGTGTCTTGTTCTAATTTGTCTTTGTG
GCCTGCTCTCTTCTGTTCTTGAAGCTGCAAGCCACAGTGAGATGAGTGAAAAGCAGTCAGTCTCAT
AGAAAAAAGCAGGGAAAAAGCAATAGAGACAAGAAGGAAAGCCAAGGAAAGGATTCTTGGGGA
AGGTCAACAGGGAAGGGTGGAGAAGGGGAAAGGAGATGACCATTATGATCTTCTAATTAGGAGTT
TAGGGGAGATCGTTTGCCTTATTCAGCAACCATGCGACTAGAAAATAAGCAATCTCTTTAAAATAA
TGCTTTACTACAGTCAACTTCAATAATCTTTTCGATAATTGGGTTGTGATTAAACTTACAGGCACAA
GACTAAATAATCCCAACGCCTTTAACTTTGCACATTGTTTTTTGTTTGTTTGGTTGGTTTTGTTTT
TAGTTTGGGGTTTTTTTTACTTTGTGTGCCCTTATATATTCAACAAATACTTCTTGGTACCCATTCTA
TTCATAGCACTCTCTTAGTCCTTGTATACAGGGGTCCTCAATCCTTGATGTGAATTAAAGTCACCTG
GGCAGCATGCTGAAAATGCAGCTTCCTAGGCCCTCCCTTCATGCAGCTTCAGGATCTCTCAGCTAT
ATTTTGATCAAACATCCAAGGAATTTCTGGTGATTCAAGGACCACACTTTGAGGAAGCTTGCTGTA
GACATGGAAAGCATATAATCCATAGTTCTTTGTCCTGTAAGACCGTATAACTGAGTTAGGGAACAG
GAGGTAGACATACATAAAGATAACGAACAACACCCAACAGTGGGTGCTACAGAAGCAAGTGAGT
AACAGAGAAAATGATGAACCAGTGACATATTAGGTGGGAAGAGGAAGAATGTTCCTACATGGAAT
TCCCTGAAGACTTCAAAAAAAAGAGTGGGCCTTTAAAAGAGAGGAGGACCATTTCAGTTGGGAA
AAATATGTAAATAAAGGCGCAGTAGCTTTATGTGGTGAGAGACTTAGGGAAAGACTGACTCAACA
TCTCTTGGCTTCATGATGATCCTTTTTGACCCACAGGTTCTTTCTCCTTTCTTATTAGGTTGCTTTTA
AGACTATTTCATAAGGGATCGCAGATGTGCATGTAAAAAGAGATTAATCACTATTGAAATGTATGT
GCTGACTGATTTGTGTGTTACACTATTGAAAAACTGTATAGACTCCAAATGGCATCTGATTATTAA
ATTCAGATGCCAGAGTCTTTGATTAACAGCATGTCTTTTTGCTCTGTATATTTCCTTCAGAAGTAG
CAGGGCTTGCAGACATCTCAAGCTATGCCACAGAAGAGTCAAACAGAGGAAGTGGTCATGAAATT
AAATGTGAAGACAGTCTATTAACTTTTGCAATACAGAACCTTTGTTTACTCATAAAATCCATATTTG
GAGCTCATTCTTTCCAAATGGATTATTATCTAAGTGTTTTTATTGGAGACTGTTTGGTACTTGTGTT
TATAGTTCTTTTTCTTTCACTCAAACAATTTTGTATATTAGAAAACAATTTCAGCAAATATTTTATG
TTTAAAAAATCAGAAGAAAATGAAGATGACCCTCTCTTTTGCCAGTACTCATAATAAATACAAAT
GAGAAGAGATTTTTATAGTACTGCATGACTCTATTATCTGGAGTACAAATCACTGCTTTTTTTTTG
TTTTGTGAGACAGGGTCTCCCTCTGTCCTCCAGGATGAGCACAAAGGCATCCTCTCGGCTCACTGC
AGCCTTGAGCTCCCTGGCTCAAGTGATCCTCCCACCTCAGCCTCCTGAATAGCTGGGACCACAGGC
ATGTGCTACCATGCCCAACTAATTTTTATTTTTTGTAGAGATGGGGACTCACTTTGCTGCCCAGGC
TGGTCTTGAATTCCTGGACTCAAGTAATCCTCCTACCTCAGCCTCACAAAGTGTTGGGATTACAGG
TGTGAGTCACTGTGCCTGGCCTTGCATTTTTTAAAGTGATAAGTAAATGCTATATGACTTCAGGT
AGAGATTATATCTCATGTTTAATTTGTATAACTGCATAAGTAGAAAAACTGTTCATGAAAATATAT
TGGCTGGGCGTGGTGGATCACACCTGTAAACTCAGCACTTTGGGAGGCTGAGGTGGGTGGATCTCC
TGAGGTCAGGAGTTCAAGACTAGCCTGGCCAACATGGAGAAACCCCATCTCTACTAAAAATACAA
AAATTAGCCGGTGTGGTGGCACATGCCTGTAATCCCAGCTACCTGGGAGGCTGAGGCAGGAGAAT
CACTTGAACCCGGGAGGCAGAGGTTGCAGTGAGCCGAGATTGCACCACTGCACTCCAGCCTGGGT
GACAGAGCAAGAGAAAAAAAAGAAAGGAAGGAAGGAAGAAATTTACTTATTCCATCTCTGTA
CACATAATTTGTAAACTTTTTTATCATCAATTATTATTATAAATTTTTTGAGACAGGGTCTCACTGT
GTTGCCCAGGCTGGAGCGTAGTGGTGTGAGCACGGCTCACTGCAGCCTCGATCACCTGGGCTCCAG
```

| Sequence Information |
|---|
| CAATCCTCCCATATCAGCCTCCTGAGTAACTGAGACTATAGGCACATGCCACCATGCCCGGTTAAT |
| TTTTGTATTTTGTAGAGACAGGGTTTCGCCATGTTACCCAGGCTGGTCTTGAACTCCTGAGCTCAAG |
| CAATCCACCTGCCTCAGCCTCCCAAAGTGCTGGGATTACAGGCATGAGCCACCACATCAGCCCATC |
| AATTATTATTAAACTCATGTGTACCAGTACAATTTCAAGCCCTCTAAGCTGCATTTAATGCTAAATT |
| GTGATATCATGTGTGTGTGTGTGTGTGTGTGTGTGTGTGTTTGAACAGAATGTTCATAT |
| GACTTCATTTCTATAATAATGTGATAATACAAATATTTGGGGTCATTTTAATCGTATTAGCATTTAT |
| CTTTACCAAATTGATTTGATTGTTGTGTAGCCACTTCTCATCTGTTACATATACACGTTTTACATATC |
| ATTCAAACTTGAAATTTCCTTAAACAACTTTCCCAGCCTGGTTTCGGATGATTGCTTGTTGAGACTT |
| TGTCCATGCTCTGTCCTCCCCTCCCCACTGTAAATACTCTTCTTTTGGGCTAGGGGGCTGTGCCCTC |
| CAGGGTATTGTTTTCCTTCCTGTTCAGTGCCCATGCTCTTGCCTGTGTTTCTCCTGTACCTTTCCCAG |
| GACCTAGCAGACAGCCGAGCACCTGCCCACTGCTCTGTAAATACTGACCTGCATCTCAAGTGGGGT |
| AGCCTTTGTGTACTTTCCCATTTCCAAGTTGATTTGCCTGTGAATCCCATATGTGAACACATATGCA |
| GATGTCCCTGATGTGCTCTTTCCTGCTTGGAGGCACATGCAAGGATGTGGCACTTTTTCTAATTGCT |
| TGAACAGTCAAGTGGATCTCTCTTAGGCAGCACTTGGCCAAAAATTCTGAATATTTAATCACTGGT |
| ACAGGATTAGTTCAGTTGGCCAAAAAGAAAAAAAAAATGTATGGATGAAATGTGAATACACTGTT |
| AACTTTTTCATCTGCCTTTATAATTAGTGTTTTTTCAATATTAAGTTTCTGCTTTTTATACTGAGTTTT |
| TAGGGAAAAAATATGGGAAGGATTCCATATTCATTGCTTCACACGATCTATAGTTCCTGAGATAAC |
| TATATAATTATGAATGTTGATACACCCATAAGAGACTTTGCTTTTTCCTCTCACACATCTGTTTTGC |
| TTTAGGCAAGAGAACTTTCTCATGCCAGAATGGCTGCAGTGGATGTAGGCAATCTGCTTTATGTTG |
| AGCCGCTACAATTCACAGATGCAAATGTTTAAAAGGTTAACATGGTTTATTTCTTCATCTGAAACAA |
| ACGTCCCTAGTCACTACTTTTGTCCTTTAAAAAAAATTGTATTCTTTTATAAATCCATTGTGTGTAA |
| TCCTTATACCCTTGTCTCATAATCCTCATATCAGAGCTGAATTAACTCTTTTGTGGCCTCCTGTGAT |
| GAATTTCAGTTGTCCTACTAGTTTCTCTTGCTGGTGTGATTGTGTCCTCTTGATGGAATTTAGGTTCT |
| TAGGGAGAGAATGAGGGAAGCAGCTTCTCTACCCAGAACAGAATCCCACTAACCGAAAGAATGCT |
| GCCCTGCAAAAAAGTTTCTAGTGTATCCATGTGTGATCTCAATTATTTAATCAACAAACATTCCAG |
| AGCATCCATTGTTTCACTGTACTAGGGAAATGGGGGCAAGACCAGGATAGTATACGGAGGCTAACC |
| TCAGCAACTGCAGTCCAGTTGGAAAGATGAAACCTAACATGATGATAGGATGGCAGCGGGTTGTG |
| AGTGTCAAACGCATGCTTCTGTACTGCGCTCCTGCTGCCTCCAAAAGCAGGGGGAGCCTTCAGTTC |
| ATCACACCTACAGCTCTGGACATTTTTTCATGTTGTTAAATTAATCTAACATTGTAGGATCTGAATT |
| TTCTATAGAAACTTTACCTAACTTTTCTTGTATTGCTAATTTGTTGTATTGAGTAAGCCTTCTGTGTA |
| GAAAACAGTTTAACTATGTTAACAACACTATGTCAAAGATTCAAAGCCTTTGAGAGCTTAGGAGA |
| AATCCAACCCCAGTCATTTTCTGACACAACTGAACACAGTACTCTGTGGTTGAAAGTTCCTGAAAC |
| TCCCAAAGCACAGGAAGGCTGACTACAGATCCTAAAGATGTTTAACTCACATAGTCCTTGGTGGCA |
| CTTACTGTTTGCAGCTGGAGGGCCTTGTATTTTCTTAAAATGCATCCTAAATAAAAACTCAAAAGC |
| CATTCAATGCTAATTCAAGTTTCATGGTTAAAGGCGCAGCTTTGCTGGCATCTAGAATTAGAACCG |
| TGTGGTGTGTCCCCAGAAAACGAGCTCTCATGGCAAAAACAGACAAACTCTACCCCCTGCCAAA |
| CTAACTGTCAGCAGAAATCTGGTCTGCTTTCTGAAATGGGATGTAGGTTTCCAAATTCTCTAGACA |
| ATCTCTTTCCAAAGCAAAGGAGAAACAAATAACTCACAGGCACCAACTGCATTTTCTGTTCAAAGC |
| AAGAAGGGTTTTCACTGTGCTGTTTTTACCTGTCATTTCACAACTCAGTTCTCTCTGGAGCACTTGT |
| ACCAAGGGTACAAGAAAGTCATGAGATCAGAGAGCTGGTTTTGGACATGCACTTAATCACTCCCA |
| TCCTTATTTCCCCTGCTTCCCTGATGCCCCTGAATAGCAGGCTCTGTCCCCGAAAGAGAAATGAGA |
| GTTAAAGAAATGACCACTTAACCTTTTCCTTTGGTAGGGAGGTTCTAGGAGGCCAGTGAAGCTTGC |
| GGGGGTCGGGAAATTTGAGAAGTGAATGGAGATTAGGAGAACAGAGTTTGCTCCAGATGAGCTTT |
| GGAGCTGTGCCTTTTCTTCTGGAACTCACTACCGGATCAAGGGGTCTAGTGGGGTGCCCACCACAC |
| TGGCCACCAGACCAGGCTTGATGGAAAGGGCCCAGAGATGGGTCCTGCTTGTGCAGTCTACAACT |
| GCCAGCATCAGCTGCCCCCTATTCCTCTCTGTGGCCCATGGTCAGCCAGAATCAGAGGGCCAAAGC |
| AATGGGCCTGTAGCTTGAGAAGCATGTCAGCAGGCTGGGGTTCAAGGCCAGGCCTACAGGCCCGC |
| AGTGGAGAGGGCAAGGCTGGCTCCAGGTCCGATGGGCAGGTTGCCAGGACGTGATTTTCAGAGCA |
| GGAAAGTGGAGTGAAGCGTGACTGGCAGTGAGTGTGAGCAGACAGCTGCAGAGTCGTCTCTGCCT |
| AGTGTTAGGCCTGGCCGCAGGCTCTGGCGGCCCTCAGCCTGACCGTAGGATGGGTCTCCCAGCTTC |
| AGCTGAAGGCAAGAAGTGCCGCTGACTTGGGGAGCTGAGCCAGACCTGGTCCTGCCCTCCTCCCT |
| GAACGTGCTCCAGGATCATCTGTCTGCCTGTTGTTCCTCACTCTTTTTAGCTCTCCACGGGGCTGGC |
| CTTTGTTGTAGACAGAAGAGAGGCACTGTGTTATGTGCCAGAAGCTCTGTCACAAGACACCTAC |
| ACCACCAATGTGCTGCCGTGCTTTTCCTCATGCTGTTCCCGTTGCCCAAGTGACCTTTCCTGCCTTT |
| CTGTGCCTGGTAAAATCGGCTTGTTCTTTGAGATCCAGTTCAAATGTAAGCTTCCTTGGCAAGTCC |
| TTCCCAGCCGCTCTGACCACCACCTTTCCTGGCAGGATTGCATACTGATTGCAACCCCCTCGGTGCC |
| CGCTCAGCGTGTTCTATGCACCTGTAGCTCTAGCCCATTATGATAGAGTTTATTTTATTCACATTCTTT |
| GTTAGATGCTGAATCTGTCCAAGACAGGGACCTGGACATCTGTCCATTCATCTCTGTATCCCTCCC |
| AGCACAGTGGCTGAAACACAGTTTGTCATTTATACATGTCTGTTTTGCAAATCCGTTATCTGAGAT |
| GAAAGCCTGTAGATTTCATTAACATCTTAGCTCTGACTAGTTGAGAAATCAAAAGTAGGGCACATG |
| GCACAGCTAACACATATTGGCGTCTTGCTGTGTGCTGCCCTAGACACCCCGTGTCCAGCAAAAAGT |
| CACACATCGTTGACCCGAGCAGAGGGAGCCCAGGGGGCCATCCTGTGTCCCTCCCAGCATCACTGC |
| AAACAGGGTGGGGGCACCAGTGGAGGCAGGAGCGCTGACCTGTCTTGAAGGCTGAGAGTAAGAT |
| GGGTCCCTTGTGGCCTTCAAAAGTATTTGGACTTCTGAAGCTGCCTGTGGCTCCGGAAATTAGGGA |
| AATGCTTTAGTGGGAGTGCTTCTGTGTGCGGGGAGGTGTAAGTGCAACATGAACTGAATCTCACTC |
| CACCCAGTACAGGATGCCCGGAGAGCATGCTGAGCTACCCTGTGCCAGCTACGTGCTCTAGAA |
| CAGCATCCTCCCAGCCACCCAGGAGGTCATGCAGGCCTCGTCATCAGAAAAGTGGCTTAAAAACC |
| ATGTGGAGTCAGACCATTTGAACACTAACTAGAAATGGGAGGCTATTAGGGAATTATTGTGAATG |
| TTCTAGGAAACATTGCTCATCTTTGCACATTAAATTCCTACTAATATAATAGTATCATGATTATGAG |
| GGGTTTATTTTTTAAGGATCCTTGTCTTTTAGGGATATATGCCAAAATATTTACCGATGAAATATG |
| ATGGTTGGAATTTGCTTGGAAATAATATGGGGAGGAGGGGGTGGGAGGTAAAGATAAAGAAAATT |
| GGCCACAAGTTGATGATTGTTGGGTACATGGTGTTTATTATGATGCTCAGTCTACTTCTGTGCATGT |
| TTGACATTTTTCATGGCAAGGTGTTTTTTTTTTTTTTTTTTTTTGAGACGGAGTCTCGCTCTGT |
| CGCCCAGGCTGGAGTGCAGTGGCGGGATCTCGGCTCACTGCAAGCTCCGCCTCCCGGGTTCACGCC |
| ATTCTCCTGCCTCAGCCTCCCAAGTAGCTGGGACTACAGGCGCCCGCCACTACGCCCGGCTAATTT |
| TTTGTATTTTTAGTAGAGACGGGGTTTCACCGTTTTAGCCGGGATGGTCTCGATCTCCTGACCTCGT |
| GATCCGCCCGCCTCGGCCTCCCAAAGTGCTGGGATTACAGGCGTGAGCCACCGCGCCCGGCCTATG |

-continued

| Sequence Information |
|---|
| TTTTTTAAGTATTTGAGAGATTAAGGGGAAACAGTATTTTGTTCTCATCCCCTCGTTTCTTGGATTT |
| GCTTTATTGTCCCTTTTCCTCACCCCTGGTTACCTCTGAGGATCTCCTAGTTAGAGAAGAGGGTCCA |
| AATTGTTGTTCTATCTACCCTTTTGGTACCTTCTTAAAAGGCCTTCCCTTAAGGTTCCCCAAATATG |
| TTTAAAAGTCTTTGGAAATTAGGTGCATTTCCTCCCATTGGCTCAGGAAGGGGTGGGGAGCAGCAT |
| ATGGTACTGGAAACCAGGCTCCCTTGAAGTGCTCCTTGCCCGGGCTTAGGCTCTGTTGAGGTGAAT |
| CACTTGCCTCCCTCCAATGAGGAGTATGCTTTCCTGAGGTTGTAGAAGAGAAATGTGCCATTTTCA |
| CTGTGCCTGTACCCAAGGGAGCCAGAATGGGAGCATTTTAAAAGAAAGACACTTTCATATGACTA |
| AATCAACCTGGAAGCCAACTGATGAAGATGTGCTATCTGATAGAGCTTGGGGACCACCAACCAAC |
| TGGGAACATAAAATGTGGAGGGCAGGCTTGGCCCTGGATTATTGACTCTCTCAAATGTTTCTATTA |
| TGTCTCACTCTTAAGGAGGGAGACTAGAAGCTCTTAAGTCCAGTAGCTTAACATTTTTCAGAGTGG |
| ATTTTTTTCTTGGCCTTATTTCTACCACCCTCGTGTTCCCAAAACACCCCTTCCATCACCACACCCA |
| ACACGGAATGCTCTGCACTCACTGTATTGTCCTCAGCCATTTCCCACCTTCATGGCCCAGCTTTCTG |
| CCAGTGCAGACCACAGATATGGTTGCAGGAAAGTGGAGAAAGAGTAGCTAATCGGAGGTGACAG |
| GGAGCGGAAGAGTAAGCATGGCGAGAGCATGCCAGCTGGTGGAGTCTTAAATGGAACTGTAGAGT |
| TCTTGGGGATGTCTGCCCATTTGAGGTAACCGTCTTGTCTAGCTTCCTGTCCACATGGCACATTCCG |
| GTGGTGTGACTTGAAGGAAGCTACCAAAACCATATTTATCACATTCCAGAGGCCAGAGGGCCTAT |
| GAGTAATCGTGAGTATGGAGACGATGAAGTTGGAATCCAGGAGAAGCTGATGGTGGAGCATAATG |
| AGGCAAATCTAATAGGCCAGAATGTCATCAGGTCAATGTAGAGTGCTGTGCGTGGGCCACCTGCA |
| AAGCGCAGGGTGAGGAGGAGTGACTGACAAGGAACTTAATAGGAGGCAACAGTGTGATGTGGCT |
| GCACAGACCTACAAATGCTTTAAAATCCAGTTGCATGGATACAGGAGGCTGAAAGCATCAATCCT |
| GTAATATATCCAGATGAGAAGTGCCAGTCCAGGAATCACATTTTGTTCCCTGTAAGTTTCTGAAGG |
| GGGCCATCTCAGTAAATGATGGTTGTTCATATGAAAGATATTATTATTTCTCTGATGGTATCTGATA |
| CTGCATGTTGCATGCAGAAGAAGATCTCTAAAGATCTTTACATATTAACAGCCTATGACATCCTTC |
| AGGTATACAGTTGTTACACATGCCAGGGGACACTGTGACTTTGTTATTGTTTTGTATTTTCTCTGCA |
| TTTGGGTTAATTTTGTTTGATTATTGTCATCCCTTTAGTTCCTAACTTACACACTAGGGTGTTAGAG |
| AGGAAGGTAATCCAGAACAGATTTTATAATAATAACAATAAAGGCCACCCTATTTTCTCTCTATTG |
| TATTGCTCAGTACTCATAGCGCATTAGTGCATTTAACGCTCACAGAAACCCAATGAAGGTAGGTGG |
| TAGTATTAGTCTCATTTTACAGAAAAGTAAAATATTAGAAAGTTAAGCAATTTGCCCCCAAGGCCG |
| CACAGCTAGAAAGCAACAAGGCAGGGACTCTGGGAGCCCAAGCTCACAGTGCCTCTCCCTGGTGT |
| TGCTTTTTCCACAGCAGTGAATAACTGCTCCCCTGAAGTGCTCCTTGCCTGGGGTTCGGCACCGCG |
| ACCAGTTCCACAGGCATCGTGTCTAAGTGTGACTGTGCCCCGGAACCCACAGAGCCACCCGGCTGC |
| TCAGTCGATGATAATCAAAAATTTTAAATTTGCTTCCATTGGACATTTCCTGCTCATCCAGCCACTTT |
| TCTTATCAGAAGACAAAGGCATGCTGACCATATGTTTATTATCATTCCTCCTCTTTCCTGCTTGTTTT |
| TCTAGTCAAGGTCAGAGAGGACCAGAAACACCCAGTGCTGAGAAGAGTGAGCCTTGCTTTCTCAG |
| AAATGGTTCCTACCTCTGTGGAAAGCAGTGAAAGAGCCTCCAGTAGCCTCTTCCTGGAGTGGTGGA |
| GGGTGGATAGAAGGAAAAACAATTAGAAGTAACAATAACGAATAGAAACAGAAAGACGTCTTTC |
| TTCCTAACAACCTCATTTTGTTTTCCTTCTAATCTTATTAAATTTTCACATACTTGGTATAAAATCAC |
| AACAGTTTAGGTTCTGATAATGTCTTATAGCTGCCTGTGTGCCTCGTTGGCTGACTTATGCTCTGAT |
| ATGTCCCTAATATGGCAGATTCTCCATACAGATAAGTGGAAAGTAACTCCTCCTACAGGTAAACTT |
| GATGGGACTGTAGGATTAAGCCTTTTGCTTGTTATGCGACTCAGCAATTATTAGGAAAAGGCTGGG |
| TGTTTTCAGCAGCCCCTGGGAAATGTGATTTATGACATGACAACGTTGGTTGGTCGGGGTCTCTGT |
| TTCACTCTCCAGTGTGCACTCATTTGAGTAAGTCTGTGAGGAACTTCCCACTTGTAAGAAACAGTA |
| TCTTGCGTGTTGCTATCACTAAACCCTGGAGGCCGGATGCTGTGTCCCTGCTAATGGTCTCTGGTTG |
| GCAAATATACATGTGACTCTTTCTGAGCAAAGTGCTATGTGTAATATGAAAGGAGCTTGAATGGGT |
| AGTCCCTGCCCTCAAGTGGCCTTGATTTTACAGGAGACTTGGCCATGGACCTCAAGATGCATGGAG |
| CACGGGGCAGCATTTGCCCATTCCCTCAGCGTGCACAGGTATAATGGCCACTGTCCGGGAGCTGGG |
| AGGTCAGAGGCCAATGACTGCAGCCAACCATACTGGGACAGAAAGGCCAGTCCCTACCAGGCTA |
| TCCACATTGGTTAAAATAGGAACCACCCATTTTTGTCTCCTCTCCAGGCTTTGAAAGCATTTGGGTA |
| ATTACAGCTTGCCTTTCTGCCTTTGGTTGTTAGTTTTAGTGTCTTAATTTATCTGCCATGTCAAAAGAT |
| TTCTCCTGATCCCTCTGAGCTCTCTCCCTTTTGCTCCTAGTGGTGTTTTCACCCTGCTTGATAAGTTA |
| GAATTGTACAGTGGTTTCCATTTCTTCTGTCATATAAACAGTAGGCAGTTCTCAACCTTCCCATCCT |
| CTCTAACTTACTCTCTACTTTTTTTCCTTAAGAGAGGCTTATGTGATGACATTGACCAAGTAAGTCC |
| TCTAACCTCAGTGATAGGGTGGTTCGGATGGGGTGGCAAGGAAAGGAAAAGGGAATTGAATCAGT |
| TTTGATTTTTTAAAAATCATGCTGAGCTGAAGTGAAACACTTTTTTTTTTCCACAAAAACTGAGTCT |
| GAAGGGATCTTTTTTTTTTTTTCATTCCACATTTTGGTTACATCTGCAGTGAGCAGTTGCAAATCCT |
| GAGAGACTTCTCTTCCCTGGCATTTGTTTCATTTTGCAAGAGTCTCACTGTGCCTGTGTCTTATGTG |
| AGCTCCTTGAAATGAAAGAACGTTAATGGCTGAAGACTGTTAGAGCCATTTGGGTGCCTGCTTATA |
| CCTTTCACTCAGCAGGACTGCCAGGGGCCCTGTCTGGCTCTGCCAGGTGCCCTCGGGTGGGAGAAT |
| AAGGGCACTGAAACAACAAATAGGCCCTTGACCAGACCTCCAGCTCCTTGCCTGCAGGGAATAGC |
| ACTGGAGTACAACGTCTAGTACAAAGTAGGTGTTCAATAAATAACCATCAAATGGGATAAAACCA |
| GTTCCTAGCCCAGCACAGGTGCAGGGTAGATGCTCAGTAAATATTTGTTGAAGAAACGAATACATT |
| ACTATATCCCATGGGGAAGACCTCTGGTCTTCATAGCACTTGCATCATTTGTAGCTCTGCAAGGG |
| CTCTGGGCTGGATCGACTAGGAAAGCAGCCTGAGCAGGGAAGCAGATGGCTGATCAAGCCCTCCA |
| GCCGAGGAGACCAGCACTGTTTCTGTGGGAACTTGGATGCCACTGACCTCACTCATGGAAGCTTGC |
| AAGAGTGGTGCAGGCCCAGTGGACCAAGGCCAGGGCTCTGTCTGCTCCCTTTGGCAGTCGGAAA |
| GCAGCACACACTTAGCTTTGCCAGGACCCAGCTTCAGCGGCCTTCATAGCCCAGTAATTACCTCGT |
| GATCAAGGGAGGGAGGGATGTGTGTAGAAATCACTTTTTAGTAGCACATATTTCTCTTGGAAAAGC |
| CCCAGTAAGCTGCCGACTTTCTCTCAAGTGTTCAAAGGATACCAGGGAACTGACGGGCTAATTTAA |
| TTGTATTAATACAAGAGGCGGCCGTCCCTAGTGCAGAGGGGAGTGCGTTAGGGAGAATTGTCTGT |
| CGGGAGGCTGGAGTTCCAGCTTCAACATGGAAGTGAAAACACTCTCCAGGAAAGCAGACGAGTCC |
| CACTGGGGAGGAAACTGACTCTCTCCATGGCCCACAAGGCCTGCTCTTCATCTGTCTGAAGAAGCC |
| TCTTTATTGCATTCAGATAAGTGTTTCACTTGAAGGAGAGCAAACACAACCAAATAATGACCTAGA |
| TGTCCCTTCCTCATGTTTTCAAACAGTCCCCCTTCTCTTTAATCCCTGCAGGAGAAAATGTCCTGGA |
| GTTGAGATCTTAGGAGACATTGGTTCATTTAAGTCCATTATGAGACCTTCACAAGGCACCCCTTAA |
| ATCTGGCAGTAGGACCACAGTTTTATCCTGGCCACAAATTTAAAGACTTTGATCCTATTCCCTCTCA |
| GGTATCAATGCAAACAGAACAATTCTAACATTTTTAGTATGGCCACCCCAACGTGGACACCAATTA |
| GCTAAGCCAGGGAACTTTACTTCTATTTCCTCATCTATGCAAAGGGGAGAACAGGTTAGATGATGT |

Sequence Information

```
CTAAGGCCCCTCAAGAACTTGAGTGCTCTTCATTCTGTAATCATTATCTCTCTAATTAGTTTCTCTTC
TCTAAACTTTATTCTCCTCCACGGCCTCTGTTTAGGGGTGGAAGGTAGATGCTGTACCCTAGTGTGT
GTTTCCCGGGGCTGTTTCTCAGCCTGCTGCTCTGTTCTCTCCACTCTCTATCTGTCCCTATTGCGATC
ATTCTCAAATCTAACTGTGACTGCAGCACTCCAGTTCATTCATTTATTCCATAATATTTCTCAAACA
CCCACACGGTGCTAGGTGCTGAATGAACAGTACACTGGTGAACAAGAGTCATGATCCCTGCTTTTT
TTGGATCATATACTTTTCTAGGGAGACATGTATTAAATATATTTAATTTAATTTAACAAATATAATT
TAAATAATATTAAATATATTAAATGAATATATAATGATAAATTGTAAGACGTGTTATGGAAGATGA
ACAGGGGTTGCCCTGATTTAATTTGGGAGGTCAAAAAATATCTGCTCTGAGGAAGTGTTATTTGAT
CTGAGACCTGGAAAAGGAGTTATCAGGCAAGGAGTTGTAGAAAGTGCTCCAGGTAGAGGAAAGA
GCTAACACAAAGACCTTTGCAGCAGGGAAGGGCTAGACTGGATGAACAGAGCTTCGTGTGCCCAA
AGAACTGAAGGAAACCAGTGTGGTTGGAACATACACAGTGAGAGCAGTGGGGTGAGATGAGACT
GGGAGAATGACAGATTAGTTAAGATAACGCTGGCTGCTGGAACAAACCAAAACTGACATTCGAAC
AGTATAGACATTTATTTCTCATTTGCAGAAGTGCAAACTAGATATTCCTGAGCAGTTAGATATCCC
TGTTCAAAGCAGTGTCTTGGAGACCACAGCTCCTTTCATTTTGCAGCTCTGCCATTTTTAATGACCT
GCCAAGGCCAGCGTGCTTCTCTGCATGGAAGGCTGTGCATGAGAGGGTTTTCTGGGCCCAGGCCTG
CCTGGAAGTGGTGCTCCCAACCGCACTCACATTCCGCCAGCACACACCCAACTGCAAGGGAGGCC
GAGAAATGTGGTCAGAGTGTGATCCCAAGAAGGAGACAGGGCAGATGACGCAGACACTGTGGGC
CATGTTGCAGTTTCAGTTTTATTCCTAGCGTGCTGAGGAGTGTGAGTGAGAGTGCACCTGTGGCAA
ATCCATCAGCACTTCTAAACCTACACGTTCAATTGCTAATGTCATGCAATTCATCTTCCTCCAAAAG
CAACATCTCTCACGTGTTCTTCCAGTGATGCCATTCCAGACCTAGCAGTCCTTTTTCCTGCTCTATT
CATCGTCTAGACTTACTTGACCAATCCAACCCTGGACTGGTTCAGTACTTCCCCGACTAGGCTCTTC
AATTGGTTTCTTTCTGCTCTGATACAGAATGCTAAGGTACGTATTTACAATGTAGACTATCCCCTTC
CAGTGACAGAGTTATTCCTGGCTGTTGTATAGAGCAACTTTTTTGTACTATCAGGTCATCCTAGAA
ACTTAATTAGTAATCAGAGTATAATGAACATGGAGATGTGTCTTTCTAAAACAGGCCTTTCATCCC
TGCTAAAAAAAAATTTTACTTGCTTCCAAGTACCTACTGAATAAAGTTCTAACTTCTATATGTTGGA
GGTACTAACGCAACCCATCTTTTCCTAACAATTCTTACTTTGTCCTCCTCAAGCCAGCCAGGGTGCT
CAACTATCCAGAGTCCAAACAAACTTGGTGAATTCTCACCTTGTACTCTTCCACACTCTGCCTGGG
ATGTCCTGTTCCTGCTCATCCTCCTCTCTGAATCCTACTGATGTTTTAGTGCAAGCCTTCATCCCCTA
AGTCTCACCTTCTCTGGGAAGTCTCCCCTCCAACCAACCAGAAATAGACTTTCCATCTCTGGAGTTC
TGTAGTGCTTACTCTTCAAAGTAATTAATGCTTAAATTAACTTGTGTCTTACCACTCCTTTGGCATT
TATCATGTATTGCCTTTTATTGACATTTATTCTCCCAATTCATTCTAAGCTTCTTAAGTAGAGATACT
TTTCCTGGTATCTAAAACAGTACCTTGCACACCCTCCAAAAAATTATTAATTAATTTAATGTTTTTC
TGTAATTCCTGTGACACCTTATACAGTTTCTTAAACATGGCAGATGCTCAAAAAATTCTTGTTGATT
TGTTATTATTGTTATTTTAATGTATAACCCCCTGTAAAATGCAAAGTCTTGGTCAGTTAAGGGGGA
GTGCTTTTTCTGGGAATTCCAGCCCCAAACGGAGGTCTGGGTAAAATGCATGGTGGAGAGGGGAG
TCTGTGAGTGCTCCTCCAGCCTCTGTGCACAGCTTCCTACTTTGCTGCTGCTGCTGCTGCTTTTTTTT
TTTTTTTTAATTGAGATGGAGTCTTGCTCTGTCACCCGGGCTGGAGTGCAGTGGTGTGATCTTGGTT
TACTGCAACCTCTGCCTCCTGGGTTCAAGCAATCTTCTCACCTCAGCCTCCTGAGTAGCTGGGACTA
CAGGTGCACACCACCACGCCCAGCTAATTTTTGTATTTTTAGTAGAAATGGGGTTTTACCATGTTG
GCCAGGCTAGTCTTGAACTCCTGACCTCAAGTGATTTGCCTGCCTCGGCCTCCCAAAGTGCCGGGA
TTACAGACGTGAGCCACCGCGACTGGCCGCTACTTTGCTTCTTCTGCTCATTCAGAAAGCCAACTC
TGGGTTTGTCACAGATTGTTTGCTTACAAATATTCCCACTTTTTCATTCACAATCCTTCTTTCCCCAA
GAAAGAGGTTGGTCGCAAGGTGTAGGGGTGTTGCCCTGGGGCTCTGTCTTTCCAATTTTCCCTTCT
ATCCAGATTTTTCATCTGCCAAACCCTATGAGAGCCAGGAGAGGGCATCAGATCAACCAGCCAAA
GCTTCAAAATCTGCCTTGACTCTGTGGGGTTCTGCTCACCTACACCTTTGTAGGGTACCATCCTCTA
GTAAAATGAGCCTCTACTATGATAGCAGGCTCCTGCATTCTATTTCTAAATCTGCCTGATTCTAAAC
ATTCTTGTTTGAGTCAGATGGGAAATACAGTTCTGTTTCATTTTTCTCCCCGTCTTAATTGGTTTTCC
GTATGCGGGTTCAGAAGTAGGGATTTTGCCATACACATCATCCTTCATGTGAGTAGGTGAGCACCAG
CATCAGGGGAAGGAAAAGAGACAAACTGACTGTTAGGGAGGGAGTCTCTCTCCAGACTCGGCTAG
CCAGCACAGCTTCAGATCCTGCCCCTCAAGTGAGTCACTTCATGAATGTGGCTAAAGTGTCTAACG
GTTGGCATTTCTCAGGAAGCATGCTGGGATTATGGATGTGAAAGTTAACATGGGTTGAGAGAGGA
CTGAGGCTTCAGCAATCTCAGAATGTCTGTCTGTTGAGCTTCATAACCAAGCTGCCAAATTCAAAT
CTGCATCTACAGATTCTTGAGCACTTGAGGCGGGTGCCCTCTGAAGCTGGACTTTTTCAAAGCTGC
TCTGAAGAGCTGGGTGGCACCTCCTTCATATTTCATTCTAAGTCAATTGCAGAGCTAAGAAACCGT
CTTTGCTTACTGTCTCAGATGTGTTTCCAGTTTTCATTGGAAAGAGAATTGTGTTCTGAATCCCAG
TTCATGTGAAACCCTGATAACTTCTCAAAATATAAAACGTCCTTACTTTCGGGGCTGCTGTCAAG
AACTAGAGGAGGCTGGAAAGAGTTGTCTCAAATGTTTGCTTTTTTACCTTTGGCAAGCATCACCTA
GTGGCCCTCATGTCAGTGACTACAGGGTTTGTGTAACATGCCTGGGTTTGGGCCATGGACAGCAAT
GTTGTGGAGGGCTGCCCTTGGAAGAACACCAGCCAGCTTCAGTTTTCTGCACTGTAATTGTTGCCA
CTGCTACCCCAGTATGGGCTCCTGGGGTCAGGAGGGATGGCATCACCAAGCTTCCCGGAGGGGGC
AGGCCCACCTGACAGCCATTAAAAGGCTGATTCCGTGGGCAGGGCCCTTTTTCCAAATTAAGTATT
AAATGAACATTATTTCATCCTTATCCAAAACTGTGCTCAGAGCCTAGACACGTCTTTCCTGCACAC
CGGAATATGAACCGTACAACACAGGGTGAGCTCAGCCTTCAGCAAGGCGTTTTGGATGGTGAGGC
TTTGTGGTTGGGATTGCACTAAATGCCATGTAGGGGGCGGGGGGTCTTTCTCCTTTCATCCCTTGC
CAGAGACTCAGCCTGGGCCATGCTCATCATCATAATCACAGGCTGAAGAGGAATATTTTGGGTTTA
GTTTCCCTTTTTTTTTTTTTTTACACACAATGCCTATTTATAACCATTTGTTGACAGACTCTACCA
ATTACTTAAAAAAACGTGTATTTAGACAGAGACAGACCAAAAATGTGAATTCAATGGTGGCCCTA
GTTCTGTATTCGATTAGCATCTGCTGGTGCCAGAACTGGAGATGGCTGTCTGTTGTCACTTTAATTG
GAGGATGATTAGAAAAAATACTTGCTTTTCTTCCAATCTTATCTTTGTTGTTACCAGCTCATCAGA
TCCGCAAGTTCATGTTTATTATGGCCATTATATGTTAAAAGCTCAGTGCATTTTCTGTCTCCACATC
ATCTATAACATCCTGTTGCCAAATCCAGTTATCTCCTTTCCTGCTTTCTCATACTTTCCCTCTCTTTG
ACATTAACCATTTTCTCCATGGAGTATTTCCCCTGGCTTCTGAGGCCTTCTTCTAGTCTAACTCCTCC
TTCTCAGCCTTTTAGAGGCCCCTTCCCCTATGCTTTGCCTTTCAAATGGTGTTTCTTTCCAGAATTCC
ATCCTCCTCCCTGTTCTTTTCAGTCCATATATTTTTTCCACCTTAAATACAGCCAGAAGAAGTGG
AGACAAGGCACCCAGTTTGAGAGTCCAGGACTTGGCAGTGCACATCGGACATTAGAGAGGGGTTA
CCCATAAAGCTATCTTAGGGGCAGCTGAATATACAGGATCTCTGTGATTCCTACCCTTACCCCAAA
AAGCAGGATGGCTCACGGGGGCAGCAGAAAGGTGATGGAGCCAGAGAGAGTAGGTAAGCTATTG
```

```
TCCATGGTGGATACAGGGAGAGACAAGCTGAAGAGGTTGAACCTGTTTTGATGGCCAAGGCCAGC
AGATGGATGTCAATATCCCTATGTGAAATACAGGAGTGGAGCACCATCGAAGGAATGATGTGAGA
AGGAAGTGAGAAGGCTGGGCTTTGTTACTGTGCAGGTTCACCTGGGCTAGAGGCACTATGGTTGG
ATACACAAAACAACAGTCTGGGTTAGAGATAAGATTCTGGAGTCTAGAATACCCAGCGAAATGTT
GGGCATGGAAACTAGAGGAACGAAAACATTGAAGAGATGAACAGTGAAAAAGAATAAGCAAAT
GAGGCTGAAAAGAATGGCAGGTAGAGGCCGGGCGCAGTGGCTCGTGCCTGTAATCCCGGCACTTT
CGGAGACCAAGGCAGGCGGATCACAAGGTCAAGAGATCGAGACCTGCCGGGCGCGGTGGCTCAC
GCCTGTAATCCCAGCACTTTGGGAGGCCGAGGCGGGCGGATCACGAGGTCAGGAGATCGAGACCA
TCCCGGCTAAAACGGTGAAACCCCGTCTCTACTAAAAAATACAAAAAATTAGCCAGGCATAGTGG
CGGGCGCCTGTAGTCCCAGCTACTTGGGAGGCTGAGGCAGGAGAATGGCGTGAACCCGGGAGGCG
GAGCTTGCAGTGAGCCGAGATCCCGCCACTGCACTCCAGCCTGGGCGACAGAGCGAGACTCTGTC
TCAAAAAAAAAAAAAAAGAGATCGAGACCATCCTGGCCAACATGGTGAAACCCGTCTCTACTA
AAAATACAAAAATTAGCTGGGCATGGTGGCGTGTGCCTGTAGTCCCAGCTACTCGGGAGGCTGAG
GCAGGAGAATCACTTGAACCCAGGAGGCAGAGGTTGCAGTGAGCCAAGATTGTGCCACCGCACTC
CAGCCTGGTGACAGAGTGAGACTCCGTCAAAAAAAAAAGAATGGCAGGTAGAAATGAGACTCCC
AAAGATGAACCCAGATGGAGCATTTTCTCTATGCCAGGCACTGCAGTAAGTGCTTTGCACGCATTG
TCTCACTTAGAGACTGAAAAGGGGAAGGACACCTTAGAAAGAAGAAAATTTCAAAAAGAGAGAC
CCTCCTTCTGCCTTGATCATATTTGTCACTCTTTCTTTACCTATTGCATTGGCCTATCCATAGGGCTC
TTCCTGGATCCTCCTGGGGAATTGGTATGTCTTTTGGAATCTCCTAGCACTTTGTGCGTTTTATTTAT
TCAGGCAACAAATGTTTATTCCACTATTTTAGAATTTATGGTGGTTAAACAAAATTATTTTATTATT
ACCTGCTGAACTCCAGCTTATTCATTCTGAAGATTTAGTGTCTAACACATATAGTGATCAACAACA
TAGGTATTTGTTTAGTAAGTAAATGAATAATATGAAATAAGTTATTTTTTCAAGACTCAAATTTAA
ACCAAAGCATGAGAAGAGCTCTTGTCAACCTATTTCAGGTATAGGTGGCTTAATTTACTACAACGG
TCATGAGTTGAGGATTCATTGAATGGTTGTTTTCTGTCATTTTTGGTTTACACTGCTCAATCAACAC
TGCTGGCTGATGTCAGACCTTAACCAATTGTTGAAGTTCCCTGTAACACCAGCACATTCTCTGAAT
ACTTACTATGCACAATGCAATAATGATTAACATTTGAACTCTGTCTAGGCTGAGTAAGCCACATCA
AAGCTCTTTTTTCACTAGGACTTTTAAAATATCAGATATGAACTGAGTGAGTAGGTGTCAGAGAAA
TTGACTTTGTAAACTGAAAATCATAAACTTAAGATTCATTTGAAATCTCATGTGGAGTGCATAT
ATAAAAATTATGAGCATTTTAATTTGTCCCCTGTAGGTAATAAATAACATCTGCAATATTCCTCCTC
ACCTTTTTCTGATTAGCTTCATGTCTGGCATATTTTTCCCAACACTCCTGTTTCGTGTTGTAAGAATT
TCTCCAAGGACAGACAGGATTCTAAGTAAGTAGTGAGGGTCTAACAGAAAACTTGCAGCAACCAG
GTTCAAGTTCAGAAATGAGGGAAGTATTTAATGGTGGTCAGGCCTCCCTATTTTACTCTTCTTTGGT
ACACGCTGGCAGAGCTGCACAGGCCCCGAGGGGTGGCAGTGCCTGTGAAAGGCACAGTGCCTGTG
AAAGGTCTATAATCTAGACCCACAAGCCAGCCCCCTCCTCCCCAAAGCTGGTGTGGCTCCCAGGCC
CCCTCACTCCCACATGTACCTGCACCCACATGGGGGCATCCAGCAGAGTGCCCTAGGCCACCAGC
ATCCCCCTAGGGTCCATGGAGCTGGAGGGACCTCTGGAGACTCCAAAGATGAACCAAGGTGGAC
ATTGGCCACCTCTGCTGGGCAGCTGCATAGAGTTTGTTTGGGAGGAAGATTTTGTCCTTAAAAGTT
TGAAAACCACTGCCTTAACTGTGTAATTTCAATAACTACTATATGATGATGATAACAATAATAGCT
AACATTTATTGAGAGCTTACTCTCTGCCAGGGACCCTATTATGGGCTTTCAATGTACTATCTCATTT
AATTCTCCCAAAAAAATCTCTGAGGCACTTACTGATTTTATCAGCTAGAAACAGAGGCTAAGTAA
AATGCCCATGGTTACAGAGTTATGAAGTAGGAGAGCTGGCCCATTTAGTCTGGCTCCAAAGCCAG
GGATCTCAATCTTGCTGCTAATACTGCTATTAATTAGCTCTGGTAAAAGTGAAGAGGCAGCCTGGA
CAACTGGAAAACAGAACAGCACATGTTTAGTAAGTGCCTATGACAGTCAGGCGTTAAATGATGCT
TGAGCCTTAGTTACTCTGAGCTTCACTCTATCCCTCTCACCCCAGTGGCCTCACCTAATTTTGGAAA
AGTTGGACAAGCAGTGAGACAGACAGGGTAAAAAGAAAAAATTGGCTTGTAAATACTCCCCGAAT
ATCCTGCCTGATAAAACATTCTTCCTCCTCTCCCTCCTCCTCCTTCCTATCACCTCTCCCTTTGCCTT
TCTCCCCAACCCCACCTCTCTTCTTTGTTTTCTGTTTTCTTTTTGCCTCCCTTATCGGTCCTGTCTTCT
TTGCCTTGTGTTAGATTCTTTAGGCTCCTATTTCAGGACAGGTCACATTTACTCTTGCTTCTACACTA
GGACACACCCTCCCCTCTTACTACTCAGTGTTAGTTCACTGGCCTCAATAAACACTGGATGTTTTTA
TTTTATTTCATGTTTGTGCACTTGAAGACTATTGAATTCATTCTGTGTGTTTTTTTTTCCAAAATGAT
ATATGAATTAGAATTGCCCTTTTGAGCCAAGAACCCTGGTGGGTTTTGTTTTGTTTTTTAACAGAGC
CGCAAGCCCAGGAATGAGAAATCAGTTCATAAAATCAATAGCAAGCAAATTTAGAATCCACTACA
GCACCTATACCCAGCTTATAGTAAGCCTGAGAAGCAGACTCCTACAGGATGAGATTGATTCCAGC
AGTGTGGTTAGATATTTGGAAATGCCTAAAGAAATGTTTATGCTCAAGTTAAGGTTGCAGCAGAAA
CCATATAACTTGAGAATTTCTGGGGCCTAAATGTACGGGCTCTACAGAATGTACTACGTTGCTTTG
TGCCTCTGCCCAGATCACTATTCTCCTTTTCCACTTTCCTCCCATGCTGCCCCCAGCACACGCATAC
TTGCCTCATCGCCTCAAAAAAAAAATAATAAAAATTGAAATCTTTCTAATGCCAATTCAGCCTTCC
AGTTTCATCTGAGACATCACTTCTTCAGGGAGATCTTCTCCTTTCCCTAGACTAATCAAGGTCCCCA
CCTTGCCTTCCTAGAGCCCCATCCCTAGCCACAACACCCATCAAAATTGATCATCACTGCTTGTCT
CCTTGCCTTCCTCCACCTGGCTGTGTGCCCAGCAACTAGGACTAGTTCAAGAAGTATTTGTTGACG
AAGTAAATCAATTTAGTTTGGGGGACCATGGCCACAGGATCAAGACACTTCTCAGCTCTCTGCTG
TCTCCTTACTCTTGCTTTCCAGACTCTGATTCCCGAGCAGTTGGGAAGACATCTTTTTGTTTCTTCCA
TTCTGAAATTCACTGACCAACTGCGTACATCCATGCTCATAAACATTTGATTTAGCTATAAAATCTA
TTTTAAATAAAAATGCCAATTAGAGTAGAAACTTCCTGCTCCTCCCTGTCCCCACTATGTGTAAGG
TAAGTGTGGAGGTGGGAAAAAGAGCGTTGTCTTCAAGGAGTGGGAGTTGAATGTCTCCTAGGTG
CCCACTGCAGGCAGCATGAAAATAATAGGATGGATACTATAGGAGGCACATTTGAGATCTTTCAA
ATTGCTCCAGCTGACCATCCATGACATGGGCTACCTGGTGAGGCAGGAAGTCCTGTGTGGGACTGT
CCTAGGGCAATAGCTGTGCAAAGACCATCATAAGTGCAACAGATGCTGCTGAAGATGGTAATTTC
AGGCAGCCTATGTTAGGCCAGGGCTCAGCTGGGCTAGACTAAGGGAACCAAAGACAGGTATGAAA
GGGACTGTAGGCTCCAGTGACCCCAAGGCAGAACCAGAATTGGGAATCTCTGTTCTATTGCACTCT
GTTTTTACAATTCTGGCCAGACCTGTAGTGTGGCATACCACTACAGGTTTATGTGGGGAAAATGTTA
CCACATATTCCCCACATAATTTTCTAACAATACCTCGTTCCCTTTGCAGCTGGTTCAGATCTCACAG
TCATAAGAGGGTTGAGCAGTTGGTCACACCTTGACTTGACAGCTGTCAGTCAGAGGCCATAGGTTC
AACATATATTGAAATGATTTCTTTCAGTTGGTCAGTTGGTTTTACCTATTTGCCTGGGCTTATGGCG
ACCACCGTGGAAATTCAAGAGACCTGTACCCAGAATCCGTGCACTTATGGTGCACAGAATGCTCA
CTACGTGTAGAATCTTATTTCCTCTTCACACTCATTCTATTTAGGTAGTATTTTGGTTCTCATTTTTG
CATACAAGGAAACAGGAACTCAGAGTGGTTAAATGACTTTATAAGATAAGAAAAAGAGCTTGTTC
```

| Sequence Information |
|---|
| TAAAGGCTATTGAAATGCCAGTGATTGATTTCTCTGAGTTACTTTTCAGAACTAGAGTGATGGCAT |
| AGGGCAAGCTTATTCAAACCCATGGCCCACGGGCTGCACGTGGCCCAGGATGGCCTTGAATGCGT |
| AACTTTTTTTTTTTTTTTGCGACAGATTCTCACTCTGTCGTCCAGGCTGGAGTACAGTGATGCGA |
| TCTCGGCTCGCTGCAACCTCCACCTCCTGGGTTCAAGTGCTTCTCATGCCTCAGCCTCCTGAGTAGC |
| TGGGATTACAGGCATGCACCGTCACACCTGGCTAATTTTTGTATTTTTAGTAGAGATGGGGTTTTAC |
| CACAGTGGCCCGGCTGGTCTCGAACTCCTGGCCTCAAGTGATCTGCCCGCCTCAGCCTCCCAAAGT |
| GCTGGGATTACAGGCGTGAGCCACCATGCCTGTAAACTTTCTGAAAATTCATAAGCTTTCTTAAAA |
| CATTATGAGTTTTCTTGCAATTTCTTTTTTTTTTAGCTCATCAGCTGTCATTAGTGTTAGTGTATTTT |
| ATGTGTGGCCCAAGACAATTCTTCTTCTTCCAGTGTGGCTCAAGGAAGCCAGAAGATTGGACACGC |
| CTGGCATACGGCATACCACTGCGCCATCCAAAACAGCTGTGCACAGCCCCACTTCCCAGCTGTTAG |
| GGGCTTTTTTCATCTTCAAAAATTAAGCAAAGAGGTTCACTAAAGCATCAGTTCAGAGTGTGGGGC |
| TTCTAGTCAGTGTATTTTAGGGAATTAATTTTAGGAAGAAACTATTTTTAGGTCCACGATTATTTTT |
| AAAAACAAAAATCTAGACAACAGTGCATACATGCACGTCTGGATATGTAAGCCCTTACCACACAG |
| CGAGATGAGAGGGTGGCCTTGGCCAAAGCCTGCAGTTGTTGGGACATTCAAAACCATGAGCAGAC |
| TGGAGATTTGAGCCACATGTGCACCAGCGCAGTCGCTCAGATGCGGCCTGGGTGCGCTGATCTGG |
| GAGGGGGACTCACGGGCTCTGGGTCTCTGACTAGCTGGCACATGAAGGACCTTAATGACTTGAAC |
| CTCACTTTCAGTTTGAGATCCTTTGAACTTTTGTTAGAGTGAGCCATAAAGAAGTGGTCAGCCAAT |
| CAGATGTTTAGTATAAACTGAACTTTAGCGTAAATAAGCTTTAAGAGACACATTTGATTTACATAA |
| TAAATAAACAAGCTACTTTTAGGAACTTTTAAGTACAAAAGTTGAAGATAGTTGCTAATTAAACCT |
| AAATCTTGCCTGTACATTAAAAACATACTCGACAGAATTTCCAGTTTTAGAAAACTCCTCAAGAACC |
| AAATTTCTGGGACAGCTGGGGTGTTTTTCTCACTTAGCCCAAGTGAGTAAGTTTTACTGTAAGTAA |
| ATATGCATACATCATTAAGTGAAGGTGGCATCACACTGGCAGGGAAAGTCAGATGGGTTATTGGC |
| GAAGAATGAAATTTTGCTGATCTTCATAAATTGTGAAATGATAAAAAACAAATAGAACTCAGTAG |
| AAATGAATGGCAGGCCAAACAAACCGGACAGAAAAGGGGCTACAGACTAAAAGTGGTAAATTAC |
| AGCTTCTACACATAAATCCTTTTTACCCCAACCCTCTTTAAATTCTGGAACATAAATGGGGGAACA |
| AATATAGACCCTTTCTAAATCCACACCAGAGAAGTGACTTTGGTTGTTTTTTGTTTGGTTTTATTTT |
| GTTTTTCTGATATAATAGTGATTTTTGCCTCCTTTCCTCCTCTTTGTAAGGTCTTGGGTAGAAGAGG |
| TTGTAAAAGAAAATGAAACTATATTATACTGATGATAATAGCTACCATTCAGTGATAGTTATTGAC |
| AGATGTTAATATCTGTTTCATAGAGCAAGGATTAAATGAGTTATACATAGAACACTTAAAGCAGTG |
| TTTTATGTTTATAAGCATGTAGTATTTAAGTATTAGATATTATTATCTTTAATGTTGGCAATTGTCTT |
| AACAATATAACAGATATTCTACTAAGCACTATATATGTCTTATCTCACTTGCTACTGTTATGTTAAT |
| TTTATAGATAGTAATCTGAGGCATGGGAAGTTTAAAAAGTTGCCTGAGATTGCACGGGTGGTAATA |
| ACTGCGCACTTTCTATATGCTGTACTTAGTACTAGACATTTTTAATGTATCGTTGCATTTAGACCTC |
| ACAACAATACTGAAACTGAGGCCTAGGGAGGCCAGCTAACACCAAGATCACACAGCCAGTGAGTG |
| ATGGAGCTGAGATTCAAACCCAAGCAGTCTGGCTCCAAAAGTGCATGTTCTATGCTACTGTGTACT |
| ATGGCCTCCTGGAGAAGGGCTGGTAGGATGCCCACTTCAATGATACAGCCCTTTCCTCCATCCTCAT |
| TACCATCCCTAGCACTGCTTTCCTTCAGGGTCACAACAGTAGGTCTTCCTAAGCCCCATTCTCCAAT |
| CATGTCCAGCTCATTGTACTTGAGCAGCATTTCGGAGAGGAAATGCCTCTAGACCCTCCCGTTCAC |
| CCTACAGCGCTGTTTGTGCCACGCTTCCTCACCACCCTGCCAAGCCCTTGCTTGCACACCTCTAAT |
| GCCAGAAAATCATCCTCCCAAGGAAACTCATTCTTTCTGTCTTGGGGAAGCTCTGTCTGGTGGAAA |
| CATATTCCTCATATTGACCCAAATGGTGCTATGTGCCTTTAACCTTTCTGTGCCTCAGTTTATTCATC |
| CATGGGACTTTCACGAGGATTAAATTAGACACCAAGTGCTTAAAACAATGCCTCATCTGTATTATG |
| TTTGCTAAATATTAGCTGCTATTACTATTTTATTATTATTAGTTCTCTCTATGGCTTCCACCCCAAAT |
| GCTTTATAGTACAAATTGAGTCCTTCTTGAATTCACTCTTTTTCACCCTTTTGTCAGCTGCAGCCTGC |
| CCTCCAGGATATGATGGTGGCCTTTGTGATGACTTTGTAGACTCAATACCATATCACTCCAGTCTGC |
| TGTACATGCATCGTTAAGAACTGTCTTTCTGGGATATTGCTTTTGTACATCATTTCCCTCTTCAGAA |
| GCCAAACTGGTTCTTGGTTGCTTTCATACTTTGGATGGATTATTAGATTCTCTACTAATTTCTTGCTG |
| ATCTCTACCCATGCTCTTCTCTCTGAGCATGAAAACTTCCTGTCTTCCATGGACTTTCCTCTTCTTAT |
| TTGCAGGTCAGCTCACATATTTATTTTGTTTAAACATTATGTAGTTAAAAGTCTCAAAGGCTATATA |
| CGAAAATGTTAACAGCAACTAATAAATTAACAGGTCATTTTTATTTTCCTTTTCATGTTTTTCTGTG |
| TTTTCCAACATATATACAACAAACATATAAATTGCATTGTTATGAAAATACTGTGTTTCCTAAAA |
| GTACAATCATAGACTGTATTATACAATACTTTCCAAGGTCAAGAGGATGCCTTGTGCAGTCAAGAG |
| AGTAGGATTGCCTTTCATGAAGATCAGAAGTATCTCCAGCCCTCCCCTCAGTCCCTTCCCTTTTTGG |
| TGAACCCATTGGAATCACTAATTAGTGTATTTCAAACTATATATATTAGCCATAGACCCTTTCTTCA |
| AACAAAAATGTAGGCCAGGTGTGGTGGCTCACACTTATAATACCTCAGCACTTTGGGAAGCCAAG |
| GTGGGAGGATGCTTGAGGCCAGGAGTTTCAGACCAGCCAGGTAACGTAGGGAAACAATTACAAA |
| AATCATAGTGGCCTCTTTAAAAATTTTTTTCTAATTTTTTTAAAATTAGCTAGGTATGGTAGCACA |
| TGCCTGTGGTCCTAACCACTCAGGAGGCTGAGGTAGGAGGATCATTTGAGCCAAGAAGTTCAAGG |
| CTGCAGTAAGCTAGTAAGCTGTGATCTCACCACTGTATTTAGCCTGAGCAACAGTGTAAGACCTT |
| ATCTCAAAAAATAAAAAATAAATTAAAAAAATGTAGAGAAGTACAACATATTTAGCAGATATTA |
| TAGATTCTTCCTTAAGGAGTTGAACTCTGTTGAAATGGAGATGGTGAACCTGGACCCCGACCCACT |
| AACTCACCATCCTATTTCAAGACAACTTCTGAGTTACTTCCAGAACCTACTTTGGGTCTGGAGAAC |
| ACAGTTCTCCACTGAAACCACCACCAGGCCACCTCATTCTGGTAACAAACAACTCCCAATTTCTAG |
| GGGTTGCTCAGATAAGGAGTGCTGTAAGTTTACTACGTATTATGTAACATATTTCATCAGTCCTAA |
| AATTTTCTGCTGATCTCCTTTTTCCCATCCAAAATCAATACACACGGCTAATCCATCTTATAGCTGA |
| ATATTTCTGTCTGGCCAGAAAGCTTTATTATCTCAGAGGTGGCTTTCAGCTCAGAAGGAAACGAGA |
| AAAATTTGTTTGTTTATACTTCTCTCTTAACTCCCTAGCTTCTGCTCATTCATCAAGCTAATAGATG |
| GAATATTTGGCTCTTCTGATTCGCCATCTGAAACCCTCTGCTCTCTTGGCTTCTGTAATGTCCTGTTT |
| AACTGGTTCACTTCCTCATATTTATTTTCCTCTCTACTCCGTTTGCTGTTTTCCTTTGGCCCTCAGTGC |
| TCTGTTTCTGGGCGTCTGCTTTCTTGCTTCCCTCCCTAGGCAGCGAATCCACTTCTAGGGTTAAGCA |
| ATCACTGCATTGCGGGTGGTGCTTAGTGTGTGCCTCAGTCTGTCAGACAGAGGCCAGTCCTATAGC |
| TCCAATATGTTGTGGAGCCGTCTACCTTGAGCTCAAGTTAATTCCTAAAATCAGTATGTCTCATTCC |
| AGATCCTTTACTCCCCACTATTTCCCGTCTGAACATCTCTATTCTGCCAATATCAACAGTATTCTC |
| TCAATCACCAAACTCAAAACCTTGGATTTATTTATCTTTTATATTCTTTTGTCACCAAATATCTTGG |
| CTTTTCACCTTGGGAACTTCTCTTAGATGTCTCTTTGCTCATCACTTCATGTCATGGAATTCCAGAAC |
| ACAGTGCTGTATTACCACATACAGTTGTTAATCAACAAATATTTCTTAAATTGGCATCTAGTCCAA |
| CTCTGTCAACGAAATTTTAAAAGTTTGTTAACATTCTAAGAAACCTCTGCCTCCTGTCTTGGGTCCT |

-continued

Sequence Information

```
GACAGTTTATCCAATACACTGTCAAGTTAATAGTGAAAACACCCAGTGCGGCCAAAGCAATCTTG
GGAAAAAATAAAAGTGGGAGGACTCAGGCTTGCTGATTTCTAAGGTTACTACTAAGCTTGACAAG
TCCTGGTAGTGTGGTACTGGCATAAGAATAGACATAGATCGCTATGTGTGTGGCTCACACCTGTA
ATCCCAGCACTTTGGGAGGCTGGATCGCTTGAGGCCAGGAGCTAGAGACCAGCCTGGCCAACATA
GTGAAACCTGTATCTATATAGATAGATAGATAGATAGATAGATAGATAGATAGATAGATAGATGG
TTATCGATTTTTTAATAACTATAGATCAATGGAATGGCATCGAGAGTCCAGAAATAAACCCTCATG
CTTATGGTCAATTGGGTTTTGACAAGGATACCAAGACAATTAAAGAGGAAAAAAATACTCTCTCA
GACAAATGGTTCTGGAGACAACTGAGATATCTATATACAAAAGGATGAAATTGGGTGGGTATGGT
GGCTCATGCCTGTAATCCCAGCACTTTGGAAGGCTGGAGTGAGAGGATTGCTTGAGGCCAGAAGA
CAAGCCTGGGTAACATTGCAAGACCCCCATCTCTATAAAAAATCAGCTGGGCATGATGGCATGTG
CCTGTAGTCCCCGCTATTCTGGAGGCTAAGGTGAGAGGATCGCTTGAGCCTAGGAGTTTAAGGATG
CAGTGAGCTAAAGCTAAGATCGCACTCCAGCCTGGGTGATGGAGTGAGATCCTGTCTCTAAAAAG
AATAAAATTGAGAATGTAATACAGAACACATTTCAGCCATTTTTTAATGCTCTGCAGTTACTCGAA
AGGTTAAACATAGACTTACCATATAACTCAGCAATTCTGCTTCTAGATATATACCCAAGAGAGGTG
AAGATGTACATCCACACTGAAATTGTACATGAATGTTAATGGTACATTACTCGTAGTCGCCAAAAA
GTATAAACAAAGAAGTGTCCATTAATTGATGAATAAAGAAAATGTGGTATATTTTTGGCAATATAC
AGGAATGAAAGGAATATTATTCATTATTTAAAAAGAATGAAGTACTGATACGTGCTACAAAATGA
ATGAACCTTGAGAACATTATGCCAAGTGAAAGAAGCCAGACACGAAAGGCCACATATTGTCTGAT
CCTATTTATATAAAATGTCCAGAATAGGTAAATCCAGAGCACAAAGTGGGTTAAGGGTTGCCTAG
GGCTGGAGGGTGTGGGAGTAAATGGGGATTAACTGCCAATGGTGCAGGGTTTCTTTCTGGGGTGA
TAAAAATGTTCTAAATATGTTACAGTGATGGTTATACAACTTTGTGAATATATCATACTAAAAAC
CATAGAATTTTACACTAAAAATGGGTGAATTTGATCATATGTGAACTATATGATATACTCTTTAAA
AATATATTTAAATTCCTCTTATGTCTCCCTATTGATTAGAAGGAAAAGTTGCCACCTCTCTGACCC
TTCTTCTGCAGCCACATCTCCCTCTGACCATAATCAAGAAGTACTCCTTGCATTTATGAACTCATGT
CATTAGATCGGGCCCATCCAGATAAATCTGAGATAATCCTCACATCTTACAGGTCTTACCTATAAT
CATACCTGCAGAGTCCCTTATGGCATGGAAGGTGATGTATTCATAGGTTCTGGGAGATTAGGATGT
TGACATTTTGAGGAACCATTATCCTGCCTATCATACCCTGTTTTATACTTCTTTCTATTGCATAAGA
GTCTCACACATGTTGACAGATGGATGGAAAAAATATATTATGCAGGTACTAACAGCAGCAACAAT
GACAGCTAAAAACTGAGCTATCTATACATCAGATAAAGTAGATTTAAAGGAGGAAAGCACTATTA
GAATTAAAGAGGGAGTTTTCAAATAATTATCCAGTCATAGAAGAGATTTTTAACATACCTCTCTC
AGTAACTGATAGAACAAGCAAACAAACAAAAATGTCCATAAAGATATAAAAGATTTGAACACCAT
AGTTAACAAACTTGACCTAAATGATATACAGAGCATTGAGCCCAACAACTTCAGACTACATGTTTT
TTACATTGGTGCTTGGATAATTCATAGTCCGTATTAGAAATGAAAATGTTGAATATCTGTTATTCAA
AAGGTTATAAAAAAAATAACAATTAAGCCCAAAGAAATAAAGGAGGGAAATAATAAAGATA
AAAGAAGTTAATGAAATAGAAAACAAACATACTACAGATAGGATCTACAAGGCCAAAAGTTTGTT
GTTTGAAAAGACCAATAAAATCAGGCCAGGTGCGGTGACTCACGCCTGTAATCCCAGCACTTTGG
GAGGCCAAGGCGGGCGGATCATGAGGTCAGGAGTTCCAGACCAGCCTGGCCAACATGGTGAAACT
CTGTCTCTACTAAAAATACAAAAAATTAGCTGGGCATGGTGGCATGCACCTGTAATCCCAGCTACT
CAGGAGGCTGAGGCAGGAGAATTGCTTGAACTCCAGAGGCAGAGGTTGCAGTGAGCCAAGATCGC
ACCACTGCACTCCAGCCTGGGTGACAGAGCAAGACTCCATCTAAAAAAAAAAAAAAAAAAAGAC
TAATAAAATCAATTAAACACTAGCAAAACGTATCTTGGGAAAAATGAAAAGCATGAATTGCCAA
TATCAGGAATAAACAGGCAATATTACTACAGATGCTACAAACATTTAAAAGATAATACAAAACAA
AAGTTCACATGTACTACACAAATTCCTAATAAAATACAAGTTATCAAAACTGACAAAGGGAGAAA
TAGAAGATCTAAATGGTCCTATACCTGCTCAGGAAATTAAATCAATAATTTCAAACCTTCCCACAA
AGAAAACTCTAGGCCTAGATGGCTTTACCAACAAACTCTTTTTTGTGGATGAATAGTATTCCATTG
TGTCTATATATCACATTTTCTTTATCCATTCATCTATTGATGGACACTTAGGTTGATTCCATATCTTG
ACTATTATAAATAGTGTTGCAATAAACATGGAGGTGCAGGTAACCCTTTAGTATACCGATTTCCTT
TCGTTTGGATAAATACCTAGTGGTGGGATTACTGCACTGTATGGTAGTTCTATTTTTAATTTTTTGA
GGAACCTCCATACTGTCTTCCATAATACCTTTACTAATTTACACTCCCACCAACAGTACACACATAC
ATTTTTAAAGCATAAAACAGTGCTATATATTATCCCTTGGCACATATGTATTCTGCATTTTAAAATG
GCTGAAGGATGCACTGAAGTCACAATAGCAGCAGCCTCTAGAGGAGTAAATGAAAGGACAGGGTT
TGAGGATAAGAACAAAGGAGACTTCAACTTCATTTTTATTGTCCAGTTTCTTTTATTTTTTTAAAA
AAAGGCAAACATGGTAAAATGTTAACATCTGTTCATTTTGGGTGATGGCTCATAGGGTGTTAGTCA
TATTATTCTTTGTAATTTTCCCTTTGTTTAATTTCTCAAAATGAAAACAATAAAGTCAAGATAATAG
TATCTTTCATAGTTTAGTCTTAGGCTTATTTATTGTTTAGGTATTTTATGTTCCTGTTTGTCTTAAGA
AAAAAATGTGTATAAATATAAGTATAGATGAGATAGTTAAATTTCCTTTTTTGTTTGTGTTCACAA
AACATGCTTGTTTTATTTAACATTCTTTGGTATCAAAATGTGGCCTTCATACAAACTTGTGAGGAGT
AAACCATGAGGGTTCACAGTTTTACCACAGTCTGTATGTTAGCAACCATTTCCTGTGATAGACATG
CTCATGCACCTCAAGTACTAGAAGTATCCATTTGTATTGGAGCCAAAATATCCGCAAGCAGAGAA
ACAAGAAGTCAAAAATATTTTCCTCTTTGGTGCTAAAGATTTGCTGCTGTGTGATTGTTGAGACTG
AAGTTCTGAAAGCACCAGTGTTTGCCGGATCTGTCTCCAGCTTGTCTCTACAAGGTCATTTCTAAA
AGACTGTCAAAAGAATGGCATGTCCCGCCTTTTCCACCACCGACACACCCTGCATGAAAACCCCAG
GAGCACAGAAGTCCTGCTTGGGTGAGGATAAGGGCTCTCAAAGTCTATTATCGAAGGAAGGCA
GACAGATGGGTTAACCACTCCAATGGAGTCTATACTTTTACAGACATATCACATATTATGACAATT
AATTATTAGGCTGGTGGTTCAGCAACCTTTCGAAGTGATCCCAAGATGATTGCTGTGACCATATTT
GAAAAGCTAACAGATAAATGTGGGCTTAAAACAGACTATATGTTATTCAGCTAGGCCTCAACCAT
AGGCATAAGTAGGAGTGAGGTGAGGGCCCTTGTGGACCCACCAGGGTCTTCCACAAGAGTAGAAC
TCTTGCCTTGTTCACTCCTTTCATAATCAGGCAAAGGAAGGAGTTATTCAAAAGGAGGAACTGAGC
ATGTTCAACCGAGACCCTTTTTGCTGTCCAATTTCCAGCCAGCCTGTCACCTGGATATATGTAAGCA
CTCTGGTCTGCTCTTGGCTGTGTGCTCTAAGGGAGCCCACTGGGTGTTCAGCAAGATCAATGGTGA
GGATTAAATCTTTCTAAGTCAAGGGTCAGTTACAAACAAGATCTCTCTGCTACAGATCTGAAGCTG
TATTCTCTCCAGTCAATTTGTCAGTAACAAAAGCAGTATTTTTGTTCCATCTGTCTATCTTCTACC
TCTTAATTGGTTTCAAACTTAAGAGGTGGTAGAGATTAGTAATTGCTCCCCACAAAAGCAAAAAAC
CAACCTGATGATCAATTAAGATCTCAAAATGATAAATTAATATAATCCATGATACCAGCCAAAA
ATTTGTATACCAAATTTGTTCTTACCCCCATAGTTATCCTGTCTGAATAGTTAACTGAGCACTGCTC
ACTTTTAGATTCCTTAAGAGTTGTTAAAAAATAAGTCTTTGTACTCTATCATGGCATGCATGAACTC
TCATAGCTTGAAATGACTGCATGAAAATGTACATTTTATAATTTCTTATACTATTTACATAGGTATA
```

Sequence Information

```
AGTATACACAGAAAGTGTGTTTAAATGTTTAACAGCCAAAAACAAAAACCAAAAAAAAGTCACTC
TGCTGTAACAGAACACTGTTCTGCATATGGCTAGCTGTACATTGGCAGAACATAGCGATTTTAAGG
ATGAATTAGTGTTGTAATCTCTTTGGGATTTCCTTTATATTTGCGGTGGTTTATGACTGACATTTCAT
GTAACTATAGCTTTCTGTTTGGATTTAATAAAAGATTCATTTCTGTGGCAAGATACACATTTGCACT
CCAGTGTTGAATAAAAGCTACTGTTCTGCAAGGGTATAAAATGCTGATTTATAACAACACGTTCCA
ATAACAGTGATCTAATTCTTTCAAACTATTTCTTCCCAGGTCCCAGGAACAGCATGGCTCCAGCAA
AGGATGACTCTTCTCTTCCAGAATATTCAGCCTTTAACACATCTGTCCATGCTGCAATTAGACATGG
AAATTGGAAACTCCTCACGGGCTACCCAGGTAGAGTCCTTAGCTTAGCAAACTTCCCTTCCCGTGG
TAGACAAAGCAGGGCTGTGTCCTCAGGGCAGTATCTCCAGTCTATCTGCCCTCCTGGGATTTGATT
CCCACGGCCATTTCTCTGGAAAGAGAGGACATTATCACTCTTGTTCTAACCGTTTCCCACCTCTTCC
TCTGTGGCTCCTCCTCAAGGCCCCTAAGCCCTACCACTTACCTCACTTTGCTCAGATACCTGAAATC
TTAAATTTGTCTTTCTAATCTTTCATGATCCCTCCTGATATATGTCCTAGAAAGACAACTATTTATTCA
GGGTTTTCTTTTCCCAATTCTAAGACTCCGCCTGTTCCCAATTACACAGCTTCCATCATTGTCATGG
TGCAAGTAAGCTTTCCCAGTGGATCATCAAGGAGAAGCTTACCGAAGTAACAAATGCCTTTTGCAA
AACATATCTCTGGGGCTGCTGAATGAGGAGATAGGAAGAAATGGTTTAACCTACTCGTCCTAACC
AAAAAAAAAAAAAAAAAAAAAAAAGAGAGAGAGAGAAAGACAGAGAGAATTAACTGTAGC
AGGGGTGAAAGGAAGAATGTCACTCTTATGCTTCATGGAAAATACGGATTTTAAATATATGTGG
CTATCAAGCACAGCACATTTAGCTAACAAAGAGAGTCTCTGAGAGCTACACCCTCAACCAGTGGT
ATAGCTGGGGAAGGAGGTTGCTCCTCTGATTATATTCTCTAAGAGTGATATCTTTTCAATACTTTTA
AAATATGTGGGATGATGGTTAAGGCTGTGATGTAATTAATCAATGTTTACAATGAGAACATTTTTG
GCGTTTGCAATATGACAAGTCTTTTTTGACTGGGATTGTCCCATGTATTGCAAGACTTTAGCATCAC
TAGCTCATGCCCACTAAATGCCAGGAGCACCCCTATGCCCTAGTCCTTGTGACAAGGACATACACA
CATGCACACGTTTCTGGGTGTCCTTGCTTGTGAAGCAGTGAGACATGTCTAGTTAAAGCACCAG
AAGTCAAGTCTGAGAAGCATCTAGAGACAGCATCTAGGGCCGCATCTTTTTATGTTTCCACACCCA
CAACCCAGTGCAGCCTTGGCCTCAGACTCCTTCCCTGAAATTAGAACCTGCCTCTGTGCTTCTCCCT
CAGTAAACTGTTTTGTTTTCTTTGCTAGGCTGTGGTTACTGGTTCCCTCCACCGTCTCAATACAATG
TTTCTGAGATACCCTCATCAGACCCACCAACCAAGACCCTCTGGCTCTTTGATATTGATCGGGACC
CTGAAGAAAGACATGACCTGTCCAGAGAATATCCTCACATCGTCACAAAGCTCCTGTCCCGCCTAC
AGTTCTACCATAAACACTCAGTCCCCGTGTACTTCCCTGCACAGGACCCCCGCTGTGATCCCAAGG
CCACTGGGGTGTGGGCCCTTGGATGTAGGATTTCAGGGAGGCTAGAAAACCTTTCAATTGGAAG
TTGGACCTCAGGCCTTTTCTCACGACTCTTGTCTCATTTGTTATCCCAACCTGGGTTCACTTGGCCCT
TCTCTTGCTCTTAAACCACACCGAGGTGTCTAATTTCAACCCCTAATGCATTTAAGAAGCTGATAA
AATCTGCAACACTCCTGCTGTTGGCTGGAGCATGTGTCTAGAGGTGGGGGTGGCTGGGTTTATCCC
CCTTTCCTAAGCCTTGGGACAGCTGGGAACTTAACTTGAAATAGGAAGTTCTCACTGAATCCTGGA
GGCTGGAACAGCTGGCTCTTTTAGACTCACAAGTCAGACGTTCGATTCCCCTCTGCCAATAGCCAG
TTTTATTGGAGTGAATCACATTTCTTACGCAAATGAAGGGAGCAGACAGTGATTAATGGTTCTGTT
GGCCAAGGCTTCTCCCTGTCGGTGAAGGATCATGTTCAGGCACTCCAAGTGAACCACCCCTCTTGG
TTCACCCCTTACTCACTTATCTCATCACAGAGCATAAGGCCCATTTTGTTGTTCAGGTCAACAGCAA
AATGCCTGCACCATGACTGTGGCTTTTAAAATAAAGAAATGTGTTTTATCGTAATTTATTTCCCCC
CAGCCATTGCTCACTCTGTCTAGACTTCCTGCCACTTCCAATTCTTCTGTGGCTTTTCCTGCCTTTCC
TTTTGACCTCAGTAGTCCTATCCCTGGGAAGGCCACTTTGCTTCTCTACCTGAGCACCCCTGATTTC
TGGAACGCTGCTGAGCCCTGCCTTACTTTTGCCCCTAGGGCTGAAGCTAGAGGCCTCCCCGTAATA
GGCGGTGGAGTTGCTCTGTGAGGATGTTCATGGTAGACACTAAGAGGGCTGGGTGGGAGATGCTT
GGCTCTGTGGCATCTGTTCAGCGAGGCTTTTCCTATATTGCATGGAGTTAGTCATTGTGATTGTAGC
TTTATTTCATAATATATTAAGACTTGCACTGCTATTTACTAGCAGTGAGAAGAAACCTCAGGAAAG
GATATGAAAAAGCAAGTGGCCAGTGTCTGGGATACTGGGCCTTGGTAAAGCAGAGGAGGGCACAC
CCACAGTCCTCTTATTCTCTGTTTTACTGCTTGTTTTGAGGTTCTGGGGTCTGGCAAAGAGGATGCA
GTTTGACACCTGCAGCCCTTTCTCAATCCCACTAATGTCTTACTAATGTGGAACAGTCCATATTAGC
TCCAGAGAGTGTCAAACCCAGAGAAATGTGTGCAAAAATGATACTCTTTTCTGCATTAGCCCCACC
ATTGTGTTCACCAATGCTTGGAACACTGCCTGAAGGCACTCATTTTTTAATTTTTATTTTATTTTTAA
TTTTTTATATCTTTATGAGACGATCTCACTCTGTCACCAGGTTGGAGTACAGTGGTACAATCACAAC
TCACCGTAGCCTCAAACTCCTGGGCTCAAGTGATTCTCCCACCTCAGGCACCCAAATAGCTGGAAC
TACAGGCATATACCGCCACACCCAGCTAATTTTATTTTTTGAAAAGACAAGGTTCCCTATGTTGCC
CAGCTGGTCTTAAACTCCTGGGCTCCAGCAATTATCCCAGCTTGGGCTCCAAAAGTGCTGGGATTA
CAGGCATGAGTCACCATGCCTGGCCTCATTTTTTAAAACAAATGAATAAATGGACAAATGAGTAA
ATGAGAAAGTCTCACACCATGAAAGATGCTAGTCCAATGAGCTGAATACAGAGGTAATATAAATG
TCTTCCAGCTGTTGCTTTTCTGTTCTCAAGCTGCCCCTCCTGGGGTAGGAGCATAATCTACATCACT
GGGCAGTCACAGGACACTCTATAGCAAGGTTGTAGCGTCCTCTCCAGTGGGGGGAGAAAAGGAAC
TGTGCCTACCAAAGGTACTCTCTTGTCAGCAATTTCCATTTCTATCTTTATGGGACACTAGAAACT
AAAAGCAACAAATAATCTGATATAAGTCCTTGTATAGTCATCCTTCAATTCAGTAGCAATATTTTC
TGGTCACTACTAACCTGTATTGTATTAAAATGAGACTATTGGAAGGAAATGGTGCTAAAACTAATA
ACATCTCTTACCAACCTTTACCCAACTCCTGGGTTGGCAAACAGCTGACCAAACTGCCATCACCTC
CCACTTGGAAGTGTATGGCCGACAGCATGAAATAGCTGAGCCCAGATGTTCCTTCTGCATCCTCCG
AATCCCAGGGCTGGGTGTAGGTAGCCGTTGGAGGCCATCGCTACAGGGCACCTATCTGTTATCGCT
GCTGTCCTCCCAACAGCTGTCTCCAGTTCTAGTTCCTTGGTTTTCAGGCACAGTGGGGGATGTTCTG
CACCCAGTGGACTTCAAAAGAGTTTTGAAGACTTAATTTTTTGTAAAACAAGTACTTGAGATTTTG
GTTTATCCATAATAGAATGTATTTCATTAGATTCTCTGATTCTATATAAGAATGTGAAAAGATTGAT
ATATTGTTGTTAGAAATAATGTTATTTCTTTCCAATTTTTTTTTTTTTTTTTGAGATGGAGTCTCG
CTCTGTCACCCAGGCTGGAGTGCAGTGGTGTGATCTCGGCTCACTGCAGCCTCTAACTCCCAGGTT
CAAGCTATTCTCCTGCCTCAGCCTCCCAAGTAGCTGGATTACAGGCATACACCACCACGCCTGGCT
ATGTTTTGTATTTTTCGTAGAGATAGGGTTTCACCATGTTGGCCAGGCTGGTCTCAAACTCCTGACC
TCAAGTGATCCACCCACTTCAGCTTCCCAAAGCACTGGGATTACAGGTGTGAGCCACTGTGCCCGG
CAAATTTTTTTACCTTTACAGAAGGTTTTGCTTATTTAATTGTGAGCTCATTTTTCTTTGTTACTTTT
GTCCCCCAGATTTGGGGACAAAATAAAATTAATCTTTTAAAATGTGTCAGCCATATGTATGGGG
CTTCCATTTGGGGTGAGGAGAAAGTTCTGGAACTAGATAGTGGTCATGGTTATACAACATCATAAA
TGCAATTACTGCCACTGAATTGTATGTTTTAAAGTGGTTAAAATGTTAAGTTTTATGTTTTATTACA
ATTTTTAAATGTGTCAACCAACTTTATAGTACATAAATTATATCTCAGTAAAGCTGTTAAATAAAT
```

-continued

Sequence Information

AAATATAGTAAAAATTTTAGAACTAAAAAAA

SEQ ID NO: 6-the cDNA sequence of the P-glucuronidase gene
(Gene ID: 2990)
GTCCTCAACCAAGATGGCGCGGATGGCTTCAGGCGCATCACGACACCGGCGCGTCACGCGACCCG
CCCTACGGGCACCTCCCGCGCTTTTCTTAGCGCCGCAGACGGTGGCCGAGCGGGGGACCGGGAAG
CATGGCCCGGGGGTCGGCGGTTGCCTGGGCGGCGCTCGGGCCGTTGTTGTGGGGCTGCGCGCTGG
GGCTGCAGGGCGGGATGCTGTACCCCCAGGAGAGCCCGTCGCGGGAGTGCAAGGAGCTGGACGG
CCTCTGGAGCTTCCGCGCCGACTTCTCTGACAACCGACGCCGGGGCTTCGAGGAGCAGTGGTACCG
GCGGCCGCTGTGGGAGGTGCGATCTCGGGCAGGGCCGGGAGGCGCCCGAAAGCCCGGCGGTGG
GAGTAGGGGAGCCCGGGCCCCCGCAGACTTCTTCCCCTGGGCGTCTCCGAGCTGGGGCCCGCAG
GAGGTTAAAGGTCAACGGGCTTGGGGGCGCCGGCTTGGGGGACGGGGGAACAGGAGCACCCTGG
AGGGCCGGGCGGATTAGGCAGGAGGAGAAAAGGCTCTTGCCGAGCCCTTTCCCGAGGTAAAGGC
TGAGTCTGTGCAGTATCCTTCCTTTCAATATTTATTTTTAATTTTTAAAAATTTTTTTGAGACTGGGT
TTGCACCTGTTTCCCAGGCTGGGGCGGAGTGGCGCCAGCCTAACTTCTGAGCTCAAGCGATTCTCC
CGCCCCAGCCTTGCAATTTAGGGGGTGCCAACACGCCTGCTAATTGAAAAAAAAAAAATTATCT
GGGCTCGGTGGCTCACACCTGTAATCCCAGCACTTTGGGAGGTGGAGGCGGGCGAATCGCCTGAG
GCCAGGAGTTTGAGACCAGGCTGGCCAACATAACAGGGTGAAACCTCATCTCTACTAAAAATATA
AAAATTAGCCAAGTGTGGTGGTTCATGCCTGTAATCCCAGCTACTTGGGAGGCTGAGTCAGGAGA
ATTGCTTGAACCCGGGAGTAGAGGTTGCAGTGAGCTGAGATCAGGATGCCACTGCACTCCAACTT
GGGCGACATAGTGAGACTACGTCTCCAAAAAAAAAAAAAAGGCAAAAAAACTTAAAAAAAAAA
AAAGATACAGGGTGTCACTATTTACCCAGGGTGGTCTCGAACTCCTGGCCTCAAGCCATCCTCCCA
CGTTGACCTCCCAAAGCGCTGATTACTGGCATGAGCCACCCACACACTCTGGCCACAGCGGCATGC
ACTGCACAGAGCTGGGCCCGGGGATCGGGAGAAGGTGACAGTTTAGATGTCCTGAGGTCAGCTCT
GCCGAGGCAGGAAGTCCCTTGGTTTTCAAGGTTCACATAGAGGACAGGACATGACATCAGGCCCA
GGACGCCACCCTGTTCCCCTCCTGACTTGGATGTGATCTGCAGAGAAGTGGAACTGGGTGAGGTC
TGGGCGGCTTTTGCCTGGTCTACATCCTCTTATTCTGACTTTGCAGCATTCAGTACAGGAGGGAAA
GAGGAGGGGCTGGGTGCCAGTGTGCACCCCACTCACAGTGTCCTAAGCAAAGCTCCCCCCATTC
CTCCAACCAGCCTTCCTCCCTGTGACAGGCAGTGGCCATCTGCCTCTTAGTCACAGGTCTGAACCTT
CTTGCCTCTGGCTGGGATGTGGCCCTGGGCTTGCTCCTGTCTCAGGAGATATTGTGCCCCATCCACT
CTGAGGAGGAACTCCTGGCCCCACTGGCCCAGGTGCACAGATCGCCCTGGCAGTTGACCTGTCATC
AGCAAGTTATCTGTCCTTTCTGCCAAGAATCCCCGCTATGTGTCAGGGCTTGTCTAGGCCTGGGG
GCACAGCCGTGCAGCACACTGGTCCTGGACCCTTTTGGGGGCCTAGGAGCTGAGCCCGGCTCTTCT
CTCCACAGTCAGGCCCCACCGTGGACATGCCAGTTCCCTCCAGCTTCAATGACATCAGCCAGGACT
GGCGTCTGCGGCATTTTGTCGGCTGGGTGTGGTACGAACGGGAGGTGATCCTGCCGGAGCGATGG
ACCCAGGACCTGCCGCACAAGAGTGGTGCTGAGGATTGGCAGTGCCCATTCCTATGCCATCGGTC
AGTGCGGCCAGGAGCAGGCAGGGCGGGTGGGGGGCACGGCTGCTGAACAGCATGGGACCTCCA
GCTGCCACCCACGGCATGTATGCTGGGGTGGGATGGTGGGGGTCCTGCCCTGCCCTGCCCTGGGG
GCTGTGCCCTGTATAGGGGGATAGGTAGCCTGATCTACCCCATTGGGATGTCATTCTTCCCGTCTG
GCTGGAAGGCCCCGGAGCCCCATGCTGCAGGTTATGTGAGGGAGTGCCCGATAGTAGGGCGCCTC
CTCATGCCCTGACCTGCAGCCCCCTCCCCGTATCTCCTGTGTCTGCAGTGGGTGAATGGGGTCGAC
ACGCTAGAGCATGAGGGGGGCTACCTCCCCTTCGAGGCCGACATCAGCAACCTGGTCCAGGTGGG
GCCCCTGCCCTCCCGGCTCCGAATCACTATCGCCATCAACAACACACTCACCCCCACCACCCTGCC
ACCAGGGACCATCCAATACCTGACTGACACCTCCAAGTGGGTACCATCCTGCCTCCATTGCACACA
CCCACCTTCCCGCCCCACCCTGTGGTCTTCCTGGTAGGGACTGGGTGGCCTTCACAGAGTGGAGGC
CTTGGATCTGGGGAGGCCAGGGAGGCCTGTGAGCTGAGGTCAGGGGACCCAGAGCAAGGGCCCA
GCAAACCACAGTCCTCCCATCCTAGGTATCCCAAGGGTTACTTTGTCCAGAACACATATTTTGACT
TTTTCAACTACGCTGGACTGCAGCGGTCTGTACTTCTGTACACGACACCCACCACCTACATCGATG
ACATCACCGTCACCACCAGCGTGGAGCAAGACAGTGGTGAGGGCTTCTGGTAGGATCCTCTCAGC
GGGGCCCAGGGTGGCTCTGTTTGTTCCCTGTTTGGAAAGCTCTCCCAGGAAAAAGGTGCTCCCAGC
ATCTCTACACCCTCACAGATTCCCTTCCACCTATGAAGCTAAAATTCAGCCTGTGTGAGCGGATAC
GGGCTCCCAAAATCACCCGTGTGGTTGACCTCGCTAGGAGAAGAGGGGTCTGGCCTAACGTCACA
CAGCTCGGGGTGGCAATCCTGTCCCTTCTCTATGGTGCTACTCTCACTCCATCTCCCCTTGCTACAC
ATCGTGCTCAAGGAACAGGCAGCTTCGGTGGGGGGGCGCCGGGCATGGTGGCTTATGCCTGTCA
TCCAGCACTTTGCAAGGAGGCCCTGGTATAAGGATCACTTGAGGCCAGTAGTTCAAGAGCAGCCT
GGGCAACATAGTGAGGCCATCACCACAAAAAATTAAAAAATTAGCCAGGGATGGTGATGTGTGCC
GGTAGTCCCAGCTGCTGAGGCAGGAGAATCACTTGAGCCTGGGAGTGTCAAGGGTGCAGTGAGCTA
TGACCACACCACTGCACTCTGGTCTGGGCAACAGACGCAGACCCTGTCTTTCTTTTTTCTTCTTTT
TTTTTTTTGAGCTGGAGTCTCGCTCTGTCGCCAGGCTGGAGTGCGATGGCGTGATCTTGGCTCACTG
CAACCTCTGCCTCCCGGGTTCAAGCGATTCTCCTGCCTCAGCCTCCCGAGTAACTGGGATTATAGG
CACCCGCCACCACGCCCGGCTAATTTTCTATTTTTTTTTAGTAGAGACAGGGTTTCACTCATTGG
CCTGACTGGTCTTGAACTCCTAACCTCAGGTGATCCACCCTCCTCGGCCTGCCAAAATGCAAGGGT
TACAGGCGTGAGCCACTGTGCCCAGCTGGGATACCCTGTTTTTTTTGTTTTTGTTTTTGTTTTGAG
ATGGAGTCTTGCTCTGTTGTCCAGGCTGGAGTGCTGTGGCGTGTTCTTGGCTCACTGCAACCTCCGC
CTCCCGGGTTCAAACAATTCTCTTGCCTCAGCCTCCTGAGCAGCTGGGATTACAGGCGTGTGCCAC
CACGTCCAGCTAATTTTTGTATTTTTAGTAGAGATGGGGTTTCACCGTTGGCCAGGCTGGTTCAA
CTCCTGACTTCGGGATCCACCCGCCTCAGTCTCCCAAAATGCTGGGATTACAGGAATGAGCCACAG
CGCTCGGTCTGTATTTAAGAAAAATTTTTGTTTTAAGTTTTTTTTCTTTTTAAAAATATATCTTTTTC
AGGGCGGGCGCGGTGGCTCATGCCTGTAATCCCAGCACTTTGGGAGGCCAAGGTGGGGGATCAC
GAGGTCAGGAGATCGCGACCATCCTGACTAACATGGTGAAACTCCGTCTCTACTAAAAATGCAAA
AAATTAGCCGGGCATGGTGGCAGGGGCCTGTAGTCCCAGCGACTCGGGAGGCTGAGGCAGGAGA
ATGGCGTGAACCTGGGAGGCAGAGCTTGCAGTGAGCCTGAGATTGCATCACTGCACTCCAGCCTAG
GGGACAGAGCGAGACTCCATGTCAAAAATAAAATAAAAAAATATATATATATCTTTTTCTTTTT
CTGAGATGAGGCTTGCACTGTGGCCCAGGCTGGAGTGCAGTGGTGAGATTATTGACAGCCGTTGTG
GGGCCGCGGTTCTAAGTTTAAAAGAATTTAGGCTGGGTGTGGTGGCTAATGCCTGTCATCCCAGCA
CTTTGGGAGTCCAAGGTGGATGGATCGCTTTAGCTGCAAAGTTTGAGACCAGCCTGGGCAACATAC
TGAGACCCTATCTAAGAAAAAATAAATAAATAAATAAATAAATGAATAAAAAAGAATTTAA Sequence Information

```
AAAAGAATCCCACAGCAAAGACAATGCACCATAGAGCAATTTATTGCCAAGGAAAGGTATTTTGG
AAGTTAAGTTTAGAACAGCCTGGGTGCACTGGCTCATGCCTGTAATCCCAGCACTTTTGGAGGCCG
AGATGGGTGGATCACTTGAGCTCAGAAGTTCAAACCAGCTTAGCCAACATTAGCTGGACATTGTG
GTGTGAGCTGCAATCCCGGCTACTCAGGAGGTTGAGATGGGAGAATTGTTTGAACCCGGGAGGT
GGAGGTTGCAGTCAGCTGAGATTGCAACACTGCACTCCAGCCTAGGTGACAGAGTGACACCCCCA
TCTCAAAAAAAATAGTGAAGTGCAAAATGCACAGTTCACCCTGAGACACAGAATTCAGGACAGGC
TGCTCGTAAGGATGAGACAGCCACCGATTATTACTGGGGAAACTCCCTTTCTGGGAGTCTTCCGTGA
TGAATTCCTAAGGAGCTGGGAAGAGGTGTTACTGTAAGCACGTTCTGGGCCGTCCTCTGGTTGCAC
ATGCGTAGTAGCTGTACATGCTTGTTCACACGTCACGTGTCTCAGTGCCGTGGTTGGCATGTCTGA
GGGACACGGTCACTTCCTTGACTACCTATCCTGCCTCAAGATCATAGCTCACTGCAGCCCCGAACT
CCTGGCTCAAGCAATCCTCCCACTTCAGCCTCCCAAGTAGCTGGGGCTGCCGGGGCTGCAAGCACG
CACCACCACGACCGGCTGATTGTTTGTATTTTTAGGGAAGAAGTGGTTTCCCTATGTTACCCAGGC
TGGTCTTGAACTCCTGGTCTCAAGCGATCCTCCCACCCCAGCCTCCTCAAGTGTTGGGATTACAGG
TGTGACCACTGCACCTGGCCAAAATCTTTTTTTAAATTAAAAAAAGCACCGGGTGCGGTGGCTCAC
ACCTGTAATCCCAGCACTTTGGGAGGCCAAGGCGGGTGGATCACTTGAGGTCAGGGGTTCAAGAC
CAGCCTGGCCAATATGACAAAACCCATCTCTACTAAAAATATAAAAATTCGCCAAGCATGGTGGT
GCACGTCTATAATCCCAGGTACTTGGGAGGCTGAGACAGGAGAATCACCTGAACCCCAGAGGTGG
AGGTTGCAGTGAGCCGAGATCATGCCACTGCACTCCAGCCTGGGGGACAGAGTGAGACTCCGTCT
CAAAAAAAAAAAATAAGAAATTAAATTTAAAAAAAGCAACAGAAACAAATGGCTGCCTGGCAGC
GGTGGCTGCAGGGCGCTCCTGTTTGTGTGACTCAGGTCGTGTCCCTCCCTCAGCCCTGGTCTCTCTT
GTTTCTTGCAGGGCTGGTGAATTACCAGATCTCTGTCAAGGGCAGTAACCTGTTCAAGTTGGAAGT
GCGTCTTTTGGATGCAGAAAACAAAGTCGTGGCGAATGGGACTGGGACCCAGGGCCAACTTAAGG
TGCCAGGTGTCAGCCTCTGGTGGCCGTACCTGATGCACGAACGCCCTGCCTATCTGTATTCATTGG
AGGTAATGGTGGTTTGGGACATGCCTAAGGGAGGTCTTTTGCCCCCATGTGGTGACCCTGGCTTCA
GCAGGAGCCCAAGACAGGTGGATGGGCAGGCATGGTCCTCTGAGCTTTCTGATGTTTCTCACCCTT
GGTGGGAGGCCCATTTTCTTTTTTTTTTTTTTTGAGATGGTCTCACTCTGTCACCCAGGCTGGAG
TGCAATGGCCTGATCACAGCTCACTGCAGCCTTGAACTCTCAGCCTGCAGCAGTCCTCCTGCCTTG
GCCTCCTGAGTAGCTGGGACTACAGGCACATGCCACCATGTCTGCCTAAATAAAAAAAATTTTGTA
GCCTGGGCAGAGTGACTCATGCCTGTAATCTCAGCATTTTGGGAGGCTGAGGTGGGTGGATCACTT
GAGGCCAAGAGTTCAAGACCAGCCTGGCCAACATGGTGAAACCCCATCTCTACTAAAAATATGAA
AATTTGCTGGGCATGGTGGCGAACACCTGTAATTCCAGCCACTCGGGAGGCTGAGGCAGGAGAAT
TGCTTGAACTCAGGAGGCAGAGGCTGCAGTGAGCTGAGATCACACCACTGCACTCCAGCCTGGGG
GACAGACTGAGACTGTCTCAGAAGAAAAACATTTTTTTTTATAGAGATGGGGTCTCAGTCTGTCA
GCAGGCTGGTCTTCAACTCCTGGACTCAAGTGATCCTCCTGCCTTAGCCTCCCAAAGTGTGGGAAC
TCCAGGCATGAGCCACCTTGTCTTGTCAAAGGGAAGGCCATGTTTTGAAGGGCAGGTTCCCAGGGT
CAGCCAGGGTAGGGCAGAACCTCTGATTGCTGCATCTCTGCTTACAGGCCCAGAGGCAGCTGCTG
GGGTGCACGAGGGGCCTTCCTGCTGGAGGGCAGGCCGGATGGGGCTCAGGCTGTCGGGGTGCTCA
CACCTGGTGCTTTGGCTGTCATAGGTGCAGCTGACTGCACAGACGTCACTGGGGCCTGTGTCTGAC
TTCTACACACTCCCTGTGGGGATCCGCACTGTGGCTGTCACCAAGAGCCAGTTCCTCATCAATGGG
AAACCTTTCTATTTCCACGGTGTCAACAAGCATGAGGATGCGGACGTGTGTTGGGGCTCCTGGGTC
CTTGTCGGGGCTGCTTCTGGTCACCCTCCACTTTCGCCTTCCCTGTGTCCTGCAGTTGAGGGCAGCT
CAGGGCAATGAGGCAAATGGCTCCAAATGGAGAGGGGCTCATGGGGTGGCTCTCCAGGGTCCTG
GCTCTCAGAGGAAGTGCAGCTTCGACAGGGACAGGGGTCACTTGGCTCTGCTATCTCCTAGATCCG
AGGGAAGGGCTTCGACTGGCCGCTGCTGGTGAAGGACTTCAACCTGCTTCGCTGGCTTGGTGCCAA
CGCTTTCCGTACCAGCCACTACCCCTATGCAGAGGAAGTGATGCAGATGTGTGACCGCTATGGGAT
TGTGGTCATCGATGAGTGTCCCGGCGTGGGCCTGGCGCTGCCGTGAGTCTCTGCTGTGCACCTGCT
CCGCCTGCCCAGCCCGGGGCGTCACCGTGACCCTCTGTCCCTTCCCTCCTGGCCCGCAGGCAGTT
CTTCAACAACGTTTCTCTGCATCACCACATGCAGGTGATGGAAGAAGTGGTGCGTAGGGACAAGA
ACCACCCCGCGGTCGTGATGTGGTCTGTGGCCAACGAGCCTGGTCCCACCTAGAATCTGCTGGCT
ACTACTTGAAGTGAGTGCTCCCTCCCTGCCCTCGGCTAGAGTGGGAAGGAGACCCTGGCAGGTGG
CTGGCCTCGGTGGGCATGTGCTGTTCAAGATCGGCCTCGTGTCCAGCCCAATGGGAAGGCCGTCCA
TACCCAGATAGTTCAGGGGACCAAATATCTACCCACCCAAATTGTGGTTTTCTTTTTGTTCTTTTT
TTTTCTTTTTGAGATGGAGTCTCACTATATGGCCCAGGCTGGAGTGCAGTGGGGTGATCTCCGCTC
ATTACAACCTCTGCCTCCTGGGTTCAAGTGATTCTCCTGCCTCAGTCCTCCTGAGTAGCTAGGATTAC
AGGCACCCATGAACCACTGTGCTGGGCTGTTTTTTTTTTTCAAAATGGGTTCTCACTCTGTTGCC
CAGGTTGGAGTGCAGCGGTGCAGTTTTGGCTTACTGCAGCCTTGACTTCCCAGGCTCAGGTGATCC
TCCTGTCTCAGCCTCCCAAGTAGCTGGGATTCTAGATGTGTGCATCACGCCCAGCTAATTTTTGCT
TTATTTTTTATTTTTTGGATATGCAGTCTCCCTCTATTGCCCAGGATGGAGTGCAGGGGCATGATCT
CAGCTCACTGCAACCTCTGCCGCTCAGGTTCAAGTGATTCTCCAGCCTCAGCCTCCCGAGTAGCTG
GGATTACAGGCACATGCCACCACGCCCAGCTAAGTTTTCCTTTTTTCCTTTTTATGAGATGGAGTCT
CACTCCGTGGCCAGGCTGGAGTGCAGTGGCGCAATCTCGTCTCACTGCAACCTTCACCTTCCAGGT
TCAAGTGATTCTCCTGCCTCAGCCTCCTGAGGAGTTGGGATTACAGGCACACGCCAACATACCCTG
CTAATTTTTGTATTTTTAGCAGAGACGGGGTTTCACCATTTTGGCTAGGATGGTCTCGATCTCTTGA
ACTCATGATCCGCCTGCCTCGGCCTCCTGAAGTGCTCGGATTACAGGCGTGAGCTACCACGCCTGG
CCAACTTTTGCATTTTTCAGTAGAGACGGGGTTTCACTATGTTGGGCCAGGCTGGTCTTGGACTACT
GACCTCAGGAGATCCACTTACCTCGGCCTCCCAGAGTGCTGGGATTACAGGCGTGAGCCACCGTGC
CCGGCTAATTAGAGACTGGGTTTCACCATGTTTGCCAGGCTGGCGTGGAACTCCTGGCCTCTAGTG
ATCCTCCTGCCTCACCTTCCCAAAGTGCTGGGATTACAGGTGTGAACCACCACACCTGGCCCCCTT
TTCTTCCTTACAATCGTGCAGTTCTAACTCAGCGTTCAGAGTTGGATTTTTCACTTGGGGTAGAAGC
AGGAGAGGTGGTAGAAATGCCTCTTGACTCATACAGCACACCCCAATTTCATGCAGTGCTTTGGGC
TGAGCCAAGTCTGCAGCAGGCAGAAGGCTCTGAGAAGTTGTTGCAGCCTGGGCCAAGGACAATTC
AGAGCTTGGGGGCACAGGGGTGTGCTCAGCAGGACTGGGTGGACAGGCCCTTTGTTGCGAAGGGG
AAGAGTACAGGCTTCCAGGAGCAGGTGTTTGAGGCTTCTTTGGGAGGTGGCCAGAGGAGATGCCT
GTTTTCTGGGGCAGGATTTGGAGGGAGCCACCCAGGCTGGAGAGGTTCAGCCAGGCTGTCACAGG
CTTTGAAGTTTCCCATCTGAGAGCCTGGCTGTTGGAGAGTGTGGGTTTGGAACTTGAGGCTAGGGG
GTTCTTTTCTGATCTGTGCCAGCCACAGCCTTCGGATAGGCAGAGCAATGATGGGGAGGGCGTAA
AAGAAGAAATGAACTGAGGAAAGAGAAGAGGAAAACAGGCTTCAACAACAGTCTAGGCTGGGTG
```

-continued

Sequence Information

```
CGGTGGCTCACGCCTGTAATCCCAGCACTTTGGGAGGCCAAGGTGGGTGGATCACCTGAGGTCAG
GAGTTTGAGACCGGCGTGGCCAACAGATATTGAAACCCTGTCTCTACTAAAAATAAAACAATTAG
CGGAACACAGAGGTGGGCGTCTGTAATCCCAGCTACTTGGAGGCTGAGGCAGGAGAATTGCTTG
AGCCCAGGAGGTGGAGGTTGCAGTGAGCCAAGATCATGTCATTGCACTCCAGCCTGGGCTACAGA
GTGAGATTCTGTCTCTCAAAAAAACAAAAACAAAAACAGTCTGTACTGTGGAGGCCTCGGGCAGG
TGCCAGGAGCTCTGAGCACAGACGGGTCCCTCTGTTGGGTTTTTCTTCCCTTCTAAGGGCCATTTCT
TCTTATTTATTTATTTTTTTGAGATGGAGTTTTGCACTTGTTGCCCAGGCTGGAGTGCAATGGC
ACAATCTCGGCTCACCACAACCTCTGCCTCCTGGGTTCAAGTGATTCTCCCGCCTCAGCCTCCCGA
GTAGCTGGGATTACAGGCATGCGCCACCACGCCCAGCTAATTTGTATTTTTAGTAGATATGGGGTT
TCTCCGTGTTGGTCAGGCTGGTCTCGAACTCCCAACCTCAGGTTATCTGCCTGCCTCAGCCTCCCAA
ATAGCTGGGGCCACAGGTGTGTGCGGCCATGTCAGGCTAAGTTTAAATTTTTTTTTTTTTCCGCA
AGATGGAGTCTTGCTTGTTGCCCAGGCTGGAGAGCACTGGTGCAATTTTGGCTCACTACAACCTCT
ACCTCCTGGGTTCAGGCAATTCTTCTGCCTCAGCCTCATGAGTAGCTGGGATTCCAGGCGCATGCC
ACCATGCCCAGCTAGGTTTTTTTGTATTTTTTGTAGAGATAGACTTTTACCATGTTGACCAGGCT
GGTCTCAAACTCTTGACCTCATGATCCACCCGCCTCGGCCTCCCAAAGTGTTGGGATTACAGGCGT
GAGCCACCATGCCCGCCCCTAATTTTTAAATTTGTTGTAGAAACAAGGTCTTGCTATGTTGCCCAG
GCTGGTCTTGAACTCCTGGTCTCTGGTAAAACTCCCAAAGTGCTGGGATTCTAGGCGTGAGCCGCC
TTGCCCGGCACTTGCACCATTTCTCTGCATGCGTCTCCACTCCCACTGCCCAGGACCTGTGGACTTA
GATTTGAGTCACTGCTGAGCACCTCGCACCTAGCCCCATGCCTGCCTCCCAGCCTGCACTCCGTTTG
CTTGATGCATTAATAAATATCCCTCCCAAATCTGCATCCATCCACCTCCTGTGTTCAAGAGCTGTTT
CAGGGCGTCAACCTCATTTTTGCCAGTGTCCAGCCTAGTGACCTCAGCTCTGTGTACCTGGAAGAG
TGGCTGCTCCTCTGGGGGTATAGGATTCGGAGATGGGGGTAGAAGGAGTGATGTTAGAGAGCTCG
GTCTAGGACTAGAGGATCATATGCCCTTATGTAAAATACATCTCAAGTTAGGGAAGAAAGCAGCG
GCTCCATGCTTTTTTTTTTTCCCCTTTGTTTTTGTTTGTTTTGAGACAGGGTCTTGCTCTGTGG
ACCAGGCTGGAGTGCAGTGGCATGATCTTGGCCCACTGCAGATCCTCCTTCTGGGTTCACGCCAT
TCTTCTGCCTCAGCCTCCTGAGTAGCTCAGACTATAGGCGCCGGCCACCACGCCCGGCTAATTTTTT
GTATTTTTAGTAGAGACGGGGTTTCACCGTGTTAGGATGGTATCGATCTCCTGACCTTGTGATCTGC
CCGCCTCGGCCTCCCAAAGTGCTGGGATTACAGGCGTGAGCCACTGCGCCCTGGCCGCTAATTTTTG
TATTTGTAGTAGATAGAGTTGGGGTTTCACCATGTTGGCCAGGCTGATCTTGAACTCCTGACCTCA
AGTGATCCACCCACCTCGGCCTCCCAAAGTGCTGGGATTACAGGTGTGAACCATCGTGCCTGGCCC
CGTGTTGTTCTGGCGGTGGAAGATGGGACAGAGAGGATGGGAGGGTGTCTGAGCCATTCCTGG
ACTGATGGAACCTGTTTCTTCTGCCTTTTGTGGACAGGATGGTGATCGCTCACACCAAATCCTTGG
ACCCCTCCCGGCCTGTGACCTTTGTGAGCAACTCTAACTATGCAGCAGACAAGGGGGTGAGCCTGG
GGGTCCCCACCCCACTTCTCCCTGCCTTTGCCTGGGCTTGTCCTGAAGCCTGGTCATGGGAACAGC
CAGGAAGAACCATGCGCTGCCAGTCTGGGTTTTATTTCATTTTCTTTTTTACTTAAAAAGATAGAGA
CAGGGTCTTGCCATGTTGCCCAGGCTGGTCTCCAACTCCTGGGCTCAAGCAATCCTCCTGCCTTGG
CCTCCCAAAGGGCTGGGGTTACAGGTGTGGGCCACCACACCCCGGCCGCAGCCAGTCTGTTTTCAC
AGATGGTCTTTGGGTTAATGAGAATTCTCCCCCTGCTTACTCGCCAGGCAGTGTGGCTTTCTCAATC
CAAGGAGGCTGGGCATAGGGAGATGGGATTTGTTTGCTCAGTTTGGACTCAGCATTTTTTGCACTT
CGATTTAATAGACTCATAAAAACATCAAAGATTTAAGGGAGCTTAGAGTTCATCTGGCCCACACCTG
GCTGATGAGAATCTCTAGGGGAAGTTTTTATGAAATGCCAGATCTCTGCATTCTGAGGTCCTGATT
TAGTACGTCCAGGGTTGGAACTTGAGTTTTTCTTTTTCTTTTGTAGAGGCAAGGTCTTACTCTCTTG
CCCTGGCTGGAGTGCAGTGGTGCAATCACAGCTCACTGCAGCCTTGAATTCCTGAGCCCAAGTGAT
CCTCCTGCCTCAGCCTCCCGAGTAGCTGGGACTCCAGGTTTTCACCACTGCGCCTAGCTAATTTTAT
ATCTTTTTGTAGAGGTGGCATCTCTCTATGTTGCCCAGGCTGGTCTCAAAGTCTTGAGCTCAAGTGA
TCTCCTGCCTTGGCCTCCCAAAGTGCTGTGATTACAGGCATGAGTTGCAGTGCCTGGCTGACATTA
GCATTCTTTATTTATTTATTTATTTTGAGATGGAATCTTGCTCTGTTGCCCAGGCTTGAGTGAA
ATGGTGCAATCTCAGCTCGCTGCAACCTCGTCCTCCCAGGTTCAAGCAATTCTGCCTCGGCCTCCTG
AGTAGCTGGGATTACAGGTGCATGCCACCACACCCAGCTAATTTTTGTATTTTTAGTAGAGATGG
GGTTTTGCCATGTTAGCCAGGCTGGTCTCAAACTGCTGATCTCAGGTGATCTGCCCACTTTGGCCTC
CCAACGTGCTGGGATTACAGGCGTGAGCCACCACACCCGGCCAGCATTTTTACTAGAAAGAAATG
TGTTCAGGACGCATTAGAAACTAGCCAGTTGGACACAGAAGCCCCTGCTGCTCAGCTGTAAGCAC
CGCTATGCTGAAGCTTGGGGTGGTCCTACTCGGTCGTCACCGCCCTGCTCCTTGGAGTGACTTTTCT
GGCCCTCTGCAGTCCACAGTGCTGCCTTGTGAAAGCTCCCTCAAGATCCTCTGTGACAGCCGGGCA
TGGTGGCTTACACCTATCATCCCAGCACTTTGGGAGGCCGAGGCAGGCAGATTACTTGAGATCAGG
AGTTCAAGACCAGCCCAGCCAACTGGTGAAACTTCATTTCTACCAAAAATACAAAAAATTAGCTG
GGCGTGGTGGCGCACGCCTGTAATCCTAGCTACTCGGGAGACTGAGGCATGAGAAGCACCTGATG
GTGGGAGGCAGAGGTTGCAGTGAGCTGAGATCGCACCACTAACATTCTAGCCTGGGCGACAGAG
GAGACTCTGTCTCCAAAACAAAACAAAAGATTTTCTGTGAGAATGACTGCATCGGCCCCTCGGGTG
GCAGCGCTTCTCCAGGGCAAGGTGAGGGGAAGCCCAGTGATGGGAGTGCTGCCTGGAGAGGAGTC
AGTTCCAGTGGTGGGGGCCCTGGGCTTTGGCTGAGGGCTGTGCGTTGGCAGCTGCTGTGCCTCTCA
CAGCCCTTCCCAGCGGCCACGTCATGAGTGTCAGTGTGGAGTCCCAGGCCTACCTCCTCTGGGCC
ACTTTGTGACCATGTTTCTTGCCTATGGCAGGGTAATTTCAGGATCTAAATTGGTACACTTGGACGT
TCTCAGCCCCAGGAGGCAGCTGTTCCCGTTCTAGGTTTTTTTTTTTTTTTTTTGGTAGAAATGGG
GGCTTGTGATGTTGCCCAGGCTGGTCTCGAACTCCTGGGATCAAGTGATCCTCCCATCTTGGCCTCC
CAATGTGCTGGGATTACAGGCATGAGCCACCGTGCCCTGCTAATTTTCTTACTACTATTTTTGTAA
TGCTGCAGTCTTGCTGTGTTGCCCAGGCTGGTCTTAAGCCATCCTCCTGCCTCAGCCTTCCCAGAGTG
CTGGGATTACATCCCCCTTACCTTCTCTGCCAGAGGAGCCCCGCAGTGTGTGAATGCTGAGTCAT
GCTGTCTACTGAGTGCTGAACGGGCTCTGCTGCTCTGGTCCTAGGCTCCGTATGTGGATGTGATCT
GTTTGAACAGCTACTACTCTTGGTATCACGACTACGGGCACCTGGAGTTGATTCAGCTGCAGCTGG
CCACCCAGTTTGAGAACTGGTATAAGAAGTATCAGAAGCCCATTATTCAGACGCAGTATGGAGCA
GAAACGATTGCAGGGTTTCACCAGGTAAGCAGTGTTGAGCTTTCTGCTTGTGTGTTCTCTCAGGGC
AGAGATGTCACTCACCTCCTCCAGCCTGACCTGCGCCCACTGCACTGCTCCCCTCGCTTCAGCTTTG
GGCTCTCCTCCCACGGCCCCGTCCACGTTCCCTCACCGCCAACAGCCAGGCCTGTGCCCCACTCAC
TTGGTCCTCAGAGGTGGCCTCCTTACTGGCTTTGTTTCCAGATAGCCTCCTATCACCCGTGCCCAAG
TGGTCTTTCTAACAGATCCAAATTTGTATTTGTTTTTGAGACCGGATCTCTCTGTCACCCAGGCTGG
AGTGTGGTGGTGCGATCACTGCTCACTGCAGCCTTAACCTCCTGGGCTCAAGTGATCCTCCCACCT
```

-continued

Sequence Information

```
CAGCCTCCTGAGTAGCTGGGACCATAGGCACATGCCAACACGCCTGGCTAATTTTTTACTTTTGT
AGAGATGGGGTCTTGCCATGTTGCCCAGACTGGTCTTGAACTCCTGGCCTCAAGTGATCTGCCTCA
GGCTCCCAAAGTGCTGGGATTACAGGTGTGAGCCTCTGCACCAGCCAGTTGAAAATTTTGGGA
GTCCTGTCATTGGCTCCCCCAGGCCCACAGGACAAAGCCCTAACCTCTGGTCAGGACACTCAGTGT
CCTCTGCTCTCTCCTGGGTTTTCATCCCCTTCTCCCCTCTATCCCAGCCACTGATCTGTTTCCACTGC
CCTCGCTTGCTCTCCTGCTCTTGCTTGAGCTGTTTCTTCTGCCTGGAATGCCCATGTTGGCACCATA
ATCACCAACTAAAATATCCTTTTTCTTAATTTTCATATTTTAGATATAGGGTCTTGCTATGTTGTCCA
GGCTGGTCTCAAACTCCTGGACTCAATTGATCTTCCTGCCTTGGCCTCCAAAAGTGCTGGAATTAC
AGGCATGATCCACTGTGCTAGCCTTTTTTTCTTTTTCTTTTTTTCAGGGTCTTGTTGTGTTGCCCAGG
CTGGAGTGCAGTGGTGTCATCATAGCTCACTGCAGCCTTGAACTAAAGGGCTGAAGTAATTCTTCC
ACCTCAGCCTCCTGAGTAGCTGGGACGACAGGCATGAACCACCATGTGCAGCCTATTTTTAAATTT
TTTTGTAAAGATGGAGTCTATCAGGCTGGTCTAGAACTCCTGGCCTTACGTGATTGTCCTGCCTCAG
ACTCCCAAAGTGCTGGGAATCCAGGCATGAGACACCATGCCCAGCCTGTCGTCATTTTTTAATCT
ATCTCATTTTTTGTCCTCCTCACCAAAGATATGTTGGTTTGTCTTGTGAGGTTTTTTTTTCCTGTG
GATTCCTGAACCCCATCCAGCCCTCATTCCCACCCCAGCCAGCTCACACTTGTTTGTCACAGCTCC
TGGTTGACACACAGGGAACAGCCACCCACAGTGGACTGCGCTGTTCTGTTTGCACCCTTAAATTTA
TCGTGCTTACAGAATGCCACTTCTGCAAACTAGTCAAGTAGGGGAAGTGGCTCTTGGATATATTTG
CTTGCGCATCCTCTTTGAAAAGGTAACCAGCTCTGAATTCTTTTTTTTTTTTGACACAGAGTTTCG
CTCTCGTTGCCTAGGCTGGAGTGCAGTGGCGCGATCTCGGCTCACTGCAATGTCCACCTCCCTGGT
TCAAGCGATTCTCATGCCTCAGCCTCCCGAGTAGCTGGGATTACAGGCATGCGCCACCACGCCCAC
CTCATTTTGTATTTTTAGTAGAGATGAGGTTTCACCATGTTGGTCAGGCTGGTCTTGAACTCCTGAC
CTCAAGTGATCCGCCCGCCTTGGCCTCCCAAAGTGCTGGGATTACAGGCATGAGCCACCGTGCCAA
GCCCTAGCTCTGAATTCTTAAGAAACTCTTGAGAGGGTCTAGGTCAGTGCTGATAGAACCTCTGCA
GTGCTGGGCATGGTGGCTCACACCTGGAATGCTGGCACTTTGGGAGGCCAAGGTCAGAGGATCTC
TTGAGCCCAGGAGTTTGAGACCAGTCTGTGCAACATAGACCCCATCTCTACAAAAAATTTAAAATT
AGTTGGGCATGGTTATGAGTGCTTGTAGTCCAAGCCACTTGGGAGGCTGAGGTGGGAGGATTGTTT
GAGCCCAGTAGGTCAAGGCTGCATTCAGCTATGATTGCACCACTGTACTCCCACCTGGGTGACAGA
GTGAGACCTTGTTTCAAAAAATAAAAAAAAAACAAACTTGCAATGATGGAAATGTTCTATATTTGCA
CTGTCTGAAATGGTACACACTAGCTACACATGGCTACTGAGGTCTTGATATATGACTAGGATAACT
GAATTGATTTAGTTTAATTAAATAAATTTTTTGAGACAGCCTCACTCTGTTGCCCAGGCTGGAGTG
CAGTGGCATAATCACAGCTCACTGCTCAACCTCCTGGGCTCAAGCGATCCTCCCTCCTTAGCCCCA
AGTAGCTTGAACTGCAGGCGTGCGCCACCACACCTGGCTAATATTTTGACTTTTTGTAGAGACTGG
GTCTCACTGTGTTGCCTAGACTAGTCTTGAAATCCTGGGCTGAAGTGATCCTCCTGTCTCGACCTCC
AAAAGTGCTGGCATTACAGACCTGAGGTACCATGCCCAGCCTGGTTTGGTTGAGTTTAATTTAATT
TAATTTTTATATATATATATATATTTATTAGAGACAGGGTCTCACTGTGTCACCCAAACTGGAGTGC
AGTGGTGTGAACACAGCTCACTGTCGCTTTGATCTCTGGGGCTCAAGCAGTCCTCCAACCTCAGCC
TCCCAAGTAGCTGGGACCACAGATGTGTGCCACTAGGCTTGGCTAATTTTGTACTTTTTGTAGAG
ATGGGGTCTTGCTATGTTGCCCAGGCTGGTCTTGAACACCTGGGCTCAAGCAGTCCTCCCACCTCA
GCCTCCCAAATTGCTGGGATGACAGACATGAGCCACTGCACCTGACTGAAAGACATATTTTGCCT
GTAGTGTAGTTTAGCCTTAAGACTGTACCAGCAGATAGAGGTGGAAAAGTAATGTGAAACGAATG
TCAAATTACGTTTATAAATAAAGCAGCTGCTCATTAAGGTTGTTTTTTTTTTTAAACCTCCTTTTTA
TTCTGGGTTACATCATTCCCTGGCTGTCTTTACCCCAGCATCAGTGAGTCCTGCAGTCACTATAGCC
CCCTGTGAAGACAGATATTTTGGTCACCATCAAGTGGATCTTTATTTTTTATCTAACATTTACAATTC
TGCCAGTTCTGACTCTTACATTCTCTTTGCCTTGAATCCTAGGATCCACCTCTGATGTTCACTGAAG
AGTACCAGAAAAGTCTGCTAGAGCAGTACCATCTGGGTCTGACTCAAAAACGCAGAAAATACGTG
GTTGGAGAGCTCATTTGGAATTTTGCCGATTTCATGACTGAACAGTGTAAGTGGCAGTTTGGCTCA
TGGGATAACGTACCCGTCCTCATTTTTTCAGGTTGCCTTTCCAATTCTGGCCATTTCAATTGTAAGA
ATATTGGAAACAAAGTTGGGGAAGCTGGTTTAATCCATGTAGGTTGCGTTGAGAATTTTCTAGGAA
AAGTAAGTTGTGTTTAGGAAGTAGGAAAGCAATCAGGCCCCCGCCTCCCAAATACGGTCAAAAAG
CAAACAGGAGAGTCAGCTATAGTGAATCGGAAATGGCTGGCTTGCCTTTTCCTTGTCTATTTTGTA
GCCAAGGAGGAACGAAAAACGGGACCTCATCATGGATTTACTTTTGGGATACACTCATTATTCCAT
AGAAGGGTACAAAGCCTGAGAAACTTAAGGTATTTCAGTCTGTTGTATATTACTTGCGAAAAGCA
GGCTTATCAAATACAGGTGAGTTTCAACGCATCTTGAATTTGGCAGCATTTACAAGTCTTCAGGCC
AGGTGTAGTGGCTCACGCCTGTAATCCCAGCACTTTGGGAGGTCAGGGTGGGAGGATCGCTTGAG
GCCAGGAGTTCAAGACCAGCCTGTTCAGCATAGCAAGACCCCATCTCTACAAAAAATAAACAGAT
TAGCTAGGCGTGGTGGTGTGTGCCTGTAGTCTCAGCTGCTTGGGAGGCTGAGGCAGGCGGATAAC
CTGAGCACAGGAGTTGGAGGCTGCAGTGAACTATGATTGCACCACTGCACAAGAGCCTGGACAAC
AGAGTGAGACTTGTCTTTAAAACACAAGATTGGTCTTCAAAGAGAATAACATCTGCGGTGTCTTGT
GAGGATGGATGAGGGGCTGCCAAGTTCGCAATGAATGTGTCCCATTTCTTCTTAGTTTATGGACTT
ACCATAAACTGAAGATAGCAGTTTGGTGGGTTGGAGAAGCATGTGGTAATGGTGGGAATTATAAT
ACATTACTTACAGGGAAAGACAGGCCTTTGAAAGGTAAAGCTAAGAGTGAGAATGGAATACAGTGG
ATGAATGAATGAACAAGATGAGGTGAGAAGGAAGAGGTAAAGGGAAAAGGAGAACAGGAAGCT
GTCCTCTGCGTGGCACCTGTGATAAATGGTTTCTGGGGACATCCCTGATGGCAGTTTTGTGGAGAG
GTGCGAGGCTTTATGCGGTAAGAAATGAGCTGCAGGCTGGGCGCAGTGGCTCAAGCCTGTGATCC
CAGCACTTTGGGAGGCCAAGGTGGACAGATCACCTGAGGTCAGGAGTTTGAGACCAGCATGGCCA
ACATGGAGAAACCCATCTCTACTAAAAATACAAAATTAGCCGGGTGTGGTAGCGCATGCCTGTA
ATGCCAGCCACTTGGGAGACTGAGGCATGAGAATCTGTTGAACCTGGGAGATGGAGGTTGCAATG
AGCTAAGATCACAGCACTGTACTCCAGCTTGAGCAATAGAGTGAGACTCTTTTTTTTTTTGAGAC
GGAGTTTTGCTCGTTTCCCAGGCTGGAGTGCAGTGGCGCTATCTCAGCCTACTGCAACCTCCACCT
CCCAGGTTCAAGCAATTCTCCTGCCTCAGCCTCCCGATTAACTGGGATTGCAGGCATGCGCCACCA
CACCCGGCTAATTTTGTATTTTTAGTAGAGACGGGGTTTCTCCATGTTGGTCAGGCTGGGTTGAAC
TACCGACCTCAGGTGATCCGCACATCTGGGCCTCCCAAAGTGCTGGGATTACAGGCATGAGCCACC
ATGGCCAGCTGAAACTCGGTCTTAAAAAGAAAAAGAAATGAGCTGCATCACGTTGGGCAAGTCA
CCTAAGCTTTTCATAAGCCTGTCCAGTGGGGATAATGCCACCTCCTTGTTGGTGTCGTAAGGGCTG
CATTTGATGAAGTACTTGGCGATGCCTGTGTTCACTTATGGAAGAAACAGTCTTGAACCTTTTGGT
GGGGAAAGCCCCCTTTCCATTTAACATTTCCATTTAGTGGTGGTCTTACTGGGGACAGAGAATGTC
CTGAGAGCACAGCCCTGACAGGTCGTTGCCAGCTGTGCTCCTCCACCAGGCTCAGCTCAGGCCTAA
```

| Sequence Information |
|---|
| TGACCACCAGTGGTGGGTGCTGCCAAGCTGGACGTCAGCCCCGGCGGACTTTGAACTCCATGAGT
AGGTCCCACGCAGGGACCTGTGGCTGGTCAGGACCCTGGCTCCCACTAGGCGCTATCTCTTCAGAA
AGGCCCAAGGCTTTTCAAGGGTAACTGTCCCAGATACCCCTAGCCCTCTGCCTACCCAGTTACCAG
ACAGCTGGGTACCCAGCATGTAAACCTTAGTTTGCAAATAAAAGATAAACTTTTAGTGCTTTTTTTT
TTTTTGGAGATGGAGTCTCACTCTGTCGCCCAGGCTGGAGTGCAGTGGCACAATCTCAGCTCACTG
CAACCTCTGCGTCCTGGGTTCAAGCGATTCTCCTGCCCCAGCCTCCTGAGTAGCTGGGACCACAGG
CACCCACCACCATGCCTGTATAATTTTTGTATTTTTAGTAGAGATGAGGTTTCACCATATTGTCCAG
GCTGGTCTTAATCTCCTGACCTTGTGATCCGCCTGCTTTGTCCTCCCAGAGTGCTGGGATTACAGGC
ATGAGCCAATGTGCCCAGCCAGTTTTTGTATTTTTAATAGAGGCGGGTTTCCTCATGTTGGCCAGG
CTGATCTTGAACTCCTGACCTCAGGTGATCCACCTGCCTCAGCCTCCCAAAGCACTGGGATTACAG
GCGTTGGCCACCACACCTGGCCACTGTTTTGGGTTTTTTTCCCCTAACAGACTAGAAAACTAGAAA
TTAACACACCAGGGAACCTGGGTGTTTGGGCAGAGCAGTGGTATTTAAATATTTCAACCCATAAAT
TGTCACTTCAGAGCAAGCATCCTGAAACTGTAAGAGGACATTTGGCTGAGCATGGTGGCTTGTGCT
TATAATCCCAGCACTTTAGGGAGGCTAAGGAGGGCAGATTGCTTGAGCCCAGTAGTTTGAGACCA
GCCTGGACAACATAATGAGACCTTGTCTTTACTAAAAAATAAAAATAAAAGATTACCGGGCATGG
TGGTGCTGGAGAGGCTGAGGCAGGAGGATTGCCTGAGCCCAGGAGGTTGAGGCTGCAGTGAGCTA
TGATTGTGTCACCGCATTCCAGCCTGGGCAACAGGGAGAAAAAAGAAAAAAAAAGACATTTCTAT
TTAGTGCCTACCTTAGCTCCAGACTGGTTCTAACTTGACCCATCAGAAGACATCTGAATCGCTTTGT
GTCTTTTTTTTTTTTTGTAGCACCGACGAGAGTGCTGGGGAATAAAAAGGGGATCTTCACTCGGC
AGAGACAACCAAAAAGTGCAGCGTTCCTTTTGCGAGAGAGATACTGGAAGATTGCCAATGAAACC
AGGTATCCCCACTCAGTAGCCAAGTCACAATGTTTGGAAAACAGCCTGTTTACTTGAGCAAGACTG
ATACCACCTGCGTGTCCCTTCCTCCCCGAGTCAGGGCGACTTCCACAGCAGCAGAACAAGTGCCTC
CTGGACTGTTCACGGCAGACCAGAACGTTTCTGGCCTGGGTTTTGTGGTCATCTATTCTAGCAGGG
AACACTAAAGGTGGAAATAAAAGATTTTCTATTATGGAAATAAAGAGTTGGCATGAAAGTGGCTA
CTGAAAAA SEQ ID NO: 7-the cDNA sequence of the β-glucocerebrosidase gene
(Gene ID: 2629)
CTCTCTCTCTCTCGCTCGCTCTCTCGCTCTCTCGCTCTCTCGCTCGCTCTCTCGCTCTCGCTCTCTC
TCTCTCTCCGGCTCGCCAGCGACACTTGTTCGTTCAACTTGACCAATGAGACTTGAGGAAGGGCTC
TGAGTCCCGCCTCTGCATGAGTGACCGTCTCTTTTCCAATCCAGGTCCCGCCCCGACTCCCCAGGG
CTGCTTTTCTCGCGGCTGCGGGTGGTCGGGCTGCATCCTGCCTTCAGAGTCTTACTGCGCGGGGCC
CCAGTCTCCAGTCCCGCCCAGGCGCCTTTGCAGGCTGCGGTGGGATTTCGTTTTGCCTCCGGTTGG
GGCTGCTGTTTCTCTTCGCCGACGGTAGGCGTAATGAATATTTCGACCTTTGGATCTTAGCTGTCCC
CTCCCTGCGTTCGCACTTAACCTTTTTCACCATTATTATTATTGTTATTATTATTATTTTTTGAG
GGAGTCTCGCCCTGTCGCCCAGGCTGGAGTGTAATGGCGCCTTCTTGGCTCACTGCAACCTCCGCC
TCCCGGGTTCAGGCGATTCTCCGACCTCAGCCTCCCAAGTACGTGGGATTACAGGCACCCGCCACC
ACGCACGGCTAATTTTTTGTATCTTTTAGTAGAGACGGGGTTTCACCATGTTGGTCAGGCTGGTCTC
CAATTCCTGACCTCGTGATCCGCCCGCCTCGGCCTGCCAAACAGCTGTGATTATAGGCGTGAGCCA
CCGCGCCCGGCCAACCATCATTATTTTTTTAACGGTAAGGATGGTCAGATTTTACTAATGAAGAA
GAGATTATAAAATCTTCAAGTCTTTATATCCACTTGCTTTTTGAGGGGTGGAGTGGGAAGAAGGTT
ATGTAATTCATACGTTCTTCAGACATGTGACAAACATTCACGGAGCCCGGCGACGAGCGTCGGGGT
TGGGATTCGCACTGGAGCTGCAGATGGGTGCCAGGATGGACTGGTCCCTACCCTCCGCTTGAACCT
AGGAGGCGGAGGTTGCAGTGAACCGAGATCGTGCCACTGCACTCCAGCCTGGGTGACAGAGATAC
TCCGTCTCAAAAAAAAAAACAAAACAAAAAACAAGCGGACTGGGCGCAGTGCCTCACCCTGTAAT
CCCAGCACTTTGCAAAGCCAAGGCGGGAGGATCCTTTGAGTTTAGGAGTTTGAGACCAACCTGCG
CAACACAGTAAGACCCCGTCTCTACAAAAAATACAGAAATTAGCCAGGTGTGGTGGTGTGCGCCT
ATAGTCCCAGCTATTCTGGAGGCTGAGGTGGGAGGATTGCTTATTCTGGAGGCAGAGGTTGCACTG
AGCCGAAATCAAGCTACTACACTCCATCCAGGGCAACATACGGAGACCCTGTCTCAAACAAACAA
ACAAAAAATTGCTCAGTACCTGGCCAAAAAAGAAGAGGCTCACTATGCAGAGGGGAAGTGGAAG
GAGATGTTTGGACTTCTAAACTCAATAGAGCAGGAGAGGCAAATGTAGAATGTGCTCAGGAAATA
TCTGTGAGATGAATGAACTTGAGGGAAGTAAGGTACTAGATATTACCTGCCCTACCCAGAACAAA
TCCTGTGCAATGTTTCCTTGAAAAGTGAGAAGTCTGGAAGGGGTGGCTACTGACATAGTGAAGCA
ACTAGTTCAATTCTACAACTTGACAGCTACCCCTGTGCCAGGCTATCTACGAGGATACTTAGAATG
CATAAGACATTCCTTCAAGGAACTCCAGGAACAGAGGCCTGACATGTTGCAATGTTTAGTGTCAAG
CAGTGTACTAGAGACACATTATCACACTCAAACCTCACAACAATTCTGTGAGGTAGGAGTTATCAC
TCCCCTTTTATAGATGAAACAGAGGCTTAGAGTGATTGATTTATTGAAAGTCAAACAGCCAGTAAA
TGGTGTAGCCAGGATTCCAAACTTGCTGTCTCACTGAGACTGTACTTAATTACTGGAGGGACCGGG
TGTGGTGGCTCATTGCTATAATCCCAACACCTTGGGAGGCTGAGGCTGTGGATCACCTGAGGTCA
GGGGTTCGAGACCAGCCTGGCCAACATGGTGAAACCCCATCTCTACTAAAAATACAAAAATTAGC
TGGGCATGGTGGTGGGCTCCTGTAATCCCAGCTACTCAGGAGGCTGAGGCAGGGCAATTGCTTGA
GCCGAGATCACACTGCACTCCAGCCTGGGCAACAGGGCAAGACTCTGTCTCAAAACCAAAAAAAA
AAAAATTACTGGAGGAACCTAGAAGAAGAAATGATCAATTTTGCTTGGAGTGTATCTAGAAAGAC
TTCACTGAGATCATTTAAAGAACAAAAAGGATGGCTGGGTCCAGCGCAGTGGCTCATGCCTGTA
ATCCCAGCACTTTCGGATACCAAGGCAGCAGATCACCTGAGGTCCAGAGTTTCAGACCAGCCTGG
CCAACATAGTGAAACCCCATCTCTACTAAAAATAAAAAAATTAGCTGGGCATGTTGGAGGGCACC
TGTAATCCCAGCTACTTGGGAGGCTGAGGCAGGAGAATCACTCGAACCCAGGAGGTGGAGGTTGC
AGTGAGCCAAGATCACGCCACTGCACTCCAGCCTGGGCAACAGAGTGAGACTCTGTCTCAAAAAA
CAACAACAACAAAAAATACAAACAAGAGACAAGTAGTTCCCAGGTGCCTACCAAGTGGTCAGGC
ACTGCACTTACCTCACTGACTGCAGTAACCACCCTTTGAGGTTGTGGCATTGCCTCCATTTTCCAGG
CAAGGAAATGGGCTGAGAGCTGGGATTAGTCAGGTCATGACTGTGTGTGCCACTCCCGCTAAATCT
CATTTGATGTGGTTCATGAGGCCACACCATGGACAGCTTCCTCCTTGTGTCCACTGAGGATATGGC
TTTGTACAACACTTTGGTTTTTGAACGACTTTACAAACCTCCCTGTCTTGTGAGGAAGGAAGAACA
GTTATTACCATCTGCATCTGATGATGAAACAAGGGACGCTGCAGAGGGAGCCGCACTGACCACTCC
CTCCCTCCAGTCCTGTCATCCCACTGCCAGTGTCCCACCCTCTTGTGCCCTGACTTCACTGGCTAA
TAACCCCCCTCACTTTTTCCTCTGTGAAGCCATCCTGGATAATTCCCACCCCACGAATGGTCCCTCC
TCATCTCAGAGAGCTCTCCATGCACACCTGTTACCGTTTCTGTCTTTATCTGTAAATATCTGTGTGT |

| Sequence Information |
|---|
| CTGACTTCCATGCCTCACACACCTCTATAGGGCAAAGACTGTCTTAAACATCTTGGTAGTGTCAGT |
| ATTTTGCACAGTGAAGTTTTTTTTTTAAATTATATCAGCTTTATTTGTACCTTTTTGACATTTCTAT |
| CAAAAAAGAAGTGTGCCTGCTGTGGTTCCCATCCTCTGGGATTTAGGAGCCTCTACCCCATTCTCC |
| ATGCAAATCTGTGTTCTAGGCTCTTCCTAAAGTTGTCACCCATACATGCCCTCCAGAGTTTTATAGG |
| GCATATAATCTGTAACAGATGAGAGGAAGCCAATTGCCCTTTAGAAATATGGCTGTGATTGCCTCA |
| CTTCCTGTGTCATGTGACGCTCCTAGTCATCACATGACCCATCCACATCGGGAAGCCGGAATTACT |
| TGCAGGGCTAACCTAGTGCCTATAGCTAAGGCAGGTACCTGCATCCTTGTTTTTGTTTAGTGGATCC |
| TCTATCCTTCAGAGACTCTGGAACCCCTGTGGTCTTCTCTTCATCTAATGACCCTGAGGGGATGGA |
| GTTTTCAAGTCCTTCCAGAGAGGTAAGAGAGAGAGCTCCCAATCAGCATTGTCACAGTGCTTCTGG |
| AATCCTGGCACTGGAATTTAATGAATGACAGACTCTCTTTGAATCCAGGGCATCATGGCTCTTTG |
| AGCAAGGCACAGATGGAGGGAGGGGTCGAAGTTGAAATGGGTGGGAAGAGTGGTGGGGAGCATC |
| CTGATTTGGGGTGGGCAGAGAGTTGTCATCAGAAGGGTTGCAGGGAGAGCTGCACCCAGGTTTCT |
| GTGGGCCTTGTCCTAATGAATGTGGGAGACCGGGCCATGGGCACCCAAAGGCAGCTAAGCCCTGC |
| CCAGGAGAGTAGTTGAGGGGTGGAGAGGGGCTTGCTTTTCAGTCATTCCTCATTCTGTCCTCAGGA |
| ATGTCCCAAGCCTTTGAGTAGGGTAAGCATCATGGCTGGCAGCCTCACAGGATTGCTTCTACTTCA |
| GGCAGTGTCGTGGGCATCAGGTGAGTGAGTCAAGGCAGTGGGGAGGTAGCACAGAGCCTCCCTTC |
| TGCCTCATAGTCCTTTGGTAGCCTTCCAGTAAGCTGGTGGTAGACTTTTAGTAGGTGCTCAATAAAT |
| CCTTTTGAGTGACTGAGACCAACTTTGGGGTGAGGATTTGTTTTTTTTCTTTTGAAACAGAGTCTT |
| ACTCTGTTGCCTGGGCTGGAGTGCAGTGGTGCAATTTTGGCTCATTCCAACCTCTGCCTCCCAGATT |
| CAAGCGATTCTCTTGCTTCAGCTTCCCAGGTAGCTGGGATTACAGGCGGCCACCACTACGCCCAGC |
| TAATTTTTGTATTTTTAGTAGAGACGGGGTTTCACCATGCTGGCAAGGCAGGTCTCAAACTCCTCA |
| CCTCAGGTGATCCGCCCACCTCGGCCTCCTAAAGTGCTAGGATTACAGGTGTGAGCCCCTGCGCCC |
| GGCCAAGGGGTGAGGAATTTTGAAACCGTGTTCAGTCTCTCCTAGCAGATGTGTCCATTCTCCATG |
| TCTTCATCAGACCTCACTCTGCTTGTACTCCCTCCCTCCCAGGTGCCCGCCCCTGCATCCCTAAAAG |
| CTTCGGCTACAGCTCGGTGGTGTGTCTGCAATGCCACATACTGTGACTCCTTTGACCCCCCGACC |
| TTTCCTGCCCTTGGTACCTTCAGCCGCTATGAGAGTACACGCAGTGGGCGACGGATGGAGCTGAGT |
| ATGGGGCCCATCCAGGCTAATCACACGGGCACAGGTAACCATTACACCCCTCACCCCTGGGCCA |
| GGCTGGGTCCTCCTAGAGGTAAATGGTGTCAGTGATCACCATGGAGTTTCCCGCTGGGTACTGATA |
| CCCTTATTCCCTGTGGATGTCCTCAGGCCTGCTACTGACCCTGCAGCCAGAACAGAAGTTCCAGAA |
| AGTGAAGGGATTTGGAGGGGCCATGACAGATGCTGCTGCTCTCAACATCCTTGCCCTGTCACCCCC |
| TGCCCAAAATTTGCTACTTAAATCGTACTTCTCTGAAGAAGGTGAGGAGGAAGGGGACAAGATGA |
| CATGAGCCATTGAAACTTTTCGTTTTTCTTTTCTTTTTTTAAAATTTTTTTGAGGCAGAATCTCACT |
| CTGCCCATTCTGTCGGCGAGACAGGAGTGCAGTGGTGTGATCTCCCCTCACAGCAACCTCTGCCTC |
| CCAGGCTATAGTGATTCTCCTGCCTCAGCCTCCTGAGTAGCTGGAATTATAGGCGTGCGCCACTAC |
| CACCTGGCTAATTTTTGTATTTTTAGTAGAGACAGGGTTTCATCATGTTGACCAGGCTAGTCTTAAA |
| CTCCTGACCTCAAATGATATACCTGCCTTGGCCTCCCGAAGTGCTGGAATTACAAGTGTGAGCCAC |
| CGAGCCCAGCAGACACTTTTCTTTTTTCTTTTTTTTTTTTGAGACAGAGTCTCGCACTGTCACCCAG |
| GCTGGAGTGCAGTGGCACAATCTCAGCTCACTGCAACCTCCACCTCCCGGGTTCAGGTGATTCTCC |
| TGTCTCAGCCTCTCGAGTACCTGGGATTACAGGTGCCTGCCACCACGCCCGGCTAATTTTTTGTATT |
| TTTAGTAGAGACAGGGTTTCACTATGTTGGCCAGGATGATTGCGAACTCCTGACCTCGTGATCTGC |
| CCACATCGGCCTCCCAAAGTGCTGGGATTACATGCGTGAGCCACTGACACTTTTCTTTGCCCTTTCT |
| TTGGACCCTGACTTCTGCCCATCCCTGACATTTGGTTCCTGTTTTAATGCCCTGTGAAATAAGATTT |
| CACCGCCTATCATCTGCTAACTGCTACGGACTCAGGCTCAGAAAGGCCTGCGCTTCACCCAGGTGC |
| CAGCCTCCACAGGTTCCAACCCAGGAGCCCAAGTTCCCTTTGGCCCTGACTCAGACACTATTAGGA |
| CTGGCAAGTGATAAGCAGAGTCCCATACTCTCCTATTGACTCGGACTACCATATCTTGATCATCCTT |
| TTCTGTAGGAATCGGATATAACATCATCCGGGTACCCATGGCCAGCTGTGACTTCTCCATCCGCAC |
| CTACACCTATGCAGACACCCCTGATGATTTCCAGTTGCACAACTTCAGCCTCCCAGAGGAAGATAC |
| CAAGCTCAAGGTAGGCATTCTAGCTTTTTCAGGCCCTGAGGGCCCTGATGTCTGGGGGTTGAGAAA |
| CTGTAGGGTAGGTCTGCTTGTACAGACATTTTGTCCCCTGCTGTTTTGTCCTGGGGGTGGGAGGGT |
| GGAGGCTAATGGCTGAACCGGATGCACTGGTTGGGCTAGTATGTGTTCCAACTCTGGGTGCTTCTC |
| TCTTCACTACCTTTGTCTCTAGATACCCCTGATTCACCGAGCCCTGCAGTTGGCCCAGCGTCCCGTT |
| TCACTCCTTGCCAGCCCCTGGACATCACCCACTTGGCTCAAGACCAATGGAGCGGTGAATGGGAA |
| GGGGTCACTCAAGGGACAGCCCGGAGACATCTACCACCAGACCTGGGCCAGATACTTTGTGAAGT |
| AAGGGATCAGCAAGGATGTGGGATCAGGACTGGCCTCCCATTTAGCCATGCTGATCTGTGTCCCAA |
| CCCTCAACCTAGTTCCACTTCCAGATCTGCCTGTCCTCAGCTCACCTTTCTACCTTCTGGGCCTTTCA |
| GCCTTGGGCCTGTCAATCTTGCCCACTCCATCAGGCTTCCTGTTCTCTCGGTCTGGCCCACTTTCTTT |
| TTATTTTTCTTCTTTTTTTTTTTTTGAGAAGGAGTCTCTCTCTGTCACCCAGGCTGGAGTGCTGT |
| GGCGCCATCTTCACTCACTGTAACCTCTGCCTCCTGAGTTCAAGCAATTCCTGCCTCAGCCTTCC |
| AAGTAGCTGGGATTATAGGCGCCTGCCACCAGGCCCAGCTGATTTTCTATTTTTAGTAGAGACGG |
| GGTTTCGCCAGGCTGTTCTCGAACTCCTGAACTCAAGTGATCCACCTGCCTCGGCTTCCCAAAGTG |
| CTGGGATTACAGGTGTGAGCCACCACCCAGCTGGTCTGGTCCACTTTCTTGGCCGGATCATTCA |
| TGACCTTTCTCTTGCCAGGTTCCTGGATGCCTATGCTGAGCACAAGTTACAGTTCTGGGCAGTGAC |
| AGCTGAAAATGAGCCTTCTGCTGGGCTGTTGAGTGGATACCCCTTCCAGTGCCTGGGCTTCACCCC |
| TGAACATCAGCGAGACTTCATTGCCCGTGACCTAGGTCCTACCCTCGCCAACAGTACTCACCACAA |
| TGTCCGCCTACTCATGCTGGATGACCAACGCTTGCTGCTGCCCCACTGGGCAAAGGTGGTAAGGCC |
| TGGACCTCCATGGTGCTCCAGTGACCTTCAAATCCAGCATCCAAATGACTGGCTCCCAAACTTAGA |
| GCGATTTCTCTACCCAACTATGGATTCCTAGAGCACCATTCCCCTGGACCTCCAGGGTGCCATGGA |
| TCCCACAGTTGTCGCTTGAAACCTTTCTAGGGGCTGGGCGAGGTGGCTCACTCATGCAAACCCAGC |
| ACTTTGGGAAGCCGAGGCGGGTGATCACCTGAGGTCAGGAGTTTAAGACCACCCTGGCCAACGTG |
| TTGAAACCCTGTGTCTACTAAAATACAAAAAAAAAAAATTATCTGGGCATGATGGTGGGTGTCTGT |
| AATCCCAGCTACTCAGGAGGCTGAGAAGGGAGAATCAGTTGAACCCGGGAGATGGTGGTTGCGGT |
| GAGCCGAGATCGCGCCACTGCACTCCAGCCTGGGAGGCTGAGCGAGACTCCATCTCGAAACAAAA |
| CAAAACAAAACTATCTAGGCTGGGGGTGGTGGTTCATGTATGTATGTGTATATACATATATATGTG |
| TTTATATGTATATATATACACACACACATACATACACACACATACACACACAAATTAGCTGG |
| GTGTGGCACCCGTGTAGTCCCAGCTACTCAGGAGGCTAATGTGGGAGGATCAGTTGACCCTAGGA |
| AGTCAAGGCTGCAGTGAGTCGTGATTGCGCCACTGTACTCCAGCCCGAGTGACAGAGTGACATCCT |
| GTCTCAAAAACAAAAAAAAATCTCCCCAAACCTCTCTAGTTGCATTCTTCCCGTCACCCAACTCCA |

-continued

Sequence Information

```
GGATTCCTACAACAGGAACTAGAAGTTCCAGAAGCCTGTGTGCAAGGTCCAGGATCAGTTGCTCTT
CCTTTGCAGGTACTGACAGACCCAGAAGCAGCTAAATATGTTCATGGCATTGCTGTACATTGGTAC
CTGGACTTTCTGGCTCCAGCCAAAGCCACCCTAGGGGAGACACACCGCCTGTTCCCAACACCATG
CTCTTTGCCTCAGAGGCCTGTGTGGGCTCCAAGTTCTGGGAGCAGAGTGTGCGGCTAGGCTCCTGG
GATCGAGGGATGCAGTACAGCCACAGCATCATCACGGTAAGCCACCCCAGTCTCCCTTCCTGCAA
AGCAGACCTCAGACCTCTTACTAGTTTCACCAAAGACTGACAGAAGCCCTTCCTGTCCAGCTTTCC
CCAGCTAGCCTGCCCTTTTGAGCAACTCTGGGGAACCATGATTCCCTATCTTCCCTTTCCTTCACAG
GTCTGCACACCTCATTGCCCCTTTTGCAACTACTGAGGCACTTGCAGCTGCCTCAGACTTCTCAGCT
CCCCTTGAGATGCCTGGATCTTCACACCCCCAACTCCTTAGCTACTAAGGAATGTGCCCCTCACAG
GGCTGACCTACCCACAGCTGCCTCTCCCACATGTGACCCTTACCTACACTCTCTGGGGACCCCCAG
TGTTGCGCCTTTGTCTCTTTGCCTTTGTCCTTACCCTAGAACCTCCTGTACCATGTGGTCGGCTGGA
CCGACTGGAACCTTGCCCTGAACCCCGAAGGAGGACCCAATTGGGTGCGTAACTTTGTCGACAGTC
CCATCATTGTAGACATCACCAAGGACACGTTTTACAAACAGCCCATGTTCTACCACCTTGGCCACT
TCAGGTGAGTGGAGGGCGGGCACCCCCATTCCATACCAGGCCTATCATCTCCTACATCGGATGGCT
TACATCACTCTACACCACGAGGGAGCAGGAAGGTGTTCAGGGTGGAACCTCGGAAGAGGCACACC
CATCCCCTTTTGCACCATGGAGGCAGGAAGTGACTAGGTAGCAACAGAAAACCCAATGCCTGAG
GCTGGACTGCGATGCAGAAAGCAGGGTCAGTGCCCAGCAGCATGGCTCCAGGCCTAGAGAGCCA
GGGCAGAGCCTCTGCAGGAGTTATGGGGTGGGTCCGTGGGTGGGTGACTTCTTAGATGAGGGTTTC
ATGGGAGGTACCCCGAGGGACTCTGACCATCTGTTCCCACATTCAGCAAGTTCATTCCTGAGGGCT
CCCAGAGAGTGGGGCTGGTTGCCAGTCAGAAGAACGACCTGGACGCAGATACTCAAGGAGGCACTGGGCTC
GATGGCTCTGCTGTTGTGGTCGTGCTAAACCGGTGAGGGCAATGGTGAGGTCTGGGAAGTGGGCT
GAAGACAGCGTTGGGGGCCTTGGCAGGATCACACTCTCAGCTTCTCCTCCCTGCTCCCTAGCTCCT
CTAAGGATGTGCCTCTTACCATCAAGGATCCTGCTGTGGGCTTCCTGGAGACAATCTCACCTGGCT
ACTCCATTCACACCTACCTGTGGCGTCGCCAGTGATGGAGCAGATACTCAAGGAGGCACTGGGCTC
AGCCTGGGCATTAAAGGGACAGAGTCAGCTCACACGCTGTCTGTGACTAAAGAGGGCACAGCAGG
GCCAGTGTGAGCTTACAGCGACGTAAGCCCAGGGGCAATGGTTTGGGTGACTCACTTTCCCCTCTA
GGTGGTGCCAGGGGCTGGAGGCCCCTAGAAAAAGATCAGTAAGCCCCAGTGTCCCCCCAGCCCCC
ATGCTTATGTGAACATGCGCTGTGTGCTGCTTGCTTTGGAAACTGGGCCTGGGTCCAGGCCTAGGG
TGAGCTCACTGTCCGTACAAACACAAGATCAGGGCTGAGGGTAAGGAAAAGAAGAGACTAGGAA
AGCTGGGCCCAAAACTGGAGACTGTTTGTCTTTCCTGGAGATGCAGAACTGGGCCCGTGGAGCAG
CAGTGTCAGCATCAGGGCGGAAGCCTTAAAGCAGCAGCGGGTGTGCCCAGGCACCCAGATGATTC
CTATGGCACCAGCCAGGAAAATGGCAGCTCTTAAAGGAGAAAATGTTTGAGCCCAGTCA

SEQ ID NO: 8-the cDNA sequence of the a-galactosidase A gene
(Gene ID: 2717)
AAACAATAACGTCATTATTTAATAAGTCATCGGTGATTGGTCCGCCCCTGAGGTTAATCTTAAAAG
CCCAGGTTACCCGCGGGAAATTTATGCTGTCCGGTCACCGTGACAATGCAGCTGAGGAACCCAGAA
CTACATCTGGGCTGCGCGCTTGCGCTTCGCTTCCTGGCCCTCGTTTCCTGGGACATCCCTGGGGCTA
GAGCACTGGACAATGGATTGGCAAGGACGCCTACCATGGGCTGGCTGCACTGGGAGCGCTTCATG
TGCAACCTTGACTGCCAGGAAGAGCCAGATTCCTGCATCAGGTATCAGATATTGGGTACTCCCTTC
CCTTTGCTTTTCCATGTGTTTGGGTGTGTTTGGGGAACTGGAGAGTCTCAACGGGAACAGTTGAGC
CCGAGGGAGAGCTCCCCCACCCGACTCTGCTGCTGCTTTTTTATCCCCAGCAAACTGTCCCGAATC
AGGACTAGCCCTAAACTTTCTCTGTGTGACCTTTCCTGGGATGGGAGTCCGGCCAGCGGCCCCTGT
TTCTTTCTCTCTCTCTCTCTCTCGTTCTCCTTCTCTTTCTCTTTCTCTTTCCTCTCTCTTTCTCTC
TCTCCCTGCCCGGTTCTCTTTTTTCACTGCTCCTTGCAGAGCAGGGCCACCCCATAGGCAGTGCC
CAAAGTAGCCCTGCCCGGTTCTATTCAGACCCTTCTTGTGAACTTCTGCTCTTCCTCTGCCGGGTGC
TAACCGTTAGAACATCTAGGGTGGGTAGGAGGAATGGGGAACTAAGATTCGTGCCATTTTTTCTCC
TTTTGGGGTCGTGGATTTCTCGGCAGTATCTCGAGGGAGTTAGAGAGACCATAAGGTCGCTGAGAT
CTCTCCCACCTCGCCCATGAGCGTGGCATCAGGCTGGAAGGTTGACATGGAGGAACTTTATCATT
TACACCTTTGCGTGAGGGTTGAGGCTGGATTAGATAGGTATTGAACATATCTGACCCTCACAATCC
TTATCTGTAAATTGGGATTACAACCTTTTAATTTCAGGGAGCTGACAAAAAAAATCTGAAAAATAG
TTCTTATCTCACACAGGTGAGTTTTCAAGGAGATAACCTATTTAAAGTACATAGCACAGCGCTTGA
CCATTCAACTGCGCTTACAGAGCAAATGTTCAATGGGAAAATGAATGTAAATCTACAAATCTGAAT
GAATATGTGTATTTTTCTGGAGAGAGGATATTTACCTTTCTTCAAATTCTCAAAGGGCTCTGTGATT
TAAAAAAGGTTAGGAATCACTGATAGATGTTGGTAAAAGGTGGCAGTCACAGTACATTTCTGTGTC
CATAAGTTATTCCTATGAATATCTTTATAGATAAAGTCAGGATGTTGGTCAGACATCACAGAAGAA
ATTGGCCTTGTAAGTTTCATGTGACCCTGTGGTACAGTATGTGGTGGCAATTTTGCCCATCACGGATT
TTTTTTTATTGGTATTTGCATCTGATTATAAAACTAATGCATGATCATTGCAAAAAATGTAGATAAA
GAAGAGCAAATGAAAATAAAGATTTCCCCCCACCGTTCCACCACCCAGAAATAATCATGGTTTA
AATGTTAATATACAACCTTACAATTGTTTCTATATAAATGAAAACATAGATTTCTTTATTTCATTA
TTTTCATAAAAAATGGATCATGTTTATGTCATGTTTGGCTAATGCTAATGACCCTGGCACCCAGTC
TGGGCTCAAATTCTGCCTCATTGTTACTTAGCCCTGTGACATTGGGTAAATTACACTTTTTTTTTTT
TTTTTTTTGAGACGGGGTCTCGCTCTGTCGCCCAGGCTGGAGTGCAGTGGCACGATCTCGGCTCA
CTGCAAGCTCCGCCTCCTGGGTTCACGCCATTCTTCTGCCTCAGCCTCCCGAGTAGCTGGGACTAC
AGGCGCCTGCCACCACGCCTGGCTCTTTTTTTTTTTTTTTTTTTAGTACAGACGGGGTTTCACC
ATGTTAGCCAGGGTGGTCTCAATCTCCTGACCTCGTGATTCGCCCGCCTCAGCCTCCCAAAGTGCT
GGTGTGAGCCACCGTGCCCAGCCTTACTTTTTTTTTGAGAGGGGGTCTCACTCTGTCACCCAGGTT
GGAGTGCAGTGGCGCGATCTCTGCTCAGTGCAAACTCCACCTCCCGGGTTTAAGCAGTTCTCCTGT
CGTAGTCTCCTGAGTAGCTGGGATTACAGGCACACCACCACGGCCAGCTAATTTTTGTATTTTCAG
TAGAGACGGGTTTCACCATGTTGCCCAAGCTGGTCTCGAACTCCTGGCCTCAAGTGATCGCCCGC
CTTGGCCTCCCAGAGTGCTGGGATTACAGGTGTGAGCCACCGCACCCGGCCTCTTTTTTCTTTTTA
GTCTATCATACCTTGCAAATACAGTGGTTCTTCCTATGTGTTGGTTTTGATATTTATGTAATCAAAC
ACATCAGTTTTTCCTTTCTGATTTCTGACTTTGGGGTCATGCTGAGAAAGTCCTTTCCTACCTGAAG
ATAATACAGTATATACGTTTCTTACTAGTATTTTTGTGGATTTTAAAATATTTAAATCTTTAGTCC
ATCTGAACTTTGTTCTTCTATCAGAAATGCCACATTTAATAAATAATAAGTCCCATGGTATCAGAT
GGCTGGAAGGACCTCTTTCGAAACTTTGTTAATTCCATTAATCTGTGTATTCTTATTCTAATGCTA
ATAGTTCCACACTAGCTTCCTTTATCTTTTTTTCTTTTTTTTTTTTTTTGAGCTGGAGTTTCGCTC
```

Sequence Information

```
TTGTTGCCCAGGCTGGAGTACAATGTCACGATCTCGGTTCACCGCAACCTCCGCCTCCCAGGTTCA
AGCAATTCTCCTGCCTCATCCTCGCGAGTAGCTGGAATTACAGGCATGCGCCACCACGCCTAGCTA
TTTTGTATTTTTAGTAGAGATGGGGTTTCTCCATGTTGGTCAGGCTGGTCTCAAACTCCCAGCCTCA
GGTGATCTGCCTGCCTCGGCCTCCCAAAATGCTGTTATTACAGGCGTGAGCCACCACGCCCAGCCT
TCATCTTTTAATGAATGTACATGTATGTAATCTTTTAGGTGAACTTTTTGTAATGTTGTGCCAAGTT
CCTTAAAAAGCCCTTTTGGAAGCTGGGCAGGTGGCCCACGCCTGTAATCCCAGCATTTTGGGAGTC
TGAGGCAGGTGGATCACTTGAGGCCAGGAGTTCAAGACTAGCCTAGCCAAAATGCAAAACCCTGT
CTCTACTAAAGATACAAAAATTAGCCGGATGCGATGGCACATGCCTGTAATCTCAGCTACTCGGGA
GGCTGAGGTAGAAGAATCGCTTGAACCGGGGAGGCAGAGGTTGCAGTGAGCCAAGATGGCGCCA
CTGCACTCCAGCCTGGGTGACAGAGGGAGACTCCATCTCAAAAAAAAAAAAAAAAAAAAAGATA
AAAAGGAAACCTAAGTACTCTTGGGCTTTGTTAAGGATTTTGTTAAATATACAAAGGATTGCAGGG
AAAATTAACTTATTTTTAATATTGAGTATGCTTATCCAAGAGCAAAATAATATTTCTCCATTTATTC
AAATCATTTAGGAGCATCATAGTTTTAACATATGGGCCTTGCACGTATCTTAAATTTATCTCTAGGC
ATTTTAGGTTGTTCAGTTGTTCTTGTGAATGGGATCTTTTTCTCCAAATAGGATTATTGTTGATATCT
GTTGATTATGTTAACTTTGTAGTTTCTGACTTTACTGAACTGTCTTCTTAGATCTAATACTCTTTTCA
ATTTCATCATATATTTCTCATTCCTATTTTGTTTGGGGTTTTAGGGCGGGAATATTAACGGGATAA
GAGAGACAAAAGAAAATCTGGAAAAACAATTCATTTTACCTTACATTGCTTGTGATTACTACCACA
CTATTACTGGGTTGGAAAAAATTGTGAAATCCCAAGGTGCCTAATAAATGGGAGGTACCTAAGTG
TTCATTTAATGAATTGTAATGATTATTGGAATTTCTCTTTCAGTGAGAAGCTCTTCATGGAGATGGC
AGAGCTCATGGTCTCAGAAGGCTGGAAGGATGCAGGTTATGAGTACCTCTGCATTGATGACTGTTG
GATGGCTCCCCAAAGAGATTCAGAAGGCAGACTTCAGGCAGACCCTCAGCGCTTTCCTCATGGGA
TTCGCCAGCTAGCTAATTATGTGAGTTTATAGATAATGTTCTTGTTCATTCAGAGGACTGTAAGCAC
TTCTGTACAGAAGCTTGTTTAGAAACAGCCCTCATGGCCGGGCGTGGTGGCTCACGCCTGTAATCC
CAACACTTTGGGAGGCCGAGGCGGGTGGATCACCTGAGGTCAAGAGTTCAAGACCAGCCTGGCCA
ACATGGTGAAACCCCAACTCTATTAAAAGTACAAAAAATTAGCTGGGCATGGTGGTGAACGCCTG
TAACCCCAGCTACTTGGGAGGCTGAGGCAGGAGAATCGCTTGAACCCAGGAGGTGGAAGTTTCAG
TGAGCTGAGATCACGCCATTGCACTCTAGCCTGGGCAACAAAAGAGAAACTCCATCTCAAAAAAA
AAAACAAGGAAAAAAAAGAAACAGCCCTCATGACACTTAGAAAGTAGAATAGCTGGCTGTTATCTG
AACATTGAATTGTAAGGCTTATCAGGTGGACTTTGCATTCCATCAGCAGACAATTTTTTTTTTTTT
TTTTTTTGAGATGGAGTCTCATTCTGTCTCCCAGGCTGGAGGGCAGTGGTGCGATCTCGGCTCACTG
CAAGCTCCACCTCCTGGGTTCATGCCATTCTCCTGCCTCAGCCTCCCAAGTAGCTGGGACCACAGG
CACCCGCCACCATGCCCAGTTAATTTTTTGTATTTTTAGTAGAGACGGGGTTTCACCATGTTAGCCA
AGATGGTCTCGATCTCCTGACCTCGTGATCCGCCCACCTCGGCCTCCCAAAGTGCTGGGATTACAG
GCATGAGCCACCGCGCCTAGCCTACAAATGTTTTGTAATAGCTCTTGAGGCCCATCTTGGAGTTCT
CCTTTTGCTAAAACCACTGAACTCTCTAGGAGGAAAAAGGAACTTGGTTCTTGACATATGTGTGCA
TGTATTTCCATATAACCTTTAGGAAGCTATTGCAATGGTACTATAAACTAGAATTTTAGAAGATAG
AAGGAAAATATTCTGGAGATCATTGAAGAGAAATGGAGTCCAACACTAGTTAAAGATGATGAAGA
CAGATTTTTTTTTTGACGGAGTCTCGCTCTGTCGCCCAGGCTGGAGTGCAGTGGCACAATCTCAGC
TCACTGCAACCCTCCACCTCTTGGGTTCAAGTGATTCTCCTGCCTCAGCCTCCCAAGTAGCTGGGAC
TACAGGCGCACACCACCACGCCCGGCTAATTTTTGTATTTTTAGTAGAGACAAGGTTTCACCATAT
TCGCCAGGCTGGTCTCGAACTCCTGACCTTGTAATCCGCCCACCTTGGCCTCCCAAAGTGCTGGGA
TTACAGGCATGAGCCACCACGCCCGGCCGATGAAGACAGATTTTATTCAGTACTACCACAGTAGA
GGAAAGAGCCAAGTTCAATTCCAAATACAACAAAGACAGGTGGAGATTTATAGCCAATGAGCAGA
TTGAGGGGGTCAGTGGATGGAATATTTAAGAAGACATCAAGGGTAGGGAGCTTCTTGCTAAAGCT
TCATGTACTTAAACAAGAAGGGTGGGGGATGAGGGAAATTGATCAGATATCAATGGTGGCAGTAT
TGACTTAGCAGGATTCTTGCTAAGAGGTCTTGCTAGGACAGACATAGGAAGCCAAGGTGGAGGTC
TAGTCGAAAAGAAGGCTCATCAGAGAAGTCTAACTAAAGTTTGGTCAAGAAGAGTCTTTGTCAAG
GTAAATCTATCATTTCCCTCAAAAGGTAATTTTCAGGATCCCATCAGGAAGATTAGCATGGCTGCT
AGCTTTCTCCTCAGTTCTGGGCTATAGCTCACATGCCTAGTTTTGAACTAGCTCAGCAGAACTGGGG
GATTTATTCTTTGTCTTCCAACAAACTCATCTGGATGATTTTGGGGGTTTGTGGGGAAAAGCCCCCA
ATACCTGGTGAAGTAACCTTGTCTCTTCCCCCAGCCTGGAATGGTTCTCTCTTTCTGCTACCTCACG
ATTGTGCTTCTACAATGGTGACTCTTTTCCTCCCTCTCATTTCAGGTTCACAGCAAAGGACTGAAGC
TAGGGATTTATGCAGATGTTGGAAATAAAACCTGCGCAGGCTTCCCTGGGAGTTTTGGATACTACG
ACATTGATGCCCAGACCTTTGCTGACTGGGGAGTAGATCTGCTAAAATTTGATGGTTGTTACTGTG
ACAGTTTGGAAAATTTGGCAGATGGTAATGTTTCATTCCAGAGATTTAGCCACAAAGGAAAGAAC
TTTGAGGCCATGGTAGCTGAGCCAAAGAACCAATCTTCAGAATTTTAAATACCCTGTCACAATACT
GGAAATAATTATTCTCCATGTGCCAGAGCTCCCATCTCTTCTCTTTCATTGTCATTAATTAATTAATT
AATTCATGTAAAATCCATGCATACCTAACCATACCTAATATTGTGCACTTATAATTCAAGAGGGCT
CTAAGAGTTAATTAGTAATTGTAACTCTCTATAACATCATTTAGGGGAGTCCAGGTTGTCAATCGG
TCACAGAGAAAGAAGCATCTTCATTCCTGCCTTTCCTCAATATACACACCATCTCTGCACTACTTCC
TCAGAACAATCCCAGCAGTCTGGGAGGTACTTTACACAATTTAAGCACAGAGCAACTGCCTGTCCC
TGCTGCTAGTTTAAACATGAACCTTCCAGGTAGCCTCTTCTTAAAATATACAGCCCCAGCTGGGCA
TGATGGCTCATGCCTGTAATCCTAGCACTTTGGGAGGCTGAGGCGGTGGATTACTTGAGGTCAGG
AGTTCGAGACCACCCTGGCCAACATGGTGAAACCCCATCTCTAGTAAAAATACAAAAATTAGCTG
ACTTTGGTGGCACATGCCTGTAATCCCAGCTACTTGGGAAGCTGAGACAGAAGAGTCACTTGAACC
TGGGAAACAGAGGTTGCAGTGAGCCAAGATCGCACCACTGCACTCCACCCTGGATGACAGACTGA
ACCCCATCTCAAAAAATTAAAATAAAATAAAATAAAATAACTATATATATAGCCCCAGCTGGAAA
TTCATTTCTTTCCCTTATTTTACCCATTGTTTTCTCATACAGGTTATAAGCACATGTCCTTGGCCCTG
AATAGGACTGGCAGAAGCATTGTGTACTCCTGTGAGTGGCCTCTTTATATGTGGCCCTTTCAAAAG
GTGAGATAGTGAGCCCAGAATCCAATAGAACTGTACTGATAGATAGAACTTGACAACAAAGGAAA
CCAAGGTCTCCTTCAAAGTCCAACGTTACTTACTATCATCCTACCATCTCTCCCAGGTTCCAACCAC
TTCTCACCATCCCCACTGCTGTAATTATAGCCTAAGCTACCCATCACCTGGAAAGTCATCCTTGTGTC
TTCCCCTTTATTTCACCATTCATGTCCTGTCTATCAACAGTCCTTCCACCAGTATCTCTAAAATATCT
CCTGAATCAGCCCACTTCCTTCCATCTTCACTACATGCACCCTGGCCTTCCAAGCTACTATCGGCTC
TCAACCAGACTGCTGGGACCACCTGATCTCTCTGCTTCCACTCTGTCTCAACCCCCATCTATTTTCC
AAGCAGCACTAGAGTTATCATATTAAAATGTAAATATCAGTTTTTTTTTAAAGAAAAAACCCTG
AGACTTAACAGAGTTATAAAAAATATAAATGTCATCATCAGTTCCCTGCTTAAAACCCTTAACTCG
```

-continued

Sequence Information

CTTCCAATTGCACTTGGAATGAAACCAAACTGCACTGATCCAGCCCTTGCCTGCCTCCCCAAAGTC
CAAGGGGTCATGGCTCTTTCCCTGGCTACACTGGTTTTCTTTCTGTCCCTCAACACTGCAAGCCTAT
TGCTGCCCCAGGGCCTTTACACTTGCTTTTTTTCTGCCTAGAACAGTTCTTCCCCAAAGATTTTTAA
AGGGCCGGGCTCCTTAACATTGAAGTCGCAGACCAAACGCCACATATGCAGACAGTTCTTCTCTAA
CTACTTTAAAATAGCCCTCTGTCCATTCATTCTTCATCACATTAACCTGTTTAATTTTCTTCTCAGAG
CTCCACACTATTTGGAAGTATTTGTTGACTTGTTACCATGTCTCCCCACTAGAGTGTAAGTTTCATG
AGGGCAGGGACCTTGTCTGACTTTGACTGTATCTCTCGCATATGGTTAAGTGTTGAATAGTTATTTA
TGGAATGAATCCCTATTATTCCCTCATTATCTCTGCAAAATAGTCTTTTTTCTCAACATCTTAAACC
TGATATCCCACCTGCCTATCTACAAACTTTTTTTTTGCGACAGAGTCTCACTGTCACCCAGGCTAGA
GTGCAGTGGCGCCATCTCGGCTCACTGCAACCTCCGCCTCCCGGGTTAAGCGATTCTCTTGCCTCA
GCCTCCCAGTAGCTGGGATTATAGGCGTGCGCTACCACATCTGGCTAATTTTTGTATTTTTAGTAGA
GATGGTTTCACCATGTTGGCCAGGCTTGTCTCGAACTCCTGACCTCAGATGATCCACCTGCCTCGG
CCTCCCAAAGTGCTGGGATTACAGGCATGAGCCACCGTGCCCAGCCTCTACAAACTTTTTATTCCA
TTAACAAACTATATGCCTGGGATTTAAGTTTTCTTAATACTTGATGGAGTCCTATGTAATTTTGCAG
CTTTTAATTTTACTAAGACCATTTTAGTTCTGATTATAGAAGTAAATTAACTTTAAGGGATTTCAAG
TTATATGGCCTACTTCTGAAGCAAACTTCTTACAGTGAAAATTCATTATAAGGGTTTAGACCTCCTT
ATGGAGACGTTCAATCTGTAAACTCAAGAGAAGGCTACAAGTGCCTCCTTTAAACTGTTTTCATCT
CACAAGGATGTTAGTAGAAAGTAAACAGAAGAGTCATATCTGTTTTCACAGCCCAATTATACAGA
AATCCGACAGTACTGCAATCACTGGCGAAATTTTGCTGACATTGATGATTCCTGGAAAAGTATAAA
GAGTATCTTGGACTGGACATCTTTTAACCAGGAGAGAATTGTTGATGTTGCTGGACCAGGGGGTTG
GAATGACCCAGATATGGTAAAAACTTGAGCCCTCCTTGTTCAAGACCCTGCGGTAGGCTTGTTTCC
TATTTTGACATTCAAGGTAAATACAGGTAAAGTTCCTGGGAGGAGGCTTTATGTGAGAGTACTTAG
AGCAGGATGCTGTGGAAAGTGGTTTCTCCATATGGGTCATCTAGGTAACTTTAAGAATGTTTCCTC
CTCTCTTGTTTGAATTATTTCATTCTTTTTCTCAGTTAGTGATTGGCAACTTTGGCCTCAGCTGGAAT
CAGCAAGTAACTCAGATGGCCCTCTGGGCTATCATGGCTGCTCCTTTATTCATGTCTAATGACCTCC
GACACATCAGCCCTCAAGCCAAAGCTCTCCTTCAGGATAAGGACGTAATTGCCATCAATCAGGAC
CCCTTGGGCAAGCAAGGGTACCAGCTTAGACAGGTAAATAAGAGTATATATTTTAAGATGGCTTTA
TATACCCAATACCAACTTTGTCTTGGGCCTAAATCTATTTTTTTCCCTTGCTCTTGATGTTACTATCA
GTAATAAAGCTTCTTGCTAGAAACATTACTTTATTTCCAAAATAATGCTACAGGATCATTTTAATTT
TTCCTACAAGTGCTTGATAGTTCTGACATTAAGAATGAATGCCAAACTAACAGGGCCACTTATCAC
TAGTTGCTAAGCAACCACACTTTCTTGGTTTTTCAGGGAGACAACTTTGAAGTGTGGGAACGACCT
CTCTCAGGCTTAGCCTGGGCTGTAGCTATGATAAACCGGCAGGAGATTGGTGGACCTCGCTCTTAT
ACCATCGCAGTTGCTTCCCTGGGTAAAGGAGTGGCCTGTAATCCTGCCTGCTTCATCACACAGCTC
CTCCCTGTGAAAAGGAAGCTAGGGTTCTATGAATGGACTTCAAGGTTAAGAAGTCACATAAATCC
CACAGGCACTGTTTTGCTTCAGCTAGAAAATACAATGCAGATGTCATTAAAAGACTTACTTTAAAA
TGTTTATTTTATTGCC

SEQ ID NO: 9-the cDNA sequence of the codon optimised GAA gene
CCAATCCAATAGCGCTGCCGCCGCGATCGCCATGGGGGTCCGACATCCTCCTTGTTCTCACCGCCT
GCTGGCCGTCTGTGCTCTGGTCTCCCTGGCTACTGCTGCTGCTGGGGCATATCCTGCTGCATGAT
TTCCTGCTGGTGCCTAGGGAGCTGAGTGGAAGCTCCCCCGTCTGGAGGAAACCCACCCTGCTCAT
CAGCAGGGAGCATCCCGACCCGGACCTCGAGATGCTCAGGCACACACCCAGGGCGGCCTAGAGCTGT
GCCCACTCAGTGCGACGTGCCCCCTAACAGCCGGTTTGACTGTGCCCCTGATAAGGCTATCACACA
GGAGCAGTGCGAAGCCAGAGGCTGCTGTTATATTCCAGCAAAACAGGGACTGCAGGGAGCACAG
ATGGGACAGCCCTGGTGTTTCTTTCCACCCTCCTACCCTTCTTATAAGCTGGAAAATCTGTCTAGTT
CAGAGATGGGCTACACAGCCACTCTGACCCGGACCACACCCACCTTCTTTCCTAAGGATATCCTGA
CACTGCGACTGGACGTGATGATGGAGACTGAAAACCGGCTGCACTTCACCATCAAGGATCCGCC
AATCGGAGATATGAAGTGCCACTGGAGACCCCCACGTCCATTCGGGCTCCAAGTCCCTGTAC
TCAGTGGAGTTCAGCGAGGAACCCTTCGGCGTGATCGTGCGGCGATCTGATGGAAGAGTGCT
GCTGAACACTACCGTCGCCCCTCTGTTCTTTGCTGACCAGTTTCTGCAGCTGAGTACTTCACTGCCT
TCTCAGTATATCACCGGCCTGGCCGAACACCTGAGTCCACTGATGCTGAGCACCTCCTGGACAAGA
ATTACTCTGTGAACAGGGACCTGGCACCTACCCCAGGAGCCAATCTGTACGGCTCTCACCCCTTC
TATCTGGCTCTGGAGGATGGCGGGAGCGCACATGGCGTGTTTCTGCTGAACTCCAATGCTATGGAC
GTGGTCCTGCAGCCCTCTCCTGCACTGAGTTGGCGGTCAACCGGAGGCATCCTGGACGTGTACATT
TTCCTGGGGCCAGAGCCCAAAAGCGTGGTCCAGCAGTACCTGGACGTGGTCGGATATCCATTCATG
CCTCCATACTGGGGGCTGGATTTCACCTGTCAGATGGGGGTATAGCTCCACCGCAATCACACGG
CAGGTGGTCGAAAACATGACCAGAGCCCATTTTCCCCTGGATGTGCAGTGGAATGACCTGGATTAC
ATGGACAGCCGACGGGACTTCACCTTCAACAAGGACGGCTTCAGGGATTTTCCTGCCATGGTGCAG
GAGCTGCATCAGGGGGGAAGAGGTACATGATGATCGTGGATCCAGCCATTTCTAGTTCAGGACC
AGCTGGCAGCTACCGACCATATGACGAAGGACTGCGACGAGGGGTGTTCATCACTAACGAGACCG
GGCAGCCACTGATTGGAAAAGTGTGGCCAGGCTCCACCGCATTCCCAGACTTCACCAATCCTACTG
CCCTGGCTTGGTGGGAAGACATGGTGGCCGAGTTCCACGACCAGGTCCCATTTGATGGAATGTGG
ATCGACATGAACGAACCCAGTAATTTCATTAGGGGATCAGAGGACGGCTGCCCTAACAATGAGCT
GGAAAATCCACCTTATGTGCCAGGAGTGGTCGGAGGGACCCTGCAGGCCGCTACAATCTGTGCCA
GCTCCCACCAGTTTCTGTCCACACACTATAACCTGCATAATCTGTACGGACTGACTGAGGCAATCG
CCTCTCATCGCGCACTGGTGAAGGCAAGGGGAACACGACCATTCGTCATTTCTAGGAGTACTTTTG
CTGGACACGGGCGCTACGCAGGACATTGGACCGGCGACGTGTGGTCAGTTGGGAACAGCTGGCT
TCAAGCGTGCCCGAGATTCTGCAGTTCAACCTGCTGGGAGTGCCTCTGGTCGGAGCAGACGTGTGC
GGGTTTCTGGGAAATACCTCCGAGGAACTGTGCGTGCGGTGGACACAGCTGGGAGCCTTCTATCCT
TTTATGCGAAACCACAATAGCCTGCTGTCCCTGCCACAGGAACCCTACTCATTCAGCGAGCCAGCC
CAGCAGGCTATGCGCAAAGCCCTGACCCTGCGATATGCTCTGCTGCCCCATCCTGTACACACTGTTT
CACCAGGCACATGTGGCCGGCGAAACTGTCGCTCGGCCTCTGTTCCTGGAGTTTCCAAAGGATTCC
TCTACATGGACTGTGGACCACCAGCTGCTGTGGGAGAAGCCCTGCTGATCACCCCGTGCTGCAG
GCTGGGAAAGCAGAGGTCACAGGCTATTTCCCACTGGGGACATGGTACGATCTGCAGACTGTGCC
AGTCGAGGCTCTGGGATCACTGCCACCACCTCCAGCAGCACCTAGAGAACCAGCAATCCACAGCG
AGGGACAGTGGGTGACACTGCCTGCCCCACTGGACACTATTAACGTGCATCTGAGGGCTGGCTAT
ATCATTCCTCTGCAGGGACCAGGCCTGACAACTACCGAGTCTCGCCAGCAGCCAATGGCTCTGGCA

| Sequence Information |
|---|
| GTGGCCCTGACCAAGGGAGGAGAAGCAAGGGGAGAGCTGTTCTGGGACGATGGAGAGAGCCTGG |
| AAGTGCTGGAGCGAGGAGCATACACACAGGTCATCTTTCTGGCCAGAAACAATACTATTGTGAAT |
| GAACTGGTGAGGGTCACCAGCGAGGGGAGCAGGACTGCAGCTGCAGAAGGTGACCGTCCTGGGAG |
| TGGCTACAGCACCTCAGCAGGTCCTGTCCAACGGCGTGCCTGTCTCCAATTTCACTTACTCTCCAG |
| ACACCAAAGTGCTGGACATCTGCGTGAGCCTGCTGATGGGCGAACAGTTTCTGGTCTCCTGGTGCT |
| GAGTCGACATTGGATTGG |
| |
| SEQ ID NO: 10-the full length β globin LCR |
| ATCTCATTGCTGTTCGTAATTGTTAGATTAATTTTGTAATATTGATATTATTCCTAGAAAGCTGAGG |
| CCTCAAGATGATAACTTTTATTTTCTGGACTTGTAATAGCTTTCTCTTGTATTCACCATGTTGTAACT |
| TTCTTAGAGTAGTAACAATATAAAGTTATTGTGAGTTTTTGCAAACACAGCAAACACAACGACCCA |
| TATAGACATTGATGTGAAATTGTCTATTGTCAATTTATGGGAAAACAAGTATGTACTTTTTCTACTA |
| AGCCATTGAAACAGGAATAACAGAACAAGATTGAAAGAATACATTTTCCGAAATTACTTGAGTAT |
| TATACAAAGACAAGCACGTGGACCTGGGAGGAGGGTTATTGTCCATGACTGGTGTGTGGAGACAA |
| ATGCAGGTTTATAATAGATGGGATGGCATCTAGCGCAATGACTTTGCCATCACTTTTAGAGAGCTC |
| TTGGGGGCCCCAGTACACAAGAGGGGACGCAGGGTATATGTAGACATCTCATTCTTTTTCTTAGTG |
| TGAGAATAAGAATAGCCATGACCTGAGTTTATAGACAATGAGCCCTTTTCTCTCTCCCACTCAGCA |
| GCTATGAGATGGCTTGCCCTGCCTCTCTACTAGGCTGACTCACTCCAAGGCCCAGCAATGGGCAGG |
| GCTCTGTCAGGGCTTTGATAGCACTATCTGCAGAGCCAGGGCCGAGAAGGGGTGGACTCCAGAGA |
| CTCTCCCTCCCATTCCCGAGCAGGGTTTGCTTATTTATGCATTTAAATGATATATTTATTTTAAAAG |
| AAATAACAGGAGACTGCCCAGCCCTGGCTGTGACATGGAAACATGTAGAATATTTTGGGTTCCAT |
| TTTTTTTTCCTTCTTTCAGTTAGAGGAAAAGGGGCTCACTGCACATACACTAGACAGAAAGTCAGG |
| AGCTTTGAATCCAAGCCTGATCATTTCCATGTCATACTGAGAAAGTCCCCACCCTTCTCTGAGCCTC |
| AGTTTCTCTTTTTATAAGTAGGAGTCTGGAGTAAATGATTTCCAATGGCTCTCATTTCAATACAAAA |
| TTTCCGTTTATTAAATGCATGAGCTTCTGTGCGGCCGCTCTAGAACTAGTGGATCCCCCGCTTCTTT |
| GAGAAACATCTTCTTCGTTAGTGGCCTGCCCCTCATTCCCACTTTAATATCCAGAATCACTATAAGA |
| AGAATATAATAAGAGGAATAACTCTTATTATAGGTAAGGGAAAATTAAGAGGCATACGTGATGGG |
| ATGAGTAAGAGAGGAGAGGGAAGGATTAATGATGATAAAATCTACTACTATTTGTTGAGACCTT |
| TTATAGTCTAATCAATTTTGCTATTGTTTTCCATCCTCACGCTAACTCCATAAAAAAACACTATTAT |
| TATCTTTATTTTGCCATGACAAGACTGAGCTCAGAAGAGTCAAGCATTTGCCTAAGGTCGGACATG |
| TCAGAGGCAGTGCCAGACCTATGTGAGACTCTGCAGCTACTGCTCATGGGCCCTGTGCTGCACTGA |
| TGAGGAGGATCAGATGGATGGGGCAATGAAGCAAAGGAATCATTCTGTGGATAAAGGAGAGCAGC |
| CATGAAGAAGTCTATGACTGTAAATTTGGGAGCAGGAGTCTCTAAGGACTTGGATTTCAAGGAATT |
| TTGACTCAGCAAACACAAGACCCTCACGGTGACTTTGCGAGCTGGTGTGCCAGATGTGTCTATCAG |
| AGGTTCCAGGGAGGGTGGGGTGGGTCAGGGCTGGCCACCAGCTATCAGGGCCCAGATGGGTTAT |
| AGGCTGGCAGGCTCAGATAGGTGGTTAGGTCAGGTTGGTGGTGCTGGGTGGAGTCCATGACTCCC |
| AGGAGCCAGGAGAGATAGACCATGAGTAGAGGGCAGACATGGGAAAGGTGGGGGAGGCACAGC |
| ATAGCAGCATTTTTCATTCTACTACTACATGGGACTGCTCCCCTATACCCCCAGCTAGGGGCAAGT |
| GCCTTGACTCCTATGTTTTCAGGATCATCATCTATAAAGTAAGAGTAATAATTGTGTCTATCTCATA |
| GGGTTATTATGAGGATCAAAGGAGATGCACACTCTCTGGACCAGTGGCCTAACAGTTCAGGACAG |
| AGCTATGGGCTTCCTATGTATGGGTCAGTGGTCTCAATGTAGCAGGCAAGTTCCAGAAGATAGCAT |
| CAACCACTGTTAGAGATATACTGCCAGTCTCAGAGCCTGATGTTAATTTAGCAATGGGCTGGGACC |
| CTCCTCCAGTAGAACCTTCTAACCAGCTGCTGCAGTCAAAGTCGAATGCAGCTGGTTAGACTTTTT |
| TTAATGAAGCTTGGTGACCGTCGTACCAGTGGGGCCTCTAAGACTAAGTCACTCTGTCTCACTGTG |
| TCTTAGCCAGTTCCTTACAGCTTGCCCTGATGGGAGATAGAGAATGGGTATCCTCCAACAAAAAAA |
| TAAATTTTCATTTCTCAAGGTCCAACTTATGTTTTCTTAATTTTTAAAAAAATCTTGACCATTCTCCA |
| CTCTCTAAAATAATCCACAGTGAGAGAAACATTCTTTTCCCCCATCCCATAAATACCTCTATTAAAT |
| ATGGAAAATCTGGGCATGGTGTCTCACACCTGTAATCCCAGCACTTTGGGAGGCTGAGGTGGGTG |
| GACTGCTTGGAGCTCAGGAGTTCAAGACCATCTTGGACAACATGGTGATACCCTGCCTCTACAAAA |
| AGTACAAAAATTAGCCTGGCATGGTGGTGTGCACCTGTAATCCCAGCTATTAGGGTGGCTGAGGC |
| AGGAGAATTGCTTGAACCCGGGAGGCGGAGGTTGCAGTGAGCTGAGATCGTGCCACTGCACTCCA |
| GCCTGGGGGACAGAGCACATTATAATTAACTGTTATTTTTTACTTGGACTCTTGTGGGAATAAGA |
| TACATGTTTTATTCTTATTTATGATTCAAGCACTGAAAATAGTGTTTAGCATCCAGCAGGTGCTTCA |
| AAACCATTTGCTGAATGATTACTATACTTTTTACAAGCTCAGCTCCCTCTATCCCTTCCAGCATCCT |
| CATCTCTGATTAAATAAGCTTCAGTTTTTCCTTAGTTCCTGTTACATTTCTGTGTGTCTCCATTAGTG |
| ACCTCCCATAGTCCAAGCATGAGCAGTTCTGGCCAGGCCCCTGTCGGGTCAGTGCCCCACCCCCG |
| CCTTCTGGTTCTGTGTAACCTTCTAAGCAAACCTTCTGGCTCAAGCACAGCAATGCTGAGTCATGA |
| TGAGTCATGCTGAGGCTTAGGGTGTGTGCCCAGATGTTCTCAGCCTAGAGTGATGACTCCTATCTG |
| GGTCCCCAGCAGGATGCTTACAGGGCAGATGGCAAAAAAAGGAGAAGCTGACCACCTGACTAA |
| AACTCCACCTCAAACGGCATCATAAAGAAAATGGATGCCTGAGACAGAATGTGACATATTCTAGA |
| ATATATTATTTCCTGAATATATATATATATATATATACACATATACGTATATATATATATATATATT |
| TGTTGTTATCAATTGCCATAGAATGATTAGTTATTGTGAATCAAATATTTATCTTGCAGGTGGCCTC |
| TATACCTAGAAGCGGCAGAATCAGGCTTTATTAATACATGTGTATAGATTTTTAGGATCTATACAC |
| ATGTATTAATATGAAACAAGGATATGGAAGAGGAAGGCATGAAAACAGGAAAAGAAAACAAACC |
| TTGTTTGCCATTTTAAGGCACCCCTGGACAGCTAGGTGGCAAAGGG |
| |
| SEQ ID NO: 11-the DNA sequence of the β globin LCR containing only |
| essential elements (NCBI reference Sequence: NC_000011.10) |
| TTTATTTTGTTTTGTTTTCTAATCAACAGAGATGGGCAAACCCATTATTTTTTCTTTAGACTTGGGA |
| TGGTGATAGCTGGGCAGCGTCAGAAACTGTGTGTGGATATAGATAAGAGCTCAGGACTATGCTGA |
| GCTGTGATGAGGGAGGGGCCTAGCTAAAGGCAGTGAGAGTCAGAATGCTCCTGCTATTGCCTTCTC |
| AGTCCCCACGCTTGGTTTCTACACAAGTAGATACATAGAAAAGGCTATAGGTTAGTGTTTGAGAGT |
| CCTGCATGATTAGTTGCTCAGAAATGCCCGATAAATATGTTATGTGTGTTTATGTATATATATGTTT |
| TATATATATATATATGTGTGTGTGTGTGTGTGTTGTGTTTACAAATATGTGATTATCATCA |
| AAACGTGAGGGCTAAAGTGACCAGATAACTTGCAAGTCCTAGGATACCAGGAAAATAAATTACAT |
| TCCAAAAATTTAACTGAGACTTTAAAAAAAAAAAAAAACAAAAAAAAACCAGTGATCCATGGA |
| CACAGGGAGGGGAACATCACACACTGGGGCCTGTTGGGGGTGGGGGGCTAGGGGAAGGATAGCA |

-continued

Sequence Information

```
TTAGGAGAAATACCTAATGTAGATGACGGGTTGATGGGTGCAGCAAACCACCATGGCACATGTAC
CCCAGAACTTAAAGCATATTAAAAAAACAGTGATCATAAAAGAAGCTCAAATTTAACTATAAGAG
ACGGAATGGCTCCCACAATTCTTAACTATAATCTTACAGAATATTCTCATTGAATAGAAGTATGCT
TATCATTAGAGATTTGGACAGCCAGGAAAGCACAGAAAAAAAAAAAGGAGCTCTGTTGCCTTAT
AGCCTAGAGGTGTTTTGAACCTCACATAACACTGATGTCCAGGCCAAGGCCATCCTTCCCATGAAG
ATGGATGAATAAGCCATATCTGACACCTATGAAATAATGTTTACTTTAGTGGCATATTGCATTAGG
CTACCTGCCTTGGCACAGTTTTTCTTTACTTTTACCTGACTGATGAAACAATTAATTGCTTACATAA
ACATGAGTGCTCTAGTTATAAATTCCAGTGTAAAAAACACCCTGGTTTCGATATTCATCTTTTGAGC
CTTTTATTTTGGTCAGAACAAGTTTTCAAGAGCAAATCTCAGCCTACAAAACAAATGAGTCCAATT
CTAGAACTCAGTAATCCCATCAAGGCTCTGCCTGCGGAGGGCTAACTAGCTCTATGCAGGCTTAGC
ACTTCCAGCTCTACTCCACTGATTTCTTTGTGTGTGCATAGCAGTGGATGTGTCAGCATACATCCTT
TTAATTATAGTTGTATATGTGTTTGACTGCTCATTCATTCATTCAAAATTGTAAAATTGCTAAGAAT
ACAGCACAAAAACAGAATAGAGGAATAAAGTTCCTGTTTTCATGGACTTGATAGTGGAAAGAGCT
TGACATTAAATAAGCAAATGAAACATGTTATATACCAATGAGATTAGGTGCTATGGAGAAAAAAA
AAAAACTGAAATGAAGGCCAGAGTGTGATTAGGACAGGGTGAAAGGGTATCGCTACTTTAAGTAG
TATGGCAGGAAAGTCCTCACTATAAAGTTAACACCTGAGAGAGTACCCATAGATGATGAGGAACC
CATTTATATGAAACTATGATTAAATATTTAGGGCATAGGGAATGGCAAATGTAAATACCCTAAAG
ATGTAAGATGCTTAGAATTTTCAAGGAATATCAATAAGGCCAATGTAGGATGAGATTCGGTGAAG
GGGAGAATAAAAGATGAGTCATAGAAGTCCTAAATTATAAAATTTGGGACACTAATAATACCTA
CATCATAGAGTTGTAAGAAAAAACACTCTACACACATACACATAAATATATATATTTATTTATATG
AGAGCTATATATATGTATCTGTAATAAACATAATATATGCATGAACAACTATTGTAGAGAATTGTA
AGGATTTGGTTTTATTATAAATGATATAGGAAACTATCAGAAGACTTTGAACAAAGAGGTGACCAT
ATATGACTTACATTTTGAAAAGACTAATTTGGATAGTATATTGGGAAGAAATTGTAGTGGGGCAGT
GGTAGAAGCAGGAAGATTGTTATGAGTCAACAGCTATAATTTAGGTGGTGGTGACAGTGACTTAG
ACCAGAGTGGTAGCATTGGAGGTGAAGGCAAGGGGTCAGCCTCTGAAAACATCCTTTCACGAAAA
ACCAACAGGATTTTCTGACAGAGAATATGGAATTGGTGTGTGTGTGTTGCACTCATGCACACTC
TAGTGCATGCTAATTTCTGGCTGTGAGTATATGTCAGAGTAAGGATTTTGAAGCTAGGCAAAGTGA
GTCTTTGGGTTGAATTTTGTCAAGGTGTTTGTTCATCACAGTCTCTACCTCAGAATTTGGCTTTAAAA
TTGGAAAGCTGGGTGGGTGGATATGGAAATGAGAAACCATCTCTGGAGCTTGTCTACACATCATA
CCTTTAGCCAAAGTGACATCAAGTATTTCTTGGATGCTGACCAGAGGCTTCTGAGCCAGGCCCCTC
TAGCTGAAGGAAGTTCACAGTTTCTTTAAGGAGGGAAAATGGTAGATAAGTCAGAGAACAATCAG
ACAGAATTCTGTTCGGTCAGGGAATTTGATGGGTTTTGTTTGTTTGTTTGTTTGTTTTCGTTTT
TCTTTAGACAGAGTCTCGCTCTGGAGGCTGGAGTGCAATGGCATGATCTCTGCTCAGTGCAAACTC
CACCTCCCCGGTTCAAGCGATTCTCCTGCCTCAGCCTCCCAAGTAGTTGGATTACAGGCTCCCGTC
ACCACGTCCAGCTAATTTTTATATTTTTAAGCAGAGACCAGGTTTCACTATGTTGGCTGGGCTGGTG
TCCAACTCCTGACCTCAAGTGATCTGCCCACCTTGGCGTCCCAAACTGCTGTGATTACAGGAGTGA
GCCACCGCACCTCAAGGAATTTGATGTTTAGGCTGTGACCTCTGCACTAGGAATGGAAGGTTAGCC
ACTCCCACCCCACCCTTCGTCCTGCAAGTACCCAATCACACTGCAGAGCCACACCTGCCTTCCTTA
GAGGCGTGCCTCCATCCCTGATGAGTTTTTCCTCCATGTGTAGAATTGAATAAGAAGGATAGAATT
CAATTTAACAAGCTTTGAGTACTTCCTATAGCCTAGGCATTGTGCTGACAACTATGTTAGAGAGAG
AAATAGACAAGCTATAAACTTTTCCTCAGGACCATCTACATAATTTCTAGGCCCAATATAAAATGA
AAATGAATAGCCCCTTTGTCAAAAATTAAGGATTTCATGTCAGGAACAGCAAGGATGTTAAACCA
AGCATGGGGCCATCAAGCTATATCTGCTATTCATGATACGAAAAAATAAAGAGTATTCTAGTTATT
TAGCCACATATTTCAAGTTTAGTCTGATATCACCCTTTAAACACTGCCACTCAACCTAAAACAATG
CTAGTCTTTCTAGACCCATCCATGGAATTTTTCCCCACTGTTTTTTTCTAATTAATTTGTGATTTA
AATGGCTCATATTCCAGCCTGTGCCACAGTTATTACACATTTAACTCACTCTCTGTATTTTGTTATC
TGTATAAATACTCTTCAGGTTGATTTCCTTTCTTAATGTTTGTGTTTATGTTAGATATGCATCATGTA
GCCTGTCTTCATTTCTATCACAAACATACACTTGAACCAAAAAGGAAGTTTTTACATAGCATCACT
AAATCTTCTCTCTGTGCTCTTAGCGAAACCAAGTAGGCTGACAAGACATCATTCATTCACAGCGAA
ACCGAGTAGACTGACAAGAGGTCATTCATTCACAAATGAATACAAAAAACAGTGTCAAGTATACG
TGAGGTCCTGTAATGGGTCCTGGGCCTGCAAAACCCTCACAGCTGCTAACCTCAAGAAGCTCAGTG
GAGACATAACATTCATCTGAAAATTCCTTGCATGTCTGTTGAACTAATTTATCTGCCTCTCCTTAAA
TTTGTTCCTTTTTGTATAGTTCCTTAAGTCATGTCACATTTCTGAAACATCTTTGCCACTGTGAACTC
CTACAGAAGCCAGCTTCAAAGCCATTCTTCTGGAAGCCTTCTCTATCCCCTTGACCTCCTGTTTTTT
CTCCCACAAGCATTATGTCTGTCTGTCATTGTTTTTCATCCTCTTGTAGTCCTTCACAGTTACCCACA
CAGGTGAACCCTTTTAGCTCTCCTGGAGGAATGTTTCTTTCCTCTCAGGATCAGAGTTGCCTACATC
TTCCTAATGCACCAAGACTGGCCTGAGATGTATCCTTAAGATGAAGACTTCCCAGTAGCACCCCAA
GTCAGATCTGACCCCGTATGTGAGCATGTGTCCTCTAACAGCACAGGCCTTTTGCCACCTAGCTGT
CCAGGGGTGCCTTAAAATGGCAAACAAGGTTTGTTTTCTTTTCCTGTTTTCATGCCTTCCTCTTCCA
TATCCTTGTTTCATATTAATACATGTGTATAGATCCTAAAAATCTATACACATGTATTAATAAAGCC
TGATTCTGCCGCTTCTAGGTATAGAGGCCACCTGCAAGATAAATATTTGATTCACAATAACTAATC
ATTCTATGGCAATTGATAACAACAAATATATATATATATATATATATACGTATATGTGTATATATAT
ATATATATTCAGGAAATAATATATTCTAGAATATGTCACATTCTGTCTCAGGCATCCATTTTCTTTA
TGATGCCGTTTGAGGTGGAGTTTTAGTCAGGTGGTCAGCTTCTCCTTTTTTTTGCCATCTGCCCTGT
AAGCATCCTGCTGGGGACCCAGATAGGAGTCATCACTCTAGGCTGAGAACATCTGGGCACACACC
CTAAGCCTCAGCATGACTCATCATGACTCAGCATTGCTGTGCTTGAGCCAGAAGGTTTGCTTAGAA
GGTTACACAGAACCAGAAGGCGGGGGTGGGGCACTGACCCCGACAGGGGCCTGGCCAGAACTGC
TCATGCTTGGACTATGGGAGGTCACTAATGGAGACACACAGAAATGTAACAGGAACTAAGGAAAA
ACTGAAGCTTATTTAATCAGAGATGAGGATGCTGGAAGGGATAGAGGGAGCTGAGCTTGTAAAAA
GTATAGTAATCATTCAGCAAATGGTTTTGAAGCACCTGCTGGATGCTAAACACTATTTTCAGTGCT
TGAATCATAAATAAGAATAAAACATGTATCTTATTCCCCACAAGAGTCCAAGTAAAAAATAACAG
TTAATTATAATGTGCTCTGTCCCCCAGGCTGGAGTGCAGTGGCACGATCTCAGCTCACTGCAACCT
CCGCCTCCCGGGTTCAAGCAATTCTCCTGCCTCAGCCACCCTAATAGCTGGGATTACAGGTGCACA
CCACCATGCCAGGCTAATTTTTGTACTTTTTGTAGAGGCAGGGTATCACCATGTTGTCCAAGATGG
TCTTGAACTCCTGAGCTCCAAGCAGTCCACCCACCTCAGCCTCCCAAAGTGCTGGGATTACAGGTG
TGAGACACCATGCCCAGATTTTCCATATTTAATAGAGGTATTTATGGGATGGGGAAAAGAATGTT
TCTCTCACTGTGGATTATTTTAGAGAGTGGAGAATGGTCAAGATTTTTTAAAAATTAAGAAAACA
```

| Sequence Information |
|---|
| TAAGTTGGACCTTGAGAAATGAAAATTTATTTTTTTGTTGGAGGATACCCATTCTCTATCTCCCATC |
| AGGGCAAGCTGTAAGGAACTGGCTAAGACACAGTGAGACAGAGTGACTTAGTCTTAGAGGCCCCA |
| CTGGTACCCAGATGAGAAGGCACCTTCATCACTCATCACAGTCAGCTCTGCCTTTCTCCTCTCTCCT |
| TTCTCATCAGAAATTTCATAAGTCTACTAGGGTCAGGCAGATCACATAAGAAAAGAGGATGCCAG |
| TTAAGGTCTGCAGTGAGTATGAGCCCATCCCTGATGAATTAAGGCAATCAACACTTTAGGCAGCCA |
| TGTTGCCATGAGAGATTAGGAGGGGCAAATGAGCCCAGAAATACCACCTACTTCTTAGATGATCT |
| TGAGCAAGTTGCTTAACTTCTTGAAGTCTCTGAAATATAGGATGATAATATGTATTAGCTAATAGA |
| ATTATGAGGATGAGATTAGTTTATTGTGTAAAGAACTAGGGACACAGTATATATTCAGTAAGTGTT |
| TTCTGTTACAGTATTATGATAAATATATACATGCAACTATTACAGTTGCATGCTACCTTAAAGAAT |
| AATTGGAGGTACAGTTATTCGGAGGTATTTCTTGACTGTTAATGTTGGCAGCAGATTCAGCTTATTT |
| TACAACACTATTCAGACCTCTCACAATAATTCCCTAGGAGATATTTAGACAACAAGCCATCATGTT |
| GTAACTTCTCATTTGTCTTTTCTCACTTACCCTCTCATTCACCCACCTCTTTTGCTCTCTGTTCCTGTG |
| AAAGTACCCTTCTACTTAGCCTACTTTTGACCAGTGTGCATGTCACTGGGCAATACAAGACCTCTG |
| AGCTTTGGCTTAGAAGGAAATACAATAATGGCTAATTTTTGAGAAAGAGGAACTCTAGCCCATCA |
| GGGAAGACATAGGGAGTTCTGTAGGAATGAGTTCTTCCATTCTTTTTTACAGATGAGAAAGACAATG |
| TGAAGCCCCAAATGATTTTAAAGTAGTTAGCATATGGAGAAATGGCTTGCATTGGTAAAATTTGGG |
| GAAACTTTGTTGTCAGACCCGGCAAAGGGAGATGCAGAGAATCTGCAGTTTCTTCTCATTTCTTGT |
| GTACCTATCACAGCACCACAGCACTATTCCTAGCATAGTTTAGGGCCCTCAGTTCTTGACGCTAGT |
| TAGAATTTCACACAAACTTAAACTAGACAAACATATGTATGTTTCTGAGGCACTGAGGTCACTGCA |
| GGATGAAGACGGAGCCAATGGGTTAGACCAGAAGAGTAAATGAACACTATAACACATAAACACT |
| CCCTTTAACCAAAGTTGCAGCTTGACCAAGGGGTCAAAGGGTAATTTGGGCAGGCATGGGCCTTC |
| AGTTTTCTCAAGTGTCTGCTTATAATTTGTCATATGACAATCTCTGTAACCCAAGAGAAAATCTCTT |
| TATTCTGAAGTTGTTTCTAAATTTTTCTTTACCTTTTTCTCCCTCAAACTTTCCTGAAGAAATGCAAT |
| TATGGTTGAGGAAGTATGGTCTGCAACTGTGGCTTGGACCACAACTTCCAATCGACAAGAAGTAA |
| AAGTAAGAAGCAAGGGCCACAGGGCAGGAATATCTACTTCTAATTTCTCGCATCCACAATATCTG |
| AGTTTGTGTTTTGCTGTGGAAAAAACACTGTCTTCAGAGGTAGCAGAACTGGGTCTACATCCTAGC |
| CTTACTACTTGGTGGTTCTGTAAGCTTGGACAAATTATTTCATGTCTTTGATTTTCGAGTCCCCAGT |
| TAATAAGAGCTCATGTAATGTAGACAGTAGGAGAGCTCAGACCATCTGACTTCTAATTACTAATTG |
| TCTACTTATTAGCTTGTGCTTTCAATAAGTTGATCTACACTACAAGTACATTGGGCTCCTCATCAAT |
| AAATGAGGTAATAATCTACTTCTGAGTATTGGTGTGAGTAAAACTAAGTTAATTCATATAATAAAC |
| TTCTTTTTTTTTTTGAGATGGAGTCTCACTCTGTCGCCTAGGCTGGAGTGCAGTGGTGCAATCTT |
| AGCTCACTGCAACCTCCACCTCCTGGGTTCAAGTGATTCTCCTGCCTCAGCCTCCTGAGTAGCTGG |
| GATTATAGACGCGTGCCACCACACCTGGCTGATTTTTTGTATTTTTTAGTAGAGAAGGGGTTTCACC |
| ATGTTGGCCAGGCTGGTCTGGAACTCCTGACCTCAGGTGATCCAATTGCCTTGGCCTCCCAAAGTG |
| CTGGGATTACAGGCATGTAATCCCATATATGAGCCACCGTGCCCGGCCTCATATGATAAACTTAAA |
| TTTGATTCTAGCATATACTAAGTACTCAAGAGGTGTTACTTATCATTAGTATTAATTATAGTATGTT |
| CAATAATACATATCTCACAGAATTACCATATGTAATGAGATTATTAAATATCATAAAATGGCACCT |
| GACATATAGAAAGATTTCAGTAAGTATTAATTCCCACTTCTCTTTCATTTACCTCCAGCCTAAATCT |
| ACACTATTTCCTCGTGTCTCTCATGTGGTTTCTAGTCCCTTCACCATCTTGTTTCCCTCTCAACTCCT |
| GTGCAGATTCCTAAAAATTTCTCATGTTCAGAACCTTGGGCTTCCATGTTTCCAGTGAAGTCAGATT |
| TTTTTAGATGGCAAAGTTGCTGTTAGACAATTTCATCTGTGCCCTGCTTAGGAGCTTAATCTTTAAT |
| GAAAGCTAAGCTTTCATTAAAAAAAGTCTAACCAGCTGCATTCGACTTTGACTGCAGCAGCTGGTT |
| AGAAGGTTCTACTGGAGGAGGGTCCCAGCCCATTGCTAAATTAACATCAGGCTCTGAGACTGGCA |
| GTATATCTCTAACAGTGGTTGATGCTATCTTCTGGAACTTGCCTGCTACATTGAGACCACTGACCCA |
| TACATAGGAAGCCCATAGCTCTGTCCTGAACTGTTAGGCCACTGGTCCAGAGAGTGTGCATCTCCT |
| TTGATCCTCATAATAACCCTATGAGATAGACACAATTATTACTCTTACTTTATAGATGATGATCCTG |
| AAAACATAGGAGTCAAGGCACTTGCCCCTAGCTGGGGGTATAGGGGAGCAGTCCCATGTAGTAGT |
| AGAATGAAAAATGCTGCTATGCTGTGCCTCCCCCACCTTTCCCATGTCTGCCCTCTACTCATGGTCT |
| ATCTCTCCTGGCTCCTGGGAGTCATGGACTCCACCCAGCACCCAACAACCTGACCTAACCACCTATC |
| TGAGCCTGCCAGCCTATAACCCATCTGGGCCCTGATAGCTGGTGGCCAGCCCTGACCCCACCCCAC |
| CCTCCCTGGAACCTCTGATAGACACATCTGGCACACCAGCTCGCAAAGTCACCGTGAGGGTCTTGT |
| GTTTGCTGAGTCAAAATTCCTTGAAATCCAAGTCCTTAGAGACTCCTGCTCCCAAATTTACAGTCAT |
| AGACTTCTTCATGGCTGTCTCCTTTATCCACAGAATGATTCCTTTGCTTCATTGCCCCATCCATCTG |
| ATCCTCCTCATCAGTGCAGCACAGGGCCCATGAGCAGTAGCTGCAGAGTCTCACATAGGTCTGGCA |
| CTGCCTCTGACATGTCCGACCTTAGGCAAATGCTTGACTCTTCTGAGCTCAGTCTTGTCATGGCAAA |
| ATAAAGATAATAATAGTGTTTTTTTATGGAGTTAGCGTGAGGATGGAAAACAATAGCAAAATTGA |
| TTAGACTATAAAAGGTCTCAACAAATAGTAGTAGATTTTATCGTCATTAATCCTTCCCTCTCCTCT |
| CTTACTCATCCCATCACGTATGCCTCTTAATTTTCCCTTACCTATAATAAGAGTTATTCCTCTTATTA |
| TATTCTTCTTATAGTGATTCTGGATATTAAAGTGGGAATGAGGGGCAGGCCACTAACGAAGAAGAT |
| GTTTCTCAAAGAAGCCATTCTCCCCACATAGATCATCTCAGCAGGGTTCAGGAAGATAAAGGAGG |
| ATCAAGGTCGAAGGTAGGAACTAAGGAAGAACACTGGGCAAGTAGGATCCAGGTTGTCCAACGCTG |
| AAAGTAGGAATCTAAGCACTAGTCTCTGGATGCTAGGAGGGCCTCTGCATGGGTAACTCTTTCAAC |
| TAGCCAGGGGCTGGACTGTGGAGAAACCATTTCCAGATAGAAGTGAGGAGATTCCAGCAGGAAAC |
| ACTTAAGAGAGGATCCCTGGAAGTTCGGGGCAGGAGGCTCCCTGTCACATGAAGGAAACCTGCTC |
| AGCGTAGGCTCTAGGTTCTTCCCTACTCTTATCCAATGGGGCTTCTGATTTTAAGCCAGTCTTCACA |
| AAGCCCCAGATTTCTACATGCTGGAGCCCTGAATGGGCAGGAAGCATTGCGGTTTCCATTTCATTC |
| AGAGCTCTTTCATACCCTGCTTCCCCATAGTTTGTCTCAACATTTCTGTTGATAATCTGATTCATGC |
| AACCAAGAATTATGAGAGAGCCTTCAGTCATGCCTAGGCCTGCATTTATTGTTGTGCATATGATGG |
| GGTAGCAGACAAGAAAACGTTAACAGCATAGACTTTCTCAGAGCTATATGAGTTTGGGAATTAAT |
| CAAGACCAGCCTTTTGCTCAGGGTAGAAATCCCCTATAGGGATTTATTCAATGATGGGTTAAAAGC |
| TTTCTATATGGTGAGGAGCTCACAGATTTTCCAAGCCCTTGCTTGTCTAGACAGCTTAATGTTTAT |
| GAAATTCTTACACACAAGAATCTTCTAATCCTGGGTTACATAATATAACTTGATTCCCTATTCCA |
| GAAGATAATATTCCCATATTCTGAAGCATTCATGCATTTGTTAAATAATAGGCATAGTGACAAGTG |
| CCAGAACTCTAACAGTCAACCAGAGAGCCACAGTTTTCAACTTCACAAAGTTAACCATCTAACTGA |
| AGACAGCAGCAATCAAAACCACCACCCCTTCTCCACATGGTGTAGTCTTTCCTGATGTCAGGGATG |
| TTAGGCTCAGGTTAGGAAAGTCAGACTATCATCCCAGAGCAGGACACAGACGAATAAAGTGTAAT |
| TTTTTAGTCACTTAGGAAAAACAGTGGAATGCAAAGAGTAAAAAATGCTTTCTGAATGGATAACTT |

Sequence Information

```
GGCCTGGGAGGCCTTTGGAAGCAGAGACTGGAGCTTAAATTTAAACATCTTTGTATCCCCAGCATC
CAGCATACAGACTGCCAAGAAGTACATGTCAATAAATATTTATTGGATAGTGAGCAAAGACATAA
TTAGGACCAAATCTCAATTCTACTATTTGCTAGTAGTTTATGTTTGTGTGTGAGAGTGTATGCTT
GAGCAAGTTGAGAGGTAGTTTTTTTAACTGTAGTAAAATGGGGATAATAATAGTATCTACCTGAAA
GAATCCAAGAGTATTAAATATGATTAATTATGCAAAGCACTAATTACAGTCTCTGATAGCCTTCAA
TAAATGTCAGTTATTTTTATTATTACAGTTAAAGATGAATGGGCATAAAGTACAGAAACACTAGTTT
TCACCTGCAGCAAGAATGATTGCAGTTAAACAAAAAATACTAGCAACATTTCTAGAGTAGTTAG
CATTTATAAGTCACTGCTTTAAACTCTTTGCATGTATTAACTCACTCGGGCTGCAGAACAATCTTAT
GAGCCTGTTAAAACTCCTGTAATCATGCTTATAATCCCAGCACTTTGGAAGGCTGAGGTGGGCAGA
TTGCTTGAGCTCCGGAGTCTGAGACCATCCTGTGTAACATGTGAAACCCATCTCTACCAAAAATA
CAAAAAATTAGCGAGGTATGGTGGTGTGTACCTGTGGTTCCAGCTACTCAGGATGTTGAGGTGGG
AGGACCGCTTGAGCCTGGGAAGTGCAAGTTGCAGTGAGCCGAGATTTTGCCACTACACTCCCATTT
GGGTGACAGAGTGAGACCCTTTCTCAAAAACAAACTAATTAAAAAACCCTCCATTTTACAGATGA
AGAAACTGAGTCATACAACTACTAAGAGAAACTGAGTCACTAATCACTCAGGTGGTCTGGCTCCA
GCATCTGTACTCTTAATCTCTGCTCTATACTGCCCAAGACTTTTATAAAGTCAAGGGTTGAGTCACT
GAAATGAGTTATTGGGATGGCTGTGTGGGAAGGGTGCTAAGTTCTTTCCTAAAGGTATGTGAGAAT
ACAAAGGAAAGAAGCATCCTCCTTTTTACACACGTGAACTAGTGCATGCAAATCTGACACTCAGTG
GGCCTGGGTGAAGGTGAGAATTTTATTGCTGAATGAGAGCCTCTGGGGACATCTTGCCAGTCAATG
AGTCTCAGGTTCAATTTCCTTCTCAGTCTTGGAGTAACAGAAGCTCATGCATTTAATAAACGGAAA
TTTTGTATTGAAATGAGAGCCATTGGAAATCATTTACTCCAGACTCCTACTTATAAAAAGAGAAAC
TGAGGCTCAGAGAAGGGTGGGACTTTCTCAGTATGACATGGAAATGATCAGGCTTGGATTCAAA
GCTCCTGACTTTCTGTCTAGTGTATGTGCAGTGAGCCCCTTTTCCTCTAACTGAAAGAAGGAAAAA
AAAATGGAACCCAAAATATTCTACATAGTTTCCATGTCACAGCCAGGGCTGGGCAGTCTCCTGTTA
TTTCTTTTAAAATAAATATATCATTTAAATGCATAAATAAGCAAACCCTGCTCGGGAATGGGAGGG
AGAGTCTCTGGAGTCCACCCCTTCTCGGCCCTGGCTCTGCAGATAGTGCTATCAAAGCCCTGACAG
AGCCCTGCCCATTGCTGGGCCTTGGAGTGAGTCAGCCTAGTAGAGAGGCAGGGCAAGCCATCTCA
TAGCTGCTGAGTGGGAGAGAGAAAAGGGCTCATTGTCTATAAACTCAGGTCATGGCTATTCTTATT
CTCACACTAAGAAAAAGAATGAGATGTCTACATATACCCTGCGTCCCCTCTTGTGTACTGGGGTCC
CCAAGAGCTCTCTAAAAGTGATGGCAAAGTCATTGCGCTAGATGCCATCCCATCTATTATAAACCT
GCATTTGTCTCCACACACCAGTCATGGACAATAACCCTCCTCCCAGGTCCACGTGCTTGTCTTTGTA
TAATACTCAAGTAATTTCGGAAAATGTATTCTTTCAATCTTGTTCTGTTATTCCTGTTTCAATGGCTT
AGTAGAAAAAGTACATACTTGTTTTCCCATAAATTGACAATAGACAATTTCACATCAATGTCTATA
TGGGTCGTTGTGTTTGCTGTGTTTGCAAAAACTCACAATAACTTTATATTGTTACTACTCTAAGAAA
GTTACAACATGGTGAATACAAGAGAAAGCTATTACAAGTCCAGAAAATAAAAGTTATCATCTTGA
GGCCTCAGCTTTCTAGGAATAATATCAATATTACAAAATTAATCTAACAATTATGAACAGCAATGA
GATAATGTGTACAAAGTACCCAGACCTATGTGGTAGAGCATCAAGGAAGCGCATTGCGGAGCAGT
TTTTTGTTTGTTTGTTTTTGTATTCTGTTTCGTGAGGCAAGGTTTCACTCTGCTGTCCAGGCTGGAGT
GCAGTGGCAAGATCATGTCTCACTGCAGCCTTGACCTCCTGAGCTCAAGGGATCCTCCCATTTCGG
CCTCCTGAGTAGCTGGGACTACAGGTGTACATCACATGCCTGGCTAATTTTTTTTTTTTTTTAAGT
AGAGACGAGGTCTTGCTATGTTGTCCAGGATAATATCAAACTCTTGAGCTCAAGCAGTCCTCCCAC
TTCTACCTCTCAAGTGCTGGAATTACAGACATGAGCCACCACTCCTGGCTTGCAGACTATTTAAAT
GACTAATTCCTGACACTACTTGAGGGATACTAGACAGTAGACAACACATCTTTAATATACCAAATG
GGTGACTGTAGGGTTGAGAGGGAGATTAGAATTCAATGTTTTATGACCAAAAAGGCTTAAATCAG
GCACAAGCTTAGGTCTTTTCAACTGTGAGGACCGGACTGAAAGTGTGCAGTTCAAGGCCCTGTAGT
TGCTGTTTAACTGTTCCCAGGTGGAAGTCTCTTCAAAGAACCACTGGTGCAAAAAGGGAACTACCT
GGGGATAAATATTTCCTCCAGAAAGGGGGAAAGTGCAAGCTCCCCTACCAAAAGCACCAGGCAAG
TCCTTGTCTATTTTCCCTGAAGTTCTCAAAGAAATGAGACCCTTGTTTACCTTTAAGATTAGAGAAG
GCTTGAAAAGTTTGAGCTGTGCCTTTGGAGGCCAACAAACTTTTCTCCTTTGTTGACCAAGTTCAGC
TCTCCTGTATGCTTCCAAGGTCTGTTGCATCAAGAGTGAGAATTGAAGGTCTTAGAAGTCTGGGATC
TCAGATGTAGGGAAAAGAGGAGATTTCCTGTTCACTCACTGTTAAGATATGGCTGAAATTTTTTGA
TCTAGTCATCTACAAAGCATGAGTTGTGGGTCAGAAATTGTTTTTCACATCTTTTGACTTCCTTTGA
CATCAGAATATAACCTAGGAATTGATTACTTAAGTGAAGGCAAGGTACTTTGGTCTGGACAGGAA
CATTTTTGAACAAGGTAGGGAGACAGCTATGAAGGCAAGCATTTATTCTATCTATCATCTATCTGTC
TATCTATCTATCTATTCTTTCATCCACTTATTTATACATTTAAACAAAAAGTATAGAGCGTAGTATA
ATTTGTAAGTGCTCAGGGCTGTGTGTGTATGGATTGTTTGAAATGAAACTAAAGTGGGAGTATAAT
TCTACTGCCCCCTTAACCCTGTGGTCCCTACACTACCCTGCAAGACTCTTAGCTGCTTAGCTTAATT
GTGAGGCTGATTTGGGGCATAGCACCCCATCCTCTCTGTCTTTCAACATCCTCATAATAACTTGAG
AATAATTTTATAAAATATCACAATAGGGTCATGTTCAGTAGGGTGATATATAAAATTAGACAAGCC
ATAGTTTGAGTTTACCCTTTTGAATAAATATATGACAAAAGGCAATTTAATTATCTTTATGAGTTTG
GAGGTATCCAGTATGAAATTTAGATAATACCTGCCTTCTAGTGTTGAAATTAGAACTTAATGATAT
AATGCATCAATGAACTTATTATAGTTCCTAGCACAAAGTAAGAATCCTTTCAATGTGTGTGTGT
GTATGTATTTATCTGTTATTAATAGGAATCTTATGGGCATTATCTCACTTAATCCTTATTAATAACT
ATGAAGCAGGTATTTATTTGAGTTTTCCAAGTGAGTTAAGTATAGCTTGAATACTTAAGGAAATA
TCCACAGGTTACATAGCTAGTATATAACTGAGAAATAATTTTATTTATATTATAAAACATTCTAAC
AATACAGATGTATATAAACTAAAAAACTGAAAGGGCTCATGCAACCCTACCTTCTCAATATCACTT
CTTCACTTAGAAAAAACCAGCCTTAGCTGTCTGCTATGAATCCTTTCAACATCCTCATAATTCTGAGAAA
TGAGAGAGAGAAATGGGGAGGGTAGAAGGAAGGAAGATAGGGTAAGAGACAGGGAAGGAGGTG
TGGGGAAAGAAATTAAATTATTCTTTTCTCTGTCTCTTGAAAGAGCTCTTTCCATTACATTGAATCA
AAGGTAATGTTGCCATTTCTGGACTCTTGAAATAAAGAAAGACCGATGTATGAAATAATTTTGAAA
GTCTATGGCATTTTCAAAATGCAAGGTGATGTCTTACTAACTAGCCTTTGCTTTATTATTAGAAATG
GGGAAGTGAGTATAGACATTTTATCAGGAGATATATTAGGAAAAAGGGAAACTGGAGAAACTGG
GAGGAGTATCCAGATGTCCTGTCCCTGTAAGGTGGGGGCACCCACCTTCAATCAAAGGG
```

SEQ ID NO: 12-the DNA sequence of the EF1α full length sequence
(NCBI Reference Sequence: NC_018917.2)

```
TTAAAGCTTAAAATTCATTTATTGTAGTGAGCAAGTTTGTAATGAATACCAGCAGGTGGTGCTCAA
GCCACAGTTGTCTAAGACACTGGGTTTCACAGGAAGTTAATCTCAATCTCAGTATATGCAAGTAAA
```

-continued

Sequence Information

```
CTGACTCATTCCTGCTTCCAGTGGGAACAATTTTTCAGTTAAATCTTGCTTCCTTGCATGTCAAGAA
TTCTCTACTGGTAAATCTTACAGGTGTCAACTTTCATTATCAGGGCATCTATTGGCCATCTATTAAA
GGCCTTACCTGTTTTTTCTGTCATCCAGCAAATCTTAGACTATTTACTTGTGTAAACATTAGATAGC
AAAGAAACTAAGGACAAAAATCTCTAGTTCAATTTAGACTTGATACCTCAGAGCACTGGCTGATG
GGAAGGCATTTTATCTAATTCAGACTCAGATGAGGGAAAACGATAACACTTCATTACAGACTTGTC
TATGGCCAATTCAAGTACCTTTGAATCTTGAGCAATACACATTGCCAGTCACTTTAAGAGGCCTTA
TCTCTTGGGCTGCTTTAACTCCTGCTTAGCATGTCCTTAAGAACACATGTCCTGGCCAGGCATGGTG
GCTCATGCCTGTAATTCCAGCACTTTAGGAGGCCGAGGCGATCACCTAAGGTCAGGAGTTTGAGAC
CAGCCTGACCAACATGGAAAAACCTCATCTCTATTAAAAACACCAAATTAGCACATGCCTGTAATC
CCAGCTACTTGGGAGGCTGAAGTAGGAGAATTGCTTGAACCCATGAGGAGGAGATTGCAGTGAGA
TTTTGCCATTGCATTCTAGCCTGGGCAACAAGAACTCCATCTTAAAAAAAAATTTTAAAAACCATC
ACACAAACAGAAAGCATGTCCTTTAATTTTACCTATCCTTCAAACTTAAGCAAAAATTTTCCTTTTA
TAACCAAAAAAAAACCTTTAGACACTTTTACATATGGGAGGTCAGGCACAGTGGCTCATGCCTGTA
ATCCCAGCAGGAAGATCGCGAAAAGCATTTTTCAAATGCACAAATGCTTAAAGATTCAGGAGTAA
GTGGGCTATTACACCTGTTAAGCCTATTACCATGTAGTTTCATTCCTCTAGTGACCAAGTAGACAAAC
TGCTAATTATCAAAGCATAAAAGGTATTAGACTCTGCAGGAGAAAAGCAATGTAGATTAGTCTAA
TTTTATAGCTACTTCAAATTGCCATCTTTTTCTATTAGAACCTTGTTCCTATTCTGAATAGCACTCAA
TAGAACTTGTGAAACCATCAAACTGGCATAAAGCTTACTCCACTGACTTCAAAATGGACCCTTCCA
CTCATAGGGTGTACACTAGCCACTACACTTATTTCTTATGTCATGGCAAATAGTCAACTTTCACTGC
CCAGTCATTTTAACCCACGTTTCAACATGCACATCCCAGTAATTTGGAAACATTTTGTTTCCAAAGA
TTCACTTAACATTGGTTTAGCAACATGAAGCTTTCTATGCAACACAAGGACTCAGTTTTTGGCCTGT
TTTAGTGACAGGCAATCAGCAACATGCTGCATTTCTCTCAGTGTTGTAATCAAAGCAACCCTCCC
ATAGCTTTAAATGATATTCCTTCCCCTTCCAATTATGTGGGGGAAAACAACCCTATTCTCCACCCA
GAAGTGTTAACTCAAGAATTACATTTTCAAGAAGTTTCCAGATTCGTAAAACCAGAATTAGATGTC
TTTCACCTAAATGTCTCGGTGTTGACCAAAGGAACACACAGGTTTCTCATTTAACTTTTTTAATGGG
TCTCAAAATTCTGTGACAAATTTTTGGTCAAGTTGTTTCCATTAAAAAGTACTGATTTTAAAAACTA
ATAACTTAAAACTGCCACACGCAAAAAAGAAAACCAAAGTGGTCCACAAAACATTCTCCTTTCCTT
CTGAAGGTTTTACGATGCATTGTTATCATTAACCAGTCTTTTACTACTAAACTTAAATGGCCAATTG
AAACAAACAGTTCTGAGACCGTTCTTCCACCACTGATTAAGAGTGGGGTGGCAGGTATTAGGGAT
AATATTCATTTAGCCTTCTGAGCTTTCTGGGCAGACTTGGTGACCTTGCCAGCTCCAGCAGCCTTCT
TGTCCACTGCTTTGATGACACCCACCGCAACTGTCTGTCTCATATCACGAACAGCAAAGCGACCTA
TTAAAAAAAAAGTTAATTATTACCCAAAGTACTGTTCAGTTGTATTTTTCATCTTTAACACAACTTT
TTTACATTTAAGTAGTCATCCTTACCCAAAGGTGGATAGTCTGAGAAGCTCTCAACACACATGGGC
TTGCCAGGAACCATATCAACAATGGCAGCATCACCAGACTTCAAGAATTTAGGGCCATCTTCCAGC
TTTTTACCAGAACGGCGATCAATCTTTTCCTTCAGCTCAGCAAACTTGCATGCAATGTGAGCCGTGT
GGCAATCCAATACAGGGGCATAGCCGGCGCTTATTTGGCCTGGATGGTTCAGGATAATCACCTTGG
AAAAAAGATTTGCGTTCAGTGCAAATCCAAAGTCTCAAATGACTTTAGCCTCTGCAGTAAGTTAAT
GTTACTTTAAATTGTTACCTGAGCAGTGAAGCCAGCTGCTTCCATTGGTGGGTCATTTTGCTGTCA
CCAGCAACGTTGCCACGACGAACATCCTTGACAGACACATTCTTGACATTGAAGCCCACATTGTCC
CCAGGAAGAGCTTCACTCAAAGCTTCATGGTGCATTTCGACAGATTTTACTTCCGTTGTAACGTTG
ACTGGAGCAAAGGTGACCACCATACCGGGTTTGAGAACACCGATCTCCACTCGGCCAACAGGAAC
AGTACCAATACCTAAAAATATTTACAGCATACTAAATACCTATGAAGGCAGACAGTACTCTATCAA
CTCAAATTCAACTTTGTTTACAGCCAACTTACCACCAATTTTGTAGACATCCTGGAGAGGCAGGCG
CAAGGGCTTGTCAGTTGGACGAGTTGGTGGTAGGATGCAGTCCAGAGCCTCAAGCAGCGTGGTTC
CACTGGCATTGCCATCCTTACGGGTGACTTTCCATCCCTTGAACCAAGGCATCTGAAACACAAGCA
TGCCAATTTGTGTAAGCATGAAATCGCCATTCCCAGAGCTTTTTAACAATGGTCTTGAAAGCCACT
TACGTTAGCACTTGGCTCCAGCATGTTGTCACCATTCCAACCAGAAATTGGCACAAATGCTACTGT
GTCGGGGTTGTAGCCAATTTTCTTAATGTAAGTGCTGACTTCCTTAACAATTTCCTCATATCTCTTC
TGGCTGTAGGGTGGCTCAGTGGAATCCATTTTGTTAACACCGACAATTAGTTGTTTCACACCCAGT
GTGTAAGCCAGAAGGGCATGCTCTCGGGTCTGCCCATTCTTGGAGATACCAGCTTCAAATTCACCA
ACACCAGCAGCAACAATCAGGACAGCACAGTCAGCCTTTAAGAAAGCAAAGACATATCCCTGTC
AACTCTCCAAATGACAAAACCAGTGTACAAAGCAAGCCTTTTGGGATAAAGAAACCTAGAATTAT
TAATCCCACCAACCTGAGATGTCCCTGTAATCATGTTTTTGATAAAGTCTCTGTGTCCTGGGGCATC
AATGATAGTCACATAGTACTTGCTGGTCTCAAATTTCCACAAGGAGATATCAATGGTGATACCACG
TTCACGCTCAGCTTTCAGTTTATCCAAGACCCAGGCATACTTGAAGGAGCCCTTTCCCATCTGTAA
GGATTAAGAGTCTTTACTTGGTTACTAAAACACAAACTCCAGCTTCAATTTCCTTGTCCCCAGCCCT
TAATTGGCAGTTTCACTTTACAACTCCAAGTCCAAAGTGATTTTAGTCACTTTGGGTTACAGAAG
CAACCAAAAATCAAACTTTTATAAGTAGGATCTTAACTATTAACATCCAAATCTACTCACTAGCAA
TACGATTACAGAAGTCACCAAAAGCAAAATTATTTCATAAGTAAGGTCTTAACTATTAGCATTCAG
ATCTAAACCACTCACTAGTTCTGGGGAAATCACCTAATGATTCTGCTGGTAAAACTCATTTTAGTT
GATCTTTCCCTTTCTGGTATTAAACATACCTCAGCAGCCTCCTTCTCAAATTTTTCAATGGTTCTTTT
GTCGATGCCACCGCATTTATAGATCAGATGGCCAGTAGTGGTGGACTTGCCCGAATCTACGTGTCC
AATGACGACAATGTTGATATGAGTCTTTTCCTTTCCCATTTTGGCTTTTAGGGGTAGTTTTCACGAC
ACCTGAAATGGAAGAAAAAAACTTTGAACCACTGTCTGAGGCTTGAGAATGAACCAAGATCCAAA
CTCAAAAGGGCAAATTCCAAGGAGAATTACATCAAGTGCCAAGCTGGCCTAACTTCAGTCTCCA
CCCACTCAGTGTGGGGAAACTCCATCGCATAAAACCCTCCCCACCCAACCTAAAGACGACTCTCC
AAAAGCTCGAGAACTAATCGAGGTGCCTGGACGGCGCCCGGTACTCCGTGGAGTCACATGAAGCG
ACGGCTGAGGACGGAAAGGCCCTTTTCCTTTGTGTGGGTGACTCACCCGCCCGCTCTCCGAGCGC
CGCGTCCTCCATTTTGAGCTCCCTGCAGCAGGGCCGGGAAGCGGCCATCTTTCCGCTCACGCAACT
GGTGCCGACCGGGCCAGCCTTGCCGCCCAGGGCGGGGCGATACACGCGGCGCGAGGCCAGGCA
CCAGAGCAGGCCGGCCAGCTTGAGACTACCCCCGTCCGATTCTCGGTGGCCGCGCTCGCAGGCCCC
GCCTCGCCGAACATGTGCGCTGGGACGCACGGGCCCCGTCGCCGCCCGCGGCCCCAAAAACCGAA
ATACCAGTGTGCAGATCTTGGCCCGCATTTACAAGACTATCTTGCCAGAAAAAAGCGTCGCAGC
AGGTCATCAAAAATTTTAAATGGCTAGAGACTTATCGAAAGCAGCGAGACAGGCGCGAAGGTGCC
ACCAGATTCGCACGCGGCGGCCCCAGCGCCCAGGCCAGGCCTCAACTCAAGCACGAGGCGAAGGG
GCTCCTTAAGCGCAAGGCCTCGAACTCTCCCACCCACTTCCAACCCGAAGCTCGGGATCAAGAATC
ACGTACTGCAGCCAGGGGCGTGGAAGTAATTCAAGGCACGCAAGGGCCATAACCCGTAAAGAGG
```

Sequence Information

CCAGGCCCGCGGGAACCACACACGGCACTTACCTGTGTTCTGGCGGCAAACCCGTTGCGAAAAAG

SEQ ID NO: 13-the DNA sequence of the EF1α used in the vector
(i.e., the EFS sequence).
GGCTCCGGTGCCCGTCAGTGGGCAGAGCGCACATCGCCCACAGTCCCCGAGAAGTTGGGGGGAGG
GGTCGGCAATTGAACCGGTGCCTAGAGAAGGTGGCGCGGGGTAAACTGGGAAAGTGATGTCGTGT
ACTGGCTCCGCCTTTTTCCCGAGGGTGGGGGAGAACCGTATATAAGTGCAGTAGTCGCCGTGAACG
TTCTTTTTCGCAACGGGTTTGCCGCCAGAACACAGGTGTCGTGACGC SEQ ID NO: 14-the DNA sequence of the HS4 PCR forward primer
TTTGCGGCCGCTATCTCATTGCTGTTCGT SEQ ID NO: 15-the DNA sequence of the H54 PCR reverse primer
TTTGCGGCCGCACAGAAGCTCATGCATT SEQ ID NO: 16-the DNA sequence of the MCS forward primer
CGATCTCGAGCCTGCAGGGATATCAT SEQ ID NO: 17-the DNA sequence of the MCS reverse primer
CGATGATATCCCTGCAGGCTCGAGAT SEQ ID NO: 18-the DNA sequence of the WP forward primer
CGGGCCACAACTCCTCATAA SEQ ID NO: 19-the DNA sequence of the WP reverse primer
TTGCTTCCCGTATGGCTTTC SEQ ID NO: 20-the sequence of the 5'-FAM, TAMRA-3' probe
FAM-TCTCCTCCTTGTATAAATCCTGGTTGCTGTCTC-TAMRA

The invention claimed is:

1. An isolated mammalian cell or an isolated mammalian cell population comprising a vector or expression cassette comprising a regulatory region comprising the nucleotide of SEQ ID NO:1 operably linked to a transgene, wherein the transgene encodes α-L-iduronidase or a biologically active truncation thereof, wherein the α-L-iduronidase is encoded by the nucleotide of SEQ ID NO: 2 or encodes α-glucosidase or a biologically active truncation thereof, wherein said α-glucosidase is encoded by the nucleotide of SEQ ID NO: 9, and wherein said regulatory sequence regulates expression of said transgene.

2. The cell population of claim 1, wherein the population is a population of human cells.

3. The cell population of claim 1, wherein the population comprises bone marrow cells.

4. The cell population of claim 1, wherein the population comprises hematopoietic stem cells or progenitor cells.

5. The cell population of claim 1, wherein the transgene has the sequence of SEQ ID NO: 2 or SEQ ID NO: 9.

6. The cell population of claim 1, wherein the cell is an erythrocyte or a macrophage.

7. The cell population of claim 1, wherein the cell population is derived from the same patient, an individual who is related to the patient, or an individual who is a tissue type match for the patient.

8. The cell population of claim 1, wherein the cell population is derived from an individual with a different genetic background from the patient to which it is administered.

9. The cell population of claim 1, wherein said transgene encodes α-L-iduronidase or encodes α-glucosidase.

* * * * *